United States Patent
Ling et al.

(10) Patent No.: US 6,613,942 B1
(45) Date of Patent: *Sep. 2, 2003

(54) GLUCAGON ANTAGONISTS/INVERSE AGONISTS

(75) Inventors: Anthony Ling, San Diego, CA (US); Vlad Gregor, Del Mar, CA (US); Javier Gonzalez, Oceanside, CA (US); Yufeng Hong, San Diego, CA (US); Dan Kiel, San Diego, CA (US); Atsuo Kuki, Encinitas, CA (US); Shenghua Shi, San Diego, CA (US); Lars Naerum, Hellerup (DK); Peter Madsen, Bagsvaerd (DK); Christian Sams, Frederiksberg (DK); Jesper Lau, Farum (DK); Michael Bruno Plewe, La Jolla, CA (US); Jun Feng, La Mesa, CA (US); Min Teng, San Diego, CA (US); Michael David Johnson, San Diego, CA (US); Kimberly Ann Teston, San Diego, CA (US); Ulla Grove Sidelmann, Vedbaek (DK); Lotte Bjerre Knudsen, Valby (DK)

(73) Assignee: Novo Nordisk A/S, Bagsvaerd (DK)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 34 days.

(21) Appl. No.: 09/220,003

(22) Filed: Dec. 23, 1998

Related U.S. Application Data

(63) Continuation-in-part of application No. 09/107,400, filed on Jun. 30, 1998, which is a continuation-in-part of application No. 09/032,516, filed on Feb. 27, 1998, which is a continuation-in-part of application No. 08/886,785, filed on Jul. 1, 1997.

(51) Int. Cl.$^7$ .................. C07C 233/00; C07C 241/00; A01N 47/28; A01N 47/10; A01N 33/02
(52) U.S. Cl. .................. 564/161; 564/251; 514/482; 514/488; 514/647; 514/651
(58) Field of Search .................. 564/161, 251; 514/482, 488, 647, 651

(56) References Cited

U.S. PATENT DOCUMENTS

| | | |
|---|---|---|
| 3,746,703 A | 7/1973 | Bruce .................. 260/562 |
| 3,836,580 A | 9/1974 | Bruce .................. 260/558 |
| 3,859,281 A | 1/1975 | Bruce .................. 260/240 |
| 3,870,680 A | 3/1975 | Schurdak |
| 3,994,987 A | 11/1976 | Cowell et al. |
| 4,334,015 A | 6/1982 | Yarian .................. 435/1 |
| 5,229,038 A | 7/1993 | Uchino et al. .................. 252/582 |
| 5,424,333 A | 6/1995 | Wing |
| 5,728,646 A | 3/1998 | Tominaga et al. |
| 5,776,954 A | 7/1998 | de Laszlo et al. |
| 5,837,719 A | 11/1998 | de Laszlo et al. |

FOREIGN PATENT DOCUMENTS

| | | |
|---|---|---|
| DE | 2 231 307 | 6/1971 |
| DE | 24 47 929 | 10/1973 |
| DE | 0 451 653 A3 | 3/1991 |
| EP | 451653 | 4/1990 |
| EP | 0 451 653 | 4/1990 |
| EP | 0 497 678 | 8/1992 |
| ES | 2 039 162 | 1/1992 |
| ES | 2 039 161 | 8/1993 |
| ES | 2039161 | 8/1993 |
| GB | 1231783 | 5/1971 |
| WO | WO 87/07027 | 11/1987 |
| WO | WO 94/22846 | 10/1994 |
| WO | WO 97/16442 | 5/1997 |
| WO | WO 97/49670 | 12/1997 |
| WO | WO 98/04528 | 2/1998 |
| WO | WO 98/21957 | 5/1998 |
| WO | WO 98/24780 | 6/1998 |
| WO | WO 98/24782 | 6/1998 |
| WO | WO 99/01423 | 1/1999 |

OTHER PUBLICATIONS

Aldrich Catalog, pp. 143 and 812 (1996).*
Fujikawa et al., "2–Pyrrolecarboxaldehyde, 2,4–Dihydroxy–5–ethylbenzaldehyde 2,4–Dihydroxy–5–isoamylbenzaldehyde" Yakugaku Zasshi, vol. 87 No. 12, pps. 1493–1500 (1967).
Fujikawa et al., Orcilaldehyde, β–Orcilaldehyde, Atranol Divaraldehyde, Yakugaku Zasshi, vol. 88 No. 10 pps. 1264–1269 (1968).
Fujikawa et al., 3–Methoxy–4–phenoxybenzaldehyde 3–Hydroxy–4–phenoxybenzaldehyde, Yakugaku Zasshi, vol. 89 No. 8, ppgs. 1119–1124 (1969).
Fujikawa et al., 3–Methoxy–2–phenoxybenzaldehyde, 3–Methoxy–4–(3–methoxyphenoxy) benzaldehyde 3–Methoxy–4–(4–methoxyphenoxy) benzaldehyde, Yakugaku Zasshi, vol. 89 No. 9, ppgs. 1266–1271 (1969).
R. Li et al., "Structure–Based Design of Parasitic Protease Inhibitors"., Bioorganic & Medicinal Chemistry, vol. 4, No. 9, pp. 1421–1427 (1996).
A.H. El–Askalany et al., "Electroreduction of Parahydroxy–Acetophenonebenzoylhydrazone (p–OHABH) Derivatives", Proc. Pakistan Acad. Sci. vol. 31 No. 3 pp. 187–196 (1994).
A. Raja et al., "Studies on antioxidants, 1 Phenolic antioxidants as stabilizers for polypropylene" Die Angewandte Makromolekulare Chemie vol. 215, (Nr. 3674) pp. 1–10 (1994).

(List continued on next page.)

*Primary Examiner*—Sreeni Padmanabhan
*Assistant Examiner*—Sikarl A. Witherspoon
(74) *Attorney, Agent, or Firm*—Richard W. Book, Esq.; Marc A. Begart, Esq.; Reza Green, Esq.

(57) ABSTRACT

Non-peptide compounds comprising a central hydrazide motif and methods for the synthesis thereof are disclosed. The compounds act to antagonize the action of the glucagon peptide hormone.

50 Claims, No Drawings

OTHER PUBLICATIONS

K. Ueno et al., "Electrochemical and Chromatographic properties of selected hydrazine and hydrazide derivatives of carbonyl compounds" Journal of Chromatography, vol. 585, pp. 225–231 (1991).

S.P. Katrolia et al., "Studies on Antifungal Agents: Aromatic Acid Hydrazones of o. Vanillin, o. Veratraldehyde, 5–Bromo–o. Vanillin and Bourbonal", Hindustan Antibiotics Bulletin vol. 31, No. 3–4, pp. 65–67 (1989).

N.D. Heindel et al., "The 1,3,4,–Oxadiazole Moiety, A Protective Synthon for Indirect Radioiodination" J. Heterocyclic Chem. vol. 22, pp. 209–210 (1985).

I. Chaaban et al., "Synthesis of Substituted 2–Acetyl–hydroquinone and 2–Acetylbenzoquinone Derivatives for an Expected Antibacterial Activity" Sci. Pharm. vol. 52, pp. 59–65 (1984).

A.K. Srivastava et al., "Studies in Organic Fluorine Compounds. Synthesis of Fluorinated Hydrazones, Aryl Esters of p–Halogenated Phenols, Fluorinated Hydroxy Ketones and their Thiosemicarbazones and Fluoro–substituted Thiazoles and their Mercury Derivatives as Possible Fungicides"., J. Indian Chem. Soc., vol. LIII, pp. 841–845 (1976).

R. Soliman et al., "Synthesis of some Azomethines and Hydrazones Having Expected Antituberculous Activity"., Pharmazie 34, H. 2., pp. 73–74(979).

E. Piscopo et al., "Biological activity of 4–hydroxyisophtalic acid derivatives. Hydrazones with antimicrobial activity", Boll.—Society Ital. Biol. Sper. (1984), 60(6), 1169–75 (English language Abstract).

Lapin et al., "Synthesis and Antiradiation Activity of Azomethines in a Series of Trihydroxy Benzaldehydes", Tr. Inst. Khim., Ural. Nauchn. Tsentr, Akad. Nauk SSSR (1978), 37, 29–34.

Madsen et al., J. Med. Chem., vol. 41, pp. 5150–5157 (1998).

Patent Abstract of Japan No. JP 11–106371 A (Apr. 1999).

Husain et al., J. Indian Chem. Soc., vol. 60, No. 6, pp. 578–579 (Jun. 1983).

Isoyama et al., "Study on Synthesis of Antitrichophytial Drugs Derived from Gallic Acid"., Nichidai Igaku Zasshi (1968), pp. 270–273.

Ulgen et al., "The In Vitro Hepatic Microsomal Metabolism of Benzoic Acid Benylidenehydrazide"., Drug Metab. Drug Interact. Freund Publishing House Ltd., vol. 13., No. 14., pp. 285–294 (1997).

Ciugureanu et al., "Sur L'Action Antigacterienne De Quelques Nouveaux Derives De L'Hydrazide"., Rev. Med. Chir. Soc.Med.Nat.Iasi, vol. 97, No. 1, pp. 433–437 (1993).

Dekelbaum et al., "Investigation of Interaction of Substituents at Hydrolysis of Carbohydrazones"., Reakst Sposobnost. Organic Soedin, pp. 637–645 (1973).

M. Tanaka., "The Studies of 5–Aminosalicylaldehyde Derivatives. III.[1)] The Preparation of 5–Aminosalicylaldehyde Hydrazones by Reduction of 5–(p–Sulfophenylazo)salicylaldehyde Hydrazone".,Bullein Chemical Society Japan., vol. 41., No. 11., pp. 2807–2810 (1968).

A.K. Bhat et al., "Chemotherapy of Fungus Infections: Part III–Alkyl or Aryl Thiosemicarbazones, Acid Hydrazones & Styryl Aryl Ketones of 5–Bromo– & 5–Nitro–salicylaldehydes"., Indian Journal of Chemistry., vol. 10, pp. 694–698 (1972).

J.T. Edward et al., Iron Chelators of the pyridoxal Isonicotinoyl hydrazone class. Relationship of the lipophilicity of the apochelator to its ability to mobilize iron from reticulocytes in vitro: reappraisal of reported partition coefficients., Can. J. Physiol. Pharmacol. vol. 75., pp. 1362–1368 (1997).

Ivanovic et al., Journal of Thermal Analysis, vol. 46, pp. 1741–1750 (1996).

Issopoulos et al., Revue Roumaine de Chimie, vol. 41, pp. 5–6 (1996).

Colonna et al, vol. 20, pp. 338–343 (1995).

Joshi et al., J. Inst. Chemists (India), vol. 64, pp. 104–107 (May, 1992).

Shah et al., Chemists (India), vol. 68, Part I, pp. 22–25 (1996) 1992.

Shaban et al., Alex. J. Pharm. Sci., vol. 6, (1) pp. 16–20 (1992).

Singh et al., U. Scientist Phyl. Sciences, vol. 7, No. 1, pp. 69–75 (1995).

Scoli et al., Rev. Med. Chir. Soc. Med. Nat. IASI, vol. 97, nr. 1, pp. 472–477 (1993).

Colonna et al., Spectroscopy Letters, vol. 27 (9), pp. 1153–1163 (1994).

Raja et al., Die Angewandte Makromolekulare Chemie, vol. 215, Nr. 3674, pp. 1–10 (1994).

Edward et al., Bio Metals, vol. 8, pp. 209–217 (1995).

El–Askalany et al., Proc. Pakistan Acad. Sci., vol. 31, No. 3, pp. 186–197 (1994).

Shah et al., J. India Chem. Soc., vol. 69, pp. 590–592 (Sep. 1992).

Baker et al., Iron Chelation In Hepatocytes vol. 15, No. 3, pp. 493–501 (1992).

Katrolia et a., Defence Research & Development Establishment, vol. 31, No. 3–4, pp. 64–71.

Zhe Li, Current Biology Ltd., vol. 1, pp. 31–37 (Sep. 1994).

Ponka et al., Biochimica et Biophysica Acta., vol. 967, pp. 122–129 (1988).

Richardson et al., The American Society of Hematology, pp. 4295–4306 (1995).

Piscopo et al., Boll. Soc. It. Biol. Sper., vol. LX, n. 6, pp. 1169–1175 (1984).

Fujikawa, et al., Yakugaku Zasshi, vol. 89, No. 9, pp. 1266–1271 (1969).

Fujikawa, et al., Yakugaku Zasshi, vol. 89, No. 8, pp. 1118–1124 (1969).

Fujikawa, et al., Yakugaku Zasshi, vol. 88, No. 10, pp. 1264–1269 (1968).

Fujikawa, et al., Yakugaku Zasshi, vol. 87, No 7, pp. 844–849 (1967) (1967).

Fujikawa, et al., Yakugaku Zasshi, vol. 87, No. 12, pp. 1493–1500.

EL–Kersh et al., Egypt J. Chem., vol., 29, No. 2, pp. 173–183 (1986).

Dologorev et al., Journal Zh. Anal. Khim, vol. 33, No. 12, pp. 2357–2361 (1978).

Tapty et al., Tartu State University, vol. 3, No. 37, pp. 619–655 (Oct. 1973).

Zhao et al., Tetrahedron, vol. 53, No. 12, pp. 4219–4230 (1997).

Rongshi Li et al., Bioorganic & Medicinal Chemistry, vol. 4, No. 9, pp. 1421–1427 (1996).

Edward et al., J. Chem. Eng. Data, vol. 33, pp. 538–540 (1988).

El-Maksoud et al., Materials and Corrosion, vol. 46, pp. 468–472 (1995).

Nakagawa et al., Pestic. Sci., vol. 43, pp. 339–345 (1995).
Soliman et al., Pharmazie, vol. 34, H. 2, pp. 73–74 (1979).
Ponka et al., Can. J. Physiol. Pharmacol., vol. 72, pp. 659–666 (1994).
Ueno et al., Journal of Chromatography, vol. 585, pp. 225–231, (1991).
El–Baradie, Bull. Fac. Sci., K.A.U., Jeddah, vol. 4, pp. 149–158 (1980).
Pajeda et al., Darbai Chemija IR Technologija, vol. 16, pp. 233–238 (1974).
Khattab et al., Indian Journal of Chemistry, vol. 15A, pp. 962–965 (Nov. 1977).
Khattab et al., Proc. Pakistan Acad. Sci., vol. 18, No. 1, pp. 1–13 (1981).
Piscopo et al., Pervenuto in redazione il, vol. 6, pp. 1636–1643 (Sep. 1982).
Brydon et al., Polymer, vol. 30, pp. 619–627 (Apr. 1989).
Chaaban et al., Sci. Pharm.,vol. 52, pp. 59–65 (1984).
Heindel et al., J. Heterocyclic Chem., vol. 22, pp. 209–210 (1985).
Habib et al., Egypt. J. Chem., vol. 30, No. 4, pp. 315–320 (1987).
Piscopo et al., Boll.—Soc. Ital. Biol. Sper., vol. 59, No. 3, pp. 344–348 (1983).
Srivastava et al., J. India Chem. Soc., vol. LIII, pp. 841–845 (Aug. 1976).
Piscopo et al., Boll. –Soc. Ital. Biol. Sper., vol. 59, No. 11, pp. 1644–1648 (1983).
Vopr. Khim. Khim. Teknol., vol. 74, pp. 85–88, (1984).
Dekelbaum et al., A Study On The Mechanism Of Hydrolysis Of Carbohydrazones, Report II, Leningrad Chemico–Pharmaceutical Institute pp. 383–389 (1981).
Lapin et al., Synthesis And Antiradiation Activity Of Azomethines In A Series Of Trihydroxy Benzaldehydes, pp. 29–34 (1984).
Vattimo et al. (1983) *Boll soc. Ital. Biol Sper*, 1649–1653 (English language Abstract).
Abstract of Lapin et al., "Synthesis and Antiradiation Activity of Azomethines in a Series of Trihydroxy Benzaldehydes", Tr. Inst. Khim., Ural. Nauchn. Tsentr. Akad. Nauk SSSR (1978), 37, 29–34.

* cited by examiner

GLUCAGON ANTAGONISTS/INVERSE AGONISTS

CROSS-REFERENCE TO RELATED APPLICATIONS

This application is a continuation-in-part application of application Ser. No. 09/107,400 filed Jun. 30, 1998 which is a continuation-in-part of application Ser. No. 09/032,516 filed Feb. 27, 1998 which is a continuation-in-part of application Ser. No. 08/886,785 filed Jul. 1, 1997, the contents of which are fully incorporated herein by reference.

FIELD OF THE INVENTION

The present invention relates to agents that act to antagonize the action of the glucagon peptide hormone. It relates particularly to non-peptide glucagon antagonists or inverse agonists.

BACKGROUND OF THE INVENTION

Glucagon is a key hormonal agent that, in cooperation with insulin, mediates homeostatic regulation of the amount of glucose in the blood. Glucagon primarily acts by stimulating certain cells (mostly liver cells) to release glucose when blood glucose levels fall. The action of glucagon is opposed by insulin which stimulates cells to take up and store glucose whenever blood glucose levels rise. Both glucagon and insulin are peptide hormones.

Glucagon is produced in the alpha islet cells and insulin in the beta islet cells of the pancreas. Diabetes mellitus, the common disorder of glucose metabolism, is characterized by hyperglycemia, and can present as type I, insulin-dependent, or type II, a form that is non-insulin-dependent in character. Subjects with type I diabetes are hyperglycemic and hypoinsulinemic, and the conventional treatment for this form of the disease is to provide insulin. However, in some patients with type I or II diabetes, absolute or relative elevated glucagon levels have been shown to contribute to the hyperglycemic state. Both in healthy animals as well as in animal models of type I and II, removal of circulating glucagon with selective and specific anti-bodies has resulted in reduction of the glycemic level (Brand et al. Diabetologia 37, 985 (1994); Diabetes 43, [suppl 1], 172A (1994); Am J Physiol 269, E469–E477 (1995); Diabetes 44 [suppl 1], 134A (1995); Diabetes 45, 1076 (1996)). These studies suggest that glucagon suppression or an action antagonistic to glucagon could be a useful adjunct to conventional antihyperglycemia treatment of diabetes. The action of glucagon can be suppressed by providing an antagonist or an inverse agonist, substances that inhibit or prevent glucagon induced response. The antagonist can be peptide or non-peptide in nature. Native glucagon is a 29 amino acid-containing peptide having the sequence:

His-Ser-Glu-Gly-Thr-Phe-Thr-Ser-Asp-Tyr-Ser-Lys-Tyr-Leu-Asp-Ser-Arg-Arg-Ala-Gln-Asp-Phe-Val-Gln-Trp-Leu-Met-Asn-Thr-$NH_2$.

Glucagon exerts its action by binding to and activating its receptor, which is part of the Glucagon-Secretin branch of the 7-transmembrane G-protein coupled receptor family (Jelinek et al. Science 259, 1614, (1993)). The receptor functions by activation of the adenylyl cyclase second messenger system and the result is an increase in cAMP levels.

Several publications disclose peptide antagonists. Probably, the most thoroughly characterized antagonist is DesHis$^1$[Glu$^9$]-glucagon amide (Unson et al., Peptides 10, 1171 (1989); Post et al., Proc. Natl. Acad. Sci. USA 90, 1662 (1993)). Other antagonists are eg DesHis$^1$,Phe$^6$[Glu$^9$]-glucagon amide (Azizh et al., Bioorganic & Medicinal Chem. Lett. 16, 1849 (1995)) or NLeu$^9$,Ala$^{11,16}$-glucagon amide (Unson et al., J. Biol. Chem. 269(17), 12548 (1994)).

Peptide antagonists of peptide hormones are often quite potent; however, they are defective as drugs because of degradation by physiological enzymes, and poor biodistribution. Therefore, non-peptide antagonists of the peptide hormones are preferred. Among the non-peptide glucagon antagonists, a quinoxaline derivative, (2-styryl-3-[3-(dimethylamino)propylmethyl-amino]-6,7-dichloroquinoxaline was found to displace glucagon from the rat liver receptor (Collins, J. L. et al. (1992) Bioorganic and Medicinal Chemistry Letters 2(9):915–918). West, R. R. et al. (1994), WO 94/14426 discloses use of skyrin, a natural product comprising a pair of linked 9,10-anthracenedione groups, and its synthetic analogues, as glucagon antagonists. Anderson, P. L., U.S. Pat. No. 4,359,474 discloses the glucagon antagonistic properties of 1-phenyl pyrazole derivatives. Barcza, S., U.S. Pat. No. 4,374,130, discloses substituted disilacyclohexanes as glucagon antagonists. WO 98/04528 (Bayer Corporation) discloses substituted pyridines and biphenyls as glucagon antagonists. Furthermore, WO 97/16442 (Merck & Co., Inc.) discloses substituted pyridyl pyrroles as glucagon antagonists and WO 98/21957 (Merck & Co., Inc.) discloses 2,4-diaryl-5-pyridylimidazoles as glucagon antagonists. These glucagon antagonists differ structurally from the present compounds.

DESCRIPTION OF THE INVENTION

Definitions

The following is a detailed definition of the terms used to describe the compounds of the invention:

"Halogen" designates an atom selected from the group consisting of F, Cl, Br or I.

The term "alkyl" in the present context designates a hydrocarbon chain or a ring that is either saturated or unsaturated (containing one or more double or triple bonds where feasible) of from 1 to 10 carbon atoms in either a linear or branched or cyclic configuration. Thus, alkyl includes for example n-octyl, methyl, ethyl, propyl, isopropyl, butyl, isobutyl, tert-butyl, allyl, propargyl, 2-hexynyl, cyclopropyl, cyclopropylmethyl, cyclopentyl, cyclohexyl, cyclooctyl, 4-cyclohexylbutyl, and the like.

Further non-limiting examples are sec-butyl, n-pentyl, isopentyl, neopentyl, tert-pentyl, n-hexyl, isohexyl, n-heptyl, n-nonyl, n-decyl, vinyl, 1-propenyl, 1-butenyl, 2-butenyl, 3-butenyl, 2-methyl-1-propenyl, 1-pentenyl, 2-pentenyl, 3-pentenyl, 4-pentenyl, 3-methyl-2-butenyl, 1-hexenyl, 3-hexenyl, 2,4-hexadienyl, 5-hexenyl, 1-heptenyl, 2,4-heptadienyl, 1-octenyl, 2,4-octadienyl, ethynyl, 1-propynyl, 1-butynyl, 2-butynyl, 3-butynyl, 1-pentynyl, 2-pentynyl, 3-pentynyl, 4-pentynyl, 1-hexynyl, 3-hexynyl, 2,4-hexadiynyl, 5-hexynyl, 1-hepynyl, 1-octynyl, 2-decynyl, cyclobutyl, cyclopentyl, 1-cyclopentenyl, 2-cyclopentenyl, 3-cyclopentenyl, 1-cyclohexenyl, 2-cyclohexenyl, 3-cyclohexenyl, 2-cyclopropylethyl, cyclobutylmethyl, 2-cyclobutylethyl, cyclohexenylmethyl, 4-cyclohexyl-2-butenyl, 4-(1-cyclohexenyl)-vinyl and the like.

The term "lower alkyl" designates a hydrocarbon moiety specified above, of from 1 to 6 carbon atoms.

"Aryl" means an aromatic ring moiety, for example: phenyl, naphthyl, furyl, thienyl, pyrrolyl, pyridyl, pyrimidinyl, pyrazolyl, imidazolyl, pyrazinyl, pyridazinyl, 1,2,3-triazinyl, 1,2,4-triazinyl, oxazolyl, isoxazolyl, 1,2,3-oxadiazolyl, 1,2,4-oxadiazolyl, 1,3,4-oxadiazolyl, 1,2,3-thiadiazolyl, 1,2,4-thiadiazolyl, 1,3,4-thiadiazolyl, thiazolyl, isothiazolyl, tetrazolyl, 1-H-tetrazol-5-yl, indolyl, quinolyl, quinazolinyl, benzofuryl, benzothiophenyl (thianaphthenyl) and the like.

Further non-limiting examples are biphenyl, anthracenyl, phenanthrenyl, fluorenyl, indenyl, 1,2,3,4-tetrahydronaphthyl, 2,3-dihydrobenzofuryl, triazolyl, pyranyl, thiadiazinyl, isoindolyl, indazolyl, 1,2,5-oxadiazolyl, 1,2,5-thiadiazolyl, benzothienyl, benzimidazolyl, benzthiazolyl, benzisothiazolyl, benzoxazolyl, benzisoxazolyl, purinyl, quinolizinyl, isoquinolyl, quinoxalinyl, naphthyridinyl, pteridinyl, carbazolyl, acridinyl, pyrrolinyl, pyrazolinyl, indolinyl, pyrrolidinyl, piperidinyl and the like.

The aryl moieties are optionally substituted by one or more substituents, for example selected from the group consisting of F, Cl, I, and Br; lower alkyl; lower alkanoyl such as formyl, acetyl, propionyl, butyryl, valeryl, hexanoyl and the like; —OH; —NO₂; —CN; —CO₂H; —O-lower alkyl; aryl; aryl-lower alkyl; —CO₂CH₃; —CONH₂; —OCH₂CONH₂; —NH₂; —N(CH₃)₂; —SO₂NH₂; —OCHF₂; —CF₃; —OCF₃ and the like. A further non-limiting example is —NH—(C=S)—NH₂.

Such aryl moieties may also be substituted by two substituents forming a bridge, for example —OCH₂O—.

"Aryl-lower alkyl" means a lower alkyl as defined above, substituted by an aryl, for example:

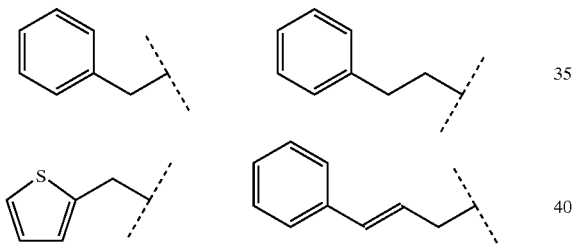

The aryl group is optionally substituted as described above.

Description of the Invention

The present invention is based on the unexpected observation that compounds having a selected nitrogen-bearing central motif and the general structural features disclosed below antagonize the action of glucagon.

Accordingly, the invention is concerned with compounds of the general formula I:

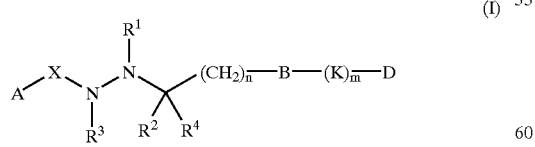

(I)

wherein:
R¹ and R² independently are hydrogen or lower alkyl or together form a valence bond;
R³ and R⁴ independently are hydrogen or lower alkyl;
n is 0, 1, 2 or 3;
m is 0 or 1;
X is >C=O, >C=S, >C=NR⁵ or >SO₂;
wherein R⁵ is hydrogen, lower alkyl, aryl-lower alkyl or —OR⁶;
wherein R⁶ is hydrogen, lower alkyl, aryl or aryl-lower alkyl;
A is

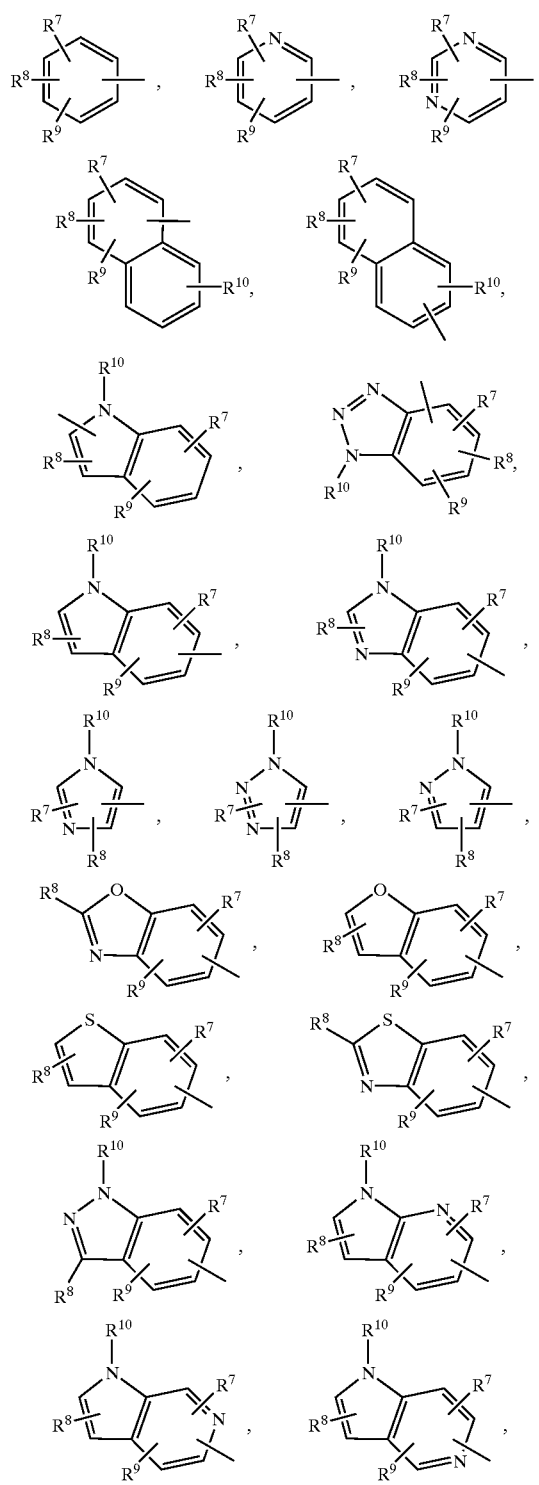

-continued

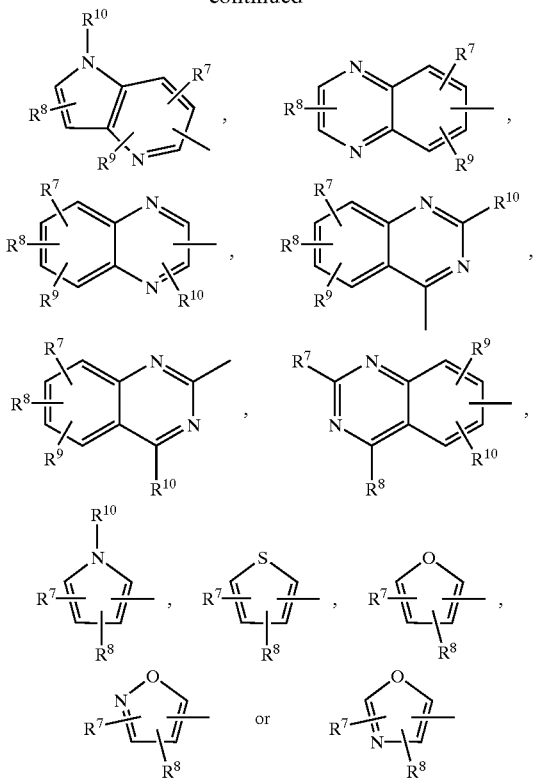

wherein:
R[7] is hydrogen, halogen, —CN, —CF$_3$, —OCF$_3$, —OCH$_2$CF$_3$, —NO$_2$, —OR[11], —NR[11]R[12], lower alkyl, aryl, aryl-lower alkyl, —SCF$_3$, —SO$_2$NR[11]R[12], —SR[11], —CHF$_2$, —OCHF$_2$, —OSO$_2$R[11], —CONR[11]R[12], —OCH$_2$CONR[11]R[12], —CH$_2$OR[11], —CH$_2$NR[11]R[12], —OCOR[11], —CO$_2$R[13] or —OSO$_2$CF$_3$;

R[8] and R[9] independently are hydrogen, halogen, —CN, —CF$_3$, —OCF$_3$, —OCH$_2$CF$_3$, —NO$_2$, —OR[11], —NR[11]R[12], lower alkyl, aryl, —SCF$_3$, —SR[11], —CHF$_2$, —OCHF$_2$, —OSO$_2$R[11], —CONR[11]R[12], —CH$_2$OR[11], —CH$_2$NR[11]R[12], —OCOR[11], —CO$_2$R[13] or —OSO$_2$CF$_3$, or R[8] and R[9] together form a bridge —OCH$_2$O— or —OCH$_2$CH$_2$O—;

wherein R[11] and R[12] independently are hydrogen, —COR[13], —SO$_2$R[13], lower alkyl or aryl;

wherein R[13] is hydrogen, lower alkyl, aryl-lower alkyl or aryl; and

R[10] is hydrogen, lower alkyl, aryl-lower alkyl or aryl; B is

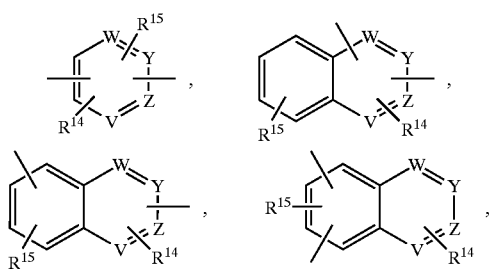

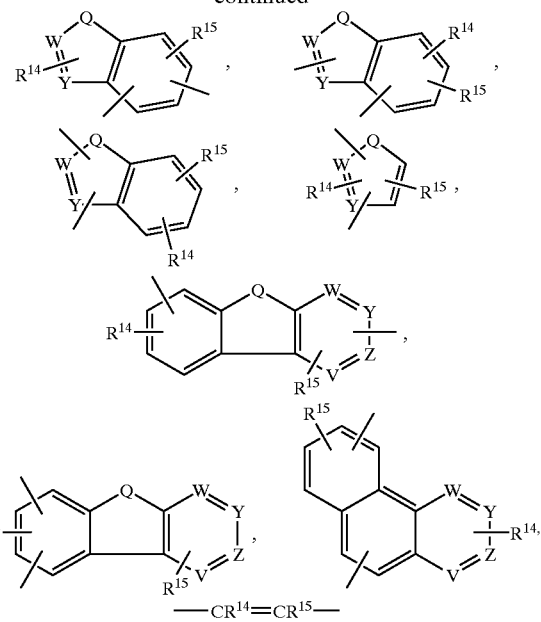

—CR[14]=CR[15]— or a valence bond;
wherein:
R[14] and R[15] independently are hydrogen, halogen, —CN, —CF$_3$, —OCF$_3$, —O(CH$_2$)$_l$CF$_3$, —NO$_2$, —OR[16], —NR[16]R[17], lower alkyl, aryl, aryl-lower alkyl, —SCF$_3$, —SR[16], —CHF$_2$, —OCHF$_2$, —OCF$_2$CHF$_2$, —OSO$_2$CF$_3$, —CONR[16]R[17], —(CH$_2$)$_l$CONR[16]R[17], —O(CH$_2$)$_l$CONR[16]R[17], —(CH$_2$)$_l$COR[16], —(CH$_2$)$_l$COR[16], —(CH$_2$)$_l$OR[16], —O(CH$_2$)$_l$OR[16], —(CH$_2$)$_l$NR[16]R[17], —O(CH$_2$)$_l$NR[16]R[17], —OCOR[16], —CO$_2$R[18], —O(CH$_2$)$_l$CO$_2$R[18], —O(CH$_2$)$_l$CN, —O(CH$_2$)$_l$Cl, or R[14] and R[15] together form a bridge —O(CH)$_l$O— or —(CH$_2$)$_l$—;

wherein l is 1, 2, 3 or 4;

R[16] and R[17] independently are hydrogen, —COR[18], —SO$_2$R[18], lower alkyl, aryl, or R[16] and R[17] together form a cyclic alkyl bridge containing from 2 to 7 carbon atoms;

wherein R[18] is hydrogen, lower alkyl, aryl or aryl-lower alkyl;

W is —N= or —CR[19]=;
Y is —N= or —CR[20]=;
Z is —N= or —CR[21]=;
V is —N= or —CR[22]=; and
Q is —NR[23]—, —O— or —S—;

wherein:
R[19], R[20], R[21] and R[22] independently are hydrogen, halogen, —CN, —CF$_3$, —OCF$_3$, —OCH$_2$CF$_3$, —NO$_2$, —OR[24], —NR[24]R[25], lower alkyl, aryl, aryl-lower alkyl, —SCF$_3$, —SR[24], —CHF$_2$, —OCHF$_2$, —OCF$_2$CHF$_2$, —OSO$_2$CF$_3$, —CONR[24]R[25], —CH$_2$CONR[24]R[25], —OCH$_2$CONR[24]R[25], —CH$_2$OR[24], —CH$_2$NR[24]R[25], —OCOR[24] or —CO$_2$R[24], or R[19] and R[20], R[20] and R[21], or R[21] and R[22] together form a bridge —OCH$_2$O—;

wherein R[24] and R[25] independently are hydrogen, —COR[26], —SO$_2$R[26], lower alkyl, aryl or aryl-lower alkyl;

wherein R[26] is hydrogen, lower alkyl, aryl or aryl-lower alkyl; and $R^{23}$ is hydrogen, lower alkyl, aryl or aryl-lower alkyl;
K is

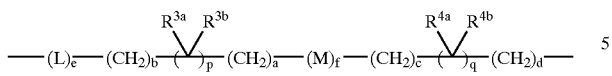

wherein:
$R^{3a}$, $R^{3b}$, $R^{4a}$ and $R^{4b}$ independently are hydrogen, halogen, —CN, —CF$_3$, —OCF$_3$, —CCH$_2$CF$_3$, —NO$_2$, —OR$^{24}$, —NR$^{24a}$R$^{25a}$, lower alkyl, aryl, aryl-lower alkyl, —SCF$_3$, —SR$^{24a}$, —CHF$_2$, —OCHF$_2$, —OCF$_2$CHF$_2$, —OSO$_2$CF$_3$, —CONR$^{24a}$R$^{25a}$, —CH$_2$CONR$^{24a}$R$^{25a}$, —OCH$_2$CONR$^{24a}$R$^{25a}$, —CH$_2$OR$^{24a}$, —CH$_2$NR$^{24a}$R$^{25a}$, —OCOR$^{24a}$ or —CO$_2$R$^{24a}$;
wherein $R^{24a}$ and $R^{25a}$ independently are hydrogen, —COR$^{26a}$, —SO$_2$R$^{26a}$, lower alkyl, aryl or aryl-lower alkyl;
wherein $R^{26a}$ is hydrogen, lower alkyl, aryl or aryl-lower alkyl; or
$R^{3a}$ and $R^{3b}$, $R^{4a}$ and $R^{4b}$, or $R^{3a}$ and $R^{4b}$ together form a bridge —(CH$_2$)$_i$—;
wherein i is 1, 2, 3 or 4;
a, b, c and d independently are 0, 1, 2, 3 or 4;
e, f and p independently are 0 or 1;
q is 0, 1 or 2; and
L and M independently are —O—, —S—, —CH=CH—, —C≡C—, —NR$^{5a}$—, —CH$_2$NR$^{5a}$—, —CO—, —OCO—, —COO—, —CONR$^{5a}$—, CONR$^{5b}$—, —NR$^{5a}$CO—, —SO—, —SO$_2$—, —OSO$_2$—, —SO$_2$NR$^{5a}$—, —NR$^{5a}$SO$_2$—, —NR$^{5a}$CONR$^{5b}$—, —CONR$^{5a}$NR$^{5b}$—, —NR$^{5a}$CSNR$^{5b}$—, —OCONR$^{5b}$—, —CH$_2$CONR$^{5b}$—, —OCH$_2$CONR$^{5b}$—, —P(O)(OR$^{5a}$)O—, —NR$^{5a}$C(O)O— or

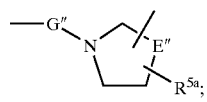

wherein $R^{5a}$ and $R^{5b}$ independently are hydrogen, lower alkyl, —OH, —(CH$_2$)$_k$—OR$^{6a}$—, —COR$^{6a}$, —(CH$_2$)$_k$—CH(OR$^{6a}$)$_2$, —(CH$_2$)$_k$—CN, —(CH$_2$)$_k$—NR$^{6a}$R$^{6b}$—, aryl, aryl-lower alkyl, —(CH$_2$)$_g$—COOR$^{43}$ or —(CH$_2$)$_g$—CF$_3$;
wherein k is 1, 2, 3 or 4;
$R^{6a}$ and $R^{6b}$ independently are hydrogen, lower alkyl, aryl or aryl-lower alkyl;
g is 0, 1, 2, 3 or 4;
$R^{43}$ is hydrogen or lower alkyl;
G" is —OCH$_2$CO—, —CH$_2$CO—, —CO— or a valence bond; and
E" is —CH$_2$—, —CH$_2$CH$_2$—, —CH=CH—, —CH$_2$NH— or —CH$_2$CH$_2$NH—;
D is hydrogen,

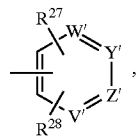 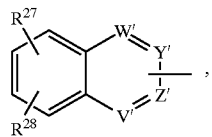

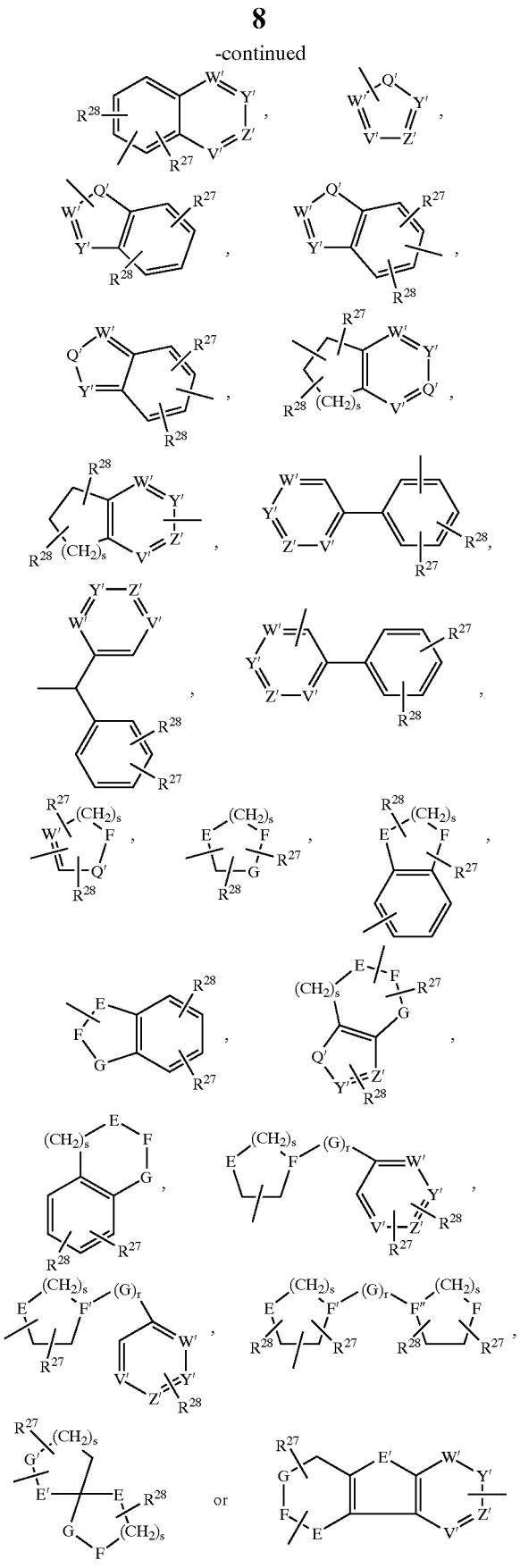

wherein:

r is 0 or 1;
s is 0, 1, 2 or 3;
E, E', F, G and G" independently are —CHR$^{38}$—, >C=O, >NR$^{39}$, —O— or —S—;
F' is >CR$^{38}$— or >N—;
Y' is —N= or —CR$^{32}$=;
Z' is —N= or —CR$^{33}$=;
V' is —N= or —CR$^{34}$=;
W' is —N= or —CR$^{35}$=; and
Q' is —NR$^{36}$—, —O— or —S—;
wherein:
R$^{27}$, R$^{28}$, R$^{32}$, R$^{33}$, R$^{34}$ and R$^{35}$ independently are hydrogen, halogen, —CN, —CF$_3$, —O(CH$_2$)$_y$CF$_3$, —(CH$_2$)$_y$NHCOCF$_3$, —NO$_2$, lower alkyl, aryl, aryl-lower alkyl, —SCF$_3$, —SR$^{29}$, —CHF$_2$, —OH$_2$, —OCF$_2$CHF$_2$, —OSO$_2$R$^{29}$, —OSO$_2$CF$_3$, —(CH$_2$)$_y$CONR$^{29}$R$^{30}$, —O(CH$_2$)$_y$CONR$^{29}$R$^{30}$, —(CH$_2$)$_y$OR$^{29}$, —(CH$_2$)$_y$NR$^{29}$R$^{30}$, —OCOR$^{29}$, —COR$^{29}$ or —CO$_2$R$^{29}$; or
R$^{27}$ and R$^{28}$, R$^{32}$ and R$^{33}$, R$^{34}$ and R$^{34}$ or R$^{34}$ and R$^{35}$ together form a bridge —OCH$_2$)$_y$O—,
wherein y is 0, 1, 2, 3 or 4; and
R$^{29}$ and R$^{30}$ independently are hydrogen, —CNR$^{31}$, —CO$_2$R$^{31}$, —SO$_2$R$^{31}$, lower alkyl, aryl or aryl-lower alkyl;
wherein R$^{31}$ is hydrogen, lower alkyl, aryl or aryl-lower alkyl;
R$^{36}$ and R$^{39}$ independently are hydrogen, lower alkyl, aryl or aryl-lower alkyl; and
R$^{38}$ is hydrogen, —OR$^{40}$, —NR$^{40}$R$^{41}$, lower alkyl, aryl, aryl-lower alkyl, —SCF$_3$, —SR$^{40}$, —CHF$_2$, —OCHF$_2$, —OCF$_2$CHF$_2$, —CONR$^{40}$R$^{41}$, —(CH$_2$)$_x$CONR$^{40}$OR$^{41}$, —O(CH$_2$)$_x$CONR$^{40}$R$^{41}$, —(CH$_2$)$_x$OR$^{40}$, —(CH$_2$)$_x$NR$^{40}$OR$^{41}$, —OCOR$^{40}$ or —CO$_2$R$^{40}$;
wherein x is 1, 2, 3 or 4;
R$^{40}$ and R$^{41}$ independently are hydrogen, —COR$^{42}$, —SO$_2$R$^{42}$, lower alkyl, aryl or aryl-lower alkyl;
wherein R$^{42}$ is hydrogen, lower alkyl, aryl or aryl-lower alkyl;
as well as any optical or geometric isomer or tautomeric form thereof including mixtures of these or a pharmaceutically acceptable salt thereof.

Where the formulae for B make it possible, R$^{19}$, R$^{20}$, R$^{21}$, R$^{22}$ and R$^{23}$ may alternatively be replaced by R$^{14}$ or R$^{15}$, respectively. In such case eg W may be selected from —N=, —CR$^{19}$— and —C$^{14}$—.

Similarly, where the formulae for D make it possible, R$^{32}$, R$^{33}$, R$^{34}$, R$^{35}$, R$^{36}$, R$^{38}$ and R$^{39}$ may alternatively be replaced by R$^{27}$ or R$^{28}$, respectively. In such case eg E may be selected from —CHR$^{38}$—, >C=O, >NR$^{39}$, —O—, —S—, —CHR$^{27}$— and >NR$^{27}$.

In a preferred embodiment the invention relates to compounds of the following general formula II.

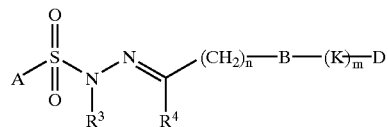

(II)

wherein A, B, K, D, R$^3$, R$^4$, n and m are as defined for formula I.

In another preferred embodiment the invention relates to compounds of the following general formula III:

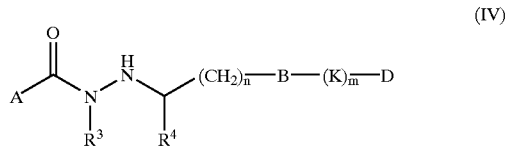

wherein A, B, K, D, R$^3$, R$^4$, n and m are as defined for formula I.

In still another preferred embodiment the invention relates to compounds of the following formula IV:

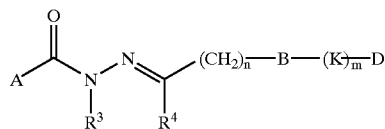

(IV)

wherein A, B, K, D, R$^3$, R$^4$, n and m are as defined for formula I.

In the compounds of the above formulae I to IV the following substituents are preferred:
R$^3$ is preferably hydrogen.
R$^4$ is preferably hydrogen.
A is preferably selected from the group consisting of:

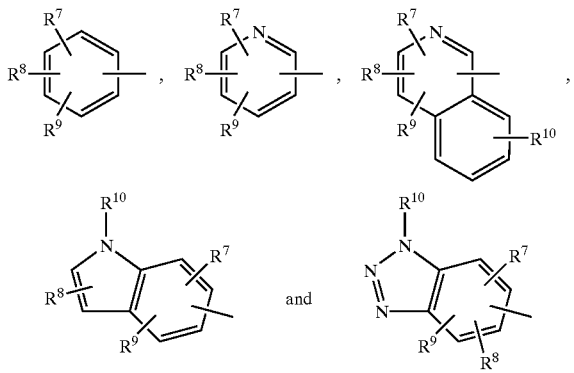

wherein R$^7$, R$^8$, R$^9$ and R$^{10}$ are as defined for formula I.
A is more preferably

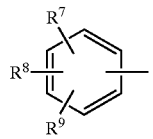

wherein R$^7$, R$^8$ and R$^9$ are as defined for formula I.
In the above embodiments of A, R$^7$ is preferably halogen, lower alkyl, —OH, —NO$_2$, —CN, —CO$_2$H, —O-lower alkyl, aryl, aryl-lower alkyl, —CO$_2$CH$_3$, —CONH$_2$, —OCH$_2$CONH$_2$, —NH$_2$, —N(CH$_3$)$_2$, —SO$_2$NH$_2$, —OCHF$_2$, —CF$_3$ or —OCF$_3$.
Preferably, R$^8$ and R$^9$ are independently hydrogen, halogen, —OH, —NO$_2$, —NH$_2$, —CN, —OCF$_3$, —SCF$_3$, —CF$_3$, —OCH$_2$CF$_3$, —O-lower alkyl such as methoxy and ethoxy, lower alkyl such as methyl and ethyl, or phenyl, and R$^{10}$ is hydrogen, lower alkyl or phenyl.
More preferably, R$^8$ and R$^9$ are independently selected from hydrogen, halogen such as —F and —Cl, —O-lower alkyl such as methoxy and ethoxy, —NH$_2$, —CN or —NO$_2$, and R$^{10}$ is hydrogen.

In a particularly preferred embodiment A is

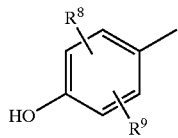

wherein R$^8$ and R$^9$ independently are hydrogen, halogen, —OH, —NO$_2$, —NH$_2$, —CN, —OCF$_3$, —SCF$_3$, —CF$_3$, —OCH$_2$CF$_3$, —O-lower alkyl such as methoxy and ethoxy, lower alkyl such as methyl and ethyl, or phenyl, preferably hydrogen, halogen such as —F and —Cl, —O-lower alkyl such as methoxy and ethoxy, —NH$_2$, —CN or —NO$_2$.

In a further particularly preferred embodiment A is

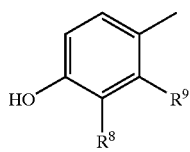

wherein R$^8$ is hydrogen, halogen such as —F or —Cl, —O-lower alkyl such as —OCH$_3$ or —OC$_2$H$_5$, —NH$_2$, —CN or —NO$_2$; and R$^9$ is hydrogen or halogen such as —F or —Cl.

In a preferred embodiment R$^8$ is halogen and R$^9$ is hydrogen.

In still a preferred embodiment the invention relates to compounds of the following formula V:

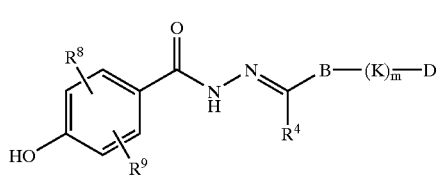

(V)

wherein R$^4$, B, K, D and m are as defined for formula I and R$^8$ and R$^9$ are as defined for formula I and preferably as defined for the preferred embodiments of A above.

B is preferably:

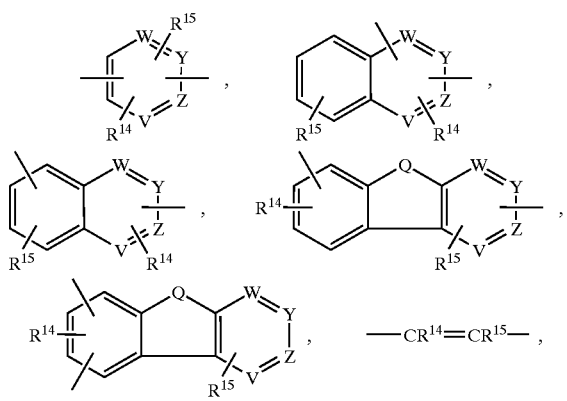

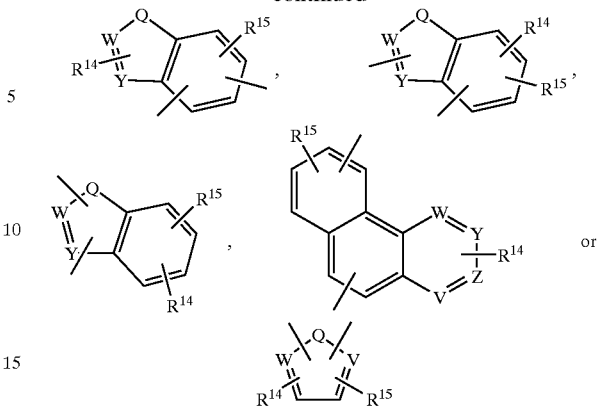

wherein V, W, Z, Y and Q are as defined for formula I; and R$^{14}$ and R$^{15}$ independently are hydrogen, halogen, —CF$_3$, —OCF$_3$, —OR$^{16}$, —NR$^{16}$R$^{17}$, lower alkyl, aryl, aryl-lower alkyl, —OSO$_2$CF$_3$, —CONR$^{16}$R$^{17}$, —CH$_2$OR$^{16}$, —CH$_2$NR$^{16}$R$^{17}$, —OCOR$^{16}$ or —CO$_2$R$^{18}$; or R$^{14}$ and R$^{15}$ together form a bridge —OCH$_2$O— or —(CH$_2$)$_l$—;

wherein l, R$^{16}$, R$^{17}$ and R$^{18}$ are as defined for formula I.

Q is preferably —O— or —NH—.

Particularly preferred compounds are those in which B is

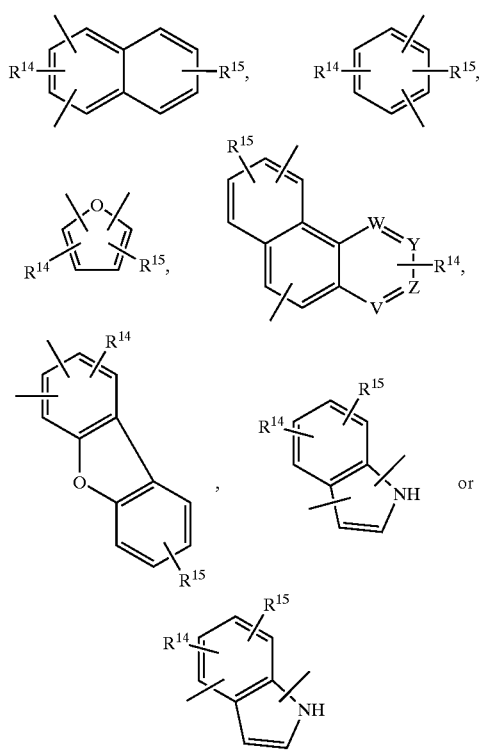

wherein V, W, Z, Y and Q are as defined for formula I; and R$^{14}$ and R$^{15}$ independently are hydrogen, halogen, —CF$_3$, —OCF$_3$, —OR$^{16}$, —NR$^{16}$R$^{17}$, lower alkyl, aryl, aryl-lower alkyl, —OSO$_2$CF$_3$, —CONR$^{16}$R$^{17}$, —CH$_2$OR$^{16}$, —CH$_2$NR$^{16}$R$^{17}$, —OCOR$^{16}$ or —CO$_2$R$^{18}$; or R$^{14}$ and R$^{15}$ together form a bridge —OCH$_2$O— or —(CH$_2$)$_l$—;

wherein l, R$^{16}$, R$^{17}$ and R$^{18}$ are as defined for formula I.

Still more preferred are compounds of the following formula VI:

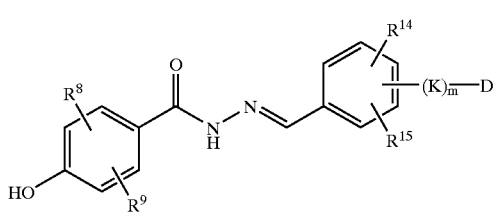

(VI)

as well as compounds of the following formula VII:

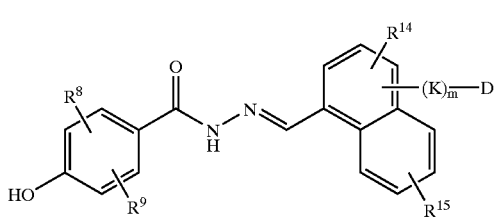

(VII)

as well as compounds of the general formulae VIIIa or VIIIb:

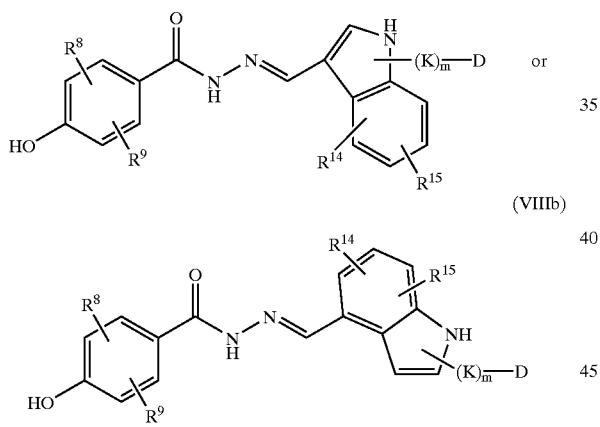

(VIIIa)

(VIIIb)

wherein $R^{14}$ and $R^{15}$ independently are hydrogen, halogen, —$CF_3$, —$OCF_3$, —$OR^{16}$, —$NR^{16}R^{17}$, lower alkyl, aryl, aryl-lower alkyl, —$OSO_2CF_3$, —$CONR^{16}R^{17}$, —$CH_2OR^{16}$, —$CH_2NR^{16}R^{17}$, —$OCOR^{16}$ or —$CO_2R^{18}$; or $R^{14}$ and $R^{15}$ together form a bridge —$OCH_2O$— or —$(CH_2)_l$—;

wherein l, $R^{16}$, $R^{14}$ and $R^{18}$ are as defined for formula I;

K, D and m are as defined for formula I; and $R^8$ and $R^9$ are as defined for formula I and preferably as defined for the preferred embodiments of A above.

In the above formulae VI, VII and VIII, $R^{14}$ and $R^{15}$ are preferably independently hydrogen, halogen, lower alkyl, aryl such as phenyl, or —O-lower alkyl such as methoxy.

In the above formulae VI and VII, K is preferably bound in para-position and in the above formulae VIIIa and VIIIb, K is preferably bound at the nitrogen atom of the indole group.

K is preferably selected from the group consisting of:

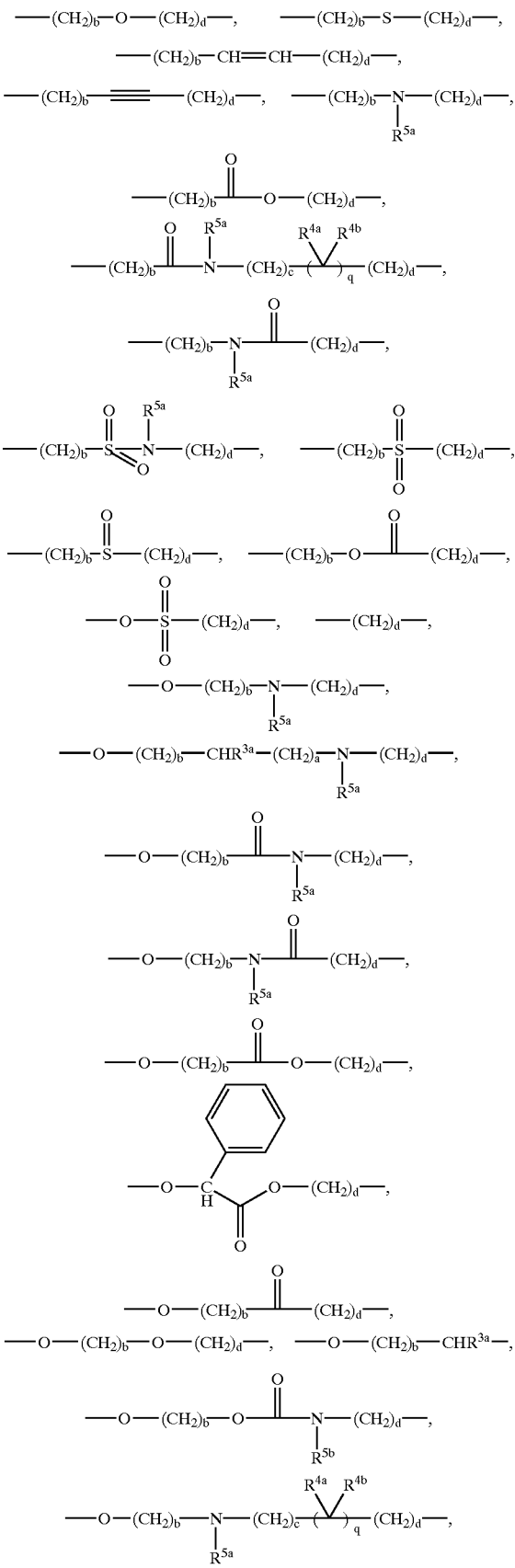

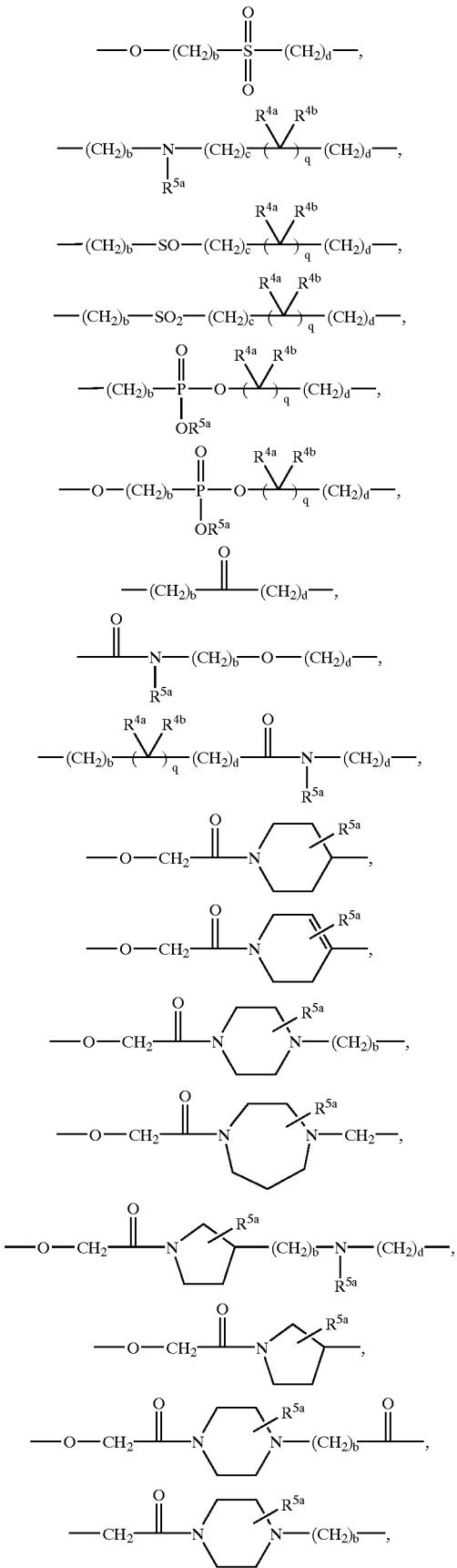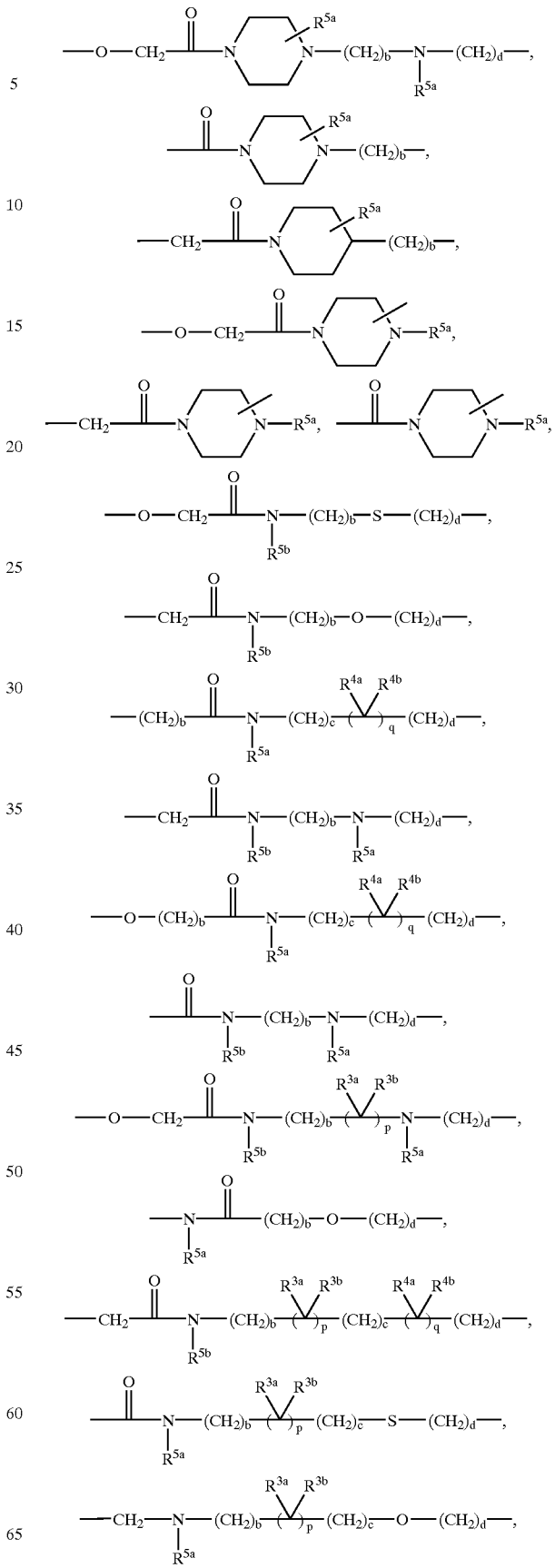

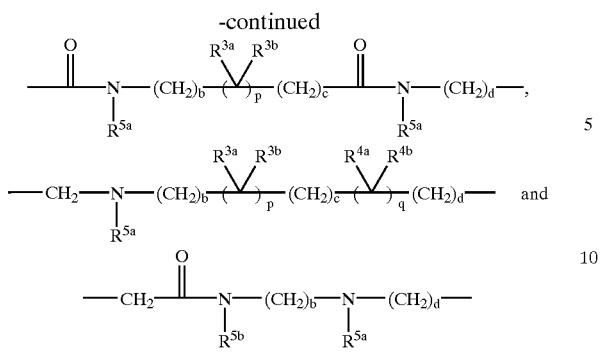
wherein $R^{3a}$, $R^{3b}$, $R^{4a}$, $R^{4b}$, $R^{5a}$, $R^{5b}$, a, b, c, d, p and q are as defined for formula I.
More preferably, K is selected from the group consisting of:
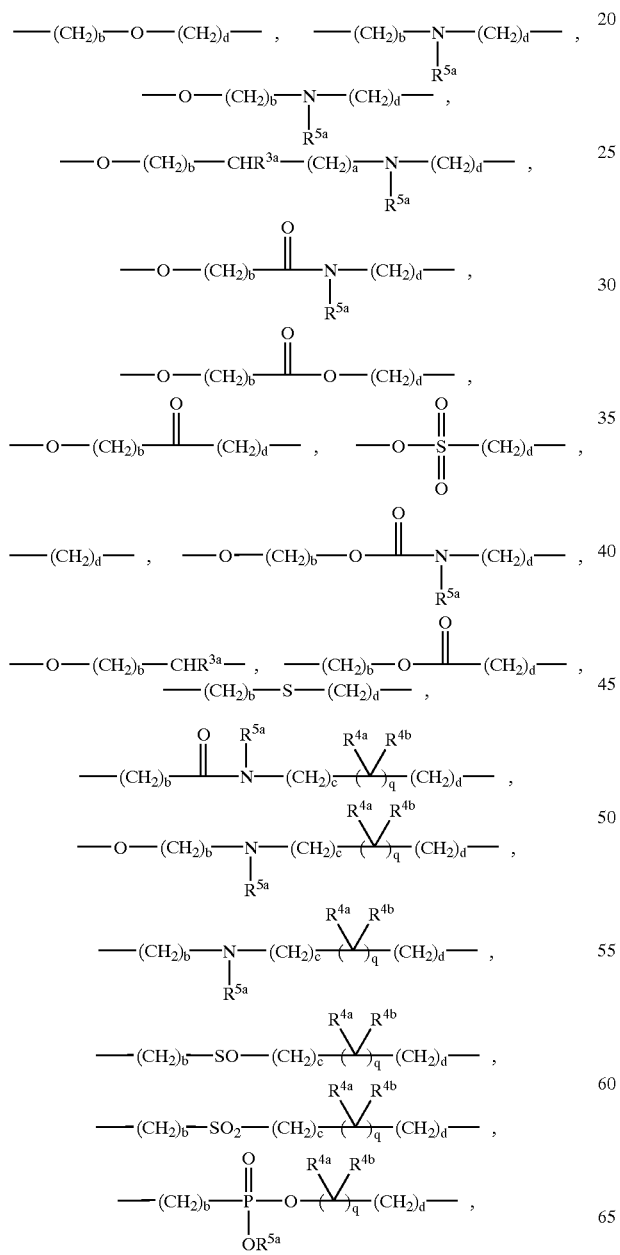
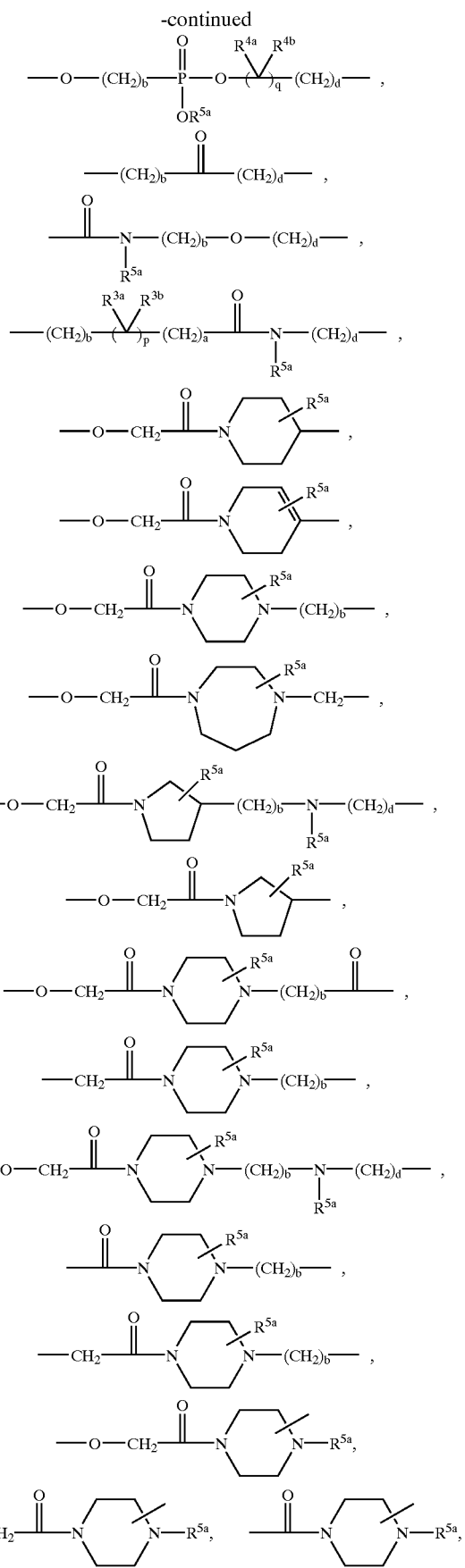

-continued
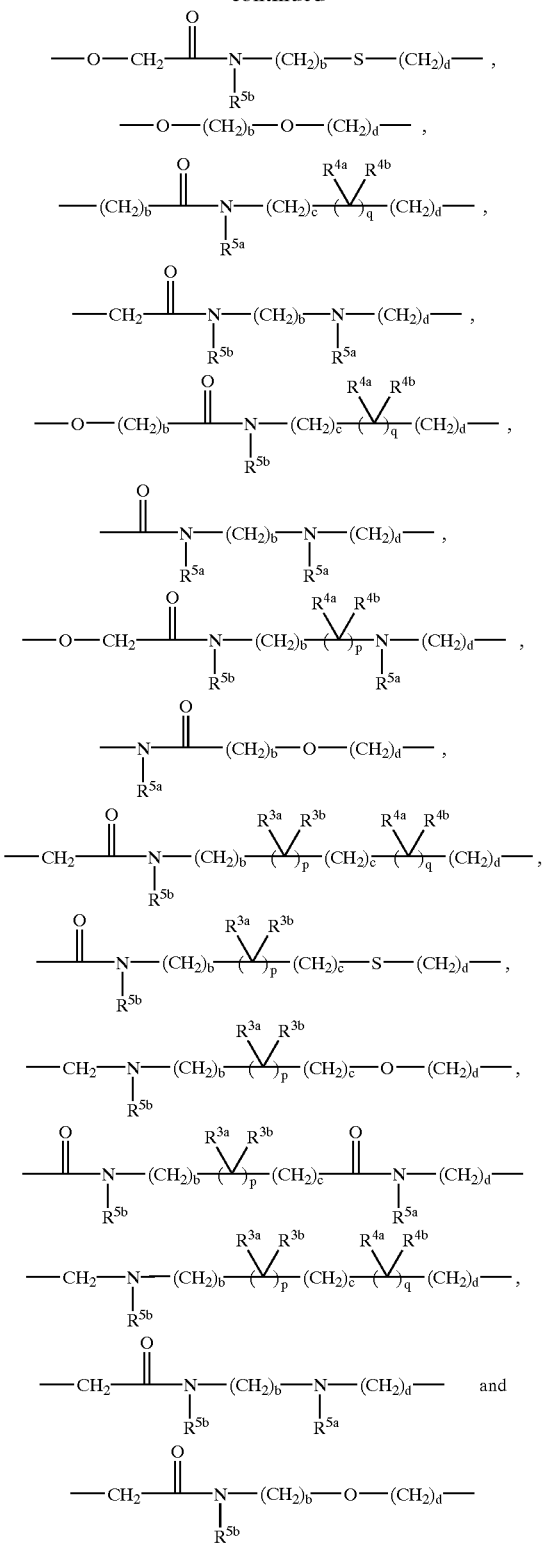
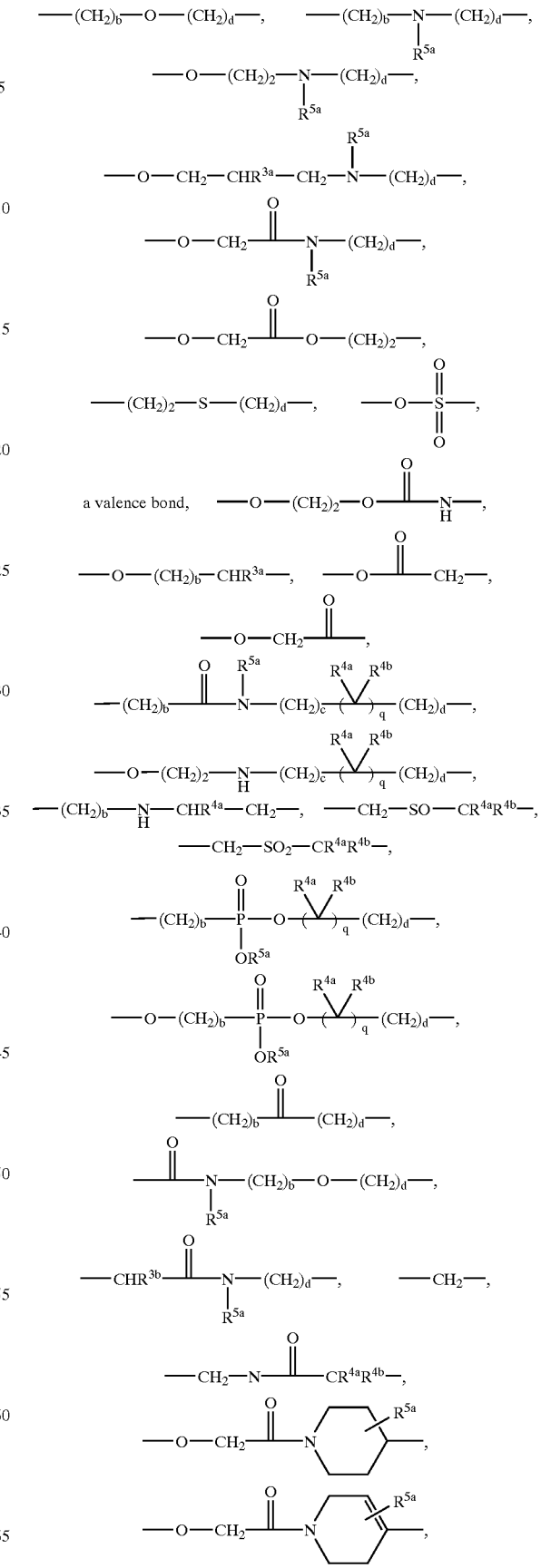
wherein $R^{3a}$, $R^{3b}$, $R^{4a}$, $R^{4b}$, $R^{5a}$, $R^{5b}$, a, b, c, d, p and q are as defined for formula I.
In a further preferred embodiment K is selected from the group consisting of:

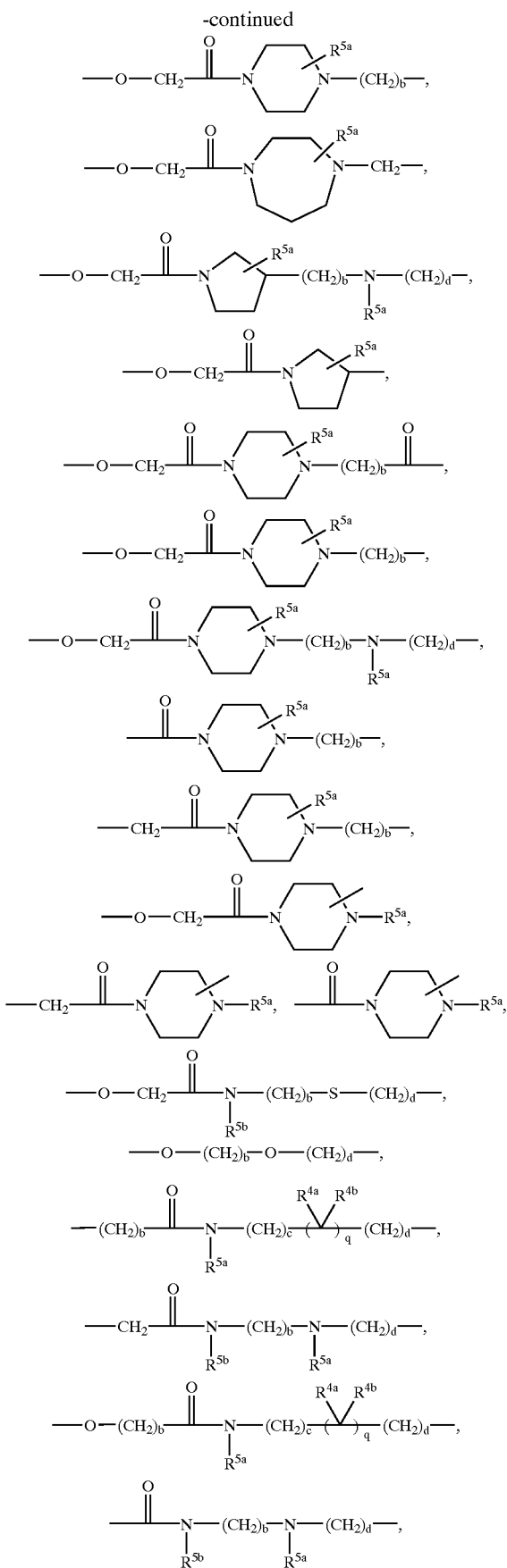

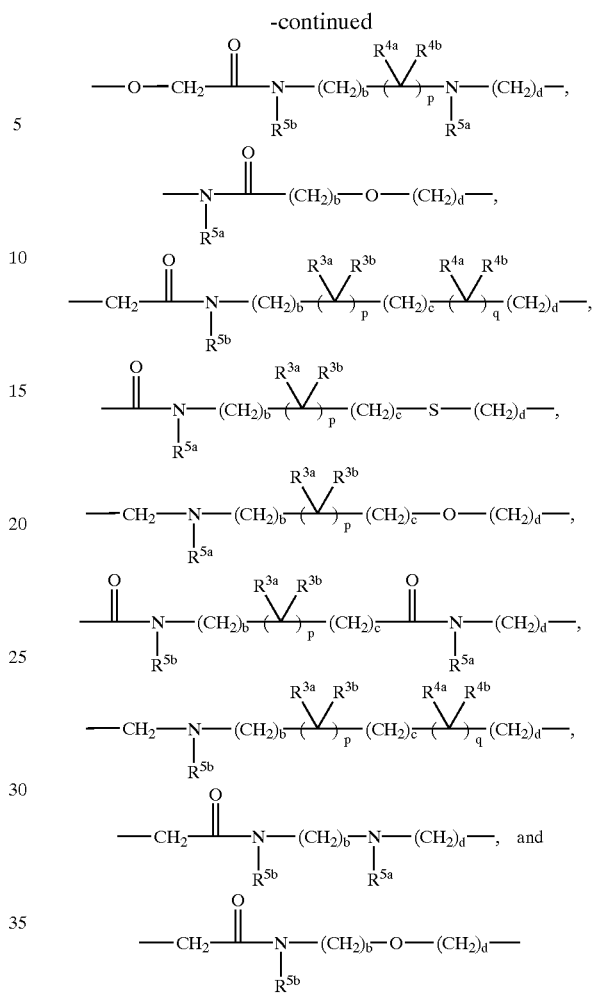

wherein $R^{3a}$, $R^{3b}$, $R^{4a}$, $R^{4b}$, $R^{5a}$, $R^{5b}$, b, c, d, p and q are as defined for formula I.

In the above embodiments of K, $R^{5a}$ and $R^{5b}$ are preferably independently hydrogen, lower alkyl, —OH, —$(CH_2)_k$OR$^{6a}$, aryl, aryl-lower alkyl, —$CH_2CF_3$, —$(CH_2)_g$COOR$^{43}$, —COOR$^{43}$, —$(CH_2)_k$—CN or —$(CH_2)_k$NR$^{6a}$R$^{6b}$ wherein g, k, $R^{43}$, $R^{6a}$ and $R^{5b}$ are as defined for formula I.

Preferably, g and k are independently 1, 2 or 3, and $R^{6a}$ and $R^{6b}$ are independently hydrogen, lower alkyl such as methyl or ethyl, or aryl such as phenyl, In the above embodiments of K, $R^{3a}$ and $R^{3b}$ are preferably independently hydrogen, halogen, —OH, —O-lower alkyl, —COO-lower alkyl, lower alkyl or aryl-lower alkyl.

In the above embodiments of K, $R^{4a}$ and $R^{4b}$ are preferably independently hydrogen, —CN, —CONH$_2$, —(CH$_2$)—N(CH$_3$)$_2$, —O-lower alkyl, —CH$_2$OH, —CH$_2$O-aryl, —N(CH$_3$)$_2$, —OH, —CO$_2$-lower alkyl or lower alkyl.

D is preferably hydrogen,

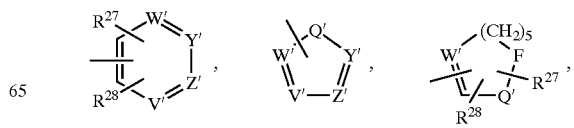

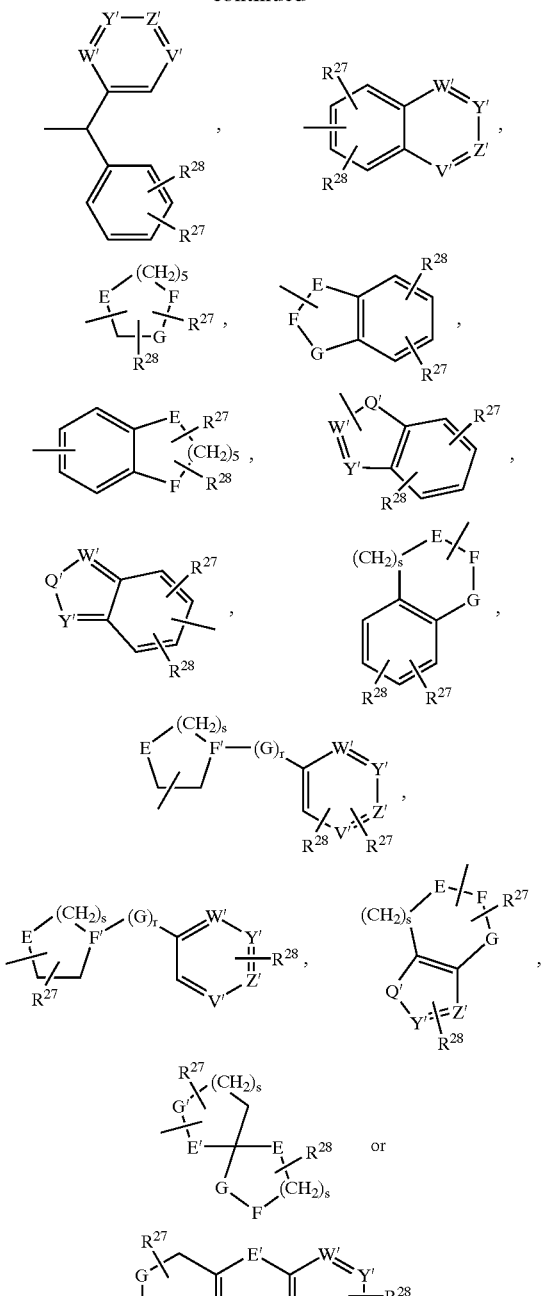
wherein s, r, $R^{27}$, $R^{28}$, V', Y', Q', Z', W', E, E', F, F', G and G' are as defined for formula I.
In still a further preferred embodiment D is hydrogen,
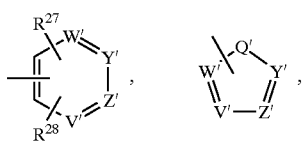
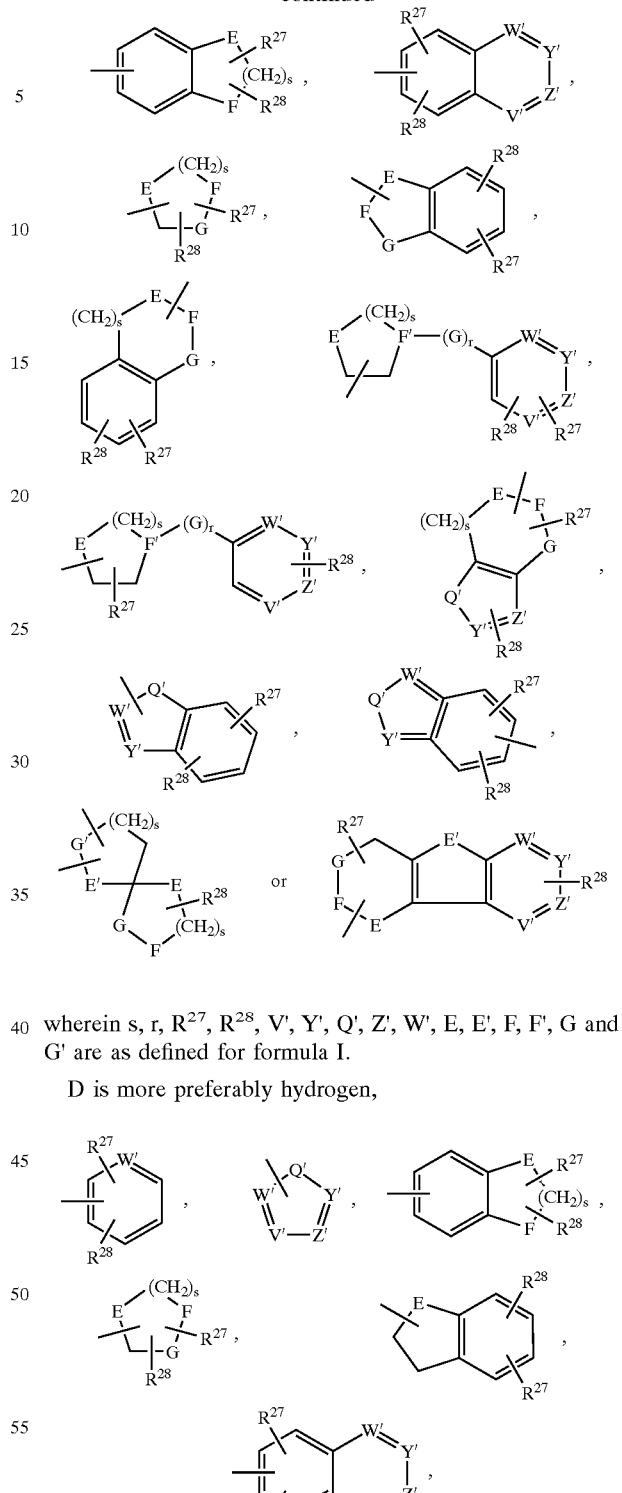
wherein s, r, $R^{27}$, $R^{28}$, V', Y', Q', Z', W', E, E', F, F', G and G' are as defined for formula I.
D is more preferably hydrogen,
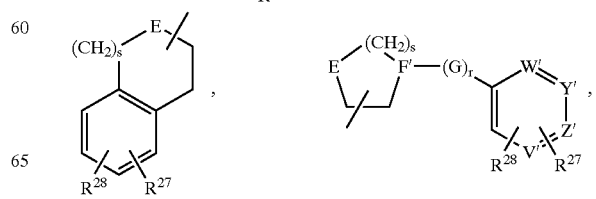

-continued

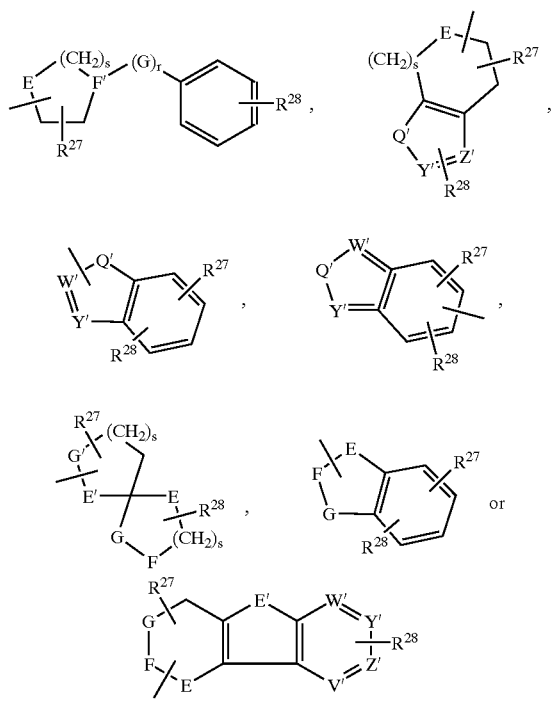

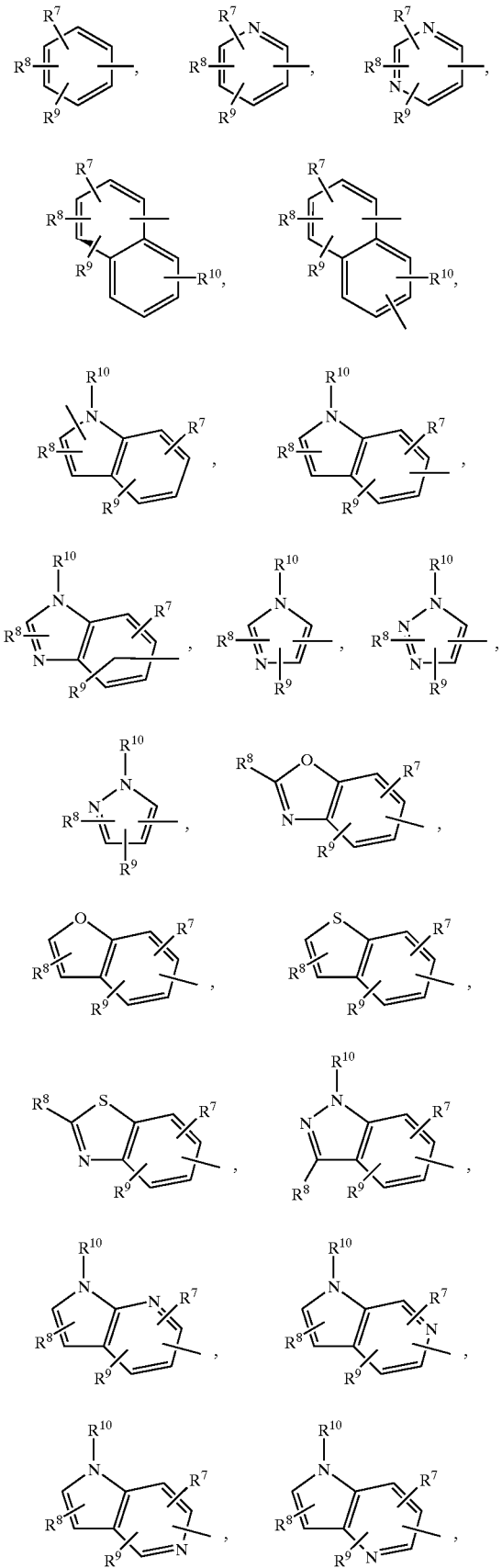

A is wherein E and E' independently are >CHR$^{38}$, >NR$^{39}$ or —O—; F, G and G' independently are >CHR$^{38}$, >C=O or >NR$^{39}$; F' is >CR$^{38}$— or >N—; and s, r, R$^{27}$, R$^{28}$, R$^{38}$, R$^{39}$, V', Y', Z', Q' and W' are as defined for formula I.

R$^{27}$ and R$^{28}$ are preferably independently hydrogen; halogen such as —Cl, —Br or —F; —CF$_3$; —OCF$_3$; —OCHF$_2$; —OCH$_2$CF$_3$; —(CH$_2$)$_y$NHCOCF$_3$; —NHCOCF$_3$; —CN; —NO$_2$; —COR$^{29}$, —COOR$^{29}$, —(CH$_2$)$_y$OR$^{29}$ or —OR$^{29}$ wherein R$^{29}$ is hydrogen, aryl or lower alkyl and y is 1, 2, 3 or 4; lower alkyl such as methyl, ethyl, 2-propenyl, isopropyl, tert-butyl or cyclohexyl; lower alkylthio; —SCF$_3$; aryl such as phenyl; —(CH$_2$)$_y$NR$^{29}$R$^{30}$ or —NR$^{29}$R$^{30}$ wherein R$^{29}$ and R$^{30}$ independently are hydrogen, —COO-lower alkyl or lower alkyl and y is 1, 2, 3 or 4; or —CONH$_2$; or R$^{27}$ and R$^{28}$ together form a bridge —OCH$_2$O—; R$^{38}$ is hydrogen; —OCHF$_2$; —OR$^{40}$ wherein R$^{40}$ is hydrogen or lower alkyl; lower alkyl such as methyl, isopropyl or tert-butyl; lower alkylthio; —SCF$_3$; —CH$_2$OH; —COO-lower alkyl or —CONH$_2$; and R$^{39}$ is hydrogen, lower alkyl, aryl or aryl-lower alkyl.

In a further embodiment the invention relates to the compounds of the formula I wherein:

R$^1$ and R$^2$ independently are hydrogen or lower alkyl or together form a valence bond;

R$^3$ and R$^4$ independently are hydrogen or lower alkyl;

X is >C=O, >C=S, >C=NR$^5$ or >SO$_2$;

n is 0, 1, 2 or 3;

m is 0 or 1;

R$^5$ is hydrogen, lower alkyl, aryl-lower alkyl, or —OR$^6$;

wherein R$^6$ is hydrogen, lower alkyl, aryl or aryl-lower alkyl;

-continued

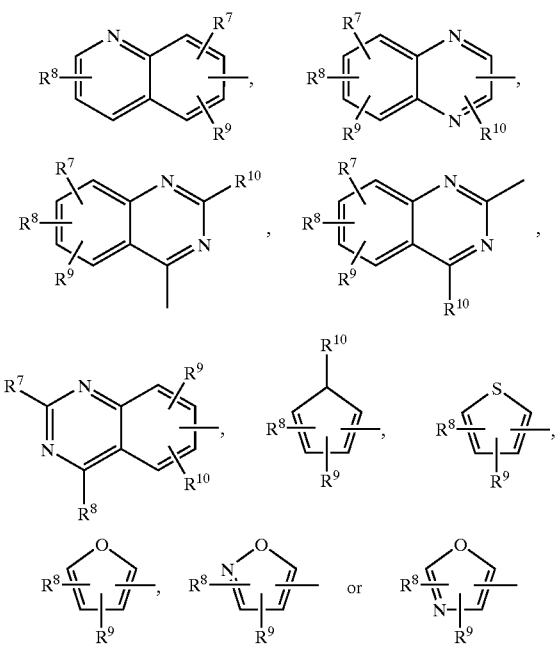

wherein

R[7] is hydrogen, halogen, —CN, —CF$_3$, —OCF$_3$, —OCH$_2$CF$_3$, —NO$_2$, —OR[11], —NR[11]R[12], lower alkyl, aryl, —SCF$_3$, —SR[11], —CHF$_2$, —OCHF$_2$, —OSO$_2$R[11], —CONR[11]R[12], —CH$_2$OR[11], —CH$_2$NR[11]R[12], —OCOR[11], —CO$_2$R[13], —OSO$_2$CF$_3$;

R[8] and R[9] independently are hydrogen, halogen, —CN, —CF$_3$, —OCF$_3$, —OCH$_2$CF$_3$, —NO$_2$, —OR[11], —NR[11]R[12], lower alkyl, aryl, —SCF$_3$, —SR[11], —CHF$_2$, —OCHF$_2$, —OSO$_2$R[11], —CONR[11]R[12], —CH$_2$OR[11], —CH$_2$NR[11]R[12], —OCOR[11], —CO$_2$R[13], —OSO$_2$CF$_3$, or R[8] and R[9] together form a bridge —OCH$_2$O—;

R[11] and R[12] independently are hydrogen, —COR[13], —SO$_2$R[13], lower alkyl or aryl;

R[13] is hydrogen, lower alkyl, aryl-lower alkyl or aryl;

R[10] is hydrogen, lower alkyl, aryl-lower alkyl or aryl;

B is

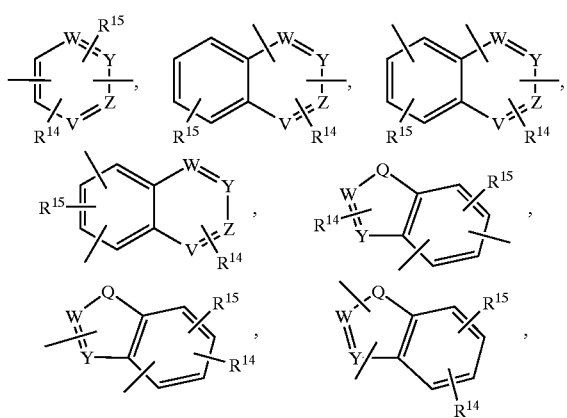

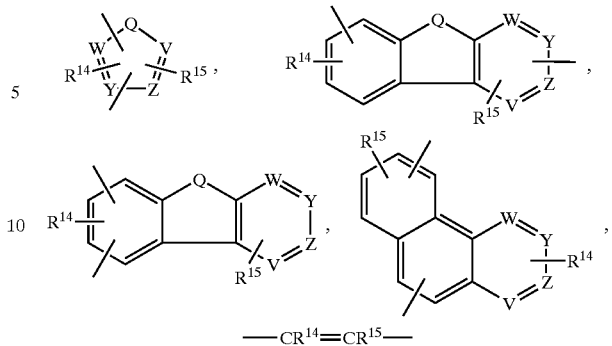

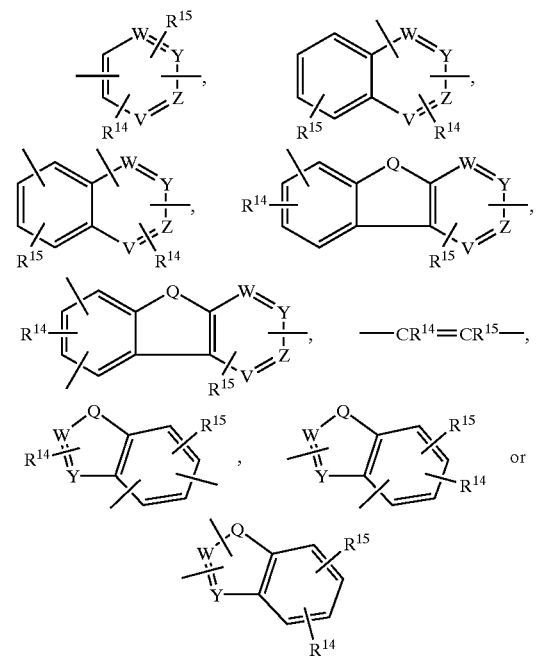

—CR[14]=CR[15]— or a valence bond; preferably

R[14] and R[15] independently are hydrogen, halogen, —CN, —CF$_3$, —OCF$_3$, —O(CH$_2$)$_l$CF$_3$, —NO$_2$, —OR[16], —NR[16]R[17], lower alkyl, aryl, —SCF$_3$, —SR[16], —CHF$_2$, —OCHF$_2$, —OCF$_2$CHF$_2$, —OSO$_2$CF$_3$, —CONR[16]R[17], —(CH$_2$)$_l$CONR[16]R[17], —O(CH$_2$)$_l$CONR[16]R[17], —(CH$_2$)$_l$COR[16], —O(CH$_2$)$_l$COR[16], —(CH$_2$)$_l$OR[16], —O(CH$_2$)$_l$R[16], —(CH$_2$)$_l$NR[16]R[17], —O(CH$_2$)$_l$NR[16]R[17], —OCOR[16], —CO$_2$R[18], —O(CH$_2$)$_l$CN, —O(CH$_2$)$_l$Cl, or R[14] and R[15] together form a bridge —O—CH$_2$—O—;

R[14] and R[15] preferably independently representing hydrogen, halogen, —CF$_3$, —OCF$_3$, —OR[16], —NR[16]R[17], lower alkyl, aryl, aryl-lower alkyl, —OSO$_2$CF$_3$, —CONR[16]R[17], —CH$_2$OR[16], —CH$_2$NR[16]R[17], —OCOR[16] or —CO$_2$R[18]; or together forming a bridge —OCH$_2$O—;

l is 1, 2, 3 or 4;

R[16] and R[17] independently are hydrogen, —COR[18], —SO$_2$R[18], lower alkyl, aryl, or R[16] and R[17] together form a cyclic alkyl bridge containing from 2 to 7 carbon atoms;

R[18] is hydrogen, lower alkyl, aryl or aryl-lower alkyl;

W is —N═ or —CR$^{19}$═;
Y is —N═ or —CR$^{20}$═;
Z is —N═ or —CR$^{21}$═;
V is —N═ or —CR$^{22}$═;
Q is —NR$^{23}$—, —O— or —S—;
wherein:
R$^{19}$, R$^{20}$, R$^{21}$ and R$^{22}$ independently are hydrogen, halogen, —CN, —CF$_3$, —OCF$_3$, —OCH$_2$CF$_3$, —NO$_2$, —OR$^{24}$, —NR$^{24}$R$^{25}$, lower alkyl, aryl, aryl-lower alkyl, SCF$_3$, —SR$^{24}$, —CHF$_2$, —OCHF$_2$, OCF$_2$CHF$_2$, —OSO$_2$CF$_3$, —CONR$^{24}$R$^{25}$, —CH$_2$CONR$^{24}$R$^{25}$, —OCH$_2$CONR$^{24}$R$^{25}$, —CH$_2$OR$^{24}$, —CH$_2$NR$^{24}$R$^{25}$, —OCOR$^{24}$ or —CO$_2$R$^{24}$, or R$^{19}$ and R$^{20}$, R$^{20}$ and R$^{21}$ or R$^{21}$ and R$^{22}$ together form a bridge —OCH$_2$O—;
R$^{24}$ and R$^{25}$ independently are hydrogen, —COR$^{26}$, —SO$_2$R$^{26}$, lower alkyl, aryl or aryl-lower alkyl;
R$^{26}$ is hydrogen, lower alkyl, aryl or aryl-lower alkyl;
R$^{23}$ is hydrogen, lower alkyl, aryl or aryl-lower alkyl;
K is

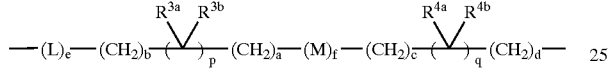

wherein:
R$^{3a}$, R$^{3b}$, R$^{4b}$ and R$^{4b}$ independently are hydrogen, halogen, —CN, —CF$_3$, —OCF$_3$, —OCH$_2$CF$_3$, —NO$_2$, —OR$^{24a}$, —NR$^{24a}$R$^{25a}$, lower alkyl, aryl, aryl-lower alkyl, SCF$_3$, —SR$^{24a}$, —CHF$_2$, —OCHF$_2$, —OCF$_2$CHF$_2$, —OSO$_2$CF$_3$, —CONR$^{24a}$R$^{25a}$, —CH$_2$CONR$^{24a}$R$^{25a}$, —OCH$_2$CONR$^{24a}$R$^{25a}$, —CH$_2$OR$^{24a}$, —CH$_2$NR$^{24a}$R$^{25a}$, —OCOR$^{24a}$ or —CO$_2$R$^{24a}$;
wherein R$^{24a}$ and R$^{25a}$ independently are hydrogen, —COR$^{26a}$, —SO$_2$R$^{26a}$, lower alkyl, aryl or aryl-lower alkyl;
R$^{26a}$ is hydrogen, lower alkyl, aryl or aryl-lower alkyl; or
R$^{3a}$ and R$^{3b}$, R$^{4a}$ and R$^{4b}$ or R$^{3a}$ and R$^{4b}$ together form a bridge —(CH$_2$)$_i$—, wherein
i is 1, 2, 3 or 4;
a, b, c and d independently are 0, 1, 2, 3 or 4;
e, f, p and q independently are 0 or 1;
L and M independently are
—O—, —S—, —CH═CH—, —C≡C—, —NR$^{5a}$—, —COO—, —CONR$^{5a}$—, —NR$^{5a}$CO—, —SO—, —SO$_2$—, —OSO$_2$—, —SO$_2$—NR$^{5a}$—, —NR$^{5a}$SO$_2$—, —NR$^{5a}$CONR$^{5b}$—, —NR$^{5a}$CSNR$^{5b}$—, —OCONR$^{5b}$ or —NR$^{5a}$C(O)O—
wherein R$^{5a}$ and R$^{5b}$ independently are hydrogen, lower alkyl, —(CH$_2$)$_k$—OH, —(CH$_2$)$_k$—NR$^{6a}$R$^{6b}$, aryl or aryl-lower alkyl;
wherein k is 2, 3 or 4;
R$^{6a}$ and R$^{6b}$ independently are hydrogen, lower alkyl or aryl-lower alkyl;
K preferably representing

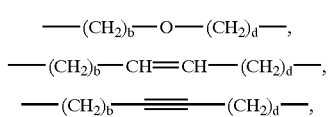

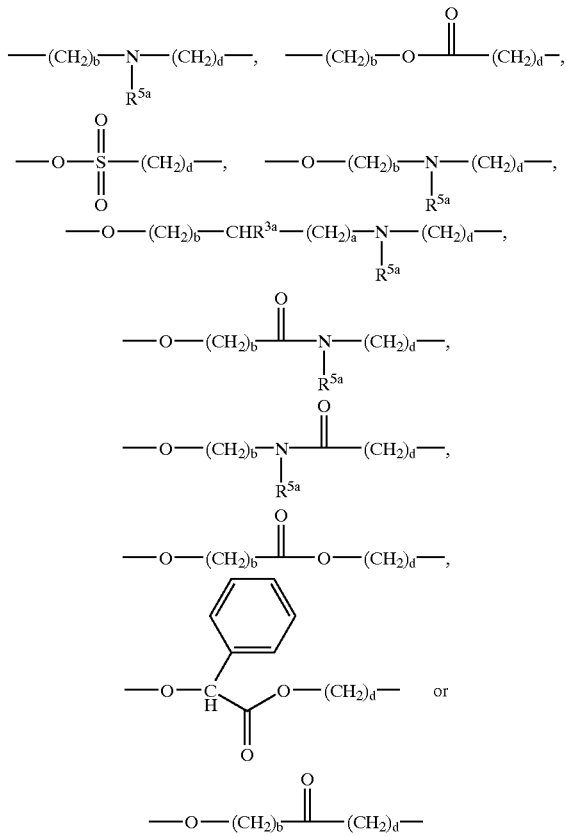

D is hydrogen or

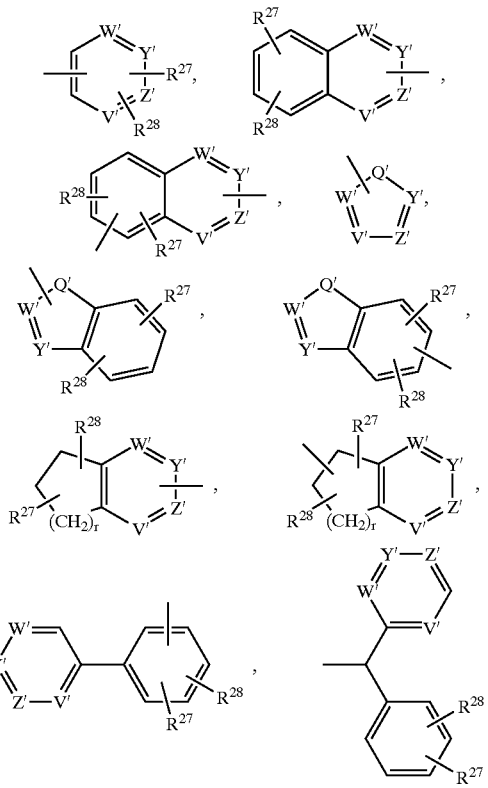

-continued

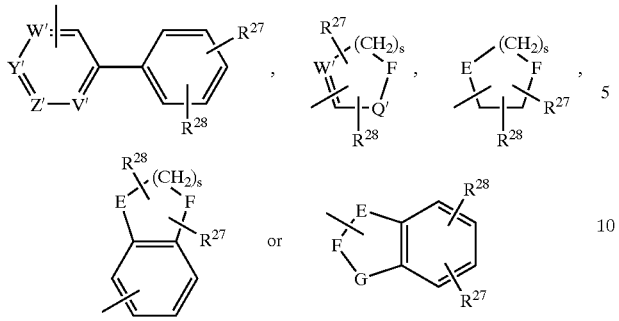

preferably hydrogen,

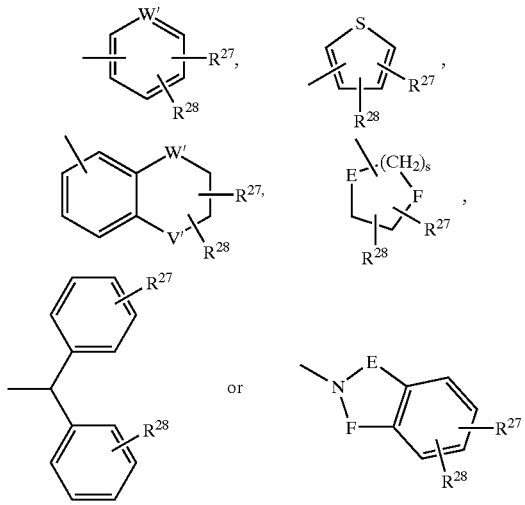

wherein:
r and s independently are 1 or 2;
E, F and G independently are —CHR$^{38}$—, >C=O, >NR$^{39}$, —O— or —S—;
Y' is —N= or —CR$^{32}$=;
Z' is —N= or —CR$^{33}$=;
V' is —N= or —CR$^{34}$=;
W' is —N= or —CR$^{35}$=;
Q' is —NR$^{36}$—, —O— or —S—;
wherein
R$^{27}$, R$^{28}$, R$^{32}$, R$^{33}$, R$^{34}$ and R$^{35}$ are independently hydrogen, halogen, —CN, —CF$_3$, —OCF$_3$, —O(CH$_2$)$_y$CF$_3$, —NO$_2$, —OR$^{29}$, —NR$^{29}$R$^{30}$, lower alkyl, aryl, aryl-lower alkyl, —SCF$_3$, —SR$^{29}$, —CHF$_2$, —OCHF$_2$, —OCF$_2$CHF$_2$, —OSO$_2$R$^{29}$, —OSO$_2$CF$_3$, —CONR$^{29}$R$^{30}$, —(CH$_2$)$_y$CONR$^{29}$R$^{30}$, —O(CH$_2$)$_y$CONR$^{29}$R$^{30}$, —(CH$_2$)$_y$OR$^{29}$, —(CH$_2$)$_y$NR$^{29}$R$^3$, —OCOR$^{29}$, —CO$_2$R$^{29}$; or R$^{27}$ and R$^{28}$, R$^{32}$ and R$^{33}$, R$^{33}$ and R$^{34}$ or R$^{34}$ and R$^{35}$ together form a bridge —OCH$_2$O—;
R$^{27}$ and R$^{28}$ preferably independently representing hydrogen, halogen, —CF$_3$, —OCF$_3$, —OCH$_2$CF$_3$, —OR$^{29}$, lower alkyl, aryl or aryl-lower alkyl, or together forming a bridge —OCH$_2$O—;
y is 1, 2, 3 or 4;
R$^{29}$ and R$^{30}$ independently are hydrogen, —COR$^{31}$, —SO$_2$R$^{31}$, lower alkyl, aryl or aryl-lower alkyl;
R$^{31}$ is hydrogen, lower alkyl, aryl or aryl-lower alkyl;
R$^{36}$ and R$^{39}$ independently are hydrogen, lower alkyl, aryl or aryl-lower alkyl;

R$^{38}$ is hydrogen, —OR$^{40}$, —NR$^{40}$R$^{41}$, lower alkyl, aryl, aryl-lower alkyl, —SCF$_3$, —SR$^{40}$, —CHF$_2$, —OCHF$_2$, —OCF$_2$CHF$_2$, —CONR$^{40}$R$^{41}$, —(CH$_2$)$_x$CONR$^{40}$R$^{41}$, —O(CH$_2$)$_x$CONR$^{40}$R$^{41}$, —(CH$_2$)$_x$OR$^{40}$, —(CH$_2$)$_x$NR$^{40}$R$^{41}$, —OCOR$^{40}$ or —CO$_2$R$^{40}$;
x is 1, 2, 3 or 4;
R$^{40}$ and R$^{41}$ independently are hydrogen, —COR$^{42}$, —SO$_2$R$^{42}$, lower alkyl, aryl or aryl-lower alkyl; and
R$^{42}$ is hydrogen, lower alkyl, aryl or aryl-lower alkyl.

In a further embodiment the invention relates to the compounds of the formula I wherein:

R$^1$ and R$^2$ independently are hydrogen or lower alkyl or together form a valence bond;

R$^3$ and R$^4$ independently are hydrogen or lower alkyl;

n is 0, 1, 2 or 3;

m is 0 or 1;

X is >C=O, >C=S, >C=NR$^5$ or >SO$_2$;

wherein R$^5$ is hydrogen, lower alkyl, aryl-lower alkyl or —OR$^6$;

wherein R$^6$ is hydrogen, lower alkyl, aryl or aryl-lower alkyl;

A is

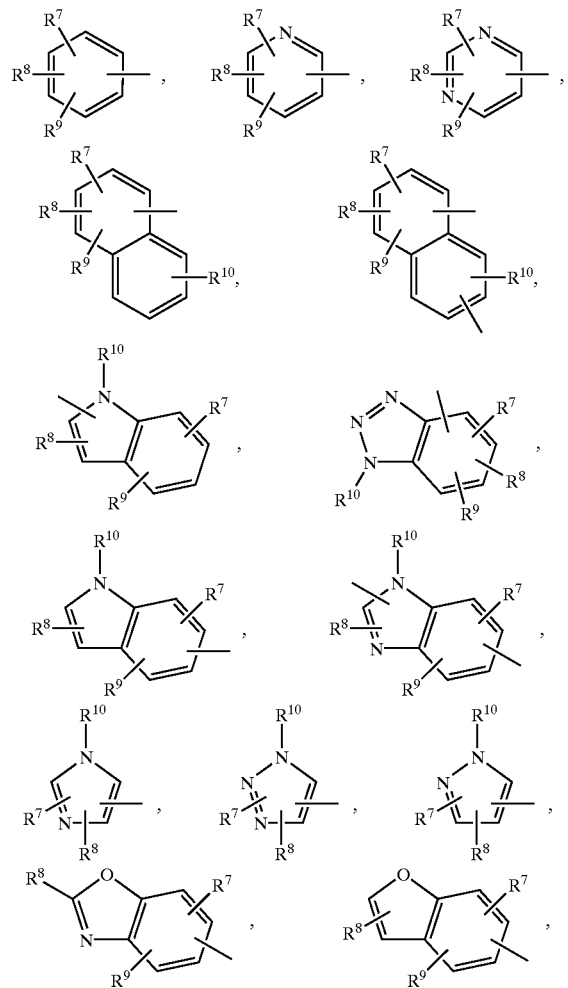

-continued

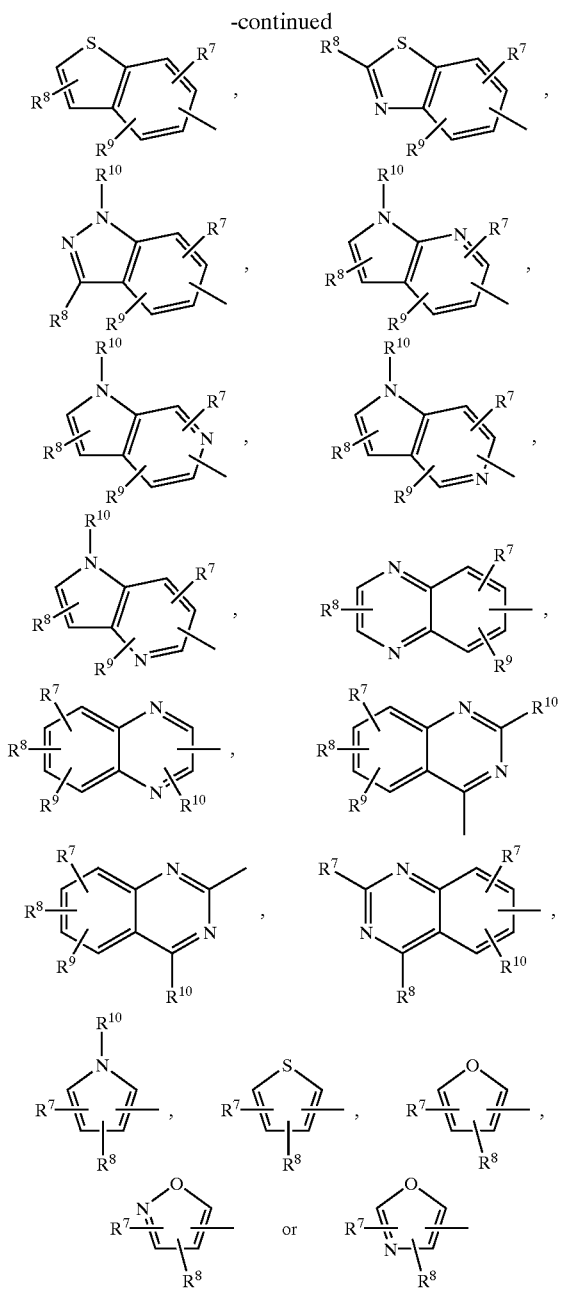

wherein:
R[7] is hydrogen, halogen, —CN, —CF$_3$, —OCF$_3$, —OCH$_2$CF$_3$, —NO$_2$, —OR[11], —NR[11]R[12], lower alkyl, aryl, —SCF$_3$, —SR[11], —CHF$_2$, —OCHF$_2$, —OSO$_2$R[11], —CONR[11]R[12], —CH$_2$OR[11], —CH$_2$NR[11]R[12], —OCOR[11], —CO$_2$R[13] or —OSO$_2$CF$_3$;

R[8] and R[9] independently are hydrogen, halogen, —CN, —CF$_3$, —OCF$_3$, —OCH$_2$CF$_3$, —NO$_2$, —OR[11], —NR[11]R[12], lower alkyl, aryl, —SCF$_3$, —SR[11], —CHF$_2$, —OCHF$_2$, —OSO$_2$R[11], —CONR[11]R[12], —CH$_2$OR[11], —CH$_2$NR[11]R[12], —OCOR[11], —CO$_2$R[13] or —OSO$_2$CF$_3$, or R[8] and R[9] together form a bridge —OCH$_2$O— or —OCH$_2$CH$_2$O—;

wherein R[11] and R[12] independently are hydrogen, —COR[13], —SO$_2$R[13], lower alkyl or aryl;

wherein R[13] is hydrogen, lower alkyl, aryl-lower alkyl or aryl; and

R[10] is hydrogen, lower alkyl, aryl-lower alkyl or aryl;

B is

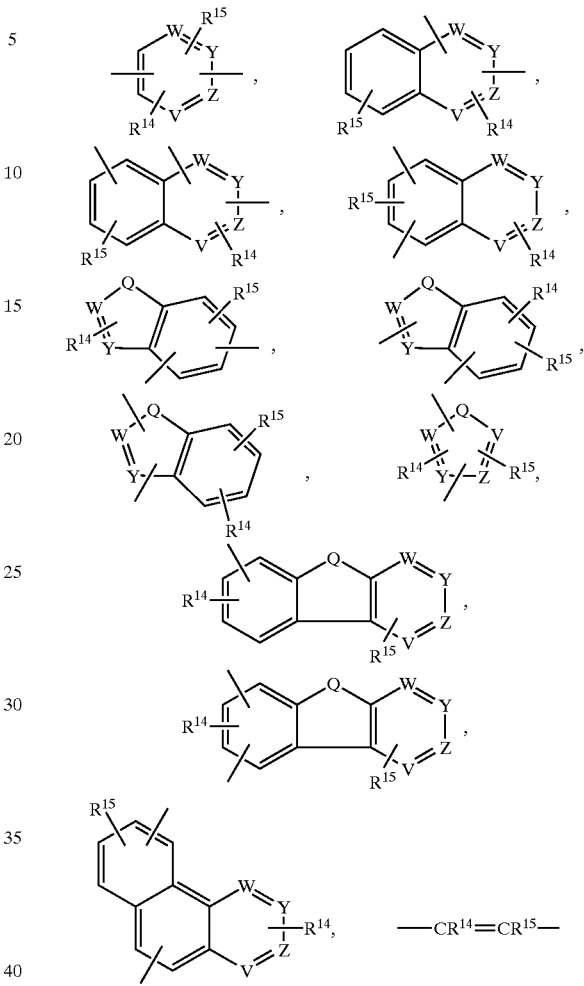

or a valence bond; preferably

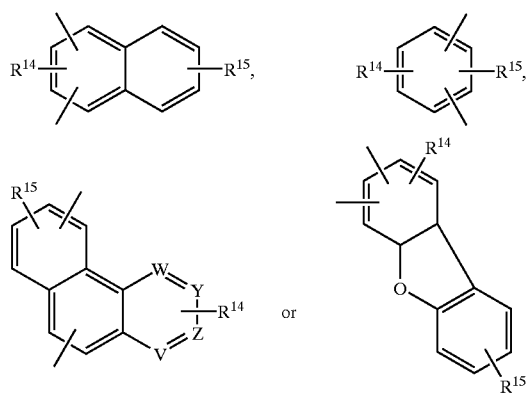

wherein:
R[14] and R[15] independently are hydrogen, halogen, —CN, —CF$_3$, —OCF$_3$, —O(CH$_2$)$_t$CF$_3$, —NO$_2$, —OR[16], —NR[16]R[17], lower alkyl, aryl, aryl-lower alkyl, —SCF$_3$, —SR[16], —CHF$_2$, —OCHF$_2$, —OCF$_2$CHF$_2$, —OSO$_2$CF$_3$, —CONR[16]R[17], —(CH$_2$)$_t$CONR[16]R[17], —O(CH$_2$)$_t$CONR[16]R[17], —(CH$_2$)$_t$COR[16], —(CH$_2$)$_t$ COR$^{16}$, —(CH$_2$)$_l$OR$^{16}$, —O(CH$_2$)$_l$OR$^{16}$, —(CH$_2$)$_l$NR$^{16}$R$^{17}$, —O(CH$_2$)$_l$NR$^{16}$R$^{17}$, —OCOR$^{16}$, —CO$_2$R$^{18}$, —O(CH$_2$)$_l$CO$_2$R$^{18}$, —O(CH$_2$)$_l$CN, —O(CH$_2$)$_l$Cl, or R$^{14}$ and R$^{15}$ together form a bridge —OCH$_2$O—;

R$^{14}$ and R$^{15}$ preferably independently representing hydrogen, halogen, —CF$_3$, —OCF$_3$, —OR$^{16}$, —NR$^{16}$R$^{17}$, lower alkyl, aryl, aryl-lower alkyl, —OSO$_2$CF$_3$, —CONR$^{16}$R$^{17}$, —CH$_2$OR$^{16}$, —CH$_2$NR$^{16}$R$^{17}$, —OCOR$^{16}$ or —CO$_2$R$^{18}$; or together forming a bridge —OCH$_2$O—;

wherein l is 1, 2, 3 or 4;

R$^{16}$ and R$^{17}$ independently are hydrogen, —COR$^{18}$, —SO$_2$R$^{18}$, lower alkyl, aryl, or R$^{16}$ and R$^{17}$ together form a cyclic alkyl bridge containing from 2 to 7 carbon atoms;

wherein R$^{18}$ is hydrogen, lower alkyl, aryl or aryl-lower alkyl;

W is —N= or —CR$^{19}$=;

Y is —N= or —CR$^{20}$=;

Z is —N= or —CR$^{21}$=;

V is —N= or —CR$^{22}$=; and

Q is —NR$^{23}$—, —O— or —S—;

wherein:

R$^{19}$, R$^{20}$, R$^2$ and R$^{22}$ independently are hydrogen, halogen, —CN, —CF$_3$, —OCF$_3$, —OCH$_2$CF$_3$, —NO$_2$, —OR$^{24}$, —NR$^{24}$R$^{25}$, lower alkyl, aryl, aryl-lower alkyl, SCF$_3$, —SR$^{24}$, —CHF$_2$, —OCHF$_2$, —OCF$_2$CHF$_2$, —OSO$_2$CF$_3$, —CONR$^{24}$R$^{25}$, —CH$_2$CONR$^{24}$R$^{25}$, —OCH$_2$CONR$^{24}$R$^{25}$, —CH$_2$OR$^{24}$, —CH$_2$NR$^{24}$R$^{25}$, —OCOR$^{24}$ or —CO$_2$R$^{24}$, or R$^{19}$ and R$^{20}$, R$^{20}$ and R$^{21}$ or R$^2$ and R$^{22}$ together form a bridge —OCH$_2$O—;

wherein R$^{24}$ and R$^{25}$ independently are hydrogen, —COR$^{26}$, —SO$_2$R$^{26}$, lower alkyl, aryl or aryl-lower alkyl;

wherein R$^{26}$ is hydrogen, lower alkyl, aryl or aryl-lower alkyl; and

R$^{23}$ is hydrogen, lower alkyl, aryl or aryl-lower alkyl;

K is

—(L)$_e$—(CH$_2$)$_b$—$\overset{R^{3a}\;R^{3b}}{\overset{\vee}{(\;)_p}}$—(CH$_2$)$_a$—(M)$_f$—(CH$_2$)$_c$—$\overset{R^{4a}\;R^{4b}}{\overset{\vee}{(\;)_q}}$—(CH$_2$)$_d$— wherein:

R$^{3a}$, R$^{3b}$, R$^{4a}$ and R$^{4b}$ independently are hydrogen, halogen, —CN, —CF$_3$, —OCF$_3$, —OCH$_2$CF$_3$, —NO$_2$, —OR$^{24a}$, —NR$^{24a}$R$^{25a}$, lower alkyl, aryl, aryl-lower alkyl, SCF$_3$, SR$^{24a}$, —CHF$_2$, —OCHF$_2$, —OCF$_2$CHF$_2$, —OSO$_2$CF$_3$, —CONR$^{24a}$R$^{25a}$, —CH$_2$CONR$^{24a}$R$^{25a}$, —OCH$_2$CONR$^{24a}$R$^{25a}$, —CH$_2$OR$^{24a}$, —CH$_2$NR$^{24a}$R$^{25a}$, —OCOR$^{24a}$ or —CO$_2$R$^{24a}$;

wherein R$^{24a}$ and R$^{25a}$ independently are hydrogen, —COR$^{26a}$, —SO$_2$R$^{26a}$, lower alkyl, aryl or aryl-lower alkyl;

wherein R$^{26a}$ is hydrogen, lower alkyl, aryl or aryl-lower alkyl; or

R$^{3a}$ and R$^{3b}$, R$^{4a}$ and R$^{4b}$ or R$^{3a}$ and R$^{4b}$ together form a bridge —(CH$_2$)$_i$—;

wherein i is 1, 2, 3 or 4;

a, b, c and d independently are 0, 1, 2, 3 or 4;

e, f and p independently are 0 or 1;

q is 0,1 or 2; and

L and M independently are

—O—, —S—, —CH=CH—, —C≡C—, —NR$^{5a}$—, —CO—, —OCO—, —COO—, —CONR$^{5a}$—, NR$^{5a}$CO—, —SO—, —SO$_2$—, —OSO$_2$—, —SO$_2$—NR$^{5a}$—, —NR$^{5a}$SO$_2$—, —NR$^{5a}$CONR$^{5b}$—, —NR$^{5a}$CSNR$^{5b}$—, —OCONR$^{5b}$— or —NR$^{5a}$C(O)O—;

wherein R$^{5a}$ and R$^{5b}$ independently are hydrogen, lower alkyl, —(CH$_2$)$_k$—OH, —(CH$_2$)$_k$—NR$^{6a}$R$^{6b}$—, aryl or aryl-lower alkyl;

wherein k is 2, 3 or 4; and

R$^{6a}$ and R$^{6b}$ independently are hydrogen, lower alkyl or aryl-lower alkyl;

K preferably representing

—O—(CH$_2$)$_d$—,  —N—,
                   |
                   H

—O—(CH$_2$)$_2$—N—(CH$_2$)$_d$—,
               |
               R$^{5a}$

—O—CH$_2$—CHR$^{3a}$—CH$_2$—N—CH$_2$—,
                          |
                          H

O
         ‖
—O—CH$_2$—C—N—(CH$_2$)$_d$—,
             |
             R$^{5a}$

O
         ‖
—O—CH$_2$—C—O—(CH$_2$)$_2$—,

O
         ‖
—O—CH$_2$—C—,

O
      ‖
—O—S— , a valence bond,
      ‖
      O

O
                ‖
—O—(CH$_2$)$_2$—O—C—N—,  —O—CHR$^{3a}$—,
                  |
                  H

O                  O   R$^{5a}$
   ‖                  ‖    |
—O—C—CH$_2$—,  —(CH$_2$)$_b$—C—N—(CH$_2$)$_d$—  and —O—(CH$_2$)$_2$—N—(CH$_2$)$_c$—$\overset{R^{4a}\;R^{4b}}{\overset{\vee}{(\;)_q}}$—(CH$_2$)$_d$—
           |
           H D is hydrogen,

,

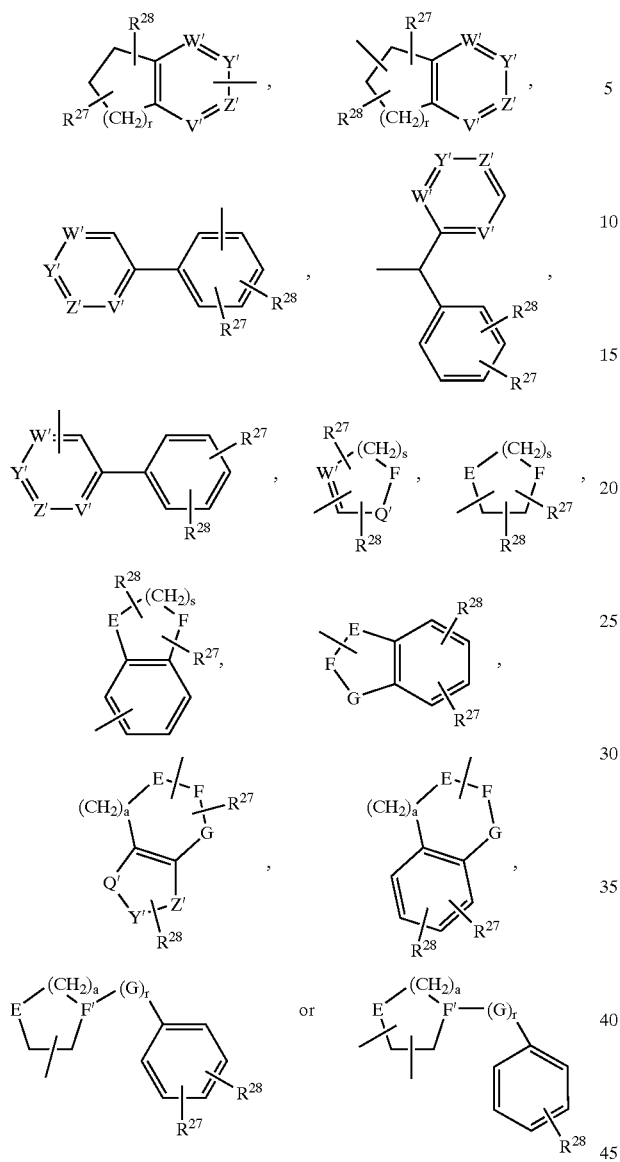
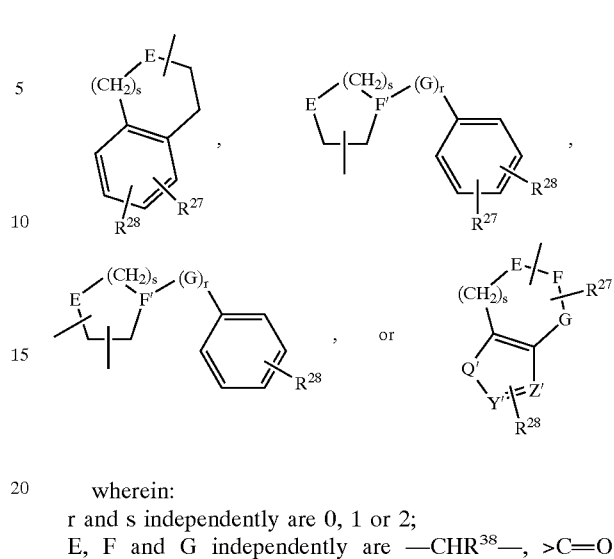
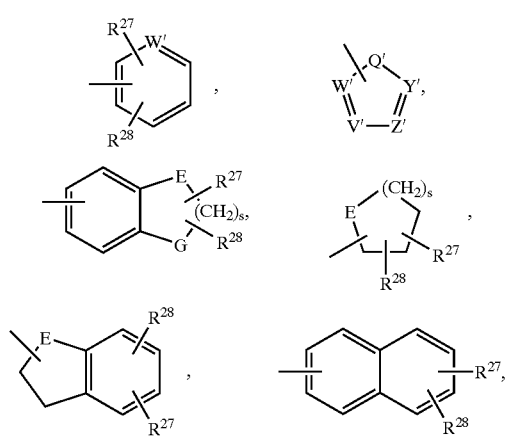

preferably hydrogen wherein:

r and s independently are 0, 1 or 2;

E, F and G independently are —CHR$^{38}$—, >C=O, >NR$^{39}$, —O— or —S—;

F' is >CR$^{38}$— or >N—;

Y' is —N= or —CR$^{32}$=;

Z' is —N= or —CR$^{33}$=;

V' is —N= or —CR$^{34}$=;

W' is —N= or —CR$^{35}$=; and

Q' is —NR$^{36}$—, —O— or —S—;

wherein:

R$^{27}$, R$^{28}$, R$^{32}$, R$^{33}$, R$^{34}$ and R$^{35}$ are independently hydrogen, halogen, —CN, —CF$_3$, —OCF$_3$, —O(CH$_2$)$_y$CF$_3$, —NO$_2$, —OR$^{29}$, —NR$^{29}$R$^{39}$, lower alkyl, aryl, aryl-lower alkyl, —SCF$_3$, —SR$^{29}$, —CHF$_2$, —OCHF$_2$, —OCF$_2$CHF$_2$, —OSO$_2$R$^{29}$, —OSO$_2$CF$_3$, —CONR$^{29}$R$^{30}$, —(CH$_2$)$_y$CONR$^{29}$R$^{30}$, —O(CH$_2$)$_y$CONR$^{29}$R$^{30}$, —(CH$_2$)$_y$OR$^{29}$, —(CH$_2$)$_y$NR$^{29}$R$^{30}$, —OCOR$^{29}$ or —CO$_2$R$^{29}$; or R$^{27}$ and R$^{28}$, R$^{32}$ and R$^{33}$, R$^{33}$ and R$^{34}$ or R$^{34}$ and R$^{35}$ together form a bridge —OCH$_2$O—;

R$^{27}$ and R$^{28}$ preferably independently representing hydrogen; halogen such as —Cl or —F; —CF$_3$; —OCF$_3$; —OCHF$_2$; —OCH$_2$CF$_3$; —OR$^{29}$ wherein R$^{29}$ is hydrogen or lower alkyl; lower alkyl such as methyl, isopropyl or tert-butyl; lower alkylthio; —SCF$_3$; —CH$_2$OH; —COO-lower alkyl; aryl or —CONH$_2$; or together forming a bridge —OCH$_2$O—;

wherein y is 1, 2, 3 or 4; and

R$^{29}$ and R$^{30}$ independently are hydrogen, —COR$^{31}$, —SO$_2$R$^{31}$, lower alkyl, aryl or aryl-lower alkyl;

wherein R$^{31}$ is hydrogen, lower alkyl, aryl or aryl-lower alkyl;

R$^{36}$ and R$^{39}$ independently are hydrogen, lower alkyl, aryl or aryl-lower alkyl; and R$^{38}$ is hydrogen, —OR$^{40}$, —NR$^{40}$R$^{41}$, lower alkyl, aryl, aryl-lower alkyl, —SCF$_3$, —SR$^{40}$, —CHF$_2$, —OCHF$_2$, —OCF$_2$CHF$_2$, —CONR$^{40}$R$^{41}$, —(CH$_2$)$_x$CONR$^{40}$R$^{41}$, —O(CH$_2$)$_x$CONR$^{40}$R$^{41}$, —(CH$_2$)$_x$OR$^{40}$, —(CH$_2$))$_x$NR$^{40}$R$^{41}$, —OCOR$^{40}$ or —CO$_2$R$^{40}$;

wherein x is 1, 2, 3 or 4;

R$^{40}$ and R$^{41}$ independently are hydrogen, —COR$^{42}$, —SO$_2$R$^{42}$, lower alkyl, aryl or aryl-tower alkyl; and wherein R$^{42}$ is hydrogen, lower alkyl, aryl or aryl-lower alkyl.

Examples of specific compounds represented by the above general formula V are the following:

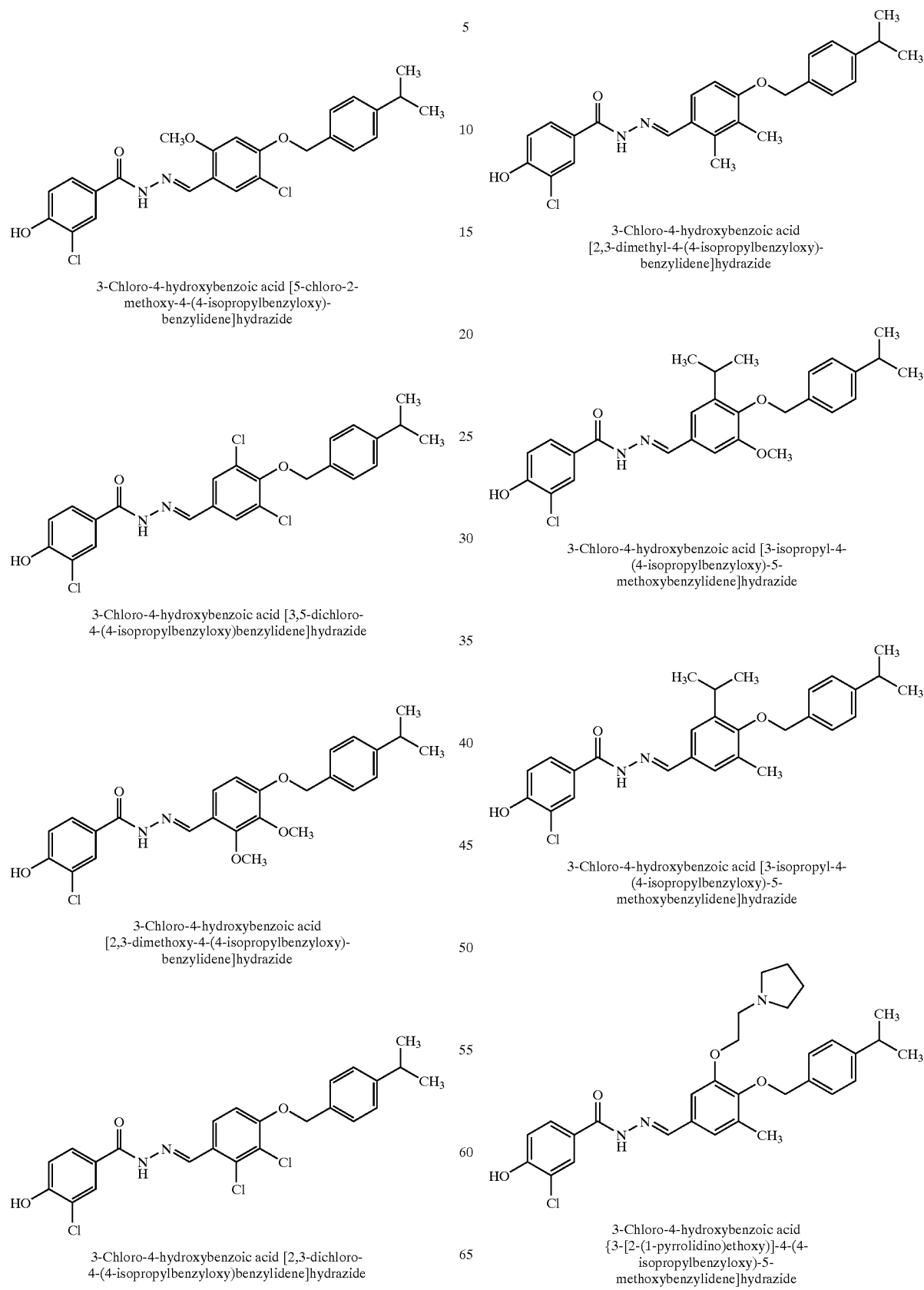

3-Chloro-4-hydroxybenzoic acid [5-chloro-2-methoxy-4-(4-isopropylbenzyloxy)-benzylidene]hydrazide 3-Chloro-4-hydroxybenzoic acid [3,5-dichloro-4-(4-isopropylbenzyloxy)benzylidene]hydrazide 3-Chloro-4-hydroxybenzoic acid [2,3-dimethoxy-4-(4-isopropylbenzyloxy)-benzylidene]hydrazide 3-Chloro-4-hydroxybenzoic acid [2,3-dichloro-4-(4-isopropylbenzyloxy)benzylidene]hydrazide 3-Chloro-4-hydroxybenzoic acid [2,3-dimethyl-4-(4-isopropylbenzyloxy)-benzylidene]hydrazide 3-Chloro-4-hydroxybenzoic acid [3-isopropyl-4-(4-isopropylbenzyloxy)-5-methoxybenzylidene]hydrazide 3-Chloro-4-hydroxybenzoic acid [3-isopropyl-4-(4-isopropylbenzyloxy)-5-methoxybenzylidene]hydrazide 3-Chloro-4-hydroxybenzoic acid {3-[2-(1-pyrrolidino)ethoxy)]-4-(4-isopropylbenzyloxy)-5-methoxybenzylidene}hydrazide -continued

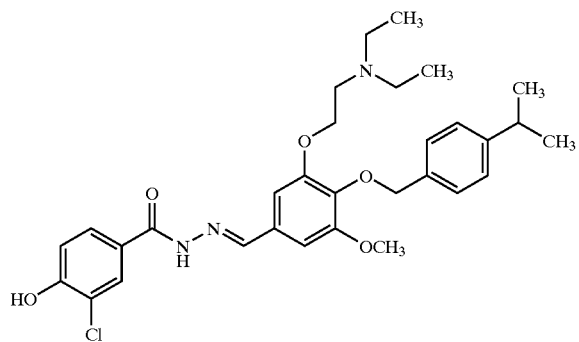

3-Chloro-4-hydroxybenzoic acid
[3-(2-diethylaminoethoxy)-4-(4-isopropyl-
benzyloxy)-5-methoxybenzylidene]hydrazide

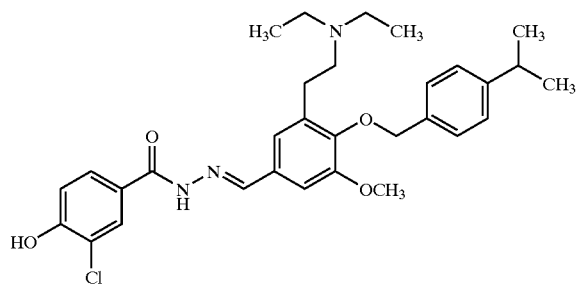

3-Chloro-4-hydroxybenzoic acid
[3-(2-diethylaminoethyl)-4-(4-
isopropylbenzyloxy)-5-methoxybenzylidene]hydrazide

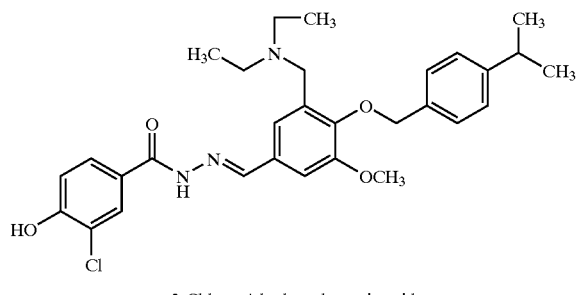

3-Chloro-4-hydroxybenzoic acid
[3-diethylaminomethyl-4-(4-
isopropylbenzyloxy)-5-methoxybenzylidene]hydrazide

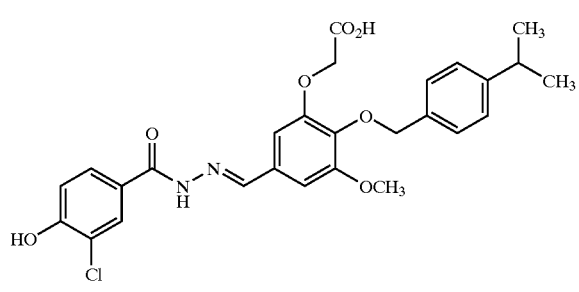

5-[(3-Chloro-4-hydroxybenzoyl)hydrazono-
methyl]-3-methoxy-2-(4-isopropylbenzyloxy)-
phenoxyacetic acid -continued

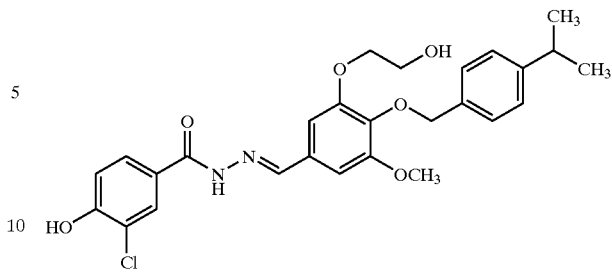

3-Chloro-4-hydroxybenzoic acid
[3-(2-hydroxyethoxy)-4-(4-isopropyl-
benzyloxy)-5-methoxybenzylidene]hydrazide

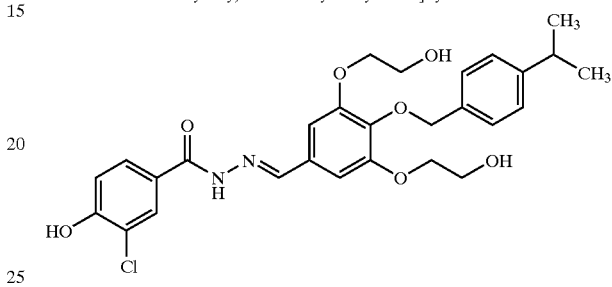

3-Chloro-4-hydroxybenzoic acid
[3,5-bis-(2-hydroxyethoxy)-4-(4-
isopropylbenzyloxy)benzylidene]hydrazide

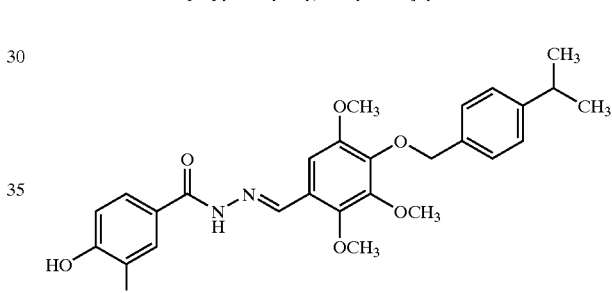

3-Chloro-4-hydroxybenzoic acid
[2,3,5-trimethoxy-4-(4-isopropylbenzyloxy)-
benzylidene]hydrazide


3-Chloro-4-hydroxybenzoic acid
[3,5-dimethoxy-4-(4-n-propylbenzyloxy)-
benzylidene]hydrazide

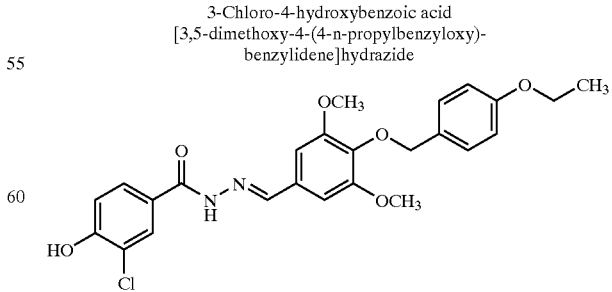

3-Chloro-4-hydroxybenzoic acid
[3,5-dimethoxy-4-(4-n-ethoxybenzyloxy)-
benzylidene]hydrazide

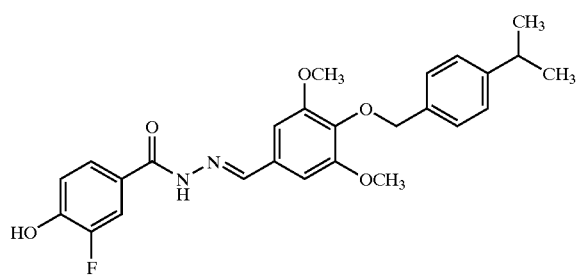

3-Fluoro-4-hydroxybenzoic acid
[3,5-dimethoxy-4-(4-isopropylbenzyloxy)-
benzylidene]hydrazide

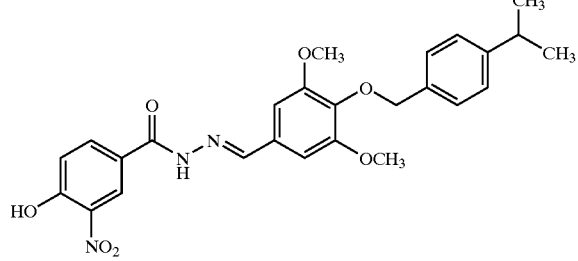

3-Nitro-4-hydroxybenzoic acid
[3,5-dimethoxy-4-(4-isopropylbenzyloxy)-
benzylidene]hydrazide

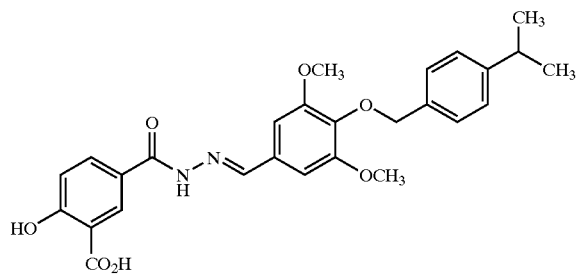

3-Carboxy-4-hydroxybenzoic acid
[3,5-dimethoxy-4-(4-isopropylbenzyloxy)-
benzylidene]hydrazide

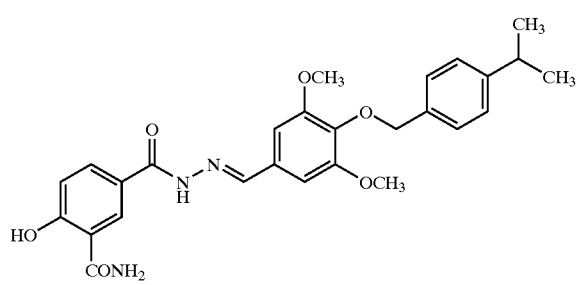

3-Carbamoyl-4-hydroxybenzoic acid
[3,5-dimethoxy-4-(4-isopropylbenzyloxy)-
benzylidene]hydrazide

3-Cyano-4-hydroxybenzoic acid
[3,5-dimethoxy-4-(4-isopropylbenzyloxy)-
benzylidene]hydrazide

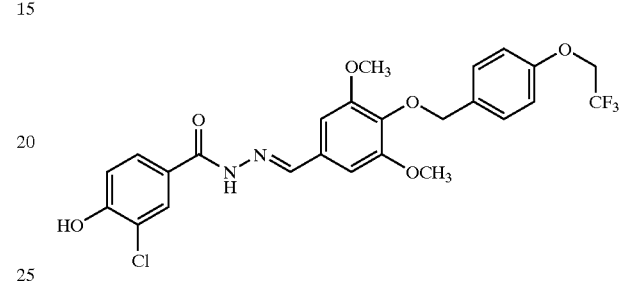

3-Chloro-4-hydroxybenzoic acid
{3,5-dimethoxy-4-[4-(2,2,2-trifluoroethoxy)-
benzyloxy]-benzylidene}hydrazide

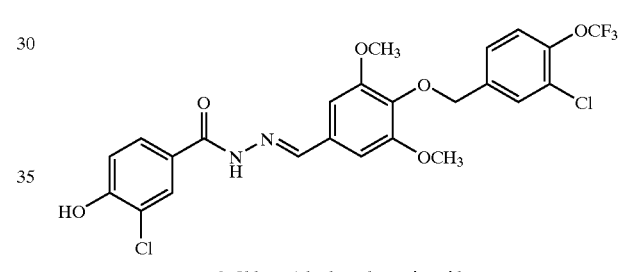

3-Chloro-4-hydroxybenzoic acid
[3,5-dimethoxy-4-(3-chloro-4-
trifluoromethoxybenzyloxy)benzylidene]hydrazide

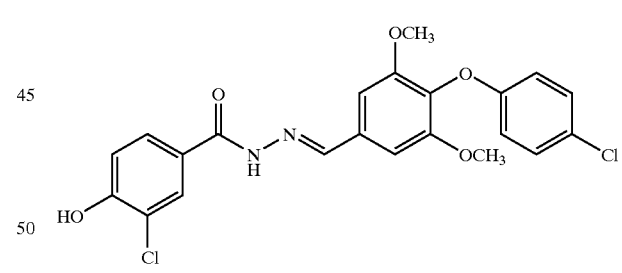

3-Chloro-4-hydroxybenzoic acid [3,5-
dimethoxy-4-(4-chlorophenoxy)
benzylidene]hydrazide

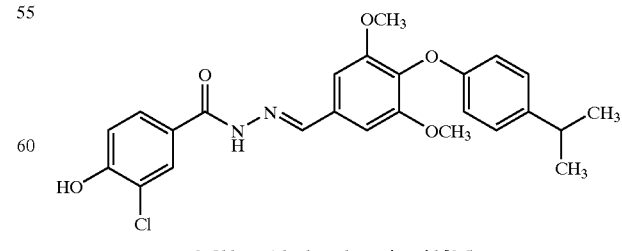

3-Chloro-4-hydroxybenzoic acid [3,5-
dimethoxy-4-(4-isopropylphenoxy)
benzylidene]hydrazide

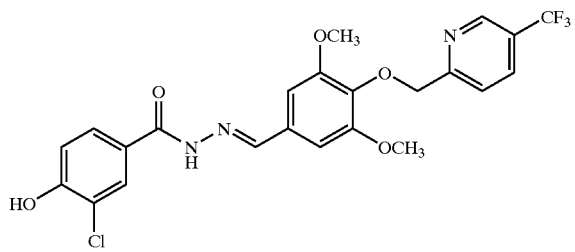

3-Chloro-4-hydroxybenzoic acid [3,5-dimethoxy-4-(4-trifluoromethyl-2-pyridylmethoxy)-benzylidene]hydrazide

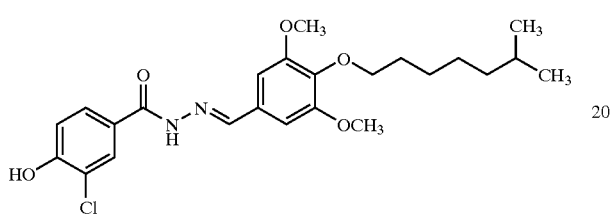

3-Chloro-4-hydroxybenzoic acid [3,5-dimethoxy-4-(6-methylheptyloxy)benzylidene]hydrazide

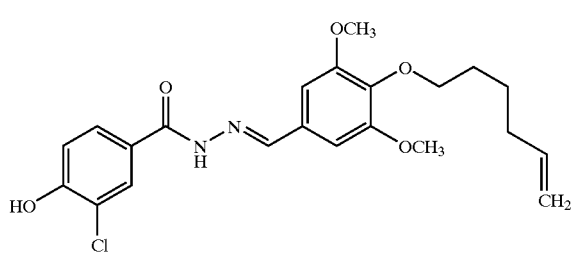

3-Chloro-4-hydroxybenzoic acid [3,5-dimethoxy-4-(5-hexenyloxy)benzylidene]hydrazide

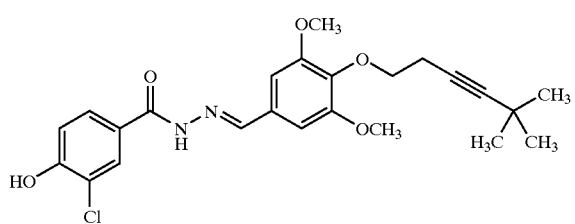

3-Chloro-4-hydroxybenzoic acid [3,5-dimethoxy-4-(5,5-dimethyl-3-hexynlyoxy)benzylidene]hydrazide

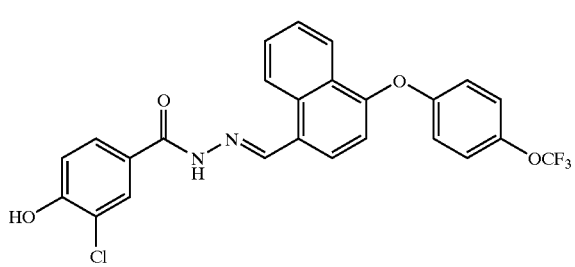

3-Chloro-4-hydroxybenzoic acid [4-(4-trifluoromethoxyphenoxy)-1-naphthylmethylene]hydrazide

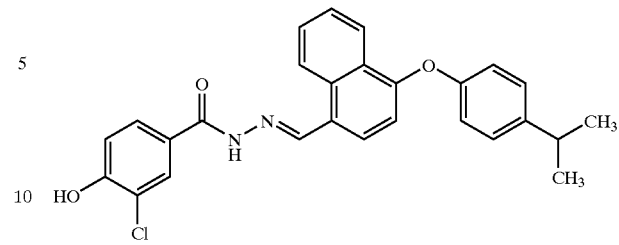

3-Chloro-4-hydroxybenzoic acid [4-(4-isopropylphenoxy)-1-naphthylmethylene]hydrazide

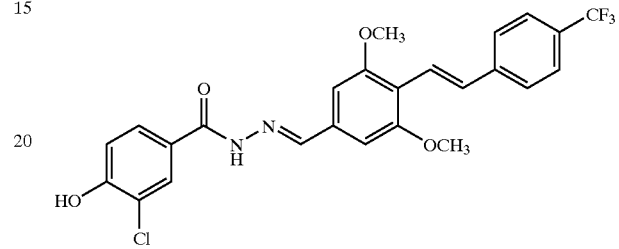

3-Chloro-4-hydroxybenzoic acid {3,5-dimethoxy-4-[2-(4-E-trifluoromethylphenyl)-ethenyl]benzylidene}hydrazide

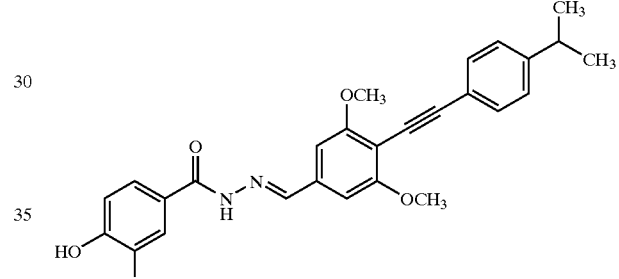

3-Chloro-4-hydroxybenzoic acid {3,5-dimethoxy-4-[(4-isopropylphenyl)-ethenyl]benzylidene}hydrazide

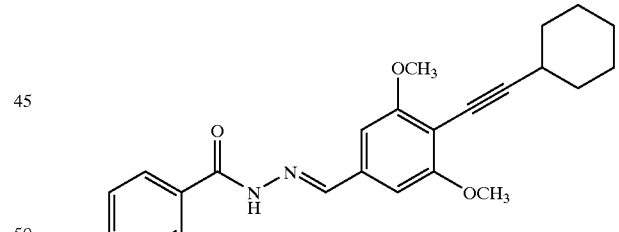

3-Chloro-4-hydroxybenzoic acid [3,5-dimethoxy-4-(cyclohexylethynyl)benzylidene]hydrazide

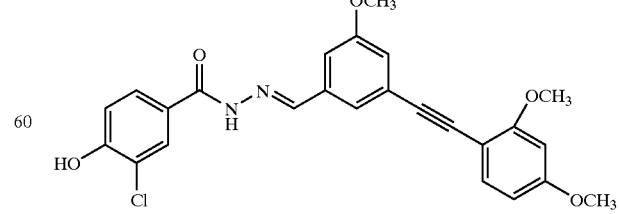

3-Chloro-4-hydroxybenzoic acid [3-(2-methoxy-4-methylphenyl)ethynyl-5-methoxybenzylidene]hydrazide -continued

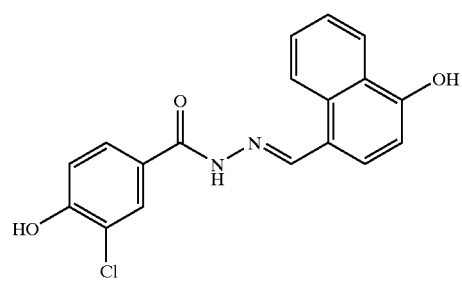

3-Chloro-4-hydroxybenzoic acid (4-hydroxy-1-naphthylmethylene)hydrazide

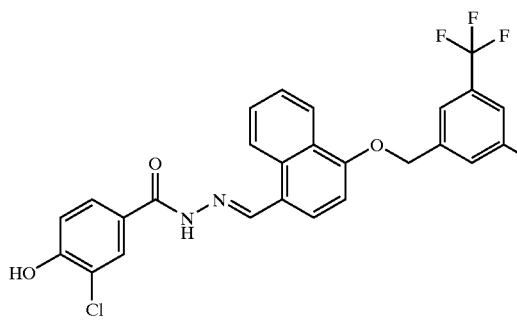

3-chloro-4-hydroxybenzoic acid [4-(3,5-bis-trifluoromethylbenzyloxy)-1-naphthylmethylene]hydrazide

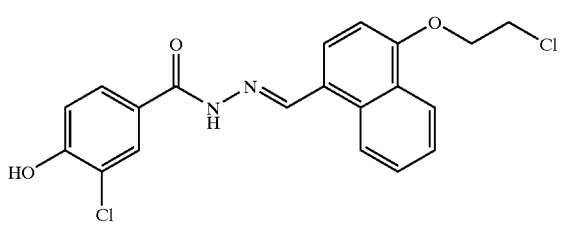

3-chloro-4-hydroxybenzoic acid [4-(2-chloroethyoxy)-1-naphthylmethylene]hydrazide

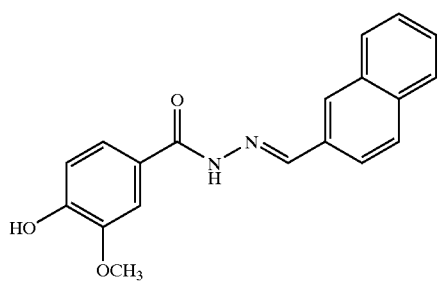

4-Hydroxy-3-methoxybenzoic acid (2-naphthylmethylene)hydrazide

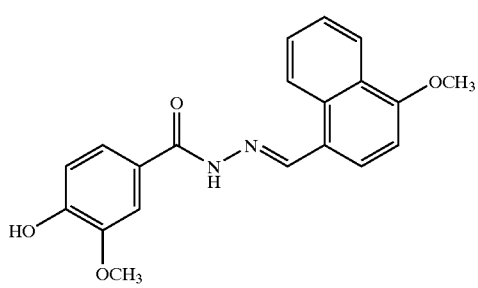

4-Hydroxy-3-methoxybenzoic acid (4-methoxy-1-naphthylmethylene)hydrazide

-continued

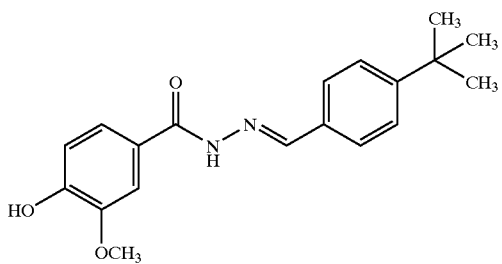

4-Hydroxy-3-methoxybenzoic acid (4-tert-butylbenzylidene)hydrazide

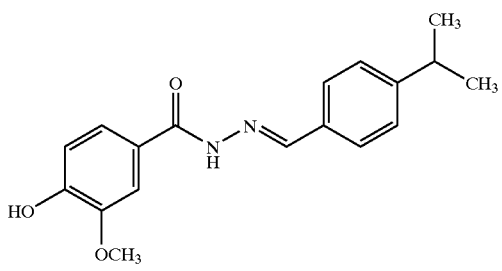

4-Hydroxy-3-methoxybenzoic acid (4-isopropylbenzylidene)hydrazide

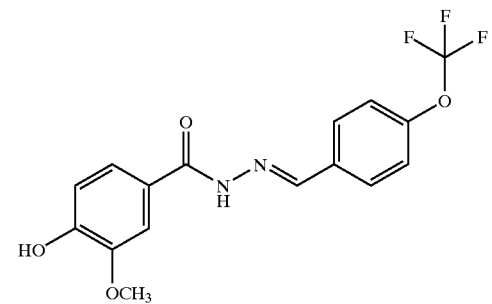

4-Hydroxy-3-methoxybenzoic acid (4-trifluoromethoxybenzylidene)hydrazide

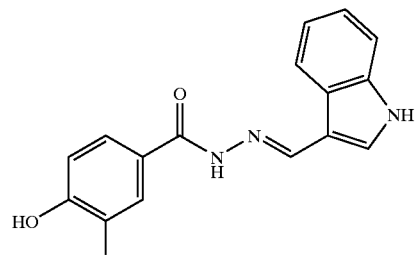

4-Hydroxy-3-methoxybenzoic acid (1H-indol-3-ylmethylene)hydrazide

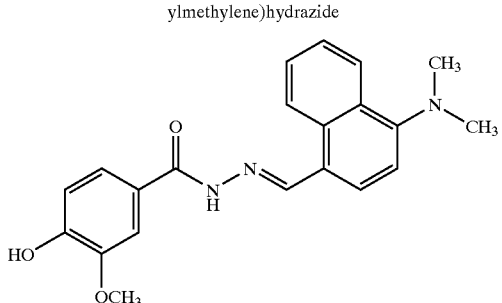

4-Hydroxy-3-methoxybenzoic acid (4-dimethylamino-1-naphthylmethylene)hydrazide

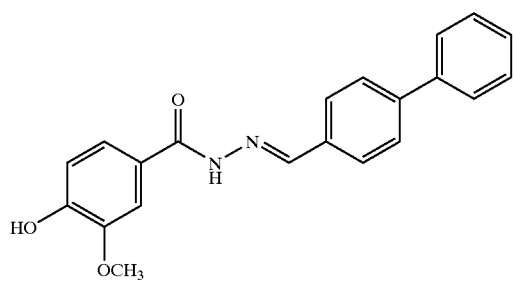

4-Hydroxy-3-methoxybenzoic acid (4-phenylbenzylidene)hydrazide

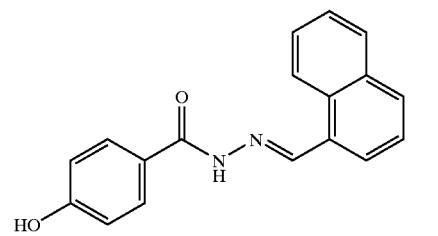

4-Hydroxybenzoic acid (1-naphthylmethylene)hydrazide

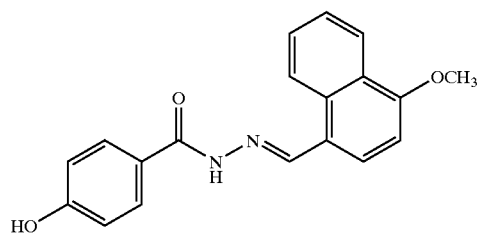

4-Hydroxybenzoic acid (4-methoxy-1-naphthylmethylene)hydrazide

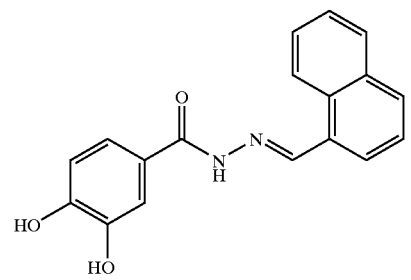

3,4-Dihydroxybenzoic acid (1-naphthylmethylene)hydrazide

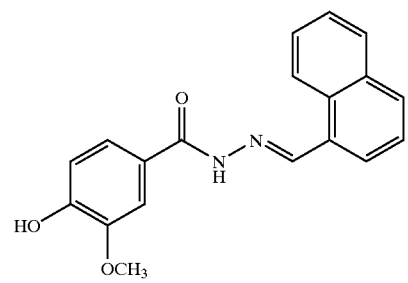

4-Hydroxy-3-methoxybenzoic acid (1-naphthylmethylene)hydrazide


4-Hydroxy-3-methoxybenzoic acid [3-(3-trifluoromethylphenoxy)benzylidene]hydrazide

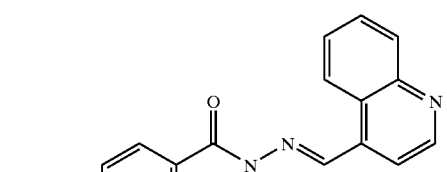

4-Hydroxy-3-methoxybenzoic acid (4-quinolinylmethylene)hydrazide

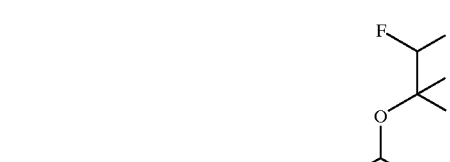

4-Hydroxybenzoic acid [3-(1,1,2,2-tetrafluoroethoxy)benzylidene]hydrazide

4-Hydroxybenzoic acid [3-(4-tert-butylphenyl)-E-but-2-enylidene]hydrazide

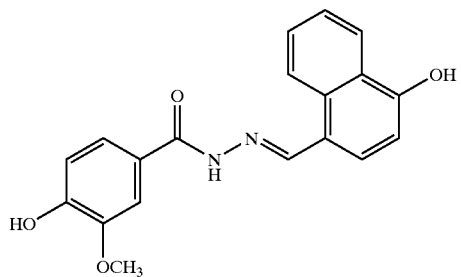

4-Hydroxy-3-methoxybenzoic acid (4-hydroxy-1-naphthylmethylene)hydrazide

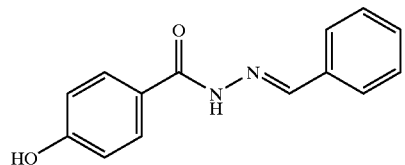

4-Hydroxybenzoic acid (benzylidene) hydrazide

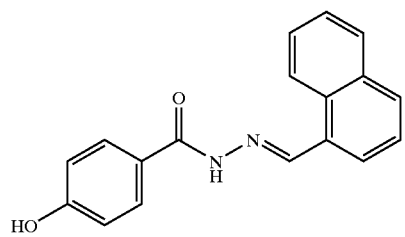

4-Hydroxybenzoic acid (1-naphthylmethylene)hydrazide

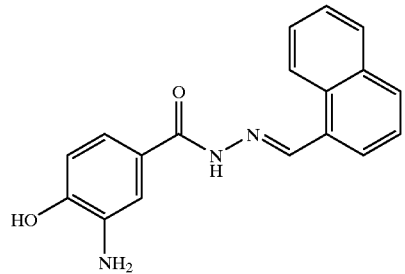

3-Amino-4-hydroxybenzoic acid (1-naphthylmethylene)hydrazide

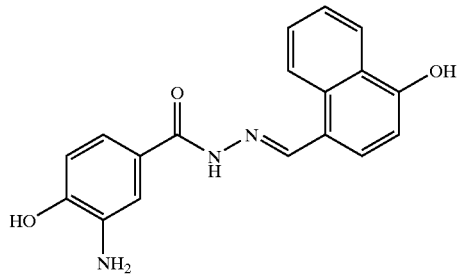

3-Amino-4-hydroxybenzoic acid (4-hydroxy-1-naphthylmethylene)hydrazide

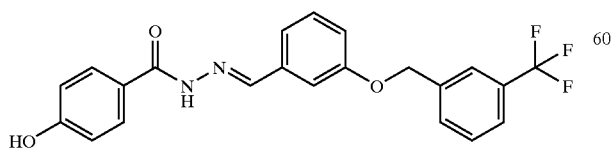

4-Hydroxybenzoic acid [3-(3-trifluoromethylbenzyloxy)benzylidene]hydrazide

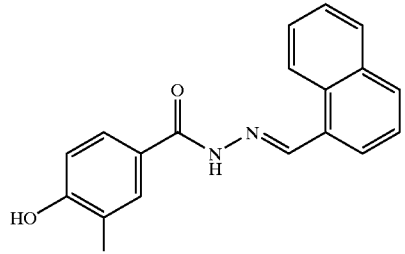

3-Chloro-4-hydroxybenzoic acid (1-naphthylmethylene)hydrazide

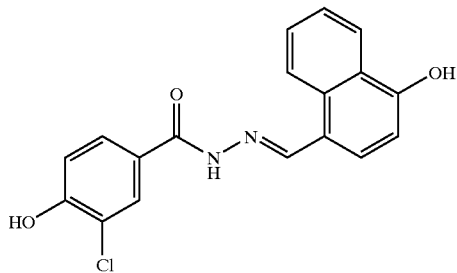

3-Chloro-4-hydroxybenzoic acid (4-hydroxy-1-naphthylmethylene)hydrazide

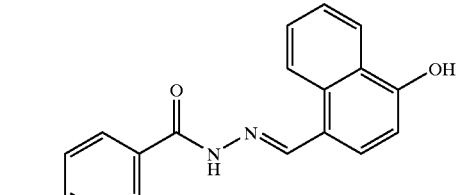

4-Hydroxybenzoic acid (4-hydroxy-1-naphthylmethylene)hydrazide

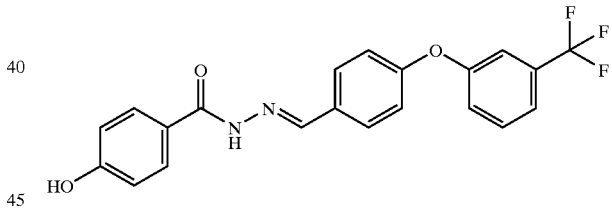

4-Hydroxybenzoic acid [4-(3-trifluoromethylphenoxy)benzylidene]hydrazide

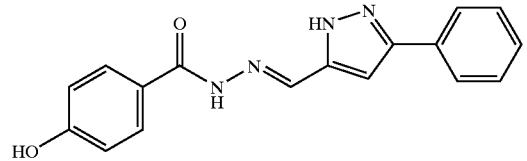

4-Hydroxybenzoic acid (5-phenyl-3-pyrazolylmethylene)hydrazide

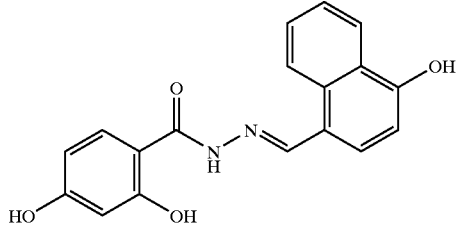

2,4-Dihydroxybenzoic acid (4-hydroxy-1-naphthylmethylene)hydrazide

-continued

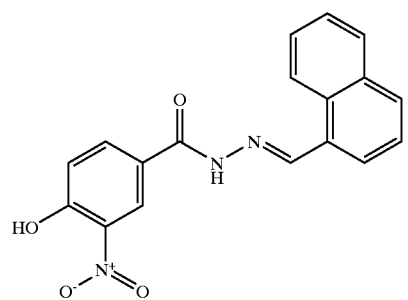

4-Hydroxy-3-nitrobenzoic acid (1-naphthylmethylene)hydrazide

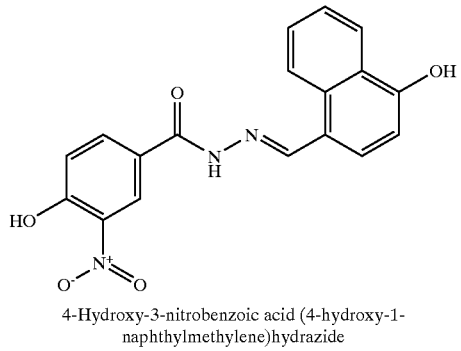

4-Hydroxy-3-nitrobenzoic acid (4-hydroxy-1-naphthylmethylene)hydrazide

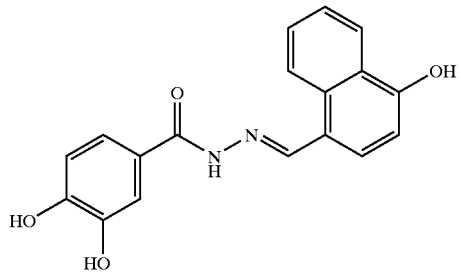

3,4-Dihyroxybenzoic acid (4-hydroxy-1-naphthylmethylene)hydrazide

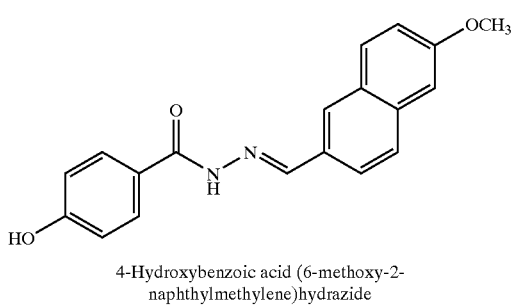

4-Hydroxybenzoic acid (6-methoxy-2-naphthylmethylene)hydrazide

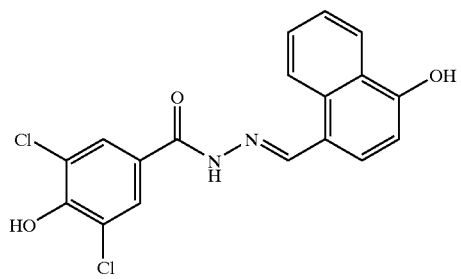

3,5-Dichloro-4-hydroxybenzoic acid (4-hydroxy-1-naphthylmethylene)hydrazide

-continued

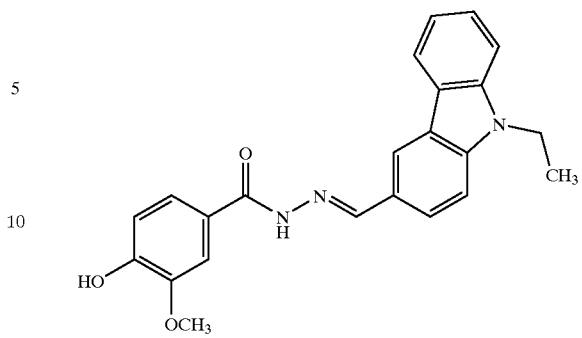

4-Hydroxy-3-methoxybenzoic acid (9-ethyl-9H-3-carbazolylmethylene)hydrazide

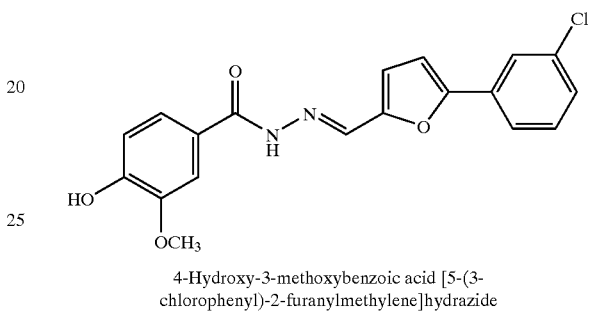

4-Hydroxy-3-methoxybenzoic acid [5-(3-chlorophenyl)-2-furanylmethylene]hydrazide

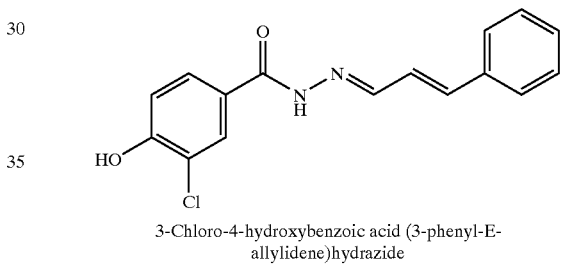

3-Chloro-4-hydroxybenzoic acid (3-phenyl-E-allylidene)hydrazide

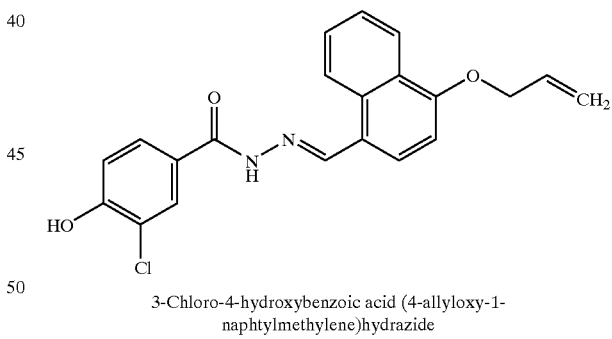

3-Chloro-4-hydroxybenzoic acid (4-allyloxy-1-naphtylmethylene)hydrazide

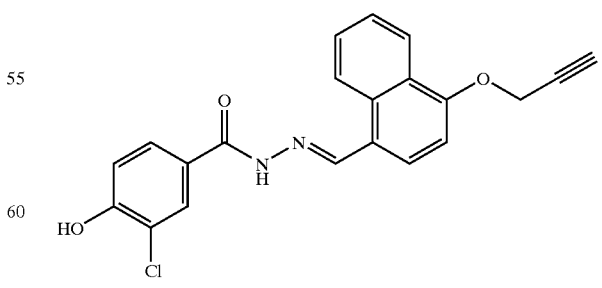

3-Chloro-4-hydroxybenzoic acid (4-ethynylmethoxy-1-naphthylmethylene)hydrazide

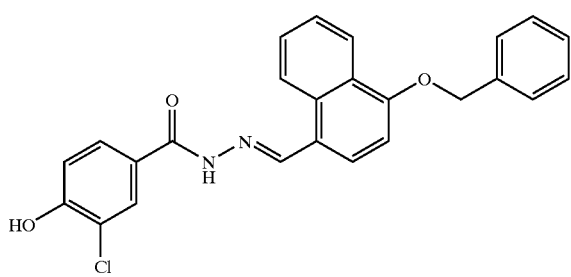

3-Chloro-4-hydroxybenzoic acid (4-benzyloxy-1-naphthylmethylene)hydrazide

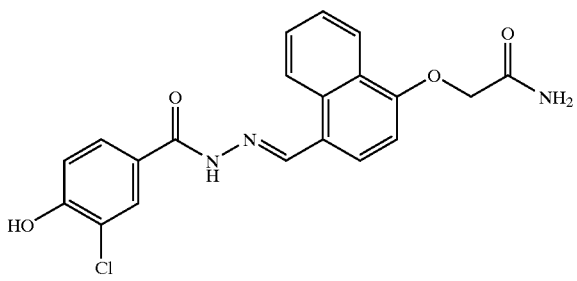

2-(4-[(3-Chloro-4-hydroxybenzoyl)hydra-zo-nomethyl]-1-naphthyloxy)acetamide

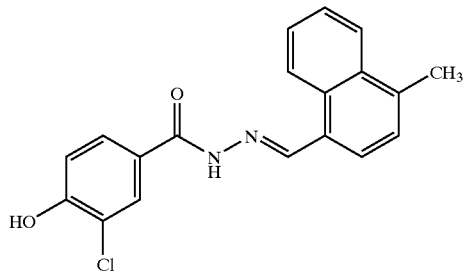

3-Chloro-4-hydroxybenzoic acid (4-methyl-1-naphthylene)hydrazide

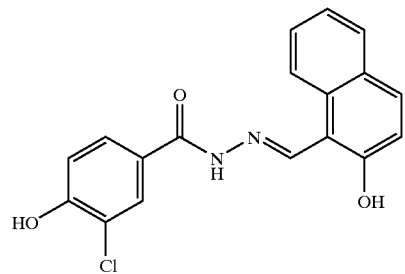

3-Chloro-4-hydroxybenzoic acid (2-hydroxy-1-naphthylmethylene)hydrazide

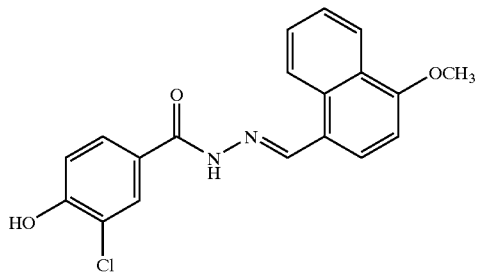

3-Chloro-4-hydroxybenzoic acid (4-methoxy-1-naphthylmethylene)hydrazide

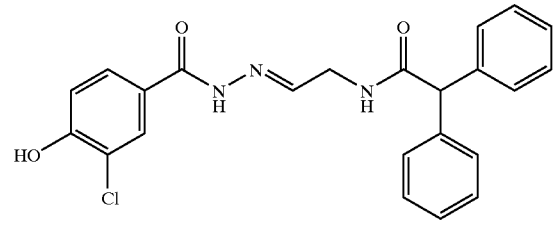

N-(2-[(3-Chloro-4-hydroxybenzoyl)hydrazono]ethyl)-2,2-diphenylacetamide

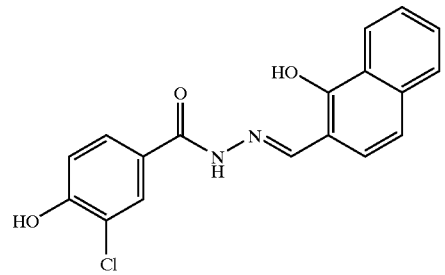

3-Chloro-4-hydroxybenzoic acid (1-hydroxy-2-naphthylmethylene)hydrazide

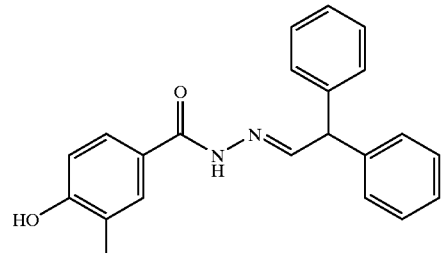

3-Chloro-4-hydroxybenzoic acid (2,2-diphenylethylidene)hydrazide

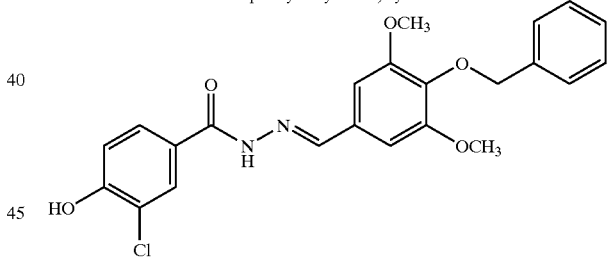

3-Chloro-4-hydroxybenzoic acid (4-benzyloxy-3,5-dimethoxybenzylidene)hydrazide

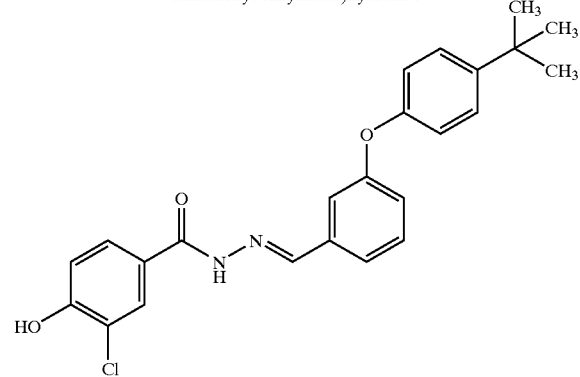

3-Chloro-4-hydroxybenzoic acid [3-(4-tert-butylphenoxy)benzylidene]hydrazide

-continued

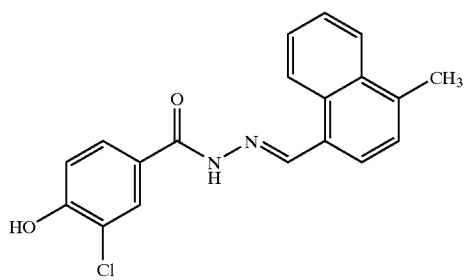

3-Chloro-4-hydroxybenzoic acid (4-methyl-1-naphthylmethylene)hydrazide

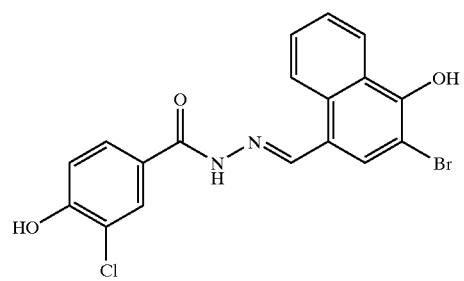

3-Chloro-4-hydroxybenzoic acid (3-bromo-4-hydroxy-1-naphthylmethylene)hydrazide

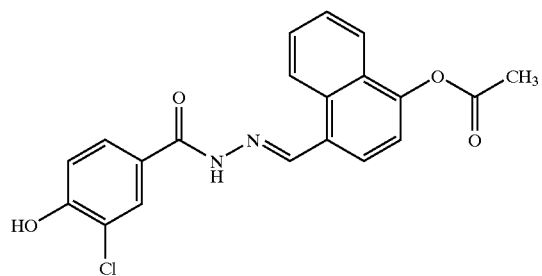

Acetic acid 4-[(3-Chloro-4-hydroxybenzoyl)hydrazonomethyl]-1-naphthyl ester

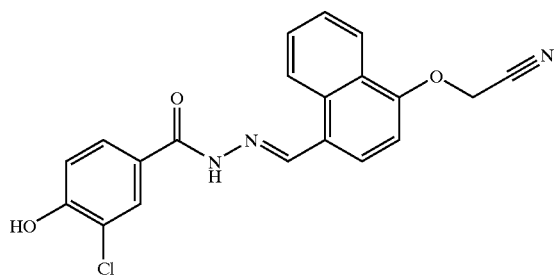

3-Chloro-4-hydroxybenzoic acid (4-cyanomethoxy-1-naphthylmethylene)hydrazide

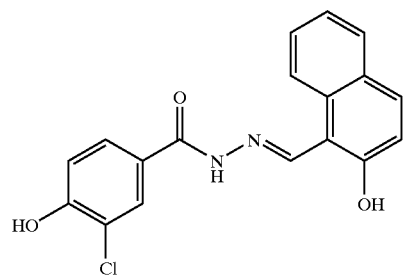

3-Chloro-4-hydroxybenzoic acid (2-hydroxy-1-naphthylmethylene)hydrazide

-continued

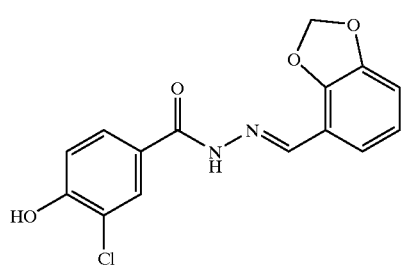

3-Chloro-4-hydroxybenzoic acid (2,3-methylenedioxybenzylidene)hydrazide

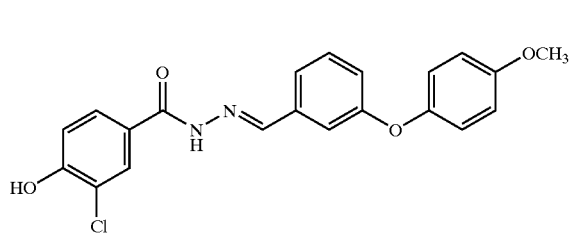

3-Chloro-4-hydroxybenzoic acid [3-(4-methoxyphenoxy)benzylidene]hydrazide

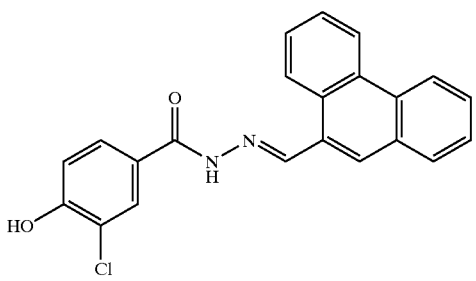

3-Chloro-4-hydroxybenzoic acid (9-phenanthrenylmethylene)hydrazide

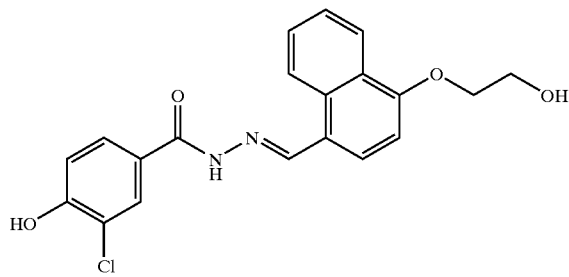

3-Chloro-4-hydroxybenzoic acid [4-(2-hydroxyethoxy)-1-naphthylmethylene]hydrazide

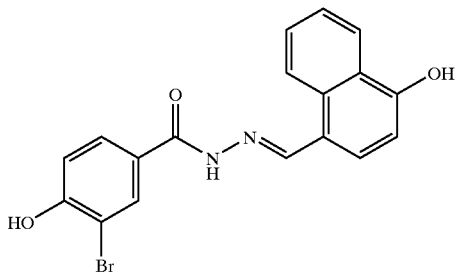

3-Bromo-4-hydroxybenzoic acid (4-hydroxy-1-naphthylmethylene)hydrazide

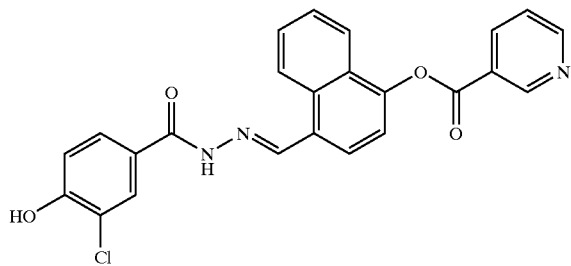

Nicotinic acid 4-[(3-chloro-4-
hydroxybenzoyl)hydrazonomethyl]-1-napthyl ester

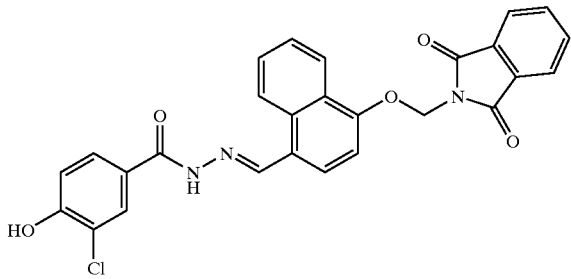

3-Chloro-4-hydroxybenzoic acid [4-(1,3-dioxo-
1,3-dihydroisoindol-2-ylmethoxy)-1-naphthylmethylene]hydrazide

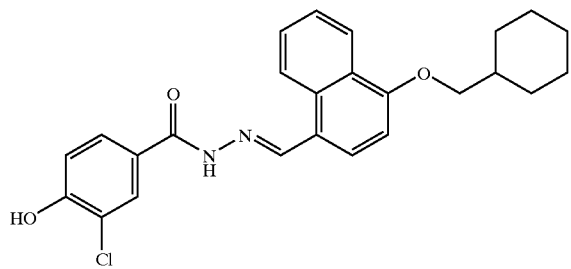

3-Chloro-4-hydroxybenzoic acid [4-
(cyclohexylmethoxy)-1-
naphthylmethylene]hydrazide

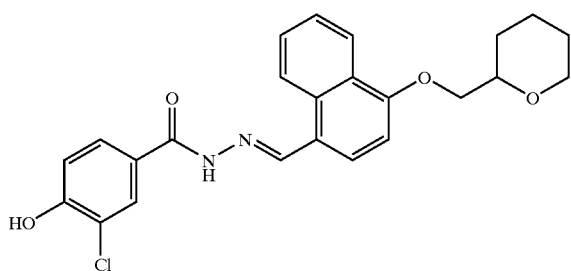

3-Chloro-4-hydroxybenzoic acid [4-
(tetrahydro-2-pyranylmethoxy)-1-
naphthylmethylene]hydrazide

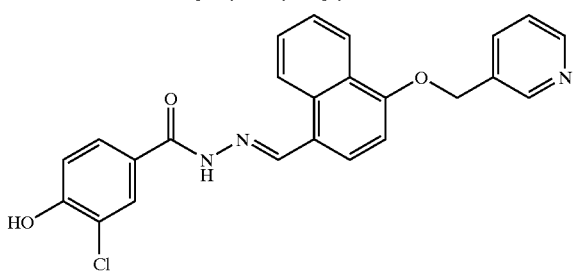

3-Chloro-4-hydroxybenzoic acid [4-
(3-pyridylmethoxy)-1-
naphthylmethylene]hydrazide

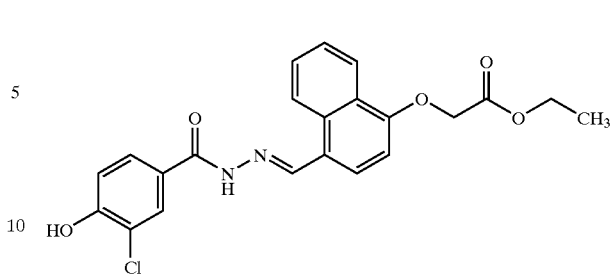

4-[(3-Chloro-4-hydroxybenzoyl)hydrazonomethyl]-1-
naphthyloxy)acetic acid ethyl ester

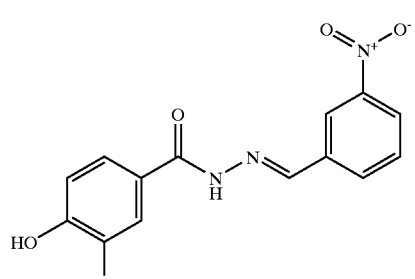

3-Chloro-4-hydroxybenzoic acid (3-
nitrobenzylidene)hydrazide

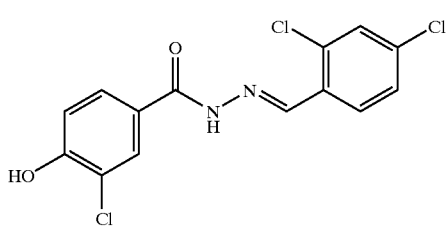

3-Chloro-4-hydroxybenzoic acid (2,4-
dichlorobenzylidene)hydrazide

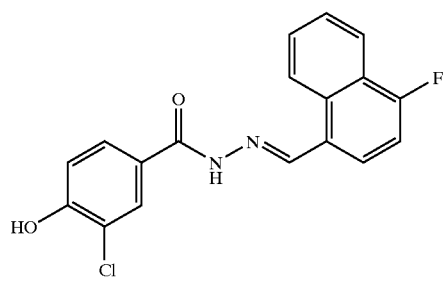

3-Chloro-4-hydroxybenzoic acid (4-fluoro-1-
naphthylmethylene)hydrazide

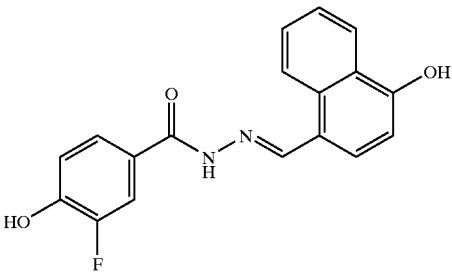

3-Fluoro-4-hydroxybenzoic acid (4-hydroxy-1-
naphthylmethylene)hydrazide

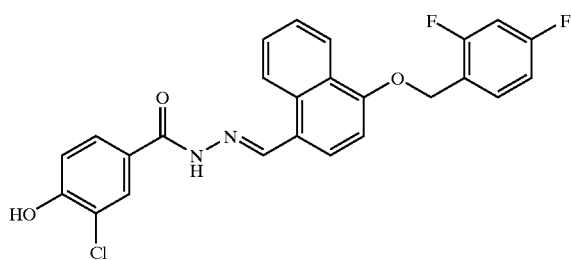

3-Chloro-4-hydroxybenzoic acid [4-(2,4-difluorobenzyloxy)-1-naphthylmethylene]hydrazide

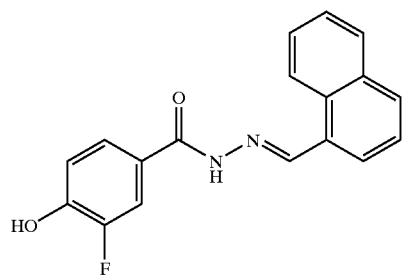

3-Fluoro-4-hydroxybenzoic acid (1-naphthylmethylene)hydrazide

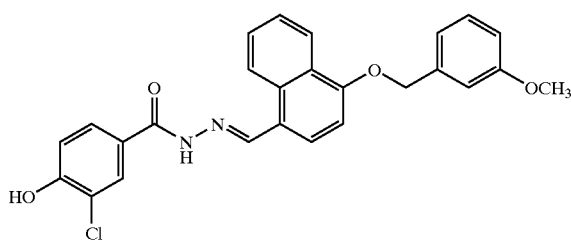

3-Chloro-4-hydroxybenzoic acid [4-(3-methoxybenzyloxy)-1-naphthylmethylene]hydrazide

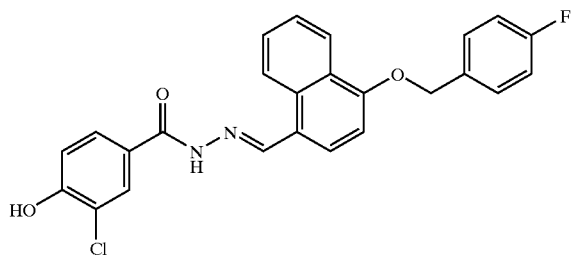

3-Chloro-4-hydroxybenzoic acid [4-(4-fluorobenzyloxy)-1-naphthylmethylene]hydrazide

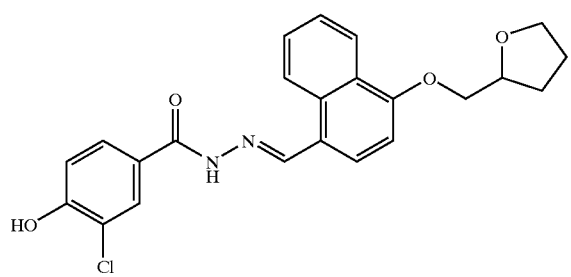

3-Chloro-4-hydroxybenzoic acid [4-(2-tetrahydrofuranylmethoxy)-1-naphthylmethylene]hydrazide

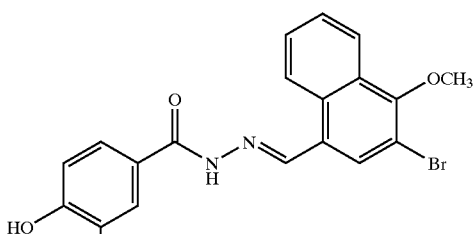

3-Chloro-4-hydroxybenzoic acid (3-bromo-4-methoxy-1-naphthylmethylmethylene)hydrazide

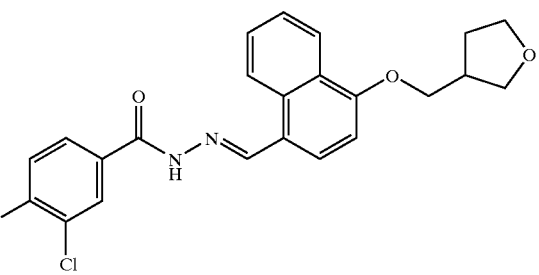

3-Chloro-4-hydroxybenzoic acid [4-(3-tetrahydrofuranylmethoxy)-1-naphthylmethylene]hydrazide

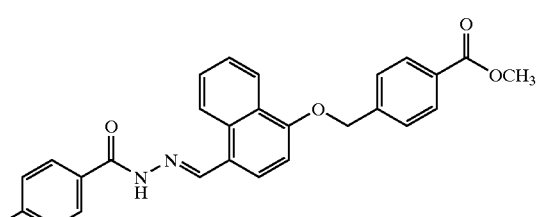

4-(4-[3-Chloro-4-hydroxybenzoyl)hydrazonomethyl]-1-naphthyloxymethyl)benzoic acid methyl ester

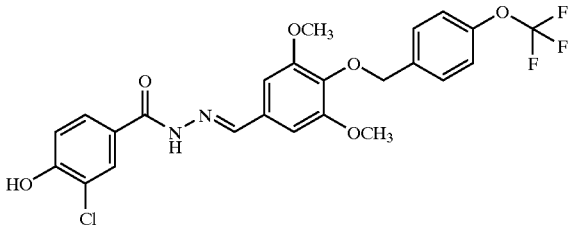

3-Chloro-4-hydroxybenzoic acid [3,5-dimethoxy-4-(4-trifluoromethoxybenzyloxy)-benzylidene]hydrazide

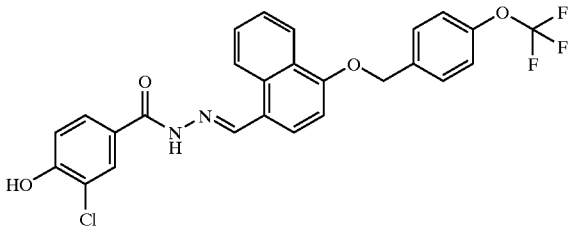

3-Chloro-4-hydroxybenzoic acid [4-(4-trifluoromethoxybenzyloxy)-1-naphthylmethylene]hydrazide -continued
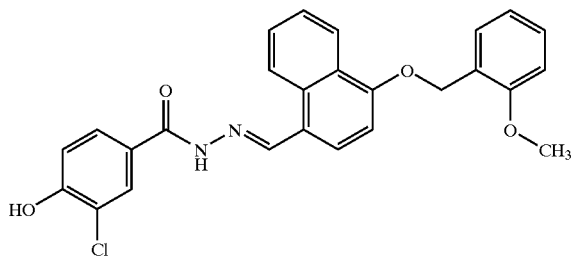
3-Chloro-4-hydroxybenzoic acid [4-(2-methoxybenzyloxy)-1-naphthylmethylene]hydrazide
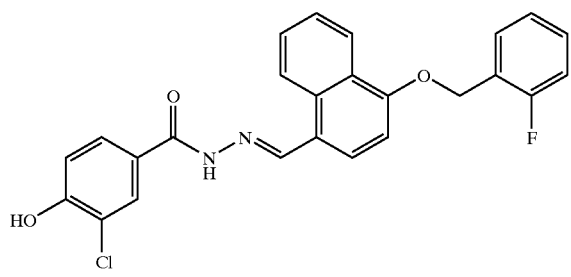
3-Chloro-4-hydroxybenzoic acid [4-(2-fluorobenzyloxy)-1-naphthylmethylene]hydrazide
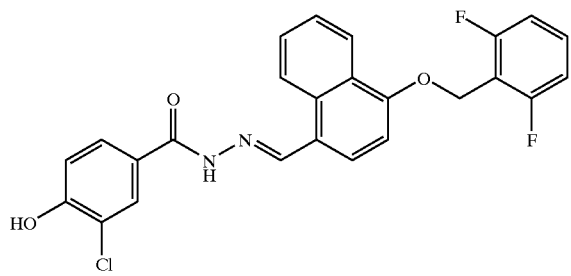
3-Chloro-4-hydroxybenzoic acid [4-(2,6-difluorobenzyloxy)-1-naphthylmethylene]hydrazide
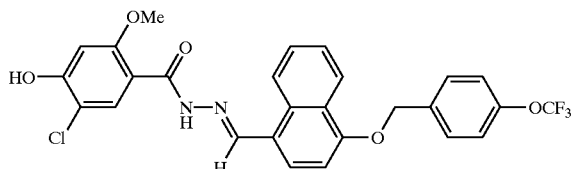
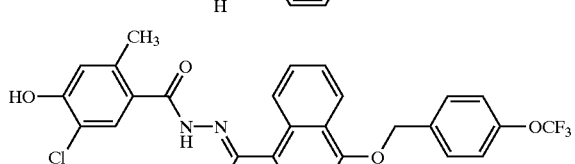
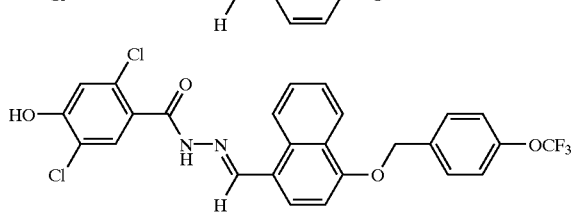
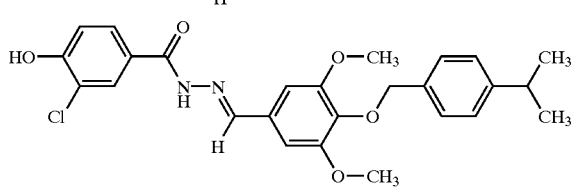
-continued
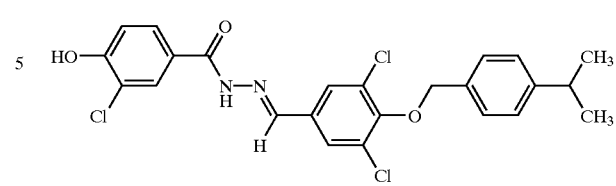
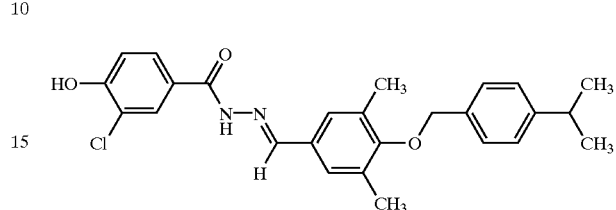
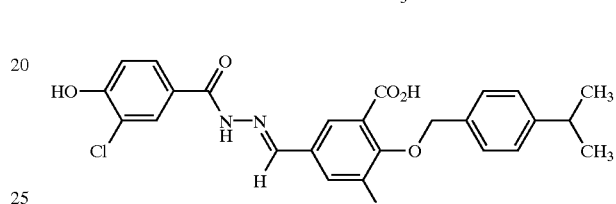

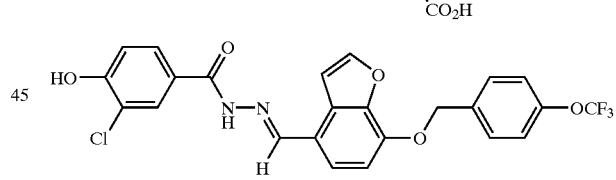
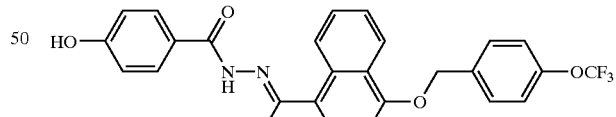
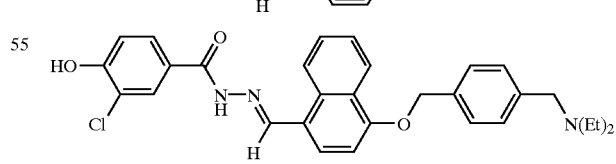
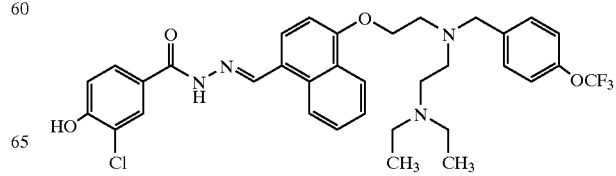

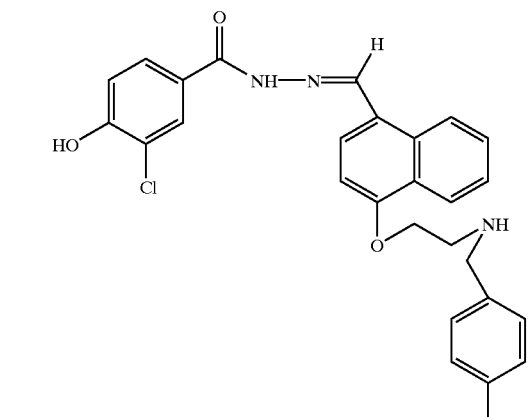
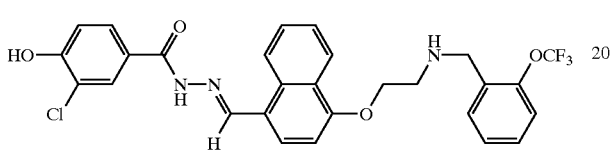
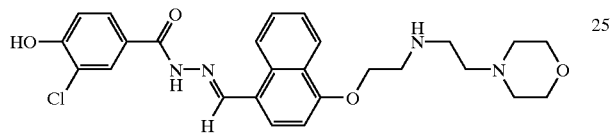
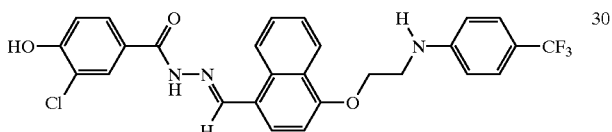
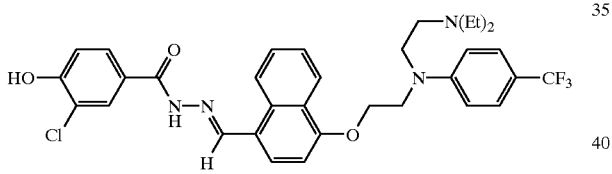
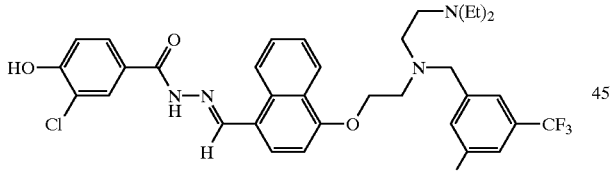

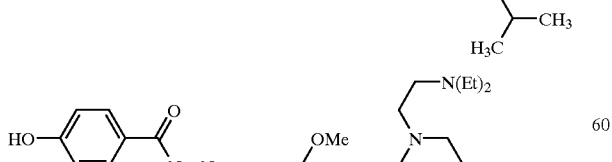
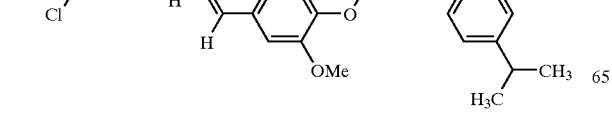
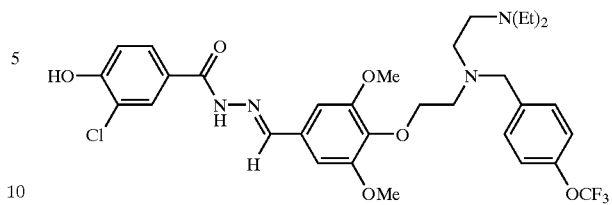
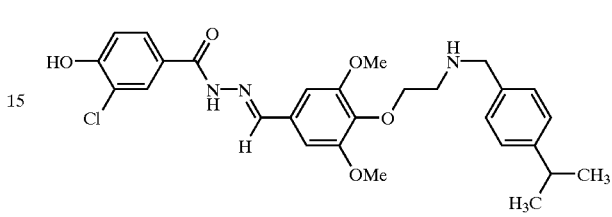
The most preferred specific compounds represented by the above general formula III are the following:
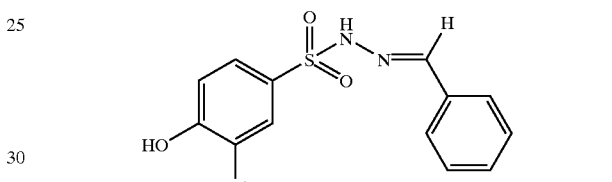
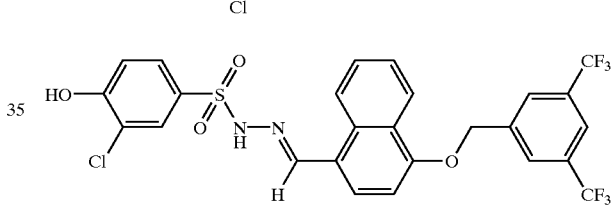
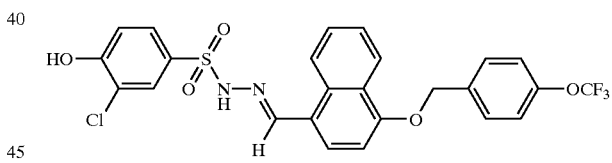
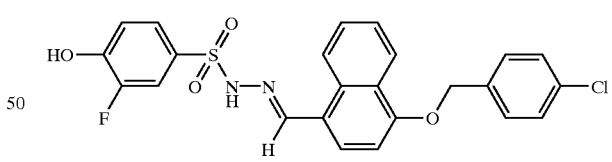
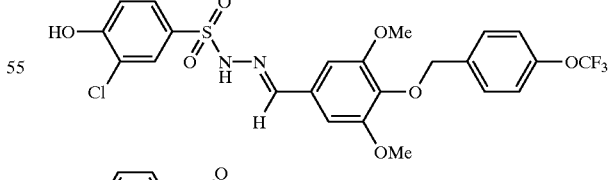
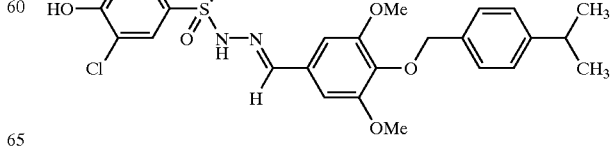

The most preferred specific compounds represented by the above general formula IV are the following:
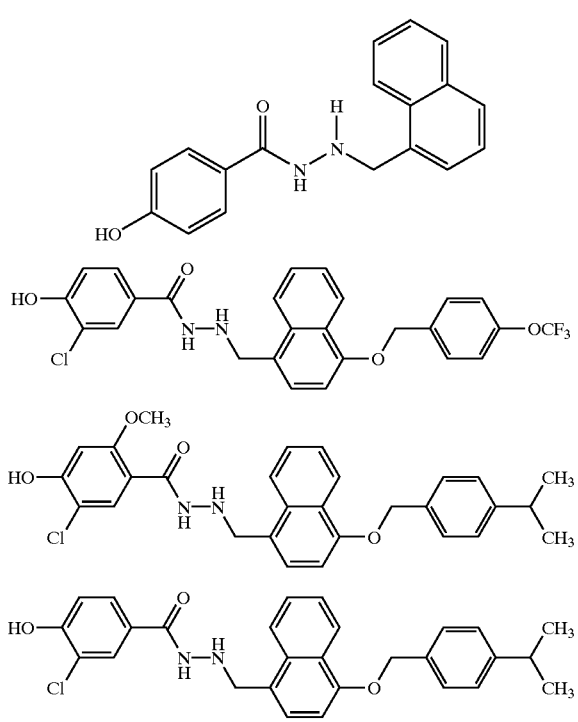
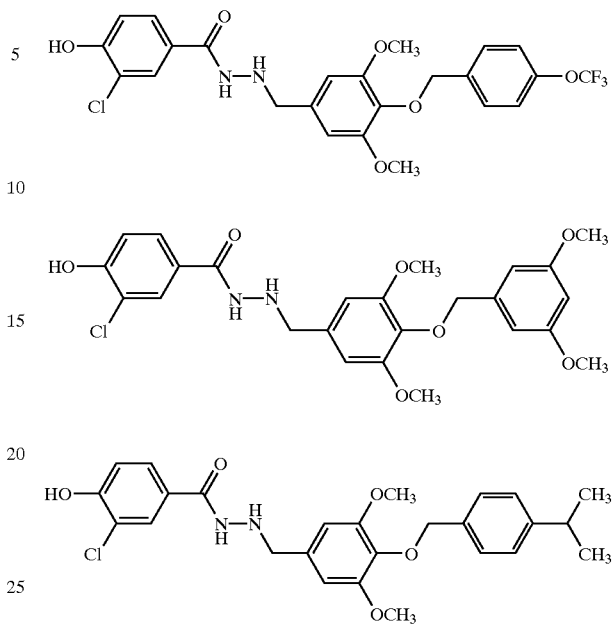
Preferred specific compounds represented by the formulae VI and VII are the following:
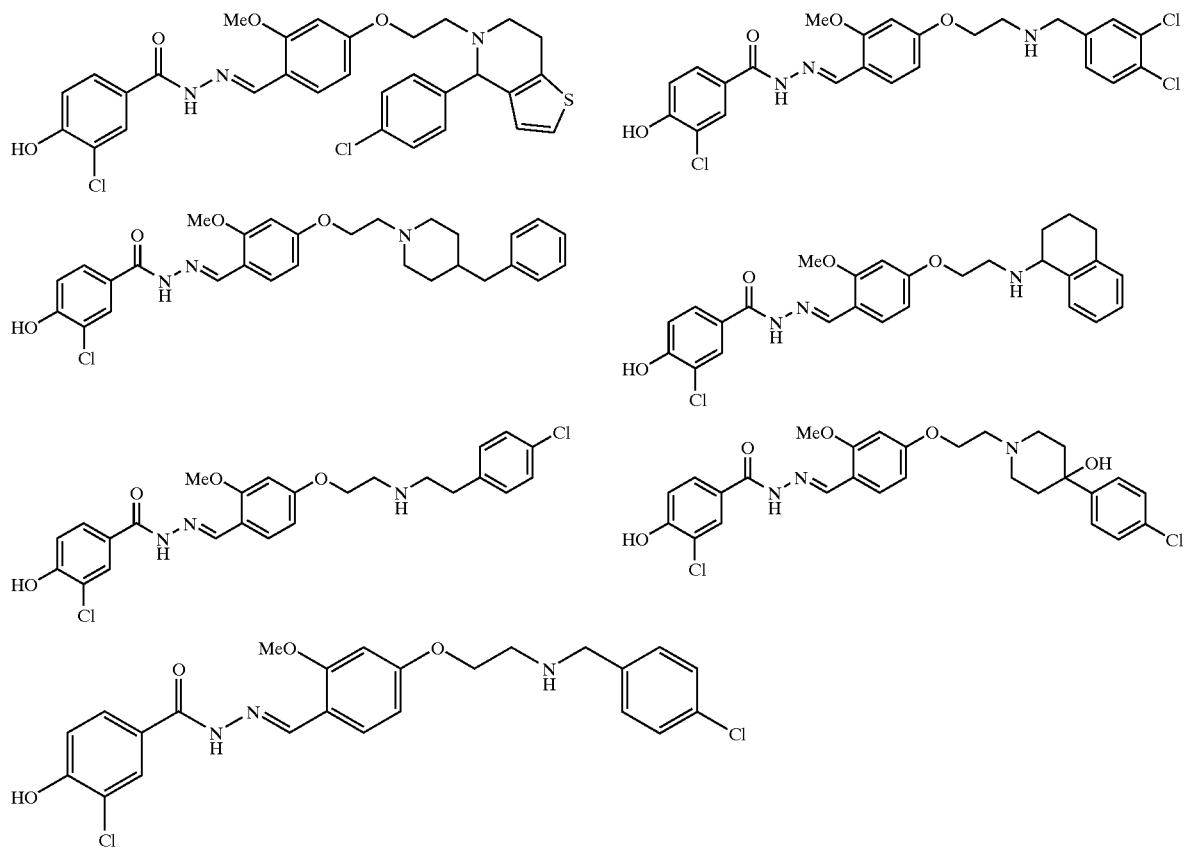

-continued
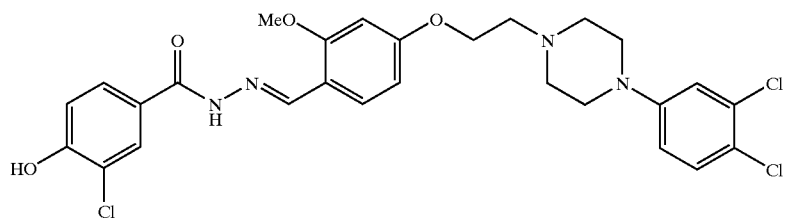
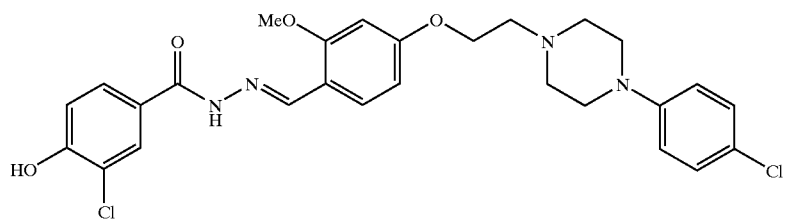
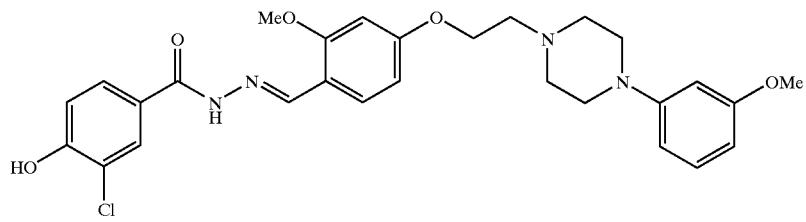
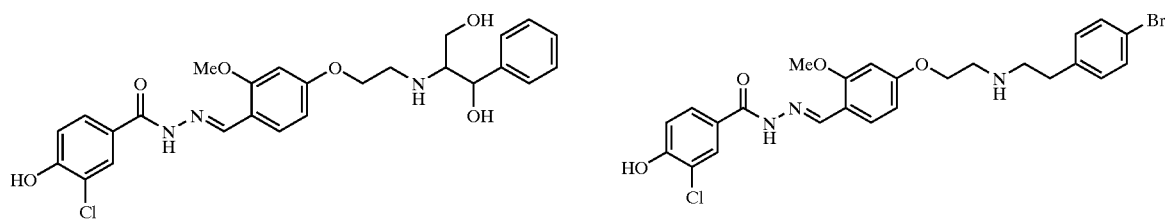
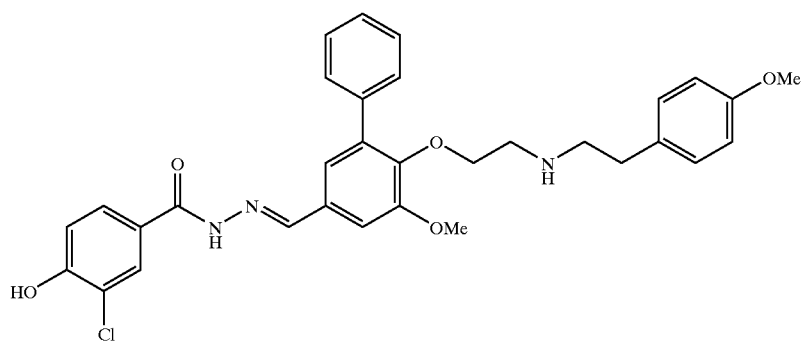
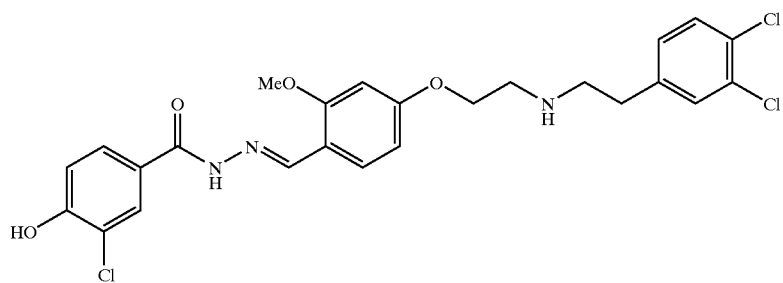

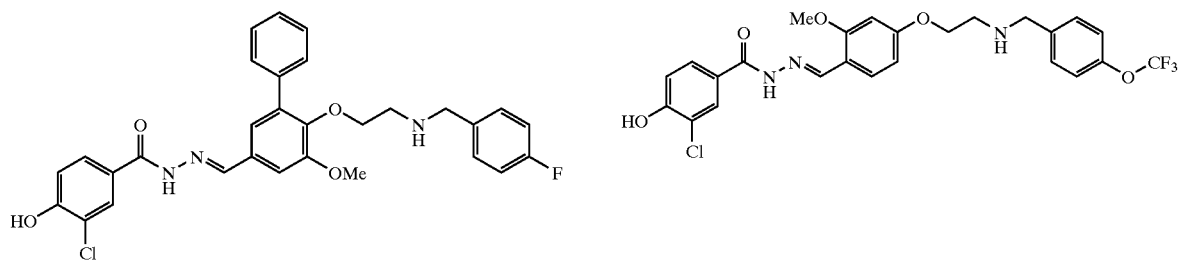
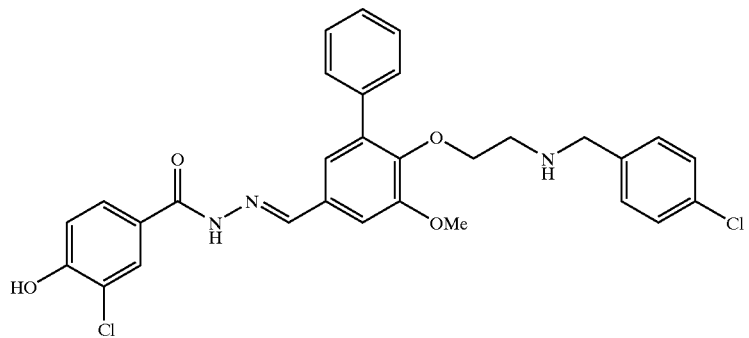
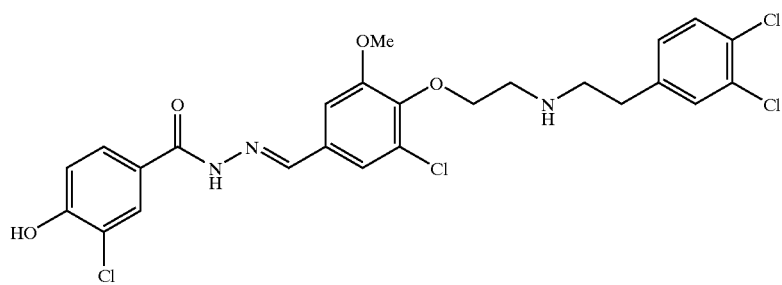
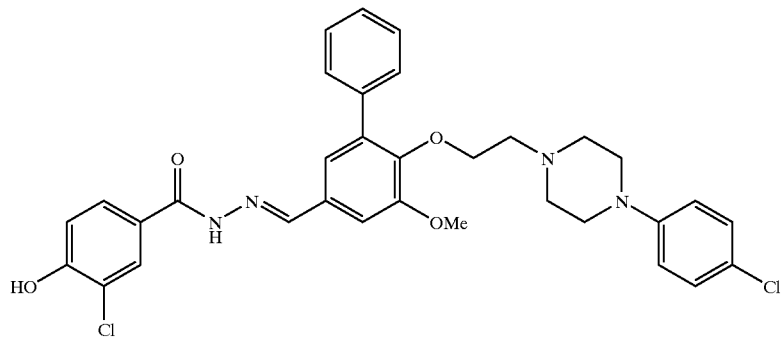
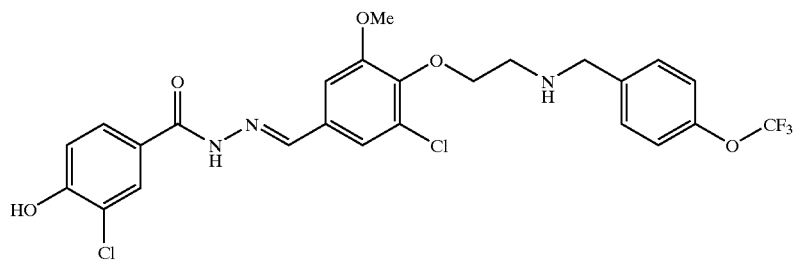

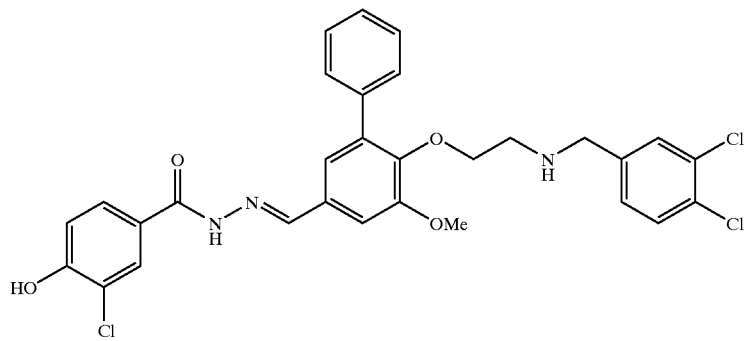
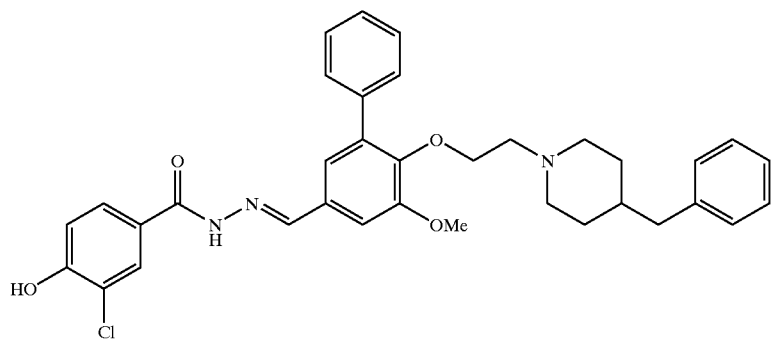
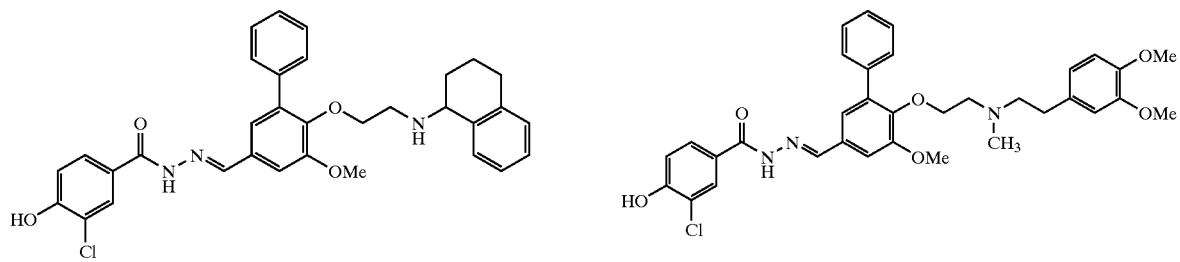
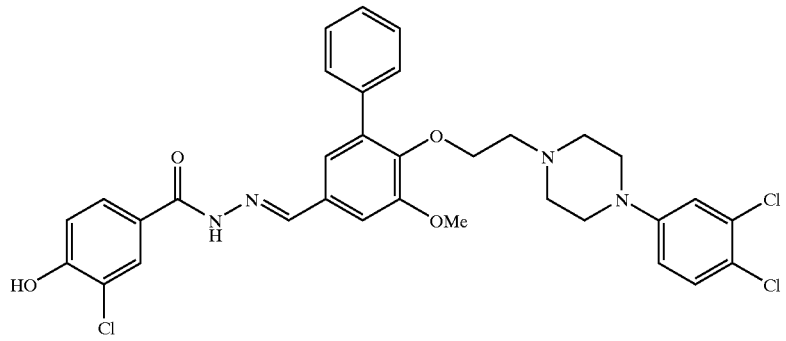
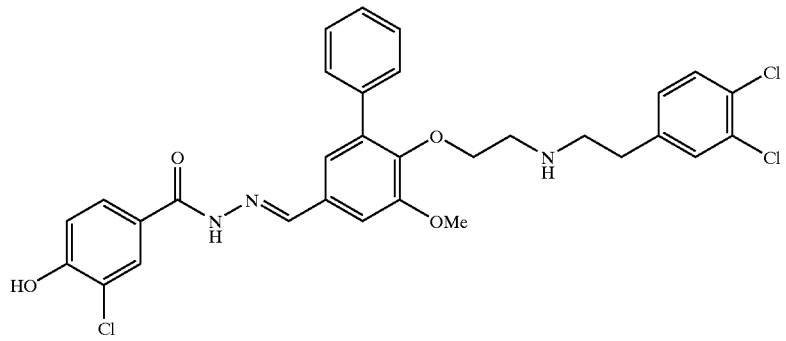

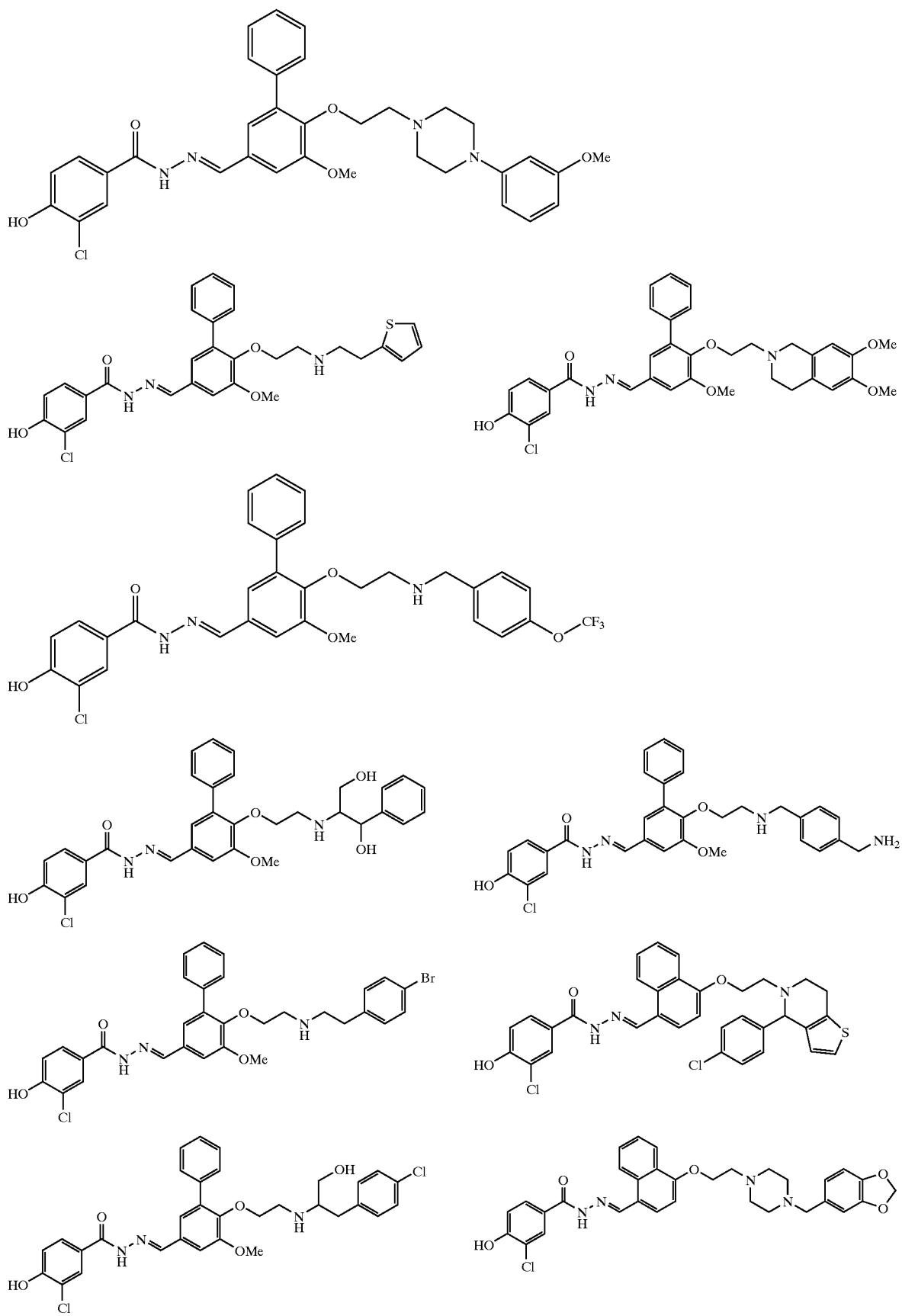

-continued
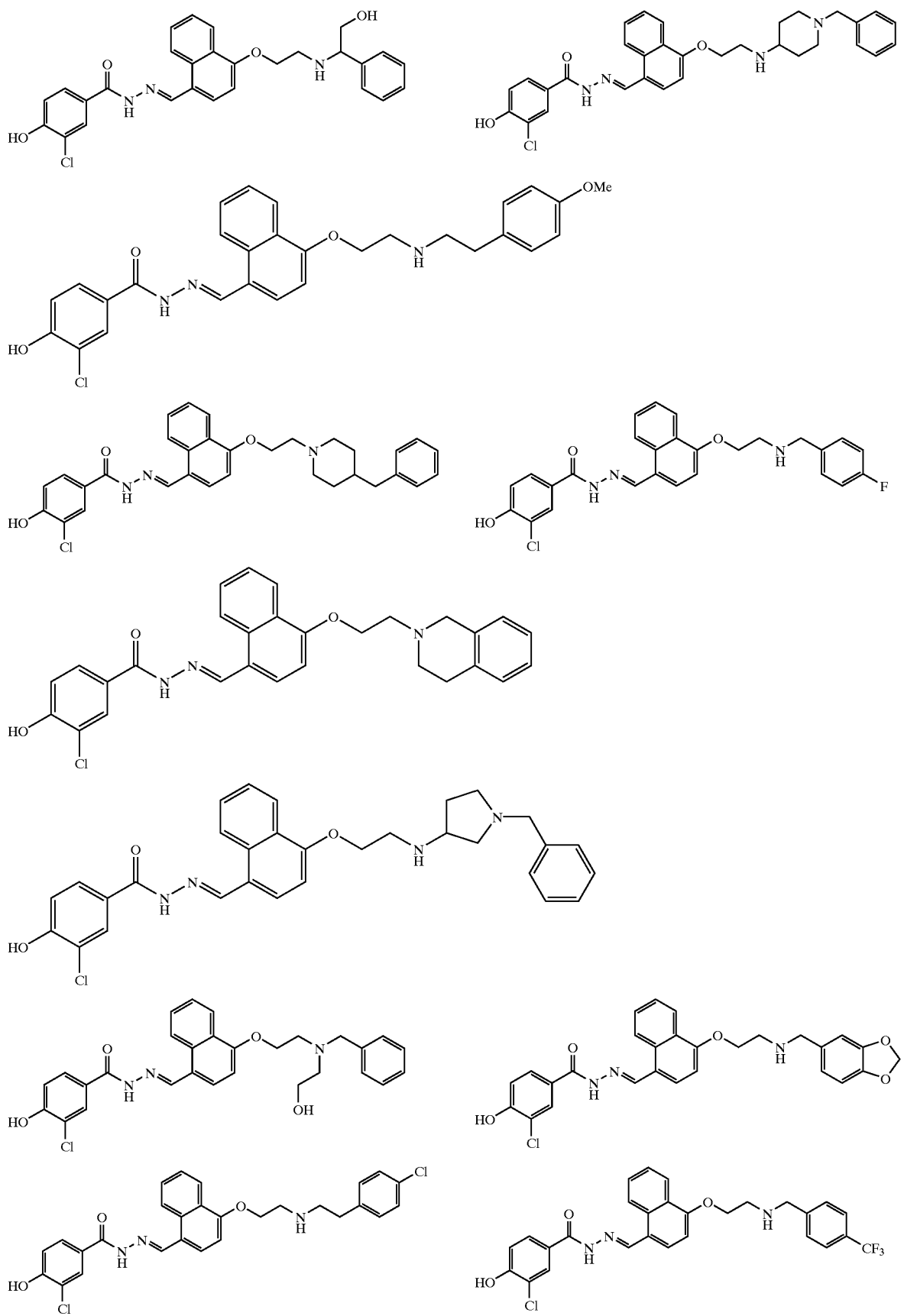

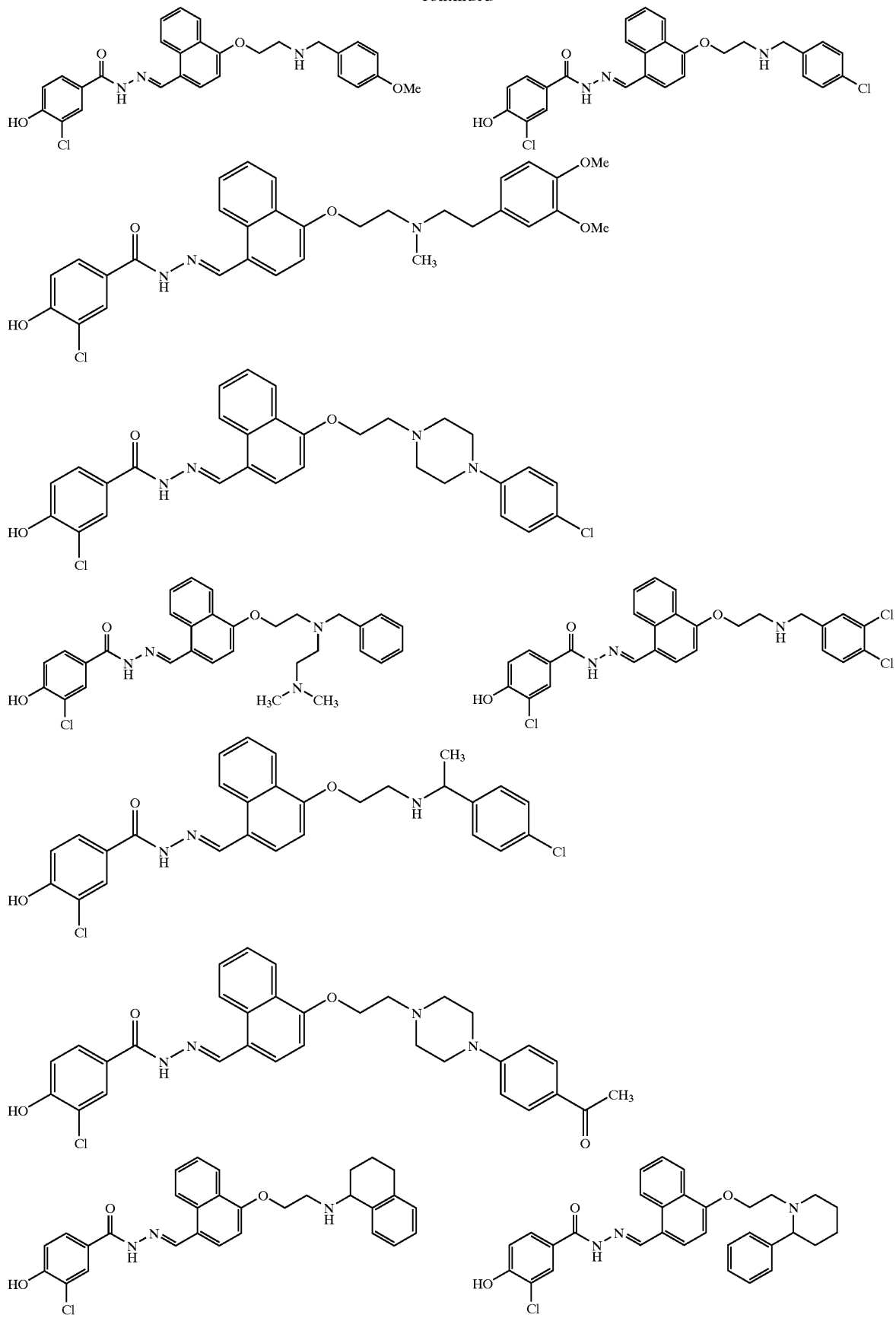

81 82
-continued
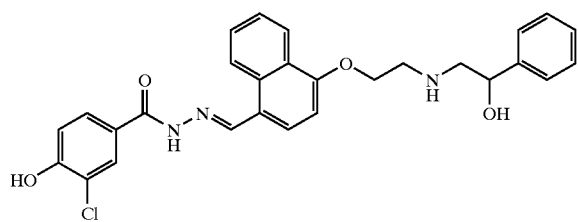
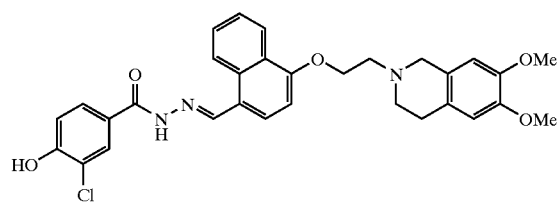
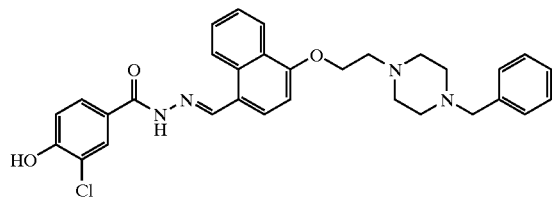
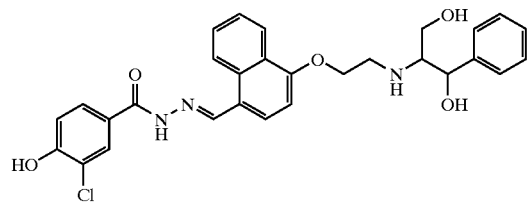
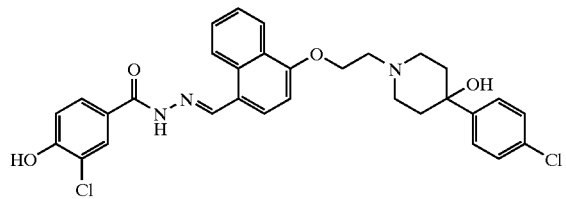
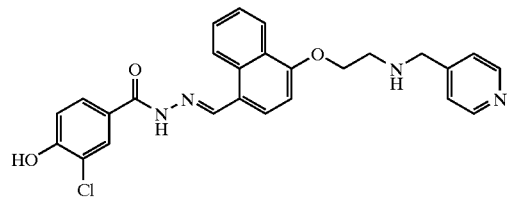
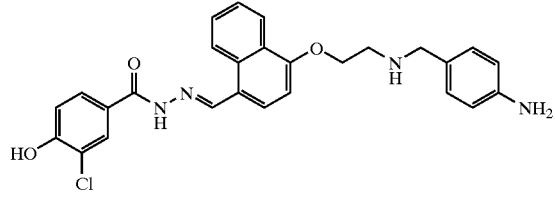
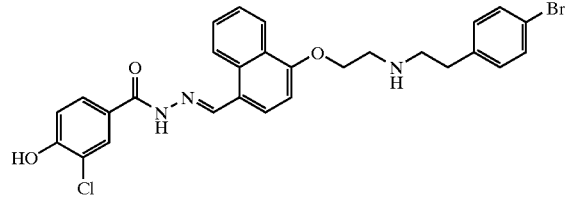
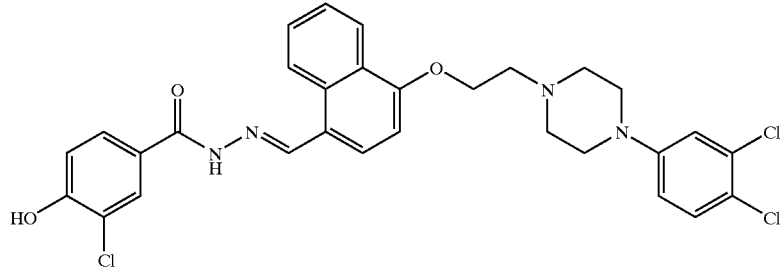
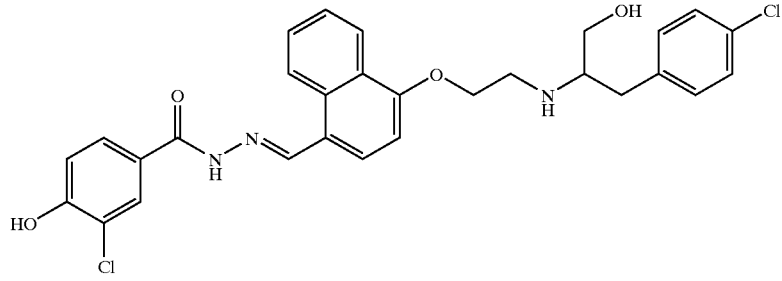
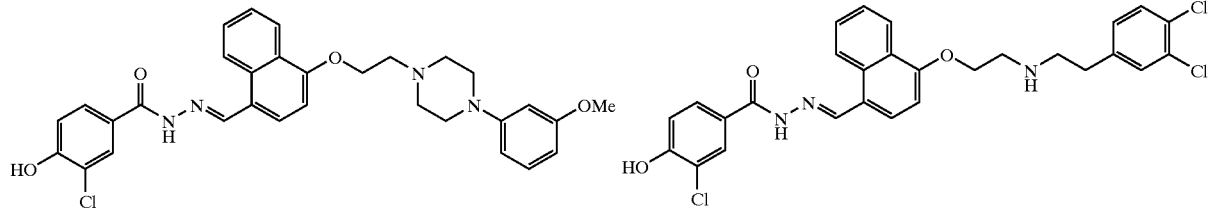
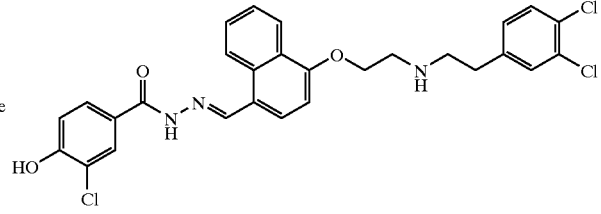

83 -continued 84
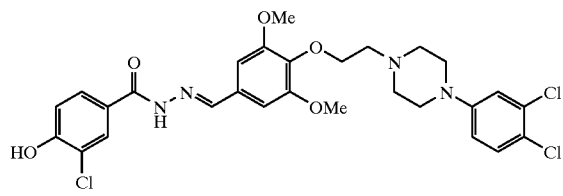
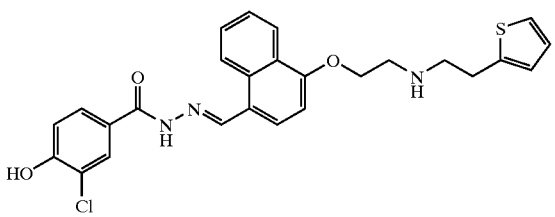
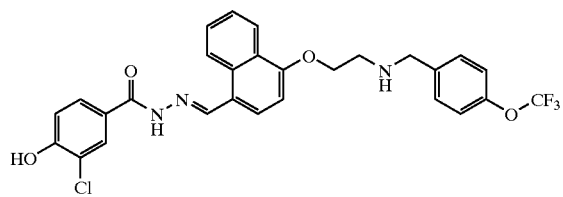
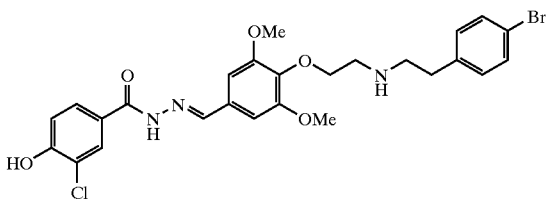
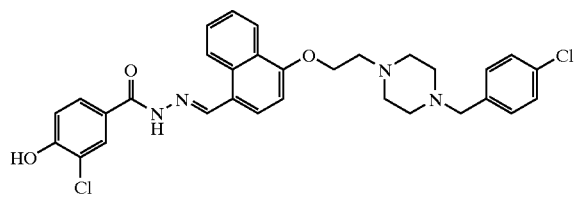
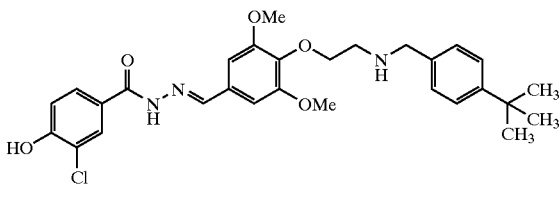
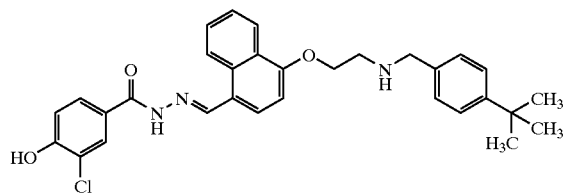
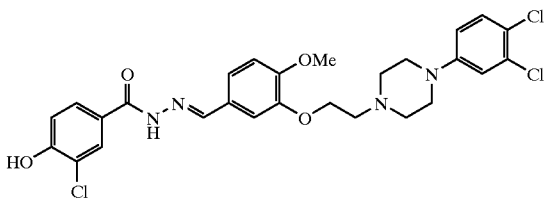
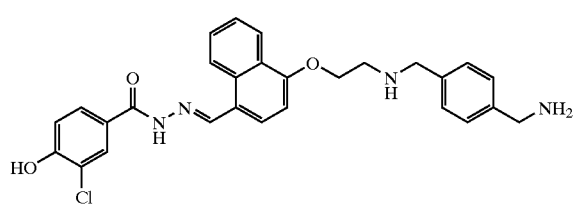
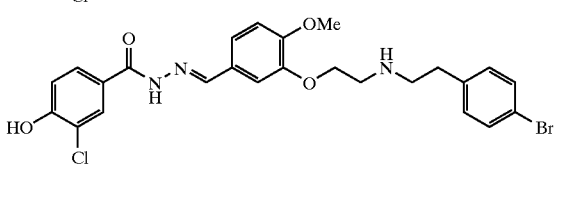
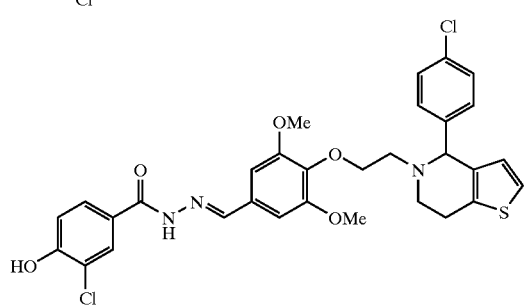
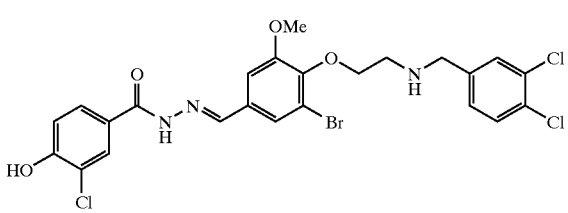
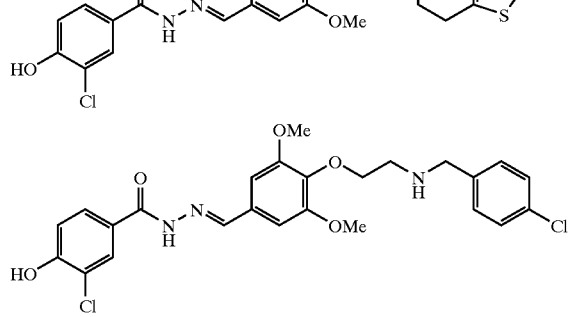
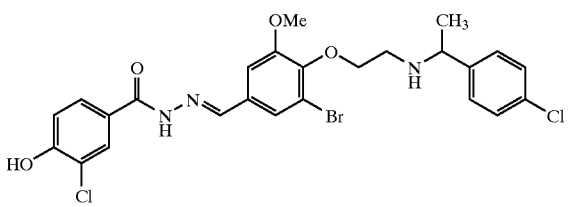
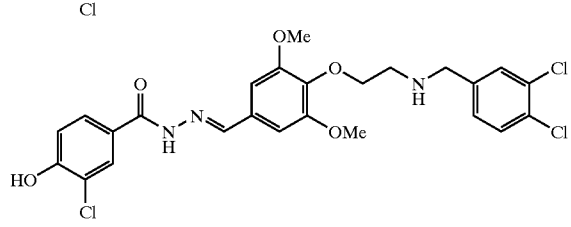
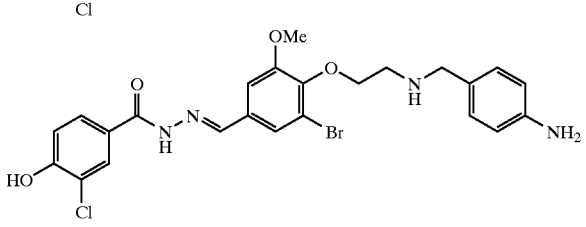

85 86
-continued
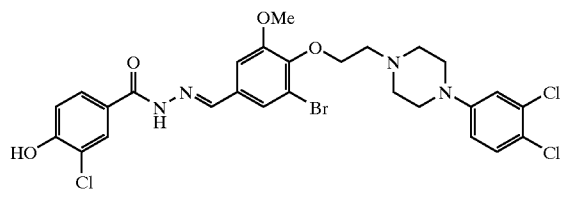
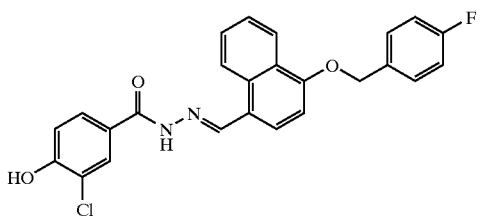
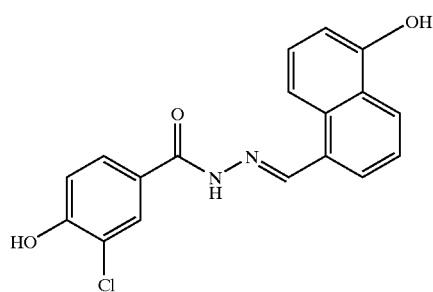
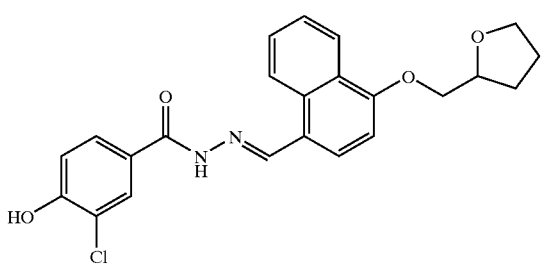
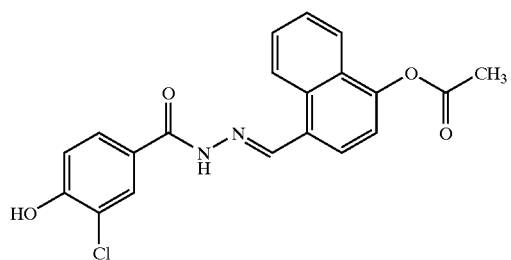
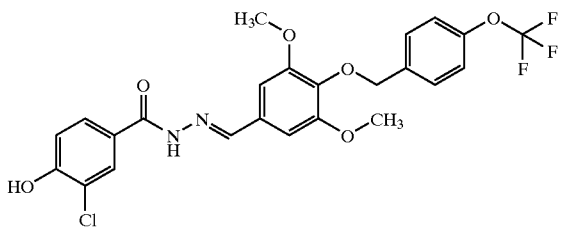
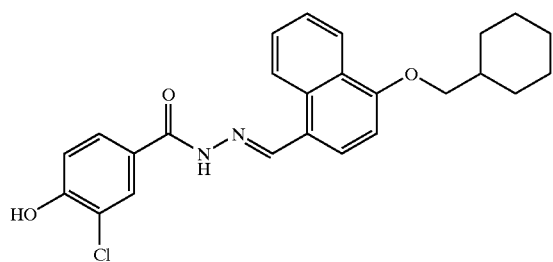
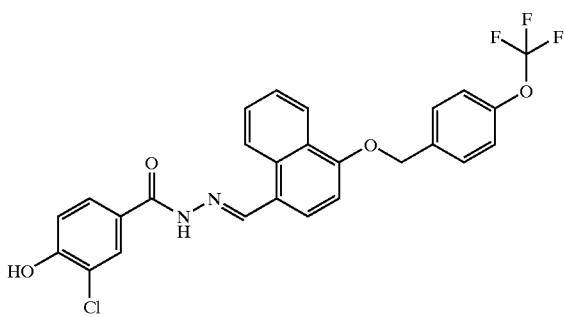
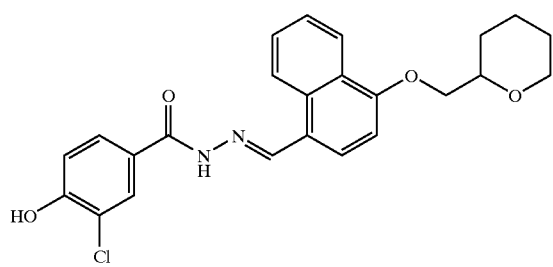
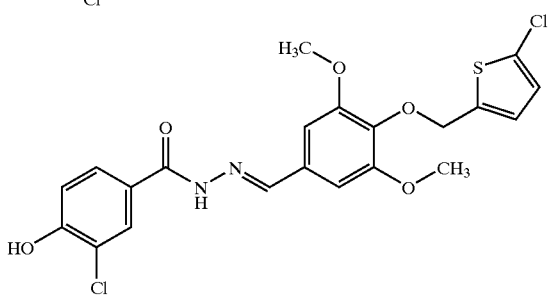
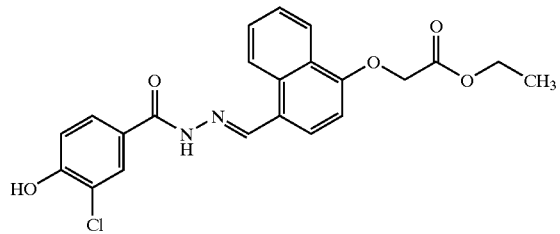
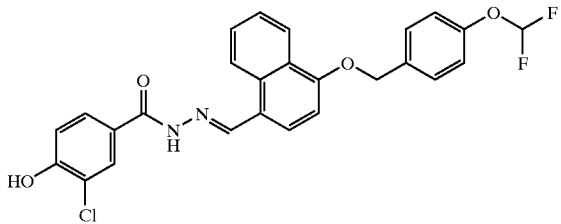

-continued
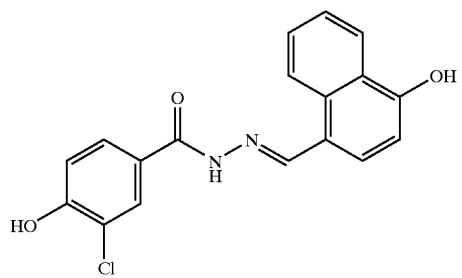
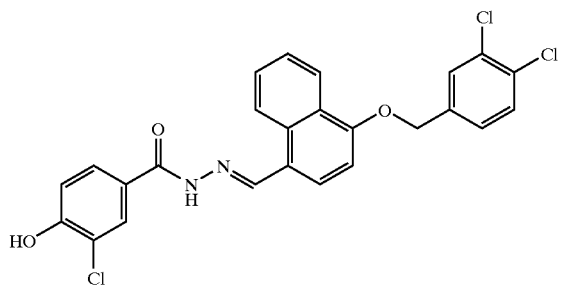
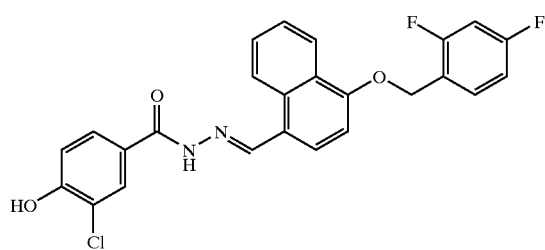
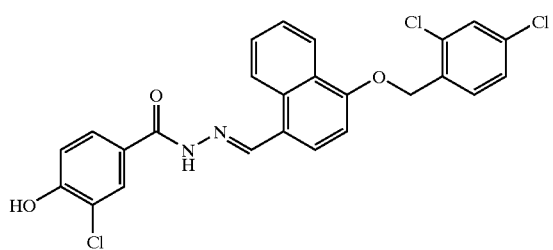
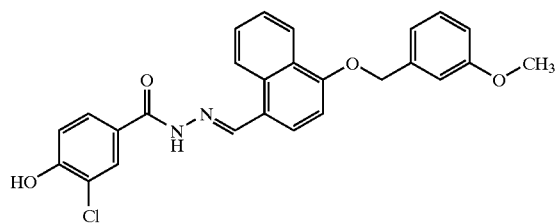
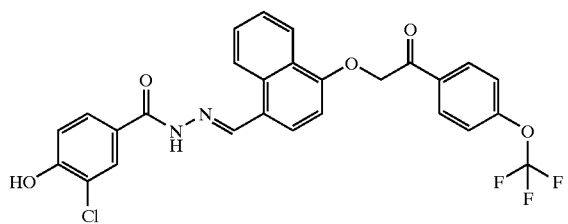
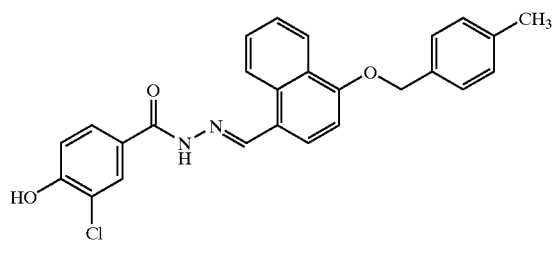
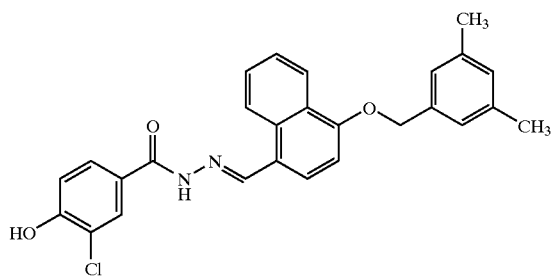
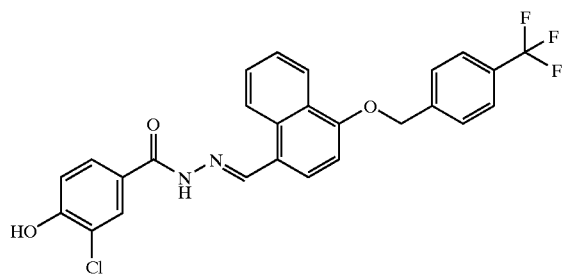
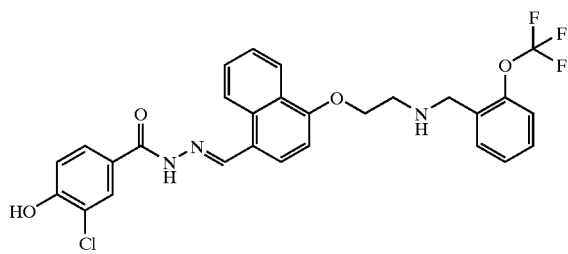
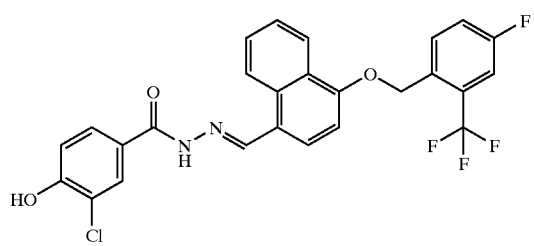
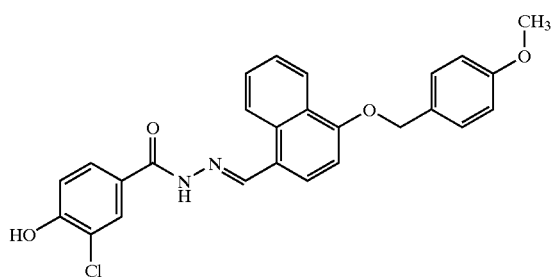

-continued
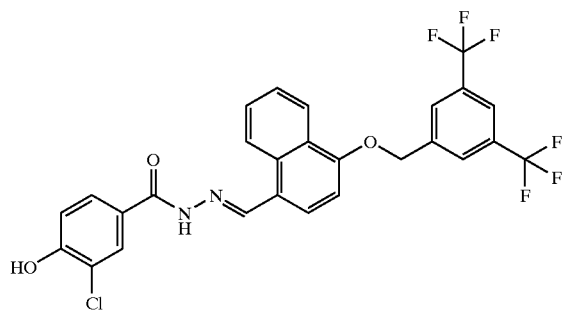
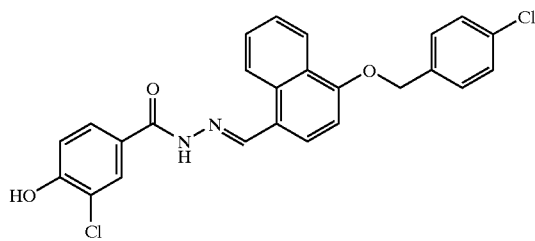
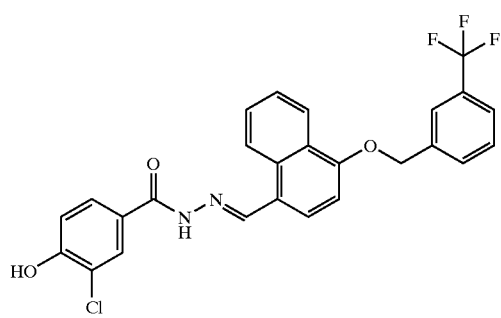
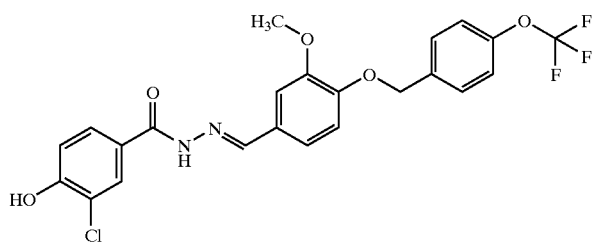
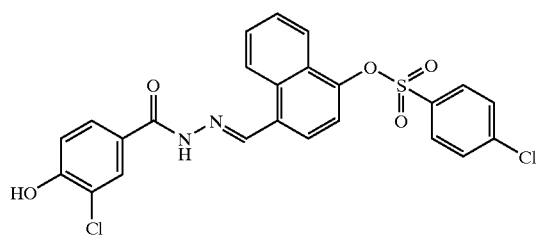
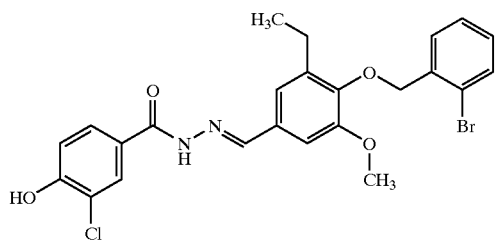
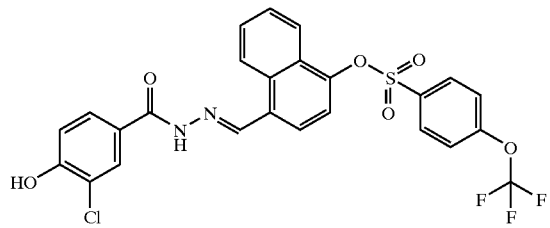
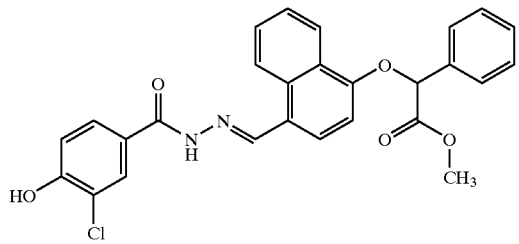
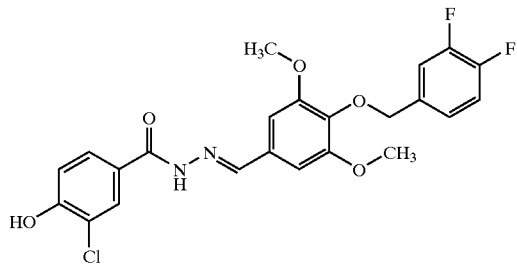
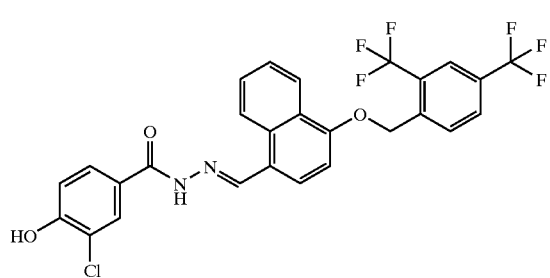
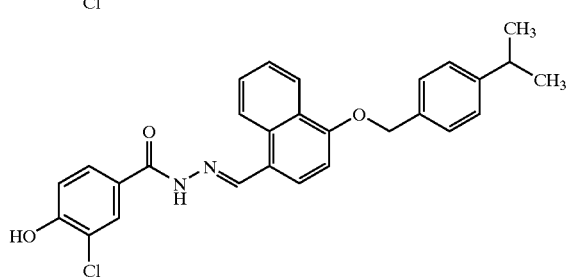

91
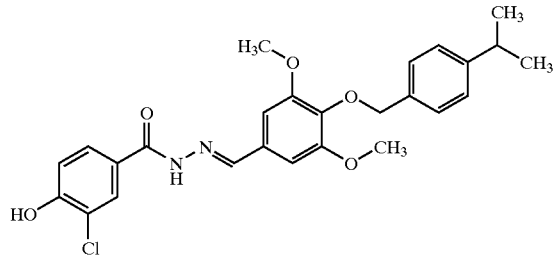
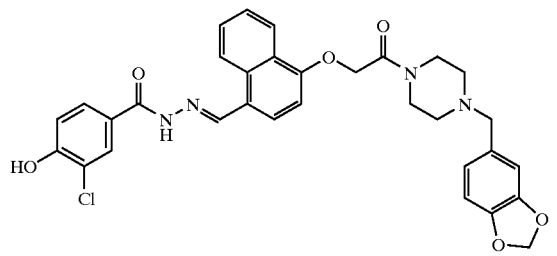
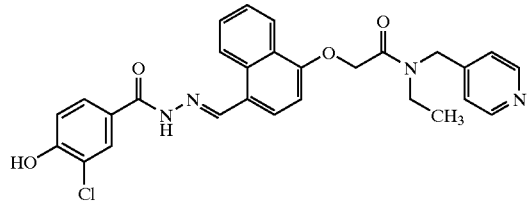
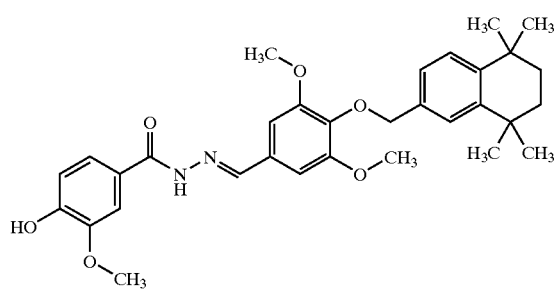
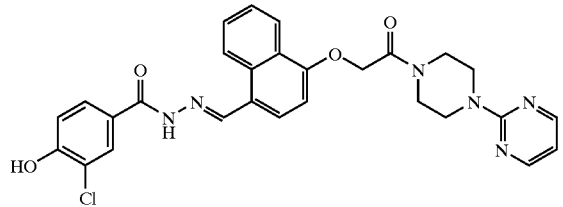
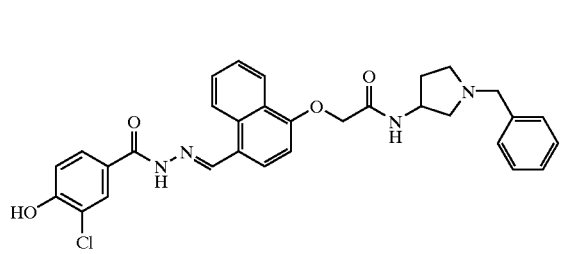
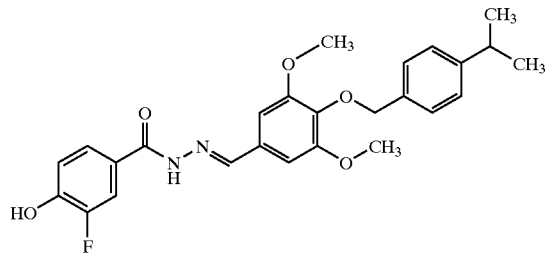
92
-continued
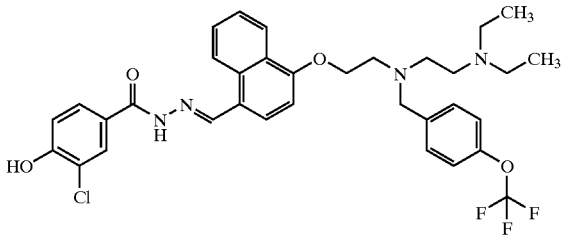
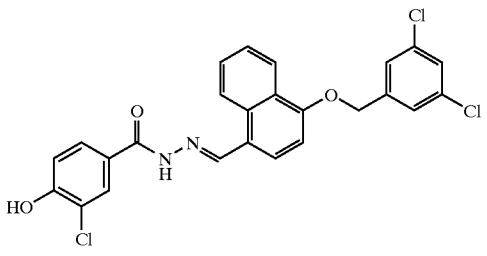
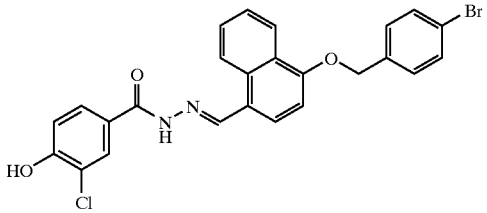
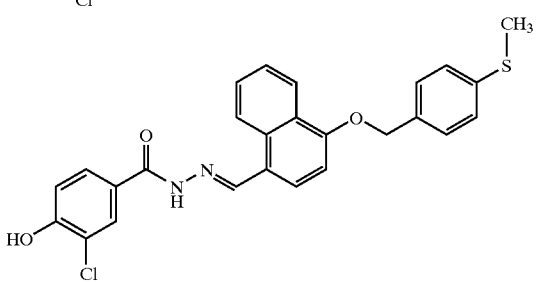
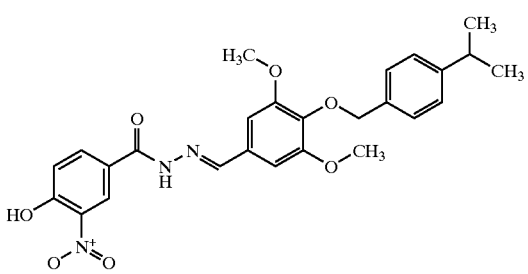
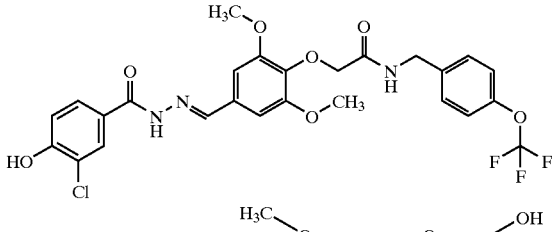
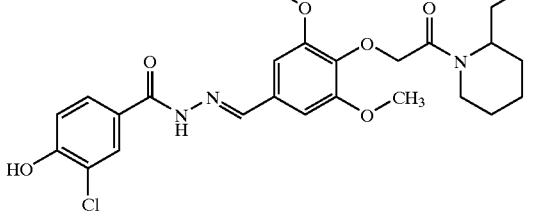

-continued
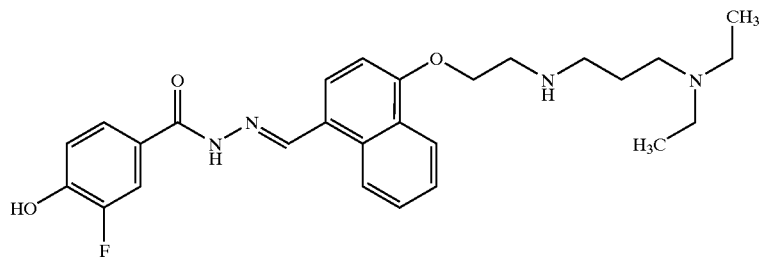
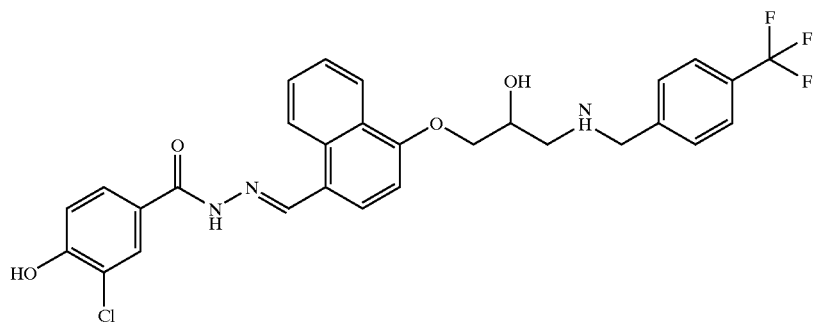
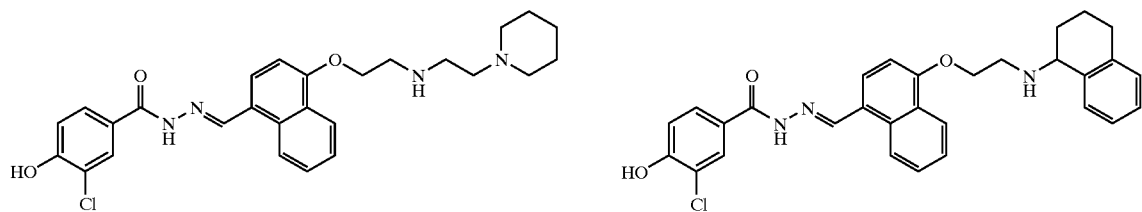
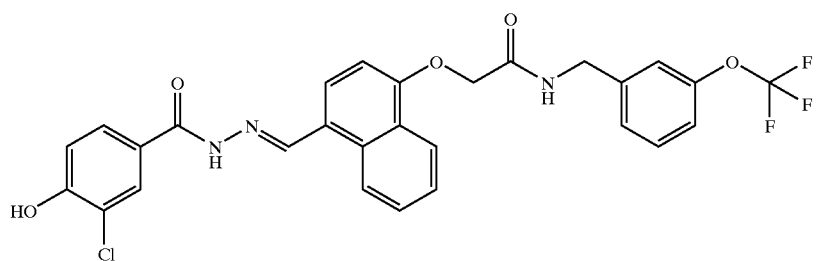
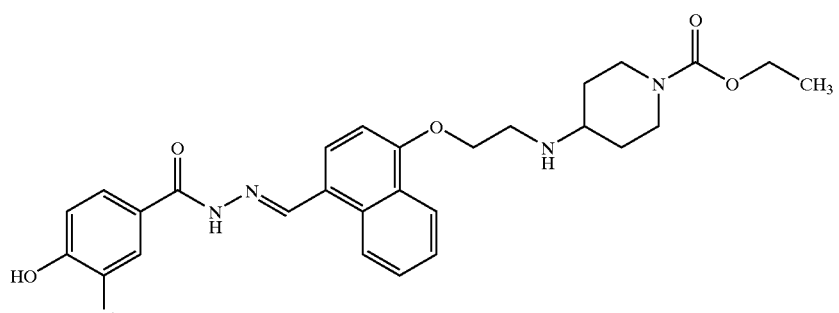
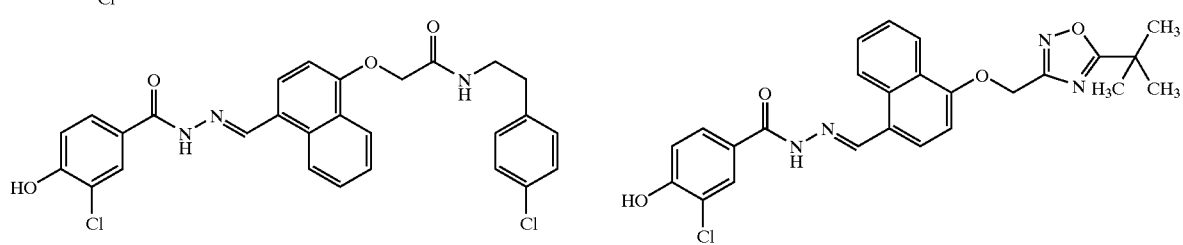

-continued
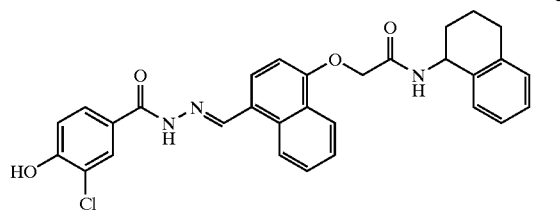
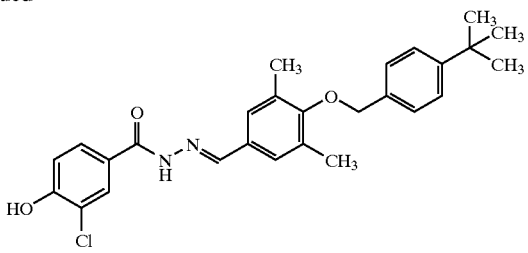
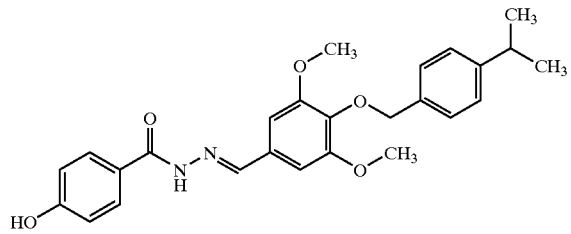
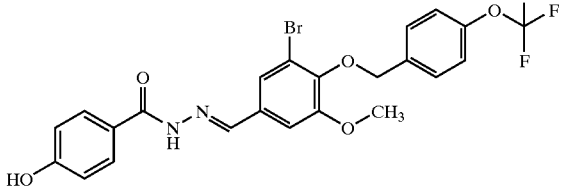
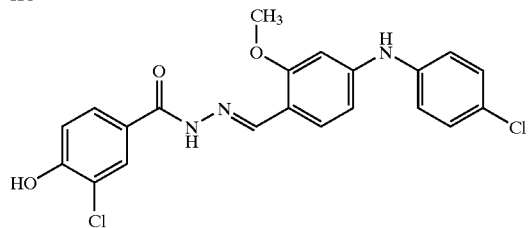
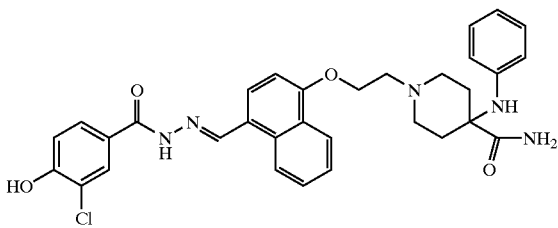
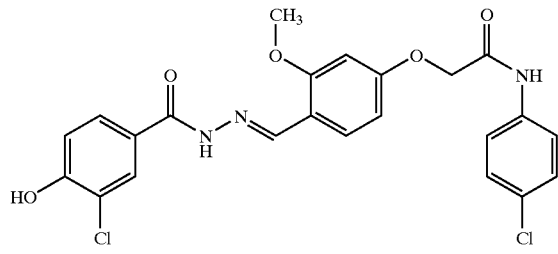
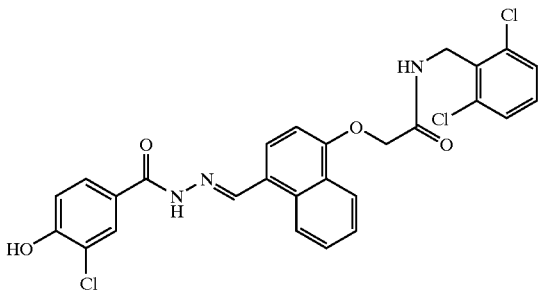
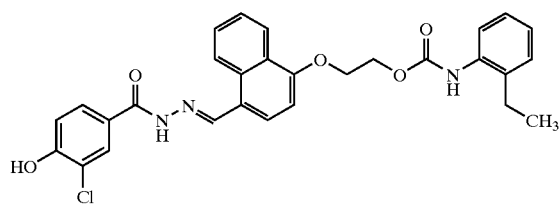
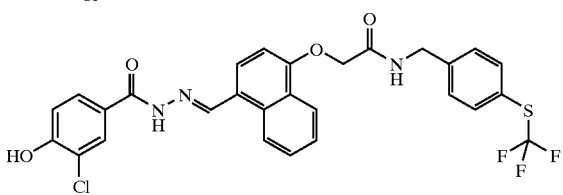
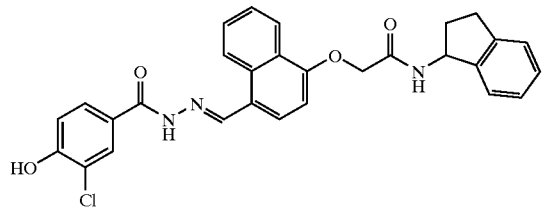
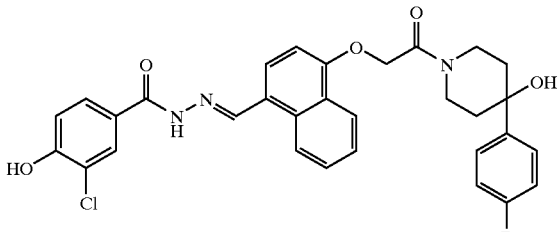
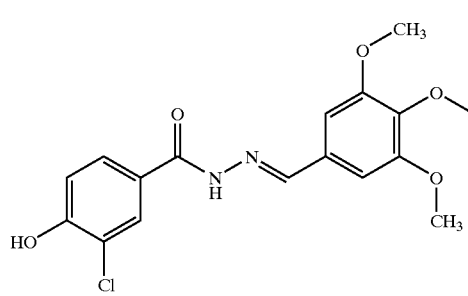

-continued
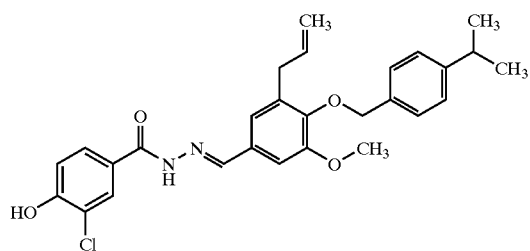
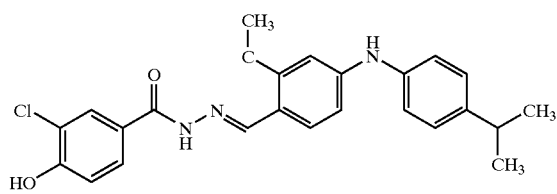
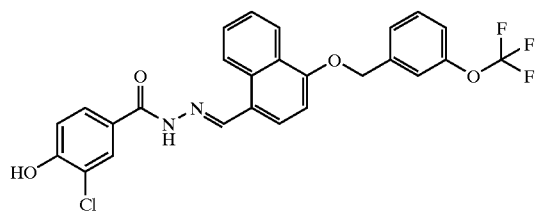
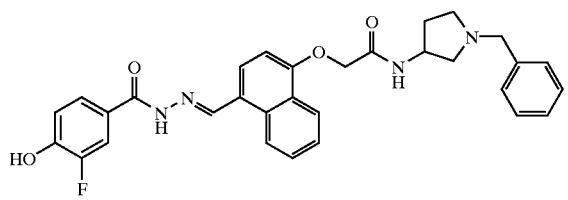
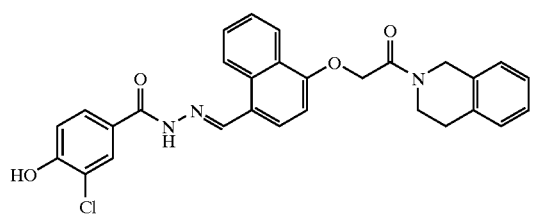
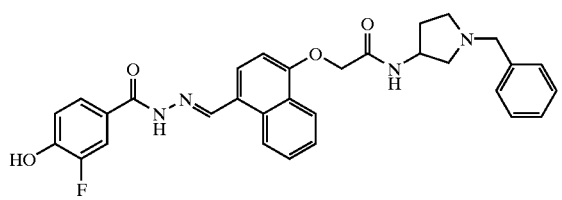
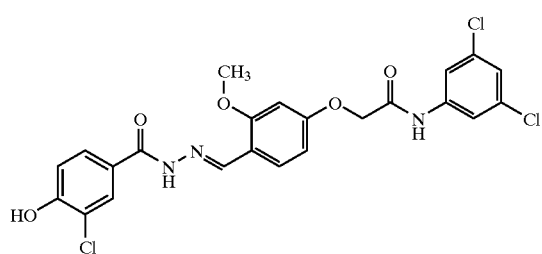
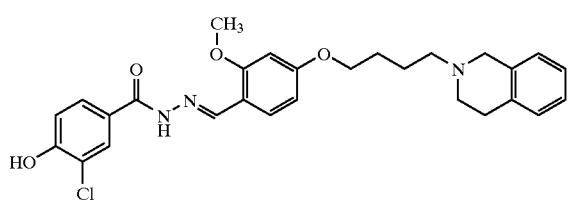
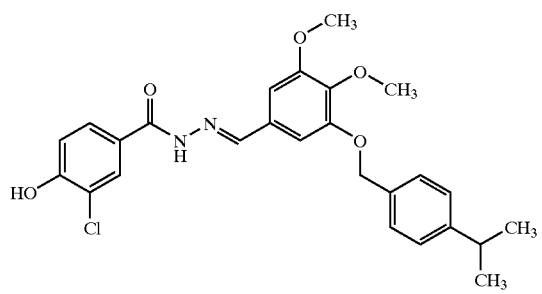
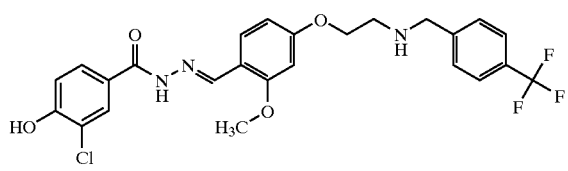
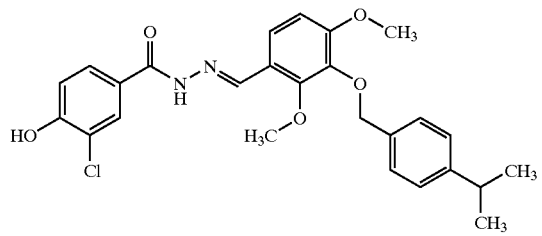
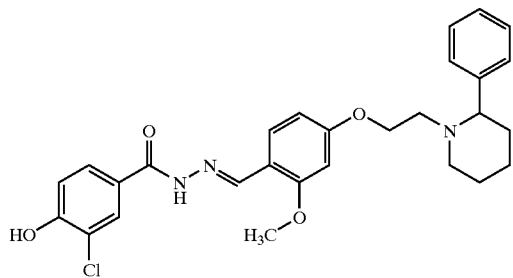

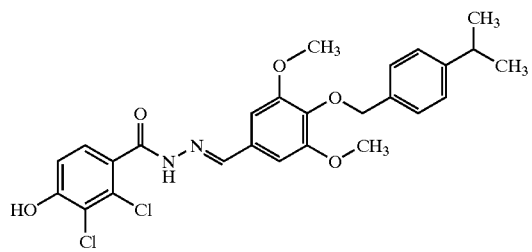

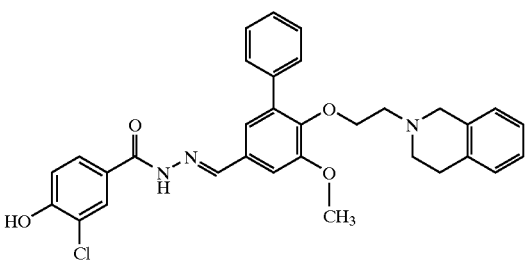

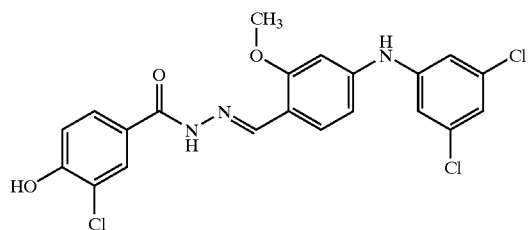

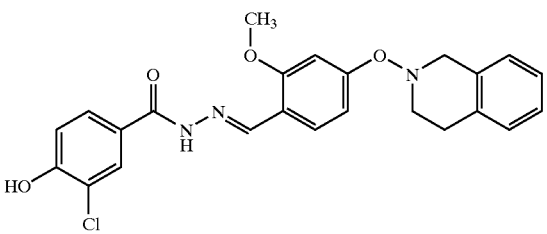

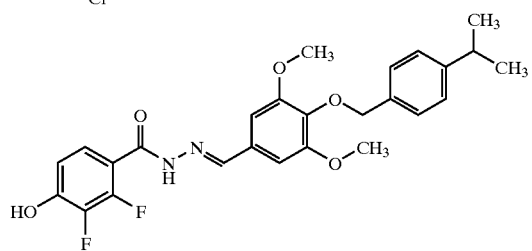

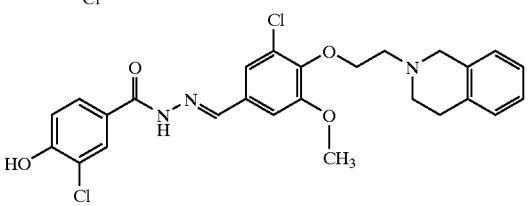

The most preferred specific compounds of formula I wherein A is a heterocyclic and/or bicyclic moiety are the following:

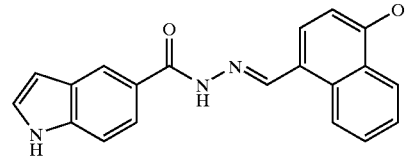

Indole-5-carboxylic acid [4-(4-trifluoromethylbenzyloxy)-1-naphthylmethylene]hydrazide

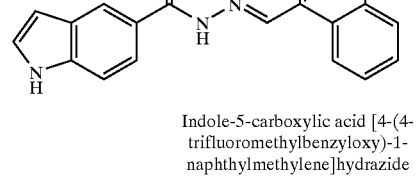

Indazole-5-carboxylic acid [4-(4-trifluoromethylbenzyloxy)-1-naphthylmethylene]hydrazide -continued

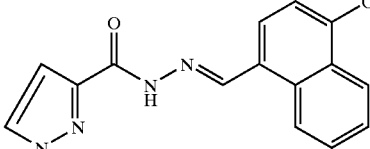

Pyrazole-3-carboxylic acid [4-(4-trifluoromethylbenzyloxy)-1-naphthylmethylene]hydrazide

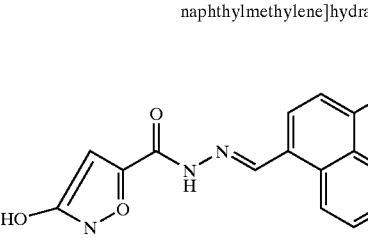

3-Hydroxyisoxazole-5-carboxylic acid [4-(4-trifluoromethylbenzyloxy)-1-naphthylmethylene]hydrazide

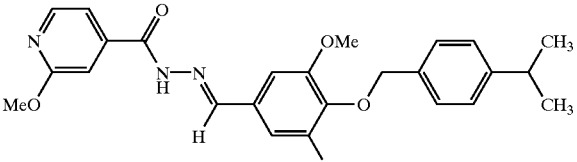

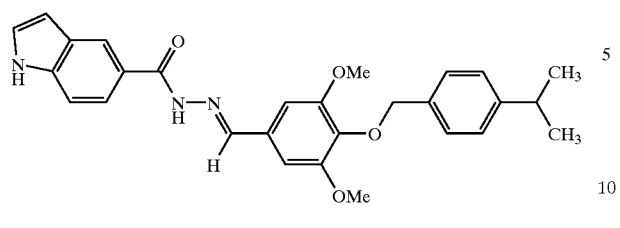
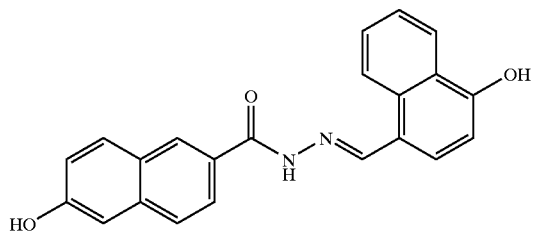
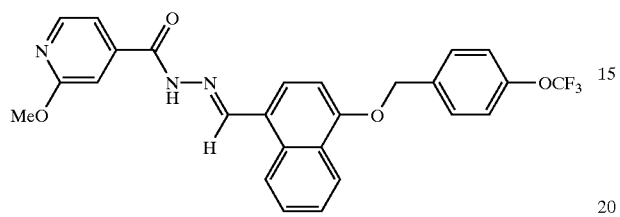
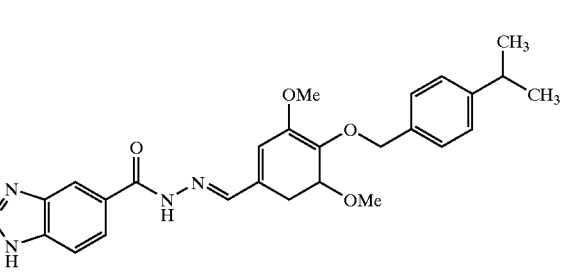

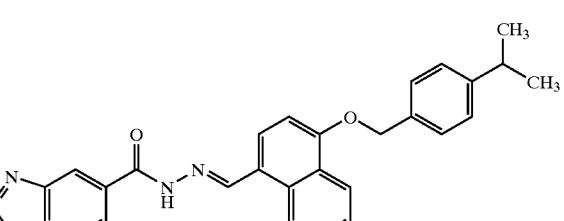
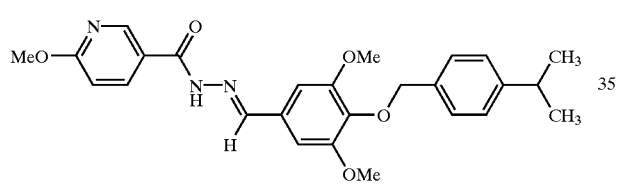
Especially preferred according to the present invention are the following compounds which show a particularly high affinity to the human glucagon receptor:
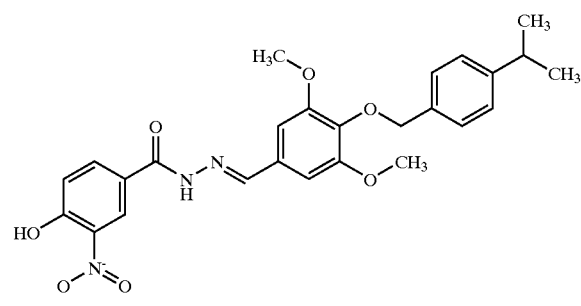
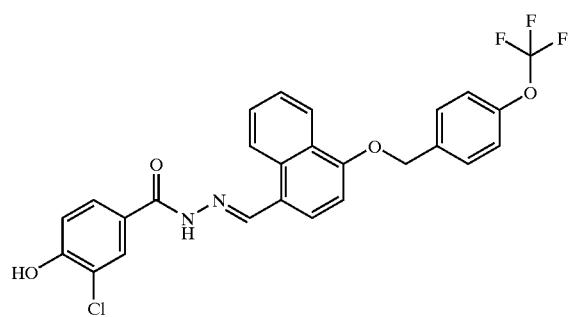
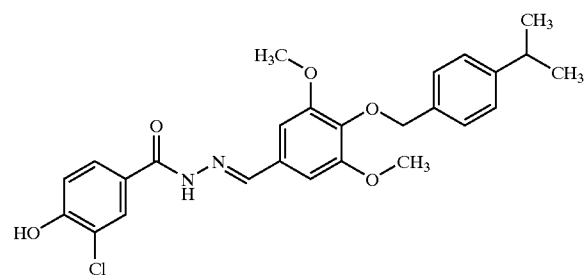
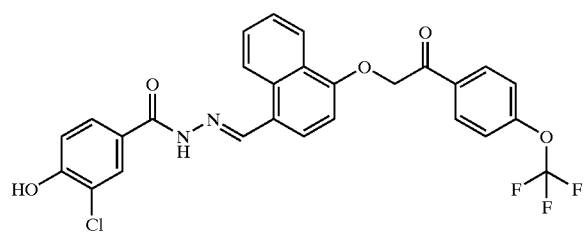

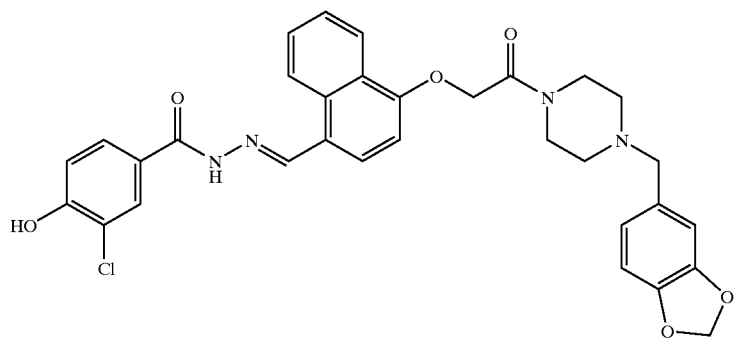
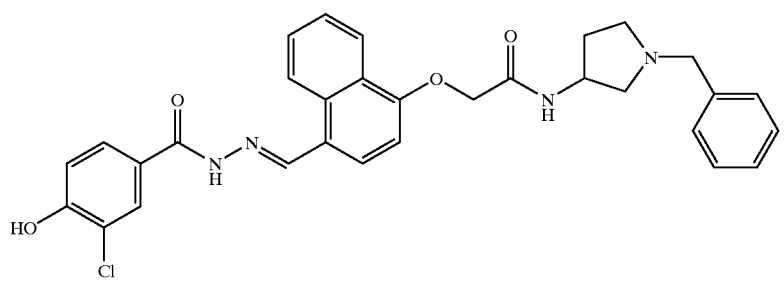
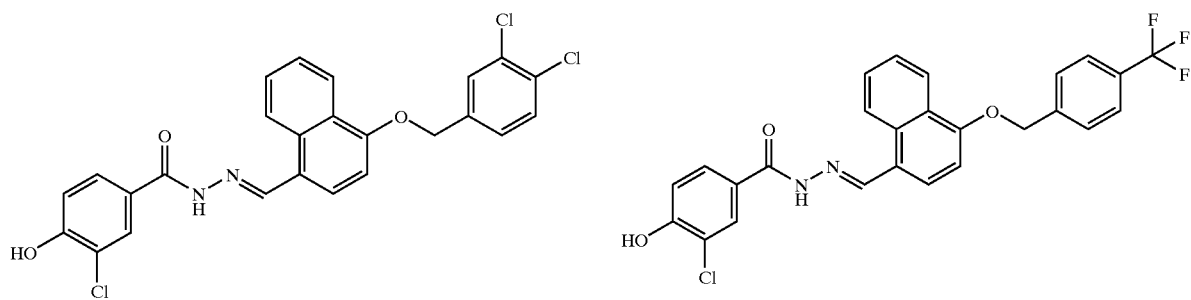
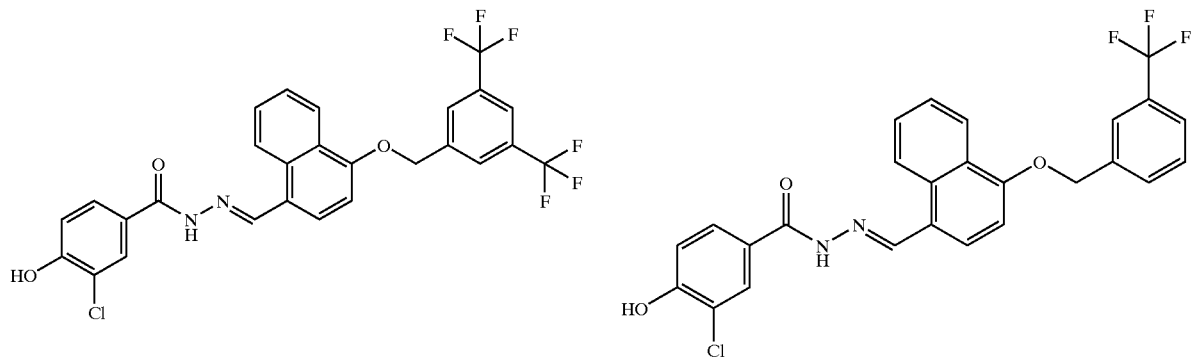
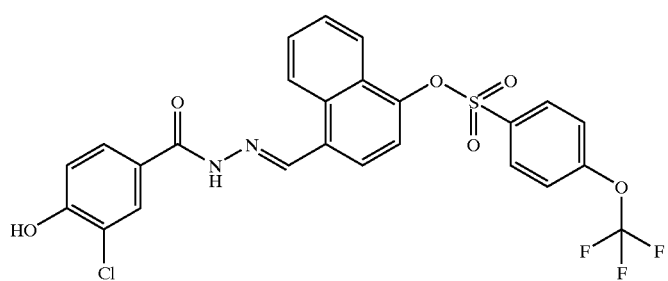

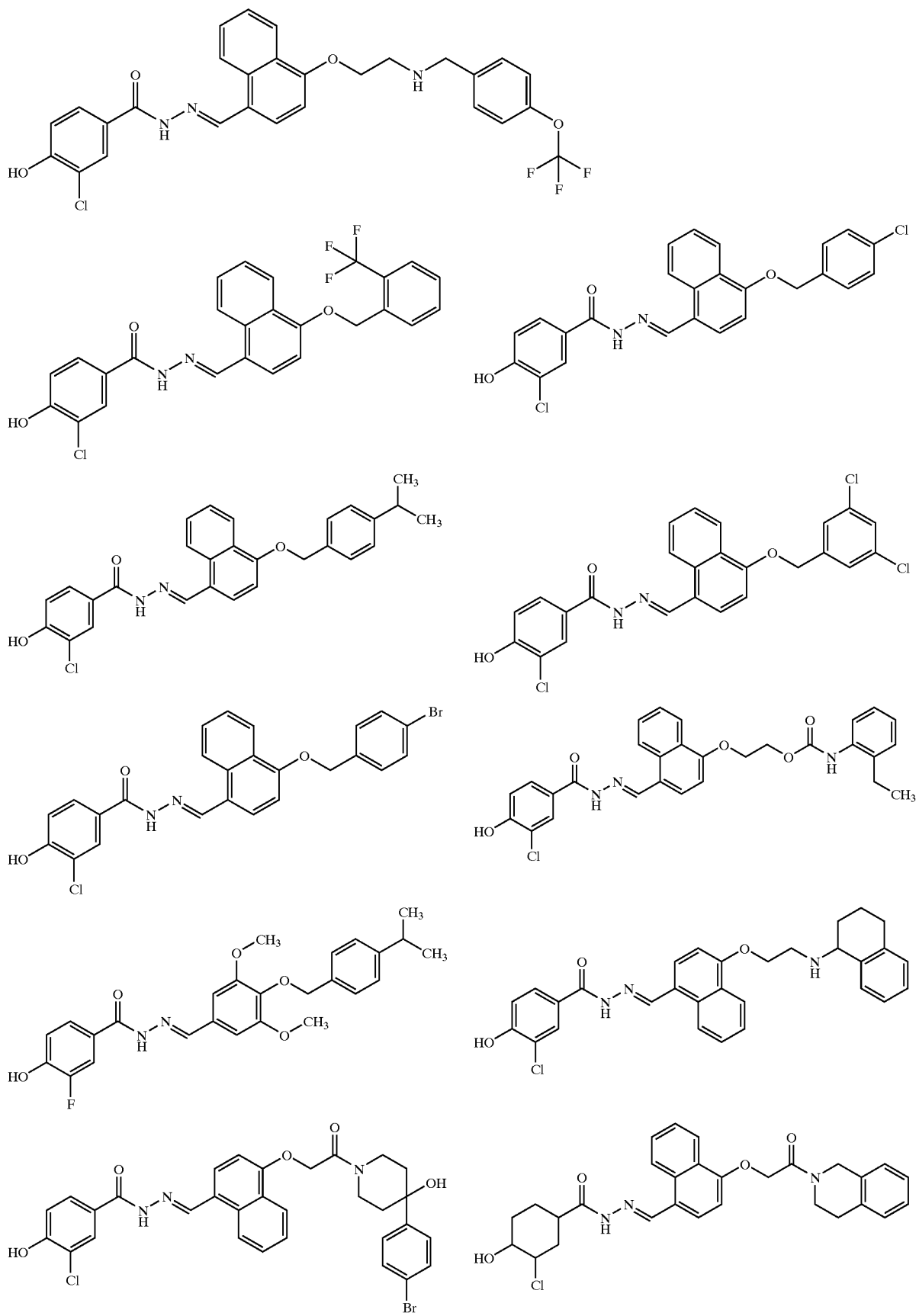

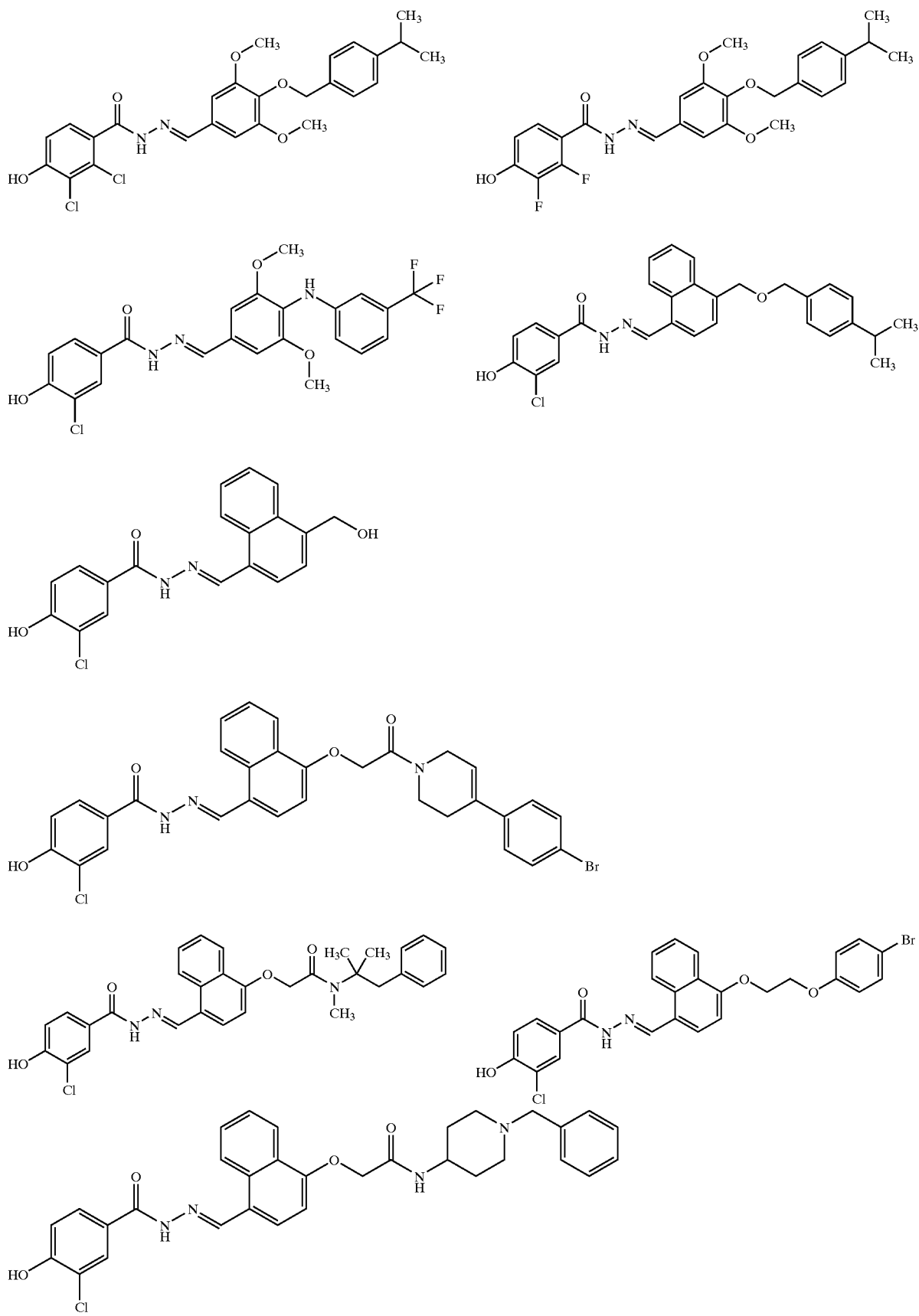

109                                                             110
-continued
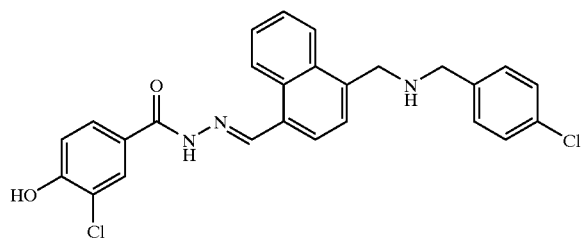
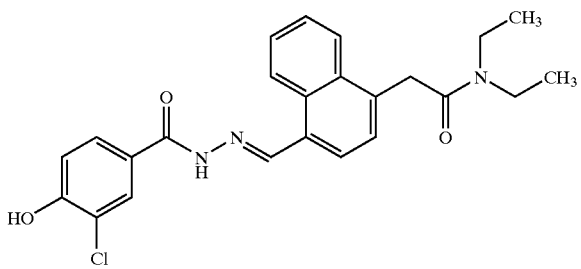
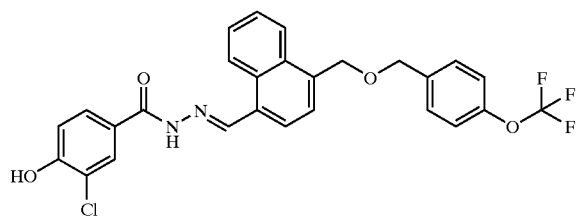
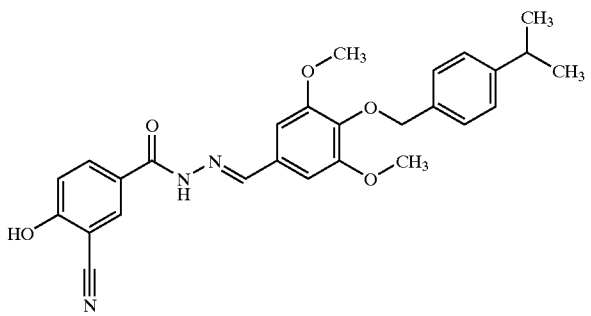
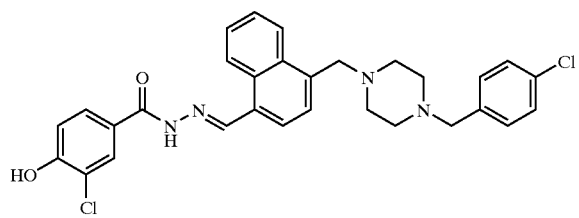
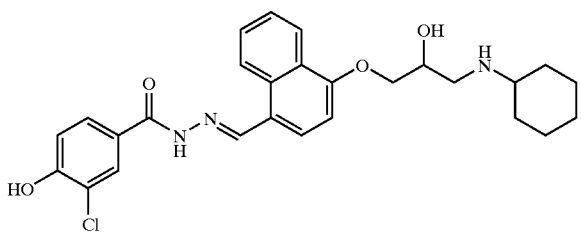
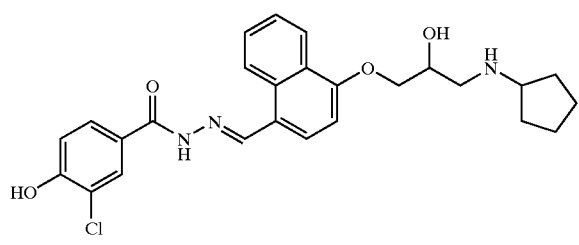
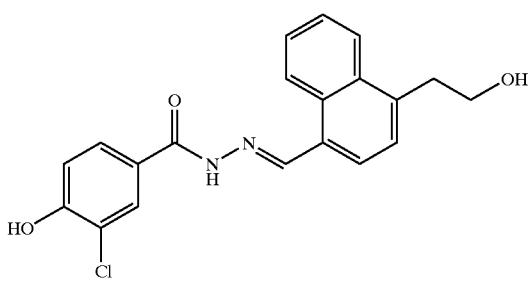
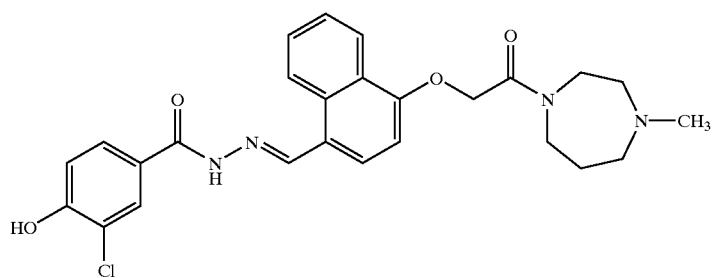
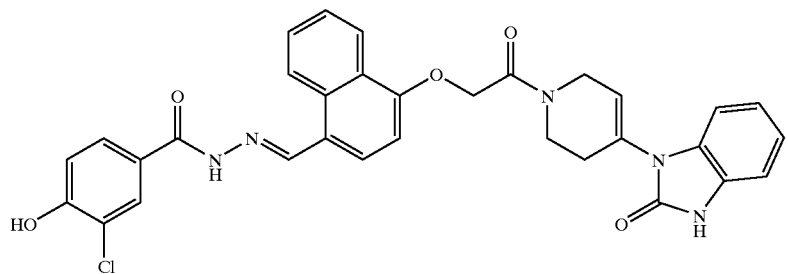

-continued
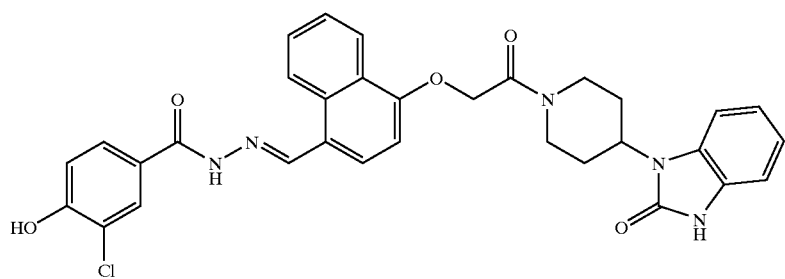
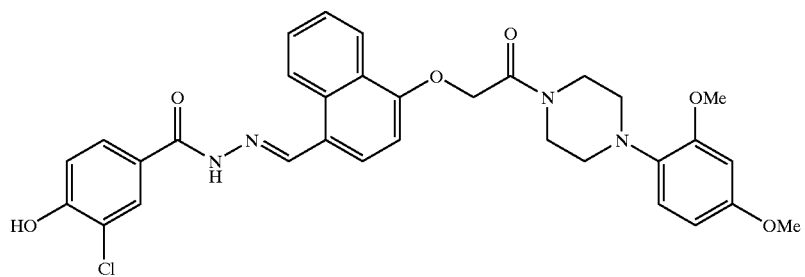
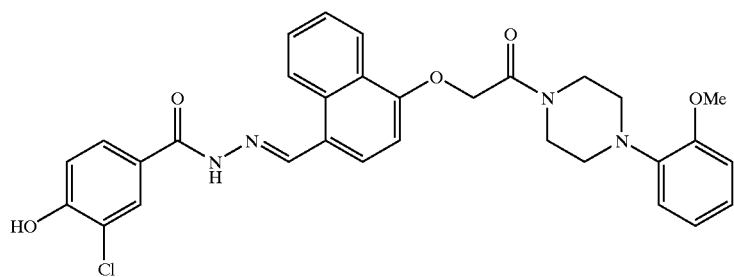
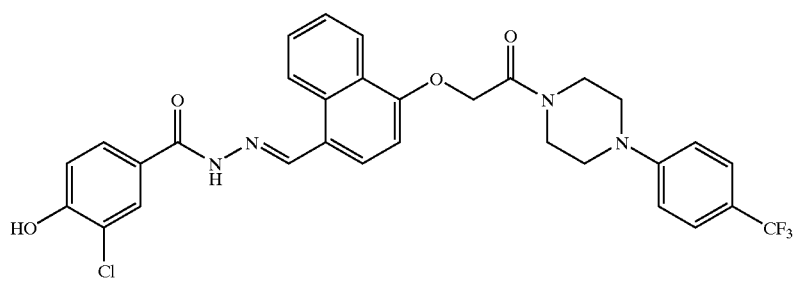
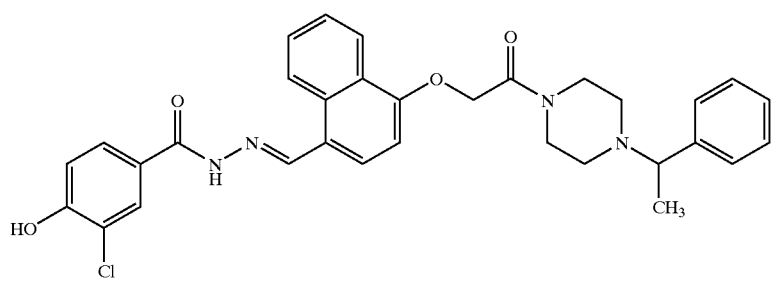
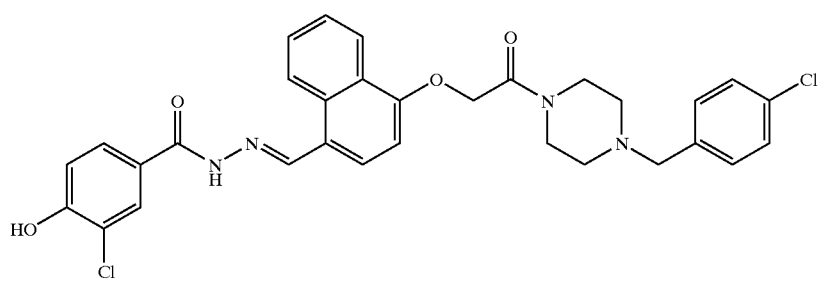

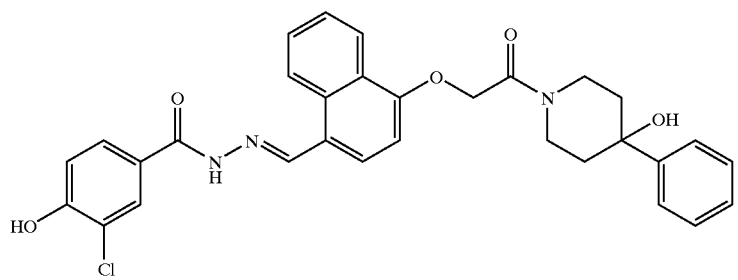
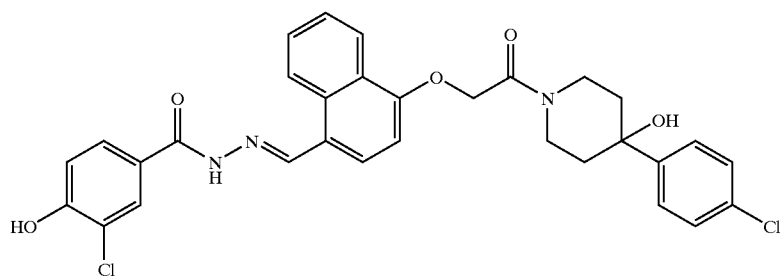
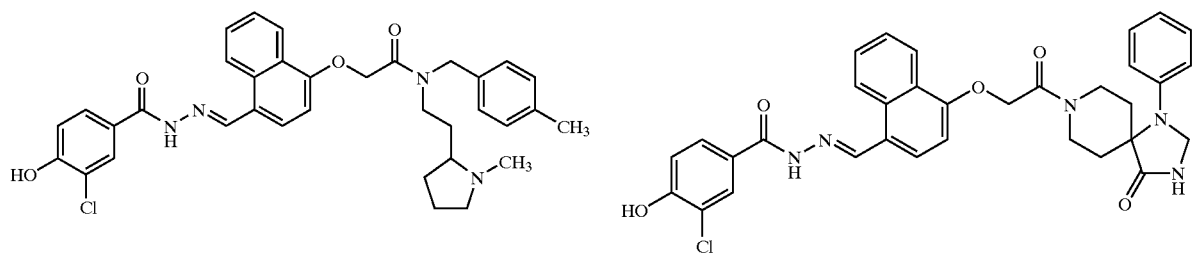
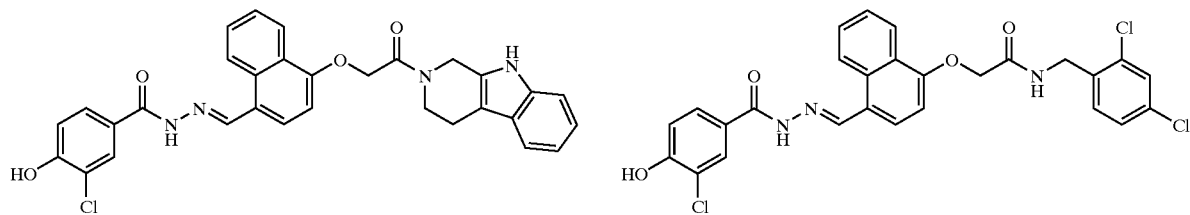
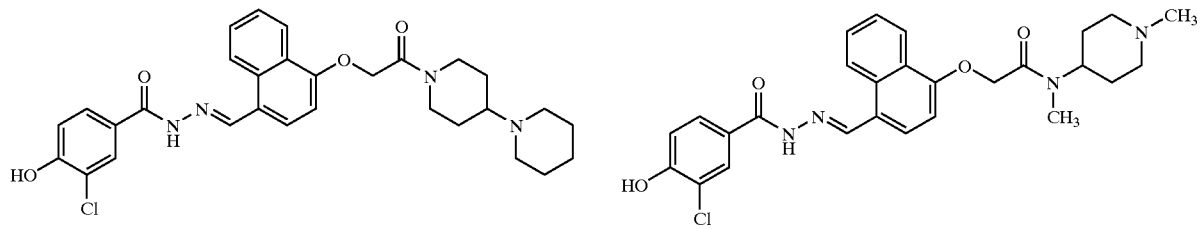
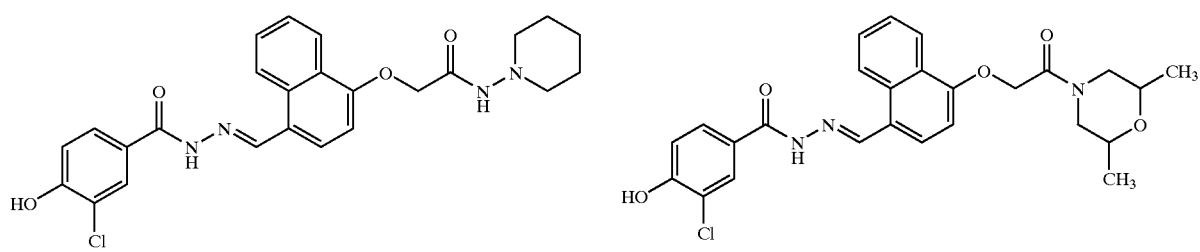

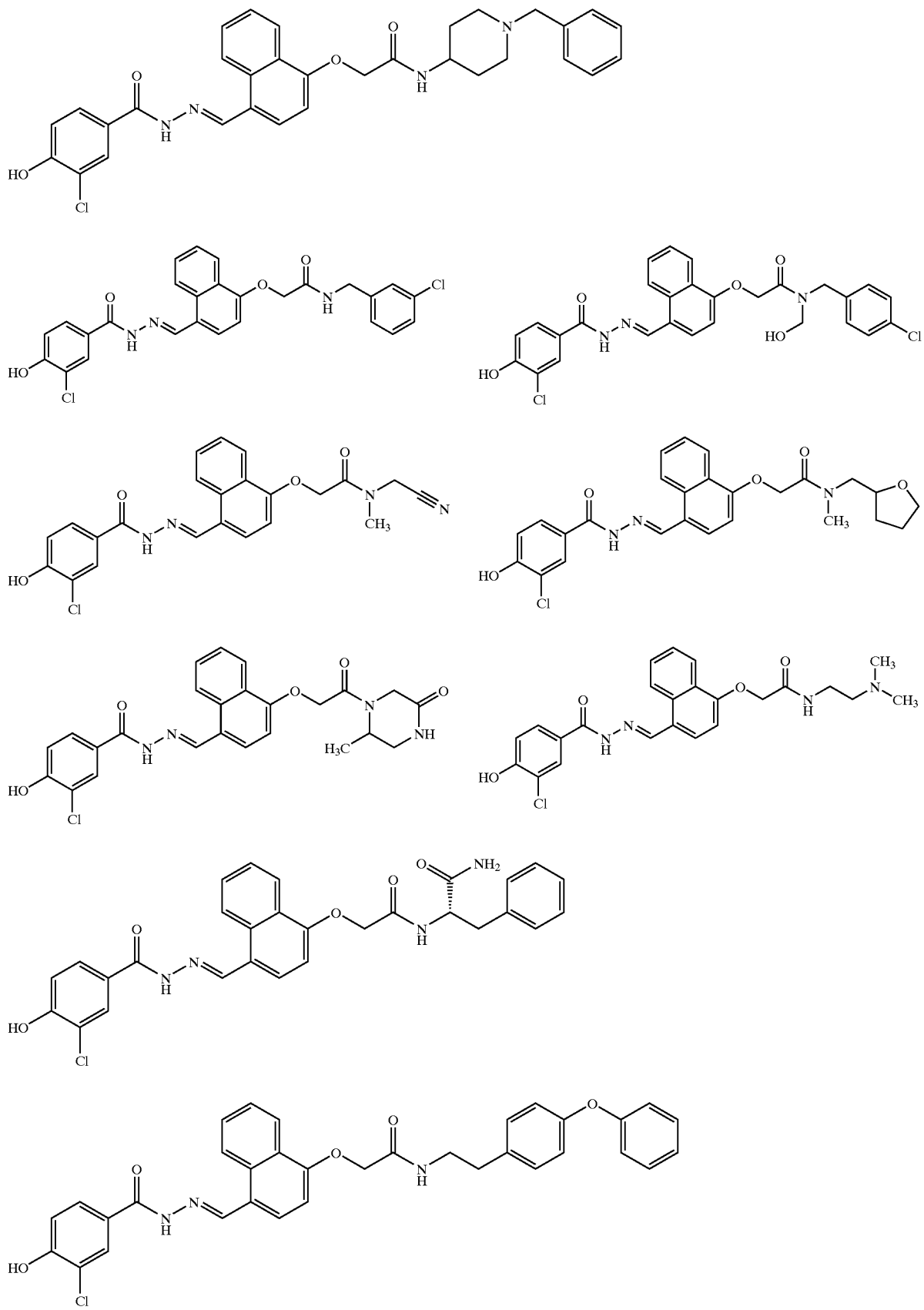

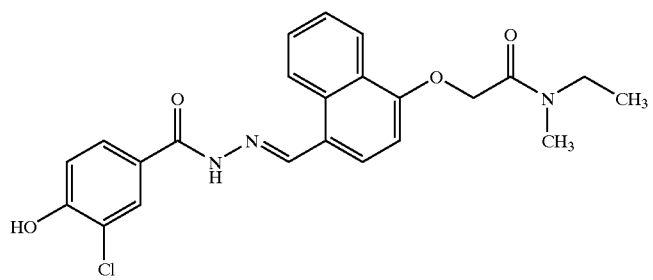
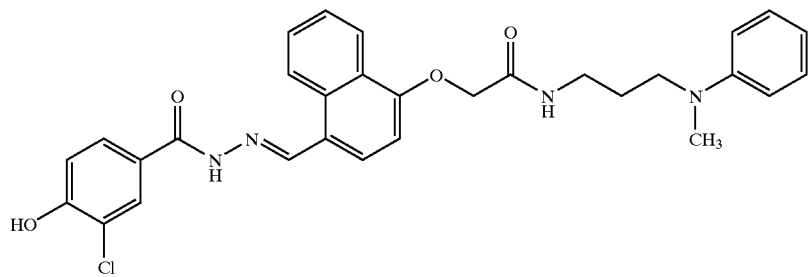
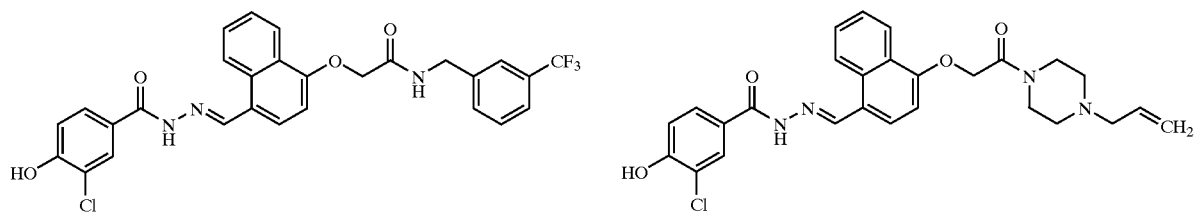
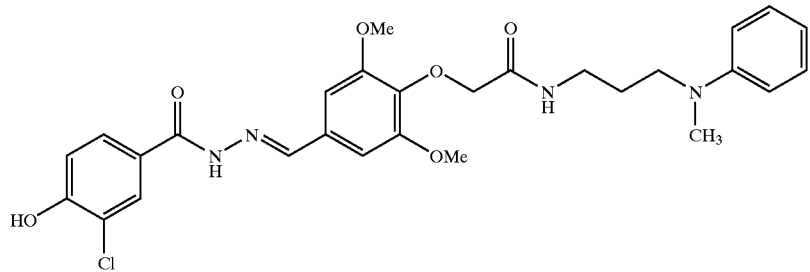
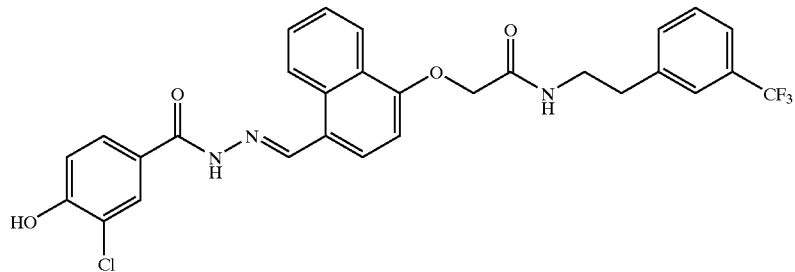
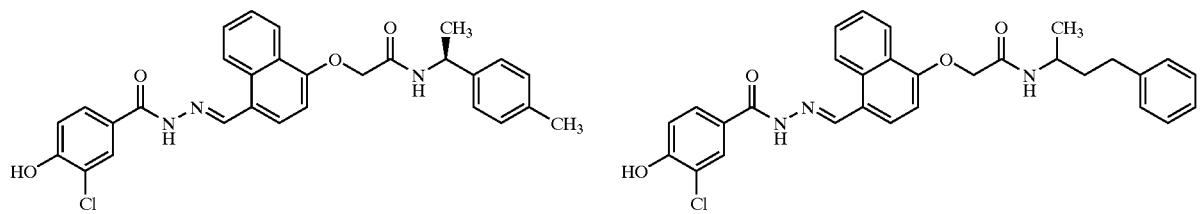

119 120
-continued
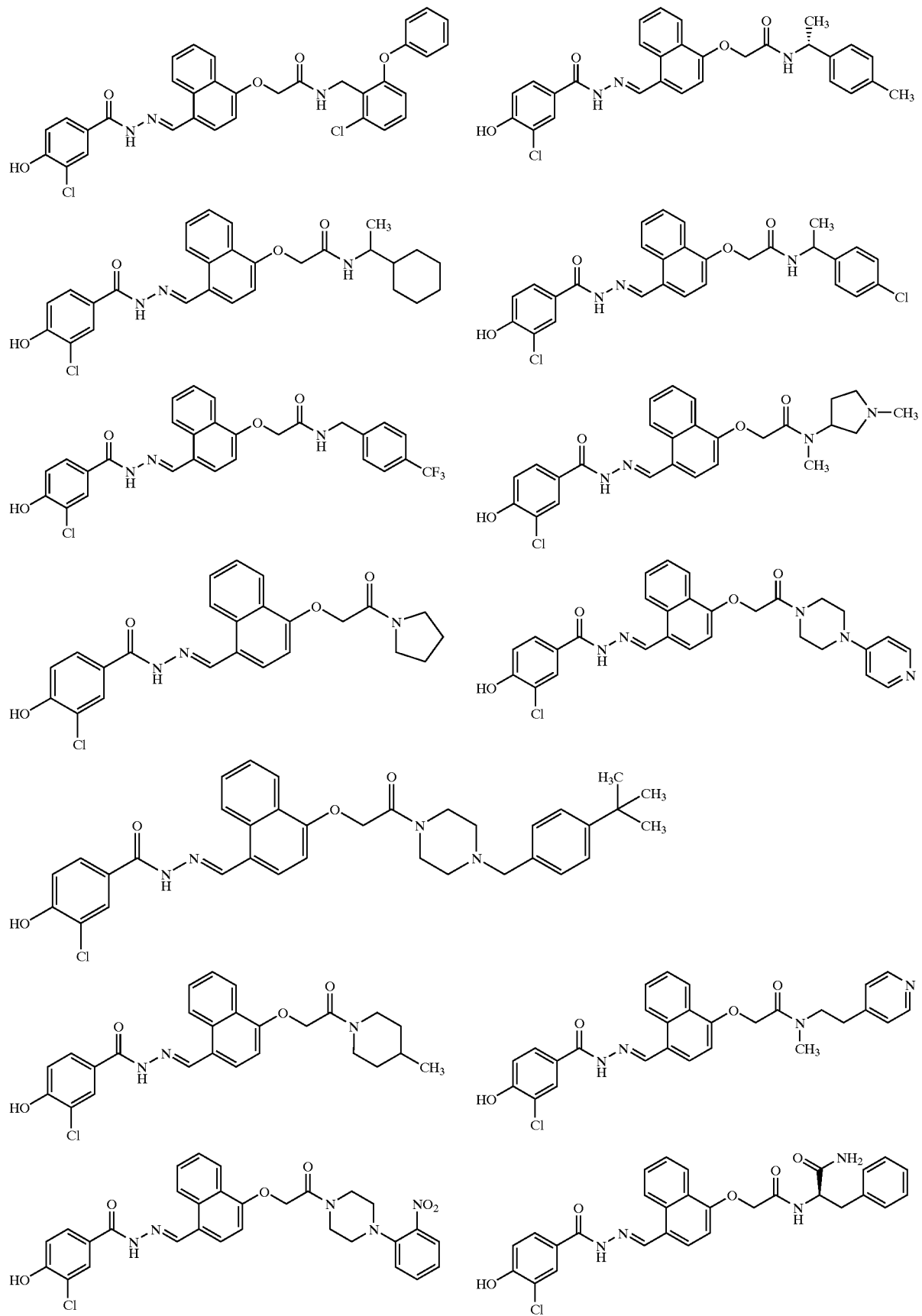

121
-continued
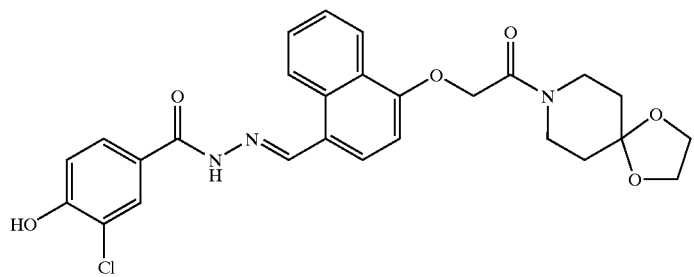
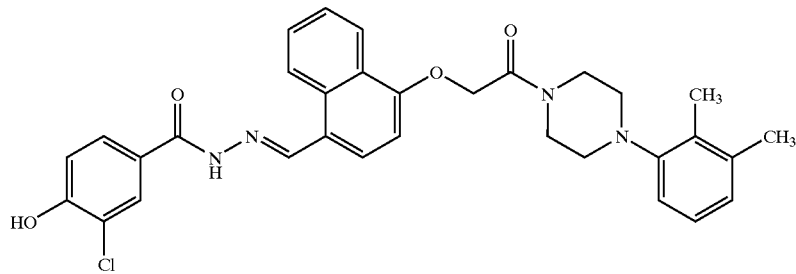
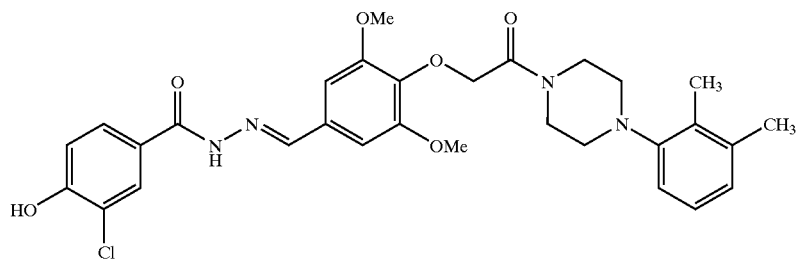
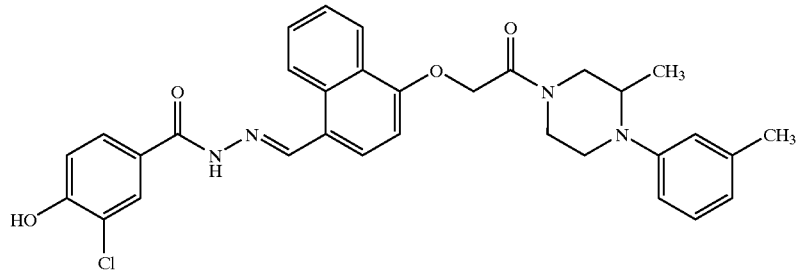
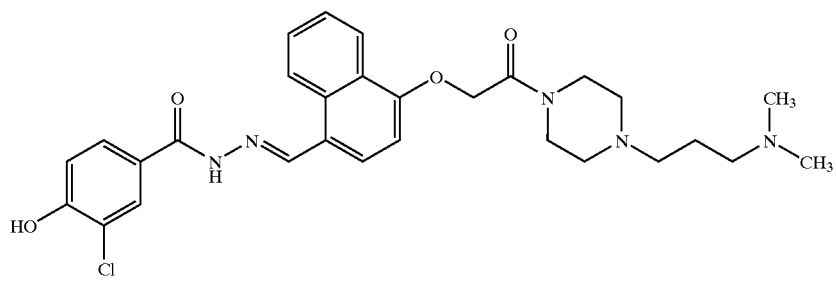
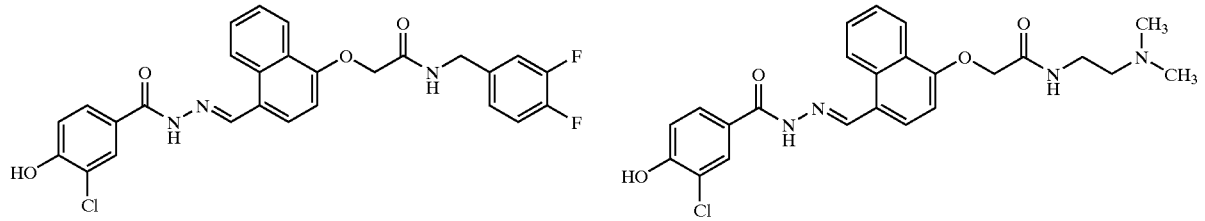

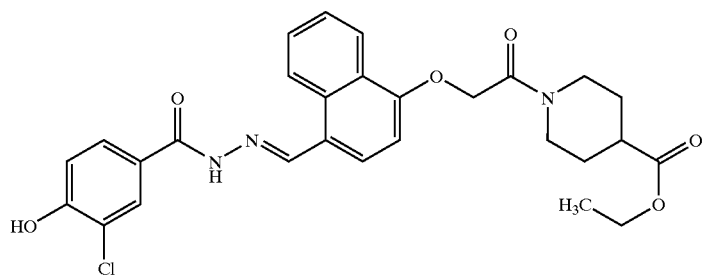
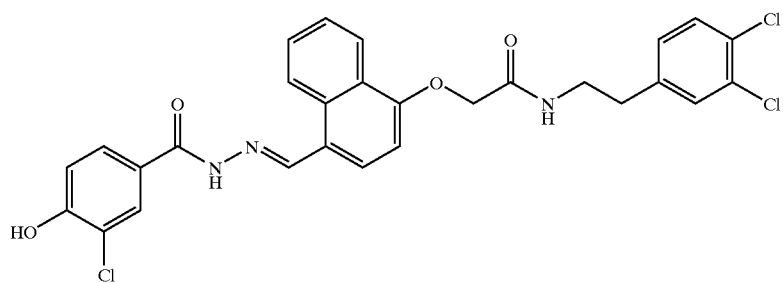
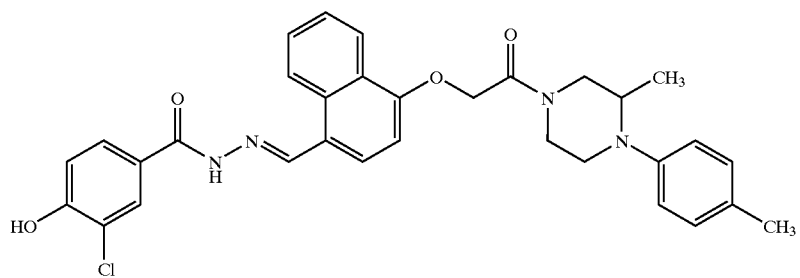
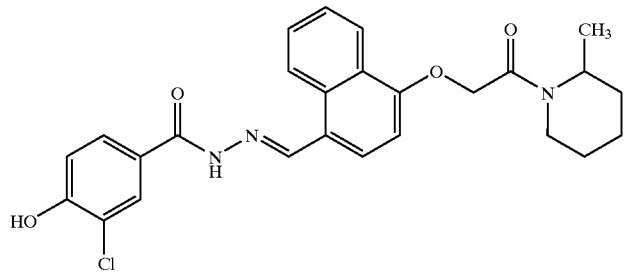
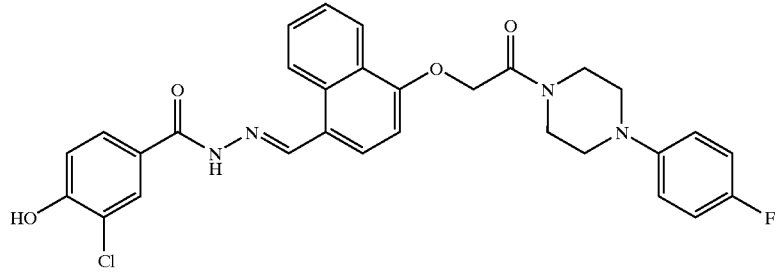
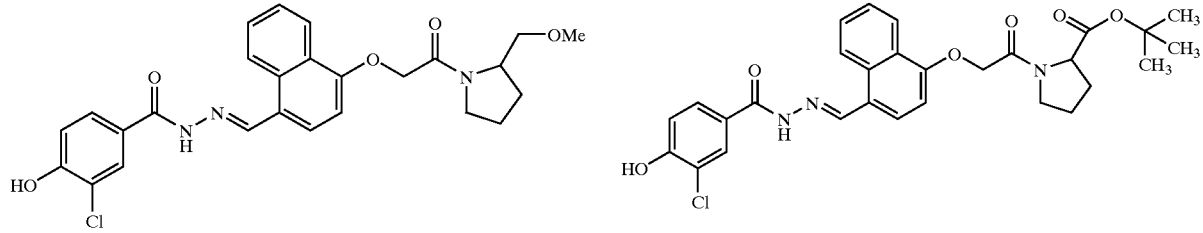

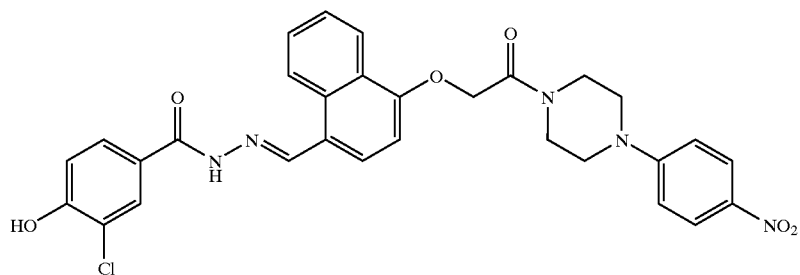
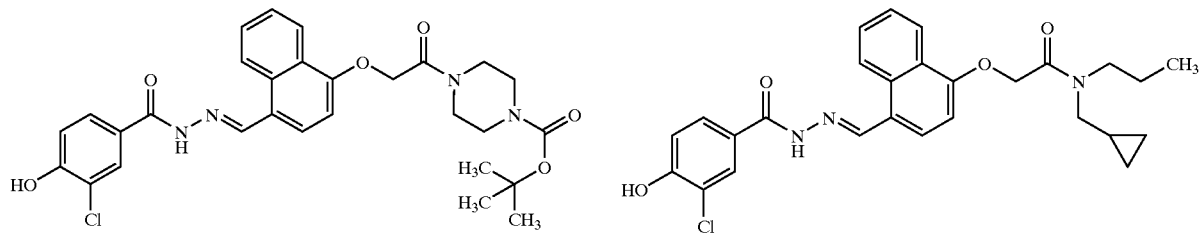
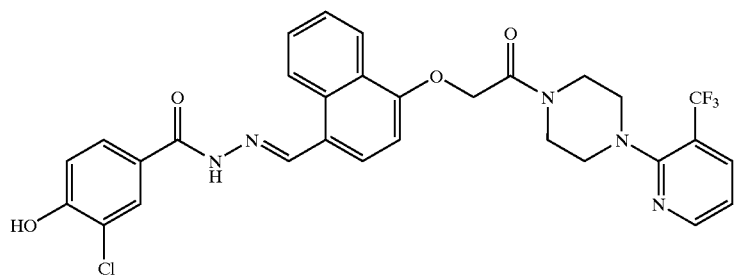
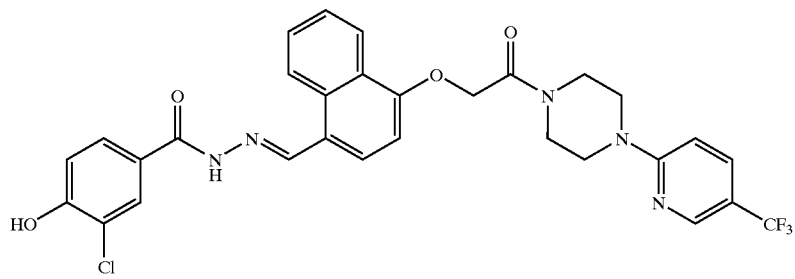
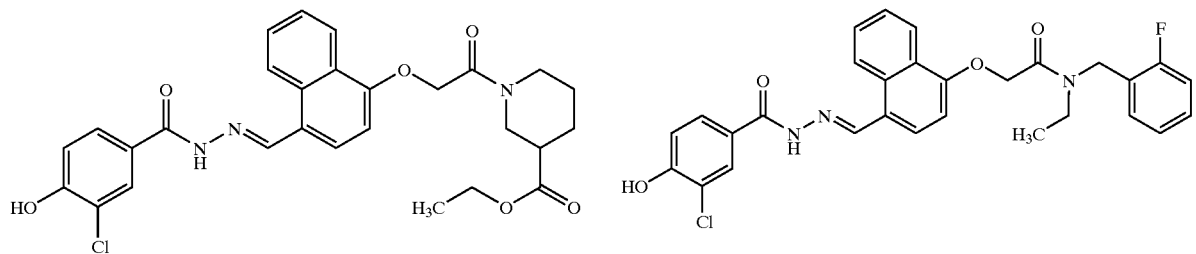
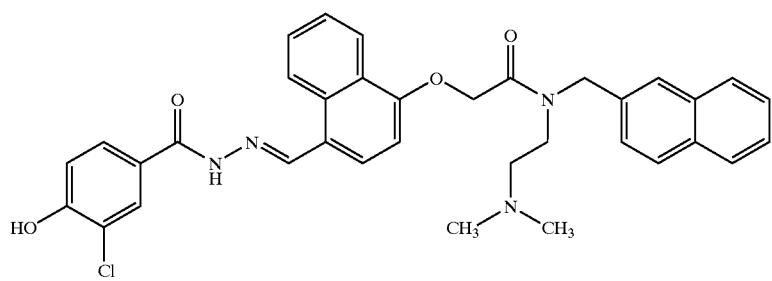

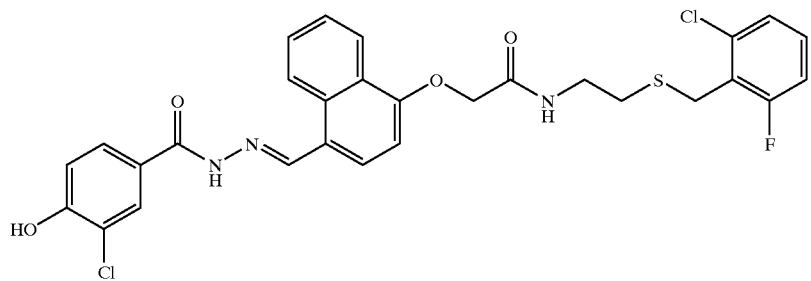
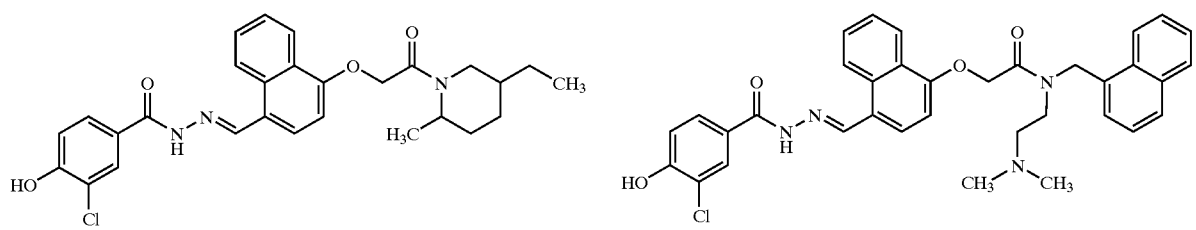
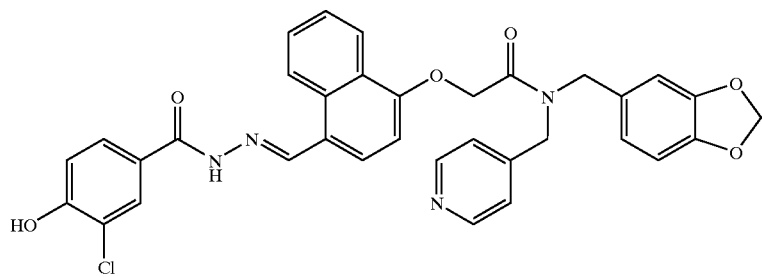
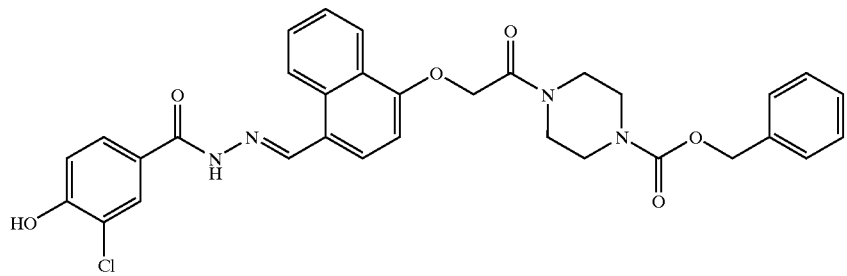
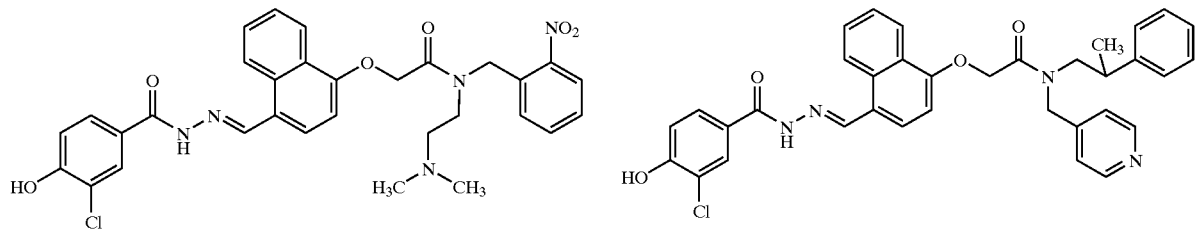
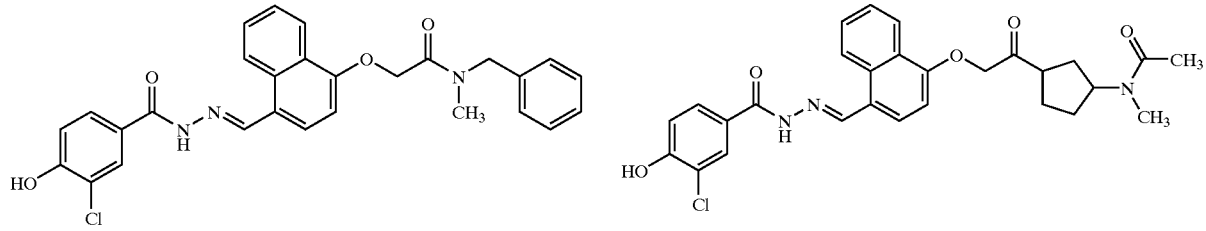

-continued
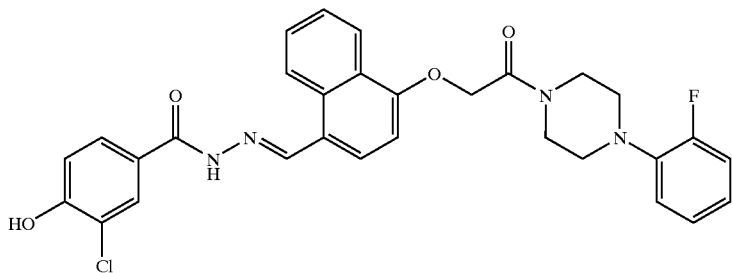
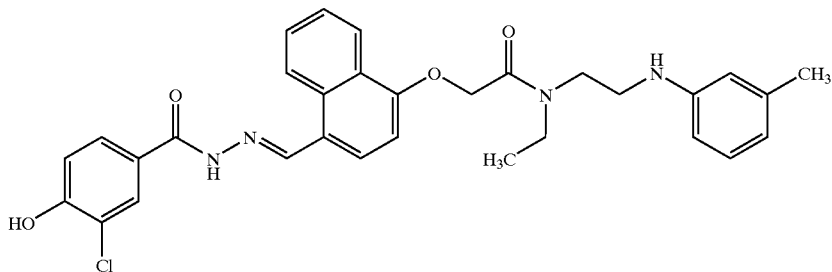
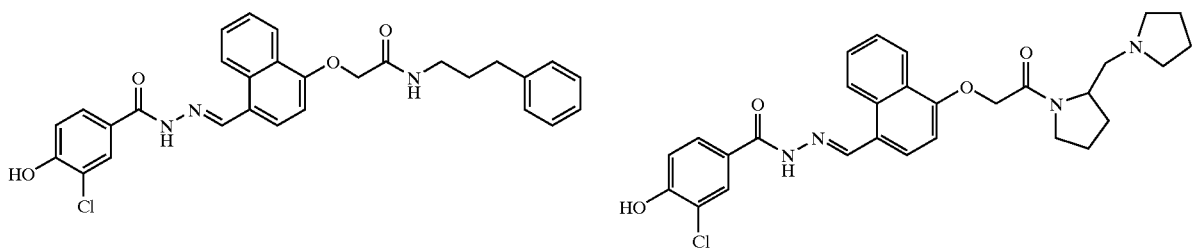
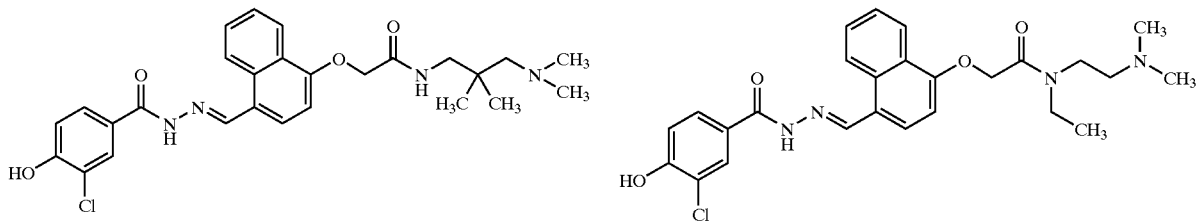
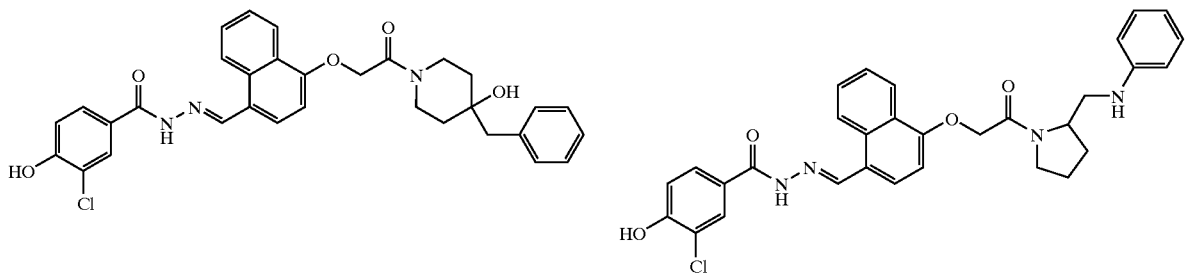
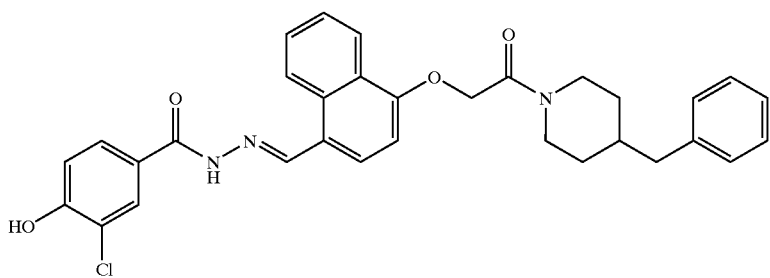

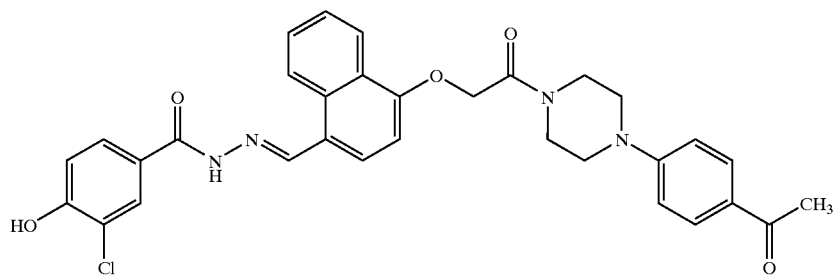
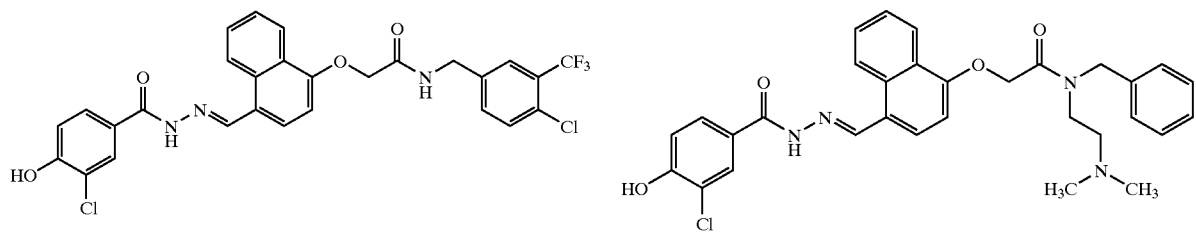
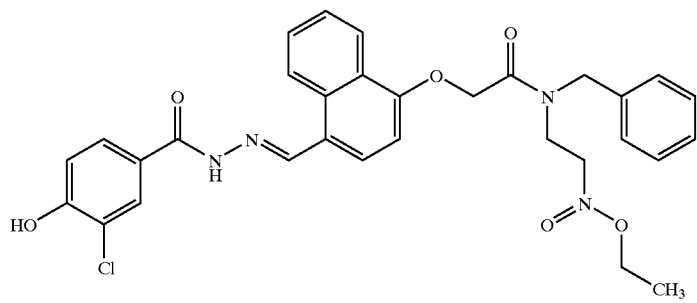
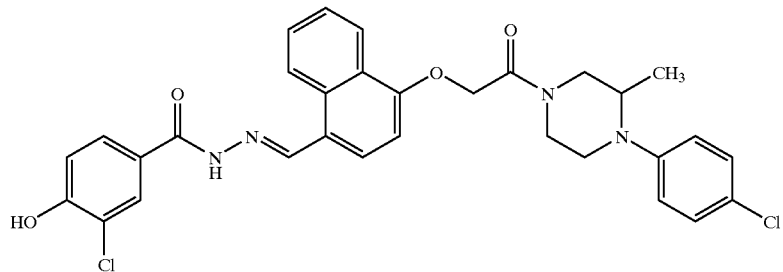
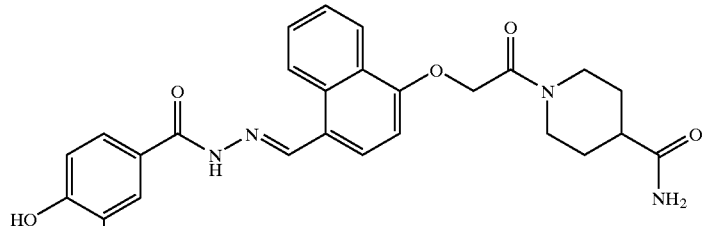
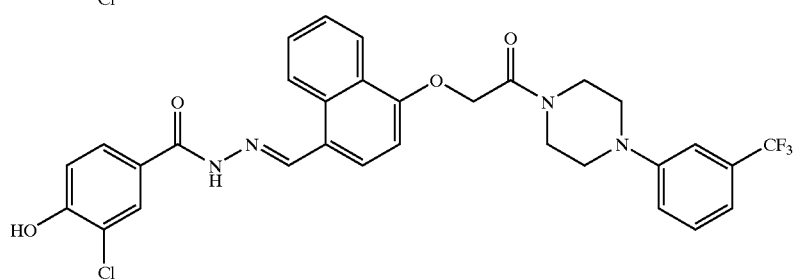

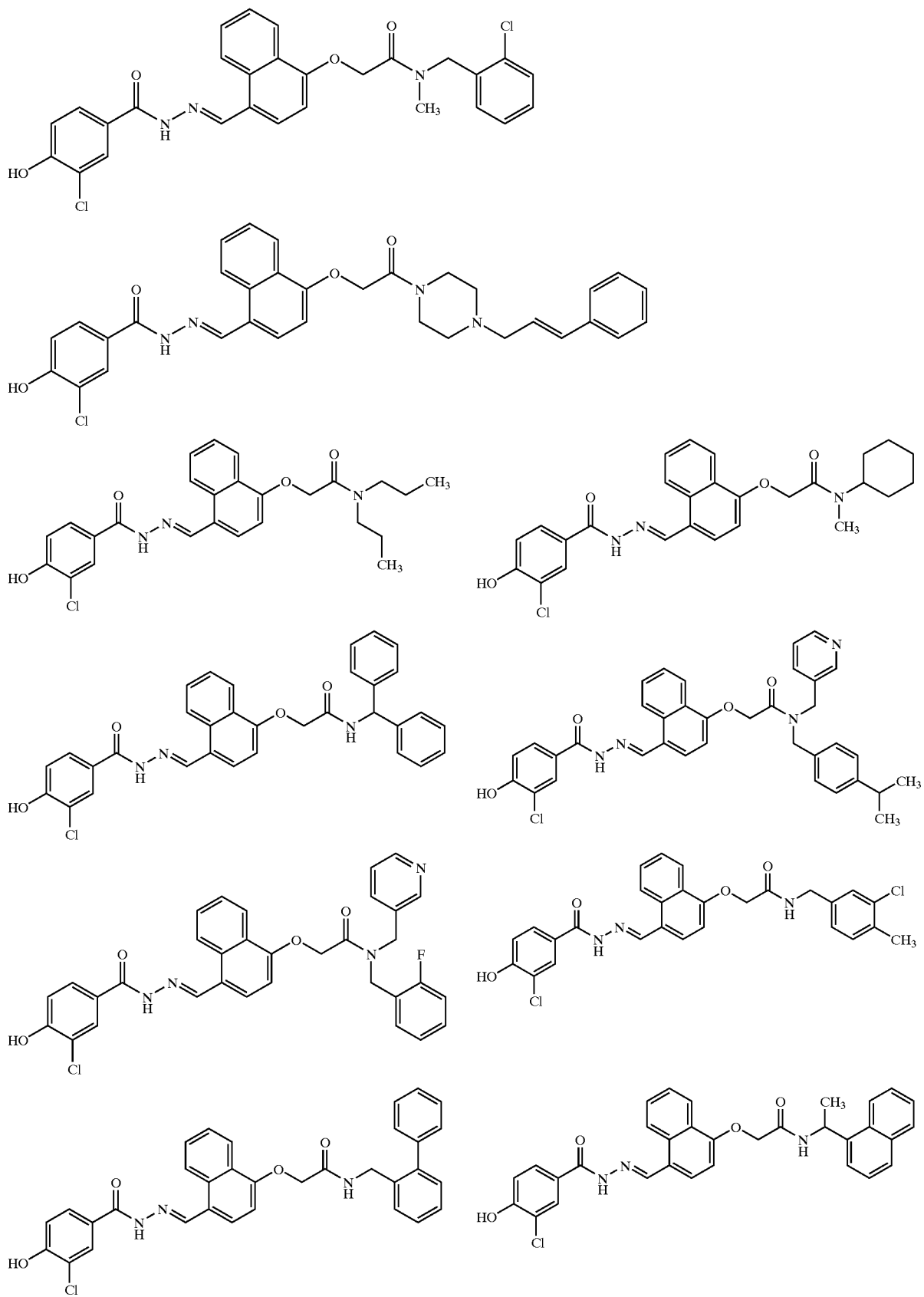

135 136
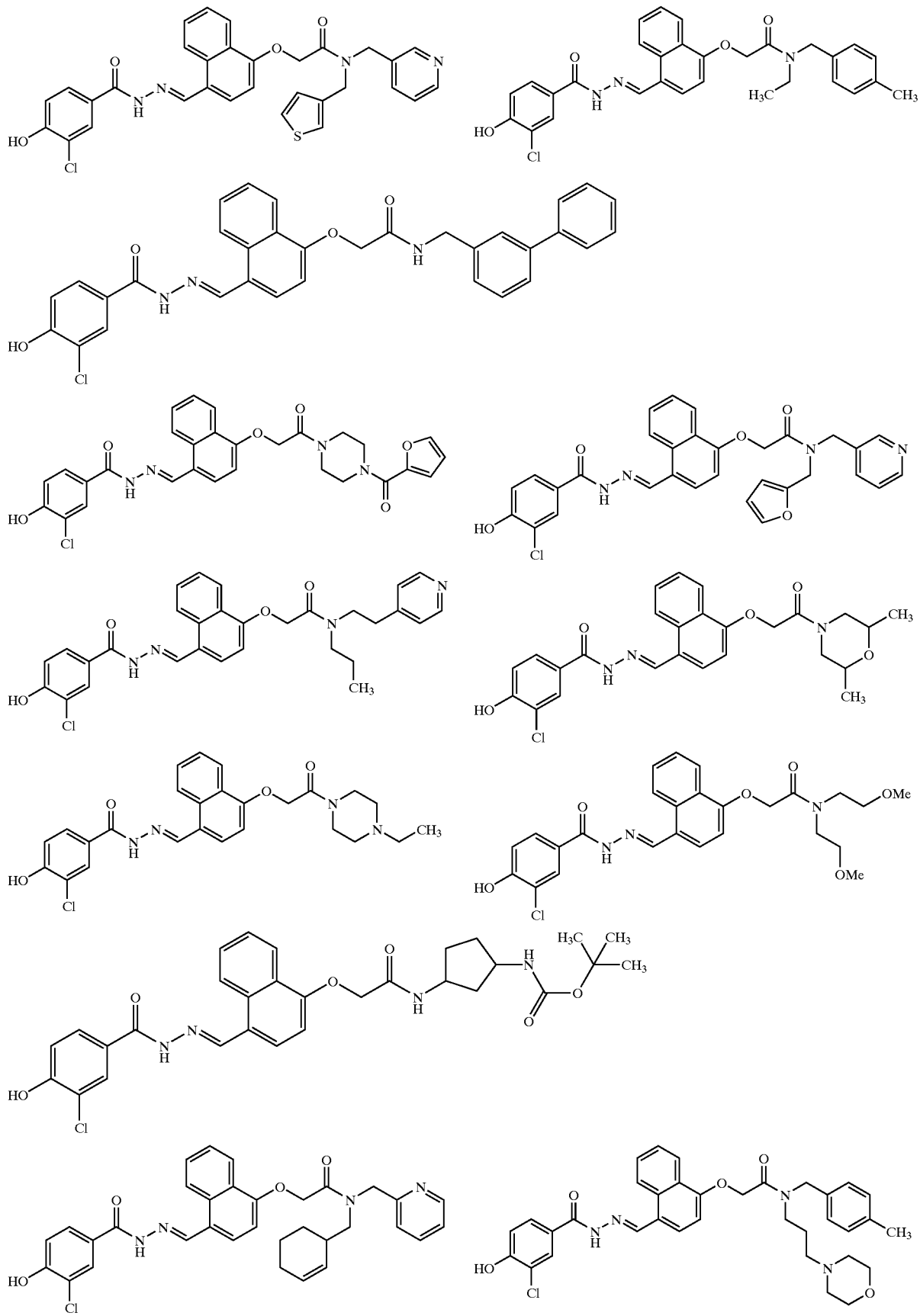

137 138
-continued
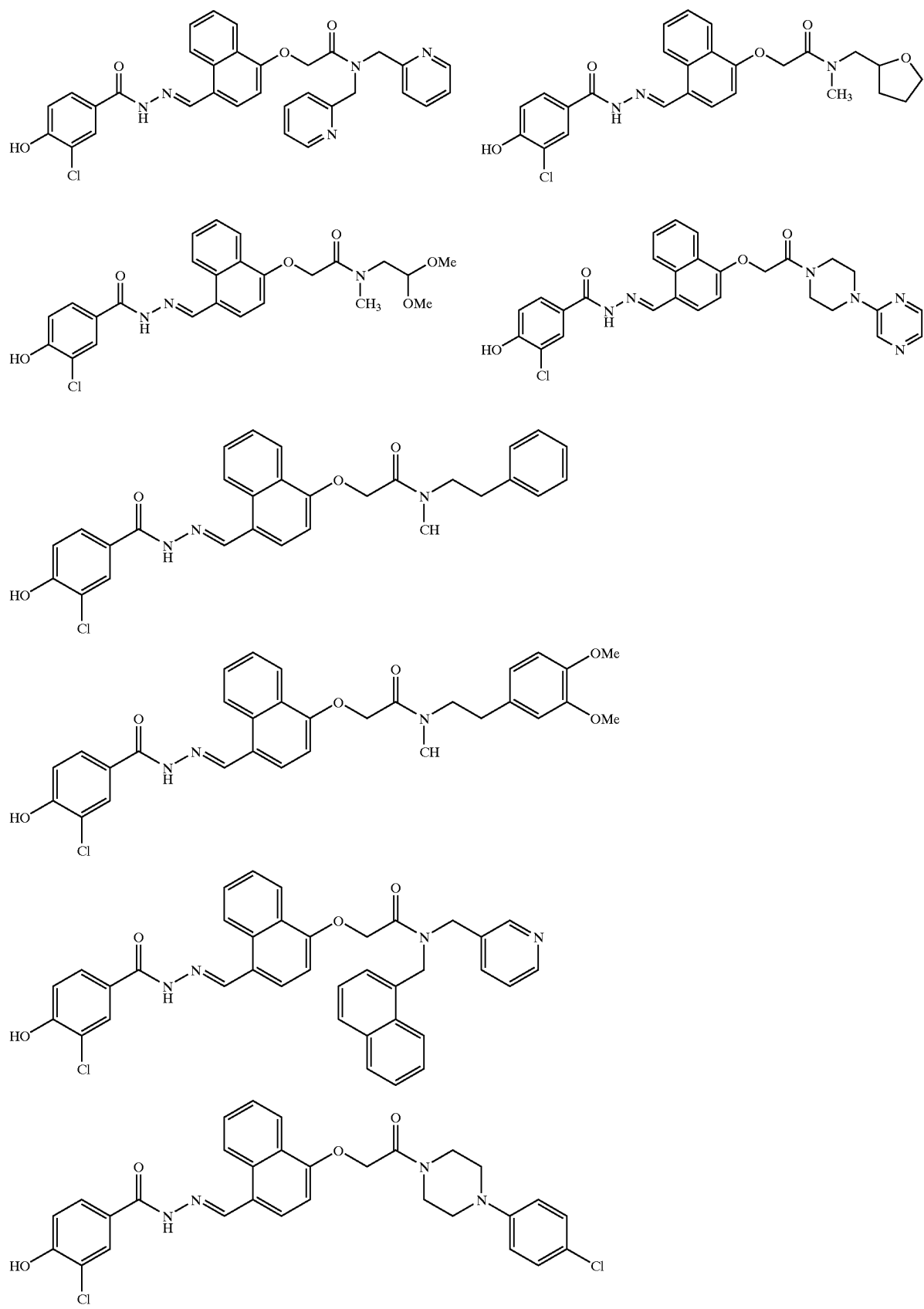

-continued
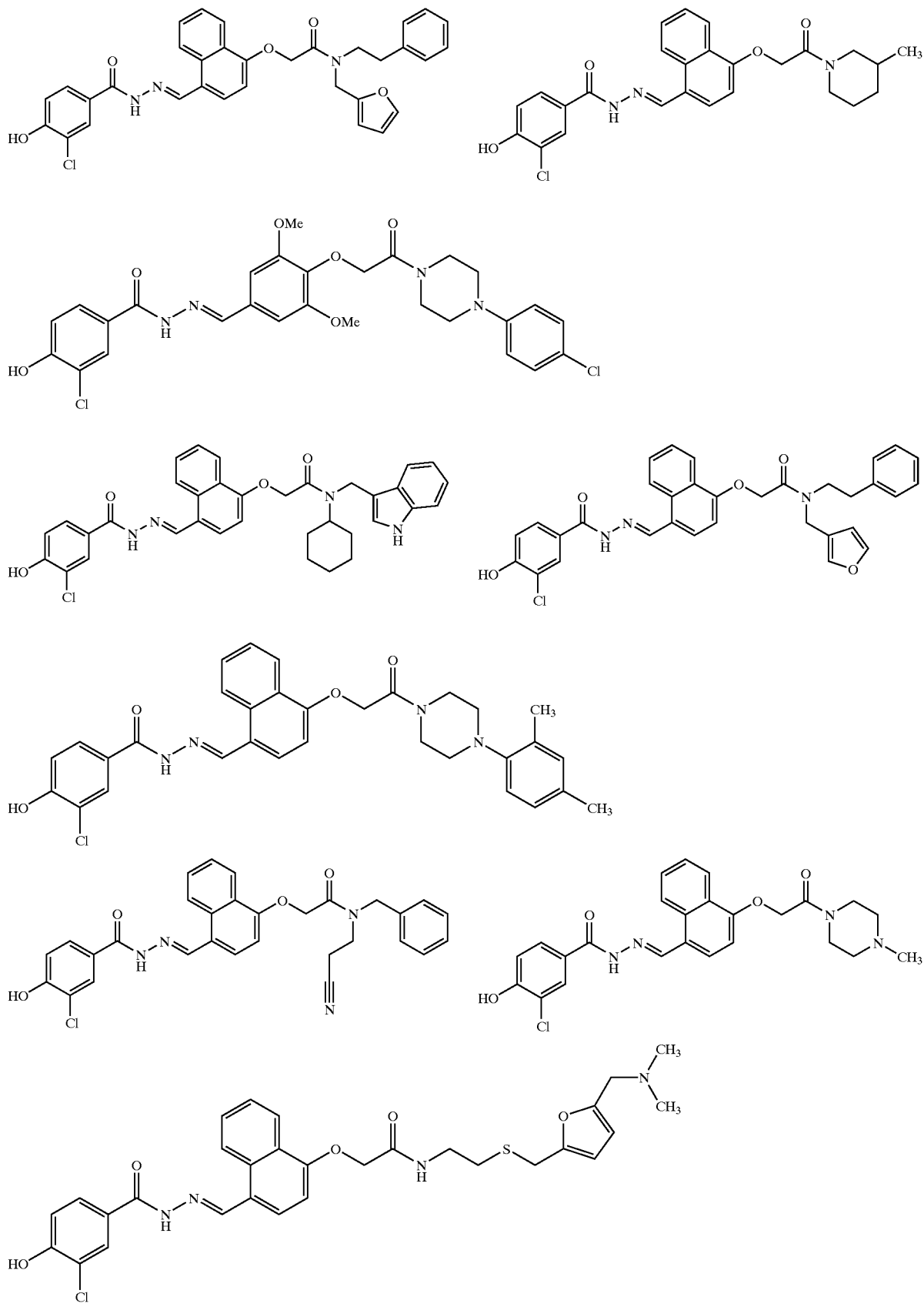

-continued
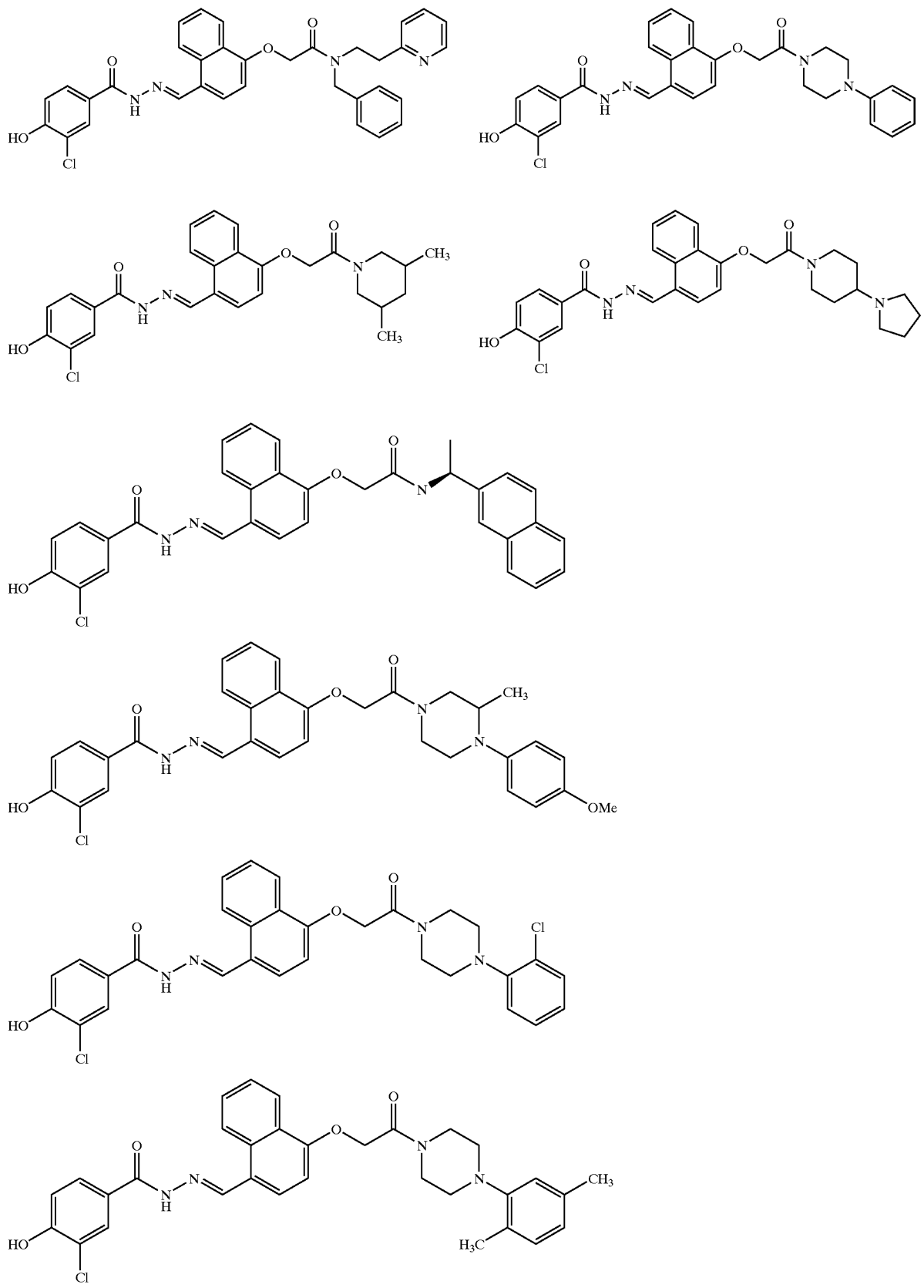

-continued
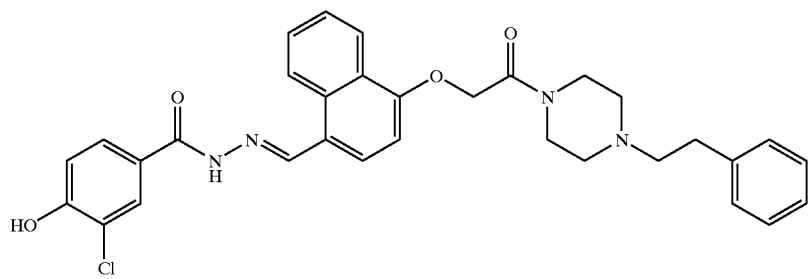
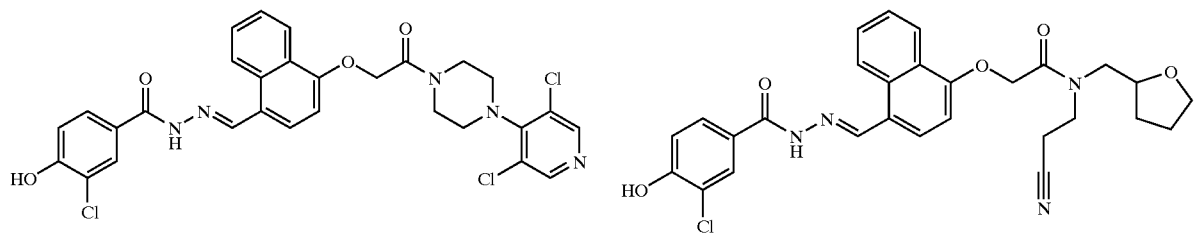
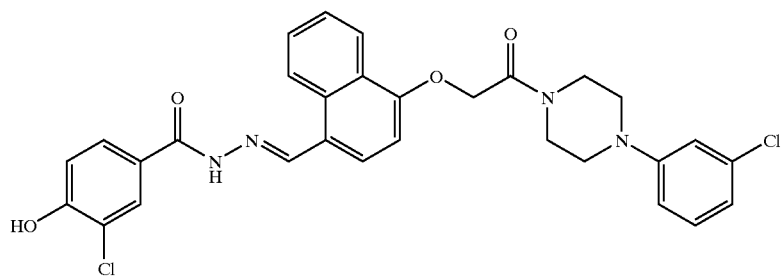
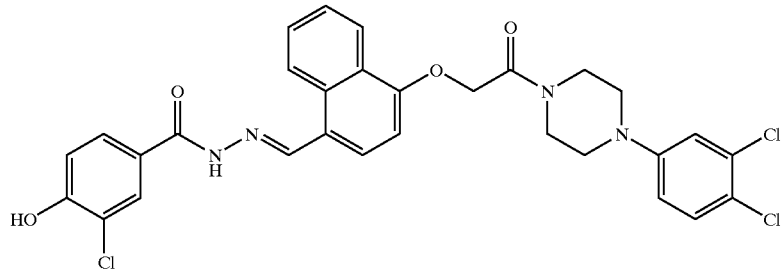
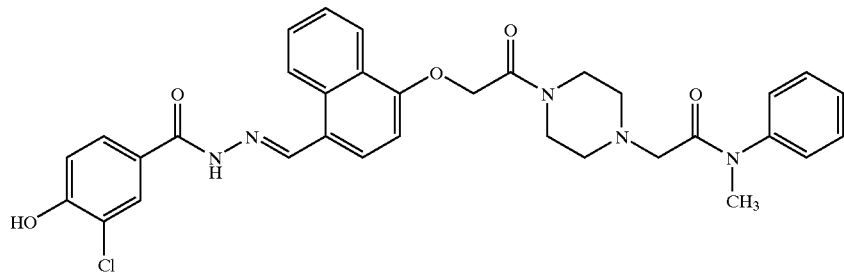
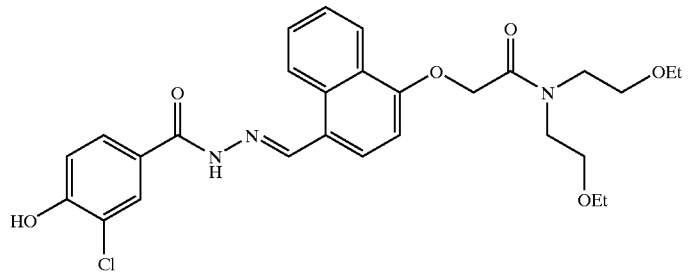

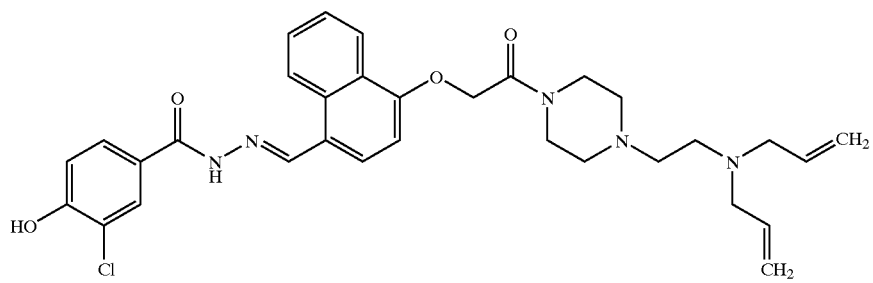
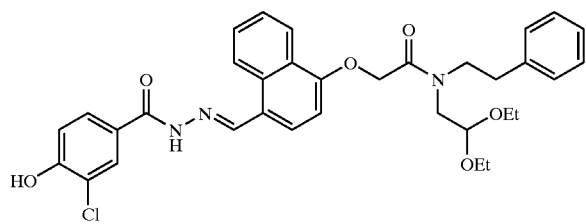
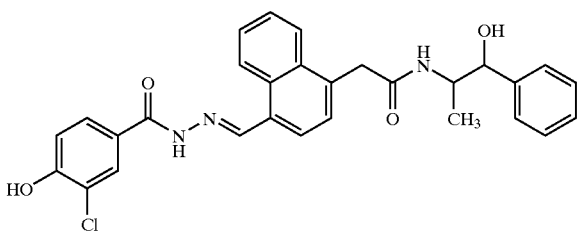
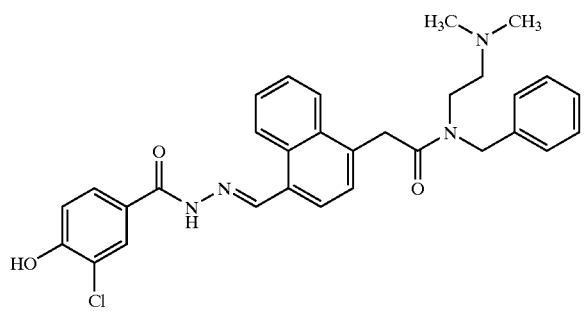
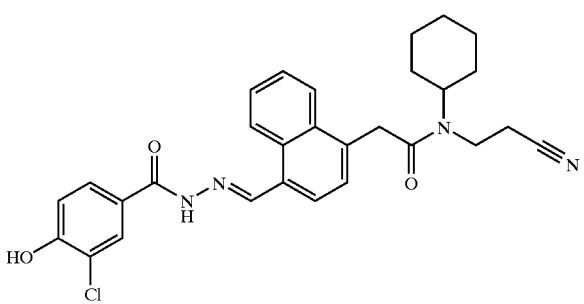
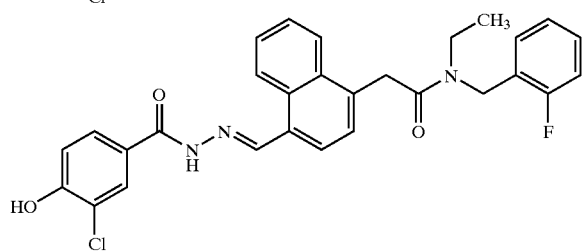
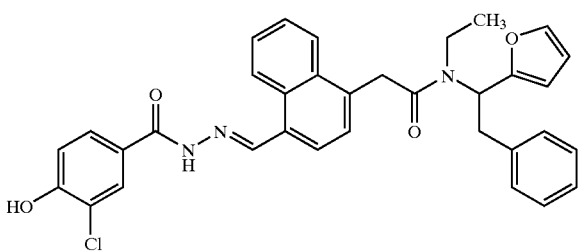
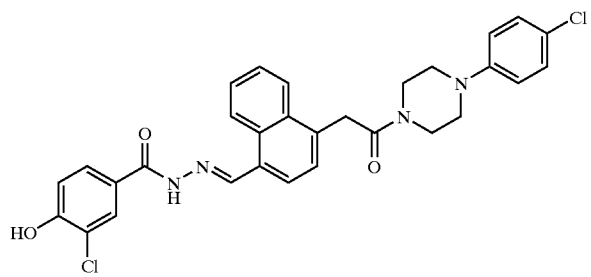
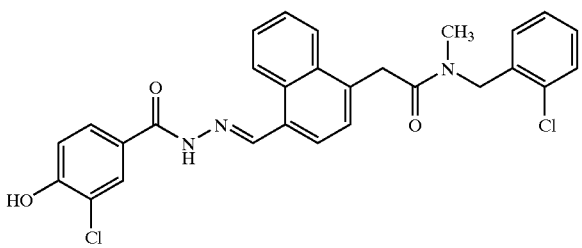
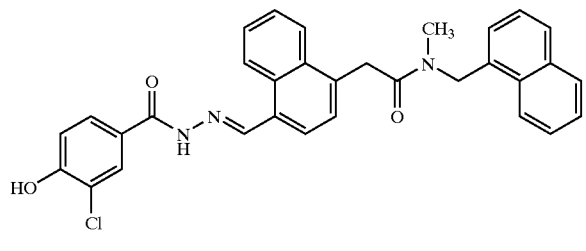
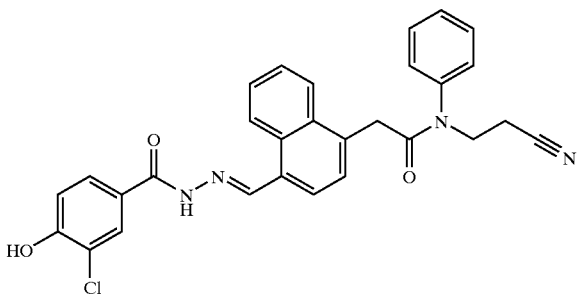

147
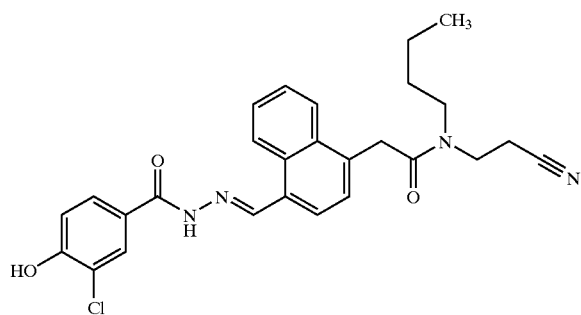
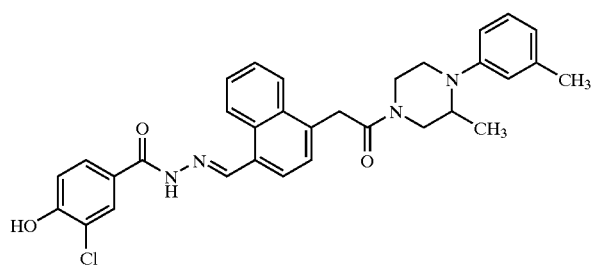
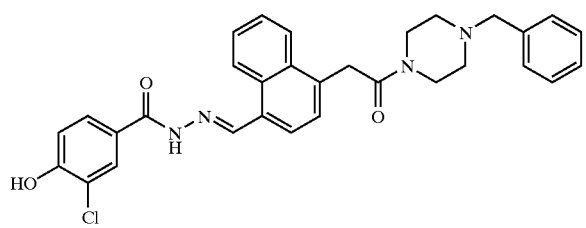
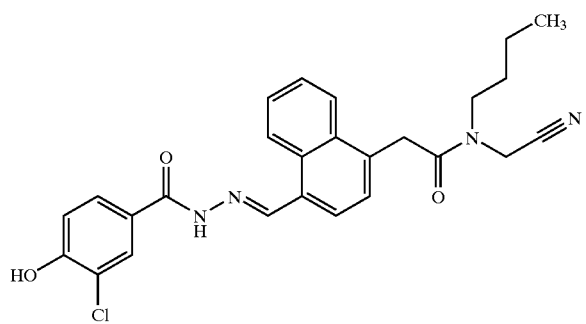
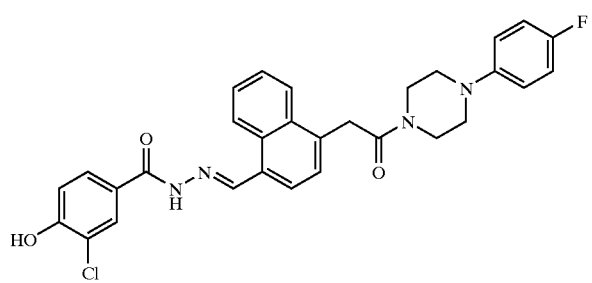
148
-continued
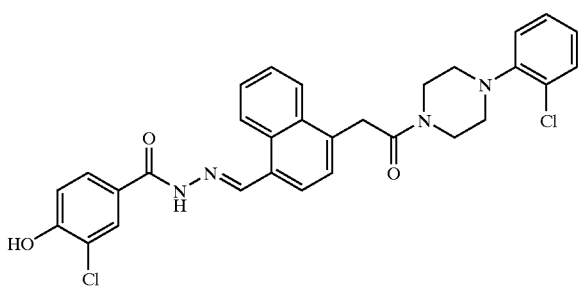
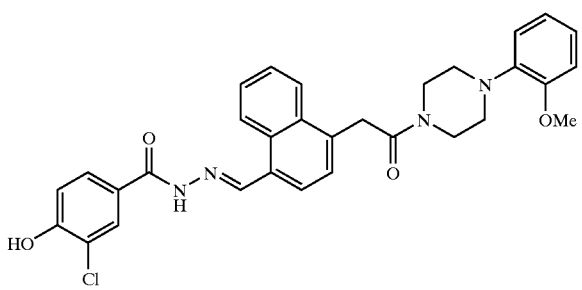
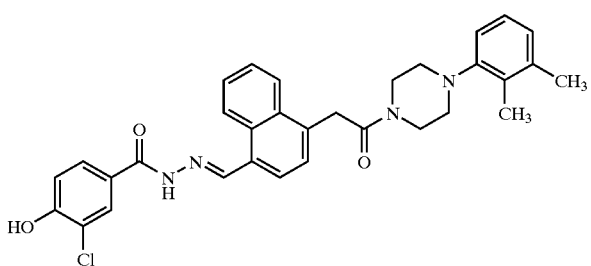
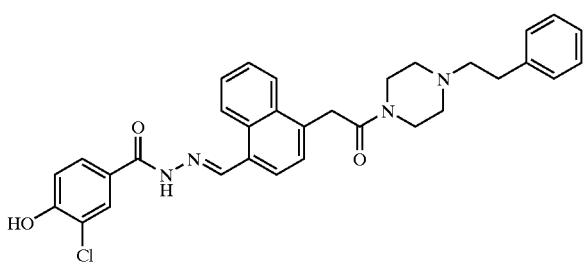
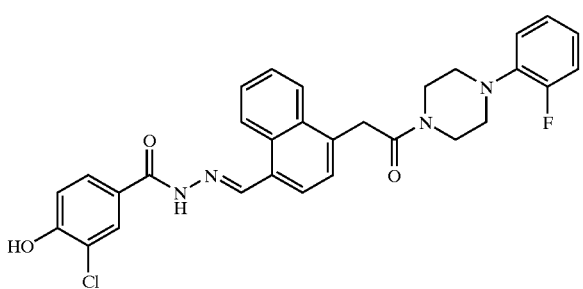

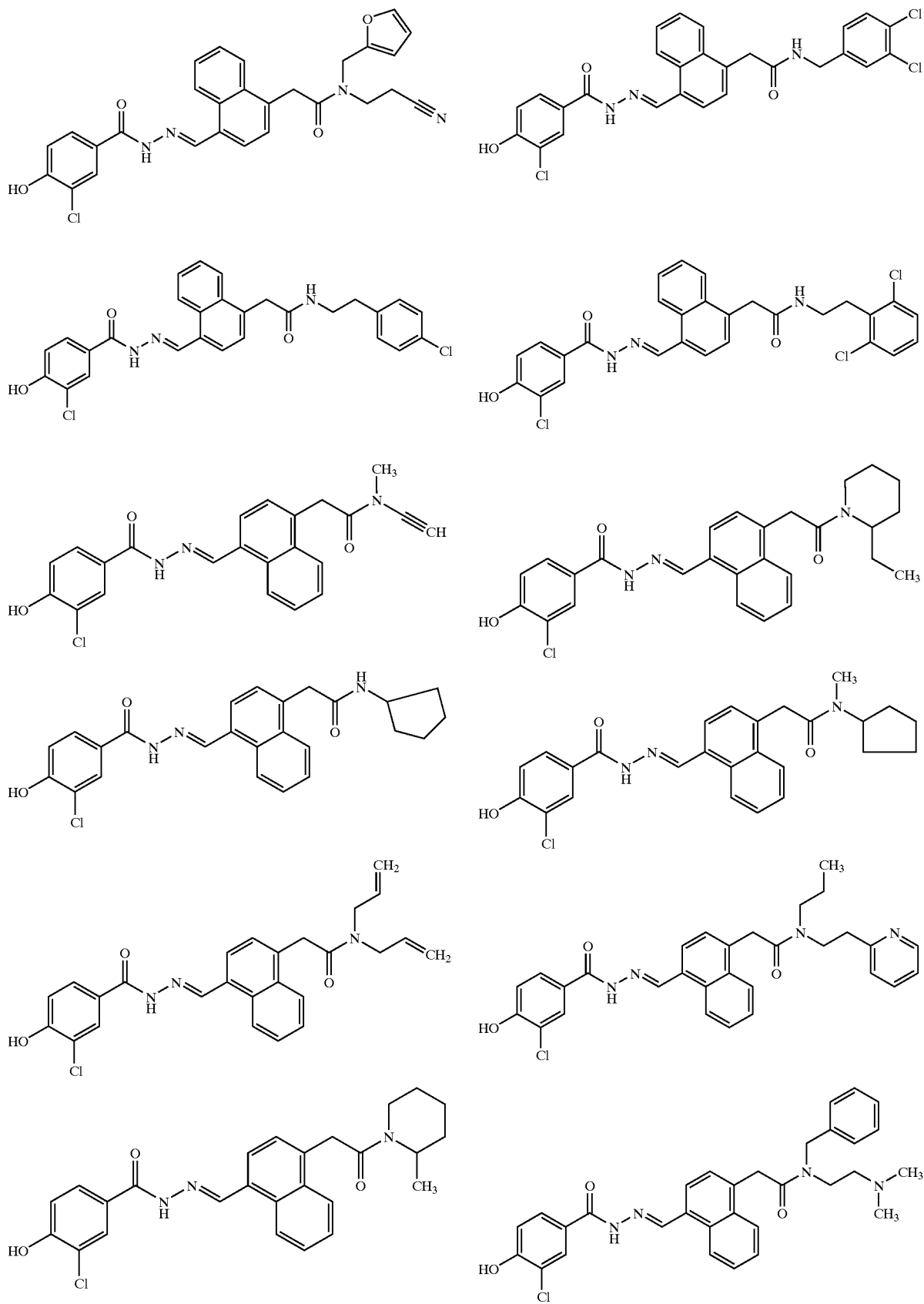

151
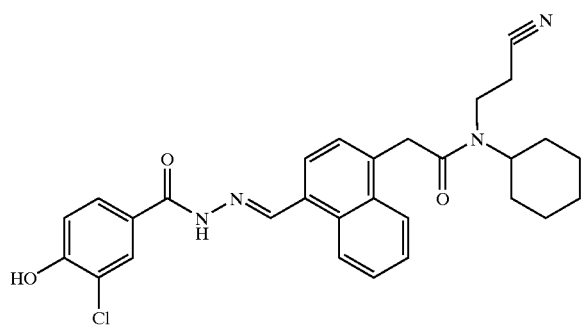
152
-continued
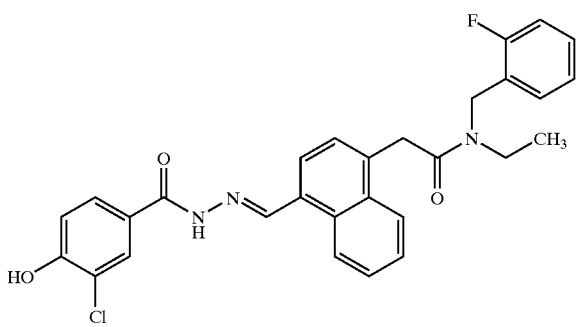
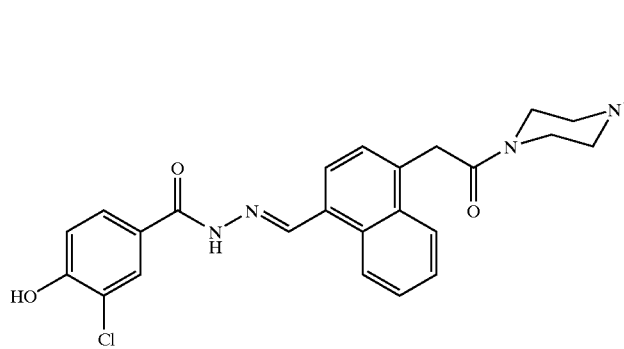
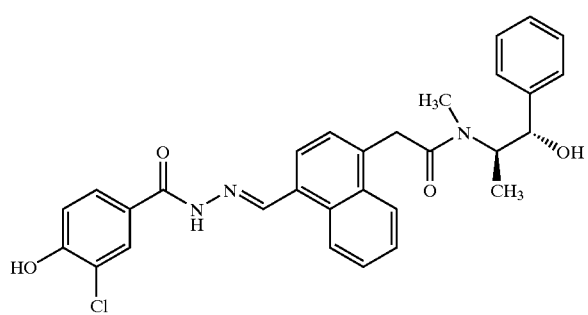
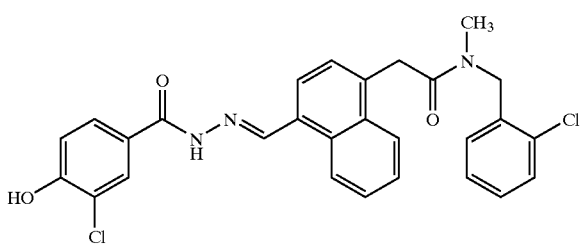
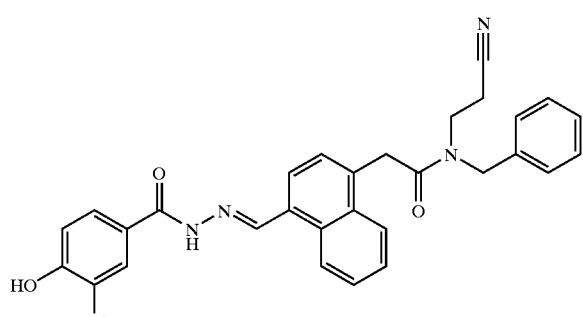
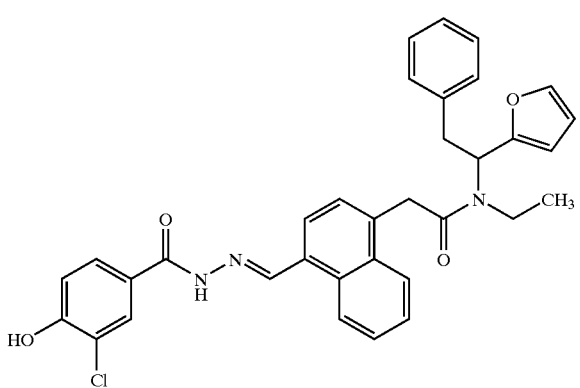
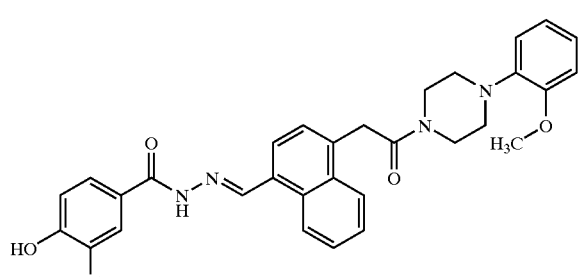
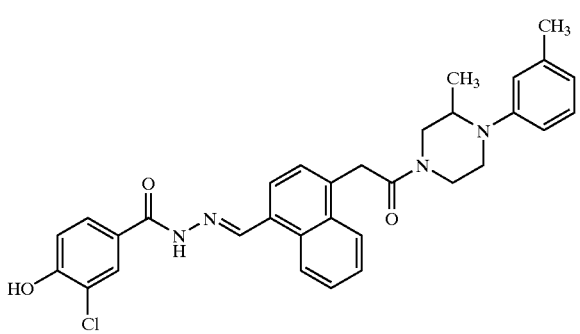

153
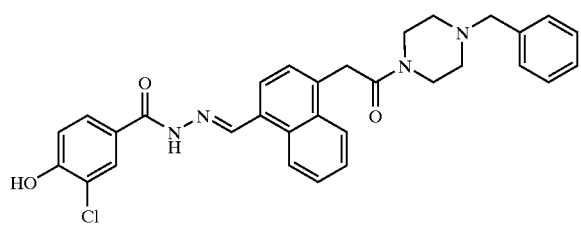
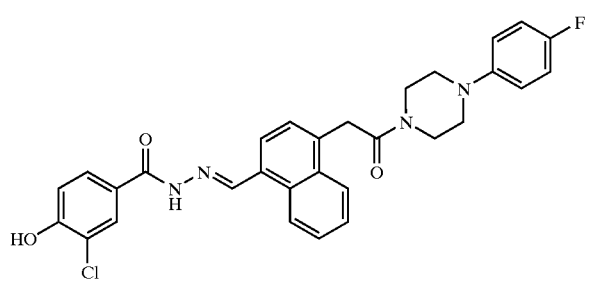
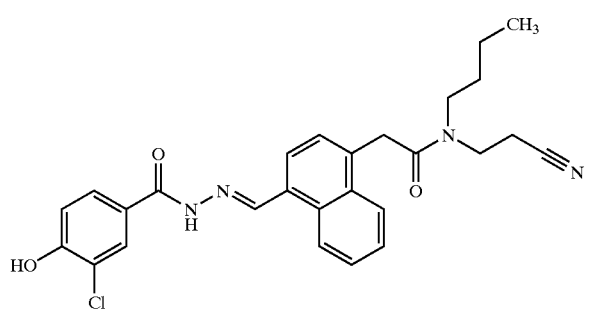
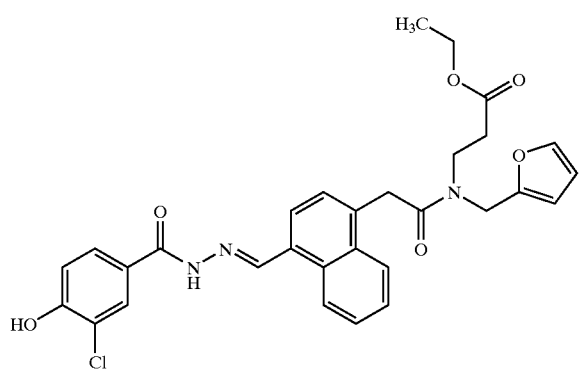
-continued
154
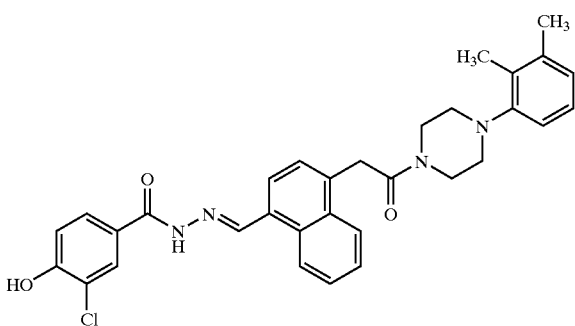
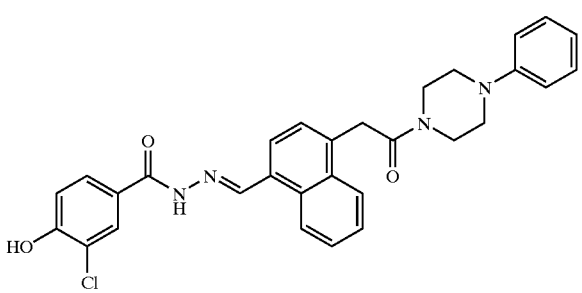
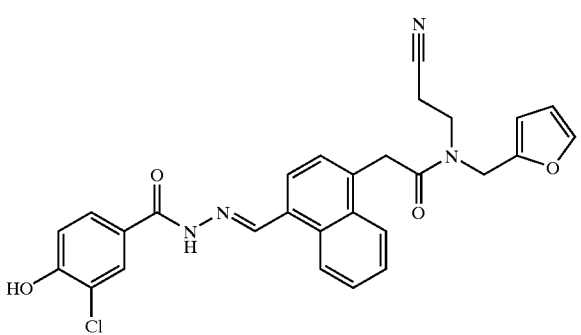
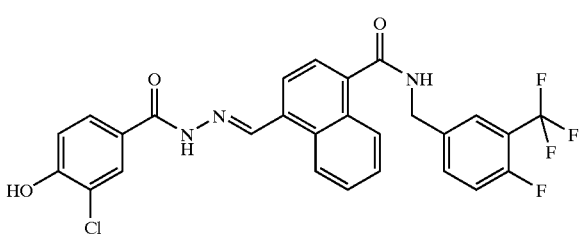
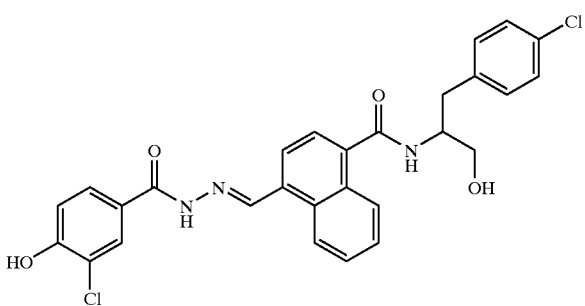

155 156
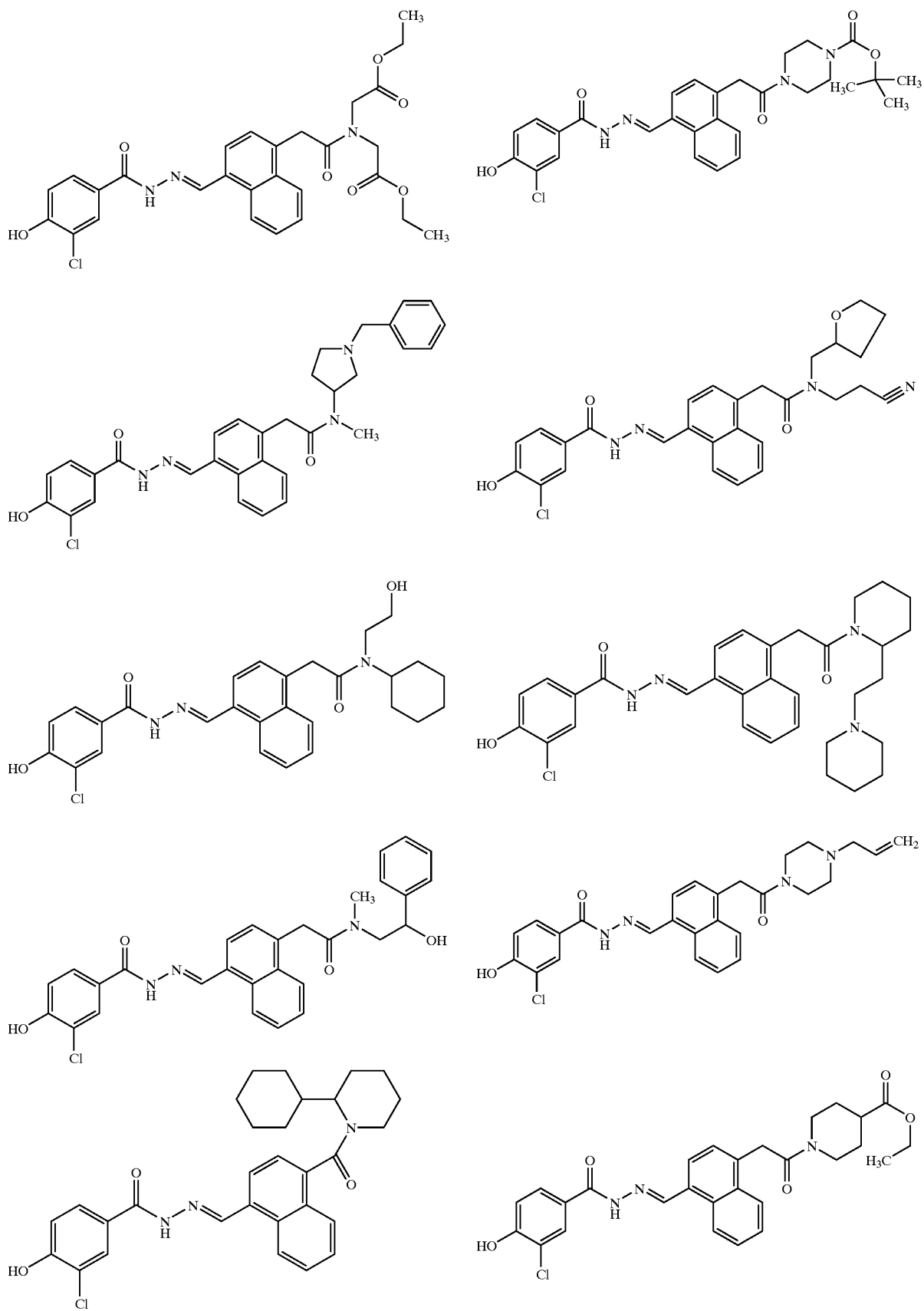
-continued

-continued
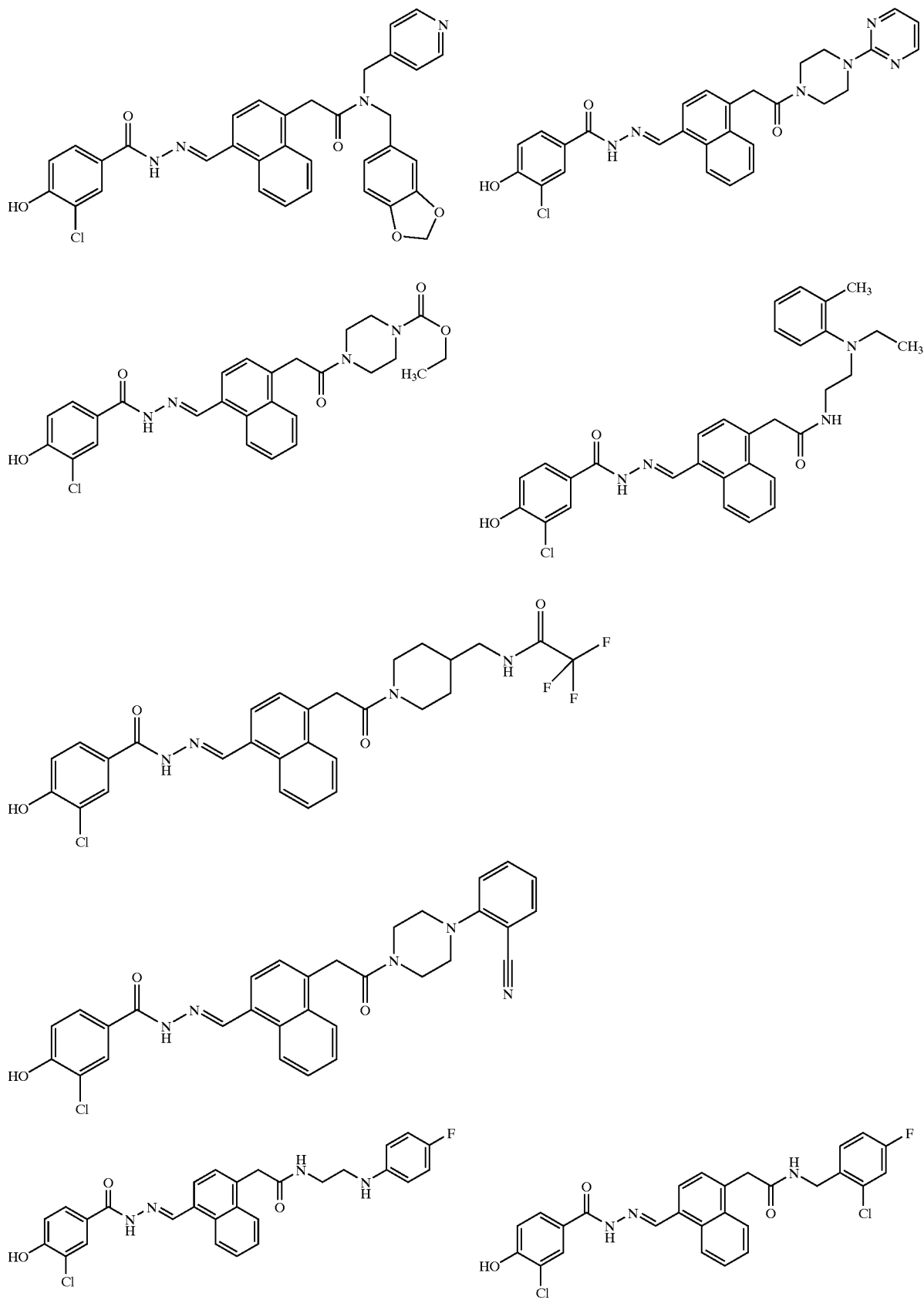

-continued
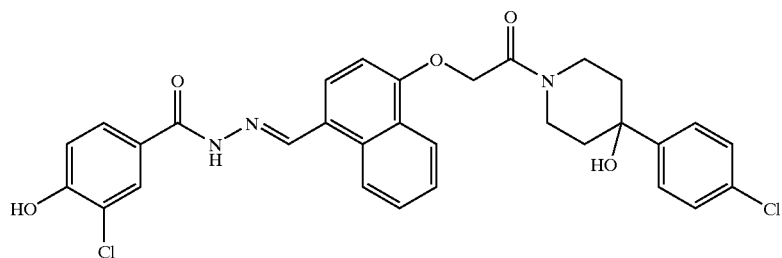
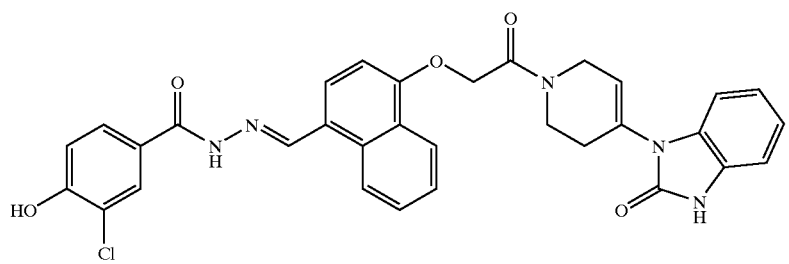
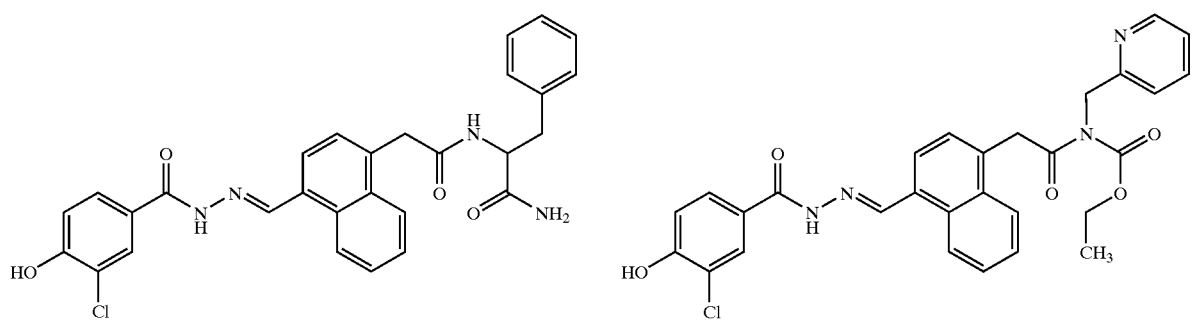
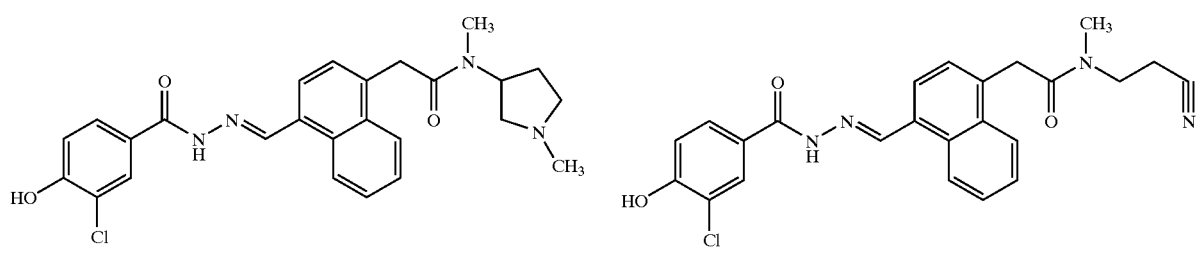
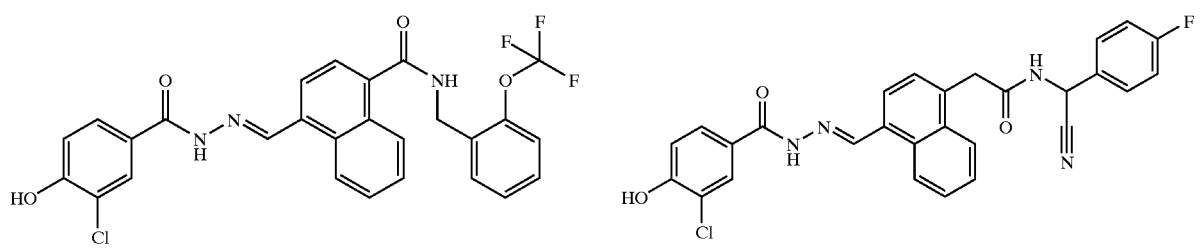
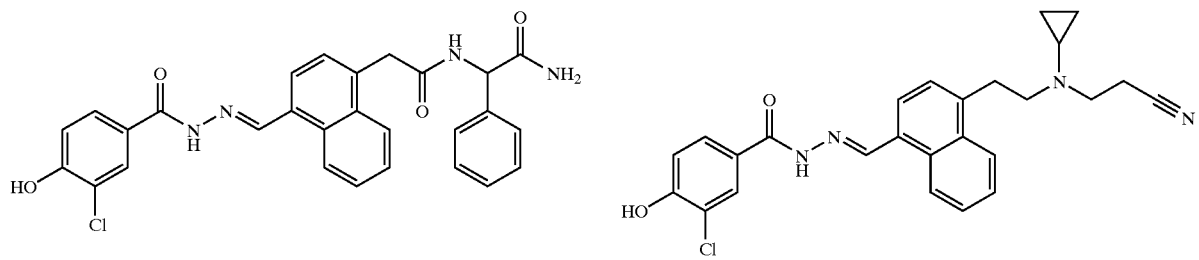

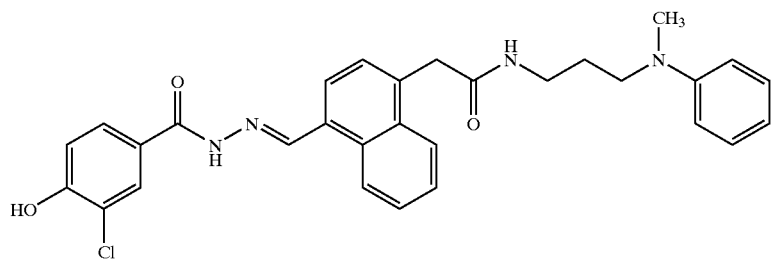
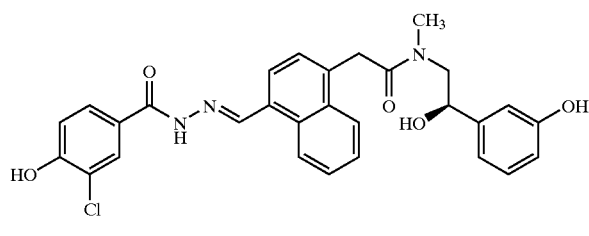
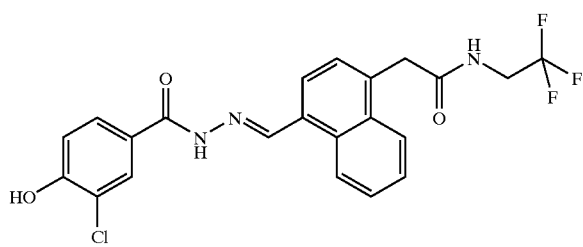
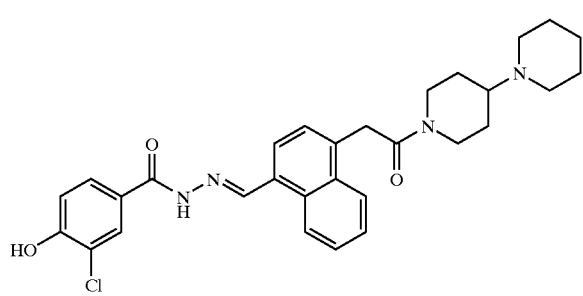
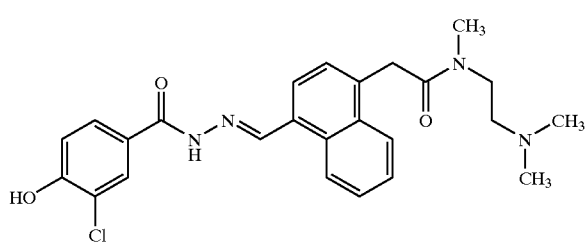
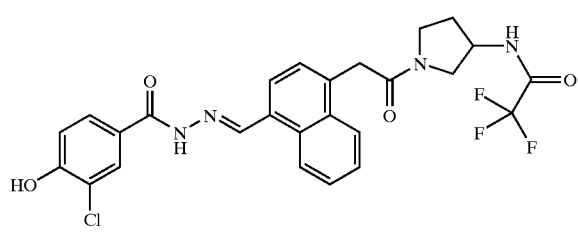
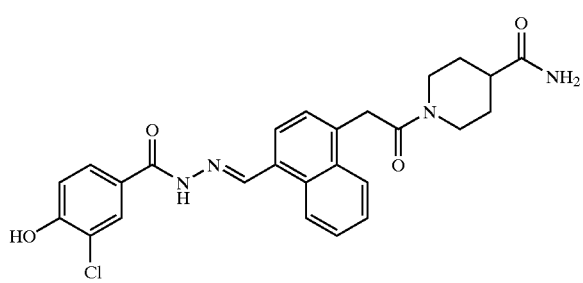
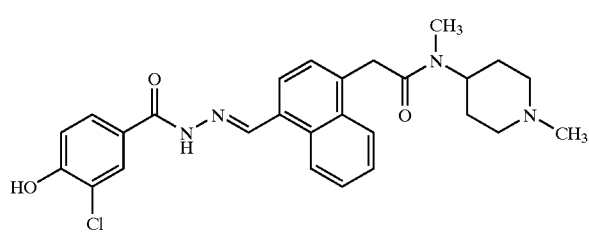
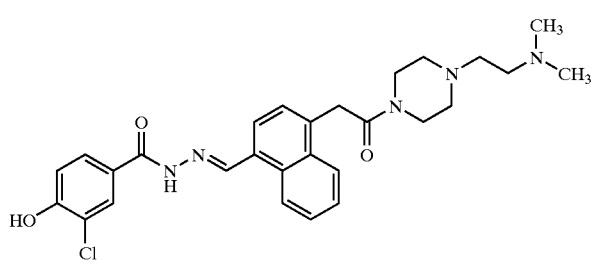
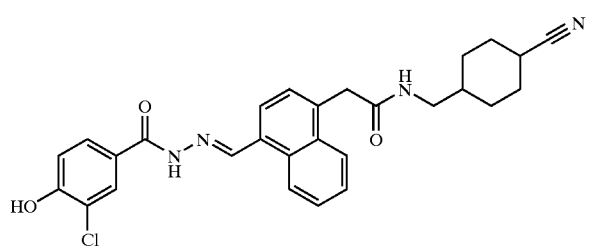
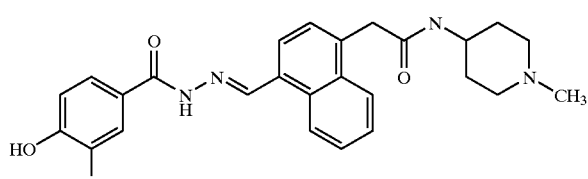

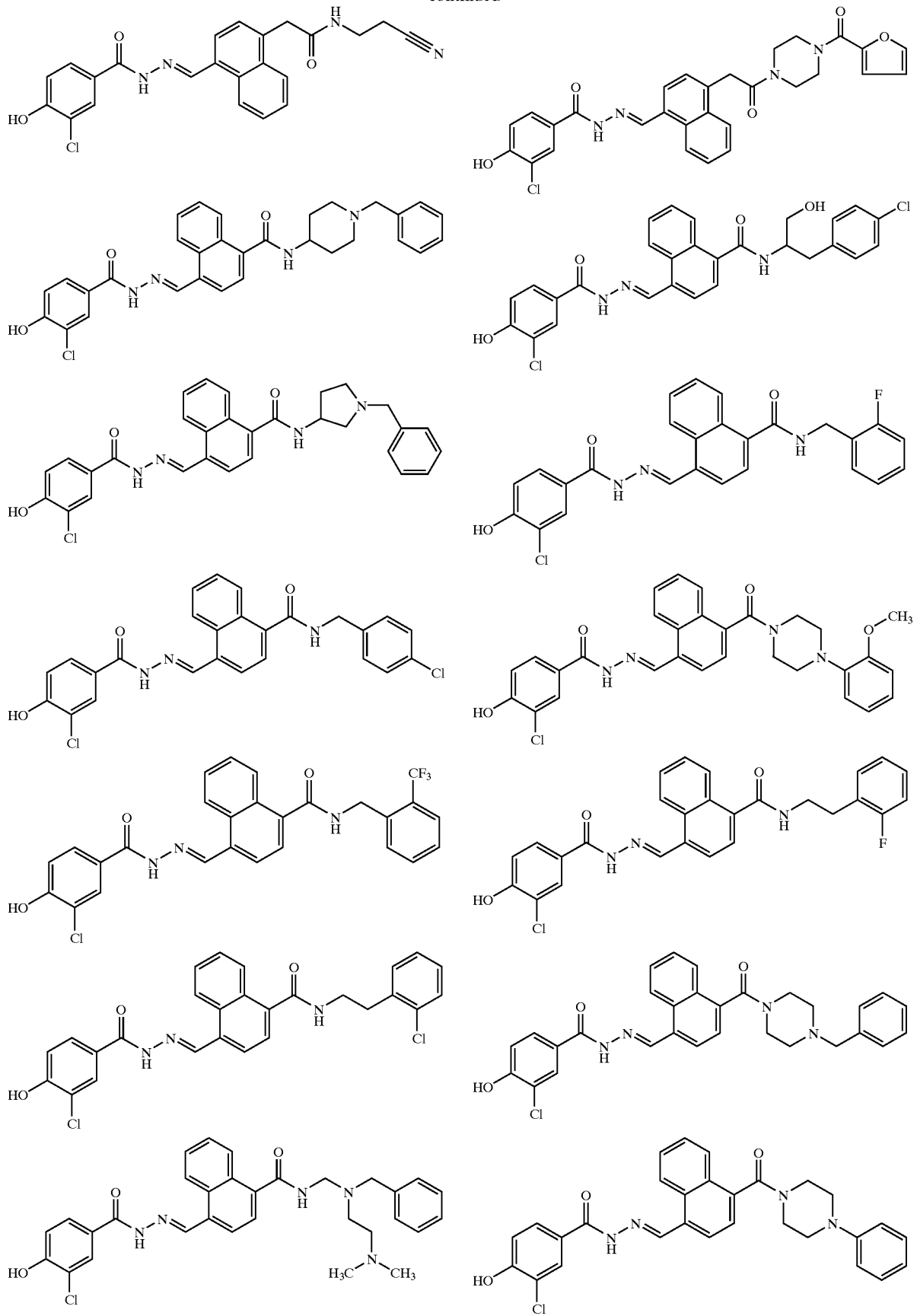

165 166
-continued
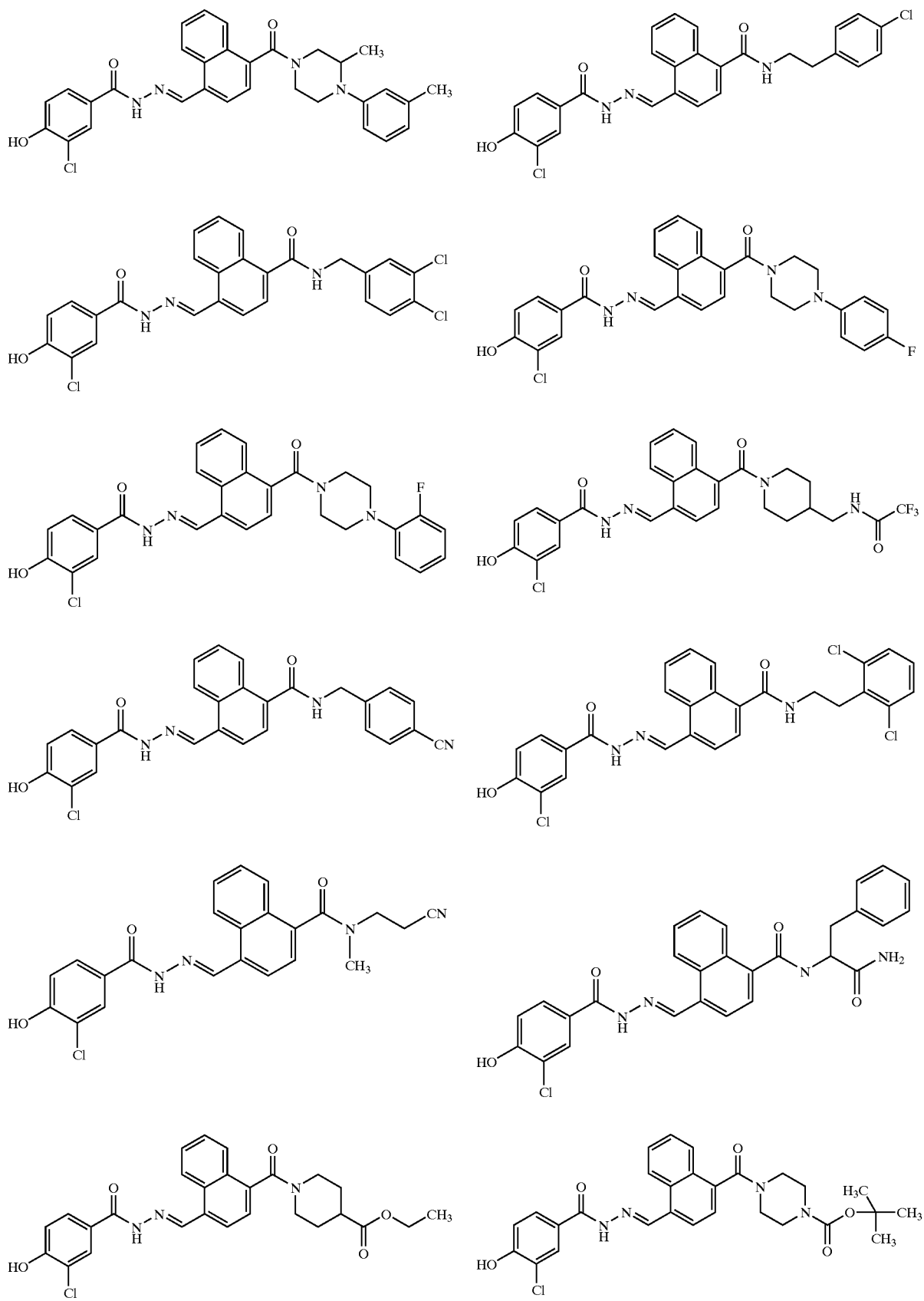

167 168
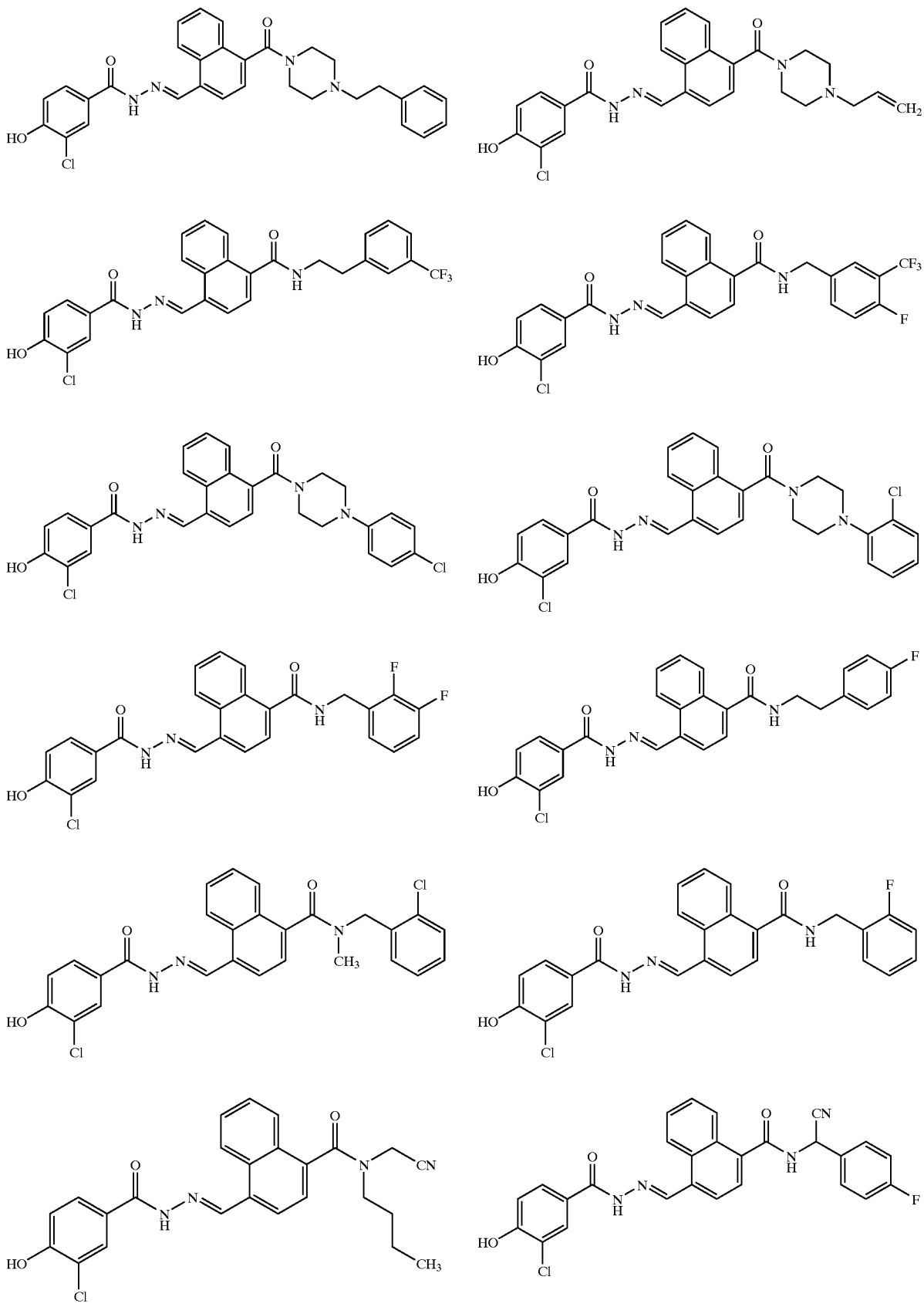

-continued
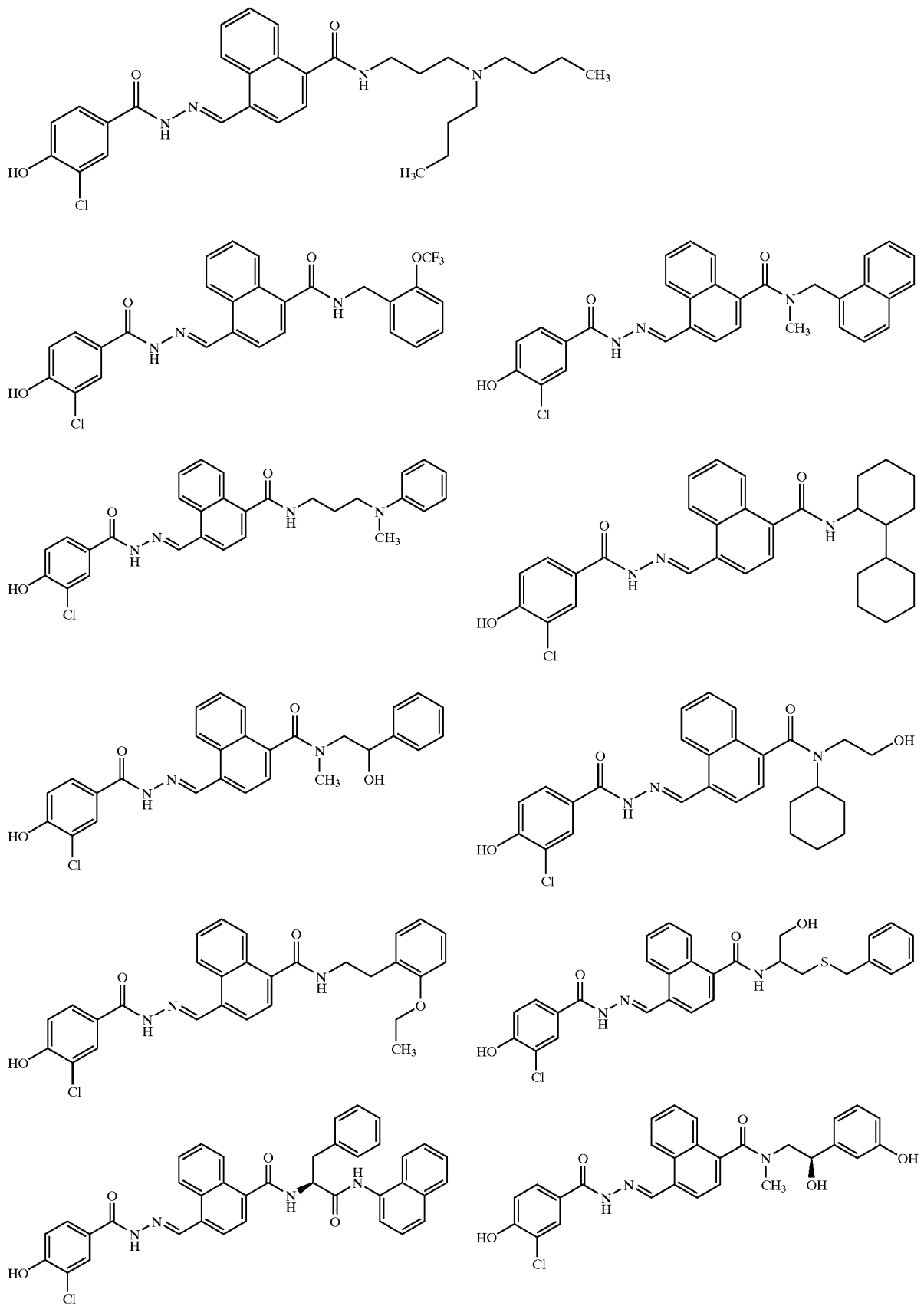

171 172
-continued
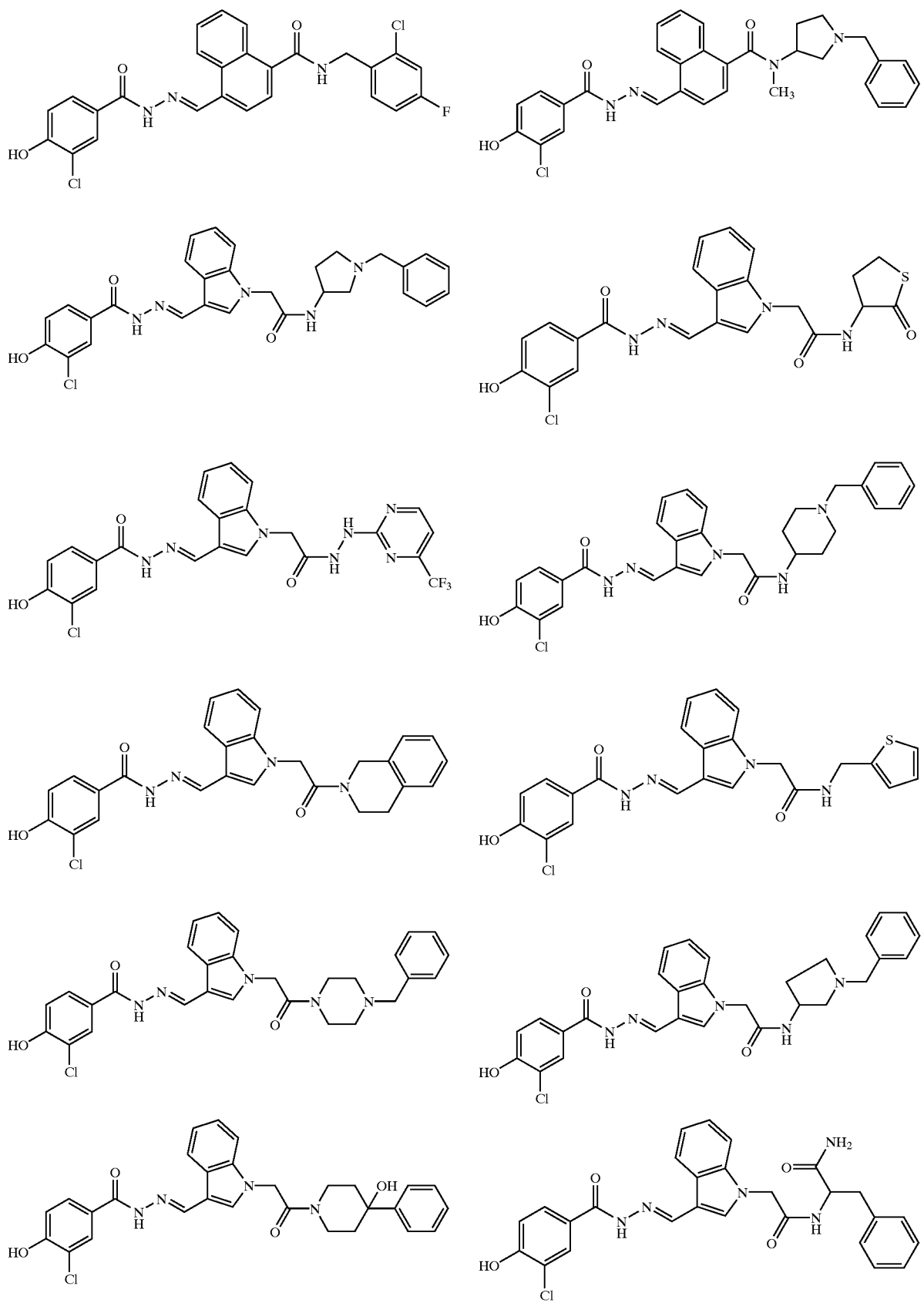

173 174
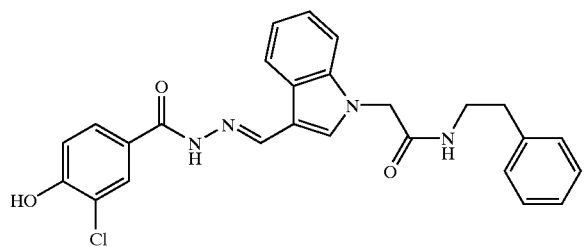
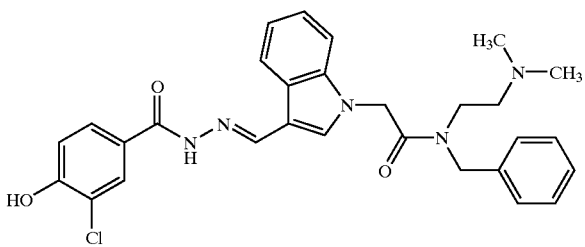
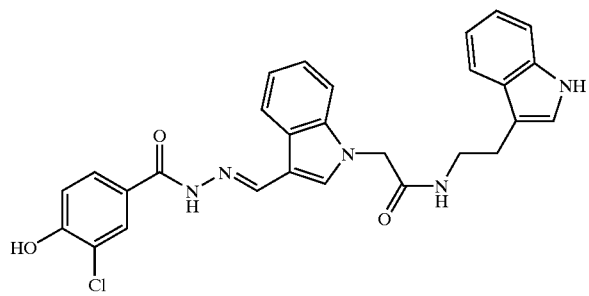
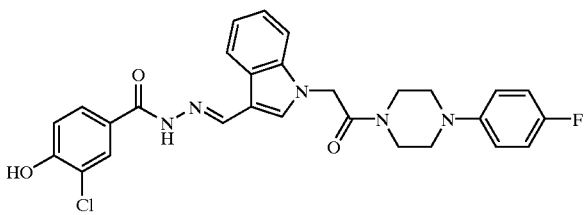
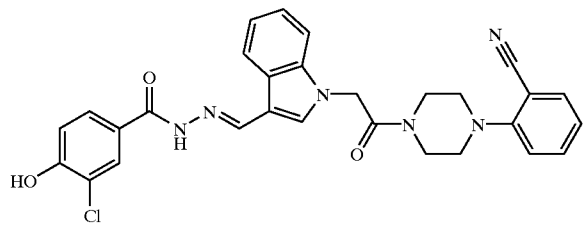
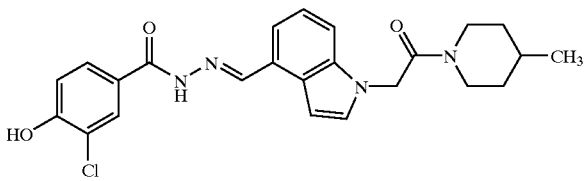
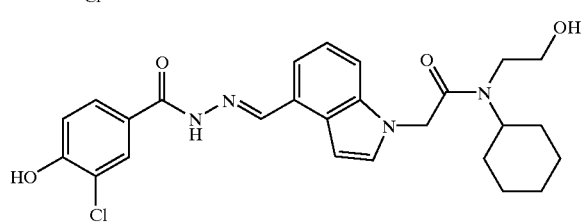
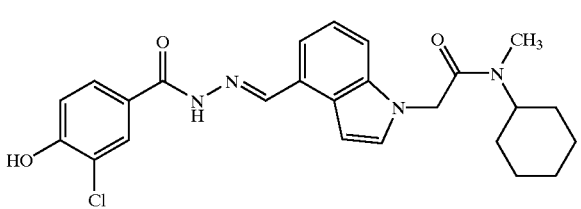
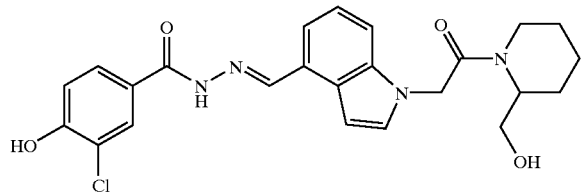
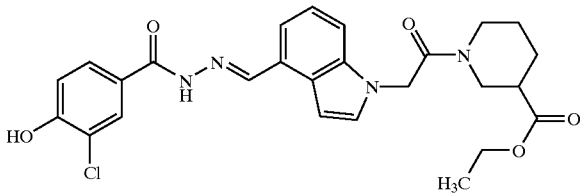
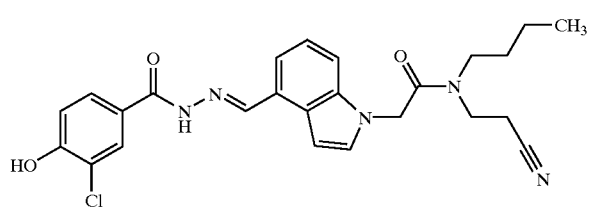
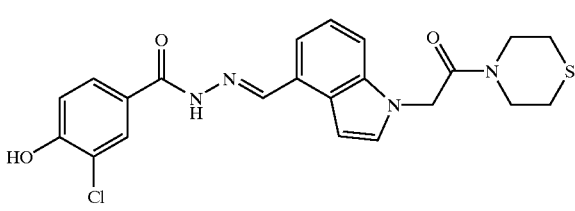
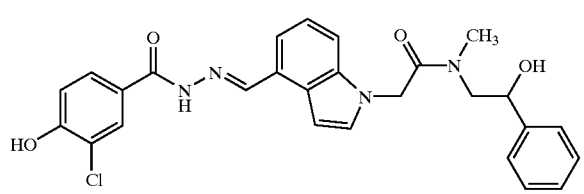
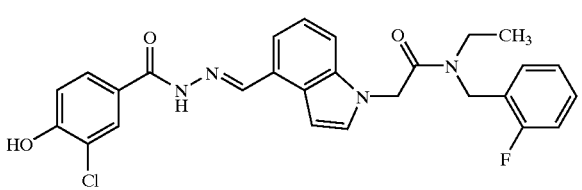

175 176
-continued
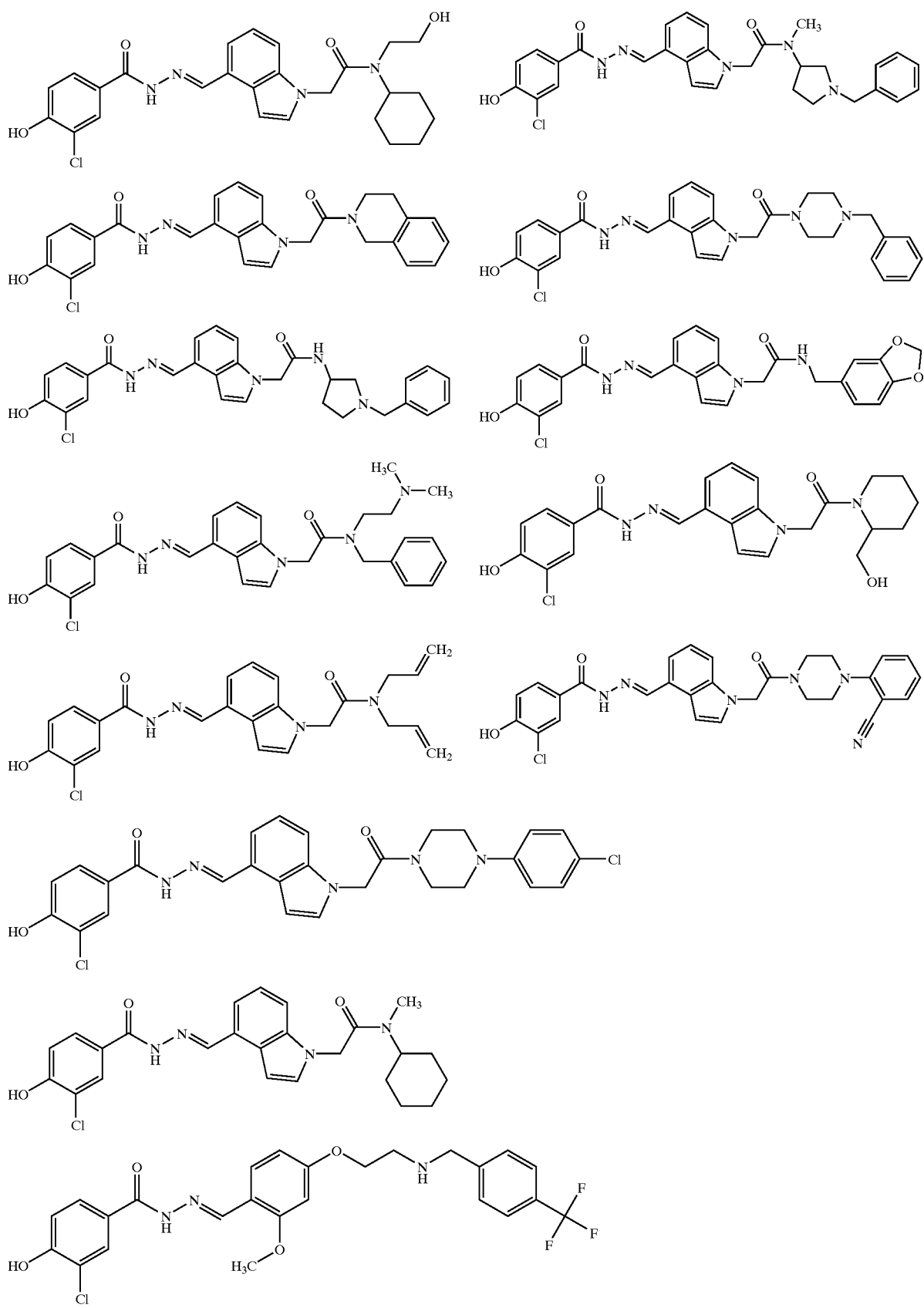

-continued
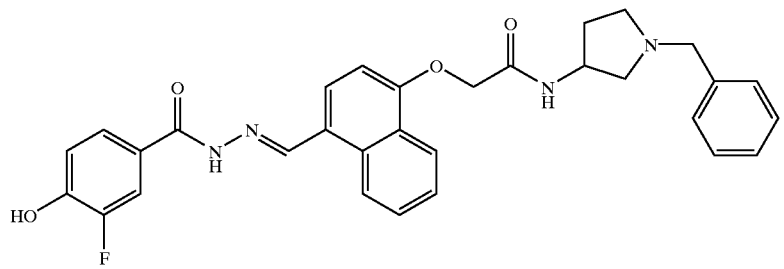
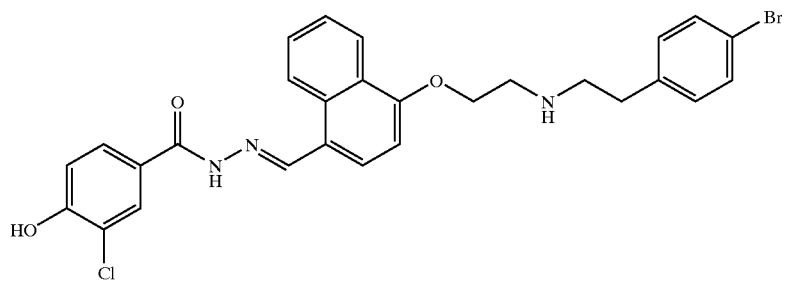
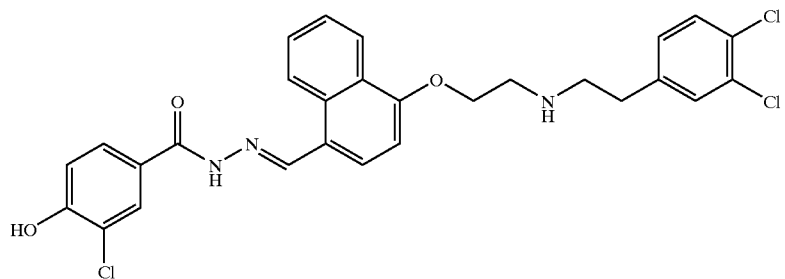
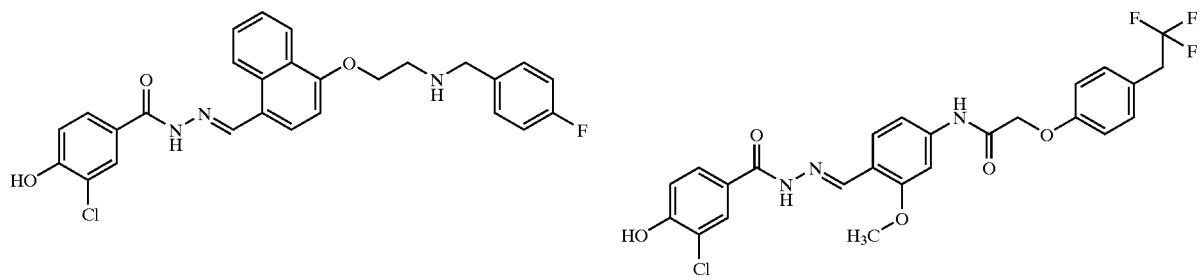
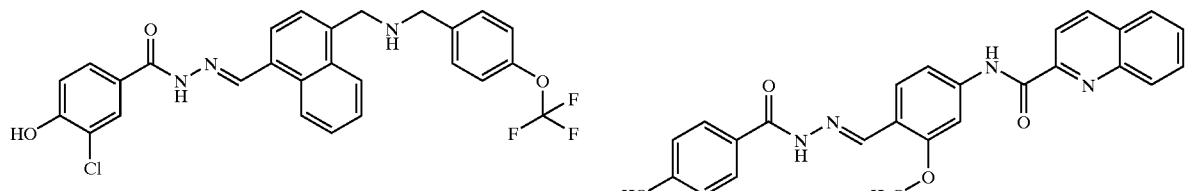
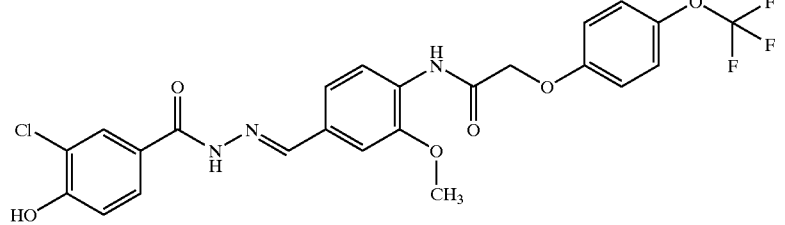

-continued
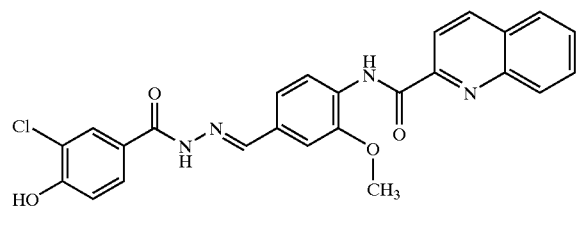
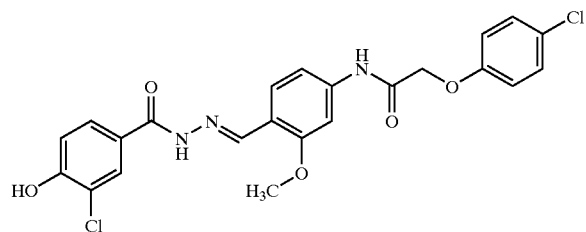
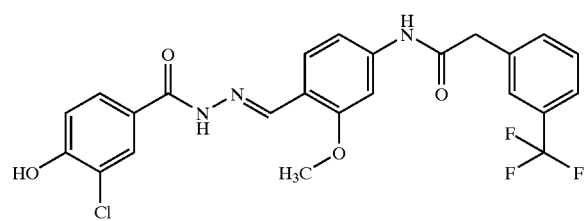
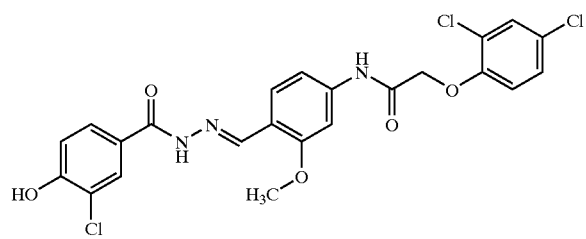
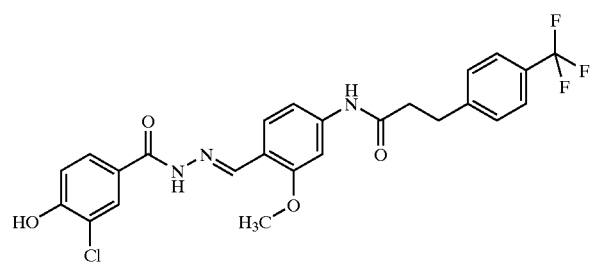
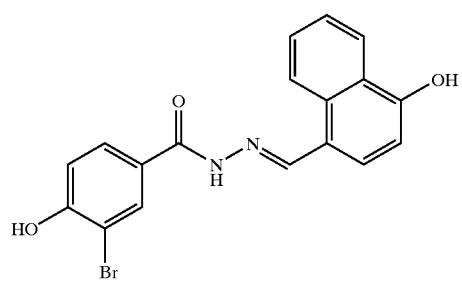
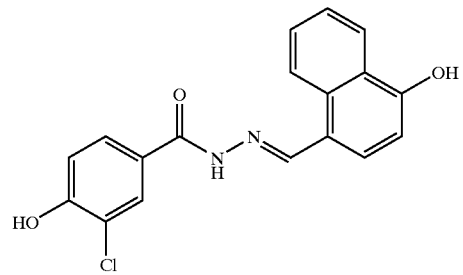
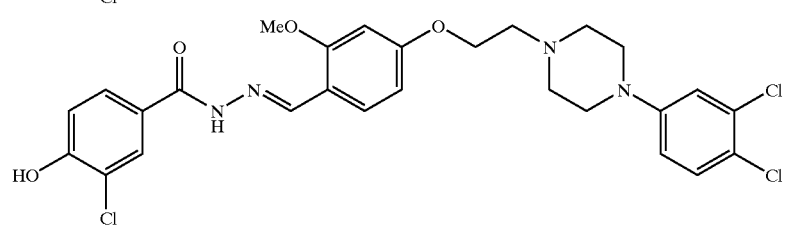
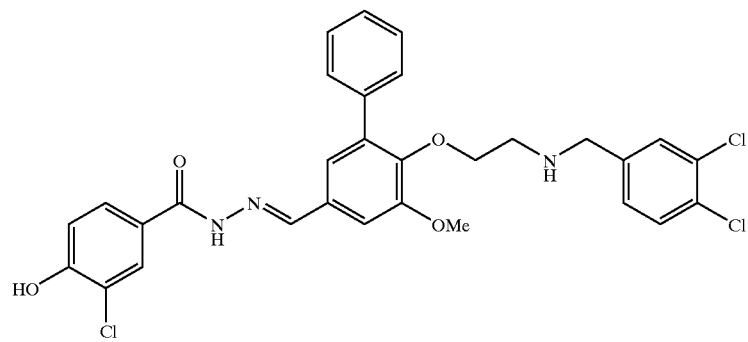

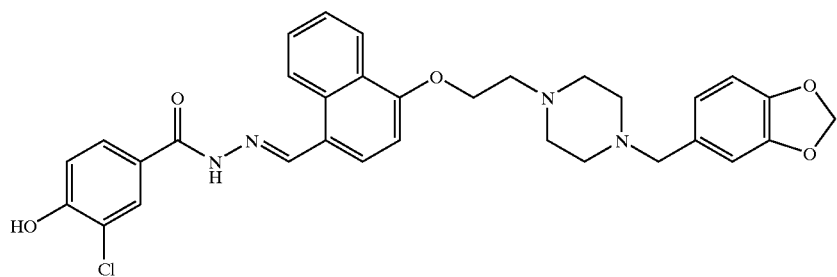
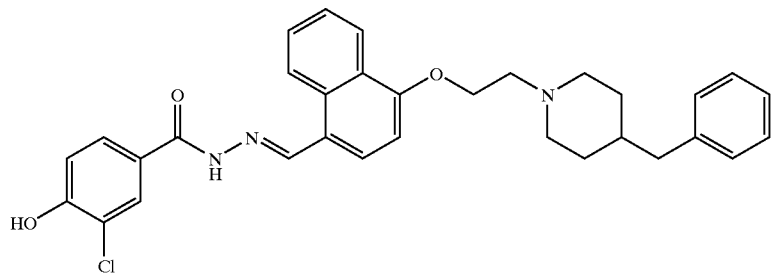
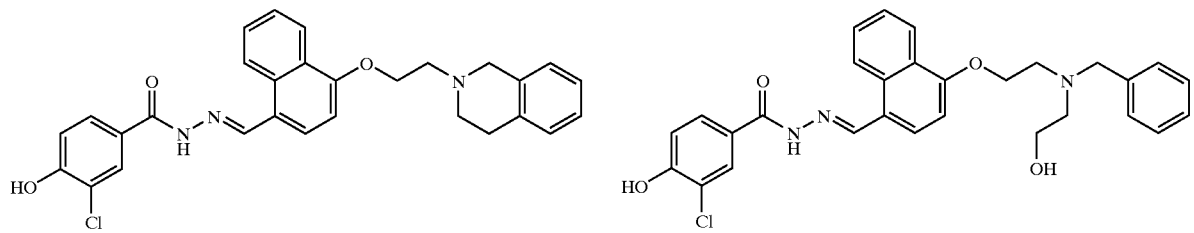
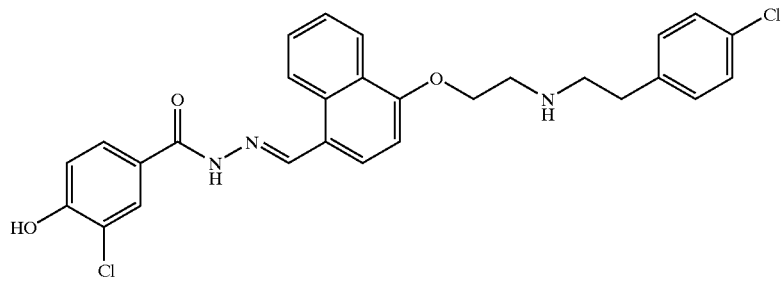
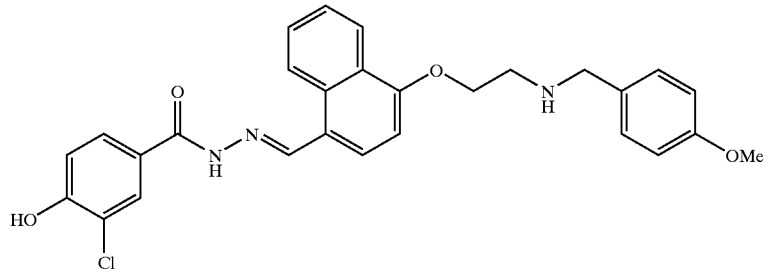
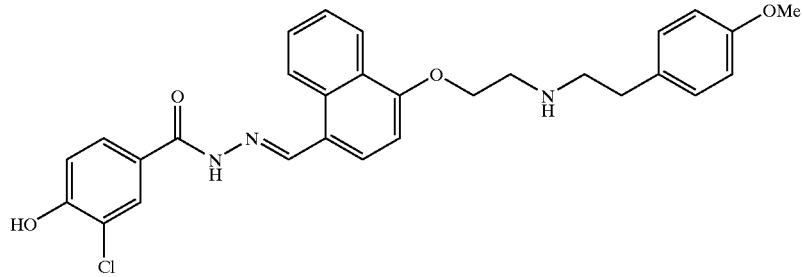

183 184
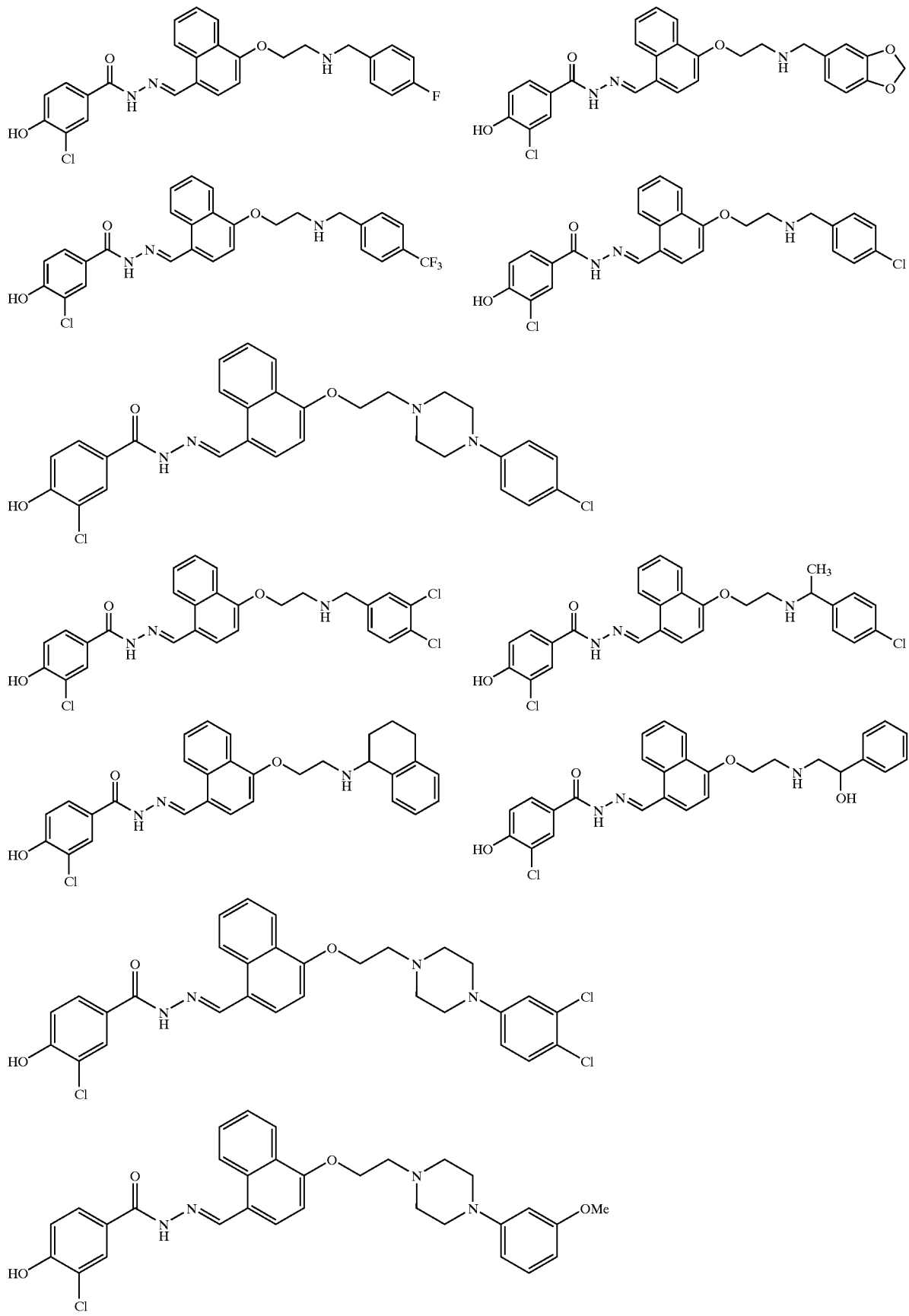
-continued

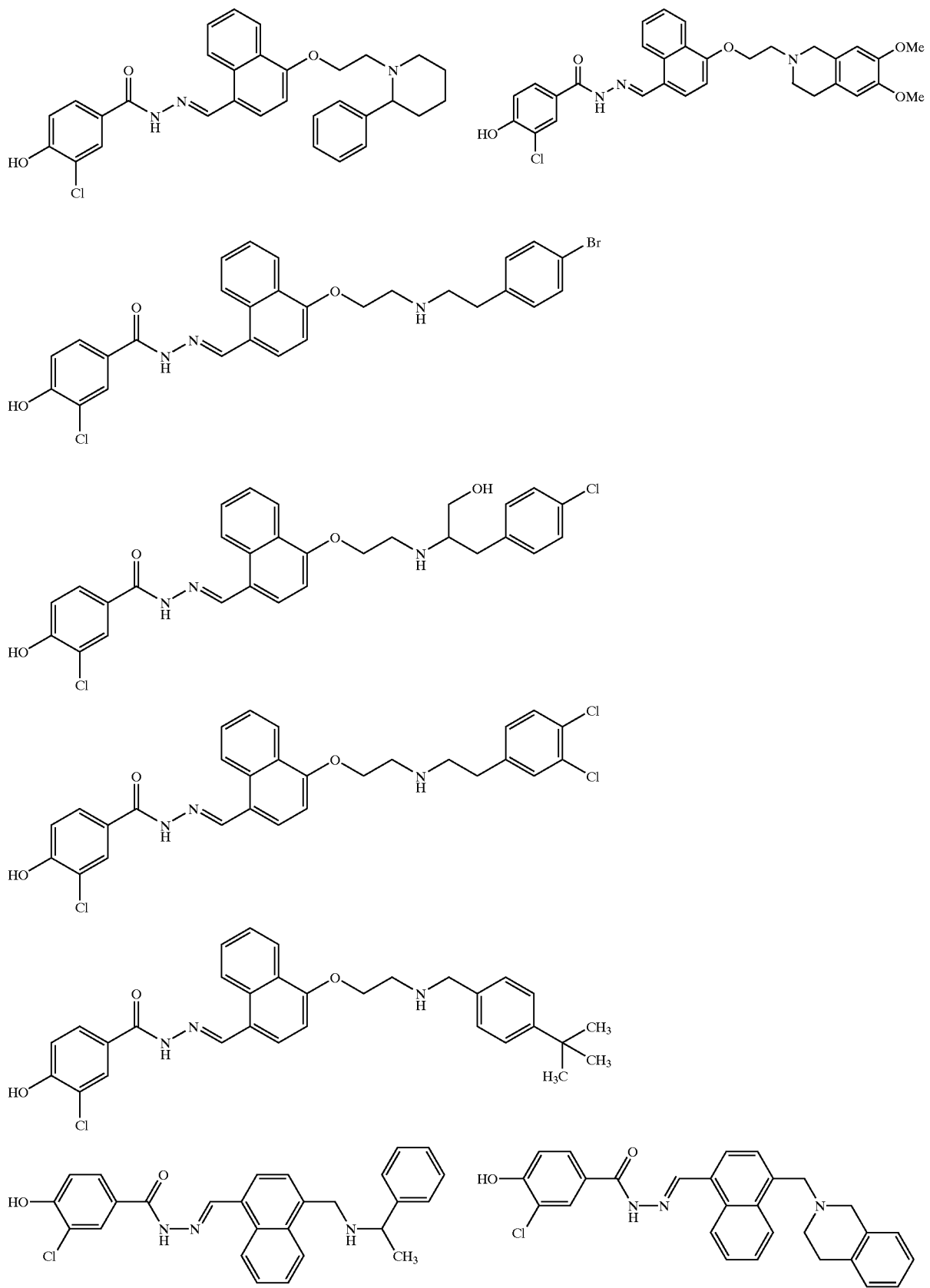

187   188
-continued
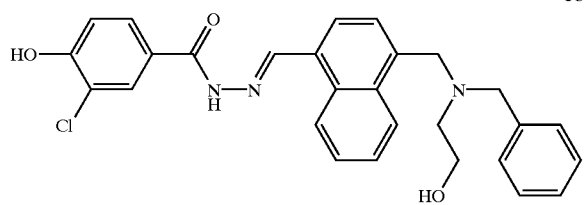
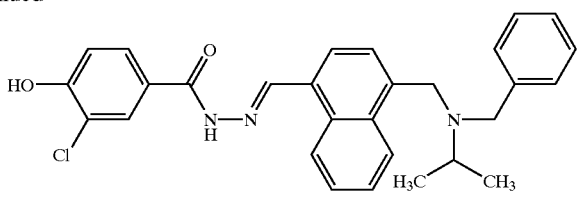
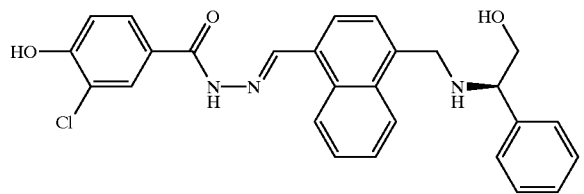
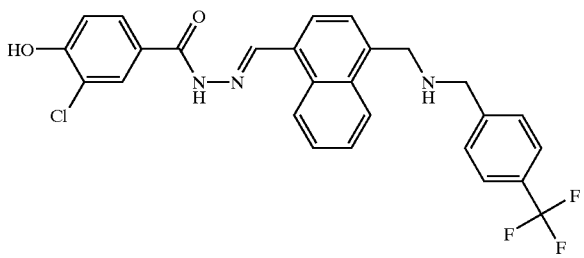
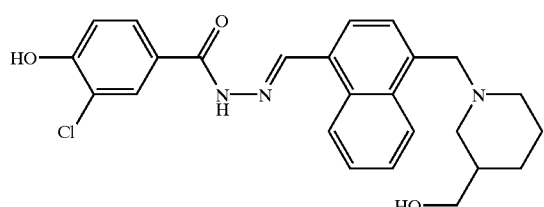
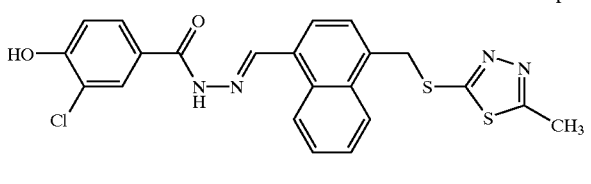
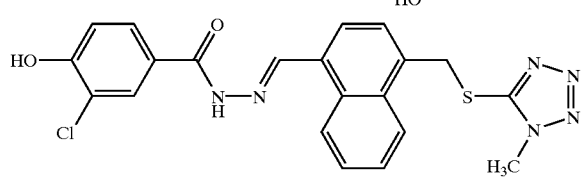
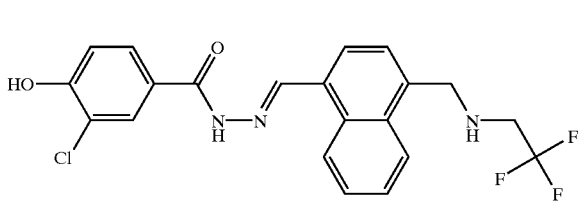
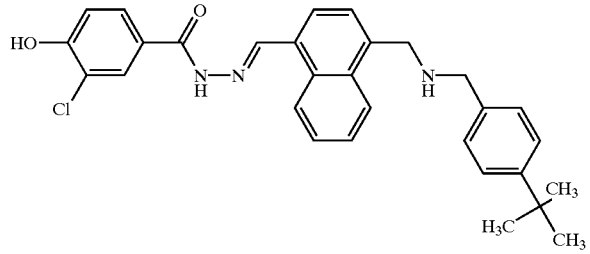
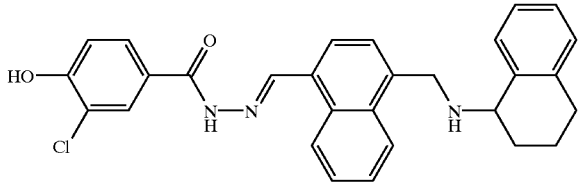
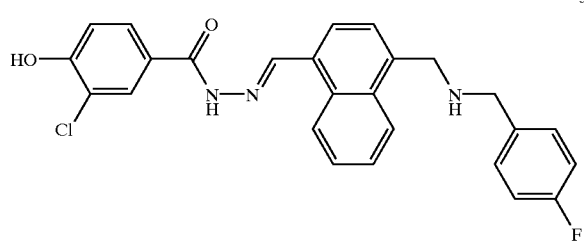
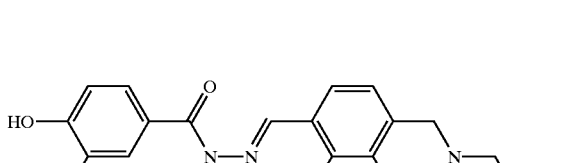
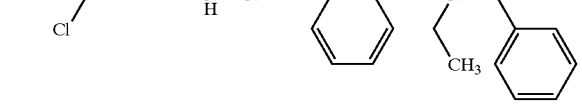
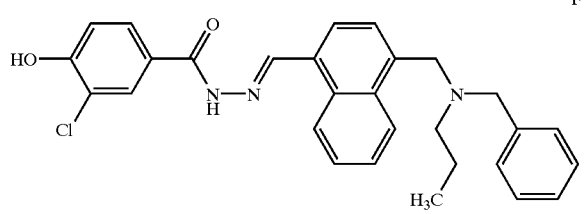
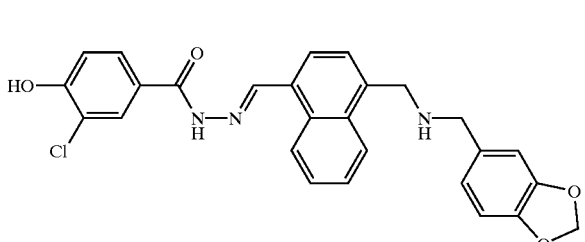
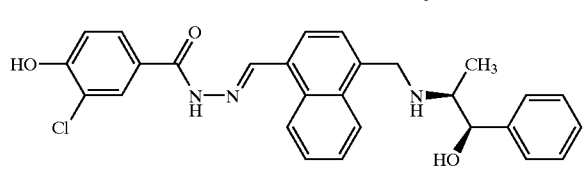
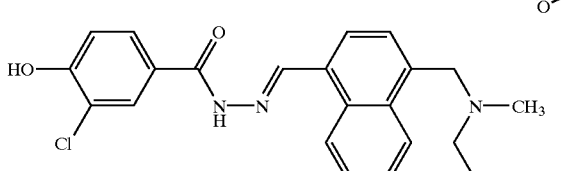

189
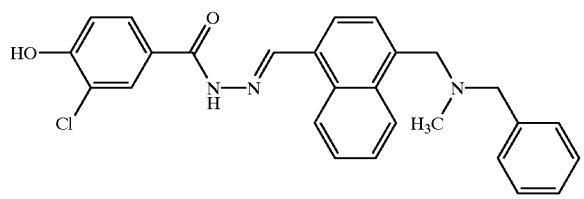
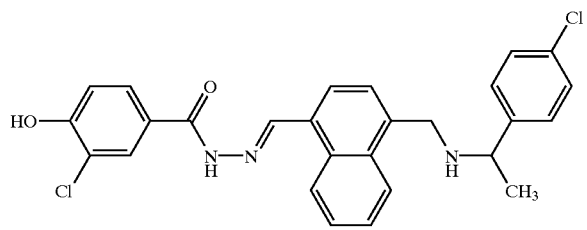
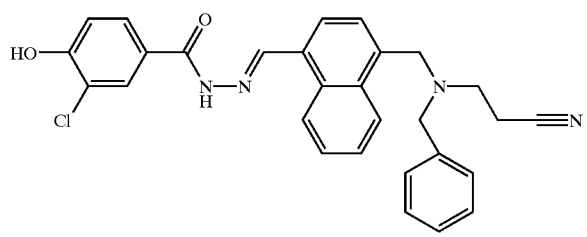
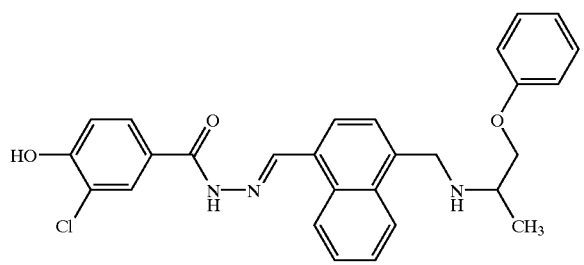
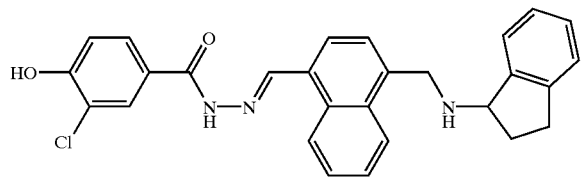
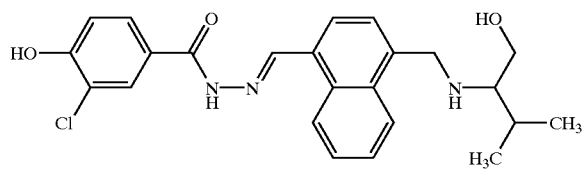
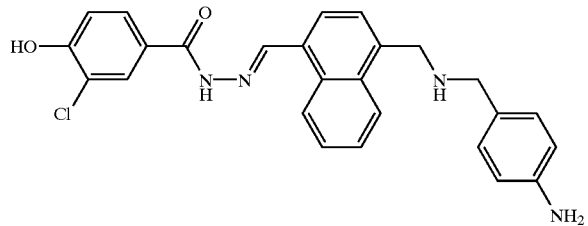
190
-continued
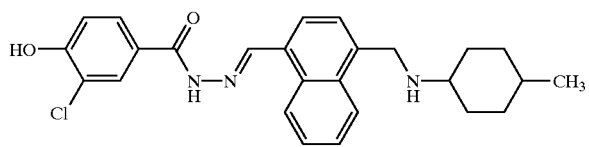
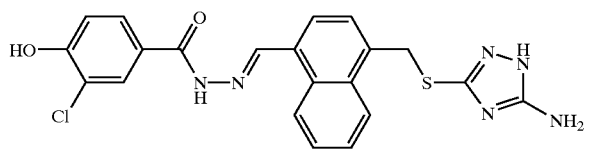
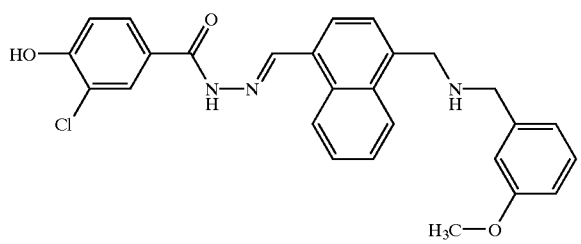
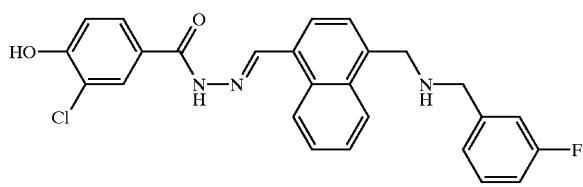
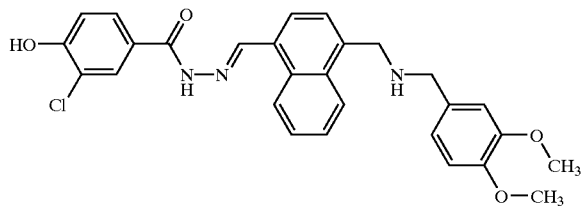
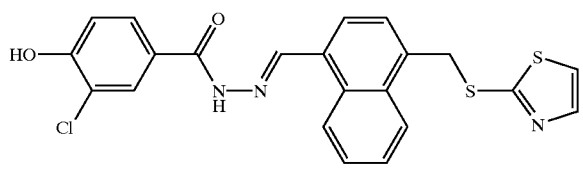
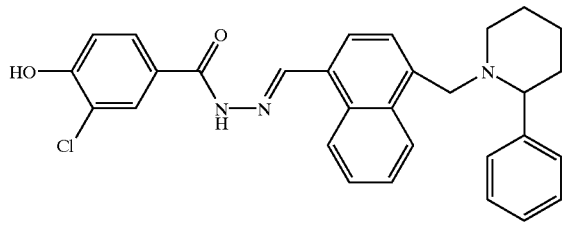

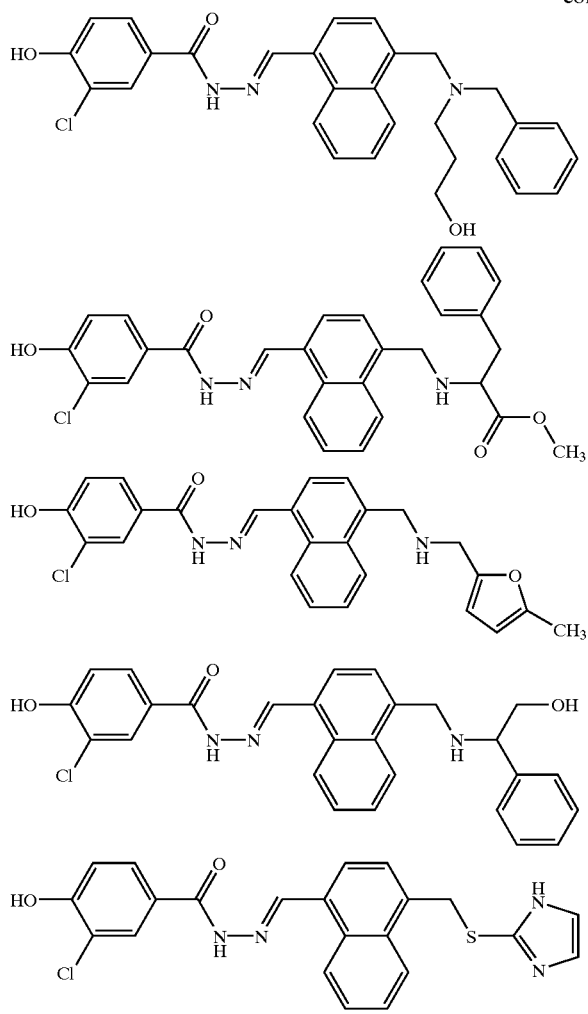
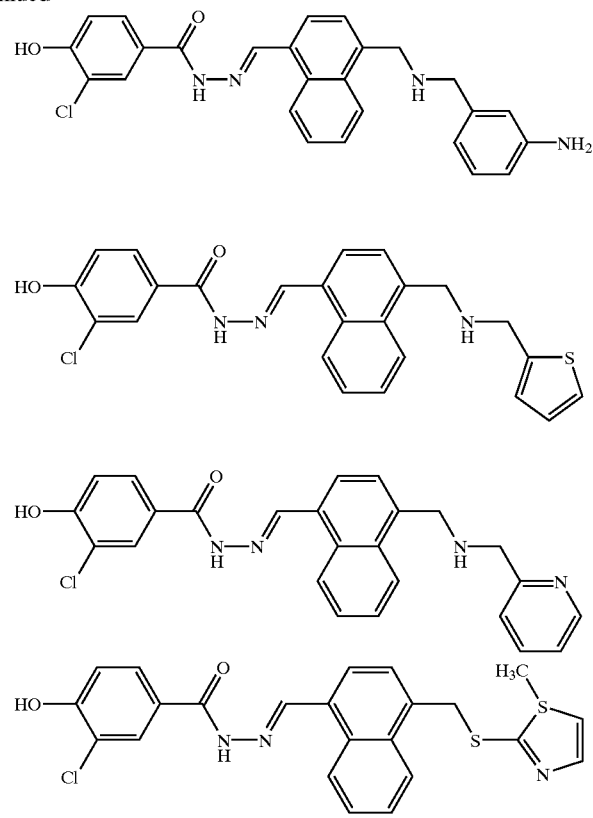

The compounds of the present invention may have one or more asymmetric centres and it is intended that any optical isomers, as separated, pure or partially purified optical isomers or racemic mixtures thereof are included in the scope of the invention.

Furthermore, one or more carbon-carbon or carbon-nitrogen double bonds may be present in the compounds which brings about geometric isomers. It is intended that any geometric isomers, as separated, pure or partially purified geometric isomers or mixtures thereof are included in the scope of the invention.

Furthermore, the compounds of the present invention may exist in different tautomeric forms, eg the following tautomeric forms:

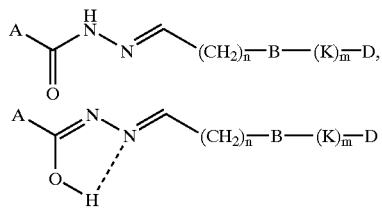

It is intended that any tautomeric forms which the compounds are able to form are included in the scope of the present invention.

Owing to their efficacy in antagonizing the glucagon receptor the present compounds may be suitable for the treatment and/or prevention of any glucagon-mediated conditions and diseases.

Accordingly, the present compounds may be applicable for the treatment of hyperglycemia associated with diabetes of any cause or associated with other diseases and conditions, eg impaired glucose tolerance, insulin resistance syndromes, syndrome X, type I diabetes, type II diabetes, hyperlipidemia, dyslipidemia, hypertriglyceridemia, glucagonomas, acute pancreatitis, cardiovascular diseases, cardiac hypertrophy, gastrointestinal disorders, diabetes as a consequence of obesity etc. Furthermore, they may be applicable as diagnostic agents for identifying patients having a defect in the glucagon receptor, as a therapy to increase gastric acid secretions, to reverse intestinal hypomobility due to glucagon administration, to reverse catabolism and nitrogen loss in states of negative nitrogen balance and protein wasting including all causes of type I and type II diabetes, fasting, AIDS, cancer, anorexia, aging and other conditions, for the treatment of any of the above conditions or diseases post-operative or during surgery and for decreasing saitety and increasing energy intake. Thus, in a further aspect the present invention relates to a pharmaceutical composition comprising, as an active ingredient, at least one compound according to the present invention together with one or more pharmaceutically acceptable carriers or excipients.

The present invention furthermore relates to methods of treating type I or type II diabetes or hyperglycemia which methods comprise administering to a subject in need thereof an effective amount of a compound according to the invention.

Moreover, the present invention relates to a method of lowering blood glucose in a mammal, comprising administering to said mammal an effective amount of a compound according to the invention.

The present invention is also concerned with the use of a compound according to the invention for the manufacture of a medicament for treating type I or type II diabetes or hyperglycemia, or for lowering blood glucose in a mammal.

Pharmaceutical Formulations and Administration Methods

The compounds according to the invention, which may also be referred to as an active ingredient, may be administered for therapy by any suitable route including oral, rectal, nasal, pulmonal, topical (including buccal and sublingual), transdermal, vaginal and parenteral (including subcutaneous, intramuscular, intravenous and intradermal), the oral route being preferred. It will be appreciated that the preferred route will vary with the condition and age of the recipient, the nature of the condition to be treated, and the chosen active ingredient.

The compounds of the invention are effective over a wide dosage range. A typical dosage is in the range of from 0.05 to about 1000 mg, preferably of from about 0.1 to about 500 mg, such as of from about 0.5 mg to about 250 mg for administration one or more times per day such as 1 to 3 times per day. It should be understood that the exact dosage will depend upon the frequency and mode of administration, the sex, age, weight and general condition of the subject treated, the nature and severity of the condition treated and any concomitant diseases to be treated as well as other factors evident to those skilled in the art.

The formulations may conveniently be presented in unit dosage form by methods known to those skilled in the art.

For parenteral routes, such as intravenous, intrathecal, intramuscular and similar administration, typically doses are on the order of about ½ the dose employed for oral administration.

The compounds of this invention are generally utilized as the free substance or as a pharmaceutically acceptable salt thereof. One example is an acid addition salt of a compound having the utility of a free base. When a compound of formula I contains a free base such salts are prepared in a conventional manner by treating a solution or suspension of a free base of formula I with a chemical equivalent of a pharmaceutically acceptable acid, for example, inorganic and organic acids, for example: maleic, fumaric, benzoic, ascorbic, pamoic, succinic, bismethylene salicylic, methanesulfonic, ethanedisulfonic, acetic, oxalic, propionic, tartaric, salicylic, citric, pyruvic, gluconic, lactic, malic, mandelic, cinnamic, citraconic, aspartic, stearic, palmitic, EDTA, glycolic, p-aminobenzoic, glutamic, benzenesulfonic, p-toluensulfonic, hydrochloric, hydrobromic, sulfuric, phosphoric or nitric acids. Physiologically acceptable salts of a compound with a hydroxy group include the anion of said compound in combination with a suitable cation such as sodium or ammonium ion.

The compounds of the invention may be administered alone or in combination with pharmaceutically acceptable carriers, in either single or multiple doses.

For parenteral administration, solutions of the novel compounds of formula I in sterile aqueous solution, aqueous propylene glycol or sesame or peanut oil may be employed. Such aqueous solutions should be suitable buffered if necessary and the liquid diluent first rendered isotonic with sufficient saline or glucose. The aqueous solutions are particularly suitable for intravenous, intramuscular, subcutaneous and intraperitoneal administration. The sterile aqueous media employed are all readily available by standard techniques known to those skilled in the art. Suitable pharmaceutical carriers include inert solid diluents or fillers, sterile aqueous solution and various organic solvents. Examples of solid carriers are lactose, terra alba, sucrose, cyclodextrin, talc, gelatin, agar, pectin, acacia, magnesium stearate, stearic acid or lower alkyl ethers of cellulose. Examples of liquid carriers are syrup, peanut oil, olive oil, phospholipids, fatty acids, fatty acid amines, polyoxyethylene or water. Similarly, the carrier or diluent may include any sustained release material known in the art, such as glyceryl monostearate or glyceryl distearate, alone or mixed with a wax. The pharmaceutical compositions formed by combining the novel compounds of formula I and the pharmaceutically acceptable carriers are then readily administered in a variety of dosage forms suitable for the disclosed routes of administration. The formulations may conveniently be presented in unit dosage form by methods known in the art of pharmacy.

Formulations of the present invention suitable for oral administration may be presented as discrete units such as capsules or tablets, each containing a predetermined amount of the active ingredient, and which may include a suitable excipient. These formulations may be in the form of powder or granules, as a solution or suspension in an aqueous or non-aqueous liquid, or as an oil-in-water or water-in-oil liquid emulsion.

If a solid carrier is used for oral administration, the preparation may be tabletted, placed in a hard gelatin capsule in powder or pellet form or it can be in the form of a troche or lozenge. The amount of solid carrier will vary widely but will usually be from about 25 mg to about 1 g.

If a liquid carrier is used, the preparation may be in the form of a syrup, emulsion, soft gelatin capsule or sterile injectable liquid such as an aqueous or non-aqueous liquid suspension or solution.

A typical tablet which may be prepared by conventional tabletting techniques may contain:

| Core: | |
|---|---|
| Active compound (as free compound or salt thereof) | 100 mg |
| Colloidal silicon dioxide (Aerosil) | 1.5 mg |
| Cellulose, microcryst. (Avicel) | 70 mg |
| Modified cellulose gum (Ac-Di-Sol) | 7.5 mg |
| Magnesium stearate | |
| Coating: | |
| HPMC approx. | 9 mg |
| *Mywacett 9-40 T approx. | 0.9 mg |

*Acylated monoglyceride used as plasticizer for film coating.

For nasal administration, the preparation may contain a compound of formula I dissolved or suspended in a liquid carrier, in particular an aqueous carrier, for aerosol application. The carrier may contain additives such as solubilizing agents, e.g. propylene glycol, surfactants, absorption enhancers such as lecithin (phosphatidylcholine) or cyclodextrin, or preservatives such as parabenes.

Optionally, the pharmaceutical composition of the invention may comprise a compound of formula I combined with one or more other pharmacologically active compounds, e.g. an antidiabetic or other pharmacologically active material, including compounds for the treatment and/or prophylaxis of insulin resistance and diseases wherein insulin resistance is the patophysiological mechanism. Suitable antidiabetics comprise insulin, GLP-1 derivatives such as those disclosed in WO 98/08871 (Novo Nordisk A/S) which is incorporated herein by reference as well as orally active hypoglycaemic agents such as sulphonylureas, e.g. glibenclamide and glipizide; biguanides, e.g. metformin; benzoic acid derivatives, e.g. repaglinide; and thiazolidinediones, e.g. troglitazone and ciglitazone, as well as PPAR and RXR agonists.

Experimental

Glucagon Binding

In the following section binding assays as well as functional assays useful for evaluating the efficacy of the compounds of the invention are described.

Glucagon Binding Assay (I)

Binding of compounds to the glucagon receptor was determined in a competition binding assay using the cloned human glucagon receptor.

In the screening setup, antagonism was determined as the ability of the compounds to inhibit the amount of cAMP formed in the presence of 5 nM glucagon.

For full characterization, antagonism was determined in a functional assay, measured as the ability of the compounds to right-shift the glucagon dose-response curve. Using at least 3 different antagonist concentrations, the $K_i$ was calculated from a Schild plot. Receptor binding was assayed using cloned human receptor (Lok et al, Gene 140, 203–209 (1994)). The receptor inserted in the pLJ6' expression vector using EcoRI/SSt1 restriction sites (Lok et al) was expressed in a baby hamster kidney cell line (A3 BHK 570-25). Clones were selected in the presence of 0.5 mg/ml G-418 and were shown to be stable for more than 40 passages. The $K_d$ was shown to be 0.1 nM.

Plasma membranes were prepared by growing cells to confluence, detaching them from the surface and resuspending the cells in cold buffer (10 mM tris/HCl), pH 7.4 containing 30 mM NaCl, 1 mM dithiothreitol, 5 mg/l leupeptin (Sigma), 5 mg/l pepstatin (Sigma), 100 mg/l bacitracin (Sigma) and 15 mg/l recombinant aprotinin (Novo Nordisk)), homogenization by two 10-s bursts using a Polytron PT 10-35 homogenizer (Kinematica), and centrifugation upon a layer of 41 w/v % sucrose at 95.000*g for 75 min. The white band located between the two layers was diluted in buffer and centrifuged at 40.000*g for 45 min. The precipitate containing the plasma membranes was suspended in buffer and stored at −80° C. until required.

Glucagon was iodinated according to the chloramine T method (Hunter and Greenwood, Nature 194, 495 (1962)) and purified using anion exchange chromatography (Jørgensen et al, Hormone and Metab. Res. 4, 223–224 (1972). The specific activity was 460 μCi/μg on day of iodination. Tracer was stored at −18° C. in aliquots and were used immediately after thawing.

Binding assays were carried out in triplicate in filter microtiter plates (MADV N65, Millipore). The buffer used in this assay was 25 mM HEPES pH 7.4 containing 0.1% human serum albumin (Sigma, grade V). Glucagon was dissolved in 0.05 M HCl, added equal amounts(w/w) of HSA and freeze-dried. On the day of use, it was dissolved in water and diluted in buffer to the desired concentrations.

175 μl of sample (glucagon or test compounds) was added to each well. Tracer (50.000 cpm) was diluted in buffer and 15 μl was added to each well. 0.5 μg freshly thawed plasma membrane protein diluted in buffer was then added in 15 μl to each well. Plates were incubated at 25° C. for 2 hours. Non specific binding was determined with $10^{-6}$ M glucagon. Bound and unbound tracer were then separated by vacuum filtration (Millipore vacuum manifold). The plates were washed once with 150 μl buffer/well. The plates were air dried for a couple of hours, whereafter filters were separated from the plates using a Millipore Puncher. The filters were counted in a γ counter.

Functional Assay (I)

The functional assay was carried out in 96 well microtiter plates (tissue culture plates, Nunc). The resulting buffer concentrations in the assay were 50 mM tris/HCl, 1 mM EGTA, 1.5 mM $MgSO_4$, 1.7 mM ATP, 20 μM GTP, 2 mM IBMX, 0.02% tween-20 and 0.1% HSA. pH was 7.4 Glucagon and proposed antagonist were added in 35 μl diluted in 50 mM tris/HCl, 1 mM EGTA, 1.85 mM $MgSO_4$, 0.0222% tween-20 and 0.111% HSA, pH 7.4. 20 μl of 50 mM tris/HCl, 1 mM EGTA, 1.5 mM $MgSO_4$, 11.8 mM ATP, 0.14 mM GTP, 14 mM iso-buthyl-methylxanthine (IBMX) and 0.1% HSA, pH 7.4 was added. GTP was dissolved immediately before the assay.

50 μl containing 5 μg plasma membrane protein was added in a tris/HCl, EGTA, $MgSO_4$, HSA buffer (the actual concentrations were dependent upon the concentration of protein in the stored plasma membranes).

The total assay volume was 140 μl. The assay was incubated for 2 hours at 37° C. with continuous shaking. Reaction was terminated by addition of 25 μl 0.5 N HCl. cAMP was measured by the use of a scintillation proximity kit (Amersham).

Glucagon Binding Assay (II)

Receptor binding was assayed using the cloned human receptor (Lok et al, Gene 140, 203–209 (1994)). The receptor inserted in the pLJ6' expression vector using EcoRI/SSt1 restriction sites (Lok et al) was expressed in a baby hamster kidney cell line (A3 BHK 570–25). Clones were selected in the presence of 0.5 mg/ml G-418 and were shown to be stable for more than 40 passages. The Kd was shown to be 0.1 nM.

Plasma membranes were prepared by growing cells to confluence, detaching them from the surface and resuspending the cells in cold buffer (10 mM tris/HCl), pH 7.4 containing 30 mM NaCl, 1 mM dithiothreitol, 5 mg/l leupeptin Sigma), 5 mg/l pepstatin (Sigma), 100 mg/l bacitracin (Sigma) and 15 mg/l recombinant aprotinin (Novo Nordisk)), homogenization by two 10-s bursts using a Polytron PT 10–35 homogenizer (Kinematica), and centrifugation. The homogenate was resuspended and centrifuged again. The final precipitate containing the plasma membranes was suspended in buffer and stored at −80° C. until required.

Binding assays were carried out in duplicate in polypropylene tubes or microtiter plates. The buffer used in this assay was 25 mM HEPES pH 7.4 containing 0.1% bovine serum albumin (Sigma, fraction V). Sample (glucagon (Bachem CA) or test compounds) was added to each tube or well. Tracer (~25000 cpm) was diluted in buffer and was added to each tube or well. 0.5 μg freshly thawed plasma membrane protein diluted in buffer was then added in aliquots to each tube or well. Tubes or plates were incubated at 37° C. for 1 hour. Non specific binding was determined with $10^{-7}$ M glucagon. Bound and unbound tracer were then separated by vacuum filtration (Brandel). The tubes or wells were washed twice with buffer. The filters or plates were counted in a gamma counter.

Functional Assay (II)

The functional assay determined the ability of the compounds to antagonize glucagonstimulated formation of cAMP in a whole-cell assay. The assay was carried out in borosilicate 5 glass 12×75 tubes. The buffer concentrations in the assay were 10 mM HEPES, 1 mM EGTA, 1.4 mM $MgCl_2$, 0.1 mM IBMX, 30 mM NaCl, 4.7 mM KCl, 2.5 mM $NaH_2PO_4$, 3mM glucose and 0.2% BSA. The pH was 7.4. Loose whole cells (0.5 ml, $10^6$/ml) were pretreated with various concentrations of compounds for 10 min at 37° C., then challenged with glucagon for 20 min. Some aliquots (500 μL) of cells were treated with test compounds (55 μL) alone to test for agonist activity. The reactions were terminated by centrifugation, followed by cell lysis with the addition of 500 μl 0.1% HCl. Cellular debris was pelleted and the supernatant containing cAMP evaporated to dryness. cAMP was measured by the use of an RIA kit (NEN, NEK-033). Some assays were carried out utilizing the adenylate cyclase FlashPlate system from NEN.

Synthesis Methods

The following synthesis protocols refer to intermediate compounds and final products identified in the specification and in the synthetic schemes. The preparation of the compounds of the present invention is described in detail using the following examples, but the chemical reactions described are disclosed in terms of their general applicability to the preparation of the glucagon antagonists of the invention. Occasionally, the reaction may not be applicable as described to each compound included within the disclosed scope of the invention. The compounds for which this occurs will be readily recognized by those skilled in the art. In all such cases, either the reactions can be successfully performed by conventional modifications known to those skilled in the art, that is, by appropriate protection of interfering groups, by changing to other conventional reagents, or by routine modification of reaction conditions. Alternatively, other reactions disclosed herein or otherwise conventional will be applicable to the preparation of the corresponding compounds of the invention. In all preparative methods, all starting materials are known or readily preparable from known starting materials. All temperatures are set forth in degrees Celsius and unless otherwise indicated, all parts and percentages are by weight when referring to yields and all parts are by volume when referring to solvents and eluents.

General Procedures for the Preparation of Alkylidene Hydrazides

The compounds of general formula I may be prepared according to one embodiment of the invention, the alkylidene hydrazides of general formula II, as indicated in Scheme I, that is, by converting an ester of a carboxylic acid, for example, an aromatic acid to a hydrazide derivative and further reacting that product compound with a substituted aldehyde or ketone to yield a substituted alkylidene hydrazide.

SCHEME I

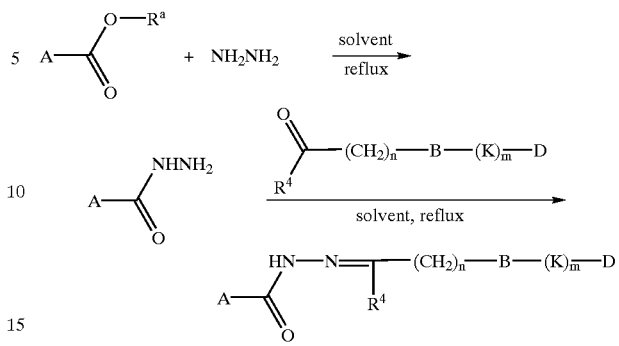

wherein A, B, K, D, m, n and $R^4$ are as defined for formula I and $R^3$ is lower alkyl.

General Procedure for the Synthesis of Precursor Hydrazides A—(C=O)—$NHNH_2$

The reaction is known (Org. Syn., Coll. Vol. II, A. H. Blatt, ed., John Wiley & Sons, New York, 1943, p. 85; Org. Syn., Coll. Vol. IV, N. Rabjohn, ed., John Wiley & Sons, New York, 1963, p. 819) and is generally performed by stirring the corresponding ester (either methyl, ethyl or other lower alkyl ester) with 2–10 molar excess of hydrazine in the presence of a solvent such as ethyl alcohol, methyl alcohol, isopropyl or tert-butyl alcohol or tetrahydrofuran, dioxane, DMSO, ethylene glycol, ethylene glycol dimethyl ester, benzene, toluene or a mixture of the above solvents or, in the absence of a solvent where excess of hydrazine acts as a solvent. The reactions are performed between 0° C. to 130° C., preferably between 20° C. to 10° C., most preferably at or about the reflux temperature of the solvent. The reactions are preferably conducted under an inert atmosphere such as $N_2$ or Ar. When the reaction is complete as judged by disappearance of the starting ester by TLC or HPLC, the solvent may be removed by concentration at atmospheric or reduced pressure.

The product can be further purified by either recrystallization from a solvent such as ethyl alcohol, methyl alcohol, isopropyl alcohol, toluene, xylene, hexane, tetrahydrofuran, diethyl ether, dibutyl ether, water or a mixture of two or more of the above. Alternatively, the product can be purified by column chromatography using dichloromethane/methanol or chloroform/methanol or isopropyl alcohol as eluent. The corresponding fractions are concentrated either at atmospheric pressure or in vacuo to provide the pure aroyl hydrazide.

Preparation of Aromatic Acid Hydrazides

The methyl or ethyl ester of the corresponding aromatic acid, such as for example a substituted benzoic acid ester, is dissolved in ethanol and hydrazine (5 eq) is added. The reaction is refluxed overnight under nitrogen. Upon cooling the substituted hydrazide derivative usually precipitates. After filtration the product is usually recrystallized from hot methanol, ethanol or isopropyl alcohol. In cases where the hydrazide does not precipitate, the reaction is concentrated under vacuo and chromatographed over silica gel using dichloromethane/methanol as the eluent. Specific examples illustrating the preparation of aromatic hydrazides are provided below.

Preparation of 5-Hydroxyindole-2-carboxylic Acid Hydrazide

To a sample of ethyl 5-hydroxyindole-2-carboxylate (5 g, 24 mmol), dissolved in ethanol (250 mL) was added hydrazine (4 mL, 121 mmol). The reaction was refluxed overnight under nitrogen. Upon cooling the reaction vessel, the desired product crystallized. The white solid was isolated by filtration. Recrystallization from hot ethanol gave the 5-hydroxyindole-3-carboxylic acid hydrazide in 85% yield.

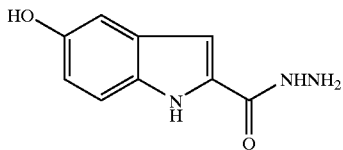

$^1$H NMR (DMSO-d$_6$): δ 4.38 (s, 2H); 6.62 (dd, 1H); 6.76 (dd, 2H); 7.13 (d, 1H); 8.70 (s, 1H); 9.57 (s, 1H); 11.21 (s, 1H); MS (FAB): m/z 192 (M+H)$^+$.

Preparation of 3-Chloro-4-hydroxybenzoic Acid Hydrazide

To a sample of methyl 3-chloro-4-hydroxybenzoate (2 g) dissolved in ethanol (50 mL) was added hydrazine (1.8 mL). The reaction was refluxed overnight under nitrogen. Upon cooling the reaction vessel, the desired product crystallized out of solution. The white solid was isolated by filtration. Recrystallization from hot ethanol gave the 3-chloro-4-hydroxybenzoic acid hydrazide in 60% yield.

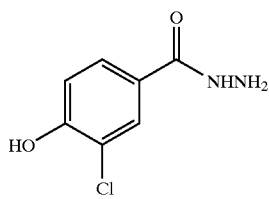

$^1$H NMR (DMSO-d$_6$): δ 4.49 (broad s, 2H), 7.05 (dd, 1H), 7.71 (dd, 1H), 7.89 (d, 1H), 9.669 (s, 1H), 10.72 (broad s, 1H).

By use of the above methodology, other hydrazides useful as intermediates in preparing the compounds of the invention are prepared, for example:

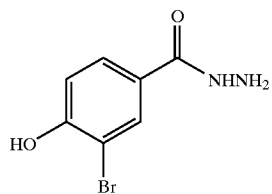

3-Bromo-4-hydroxybenzoic Acid Hydrazide
$^1$H NMR (DMSO-d$_6$): δ 9.95 (s, 1H), 9.65 (d, 1H), 9.61 (broad s, 1H), 6.95 (d, 1H), 4.40 (broad s, 2H); MS m/z 233.1.

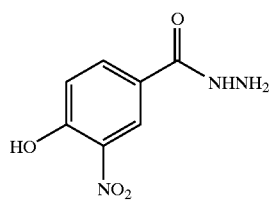

3-Nitro-4-hydroxybenzoic Acid Hydrazide
$^1$H NMR (DMSO-d$_6$): δ 9.28 (broad s, 1H), 8.28 (s, 1H), 7.52 (d, 1H), 6.41 (d, 1H). MS m/z 198.

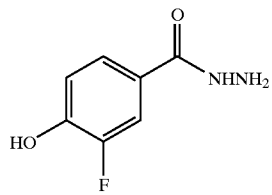

3-Fluoro-4-hydroxybenzoic Acid Hydrazide
$^1$H NMR (DMSO-d$_6$): δ 9.45 (broad s, 1H), 7.5 (d, 1H), 7.43 (d, 1H), 6.85 (t, 1H), 5.55 (broad s, 3H).

Preparation of 2-Chloro-4-hydroxybenzoic Acid Hydrazide, 2,3-Dichloro-4-hydroxybenzoic Acid Hydrazide and 2,5-Dichloro-4-hydroxybenzoic Acid Hydrazide

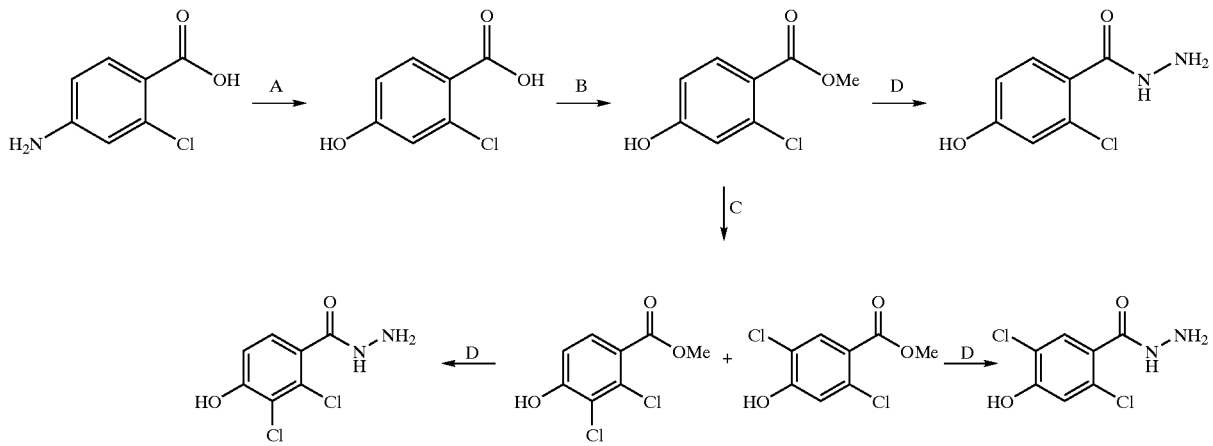

Preparation of 2-Chloro-4-hydroxybenzoic Acid Hydrazide

Step A:

4-amino-2-chlorobenzoic acid (10 g, 58 mmol) was dissolved in $H_2SO_4$ (12 N, 120 mL) with heating. After cooling the solution in an ice-bath aqueous $NaNO_2$ (2.5 M, 25 mL) was added dropwise such that the internal temperature remained at 5° C. Urea was added to the mixture for after stirring for 15 minutes to destroy excess $NaNO_2$ (monitored by starch iodine test). $CuSO_4$ (100–200 mg) was added and the mixture was heated to 90° C. until evolution of gas stopped. After cooling, the mixture was extracted with ethyl ether (3×). The combined organic fractions were extracted with 3N NaOH (3×). The combined aqueous layer was acidified with conc. HCl and the product was extracted with ethyl ether (3×). The organic fractions were washed with water, brine, and dried over $MgSO_4$. The crude product was introduced into a silica gel column and eluted with ethyl acetate/hexane (1/1) to afford 2-chloro-4-hydroxybenzoic acid.

$_1$H NMR (DMSO-D6): δ 6.97 (dd, 1H), 7.05 (d, 1H), 7.95 (d, 1H), 10.90 (brd s, 1H).

Step B:

To a solution 2-chloro-4-hydroxybenzoic acid in anhydrous methanol was added thionyl chloride (1.5 eq). After stirring the solution at room temperature for 16 hours, the solvent was evaporated. The residue was taken up in ethyl acetate and washed with saturated aqueous sodium bicarbonate, water, brine, and dried over $MgSO_4$ and concentrated in vacuo to give methyl 2-chloro-4-hydroxybenzoate.

Step C:

To a solution of methyl 2-chloro-4-hydroxybenzoate (13.6 g, 73.1 mmol) in acetic acid (300 mL) was added N-chlorosuccinimide (9.8 g, 73.7 mmol). The solution was refluxed for 24 h and the solvent was evaporated under vacuo. The residue was taken up in chloroform, washed with water, brine, dried over magnesium sulfate, filtered and concentrated. Methyl 2,3-dichloro-4-hydroxybenzoate precipitated out of ethyl acetate. Chromatography of the residue using ethyl acetate/hexane (1/9 to 3/7) afforded methyl 2,5-dichloro-4-hydroxybenzoate (1.4 g, 60%) as well as an additional batch of methyl 2,3-dichloro-4-hydroxybenzoate isomer (total of 8.4 g, 10%).

Methyl 2,3-dichloro-4-hydroxybenzoate:
$^1$H NMR (DMSO-D6) δ 3.81 (s, 3H), 7.02 (d, 1H), 7.70 (d 1H), 11.52 (s, 1H); MS (APCI): 221, 223.

Methyl 2,5-dichloro-4-hydroxybenzoate:
$^1$H NMR (CDCl$_3$): δ 3.90 (s, 3H), 6.00 (s, 1H), 7.14 (s, 1H), 7.27 (s, 1H), 7.96 (s, 1H); MS (APCI): 221.9.

Step D:

The title compound was prepared according to the general procedure for the synthesis of precursor hydrazides A—(C=O)—NHNH$_2$.

$^1$H NMR (DMSO-D6): δ 6.82 (dd, 1H), 6.90 (d, 1H), 7.79 (d, 1H, 10.68 (brd s, 1H).

Preparation of 2,3-Dichloro-4-hydroxybenzoic Acid Hydrazide and 2,5-dichloro-4-hydroxybenzoic Acid Hydrazide (Step D)

The 2,3-dichloro-4-hydroxybenzoic Acid Hydrazide was prepared from the methyl 2,3-dichloro-4-hydroxybenzoate above according to the general procedure for the synthesis of precursor hydrazides A—(C=O)—NHNH$_2$ with the exception that pentanol was the solvent of choice. The product was purified via silica gel column chromatography using CH2Cl$_2$/MeOH (95/5 to 80/20), yield=50%.

2,5-dichloro-4-hydroxybenzoic acid hydrazide was prepared in a similar way starting from 2,5-dichloro-4-hydroxybenzoate.

2,3-Dichloro-4-hydroxybenzoic Acid Hydrazide:
$^1$H NMR (DMSO-D6) δ 4.41 (brd s, 2H), 6.99 (1, 1H), 7.37 (s, 1H), 9.46 (s, 1H), 11.04 (s, 1H).

2,5-Dichloro-4-hydroxybenzoic Acid Hydrazide:
$^1$H NMR (DMSO-D6) δ 4.48 (brd s, 3H), 6.92 (d, 2H), 7.18 (d, 2H), 9.45 (brd s, 1H).

Preparation of 2,3-Dichloro-4-hydroxybenzoic Acid Hydrazide

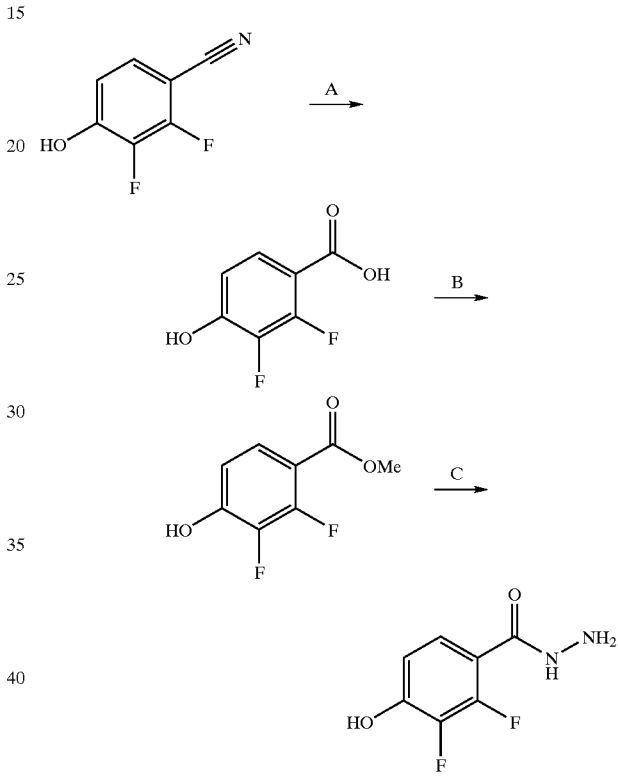

Step A:

A mixture of 2,3-difluoro-4-cyanophenol (1 g, 6.45 mmol) in water (8 mL), H$_2$SO$_4$ (8 mL), and acetic acid (8 mL) was refluxed for 48 hours. The solvents were removed by rotary evaporation to give a slurry which was poured onto ice. The product precipitated out of solution and filtered. The solid was washed with water and dried to give 2,3-difluoro-4-hydroxybenzoic acid (800 mg, 71%).

$^1$H NMR (DMSO-D$_6$): δ 6.87 (t, 1H), 7.60 (t, 1H), 11.28 (s, 1H), 12.53 (brd s, 1H).

Step B:

To the 2,3-difluoro-4-hydroxybenzoic acid (800 mg, 5.1 mmol) dissolved in anhydrous methanol (50 mL) was added thionyl chloride (0.55 mL, 7.3 mmol). After stirring the solution at room temperature for 16 hours, the solvent was evaporated. The residue was taken up in ethyl acetate and washed with saturated aqueous sodium bicarbonate, water, brine, and dried over MgSO$_4$ to give methyl 2,3-difluoro-4-hydroxybenzoate (540 mg, 62%).

$^1$H NMR (CDCl$_3$): δ 3.92 (s, 3H), 6.34 (brd s, 1H), 6.82 (dt, 1H), 7.68 (dt, 1H).

Step C:

The 2,3-difluoro-4-hydroxybenzoic acid hydrazide was prepared from the methyl 2,3-difluoro-4-hydroxybenzoate above according to the general procedure for the synthesis of precursor hydrazides A—(C=O)—NHNH$_2$. The product was purified via silica gel column chromatography using CH2Cl$_2$/MeOH (95/5 to 80/20) to afford the title compound.

$^1$H NMR (DMSO-D$_6$): δ 4.48 (s, 2H), 6.80 (m, 1H), 7.22 (m, 1H), 9.36 (s, 1H), 10.89 (s, 1H); MS (APCI): 189.

Preparation of 3-Cyano-4-hydroxybenzoic Acid Hydrazide, Trifluoroacetate washed with brine containing sodium metabisulfite, dried over sodium sulfate, filtered, and the solvent removed in vacuo. The resulting solids were purified by flash chromatography on silica gel (20% ethyl acetate/hexane) to afford methyl-3-cyano-4-hydroxybenzoate, 0.93g (73%).

$^1$H NMR (DMSO-D$_6$): δ 3.79 (s, 3H), 7.07 (d, J=8.7, 1H), 8.02 (dd, J=8.7, 1.9, 1H), 8.10 (d, J=1.9, 1H).

Step C:

Methyl-3-cyano-4-hydroxybenzoate (2.71 g, 15.3 mmol) was dissolved in 50 mL of THF. The solution was chilled in an ice bath, and 2.0M potassium hydroxide (17 mL, 34 mmol) was added dropwise. The resulting mixture was

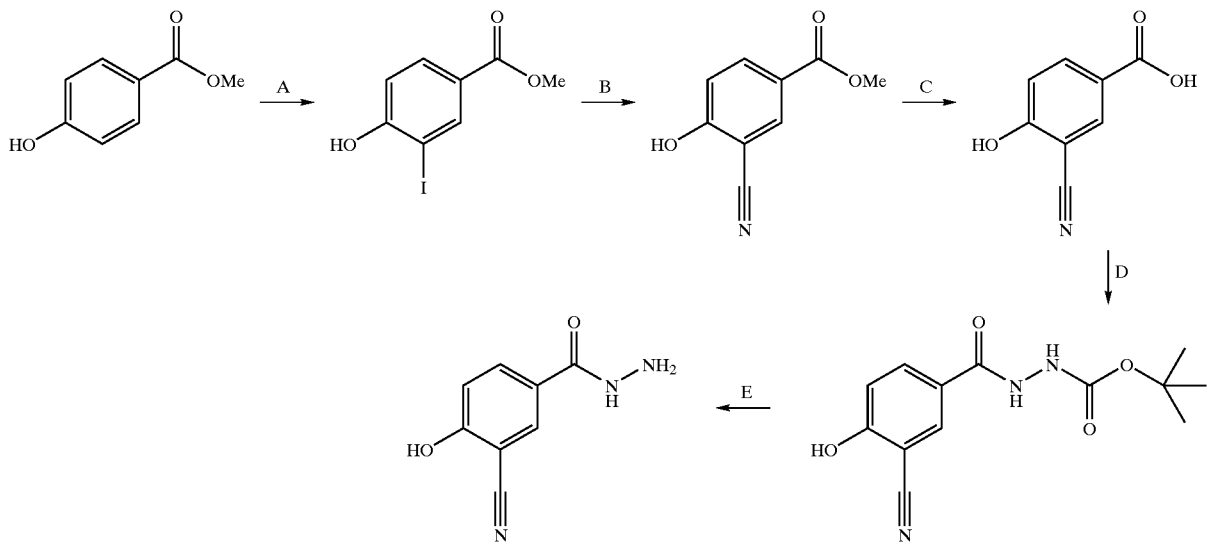

Step A:

Methyl-4-hydroxybenzoate (35.5 g, 0.233 mol) was dissolved in 200 mL of warm (65° C.) acetic acid. A solution of iodine monochloride (37.8 g, 0.233 mol) in 50 mL of acetic acid was added slowly (40 minutes) to the methyl-4-hydroxybenzoate solution, while maintaining a temperature of 65° C. and vigorous stirring. The product crystallizes from solution upon cooling to room temperature and standing overnight. The crystals were collected on a filter, washed with water, then dried under vacuum. Methyl-4-hydroxy-3-iodobenzoate was obtained as white crystals (28.6 g, 44%).

$^1$H NMR (DMSO-D$_6$): δ 3.79 (s, 3H), 6.95 (d, J=8.3, 1H), 7.81 (dd, J=8.3, 2.2, 1H), 8.22 (d, J=2.2, 1H); $^{13}$C NMR (DMSO-D$_6$) δ 52.8, 85.2, 115.5, 123.0, 132.0, 141.0, 161.9, 165.6; MS (APCI, neg): 277.

Step B:

Methyl-4-hydroxy-3-iodobenzoate (2.00 g, 7.2 mmol) was dissolved into 5 mL of dry DMF. Copper(I) cyanide (0.72 g, 8.0 mmol) and a small crystal of sodium cyanide was added. The mixture was flushed with nitrogen, placed in an oil heating bath (100–110° C.), and stirred overnight. TLC indicated nearly complete reaction. The mixture was cooled and the solids removed by filtration. The solids were extracted with DMF (3 mL). The filtrate and washings were taken up in 100 mL of ethyl acetate, then washed with 3 portions of saturated sodium chloride solution. The solids and aqueous washings were combined, and shaken with a mixture of 50 mL of ethyl acetate and a ferric chloride solution (4 g of hydrated ferric chloride in 7 mL of conc. hydrochloric acid). The ethyl acetate layers were combined, stirred at room temperature overnight. TLC indicated complete reaction. The THF was removed by rotary evaporation. The aqueous residue was acidified with aqueous trifluoroacetic acid and purified by reverse-phase HPLC (C-18, 0.1% TFA in water and acetonitrile). 3-Cyano-4-hydroxybenzoic acid was obtained as a white powder (2.1 g, 84%) after lyophilization.

$^1$H NMR (DMSO-D$_6$): δ 7.09 (d, J=9.0, 1H), 8.00 (dd, J=9.0, 2.3, 1H), 8.07 (d, J=2.3, 1H) 12.50 (br s, 2H); MS (APCI, neg): 162. IR: 2252 cm$^{-1}$, CN.

Step D:

3-Cyano-4-hydroxybenzoic acid (1.88 g, 11.5 mmol) was dissolved in 20 mL of methylene chloride/DMF (1/1) and chilled in an ice-bath. Diisopropylethylamine (12 mL, 69 mmol), t-butyl carbazate (1.76 g, 13.3 mmol), and PyBroP (bromo-tris-pyrrolidino-phosphonium hexafluorophosphate, 6 g, 12.9 mmol) were added, and the mixture was stirred to form a clear solution. The solution stood in the refrigerator overnight. TLC indicated that the reaction was not complete, so additional diisopropylethylamine (22 mL, 127 mmol), t-butyl carbazate (0.85 g, 6.4 mmol) and PyBroP (3.0 g, 6.4 mmol) were added. After 8 more hours at 0° C., the reaction was worked up as follows. The solution was reduced by rotary evaporation. The remaining DMF solution was diluted with 100 mL of ethyl acetate, and washed with several portions of 0.1 M HCl (until the wash remained acidic to litmus paper). The ethyl acetate layer was further washed with 3 portions of brine, dried over magnesium sulfate, filtered, and reduced to an oil in vacuo. The oil was purified by chromatography on silica gel (6:4 hexane:ethyl acetate) to afford tert-butyloxycarbonyl (3-cyano-4-hydroxy)benzoic acid hydrazide as a white solid (1.8 g, 56%).

$^1$H NMR (DMSO-D$_6$): δ 1.42 (s, 9H), 7.09 (d, J=8.7, 1H), 7.98 (m, 1H), 8.11 (br s, 1H), 8.92 (s, 1H), 10.15 (s, 1H), 11.73 (br s, 1H); MS (APCI, neg): 276; IR: 2232 cm$^{-1}$, CN.

Step E:

The Boc-hydrazide (1.8 g, 6.5 mmol) was suspended in 50 mL of chloroform and cooled in an ice-bath. Trifluoroacetic acid was added with stirring, and the resulting solution stood for 4 hours at 0° C. TLC indicated complete reaction. Solvent and excess TFA were removed by rotary evaporation. The remaining oil was purified by reverse-phase liquid chromatography (Aquasil C-18 column, water/acetonitrile/0.1% TFA). The title compound was obtained as a white solid (0.24 g, 13%).

$^1$H NMR (DMSO-D$_6$): δ 7.16 (d, J=9.0, 1H), 8.00 (dd, J=1.5, 9.0, 1H), 8.14 (d, J=1.5, 1H), 10.47 (br s, 5H); MS (APCI, neg): 176.

Preparation of 4-Hydroxynaphthoic Acid Hydrazide

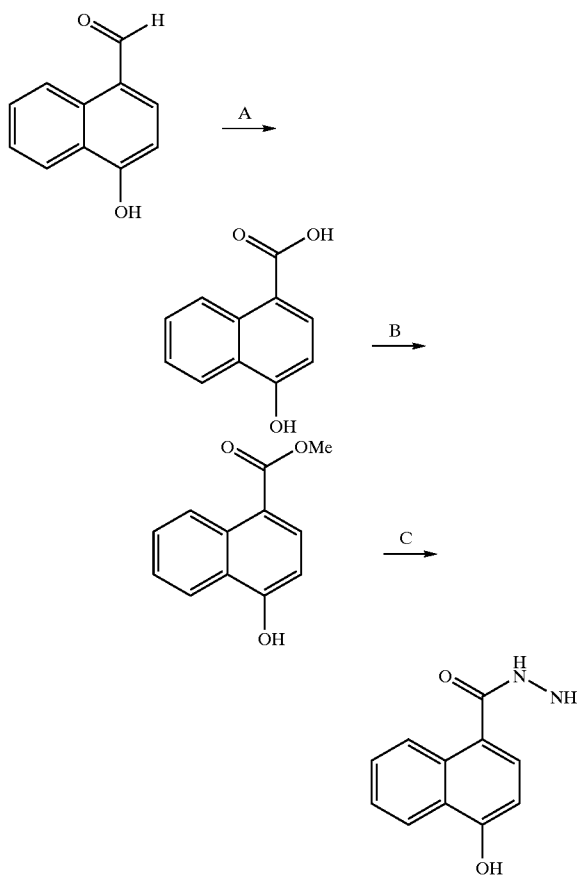

Step A:

Silver nitrate (17 g, 0.1 mol) was dissolved in water (10 mL) and treated with 1 N NaOH (300 mL, 0.3 mol). The brown precipitate which was formed was stirred for 30 minutes and the supernatant was decanted. The brown silver oxide was washed with additional volumes of water (3×).

To the silver oxide above was added 1N NaOH (150 mL) and 4-hydroxynaphthaldehyde (1 g, 6 mmol)). The mixture was heated to 70° C. for 10 minutes after which additional amounts of 4-hydroxynaphthaldehyde (5.5 g, 32 mmol) was added in portions. The mixture was kept at 80° C. for 16 hours. TLC analysis indicated incomplete conversion. An additional portion of silver oxide was prepared as above and added to the reaction mixture. After heating the mixture for an additional 6 hours, the mixture was cooled and acidified with 1N HCl. The aqueous layer was extracted with ethyl acetate (3×) and upon concentration 4-hydroxynaphthoic acid precipitated (3.7 g, 60%) out of solution.

$^1$H NMR (DMSO-D6): δ 6.69 (d, 1H), 7.28 (t, 1H), 7.39 (t, 1H), 7.93 (d, 1H), 8.03 (d, 1H), 8.82 (d, 1H), 10.82 (s, 1H), 12.29 (s, 1H).

Step B:

To a solution 4-hydroxynaphthoic acid in anhydrous methanol at 0° C. was added thionyl chloride (1.5 eq). After stirring the solution at room temperature for 16 hours, the solvent was evaporated. The residue was taken up in ethyl acetate and washed with saturated aqueous sodium bicarbonate, water, brine, and dried over MgSO$_4$ to give methyl 4-hydroxynaphthoate.

$^1$H NMR (DMSO-D6): δ 3.87 (s, 3H), 6.92 (d, 1H), 7.53 (t, 1H), 7.65 (t, 1H), 8.13 (d, 1H), 8.26 (d, 1H), 8.93 (d, 1H), 11.16 (s, 1H).

Step C:

The title compound was prepared from methyl 4-hydroxynaphthoate according to the procedure for the synthesis of precursor hydrazides A—(C=O)—NHNH$_2$.

$^1$H NMR (DMSO-D6): δ 6.60 (d, 1H), 7.28 (m, 3H), 7.95 (d, 1H), 8.07 (d, 1H), 9.25 (brd s, 1H).

Moreover, by use of the above methodology, the following hydrazides useful as intermediates in preparing the compounds of the invention may be prepared:

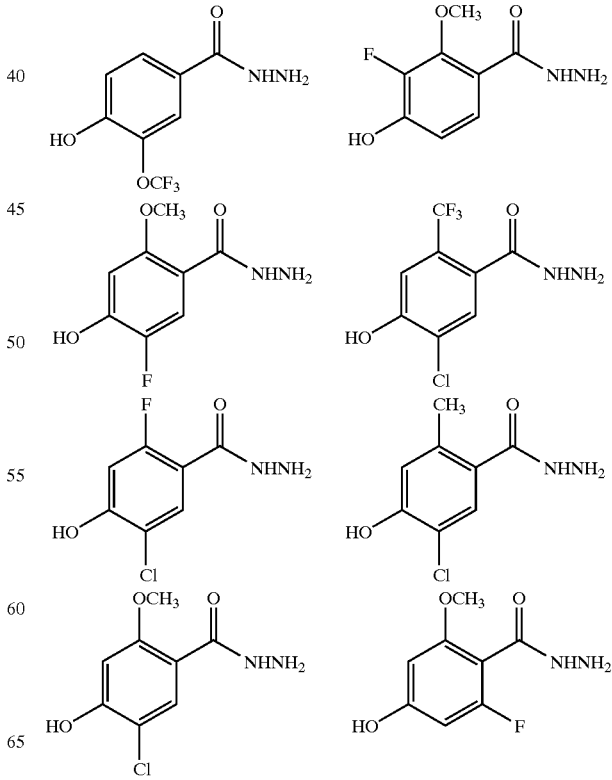

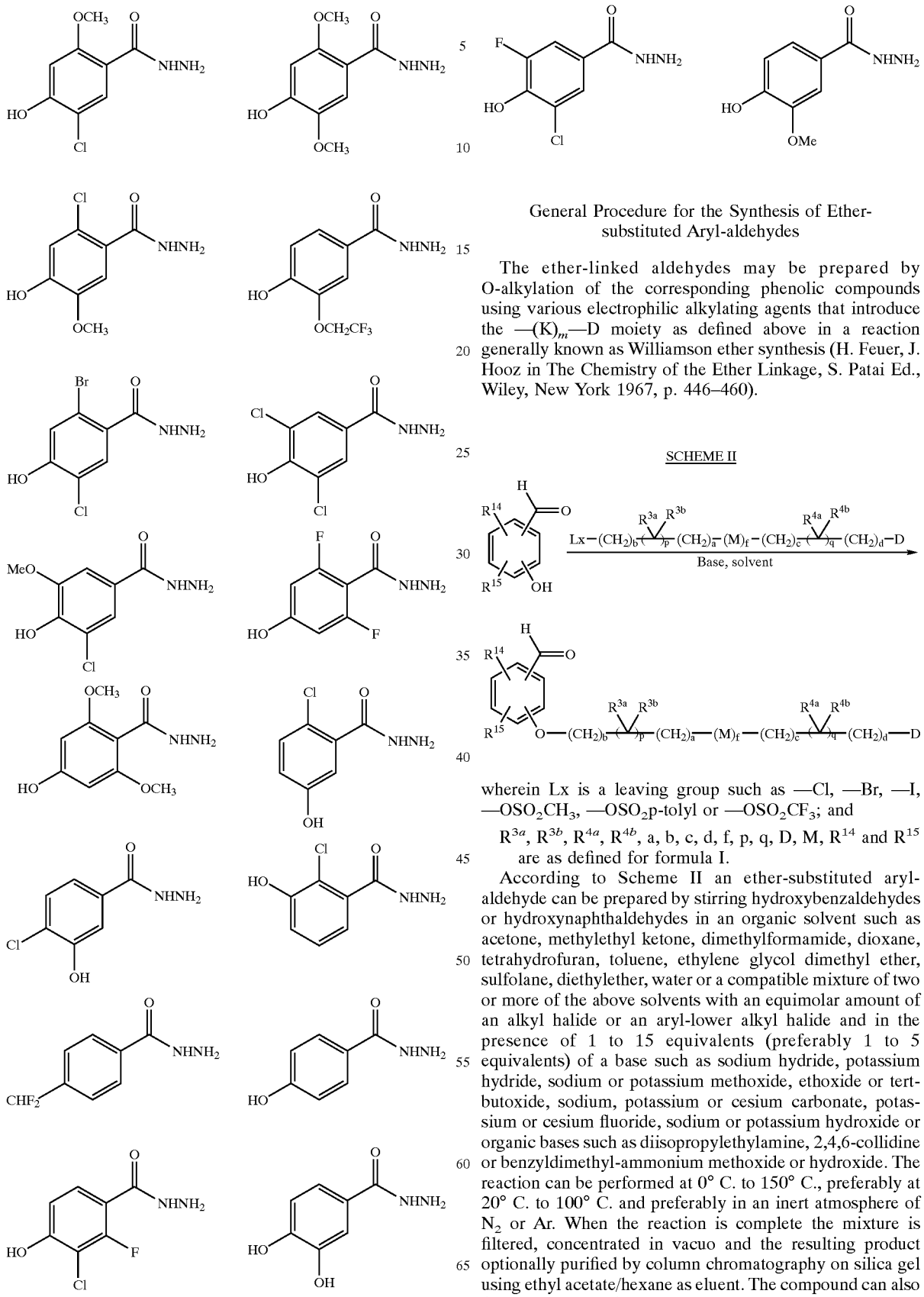

General Procedure for the Synthesis of Ether-substituted Aryl-aldehydes

The ether-linked aldehydes may be prepared by O-alkylation of the corresponding phenolic compounds using various electrophilic alkylating agents that introduce the —$(K)_m$—D moiety as defined above in a reaction generally known as Williamson ether synthesis (H. Feuer, J. Hooz in The Chemistry of the Ether Linkage, S. Patai Ed., Wiley, New York 1967, p. 446–460).

SCHEME II

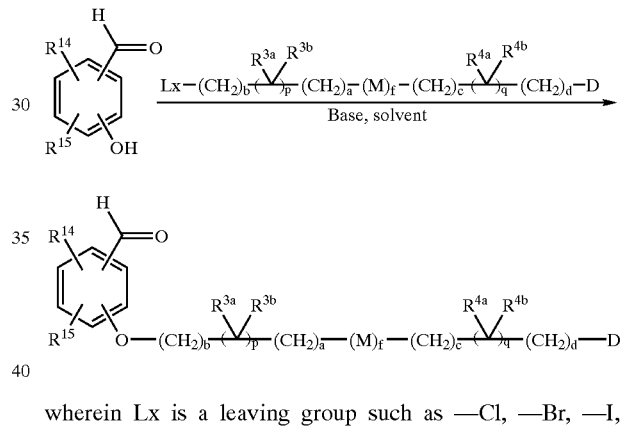

wherein Lx is a leaving group such as —Cl, —Br, —I, —$OSO_2CH_3$, —$OSO_2$p-tolyl or —$OSO_2CF_3$; and $R^{3a}$, $R^{3b}$, $R^{4a}$, $R^{4b}$, a, b, c, d, f, p, q, D, M, $R^{14}$ and $R^{15}$ are as defined for formula I.

According to Scheme II an ether-substituted aryl-aldehyde can be prepared by stirring hydroxybenzaldehydes or hydroxynaphthaldehydes in an organic solvent such as acetone, methylethyl ketone, dimethylformamide, dioxane, tetrahydrofuran, toluene, ethylene glycol dimethyl ether, sulfolane, diethylether, water or a compatible mixture of two or more of the above solvents with an equimolar amount of an alkyl halide or an aryl-lower alkyl halide and in the presence of 1 to 15 equivalents (preferably 1 to 5 equivalents) of a base such as sodium hydride, potassium hydride, sodium or potassium methoxide, ethoxide or tert-butoxide, sodium, potassium or cesium carbonate, potassium or cesium fluoride, sodium or potassium hydroxide or organic bases such as diisopropylethylamine, 2,4,6-collidine or benzyldimethyl-ammonium methoxide or hydroxide. The reaction can be performed at 0° C. to 150° C., preferably at 20° C. to 100° C. and preferably in an inert atmosphere of $N_2$ or Ar. When the reaction is complete the mixture is filtered, concentrated in vacuo and the resulting product optionally purified by column chromatography on silica gel using ethyl acetate/hexane as eluent. The compound can also (when appropriate) be purified by recrystallization from a suitable solvent such as ethyl alcohol, ethyl acetate, isopropyl alcohol, water, hexane, toluene or their compatible mixture. Specific examples illustrating the preparation of ether-substituted aryl-aldehydes are provided below.

Preparation of 4-(2-Tetrahydropyranylmethoxy)-1-naphthaldehyde

A mixture of 4-hydroxynaphthaldehyde (1 g, 5.8 mmol), 2-bromomethyl tetrahydropyran (1 g, 5.8 mmol) and powdered $K_2CO_3$ (1.2 g, 8.7 mmol) in dimethyl formamide was stirred at 60° C. overnight. The mixture was taken up in water and ethyl acetate. The organic layer was separated and washed with water, brine, dried over $MgSO_4$, filtered, and concentrated. The product was purified by silica gel column chromatography using ethyl acetate/hexane.

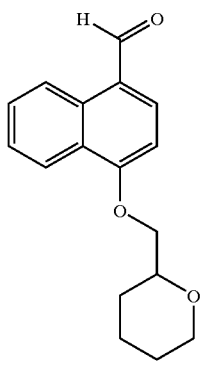

$^1$H NMR (DMSO-$d_6$): δ 1.48 (m, 4H), 1.74 (d, 1H), 1.84 (m, 1H), 3.44 (m, 1H), 3.78 (m, 1H), 3.92 (d, 1H), 4.23 (m, 2H), 7.17 (d, 1H), 7.64 (t, 1H), 7.74 (t, 1H), 8.11 (d, 1H), 8.27 (d, 1H), 9.22 (d, 1H), 10.17 (s, 1H).

Preparation of 4-[(3,5-bis-Trifluoromethyl)benzyloxy]-1-naphthaldehyde

A mixture of 4-hydroxynaphthaldehyde (1 g, 5.8 mmol), 3,5-bis-trifluoromethylbenzylbromide (1.8 g, 5.8 mmol), and powdered $K_2CO_3$ (1.2 g, 8.7 mmol) was stirred in acetone (40 mL) overnight. The mixture was poured onto 200 mL of ice-chips and stirred until the ice melted. The yellow precipitate, 4-((3,5-bis-trifluoromethyl)benzyloxy)-1-naphthaldehyde, was collected and dried.

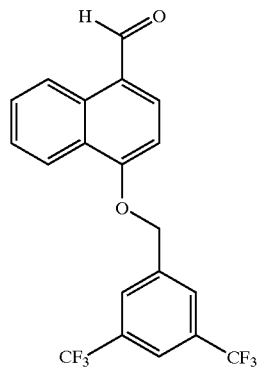

$^1$H NMR (DMSO-$d_6$): δ 5.58 (s, 2H), 7.07 (d, 1H), 7.22 (d, 1H), 7.63 (t, 1H), 7.69 (t, 1H), 7.79 (d, 1H), 7.86 (d, 1H), 7.99 (s, 1H), 8.14 (s, 1H), 8.30 (s, 3H), 8.94 (s, 1H), 8.97 (d, 1H), 11.0 (broad s, 1H), 11.69 (s, 1H); MS (ESI) m/z 675.2 $(M+H)_+$.

Preparation of 4-(2-Chloroethoxy)-1-naphthaldehyde

To a solution of 4-hydroxy-1-naphthaldehyde (8.6 g, 50 mmoles) and potassium carbonate (13.8 g, 100 mmoles) in N,N-dimethylformamide (DMF)(40 mL) was added 1-bromo-2-chloroethane (7.4 g, 50 mmoles). The mixture was heated at 60° C. overnight. The solution was diluted with ethyl acetate (500 mL), extracted with water and brine. The organic layer was dried over magnesium sulfate and the solvent was evaporated to obtain 12.1 g product (52% yield).

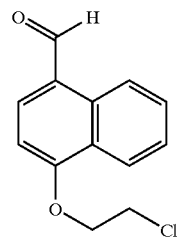

MS (Cl): 403, 405, 407. $^1$H NMR (CDCl$_3$): δ 10.2 (s, 1H), 9.3 (d, 1H), 8.35 (d, 1H), 7.85 (d, 1H), 7.65 (m, 1H), 7.5 (m, 1H), 7.1 (d, 1H), 4.35 (t, 2H), 4.15 (t, 2H).

The products were used as such in further transformations.

By application of the above methodology the following substituted aldehyde intermediates were synthesized:

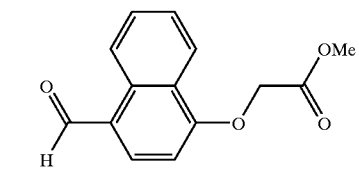

4-carbomethoxymethoxy-1-naphthaldehyde
m.p.: 115–116° C.

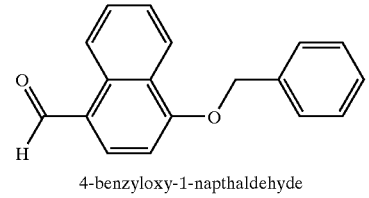

4-benzyloxy-1-napthaldehyde

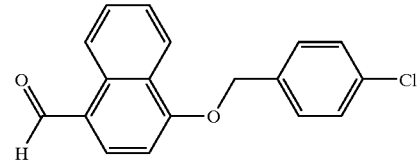

4-(4-chlorobenzyloxy)-1-naphthaldehyde

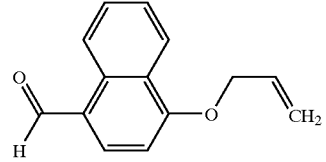

4-allyloxy-1-naphthaldehyde

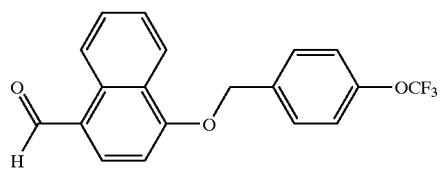

4-(4-trifluoromethoxybenzyloxy)-1-naphthaldehyde

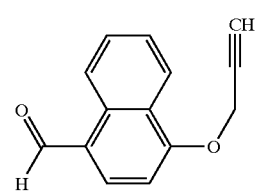

4-propargyloxy-1-naphthaldehyde

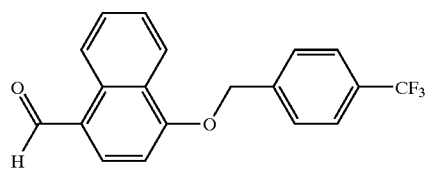

4-(4-trifluoromethylbenzyloxy)-1-naphthaldehyde

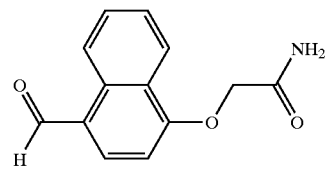

2-[(4-carboxaldehydo)-1-
naphthyloxy]acetamide
m.p. 174–175° C.

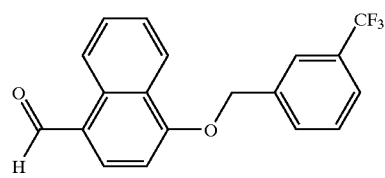

4-(3-trifluoromethylbenzyloxy)-1-naphthaldehyde

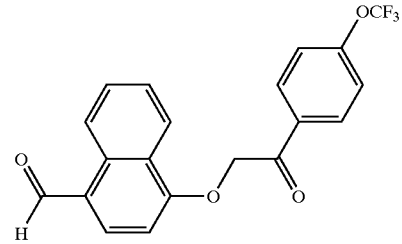

4-(2-(4-trifluoromethoxyphenyl)-2-oxo-
ethoxy)-1-naphthaldehyde
m.p. 112–114° C.

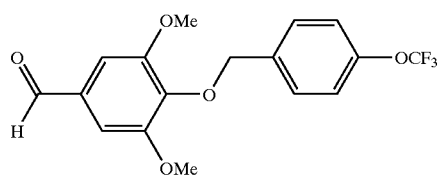

4-(4-trifluoromethoxybenzyloxy)-3,5-dimethoxybenzaldehyde

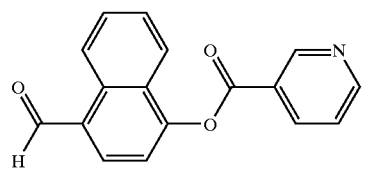

Nicotinic acid 4-formyl-1-naphthyl ester
m.p. 142–143° C.

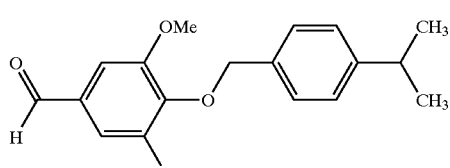

4-(4-isopropylbenzyloxy)-3,5-dimethoxybenzaldehyde
(oil)

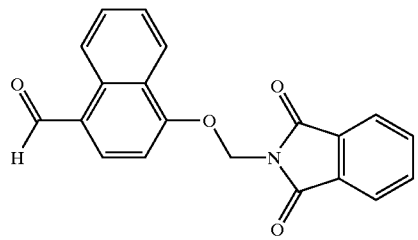

4-(1,3-dioxo-1,3-dihydroisoindol-2-ylmethoxy)-
1-naphthaldehyde
m.p. 191–192° C.

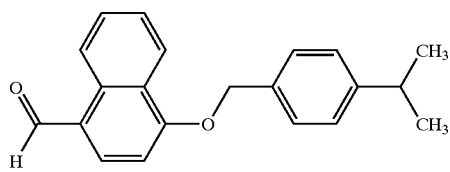

4-(4-isopropylbenzyloxy)-1-naphthaldehyde

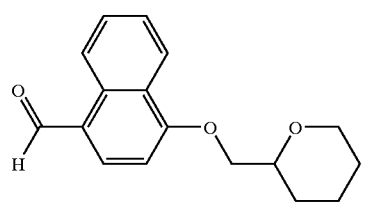

4-(tetrahydro-2-pyranylmethoxy)-1-
naphthaldehyde

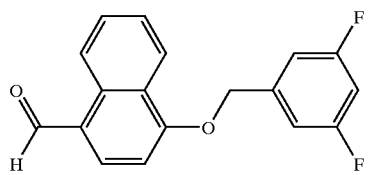

4-(3,5-difluorobenzyloxy)-1-naphtaldehyde
m.p. 100–101° C.

Preparation of 3-Allyl-4-hydroxy-5-methoxy-benzaldehyde

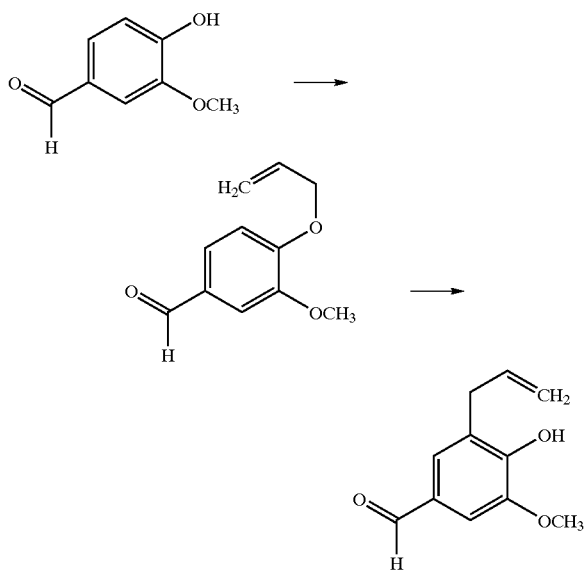

To a solution of vanillin (1.0 g, 6.57 mmol) in acetone (30 mL) was added potassium carbonate (4.50 g, 32.8 mmol) and allyl bromide (0.62 mL, 7.3 mmol). The mixture was heated under reflux for 6 h. TLC showed appearance of a new spot. Potassium salts were removed by filtration and the filtrate was concentrated to a syrup. A small sample was purified using prep TLC using hexane/ethyl acetate 7:3 as developing solvent. $^1$H NMR (CDCl$_3$) δ=3.94 (s, 3H), 4.67–4.83 (m, 2H), 5.30–5.55 (m, 2H), 6.01–6.21 (m, 1H), 6.98 (d, J=9 Hz, $_1$H), 7.40–7.56 (m, 2H), 9.85 (s, 1H); MS (APCI): 193.6.

The crude syrup was heated neat in an oil bath at 200° C. for 6 h. The crude material was dissolved in chloroform and filtered through a pack of silica gel. The crude product (yield 72%) was used as is in the next step for O-alkylation. A small portion was purified using prep-TLC to give a pure sample of 3-allyl-4-hydroxy-5-methoxy-benzaldehyde. $^1$H NMR (CDCl$_3$) δ=3.46 (d, J=6 Hz, 2H), 3.96 (s, 3H), 5.02–5.22 (m, 2H), 5.94–6.11 (m, 1H), 6.30 (s, 1H), 7.45 (s, 2H), 9.80 (s, 1H); MS (APCI): 193.3.

Preparation of 3-Allyl-4-(4-isopropylbenzyloxy)-5-methoxybenzaldehyde

The crude 3-allyl-4-hydroxy-5-methoxy-benzaldehyde was taken up in acetone and treated with 4-isopropylbenzyl chloride in the presence of potassium carbonate to give the desired product.

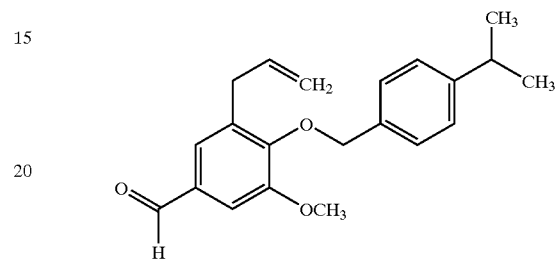

$^1$H NMR (CDCl$_3$) δ=1.26 (d, J=7 Hz, 6H), 2.92 (m, 1H), 3.38 (d, J=7 Hz, 2H), 3.95 (s, 3H), 4.98–5.12 (m, 4H), 5.93–5.75 (m, 1H), 7.20–7.43 (m, 6H), 9.87 (s, 1H).

General Procedure for the Synthesis of Compounds of Formulae IXa and IXb

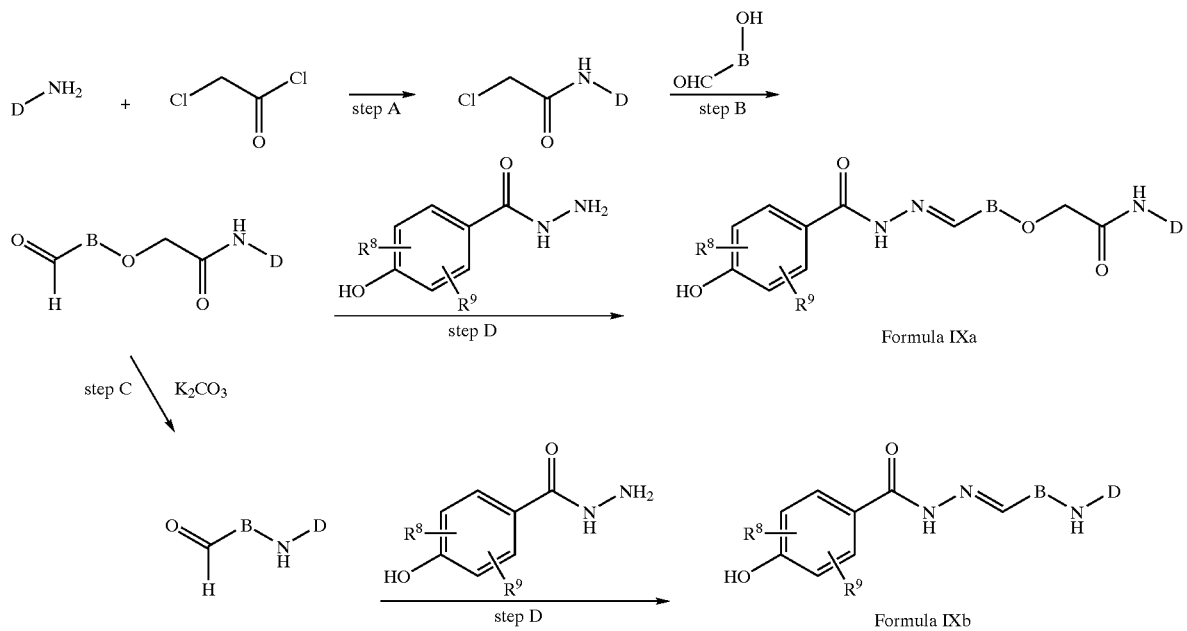

In the above formulae B, D, R$^8$ and R$^9$ have the same meanings as defined for formula I.

Step A:

To a solution of aniline (or an aniline derivative) (1 eq.) in THF was added dropwise chloroacetyl chloride (1.2 eq.). After stirring at room temperature overnight, 100 mL water was added, and the mixture was extracted with ethyl acetate. The organic phase was washed twice with dilute hydrochloric acid, twice with water, dried over Mg SO$_4$ and then concentrated to give pure product.

Step B:

To a solution of chloroacetanilide (or a derivative thereof) (1.2 eq.) and 2-methoxy-4-hydroxy benzaldehyde (or another aromatic aldehyde substituted with a hydroxy group) (1 eq.) in DMSO was added potassium carbonate (1.5 eq.). After stirring overnight at room temperature, 100 ml water was added. The mixture was extracted with ethyl acetate, the organic extracts were washed twice with a satd. sodium bicarbonate solution, twice with water, and dried over $MgSO_4$. After concentration in vacuo, the product was obtained.

The following two aldehydes were prepared as examples of compounds that can be prepared using this methodology:
N-(4-Chlorophenyl)-2-(4-formyl-3-methoxyphenoxy) acetamide:

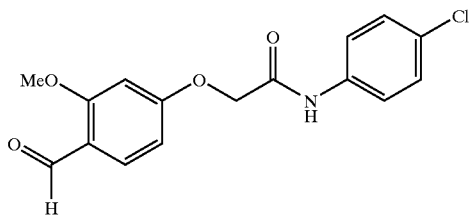

$^1H$ NMR ($CDCl_3$): δ 4.28 (s, 3H), 5.01 (s, 2H), 6.90 (d, J=2.2 Hz, 1H), 6.97 (dd, J=8.6, 2.1 Hz, 1H), 7.67 (d, J=8.9 Hz, 2H), 7.89 (d, J=8.8 Hz, 2H), 8.20 (d, J=8.6 Hz, 1H), 8.51 (s, 1H), 10.66 (s, 1H); MS (APCI): 319.9.
N-(4-Isopropylphenyl)-2-(4-formyl-3-methoxyphenoxy) acetamide:

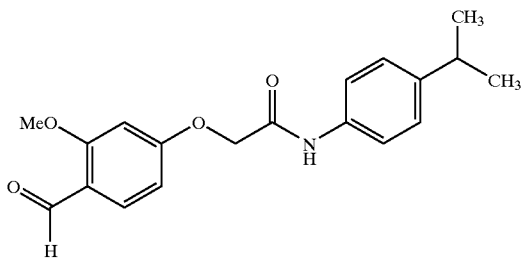

$^1H$ NMR (DMSO-D6): δ 2.07 (d, J=6.9 Hz, 6H), 2.70 (m, J=6.9 Hz, 1H), 3.77 (s, 3H), 4.68 (s, 2H), 6.56 (dd, J=8.7, 2.1 Hz, 1H), 6.66 (d, J=2.1 Hz, 1H), 7.06 (d, J=8.5 Hz, 2H), 7.39 (d, J=8.50 Hz, 2H), 7.55 (d, J=8.7 Hz, 1H), 9.93 (s, 1H), 10.05 (s, 1H); MS (APCI): 328.

This type of aldehydes can be coupled to hydrazides using the methodology as described in step D to give a compound of formula IXa. Alternatively these compounds can undergo rearrangement by treatment with base as described below (step C), followed by coupling to a hydrazide (step D) to give a compound of formula IXb.

Step C:

The mixture of aldehyde (1 eq.) and potassium carbonate (1.5 eq.) in acetonitrile was refluxed. The reaction was monitored by TLC (hexane:ethyl acetate=2:1). When TLC showed almost complete conversion (about 48 h), 100 ml water was added. The mixture was extracted with ethyl acetate, the organic extracts were dried over $MgSO_4$, and concentrated to give the desired product which can be further purified by column chromatography, or used directly for the next step.

The following two aldehydes were prepared as examples of compounds that can be prepared using this methodology:
4-(4-Chlorophenylamino)-2-methoxybenzaldehyde:

Prepared from N-(4-chlorophenyl)-2-(4-formyl-3-methoxyphenoxy)acetamide using the procedure described in step C above.

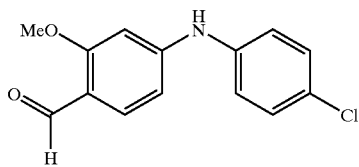

$^1H$ NMR ($CDCl_3$): δ 3.84 (s, 3H), 6.14 (s, 1H), 6.45 (d, J=2.0 Hz, 1H), 6.54 (dd, J=8.4, 1.8 Hz, 1H), 7.14 (d, J=8.7 Hz, 2H), 7.33 (d, J=8.7 Hz, 2H), 7.74 (d, J=8.5 Hz, 1H), 10.22 (s, 1H); MS (APCI): 261.9.
4-(4-Isopropylphenylamino)-2-methoxybenzaldehyde:

Prepared from N-(4-isopropylphenyl)-2-(4-formyl-3-methoxyphenoxy)acetamide using the procedure described in step C above.

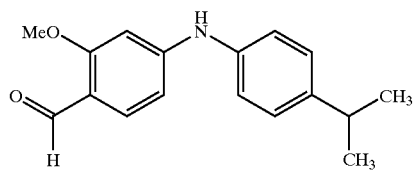

$^1H$ NMR ($CDCl_3$) δ 1.26 (d, J=6.9 Hz, 6H), 2.88 (m, J=6.9 Hz, 1H), 3.84 (s, 3H), 6.50 (d, J=1.9 Hz, 1H), 6.55 (dd, J=8.6, 1.8 Hz, 1H), 6.96 (s, 1H), 7.15 (d, 2H, J=8.5 Hz, 2H), 7.22 (d, J=8.5 Hz, 2H), 7.69 (d, J=8.5 Hz, 1H), 10.18 (s, 1H); MS (APCI): 269.

Step D:

The resulting carbonyl compounds are treated with the corresponding acylhydrazide in a solvent. The solvent may be one of the following: ethyl alcohol, methyl alcohol, isopropyl alcohol, tert-butyl alcohol, dioxane, tetrahydrofuran, toluene, chlorobenzene, anisole, benzene, chloroform, dichloromethane, DMSO, acetic acid, water or a compatible mixture of two or more of the above solvents. A catalyst such as acetic acid can be added. A dehydrating reagent such as triethylorthoformate can also be added to the reaction mixture. The reaction is performed by stirring the reaction mixture preferably under an inert atmosphere of $N_2$ or Ar at temperatures between 0° C. to 140° C., preferably between 10° C. to 80° C. In many cases the product simply crystallizes out when the reaction is completed and is isolated by suction filtration. It can be further recrystallized if necessary from a solvent such as the above described reaction solvents. The product can also be isolated by concentration of the reaction mixture in vacuo, followed by column chromatography on silica gel using a solvent system such as chloroform/methanol or dichloromethane/methanol or chloroform/ethyl acetate to give a compound of formula IXb.

The following compounds of formulae IXa or IXb according to the invention were prepared as examples of compounds that can be prepared using this methodology:

EXAMPLE 1

3-Chloro-4-hydroxybenzoic Acid [4-(4-Chlorophenylamino)-2-methoxybenzylidene] hydrazide

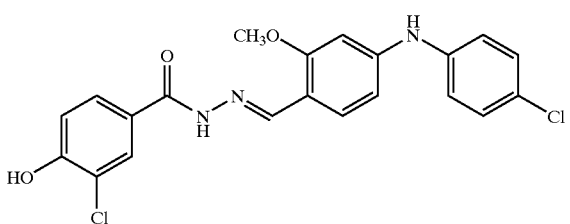

¹H NMR (DMSO-D6): δ 3.81 (s, 3H), 6.72–6.67 (m, 2H), 7.04 (d, J=8.5 Hz, 1H), 7.17 (d, J=8.7 Hz, 2H), 7.31 (d, J=8.7 Hz, 2H), 7.77–7.70 (m, 2H), 7.96 (d, J=1.6 Hz, 1H), 8.65 (s, 1H), 8.70 (s, 1H), 10.87 (s, 1H), 11.51 (s, 1H); MS (APCI): 430.

EXAMPLE 2

3-Chloro-4-hydroxybenzoic Acid [4-(4-Isopropylphenylamino)-2-methoxybenzylidene]hydrazide

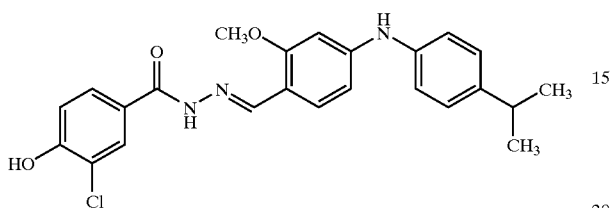

¹H NMR (DMSO-D6): δ 1.18 (2s, 6H), 2.86 (m, 1H), 3.79 (s, 3H), 6.65 (m, 2H), 7.03 (d, 1H), 7.11 (d, 2H), 7.19 (d, 2H), 7.70 (d, 1H), 7.75 (dd, 1H), 7.97 (s, 1H), 8.49 (s, 1H), 8.64 (s, 1H), 10.88 (s, 1H), 11.48 (s, 1H); MS (FAB): 438.16.

EXAMPLE 3

2-{4-[(3-Chloro-4-hydroxybenzoyl)hydrazonomethyl]-3-methoxyphenoxy}-N-(4-chlorophenyl)acetamide

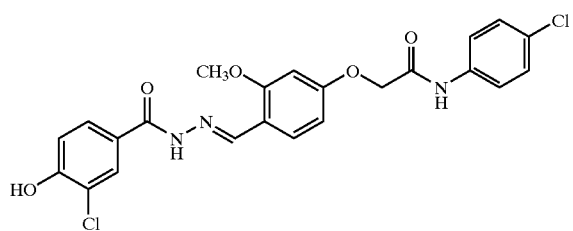

¹H NMR (DMSO-D₆): δ 3.66 (s, 3H), 4.57 (s, 2H), 6.48 (d, 1H), 6.55 (s, 1H), 6.83 (d, 1H), 7.20 (d, 2H), 7.48 (d, 2H), 7.56 (dd, 1H), 7.58 (d, 1H), 7.77 (d, 1H), 8.48 (s, 1H), 10.05 (s, 1H), 10.72 (brd s, 1H), 11.40 (s, 1H); MS (APCI): 487.8.

EXAMPLE 4

2-{4-[(3-Chloro-4-hydroxybenzoyl)hydrazonomethyl]-3-methoxyphenoxy}-N-(4-isopropylphenyl)acetamide ¹H NMR (DMSO-D₆): δ 1.17 (2 s, 6H), 2.85 (m, 1H), 3.87 (s, 3H), 4.76 (s, 2H), 6.70 (d, 1H), 6.76 (d, 1H), 7.05 (d, 1H), 7.20 (d, 2H), 7.55 (d, 2H), 7.77 (dd, 1H), 7.80 (d, 1H), 7.98 (s, 1H), 8.70 (s, 1H), 10.03 (s, 1H), 10.92 (s, 1H), 11.62 (s, 1H); MS (FAB): 496.16.

EXAMPLE 5

2-{4-[(3-Chloro-4-hydroxybenzoyl)hydrazonomethyl]-3-methoxyphenoxy}-N-(3,5-dichlorophenyl)acetamide

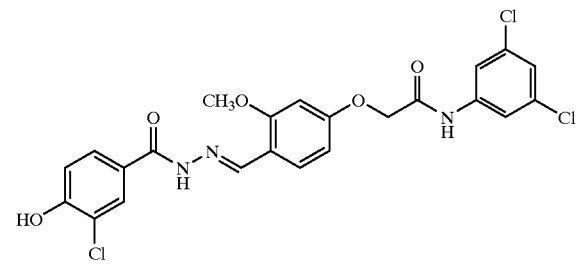

¹H NMR (DMSO-D₆): δ 4.06 (s, 3H), 4.94 (s, 2H), 6.8 (d, 1H), 6.88 (s, 1H), 7.20 (d, 1H), 7.45 (s, 1H), 7.90 (m, 3H), 8.10 (s, 1H), 8.82 (s, 1H), 10.62 (s, 1H), 11.07 (brd s, 1H), 11.75 (s, 1H); MS (APCI): 524.8.

General Procedure for the Synthesis of Alkylidene Hydrazides of Formula II According to the Invention The acylhydrazides are treated with the corresponding carbonyl compounds, such as aldehydes or ketones, in a solvent. The solvent may be one of the following: ethyl alcohol, methyl alcohol, isopropyl alcohol, tert-butyl alcohol, dioxane, tetrahydrofuran, toluene, chlorobenzene, anisole, benzene, chloroform, dichloromethane, DMSO, acetic acid, water or a compatible mixture of two or more of the above solvents. The reaction is performed by stirring the reaction mixture preferably under an inert atmosphere of N₂ or Ar at temperatures between 0° C. to 140° C., preferably between 10° C. to 80° C. In many cases the product simply crystallizes out when the reaction is completed and is isolated by suction filtration. It can be further recrystallized if necessary from a solvent such as the above described reaction solvents. The product can also be isolated by concentration of the reaction mixture in vacuo, followed by column chromatography on silica gel using a solvent system such as chloroform/methanol or dichloromethane/methanol

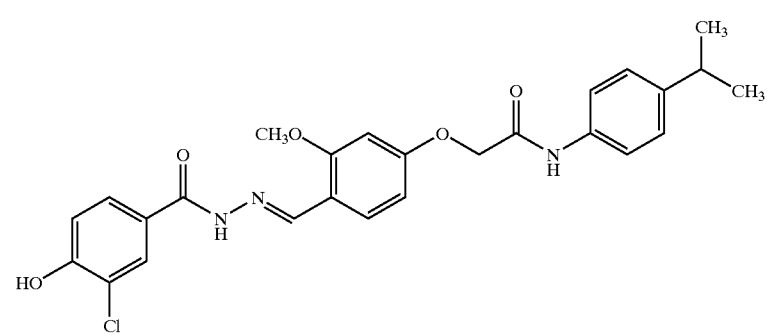

EXAMPLE 6

3-Chloro-4-hydroxybenzoic Acid (4-Hydroxy-1-naphthylmethylene)hydrazide

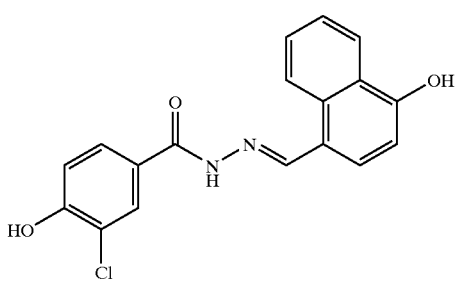

To a solution of 3-chloro-4-hydroxybenzoic acid hydrazide (200 mg, 1.1 mmol) in DMSO (2 ml) was added 4-hydroxynaphthaldehyde and a catalytic amount of glacial acetic acid (5 drops). The reaction was stirred overnight under nitrogen and diluted with ethyl acetate. The solution was washed with saturated sodium bicarbonate, water, brine, and dried over MgSO$_4$. The organic volume was concentrated in vacuo to give the crude product. The product was purified by silica gel column chromatography using CH$_2$Cl$_2$/MeOH as the mobile phase.

$^1$H NMR (DMSO-d$_6$): δ 6.89 (d, 2H), 7.02 (d, 1H), 7.47 (t, 1H), 7.58 (t, 1H), 7.66 (d, 1H), 7.73 (d, 1H), 7.93 (s, 1H), 8.17 (d, 1H), 8.84 (s, 1H), 8.88 (d, 1H), 10.73 (s, 1H), 10.88 (s, 1H), 11.54 (s, 1H); MS (ESI): m/z 341.04 (M+H)$^+$.

EXAMPLE 7

3-Chloro-4-hydroxybenzoic Acid [4-(3,5-bis-Trifluoromethylbenzyloxy)-1-naphthylmethylene]-hydrazide

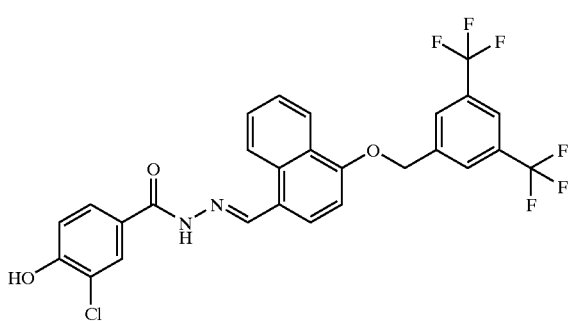

To a solution of 3-chloro-4-hydroxybenzoic acid hydrazide (200 mg, 1.1 mmol) in DMSO (2 mL) was added 4-(3,5-bis-trifluoromethylbenzyloxy)-1-naphthaldehyde (440 mg, 1.1 mmol) and a catalytic amount of glacial acetic acid (5 drops). The reaction was stirred overnight under nitrogen and diluted with ethyl acetate. The solution was washed with saturated sodium bicarbonate, water, brine, and dried over MgSO$_4$. The organic volume was concentrated under vacuo to give the crude product. The product was purified by silica gel column chromatography using CH$_2$Cl$_2$/MeOH as the mobile phase.

$^1$H NMR (DMSO-d$_6$): δ 3.77 (s, 6H), 4.91 (s, 2H), 6.95 (s, 2H), 6.99 (d, 1H), 7.30 (d, 2H), 7.52 (d, 2H), 7.68 (m, 1H), 7.89 (s, 1H), 8.29 (s, 1H), 10.90 (broad s, 1H), 11.69 (s, 1H); MS (ESI): m/z 525.37 (M+H)$^+$.

EXAMPLE 8

3-Chloro-4-hydroxybenzoic Acid [4-(2-Chloroethoxy)-1-naphthylmethylene]hydrazide

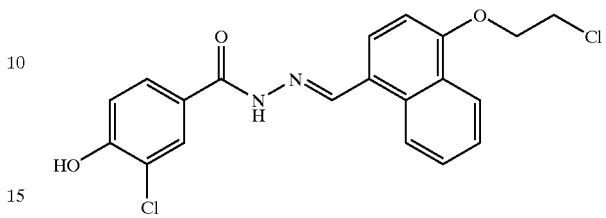

A solution of 1-(4-chloroethoxy)naphthaldehyde (2.35 g, 10 mmoles), 3-chloro-4-hydroxy benzoic acid hydrazide (1.87 g, 10 mmoles), glacial acetic acid (0.2 mL) and dimethylsulfoxide (DMSO)(15 mL) was stirred at room temperature overnight. Ethyl acetate (100 mL) was added. The solution was extracted with water and brine which induced precipitation. The product (3.1 g, 77% yield) was obtained by suction filtration. The product was purified by recrystallization from ethyl acetate.

MS (Cl): 235. $^1$H NMR (DMSO-d$_6$): δ 11.5 (s, 1H), 10.7 (s, 1H), 8.7 (bs, 2H), 8.1 (m, 1H), 7.8 (s, 1H), 7.6–7.3 (m, 2H), 7.0 (m, 2H), 4.3 (t, 2H), 3.7 (t, 2H).

By application of the above methodology the following compounds of the invention are synthesized employing the following general procedure:

To a solution of 1 mmol of an arylcarboxylic Acid Hydrazide in 2 ml of anhydrous DMSO was added 1 mmol of the carbonyl compound (an aldehyde or ketone), followed by a catalytic amount of glacial acetic acid. The reaction was stirred overnight under nitrogen and diluted with ethyl acetate. The organic layer was washed with saturated sodium bicarbonate, water, brine, and dried over MgSO$_4$. Upon partial concentration of the solvent in vacuo, the alkylene hydrazides usually precipitated. The alkylene hydrazides were further purified by recrystallization from hot ethanol or ethyl acetate, or chromatographed using CH$_2$Cl$_2$/MeOH as an eluent.

EXAMPLE 9

4-Hydroxy-3-methoxybenzoic Acid (2-Naphthylmethylene)hydrazide

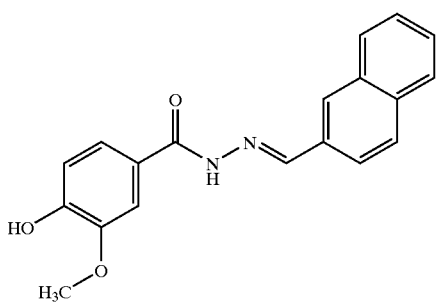

$^1$H NMR (DMSO-d$_6$) δ 3.66 (s, 3H), 6.67 (d, J=8.2 Hz, 1H), 7.32–7.47 (m, 5H), 7.74 (d, J=7.2 Hz, 1H), 7.79 (d, J=8.2 Hz, 2H), 8.60 (d, J=8.2 Hz, 1H), 9.11 (s, 1H), 11.80 (s, 1H). APCI m/z: 321

EXAMPLE 10

4-Hydroxy-3-methoxybenzoic Acid (4-Methoxy-1-naphthylmethylene)hydrazide

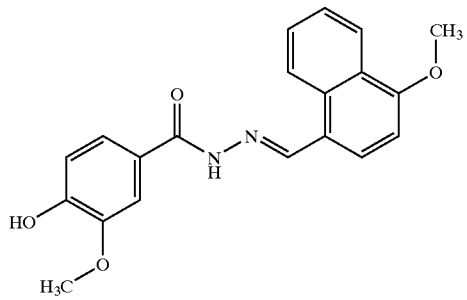

$^1$H NMR (CDCl$_3$): δ 4.80 (s, 3H), 3.86 (s, 3H), 6.00 (s, 1H), 6.59 (d, 1H), 6.83 (d, 1H), 7.39 (m, 3H), 7.52 (s, 1H), 7.73 (s, 1H), 8.18 (d, 1H), 8.58 (d, 1H), 8.88 (s, 1H), 9.95 (s, 1H). MS (APCI): 351.

EXAMPLE 11

4-Hydroxy-3-methoxybenzoic Acid (4-tert-Butylbenzylidene)hydrazide

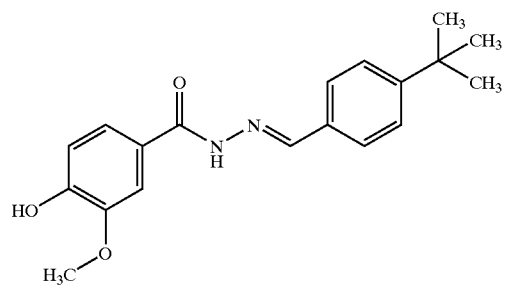

$^1$H NMR (CDCl$_3$): δ 1.30 (s, 9H), 3.91 (s, 3H), 6.16 (s, 1H), 6.88 (d, 1H), 7.23–7.78 (m, 6H), 8.28 (s, 1H), 9.58 (s, 1H). MS (APCI): 327.

EXAMPLE 12

4-Hydroxy-3-methoxybenzoic Acid (4-Isopropylbenzylidene)hydrazide

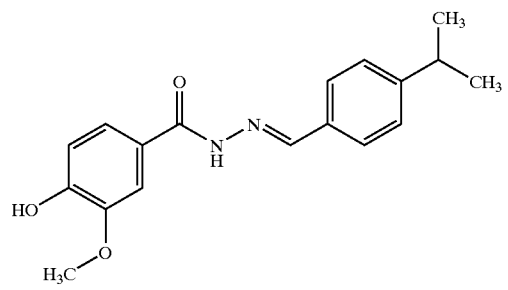

$^1$H NMR (CDCl$_3$) δ 1.29 (d, 6H), 2.94 (q, 1H), 3.98 (s, 3H), 6.13 (s, 1H), 6.97 (d, 1H), 7.20–7.80 (m, 6H), 8.29 (s, 1H), 9.38 (s, 1H). MS (APCI): 313.

EXAMPLE 13

4-Hydroxy-3-methoxybenzoic Acid (4-Trifluoromethoxybenzylidene)hydrazide

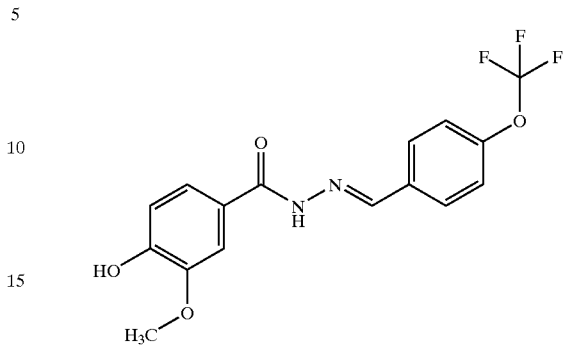

$^1$H NMR (DMSO-d$_6$): δ 4.01 (s, 3H), 7.04 (d, J=8.1 Hz, 1H), 7.60 –7.65 (m, 4H), 8.01 (d, J=8.4 Hz, 2H), 8.63 (s, 1H), 9.92 (s, 1H), 11.89 (s, 1H). MS (APCI): 355, 313, 222, 205.

EXAMPLE 14

4-Hydroxy-3-methoxybenzoic Acid (1H-indol-3-ylmethylene)hydrazide

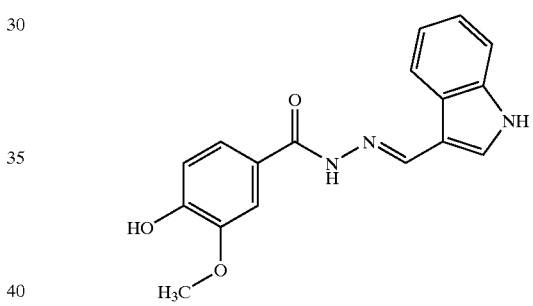

$^1$H NMR (DMSO-d$_6$) δ 3.79 (s, 3H), 6.80 (d, J=8.2 Hz, 1H), 7.11 (m, 2H), 7.38 (m, 3H), 7.73 (d, J=2.0 Hz, 1H), 8.53 (d, J=7.5 Hz, 1H), 8.53 (s, 1H), 9.58 (s, 1H), 11.23 (s, 1H), 11.49 (s, 1H). MS (APCI): 310.

EXAMPLE 15

4-Hydroxy-3-methoxybenzoic Acid (4-Dimethylamino-1-naphthylmethylene)hydrazide

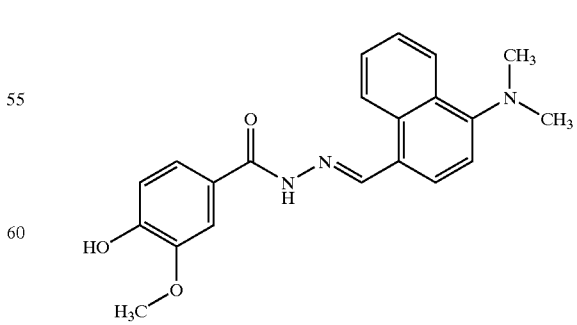

$^1$H NMR (DMSO-d$_6$): δ 3.05 (s, 6H), 4.03 (s, 3H), 7.06 (d, J=8.1 Hz, 1H), 7.33 (d, J=8.0 Hz, 1H), 7.63–7.80 (m,

4H), 7.97 (d, J=8.0 Hz, 1H), 8.38 (d, J=7.9 Hz, 1H), 9.10 (d, J=8.4 Hz, 1H), 9.15 (s, 1H), 9.90 (s, 1H), 11.73 (s, 1H). MS (APCI): 364.

EXAMPLE 16

4-Hydroxy-3-methoxybenzoic Acid (4-Phenylbenzylidene)hydrazide

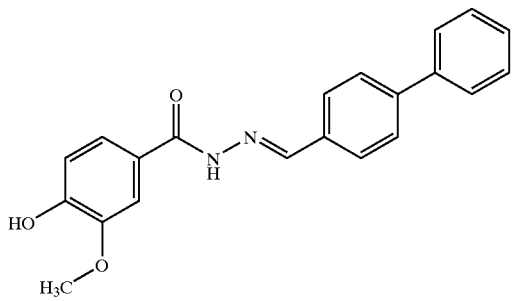

$^1$H NMR (DMSO-d$_6$): δ 4.02 (s, 3H), 7.04 (d, J=8.2 Hz, 1H), 7.63–7.68 (m, 5H), 7.88–7.96 (m, 6H), 8.64 (s, 1H), 9.91 (s, 1H), 11.83 (s, 1H). MS (APCI): 347.

EXAMPLE 17

4-Hydroxybenzoic Acid (1-Naphthylmethylene)hydrazide

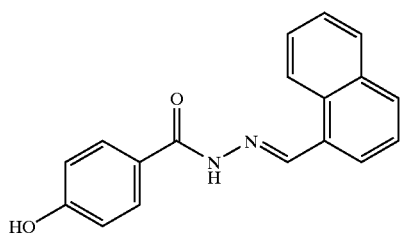

$^1$H NMR (DMSO-d$_6$): δ 6.82 (d, J=8.2 Hz, 2H), 7.48–7.68 (m, 3H), 7.72–7.88 (m, 3H), 7.95 (d, J=8.2 Hz, 2H), 8.80 (d, 1H), 9.04 (s, 1H), 10.14 (s, 1H). MS (APCI): 291.

EXAMPLE 18

4-Hydroxybenzoic Acid (4-Methoxy-1-naphthylmethylene)hydrazide

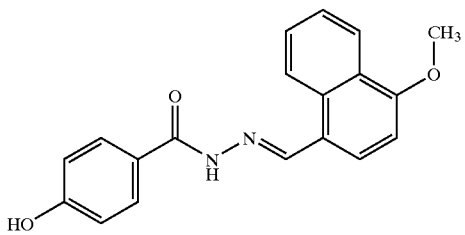

$^1$H NMR (DMSO-d$_6$): δ 3.97 (s, 3H), 6.82 (d, J=8.6 Hz, 2H), 7.04 (d, J=8.2 Hz, 1H), 7.52 (dd, J=7.3, 7.7 Hz, 1H), 7.62 (dd, J=6.8, 7.7 Hz, 1H), 7.77 (d, J=8.5 Hz, 3H), 8.19 (d, J=8.2 Hz, 1H), 8.89 (m, 2H), 10.06 (s, 1H). MS (APCI): 321.

EXAMPLE 19

3,4-Dihydroxybenzoic Acid (1-Naphthylmethylene)hydrazide

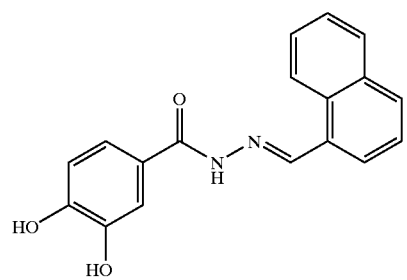

$^1$H NMR (DMSO-d$_6$): δ 6.64 (d, J=8.6 Hz, 1H), 7.13 (d, J=8.2 Hz, 1H), 7.19 (d, J=2.0 Hz, 1H), 7.36–7.42 (m, 3H), 7.68 (d, J=8.2 Hz, 1H), 7.80 (d, J=8.2 Hz, 2H), 8.65 (d, J=8.2 Hz, 1H), 8.88 (s, 1H), 9.07 (s, 1H), 9.46 (s, 1H), 11.45 (s, 1H). MS (APCI): 307.

EXAMPLE 20

4-Hydroxy-3-methoxybenzoic Acid (1-Naphthylmethylene)hydrazide

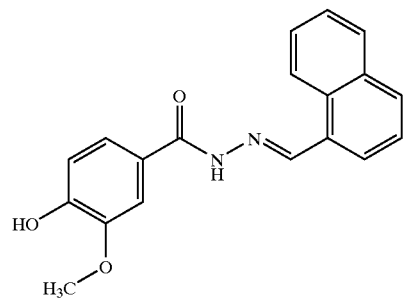

$^1$H NMR (DMSO-d$_6$) δ 3.94 (s, 3H), 6.74 (d, 1H), 7.37–7.52 (m, 6H), 7.77 (d, 1H), 7.89 (d, 2H), 8.67 (d, 1H), 9.93 (s, 1H), 10.90 (s, 1H). MS (APCI): 321.

EXAMPLE 21

4-Hydroxy-3-methoxybenzoic Acid [3-(3-Trifluoromethylphenoxy)benzylidene]hydrazide

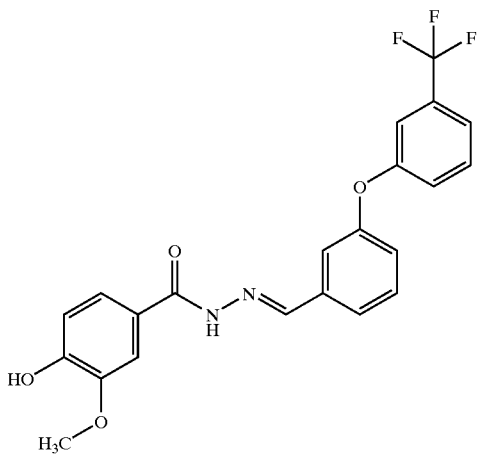

$^1$H NMR (DMSO-$d_6$) δ 3.83 (s, 3H), 6.85 (d, 1H), 7.16 (dd, 1H), 7.36 (m, 5H), 7.44 (m, 3H), 7.61 (t, 1H), 8.43 (s, 1H), 1.75 (s, 1H), 11.69 (s, 1H). MS (APCI): 431.

EXAMPLE 22

4-Hydroxy-3-methoxybenzoic Acid (4-Quinolinylmethylene)hydrazide

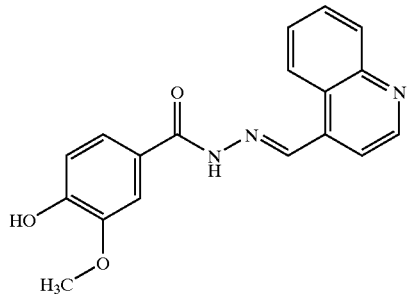

$^1$H NMR (DMSO-$d_6$): δ 3.58 (s, 3H), 6.52 (d, J=8.0 Hz, 1H), 7.28 (d, J=7.8 Hz, 2H), 7.47 (dd, J=J=8.1 Hz, 1H), 7.59 (m, 2H), 7.86 (d, J=8.4 Hz, 1H), 8.50 (d, J=8.4 Hz, 1H), 8.73 (d, J=4.5 Hz, 1H), 8.94 (s, 1H). MS (APCI): 322.

EXAMPLE 23

4-Hydroxybenzoic Acid [3-(1,1,2,2-Tetrafluoroethoxy)benzylidene]hydrazide

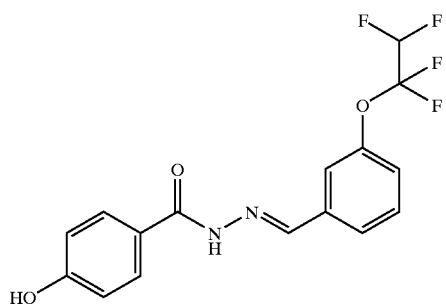

$^1$H NMR (DMSO-$d_6$) δ 6.49–6.78 (m, 3H), 7.10 (d, 1H), 7.32 (t, 1H), 7.41 (m, 2H), 7.57 (d, 2H), 8.23 (s, 1H), 10.01 (s, 1H), 11.59 (s, 1H). MS (APCI): 357.

EXAMPLE 24

4-Hydroxybenzoic Acid [3-(4-tert-Butylphenyl)but-2-enylidene]hydrazide

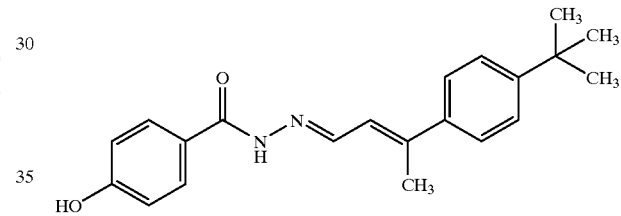

$^1$H NMR (DMSO-$d_6$) δ 1.15 (s, 9H), 1.99 (s, 3H), 6.64 (s, 1H), 6.17 (d, 2H), 7.29 (s, 4H), 7.64 (d, 2H), 8.06 (s, 1H), 9.98 (s, 1H), 11.36 (s, 1H). MS (APCI): 337.

EXAMPLE 25

4-Hydroxy-3-methoxybenzoic Acid (4-Hydroxy-1-naphthylmethylene)hydrazide

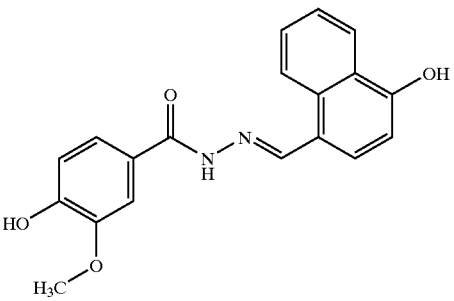

$^1$H NMR (DMSO-$d_6$): δ 3.90 (s, 3H), 6.89 (d, 1H), 6.99 (d, 1H), 7.19 (d, 1H), 7.45–7.80 (m, 5H), 8.22 (d, 1H), 8.90 (s, 2H), 9.62 (s, 1H), 10.68 (s, 1H). MS (APCI): 337.

EXAMPLE 26

4-Hydroxybenzoic Acid (Benzylidene)hydrazide

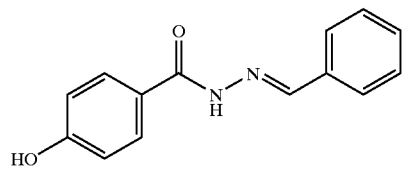

$^1$H NMR (DMSC-d$_6$): δ 6.86 (d, 2H), 7.41–7.52 (3H), 7.72 (d, 2H), 7.82 (d, 2H), 8.41 (s, 1H), 10.14 (s, 1H). MS (APCI): 241.

EXAMPLE 27

3-Amino-4-hydroxybenzoic Acid (1-Naphthylmethylene)hydrazide

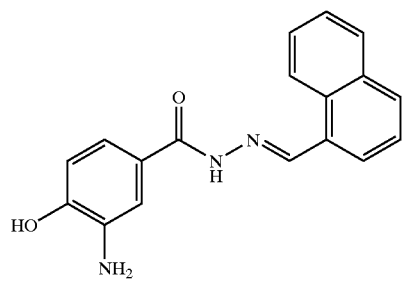

$^1$H NMR (DMSO-d$_6$): δ 4.71 (bs, 2H), 6.68 (d, J=8.1 Hz, 1H), 7.01 (dd, J=2.0, 8.2 Hz, 1H), 7.17 (d, J=2.0 Hz, 1H), 7.51–7.62 (m, 3H), 7.84 (d, J=7.2 Hz, 1H), 7.94 (d, J=8.0 Hz, 2H), 8.75 (d, J=7.6 Hz, 1H), 9.01 (s, 1H), 9.70 (s, 1H), 11.54 (s, 1H). MS (APCI): 306.

EXAMPLE 28

3-Amino-4-hydroxybenzoic Acid (4-Hydroxy-1-Naphthylmethylene)hydrazide

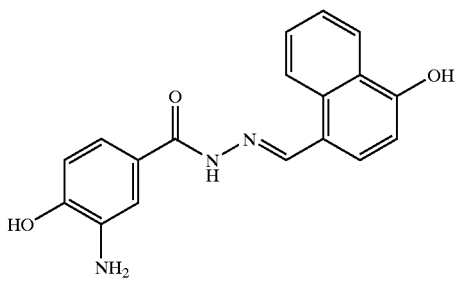

$^1$H NMR (DMSO-d$_6$): δ 4.68 (bs, 2H), 6.67 (d, J=8.2 Hz, 1H), 6.91 (d, J=7.3 Hz, 1H), 7.03 (d, J=8.2 Hz, 1H), 7.15 (s, 1H), 7.43–7.65 (m, 3H), 8.16 (d, J=8.2 Hz, 1H), 8.83 (m, 2H), 10.71 (s, 1H), 11.34 (s, 1H). MS (APCI): 322.

EXAMPLE 29

4-Hydroxybenzoic Acid [3-(3-Trifluoromethylbenzyloxy)benzylidene]hydrazide

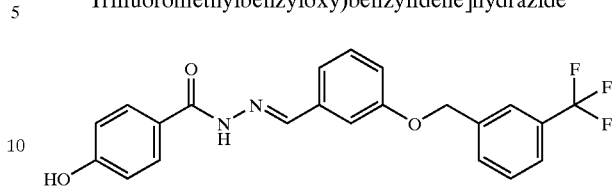

$^1$H NMR (DMSO-d$_6$): δ 5.28 (s, 2H), 6.88 (d, 2H), 7.12 (m, 1H), 7.24–7.50 (m, 3H), 7.55–7.92 (m, 6H), 8.41 (s, 1H), 10.16 (s, 1H), 10.86 (s, 1H). MS (APCI): 415.

EXAMPLE 30

3-Chloro-4-hydroxybenzoic Acid (1-Naphthylmethylene)hydrazide

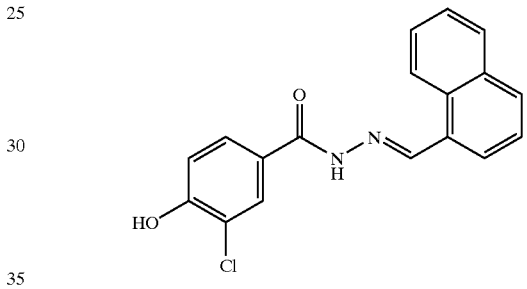

$^1$H NMR (DMSO-d$_6$): δ 7.03 (d, J=8.2 Hz, 1H), 7.52–7.62 (m, 3H), 7.74 (d, J=8.2 Hz, 1H), 7.86 (d, J=7.0 Hz, 1H), 7.96 (m, 3H), 8.79 (d, J=8.2 Hz, 1H), 9.01 (s, 1H), 10.94 (s, 1H), 11.76 (s, 1H). MS (APCI): 325.

EXAMPLE 31

3-Chloro-4-hydroxybenzoic Acid (4-Hydroxy-1-naphthylmethylene)hydrazide

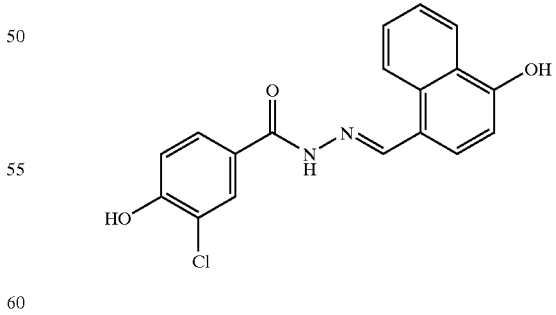

$^1$H NMR (DMSO-d$_6$): δ 6.90 (d, J=8.0 Hz, 1H), 7.02 (d, J=8.5 Hz, 1H), 7.50 (dd, J=J'=7.8 Hz, 1H), 7.58 (dd, J=7.1, 8.0 Hz, 1H), 7.65 (d, J=8.0 Hz, 1H), 7.72 (d, J=8.5 Hz, 1H), 7.93 (s, 1H), 8.17 (d, J=8.2 Hz, 1H), 8.83 (s, 1H), 8.88 (d, J=8.5 Hz, 1H), 10.73 (s, 1H), 10.88 (s, 1H), 11.54 (s, 1H). MS (APCI): 343, 341.

EXAMPLE 32

4-Hydroxybenzoic Acid (4-Hydroxy-1-naphthylmethylene)hydrazide

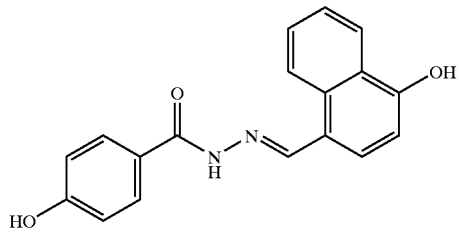

$^1$H NMR (DMSO-d$_6$): δ 6.88 (d, 2H), 6.98 (d, 1H), 7.55 (dd, 1H), 7.64 (dd, 1H), 7.71 (d, 1H), 7.82 (d, 2H), 8.22 (d, 1H), 8.94 (m, 2H), 10.11 (s, 1H), 10.77 (s, 1H). MS (APCI): 307.

EXAMPLE 33

4-Hydroxybenzoic Acid [4-(3-Trifluoromethylphenoxy)benzylidene]hydrazide

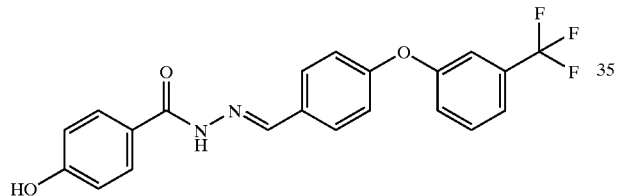

$^1$H NMR (DMSO-d$_6$): δ 6.81 (d, 2H), 6.98 (d, 1H), 7.13 (dd, 1H), 7.30–7.48 (m, 3H), 7.48–7.60 (m, 3H), 7.68 (dd, 1H), 7.81 (d, 2H), 8.41 (s, 1H). MS (APCI): 401.

EXAMPLE 34

4-Hydroxybenzoic Acid (5-Phenyl-3-pyrazolylmethylene)hydrazide

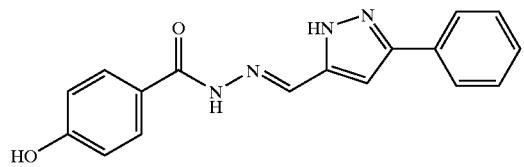

$^1$H NMR (DMSO-d$_6$): δ 6.81 (d, 2H), 7.40–7.62 (m, 5H), 7.78 (d, 2H), 8.09 (s, 1H), 8.50 (s, 1H). MS (APCI): 307.

EXAMPLE 35

2,4-Dihydroxybenzoic Acid (4-Hydroxy-1-naphthylmethylene)hydrazide

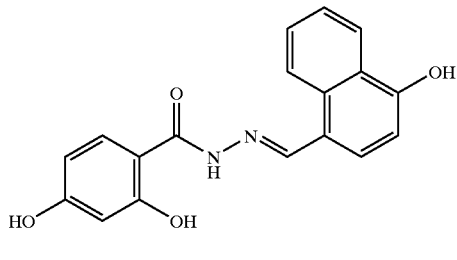

$^1$H NMR (DMSO-d$_6$): 6.35 (s, 1H), 6.39 (d, 1H), 6.99 (d, 1H), 7.51 (dd, 1H), 7.65 (dd, 1H), 7.73 (d, 1H), 7.82 (d, 1H), 8.26 (d, 1H), 8.88 (s, 1H), 8.98 (d, 1H), 10.0–11.0 (m, 4H). MS (APCI): 323.

EXAMPLE 36

4-Hydroxy-3-nitrobenzoic Acid (1-Naphthylmethylene)hydrazide

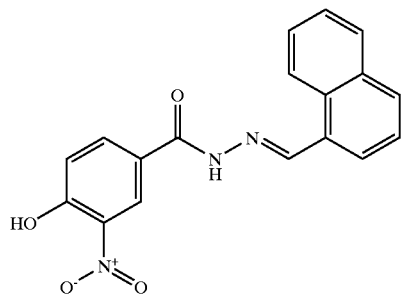

$^1$H NMR (DMSO-d$_6$): δ 6.15 (d, J=9.3 Hz, 1H), 7.37–7.48 (m, 4H), 6.70 (d, J=7.1 Hz, 1H), 7.78–7.82 (m, 2H), 8.29 (s, 1H), 8.43 (d, J=8.5 Hz, 1H), 8.85 (s, 1H).

EXAMPLE 37

4-Hydroxy-3-nitrobenzoic Acid (4-Hydroxy-1-naphthylmethylene)hydrazide

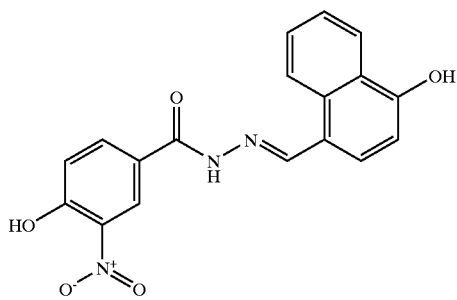

$^1$H NMR (DMSO-d$_6$): δ 6.24 (d, J=9.3 Hz, 1H), 6.83 (d, J=8.0 Hz, 1H), 7.37–7.52 (m, 3H), 7.57 (d, J=8.0 Hz, 1H), 8.10 (d, J=8.0 Hz, 1H), 8.34 (s, 1H), 8.76 (s, 1H), 8.79 (s, 1H), 10.57 (s, 1H), 11.17 (m, 1H).

EXAMPLE 38

3,4-Dihydroxybenzoic Acid (4-Hydroxy-1-naphthylmethylene)hydrazide

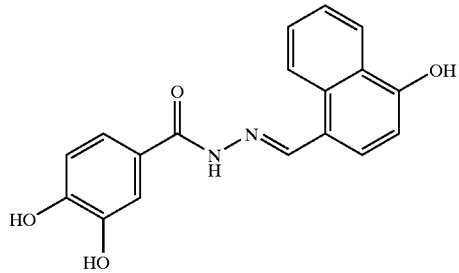

$^1$H NMR (DMSO-d$_6$): δ 6.86 (d, 1H), 6.98 (d, 1H), 7.32 (d, 1H), 7.42 (s, 1H), 7.56 (dd, 1H), 7.63 (dd, 1H), 7.71 (d, 1H), 8.24 (d, 1H), 8.88 (s, 1H), 8.92 (m, 2H), 9.26 (s, 1H), 9.54 (s, 1H), 10.75 (s, 1H). MS (APCI): 323.

EXAMPLE 39

4-Hydroxybenzoic Acid (6-Methoxy-2-naphthylmethylene)hydrazide

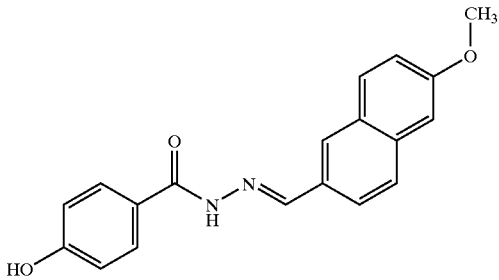

$^1$H NMR (DMSO-d$_6$): δ 3.89 (s, 3H), 6.86 (d, J=8.6 Hz, 2H), 7.22 (dd, J=2.3, 8.9 Hz, 1H), 7.37 (d, J=2.3 Hz, 1H), 7.80–7.93 (m, 6H), 8.04 (s, 1H), 8.53 (s, 1H), 11.67 (s, 1H). MS (APCI): 321.

EXAMPLE 40

3,5-Dichloro-4-hydroxybenzoic Acid (4-Hydroxy-1-naphthylmethylene)hydrazide

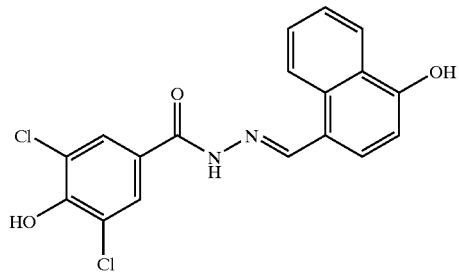

$^1$H NMR (DMSO-d$_6$): δ 6.98 (d, 1H), 7.58 (dd, 1H), 7.68 (dd, 1H), 7.78 (d, 1H), 8.02 (s, 2H), 8.27 (d, 1H), 8.90 (s, 1H), 8.96 (d, 1H), 10.81 (s, 1H), 10.98 (s, 1H), 11.67 (s, 1H). MS (APCI): 375, 377.

EXAMPLE 41

6-Hydroxy-2-naphthoic Acid (4-Hydroxy-1-naphthylmethylene)hydrazide

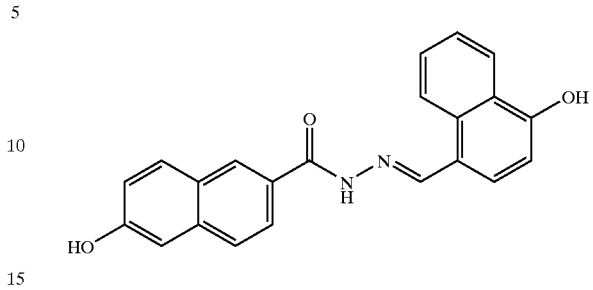

$^1$H NMR (DMSO-d$_6$): δ 6.04 (d, 2H), 6.33 (m, 1H), 6.62 (dd, 2H), 6.79 (dd, 2H), 7.06 (d, 2H), 7.44 (d, 2H), 8.27 (d, 2H), 8.39 (s, 2H).

EXAMPLE 42

4-Hydroxy-3-methoxybenzoic Acid (9-Ethyl-9H-3-carbazolylmethylene)hydrazide

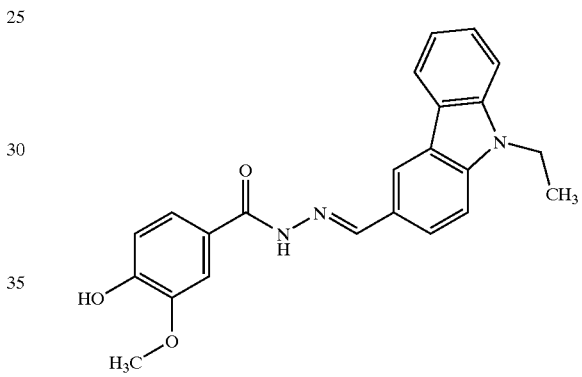

$^1$H NMR (DMSO-d$_6$) δ 1.34 (t, J=7.0 Hz, 3H), 3.88 (s, 3H), 4.47 (q, J=7.0 Hz, 2H), 6.90 (d, J=8.0 Hz, 1H), 7.25 (t, J=7.5 Hz, 1H), 7.47–7.54 (m, 3H), 7.64 (d, J=8.2 Hz, 1H), 7.69 (d, J=8.5 Hz, 1H), 7.89 (d, J=8.5 Hz, 1H), 8.24 (d, J=7.7 Hz, 1H), 8.45 (s, 1H), 8.62 (s, 1H), 9.62 (s, 1H), 11.51 (s, 1H). MS (APCI): 388.

EXAMPLE 43

4-Hydroxy-3-methoxybenzoic Acid [5-(3-Chlorophenyl)-2-furanylmethylene]hydrazide

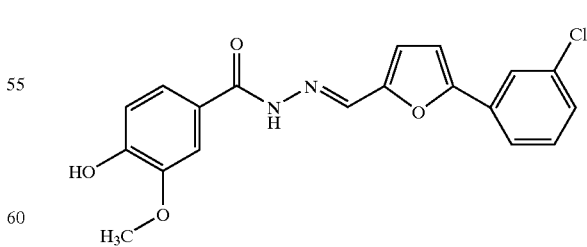

$^1$H NMR (DMSO-d$_6$): δ 3.93 (s, 3H), 6.97 (d, J=8.2 Hz, 1H), 7.14 (d, J=3.5 Hz, 1H), 7.37 (d, J=3.5 Hz, 1H), 7.48–7.63 (m, 4H), 7.84 (d, J=8.0 Hz, 1H), 7.93 (s, 1H), 8.47 (s, 1H), 9.85 (s, 1H), 11.75 (s, 1H). MS (APCI): 371.

EXAMPLE 44 3-Chloro-4-hydroxybenzoic Acid (3-Phenylallylidene)hydrazide

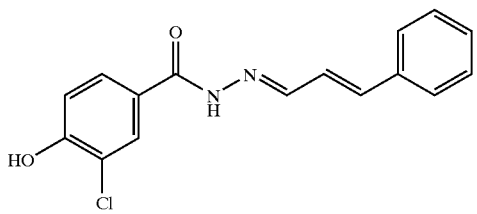

¹H NMR (DMSO-d₆): δ 7.00 (m, 3H), 7.22–7.40 (m, 3H), 7.57 (d, 2H), 7.69 (d, 1H), 7.89 (s, 1H), 8.12 (d, 1H), 11.0 (s, 1H), 12.0 (s, 1H). MS (APCI): 301.

EXAMPLE 45

3-Chloro-4-hydroxybenzoic Acid (4-Allyloxy-1-naphtylmethylene)hydrazide

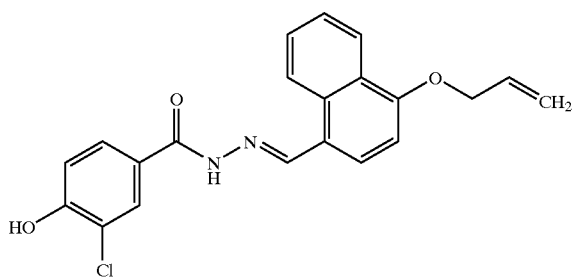

¹H NMR (DMSO-d₆): δ 4.68 (m, 2H), 5.21 (d, 1H), 5.38 (d, 1H), 5.90 –6.10 (m, 1H), 6.86 (dd, 2H), 7.42 (dd, 1H), 7.53 (dd, 1H), 7.67 (dd, 2H), 7.86 (s, 1H), 8.18 (d, 1H), 8.78 (s, 1H), 8.82 (d, 1H), 10.9 (s, 1H), 12.0 (s, 1H). MS (APCI): 381.

EXAMPLE 46

3-Chloro-4-hydroxybenzoic Acid (4-Ethynylmethoxy-1-naphthylmethylene)hydrazide

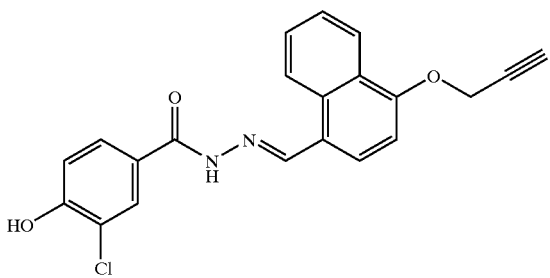

¹H NMR (DMSO-d₆): δ 3.60 (s, 1H), 5.06 (s, 2H), 6.99 (d, 1H), 7.12 (d, 1H), 7.55 (t, 1H), 7.66 (t, 1H), 7.73 (t, 1H), 7.93 (s, 1H), 8.02 (d, 1H), 8.16 (t, 1H), 8.86 (d, 1H), 9.27 (d, 1H), 10.90 (s, 1H), 11.62 (s, 1H). MS (APCI): 378.

EXAMPLE 47

3-Chloro-4-hydroxybenzoic Acid (4-Benzyloxy-1-naphthylmethylene)hydrazide

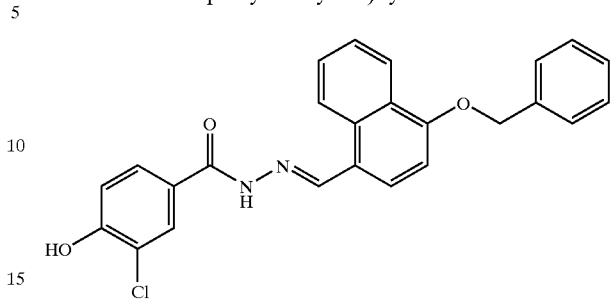

¹H NMR (DMSO-d₆): δ 5.40 (s, 2H), 7.08 (d, 1H), 7.08 (s, 1H), 7.39 (d, 1H), 7.43 (m, 3H), 7.70 (m, 5H), 8.00 (s, 1H), 8.01 (d, 1H), 8.33 (t, 1H), 8.94 (d, 1H), 9.35 (d, 1H), 10.98 (s, 1H), 11.69 (s, 1H). MS (APCI): 431, 433.

EXAMPLE 48

2-(4-[(3-Chloro-4-hydroxybenzoyl)hydrazonomethyl]-1-naphthyloxy)acetamide

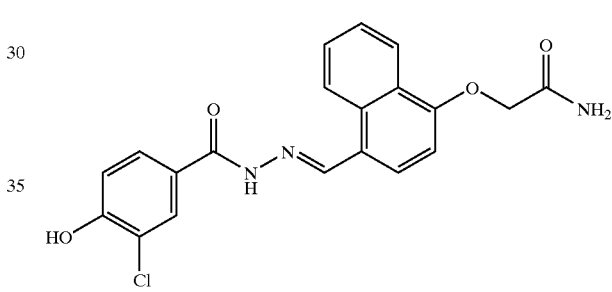

¹H NMR (DMSO-d₆): δ 4.68 (d, 2H), 6.94 (d, 1H), 6.98 (dd, 1H), 7.40–7.86 (m, 5H), 8.00 (m, 1H), 8.48 (dd, 1H), 8.93 (m, 1H), 9.38 (m, 1H). MS (APCI): 398.

EXAMPLE 49

3-Chloro-4-hydroxybenzoic Acid (4-Methyl-1-naphthylmethylene)hydrazide

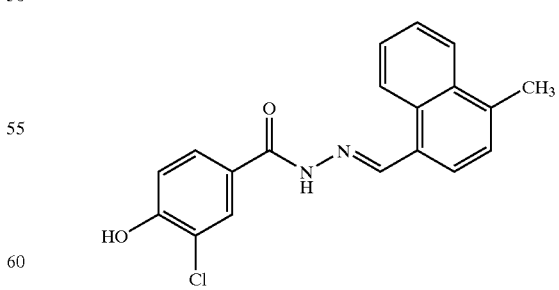

¹H NMR (DMSO-d₆): δ 2.70 (s, 3H), 7.10 (d, 1H), 7.49 (d, 1H), 7.67 (m, 2H), 7.81 (m, 2H), 8.00 (s, 1H), 8.11 (d, 1H), 8.88 (d, 1H), 9.07 (s, 1H), 11.0 (s, 1H). MS (APCI): 339, 341.

EXAMPLE 50

3-Chloro-4-hydroxybenzoic Acid (2-Hydroxy-1-naphthylmethylene)hydrazide

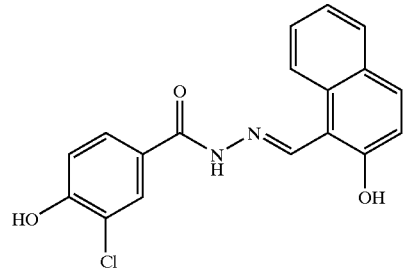

$^1$H NMR (DMSO-d$_6$): δ 6.98 (d, 1H), 7.98 (d, 1H), 7.29 (dd, 1H), 7.48 (dd, 1H), 7.69 (d, 1H), 7.78 (dd, 2H), 7.90 (s, 1H), 8.06 (d, 1H), 9.32 (s, 1H), 11.00 (s, 1H). MS (APCI): 341.

EXAMPLE 51

3-Chloro-4-hydroxybenzoic Acid (4-Methoxy-1-naphthylmethylene)hydrazide

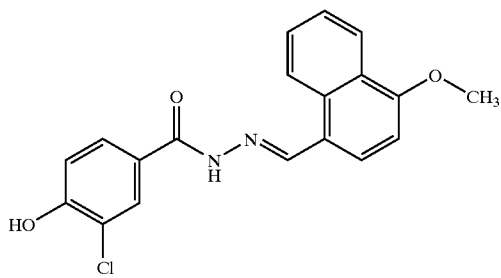

$^1$H NMR (DMSO-d5): δ 4.05 (s, 3H), 7.06 (m, 2H), 7.59 (dd, 1H), 7.70 (dd, 1H), 7.81 (d, 1H), 7.86 (d, 1H), 8.00 (s, 1H), 8.27 (d, 1H), 8.93 (s, 1H), 8.99 (d, 1H), 11.00 (s, 1H). MS (APCI): 341, 339.

EXAMPLE 52

N-(2-[(3-Chloro-4-hydroxybenzoyl)hydrazono]ethyl)-2,2-diphenylacetamide

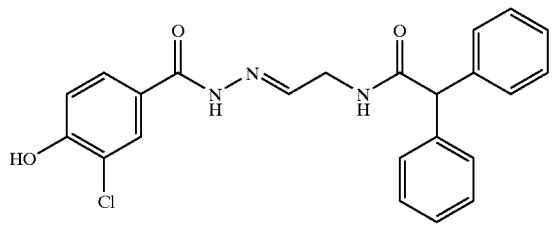

$^1$H NMR (DMSO-d$_6$) δ 3.85 (t, 2H), 4.93 (s, 2H), 7.16–7.25 (m, 10H), 7.26 (m, 1H), 7.62 (d, 1H), 7.82 (s, 1H), 8.69 (t, 1H), 10.85 (s, 1H), 11.39 (s, 1H). MS (APCI): 422.

EXAMPLE 53

3-Chloro-4-hydroxybenzoic Acid (1-Hydroxy-2-naphthylmethylene)hydrazide

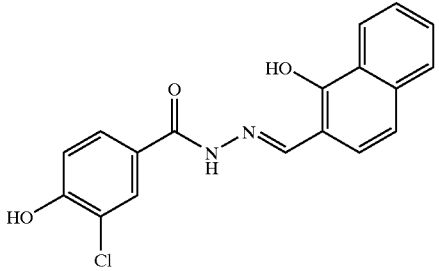

$^1$H NMR (DMSO-d$_6$): δ 6.99 (d, 1H), 7.22 (d, 1H), 7.37 –7.56 (m, 4H), 7.68 (dd, 1H), 7.77 (d, 1H), 7.90 (s, 1H), 8.19 (d, 1H), 8.58 (s, 1H), 11.00 (s, 1H). MS (APCI): 341.

EXAMPLE 54

3-Chloro-4-hydroxybenzoic Acid (2,2-Diphenylethylidene)hydrazide

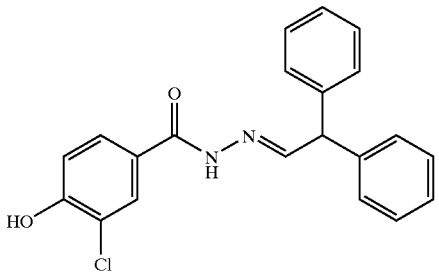

$^1$H NMR (DMSO-d$_6$): δ 4.94 (d, 1H), 6.98 (d, 1H), 7.11–7.22 (m, 5H), 7.22–7.34 (m, 4H), 7.68 (d, H), 7.82 (s, 1H), 8.19 (d, 1H), 11.00 (s, 1H). MS (APCI): 365, 367.

EXAMPLE 55

3-Chloro-4-hydroxybenzoic Acid (4-Benzyloxy-3,5-dimethoxybenzylidene)hydrazide

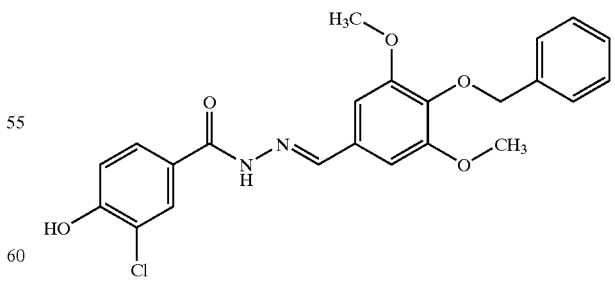

$^1$H NMR (DMSO-d$_6$): δ 3.86 (s, 6H), 4.98 1(s, 2H), 7.03 (s, 2H), 7.09 (d, 1H), 7.25–7.33 (m, 3H), 7.48 (m, 2H), 7.89 (dd, 1H), 7.99 (s, 1H), 8.32 (s, 1H), 11.00 (s, 1H). MS (APCI): 441.

EXAMPLE 56

3-Chloro-4-hydroxybenzioc Acid [3-(4-tert-Butylphenoxy)benzylidene]hydrazide

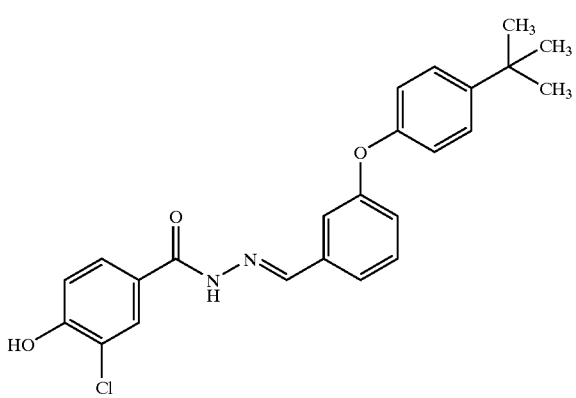

¹H NMR (DMSO-d₆): δ 1.05 (s, 9H), 6.90 (m, 3H), 7.09 (d, 1H), 7.30 (t, 1H), 7.40 (m, 3H), 7.69 (m, 2H), 7.88 (s, 1H), 8.44 (s, 1H), 10.60 (s, 1H), 11.55 (s, 1H). MS (APCI): 423.

EXAMPLE 57

3-Chloro-4-hydroxybenzoic Acid (4-methyl-1-naphthylmethylene)hydrazide

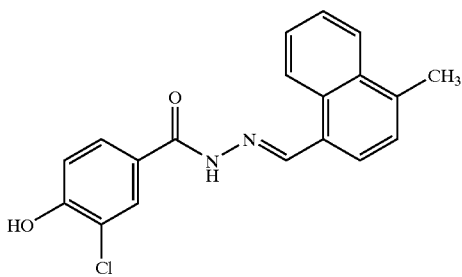

¹H NMR (DMSO-d₆): δ 2.64 (s, 3H), 7.03 (d, J=8.5 Hz, 1H), 7.41 (d, J=7.4 Hz, 1H), 7.58 (m, 2H), 7.78 (m, 2H), 7.95 (d, J=2.0 Hz, 1H), 8.06 (dd, J=2.0, 8.0 Hz, 1H), 8.82 (d, J=8.0 Hz, 1H), 9.07 (s, 1H), 10.93 (s, 1H), 11.71 (s, 1H). MS (APCI): 337, 339.

EXAMPLE 58

3-Chloro-4-hydroxybenzoic Acid (3-Bromo-4-hydroxy-1-naphthylmethylene)hydrazide

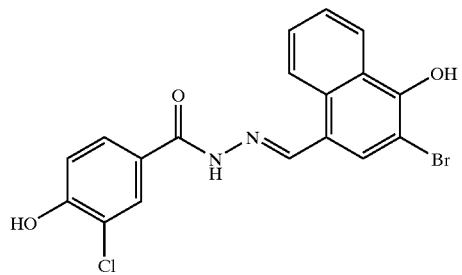

¹H NMR (CDCl₃): δ 7.02 (d, J=8.5 Hz, 1H), 7.51 –7.62 (m, 4H), 7.80 (dd, J=2.0, 8.5 Hz, 1H), 8.00 (d, J=2.0 Hz, 1H), 8.21 (s, 1H), 8.59 (d, J=8.5 Hz, 1H), 8.91 (s, 1H). MS (APCI): 421, 423.

EXAMPLE 59

Acetic Acid 4-[(3-Chloro-4-hydroxybenzoyl)hydrazonomethyl]-1-naphthyl Ester

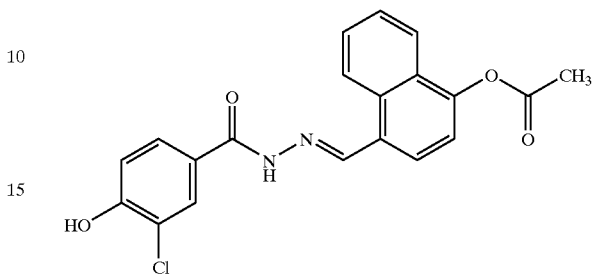

¹H NMR (DMSO-d₆): δ 2.63 (s, 3H), 7.03 (d, J=8.5 Hz, 1H), 7.36 (d, J=8.0 Hz, 1H), 7.60 (dd, J=7.0, 7.5 Hz, 1H), 7.68 (dd, J=7.0, 8.0 Hz, 1H), 7.75 (dd, J=1.4, 8.0 Hz, 1H), 7.89 (d, J=8.0 Hz, 1H), 7.97 (d, J=8.0 Hz, 2H), 8.85 (d, J=8.5 Hz, 1H), 9.08 (s, 1H), 11.0 (s, 1H), 11.78 (s, 1H). MS (APCI): 383.

EXAMPLE 60

3-Chloro-4-hydroxybenzoic Acid (4-Cyanomethoxy-1-naphthylmethylene)hydrazide

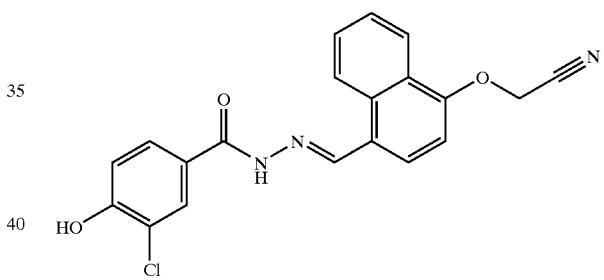

¹H NMR (DMSO-d₆): δ 5.40 (s, 2H), 7.00 (d, 1H), 7.21 (d, 1H), 7.58–7.80 (m, 3H), 7.82 (d, 1H), 7.96 (s, 1H), 8.18 (d, 1H), 8.90 (s, 2H), 9.28 (s, 1H), 11.62 (s, 1H). MS (APCI): 380, 382.

EXAMPLE 61

3-Chloro-4-hydroxybenzoic Acid (2-Hydroxy-1-naphthylmethylene)hydrazide

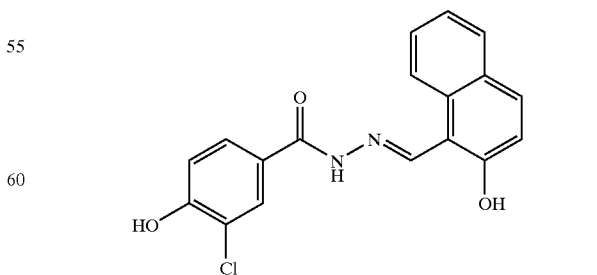

¹H NMR (DMSO-d₆): δ 7.18 (d, 1H), 7.30 (d, 1H), 7.50 (dd, 1H), 7.68 (dd, 1H), 7.88 (d, 1H), 7.95 (m, 2H), 8.08 (s,

1H), 8.29 (d, 1H), 9.51 (s, 1H), 11.12 (s, 1H), 12.12 (s, 1H). MS (APCI): 341, 343.

EXAMPLE 62

3-Chloro-4-hydroxybenzoic Acid (2,3-Methylenedioxybenzylidene)hydrazide

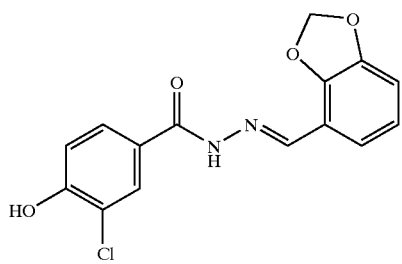

$^1$H NMR (DMSO-$d_6$): δ 6.06 (s, 2H), 6.86 (dd, 1H), 6.90 (dd, 1H), 7.01 (d, 1H), 7.25 (d, 1H), 7.71 (dd, 1H), 7.92 (s, 1H), 8.49 (s, 1H), 10.93 (s, 1H), 11.70 (s, 1H). MS (APCI): 319, 321.

EXAMPLE 63

3-Chloro-4-hydroxybenzoic Acid [3-(4-Methoxyphenoxy)benzylidene]hydrazide

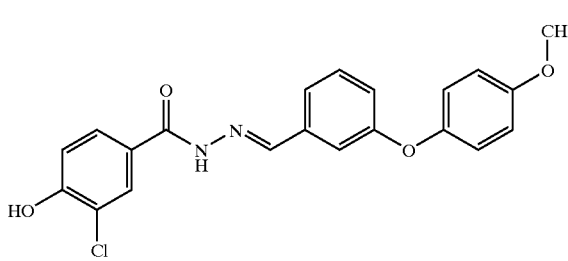

$^1$H NMR (DMSO-$d_6$): δ 3.98 (s, 3H), 7.38 (m, 6H), 7.48 (s, 1H), 7.72 (m, 2H), 7.97 (d, 1H), 8.19 (s, 1H), 8.64 (s, 1H), 11.93 (s, 1H). MS (APCI): 397, 399.

EXAMPLE 64

3-Chloro-4-hydroxybenzoic Acid (9-Phenanthrenylmethylene)hydrazide

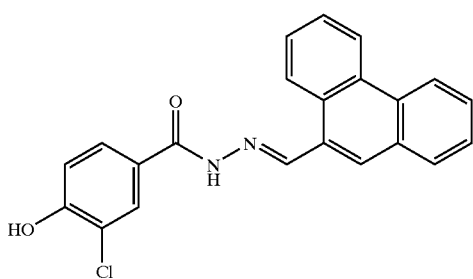

$^1$H NMR (DMSO-$d_6$): δ 7.02 (d, 1H), 7.52–7.83 (m, 5H), 7.99 (d, 1H), 8.08 (d, 1H), 8.21 (s, 1H), 8.82 (d, 1H), 8.89 (dd, 1H), 8.96 (dd, 1H), 9.06 (s, 1H), 10.96 (s, 1H), 11.82 (s, 1H). MS (APCI): 375, 377.

EXAMPLE 65

3-Chloro-4-hydroxybenzoic Acid [4-(2-Hydroxyethoxy)-1-naphthylmethylene]hydrazide

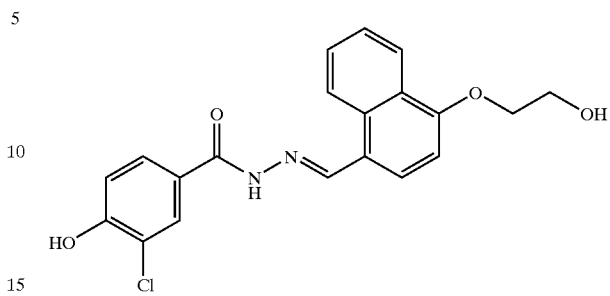

$^1$H NMR (DMSO-$d_6$): δ 3.81 (t, J=4.8 Hz, 2H), 4.16 (t, J=4.8 Hz, 2H), 6.46 (d, J=8.5 Hz, 1H), 7.01 (d, J=8.5 Hz, 1H), 7.51–7.61 (m, 3H), 7.72 (d, J=8.2 Hz, 1H), 7.82 (d, J=2.1 Hz, 1H), 8.30 (d, J=8.2 Hz, 1H), 8.85 (s, 1H), 8.87 (d, J=8.5 Hz, 1H), 11.38 (s, 1H). MS (APCI): 385, 387.

EXAMPLE 66

3-Bromo-4-hydroxybenzoic Acid (4-Hydroxy-1-naphthylmethylene)hydrazide

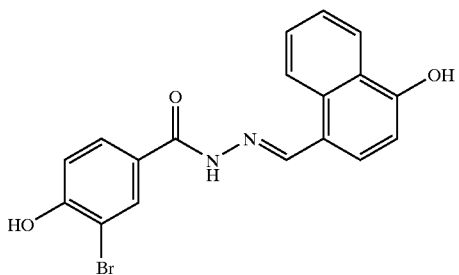

$^1$H NMR (DMSO-$d_6$): δ 6.90 (d, J=8.0 Hz, 1H), 7.00 (d, J=8.0 Hz, 1H), 7.47 (dd, J=J'=8.0 Hz, 1H), 7.58 (dd, J=J''=8.0 Hz, 1H), 7.66 (d, J=8.0 Hz, 1H), 7.77 (dd, J=2.0, 8.0 Hz, 1H), 8.08 (d, J=2.0 Hz, 1H), 8.17 (d, J=8.0 Hz, 1H), 8.83 (s, 1H), 8.88 (d, J=8.0 Hz, 1H), 10.73 (s, 1H), 11.53 (s, 1H). MS (APCI): 385, 387.

EXAMPLE 67

Nicotinic Acid 4-[(3-Chloro-4-hydroxybenzoyl)hydrazonomethyl]-1-naphthyl Ester

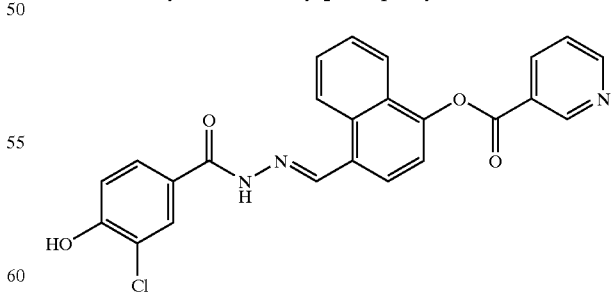

$^1$H NMR (DMSO-$d_6$): δ 7.04 (d, J=8.5 Hz, 1H), 7.58 (d, J=8.0 Hz, 1H), 7.64–7.69 (m, 4H), 7.74–8.02 (m, 3H), 8.56 (dd, J=2.0, 8.0 Hz, 1H), 8.91 (m, 2H), 9.05 (s, 1H), 8.35 (d, J=1.8 Hz, 1H), 10.96 (s, 1H), 11.84 (s, 1H). MS (APCI): 446, 448.

EXAMPLE 68

3-Chloro-4-hydroxybenzoic Acid [4-(1,3-Dioxo-1,3-dihydroisoindol-2-ylmethoxy)-1-naphthylmethylene]hydrazide

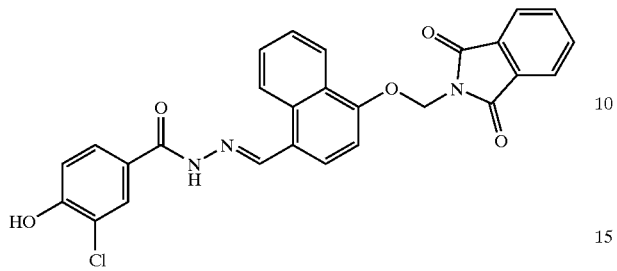

$^1$H NMR (DMSO-$d_6$): δ 5.78 (s, 2H), 7.03 (d, J=8.5 Hz, 1H), 7.37 (d, J=8.2 Hz, 1H), 7.48 (m, 1H), 7.61 (m, 1H), 7.73–7.81 (m, 8H), 8.90 (m, 2H), 10.91 (s, 1H), 11.67 (s, 1H). MS (APCI): 500, 502.

EXAMPLE 69

3-Chloro-4-hydroxybenzoic Acid [4-(Cyclohexylmethoxy)-1-naphthylmethylene]hydrazide

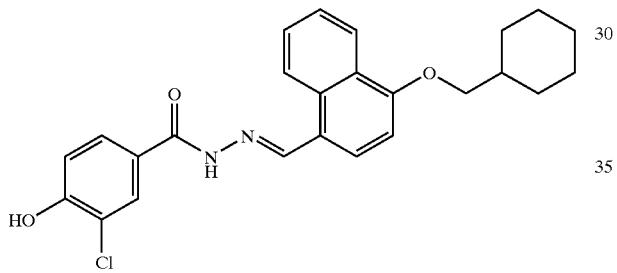

$^1$H NMR (DMSO-$d_6$): δ 1.08–1.19 (m, 4H), 1.66–1.72 (m, 3H), 1.83–1.92 (m, 3H), 3.21 (m, 1H), 3.95 (m, 2H), 6.99 (d, J=8.1 Hz, 1H), 7.03 (d, J=8.5 Hz, 1H), 7.53 (dd, J=J'=7.4 Hz, 1H), 7.62 (dd, J=J'=7.5 Hz, 1H), 7.72–7.93 (m, 2H), 7.94 (d, J=2.1 Hz, 1H), 8.22 (d, J=8.0 Hz, 1H), 8.87 (s, 1H), 8.90 (d, J=8.5 Hz, 1H), 10.94 (s, 1H), 11.60 (s, 1H). MS (APCI): 437, 439.

EXAMPLE 70

3-Chloro-4-hydroxybenzoic Acid [4-(Tetrahydro-2-pyranylmethoxy)-1-naphthylmethylene]hydrazide

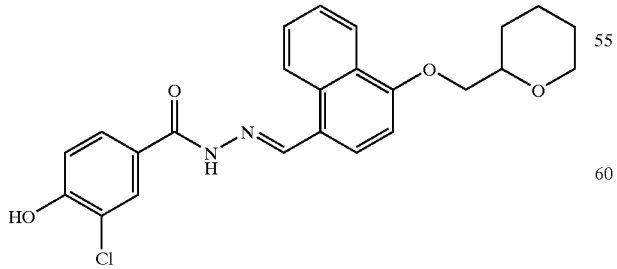

$^1$H NMR (DMSO-$d_6$): δ 1.35 (m, 3H), 1.60–1.71 (m, 2H), 3.15–3.38 (m, 2H), 3.64 (m, 1H), 3.78 (m, 1H), 4.02 (m, 2H), 6.94 (d, J=8.5 Hz, 2H), 7.46 (dd, J=J'=7.4 Hz, 1H), 7.54 (dd, J=J'=8.2 Hz, 1H), 7.66 (m, 2H), 7.86 (d, J=2.1 Hz, 1H), 8.13 (d, J=8.0 Hz, 1H), 8.78 (s, 1H), 8.83 (d, J=8.5 Hz, 1H), 10.83 (s, 1H), 11.52 (s, 1H). MS (APCI): 439, 441.

EXAMPLE 71

3-Chloro-4-hydroxybenzoic Acid [4-(3-Pyridylmethoxy)-1-naphthylmethylene]hydrazide

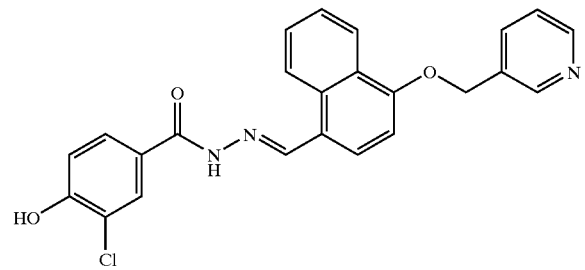

$^1$H NMR (DMSO-$d_6$): δ 5.28 (m, 2H), 6.94 (d, J=8.5 Hz, 1H), 7.10 (d, J=8.5 Hz, 1H), 7.34 (dd, J=4.8, 7.8 Hz, 1H), 7.45 (dd, J'=7.6 Hz, 1H), 7.54 (dd, J=J'=7.5 Hz, 1H), 7.66 (d, J=8.5 Hz, 1H), 7.70 (d, J=8.2 Hz, 1H), 7.86 (m, 2H), 8.15 (d, J=8.0 Hz, 1H), 8.45 (dd, J=1.5, 4.8 Hz, 1H), 8.65 (s, 1H), 8.81 (m, 2H), 10.90 (s, 1H), 11.56 (s, 1H). MS (APCI): 432, 434.

EXAMPLE 72

4-[(3-Chloro-4-hydroxybenzoyl)hydrazonomethyl]-1-naphthyloxy)acetic Acid Ethyl Ester

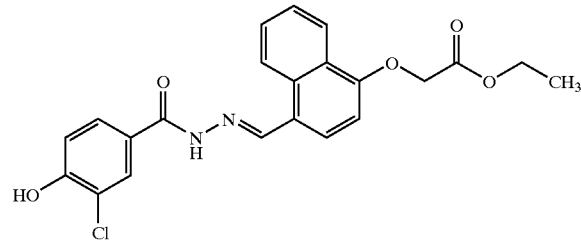

$^1$H NMR (DMSO-$d_6$): δ 1.25 (t, J=7.0 Hz, 3H), 4.25 (q, J=7.0 Hz, 2H), 5.11 (s, 2H), 7.06 (d, J=8.2 Hz, 1H), 7.13 (d, J=8.5 Hz, 1H), 7.64–7.70 (m, 2H), 7.76 (d, J=8.2 Hz, 2H), 8.04 (d, J=2.1 Hz, 1H), 8.36 (d, J=8.2 Hz, 1H), 8.97 (s, 1H), 9.02 (d, J=8.5 Hz, 1H), 11.01 (s, 1H), 11.74 (s, 1H). MS (APCI): 427, 429.

EXAMPLE 73

3-Chloro-4-hydroxybenzoic Acid (3-Nitrobenzylidene)hydrazide

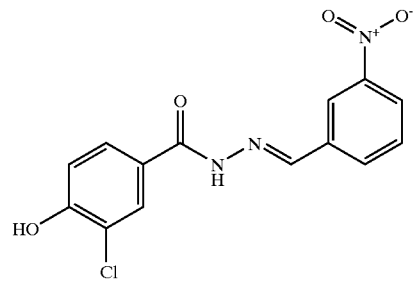

$^1$H NMR (DMSO-$d_6$): δ 7.13 (d, J=8.5 Hz, 1H), 7.79–7.86 (m, 2H), 8.03 (d, J=2.1 Hz, 1H), 8.18 (d, J=7.5 Hz, 1H), 8.30 (d, J=8.0 Hz, 1H), 8.58 (s, 2H), 11.08 (s, 1H), 12.05 (s, 1H). MS (APCI): 320, 322.

EXAMPLE 74

3-Chloro-4-hydroxybenzoic Acid (2,4-Dichlorobenzylidene)hydrazide

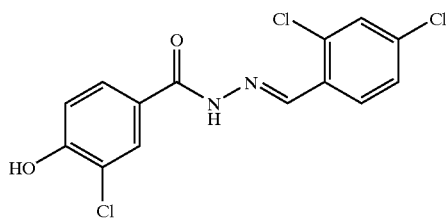

$^1$H NMR (DMSO-$d_6$): δ 7.02 (d, J=8.5 Hz, 1H), 7.46 (d, J=8.2 Hz, 1H), 7.66 (s, 1H), 7.73 (d, J=8.2 Hz, 1H), 7.95 (m, 2H), 8.71 (s, 1H), 11.97 (s, 1H), 11.94 (s, 1H). MS (APCI): 345.

EXAMPLE 75

3-Chloro-4-hydroxybenzoic Acid (4-Fluoro-1-naphthylmethylene)hydrazide

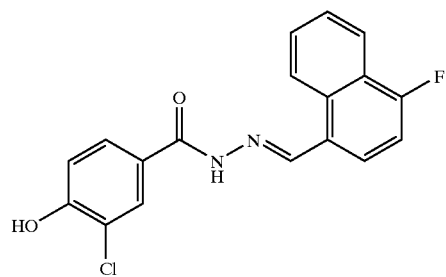

$^1$H NMR (DMSO-$d_6$): δ 7.00 (d, J=8.5 Hz, 1H), 7.33 (dd, J=8.2, 10.3 Hz, 1H), 7.62–7.72 (m, 3H), 7.82 (m, 1H), 7.91 (d, J=1.9 Hz, 1H), 8.04 (d, J=8.1 Hz, 1H), 8.09 (m, 1H), 8.91 (s, 1H), 10.81 (s, 1H), 11.67 (s, 1H). MS (APCI): 343.

EXAMPLE 76

3-Fluoro-4-hydroxybenzoic Acid (4-Hydroxy-1-naphthylmethylene)hydrazide

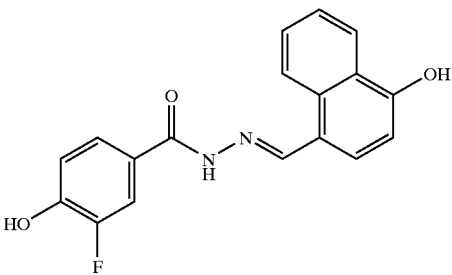

$^1$H NMR (DMSO-$d_6$): δ 6.90 (d, J=8.0 Hz, 1H), 7.00 (t, J=8.6 Hz, 1H), 7.44–7.72 (m, 6H), 8.17 (d, J=8.6 Hz, 1H), 8.84 (s, 1H), 8.89 (d, J=8.5 Hz, 1H), 10.60 (s, 1H), 11.50 (s, 1H). MS (APCI): 325.

EXAMPLE 77

3-Chloro-4-hydroxybenzoic Acid [4-(2,4-Difluorobenzyloxy)-1-naphthylmethylene]hydrazide

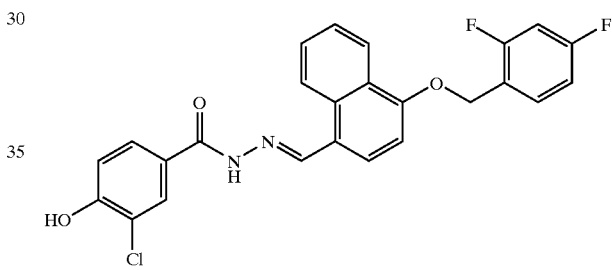

$^1$H NMR (DMSO-$d_6$): δ 5.33 (s, 2H), 7.03 (d, J=8.5 Hz, 1H), 7.12 (m, 1H), 7.21 (d, J=8.2 Hz, 1H), 7.31 (m, 1H), 7.52 (m, 1H), 7.54 (m, 1H), 7.69–7.80 (m, 3H), 7.94 (s, 1H), 8.16 (d, J=8.2 Hz, 1H), 8.90 (m, 2H), 10.91 (s, 1H), 11.63 (s, 1H). MS (APCI): 467, 469.

EXAMPLE 78

3-Fluoro-4-hydroxybenzoic Acid (1-Naphthylmethylene)hydrazide

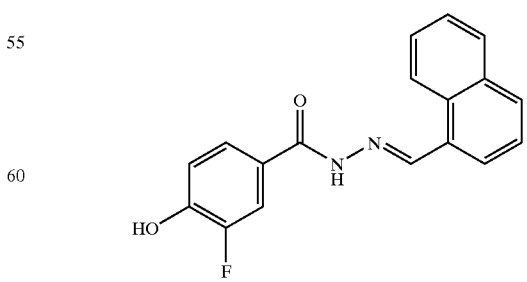

MS (APCI): 309.

EXAMPLE 79

3-Chloro-4-hydroxybenzoic Acid [4-(3-Methoxybenzyloxy)-1-naphthylmethylene]hydrazide

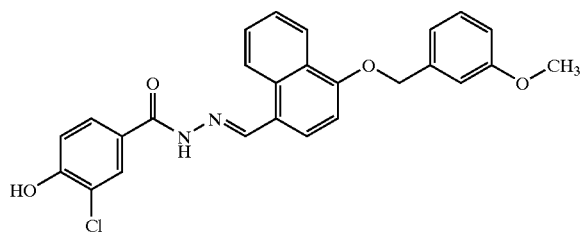

$^1$H NMR (DMSO-$d_6$): δ 3.71 (s, 3H), 5.29 (s, 2H), 6.87 (d, J=8.5 Hz, 1H), 7.00–7.14 (m, 4H), 7.29 (t, J=8.0 Hz, 1H), 7.55 (m, 1H), 7.68 (m, 1H), 7.75 (m, 2H), 7.94 (d, J=2.0 Hz, 1H), 8.25 (d, J=8.0 Hz, 1H), 8.87 (s, 1H), 8.92 (d, J=8.5 Hz, 1H), 11.00 (s, 1H), 11.62 (s, 1H). MS (APCI): 461.

EXAMPLE 80

3-Chloro-4-hydroxybenzoic Acid [4-(4-Fluorobenzyloxy)-1-naphthylmethylene]hydrazide

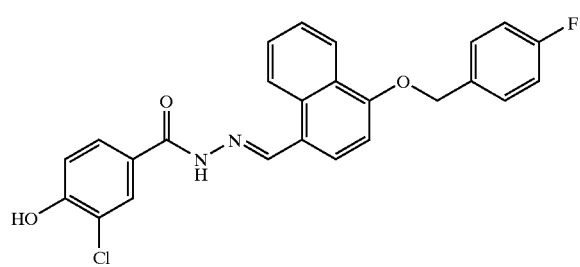

$^1$H NMR (DMSO-$d_6$): δ 5.30 (s, 2H), 7.02 (d, J=8.5 Hz, 1H), 7.13–7.25 (m, 3H), 7.53–7.60 (m, 4H), 7.79 (m, 2H), 7.94 (d, J=2.0 Hz, 1H), 8.23 (d, J=8.0 Hz, 1H), 8.88 (s, 1H), 8.92 (d, J=8.5 Hz, 1H), 10.93 (s, 1H), 11.63 (s, 1H). MS (APCI): 449, 451.

EXAMPLE 81

3-Chloro-4-hydroxybenzoic Acid [4-(2-Tetrahydrofuranylmethoxy)-1-naphthylmethylene]hydrazide

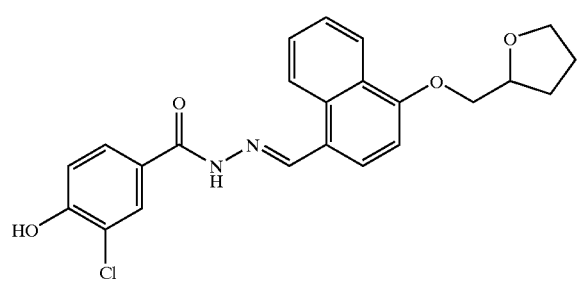

$^1$H NMR (DMSO-$d_6$): δ 1.77–2.04 (m, 4H), 3.68 (m, 1H), 3.78 (m, 1H), 4.12–4.16 (m, 2H), 4.26 (m, 1H), 7.02 (d, J=8.5 Hz, 1H), 7.04 (d, J=8.2 Hz, 1H), 7.53 (m, 1H), 7.62 (m, 1H), 7.74 (m, 2H), 7.94 (d, J=2.0 Hz, 1H), 8.20 (d, J=8.2 Hz, 1H), 8.87 (s, 1H), 8.90 (d, J=8.5 Hz, 1H), 10.93 (s, 1H), 11.61 (s, 1H). MS (APCI): 425, 427.

EXAMPLE 82

3-Chloro-4-hydroxybenzoic Acid (3-Bromo-4-methoxy-1-naphthylmethylene)hydrazide

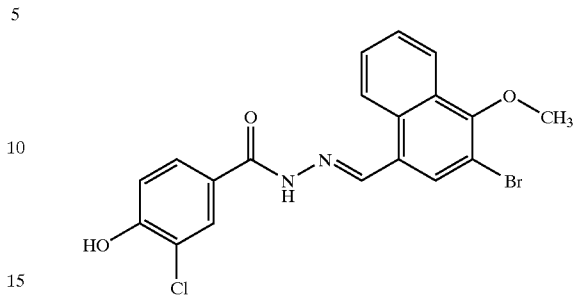

$^1$H NMR (DMSO-$d_6$): δ 3.91 (s, 3H), 7.03 (d, J=8.5 Hz, 1H), 7.65–7.76 (m, 3H), 7.94 (d, J=2.0 Hz, 1H), 8.02 (s, 1H), 8.12 (d, J=8.0 Hz, 1H), 8.71 (d, J=8.0 Hz, 1H), 8.95 (s, 1H), 10.96 (s, 1H), 11.85 (s, 1H). MS (APCI): 433, 435.

EXAMPLE 83

3-Chloro-4-hydroxybenzoic Acid [4-(3-Tetrahydrofuranylmethoxy)-1-naphthylmethylene]hydrazide

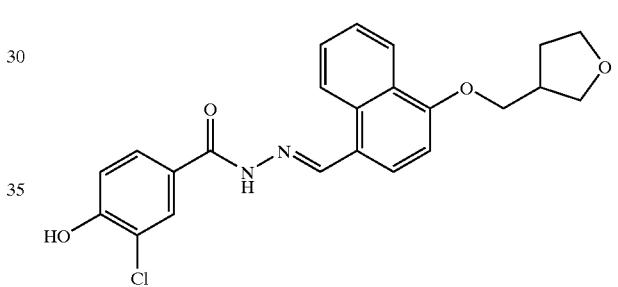

$^1$H NMR (DMSO-$d_6$): δ 1.92 (m, 1H), 2.10 (m, 1H), 2.77 (m, 1H), 3.28–3.88 (m, 4H), 4.12 (m, 2H), 7.03 (d, J=8.5 Hz, 1H), 7.04 (d, J=8.2 Hz, 1H), 7.55 (m, 1H), 7.62 (m, 1H), 7.74 (d, J=8.5 Hz, 1H), 7.76 (d, J=8.0 Hz, 1H), 7.94 (d, J=2.0 Hz, 1H), 8.20 (d, J=8.0 Hz, 1H), 8.88 (s, 1H), 8.90 (d, J=8.5 Hz, 1H), 10.91 (s, 1H), 11.63 (s, 1H). MS (APCI): 425, 427.

EXAMPLE 84

4-(4-[3-Chloro-4-hydroxybenzoyl]hydrazonomethyl]-1-naphthyloxymethyl)benzoic Acid Methyl Ester

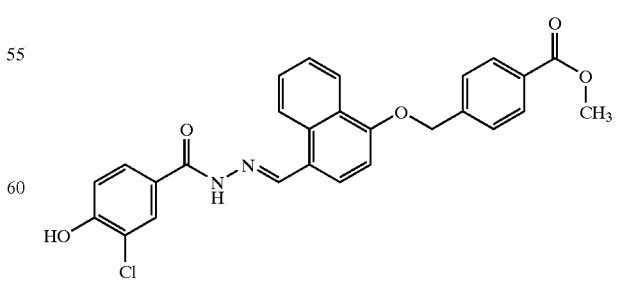

$^1$H NMR (DMSO-$d_6$): δ 3.80 (s, 3H), 5.43 (s, 2H), 7.03 (d, J=8.5 Hz, 1H), 7.12 (d, J=8.2 Hz, 1H), 7.54 (m, 1H), 7.57

(d, J=8.0 Hz, 4H), 7.93–7.99 (m, 3H), 8.30 (d, J=8.0 Hz, 1H), 8.87 (s, 1H), 8.93 (d, J=8.5 Hz, 1H), 10.91 (s, 1H), 11.63 (s, 1H). MS (APCI): 489, 491.

EXAMPLE 85

3-Chloro-4-hydroxybenzoic Acid [3,5-Dimethoxy-4-(4-trifluoromethoxybenzyloxy)benzylidene]hydrazide

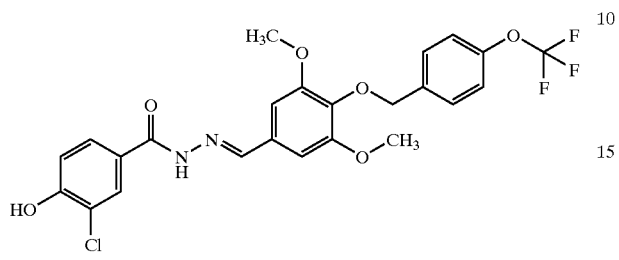

$^1$H NMR (DMSO-$d_6$): δ 3.76 (s, 6H), 4.91 (s, 2H), 6.95–7.00 (m, 3H), 7.30 (d, J=8.2 Hz, 2H), 7.52 (d, J=8.5 Hz, 2H), 7.68 (d, J=2.0, 8.5 Hz, 1H), 7.88 (s, 1H), 8.29 (s, 1H), 10.91 (s, 1H), 11.69 (s, 1H). MS (APCI): 525, 527.

EXAMPLE 86

3-Chloro-4-hydroxybenzoic Acid [4-(4-Trifluoromethoxybenzyloxy)-1-naphthylmethylene]hydrazide

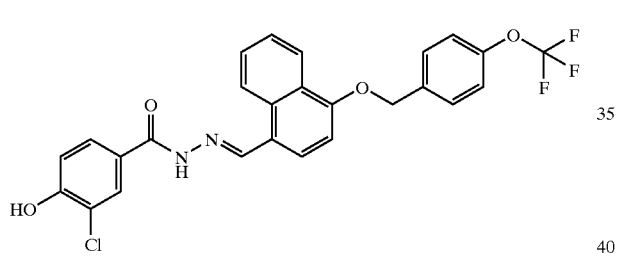

$^1$H NMR (DMSO-$d_6$): δ 5.36 (s, 2H), 7.02 (d, J=8.4 Hz, 1H), 7.14 (d, J=8.2 Hz, 1H), 7.39 (d, J=8.2 Hz, 2H), 7.56 (m, 1H), 7.62 (m, 3H), 7.76 (m, 2H), 7.94 (d, J=2.0 Hz, 1H), 8.26 (d, J=8.3 Hz, 1H), 8.88 (s, 1H), 8.93 (d, J=8.5 Hz, 1H), 10.91 (s, 1H), 11.63 (s, 1H). MS (APCI): 515, 517.

EXAMPLE 87

3-Chloro-4-hydroxybenzoic Acid [4-(2-Methoxybenzyloxy)-1-naphthylmethylene]hydrazide

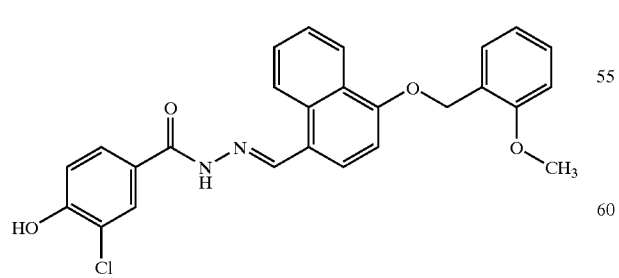

$^1$H NMR (DMSO-$d_6$): δ 3.79 (s, 3H), 5.27 (s, 2H), 6.95 (m, 1H), 7.03 (d, J=8.5 Hz, 1H), 7.04 (d, J=8.2 Hz, 1H), 7.13 (d, J=8.5 Hz, 1H), 7.31 (m, 1H), 7.46–7.53 (m, 2H), 7.61 (m, 1H), 7.76 (m, 2H), 7.94 (d, J=2.0 Hz, 1H), 8.22 (d, J=8.3 Hz, 1H), 8.88 (s, 1H), 8.92 (d, J=8.5 Hz, 1H), 10.90 (s, 1H), 11.62 (s, 1H). MS (APCI): 461, 463.

EXAMPLE 88

3-Chloro-4-hydroxybenzoic Acid [4-(2-Fluorobenzyloxy)-1-naphthylmethylene]hydrazide

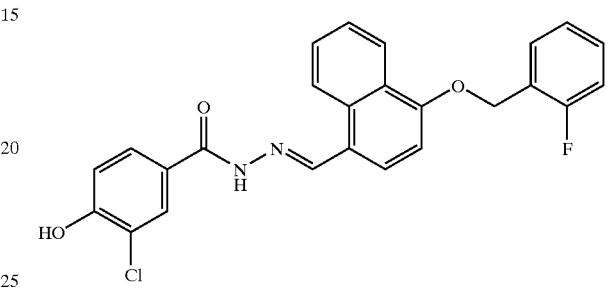

$^1$H NMR (DMSO-$d_6$): δ 5.36 (s, 2H), 7.03 (d, J=8.5 Hz, 1H), 7.19–7.28 (m, 3H), 7.39 (m, 1H), 7.53 (m, 1H), 7.63 (m, 2H), 7.72–7.80 (m, 2H), 7.94 (d, J=2.1 Hz, 1H), 8.19 (d, J=8.3 Hz, 1H), 8.88 (s, 1H), 8.92 (d, J=8.5 Hz, 1H), 10.90 (s, 1H), 11.64 (s, 1H). MS (APCI): 449, 451.

EXAMPLE 89

3-Chloro-4-hydroxybenzoic Acid [4-(2,6-Difluorobenzyloxy)-1-naphthylmethylene]hydrazide

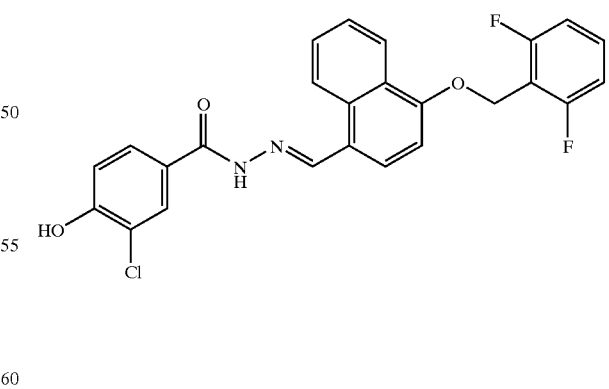

$^1$H NMR (DMSO-$d_6$): δ 5.34 (s, 2H), 7.03 (d, J=8.5 Hz, 1H), 7.16 (d, J=8.2 Hz, 1H), 7.18 (d, J=8.0 Hz, 1H), 7.27 (d, J=8.2 Hz, 1H), 7.51 (m, 2H), 7.72 (m, 1H), 7.74 (d, J=8.0 Hz, 1H), 7.78 (d, J=8.0 Hz, 1H), 7.94 (d, J=2.1 Hz, 1H), 8.03 (d, J=8.3 Hz, 1H), 8.89 (s, 1H), 8.91 (d, J=8.5 Hz, 1H), 10.97 (s, 1H), 11.65 (s, 1H). MS (APCI): 467, 469.

EXAMPLE 90

4-Hydroxy-3-methoxybenzoic Acid [3,5-Dimethoxy-4-(5,5,8,8-tetramethyl-5,6,7,8-tetrahydronaphth-1-ylmethoxy)benzylidene]hydrazide

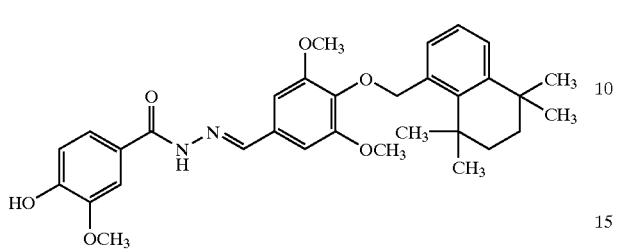

$^1$H NMR (DMSO-d$_6$): δ 1.2 (s, 12H), 1.63 (s, 4H), 3.82 (s, 6H), 3.85 (s, 3H), 4.90 (s, 2H), 6.88 (d, 1H), 7.01 (s, 2H), 7.18 (d, 1H), 7.29 (d, 1H), 7.38 (s, 1H), 7.44 (d, 1H), 7.48 (s, 1H), 8.40 (brd s, 1H), 11.62 (s, 1H); MS (APCI): 547.1.

EXAMPLE 91

3-Fluoro-4-hydroxybenzoic Acid [4-(4-Isopropylbenzyloxy)-3,5-dimethoxybenzylidene]hydrazide

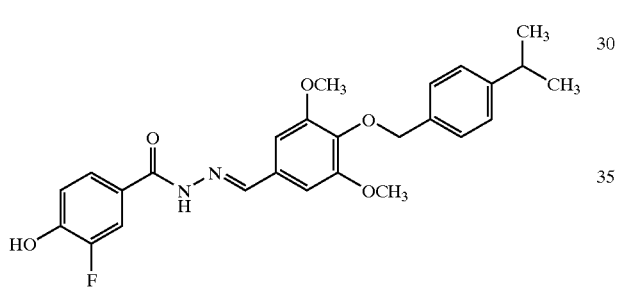

$^1$H NMR (DMSO-d$_6$): δ 1.05 (d, 6H), 2.67 (m, 1H), 3.61 (s, 6H), 4.69 (s, 2H), 6.79 (s, 2H), 6.86 (t, 1H), 7.01 (d, 2H), 7.24 (d, 1H), 7.44 (dd, 1H), 7.51 (d, 1H), 8.10 (brd s, 1H), 10.32 (s, 1H), 11.41 (s, 1H); MS (APCI): 467.19.

EXAMPLE 92

3-Chloro-4-hydroxybenzoic Acid [4-(4-tert-Butylbenzyloxy)-3,5-dimethylbenzylidene]hydrazide

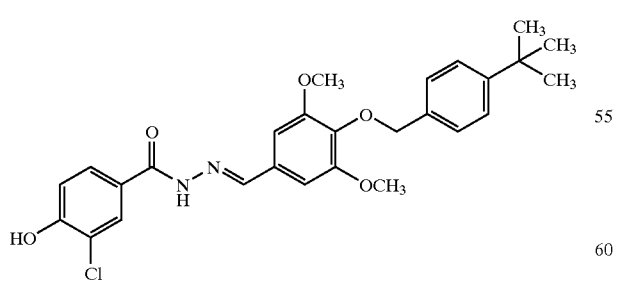

$^1$H NMR (DMSO-d$_6$): δ 1.06 (s, 9H), 1.99 (s, 6H), 4.55 (s, 2H), 6.83 (d, 1H), 7.19 (s, 6H), 7.52 (d, 1H), 7.73 (s, 1H), 8.09 (s, 1H), 10.74 (brd s, 1H), 11.44 (s, 1H); MS (FAB): 465.6.

EXAMPLE 93

3-Chloro-4-hydroxybenzoic Acid [3-Bromo-5-methoxy-4-(4-trifluoromethoxybenzyloxy)benzylidene]hydrazide

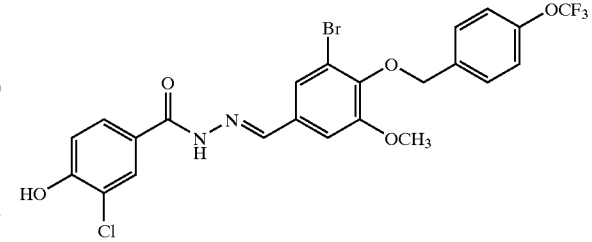

$^1$H NMR (DMSO-d$_6$): δ 3.92 (s, 3H), 5.07 (s, 2H), 7.07 (d, 1H), 7.40 (m, 3H), 7.52 (s, 1H), 7.63 (d, 2H), 7.77 (dd, 1H), 7.97 (d, 1H), 8.35 (s, 1H), 11.00 (brd s, 1H), 11.86 (s, 1H); MS (FAB): 575.0.

EXAMPLE 94

4-Hydroxybenzoic Acid [4-(4-Isopropylbenzyloxy)-3,5-dimethoxybenzylidene]hydrazide

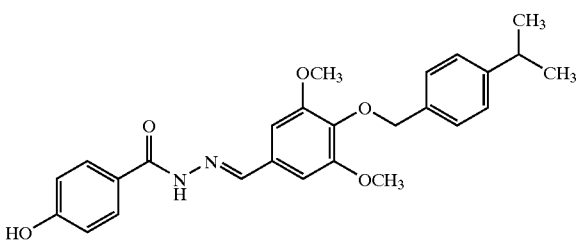

$^1$H NMR (DMSO-d$_6$): δ 1.05 (d, 6H), 2.71 (m, 1H), 3.67 (s, 6H), 4.75 (s, 2H), 6.70 (d, 2H), 6.85 (s, 2H), 7.14 (d, 2H), 7.21 (d, 2H), 7.64 (d, 2H), 8.21 (brd s, 1H), 9.97 (brd s, 1H), 11.47 (s, 1H); MS (APCI): 448.9.

EXAMPLE 95

2-Chloro-4-hydroxybenzoic Acid [4-(4-Isopropylbenzyloxy)-3,5-dimethoxybenzylidene]hydrazide

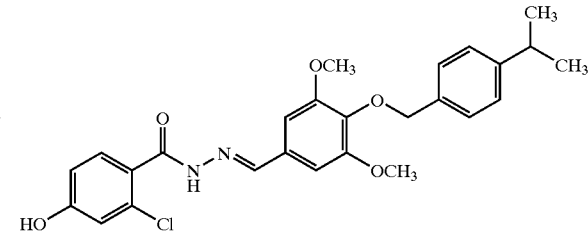

$^1$H NMR (DMSO-D$_6$): d 1.18 (d, 6H), 2.87 (septet, 1H), [3.68 (s, 1H)+3.81 (s, 5H), 6H], [4.83 (s, 0.5H)+4.90 (s, 1.5H), 2H], [6.76 (s, 0.5H)+7.01 (s, 1.5H), 2H], [6.80 (dd, 1H)+6.88 (d, 1H), 2H], 7.23 (d, 2H), 7.35 (d, 2H), 7.38 (m, 1H), [7.91 (s, 0.3H)+8.18 (s, 0.7H), 2H], 10.17 (s, 0.7H)+11.73 (s, 0.3H), 1H]; MS (APCI): 483.0.

EXAMPLE 96

3-Chloro-4-hydroxybenzoic Acid [3-(4-Isopropylbenzyloxy)-4,5-dimethoxybenzylidene]hydrazide

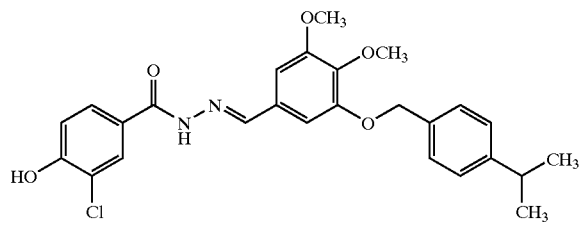

¹H NMR (DMSO-d₆): δ 1.05 (d, 6H), 2.70 (m, 1H), 3.54 (s, 3H), 3.66 (s, 3H), 4.94 (s, 2H), 6.87 (m, 3H), 7.08 (d, 2H), 7.20 (d, 2H), 7.56 (dd, 1H), 7.77 (s, 1H), 8.15 (s, 1H), 10.76 (s, 1H), 11.52 (s, 1H); MS (APCI): 483.7.

EXAMPLE 97

3-Chloro-4-hydroxybenzoic Acid [3-(4-Isopropylbenzyloxy)-2,4-dimethoxybenzylidene]hydrazide

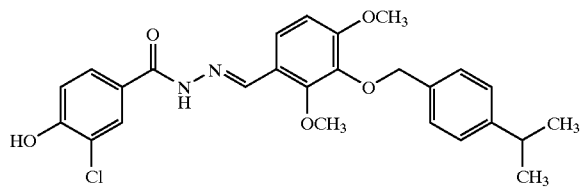

¹H NMR (DMSO-d₆): δ 1.20 (d, 6H), 2.89 (m, 1H), 3.85 (s, 6H), 4.95 (s, 2H), 6.95 (d, 1H), 7.07 (d, 1H), 7.22 (d, 2H), 7.40 (d, 2H), 7.64 (d, 1H), 7.78 (dd, 1H), 7.97 (d, 1H), 8.62 (s, 1H), 11.68 (s, 1H); MS (APCI): 483.8.

EXAMPLE 98

3-Chloro-4-hydroxybenzoic Acid [4-(3-Trifluoromethoxybenzyloxy)naphth-1-ylmethylene]hydrazide

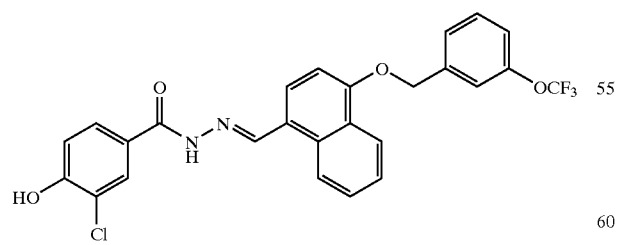

¹H NMR (DMSO-d₆): δ 5.46 (s, 2H), 7.10 (d, 1H), 7.20 (d, 1H), 7.37 (d, 1H), 7.65 (m, 5H), 7.82 (m, 2H), 8.01 (s, 1H), 8.32 (d, 1H), 8.97 (m, 2H), 11.70 (s, 1H); MS (APCI): 514.8.

EXAMPLE 99

3-Chloro-4-hydroxy-benzoic Acid [4-(4-Isopropylbenzyloxy)-8-methoxynaphthalen-1-ylmethylene]-hydrazide

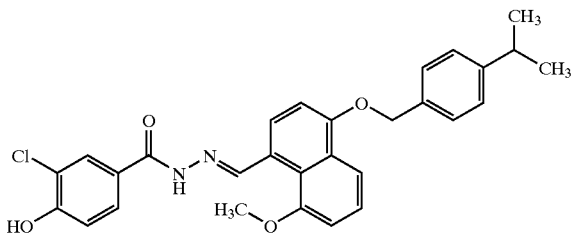

4-hydroxy-8-methoxynaphthalene-1-carbaldehyde (2 g, 9.9 mmol) was dissolved in DMF (25 mL). To this mixture potassium carbonate (6.8 g, 50 mmol) and 4-isopropylbenzylchloride (1.8 g, 10.4 mmol) were added and the resulting mixture was stirred at room temperature for 16 hours. Water (100 mL) was added and the resulting mixture was extracted with diethyl ether (3×100 mL). The combined organic extracts were washed with saturated sodium chloride (100 mL), dried (MgSO₄) and evaporated in vacuo to afford 3.0 g crude product. This was purified using column chromatography on silica gel (300 mL) eluting with a mixture of ethyl acetate and heptane (1:4). This afforded 2.57 g (81%) of 4-isopropylbenzyloxy-8-methoxynaphthalene-1-carbaldehyde.

Calculated for $C_{22}H_{22}O_3$: C, 79.02%; H, 6.63%. Found: C, 79.10%, H, 6.69%, C, 79.17%, H, 6.69%.

3-Chloro-4-hydroxybenzoic acid hydrazide (205 mg, 1.1 mmol) was dissolved in DMSO (2 mL) and the above 4-isopropylbenzyloxy-8-methoxynaphthalene-1-carbaldehyde (365 mg, 1.1 mmol) and glacial acetic acid (5 drops) were added and the resulting mixture was stirred at room temperature for 20 minutes. More DMSO (2 mL) was added and the mixture was stirred at room temperature for 16 hours. The solid was collected by filtration and washed successively with DMSO and ethyl acetate to afford 330 mg (66%) of the title compound.

M.p.: >250° C.

EXAMPLE 100

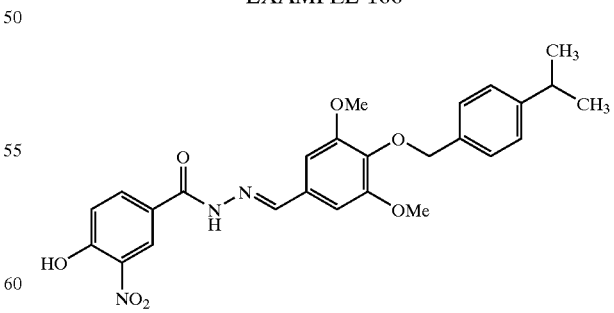

¹H NMR (DMSO-d₆) δ 1.13 (d, 6H), 2.82 (sept, 1H), 3.77 (s, 6H), 4.8 (s, 2H), 7.15 (s, 1H), 7.18 (s, 2H), 7.30 (d, 2H), 8.00 (dd, 1H), 8.30 (s, 1H), 8.44 (s, 1H), 11.84 (s, 1H); MS (APCI): 494.0.

EXAMPLE 101

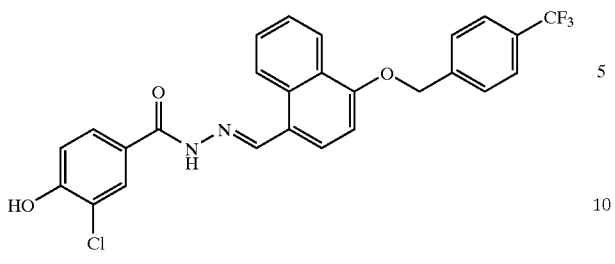

$^1$H NMR (DMSO-d$_6$) δ 5.38 (s, 2H), 6.95 (d, 1H), 7.06 (d, 1H), 7.49 (t, 1H), 7.56 (t, 1H), 7.65–7.71 (m, 6H), 7.87 (d, 1H), 8.22 (d, 1H), 8.80 (s, 1H), 8.86 (d, 1H), 10.82 (s, 1H), 11.55 (s, 1H); MS (FAB): 499.

EXAMPLE 102

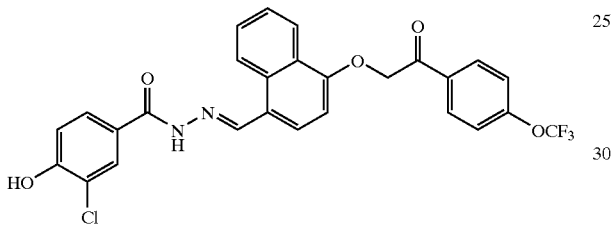

$^1$H NMR (DMSO-d$_6$) δ 5.85 (s, 2H), 7.05 (t, 2H), 7.52–7.63 (m, 4H), 7.73 (m, 2H), 7.95 (s, 1H), 8.16 (d, 2H), 8.33 (d, 1H), 8.90 (s, 1H), 8.93 (s, 1H), 10.90 (brd s, 1H), 11.63 (s, 1H); MS (FAB): 543.

EXAMPLE 103

3-Chloro-4-hydroxybenzoic Acid {4-[2-(4-Bromophenoxy)ethoxy]-3,5-dimethoxybenzylidene}hydrazide

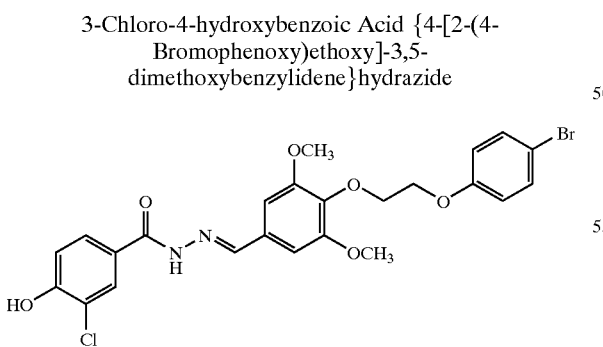

$^1$H NMR (DMSO-d$_6$): δ 3.78 (s, 6H), 4.21 (m, 4H), 6.87 (d, 2H), 7.00 (s, 2H), 7.05 (d, 1H), 7.44 (d, 2H), 7.75 (dd, 1H), 7.96 (s, 1H), 8.36 (s, 1H), 10.95 (brd s, 1H), 11.66 (s, 1H); MS (APCI): 548.8.

EXAMPLE 104

3-Chloro-4-hydroxybenzoic Acid [4-(3-Methoxy-3-(4-methylphenyl)-propyloxy)naphth-1-ylmethylene]hydrazide

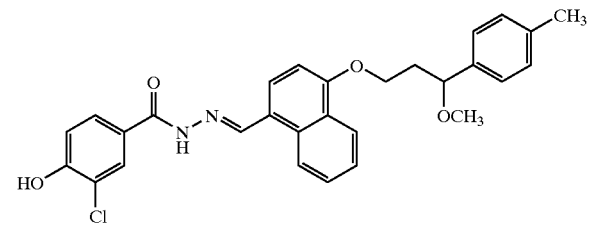

MS (APCI): 502.9.

EXAMPLE 105

(2-Ethylphenyl)carbamic Acid 2-{4-[(3-Chloro-4-hydroxybenzoyl)hydrazonomethyl]-naphth-1-yloxy}ethyl Ester

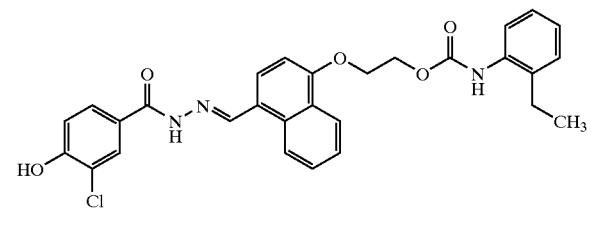

$^1$H NMR (CDCl$_3$): δ 1.12 (t, 3H), 2.50 (qt, 2H), 3.69 (t, 2H), 4.39 (t, 2H), 5.20 (t, 1H), 6.57 (t, 1H), 6.74 (d, 1H), 6.97 (d, 1H), 7.08 (m, 3H), 7.57 (t, 1H), 7.67 (t, 1H), 7.81 (t, 2H), 8.01 (s, 1H), 8.35 (d, 1H), 8.95 (m, 2H), 11.67 (s, 1H).

EXAMPLE 106

3-Chloro-4-hydroxybenzoic Acid [3-Allyl-4-(4-isopropylbenzyloxy)-5-methoxybenzylidene]hydrazide

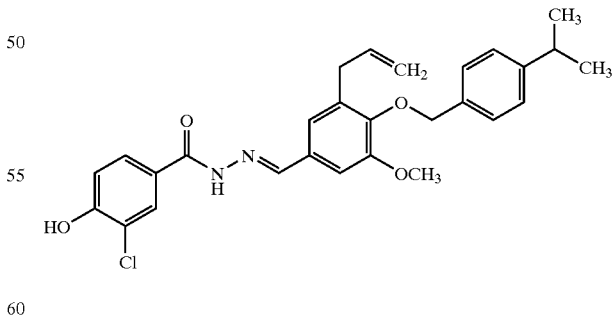

$^1$H NMR (DMSO-d$_6$): δ 1.13 (d, 6H), 2.80 (m, 1H), 3.20 (m, 2H), 3.85 (s, 3H), 4.82 (s, 2H), 5.00 (d, 2H), 5.70 (m, 1H), 6.96 (s, 1H), 7.05 (s, 1H), 7.20 (d, 2H), 7.30 (d, 2H), 7.70 (d, 1H), 7.89 (s, 1H), 8.28 (s, 1H), 10.80 (brd s, 1H), 11.61 (s, 1H); MS (APCI): 493.1.

Similarly, the following compounds were made:

EXAMPLE 107

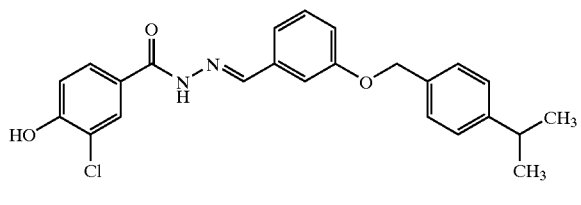

¹H NMR (DMSO-D₆): δ 0.99 (d, 6H), 2.68 (septet, 1H), 4.89 (s, 2H), 6.84 (d, 2H), 7.06 (m, 2H), 7.16 (m, 3H), 7.55 (d, 1H), 7.75 (s, 1H), 8.18 (s, 1H), 10.75 (s, 1H), 11.52 (s, 1H); MS (APCI): 423.7, 425.6.

EXAMPLE 108

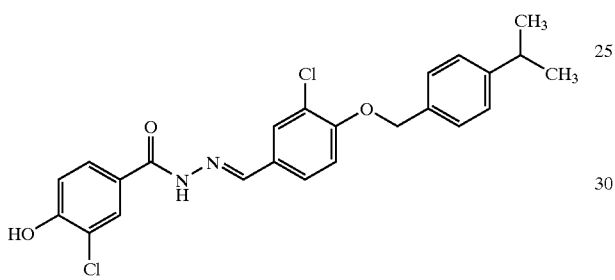

¹H NMR (DMSO-D₆): δ 1.18 (d, 1H), 2.88 (septet, 1H), 5.20 (s, 2H), 7.04 (d, 1H), 7.28 (t, 2H), 7.30 (s, 1H), 7.38 (d, 2H), 7.62 (d, 1H), 7.73 (dd, 1H), 7.79 (s, 1H), 7.94 (d, 1H), 8.32 (s, 1H), 11.94 (s, 1H), 11.72 (s, 1H); MS (APCI): 457.4, 459.1.

EXAMPLE 109

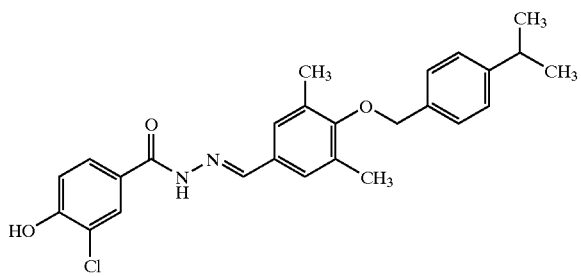

¹H NMR (DMSO-D₆): δ 1.1 (d, 6H), 2.2 (s, 6H), 2.8 (septet, 1H), 4.7 (s, 2H), 7.0 (d, 1H), 7.2 (d, 2H), 7.4 (d, 4H), 7.7 (d, 1H), 7.9 (s, 1H), 8.2 (s, 1H), 10.9 (s, 1H), 11.6 (s, 1H); MS (APCI): 451.6, 453.3.

EXAMPLE 110

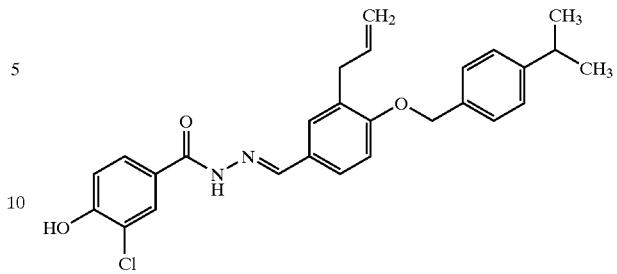

¹H NMR (DMSO-D₆): δ 1.1 (d, 6H), 2.8 (septet, 1H), 3.3 (d, 1H), 5.0 (d, 1H), 5.1 (d, 1H), 5.2 (s, 2H), 5.9 (m, 1H), 7.0 (d, 1H), 7.1 (d, 1H), 7.2 (d, 2H), 7.3 (d, 2H), 7.4 (d, 1H), 7.5 (s, 1H), 7.7 (dd, 1H), 7.9 (d, 1H), 8.3 (s, 1H), 10.9 (brd s, 1H), 11.5 (s, 1H); MS (APCI): 463.5, 465.1.

EXAMPLE 111

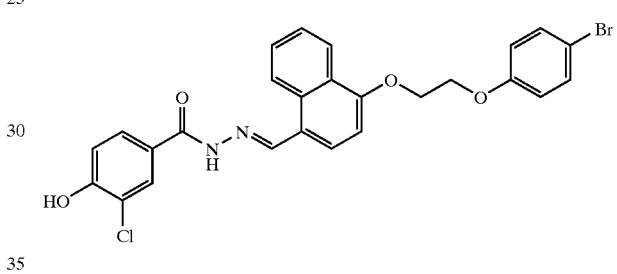

¹H NMR (DMSO-D₆): δ 4.47 (t, 2H), 4.54 (t, 2H), 7.01 (d, 2H), 7.07 (d, 1H), 7.14 (d, 1H), 7.45 (d, 2H), 7.53 (t, 1H), 7.27 (d, 1H), 7.79 (m, 2H), 7.96 (d, 1H), 8.17 (d, 1H), 8.91 (s, 1H), 8.94 (d, 1H), 10.92 (s, 1H), 11.64 (s, 1H), MS (APCI): 539.3, 541.1, 543.1.

EXAMPLE 112

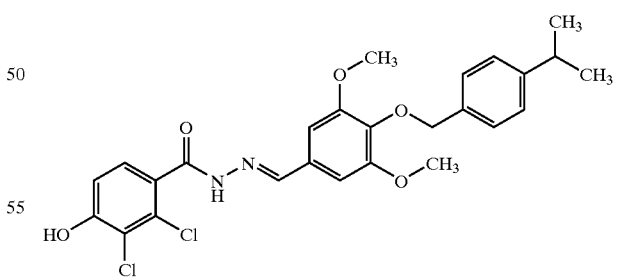

¹H NMR (DMSO-D₆): δ 1.18 (d, 6H), 2.87 (septet, 1H), [3.67 (s, 1.5H)+3.81 (s, 4.5H), 6H], [4.83 (s, 0.5H)+4.90 (s, 1.5H), 2H], 6.73 (s, 0.5H)+[7.02 (m, 2.5H), +7.27 (m, 2.5H)+7.37 (m, 2.5H), 8H], [7.92 (s, 0.3H)+8.17 (s, 0.7H), 1H], [10.96 (s, 0.3H)+11.12 (s, 0.7H), 1H], [11.82 (s, 0.7H)+11.95 (s, 0.3H), 1H]; MS (APCI): 517.6, 519.2.

EXAMPLE 113

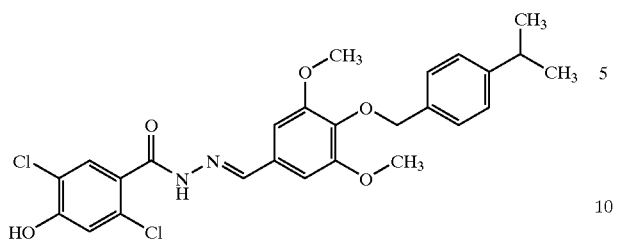

¹H NMR (DMSO-D₆): δ 1.19 (d, 6H), 2.89 (septet, 1H), [3.68 (s, 1.5H)+3.82 (s, 4.5H), 6H], [4.84 (s, 0.5H)+4.89 (s, 1.5H), 2H], [6.76 (s, 0.5H)+7.02 (m, 2.5H), 3H], 7.20 (m, 2H), 7.34 (m, 2H), [7.50 (s, 0.3H)+7.62 (s, 0.7H), 1H], 7.92 (s, 0.3H)+8.18 (s, 0.7H), 1H], 11.17 (brd s, 1H), 11.81 (s, 0.7H)+11.96 (s, 0.3H), 1H]; MS (APCI): 517.7, 519.2.

EXAMPLE 114

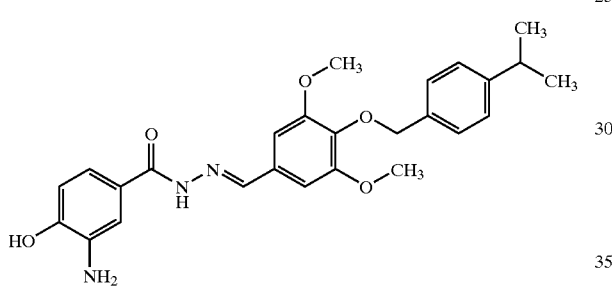

¹H NMR (DMSO-D₆): δ 1.20 (d, 6H), 2.87 (septet, 1H), 3.82 (s, 6H), 4.89 (s, 2H), 6.69 (d, 1H), 6.98 (m, 3H), 7.21 (m, 3H), 7.36 (d, 2H), 8.32 (s, 1H), 9.8 (brd s, 1H), 11.50 (s, 1H); MS (APCI): 464.7.

EXAMPLE 115

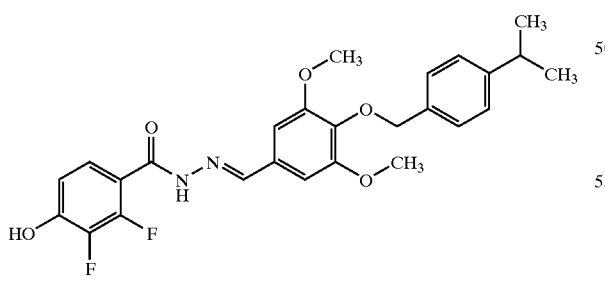

¹H NMR (DMSO-D₆): δ 1.19 (d, 6H), 2.30 (septet, 1H), [3.71 (s)+3.82 (s), 6H], 4.90 (s, 2H), [6.81 (m, 1.5H)+6.88 (s, 1.5H), 3H], [7.24 (s, 0.2H)+8.24 (s, 0.8H), 1H], 11.05 (brd, 1H), 11.69 (s, 0.75H)+11.94 (s, 0.25H), 1H]; MS (APCI): 485.5, 486.3.

EXAMPLE 116

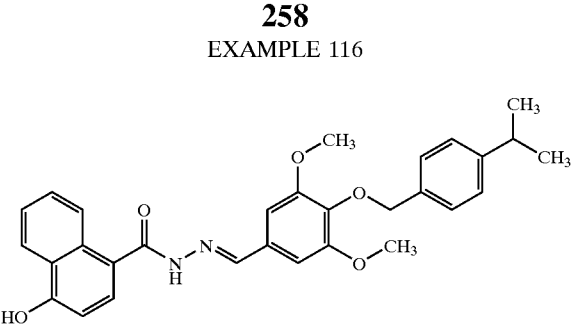

¹H NMR (DMSO-D₆): δ 1.19 (d, 6H), 2.88 (septet, 1H), 3.83 (s, 6H), 4.90 (s, 2H), 6.87 (d, 1H), 7.03 (s, 2H), 7.23 (d, 2H), 7.36 (d, 2H), 7.53 (m, 3h), 8.26 (m, 3H), 10.73 (s, 1H), 11.82 (s, 1H); MS (APCI): 499.8.

EXAMPLE 117

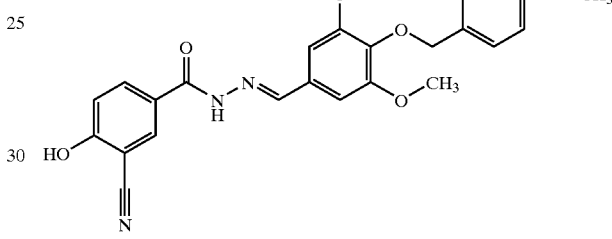

¹H NMR (DMSO-D₆): δ 1.20 (d, J=6.9, 6H), 2.89 (sept, J=6.9, 1H), 3.84 (s, 6H), 4.91 (s, 2H), 7.03 (br s, 2H), 7.12 (d, J=8.8, 1H), 7.23 (d, J=8.0, 2H), 7.37 (d, J=8.0, 2H), 8.04 (dd, J=2.2, 8.8, 1H), 8.21 (br s, 1H), 8.35 (br s, 1H), 11.78 (s, 1H), 11.89 (br s, 1H); MS (APCI, neg): 472.

Preparation of Acyl-hydrazones of 4-(2-Hydroxyethyl)-1-naphthaldehyde

General Procedure for Synthesis of Compounds of the General Formula X

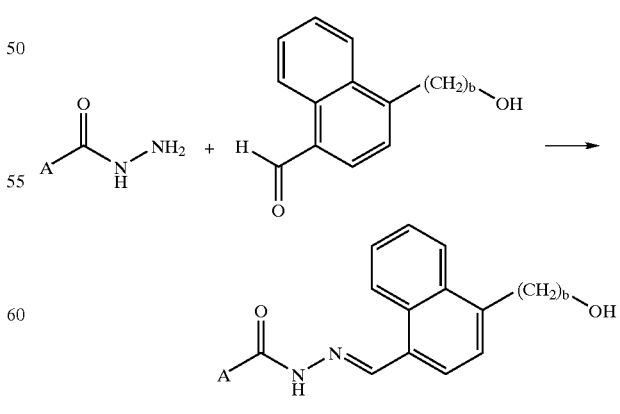

formula X wherein b is 1, 2, 3 or 4

Preparation of 4-(2-Hydroxyethyl)-1-naphthaldehyde

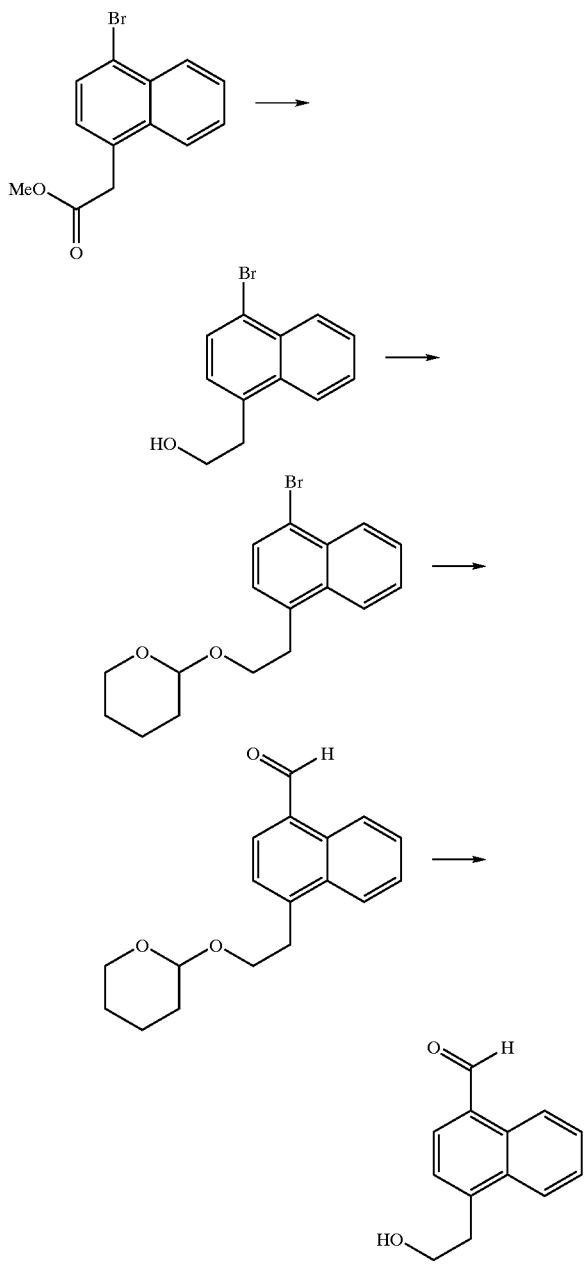

1-Bromo-4-(2-hydroxyethyl)naphthalene:

To a solution of methyl 4-bromo naphthalene acetate (2.0 g, 7.16 mmol) in anhydrous THF 15 mL) was added drop wise at 0° C. 1 M lithium aluminum hydride in THF (4 mL). The mixture was stirred at room temperature for 16 h, diluted with water (5 ml), acidified with conc. hydrochloric acid, and extracted with ethyl acetate (3×20 mL). The combined organic extracts were dried (MgSO$_4$), and concentrated to provide a 1.71 g (95%) colorless oil (1.71 g, 95%). A similar synthetic reference is described in A. A. Kiprianov, A. A. Shulezhko. Zh. Org. Khim. 2 (1966), 1852, English translation: J. Org. Chem. (USSR) 2 (1966) 1820].

$^1$H NMR (CDCl$_3$) δ=2.36 (s, 1H), 3.33 (t, J=6.7 Hz, 2H), 3.99 (t, J=6.7 Hz, 2H), 7.24 (d, J=7.3 Hz, 1H), 7.58–7.63 (m, 2H), 7.73 (d, J=7.6 Hz, 1H), 7.61 (m, 1H), 8.31 (dd, J=1.1, 8.0 Hz, 1H). GCMS (pos.) 250, 252.

1-Bromo-4-(2-tetrahydropyranyloxyethyl)naphthalene:

To a solution of 1-bromo-4-(2-hydroxyethyl)naphthalene (1.71 g, 6.8 mmol) in dichloromethane (20 mL) was added 3,4-dihydro-2H-pyrane (1 mL, 0.92 g, 11.0 mmol) and p-toluene sulfonic acid (80 mg). The mixture was stirred at room temperature for 90 min, diluted with dichloromethane (20 mL), washed with satd. NaHCO$_3$ sol. (20 mL), dried (MgSO$_4$), and concentrated. Flash chromatography using hexane/ethyl acetate 9:1 as eluent provided 1.69 g (75%) of a colorless oil.

$^1$H NMR (CDCl$_3$) δ=1.51–1.60 m (6H), 3.37 (t, J=7.2 Hz, 2H), 3.39–3.47 (m, 1H), 3.74 (t, J=7.2 Hz, 2H), 4.08 (dd, J=2.4, 7.5 Hz, 1H), 4.60 (m, 1H), 7.25 (d, J=7.3 Hz, 1H), 7.56–7.61 (m, 2H), 7.72 (d, J=7.6 Hz, 1H), 8.09–8.12 (m, 1H), 8.29 (dd, J=2.5, 7.1 Hz, 1H). GCMS (pos), 334, 336.

1-Formyl-4-(2-tetrahydropyranyloxyethyl)naphthalene:

A solution of 1-bromo-4-(2-tetrahydropyranyloxyethyl)naphthalene in anhydrous THF (15 mL) under nitrogen was cooled to −78° C. n-Butyl lithium (1.4 mL of a 2.5 M solution in hexane) was added via syringe, and the mixture was stirred at the same temperature for 30 min. DMF (1.1 mL) was added, and the mixture was allowed to reach room temperature. It was diluted with satd. NH$_4$Cl solution (10 mL), extracted with ether (3×10 ml), dried (MgSO$_4$) and concentrated. Flash chromatography using hexane/ethyl acetate 5:1 as eluent provided 408 mg (54%) of a colorless oil.

$^1$H NMR (CDCl$_3$) δ=1.48–1.69 m (6H), 3.45–3.50 (m, 3H), 3.69–3.85 (m, 2H), 4.07–4.17 (m, 1H), 4.61 (m, 1H), 7.58 (d, J=7.3 Hz, 1H), 7.62–7.73 (m, 2H), 7.92 (d, J=7.3 Hz, 1H), 8.20 (d, J=1.0, 8.1 Hz, 1H), 10.36 (s, 1H). GCMS: 284.

1-Formyl-4-(2-hydroxyethyl)naphthalene:

1-Formyl-4-(2-tetrahydropyranyloxyethyl)naphthalene (400 mg, 1.40 mmol) was dissolved in methanol (15 mL), and p-toluene sulfonic acid (45 mg) was added. The mixture was stirred at room temperature for 16 h, and concentrated. The residue was dissolved in ethyl acetate (3×10 mL), washed with satd. NaHCO$_3$ (20 mL), dried (MgSO$_4$) and concentrated. Purification by flash chromatography using hexane/ethyl acetate 3:1 as eluent provided 182 mg (65%) of a colorless oil.

$^1$H NMR (CDCl$_3$) δ=2.09 (s, 1H), 3.40 (t, J=6.6 Hz, 2H), 4.02 (t, J=6.6 Hz, 2H), 7.54 (d, J=7.3 Hz, 1H), 7.61–7.71 (m, 2H), 7.88 (d, J=7.3 Hz, 1H), 8.13 (dd, J=1.3, 8.0 Hz, 1H), 9.29 (dd, J=1.3, 8.0 Hz, 1H), 10.28 (s, 1H). GCMS: 200.

The following compounds were prepared according to the general procedure for the synthesis of alkylidene hydrazones from the condensation of 1-formyl-4-(2-hydroxyethyl)naphthalene (from step D) with 4-hydroxy benzoic acid hydrazides.

EXAMPLE 118

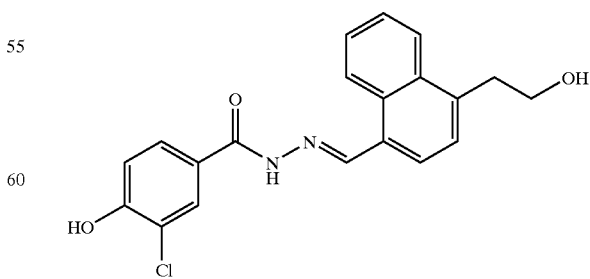

$^1$H NMR (DMSO-D$_6$) δ=3.25 (t, J=6.5 Hz, 2H), 3.73 (dt, J=J'=6.5 Hz, 2H), 4.84 (t, J=6.5 Hz, 1H), 7.08 (d, J=8.5 Hz,

1H), 7.49 (d, J=7.4 Hz, 1H), 7.60–7.68 (m, 2H), 7.80 (dd, J=1.8, 7.4 Hz, 1H), 7.84 (d, J=7.3 Hz, 1H), 8.00 (d, J=1.8 Hz, 1H), 9.19 (d, J=6.7 Hz, 1H), 8.85 (d, J=7.7 Hz, 1H), 9.05 (s, 1H), 10.98 (s, 1H), 11.76 (s, 1H); MS (APCI, pos.): 369.4, 371.2.

EXAMPLE 119

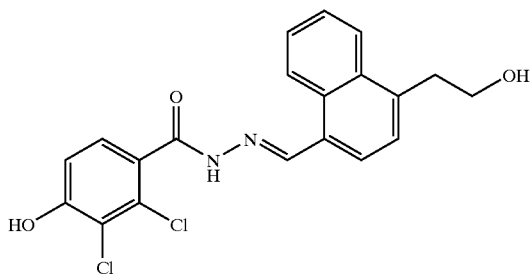

$^1$H NMR (DMSO-D6) δ=3.18 (t, J=7.0 Hz, 1H), 3.25 (t, J=7.0 Hz, 1H), 3.65 (dd, J=7.0 Hz, 1H), 3.74 (dd, J=5.3, 7.0 Hz, 1H), 4.74 (t, J=5.3 Hz, 0.5H), 4.79 (t, J=5.3 Hz, 0.5H), 7.04 (d, J=8.3 Hz, 0.5H), 7.05 (d, J=8.3 Hz, 0.5H), 7.25 (d, J=8.3 Hz, 0.5H), 7.28 (d, J=8.3 Hz, 0.5H), 7.38 (d, J=7.4 Hz, 0.5H), 7.43 (d, J=8.4 Hz, 0.5H), 7.47–7.57 (m, 1.5H), 7.61–7.72 (m, 1H), 7.82 (d, J=7.2 Hz, 0.5H), 8.10 (d, J=8.6 Hz, 0.5H), 8.19 (dd, J=2.2, 7.2 Hz, 0.5H), 8.45 (d, J=8.6 Hz, 0.5H), 8.48 (s, 0.5H), 8.85 (s, 0.5H), 8.87 (dd, J=2.2, 6.5 Hz, 0.5H), 11.00 (s, 0.5H), 11.15 (s, 0.5H), 11.86 (s, 0.5H), 11.92 (s, 0.5H); MS (APCI, pos.): 403.4, 405.2, 406.1.

Preparation of Acylhydrazones of 4-Hydroxymethylnaphthaldehyde

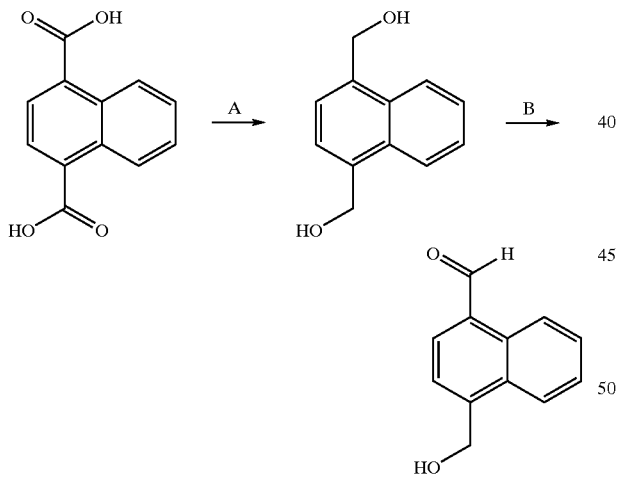

Step A:

The 1,4-Naphthalenedicarboxylic acid (25 g, 116 mmol) was dripped into a mixture of Lithium Aluminum Hydride (15 g, 395 mmol) in 600 mL of anhydrous THF and refluxed for two days. The mixture was cooled in an ice bath and excess LAH was decomposed by the slow addition of methanol followed by ice chips. THF was removed under vacuum and the residue was acidified with 1N HCl. The product was extracted with ethyl acetate (3×), washed with aqueous sodium bicarbonate (3×), water, brine, and dried over magnesium sulfate. 1,4-Bishydroxymethylnaphthalene (70%) was obtained as a solid after evaporation of the solvent and can be used in the subsequent oxidation step without further purification. A portion of the material was purified by column chromatography using hexane/ethyl acetate (80/20 to 75/25) for characterization purposes.

$^1$H NMR (DMSO-D6): δ 5.19 (s, 4H), 7.77 (m, 4H), 8.32 (m, 2H).

Step B:

To a solution of 1,4-bishydroxymethylnaphthalene (12 g, 65 mmol) in ethyl acetate (300 ml) was added manganese dioxide (28 g, 325 mmol). After stirring for 45 minutes most of the starting material had disappeared and two new spots (mono aldehyde and dialdehyde) were seen on TLC. The upper spot corresponds to the dialdehyde. The mixture was passed through a bed of Celite and eluted with additional volumes of ethyl acetate. The solvent was evaporated and 4-hydroxymethylnaphthaldehyde was purified by column chromatography using hexane/ethyl acetate (80/20 to 75/25) in 50% yield.

$^1$H NMR (DMSO-D6): δ 5.19 (s, 2H), 5.71 (brd s, 1H), 7.73 (t, 1H), 7.78 (t, 1H), 7.95 (d, 1H), 8.26 (m, 2H), 9.34 (d, 1H), 10.46 (s, 1H).

Examples of products employing the above aldehyde:

EXAMPLE 120

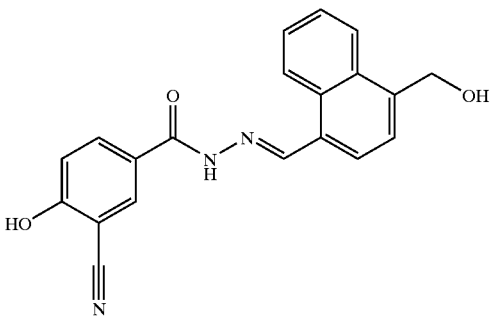

The above compound was prepared according to the general procedure for the synthesis of alkylidene hydrazones from the condensation of the above aldehyde with 3-cyano-4-hydroxybenzoic acid hydrazide.

$^1$H NMR (DMSO-D$_6$): δ 5.02 (s, 2H), 5.44 (s, 1H), 7.14 (d, 1H), 7.69 (m, 3H), 7.91 (d, 1H), 8.10 (d, 1H), 8.14 (d, 1H), 8.27 (s, 1H), 8.87 (d, 1H), 9.06 (s, 1H), 11.84 (brd s, 2H); MS (ACPI): 346.3, 347.2.

EXAMPLE 121

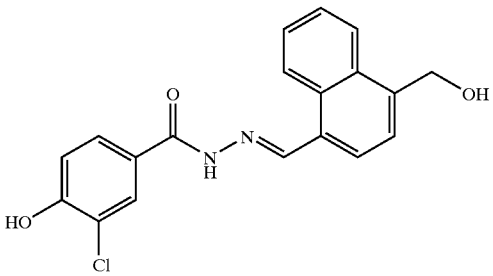

The above compound was prepared according to the general procedure for the synthesis of alkylidene hydrazones from the condensation of the above aldehyde with 3-chloro-4-hydroxybenzoic acid hydrazide.

EXAMPLE 122

¹H NMR (DMSO-D₆): δ 5.02 (s, 2H), 5.43 (t, 1H), 7.10 (d, 1H), 7.66 (m, 3H), 7.80 (d, 1H), 7.90 (d, 1H), 8.02 (s, 1H), 8.15 (d, 1H), 8.87 (d, 1H), 9.08 (s, 1H), 10.98 (s, 1H), 11.79 (s, 1H); MS (APCI): 355.5.

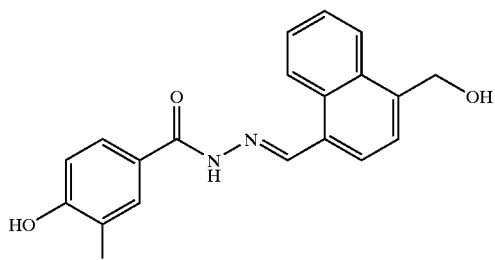

The above compound was prepared according to the general procedure for the synthesis of alkylidene hydrazones from the condensation of the above aldehyde with 3-fluoro-4-hydroxybenzoic acid hydrazide.

¹H NMR (DMSO-D₆): d 4.84 (s, 2H), 6.91 (t, 1H), 7.43–7.53 (m, 4H), 7.62 (d, 1H), 7.72 (d, 1H), 7.96 (d, 1H), 8.68 (d, 1H), 8.98 (s, 1H), 11.71 (brd s, 1H); MS (APCI): 339.4, 340.3.

The compounds of formula II can also be prepared by parallel synthesis using the protocol mentioned above in a combinatorial approach. Thousands of compounds of formula II can thus be prepared by this combinatorial approach which can be semi- or fully automated. The automation of this protocol can be performed using solution phase combinatorial chemistry in e.g. a 96 well setup using an automated synthesizer device. In the first step of the synthesis the aldehydes or ketones may be prepared according to Scheme II by a combination of a selected number of aldehydes or ketones with a selected number of alkylating reagents. In the second step the formed aldehydes/ketones can be combined with a selected number of the hydrazides (which may be synthesized according to Scheme I) thereby generating a predetermined very large number of compounds as single entities.

The synthesized compounds mentioned above are examples of such compounds that can be prepared using this combinatorial methodology.

By application of the above methodology, the following compounds may also be synthesized:

EXAMPLE 123

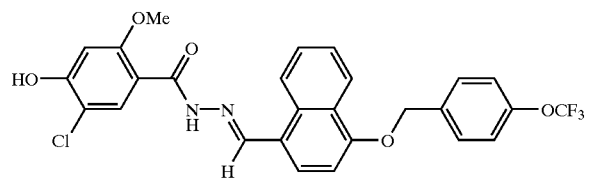

EXAMPLE 124

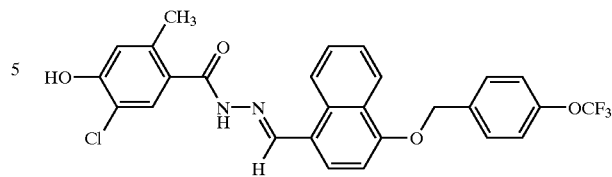

EXAMPLE 125


EXAMPLE 126

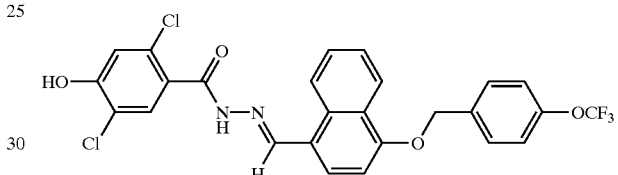

EXAMPLE 127

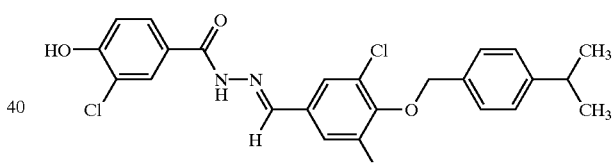

EXAMPLE 128

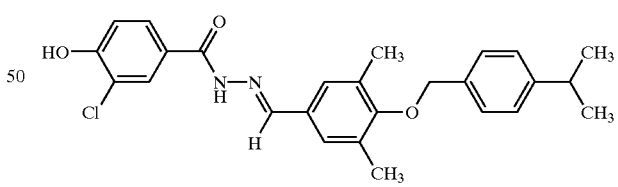

EXAMPLE 129

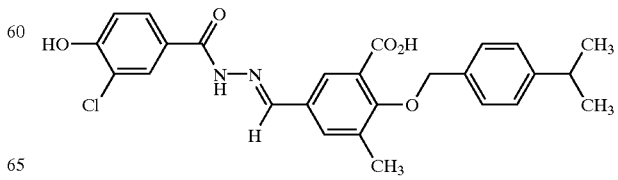

EXAMPLE 130
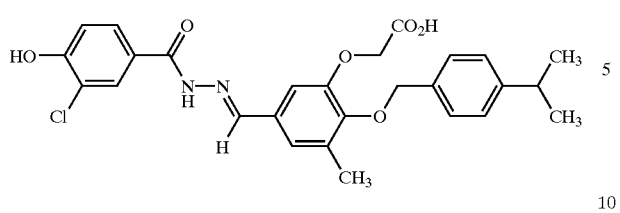
EXAMPLE 135
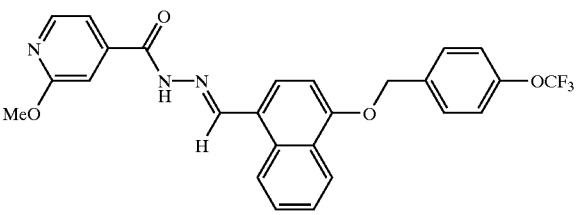
EXAMPLE 131
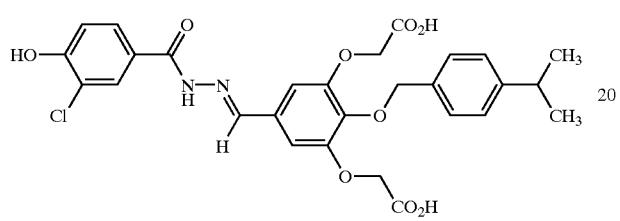
EXAMPLE 136
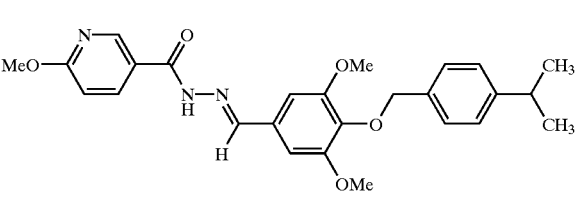
EXAMPLE 132
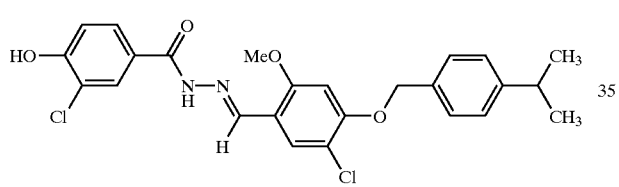
EXAMPLE 137
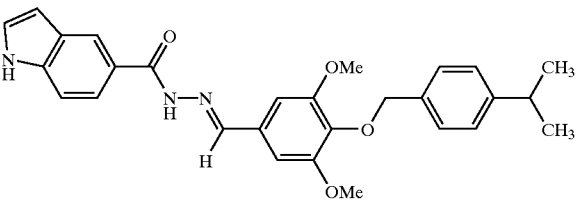
EXAMPLE 133
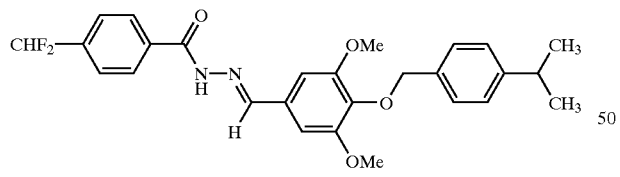
EXAMPLE 138
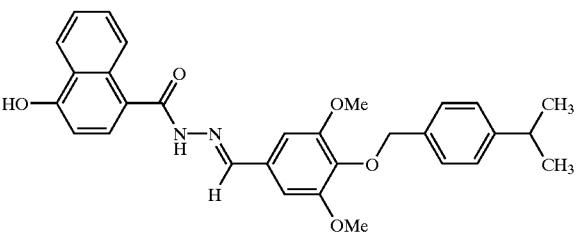
EXAMPLE 134
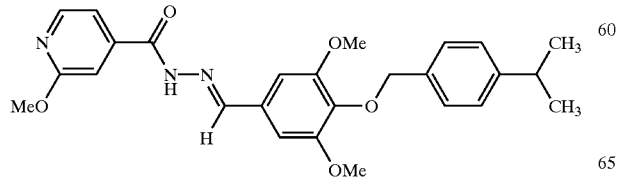
EXAMPLE 139
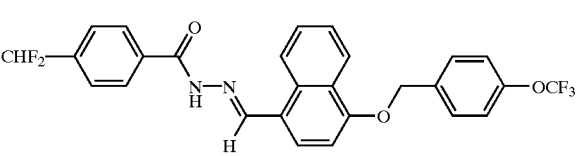

EXAMPLE 140

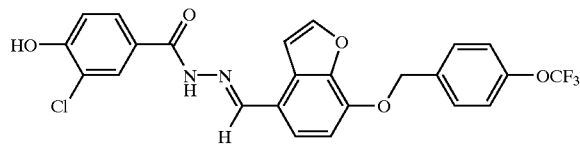

EXAMPLE 141

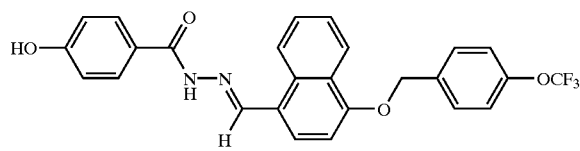

EXAMPLE 142

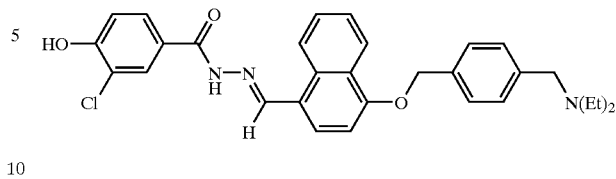

General Procedure for the Synthesis of Further Derivatized Hydrazides of Formula II The compounds of general formula I may be prepared according to one embodiment of the invention, the alkylidene hydrazides of general formula II, as indicated in Scheme III, that is, by converting an alkylidene hydrazide (prepared according to the general method shown in Scheme I, and more specifically as in example 8) into a further derivatized alkylidene hydrazide. Thus, by reacting an amine with an alkylidene hydrazide that contains a leaving group $X_L$ (Scheme III) a new alkylidene hydrazide containing an amine in the group K of formula II can be formed.

SCHEME III

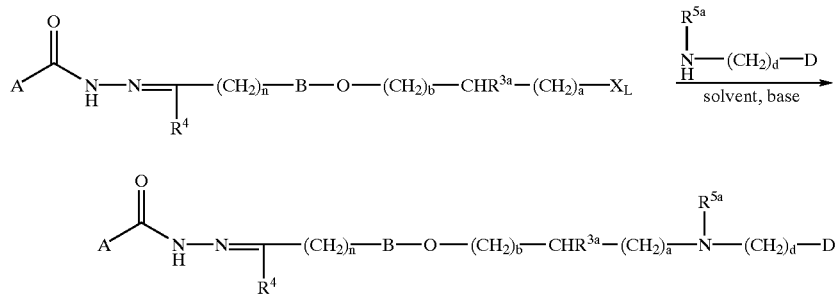

wherein A, B, D, n, $R^4$, $R^{3a}$a, b and d are as defined for formula I and $R^{5a}$ is lower alkyl. Specific examples illustrating the preparation of further derivatized hydrazides of formula II are provided below:

EXAMPLE 143

3-Chloro-4-hydroxybenzoic Acid {4-[2-[N'-(2-N,N-Diethylaminoethyl)-N'-(4-trifluoromethoxy-benzylamino)]]ethoxy-1-naphthylmethylene}hydrazide

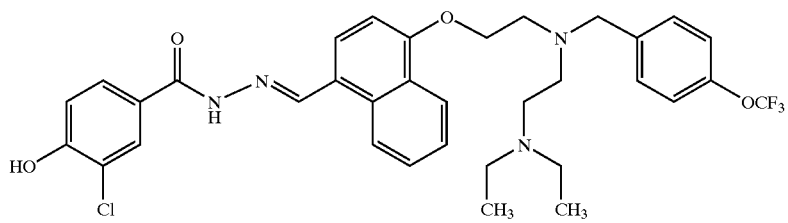

N,N-Diethyl-N'-(4-trifluoromethoxybenzyl)ethylenediamine:

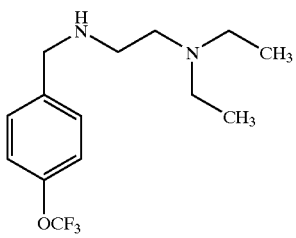

A solution of (4-trifluoromethoxy)benzaldehyde (1.9 g, 10 mmoles), N,N-diethylethylene-diamine (1.16 g, 10 mmoles), zinc chloride (1.36 g, 10 mmoles) and sodium cyanoborohydride (1.26 g, 20 mmoles) in methanol (10 mL) in a dry 100 mL round-bottom flask was stirred at room temperature for 8 hours. Water (20 mL) was then added and most of the methanol was removed in vacuo. The residue was distributed between ethyl acetate and 1N HCl. The acidic aqueous phase was basified with excess of sodium hydroxide. Crude N,N-diethyl-N'-(4-trifluoromethoxybenzyl)ethylenediamine was obtained. The crude product was used in the following reaction without further purification.

MS (CI): 291. $^1$H NMR (CDCl$_3$): δ 7.4 (m, 2H), 7.2 (m, 2H), 3.9 (bs, 2H), 3.1–2.6 (m, 9H), 1.4–1.1 (t, 6H).

To a flask containing N,N-diethyl-N'-(4-trifluoromethoxybenzyl)ethylenediamine (0.29 g, 1 mmole) in DMF (5 mL) was added [1-(4-chloroethoxy)naphthyl](3-chloro-4-hydroxy)benzoic acid hydrazide (0.41 g, 1 mmole) and triethylamine (0.1 g, 1 mmole). The resulting solution was heated at 80° C. overnight. Removal of most of the solvent in vacuo followed by flash chromatography (10:1 CHCl$_3$/MeOH) on silica gel provided the title compound as a brown solid.

$^1$H NMR (DMSO-d$_6$): δ 11.7 (1H), 9.0 bs, 2H), 8.4–7.0 (m, 12H), 4.75 (bs, 1H), 4.65 (bs, 1H), 4.55 (t, 1H), 4.35 (t, 1H), 4.15 (t, 1H), 3.9 (bs, 1H), 3.5 (q, 4H), 3.05 (t, 1H), 1.3 (t, 3H), 0.95 (t, 3H). M.p.: 134–136° C. MS (CI): 657, 659.

EXAMPLE 144

3-Chloro-4-hydroxybenzoic Acid {4-[2-(4-Trifluoromethoxy)benzylaminoethoxy]-1-naphthylmethylene}hydrazide

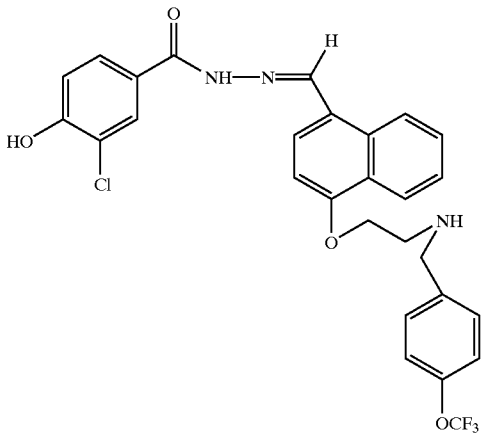

To a flask containing 4-trifluoromethoxybenzylamine (0.29 g, 1 mmole) in DMF (5 mL) was added 3-chloro-4-hydroxybenzoic acid [4-(2-chloroethoxy)-1-naphthylmethylene]hydrazide (0.403 g, 1 mmole) and triethylamine (0.1 g, 1mmole). The resulting solution was heated at 80° C. for 16 hours. Removal of most of the solvent in vacuo, followed by flash chromatography (10:1 CHCl$_3$/MeOH) on silica gel provided the title compound as a brown solid.

$^1$H NMR (DMSO-d$_6$): δ 11.6 (s, 1H), 9.0 (m 2H), 8.3 (m 1H), 8.0 (m, 1H), 7.8 (s, 2H), 7.7 (m, 1H), 7.6 (m, 1H), 7.5 (m, 3H), 7.3 (m, 2H), 7.1 (m, 2H), 4.3 (t, 2H), 3.9 (s, 2H), 3.0 (t, 2H). MS (CI): 557, 559.

By application of the above methodology the following compounds of the invention were synthesized:

EXAMPLE 145

3-Chloro-4-hydroxybenzoic Acid {3,5-Dimethoxy-4-[2-(4-trifluoromethoxybenzylamino)-ethoxy]benzylidene}hydrazide

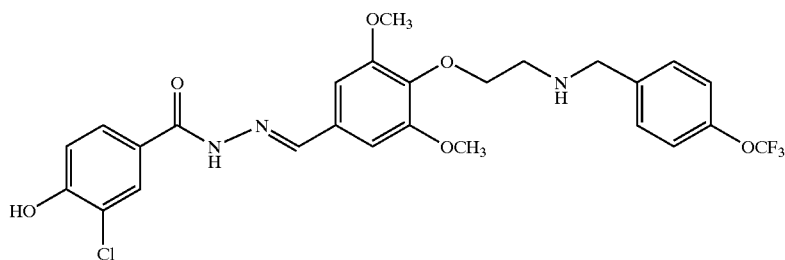

271

¹H NMR (CD₃OD): δ 2.90 (brd t, 2H), 3.75 (s, 6H), 3.89 (s, 2H), 4.08 (brd t, 2H), 6.87 (d, 1H), 7.10 (s, 2H), 7.20 (d, 2H), 7.43 (d, 2H), 7.65 (m, 1H), 7.82 (m, 1H), 8.11 (brd s, 1H); MS (APCI): 567.9.

EXAMPLE 146

3-Chloro-4-hydroxybenzoic Acid {4-[2-(2-Piperidin-1-yl-ethylamino)ethoxy]naphth-1-ylmethylene}hydrazide

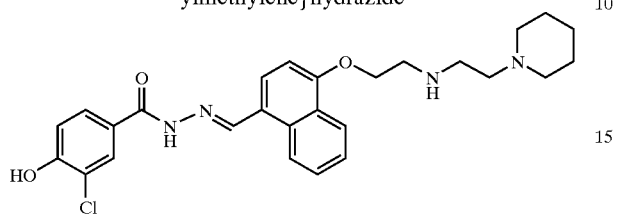

272

¹H NMR (DMSO-d₆): δ 1.53 (m, 2H), 1.74 (m, 4H), 3.12 (m, 2H), 3.40 (m, 2H), 3.54 (m, 2H), 3.63 (m, 4H), 4.52 (s, 2H), 7.10 (d, 1H), 7.14 (d, 1H), 7.60 (t, 1H), 7.71 (m, 1H), 7.80 (dd, 1H), 7.83 (d, 1H), 8.00 (d, 1H), 8.51 (d, 1H), 8.95 (d, 1H), 8.98 (s, 1H), 11.69 (s, 1H); MS (APCI): 495.0.

EXAMPLE 147

3-Chloro-4-hydroxybenzoic Acid {4-[2-(3-Diethylaminopropylamino)ethoxy]naphth-1-ylmethylene}hydrazide

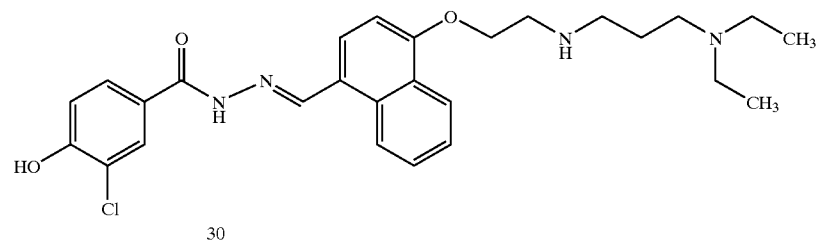

¹H NMR (DMSO-d₆): δ 1.21 (t, 6H), 2.10 (m, 2H), 3.14 (m, 10H), 4.52 (t, 2H), 7.10 (d, 1H), 7.14 (d, 1H), 7.63 (t, 1H), 7.73 (m, 1H), 7.80 (dd, 1H), 7.84 (d, 1H), 8.00 (d, 1H), 8.46 (d, 1H), 8.93 (s, 1H), 8.98 (m, 1H), 9.20 (m, 2H), 9.69 (m, 1H), 11.00 (s, 1H), 11.69 (s, 1H); MS (APCI): 497.0.

EXAMPLE 148

1-(2-{4-[(3-Chloro-4-hydroxybenzoyl)hydrazonomethyl]naphth-1-yloxy}ethyl)-4-phenylaminopiperidine-4-carboxylic Acid Amide

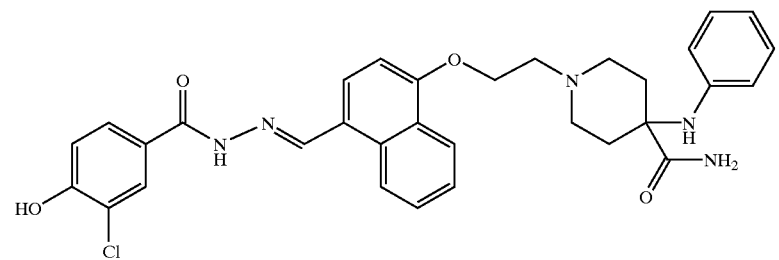

¹H NMR (DMSO-d₆): δ 1.16 (m, 2H), 1.88 (m, 2H), 2.03 (m, 2H), 2.80 (m, 2H), 2.92 (m, 2H), 4.37 (m, 2H), 4.40 (brd s, 2H), 4.44 (s, 1H), 6.55–6.62 (m, 3H), 6.96 (s, 1H), 7.03–7.16 (m, 5H), 7.61 (dd, 1H), 7.68 (dd, 1H), 8.00 (d, 1H), 8.27 (d, 1H), 8.94 (s, 1H), 8.97 (s, 1H), 11.63 (s, 1H); MS (APCI): 586.4.

EXAMPLE 149

4-(2-{4-[(3-Chloro-4-hydroxybenzoyl)hydrazonomethyl]naphth-1-yloxy}ethylamino)piperidine-1-carboxylic Acid Ethyl Ester

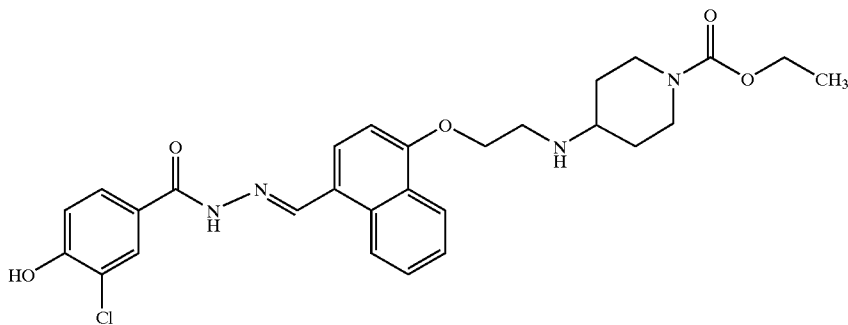

¹H NMR (DMSO-d₆): δ 1.10 (t, 3H), 1.15–1.23 (m, 2H), 1.86 (m, 2H), 2.79 (m, 3H), 3.30 (m, 2H), 3.87 (m, 2H), 3.94 (q, 2H), 4.28 (m, 2H), 7.03 (d, 1H), 7.05 (m, 1H), 7.51–7.63 (m, 3H), 7.13 (d, 1H), 7.75 (m, 1H), 7.93 (d, 1H), 8.29 (d, 1H), 8.87 (m, 2H), 11.55 (s, 1H); MS (APCI): 539.1, 541.0.

EXAMPLE 150

3-Chloro-4-hydroxybenzoic Acid {4-[2-(1,2,3,4-Tetrahydronaphth-1-ylamino)ethoxy]-naphth-1-ylmethylene}hydrazide

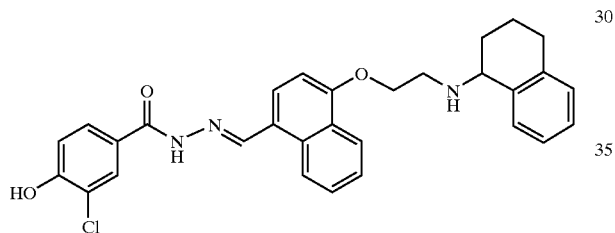

¹H NMR (DMSO-d₆): δ 1.76 (m, 1H), 2.04 (m, 1H), 2.17 (m, 2H), 2.75–2.94 (m, 2H), 3.61 (m, 2H), 4.55 (m, 2H), 4.71 (s, 1H), 7.11 (d, 1H), 7.13 (d, 1H), 7.23–7.35 (m, 3H), 7.61 (d, 1H), 7.67 (d, 1H), 7.71 (dd, 1H), 7.81 (dd, 1H), 7.86 (d, 1H), 8.01 (d, 1H), 8.48 (d, 1H), 8.94 (m, 1H), 8.99 (m, 1H), 9.22 (m, 2H), 11.00 (s, 1H), 11.64 (s, 1H); MS (APCI): 514.0, 516.0.

EXAMPLE 151

1-(2-{4-[(3-Chloro-4-hydroxybenzoyl)hydrazonomethyl]naphth-1-yloxy}ethyl)piperidine-4-carboxylic Acid Amide

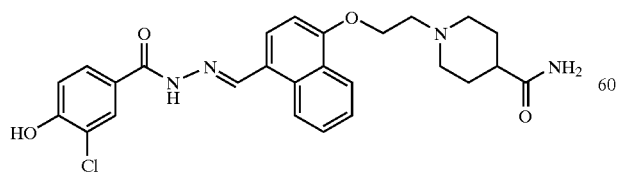

MS (APCI): 495.0.

EXAMPLE 152

3-Chloro-4-hydroxybenzoic Acid {4-[2-(2-Trifluoromethoxybenzylamino)-ethoxy]-1-naphthylmethylene}hydrazide

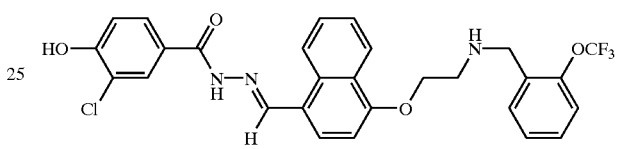

EXAMPLE 153

3-Chloro-4-hydroxybenzoic Acid {4-[2-(4-Morpholinylethylamino)ethoxy]-1-naphthylmethylene}hydrazide


By application of the above methodology the following compounds may also be synthezised:

EXAMPLE 154

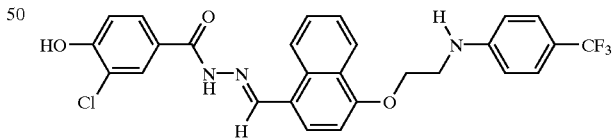

EXAMPLE 155

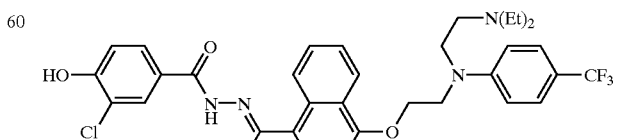

EXAMPLE 156

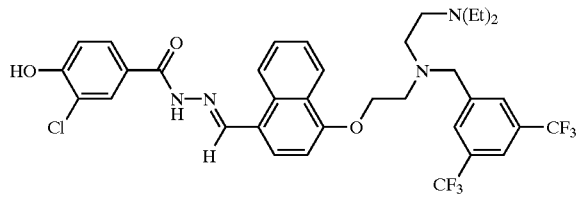

EXAMPLE 157

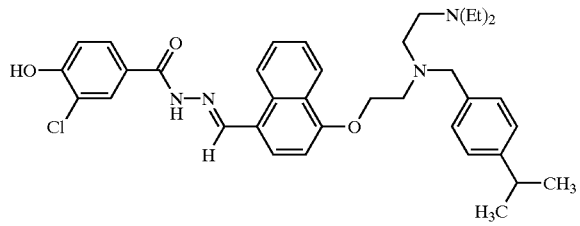

EXAMPLE 158

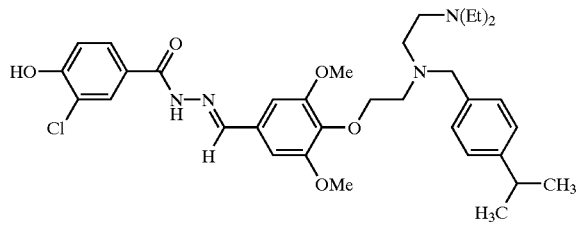

EXAMPLE 159

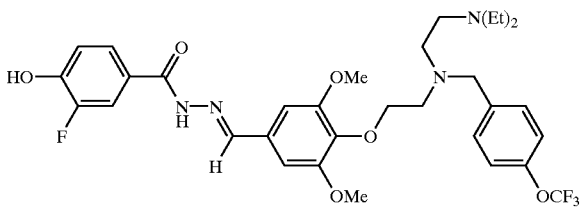

EXAMPLE 160

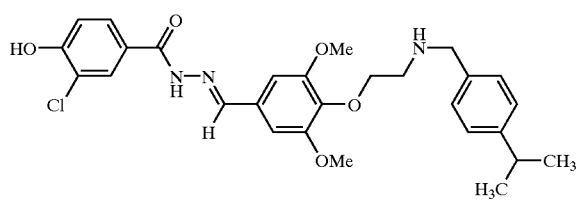

General Procedures for the Preparation of Alkylidene Arylsulfonyl Hydrazides According to the Invention The compounds of general formula I are prepared according to one embodiment of the invention, the alkylidene arylsulfonyl hydrazides of general formula III, that is, by converting an arylsulfonyl halide, for example chloride or bromide to the corresponding hydrazide derivative and further reacting the product arylsulfonyl hydrazide compound with a substituted aldehydes or ketones to yield alkylidene arylsulfonyl hydrazide derivatives as illustrated in Scheme IV.

SCHEME IV

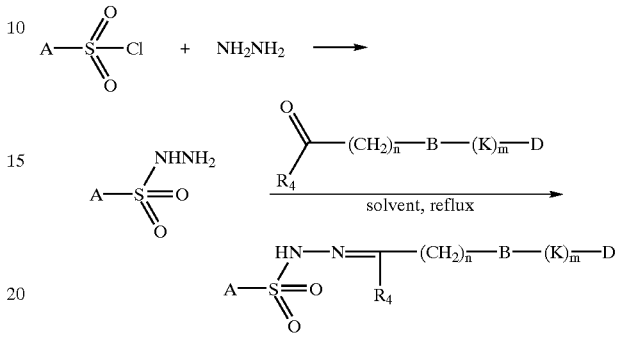

wherein A, B, K, D, m, n and $R^4$ are as defined for formula I.

The synthesis of the arylsulfonylhydrazide precursors is performed by application of general methodology, for example as described by Friedman, L.; Litle, R. L; Reichle, W. R. in *Org. Synth. Coll. Vol. V*, 1973, 1055–1057, by slowly adding the arylsulfonyl chloride either neat, or in a solution in an inert solvent such as tetrahydrofuran, dimethyl ether, dioxane or diethyl ether to an excess of hydrazine, either neat or in solution in the one of the above solvents or a mixture of these at −20° C. to 100° C., preferably between 0° C. to 60° C. When the reaction is judged to be completed, the excess of solvent and volatile reagents is removed by distillation either at atmospheric pressure or in vacuo. The residual product can be further purified by recrystallization from a solvent such as methyl alcohol, ethyl alcohol, isopropyl alcohol, water, toluene, acetic acid, dioxane, tetrahydrofuran or a mixture of two or more of the above solvents when compatible.

Alternatively, the product can be purified by column chromatography using dichloromethane/methanol or chloroform/methanol or isopropyl alcohol as eluent. The corresponding fractions are concentrated either at atmospheric pressure or in vacuo to provide the pure arylsulfonyl hydrazide.

By use of the above methodology the following compounds can be prepared:

EXAMPLE 161

3-Chloro-4-hydroxybenzenesulfonic Acid (Benzylidene)hydrazide

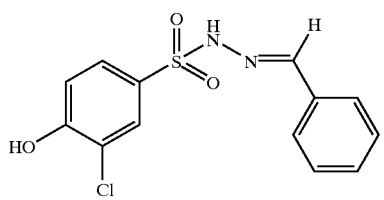

3-Chloro-4-hydroxybenzenesulfonyl Hydrazide

A solution of 4.82 g (21.2 mmol) 3-chloro-4-hydroxybenzenesulfonyl chloride, (prepared according to the procedure described by Popoff, I. C.; Frank, J. R.; Whitaker R. L.; Miller H. J., Demaree K. D. *J. Agr. Food Chem.* 1969, 17, 810.) in 15 ml THF was added dropwise with stirring to 3.4 ml 50% hydrazine hydrate (54.4 mmol, 2.5 eq.) at such a rate that the temperature is maintained below 10° C. A precipitate formed after the addition was completed. The mixture was stirred for an additional 30 min, and cooled to 0° C. The solid was collected in a Büchner funnel, washed several times with distilled water, and air dried. Recrystallization from methanol provided 1.20 g 3-chloro-4-hydroxybenzenesulfonyl hydrazide as a white solid.

H NMR (DMSO-d$_6$): δ 4.78 (bs, 4H), 6.72 (d, J=8.6 Hz, 1H), 7.35 (dd, J=2.3, 8.6 Hz, 1H), 5.55 (J=2.2 Hz, 1H); MS (CI): m/z 223, 221.

To a solution of 105 mg (0.48 mmol) of the above 3-chloro-4-hydroxybenzenesulfonyl hydrazide in 5 ml methanol was added 0.05 ml (52 mg, 0.49 mmol) benzaldehyde and one drop of acetic acid. After 30 min the mixture was concentrated. Flash chromatography (silica gel, 2:1 hexane/ethylacetate) provided 67 mg (45%) of the title compound as a solid.

$^1$H (DMSO-d$_6$): δ 7.10 (d, J=8.6 Hz, 1H), 7.38 (m, 3H), 7.55 (dd, J=2.3, 6.0 Hz, 2H), 7.66 (d, J=2.2, 8.6 Hz, 1H), 7.76 (d, J=2.2 Hz, 1H), 7.90 (s, 1H), 11.3 (m, 2H). MS (CI): m/z 311.

EXAMPLE 162

3-Chloro-4-hydroxy-benzenesulfonic Acid [4-(4-Trifluoromethoxybenzyloxy)-1-naphthylmethylene] hydrazide To a solution of 3-chloro-4-hydroxy-benzene sulfonyl hydrazide (105 mg, 0.48 mmol) in 5 ml methanol was added 4-trifluoromethoxybenzyloxy-1-naphthaldehyde (163 mg, 0.49 mmol) and a catalytical amount of glacial acetic acid (5 drops). The reaction mixture was stirred overnight, and filtered. The filtrate was concentrated under vacuo to give the crude product. Flash chromatography (silica gel, 1:1 hexane/ethylacetate) provided 145 mg (56%) of the title compound as a solid.

$^1$H NMR (DMSO-d$_6$) δ 5.27 (s, 2H), 6.06 (s, 1H), 6.83 (d, J=8.1 Hz, 1H), 7.10 (d, J=8.1 Hz, 1H), 7.26 (d, J=7.3 Hz, 2H), 7.50–7.60 (m, 5H), 7.80 (s, 1H), 7.85 (dd, J=3.0, 8.2 Hz, 1H), 8.08 (d, J=2.1 Hz, 1H), 8.26 (s, 1H), 8.36 (d, J=7.76 Hz, 1H), 8.67 (d, J=8.5 Hz, 1H). CIMS m/z: 551, 553.

By using the above methodology, the following compounds may be prepared:

EXAMPLE 163

EXAMPLE 164

EXAMPLE 165

EXAMPLE 166

Synthesis of Alkylhydrazides According to the Invention

The alkylidene hydrazide derivatives given above can be reduced to the dihydroderivatives by the method given in Scheme V:

SCHEME V where A, R$^4$, B, K, D, m and n are as defined for formula I.

The alkylhydrazide derivatives can be prepared by reduction (i.e. Lane, C. F.(1975), Synthesis, p.135) of the corresponding alkylidene hydrazides using a metal hydride, such as sodium borohydride or sodium cyanoborohydride. The alkylidene hydrazide derivative is treated with between 1–10 equivalents, preferentially 1–3 equivalents, of sodium cyanoborohydride in a solvent such as methyl alcohol, ethyl alcohol, isopropyl alcohol, tetrahydrofuran, dioxane, water or a compatible mixture of two or more solvents. Optionally a small amount of an acid is used as a catalyst such as hydrochloric acid, trifluoroacetic acid, acetic acid, or sulfuric acid. The reactions are performed at 0° C. to 60° C., preferably at 10° C. to 30° C. When the reaction is complete as judged by HPLC or TLC (silica gel, 1% methanol in dichloromethane as eluent) the solvent(s) are removed and the residue is chromatographed on a silica gel column using 1% methanol in dichloromethane or chloroform as an eluent. The corresponding fractions are concentrated to give the desired product. Specific examples illustrating the preparation of alkylhydrazides according to the invention are provided below.

EXAMPLE 167

4-Hydroxybenzoic Acid (1-Naphthylmethyl) hydrazide

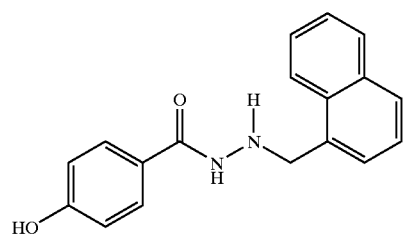

4-Hydroxybenzoic acid (1-naphthylmethylene)hydrazide (100 mg, 0.34 mmol) was dissolved in methanol (10 mL) and treated with sodium cyanoborohydride (236 mg, 4.1 mmol) followed by two drops of trifluoroacetic acid. After stirring the reaction solution for three hours at room temperature, the solvent was evaporated in vacuo. The residue was introduced into a silica gel column and eluted with dichloromethane/methanol (99/1). Evaporation of the corresponding fractions in vacuo gave the title compound in 30% yield. MS (ESI) m/z 293 (M+H)$^+$.

Using the same methodology as described above the following compound was prepared:

EXAMPLE 168

3-Chloro-4-hydroxybenzoic Acid N-[4-(4-Isopropylbenzyloxy)-3,5-dimethoxybenzyl] hydrazide

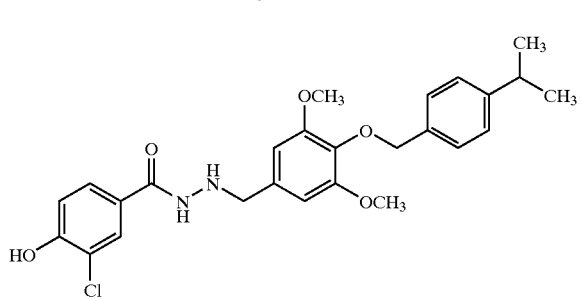

$^1$H NMR (DMSO-d$_6$): δ 1.18 (d, 6H), 2.87 (m, 1H), 3.75 (s, 6H), 3.90 (m, 2H), 4.80 (s, 2H), 5.43 (brd s, 1H), 6.68 (s, 2H), 6.98 (d, 1H), 7.20 (d, 2H), 7.34 (d, 2H), 7.64 (dd, 1H), 7.87 (d, 1H), 9.89 (brd s, 1H), 10.80 (s, 1H); MS (APCI): 485.2.

Furthermore, the following compounds may also be prepared:

EXAMPLE 169

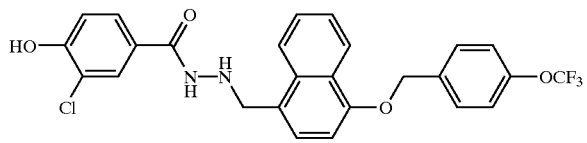

EXAMPLE 170

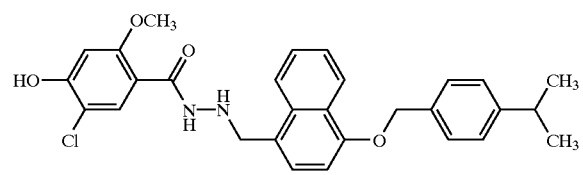

EXAMPLE 171

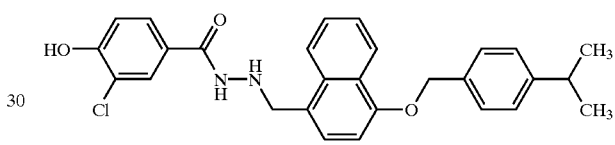

EXAMPLE 172

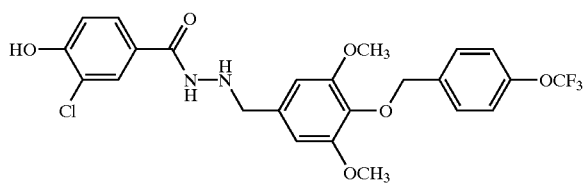

EXAMPLE 173

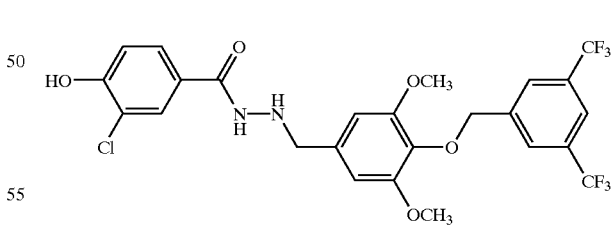

General Procedure for Synthesis of Compounds of the General Formula XI

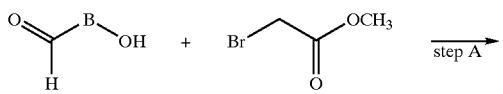

-continued

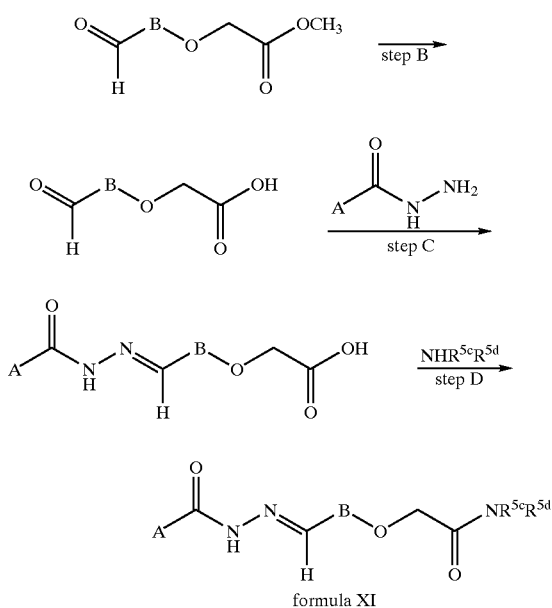

formula XI

A and B are as defined for formula I and —NR$^{5c}$R$^{5d}$ is

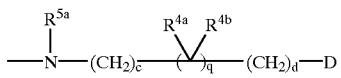

where R$^{5a}$, R$^{4a}$, R$^{4b}$, c, q, d and D are as defined for formula I or
—D' where —D' is defined as a subset of —D that contains a primary or secondary amine that can react as a nucleophile.

Step A: The reaction is known and is generally performed by stirring hydroxy benzaldehyde, hydroxy naphthaldehyde or the like together with a bromo acetic acid ester (either methyl, ethyl or other lower alkyl ester) in the presence of a base such as lithium, sodium, potassium or cesium carbonate in a solvent such as acetone, 2-methyl-3-pentanone, tetrahydrofuran, dioxane, DMSO, DMF, ethylene glycol, benzene, toluene or a mixture of the above solvents. The reactions are performed between 0° C. to 130° C., preferably between 20° C. to 100° C., most preferably at or about the reflux temperature of the solvent. The reactions are preferably conducted under an inert atmosphere such as N$_2$ or Ar. When the reaction is complete as judged by disappearance of the starting ester by TLC or HPLC, the solvent may be removed by concentration at atmospheric or reduced pressure. The product can be further purified by either recrystallization from a solvent such as ethyl alcohol, methyl alcohol, isopropyl alcohol, toluene, xylene, hexane, tetrahydrofuran, diethyl ether, dibutyl ether, water or a mixture of two or more of the above. Alternatively, the product can be purified by column chromatography using dichloromethane/methanol or chloroform/methanol or isopropyl alcohol as eluent.

Step B: The resulting derivative of acetic ester is then saponified using methods well-known to those skilled in the art such as dissolving the compound in an appropriate solvent such as a lower alcohol (e.g methanol, ethanol or isopropanol), DMF, dioxane or DMSO and adding an aqueous base like lithium, sodium or potassium hydroxide. The reactions are performed between 0° C. to 130° C., preferably between 20° C. to 100° C. When the reaction is complete as judged by disappearance of the staring ester by TLC or HPLC, the solvent may be removed by concentration at atmospheric or reduced pressure. The product can then be isolated by pouring the residue into water or cooled water and acidifying the mixture using an inorganic acid such as hydrochloric acid or sulfuric acid. The product can then be isolated either by filtration or by extraction using a solvent such as ethyl acetate, toluene, dichloromethane or diethylether and the solvent may then be removed by concentration at atmospheric or reduced pressure. The product can be further purified by either recrystallization from a solvent such as ethyl alcohol, methyl alcohol, isopropyl alcohol, toluene, xylene, hexane, tetrahydrofuran, diethyl ether, dibutyl ether, water or a mixture of two or more of the above. Alternatively, the product can be purified by column chromatography using dichloromethane/methanol or chloroform/methanol or isopropyl alcohol as eluent.

Step C: The resulting carbonyl compounds are treated with an acylhydrazide in a solvent. The solvent may be one of the following: ethyl alcohol, methyl alcohol, isopropyl alcohol, tert-butyl alcohol, dioxane, tetrahydrofuran, toluene, chlorobenzene, anisole, benzene, chloroform, dichloromethane, DMSO, acetic acid, water or a compatible mixture of two or more of the above solvents. A catalyst such as acetic acid can be added. A dehydrating reagent such as triethylorthoformate can also be added to the reaction mixture. The reaction is performed by stirring the reaction mixture preferably under an inert atmosphere of N$_2$ or Ar at temperatures between 0° C. to 140° C., preferably between 10° C. to 80° C. In many cases the product simply crystallizes out when the reaction is completed and is isolated by suction filtration. It can be further recrystallized if necessary from a solvent such as the above described reaction solvents. The product can also be isolated by concentration of the reaction mixture in vacuo, followed by column chromatography on silica gel using a solvent system such as chloroform/methanol or dichloromethane/methanol or chloroform/ethyl acetate.

Step D: The resulting acid is then coupled to a primary or secondary amine using one of the methods well-known to those skilled in the art. This coupling can be performed using one of the standard amide or peptide synthesis procedures such as by generating an active ester, an anhydride or an acid halide that can then react with the amine to give a compound of formula XI. Step D can also be done combinatorially with a selected number of amines. The product can then be isolated either by filtration or by extraction using a solvent such as ethyl acetate, toluene, dichloromethane or diethylether and the solvent may then be removed by concentration at atmospheric or reduced pressure. The product can be further purified by either recrystallization from a solvent such as ethyl alcohol, methyl alcohol, isopropyl alcohol, toluene, xylene, hexane, tetrahydrofuran, diethyl ether, dibutyl ether, water or a mixture of two or more of the above. Alternatively, the product can be purified by column chromatography using dichloromethane/methanol or chloroform/methanol or isopropyl alcohol as eluent giving a compound of formula XI.

Specific examples illustrating the preparation of compounds of the general formula XI according to the invention are provided below.

EXAMPLE 174

2-{4-[(3-Chloro-4-hydroxy-benzoyl)hydrazonomethyl]naphthyl-1-yloxy}-N-(4-chlorophenyl)acetamide

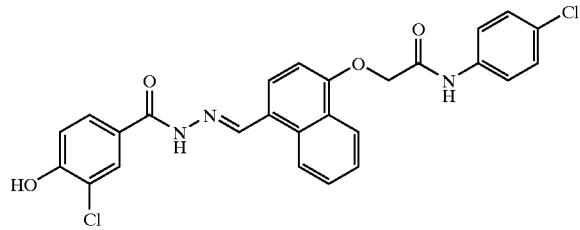

Step A: Hydroxynaphthaldehyde ((10 g, 58 mmol), potassium carbonate (16 g, 110 mmol), and methyl bromoacetate (16 g, 100 mmol) were refluxed in acetone (120 mL) overnight. The reaction mixture was poured into an Erlenmeyer flask containing approximately 500 mL of ice chips. The mixture was stirred until all of the ice was melted. (4-Formylnaphth-1-yloxy) acetic acid methyl ester (13 g, 50 mmol) was filtered and dried in vacuo overnight.

$^1$H NMR (CDCl$_3$): δ 3.86 (s, 3H), 4.93 (s, 2H), 6.80 (d, 1H), 7.61 (t, 1H), 7.72 (t, 1H), 7.90 (d, 1H), 8.42 (d, 1H), 9.29 (d, 1H), 10.22 (s, 1H).

Step B: The above ester (13 g, 50 mmol) was dissolved in methanol (100 mL) and 2 M NaOH (40 mL) was added. The reaction solution was stirred overnight and concentrated to approximately 100 mL under vacuo. The residue was poured into approximately 500 mL of ice chips and the mixture was acidified (by pH paper) with the addition of 3N HCl. The mixture was stirred until all of the ice was melted. (4-Formylnaphth-1-yloxy) acetic acid was filtered and washed with water.

Step C: To a solution of 3-chloro-4-hydroxybenzoic acid hydrazide (2 g, 10.7 mmol) in DMSO (20 mL) was added the above (4-formylnaphth-1-yloxy) acetic acid (3 g, 13 mmol) and a catalytic amount of acetic acid (10 drops). The solution was stirred overnight and diluted with ethyl acetate. The solution was washed with water (3×), brine, and dried over MgSO$_4$. The volume was reduced to approximately 100 mL and placed in an ice-bath. The resulting solid was filtered and washed with cold ethyl acetate to afford {4-[(3-chloro-4-hydroxy-benzoyl)hydrazonomethyl]naphth-1-yloxy}acetic acid.

$^1$H NMR (DMSO-d$_6$): δ 4.91 (s, 2H), 6.95 (d, 1H), 7.02 (d, 1H), 7.55 (t, 1H), 7.64 (t, 1H), 7.74 (d, 1H), 7.92 (d, 1H), 8.27 (d, 1H), 8.90 (m, 2H), 10.92 (brd s, 1H), 11.63 (s, 1H), 13.14 (brd s, 1H).

Step D: To a solution of the hydrazone-carboxylic acid (50 mmol) in anhydrous DMSO was added a solution of carbonyldiimidazole (55 mmol) in anhydrous DMSO. After the evolution of gases ceased (approximately 3–4 minutes), the amine was added and the reaction mixture was stirred for 3 hours. The mixture was diluted with ethyl acetate and washed with water, brine, and dried over magnesium sulfate. Evaporation of the solvent afforded the crude material, which was purified by reverse phase HPLC chromatography to give the title compound.

$^1$H NMR (DMSO-d$_6$): δ 4.99 (s, 2H), 7.04 (m, 2H), 7.36 (d, 2H), 7.65 (m, 4H), 7.79 (t, 2H), 7.99 (s, 1H), 8.40 (d, 1H), 8.72 (s, 1H), 8.92 (d, 1H), 10.42 (s, 1H), 10.96 (s, 1H), 11.69 (s, 1H); MS (APCI): 507.9.

By using the same methodology, the following compounds were prepared:

EXAMPLE 175

N-(1-Benzylpyrrolidin-3-yl)-2-{4-[(3-chloro-4-hydroxy-benzoyl)hydrazonomethyl]naphth-1-yloxy}acetamide

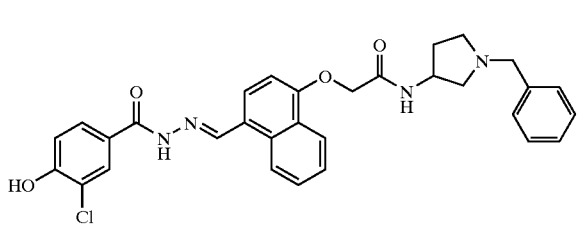

$^1$H NMR (DMSO-d$_6$): δ 1.96 (m, 2H), 2.32 (m, 5H), 4.58 (s, 2H), 6.78 (d, 1H), 6.92 (d, 1H), 7.15 (m, 5H), 7.47 (t, 1H), 7.52 (t, 1H), 7.62 (d, 2H), 7.82 (d, 1H), 8.18 (m, 2H), 8.78 (d, 2H), 10.75 (brd s, 1H), 11.52 (s, 1H); MS (APCI): 556.9.

EXAMPLE 176

2-{4-[(3-Chloro-4-hydroxybenzoyl)hydrazonomethyl]naphth-1-yloxy}-N-indan-1-yl-acetamide

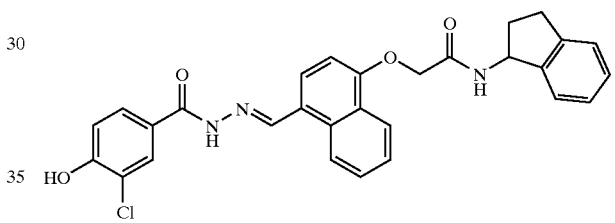

$^1$H NMR (DMSO-d$_6$): δ 1.94 (m, 1H), 2.40 (m, 1H), 2.80–3.07 (m, 3H), 4.87 (s, 2H), 7.04 (d, 1H), 7.10 (d, 1H), 7.21 (m, 4H), 7.61 (t, 1H), 7.69 (t, 1H), 7.80 (t, 2H), 8.10 (s, 1H), 8.42 (d, 1H), 8.64 (d, 1H), 8.98 (m, 2H), 11.00 (brd s, 1H), 11.68 (s, 1H); MS (APCI): 514, 516.

EXAMPLE 177

2-{4-[(3-Chloro-4-hydroxybenzoyl)hydrazonomethyl]naphth-1-yloxy}-N-(1,2,3,4-tetrahydronaphthalen-1-yl)acetamide

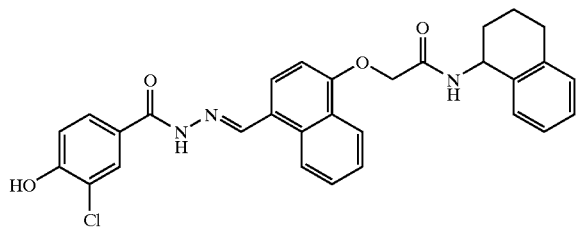

$^1$H NMR (DMSO-d$_6$): δ 1.75 (m, 2H), 1.92 (m, 2H), 2.74 (m, 2H), 4.87 (m, 2H), 5.12 (m, 1H), 7.12 (m, 6H), 7.61 (t, 1H), 7.74 (t, 1H), 7.84 (m, 2H), 8.01 (s, 1H), 8.40 (d, 1H), 8.62 (d, 1H), 8.97 (m, 2H), 11.72 (s, 1H); MS (APCI): 528, 530.

EXAMPLE 178

2-{4-[(3-Chloro-4-hydroxybenzoyl)hydrazonomethyl]naphth-1-yloxy}-N-[2-(4-chlorophenyl)ethyl]acetamide

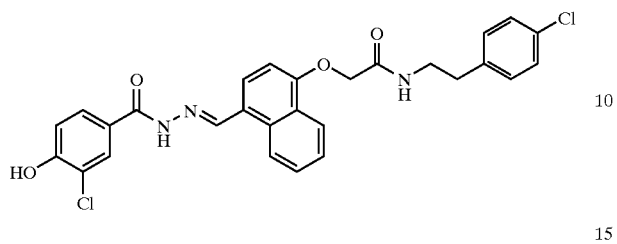

¹H NMR (DMSO-d₆): δ 2.40 (t, 2H), 2.79 (t, 2H), 4.74 (s, 2H), 6.96 (d, 1H), 7.10 (d, 1H), 7.63 (t, 1H), 7.69 (t, 1H), 7.72 (m, 2H), 7.81 (s, 1H), 8.01 (m, 2H), 8.23 (t, 1H), 8.40 (d, 1H), 8.95 (s, 1H), 9.01 (d, 1H), 10.98 (brd s, 1H), 11.70 (s, 1H); MS (APCI) 538.8, 537.8.

EXAMPLE 179

2-{4-[(3-Chloro-4-hydroxybenzoyl)hydrazonomethyl]naphth-1-yloxy}-N-[3-(4-methylpiperazin-1-yl)propyl]acetamide

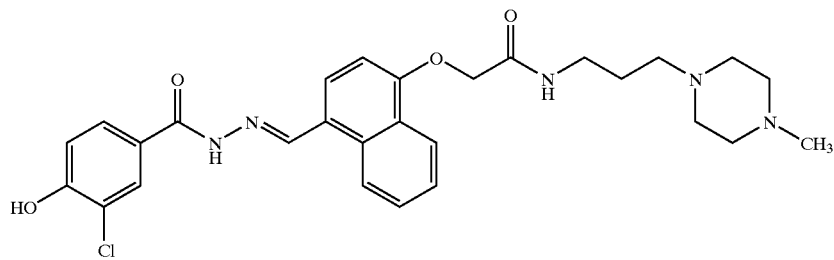

¹H NMR (DMSO-d₆): δ 1.50 (m, 2H), 2.26 (m, 2H), 2.48 (m, 5H), 3.01 (m, 8H), 4.53 (s, 2H), 6.78 (d, 1H), 6.89 (d, 1H), 7.38 (t, 1H), 7.47 (t, 1H), 7.5 (t, 2H), 7.76 (d, 1H), 8.01 (t, 1H), 8.22 (d, 1H), 8.68 (d, 1H), 8.74 (s, 1H), 10.74 (brd s, 1H), 11.45 (s, 1H); MS (APCI): 538.0.

EXAMPLE 180

3-Chloro-4-hydroxybenzoic Acid {4-[2-(1,2,3,4-Tetrahydroisoquinolin-2-yl)-2-oxoethoxy]naphth-1-ylmethylene}hydrazide

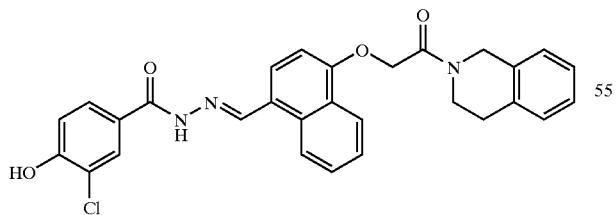

¹H NMR (DMSO-d₆): δ 2.90 (d, 2H), 2.75 (m, 2H), 4.70 (d, 2H), 5.24 (s, 2H), 6.90 (t, 2H), 7.10 (m, 4H), 7.66 (m, 4H), 8.01 (s, 1H), 8.34 (t, 1H), 8.95 (m, 2H), 10.97 (brd s, 1H), 11.68 (brd s, 1H); MS (APCI): 514.2.

EXAMPLE 181

2-{4-[(3-Chloro-4-hydroxy-benzoyl)hydrazonomethyl]naphth-1-yloxy}-N-(3-trifluoromethoxybenzyl)acetamide

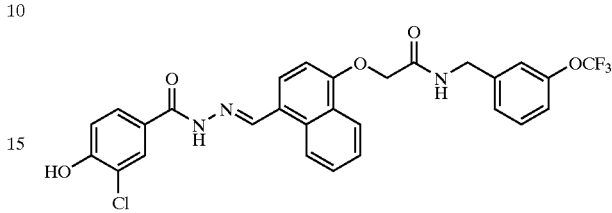

¹H NMR (DMSO-d₆): δ 4.49 (d, 2H), 4.90 (s, 2H), 7.13 (m, 2H), 7.42 (m, 4H), 7.59 (dd, 1H), 7.68 (dd, 1H), 7.78 (m, 2H), 8.03 (s, 1H), 8.51 (d, 1H), 8.79 (t, 1H), 9.0 (m, 2H), 10.85 (brd s, 1H), 11.72 (s, 1H); MS (APCI): 572.1.

EXAMPLE 182

3-Chloro-4-hydroxybenzoic Acid (4-{2-[4-(4-Bromophenyl)-4-hydroxypiperidin-1-yl]-2-oxoethoxy}naphth-1-ylmethylene)hydrazide

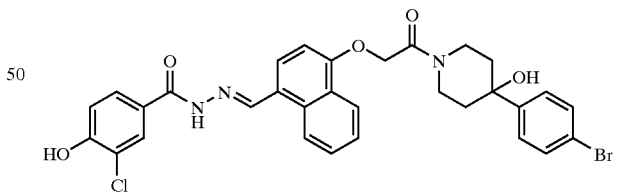

MS (APCI): 636, 638.

EXAMPLE 183

2-{4-[(3-Chloro-4-hydroxybenzoyl)hydrazonomethyl]naphth-1-yloxy}-N-(4-trifluoromethylsulfanylbenzyl)acetamide

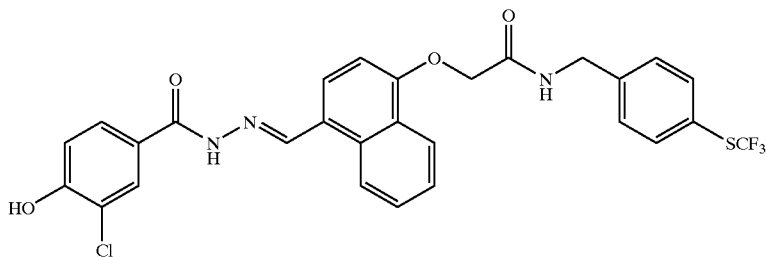

¹H NMR (DMSO-d₆): δ 4.48 (d, 2H), 4.88 (s, 2H), 7.08 (m, 2H), 7.45 (d, 2H), 7.68 (m, 4H), 7.82 (m, 2H), 8.01 (d, 1H), 8.52 (d, 1H), 8.87 (t, 1H), 8.96 (s, 1H), 9.01 (d, 1H), 10.98 (brd s, 1H), 11.72 (s, 1H); MS (APCI): 588.2.

EXAMPLE 184

2-{4-[(3-Chloro-4-hydroxy-benzoyl)hydrazonomethyl]naphth-1-yloxy}-N-(3,4-dichlorobenzyl)acetamide

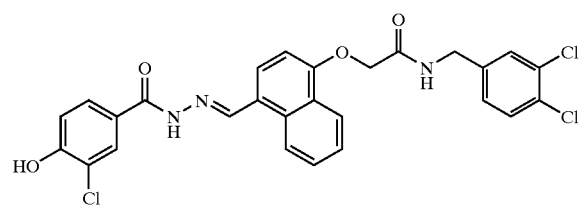

¹H NMR (DMSO-d₆): δ 4.42 (d, 2H), 4.91 (s, 2H), 7.08 (d, 1H), 7.11 (d, 1H), 7.22 (d, 1H), 7.48–7.76 (m, 4H), 7.82 (d, 2H), 8.04 (d, 1H), 8.51 (dd, 1H), 8.83 (m, 1H), 8.91 (s, 1H), 10.02 (d, 1H), 11.00 (brd s, 1H), 11.73 (s, 1H); MS (APCI): 556.0.

EXAMPLE 185

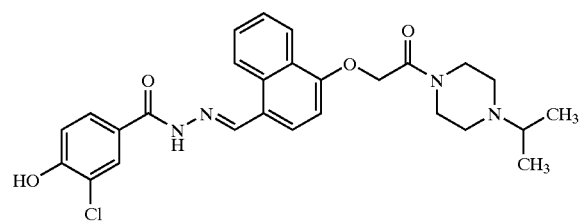

¹H NMR (DMSO-D₆): δ 0.97 (d, 6H), 2.42 (m, 2H), 2.50 (m, 2H), 2.68 (septet, 1H), 3.49 (m, 4H), 5.12 (s, 2H), 7.03 (d, 1H), 7.08 (d, 1H), 7.60 (t, 1H), 7.68 (t, 1H), 7.80 (d, 2H), 8.01 (d, 1H), 8.33 (d, 1H), 8.94 (s, 1H), 9.00 (d, 1H), 11.68 (s, 1H); MS (APCI, neg.): 507.1, 509.1.

EXAMPLE 186

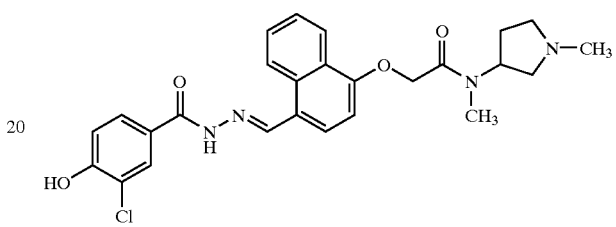

¹H NMR (DMSO-D₆): δ 1.75 (m, 2H), 2.25 (m, 2H), 2.24 (d, 3H), 2.39 (quintet, 1H), 3.26 (m, 2H), [2.84 (s, 1.5H)+3.04 (s, 1.5H), 3H], 5.16 (d, 2H), 6.72 (t, 1H), 7.07 (d, 1H), 7.62 (t, 1H), 7.68 (t, 1H), 7.78 (dd, 2H), 8.00 (d, 1H), 8.34 (m, 1H), 8.94 (s, 1H), 9.00 (d, 1H), 11.65 (brd s, 1H); MS (APCI): 495.2, 497.2.

EXAMPLE 187

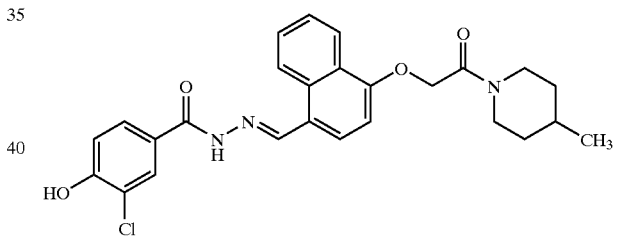

¹H NMR (DMSO-D₆): δ 0.86 (s, 3H), 1.48 (m, 4H), 2.38 (t, 1H), 2.72 (m, 1H), 3.09 (t, 1H), 3.84 (t, 1H), 4.18 (t, 1H), 5.09 (m, 2H), 7.03 (d, 1H), 7.11 (d, 1H), 7.59 (t, 1H), 7.64 (t, 1H), 7.82 (d, 2H), 8.01 (s, 1H), 8.33 (d, 1H), 8.94 (s, 1H), 9.00 (d, 1H), 11.0 (brd, 1H), 11.69 (brd s, 1H); MS (APCI): 480.1, 482.1.

EXAMPLE 188

¹H NMR (DMSO-D₆): δ 2.88 (s, 1.5H)+(s, 1.5H), 3H], 2.95 (t, 1H), 3.01 (s, 1.5H), 3.10 (s, 1.5H), 3.10 (t, 1H), 3.69 (t, 1H), 3.81 (t, 1H), 5.05 (d, 2H), [6.66+6.95 (d), 1H], 7.10

(d, 1H), [7.20+7.38 (d), 1 H], 7.29 (d, 1H), 7.67 (m, 5H), 8.01 (s, 1H), 8.30 (t, 1H), 8.53 (dd, 1H), 8.97 (m, 2H), 11.67 (brd s, 1H): MS (APCI): 517.3, 519.2.
EXAMPLE 189
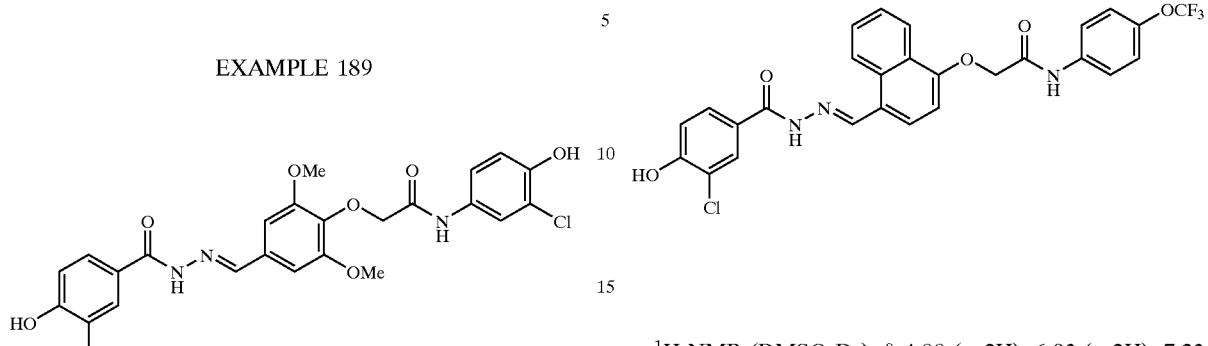
¹H NMR (DMSO-D₆): δ 3.88 (s, 6H), 4.75 (s, 2H), 6.93 (d, 1H), 7.08 (m, 3H), 7.34 (dd, 1H), 7.74 (dd, 1H), 7.79 (d, 1H), 7.95 (s, 1H), 8.37 (s, 1H), 9.74 (s, 1H), 10.03 (m, 1H), 10.96 (brd s, 1H), 11.76 (brd s, 1H); MS (APCI): 534.4, 536.2.
EXAMPLE 190
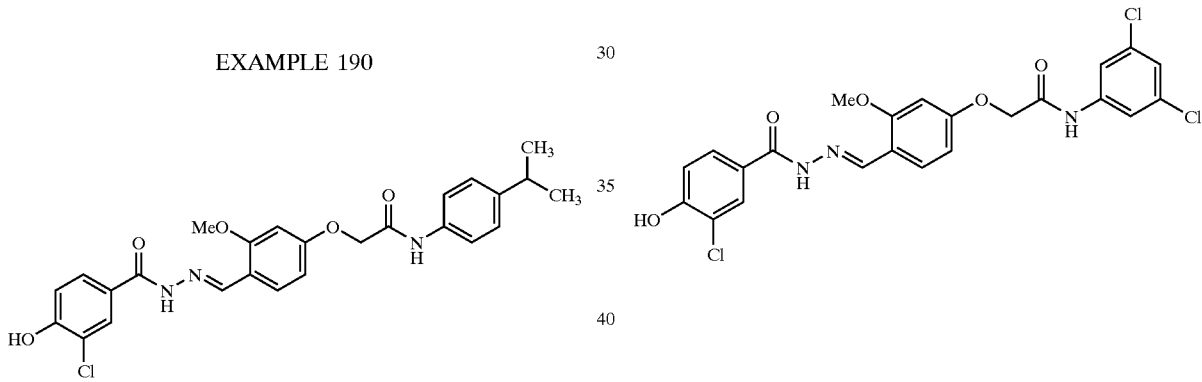
¹H NMR (DMSO-D₆): δ 1.18 (d, 6H), 2.85 (m, 1H), 3.87 (s, 3H), 4.76 (s, 2H), 6.71 (d, 1H), 6.78 (d, 1H), 7.06 (d, 1H), 7.20 (d, 2H), 7.58 (d, 2H), 7.78 (dd, 1H), 7.82 (d, 1H), 7.99 (d, 1H), 8.70 (s, 1H), 10.04 (s, 1H), 10.92 (brd s, 1H), 11.62 (brd s, 1H); MS (APCI): 496.5, 498.2.
EXAMPLE 191
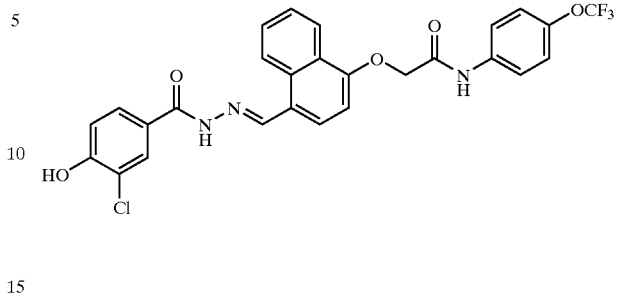
¹H NMR (DMSO-D₆): δ 4.88 (s, 2H), 6.93 (t, 2H), 7.23 (d, 2H), 7.47–7.70 (m, 6H), 7.86 (d, 1H), 8.30 (d, 1H), 8.80 (s, 1H), 8.87 (d, 1H), 10.34 (s, 1H), 10.82 (brd s, 1H), 11.55 (brd s, 1H); MS (APCI): 558.5, 560.0.
EXAMPLE 192
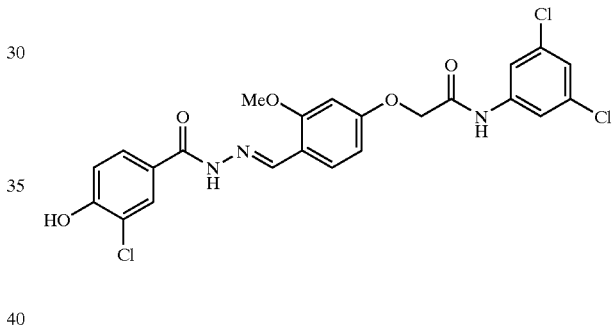
¹H NMR (DMSO-D₆): δ 4.06 (s, 3H), 4.94 (s, 2H), 6.81 (d, 1H), 6.89 (s, 1H), 7.19 (d, 1H), 7.45 (s, 1H), 7.90 (m, 3H), 8.10 (s, 1H), 8.82 (s, 1H), 10.62 (s, 1H), 11.07 (brd s, 1H), 11.75 (s, 1H); MS (APCI): 523.3, 524.8, 526.6.
EXAMPLE 193
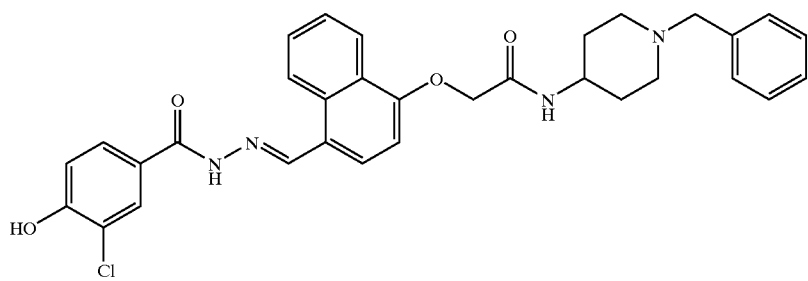

¹H NMR (DMSO-D₆): δ 1.68 (m, 2H), 2.01 (m, 2H), 3.05 (m, 2H), 3.35 (m, 2H), 3.86 (m, 1H), 4.26 (s, 2H), 4.81 (s, 2H), 6.95 (d, 1H), 7.09 (d, 1H), 7.46 (s, 5H), 7.59 (m, 1H), 7.66 (t, 1H), 7.77 (d, 1H), 7.98 (d, 1H), 8.34 (d, 1H), 8.41 (d, 1H), 8.92 (m, 2H), 9.65 (brd s, 1H), 11.02 (brd s, 1H), 11.80 (brd s, 1H); MS (APCI): 571.3, 572.3, 573.3.
EXAMPLE 194
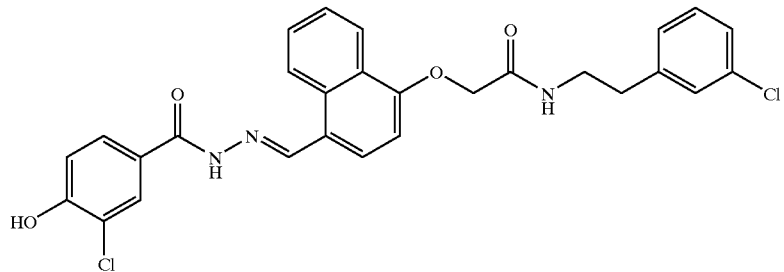
¹H NMR (DMSO-D₆): δ 2.79 (t, 2H), 3.43 (qt, 2H), 4.71 (s, 2H), 6.95 (d, 1H), 7.08 (d, 1H), 7.17 (m, 1H), 7.26–7.30 (m, 3H), 7.61 (t, 1H), 7.67 (t, 1H), 7.76 (m, 2H), 7.99 (d, 1H), 8.24 (t, 1H), 8.38 (d, 1H), 8.91 (s, 1H), 8.98 (d, 1H), 10.94 (s, 1H), 11.67 (s, 1H); MS (APCI): 536.3, 538.2, 539.1.
EXAMPLE 195
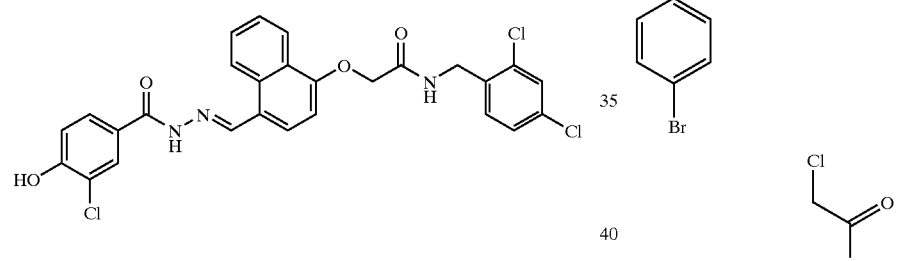
¹H NMR (DMSO-D₆): δ 4.42 (d, 2H), 4.87 (s, 2H), 7.06 (m, 2H), 7.38 (d, 2H), 7.60 (t, 1H), 7.63 (m, 1H), 7.80 (t, 1H), 7.99 (d, 1H), 8.49 (d, 1H), 8.79 (t, 1HJ), 8.93 (s, 1H), 8.98 (d, 1H), 10.95 (s, 1H), 11.68 (s, 1H); MS (APCI): 558.2, 560.1.
EXAMPLE 196
4-(4-Bromophenyl-3,4-dihydropiperadinylacetamideoxy)naphth-1-yl methylene-3-chloro-4-hydroxybenzoic Acid Hydrazone
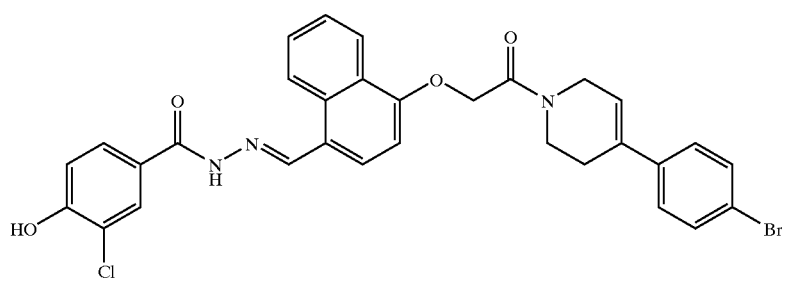
Reaction scheme:

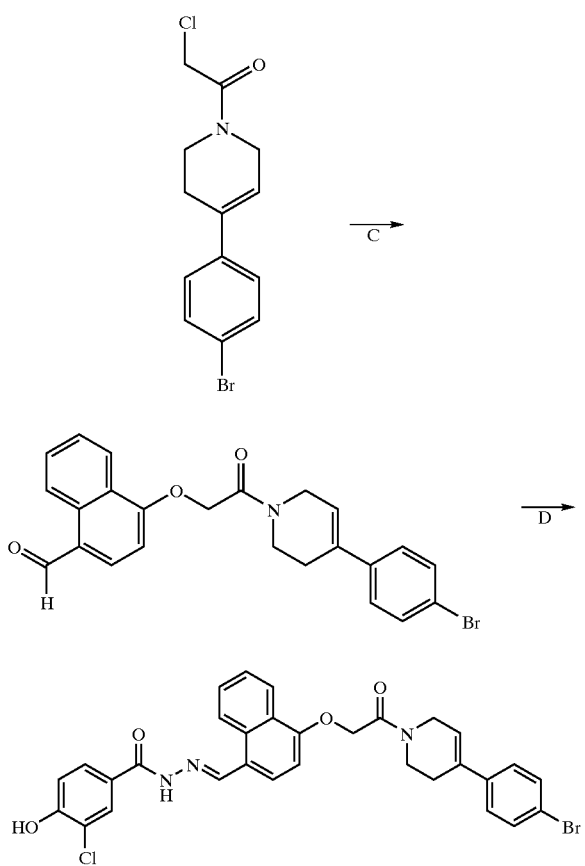

4-(4-Bromophenyl)-4-pipendinol Choroacetamide (Step A):

To a solution of 4-(4-bromophenyl)-4-piperidinol (5 g, 19.5 mmol) and diisopropylethylamine (2.8 g, 21.5 mmol) in DMF (30 mL) was added dropwise chloroacetylchloride (2.2 g, 21.5 mmol). After stirring the mixture for one hour, the mixture was diluted with ethyl acetate and washed with aqueous sodium bicarbonate (2x), 1 N HCl (3x), water, brine, and dried over MgSO$_4$. The solution was concentrated and chromatographed over silica gel with ethyl acetate to give the product as a brown solid (4 g, 62%).

$^1$H NMR (DMSO-D$_6$): δ 1.21 (d, 2H), 1.71 (t, 1H), 1.96 (t, 1H), 2.71 (t, 1H), 3.37 (t, 1H), 3.70 (d, 1H), 4.27 (d, 1H), 4.54 (s, 2H), 5.26 (s, 1H), 7.42 (d, 2H), 7.51 (d, 2H).

4-(4-Bromophenyl)-3,4-dihydropiperidine Chloroacetamide (Step B):

To a solution of 4-(4-bromophenyl)-4-piperidinol chloroacetamide (4 g, 12 mmol) and diisopropylethylamine (4.6 mL, 26 mmol) in THF (40 mL) cooled in an ice-bath was added methanesulfonyl chloride (2 mL, 26 mmol) and the mixture was refluxed for 16 hours under a nitrogen blanket. The reaction mixture was diluted with ethyl acetate and washed with 1 N HCl (2x), aqueous NaHCO$_3$ (2x), brine (2x), and dried over MgSO$_4$. The solvent was evaporated and the product was chromotographed over silica gel with ethyl acetate/hexane (4/6). The product was obtained as a yellow solid (1.5 g, 32%).

$^1$H NMR (DMSO-D$_6$): δ 2.44 (t, 2H), 3.62 (m, 2H), 4.14 (dd, 2H), 4.42 (d, 2H), 6.21 (s, 1H), 7.36 (m, 2H), 7.51 (d, 2H).

4(-4-Bromophenyl-3,4-dihydropiperadinylacetamideoxy) naphthaldehyde (Step C):

A mixture of 4-(4-bromophenyl)-3,4-dihydropiperidine chloroacetamide (1.5 g, 4.8 mmol) 4-hydroxynapthaldehyde (1.2 g , 7 mmol), and powdered potassium carbonate (1 g, 7.2 mmol) in acetonitrile (50 mL) was refluxed for 16 hours. The mixture was diluted with ethyl acetate and washed with brine (3x), dried over MgSO$_4$, and concentrated. Silica gel chromatography with ethyl acetate/hexane (1/1) provided the product (1.4 g, 65%).

$^1$H NMR (DMSO-D$_6$): δ 2.27–2.32 (m, 2H), 3.49–3.55 (m, 2H), 3.94 (brd s, 1H), 4.06 (brd s, 1H), 5.08 (s, 1H), 5.13 (s, 1H), 6.05 (s, 1H), 6.97 (t, 1H), 7.20 (t, 1H), 7.34 (d, 2H), 7.42–7.47 (m, 1H), 7.52–7.57 (m, 1H), 7.92 (d, 1H), 8.16 (d, 1H), 9.01 (d, 1H), 9.97 (s, 1H).

4(-4-Bromophenyl-3,4-dihydropiperadinylacetamideoxy) naphth-1-yl Methylene-3-chloro-4-hydroxybenzoic Acid Hydrazone (Step D):

The title compound was prepared according to the general procedure for the synthesis of alkylidene hydrazides from the condensation of 3-chloro-4-hydroxybenzoic acid hydrazide and 4-(4-bromophenyl-3,4-dihydropiperadinylacetamideoxy)naphthaldehyde:

$^1$H NMR (DMSO-D$_6$): δ 2.47–2.58 (m, 2H), 3.72 (br s, 2H), 4.13 (s, 1H), 4.26 (s, 1H), 5.14 (s, 1H), 5.18 (s, 1H), 6.23 (s, 1H), 6.50–6.53 (m, 1H), 7.03–7.06 (m, 1H), 7.35–7.38 (m, 2H), 7.52 (d, 2H), 7.58 (d, 2H), 7.59–7.67 (m, 1H), 7.75 (d, 1H), 7.84 (s, 1H), 8.32 (d, 1H), 8.89 (s, 1H), 8.92 (s, 1H), 11.41 (s, 1H); MS (APCI): 618.1, 620.1, 621.1, 622.1.

EXAMPLE 197:

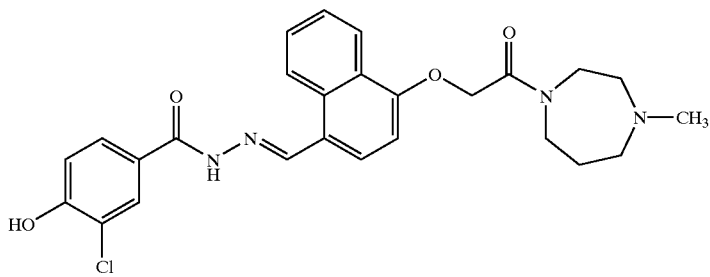

EXAMPLE 198:
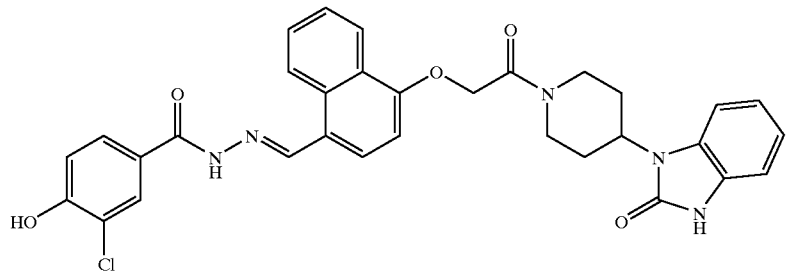
EXAMPLE 199:
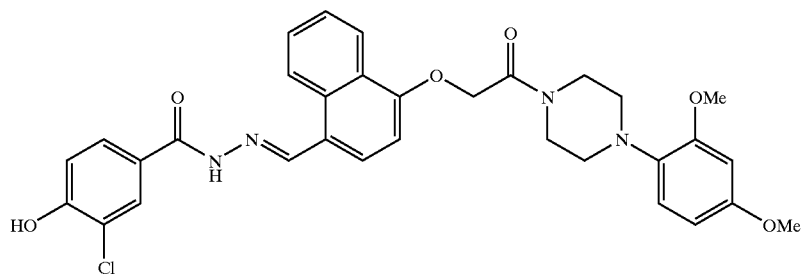
EXAMPLE 200:
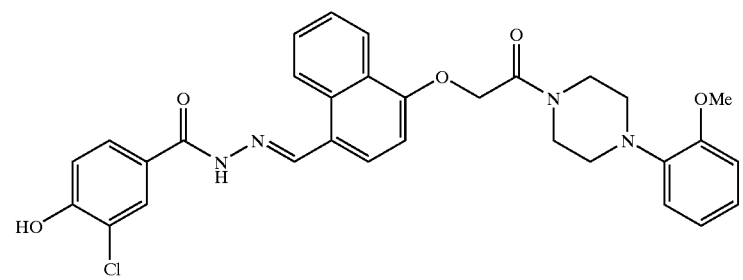
EXAMPLE 201:
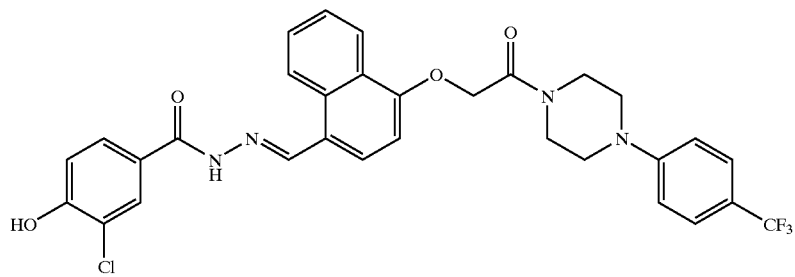
EXAMPLE 202:
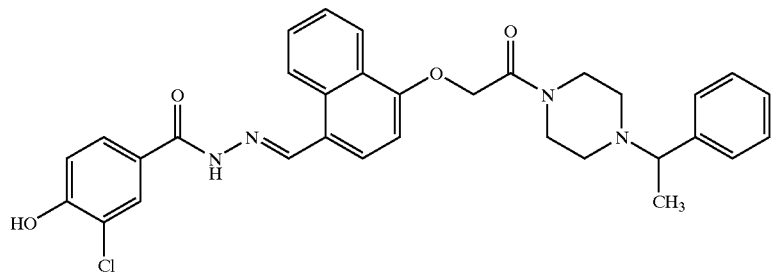

EXAMPLE 203:
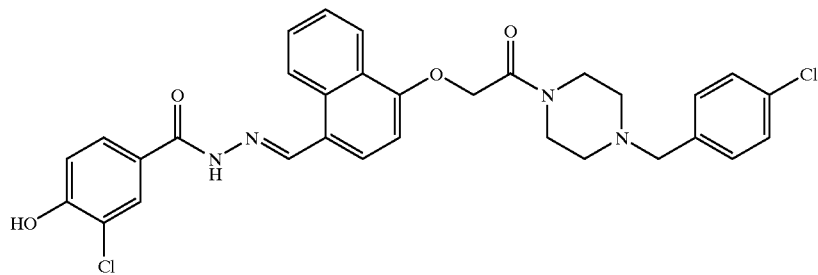
EXAMPLE 204:
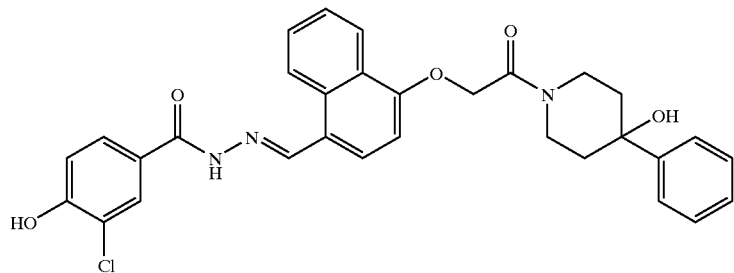
EXAMPLE 205:
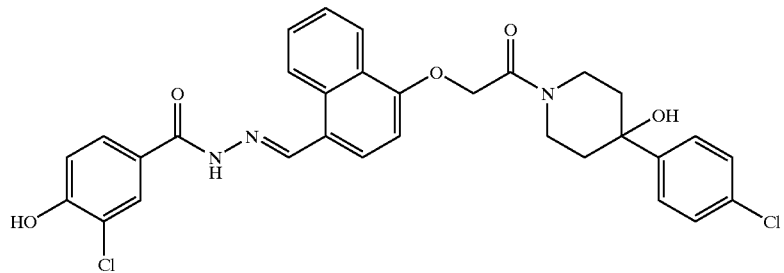
EXAMPLE 206:
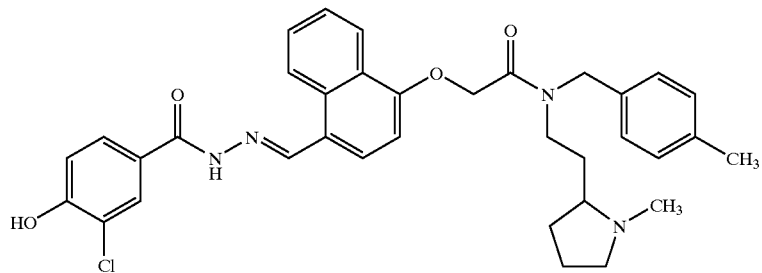
EXAMPLE 207:
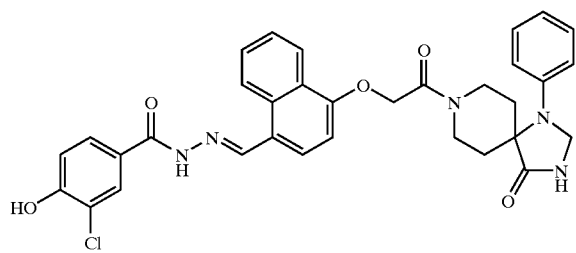
EXAMPLE 208:
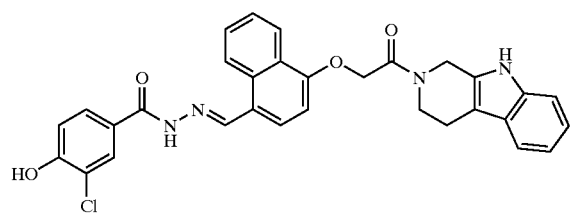

EXAMPLE 209:
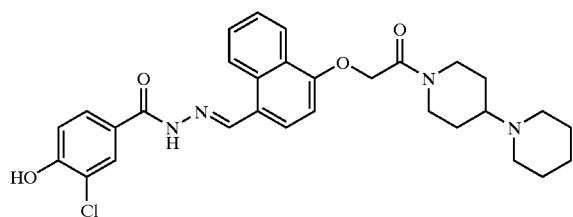
EXAMPLE 210:
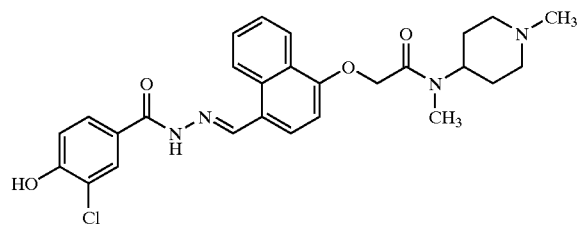
EXAMPLE 211:
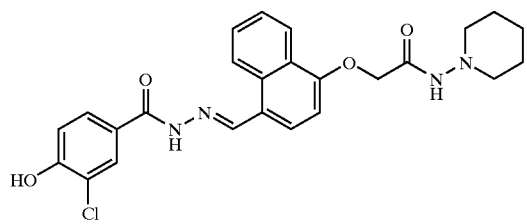
EXAMPLE 212:
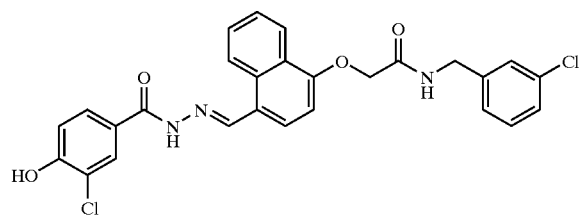
EXAMPLE 213:
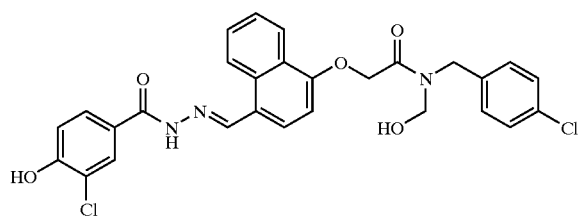
EXAMPLE 214:
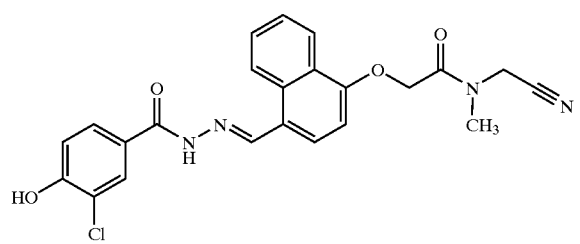
EXAMPLE 215:
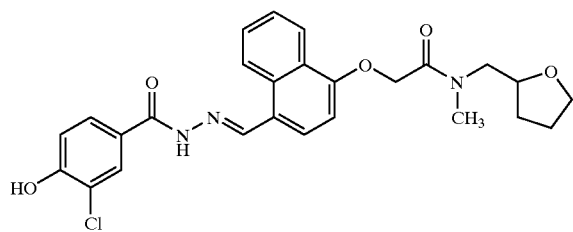
EXAMPLE 216:
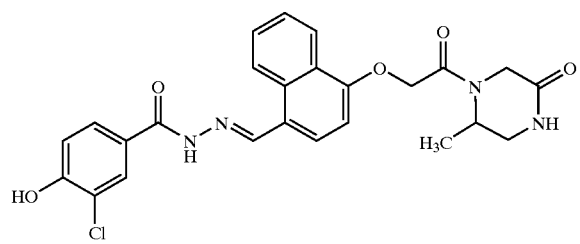
EXAMPLE 217:
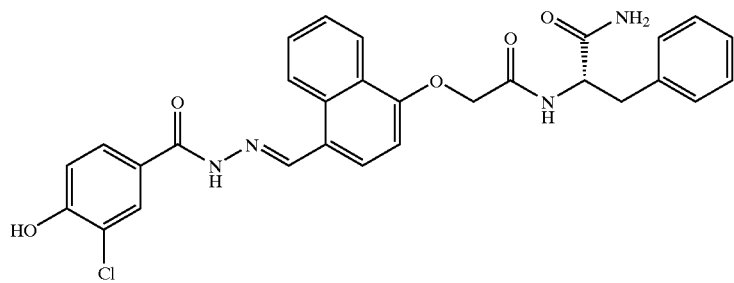

EXAMPLE 218:
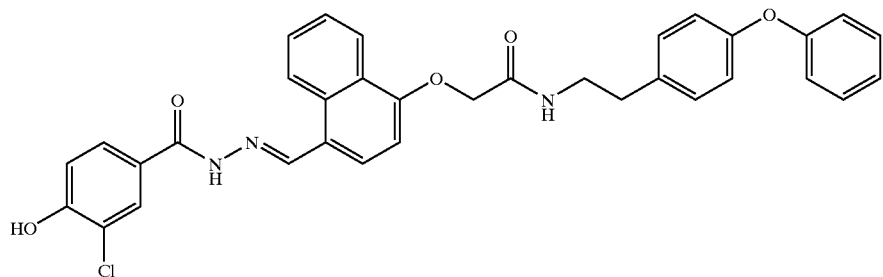
EXAMPLE 219:
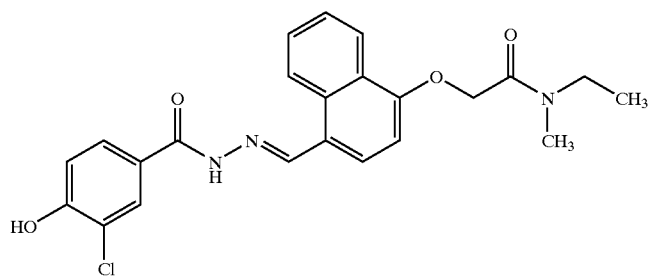
EXAMPLE 220:
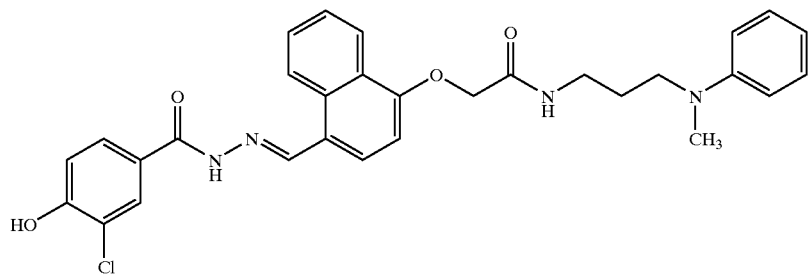
EXAMPLE 221:
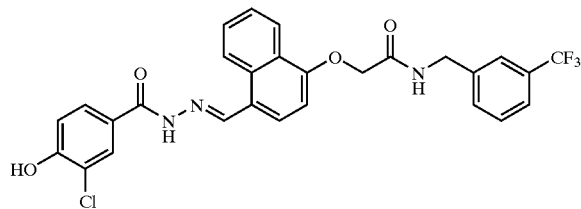
EXAMPLE 222:
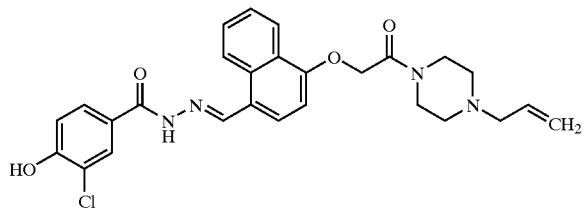
EXAMPLE 223:
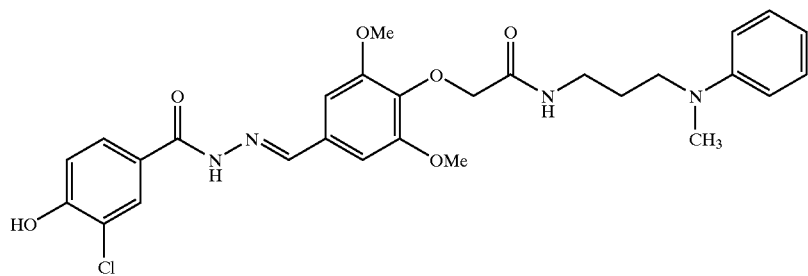

EXAMPLE 224:
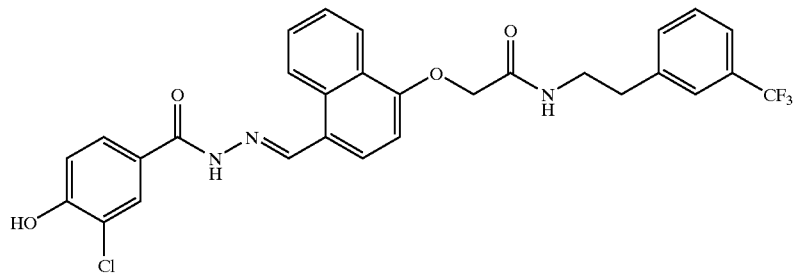
EXAMPLE 225:
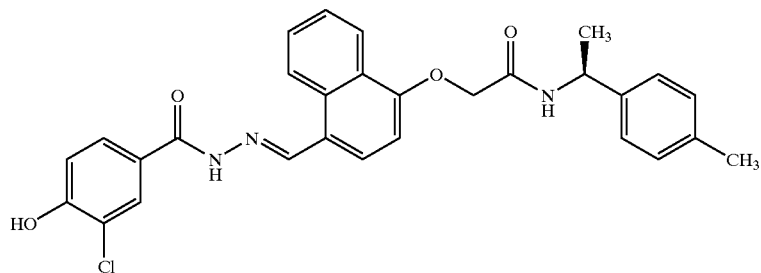
EXAMPLE 226:
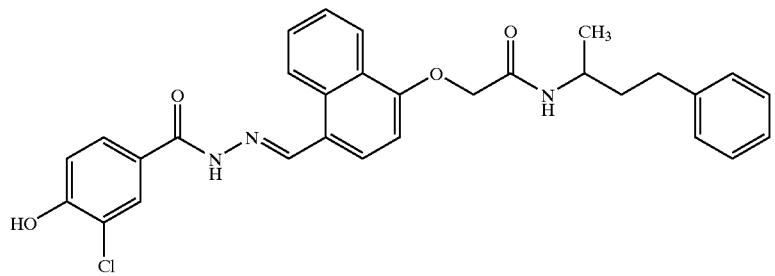
EXAMPLE 227:
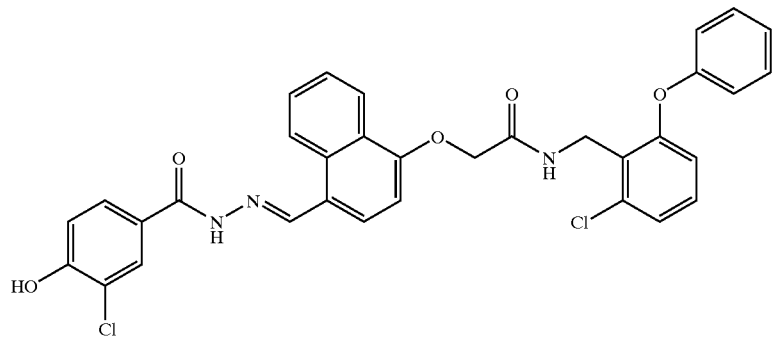
EXAMPLE 228:  EXAMPLE 229:
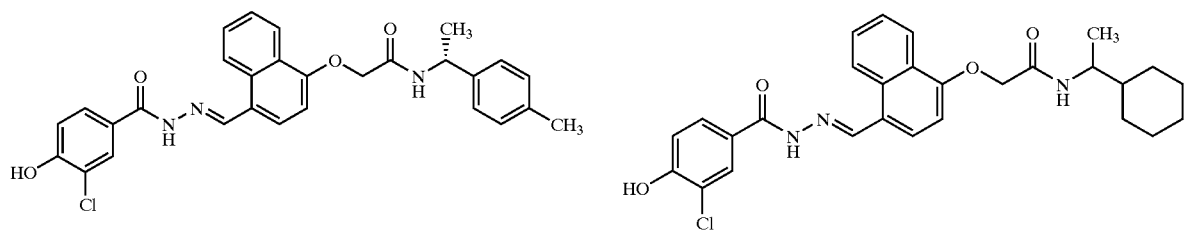

EXAMPLE 230:
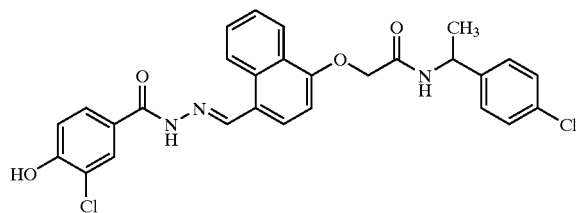
EXAMPLE 231:
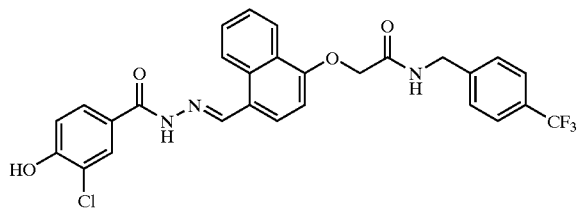
EXAMPLE 232:
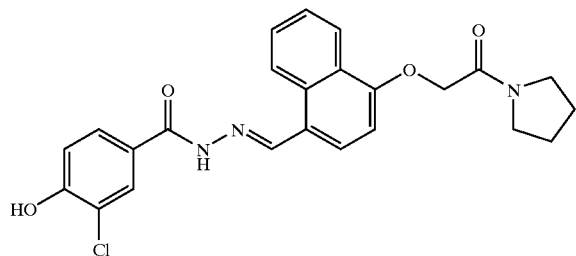
EXAMPLE 233:
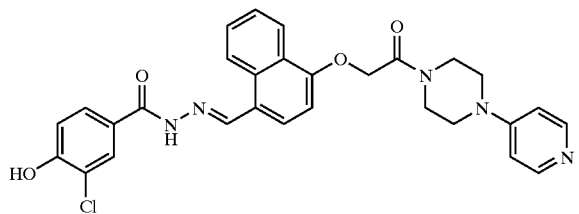
EXAMPLE 234:
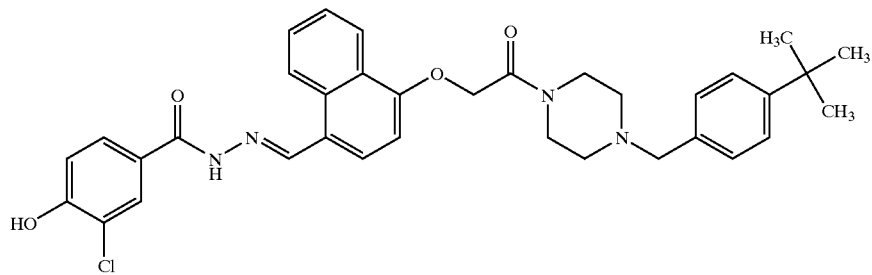
EXAMPLE 235:
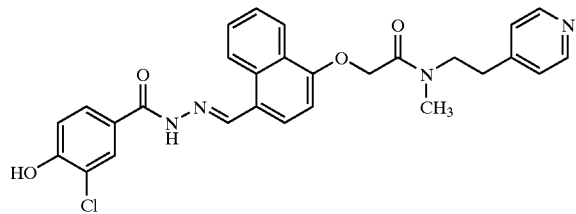
EXAMPLE 236:
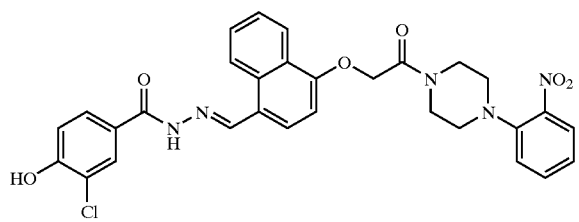
EXAMPLE 237:
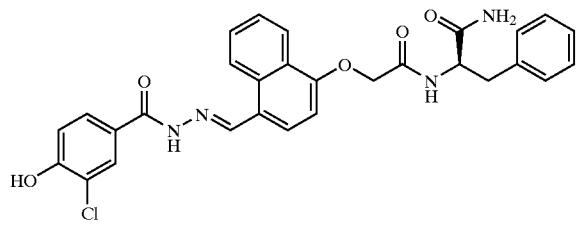
EXAMPLE 238:
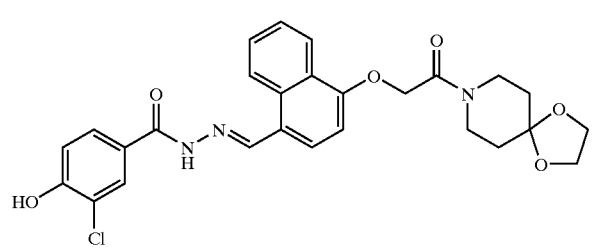

EXAMPLE 239:
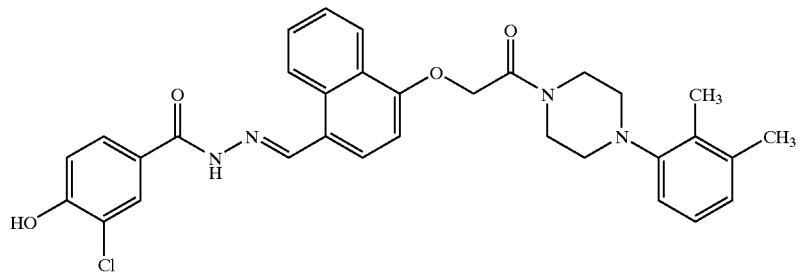
EXAMPLE 240:
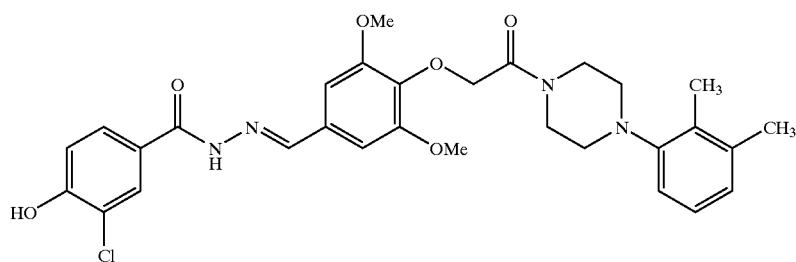
EXAMPLE 241:
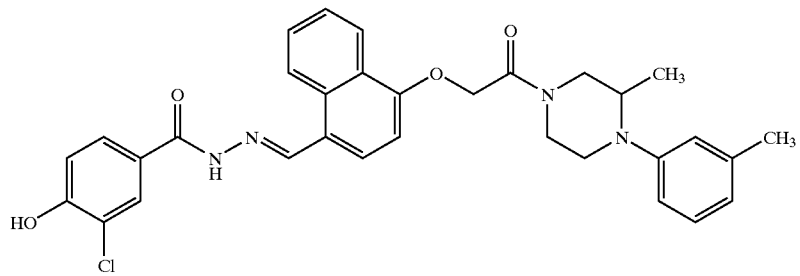
EXAMPLE 242:
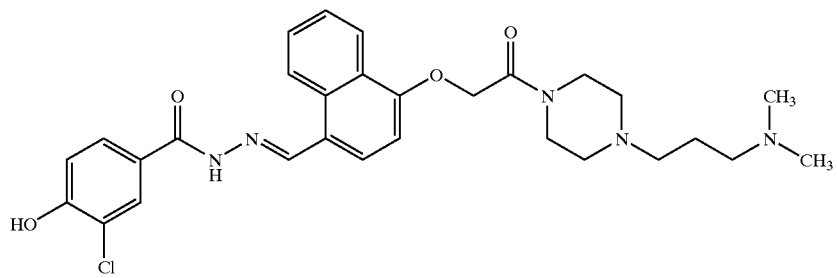
EXAMPLE 243:
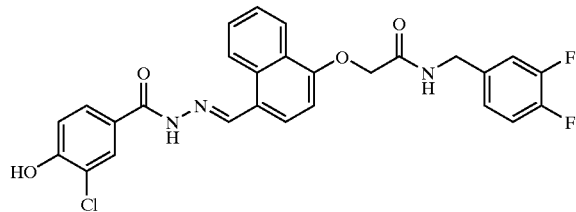
EXAMPLE 244:
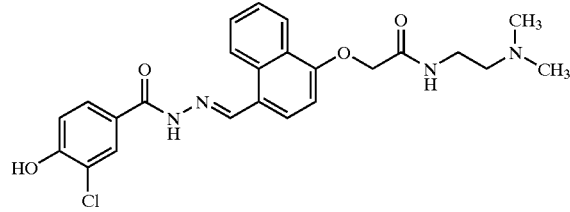

EXAMPLE 245:
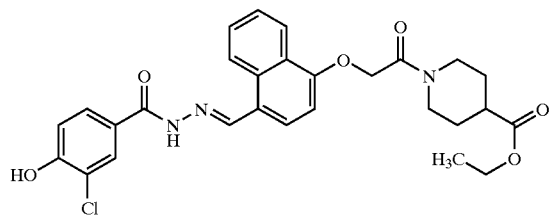
EXAMPLE 246:
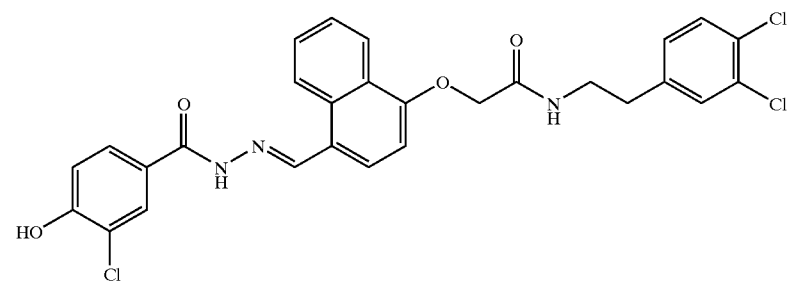
EXAMPLE 247:
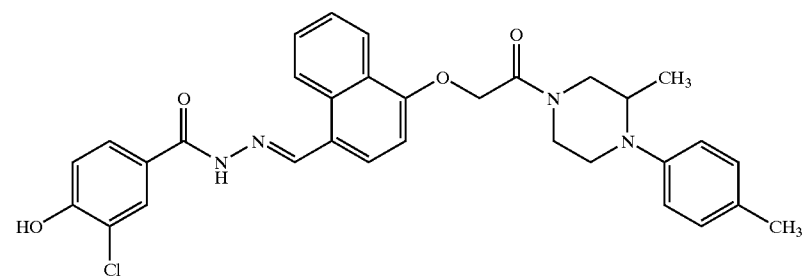
EXAMPLE 248:
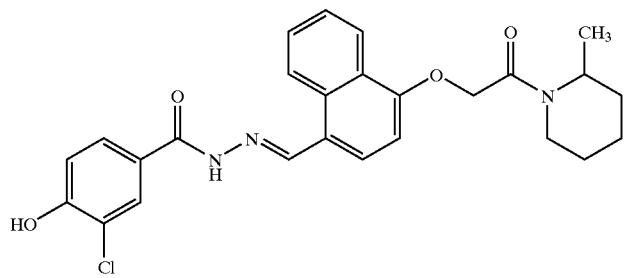
EXAMPLE 249:
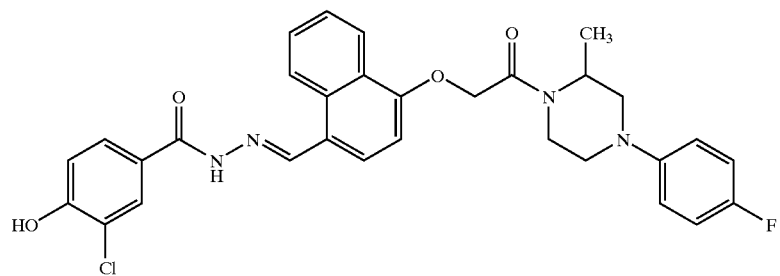

EXAMPLE 250:
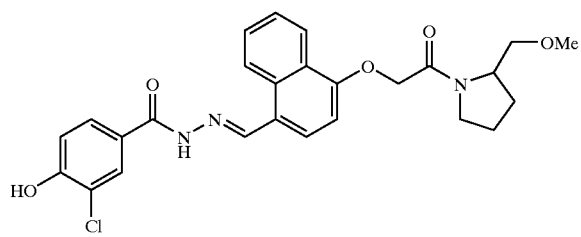
EXAMPLE 251:
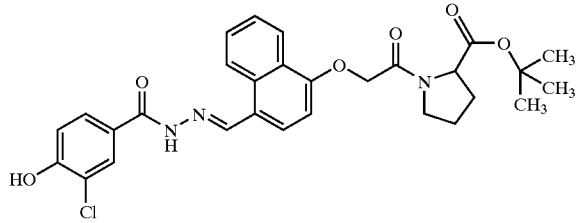
EXAMPLE 252:
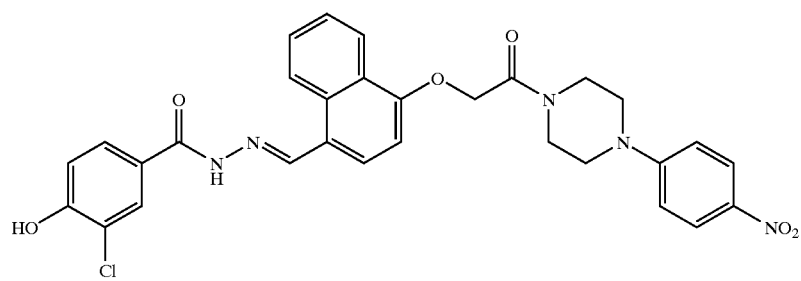
EXAMPLE 253:
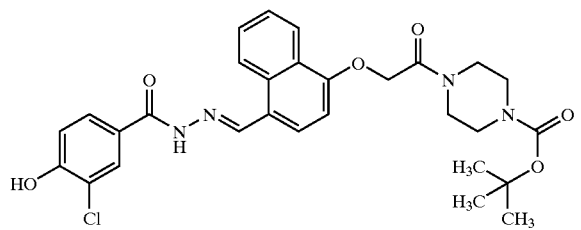
EXAMPLE 254:
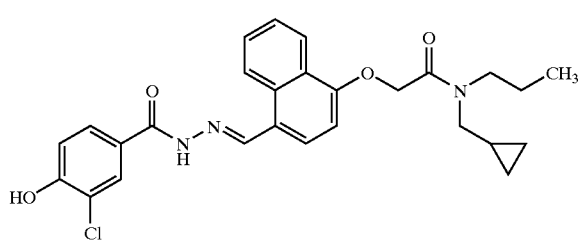
EXAMPLE 255:
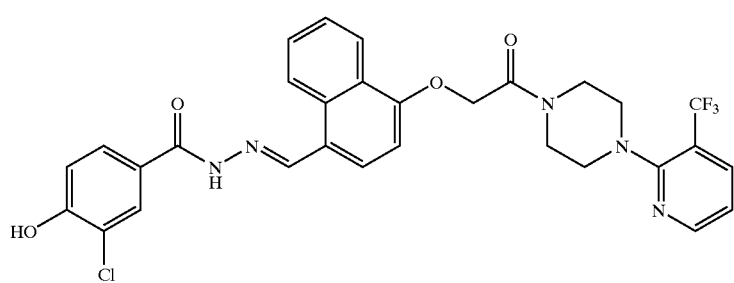
EXAMPLE 256:
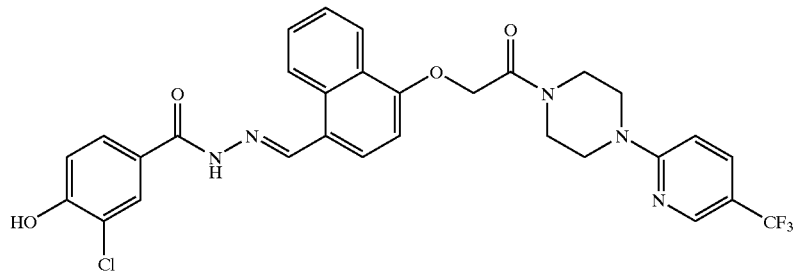

EXAMPLE 257:
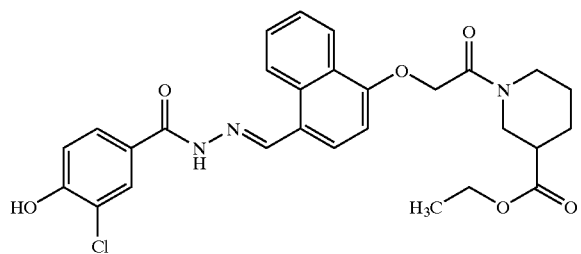
EXAMPLE 258:
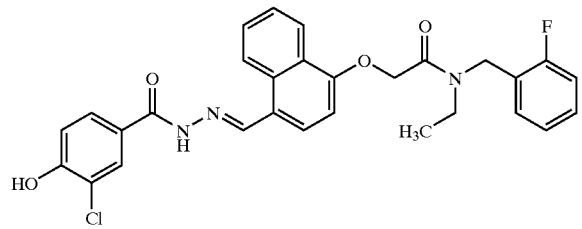
EXAMPLE 259:
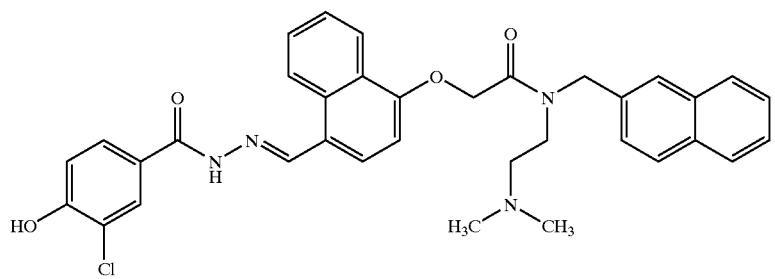
EXAMPLE 260:
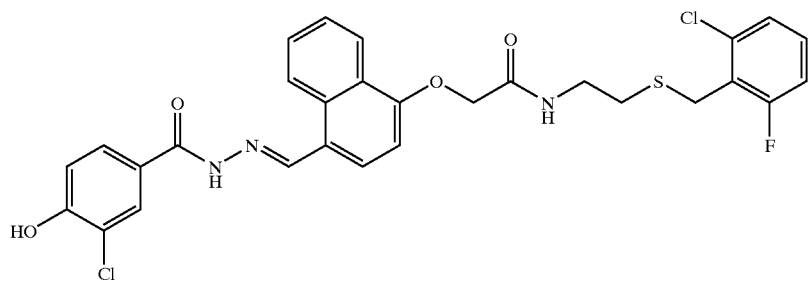
EXAMPLE 261:
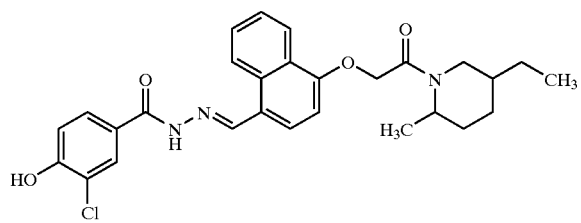
EXAMPLE 262:
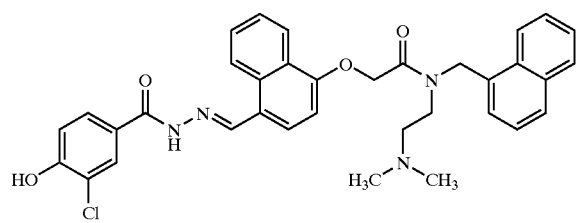
EXAMPLE 263:
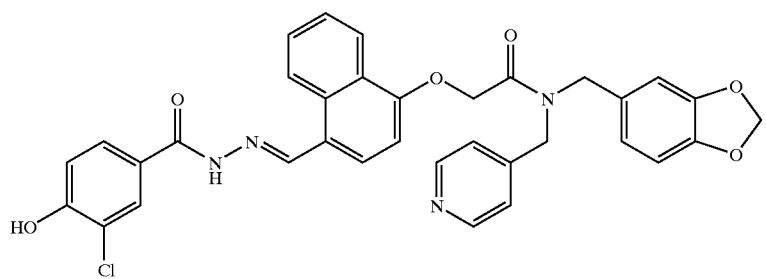

EXAMPLE 264:
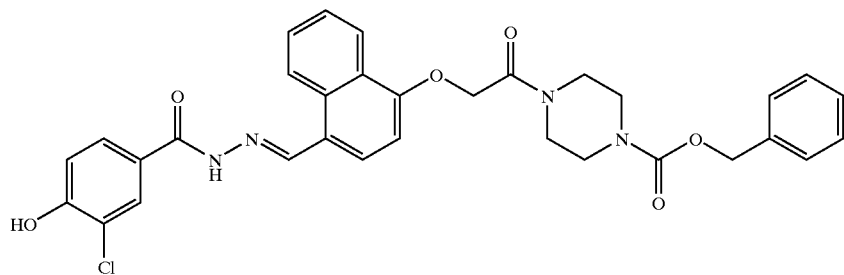
EXAMPLE 265:
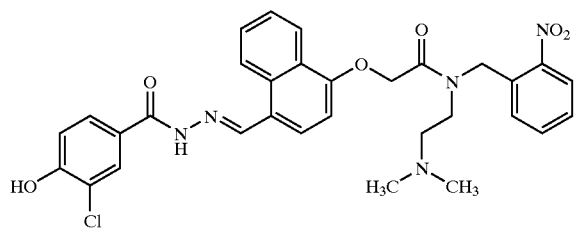
EXAMPLE 266:
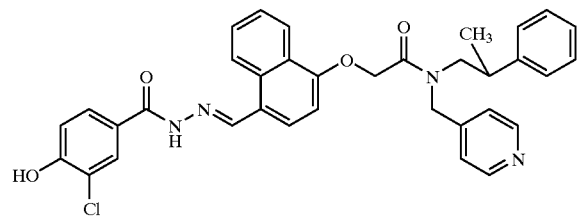
EXAMPLE 267:
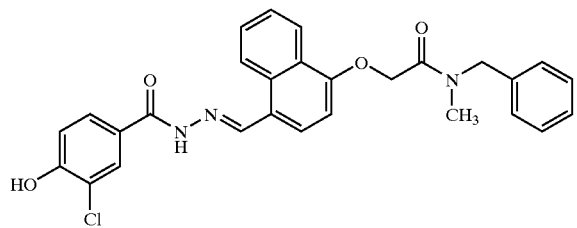
EXAMPLE 268:
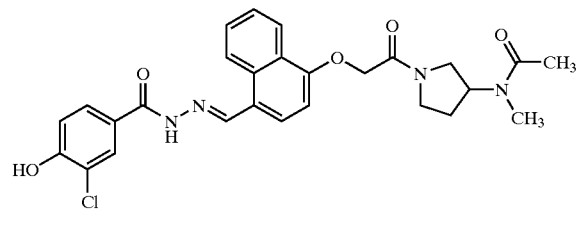
EXAMPLE 269:
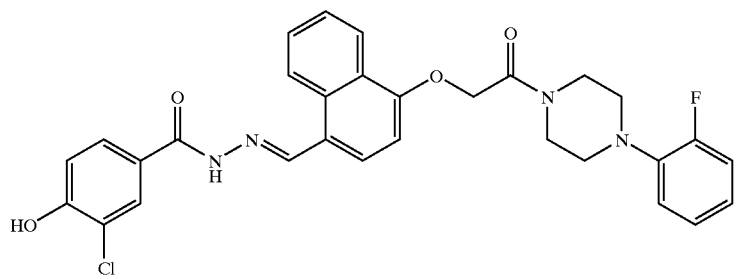
EXAMPLE 270:
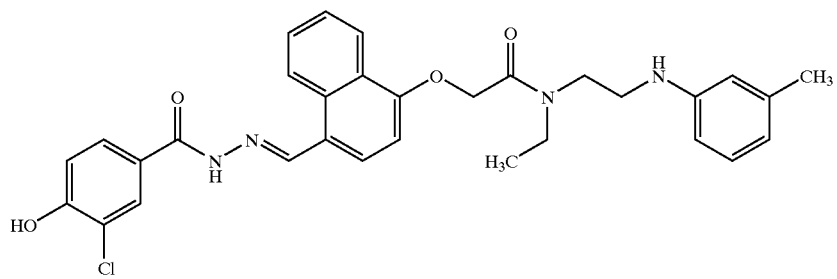

EXAMPLE 271:
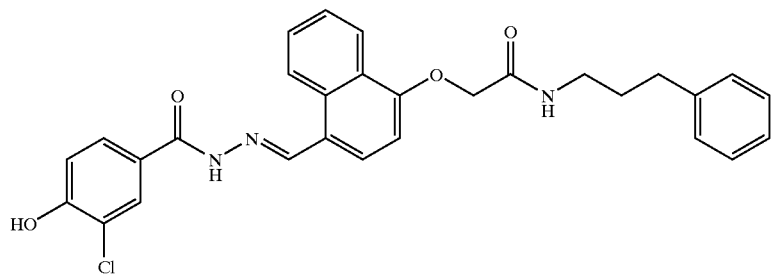
EXAMPLE 272:
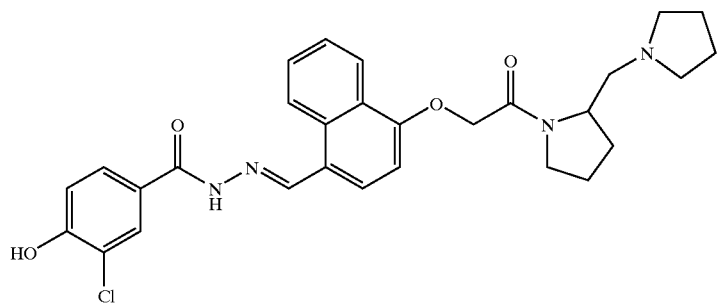
EXAMPLE 273:
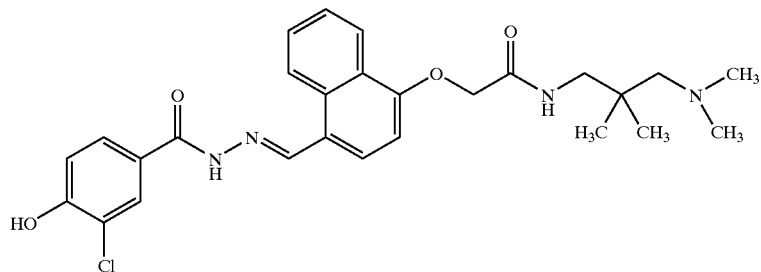
EXAMPLE 274:
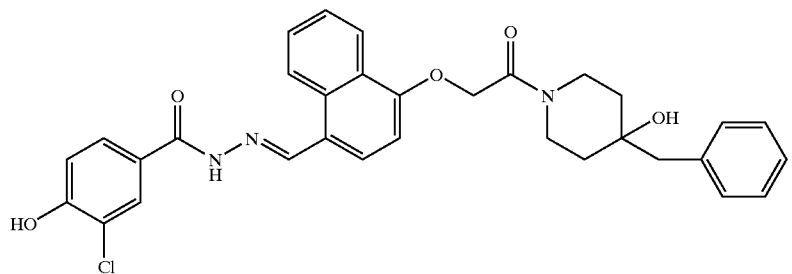
EXAMPLE 275:
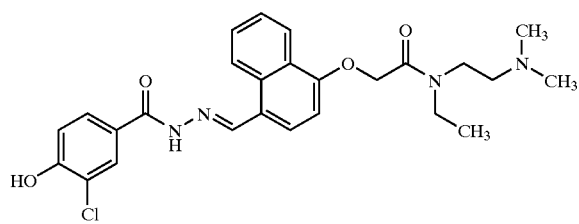
EXAMPLE 276:
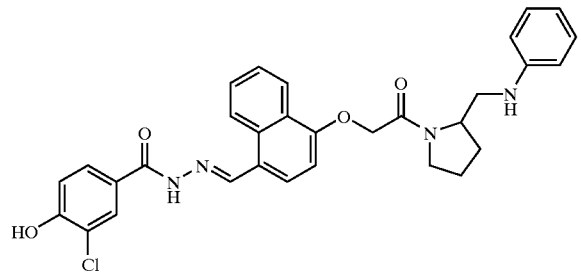

EXAMPLE 277:
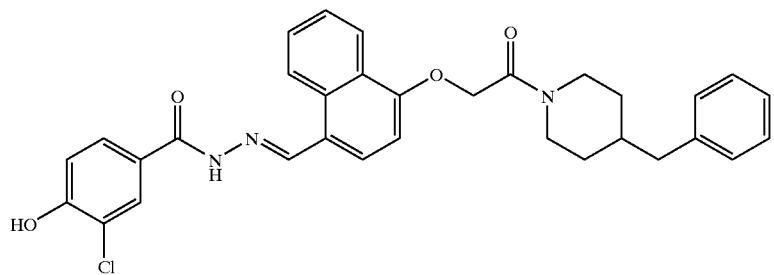
EXAMPLE 278:
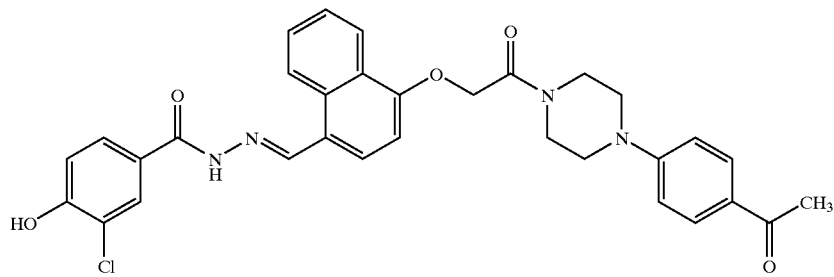
EXAMPLE 279:
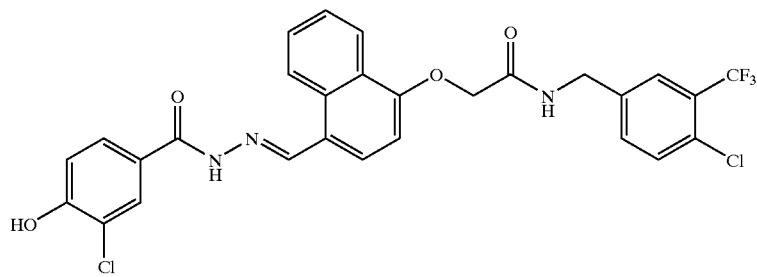
EXAMPLE 280:                                                EXAMPLE 281:
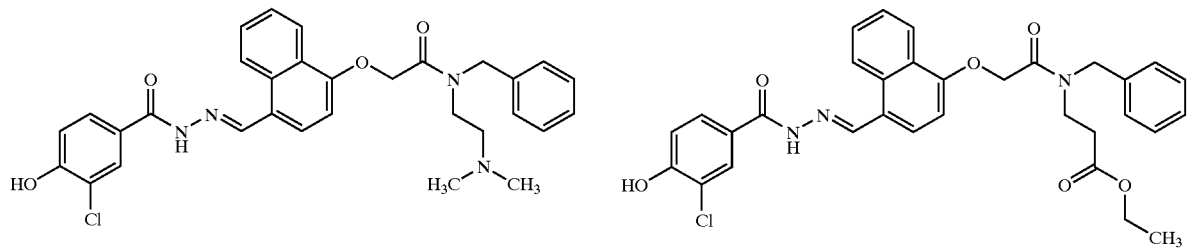
EXAMPLE 282:
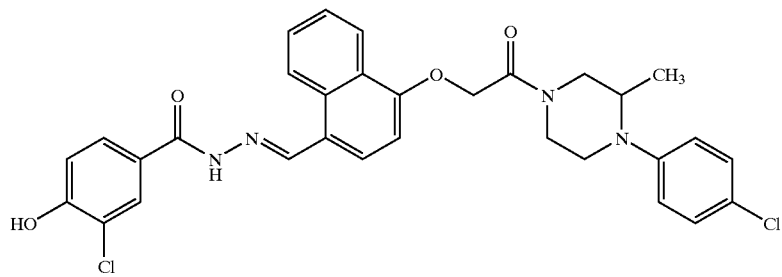

EXAMPLE 283:
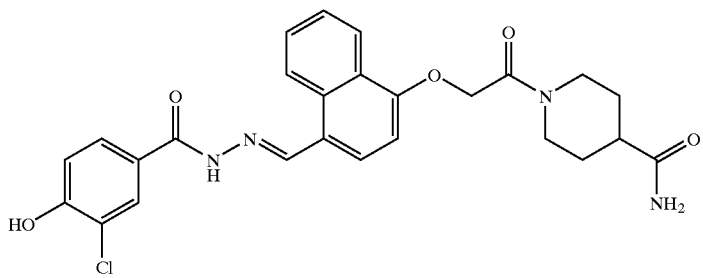
EXAMPLE 284:
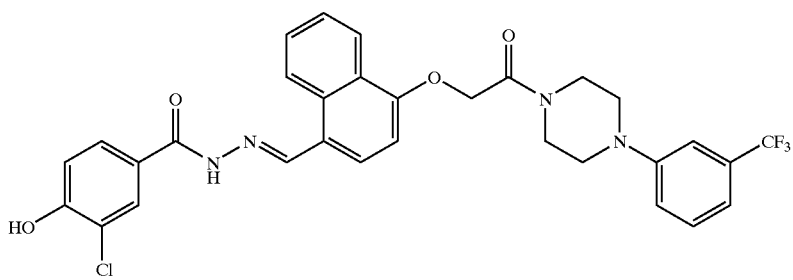
EXAMPLE 285:
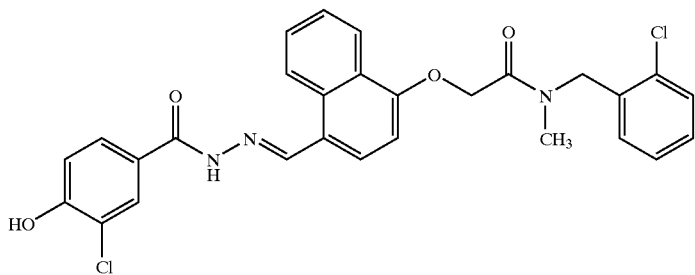
EXAMPLE 286:
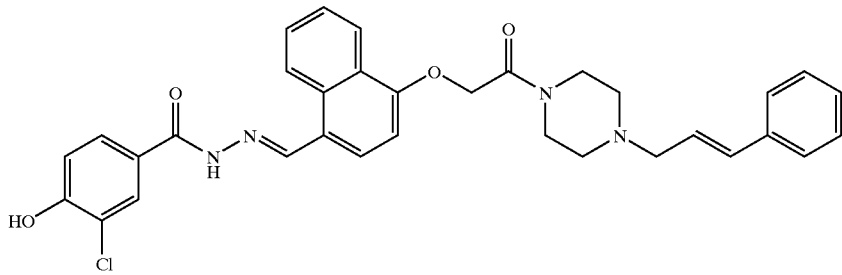
EXAMPLE 287:
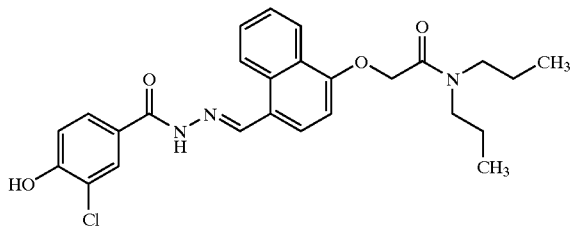
EXAMPLE 288:
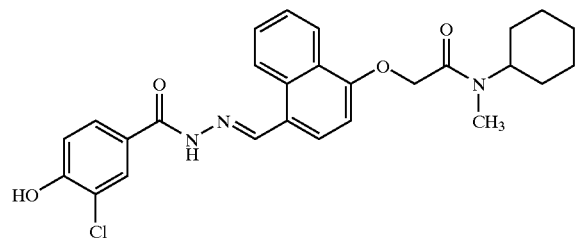

EXAMPLE 289:
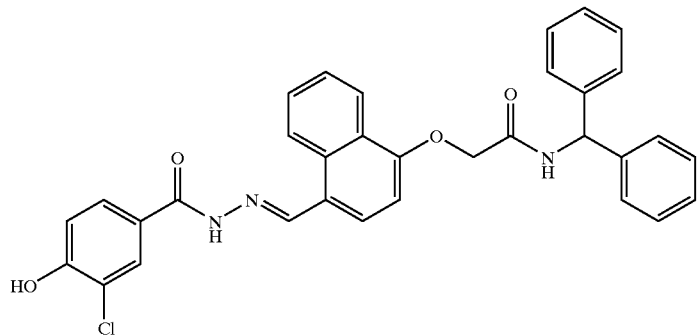
EXAMPLE 290:
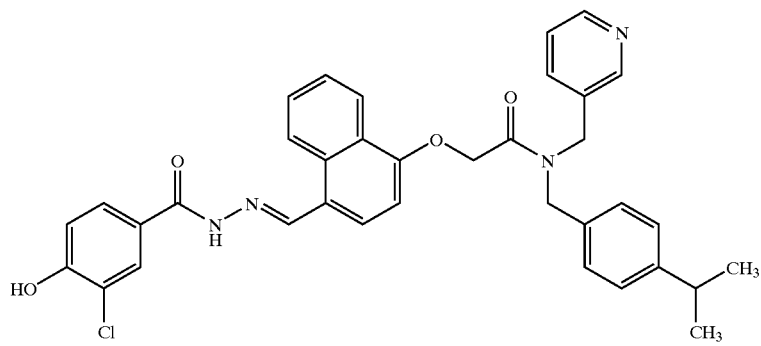
EXAMPLE 291:
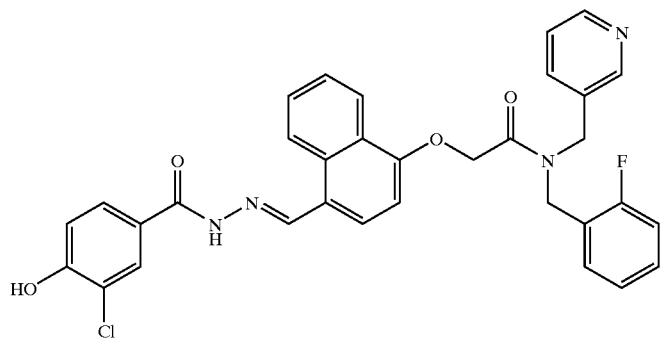
EXAMPLE 292:
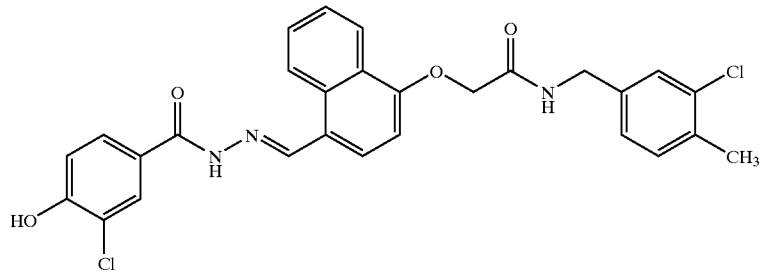

EXAMPLE 293:
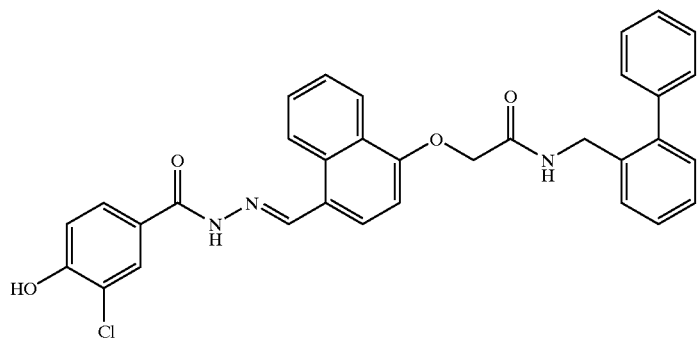
EXAMPLE 294:
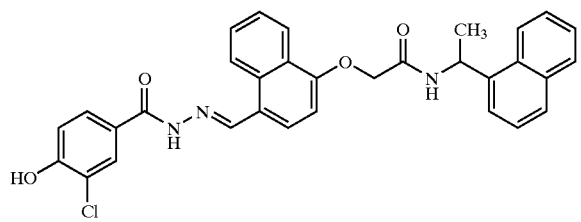
EXAMPLE 295:
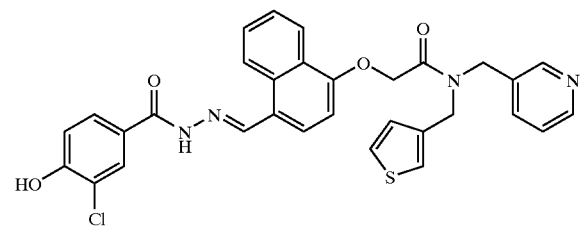
EXAMPLE 296:
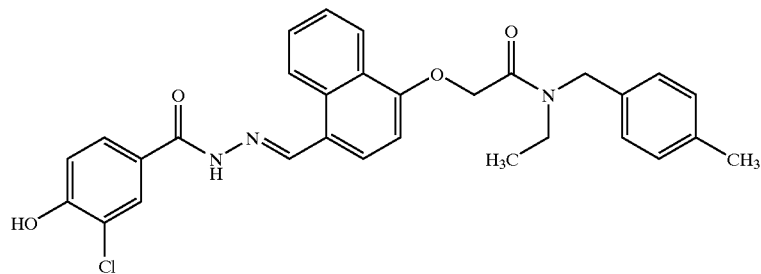
EXAMPLE 297:
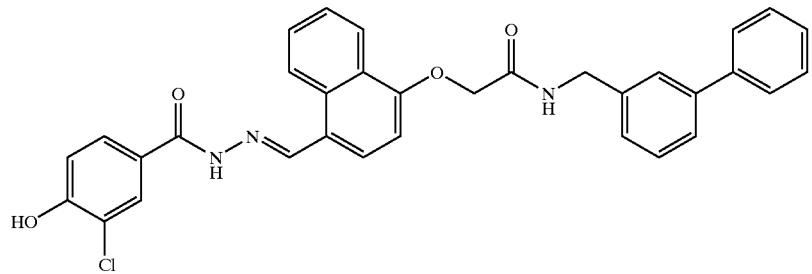
EXAMPLE 298:
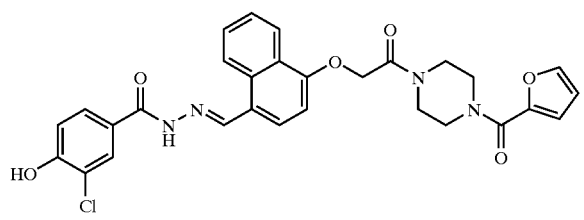
EXAMPLE 299:
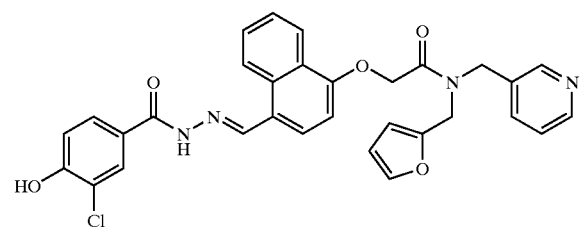

EXAMPLE 300:
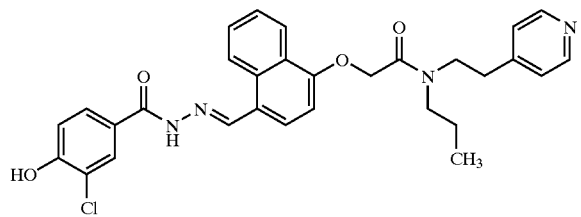
EXAMPLE 301:
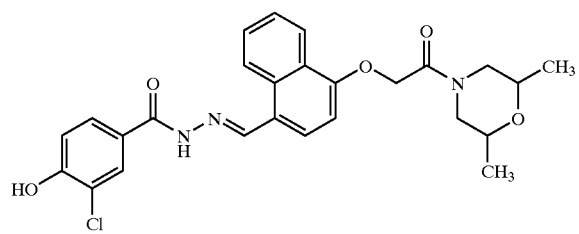
EXAMPLE 302:
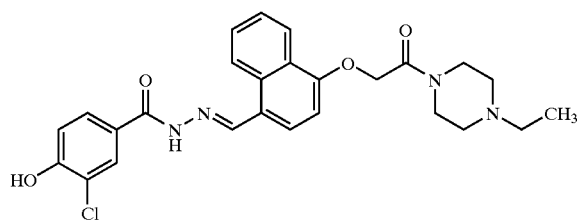
EXAMPLE 303:
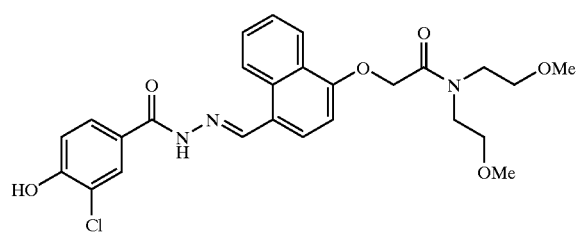
EXAMPLE 304:
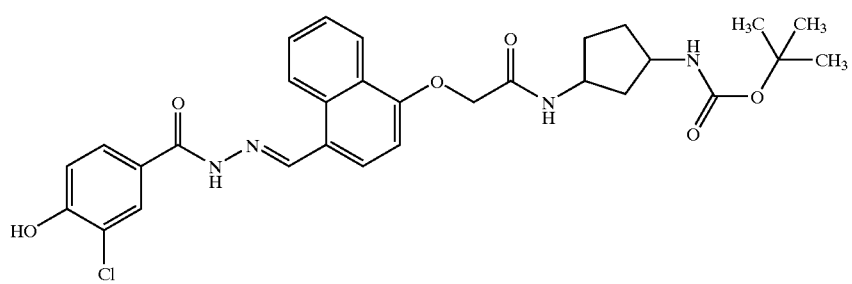
EXAMPLE 305:
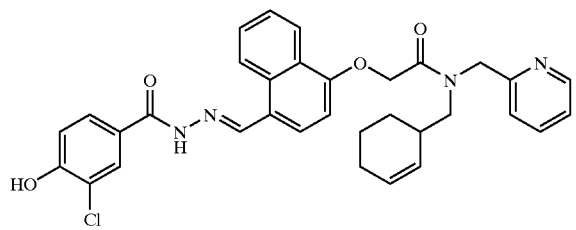
EXAMPLE 306:
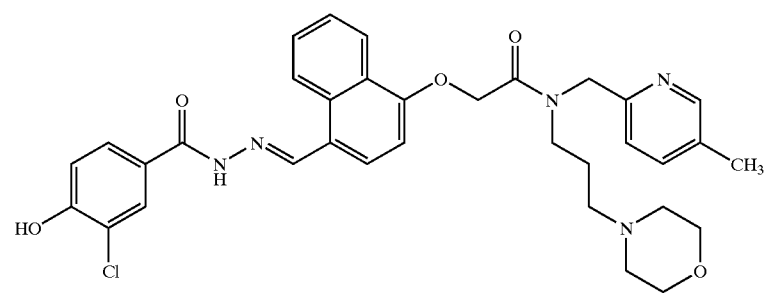

EXAMPLE 307:
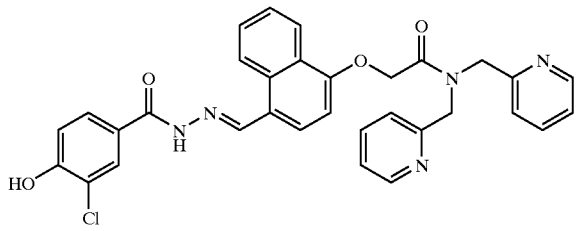
EXAMPLE 308:
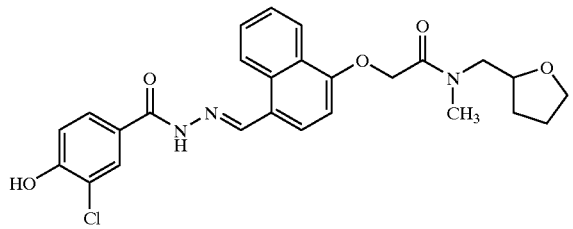
EXAMPLE 309:
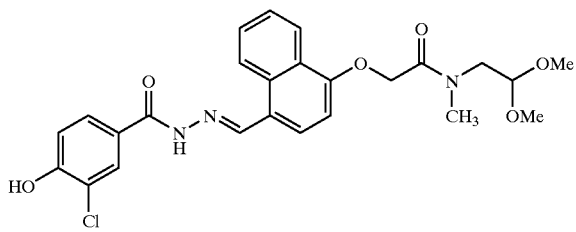
EXAMPLE 310:
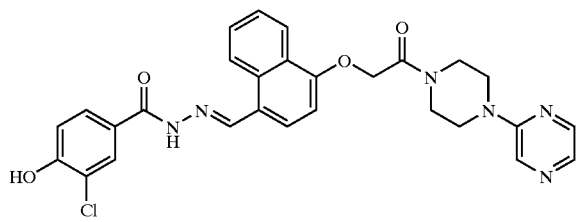
EXAMPLE 311:
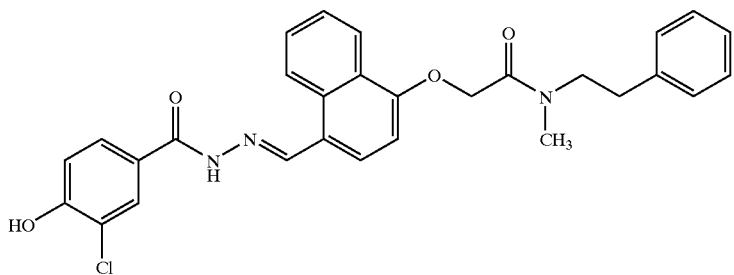
EXAMPLE 312:
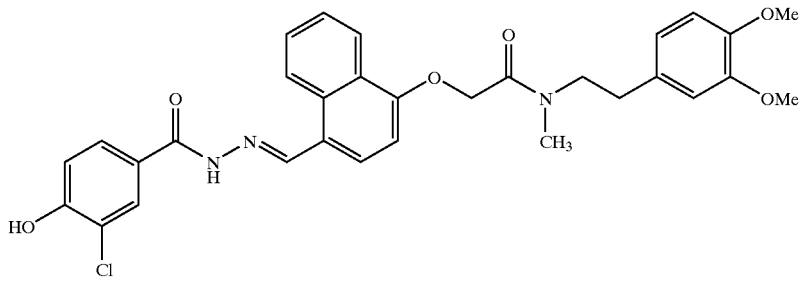
EXAMPLE 313:
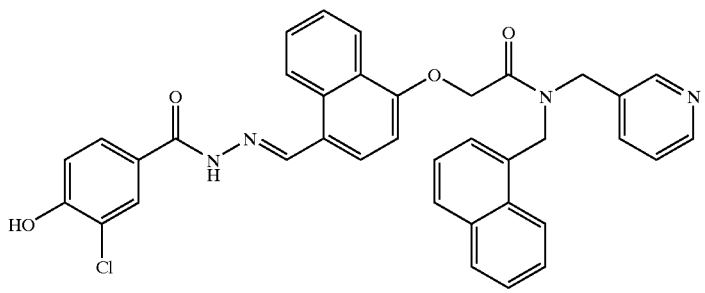

EXAMPLE 314:
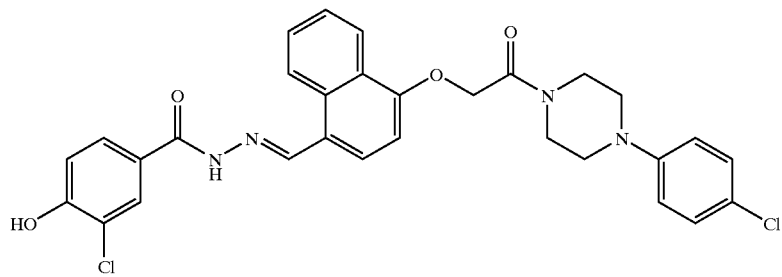
EXAMPLE 315:
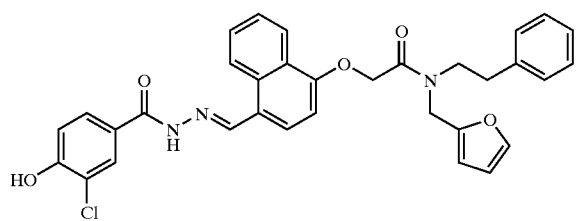
EXAMPLE 316:
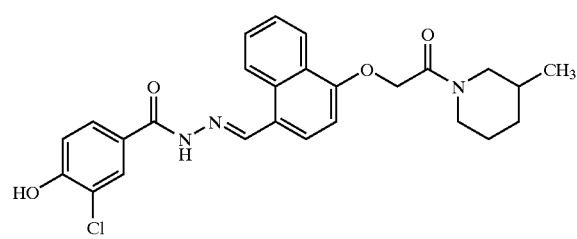
EXAMPLE 317:
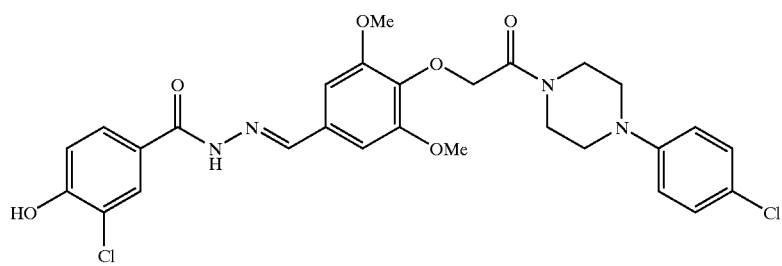
EXAMPLE 318:
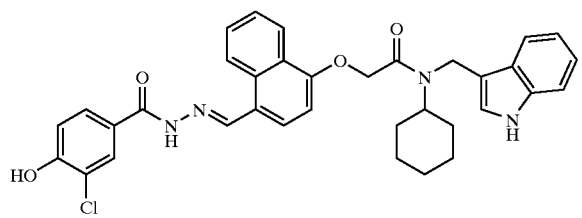
EXAMPLE 319:
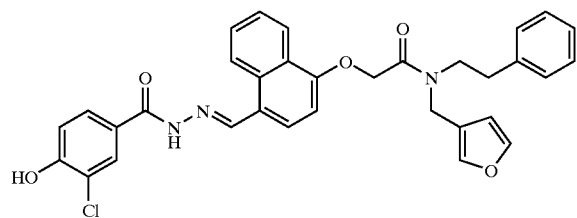
EXAMPLE 320:
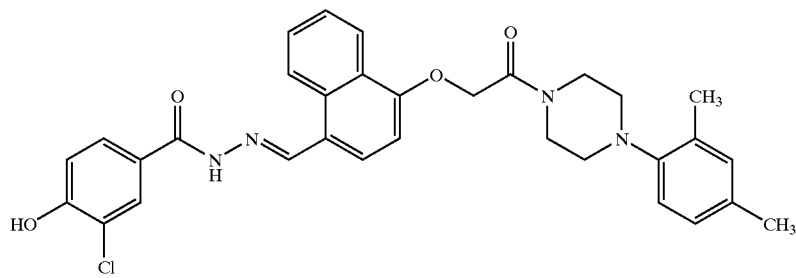

EXAMPLE 321:
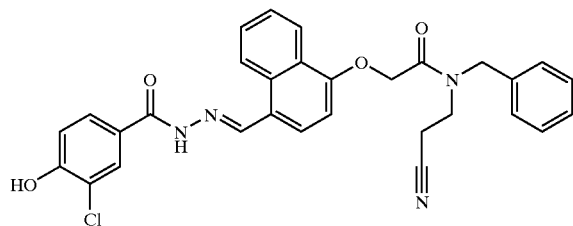
EXAMPLE 322:
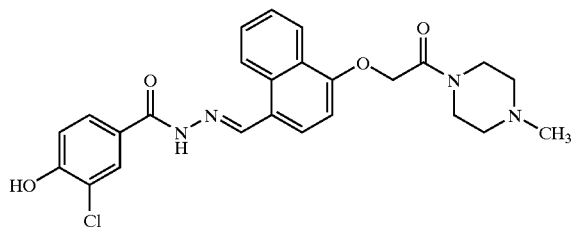
EXAMPLE 323:
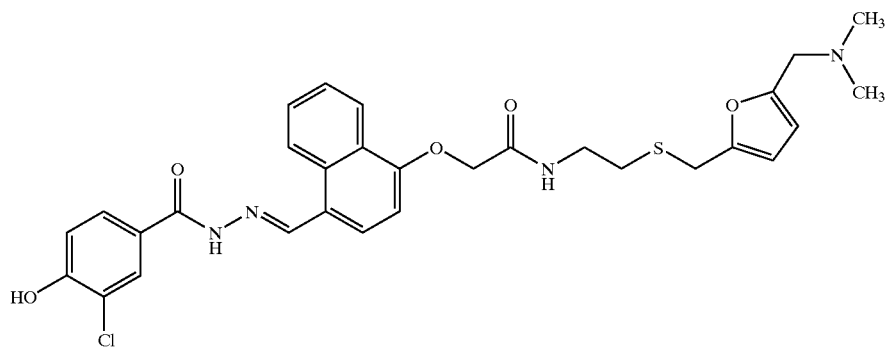
EXAMPLE 324:
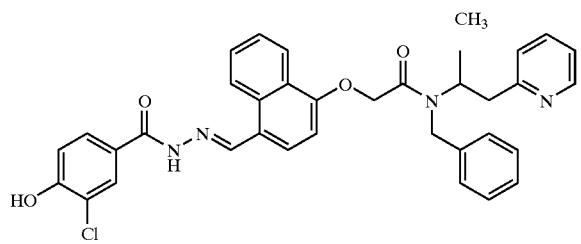
EXAMPLE 325:
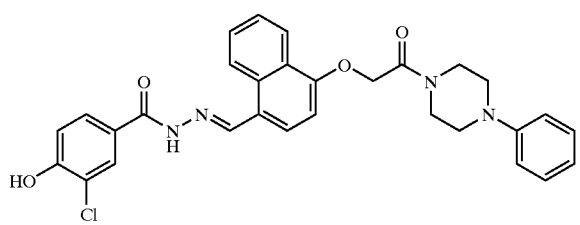
EXAMPLE 326:
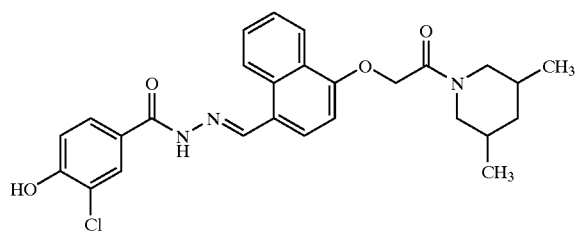
EXAMPLE 327:
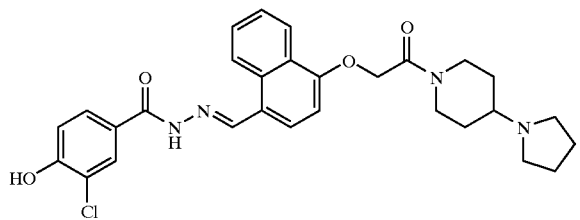
EXAMPLE 328:
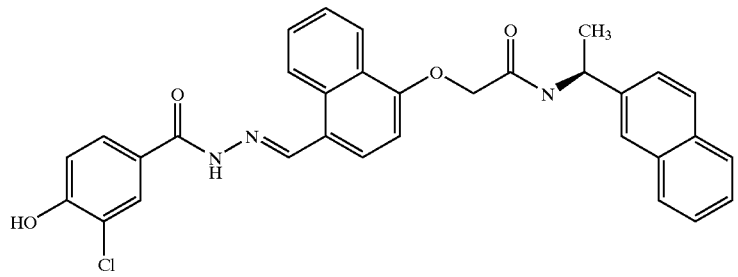

EXAMPLE 329:
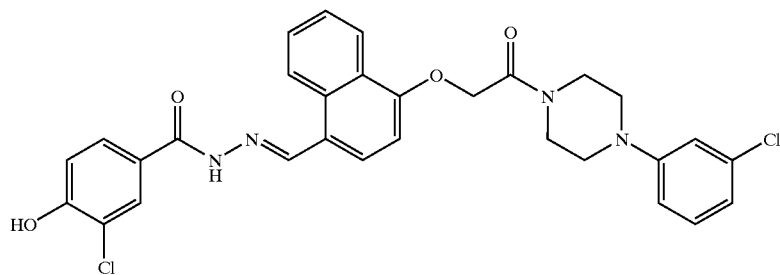
EXAMPLE 330:
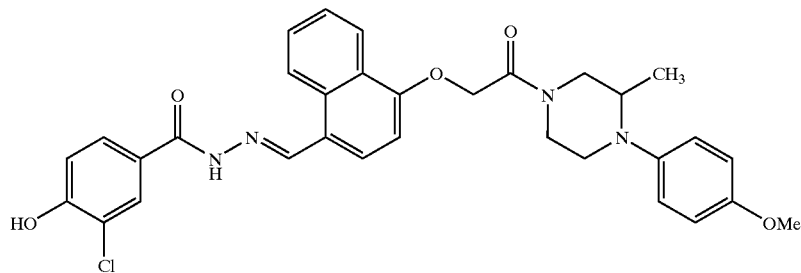
EXAMPLE 331:
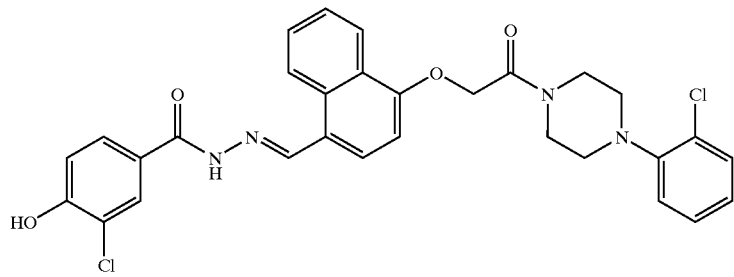
EXAMPLE 332:
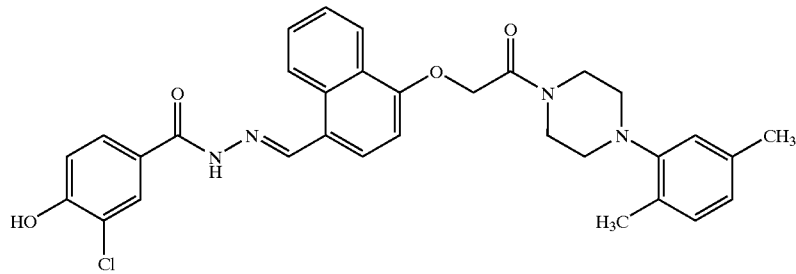
EXAMPLE 333:
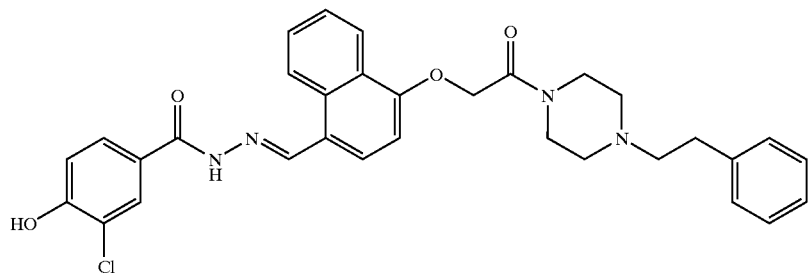

EXAMPLE 334:
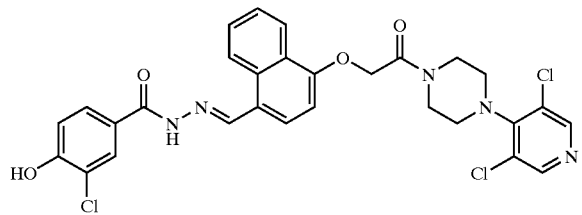
EXAMPLE 335:
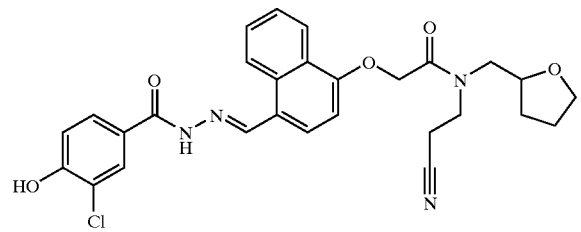
EXAMPLE 336:
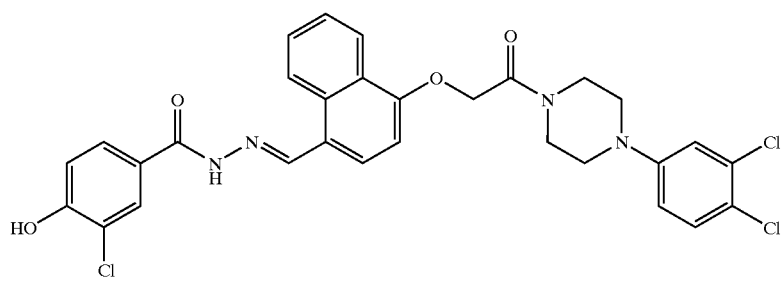
EXAMPLE 337:
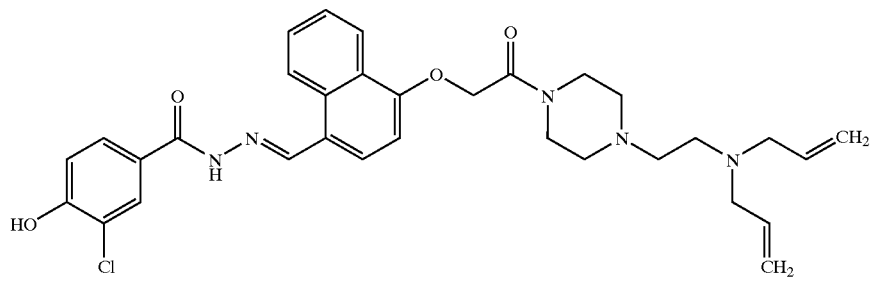
EXAMPLE 338:
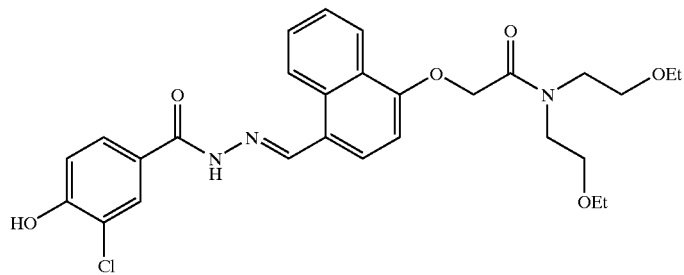
EXAMPLE 339:
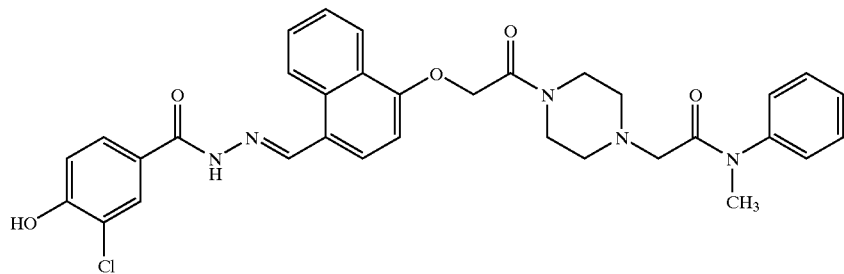

EXAMPLE 340:

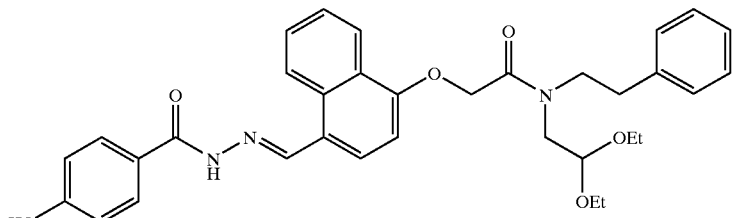

EXAMPLE 341:

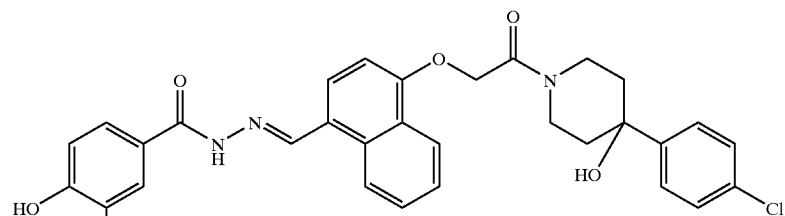

EXAMPLE 342:

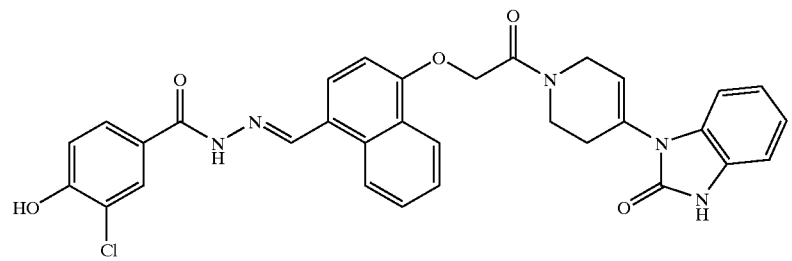

General Procedure for Synthesis of Compounds of the General Formula XII

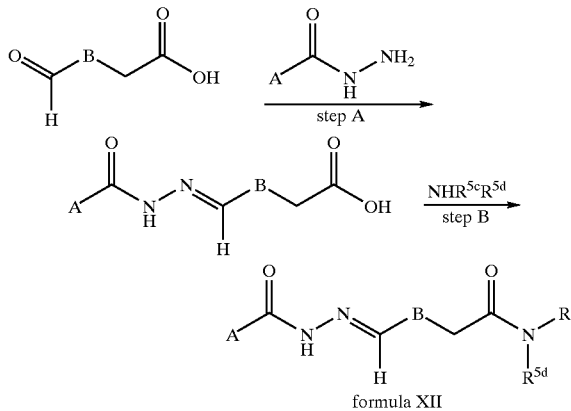

A and B are as defined for formula I and —NR$^{5c}$R$^{5d}$ is

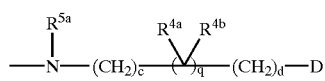

where R$^{5a}$, R$^{4a}$, R$^{4b}$, c, q, d and D are as defined for formula I or —D' where —D' is defined as a subset of —D that contains a primary or secondary amine that can react as a nucleophile.

Step A: The carbonyl compounds are treated with an acylhydrazide in a solvent. The solvent may be one of the following: ethyl alcohol, methyl alcohol, isopropyl alcohol, tert-butyl alcohol, dioxane, tetrahydrofuran, toluene, chlorobenzene, anisole, benzene, chloroform, dichloromethane, DMSO, acetic acid, water or a compatible mixture of two or more of the above solvents. A catalyst such as acetic acid can be added. A dehydrating reagent such as triethylorthoformate can also be added to the reaction mixture. The reaction is performed by stirring the reaction mixture preferably under an inert atmosphere of N$_2$ or Ar at temperatures between 0° C. to 140° C., preferably between 10° C. to 80° C. In many cases the product simply crystallizes out when the reaction is completed and is isolated by suction filtration. It can be further recrystallized if necessary from a solvent such as the above described reaction solvents. The product can also be isolated by concentration of the reaction mixture in vacuo, followed by column chromatography on silica gel using a solvent system such as chloroform/methanol or dichloromethane/methanol or chloroform/ethyl acetate.

Step B: The resulting acid is then coupled to a primary or secondary amine using one of the methods well-known to those skilled in the art. This coupling can be performed using one of the standard amide or peptide synthesis procedures such as by generating an active ester, an anhydride or an acid halide that can then react with the amine to give a compound of formula XII. Step B was also done combinatorially with a preactivated acid and a selection of amines. The product can then be isolated either by filtration or by extraction using a solvent such as ethyl acetate, toluene, dichloromethane or diethylether and the solvent may then be removed by concentration at atmospheric or reduced pressure. The product can be further purified by either recrystallization from a solvent such as ethyl alcohol, methyl alcohol, isopropyl alcohol, toluene, xylene, hexane, tetrahydrofuran, diethyl ether, dibutyl ether, water or a mixture of two or more of the above. Alternatively, the product can be purified by column chromatography using dichloromethane/methanol or chloroform/methanol or isopropyl alcohol as eluent giving a compound of formula XII.

Specific examples illustrating the preparation of compounds of the general formula XII according to the invention are provided below.

Preparation of 4-Formyl-1-naphthylacetic Acid

This compound was prepared from the reduction of 4-cyano-1-naphthylacetic acid in the presence of 85% formic acid and Raney alloy as described in the literature. References: 1) A. A. Shulezhko and A. I. Kiprianov, J. org. Chem., (USSR) English translation, 4, 1968, p.1052. 2) Zh. Org. Khim., 4, 1968, p. 1089.

Preparation of 4-[3-Chloro-4-hydroxybenzoyl)-hydrazonomethyl]-1-naphthylacetic Acid (Step A)

This compound was prepared according to the general procedure for the synthesis of alkylidene hydrazides from the condensation of 4-formyl-1-naphthylacetic acid above and 3-chloro-4-hydroxybenzoic acid hydrazide.

$^1$H NMR (DMSO-D$_6$): δ 4.1 (s, 2H), 7.1 (d, 1H), 7.5 (d, 1H), 7.7 (qt, 2H), 7.8 (d, 1H), 7.9 (d, 1H), 8.0 (s, 1H), 8.1 (d, 1H), 8.8 (d, 1H), 9.1 (s, 1H), 11.0 (brd s, 1H), 11.8 (s, 1H), 12.2 (brd s, 1H); MS (APCI): 383.4, 385.2.

Preparation of (3-Formylindolyl)acetic Acid
Ethyl (3-Formylindolyl)acetate:
3-Formylindole (10.0 g, 69 mmoles) was dissolved in DMF (100 ml). Under N$_2$ was a 60% suspension of NaH in mineral oil (3.0 g) added in portions with cooling (temp<15° C.). At <15° C. was a solution of ethyl bromoacetate (8.4 ml) in DMF (15 ml) added drop wise over 30 minutes. The resulting mixture was stirred at room temperature for 16 hours and evaporated in vacuo. The residue was added water (300 ml) and extracted with ethyl acetate (2×150 ml), the combined organic extracts were washed with satd. NH$_4$Cl, dried (MgSO$_4$) and concentrated to afford 15.9 g ethyl (3-formylindolyl)acetate.

$^1$H NMR (CDCl$_3$) δ 1.26 (t, 3H), 4.22 (q, 2H), 4.90 (s, 2H), 7.21–7.35 (m, 3H), 7.72 (s, 1H), 8.30 (d, 1H), 10.0 (s, 1H).
(3-Formylindolyl)acetic Acid:
Ethyl (3-formylindolyl)acetate (15.9 g) was dissolved in 1,4-dioxane (100 ml) and added 36% aq. NaOH (10 ml). The resulting mixture was stirred at room temperature for 4 days. Water (500 ml) was added and the mixture was washed with diethyl ether (150 ml). The aqueous phase was made acidic with 5N HCl and extracted with ethyl acetate (250+150 ml). The combined organic extracts were dried (MgSO$_4$) and evaporated in vacuo to afford 10.3 g (73% over two steps) of (3-formylindolyl)acetic acid.

$^1$H NMR (DMSO-d$_6$) δ 4.94 (s, 2H), 7.27–7.36 (m, 3H), 7.98 (s, 1H), 8.25 (d, 1H), 10.0 (s, 1H), 12.5 (bs, 1H).

Preparation of (4-Formylindolyl)acetic Acid
4-Formylindole:
This compound was synthesized according to F. Yamada, M. Somei, Heterocycles 26 (1987) 1173.
$^1$H NMR (CDCl$_3$) δ 7.28–7.36 (m, 2H), 7.41 (t, J=3.0 Hz, 1H), 7.60–7.70 (m, 2H), 8.62 (brd s, 1H), 10.20 (s, 1H). GC-MS (pos.): 146.
Ethyl (4-Formylindolyl)acetate:
This compound was synthesized according to the general procedure for N-alkylation of indoles.
$^1$H NMR (CDCl$_3$) δ 1.13 (t, J=6.9 Hz, 3H), 4.15 (q, J=7.2 Hz, 2H), 4.86 (s, 2H), 7.22–7.35 (m, 3H), 7.49 (d, J=8.6 Hz, 1H), 7.60 (d, J=7.3 Hz, 1H), 10.20 (s, 1H).
(4-Formylindolyl)acetic Acid:
This compound was synthesized according to the general procedure for saponification of esters.
$^1$H NMR (DMSO-d$_6$) δ 5.15 (s, 2H), 7.12 (d, J=3.0 Hz, 1H), 7.36 (d, J=7.9 Hz, 1H), 7.61 (d, J=3.1 Hz, 1H), 7.71 (d, J=7.3 Hz, 1H), 7.82 (d, J=8.2 Hz, 1H), 10.20 (s, 1H), 12.94 (brd s, 1H).

Preparation of (5-Formylindolyl)acetic Acid
5-Cyano-N-tosylindole:
In a 100 mL round-bottom flask was placed NaH (0.4 g, 60% dipersion in mineral oil, 10 mmol) and anhydrous THF (10 mL) was added. To the suspension was added a solution of 5-cyanoindole (1.0 g, 7 mmol) in anhydrous THF (10 mL) by syringe at 0° C. The mixture was stirred for 10 min, and tosyl chloride (1.6 g, 8.4 mmol) was added. After stirring at room temperature for 2 h, water (100 mL) was added. The mixture was extracted with ethyl acetate (3×50 mL), dried (MgSO$_4$), and concentrated. The residue was purified by column chromatography using hexane: ethyl acetate=2:1 as eluent to yield 1.86 g (92%) of the desired product.
$^1$H NMR (CDCl$_3$) δ 2.32 (s, 3H), 6.65 (d, J=3.6 Hz, 1H), 7.19 (d, J=7.9 Hz, 2H), 7.41 (d, J=8.6 Hz, 1H), 7.57 (d, J=3.6 Hz, 1H), 7.63 (s, 1H), 7.75 (d, J=8.3 Hz, 1H), 7.99 (d, J=8.6 Hz, 1H).
5-Formyl-N-tosylindole:
To a solution of 5-cyano-N-tosylindole (0.66 g, 2.2 mmol) in anhydrous THF (20 mL), was added 1M DIBAL in hexane (4 mL, 4 mmol) via syringe at 0° C. The mixture was stirred at room temperature for 16 h, poured into ice-cooled 1N hydrochloric acid (50 mL), extracted with ethyl acetate (3×80 mL). The combined organic extracts were dried (MgSO$_4$), and concentrated to give an oil. After a short column chromatography using hexane/ethyl acetate 2:1 as eluent 0.62 g (95%) pure 5-formyl-N-tosylindole was obtained.
$^1$H NMR (CDCl$_3$) δ 2.29 (s, 3H), 6.74 (d, J=3.7 Hz, 1H), 7.21 (d, J=8.3 Hz, 2H), 7.65 (d, J=3.7 Hz, 1H), 7.77 (d, J=8.4 Hz, 2H), 7.82 (dd, J=1.4, 8.6 Hz, 1H), 8.02 (d, J=1.1 Hz, 1H), 8.09 (d, J=8.6 Hz, 1H), 9.99 (s, 1H).
5-Formylindole:
5-formyl-N-tosylindole (0.5 g, 1.7 mmol) was dissolved in a mixture of methanol (10 mL) containing 5% aqueous KOH solution (5 mL). The mixture was refluxed for 3 h, neutralized with 1N hydrochloric acid, and extracted with ethyl acetate (3×50 mL). The combined organic extracts were dried (MgSO$_4$), and concentrated. The residue was purified by short column chromatography to provide 240 mg (97%) of the desired product.
$^1$H NMR (CDCl$_3$) δ 6.70 (t, J=2.1 Hz, 1H), 7.32 (t, J=2.3 Hz, 1H), 7.49 (d, J=8.4 Hz, 1H), 7.78 (dd, J=1.5, 8.6 Hz, 1H), 8.19 (s, 1H), 9.45 (b, 1H), 10.15 (s, 1H). GC-MS (pos.): 146.

343

Ethyl (5-Formylindolyl)acetate:

This compound was synthesized according to the general procedure for N-alkylation of indoles.

$^1$H NMR (CDCl$_3$) δ 1.27 (t, J=6.8 Hz, 3H), 4.22 (q, J=7.2 Hz, 2H), 4.87 (s, 2H), 6.70 (d, J=3.4 Hz, 1H), 7.18 (d, J=3.0 Hz, 1H), 7.36 (d, J=8.7 Hz, 1H), 7.78 (d, J=8.3 Hz, 1H), 8.14 (s, 1H), 10.01 (s, 1H).

(5-Formylindolyl)acetic Acid:

This compound was synthesized according to the general procedure for saponification of esters.

$^1$H NMR (DMSO-d$_6$) δ 5.10 (s, 2H), 6.66 (d, J=3.0 Hz, 1H), 7.48 (d, J=3.0 Hz, 1H), 7.56 (d, J=8.7 Hz, 1H), 7.66 (d, J=8.3 Hz, 1H), 8.17 (s, 1H), 9.97 (s, 1H), 12.9 (brd s, 1H).

General Procedure for Preparation of [(3-Chloro-4-hydroxybenzoyl)hydrazonomethyl]indolyl Acetic Acids These compounds were prepared according to the general procedure for the synthesis of alkylidene hydrazones by condensation of the various formylindolylacetic acids with 3-chloro-4-hydroxy benzoic acid hydrazide.

3-[(3-Chloro-4-hydroxybenzoyl)hydrazonomethyl]indolyl Acetic Acid:

$^1$H NMR (DMSO-D$_6$): δ 2.81 (t, J=6.5, 2H), 4.43 (t, J=6.5, 2H), 7.06 (d, J=8.5, 1H), 7.15–7.28 (m, 2H), 7.56 (d, J=8.1, 1H), 7.75 (d, J=8.5, 1H), 7.83 (s, 1H), 7.95 (s, 1H), 8.27 (d, J=7.65, 1H), 8.54 (s, 1H), 10.88 (br s, 1H), 11.41 (s, 1H). LRMS calcd for C$_{19}$H$_{16}$Cl$_1$N$_3$O$_4$ (M−H) 384, found 384.0.

4-[(3-Chloro-4-hydroxybenzoyl)hydrazonomethyl]indolyl Acetic Acid:

$^1$H NMR (DMSO-d$_6$) δ 5.09 (s, 2H), 7.09 (d, J=8.6 Hz, 1H), 7.16–7.25 (m, 2H), 7.32 (d, J=7.2 Hz, 1H), 7.45–7.55 (m, 2H), 7.81 (d, J=8.2 Hz, 1H), 8.01 (d, J=1.8 Hz, 1H), 8.68 (s, 1H), 10.96 (s, 1H), 11.71 (s, 1H), 12.90 (b, 1H). MS (APCI, neg.): 370.

5-[(3-Chloro-4-hydroxybenzoyl)hydrazonomethyl]indolyl Acetic Acid:

$^1$H NMR (DMSO-d$_6$) δ 5.09 (s, 2H), 6.35 (d, J=2.9 Hz, 1H), 7.06 (d, J=8.6 Hz, 1H), 7.39 (d, J=3.1 Hz, 1H), 7.47 (d, J=8.6 Hz, 1H), 7.61 (d, J=8.6 Hz, 1H), 7.76 (d, J=8.5 Hz, 1H), 7.83 (s, 1H), 7.97 (s, 1H), 8.48 (s, 1H), 10.93 (s, 1H), 11.58 (s, 1H), 12.90 (brd s, 1H). MS (APCI, neg.): 370.

4-[3-Chloro-4-hydroxybenzoyl)-hydrazonomethyl]-1-naphthylacetamides and the Various Indolacetamides (Step B)

General Library Production Procedures

To solutions of 4-[(3-chloro-4-hydroxybenzoyl)-hydrazonomethyl]naphthylacetic acid and the various indolylacetic acids in DMSO was added carbonyldiimidazole (1.2 eq). The solution was agitated for 5 minutes and diluted with DMSO to a concentration of 50 mM. The solution was then dispensed into 88 deep well plates containing solutions of amines in DMSO (50 mM). The plates were covered and agitated for 16 hours. The products were purified by HPLC.

Examples of compounds of the formula XII:

344

EXAMPLE 343

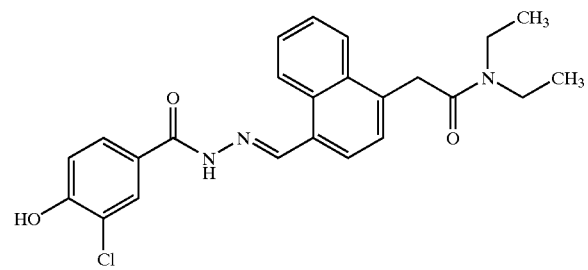

$^1$H NMR (DMSO-D$_6$): δ 1.06 (t, 3H), 1.17 (t, 3H), 3.31 (qt, 2H), 3.50 (qt, 2H), 4.19 (s, 2H), 7.10 (d, 1H), 7.45 (d, 1H), 7.64 (quintet, 2H), 7.83 (d, 1H), 7.88 (d, 1H), 7.98 (m, 2H), 8.87 (d, 1H), 9.09 (s, 1H), 10.99 (brd s, 1H), 11.80 (brd s, 1H); ms (APCI); 438.1, 440.1.

EXAMPLE 344

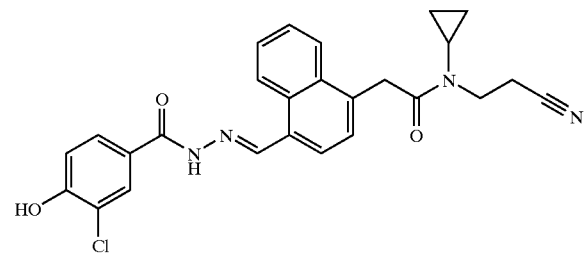

$^1$H NMR (DMSO-D$_6$): δ 0.98 (d, 4H), 2.76 (t, 2H), 3.02 (quintet, 1H), 3.59 (t, 2H), 4.40 (s, 2H), 7.10 (d, 1H), 7.48 (d, 1H), 7.48 (d, 1H), 7.59 (qt, 1H), 7.67 (t, 1H), 7.81 (d, 1H), 7.89 (d, 1H), 7.97 (d, 1H), 8.02 (s, 1H), 8.84 (d, 1H), 9.09 (s, 1H), 10.99 (brd s, 1H), 11.80 (brd s, 1H); MS (APCI, neg.): 473.1, 475.1.

EXAMPLE 345

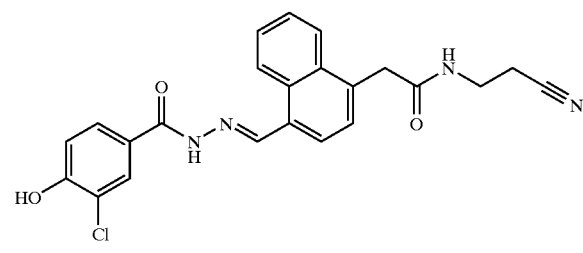

$^1$H NMR (DMSO-D$_6$): δ 2.50 (2H), 2.68 (t, 2H), 4.00 (s, 2H), 7.10 (d, 1H), 7.53 (d, 1H), 7.65 (tt, 2H), 7.80 (dd, 1H), 7.90 (d, 1H), 8.02 (d, 1H), 8.14 (d, 1H), 8.62 (t, 1H), 8.84 (d, 1H), 9.09 (s, 1H), 11.0 (brd s, 1H) 11.80 (s, 1H); MS (APCI): 433.1, 435.1.

EXAMPLE 346

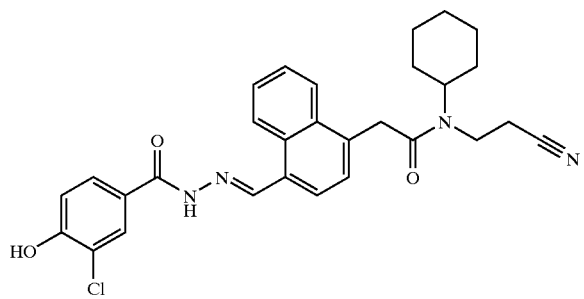

$^1$H NMR (DMSO-D$_6$): δ 1.08 (m, 4H), 1.54 (m, 6H), 2.70 (t, 2H), 3.45 (t, 2H), 3.76 (m, 1H), 4.30 (s, 2H), 7.06 (d, 1H), 7.49 (d, 1H), 7.64 (m, 2H), 7.80 (d, 1H), 7.88 (d, 1H), 8.01 (s, 1H), 8.07 (d, 1H), 8.83 (d, 1H), 9.09 (s, 1H), 10.5 (brd d, 1H), 11.78 (brd s, 1H); MS (APCI, neg.): 515.2.

EXAMPLE 347

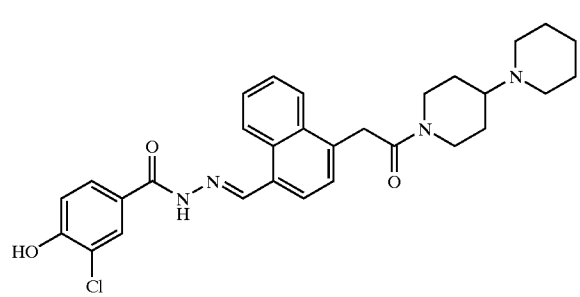

$^1$H NMR (DMSO-D$_6$): δ 1.26 (m, 2H), 1.37 (m, 4H), 1.67 (m, 2H), 2.43 (m, 4H), 2.62 (m, 3H), 3.10 (t, 2H), 3.90 (d, 1H), 4.32 (s, 2H), 4.48 (d, 1H), 7.10 (d, 1H), 7.31 (d, 1H), 7.48 (m, 2H), 7.81 (d, 1H), 7.88 (d, 1H), 8.03 (m, 2H), 8.85 (d, 1H), 9.08 (brd s, 1H), 11.76 (brd s, 1H): MS (APCI): 533.2.

EXAMPLE 348

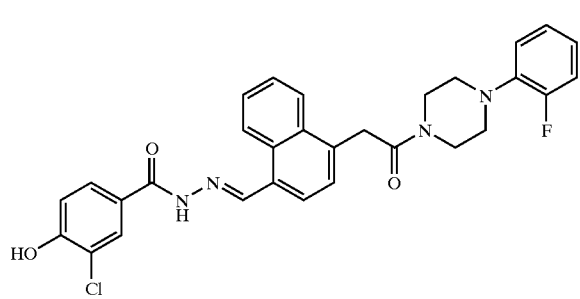

$^1$H NMR (DMSO-D$_6$): δ 3.03 (m, 4H), 3.68 (t, 2H), 3.79 (t, 2H), 4.30 (s, 2H), 7.14 (m, 5H), 7.47 (d, 1H), 7.66 (quintet, 2H), 7.82 (d, 1H), 7.88 (d, 1H), 8.02 (d, 1H), 8.07 (d, 1H), 8.87 (d, 1H), 9.10 (s, 1H), 10.99 (s, 1H), 11.80 (s, 1H); MS (ACPI): 545.6.

EXAMPLE 349

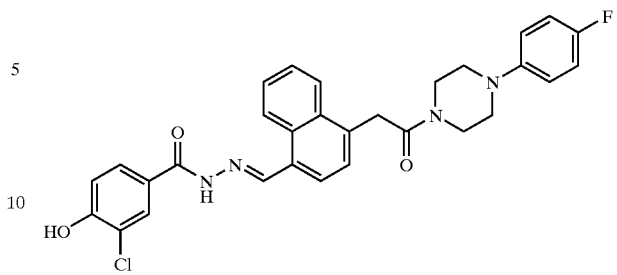

$^1$H NMR (DMSO-D$_6$): δ 3.10 (d, 4H), 3.67 (d, 4H), 4.30 (s, 2H), 7.00 (m, 2H), 7.09 (m, 3H), 7.47 (d, 1H), 7.62 (quintet, 2H), 7.82 (d, 1H), 7.88 (d, 1H), 8.03 (s, 1H), 8.06 (d, 1H), 8.85 (d, 1H), 9.10 (s, 1H), 10.99 (s, 1H), 11.80 (s, 1H); MS (ACPI): 544.5, 545.3.

EXAMPLE 350

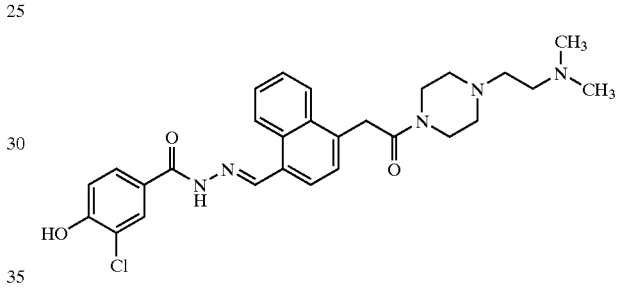

$^1$H NMR (DMSO-D$_6$): δ 2.15 (s, 6H), 2.39 (m, 8H), 3.51 (d, 4H), 4.22 (s, 2H), 7.03 (d, 1H), 7.43 (d, 1H), 7.64 (quintet, 2H), 7.77 (d, 1H), 7.87 (d, 1H), 7.99 (s, 1H), 8.02 (d, 1H), 8.83 (d, 1H), 9.08 (s, 1H), 11.80 (brd s, 1H); MS (APCI): 522.2.

EXAMPLE 351

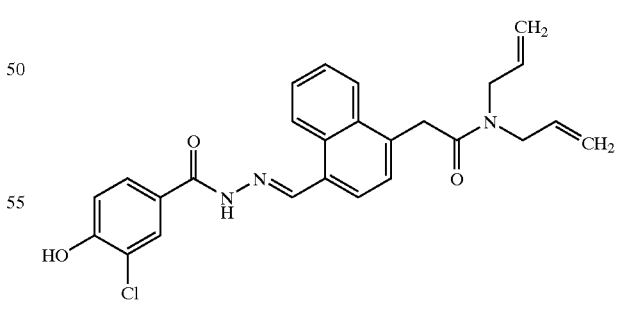

$^1$H NMR (DMSO-D$_6$): δ 3.93 (d, 2H), 4.10 (d, 2H), 4.23 (s, 2H), 5.20 (m, 4H), 5.79 (m, 1H), 5.94 (m, 1H), 7.10 (d, 1H), 7.78 (d, 1H), 7.63 (m, 2H), 7.80 (d, 1H), 7.83 (d, 1H), 7.95 (d, 1H), 8.02 (d, 1H), 8.85 (d, 1H), 9.10 (s, 1H), 11 (brd s, 1H), 11.80 (brd s, 1H); MS (ACPI): 462.2.

EXAMPLE 352

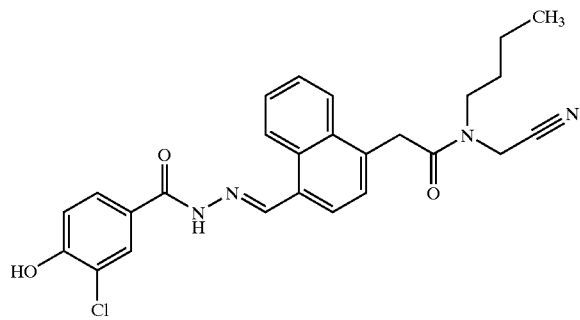

$^1$H NMR (DMSO-D$_6$): δ 0.9 (t, 3H), 1.30 (sextet, 2H), 1.54 (sextet, 2H), 3.56 (t, 2H), 4.31 (s, 2H), 4.39 (s, 2H), 7.06 (d, 1H), 7.48 (d, 1H), 7.65 (quintet, 2H), 7.79 (dd, 1H), 7.87 (d, 1H), 7.97 (d, 1H), 8.01 (d, 1H), 8.85 (d, 1H), 9.09 (s, 1H), 11.79 (s, 1H); MS (APCI): 477.01, 479.2.

EXAMPLE 353

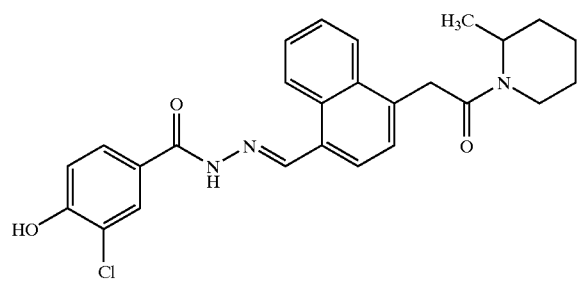

$^1$H NMR (DMSO-D$_6$): δ 1.17 (m, 4H), 1.54 (m, 4H), 2.68 (m, 1H), 3.77 (d, 1H), 4.18 (s, 2H), 4.33 (m, 1H), 4.76 (brd, 1H), 7.10 (d, 1H), 7.43 (m, 1H), 7.65 (quintet, 2H), 7.81 (d, 1H), 7.88 (d, 1H), 8.02 (s, 1H), 8.04 (d, 1H), 8.84 (d, 1H), 9.09 (s, 1H), 11.79 (s, 1H); MS (APCI): 464.1, 466.2.

EXAMPLE 354

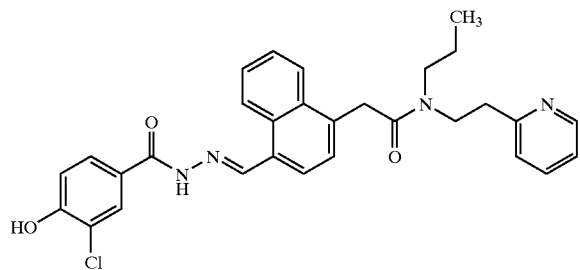

$^1$H NMR (DMSO-D$_6$): δ 0.85 (qt, 3H), 1.53 (m, 2H), 3.00 (dt, 2H), 3.29 (quintet, 2H), 3.77 (dt, 2H), 4.13 (d, 2H), 7.05 (d, 1H), 7.26 (m, 2H), 7.36 (d, 1H), 7.52 (qt, 1H), 7.69 (m, 2H), 7.87 (m, 2H), 7.95 (d, 1H), 8.00 (s, 1H), 7.87 (dd, 1H), 8.84 (t, 1H), 9.07 (brd, 1H), 11.76 (brd s, 1H); MS (APCI): 529.2, 529.7, 531.2.

EXAMPLE 355

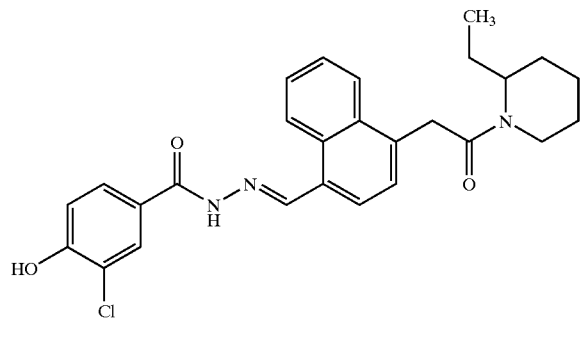

$^1$H NMR (DMSO-D$_6$): δ 0.85 (qt, 3H), 1.33 (m, 1H), 1.65 (m, 7H), 2.60 (t, 0.5H), 3.10 (t, 0.5H), 3.80 (m, 1H), 4.21 (s, 2H), 4.24 (m, 1H), 7.11 (d, 1H), 7.45 (t, 1H), 7.65 (m, 2H), 7.75 (d, 1H), 7.89 (d, 1H), 8.01 (d, 1H), 8.05 (d, 1H), 8.83 (d, 1H), 9.09 (s, 1H), 11.80 (s, 1H); MS (APCI): 478.4, 480.3.

EXAMPLE 356

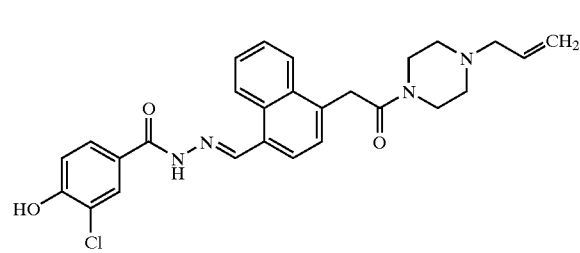

$^1$H NMR (DMSO-D$_6$): δ 2.36 (m, 4H), 2.97 (d, 2H), 3.50 (m, 2H), 3.60 (m, 2H), 4.23 (s, 2H), 5.17 (t, 2H), 5.86 (m, 1H), 7.08 (d, 1H), 7.43 (d, 1H), 7.64 (quintet, 2H), 7.79 (dd, 1H), 7.87 (d, 1H), 8.01 (s, 1H), 8.04 (d, 1H), 8.83 (d, 1H), 9.09 (d, 1H), 11.79 (brd s, 1H); MS (APCI):4.91.2, 493.2.

EXAMPLE 357

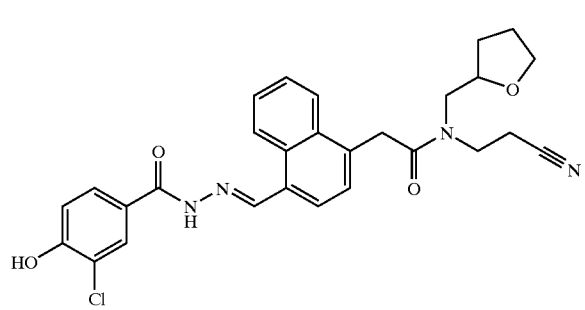

$^1$H NMR (DMSO-D$_6$): δ 1.50 (m, 1H), 1.90 (m, 2H), 1.95 (m, 1H), 2.72 (t, 1H), 2.95 (t, 1H), 3.30 (m, 1H), 3.55 (m, 1H), 3.65 (t, 2H), 3.75 (m, 1H), 3.92 (t, 1H), 4.12 (t, 1H), 4.35 (d, 2H), 7.11 (d, 1H), 7.48 (m, 1H), 7.65 (t, 1H), 7.68 (t, 1H), 7.8 (dd, 1H), 7.87 (d, 1H), 8.00 (d, 1H), 8.03 (d, 1H), 8.83 (d, 1H), 9.10 (s, 1H), 11.80 (brd s, 1H); MS (APCI): 519.5, 521.2, 522.2.

EXAMPLE 358

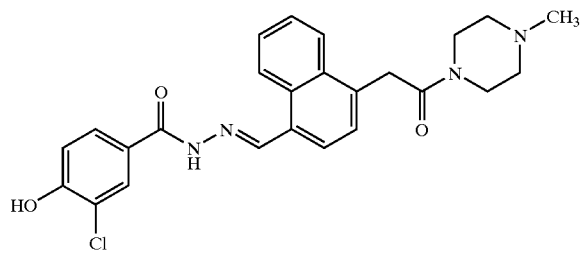

$^1$H NMR (DMSO-D$_6$): δ 2.19 (s, 3H), 2.30 (m, 4H), 3.50 (T, 2H), 3.58 (T, 2H), 4.22 (S, 2H), 7.03 (D, 1H), 7.43 (D, 1H), 7.64 (quint, 2H) 7.77 (dd, 1H), 7.87 (d, 1H), 7.99 (d, 1H), 8.04 (s, 1H), 8.83 (d, 1H), 9.09 (s, 1H), 11.80 (brd s, 1H); MS (APCI): 465.2, 467.3.

EXAMPLE 359

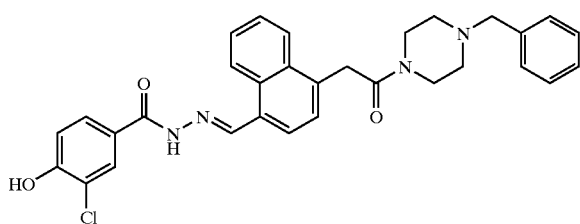

$^1$H NMR (DMSO-D$_6$): δ 2.38 (m, 4H), 3.51 (s, 4H), 3.61 (t, 2H), 4.22 (s, 2H), 7.08 (d, 1H), 7.31 (m, 5H), 7.43 (d, 1H), 7.61 (quintet, 2H), 7.82 (dd, 1H), 7.88 (d, 1H), 8.00 (s, 1H), 8.02 (d, 1H), 8.85 (d, 1H), 9.10 (s, 1H), 11.80 (brd s, 1H); MS (APCI): 541.4, 543.1.

EXAMPLE 360

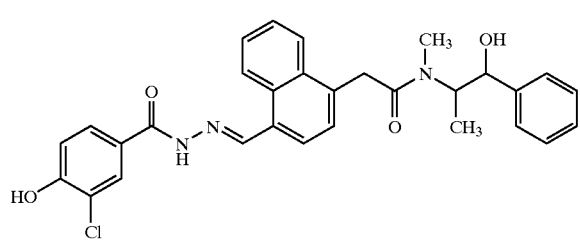

$^1$H NMR (DMSO-D$_6$): δ 1.33 (dd, 3H), 2.76 (s, 1.5H), 2.96 (s, 1.5H), 3.61 (d, 1H), 4.14 (quintet, 1H), 4.65 (m, 2H), 7.10 (m, 2H), 7.33 (s, 3H), 7.42 (m, 3H), 7.54 (m, 2H), 8.02 (t, 1H), 8.80 (m, 1H), 9.07 (brd, 1H), 11.80 (brd s, 1H); MS (APCI): 530.2, 532.2.

EXAMPLE 361

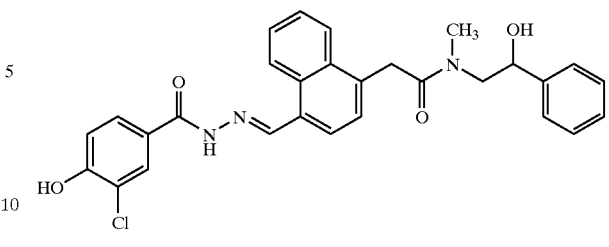

$^1$H NMR (DMSO-D$_6$): δ [2.94 (s, 1.5H) +3.10 (s, 1.5H), 3H], 3.54 (m, 2H), 4.00 (d, 1H), 4.28 (d, 1H), 4.81 (t, 1H), 4.96 (t, 1H), 7.09 (d, 1H), 7.35 (m, 3H), 7.43 (m, 3H), 7.61 (m, 2H), 7.83 (m, 3H), 8.04 (s, 1H), 8.85 (t, 1H), 9.11 (d, 1H), 11.80 (brd s, 1H); MS (APCI): 516.3, 518.2.

EXAMPLE 362

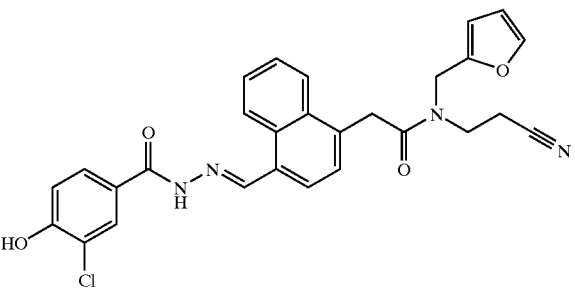

$^1$H NMR (DMSO-D$_6$): δ 2.75 (t, 1H), 2.95 (t, 1H), 3.59 (t, 1H), 3.80 (t, 1H), 4.38 (brd s, 3H), 4.61 (s, 1H), 4.84 (s, 1H), 6.40 (d, 1H), 6.53 (d, 1H), 7.05 (d, 1H), 7.45 (t, 1H), 7.58 (m, 3H), 7.81 (m, 3H), 8.00 (brd, 2H), 8.83 (d, 1H), 9.10 (s, 1H), 11.78 (brd s, 1H); MS (APCI, neg.): 513.3, 514.2.

EXAMPLE 363

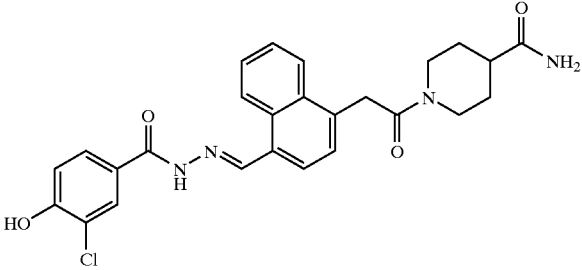

$^1$H NMR (DMSO-D$_6$): δ 1.50 (m, 2H), 1.68 (d, 2H), 2.28 (t, 1H), 2.59 (t, 1H), 3.05 (t, 1H), 3.96 (d, 1H), 4.16 (s, 2H), 4.32 (d, 1H), 6.74 (brd s, 1H), 6.95 (d, 1H), 7.22 (brd s, 1H), 7.36 (d, 1H), 7.57 (quintet, 2H), 7.71 (dd, 1H), 7.79 (d, 1H), 7.92 (dd, 1H), 7.96 (d, 1H), 8.76 (d, 1H), 9.01 (s, 1H), 11.80 (brd s, 1H); MS (ACPI): 493.1, 495.2.

EXAMPLE 364
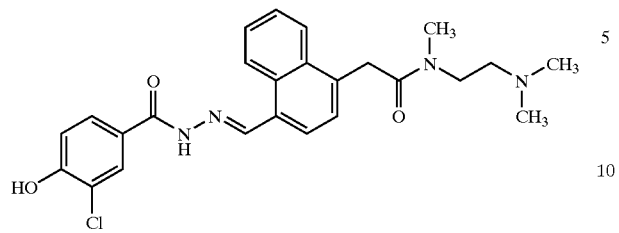
¹H NMR (DMSO-D₆): δ 2.10 (s, 3H), 2.15 (s, 3H), 2.29 (t, 1H), 2.40 (t, 1H), 2.80 (s, 1H), 3.05 (s, 2H), 3.36 (t, 1H), 3.46 (t, 1H), 4.16 (d, 2H), 7.01 (d, 1H), 7.38 (t, 1H), 7.56 (m, 2H), 7.72 (dd, 1H), 7.79 (d, 1H), 7.94 (m, 2H), 8.77 (d, 1H), 9.02 (s, 1H), 11.71 (brd s, 1H); MS (ACPI): 467.3, 469.1.
EXAMPLE 365
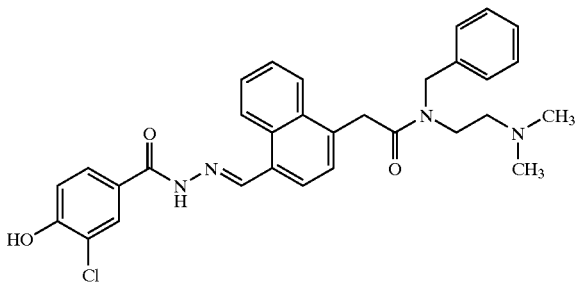
¹H NMR (DMSO-D₆): δ 2.11 (s, 3H), 2.14 (s, 3H), 2.33 (t, 1H), 2.39 (t, 1H), 3.37 (t, 1H), 3.46 (t, 1H), 4.14 (s, 1H), 4.32 (s, 1H), 4.55 (s, 1H), 4.74 (s, 1H), 7.05 (d, 1H), 7.23 (d, 1H), 7.29 (m, 3H), 7.38 (t, 1H), 7.43 (d, 1H), 7.57 (m, 2H), 7.81 (m, 2H), 7.97 (s, 1H), 8.06 (d, 1H), 8.79 (t, 1H), 9.05 (s, 1H), 11.75 (brd s, 1H); MS (APCI): 543.2, 545.2.
EXAMPLE 366:
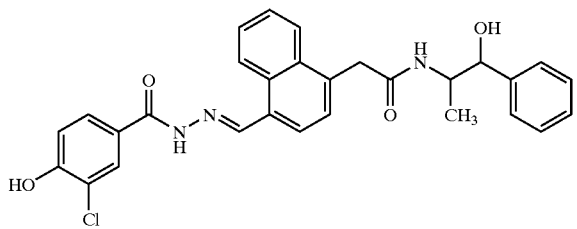
EXAMPLE 367:
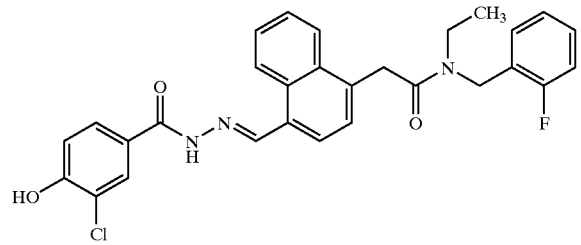
EXAMPLE 368:
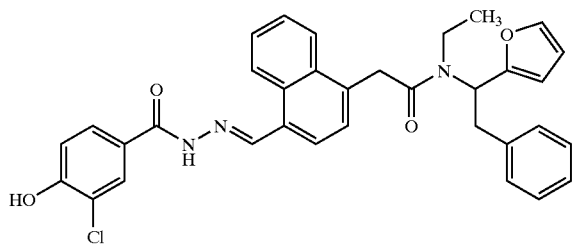
EXAMPLE 369:
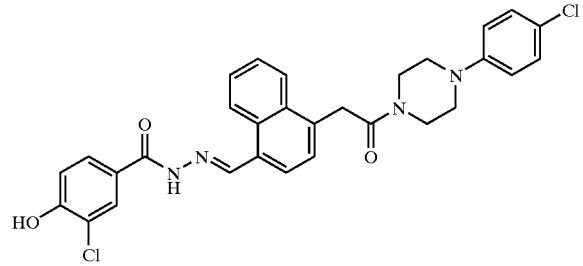
EXAMPLE 370:
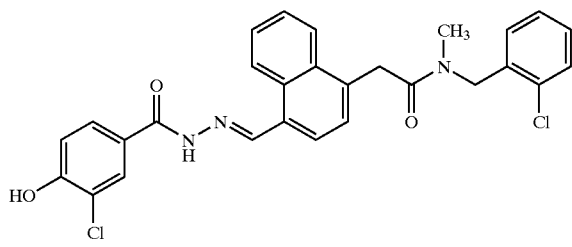
EXAMPLE 371:
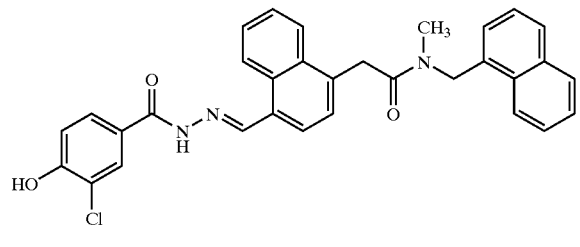

EXAMPLE 372:
EXAMPLE 373:
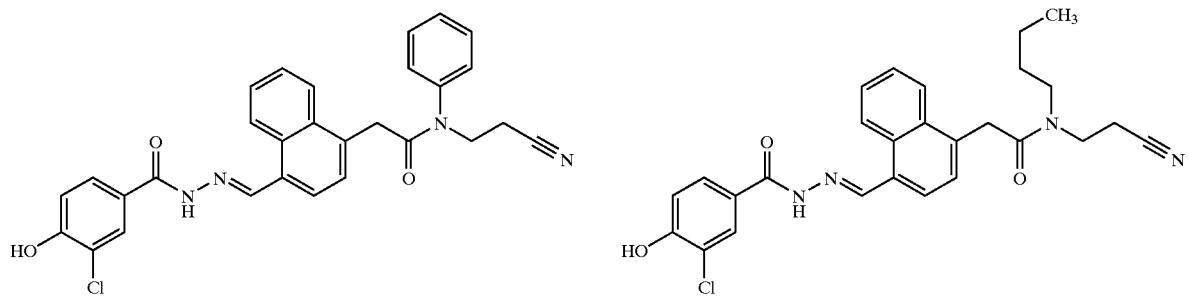
EXAMPLE 374:
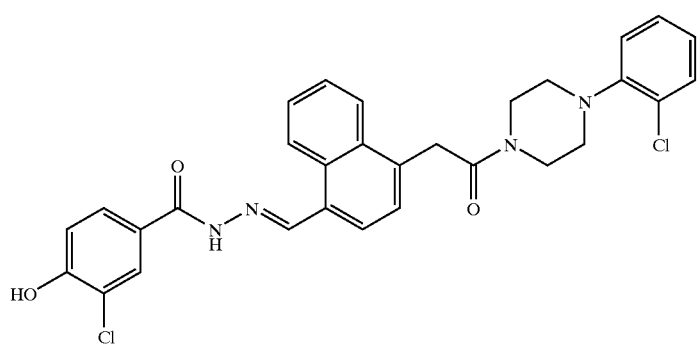
EXAMPLE 375:
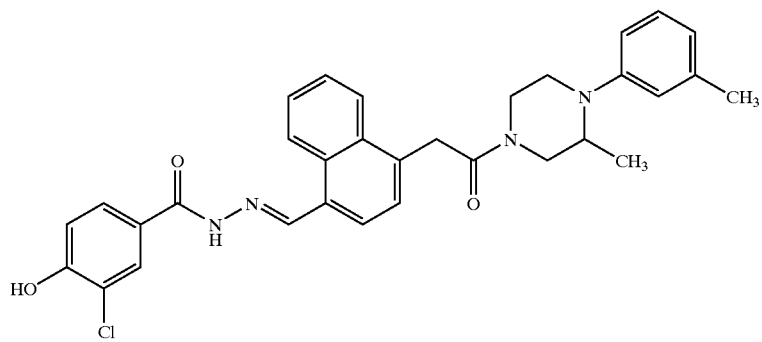
EXAMPLE 376:
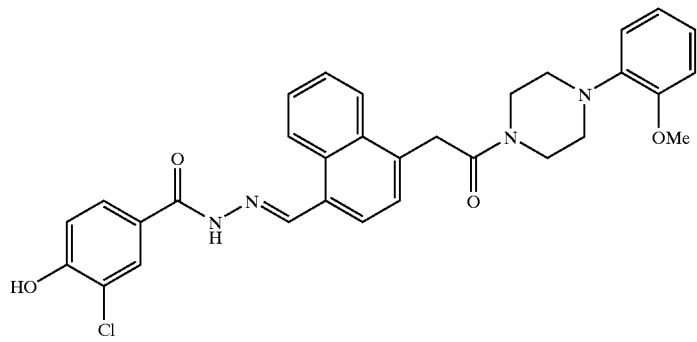

EXAMPLE 377:
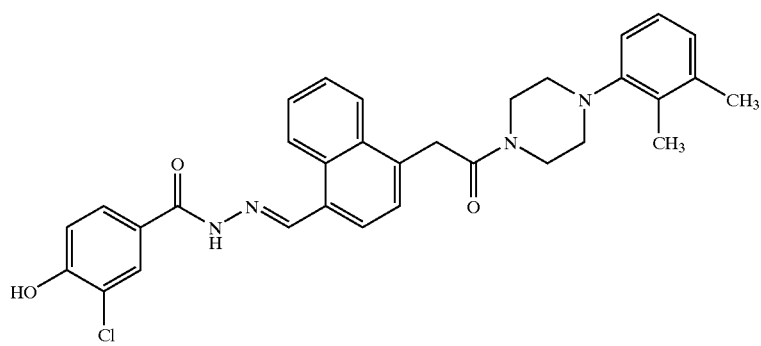
EXAMPLE 378:
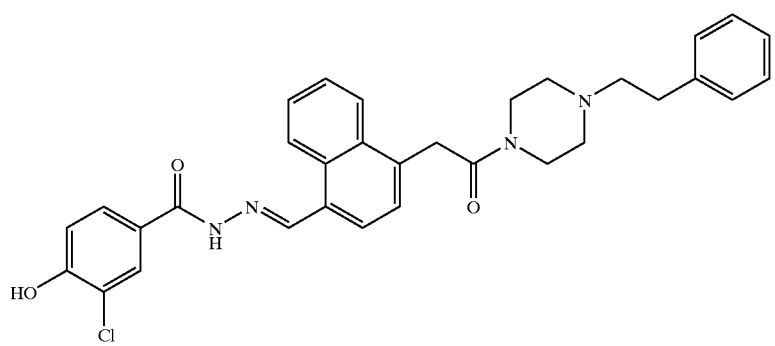
EXAMPLE 379:
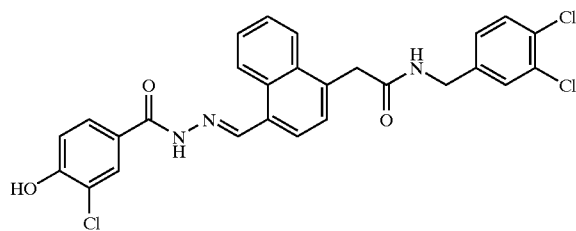
EXAMPLE 380:
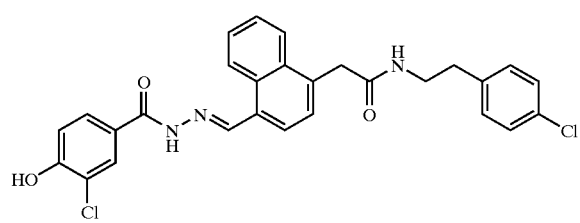
EXAMPLE 381:
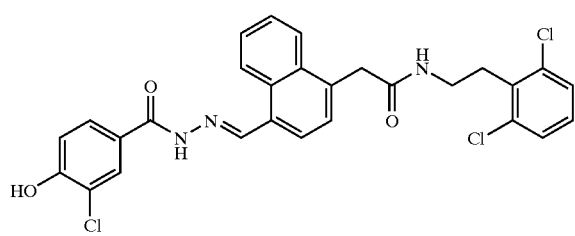
EXAMPLE 382:
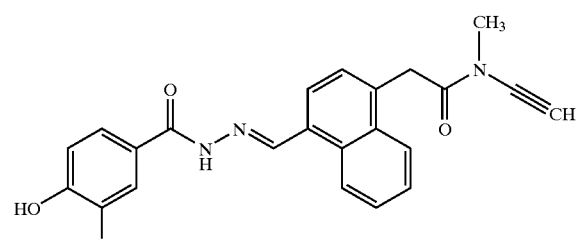
EXAMPLE 383:
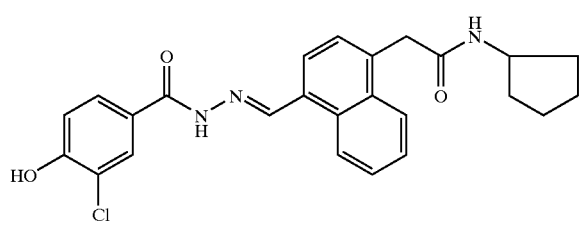
EXAMPLE 384:
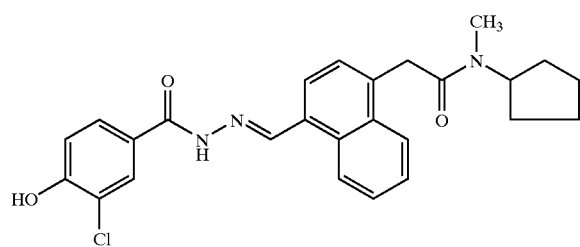

EXAMPLE 385:
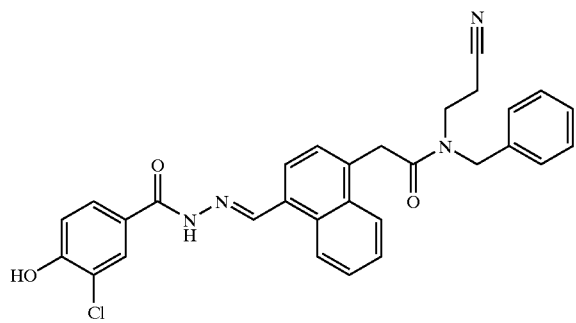
EXAMPLE 386:
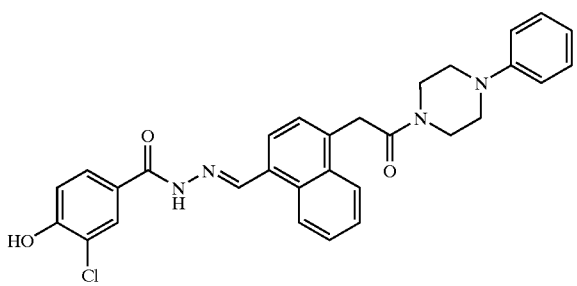
EXAMPLE 387:
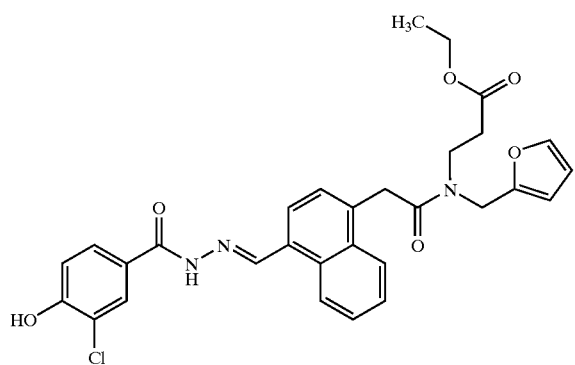
EXAMPLE 388:
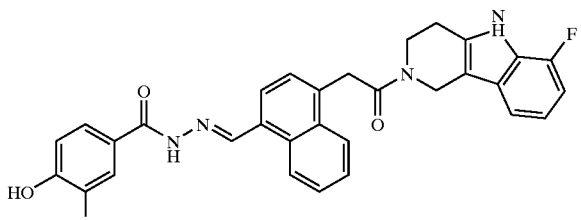
EXAMPLE 389:
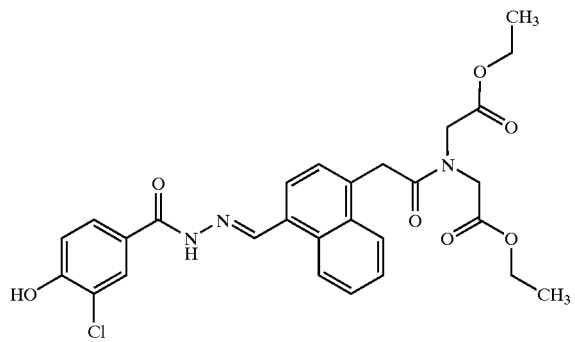
EXAMPLE 390:
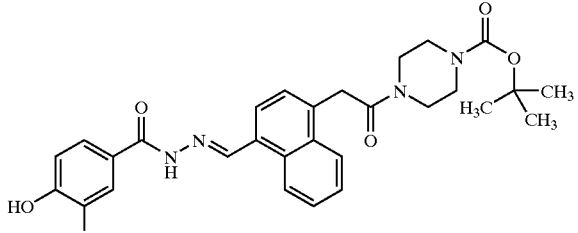
EXAMPLE 391:
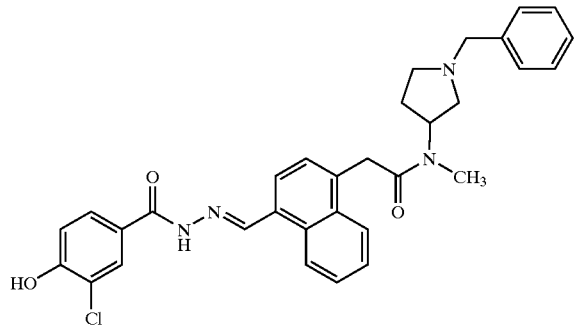
EXAMPLE 392:
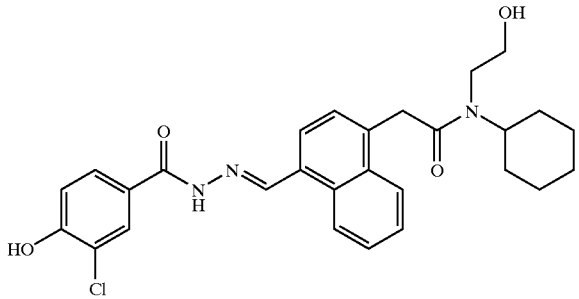

-continued
EXAMPLE 393:
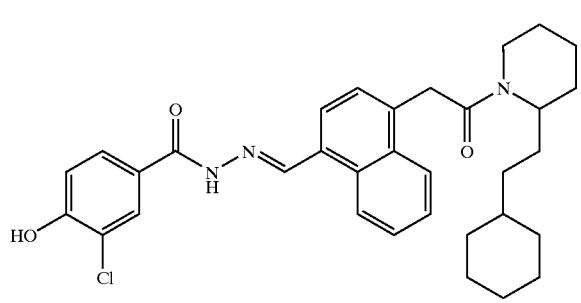
EXAMPLE 394:
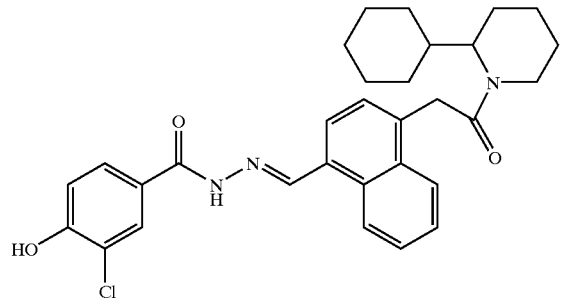
EXAMPLE 395:
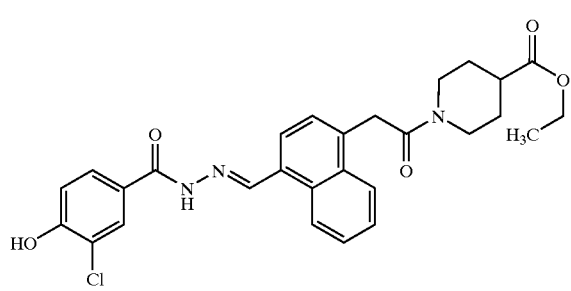
EXAMPLE 396:
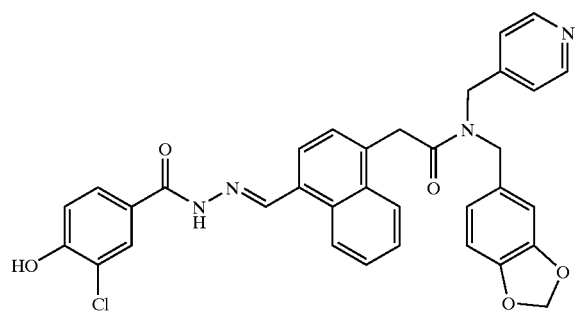
EXAMPLE 397:
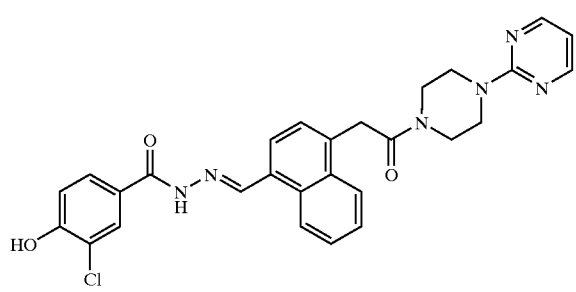
EXAMPLE 398:
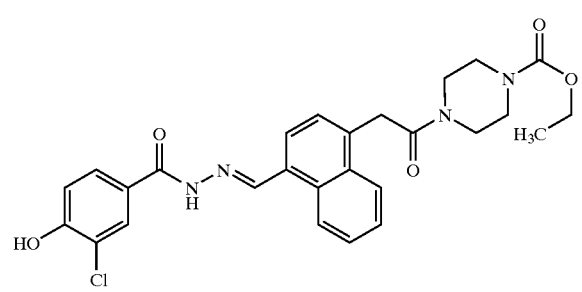
EXAMPLE 399:
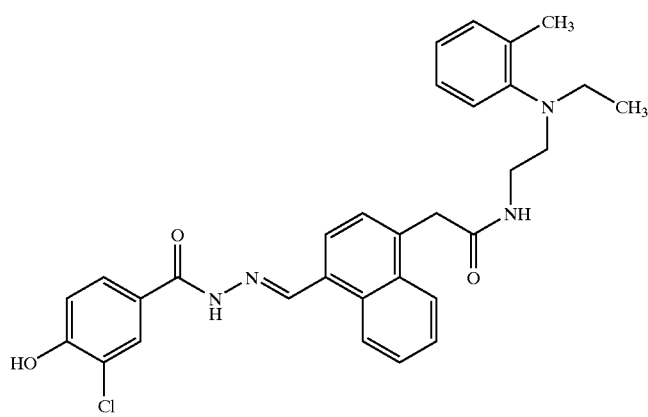

EXAMPLE 400:
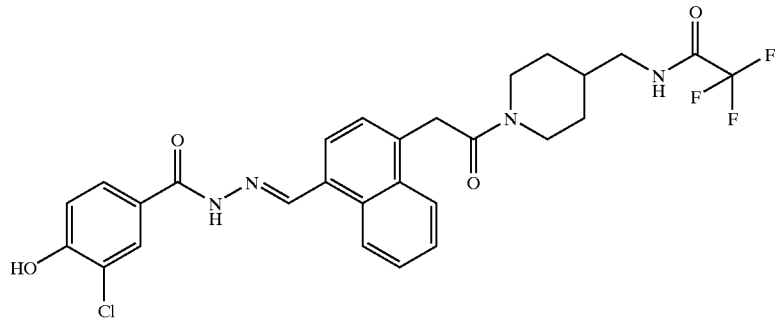
EXAMPLE 401:
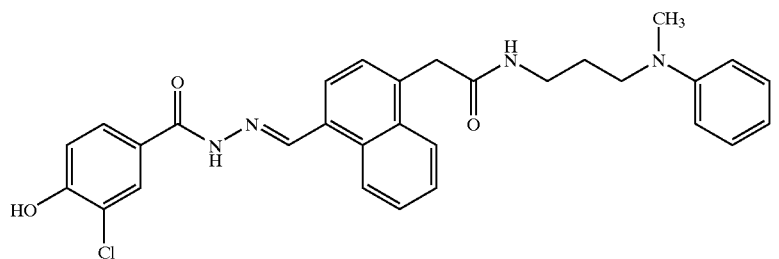
EXAMPLE 402:
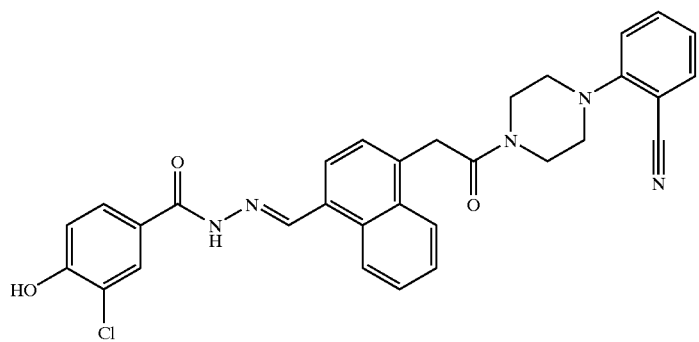
EXAMPLE 403:
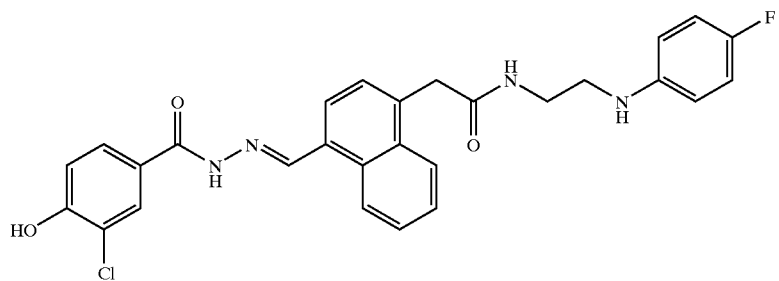

EXAMPLE 404:
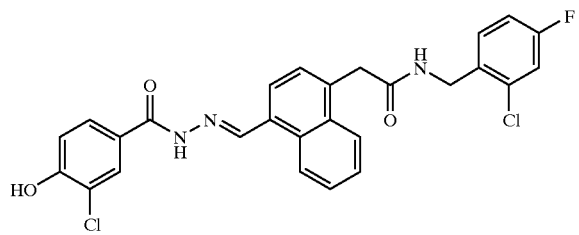
EXAMPLE 405:
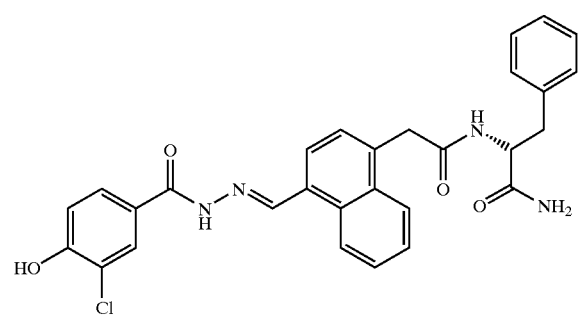
EXAMPLE 406:
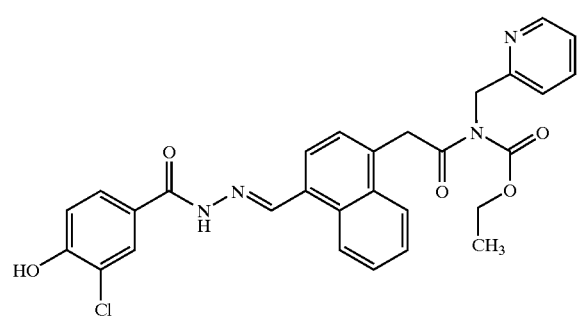
EXAMPLE 407:
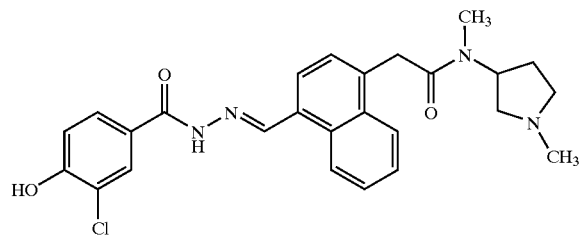
EXAMPLE 408:
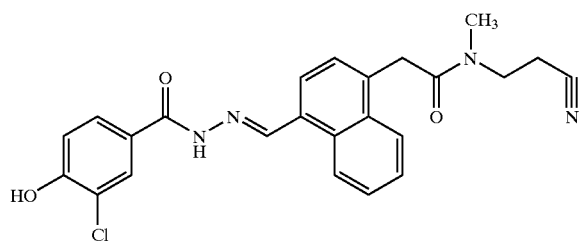
EXAMPLE 409:
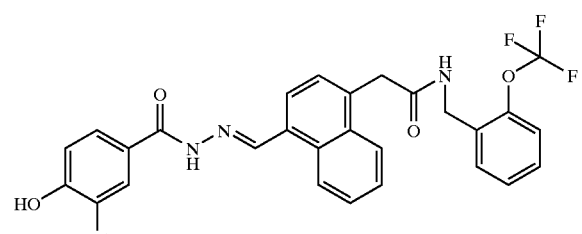
EXAMPLE 410:
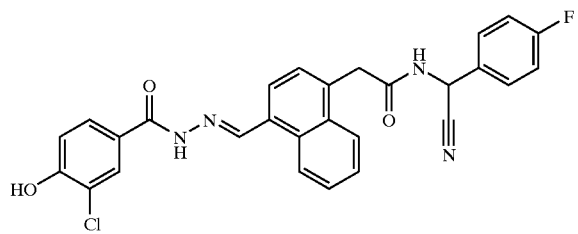
EXAMPLE 411:
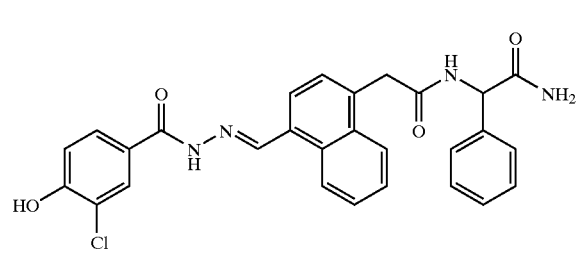
EXAMPLE 412:
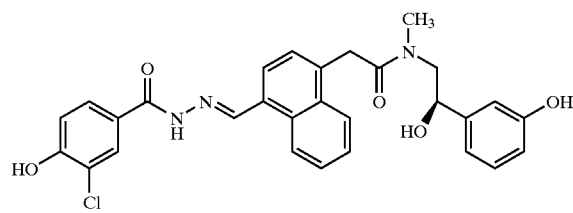
EXAMPLE 413:
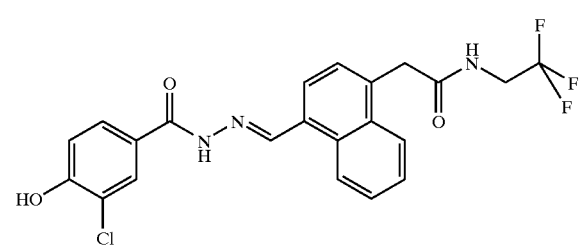

EXAMPLE 414:
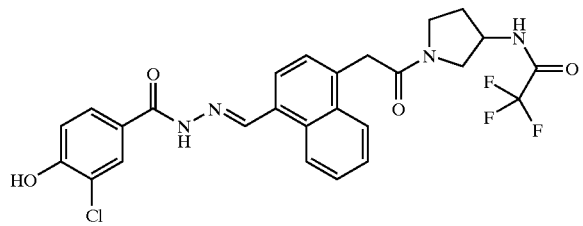
EXAMPLE 415:
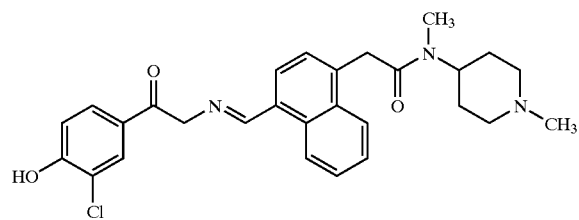
EXAMPLE 416:
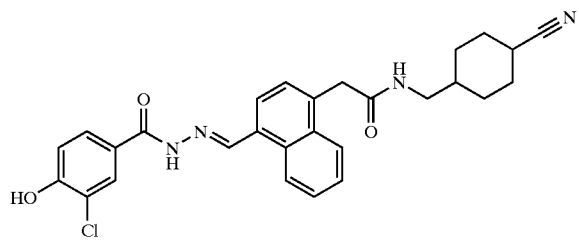
EXAMPLE 417:
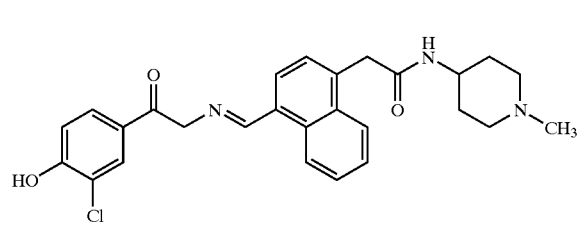
EXAMPLE 418:
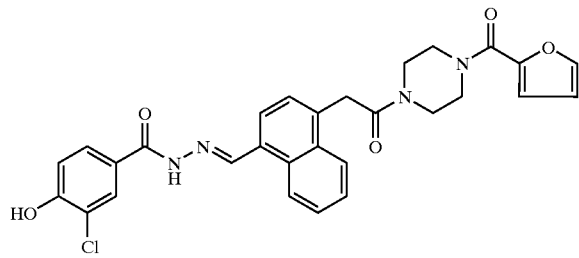
EXAMPLE 419:
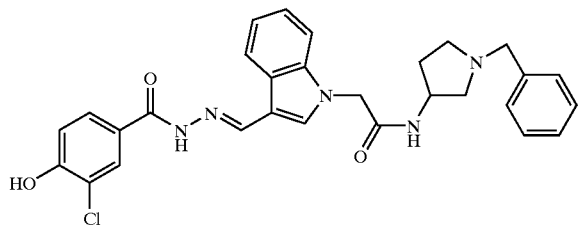
EXAMPLE 420:
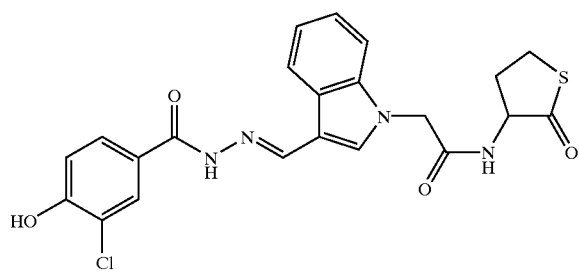
EXAMPLE 421:
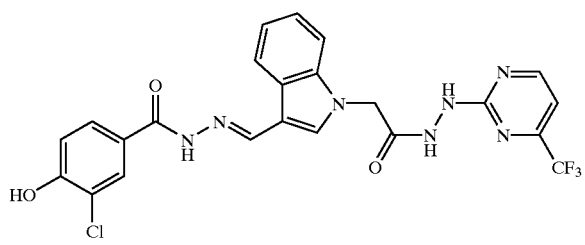
EXAMPLE 422:
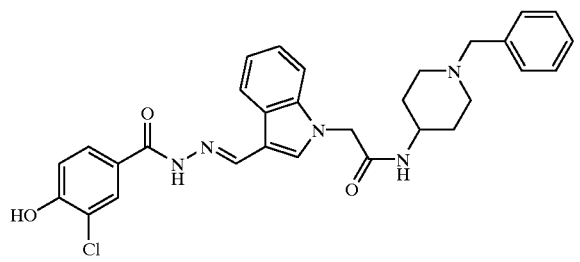
EXAMPLE 423:
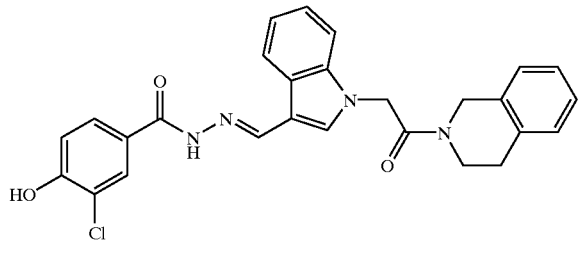

EXAMPLE 424:
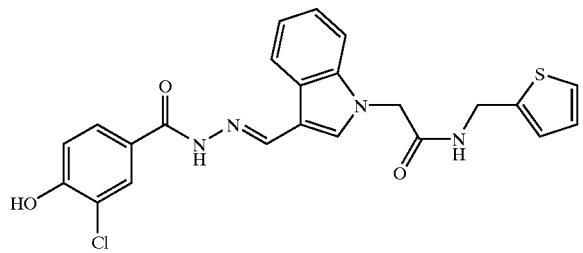
EXAMPLE 425:
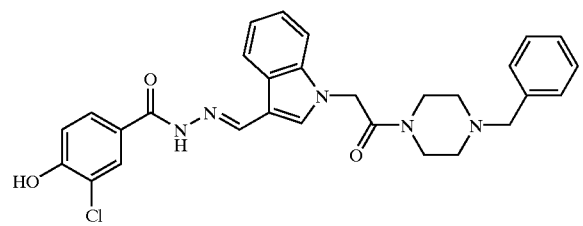
EXAMPLE 426:
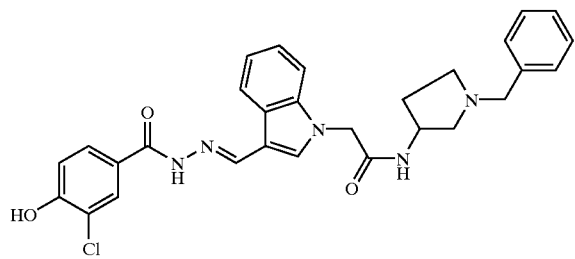
EXAMPLE 427:
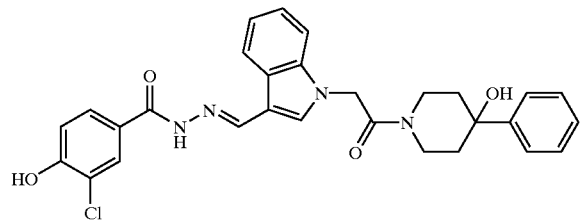
EXAMPLE 428:
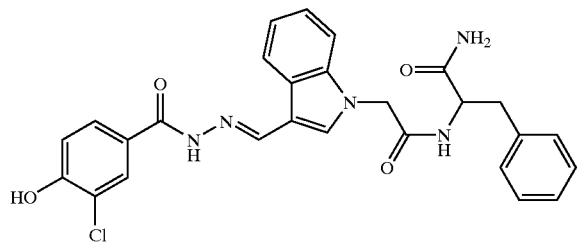
EXAMPLE 429:
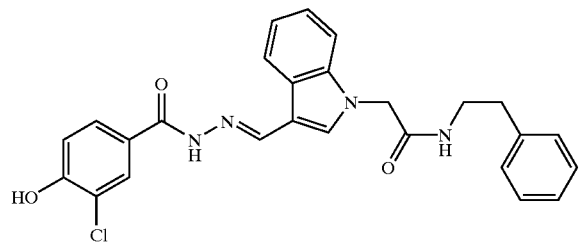
EXAMPLE 430:
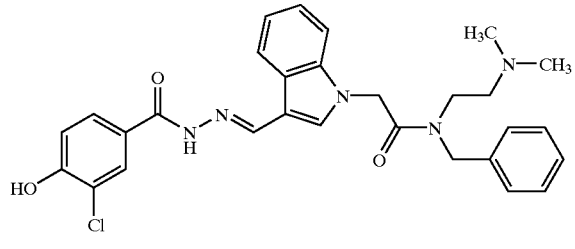
EXAMPLE 431:
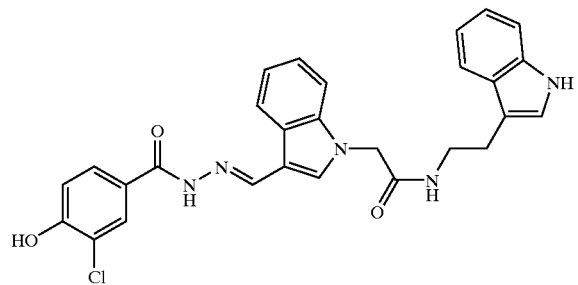
EXAMPLE 432:
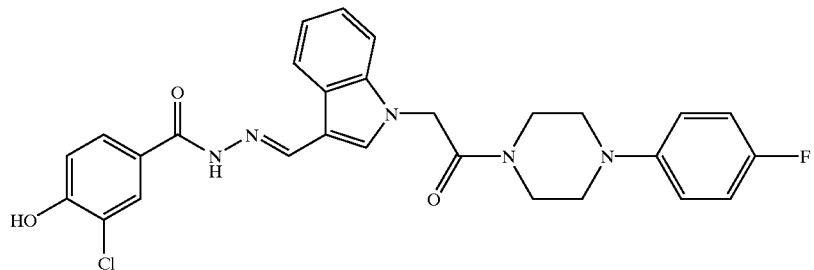

EXAMPLE 433:
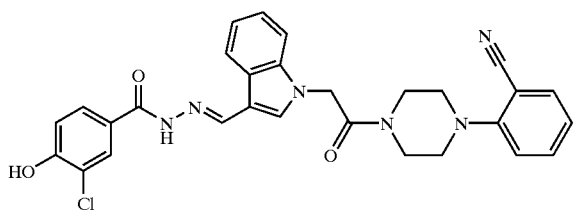
EXAMPLE 434:
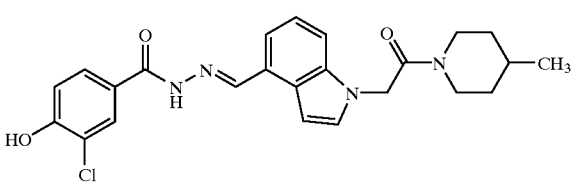
EXAMPLE 435:
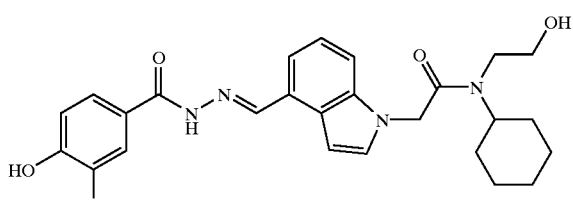
EXAMPLE 436:
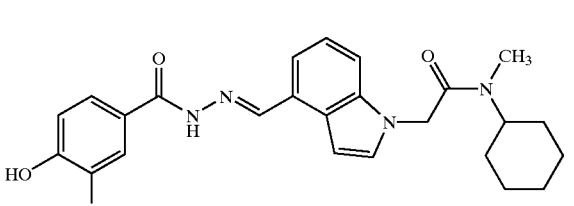
EXAMPLE 437:
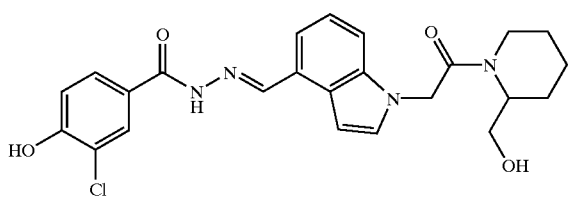
EXAMPLE 438:
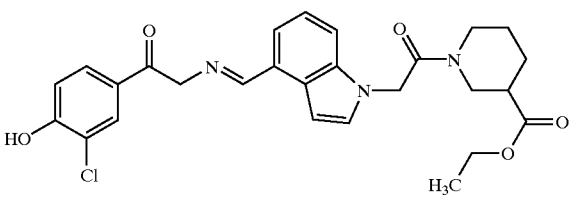
EXAMPLE 439:
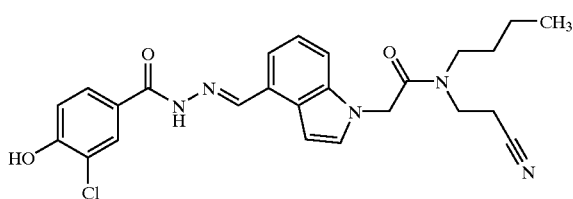
EXAMPLE 440:
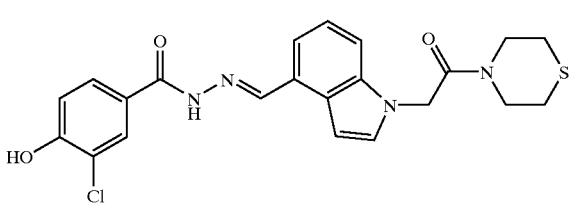
EXAMPLE 441:
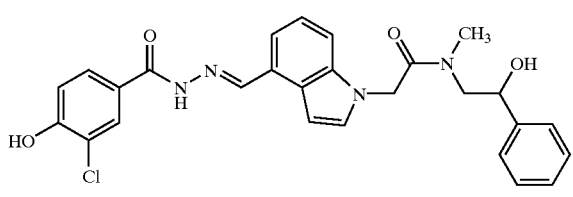
EXAMPLE 442:
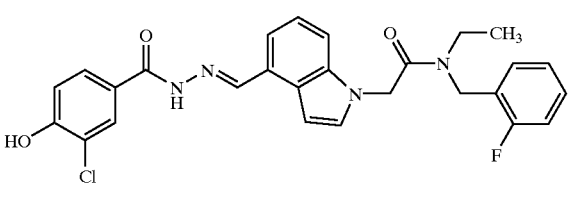
EXAMPLE 443:
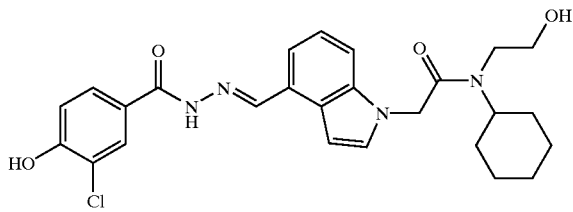
EXAMPLE 444:
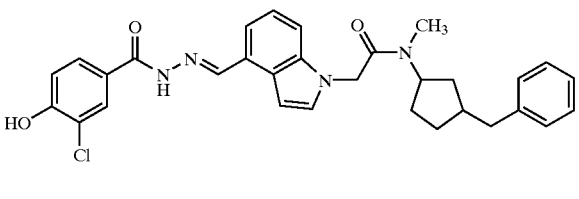
EXAMPLE 445:
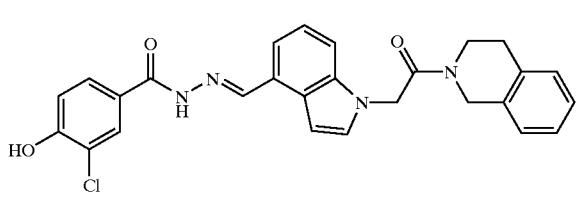
EXAMPLE 446:
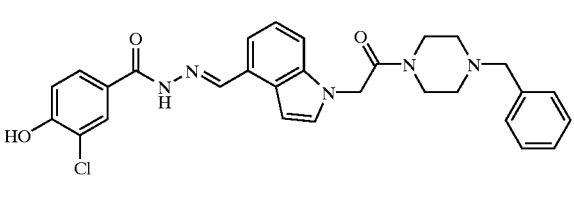

EXAMPLE 447:
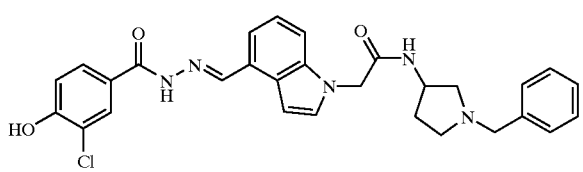
EXAMPLE 448:
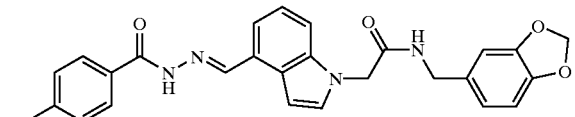
EXAMPLE 449:
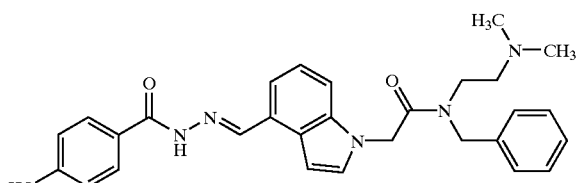
EXAMPLE 450:
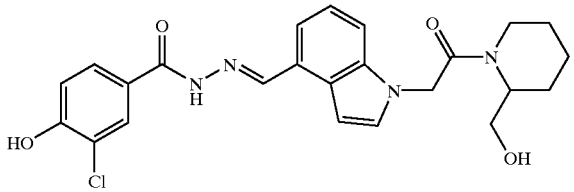
EXAMPLE 451:
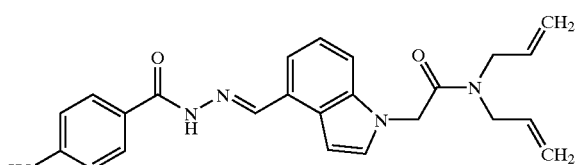
EXAMPLE 452:
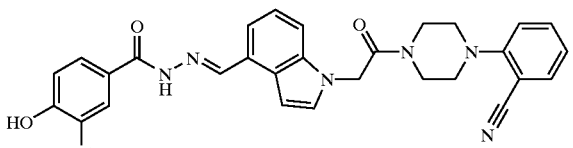
EXAMPLE 453:
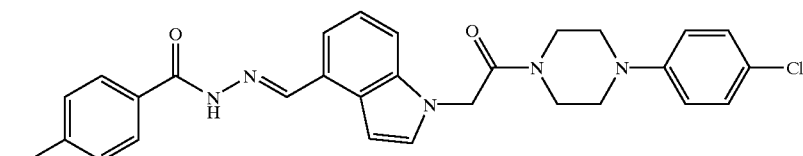
EXAMPLE 454:
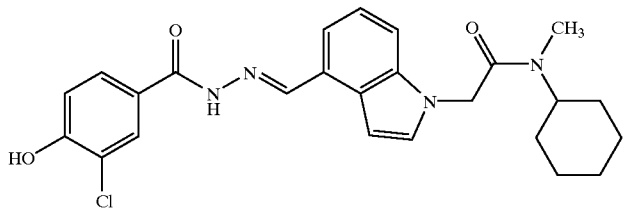
General Procedure for Synthesis of Compounds of the General Formula XIII
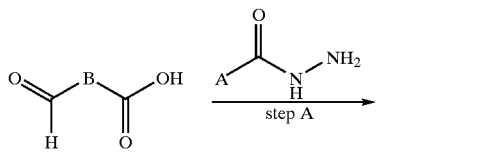
-continued
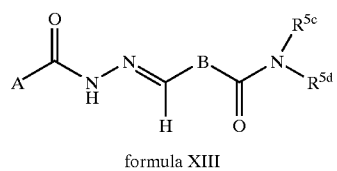
formula XIII
A and B are as defined for formula I and —NR$^{5c}$CR$^{5d}$ is
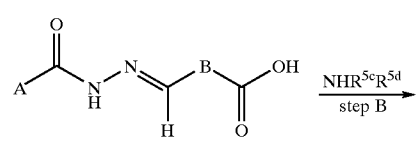
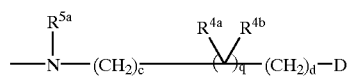

where $R^{5a}, R^{4a}, R^{4b}$, c, q, d and D are as defined for formula I or —D' where —D' is defined as a subset of —D that contains a primary or secondary amine that can react as a nucleophile.

Step A: The carbonyl compounds are treated with an acylhydrazide in a solvent. The solvent may be one of the following: ethyl alcohol, methyl alcohol, isopropyl alcohol, tert-butyl alcohol, dioxane, tetrahydrofuran, toluene, chlorobenzene, anisole, benzene, chloroform, dichloromethane, DMSO, acetic acid, water or a compatible mixture of two or more of the above solvents. A catalyst such as acetic acid can be added. A dehydrating reagent such as triethylorthoformate can also be added to the reaction mixture. The reaction is performed by stirring the reaction mixture preferably under an inert atmosphere of $N_2$ or Ar at temperatures between 0° C. to 140° C., preferably between 10° C. to 80° C. In many cases the product simply crystal out when the reaction is completed and is isolated by suction filtration. It can be further recrystallized if necessary from a solvent such as the above described reaction solvents. The product can also be isolated by concentration of the reaction mixture in vacuo, followed by column chromatography on silica gel using a solvent system such as chloroform/methanol or dichloromethane/methanol or chloroform/ethyl acetate.

Step B: The resulting acid is then coupled to a primary or secondary amine using one of the methods well-known to those skilled in the art. This coupling can be performed using one of the standard amide or peptide synthesis procedures such as by generating an active ester, an anhydride or an acid halide that can then react with the amine to give a compound of formula XIII. The product can then be isolated either by filtration or by extraction using a solvent such as ethyl acetate, toluene, dichloromethane or diethylether and the solvent may then be removed by concentration at atmospheric or reduced pressure. The product can be further purified by either recrystallization from a solvent such as ethyl alcohol, methyl alcohol, isopropyl alcohol, toluene, xylene, hexane, tetrahydrofuran, diethyl ether, dibutyl ether, water or a mixture of two or more of the above. Alternatively, the product can be purified by column chromatography using dichloromethane/methanol or chloroform/methanol or isopropyl alcohol as eluent giving a compound of formula XIII.

Specific examples illustrating the preparation of compounds of the general formula XIII according to the invention are provided below.

Preparation of 4-Formylnaphthoic Acid is Depicted Below

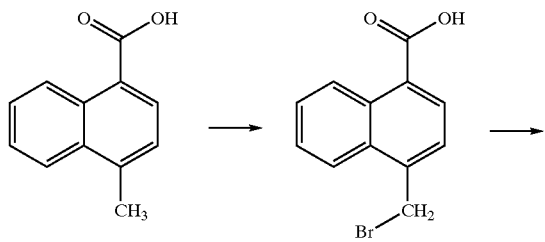

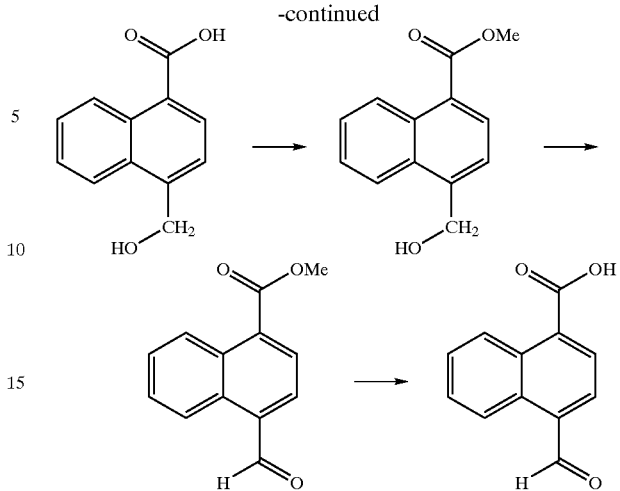

4-Bromomethylnaphthoic Acid:

A mixture of 4-methylnaphthoic acid (10 g, 54 mmol), N-bromosuccinimide (10 g, 56 mmol) and AIBN (100 mg) in $CCl_4$ (250 mL) was refluxed for 3 hr. The reaction mixture was concentrated and dissolved in ethyl acetate. The organic layer was washed with water, brine and dried over $MgSO_4$. Evaporation of the solvent gave the desired product (16 g, 80%).

$^1$H NMR (DMSO-$D_6$): δ 5.24 (s, 2H), 7.73 (m, 3H), 8.03 (d, 1H), 8.28 (d, 1H), 8.86 (d, 1H), 13.29 (brd s, 1H).

4-Hydroxymethylnaphthoic Acid:

4-Bromomethylnaphthoic acid (16 g, 160 mmol) in an aqueous solution of $K_2CO_3$ (10%, 100 mL) was stirred at 70° C. for 30 minutes. The reaction mixture was cooled and made acidic with conc. HCl. The resulting precipitate was filtered and dried to give the desired product as a yellow solid in quantitative yield.

$^1$H NMR (DMSO-$D_6$); δ 5.01 (s, 2H), 5.96 (s, 1H), 7.70 (m, 3H), 8.10 (m, 2H), 8.90 (d, 1H).

Methyl 4-Hydroxymethylnaphthoate:

A mixture of 4-hydroxymethylnaphthoic acid (10 g, 50 mmol), methanol (300 mL), and conc. $H_2SO_4$ (2 mL) was refluxed overnight. The insolubles were filtered off and the filtrate was concentrated. The residue was taken up in ethyl acetate and washed with aqueous $NaHCO_3$ (2x), brine, dried over $MgSO_4$, and concentrated to give a yellow oil. Silica gel column chromatography using ethyl acetate/hexane (1/3) gave the desired product as a yellow oil (3.3 g, 35%).

$^1$H NMR ($CDCl_3$): δ 2.05 (t, 1H), 4.01 (s, 3H), 5.22 (s, 2H), 7.66 (m, 3H), 8.09 (d, 1H), 8.16 (d, 1H), 8.96 (d, 1H).

Methyl 4-Formylnaphthoate:

To a solution of methyl 4-hydroxymethylnaphthoate above (3.3, 15.3 mmol) in dichloromethane (20 mL) was added $MnO_2$ (6.6 g, 76 mmol). After stirring the dark mixture for 16 hours, the insolubles were filtered through a bed of Celite. Evaporation of the solvent gave the desired product as a white solid in quantitative yield.

$^1$H NMR ($CDCl_3$): δ 4.06 (S, 3H), 7.75 (m, 2H), 8.03 (d, 1H), 8.20 (d, 1H), 8.80 (d, 1H), 9.27 (d, 1H), 10.50 (s, 1H).

4-Formylnaphthoic Acid:

A mixture of the methyl 4-formylnaphthoate above (2.3 g, 1 mmol) and $Na_2CO_3$ (1.25 g, 12 mmol) in water (30 mL) was heated in a water bath for approximately 2 hr until a clear solution was obtained. The solution was cooled and filtered. The filtrate was acidified with conc. HCl to give a yellow precipitate. The solids were collected and dried over night to give the desired product (1.86 g, 87%).

¹H NMR (DMSO-D₆): δ 7.76 (m, 2H), 8.22 (m, 2H), 8.71 (d, 1H), 9.20 (d, 1H), 10.49 (s, 1H).

4-[(3-Chloro-4-hydroxybenzoyl)hydrazonomethyl] naphthoic Acid (Step A)

To a solution of 3-chloro-4-hydroxybenzoic acid hydrazide (1.53 g, 8.23 mmol) in DMSO (20 mL) was added a solution of 4-formylnaphthoic acid (1.65 g, 8.23 mmol) in DMSO (2 mL). After stirring the solution for 16 hr, the reaction was diluted with ethyl acetate (30 mL) and water (30 mL). A precipitate formed. The precipitate was collected, washed with hexane and dried to give the product as a white solid in quantitative yield.

¹H NMR (DMSO-D₆): δ 4.70 (d, 1H), 7.70 (m, 2H), 7.83 (d, 1H), 8.03 (m, 2H), 8.18 (d, 1H), 8.72 (s, 1H), 8.90 (d, 1H), 9.17 (s, 1H), 11.0 (brd s, 1H), 11.94 (s, 1H), 13.4 (brd s, 1H); MS (APCI, neg): 368.5, 370.2).

General Procedure

Derivatives of 4-[(3-Chloro-4-hydroxybenzoyl) hydrazonomethyl]naphthamides (Step B)

To a solution of a derivative of 4-[(4-hydroxybenzoyl)-hydrazonomethyl]naphthoic acid in DMSO was added carbonyldiimidazole (1.2 eq). The solution was agitated for 5 minutes and diluted with DMSO to a concentration of 50 mM. The solution was then dispensed into 88 deep well plates containing solutions of amines in DMSO (50 mM). The plates were covered and agitated for 16 hours. The products were purified by HPLC.

The following compounds of formula XII were prepared:

EXAMPLE 455

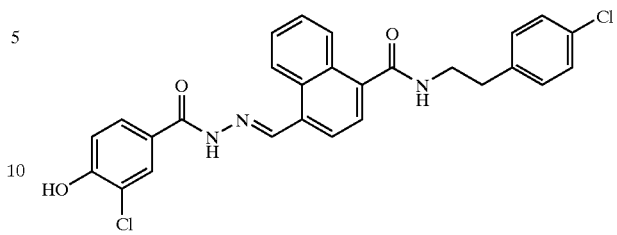

¹H NMR (DMSO-D₆): δ 2.91 (t, 2H), 3.67 (t, 2H), 7.12 (d, 1H), 7.38 (qt, 4H), 7.58 (t, 2H), 7.70 (t, 1H), 7.50 (d, 1H), 7.95 (d, 2H), 8.03 (s, 1H), 8.69 (brd t, 1H), 8.81 (d, 1H), 9.12 (s, 1H), 11.02 (s, 1H), 11.89 (s, 1H); MS (APCI): 507.3, 508.5.

EXAMPLE 456

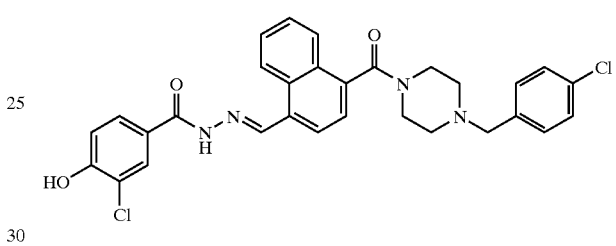

¹H NMR (DMSO-D₆): δ 2.20 (brd m, 1H), 2.30 (brd m, 1H), 2.55 (m, 2H), 3.10 (brd m, 2H), 3.50 (s, 2H), 3.72 (brd m, 1H), 3.85 (brd m, 1H), 7.10 (d, 1H), 7.36 (qt, 4H), 7.53 (d, 1H), 7.70 (m, 2H), 7.82 (m, 2H), 7.95 (d, 1H), 8.03 (s, 1H), 8.88 (d, 1H), 9.11 (s, 1H), 11.00 (brd s, 1H), 11.89 (s, 1H); MS (APCI, neg.): 559.2, 561.2.

EXAMPLE 457:

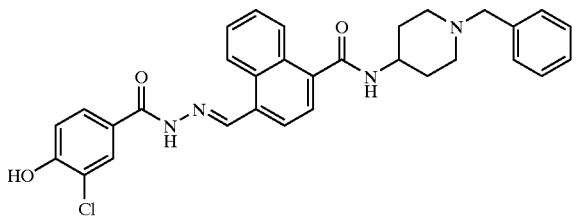

EXAMPLE 458:

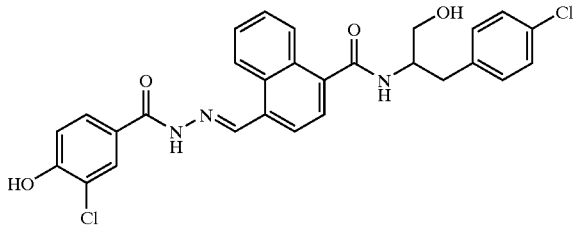

EXAMPLE 459:

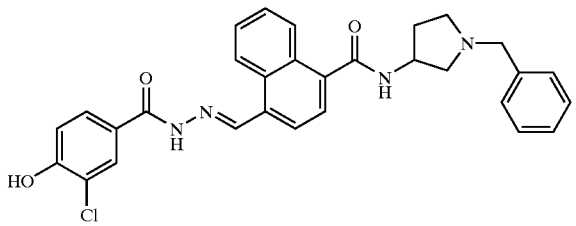

EXAMPLE 460:

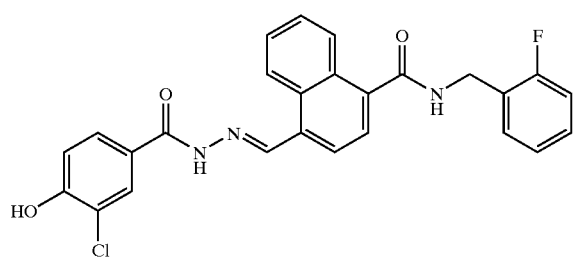

EXAMPLE 461:
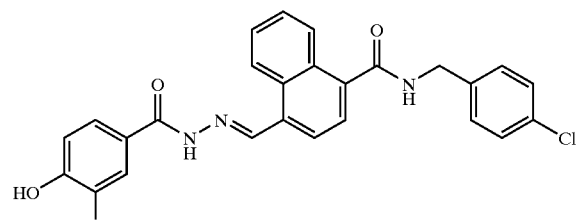
EXAMPLE 462:
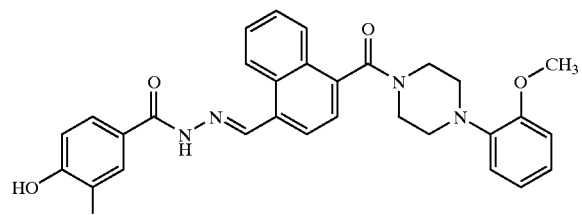
EXAMPLE 463:
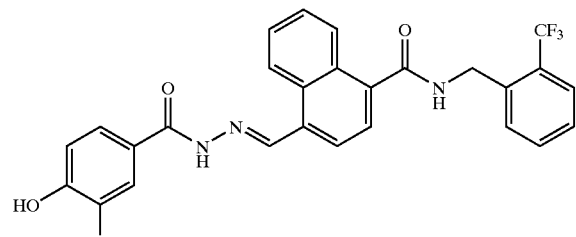
EXAMPLE 464:
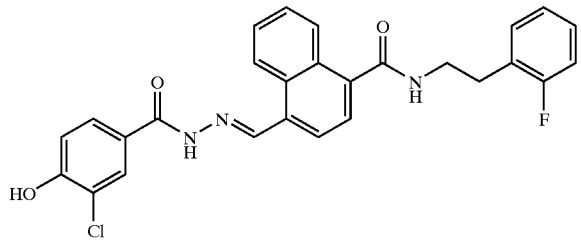
EXAMPLE 465:
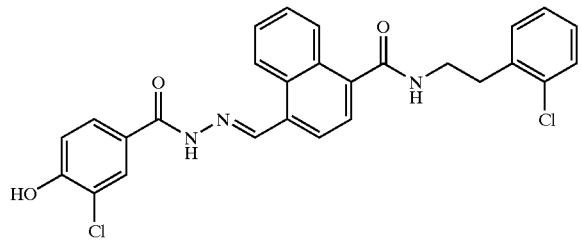
EXAMPLE 466:
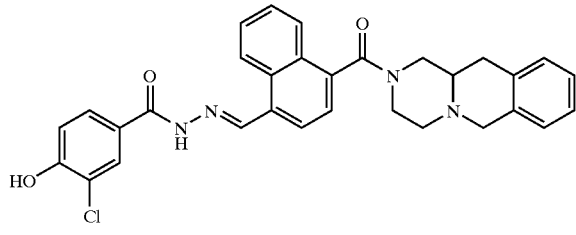
EXAMPLE 467:
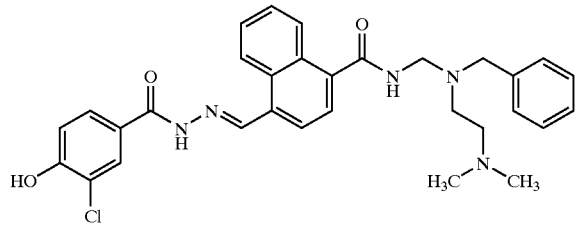
EXAMPLE 468:
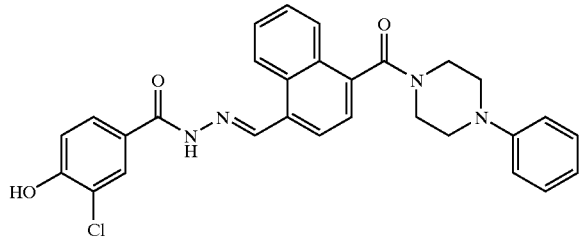
EXAMPLE 469:
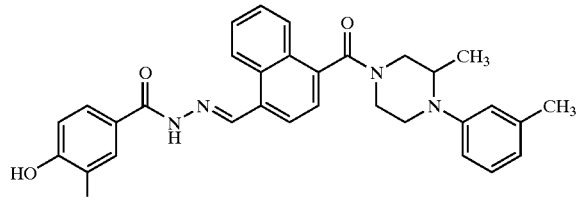
EXAMPLE 470:
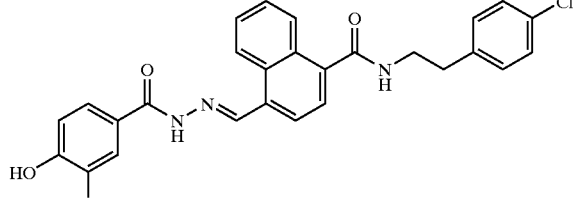
EXAMPLE 471:
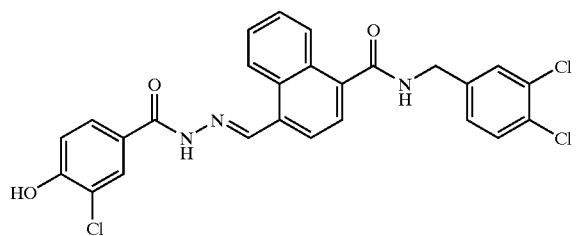
EXAMPLE 472:
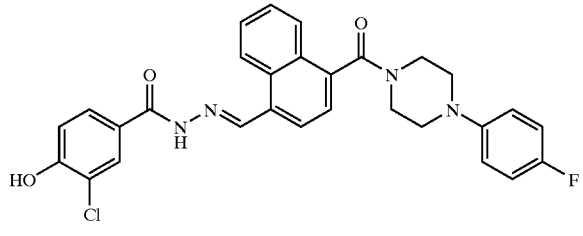

EXAMPLE 473:
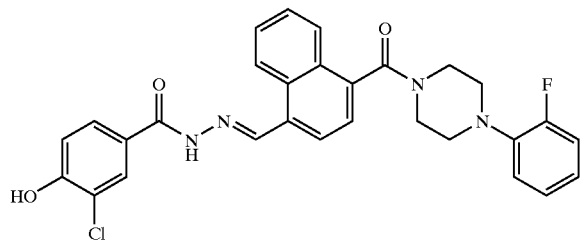
EXAMPLE 474:
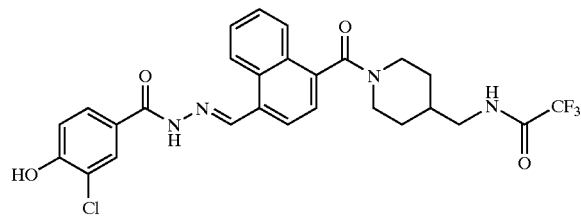
EXAMPLE 475:
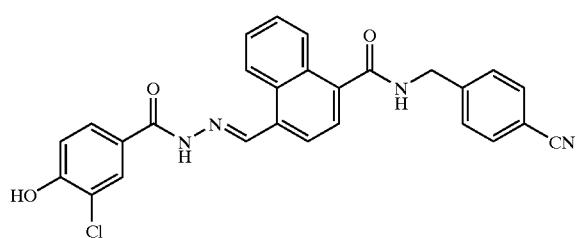
EXAMPLE 476:
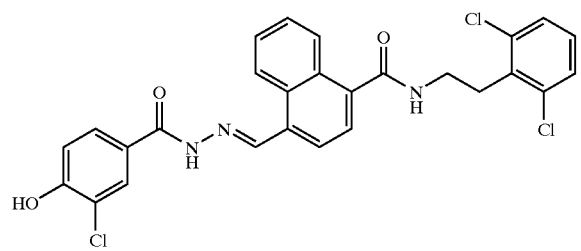
EXAMPLE 477:
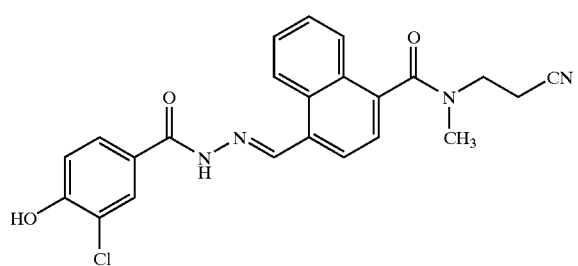
EXAMPLE 478:
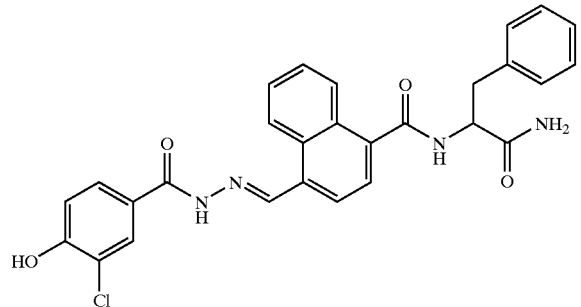
EXAMPLE 479:
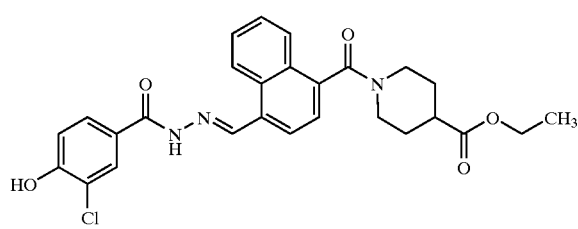
EXAMPLE 480:
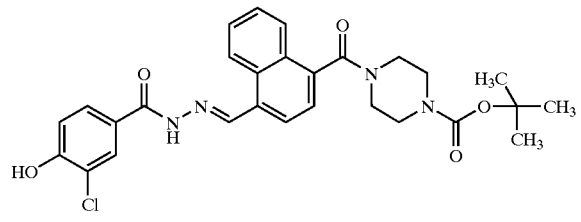
EXAMPLE 481:
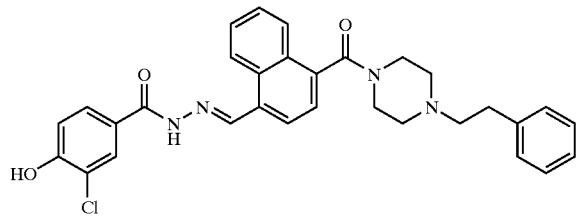
EXAMPLE 482:
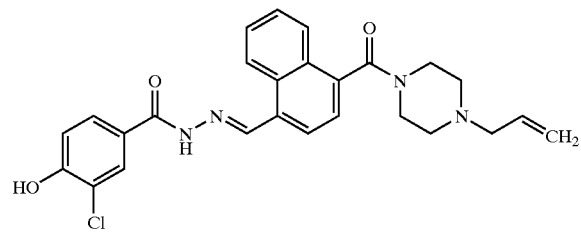

EXAMPLE 483:
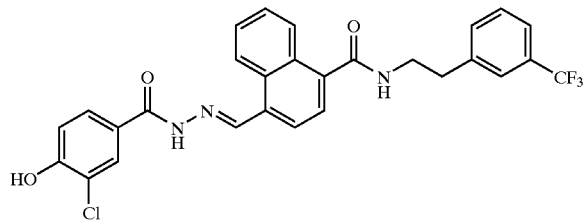
EXAMPLE 484:
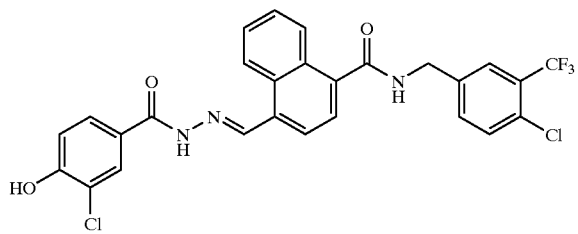
EXAMPLE 485:
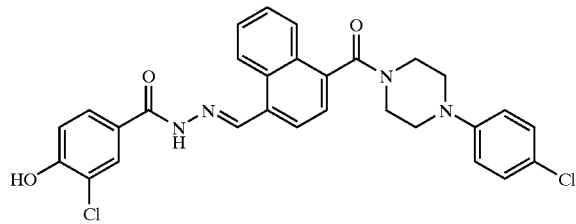
EXAMPLE 486:
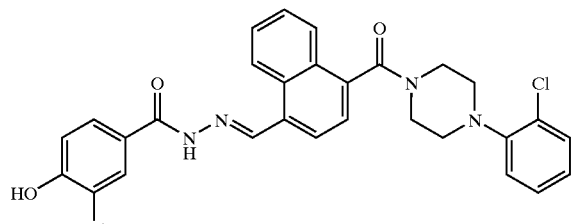
EXAMPLE 487:
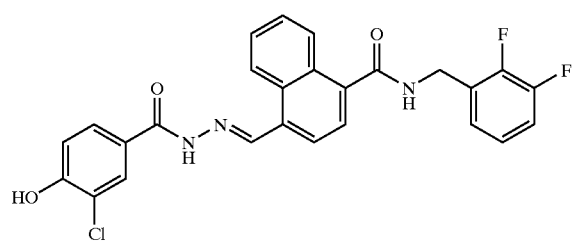
EXAMPLE 488:
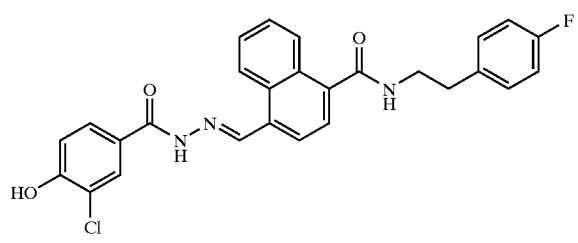
EXAMPLE 489:
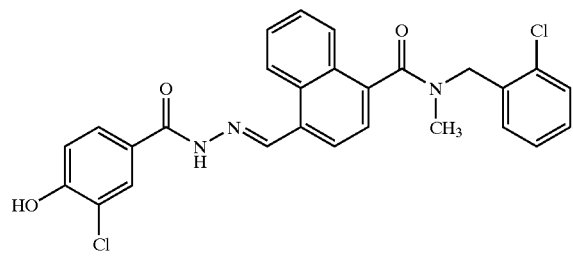
EXAMPLE 490:
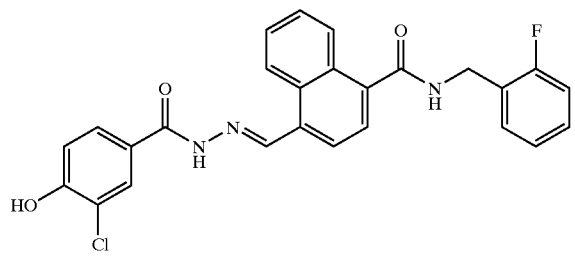
EXAMPLE 491:
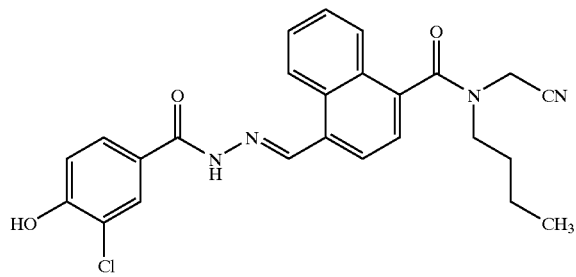
EXAMPLE 492:
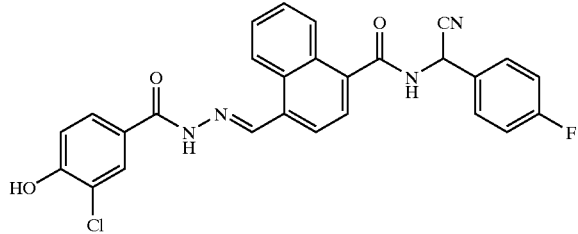

EXAMPLE 493:
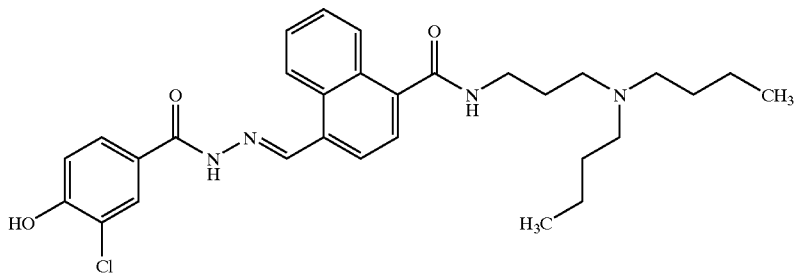
EXAMPLE 494:
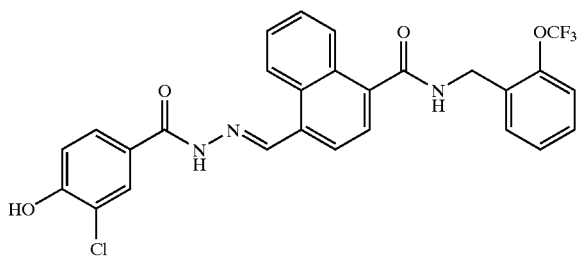
EXAMPLE 495:
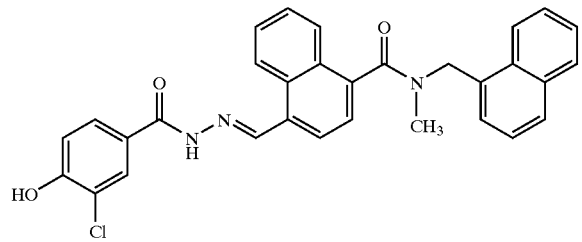
EXAMPLE 496:
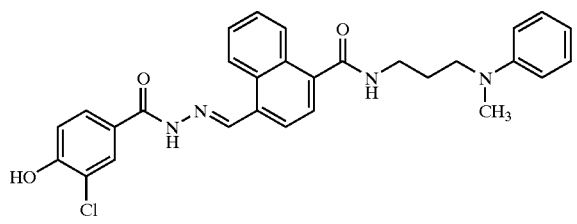
EXAMPLE 497:
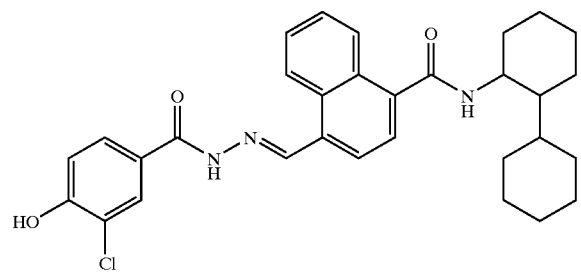
EXAMPLE 498:
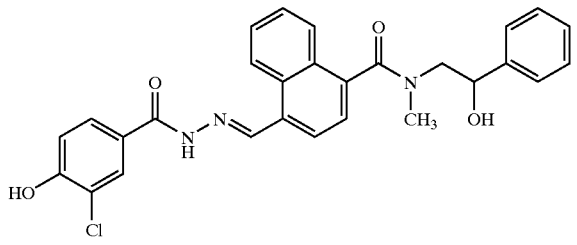
EXAMPLE 499:
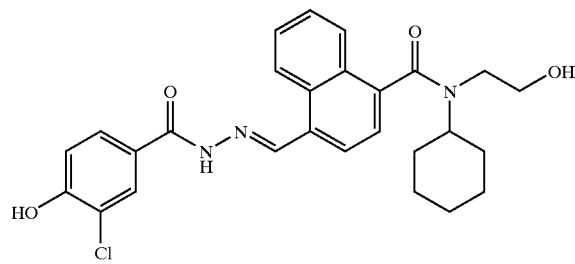
EXAMPLE 500:
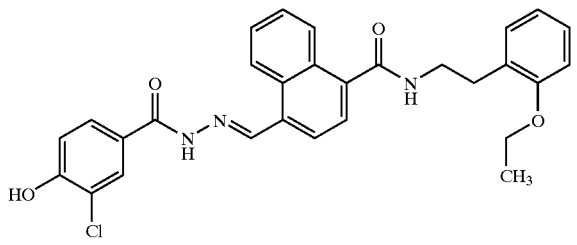
EXAMPLE 501:
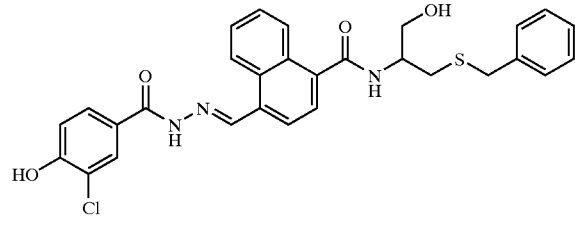

EXAMPLE 502:

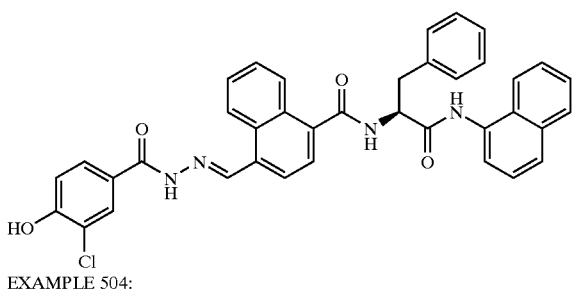

EXAMPLE 504:

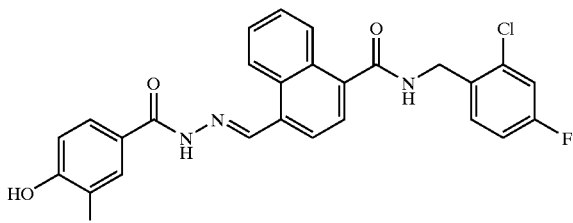

EXAMPLE 506:

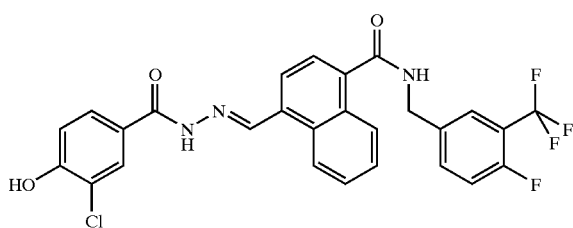

EXAMPLE 503:

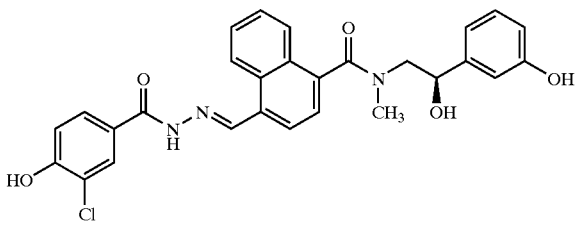

EXAMPLE 505:

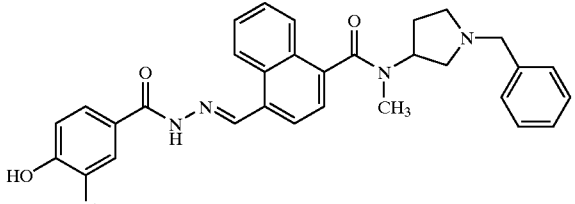

EXAMPLE 507:

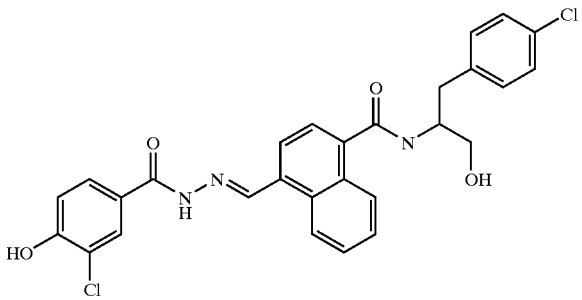

General Procedure for Synthesis of Compounds of the General Formula XIV

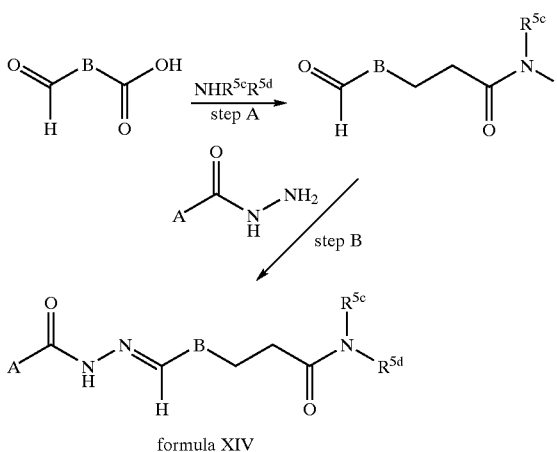

formula XIV

A and B are as defined for formula I and —NR$^{5a}$R$^{5d}$ is

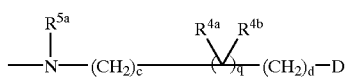

where R$^{5a}$, R$^{4a}$, R$^{4b}$, c, q, d and D are as defined for formula I or —D' where —D' is defined as a subset of —D that contains a primary or secondary amine that can react as a nucleophile.

Step A: The acid is coupled to a primary or secondary amine using one of the methods well-known to those skilled in the art. This coupling can be performed using one of the standard amide or peptide synthesis procedures such as by generating an active ester, an anhydride or an acid halide that can then react with the amine to give a compound of formula XIV. The product can then be isolated either by filtration or by extraction using a solvent such as ethyl aceate, toluene, dichloromethane or diethylether and the solvent may then be removed by concentration at atmospheric or reduced pressure. The product can be further purified by either recrystallization from a solvent such as ethyl alcohol, methyl alcohol, isopropyl alcohol, toluene, xylene, hexane, tetrahydrofuran, diethyl ether, dibutyl ether, water or a mixture of two or more of the above. Alternatively, the product can be purified by column chromatography using dichloromethane/methanol or chloroform/methanol or isopropyl alcohol as eluent giving a compound of formula XIV.

Step B: The carbonyl compounds are then treated with an acylhydrazide in a solvent. The solvent may be one of the following: ethyl alcohol, methyl alcohol, isopropyl alcohol, tert-butyl alcohol, dioxane, tetrahydrofuran, toluene, chlorobenzene, anisole, benzene, chloroform, dichloromethane, DMSO, acetic acid, water or a compatible mixture of two or more of the above solvents. A catalyst such as acetic acid can be added. A dehydrating reagent such as triethylorthoformate can also be added to the reaction mixture. The reaction is performed by stirring the reaction mixture preferably under an inert atmosphere of $N_2$ or Ar at temperatures between 0° C. to 140° C., preferably between 10° C. to 80° C. In many cases the product simply crystallizes out when the reaction is completed and is isolated by suction filtration. It can be further recrystallized if necessary from a solvent such as the above described reaction solvents. The product can also be isolated by concentration of the reaction mixture in vacuo, followed by column chromatography on silica gel using a solvent system such as chloroform/methanol or dichloromethane/methanol or chloroform/ethyl acetate.

Specific examples illustrating the preparation of compounds of the general formula XIV according to the invention are provided below.

The Preparation of 3-(4-Formylnaphthalene) propanoic Acid is Depicted Below

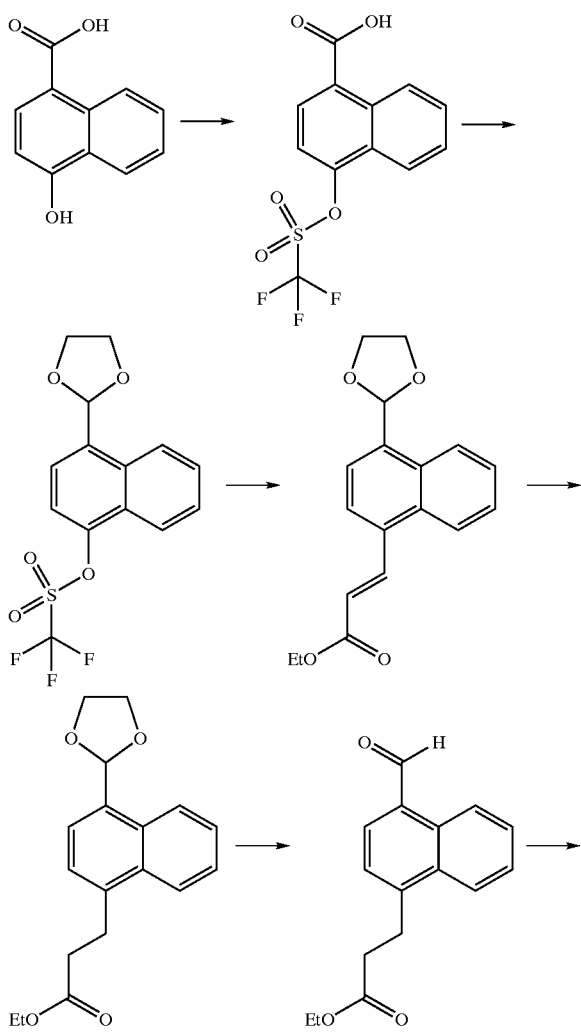

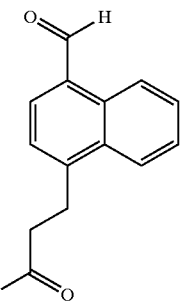

4-Trifluoromethylsulfonyloxy Naphthaldehyde:

To a solution of 4-hydroxy naphthaldehyde (34.4 g, 0.20 mol) in dichloromethane (200 mL) and pyridine (19 mL, 18.58 g, 0.23 mol) was added dropwise at 0° C. trifluoromethane sulfonic anhydride (46.75 g, 0.16 mol). The mixture was stirred at 0° C. for 2 hr and at room temperature for 16 hr. It was poured into water (200 mL), and extracted with ether (3×100 mL). The combined organic extracts were washed with water (100 mL), 0.1 N hydrochloric acid (2×100 mL), water (100 mL), brine (100 mL), dried ($MgSO_4$), and concentrated.

$^1$H NMR ($CDCl_3$) δ 7.89–7.97 (m, 3H), 8.09 (dd, J=2.8, 6.5 Hz, 1H), 8.33 (d, J=8.0 Hz,1H), 9.24 (dd, J=2.8, 6.5 Hz, 1H), 10.45 (s, 1H).

2-(4-Trifluoromethylsulfonyloxy naphthyl)dioxolane:

A solution of 4-trifluoromethylsulfonyloxy naphthaldehyde (4.09 g, 13.4 mmol), ethylene glycol (1.5 mL, 1.67 g, 26.9 mmol), and p-toluene sulfonic acid (250 mg) in toluene (250 mL) was refluxed for 16 hr using a Dean-Stark trap. The solution was allowed to reach room temperature, was washed with satd. $NaHCO_3$-sol. (2×80 mL), brine (80 mL), dried ($MgSO_4$), and concentrated to give a yellow oil (4.79 g, quant).

$^1$H NMR ($CDCl_3$) δ 4.19 (m, 4H), 6.47 (s, 1H), 7.47 (d, J=8.0 Hz, 1H), 7.66–7.70 (m, 2H), 7.81 (d, J=8.0 Hz, 1H), 8.13 (dd, J=3.3, 6.3 Hz, 1H), 8.30 (dd, J=3.3, 6.3 Hz, 1H). GCMS: 348.

2-[4-(2-Ethoxycarbonylvinyl)naphthyl]dioxolane:

Nitrogen was passed through a solution of 2-(4-trifluoromethylsulfonyloxynaphthyl) dioxolane (2.46 g, 7.06 mmol), ethyl acrylate (2.3 mL, 2.1 g, 21.2 mmol), triethylamine (4.3 g, 42.3 mmol) in DMF (6 mL) for 15 min, and bis(triphenylphosphine)palladium dichloride was added. The well stirred solution was heated at 90° C. for 8 hr, and concentrated. The residue was dissolved in ethyl acetate (50 mL), washed with brine (2×50 mL), dried ($Na_2SO_4$), and concentrated. Purification by flash chromatography using hexane/ethyl acetate 9:1 as eluent provided a yellow solid (1.13 g, 53%).

$^1$H NMR ($CDCl_3$) δ 1.38 (t, J=7.0 Hz, 3H), 3.74–4.22 (m, 4H), 8.65 (q, J=7.0 Hz, 2H), 6.50 (s, 1H), 6.53 (d, J=15.7 Hz, 1H), 7.58–7.62 (m, 2H), 7.74 (d, J=7.5 Hz, 1H), 7.80 (d, J=7.5 Hz, 1H), 8.21–8.28 (m, 2H), 8.52 (d, J=15.2 Hz, 1H).

2-[4-(2-Ethoxycarbonylethyl)naphthyl]dioxolane:

To a solution of 2-[4-(2-ethoxycarbonylvinyl)naphthyl] dioxolane (701 mg, 2.35 mmol) in ethyl acetate (15 mL) was added palladium (5% on $BaCO_3$, 51 mg). The mixture was stirred under a hydrogen atmosphere for 16 hr, filtered by suction through Celite and concentrated to provide 689 mg (98%) of a colorless oil.

$^1$H NMR ($CDCl_3$) δ 1.25 (t, J=7.0 Hz, 3H), 2.75 (t, J=8.0 Hz, 2H), 3.43 (t, J=8.0 Hz, 2H), 4.12–4.22 (m, 6H), 6.46 (s, 1H), 7.37 (d, J=7.3 Hz, 1H), 7.54–7.70 (m, 2H), 7.70 (d, J=7.3 Hz, 1H), 8.07 (dd, J=3.3, 6.5 Hz, 1H), 8.26 (dd, J=3.3, 6.5 Hz, 1H).

Ethyl 3-(4-Formylnaphthalene)propanoic Acid:

To a solution of 2-[4-(2-ethoxycarbonylethyl)naphthyl]dioxolane (689 mg, 2.29 mmol) in THF (15 mL) was added 6N hydrochloric acid (2 mL). The mixture was stirred for 16 hr at room temperature, diluted with ethyl acetate (20 mL), washed with satd. NaHCO$_3$ solution (20 mL), dried (MgSO$_4$), and concentrated to give the product as a colorless oil (407 mg, 68%) that crystallized upon sitting.

3-(4-Formylnaphthalene)propanoic Acid:

Ethyl 3-(4-formylnaphthalene)propanoic acid (310 mg, 1.2 mmol) was suspended in water (10 mL), and Na$_2$CO$_3$ (130 mg, 1.2 mmol) was added. The mixture was refluxed for 5 hr, and allowed to cool to room temperature. After acidification with conc. hydrochloric acid, a precipitate was formed. The precipitate was collected by suction, and dried at 80° C. in vacuum for 16 hr to give a white solid (300 mg, 73%).

$^1$H NMR (DMSO-D$_6$) δ 2.69 (t, J=7.0 Hz, 2H), 3.39 (t, J=7.0 Hz, 2H), 7.66–7.77 (m, 2H), 8.10 (d, J=7.3 Hz, 1H), 8.23 (dd, J=1.1, 8.0 Hz, 1H), 9.22 (dd, J=1.1 , 9.0 Hz, 1H), 10.33 (s, 1H), 12.30 (br s, 1H).

General Procedure (Step A)

Preparation of 3-(4-Formylnaphthalene)propanamides

To a solution of 3-(4-formylnaphthalene)propanoic acid (100 mg, 0.437 mmol) in DMF (3 mL) was added carbonyl diimidazole (140 mg, 0.863 mmol). The mixture was stirred at room temperature for 1 hr, and amine (1.3 equivalents) was added. After stirring at room temperature for 16 hr, the mixture was diluted with ethylacetate (5 mL), extracted with water (5 mL), 1 N hydrochloric acid (5 mL), and water (3×5 mL), dried (MgSO$_4$) and concentrated. After flash chromatography using hexane/ethylacetate 1:1 pure amide was isolated.

Examples of Amides

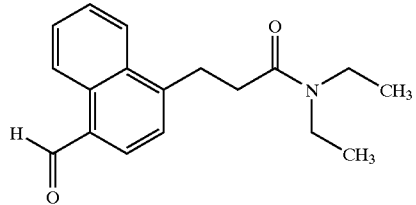

$^1$H NMR (CDCl$_3$) δ 1.06 (t, J=7.0 Hz, 3H), 1.12 (t, J=7.0 Hz, 3H), 2.79 (t, J=8.0 Hz, 2H), 3.50 (t, J=8.0 Hz, 2H), 4.12 (q, J=7.1 Hz, 2H), 7.54 (d, J=7.3 Hz, 1H), 7.64–7.71 (m, 2H), 7.92 (d, J=7.3 Hz, 1H), 8.18 (dd, J=1.3, 8.0 Hz, 1H), 9.34 (dd, J=1.3, 8.0 Hz, 1H), 10.34 (s, 1H). MS (APCI, pos.) 284.1.

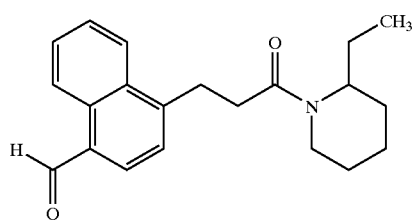

$^1$H NMR (CDCl$_3$) δ 0.77 (t, J=7.0 Hz, 3H), 0.86 (t, J=7.0 Hz, 3H), 1.15–1.82 (m, 8H), 2.58 (dt, 0.5H), 2.65–2.88 (m, 2H), 2.92 (dt, 0.5H), 3.39–3.60 (m, 2.5H), 3.62–3.73 (m, 0.5H), 4.58 (dd, 0.5H), 4.73 (m, 0.5H), 7.56 (d, J=7.3 Hz, 1H), 7.91 (d, J=7.3 Hz, 1H), 7.61–7.72 (m, 2H), 8.16 (d, J=8.3 Hz, 1H), 9.33 (d, J=8.0 Hz, 1H), 10.34 (s, 1H). MS (APCI, pos.) 325.2.

Derivatives of 4-[(4-Hydroxybenzoyl)hydrazonomethyl]naphthylpropanamides (Step B):

These compounds were prepared according to the general procedure for the synthesis of alkylidene hydrazones from the condensation of 4-formyl-1-naphthyl propanamides (from step A) and 4-hydroxybenzoic acid hydrazide derivatives.

EXAMPLE 508

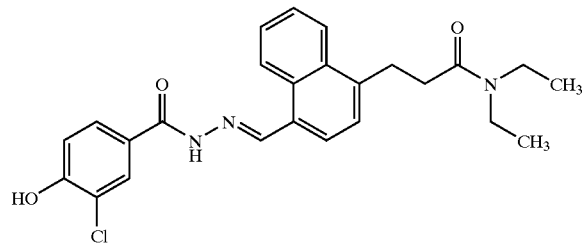

$^1$H NMR (DMSO-D$_6$) δ 0.95–1.02 (m, 6H), 2.69 (t, J=7.3 Hz, 2H), 3.19 (q, J=7.0 Hz, 2H), 3.25 (q, J=7.0 Hz, 2H), 3.33 (t, J=7.3 Hz, 2H), 7.08 (d, J=8.5 Hz, 1H), 7.49 (d, J=7.5 Hz, 1H), 7.65 (m, 2H), 7.81 (m, 2H), 8.00 (d, J=2.0 Hz, 1H), 9.17 (dd, J=2.4, 6.5 Hz, 1H), 8.87 (d, J=7.6 Hz, 1H), 9.05 (s, 1H), 11.00 (s, 1H), 11.77 (s, 1H). MS (APCI, pos.): 452.2, 454.2.

EXAMPLE 509

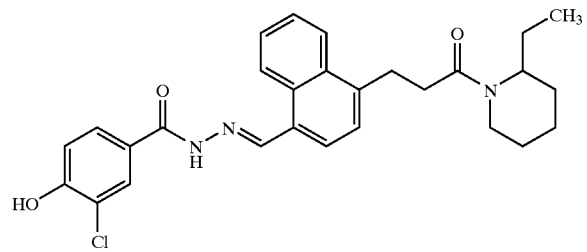

$^1$H NMR (DMSO-D$_6$) δ 0.68 (t, J=7.5 Hz, 3H), 0.75 (t, J=7.5 Hz, 3H), 0.76 (dd, 0.5H), 0.90 (dd, 0.5H), 1.02–1.68 (m, 8H), 2.49 (m, 0.5H), 2.75 (m, 2H), 2.90 (t, J=14.0 Hz, 0.5H), 3.33 (m, 2H), 3.61 (d, J=12.0 Hz, 0.5H), 3.75 (m, 0.5H), 4.36 (d, J=12.0 Hz, 0.5H), 4.53 (m, 0.5H), 7.08 (d, J=8.5 Hz, 1H), 7.50 (d, J=7.5 Hz, 1H), 7.64–7.66 (m, 2H), 7.80 (dd, J=1.9, 8.5 Hz, 1H), 7.83 (d, J=7.5 Hz, 1H), 8.00 (d, J=1.9 Hz, 1H), 8.17 (m, 1H), 8.88 (d, J=7.5 Hz, H), 7.25 (s, 1H), 11.0 (s, 1H), 11.76 (s, 1H). MS (APCI, pos.): 492.1, 494.1.

EXAMPLE 510

Ethyl 4-[(3-Chloro-4-hydroxybenzoyl)hydrazonomethyl]naphthyl Propanate

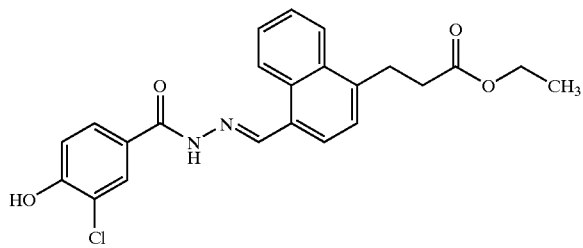

The compound was prepared according to the general procedure for the synthesis of alkylidene hydrazones from the condensation of ethyl 4-formyl-1-naphthylpropanate (from step E) and 3-chloro-4-hydroxy benzoic acid hydrazide.

$^1$H NMR (DMSO-D$_6$) δ 1.14 (t, J=7.0 Hz, 3H), 2.73 (t, J=7.5 Hz, 2H), 3.35 (t J=7.5 Hz, 2H), 4.02 (q, J=7.0 Hz, 2H), 7.08 (d, J=8.6 Hz, 1H), 7.66 (m, 2H), 7.79 (dd, J=1.8, 8.6 Hz, 1H), 7.86 (d, J=7.5 Hz, 1H), 8.85 (d, J=7.7 Hz, 1H), 9.05 (s, 1H), 11.0 (brd s, 1H), 11.78 (s, 1H). MS (APCI, pos.): 425.5, 427.3.

EXAMPLE 511

3-Chloro-4-hydroxy Benzoic Acid (4-Trifluoromethylsulfonyloxy naphthylidene) hydrazide

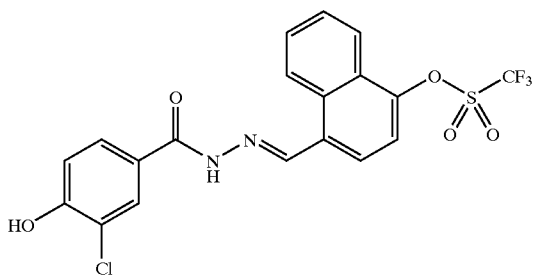

The compound was prepared according to the general procedure for the synthesis of alkylidene hydrazones from the condensation of 4-trifluoromethylsulfonyloxy naphthaldehyde 3-chloro-4-hydroxy benzoic acid hydrazide.

$^1$H NMR (DMSO-D$_6$) δ 7.09 (d, J=8.7 Hz, 1H), 7.68–7.95 (m, 4H), 8.00–8.10 (m, 3H), 8.90 (s, 1H), 9.10 (s, 1H), 11.02 (s, 1H), 11.96 (s, 1H). MS (APCI, pos.): 473.2, 475.1.

General Procedure for Synthesis of Compounds of the General Formula XV

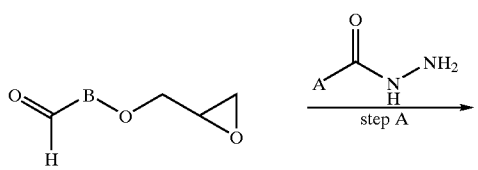

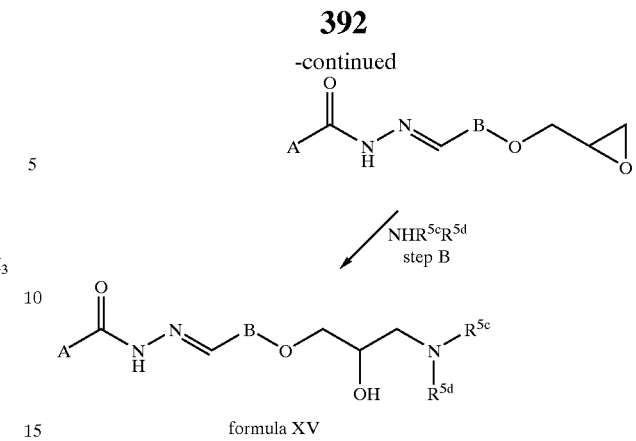

formula XV

A and B are as defined for formula I and —NR$^{5c}$R$^{5d}$ is $$-\underset{R^{5a}}{\overset{|}{N}}-(CH_2)_c-\overset{R^{4a}\ R^{4b}}{\vee}-(CH_2)_d-D$$

where R$^{5a}$, R$^{4a}$, R$^{4b}$, c, q, d and D are as defined for formula I or —D' where —D' is defined as a subset of —D that contains a primary or secondary amine that can react as a nucleophile.

Step A: The carbonyl compounds are treated with an acylhydrazine in a solvent. The solvent may be one of the following: ethyl alcohol, methyl alcohol, isopropyl alcohol, tert-butyl alcohol, dioxane, tetrahydrofuran, toluene, chlorobenzene, anisole, benzene, chloroform, dichloromethane, DMSO, acetic acid, water or a compatible mixture of two or more of the above solvents. A catalyst such as acetic acid can be added. A dehydrating reagent such as triethylorthoformate can also be added to the reaction mixture. The reaction is performed by stirring the reaction mixture preferably under an inert atmosphere of N$_2$ or Ar at temperatures between 0° C. to 140° C., preferably between 10° C. to 80° C. In many cases the product simply crystallizes out when the reaction is completed and is isolated by suction filtration. It can be further recrystallized if necessary from a solvent such as the above described reaction solvents. The product can also be isolated by concentration of the reaction mixture in vacuo, followed by column chromatography on silica gel using a solvent system such as chloroform/methanol or dichloromethane/methanol or chloroform/ethyl acetate.

Step B: The epoxide is then ring opened by a primary or secondary amine using one of the methods well-known to those skilled in the art to give a compound of formula XV. The solvent may be one of the following: ethyl alcohol, methyl alcohol, isopropyl alcohol, tert-butyl alcohol, dioxane, tetrahydrofuran, toluene, chlorobenzene, anisole, benzene, chloroform, dichloromethane, DMSO, DMF, NMP, water or a compatible mixture of two or more of the above solvents. The product can then be isolated either by filtration or by extraction using a solvent such as ethyl acetate, toluene, dichloromethane or diethylether and the solvent may then be removed by concentration at atmospheric or reduced pressure. The product can be further purified by either recrystallization from a solvent such as ethyl alcohol, methyl alcohol, isopropyl alcohol, toluene, xylene, hexane, tetrahydrofuran, diethyl ether, dibutyl ether, water or a mixture of two or more of the above. Alternatively, the product can be purified by column chromatography using dichloromethane/methanol or chloroform/methanol or isopropyl alcohol as eluent giving a compound of formula XV.

Specific examples illustrating the preparation of compounds of the general formula XV according to the invention are provided below.

The preparation of 4-(2,3-epoxypropanoxy)-1-naphthaldehyde is depicted below

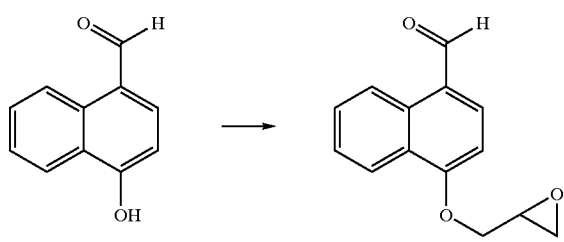

4-(2,3-Epoxypropanoxy)-1-naphthaldehyde:

To a solution of 4-hydroxy-1-naphthaldehyde (1 g, 5.8 mmol) in DMSO (20 mL) was added $K_2CO_3$(1 g, 7.2 mmol). The mixture was stirred at room temperature for 30 min, and then 2,3-epoxypropyl bromide (0.96 g, 7 mmol) was added. After stirring for 24 hr, water (100 mL) was added. The mixture was extracted with ethyl acetate (3×80 mL), dried ($MgSO_4$), and concentrated to give a brown solid (1.23 g, 93%).

$^1$H NMR (CDCl$_3$) δ 2.88 (dd, J=2.6, 4.8 Hz, 1H), 3.02 (dd, J=4.0, 4.6 Hz, 1H), 3.51–3.57 (m, 1H), 4.22 (dd, J=5.8, 11.1 Hz, 1H), 4.55 (dd, J=2.8, 11.1 Hz, 1H), 6.94 (d, J=8.1 Hz, 1H), 7.60 (t, J=7.2 Hz, 1H), 7.71 (t, J=7.7 Hz, 1H), 7.92 (d, J=8.0 Hz, 1H), 8.89 (d, J=8.4 Hz, 1H), 9.31 (d, J=8.6 Hz, 1H), 10.22 (s, 1H).

General Procedure

4-Hydroxybenzoic Acid 4-(2,3-Epoxypropanoxy)-1-naphthylidene Hydrazide Derivatives (Step A)

The compound was prepared according to the general procedure for the synthesis of alkylidene hydrazones from the condensation of the above epoxy-aldehyde with 4-hydroxy benzoic acid hydrazide derivatives.

$^1$H NMR (DMSO-d$_6$) δ 2.84 (dd, J=2.2, 4.9 Hz, 1H), 2.92 (dd, J=4.5, 4.5 Hz, 1H), 3.45–3.57 (m, 1H), 4.11 (dd, J=6.4, 11.3 Hz, 1H), 4.60 (d, J=11.3 Hz, 1H), 7.02–7.18 (m, 2H), 7.55–7.90 (m, 4H), 7.99 (d, J=1.9 Hz, 1H), 8.29 (d, J=8.3 Hz, 1H), 8.90–9.05 (d, 2H), 10.94 (s, 1H), 11.66 (s, 1H). MS (APCI, negative): 395.

General Procedure for Epoxide Ring Opening (Step B)

A mixture of epoxide (0.2 mmol) and amine (0.3 mmol) in 10 mL ethanol was refluxed for 4 hr. A red oil was obtained after concentration. Products were purified by preparatory HPLC.

Examples of Compounds of Formula XV

EXAMPLE 512

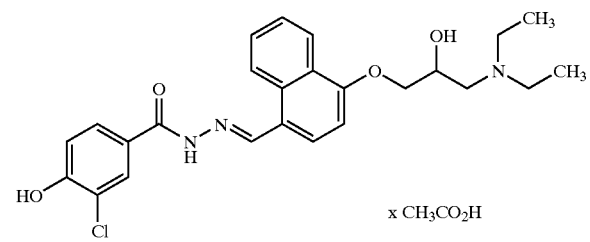

x CH$_3$CO$_2$H $^1$H NMR (DMSO-d$_6$) δ 0.95 (t, J=6.9 Hz, 6H), 1.90 (s, 3H), 2.50, 2.62 (2q, J=6.6 Hz, 4H), 2.70 (dd, J=6.6, 13.0 Hz, 1H), 2.88 (dd, J=7.0, 14.2 Hz, 1H), 3.95–4.35 (m, 3H), 7.02 (d, J=8.7 Hz, 1H), 7.06 (d, J=8.3 Hz, 1H), 7.55–7.85 (m, 4H), 7.96 (d, J=1.9 Hz, 1H), 8.36 (d, J=8.3 Hz, 1H), 8.85–9.05 (d, 2H), 11.60 (s, 1H); MS (APCI, pos.): 470.

EXAMPLE 513

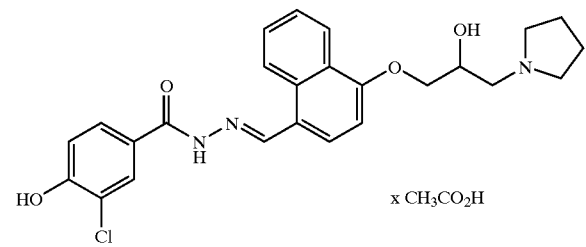

x CH$_3$CO$_2$H $^1$H NMR (DMSO-d$_6$) δ 1.67 (brd s, 4H), 1.88 (s, 3H), 2.50–2.85 (m, 6H), 4.0–4.3 (m, 3H), 7.00–7.12 (t, 2H), 7.55–7.85 (m, 4H), 7.97 (s, 1H), 8.36 (d, J=8.3 Hz, 1H), 8.85–9.05 (d,2H), 11.63 (s, 1H); MS (APCI, pos.): 468.

EXAMPLE 514

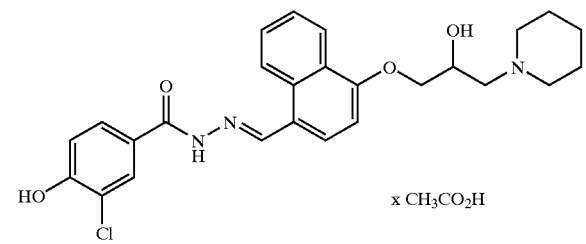

x CH$_3$CO$_2$H $^1$H NMR (DMSO-d$_6$) δ 1.30–1.55 (m, 6H), 1.88 (s, 3H), 2.35–2.60 (m, 6H), 4.05–4.30 (m, 3H), 7.04 (d, J=8.5 Hz, 1H), 7.12 (d, J=8.3 Hz, 1H), 7.55–7.85 (m, 4H), 7.97 (d, J=2.1 Hz, 1H), 8.36 (d, J=8.2 Hz, 1H), 8.85–9.05 (d, 2H), 11.62 (s, 1H); MS (APCI, pos.): 470.

EXAMPLE 515

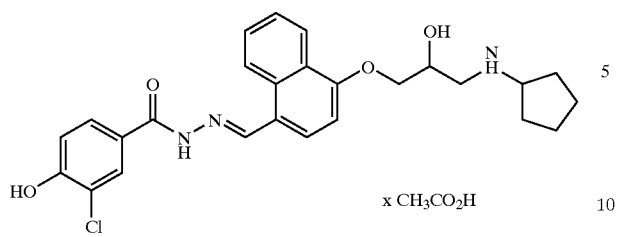

x CH₃CO₂H

¹H NMR (DMSO-d₆) δ 1.25–1.82 (m, 8H), 1.88 (s, 3H), 2.68–2.90 (m, 2H), 3.08 (m, 1H), 4.0–4.25 (m, 3H), 7.03 (d, J=8.6 Hz, 1H), 7.07 (d, J=8.3 Hz, 1H), 7.52–7.85 (m, 4H), 7.97 (d, J=1.4 Hz, 1H), 8.34 (d, J=8.4 Hz, 1H), 8.85–9.0 (d, 2H), 11.61 (s, 1H); MS (APCI, pos.): 482.

EXAMPLE 516

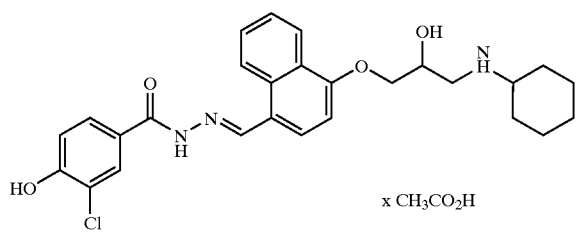

x CH₃CO₂H

¹H NMR (DMSO-d₆) δ 0.95–1.80 (m, 10H), 1.88 (s, 3H), 2.45 (m, 1H), 2.70–2.90 (m, 2H), 3.98–4.30 (m, 3H), 7.02 (d, J=8.52 Hz, 1H), 7.07 (d, J=8.2 Hz, H), 7.52–7.75 (m, 4H), 7.97 (d, J=2.05 Hz, 1H), 8.34 (d, J=8.33 Hz, 1H), 8.87–9.00 (m, 2H), 11.61 (s, 1H); MS (APCI, pos.): 496.

EXAMPLE 517

3-Chloro-4-hydroxybenzoic Acid 4-(3-Hydroxypropyl)naphthylmethylene Hydrazide

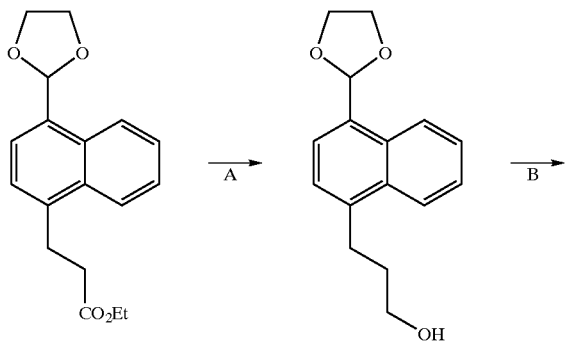

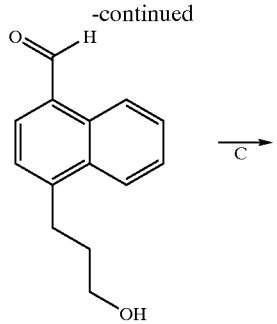

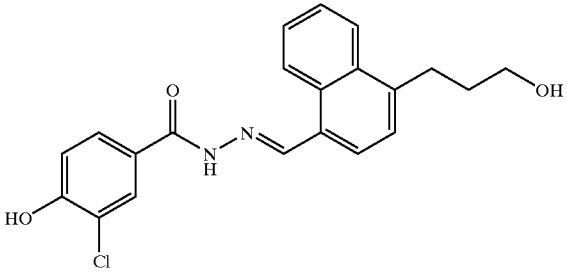

2-[4-(3-Hydroxypropyl)naphthyl]dioxolane (step A):

To a solution of 2-[4-(2-ethoxycarbonylethyl)naphthyl] dioxolane (210 mg, 0.70 mmol) in anhydrous THF (5 mL) was added at 0° C. 1M lithium aluminum hydride in THF (0.5 mL). THF (5 mL) was added and the mixture was stirred at room temperature for 16 hr, diluted with water (10 mL), acidified with conc. hydrochloric acid, and extracted with ether (3×10 mL). The combined organic extracts were dried (MgSO₄), and concentrated. The residue was purified by flash chromatography using hexane/ethyl acetate 2:1 as eluent to provide 67 mg (37%) of a colorless oil.

¹H NMR (CDCl₃) δ 1.51 (brd s, 1H), 1.99–2.04 (m, 2H), 3.19 (t, J=7.4 Hz, 2H), 3.75 (t, J=6.3 Hz, 2H), 4.16–4.22 (m, 4H), 6.47 (s, 1H), 7.35 (d, J=7.3 Hz, 1H), 7.52–7.70 (m, 2H), 7.70 (d, J=7.3 Hz, 1H), 8.11 (d, J=9.8 Hz, 1H), 8.25 (d, J=9.8 Hz, 1H). GCMS: 258.

1-Formyl-4-(3-hydroxypropyl)naphthalene (Step B):

To a solution of 2-[4-(3-hydroxypropyl)naphthyl] dioxolane (67 mg, 0.26 mmol) in anhydrous THF (5 mL) was added 1 N hydrochloric acid (1 mL). The mixture was stirred at room temperature for 48 hr, diluted with ethyl ether (20 mL), washed with satd. NaHCO₃ solution (2×10 mL), dried (MgSO₄), concentrated and coevaporated with CHCl₃ (3×10 mL) to yield 40 mg (72%) of a colorless oil.

¹H NMR (CDCl₃) δ 1.56 (brd s, 1H), 2.02–2.08 (m, 2H), 3.27 (t, J=7.5 Hz, 2H), 3.78 (t, J=6.4 Hz, 2H), 7.53 (d, J=7.3 Hz, 1H), 7.62–7.70 (m, 2H), 7.92 (d, J=7.3 Hz, 1H), 9.17 (d, J=8.3 Hz, 1H), 9.34 (d, J=8.6 Hz, 1H), 10.34 (s, 1H).

3-Chloro-4-hydroxybenzoic Acid 4-(3-Hydroxypropyl) naphthylmethylene Hydrazide (Step C):

This compound was prepared according to the general procedure for the synthesis of alkylidene hydrazones by condensation of 1-formyl-4-(3-hydroxypropyl) naphthalene from step B and 3-chloro-4-hydroxy benzoic acid hydrazide.

¹H NMR DMSO-D₆ δ 1.83 (m, 2H), 3.12 (t, J=7.5 Hz, 2H), 3.51 (dt, J=4.9, 7.0 Hz, 2H), 7.09 (d, J=8.5 Hz, 1H), 7.47 (d, J=7.5 Hz, 1H), 7.65 (m, 2H), 7.80 (dd, J=2.0, 8.5 Hz, 1H), 7.86 (d, J=7.5 Hz, 1H), 8.00 (d, J=2.0 Hz, 1H), 8.19 (dd, J=2.5, 7.0 Hz, 1H), 8.84 (d, J=8.4 Hz, 1H), 9.05 (s, 1H), 10.98 (s, 1H), 11.76 (s, 1H). MS (APCI, pos.): 383.1, 385.1.

EXAMPLE 518

4-[(3-Chloro-4-hydroxybenzoyl)hydrazonomethyl] naphthyl Diethylacrylamide

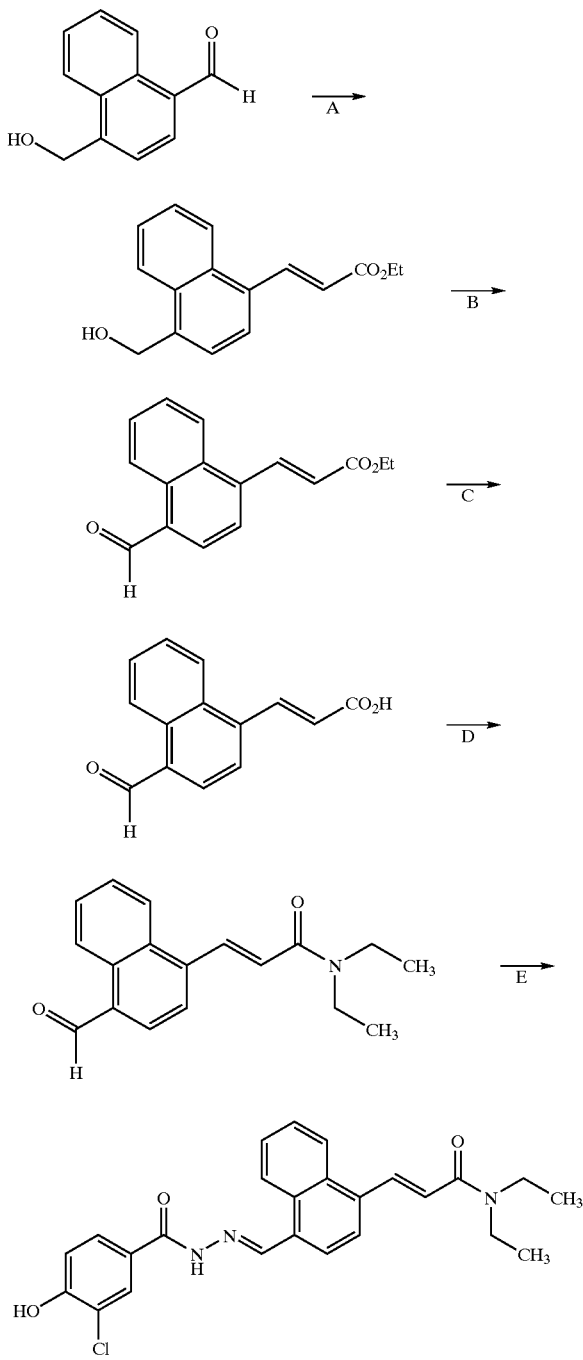

Ethyl(4-Hydroxymethyl)naphthalene Acrylate (Step A):

To a suspension of sodium hydride (160 mg, 60% dispersion in mineral oil, 4.00 mmol) in THF (10 mL) at 0° C. was added triethylphosphonoacetate (0.77 mL, 670 mg, 3.88 mmol). The mixture was stirred at 0° C. for 1 hr, and 4-hydroxymethyl naphthaldehyde (600 mg, 3.2 mmol) in THF (5 mL) was added at the same temperature. The mixture was stirred at room temperature for 16 hr, diluted with satd. NH$_4$Cl-solution (10 mL), and extracted with ethyl acetate (3×10 mL). The combined organic extracts were dried (MgSO$_4$), and concentrated, to provide 900 mg of a colorless oil, which was used without further purification in the next step.

$^1$H NMR (CDCl$_3$) δ 1.37 (t, J=7.1 Hz, 3H), 1.86 (brd s, 1H), 4.32 (q, J=7.1 Hz, 2H), 5.17 (s, 2H), 6.50 (d, J=15.7 Hz, 1H), 7.54–7.62 (m, 2H), 7.70 (d, J=7.4 Hz, 1H), 8.13 (dd, J=2.8, 9.8 Hz, 1H), 8.21 (dd, J=2.8, 9.8 Hz, 1H), 8.49 (d, J=15.7 Hz, 1H).

Ethyl 4-Formylnaphthalene Acrylate (Step B):

The crude material (900 mg) from step A was dissolved in chloroform (10 mL), and manganese dioxide (1.5 g, 17 mmol) was added. After stirring at room temperature for 16 h, the suspension was filtered by suction through Celite, and the filtrate was concentrated. Flash chromatography using hexane/ethyl acetate 5:1 provided 491 mg (60% over 2 steps) of a colorless oil.

$^1$H NMR (CDCl$_3$) δ 1.39 (t, J=7.1 Hz, 3H), 1.86 (brd s, 1H), 4.34 (q, J=7.1 Hz, 2H), 6.60 (d, J=15.7 Hz, 1H), 7.68–7.75 (m, 2H), 7.85 (d, J=7.4 Hz, 1H), 8.00 (d, J=7.4 Hz, 1H), 8.25 (d, J=8.1 Hz, 1H), 8.50 (d, J=15.7 Hz, 1H), 9.31 (dd, J=1.3, 8.1 Hz, 1H), 10.43 (s, 1H). MS (APCI, neg.): 254.1.

4-Formylnaphthalene Acrylic Acid (Step C):

A suspension of ethyl 4-formylnaphthalene acrylate (391 mg, 1.53 mmol), sodium carbonate (195 mg, 1.84 mmol) in water (10 mL) was refluxed for 16 hr. The cold solution was filtered, and the filtrate was acidified with conc. hydrochloric acid. The precipitate was collected by suction and dried for 48 hr in vacuum to give the product (325 mg, 94%) as a yellow solid.

$^1$H NMR (DMSO-D$_6$) δ 6.72 (d, J=15.7 Hz, 1H), 7.71–7.75 (m, 2H), 8.12 (d, J=7.45 Hz, 1H), 8.20 (d, J=7.5 Hz, 1H), 8.30 (d, J=8.0 Hz, 1H), 8.40 (d, J=15.7 Hz, 1H), 9.21 (d, J=8.0 Hz, 1H), 10.43 (s, 1H).

4-Formylnaphthalene Diethyl Acrylamide (Step D):

To a solution of 4-formylnaphthalene acrylic acid (210 mg, 0.92 mmol) in DMF (4 mL) was added carbonyl diimidazole (180 mg, 1.10 mmol). The mixture was stirred at room temperature for 1 hr, and diethylamine (0.1 mL, 71 mg, 0.97 mmol) was added. After stirring at room temperature for 16 hr, the mixture was diluted with ethylacetate (5 mL), extracted with water (5 mL), 1 N hydrochloric acid (5 mL), and water (3×5 mL), dried (MgSO$_4$) and concentrated. After flash chromatography using hexane/ethylacetate 1:1, 115 mg (43%) of a yellow oil was obtained.

$^1$H NMR (CDCl$_3$) δ 1.25 (t, J=7.1 Hz, 3H), 1.30 (t, J=7.1 Hz, 3H), 3.55 (m, 4H), 6.97 (d, J=15.7 Hz, 1H), 7.63–7.76 (m, 2H), 7.80 (d, J=7.4 Hz, 1H), 7.99 (d, J=7.4 Hz, 1H), 8.29 (d, J=8.3 Hz, 1H), 8.51 (d, J=15.7 Hz, 1H), 9.30 (d, J=8.3 Hz, 1H), 10.43 (s, 1H).

4-[(3-Chloro-4-hydroxybenzoyl)hydrazonomethyl]naphthyl Diethylacrylamide (Step E):

The compound was prepared according to the general procedure for the synthesis of alkylidene hydrazones from the condensation of 4-formyl-1-naphthyl diethylacrylamide (from step D) and 3-chloro-4-hydroxy benzoic acid hydrazide.

$^1$H NMR (DMSO-D$_6$) δ 1.11 (t, J=7.0 Hz, 3H), 1.18 (t, J=7.0 Hz, 3H), 3.42 (q, J=7.0 Hz, 1H), 3.56 (q, J=7.0 Hz, 2H), 7.10 (d, J=8.5 Hz, 1H), 7.22 (d, J=15.1 Hz, 1H), 7.67–7.72 (m, 2H), 7.81 (d, J=8.3 Hz, 1H), 7.96–8.03 (m, 2H), 8.06 (d, J=7.7 Hz, 1H), 8.26 (dd, J=2.1, 7.2 Hz, 1H), 8.32 (d, J=15.1 Hz, 1H), 8.83 (d, J=7.0 Hz, 1H), 9.13 (s, 1H), 11.00 (s, 1H), 11.86 (s, 1H). MS (APCI, pos.): 450.3.

EXAMPLE 519

Ethyl 4-[(3-Chloro-4-hydroxybenzoyl)hydrazonomethyl]naphthyl Acrylate

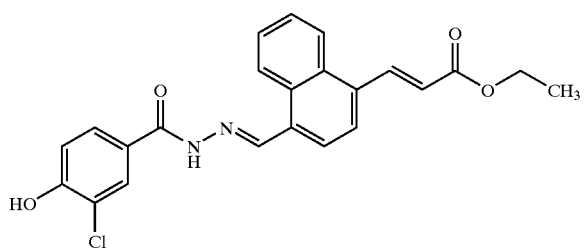

The compound was prepared according to the general procedure for the synthesis of alkylidene hydrazones from the condensation of ethyl 4-formyl-1-naphthyl acrylate (from step B) and 3-chloro-4-hydroxy benzoic acid hydrazide.

$^1$H NMR (DMSO-D$_6$) δ 1.29 (t, J=7.1 Hz, 3H), 4.25 (q, J=7.1 Hz, 2H), 6.75 (d, J=15.7 Hz, 1H), 7.10 (d, J=8.5 Hz, 1H), 7.71 (m, 2H), 7.92 (d, J=8.5 Hz, 1H), 8.01 (m, 2H), 8.07 (d, J=8.0 Hz, 1H), 8.46 (d, J=15.7 Hz, 1H), 8.81 (d, J=7.1 Hz, 1H), 9.13 (s, 1H), 11.00 (s, 1H), 11.89 (s, 1H). MS (APCI, pos.): 421.1, 423.0.

EXAMPLE 520

4-[(3-Chloro-4-hydroxybenzoyl)hydrazonomethyl] naphthyl Acrylate

The compound was prepared according to the general procedure for the synthesis of alkylidene hydrazones from the condensation of 4-formyl-1-naphthyl acrylate (from step C) and 3-chloro-4-hydroxy benzoic acid hydrazide.

$^1$H NMR (DMSO-D6) δ 6.65 (d, J=15.6 Hz, 1H), 7.09 (d, J=8.5 Hz, 1H), 7.66–7.74 (m, 2H), 7.81 (d, J=8.5 Hz, 1H), 7.97–8.05 (m, 3H), 8.29 (dd, J=2.2, 7.1 Hz, 1H), 8.41 (d, J=15.6 Hz, 1H), 8.82 (d, J=7.6 Hz, 1H), 9.12 (s, 1H), 10.92 (s, 1H), 11.89 (s, 1H), 12.62 (s, 1H). MS (APCI, pos.): 394.1, 395.3.

General Procedure for the Synthesis of Substituted Piperazine-aryl-aldehydes Followed by Hydrazone Formation The substituted piperazine-aryl-aldehydes may be prepared by N-alkylation of the corresponding unsubstituted piperazine-aryl-aldehydes using various electrophilic alkylating agents that introduce the —(K)$_m$—D moiety as defined above.

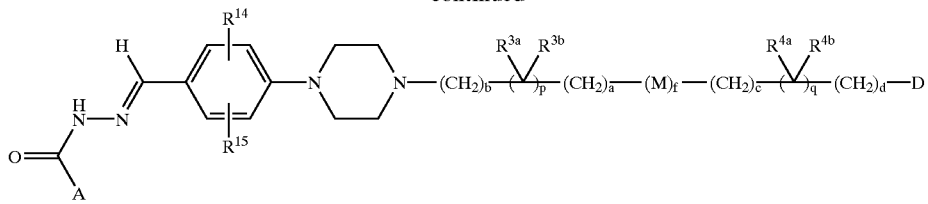

wherein Lx is a leaving group such as —Cl, —Br, —I, —OSO$_2$CH$_3$, —OSO$_2$p-tolyl or —OSO$_2$CF$_3$; and A, R$^{3a}$, R$^{3b}$, R$^{4a}$, R$^{4b}$, a, b, c, d, f, p, q, D, M, R$^{14}$ and R$^{15}$ are as defined for formula I.

According to the above scheme the substituted piperazine-aryl-aldehydes can be prepared by stirring piperazinylbenzaldehydes or piperazinylnaphthaldehydes in an organic solvent such as acetone, methylethyl ketone, dimethylformamide, DMSO, dioxane, tetrahydrofuran, toluene, ethylene glycol dimethyl ether, sulfolane, diethylether, water or a compatible mixture of two or more of the above solvents with an equimolar amount of an alkyl halide or an aryl-lower alkyl halide and in the presence of 1 to 15 equivalents (preferably 1 to 5 equivalents) of a base such as sodium hydride, potassium hydride, sodium or potassium methoxide, ethoxide or tert-butoxide, sodium, potassium or cesium carbonate, potassium or cesium fluoride, sodium or potassium hydroxide or organic bases such as diisopropylethylamine, 2,4,6-collidine or benzyldimethyl-ammonium methoxide or hydroxide. The reaction can be performed at 0° C. to 150° C., preferably at 20° C. to 100° C. and preferably in an inert atmosphere of N$_2$ or Ar. When the reaction is complete the mixture is filtered, concentrated in vacuo and the resulting product optionally purified by column chromatography on silica gel using ethyl acetate/hexane as eluent. The compound can also (when.appropriate) be purified by recrystallization from a suitable solvent such as ethyl alcohol, ethyl acetate, isopropyl alcohol, water, hexane, toluene or their compatible mixture. Specific examples illustrating the preparation of unsubstituted piperazine-aryl-aldehydes are provided below.

The following step, the hydrazone formation is described above in general and below in detail.

Preparation of 4-Piperazinyl-2,5-dimethylbenzaldehyde 4-(2,5-Dimethylphenyl)-1-benzylpiperazine:

A solution of 2,5-dimethylphenylpiperazine (20 g, 105 mmol) was prepared in acetonitrile (300 mL) and cooled to 0° C. Benzyl bromide (19 g, 111 mmol) was added and the reaction mixture was stirred for 15 minutes before potassium carbonate (16 g, 116 mmol) was added. After stirring the mixture for two hours, the acetonitrile was evaporated and the residue taken up in water and ethyl acetate. The organic layer was separated and washed with brine and dried over magnesium sulfate. The benzylated product was purified by silica gel column chromatography using gradient hexane/ethyl acetate (10/0 to 8/2). The product (21 g, 71%) was obtained as an oil.

$^1$H NMR (CDCl$_3$) δ 2.24 (s, 3H), 2.29 (s, 3H), 2.60 (brd s, 4H), 2.92 (brd s, 4H), 3.55 (s, 2H), 6.78 (m, 1H), 6.84 (s, 1H), 7.04 (m, 1H), 7.30 (m, 5H).

4-(2,5-Dimethyl-4-formylphenyl)-1-benzylpiperazine:

The 4-(2,5-dimethylphenyl)-1-benzylpiperazine (10 g, 36 mmol) was dissolved in anhydrous DMF (30 mL, 390 mmol) and cooled to 0° C. Fresh POCl$_3$ (70 mL, 750 mmol) was added drop wise with stirring. Once the addition was completed the dark mixture was warmed to 75° C. for five hours or until TLC analysis indicated the disappearance of the starting material. The excess phosphorous oxychloride was distilled off and the entire mixture was diluted with ethyl acetate and added slowly to 500 mL of ice-chips. The solution was neutralized and made basic with concentrated NaOH. The neutralization and basification must be done at low temperatures to avoid creating by-products. The formylated product was extracted with ethyl acetate (5x). The organic layer was washed with water (2x), brine, dried over magnesium sulfate and purified by silica gel column chromatography using gradient hexane/ethyl acetate (10/0 to 8/2). The product (9 g, 81%) was obtained as an oil.

$^1$H NMR (CDCl$_3$) δ 2.29 (s, 3H), 2.28 (s+t, 7H), 3.03 (t, 4H), 3.59 (s, 2H), 6.75 (s, 1H), 7.31 (m, 5H), 7.58 (s, 1H), 10.12 (s, 1H).

4-(2,5-Dimethyl-4-formylphenyl)-1-(1-chloroethoxycarbonyl)piperazine:

The 4-(2,5-dimethyl-4-formylphenyl)-1-benzylpiperazine (9 g, 29 mmol) was dissolved in anhydrous 1,2-dichloroethane (100 mL) and 1-chloroethyl chloroformate (4.5 g, 31.5 mmol) was added. The solution was refluxed for 30 minutes or until TLC analysis indicated the disappearance of the starting material. The product was just slightly less polar than the starting material by TLC using hexane/EtOAc (3/1). Dichloroethane was evaporated and the residue was chromatographed using gradient hexane/EtOAc (10/0 to 8/2) to give the product (6 g, 64%) as an oil.

$^1$H NMR (CDCl$_3$) δ 1.84 (d, 3H), 2.32 (s, 3H), 2.61 (s, 3H), 2.99 (brd m, 4H), 3.70 (brd m, 4H), 6.62 (qt, 1H), 6.76 (s, 1H), 7.62 (s, 1H), 10.14 (s, 1H).

4-Piperazinyl-2,5-dimethylbenzaldehyde:

To a solution of the dimethylphenylpiperazinylcarbamate above (6 g, 18.5 mmol) in THF (50 mL) was added 1 N HCl (50 mL, 50 mmol). The mixture was warmed to approximately 80° C. until the evolution of CO$_2$ stopped. Most of the THF was removed by rotary evaporation and the residue was lyophilized to give the product as the dihydrochloride salt (5.5 g, 99%).

$^1$H NMR (DMSO-D$_6$) δ 2.2 (s, 3H), 2.50 (s, 3H), 3.13 (brd s, 8H), 6.85 (s, 1H), 7.54 (s, 1H), 9.49 (brd s, 2H), 10.02 (s, 1H).

4-Piperazinyl-2,3-dimethylbenzaldehyde:

4-Piperazinyl-2,3-dimethylbenzaldehyde was prepared in the same fashion as above. Formylation of the N-benzyl-piperazinyl-2,3-dimethylbenzene was much slower and required overnight heating at 70° C. All other steps were otherwise very similar and the yields were comparable.

$^1$H NMR (DMSO-D$_6$) δ 2.15 (s, 3H), 2.47 (s, 3H), 3.07 (brd m, 4H), 3.17 (brd m, 4H), 5.90 (brd s, 1H, NH), 7.02 (d, 1H), 7.50 (d, 1H), 9.54 (brd s, 2H, NH$_2$), 10.10 (s, 1H).

4-piperazinyl-3,5-dimethylbenzaldehyde:

4-Piperazinyl-3,5-dimethylbenzaldehyde was prepared in the same manner as above.

General Library Procedure for N-alkylation and Hydrazone Formation

To a solution of the unsubstituted piperazinyl-aryl-aldehyde in DMSO dispensed into 88 deep well plates were added solutions of desired alkylating agents (1 eq) in DMSO followed by diisopropylethylamine (5 eq). Solid potasssium carbonate (5 eq) may also be substituted. After stirring the solutions for 16 hours, a solution of 4-hydroxybenzoic acid hydrazide derivative (1 eq) in DMSO and a solution of acetic acid (catalytic) in DMSO were added into each well. The reaction mixtures were agitated for 16 hours to give the crude products which were purified by HPLC.

Examples of products:

EXAMPLE 521

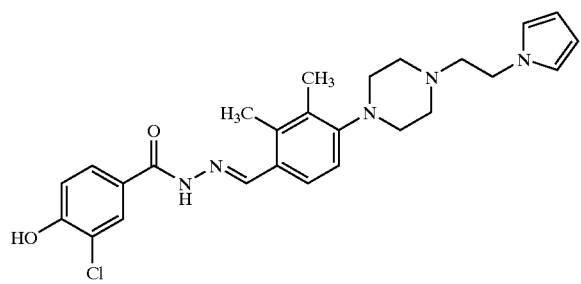

$^1$H NMR (DMSO-D$_6$): δ 2.26 (s, 3H), 2.38 (s, 3H), 2.65 (brd s, 4H), 2.73 (t, 2H), 2.89 (brd s, 4H), 4.07 (t, 2H), 6.03 (d, 2H), 6.84 (t, 2H), 7.02 (d, 1H), 7.13 (d, 1H), 7.72 (d, 1H), 7.82 (dd, 1H), 8.01 (s, 1H), 8.86 (brd s, 1H), 11.68 (brd s, 1H); MS (APCI): 480.7, 482.3.

EXAMPLE 522

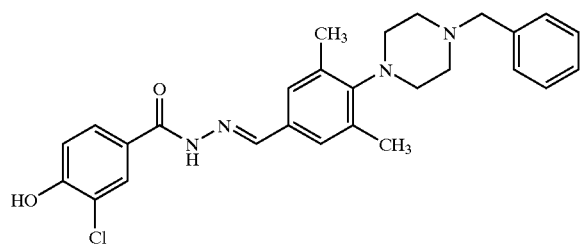

$^1$H NMR (DMSO-D$_6$): δ 2.49 (s, 6H), 2.68 (brd s 4H), 3.22 (brd s, 4H), 3.72 (s, 2H), 7.22 (d, 1H), 7.44 (m, 1H), 7.52 (m, 6H), 7.92 (dd, 1H), 8.13 (s, 1H), 8.46 (s, 1H), 11.12 (brd s, 1H), 11.80 (s, 1H); MS (APCI): 477.5, 479.2.

EXAMPLE 523

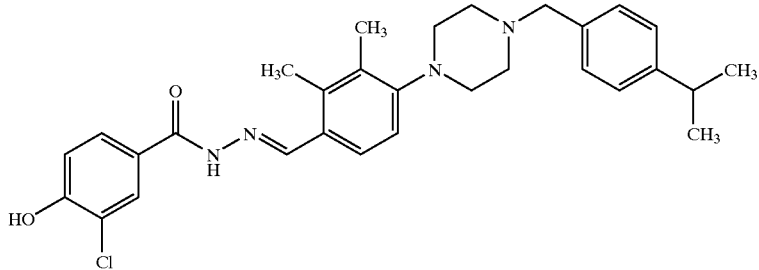

$^1$H NMR (DMSO-D$_6$): δ 1.25 (s, 3H), 1.27 (s, 3H), 2.26 (s, 3H), 2.38 (s, 3H), 2.57 (brd s, 4H), 2.95 (brd s, 4H), 3.56 (s, 2H), 7.02 (d, 1H), 7.12 (d, 1H), 7.30 (qt, 4H), 7.72 (d, 1H), 7.82 (d, 1H), 8.01 (s, 1H), 8.83 (s, 1H), 11.0 (brd s, 1H), 11.1 (s, 1H); MS (APCI): 519.7, 521.5.

EXAMPLE 524

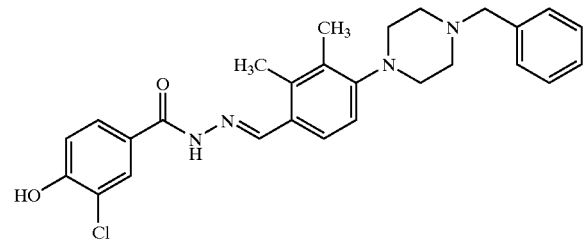

$^1$H NMR (DMSO-D$_6$): δ 2.22 (s, 3H), 2.33 (s, 3H), 3.17 (brd s, 4H), 3.23 (m, 2H), 3.36 (m, 2H), 4.41 (s, 2H), 6.98 (d, 1H), 7.10 (d, 1H), 7.48 (m, 3H), 7.68 (m, 3H), 7.71 (d, 1H), 7.97 (s, 1H), 8.83 (s, 1H), 11.00 (s, 1H), 11.02 (brd s, 1H), 11.69 (s, 1H); MS (APCI): 477.4, 479.2.

EXAMPLE 525

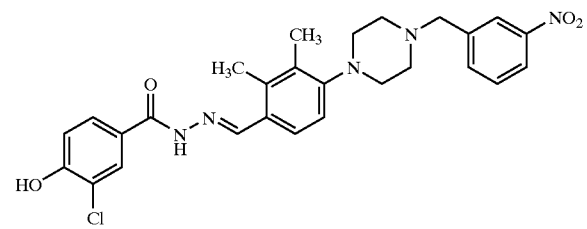

$^1$H NMR (DMSO-D$_6$): δ 2.20 (s, 3H), 2.31 (s, 3H), 2.59 (s, 4H), 2.87 (s, 4H), 3.69 (s, 2H), 6.98 (d, 1H), 7.02 (d, 1H), 7.64 (m, 2H), 7.75 (dd, 1H), 7.82 (d, 1H), 7.94 (d, 1H), 8.12 (dd, 1H), 8.19 (s, 1H), 8.74 (s, 1H), 10.94 (brd s, 1H), 11.54 (s, 1H); MS (APCI): 522.2, 524.3.

EXAMPLE 526

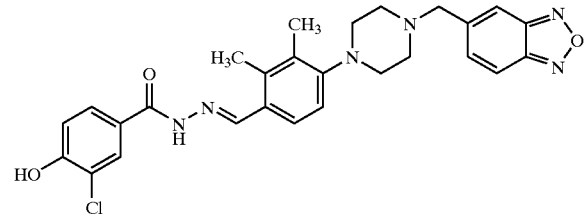

$^1$H NMR (DMSO-D$_6$): δ 2.20 (s, 3H), 2.31 (s, 3H), 2.62 (brd s, 4H), 2.87 (brd s, 4H), 3.68 (s, 2H), 6.98 (d, 1H), 7.04 (d, 1H), 7.55 (d, 1H), 7.61 (d, 1H), 7.74 (dd, 1H), 7.91 (s, 1H), 7.92 (d, 1H), 8.01 (d, 1H), 8.74 (s, 1H), 10.93 (brd s, 1H), 11.54 (s, 1H); MS (APCI): 519.2, 521.3.

EXAMPLE 527

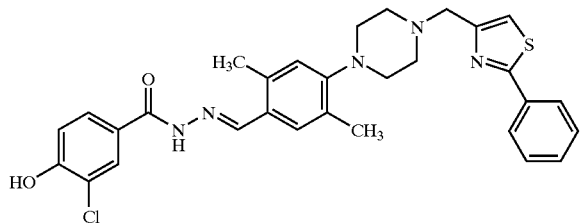

$^1$H NMR (DMSO-D$_6$): δ 2.21 (s, 3H), 2.37 (s, 3H), 2.66 (brd s, 4H), 2.91 (brd s, 4H), 3.76 (s, 2H), 6.83 (s, 1H), 7.05 (d, 1H), 7.62 (s, 1H), 7.69 (s, 1H), 7.75 (dd, 1H), 7.86 (d, 2H), 7.94 (s, 1H), 8.15 (d, 2H), 8.60 (s, 1H), 10.92 (brd s, 1H), 11.55 (s, 1H); MS (APCI): 628.3, 630.2, 631.2.

General Procedure for the Synthesis of N-Substituted Indole Aldehydes Followed by Hydrazone Formation:

The N-substituted indole aldehydes may be prepared by N-alkylation of the corresponding unsubstituted indole aldehydes using various electrophilic alkylating agents that introduce the —(K)$_m$—D moiety as defined above.

According to the above scheme the N-substituted indole aldehydes can be prepared by stirring formylindoles in an organic solvent such as acetone, methylethyl ketone, dimethylformamide, DMSO, dioxane, tetrahydrofuran, toluene, ethylene glycol dimethyl ether, sulfolane, diethylether, water or a compatible mixture of two or more of the above solvents with an equimolar amount of an alkyl halide or an aryl-lower alkyl halide and in the presence of 1 to 15 equivalents (preferably 1 to 5 equivalents) of a base such as sodium hydride, potassium hydride, sodium or potassium methoxide, ethoxide or tert-butoxide, sodium, potassium or cesium carbonate, potassium or cesium fluoride, sodium or potassium hydroxide or organic bases such as diisopropylethylamine, 2,4,6-collidine or benzyldimethyl-ammonium methoxide or hydroxide. The reaction can be performed at 0° C. to 150° C., preferably at 20° C. to 100° C. and preferably in an inert atmosphere of N$_2$ or Ar. When the reaction is complete the mixture is filtered, concentrated in vacuo and the resulting product optionally purified by column chromatography on silica gel using ethyl acetate/hexane as eluent. The compound can also (when appropriate) be purified by recrystallization from a suitable solvent such as ethyl alcohol, ethyl acetate, isopropyl alcohol, water, hexane, toluene or their compatible mixture.

The following step, the hydrazone formation is described above in general and below in detail.

Library Procedure for Indole Alkylation (Step A)

Preparation of the Sodium Salt of the Indole

Indole-3-carboxaldehyde (1.45 g) was dissolved into 8.6 mL of dry DMF in a dried and cooled 3 100 mL 3-necked roundbottom flask.

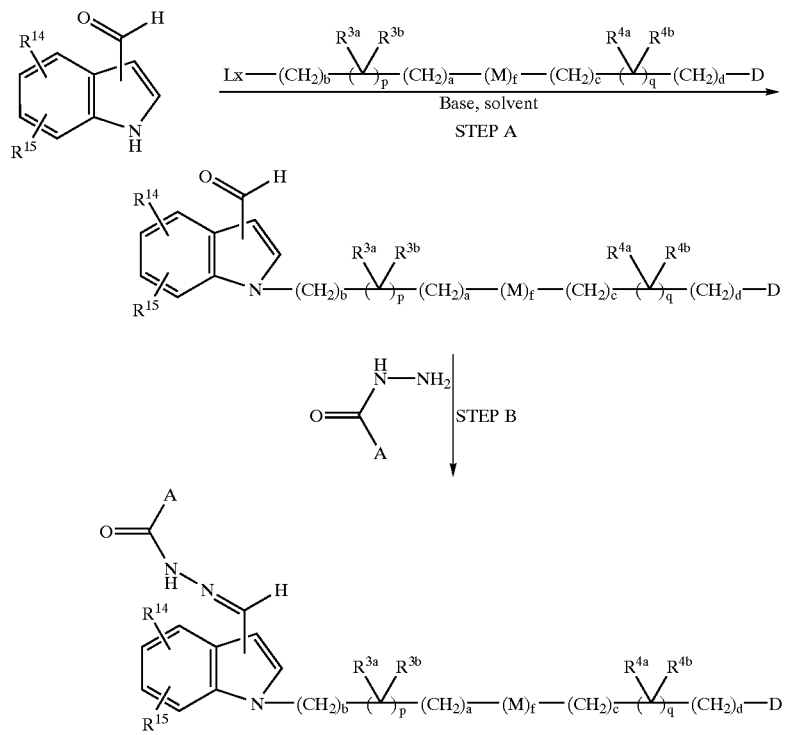

wherein Lx is a leaving group such as —Cl, —Br, —I, —OSO$_2$CH$_3$, —OSO$_2$p-tolyl or —OSO$_2$CF$_3$; and A, R$^{3a}$, R$^{3b}$, R$^{4a}$, R$^{4b}$, a, b, c, d, f, p, q, D, M, R$^{14}$ and R$^{15}$ are as defined for formula I.

Evolution of large amounts of hydrogen gas occurs during this step. Care should be taken to keep the flow of inert gas steady and maintain adequate venting to accommodate the hydrogen gas evolution.

While maintaining a steady flow of nitrogen or argon through the 3-necked round bottomed flask, 1.1 equivalent of sodium hydride (0.27 g of dry 95% reagent) was transferred to the indole solution. The mixture was stirred for 15 minutes, while maintaining flow of inert gas. Proceeded promptly to the next step.

Preparation of the Alkyl Halide Solutions

Amber glass vials (for preparing stock solutions) were dried for at least four hours at 110° C., then were allowed to cool under an argon atmosphere in a desiccator. Alkyl halides solutions (1.0 M) were prepared in anhydrous DMF in the dried vials. Each alkyl halide solution (100 µL) was added to its corresponding well of a deep-well plate (1×88×1 format).

Alkylation of the Indole Sodium Salt

100 µL of the 1.0 M indole salt solution was quickly delivered to each alkyl halide in the deep-well plates. The plates were vortexed briefly to mix, then allowed to react for two hours.

Library Procedure for
Hydrazone Formation (Step B)

Acyl Hydrazone Formation

3-Chloro-4-hydroxybenzoic acid hydrazide (1.86 g) was dissolved in 5 mL of dry DMSO, followed by trifluoroacetic acid (0.77 mL). The resulting solution was diluted to a final volume of 10.0 mL. 100 µL of the 1.0 M acid hydrazide TFA salt solution was added to each well of the deep-well plate. The plate was vortexed for one minute to mix, then allowed to react for 30 minutes.

The products were purified by chromatography on silica gel with ethyl acetate/hexane eluent.

The following compounds were prepared:

EXAMPLE 528

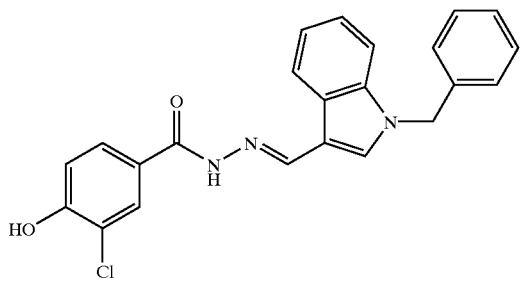

$^1$H NMR (DMSO-D$_6$): δ 5.46 (s, 2H), 7.10 (d, J=8.7, 2H), 7.20 (m, 2H), 7.28 (m, 5H), 7.51 (d, J=7.53, 1H), 7.79 (d, J=7.9, 1H), 7.99 (s, 1H), 8.01 (s, 1H), 8.33 (d, J=6.96, 1H), 8.62 (s, 1H), 10.9 (s, 1H), 11.5 (s, 1H); LRMS calcd for C$_{26}$H$_{24}$Cl$_1$N$_3$O$_2$ (M–H) 402, found 402.1.

EXAMPLE 529

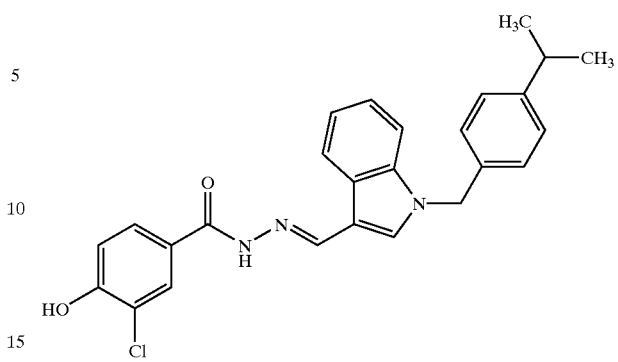

$^1$H NMR (DMSO-D$_6$): δ 1.14 (d, J=6.8, 6H), 2.81 (sept, J=6.9, 1H), 5.41 (s, 2H), 7.07 (d, J=8.3, 1H), 7.20 (m, 6H), 7.54 (d, J=7.6, 1H), 7.77 (d, J=7.9, 1H), 7.97 (s, 1H), 8.01 (s, 1H), 8.29 (d, J=7.2, 1H), 8.59 (s, 1H), 10.88 (s, 1H), 11.44 (s, 1H). LRMS calcd for C$_{26}$H$_{24}$Cl$_1$N$_3$O$_2$ (M–H) 445, found 445.9.

EXAMPLE 530

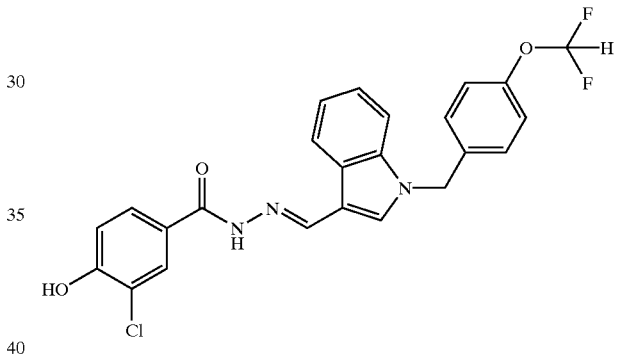

$^1$H NMR (DMSO-D$_6$): δ 5.47 (s, 2H), 7.08, (d, J=8.7, 1H), 7.13–7.25 (m, 5H), 7.18 (t, J=74.2, 1H), 7.35 (d, J=8.7, 1H), 7.54 (d, J=7.9, 1H), 7.77 (dd, J=8.7, 1.7, 1H), 7.97 (d, J=1.7, 1H), 8.02 (s, 1H), 8.30 (d, J=7.2, 1H), 8.59 (s, 1H), 10.89 (s, 1H), 11.45 (s, 1H). LRMS calcd for C$_{24}$H$_{18}$Cl$_1$F$_2$N$_3$O$_3$ (M–H) 468, found 468.1.

EXAMPLE 531

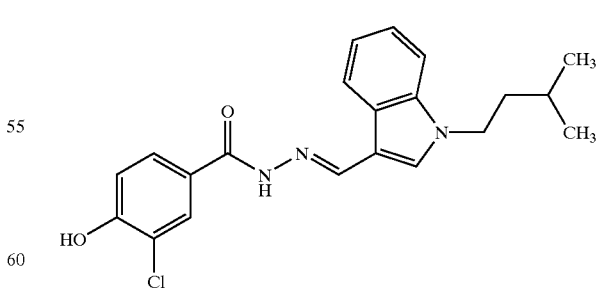

$^1$H NMR (DMSO-D$_6$): δ 0.94 (d, J=6.2, 6H), 1.54 (sept, J=6.2, 1H), 1.66–1.73 (m, 2H), 4.23 (t, J=7.0, 2H), 7.08 (d, J=8.7, 1H), 7.16–7.29 (m, 2H), 7.54 (d, J=7.95, 1H), 7.77 (d, J=8.7, 1H), 7.88 (s, 1H), 7.97 (s, 1H), 8.29 (d, J=7.5, 1H), 8.57 (s, 1H), 10.88 (s, 1H). 11.42 (s, 1H). LRMS calcd for $C_{21}H_{22}Cl_1N_3O_2$ (M+H) 384, found 384.2.

EXAMPLE 532

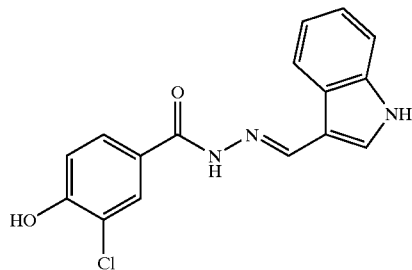

$^1$H NMR (DMSO-$D_6$): δ 7.06 (d, J=8.5, 1H), 7.12–7.26 (m, 3H), 7.46–7.49 (M, 2H), 7.78 (d, J=8.1, 1H), 7.99 (s, 1H), 11.33 (s, 1H), 11.65 (s, 1H). LRMS calcd for $C_{16}H_{12}Cl_1N_3O_2$ (M−H) 312, found 312.0.

General Procedure for the Synthesis of Alkyl/aryl-sulfonyloxy Aryl-aldehydes Followed by Hydrazone Formation The alkyl/aryl-sulfonyloxy aryl-aldehydes may be prepared by 0-sulfonylation of the corresponding phenolic compounds using various electrophilic sulfonylating agents that introduce the —(K)$_m$—D moiety as defined above.

wherein Lx is a leaving group such as —Cl, —Br, —I, —OSO$_2$CH$_3$, —OSO$_2$p-tolyl or —OSO$_2$CF$_3$; and A, $R^{3a}$, $R^{3b}$, $R^{4a}$, $R^{4b}$, a, b, c, d, f, p, q, D, M, $R^{14}$ and $R^{15}$ are as defined for formula I.

According to the above scheme an alkyl/aryl-sulfonyloxyaryl aldehyde can be prepared by stirring hydroxybenzaldehydes or hydroxynaphthaldehydes in an organic solvent such as acetone, methylethyl ketone, dimethylformamide, dioxane, tetrahydrofuran, toluene, ethylene glycol dimethyl ether, sulfolane, diethylether, water or a compatible mixture of two or more of the above solvents with an equimolar amount of an alkylsulfonylhalide, arylsulfonylhalide or an aryl-lower alkyl sulfonyihalide and in the presence of 1 to 15 equivalents (preferably 1 to 5 equivalents) of a base such as sodium hydride, potassium hydride, sodium or potassium methoxide, ethoxide or tert-butoxide, sodium, potassium or cesium carbonate, potassium or cesium fluoride, sodium or potassium hydroxide or organic bases such as diisopropylethylamine, 2,4,6-collidine or benzyldimethyl-ammonium methoxide or hydroxide. The reaction can be performed at 0° C. to 150° C., preferably at 20° C. to 100° C. and preferably in an inert atmosphere of $N_2$ or Ar. When the reaction is complete the mixture is filtered, concentrated in vacuo and the resulting product optionally purified by column chromatography on silica gel using ethyl acetate/hexane as eluent. The compound can also (when appropriate) be purified by recrystallization from a suitable solvent such as ethyl alcohol, ethyl acetate, isopropyl alcohol, water, hexane, toluene or their compatible mixture.

The following hydrazone formation step is described above in general.

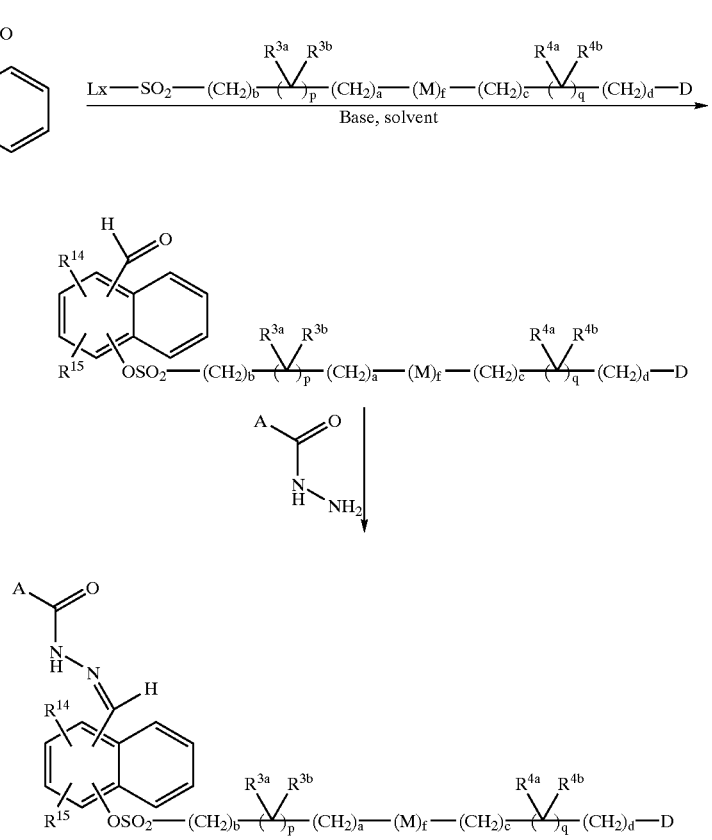

Examples of Compounds Synthesized Using the Methodology Described are Given Below:

EXAMPLE 533

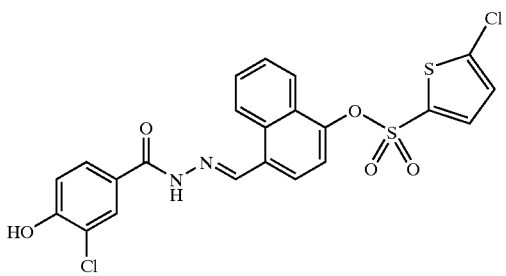

$^1$H NMR (DMSO-D$_6$): δ 7.03 (d, 1H), 7.28 (d, 1H), 7.39 (d, 1H), 7.61 (t, 1H), 7.67 (t, 1H), 7.75 (m, 2H), 7.87 (d, 2H), 7.95 (s, 1H), 8.75 (d, 1H), 9.02 (s, 1H), 11.00 (s, 1H), 11.88 (s, 1H); MS (APCI): 521.0, 523.0.

EXAMPLE 534

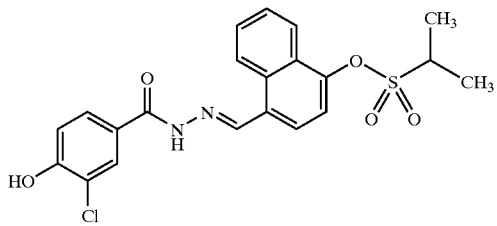

$^1$H NMR (DMSO-D$_6$): δ 1.38 (d, 6H), 3.91 (septet, 1H), 6.97 (d, 1H), 7.46 (d, 1H), 7.61 (m, 2H), 7.71 (d, 1H), 7.81 (d, 1H), 7.89 (s, 1H), 8.01 (d, 1H), 8.69 (d, 1H), 9.11 (s, 1H), 11.00 (brd s, 1H), 11.98 (s, 1H); MS (APCI, neg.): 445.0, 487.0, 339-iprso$_2$.

General Procedures for the Preparation of Alkylidene Hydrazides According to the Invention Involving Parallel Synthesis on a Solid Support:

The compounds of Examples 535 to 614 were prepared according to the following equation Resin—[Building block 1]→

Resin—[Building block 1]—[Building block 2]→Resin—[Building block 1]—[Building block 2]—[Building block 3]

and were simultaneously deprotected and cleaved from the resin with 50% trifluoroacetic acid in dichloromethane to give the desired compounds as individual entities according to the following formula

[Building block 1]—[Building block 2]—[Building block 3].

The following 80 compounds were prepared as single entities by parallel synthesis on a solid support. Preparation of Resin—[Building block 1]—[Building block 2] was done manually, whereas the attachment of [Building block 3] and cleavage from the resin were performed on an Advanced ChemTech Model 384 HTS.

The starting resins, Resin—[Building block 1]—[Building block 2], were all prepared as described below.

The resin used was a polystyrene resin with a Wang linker and the substitution capacity was 0.9 mmol/g.

All 80 compounds are based on attachment of [Building block 3] to Resin—[Building block 1]—[Building block 2] in a fully combinatorial way using a Heck reaction according to the following scheme:

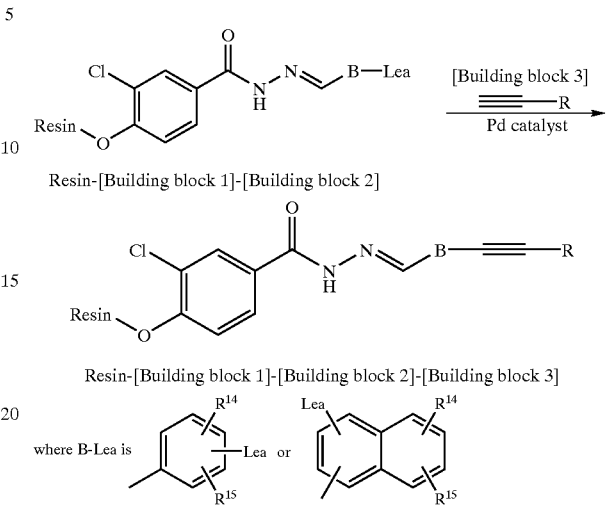

wherein Lea is a leaving group and preferably is selected from bromo, iodo and trifluoromethanesulfonyloxy, and R$^{14}$ and R$^{15}$ are as defined for formula I.

The following resin, here depicted as Resin—[Building block 1] was used:

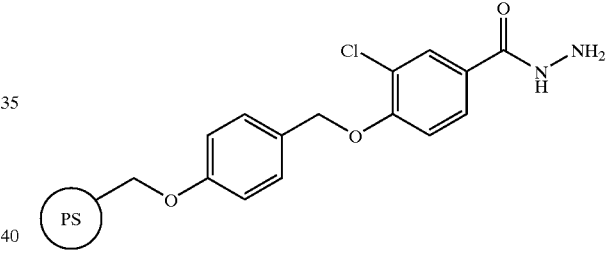

where PS is polystyrene. In the following "Resin" is the polystyrene resin with the Wang linker:

where

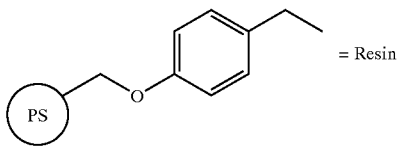

The following building blocks were used:

[Building block 2]:

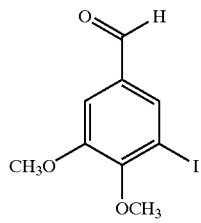

3,4-dimethoxy-5-iodobenzaldehyde

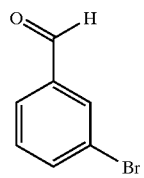

3-Bromobenzaldehyde

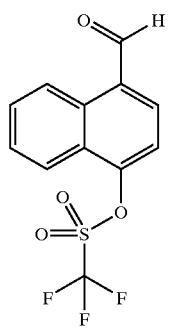

Trifluoromethanesulfonic acid 4-formyl-1-naphthyl ester

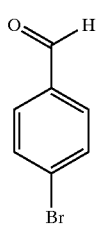

4-Bromobenzaldehyde

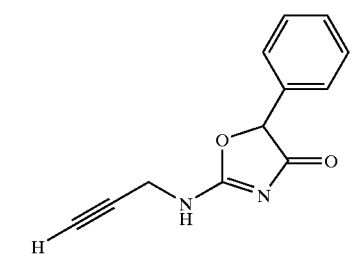

5-Phenyl-2-(2-propynylamino)-2-oxazolin-4-one

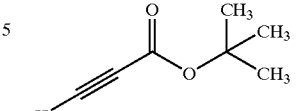
tert-Butyl propiolate

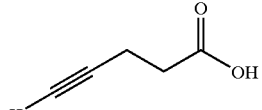
4-Pentynoic acid

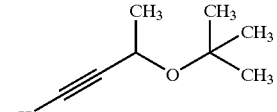
tert-Butyl 1-methyl-2-propynyl ether

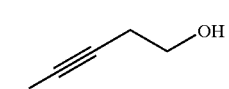
3-Butyn-1-ol

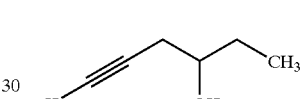
5-Hexyn-3-ol

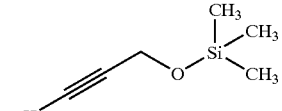
O-Trimethylsilylpropargyl alcohol

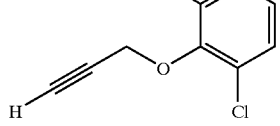
3-(2,6-Dichlorophenoxy)prop-1-yne

[Building block 3]:

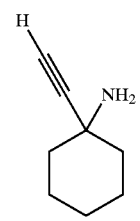

1-Ethynylcyclohexylamine

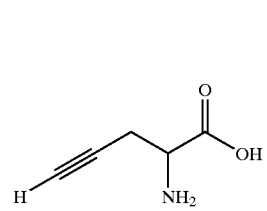

2-Amino-4-pentynoic acid

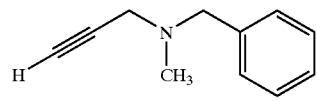

N-Methyl-N-propargylbenzylamine

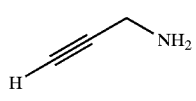

Propargylamine

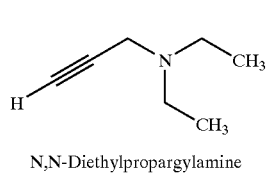

N,N-Diethylpropargylamine

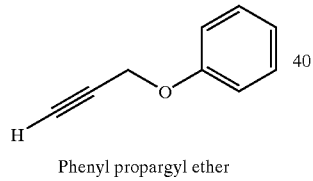

Phenyl propargyl ether

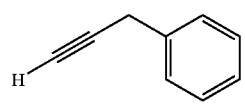

3-Phenyl-1-propyne

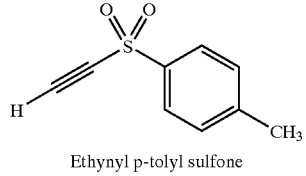

Ethynyl p-tolyl sulfone

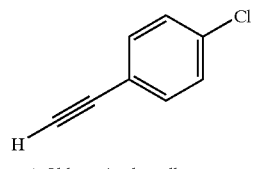

1-Chloro-4-ethynylbenzene

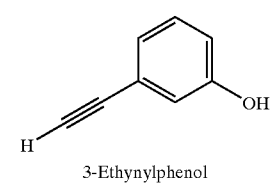

3-Ethynylphenol

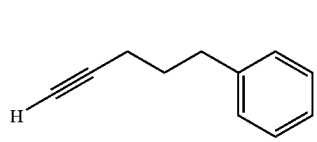

5-Phenyl-1-pentyne

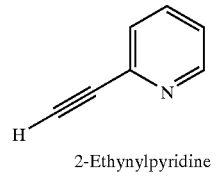

2-Ethynylpyridine

By combination of these building blocks in a fully combinatorial way 1×4×20=80 compounds were prepared.

Preparation of [Building Block 2]

Preparation of 3,4-Dimethoxy-5-iodobenzaldehyde

Iodomethane (2.5 mL, 40 mmoles) was added to a mixture of 5-iodovanillin (10 g, 36 mmoles), potassium carbonate (25 g, 180 mmoles) in DMF (100 ml) and the resulting mixture was stirred at room temperature for 16 hours. The mixture was poured into water (0.5 L) and extracted with ethyl acetate (2×200 mL). The combined organic phases were washed with water (200 mL), dried over MgSO$_4$ and evaporated in vacuo to afford 9.78 g (93%) of 3,4-dimethoxy-5-iodobenzaldehyde, m.p. 58–63° C.

Preparation of Trifluoromethanesulfonic Acid 4-Formyl-1-naphthyl Ester

4-Hydroxy-1-naphthaldehyde (10 g, 58 mmoles) was dissolved in pyridine (50 ml) and the mixture was cooled to 0° C. Trifluoromethanesulfonic anhydride (11.7 mL, 70 mmoles) was added dropwise while maintaining the temperature below 5° C. When the addition was completed the mixture was stirred at room temperature for 30 minutes. Diethyl ether (200 mL) was added and the mixture was successively washed with water (2×250 mL), 3 N hydrochloric acid (200 mL), and saturated NaCl (200 mL). The organic phase was dried over MgSO$_4$ and evaporated in vacuo. The residue was purified by column chromatography on silica gel (800 mL) eluting with a mixture of ethyl acetate and heptane (1:4). Pure fractions eluting with $R_f$=0.46 were pooled and evaporated in vacuo to afford 8.35 g (47%) of trifluoromethanesulfonic acid 4-formyl-1-naphthyl ester, m.p. 44–47° C. The other [Building block 2]'s (3-Bromobenzaldehyde and 4-bromobenzaldehyde) are commercially available.

Preparation of Resin—[Building Block 1]
(Resin Bound 3-Chloro-4-hydroxybenzoic Acid Hydrazide)

Polystyrene resin (15 g) loaded with the Wang linker (0.92 mmoles/g), was successively washed with DMF (3×40 mL) and CH$_2$Cl$_2$ (3×40 mL). The resin was suspended in CH$_2$Cl$_2$ (80 mL) and diisopropylethylamine (60 mL) was added. The mixture was cooled to 0° C. and methanesulfonyl chloride (5.8 mL) dissolved in CH$_2$Cl$_2$ (30 mL) was added drop wise while maintaining the temperature below 5° C. When addition was complete the mixture was stirred at 0° C. for 30 minutes and at room temperature for 30 minutes. The resin was successively washed with CH$_2$Cl$_2$ (3×80 mL) and N-methylpyrrollidone (NMP) (3×80 mL). This resin and cesium carbonate (12.3 g) were added to ethyl 3-chloro-4-hydroxybenzoate (15 g) dissolved in NMP (200 mL) and the mixture was stirred at 80° C. for 4 hours. After cooling the resin was successively washed with NMP (3×80 mL) and methanol (3×80 mL).

The above resin was suspended in 1,4-dioxane (150 mL) and water (36 mL). Lithium hydroxide (2.6 g) was added and the mixture was stirred at 60° C. under N$_2$ for 16 hours. After cooling the resin was successively washed with DMF (3×80 mL), CH$_2$Cl$_2$ (3×80 mL) and methanol (80 mL) and dried in vacuo at 50° C. for 3 days.

The above resin (3.0 g) was suspended in CH$_2$Cl$_2$ (20 mL) and 1-hydroxybenzotriazole (0.6 g), N-(3-dimethylaminopropyl)-N'-ethylcarbodiimide, hydrochloride (0.9 g) and DMF (10 mL) were added. The mixture was shaken at room temperature for 45 minutes, hydrazine hydrate (300 µL) was added, and the mixture was shaken overnight at room temperature. The resin was successively washed with DMF (3×20 mL) and CH$_2$Cl$_2$ (3×20 mL) to afford resin bound 3-chloro-4-hydroxybenzoic acid hydrazide (Resin—[Building block 1]).

Preparation of Resin—[Building Block 1]—[Building Block 2]

Preparation of Resin Bound 3-Chloro-4-hydroxybenzoic Acid (3,4-Dimethoxy-5-iodobenzylidene)hydrazide The above resin (Resin—[Building block 1]) (4 g) was suspended in DMF (50 mL) and 3,4-dimethoxy-5-iodobenzaldehyde (5.8 g) and triethyl orthoformate (25 mL) were added and the mixture was shaken for 16 hours at room temperature. The resin was successively washed with DMF (4×40 mL) and CH$_2$Cl$_2$ (6×40 mL), and dried in vacuo at 50° C. for 16 hours to afford resin bound 3-chloro-4-hydroxybenzoic acid (3,4-dimethoxy-5-iodobenzylidene)hydrazide.

Preparation of Resin Bound Trifluoromethanesulfonic Acid 4-[(3-Chloro-4-hydroxybenzoyl)hydrazonomethyl]naphthalen-1-yl ester Similarly as described above but using trifluoromethanesulfonic acid 4-formyl-1-naphthyl ester instead of 3,4-dimethoxy-5-iodobenzaldehyde resin bound was trifluoromethanesulfonic acid 4-[(3-chloro-4-hydroxybenzoyl)hydrazonomethyl]naphthalen-1-yl ester obtained.

Preparation of Resin Bound 3-Chloro-4-hydroxybenzoic Acid (3-Bromobenzylidene) hydrazide Similarly as described above but using 3-bromobenzaldehyde instead of 3,4-dimethoxy-5-iodobenzaldehyde resin bound 3-chloro-4-hydroxybenzoic acid (3-bromobenzylidene)hydrazide) was obtained.

Preparation of Resin Bound 3-Chloro-4-hydroxybenzoic Acid (4-Bromobenzylidene) hydrazide Similarly as described above but using 4-bromobenzaldehyde instead of 3,4-dimethoxy-5-iodobenzaldehyde resin bound 3-chloro-4-hydroxybenzoic acid (4-bromobenzylidene)hydrazide) was obtained.

EXAMPLE 535

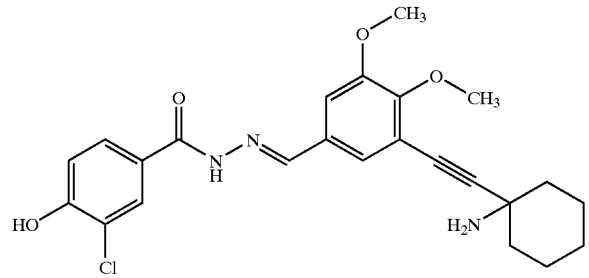

3-Chloro-4-hydroxybenzoic Acid [3-(1-Aminocyclohexylethynyl)-4,5-dimethoxybenzylidene]-hydrazide To the resin bound 3-chloro-4-hydroxybenzoic acid (3-bromobenzylidene)hydrazide (0.05 mmoles) was added copper (I) iodide (10 mg). Diisopropylethylamine (0.2 mL), a solution of triphenylphosphine in NMP (0.4 M, 0.5 mL), a solution of tetrabutylammonium chloride in water (0.66 M, 0.3 mL), a solution of palladium (II) acetate in NMP (0.16 M, 0.25 mL) and a solution of 1-ethynylcyclohexylamine ([Building block 3]) in NMP (1 M, 0.5 mL) were added successively, and the mixture was shaken at 90° C. for 15 hours. The resin was repeatedly washed with NMP (1.5 mL, 3 times), 50% water in DMF (1.5 mL, 3 times), NMP (1.5 mL, 2 times), 1% sodium diethylaminodithiocarbamate trihydrate (1.5 mL, 9 times), NMP (1.5 mL, 5 times), and CH$_2$Cl$_2$ (1.5 mL, 6 times) for 2 minutes and filtered.

The compound was cleaved off the resin by shaking for 45 minutes at room temperature with a 50% solution of trifluoroacetic acid in CH$_2$Cl$_2$ (1.5 mL). The mixture was filtered and the resin was extracted with CH$_2$Cl$_2$ (0.5 mL). The combined CH$_2$Cl$_2$ extracts were concentrated in vacuo. The residue was dissolved in a 1:1 mixture of methanol and CH$_2$Cl$_2$ (1 mL) and concentrated in vacuo to give the title compound.

The final product obtained was characterized by analytical RP-HPLC (retention time) and by LC-MS (molecular mass).

The RP-HPLC analysis was performed on a Waters HPLC system consisting of Waters™ 600S Controller, Waters™ 996 Photodiode Array Detector, Waters™ 717 Autosampler, Waters™ 616 Pump, Waters™ 3 mm×150 mm 3.5 µ C-18 Symmetry column and Millenium QuickSet Control Ver. 2.15 using UV detection at 214 nm. A gradient of 5% to 90% acetonitrile/0.1% trifluoroacetic acid/water during 15 minutes at 1 mL/minute.

The LC-MS analysis was performed on a PE Sciex API 100 LC/MS System using a Waters™ 3 mm×150 mm 3.5 µ C-18 Symmetry column and positive ionspray with a flow rate at 20 µL/minute.

EXAMPLES 536 TO 614

A library of the following 79 compounds can be prepared in parallel as individual entities analogously to example 535 on an Advanced ChemTech Model 384 HTS using the following ChemFile to control the operation of the synthesizer. The 4 resins of type Resin—[Building block 1]—[Building block 2] are equally distributed in the 80 wells in the synthesizer prior to the initialization of the device.

ChemFile C:\ACT\90250004.CHM Page 1
1 Empty RB_Heating_All_1to36 for 2.000 minute(s)
2 REM Addition of DIPEA
3 Transfer 200 ul from Monomers_1to36 [25] ( ) to RB_Heating_All_1to96 [1–80] using DCE
4 Mix for 1.00 minutes at 600 rpm(s)
5 REM Addition of Ph3P in NMP
6 Transfer 500 µl from Monomers_1to36 [21] ( ) to RB Heating_All 1 to 96 [1–80] using DCE
7 REM Addition of Bu4NCl in water
8 Transfer 300 ul from Monomers_1to36 [22] ( ) to RB Heating_All_1to96 [1–80] using DCE
9 Mix for 1.00 minutes at 600 rpm(s)
10 REM Addition of Pd(OAc)2 in NMP
11 Transfer 250 µl from Monomers_1to36 [22] ( ) to RB_Heating_All_1to96 [1–80] using DCE
12 Mix for 2.00 minutes at 600 rpm(s)
13 Dispense Sequence C:\ACT\ALKYNES.DSP with 500 µl to RB_Heating_All_1to96 rack
14 Set Temperature to 90.0 degrees Celsius
15 Mix for 15.00 minutes at 600 rpm(s)
16 Wait for 15.000 minute(s)
17 Repeat from step 15, 47 times
18 Turn Temperature Controller Off
19 Mix for 15.00 minutes at 600 rpm(s)
20 Wait for 15.000 minute(s)
21 Repeat from step 19, 7 times
22 Empty RB_Heating_All_1to96 for 2.000 minute(s)
23 Dispense System Fluid NMP1 1500 µl to RB_Cleavage_All_1to96 [1–80]
24 Mix for 3.00 minutes at 600 rpm(s)
25 Empty RB_Heating_All_1to96 for 2.000 minute(s)
26 Repeat from step 23, 2 times
27 REM Wash with 50% H2O/NMP
28 Transfer 1500 µl from Reagent_3 [1] ( ) to RB_Heating_All_1to96 [1–80] using NMP1
29 Mix for 3.00 minutes at 600 rpm(s)
30 Empty RB_Heating_All_1to96 for 2.000 minute(s)
31 Repeat from step 28, 2 times
32 Dispense System Fluid NMP1 1500 µl to RB_Cleavage_All_1to96 [1–80]
33 Mix for 3.00 minutes at 600 rpm(s)
34 Empty RB_Heating_All_1to96 for 2.000 minute(s)
35 Repeat from step 32, 1 times
36 REM Wash with Sodium diethylaminodithiocarbamate
37 Transfer 1500 µl from Reagent_3 [1] ( ) to RB_Heating_All_1to96 [1–80] using NMP1
38 Mix for 3.00 minutes at 600 rpm(s)
39 Empty RB_Heating_All_1to96 for 2.000 minute(s)
40 Repeat from step 37, 2 times
41 Transfer 1500 µl from REAGENT_4 [1] ( ) to RB_Heating_All_1to96 [1–80] using NMP1
42 Mix for 3.00 minutes at 600 rpm(s)
43 Empty RB_Heating_All_1to96 for 2.000 minute(s)
44 Repeat from step 41, 2 times
45 Transfer 1500 µl from REAGENT_5 [1] ( ) to RB_Heating_All_1to96 [1–80] using NMP1
46 Mix for 2.00 minutes at 600 rpm(s)
47 Empty RB_Heating_All_1to96 for 2.000 minute(s)
48 Repeat from step 45, 2 times
49 Dispense System Fluid NMP1 1500 µl to RB Cleavage_All_1to96 [1–80]
50 Mix for 3.00 minutes at 600 rpm(s)
51 Empty RB_Heating_All_1to96 for 2.000 minute(s)
52 Repeat from step 49, 4 times
53 Dispense System Fluid DCE1 1500 µl to RB_Cleavage_All_1to96 [1–80]
54 Mix for 3.00 minutes at 600 rpm(s)
55 Empty RB_Heating_All1 to 96 for 2.000 minute(s)
56 Repeat from step 53, 5 times
57 REM Cleavage from Resin
58 REM with 50% TFA/DCM
59 Transfer 1500 µl from Reagent_3 [1] ( ) to RB_Cleavage_All_1to96 [1–80] using DCM1
60 Mix for 45.00 minutes at 600 rpm(s)
61 Empty RB_Cleavage_All_1to96 for 1.000 minute(s)
62 Dispense System Fluid DCM1 500 µl to RB_Cleavage_All_1to96 [1–80]
63 Mix for 1.00 minutes at 300 rpm(s)
64 Empty RB_Cleavage_All_1to96 for 1.000 minute(s)
65
66

Dispense Sequence C:\ACT\ALKYNES.DSP is a subroutine that controls the combinatorial addition of the solutions of the 20 alkynes of type [Building block 3] into the 80 wells in the synthesizer.

The library containing the compounds listed below was synthesized. A subset of the library obtained was characterized by analytical RP-HPLC (retention time) and by LC-MS (molecular mass).

EXAMPLE 536:

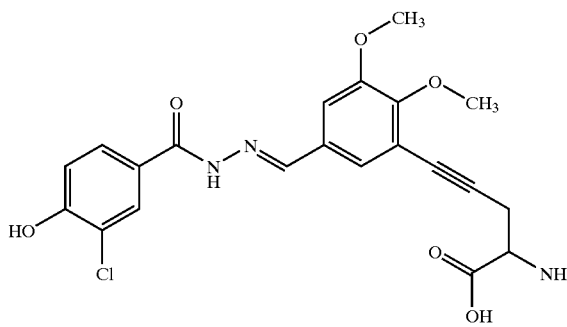

2-Amino-5-{5-[(3-chloro-4-hydroxybenzoyl)hydrazonomethyl]-2,3-dimethoxyphenyl}-4-pentynoic acid

EXAMPLE 537:

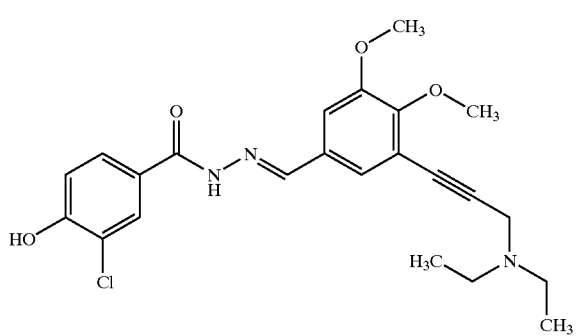

3-Chloro-4-hydroxybenzoic acid [3-(3-diethylamino-1-propynyl)-4,5-dimethoxybenzylidene]hydrazide

EXAMPLE 538:

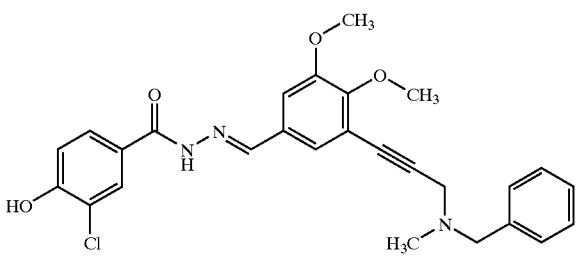

3-Chloro-4-hydroxybenzoic acid{3-[3(benzylmethylamino)-1-propynyl]-4,5-dimethoxybenzylidene}hydrazide

EXAMPLE 539:

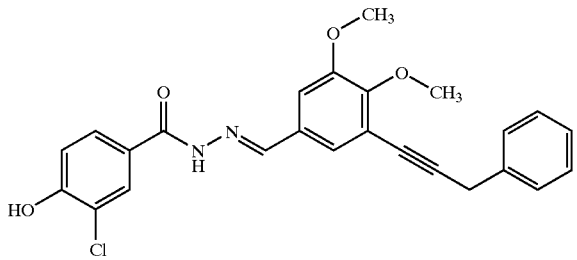

3-Chloro-4-hydroxybenzoic acid [3,4-dimethoxy-5-(3-phenyl-1-propynyl)benzylidene]hydrazide

EXAMPLE 540:

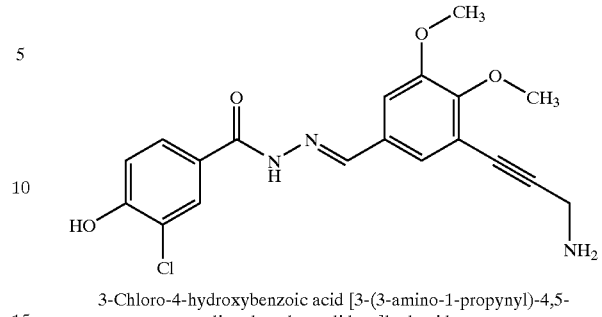

3-Chloro-4-hydroxybenzoic acid [3-(3-amino-1-propynyl)-4,5-dimethoxybenzylidene]hydrazide

EXAMPLE 541:

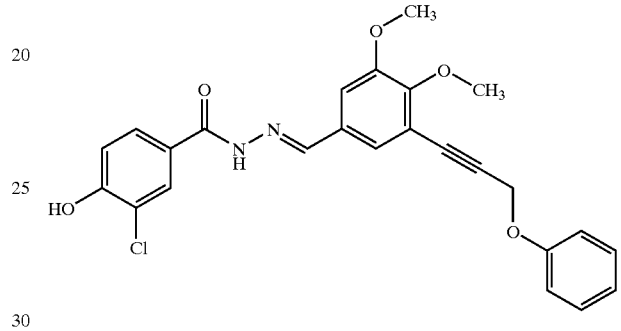

3-Chloro-4-hydroxybenzoic acid [3,4-dimethoxy-5-(3-phenoxy-1-propynyl)benzylidene]hydrazide

EXAMPLE 542:

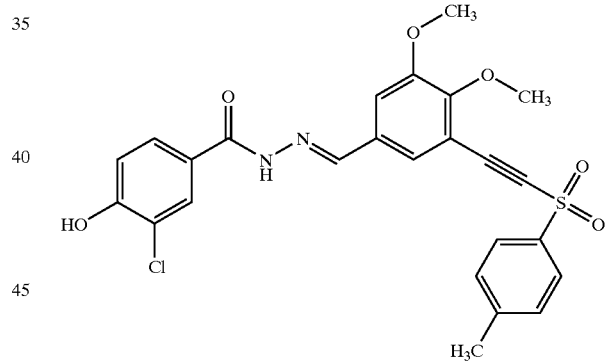

3-Chloro-4-hydroxybenzoic acid [3,4-dimethoxy-5-(toluene-4-sulfonylethynyl)-benzylidene]hydrazide

EXAMPLE 543:

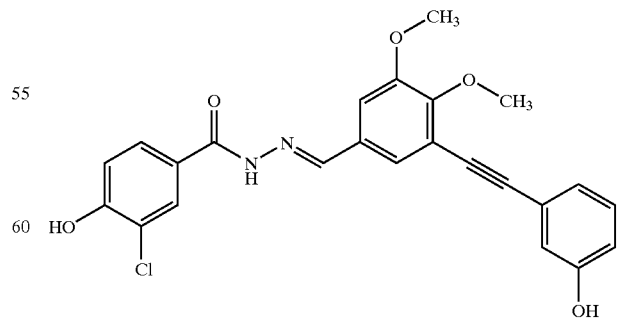

3-Chloro-4-hydroxybenzoic acid [3-(3-hydroxyphenylethynyl)-4,5-dimethoxybenzylidene]hydrazide

EXAMPLE 544:

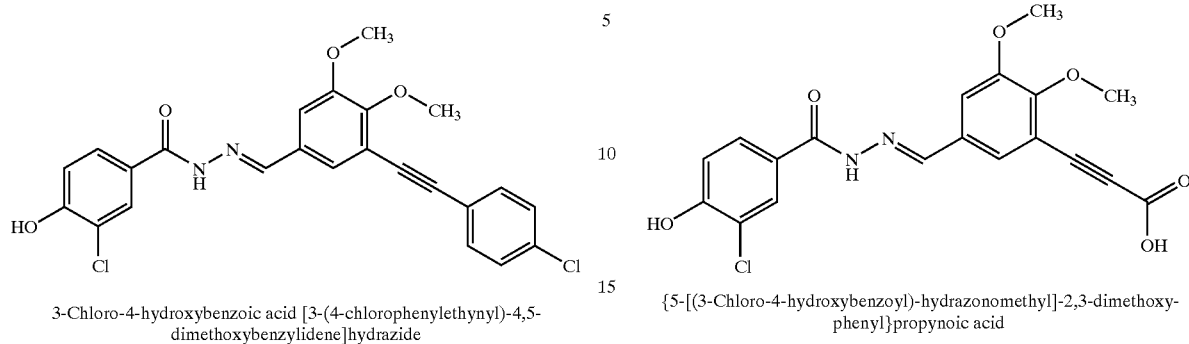

3-Chloro-4-hydroxybenzoic acid [3-(4-chlorophenylethynyl)-4,5-dimethoxybenzylidene]hydrazide

EXAMPLE 545:

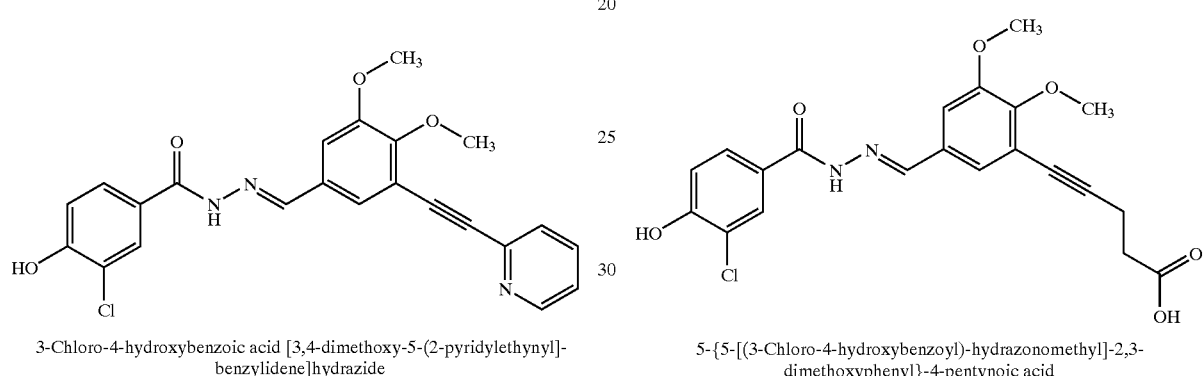

3-Chloro-4-hydroxybenzoic acid [3,4-dimethoxy-5-(2-pyridylethynyl)-benzylidene]hydrazide

EXAMPLE 546:

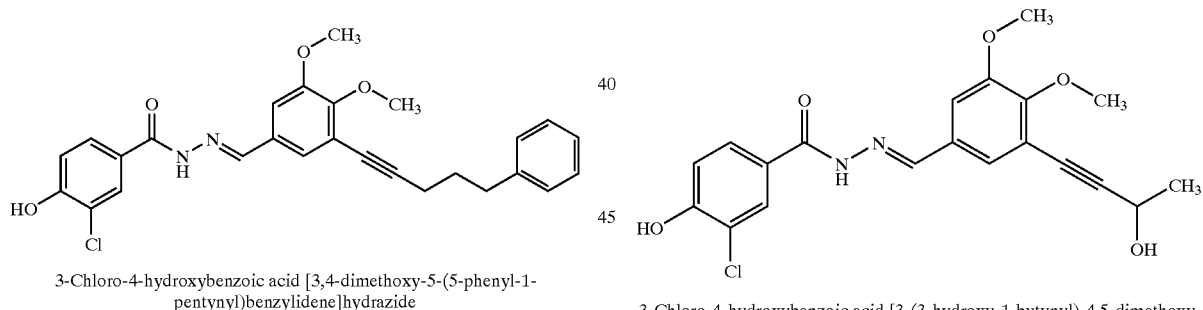

3-Chloro-4-hydroxybenzoic acid [3,4-dimethoxy-5-(5-phenyl-1-pentynyl)benzylidene]hydrazide

EXAMPLE 547:

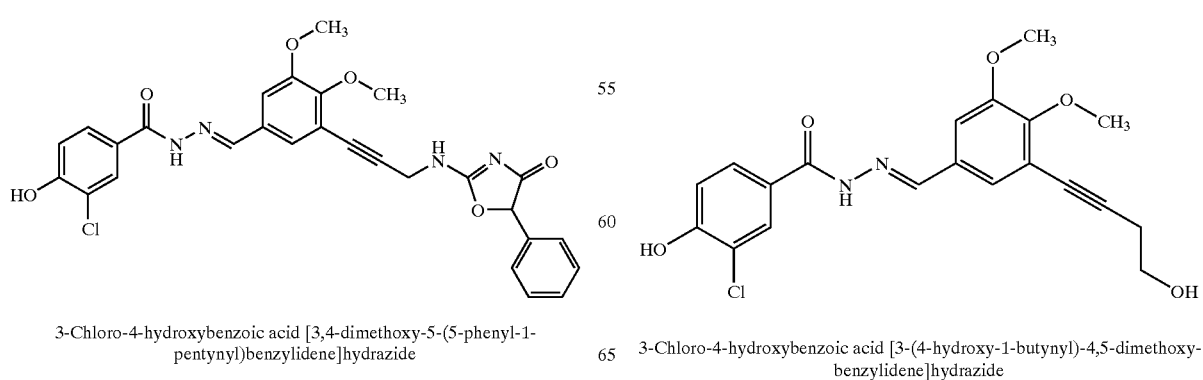

3-Chloro-4-hydroxybenzoic acid [3,4-dimethoxy-5-(5-phenyl-1-pentynyl)benzylidene]hydrazide

EXAMPLE 548:

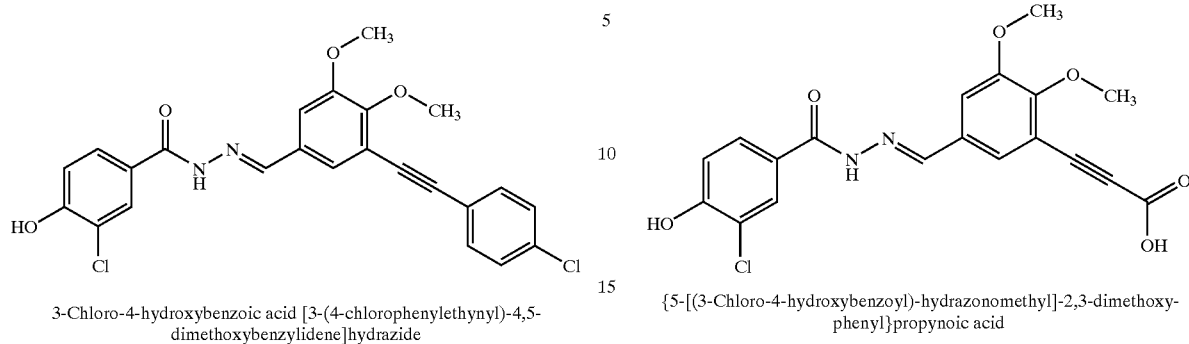

{5-[(3-Chloro-4-hydroxybenzoyl)-hydrazonomethyl]-2,3-dimethoxy-phenyl}propynoic acid

EXAMPLE 549:

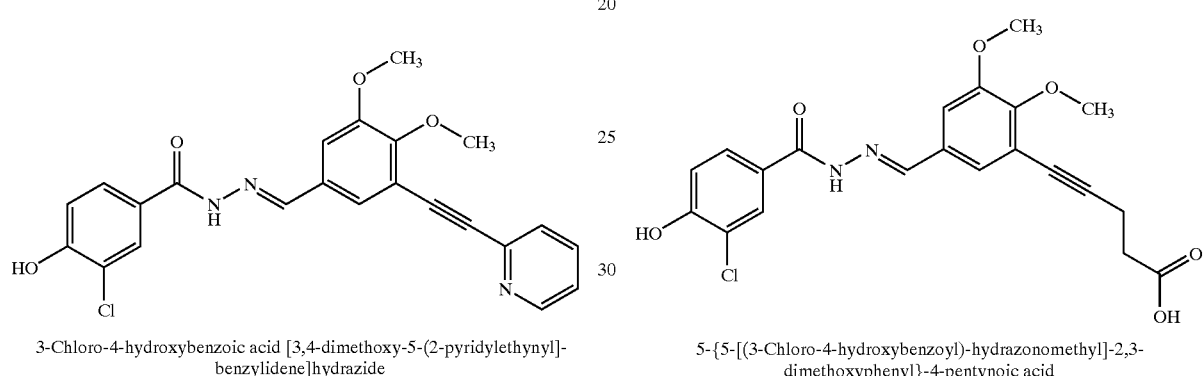

5-{5-[(3-Chloro-4-hydroxybenzoyl)-hydrazonomethyl]-2,3-dimethoxyphenyl}-4-pentynoic acid

EXAMPLE 550:

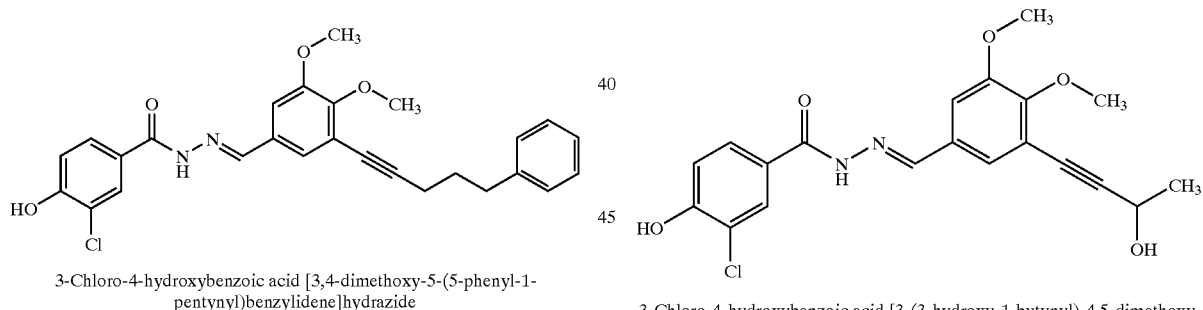

3-Chloro-4-hydroxybenzoic acid [3-(3-hydroxy-1-butynyl)-4,5-dimethoxy-benzylidene]hydrazide

EXAMPLE 551:

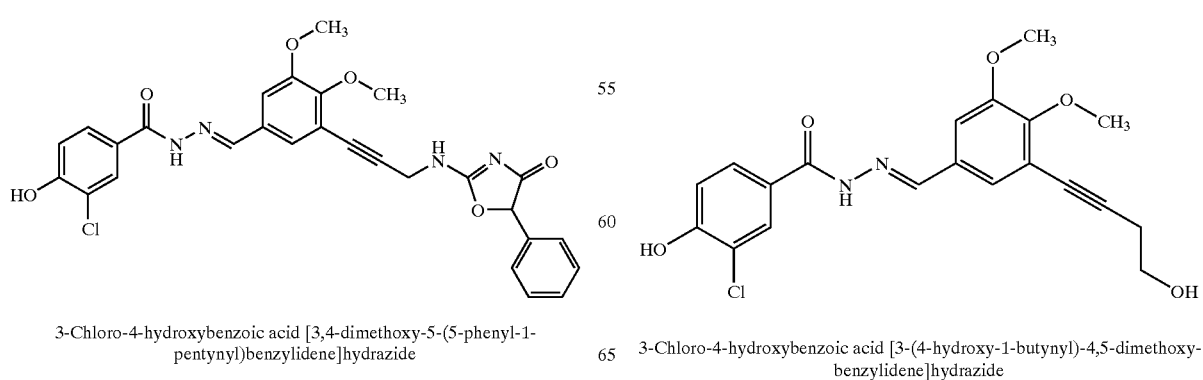

3-Chloro-4-hydroxybenzoic acid [3-(4-hydroxy-1-butynyl)-4,5-dimethoxy-benzylidene]hydrazide

EXAMPLE 552:

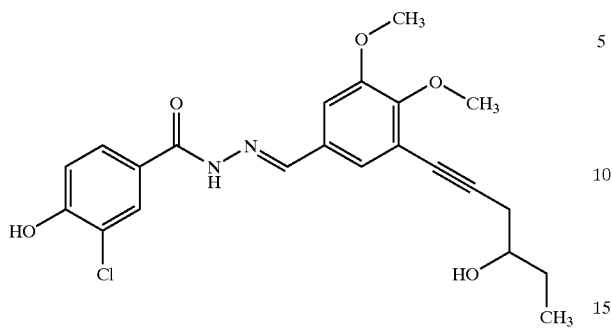

3-Chloro-4-hydroxybenzoic acid [3-(4-hydroxy-1-hexynyl)
-4,5-dimethoxy-benzylidene]hydrazide

EXAMPLE 553:

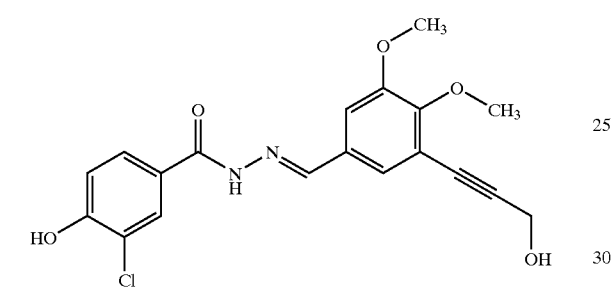

3-Chloro-4-hydroxybenzoic acid [3-(3-hydroxy-1-propynyl)-4,5-dimethoxy
benzylidene]hydrazide

EXAMPLE 554:

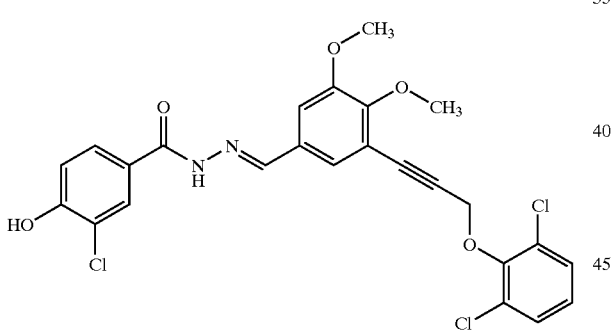

3-Chloro-4-hydroxybenzoic acid {3-[3-(2,6-dichlorophenoxy)-
1-propynyl]-4,5-dimethoxybenzylidene}hydrazide

EXAMPLE 555:

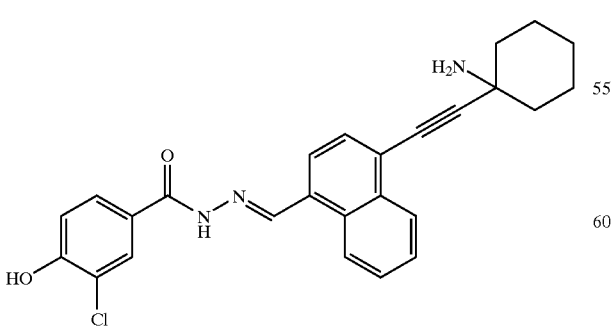

3-Chloro-4-hydroxybenzoic acid [4-(1-aminocyclohexylethynyl)-1-
naphthylmethylene]hydrazide

EXAMPLE 556:

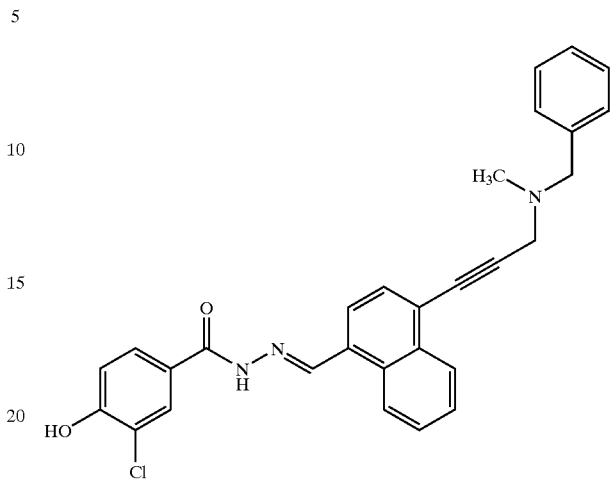

3-Chloro-4-hydroxy benzoic acid [4-(3-benzylmethylamino-1-propynyl)-
1-naphthylmethylene]hydrazide

EXAMPLE 557:

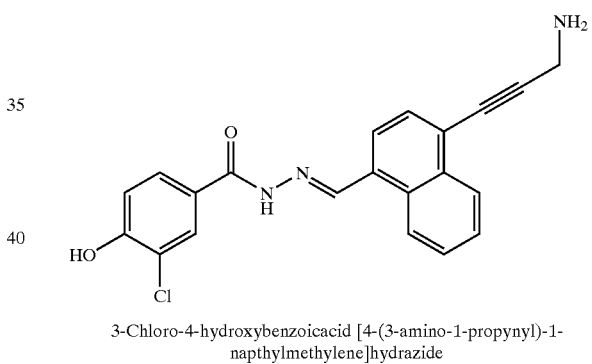

3-Chloro-4-hydroxybenzoicacid [4-(3-amino-1-propynyl)-1-
napthylmethylene]hydrazide

EXAMPLE 558:

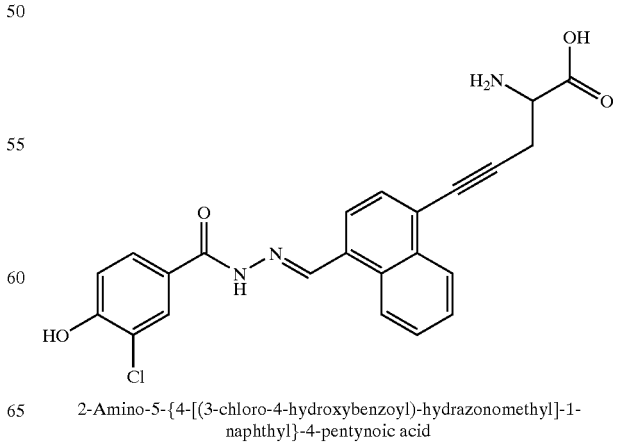

2-Amino-5-{4-[(3-chloro-4-hydroxybenzoyl)-hydrazonomethyl]-1-
naphthyl}-4-pentynoic acid

EXAMPLE 559:

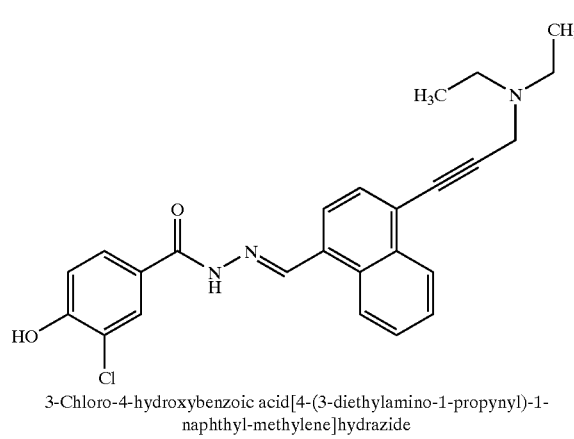

3-Chloro-4-hydroxybenzoic acid[4-(3-diethylamino-1-propynyl)-1-naphthyl-methylene]hydrazide

EXAMPLE 560:

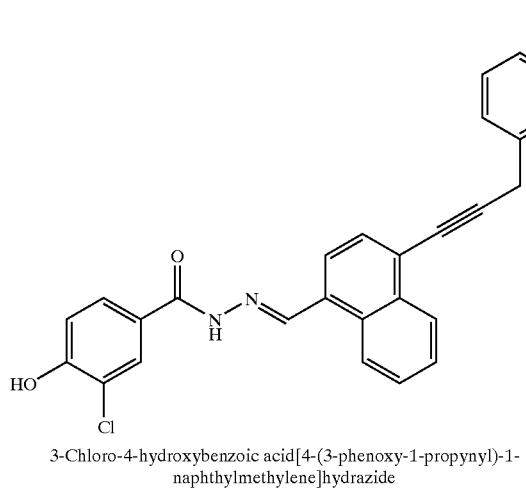

3-Chloro-4-hydroxybenzoic acid[4-(3-phenoxy-1-propynyl)-1-naphthylmethylene]hydrazide

EXAMPLE 561:

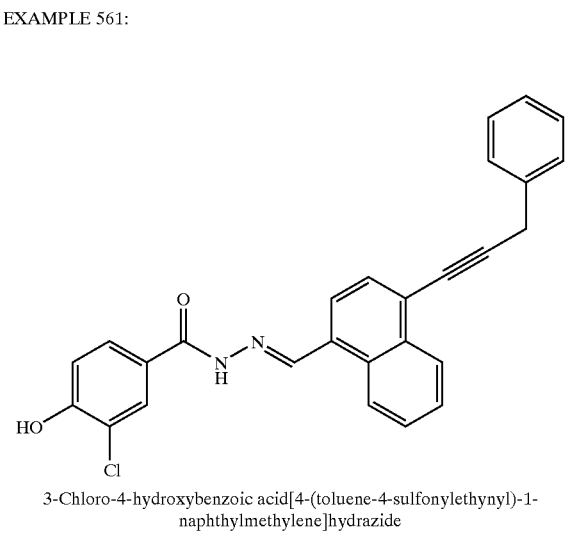

3-Chloro-4-hydroxybenzoic acid[4-(toluene-4-sulfonylethynyl)-1-naphthylmethylene]hydrazide

EXAMPLE 562:

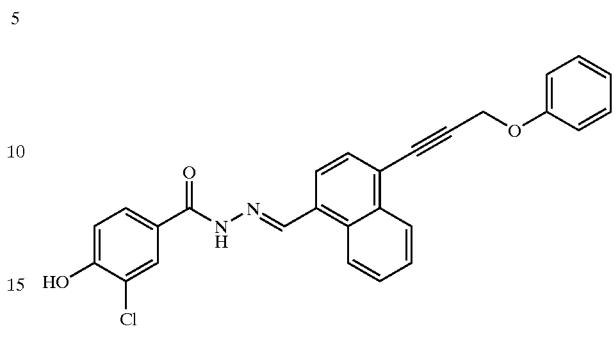

3-Chloro-4-hydroxybenzoic acid[4-(3-phenoxy-1-propynyl)-1-naphthylmethylene]-hydrazide

EXAMPLE 563:

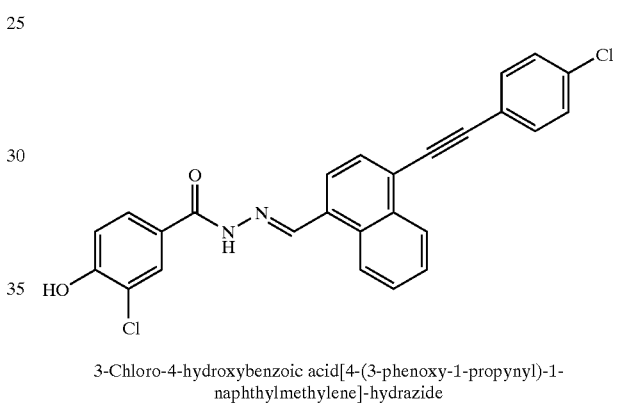

3-Chloro-4-hydroxybenzoic acid[4-(3-phenoxy-1-propynyl)-1-naphthylmethylene]-hydrazide

EXAMPLE 564:

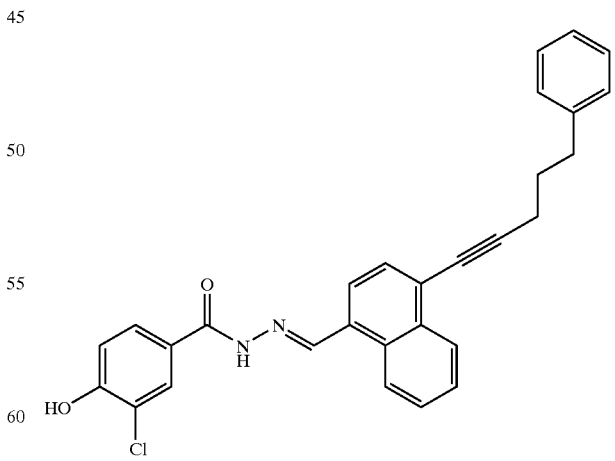

3-Chloro-4-hydroxybenzoic acid[4-(5-phenyl-1-pentynyl)-1-naphthylmethylene]hydrazide

EXAMPLE 565:

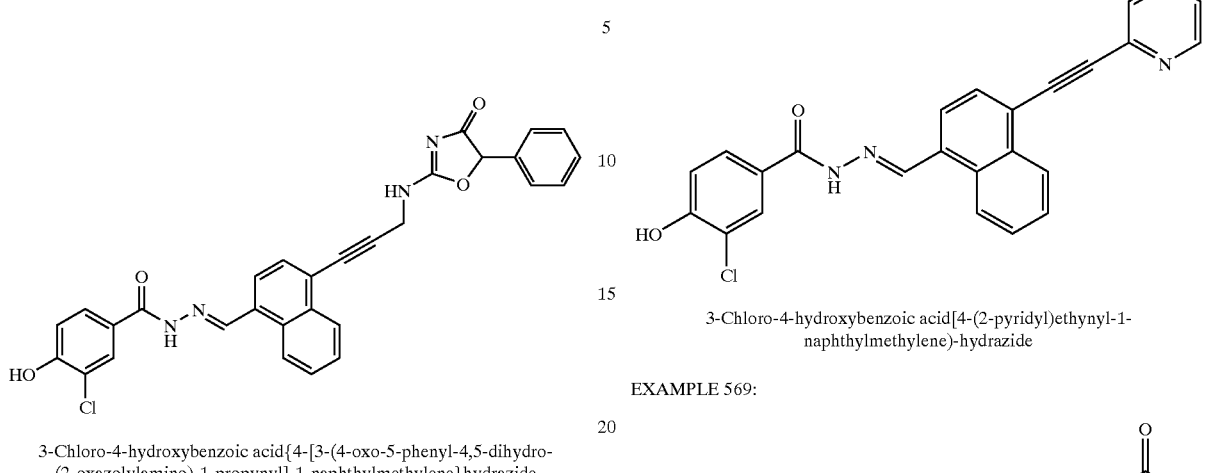

3-Chloro-4-hydroxybenzoic acid{4-[3-(4-oxo-5-phenyl-4,5-dihydro-(2-oxazolylamino)-1-propynyl]-1-naphthylmethylene}hydrazide

EXAMPLE 566:

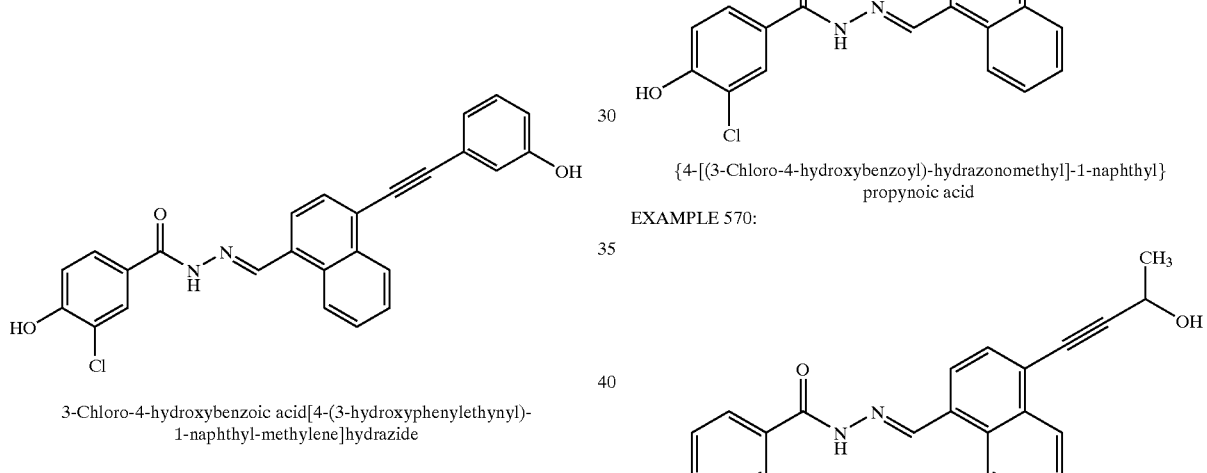

3-Chloro-4-hydroxybenzoic acid[4-(3-hydroxyphenylethynyl)-1-naphthyl-methylene]hydrazide

EXAMPLE 567:

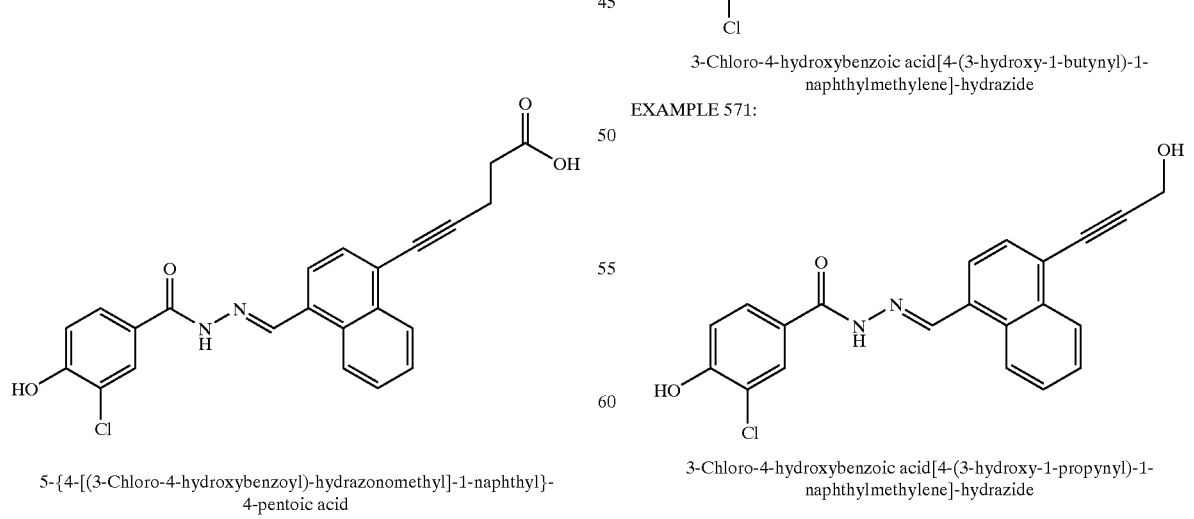

5-{4-[(3-Chloro-4-hydroxybenzoyl)-hydrazonomethyl]-1-naphthyl}-4-pentoic acid

EXAMPLE 568:

3-Chloro-4-hydroxybenzoic acid[4-(2-pyridyl)ethynyl-1-naphthylmethylene)-hydrazide

EXAMPLE 569:

{4-[(3-Chloro-4-hydroxybenzoyl)-hydrazonomethyl]-1-naphthyl} propynoic acid

EXAMPLE 570:

3-Chloro-4-hydroxybenzoic acid[4-(3-hydroxy-1-butynyl)-1-naphthylmethylene]-hydrazide

EXAMPLE 571:

3-Chloro-4-hydroxybenzoic acid[4-(3-hydroxy-1-propynyl)-1-naphthylmethylene]-hydrazide

429
-continued

EXAMPLE 572:

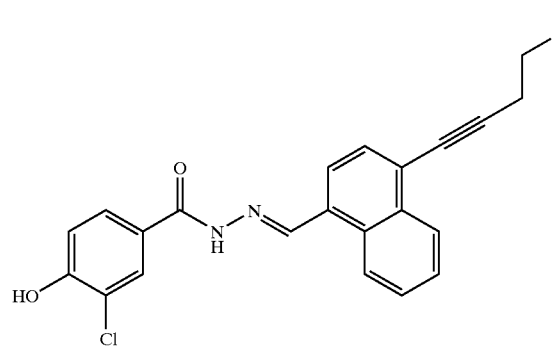

3-Chloro-4-hydroxybenzoic acid[4-(4-hydroxy-1-butynyl)-1-naphthylmethylene]-hydrazide

EXAMPLE 573:

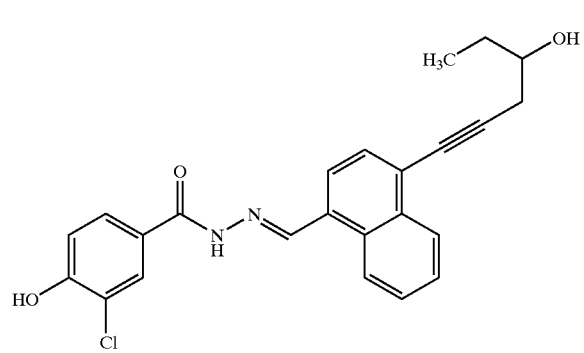

3-Chloro-4-hydroxybenzoic acid[4-(4-hydroxy-1-hexynyl)-1-naphthylmethylene]-hydrazide

EXAMPLE 574:

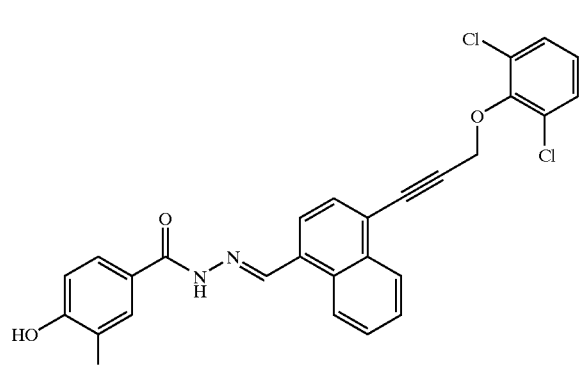

3-Chloro-4-hydroxybenzoic acid{4-[3-(2,6-dichlorophenoxy)-1-propynyl]-1-naphthylmethylene}hydrazide

EXAMPLE 575:

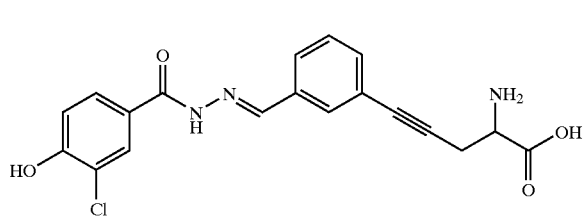

2-Amino-5-{3-[(3-chloro-4-hydroxy-benzoyl)hydrazonomethyl]phenyl}-4-pentynoic acid

430
-continued

EXAMPLE 576:

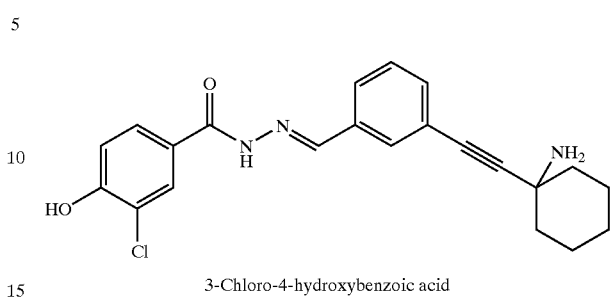

3-Chloro-4-hydroxybenzoic acid [3-(1-aminocyclohexylethynyl)benzylidene]-hydrazide

EXAMPLE 577:

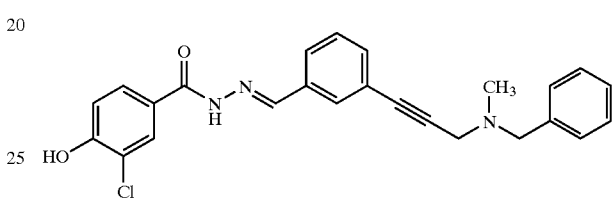

3-Chloro-4-hydroxybenzoic acid{3-[3-(benzylmethylamino)-1-propynyl]benzylidene}hydrazide

EXAMPLE 578:

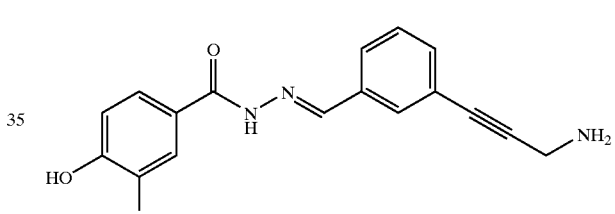

3-Chloro-4-hydroxybenzoic acid{3-[3-(benzylmethylamino)-1-propynyl]benzylidene}hydrazide

EXAMPLE 579:

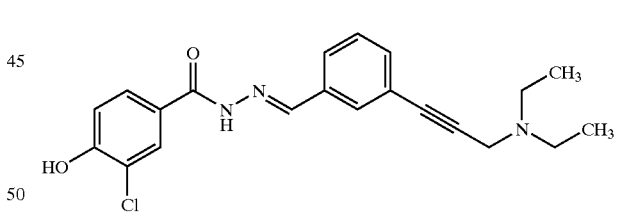

3-Chloro-4-hydroxybenzoic acid[3-(3-diethylamino-1-propynyl)benzylidene]-hydrazide

EXAMPLE 580:


3-Chloro-4-hydroxybenzoic acid[3-(toluene-4-sulfonylethynyl)benzylidene]hydrazide

EXAMPLE 581:

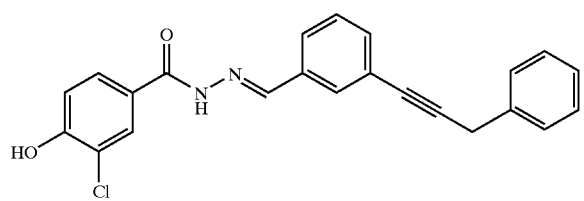

3-Chloro-4-hydroxybenzoic acid[3-(3-phenyl-1-propynyl)benzylidene]
hydrazide

EXAMPLE 582:

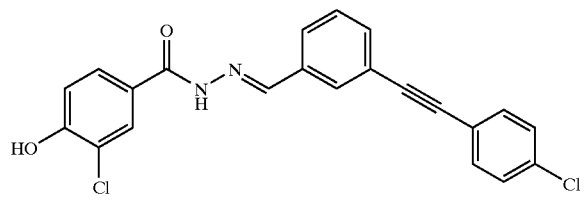

3-Chloro-4-hydroxybenzoic acid[3-(4-chlorophenylethynyl)benzylidene]
hydrazide

EXAMPLE 583:

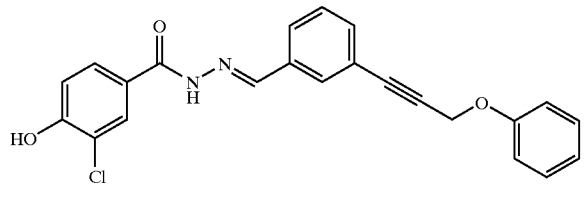

3-Chloro-4-hydroxybenzoic acid[3-(3-phenoxy-1-
propynyl)benzylidene]hydrazide

EXAMPLE 584:

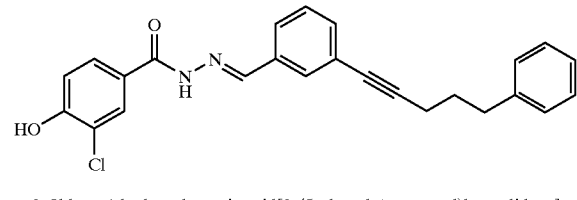

3-Chloro-4-hydroxybenzoic acid[3-(5-phenyl-1-pentynyl)benzylidene]
hydrazide

EXAMPLE 585:

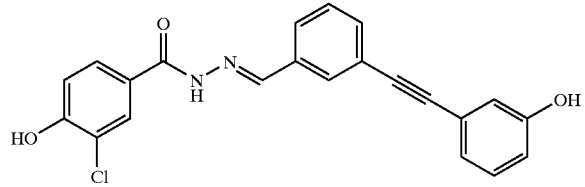

3-Chloro-4-hydroxybenzoic acid
[3-(3-hydroxyphenylethynyl)benzylidene]-hydrazide

EXAMPLE 586:

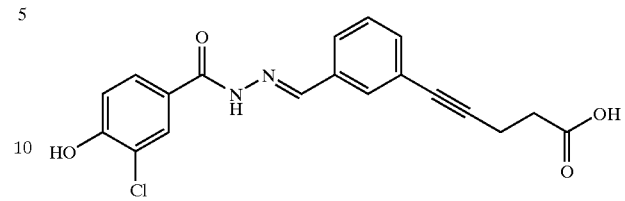

5-{3-[(3-Chloro-4-hydroxybenzoyl)-hydrazonomethyl]phenyl}-
4-pentynoic acid

EXAMPLE 587:

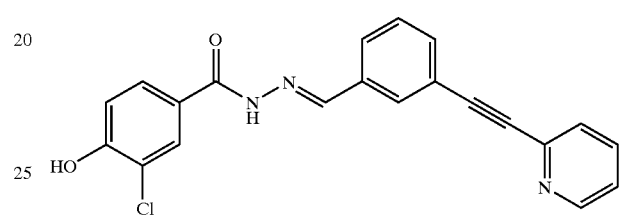

3-Chloro-4-hydroxybenzoic acid
[3-(2-pyridylethynyl)benzylidene]hydrazide

EXAMPLE 588:

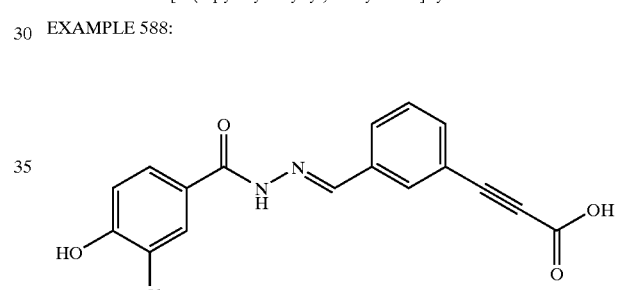

{3-[(3-chloro-4-hydroxybenzoyl)-hydrazonomethyl]phenyl}
propynoic acid

EXAMPLE 589:

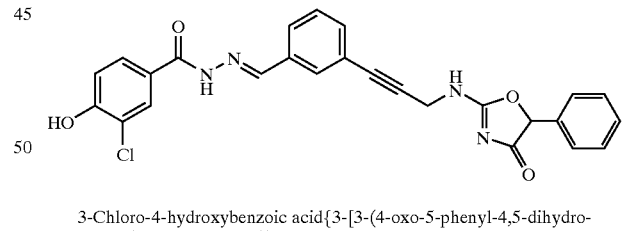

3-Chloro-4-hydroxybenzoic acid{3-[3-(4-oxo-5-phenyl-4,5-dihydro-
(2-oxazolylamino))-1-propynyl]benzylidene}hydrazide

EXAMPLE 590:

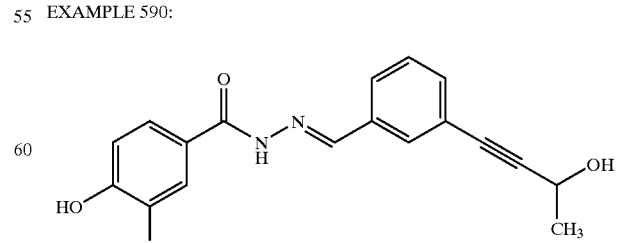

3-Chloro-4-hydroxybenzoic acid[3-(3-hydroxy-1-
butynyl)benzylidene]hydrazide

EXAMPLE 591:

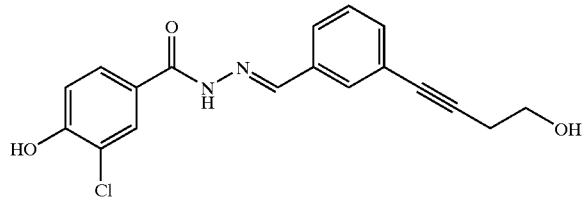

3-Chloro-4-hydroxybenzoic acid[3-(4-hydroxy-1-butynyl)benzylidene]hydrazide

EXAMPLE 592:

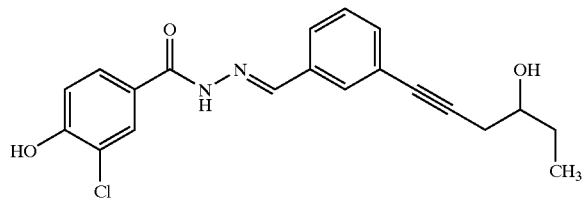

3-Chloro-4-hydroxybenzoic acid[3-(4-hydroxy-1-hexynyl)benzylidene]hydrazide

EXAMPLE 593:

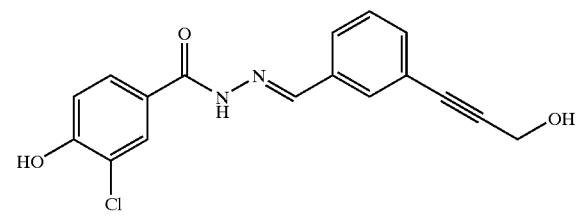

3-Chloro-4-hydroxybenzoic acid[3-(3-hydroxy-1-propynyl)benzylidene]hydrazide

EXAMPLE 594:

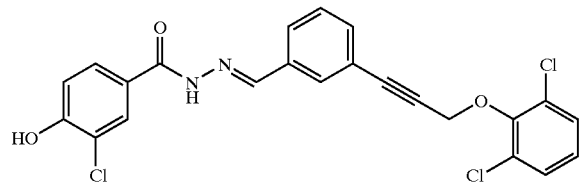

3-Chloro-4-hydroxybenzoic acid{3-[3-(2,6-dichlorophenoxy)-1-propynyl]benzylidene}-hydrazide

EXAMPLE 595:

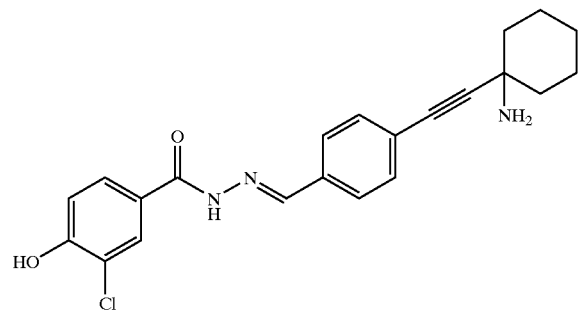

3-Chloro-4-hydroxybenzoic acid[4-(1-aminocyclohexylethynyl)benzylidene]-hydrazide

EXAMPLE 596:

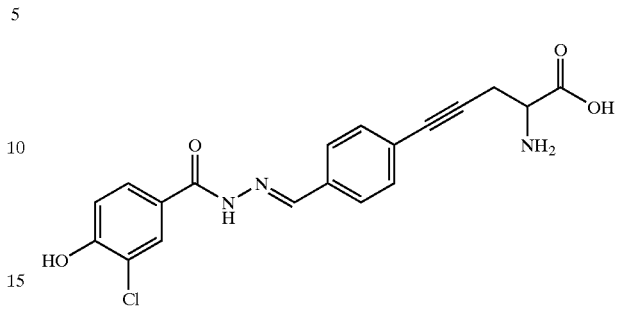

2-Amino-5-{4-[(3-chloro-4-hydroxybenzoyl)-hydrazonomethyl]phenyl}-4-pentynoic acid

EXAMPLE 597:

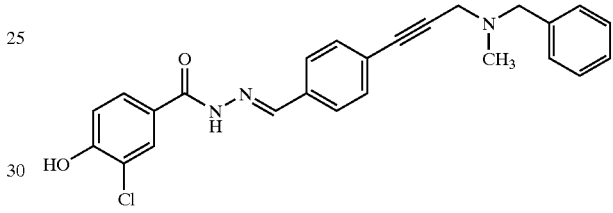

3-Chloro-4-hydroxybenzoic acid{4-[3-(benzylmethylamino)-1-propynyl]-benzylidene}hydrazide

EXAMPLE 598:

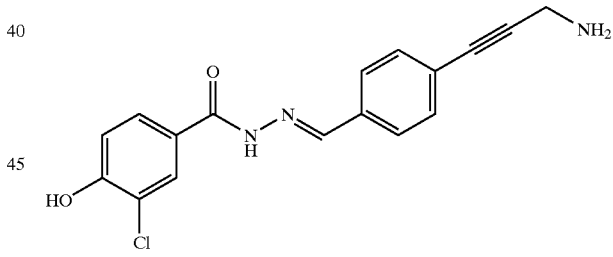

3-Chloro-4-hydroxybenzoic acid[4-(3-amino-1-propynyl)benzylidene]hydrazide

EXAMPLE 599:

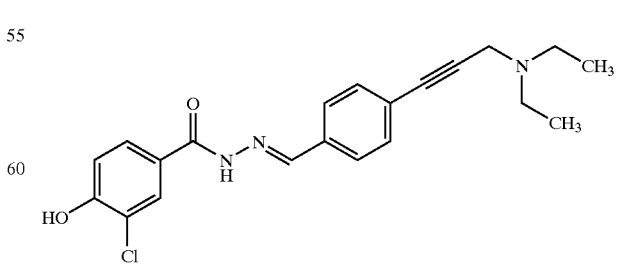

3-Chloro-4-hydroxybenzoic acid[4-(3-diethylamino-1-propynyl)benzylidene]-hydrazide

EXAMPLE 600:

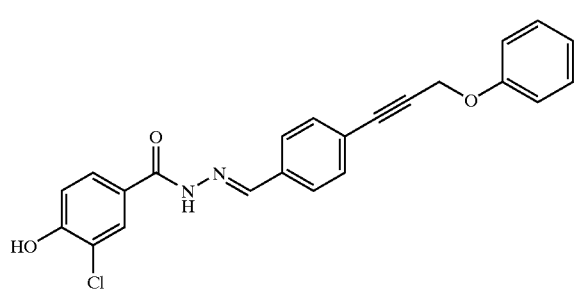

3-Chloro-4-hydroxybenzoic acid[4-(3-diethylamino-1-propynyl)benzylidene]-hydrazide

EXAMPLE 601:

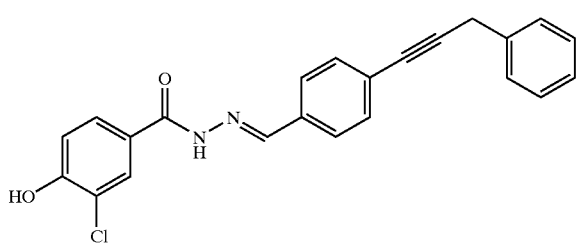

3-Chloro-4-hydroxybenzoic acid[4-(3-diethylamino-1-propynyl)benzylidene]-hydrazide

EXAMPLE 602:

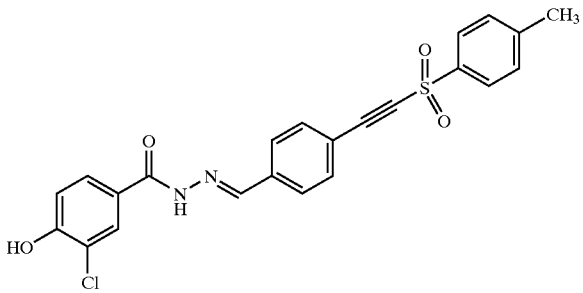

3-Chloro-4-hydroxybenzoic acid[4-(toluene-4-sulfonylethynyl)benzylidene]hydrazide

EXAMPLE 603:

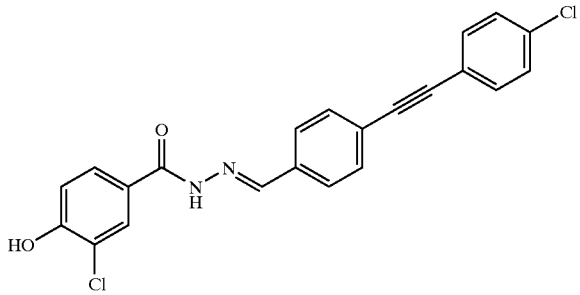

3-Chloro-4-hydroxybenzoic acid[4-(4-chlorophenylethynyl)benzylidene]hydrazide

EXAMPLE 604:

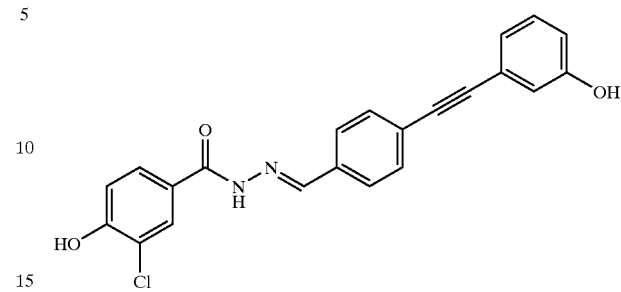

3-Chloro-4-hydroxybenzoic acid[4-(3-hydroxyphenylethynyl)benzylidene]hydrazide

EXAMPLE 605:

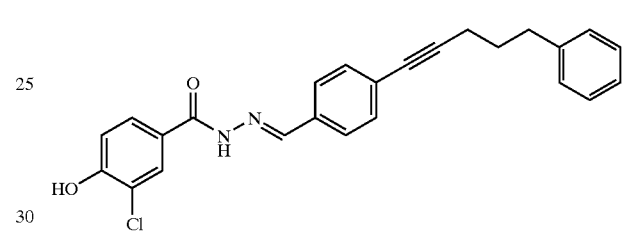

3-Chloro-4-hydroxybenzoic acid[4-(5-phenyl-1-pentynyl)benzylidene]hydrazide

EXAMPLE 606:

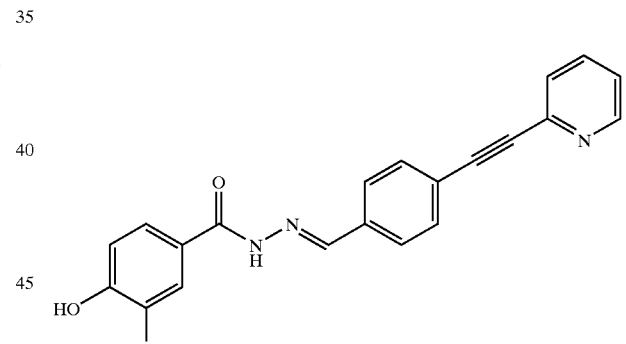

3-Chloro-4-hydroxybenzoic acid[4-(2-pyridylethynyl)benzylidene]hydrazide

EXAMPLE 607:

3-Chloro-4-hydroxybenzoic acid{4-[3-(4-oxo-5-phenyl-4,5-dihydro-(2-oxazolylamino)-1-propynyl]benzylidene}hydrazide

EXAMPLE 608:

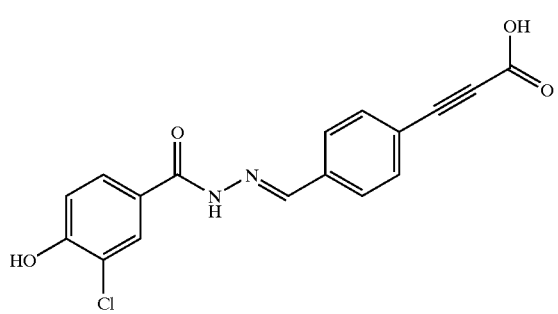

{4-[(3-Chloro-4-hydroxybenzoyl)hydrazonomethyl]-phenyl}
propynoic acid

EXAMPLE 609:

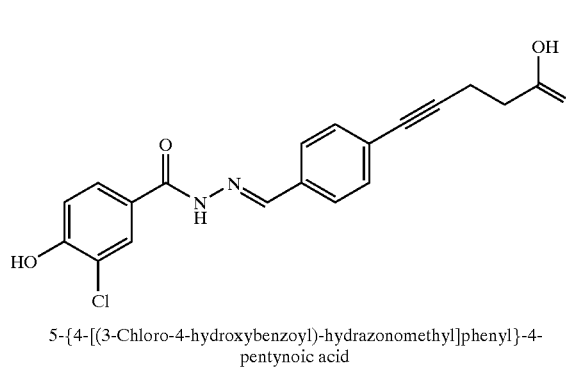

5-{4-[(3-Chloro-4-hydroxybenzoyl)-hydrazonomethyl]phenyl}-4-
pentynoic acid

EXAMPLE 610:

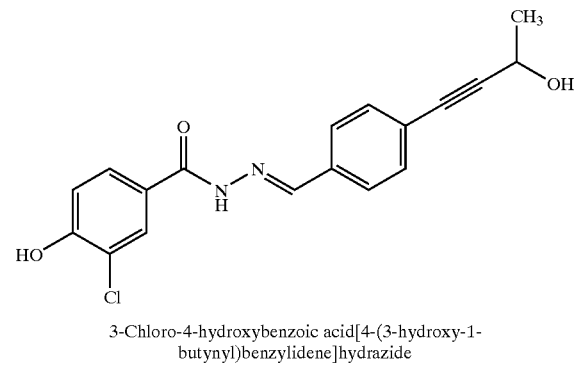

3-Chloro-4-hydroxybenzoic acid[4-(3-hydroxy-1-
butynyl)benzylidene]hydrazide

EXAMPLE 611:

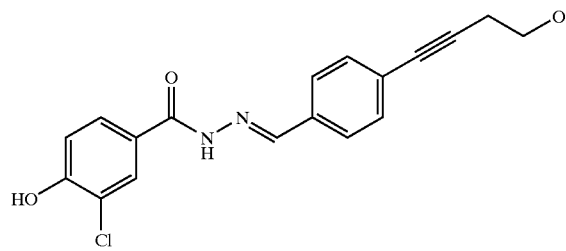

3-Chloro-4-hydroxybenzoic acid[4-(4-hydroxy-1-
butynyl)benzylidene]hydrazide

EXAMPLE 612:

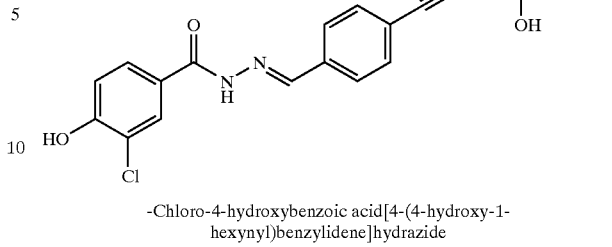

-Chloro-4-hydroxybenzoic acid[4-(4-hydroxy-1-
hexynyl)benzylidene]hydrazide

EXAMPLE 613:

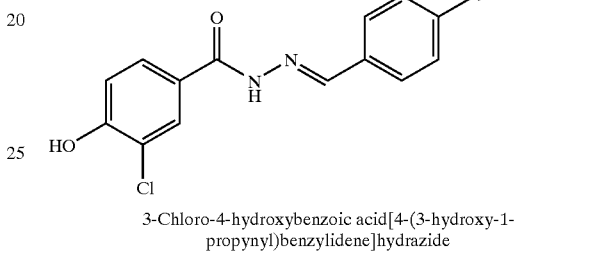

3-Chloro-4-hydroxybenzoic acid[4-(3-hydroxy-1-
propynyl)benzylidene]hydrazide

EXAMPLE 614:

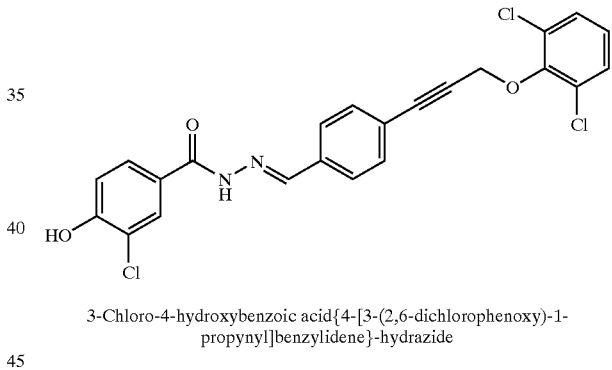

3-Chloro-4-hydroxybenzoic acid{4-[3-(2,6-dichlorophenoxy)-1-
propynyl]benzylidene}-hydrazide General Procedure for the
Preparation of Examples 615 to 694

The following 80 compounds were prepared as single entities by parallel synthesis on a solid support. The attachment of [Building block 3] and cleavage from the resin were performed on an Advanced ChemTech Model 384 HTS.

The compounds were prepared according to the following equation:

Resin—[Building block 1]→

Resin—[Building block 1]—[Building block 2]→

Resin—[Building block 1]—[Building block 2]—
[Building block 3]

and were simultaneously cleaved (and deprotected when protected) from the resin with 50% trifluoroacetic acid in dichloromethane to give the desired compounds as individual entities according to the following formula:

[Building block 1]—[Building block 2]—[Building block 3].

The starting resins, Resin—[Building block 1]—[Building block 2], were all prepared as described above.

The resin used was a polystyrene resin loaded with a Wang linker and the substitution capacity was 0.9 mmol/g.

All 80 compounds are based on attachment of [Building block 3] to Resin—[Building block 1]—[Building block 2] in a fully combinatorial way using a Suzuki reaction according to the following scheme.

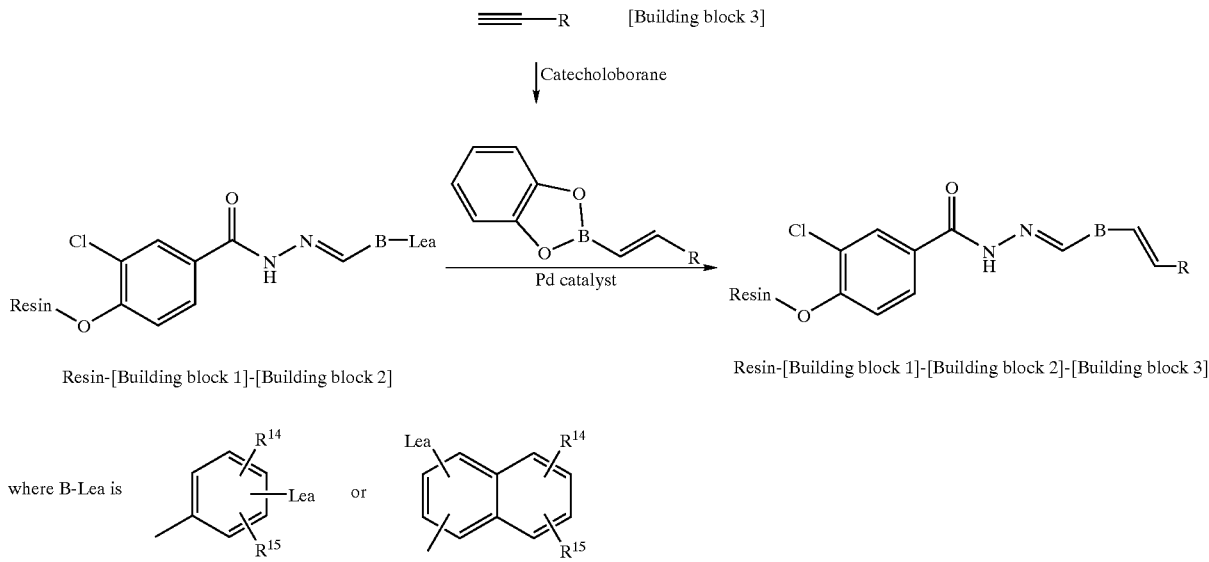

wherein Lea is a leaving group and $R^{14}$ and $R^{15}$ are as defined for formula I.

The starting materials used were the same as those use in examples 535 to 614, i.e. Resin—[Building block 1], [Building block 2] and [Building block 3] were the same as those used in examples 535 to 614, the only difference being the products in examples 615 to 694 are having double bonds as compared to the products in examples 535 to 614 having triple bonds.

EXAMPLE 615

3-Chloro-4-hydroxybenzoic Acid {3-[2-(1-Aminocyclohexyl)vinyl]-4,5-dimethoxybenzylidene}hydrazide

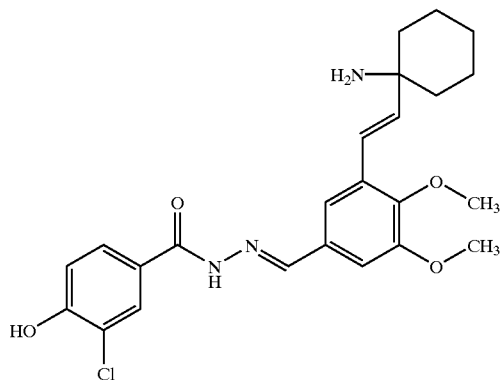

Preparation of a 1,4-Dioxane/THF Solution of 1-(2-Benzo[1,3,2]dioxaborol-2-ylvinyl)cyclohexylamine To a solution of 1-ethynylcyclohexylamine ([Building block 3]) in 1,4-dioxane (1 M, 0.5 mL) was added a solution of catecholborane in THF (1 M, 0.5 mL) and the mixture was heated at 60° C. for 4 hours. The solution was cooled to room temperature and used directly in the Suzuki coupling reaction.

To the resin bound 3-chloro-4-hydroxybenzoic acid (3-bromobenzylidene)hydrazide (0.05 mmoles) was added a solution of cesium carbonate in water (1.25 M, 0.2 mL), a solution of triphenylphosphine and tetrabutylammonium chloride in NMP (both 0.4 M, 0.5 mL), a solution of palladium (II) acetate in NMP (0.16 M, 0.25 mL), was mixed and the solution of 1-(2-benzo[1,3,2]dioxaborol-2-ylvinyl)cyclohexylamine in 1,4-dioxane/THF (prepared as described above) was added and the mixture was shaken at 70° C. for 15 hours. The resin was repeatedly washed with NMP (1.5 mL, 3 times), 50% water in DMF (1.5 mL, 3 times), NMP (1.5 mL, 2 times), 1% sodium diethylaminodithiocarbamate trihydrate (1.5 mL, 9 times), NMP (1.5 mL, 5 times) and $CH_2Cl_2$ (1.5 mL, 6 times) for 2 minutes and filtered.

The compound was cleaved off the resin by shaking for 45 minutes at room temperature with a 50% solution of trifluoroacetic acid in $CH_2Cl_2$ (1.5 mL). The mixture was filtered and the resin was extracted with $CH_2Cl_2$ (0.5 mL). The combined $CH_2Cl_2$ extracts were concentrated in vacuo. The residue was dissolved in a 1:1 mixture of methanol and $CH_2Cl_2$ (1 mL) and concentrated in vacuo to give the title compound.

The final product obtained was characterized by analytical RP-HPLC (retention time) and by LC-MS (molecular mass).

The RP-HPLC analysis was performed on a Waters HPLC system consisting of Waters™ 600S Controller, Waters™ 996 Photodiode Array Detector, Waters™ 717 Autosampler, Waters™ 616 Pump, Waters™ 3 mm×150 mm 3.5 µ C-18 Symmetry column and Millenium QuickSet Control Ver. 2.15 using UV detection at 214 nm. A gradient of 5% to 90% acetonitrile/0.1% trifluoroacetic acid/water at 15 minutes at 1 mL/minute. The LC-MS analysis was performed on a PE Sciex API 100 LC/MS System using a Waters™ 3 mm×150 mm 3.5 μ C-18 Symmetry column and positive ionspray with a flow rate at 20 μL/minute.

EXAMPLES 616 TO 694

A library of the following 79 compounds can be prepared in parallel as individual entities analogously to example 615 on an Advanced ChemTech Model 496 HTS using the following ChemFile to control the operation of the synthesizer. The 4 resins of type Resin—[Building block 1]—[Building block 2] are equally distributed in the 80 wells in the synthesizer prior to the initialization of device.

ChemFile C:\ACT\90250003.CHM Page 1

1 Empty RB_Heating_All_1to96 for 2.000 minute(s)
2
3 REM Addition of Cs2C03 in water
4
5 Transfer 200 μl from Monomers_1to36 [25] ( ) to RB_Heating_All_1to96 [1–80] using DCE
6 Mix for 1.00 minutes at 600 rpm(s)
7
8 REM Addition of Ph3P+Bu4NCl in NMP
9
10 Transfer 500 μl from Monomers_1to36 [21] ( ) to RB_Heating_All_1to96 [1–80] using DCE
11 Mix for 1.00 minutes at 600 rpm(s)
12
13 REM Addition of Pd(OAc)2 in NMP
14
15 Transfer 500 μl from Monomers_1to36 [22] ( ) to RB_Heating_All_1to96 [1–80] using DCE
16 Mix for 2.00 minutes at 600 rpm(s)
17 Dispense Sequence C:\ACT\ALKYNES.DSP with 500 μl to RB_Heating_All_1to96 rack
18 Set Temperature to 70.0 degrees Celsius
19 Mix for 15.00 minutes at 600 rpm(s)
20 Wait for 15.000 minute(s)
21 Repeat from step 19, 29 times
22 Turn Temperature Controller Off
23 Mix for 15.00 minutes at 600 rpm(s)
24 Wait for 15.000 minute(s)
25 Repeat from step 23, 7 times
26 Empty RB_Heating_All 1 to 96 for 2.000 minute(s)
27 Dispense System Fluid NMP1 1500 μl to RB_Cleavage_All_1to96 [1–80]
28 Mix for 3.00 minutes at 600 rpm(s)
29 Empty RB_Heating_All_1to96 for 2.000 minute(s)
30 Repeat from step 27, 2 times
31
32 REM Wash with 50% H2O/NMP
33
34 Transfer 1500 μl from Reagent_3 [1] ( ) to RB_Heating_All_1to96 [1–80] using NMP1
35 Mix for 3.00 minutes at 600 rpm(s)
36 Empty RB_Heating_All_1to96 for 2.000 minute(s)
37 Repeat from step 34, 2 times
38 Dispense System Fluid NMP1 1500 μl to RB_Cleavage_All_1to96 [1–80]
39 Mix for 3.00 minutes at 600 rpm(s)
40 Empty RB_Heating_All_1to96 for 2.000 minute(s)
41 Repeat from step 38, 1 times
42
43 REM Wash with Sodium diethylaminodithiocarbamate
44
45 Transfer 1500 μl from Reagent$_{13}$ 3 [1] ( ) to RB_Heating_All_1to96 [1–80] using NMP1
46 Mix for 3.00 minutes at 600 rpm(s)
47 Empty RB_Heating_All_1to96 for 2.000 minute(s)
48 Repeat from step 45, 2 times
49 Transfer 1500 μl from REAGENT_4 [1] ( ) to RB_Heating_All_1to96 [1–80] using NMP1
50 Mix for 3.00 minutes at 600 rpm(s)
51 Empty RB_Heating_All_1to96 for 2.000 minute(s)
52 Repeat from step 49, 2 times
53 Transfer 1500 μl from REAGENT_5 [1] ( ) to RB_Heating All_1to96[1–80] using NMP1
54 Mix for 2.00 minutes at 600 rpm(s)
55 Empty RB_Heating_All_1to96 for 2.000 minute(s)
56 Repeat from step 53, 2 times
57 Dispense System Fluid NMP1 1500 μl to RB_Cleavage_All_1to96 [1–80]
58 Mix for 3.00 minutes at 600 rpm(s)
59 Empty RB_Heating_All_1to96 for 2.000 minute(s)
60 Repeat from step 57, 4 times
61 Dispense System Fluid DCE1 1500 μl to RB_Cleavage_All_1to96 [1–80]
62 Mix for 3.00 minutes at 600 rpm(s)
63 Empty RB Heating_All _1to96 for 2.000 minute(s)
64 Repeat from step 61, 5 times
65
66 REM Cleavage from Resin
67 REM with 50% TFA/DCM
68
69 Transfer 1500 μl from Reagent_3 [1] ( ) to RB_Cleavage_All_1to96 [1–80] using DCM1
70 Mix for 45.00 minutes at 600 rpm(s)
71 Empty RB_Cleavage_All_1to96 for 1.000 minute(s)
72 Dispense System Fluid DCM1 500 μl to RB_Cleavage_All_1to96 [1–80]
73 Mix for 1.00 minutes at 300 rpm(s)
74 Empty RBCleavage_All_1to96 for 1.000 minute(s)
75

Dispense Sequence C:\ACT\ALKYNES.DSP is a subroutine that controls the combinatorial addition of the solutions of the 20 2-vinyl-benzo[1,3,2]dioxaboroles of type [Building block 3] into the 80 wells in the synthesizer.

The library containing the compounds listed below was synthesized. A subset of the library obtained was characterized by analytical RP-HPLC (retention time) and by LC-MS (molecular mass).

EXAMPLE 616:

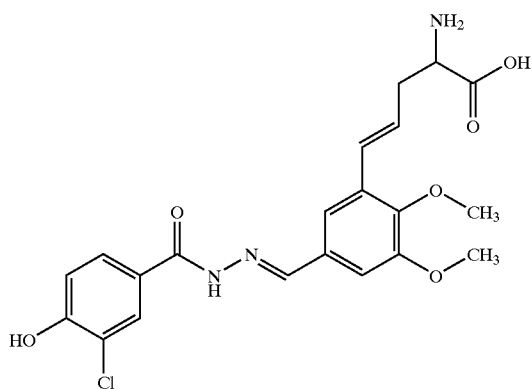

2-Amino-5-{5-[(3-chloro-4-hydroxybenzoyl)-
hydrazonomethyl]-2, 3-dimethoxyphenyl}-4-pentenoic
acid

EXAMPLE 617:

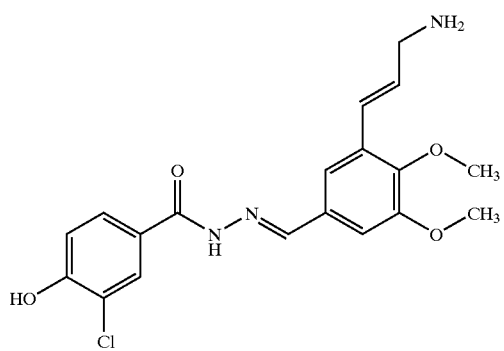

3-Chloro-4-hydroxybenzoic acid[3-(3-amino-1-propenyl)-4, 5-
dimethoxy-benzylidene]hydrazide

EXAMPLE 618:

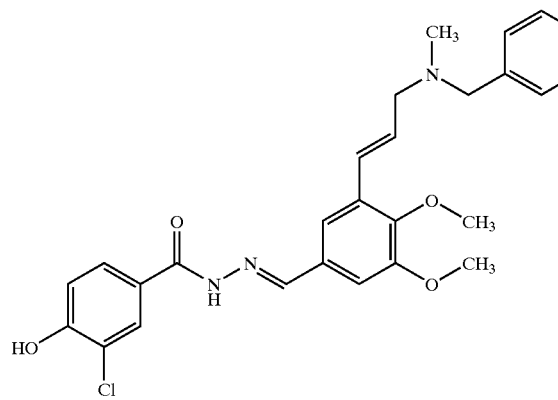

3-Chloro-4-hydroxybenzoic acid{3-[3-(benzylmethylamino)propenyl]
-4, 5-dimethoxybenzylidene}hydrazide

EXAMPLE 619:

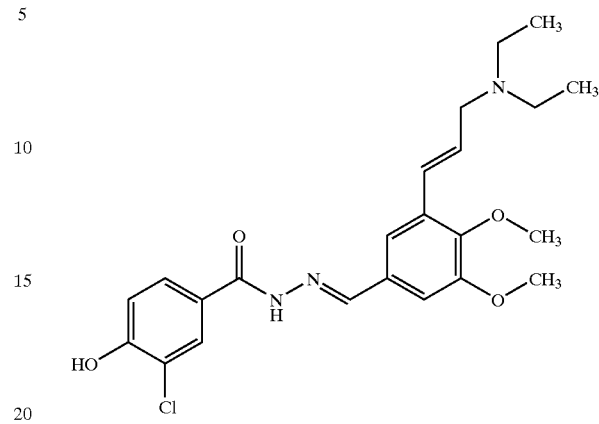

3-Chloro-4-hydroxybenzoic acid[3-(3-diethylamino-1-propenyl)
-4, 5-dimethoxybenzylidene]hydrazide

EXAMPLE 620:

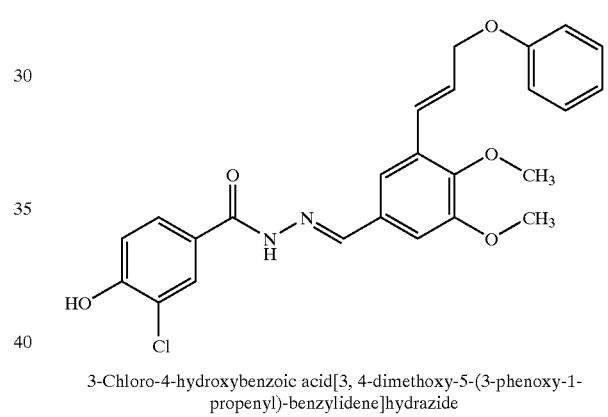

3-Chloro-4-hydroxybenzoic acid[3, 4-dimethoxy-5-(3-phenoxy-1-
propenyl)-benzylidene]hydrazide

EXAMPLE 621:

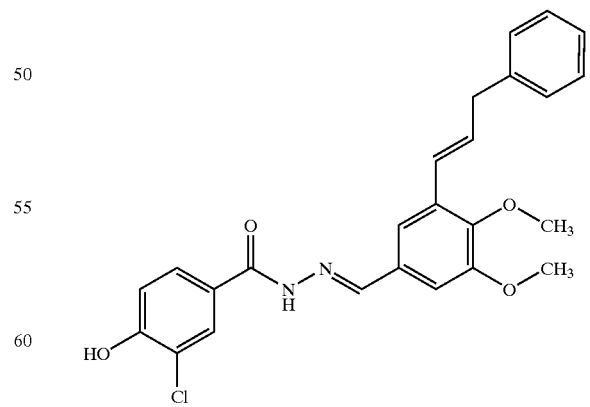

3-Chloro-4-hydroxybenzoic acid[3, 4-dimethoxy-5-(3-phenyl-1-
propenyl)-benzylidene]hydrazide

EXAMPLE 622:

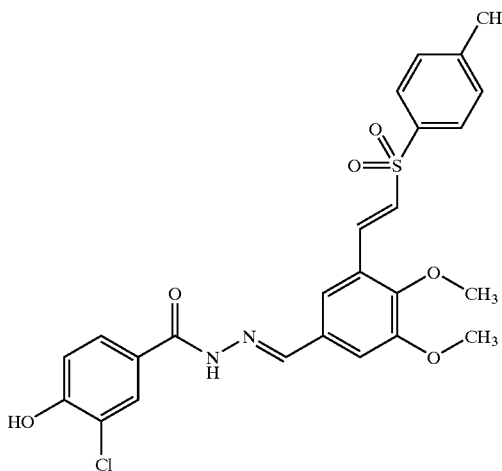

3-Chloro-4-hydroxybenzoic acid{3, 4-dimethoxy-5-[2-(toluene-4-sulfonyl)vinyl]-benzylidene}hydrazide

EXAMPLE 623:

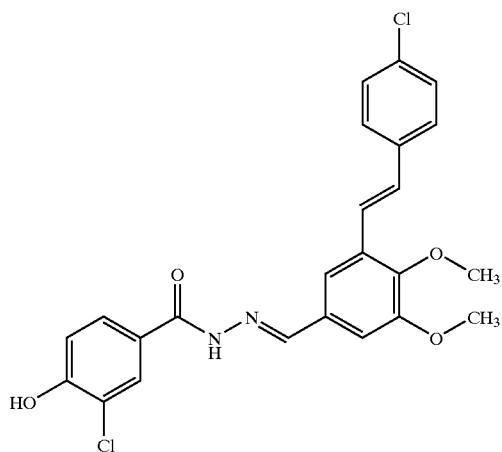

3-Chloro-4-hydroxybenzoic acid{3-[2-(4-chlorophenyl)vinyl]-4, 5-dimethoxybenzylidene}hydrazide

EXAMPLE 624:

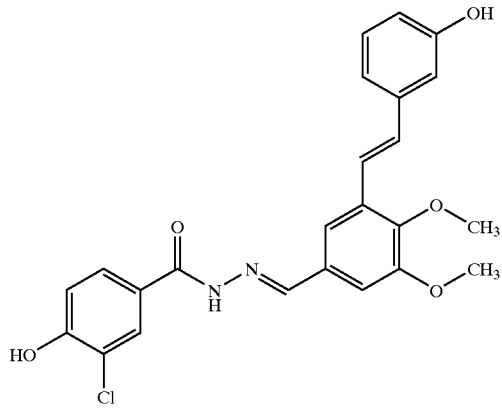

3-Chloro-4-hydroxybenzoic acid{3-[2-(3-hydroxyphenyl)vinyl]-4, 5-dimethoxy-benzylidene}hydrazide

EXAMPLE 625:

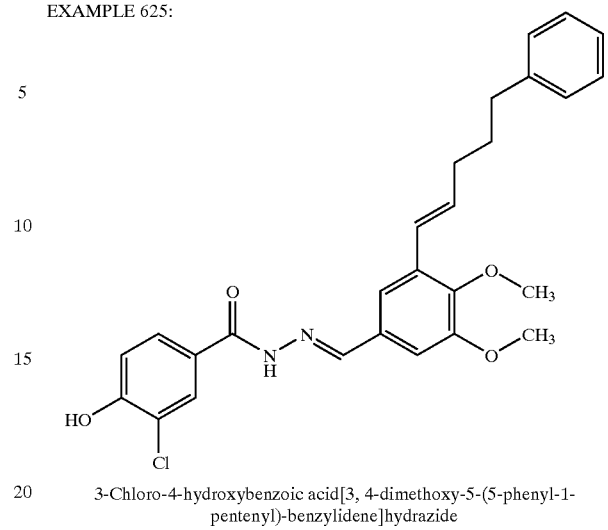

3-Chloro-4-hydroxybenzoic acid[3, 4-dimethoxy-5-(5-phenyl-1-pentenyl)-benzylidene]hydrazide

EXAMPLE 626:

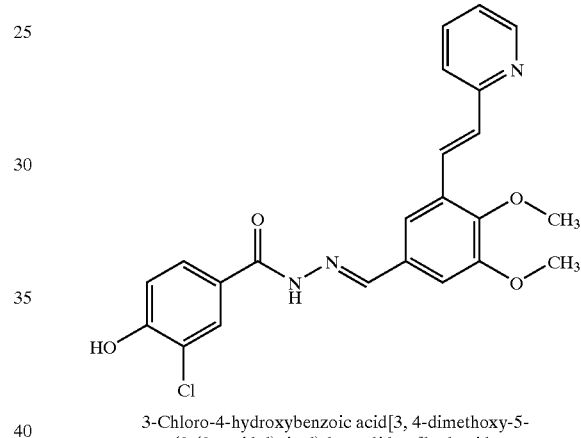

3-Chloro-4-hydroxybenzoic acid[3, 4-dimethoxy-5-(2-(2-pyridyl)vinyl)-benzylidene]hydrazide

EXAMPLE 627:

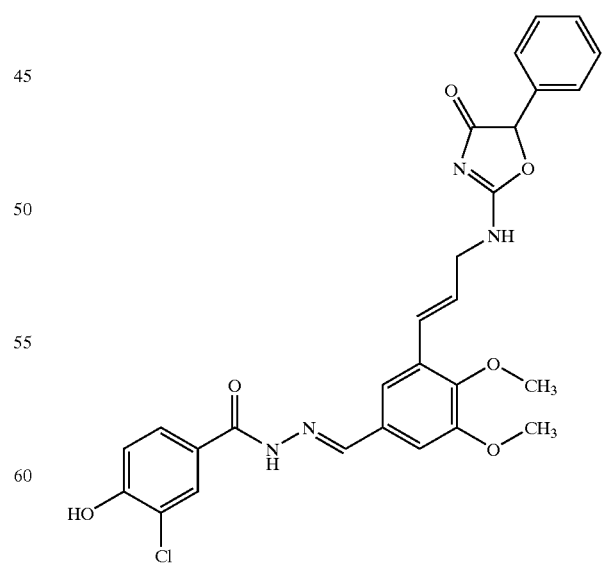

3-Chloro-4-hydroxybenzoic acid{3, 4-dimethoxy-5-[3-(4-oxo-5-phenyl-4, 5-dihydro-2-oxazolylamino)-1-propenyl]-benzylidene}hydrazide

EXAMPLE 628:

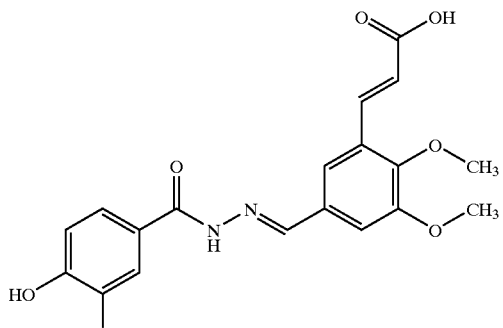

3-{5-[(3-Chloro-4-hydroxybenzoyl)-hydrazonomethyl]-2, 3-dimethoxyphenyl}-acrylic acid

EXAMPLE 629:

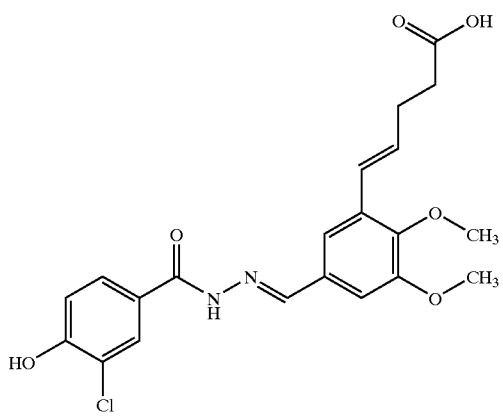

5-{5-[(3-Chloro-4-hydroxybenzoyl)-hydrazonomethyl]-2, 3-dimethoxyphenyl}-4-pentenoic acid

EXAMPLE 630:

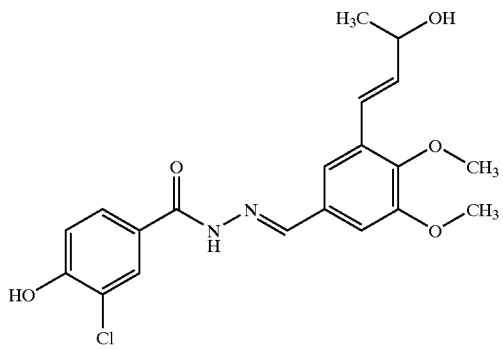

3-Chloro-4-hydroxybenzoic acid[3-(3-hydroxy-1-butenyl)-4, 5-dimethoxy-benzylidene]hydrazide

EXAMPLE 631:

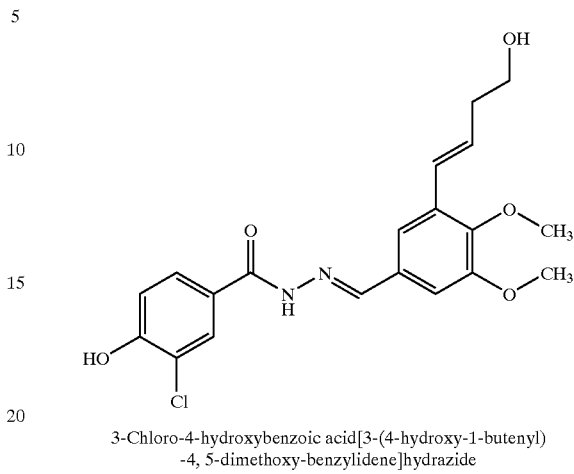

3-Chloro-4-hydroxybenzoic acid[3-(4-hydroxy-1-butenyl)-4, 5-dimethoxy-benzylidene]hydrazide

EXAMPLE 632:

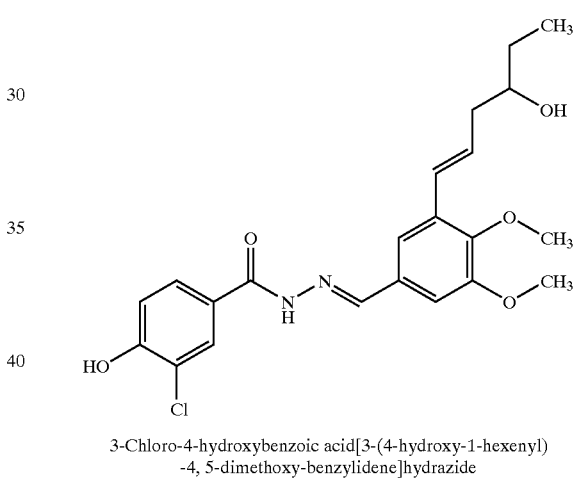

3-Chloro-4-hydroxybenzoic acid[3-(4-hydroxy-1-hexenyl)-4, 5-dimethoxy-benzylidene]hydrazide

EXAMPLE 633:

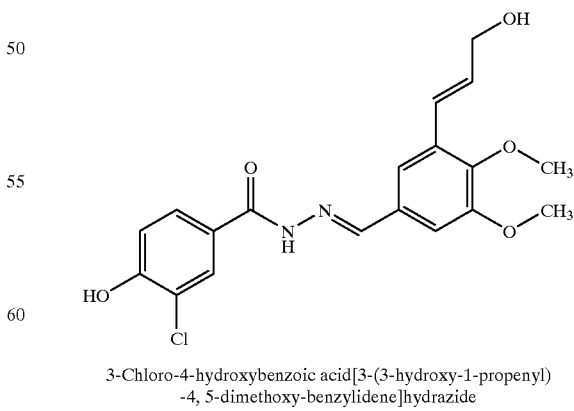

3-Chloro-4-hydroxybenzoic acid[3-(3-hydroxy-1-propenyl)-4, 5-dimethoxy-benzylidene]hydrazide

EXAMPLE 634:

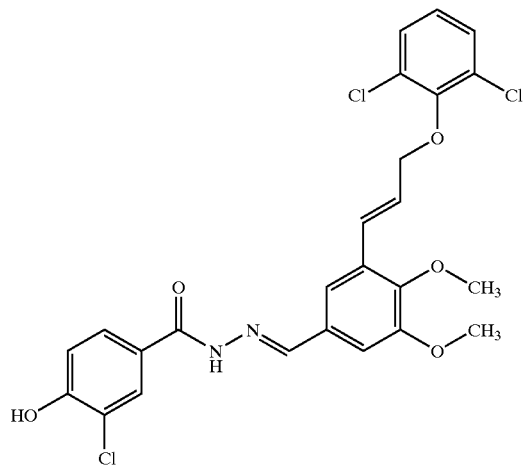

3-Chloro-4-hydroxybenzoic acid{3-[3-(2, 6-dichlorophenoxy)
-1-propenyl]-4, 5-dimethoxybenzylidene}hydrazide

EXAMPLE 635:

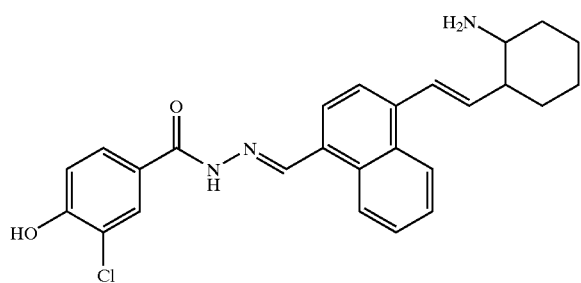

3-chloro-4-hydroxybenzoic acid{4-[2-(1-aminocyclohexyl)
vinyl]-1-naphthyl-methylene}hydrazide

EXAMPLE 636:

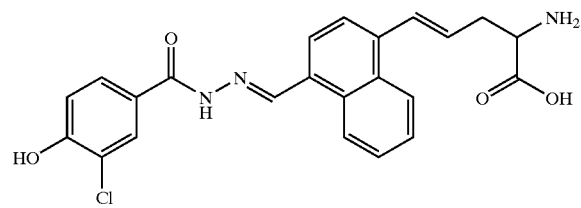

2-Amino-5-{4-[(3-chloro-4-hydroxybenzoyl)-hydrazonomethyl]
-1-naphthyl}-4-pentenoic acid

EXAMPLE 637:

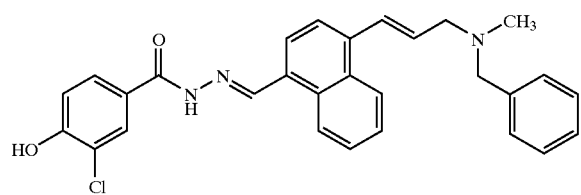

3-Chloro-4-hydroxybenzoic acid{4-[3-benzylmethlamino)propenyl]
-1-naphthylmethylene}hydrazide

EXAMPLE 638:

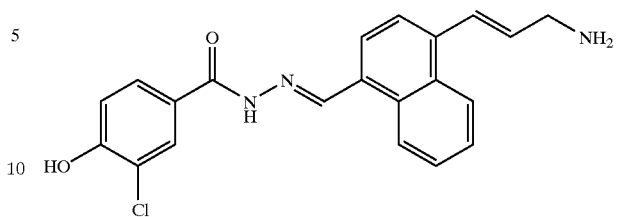

3-Chloro-4-hydroxybenzoic acid[4-(3-amino-1-propenyl)
-1-naphthylmethylene]hydrazide

EXAMPLE 639:

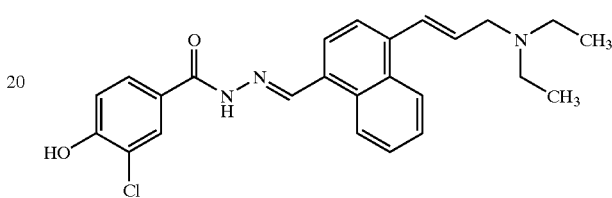

3-Chloro-4-hydroxybenzoic acid[4-(3-diethylamino-1-propenyl)
-1-naphthyl-methylene]hydrazide

EXAMPLE 640:

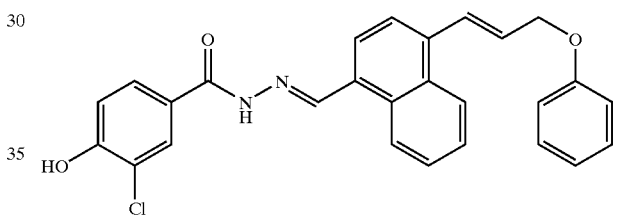

3-Chloro-4-hydroxybenzoic acid[4-(3-phenoxy-1-propenyl)
-1-naphthyl-methylene]hydrazide

EXAMPLE 641:

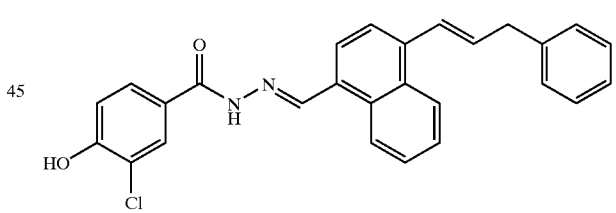

3-Chloro-4-hydroxybenzoic acid[4-(3-phenyl-1-propenyl)
-1-naphthylmethylene]hydrazide

EXAMPLE 642:

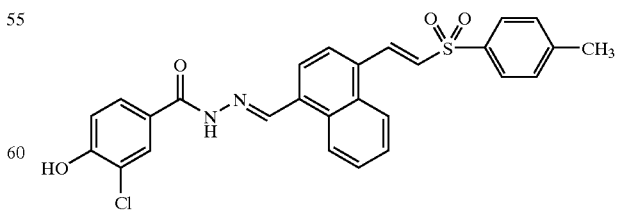

3-Chloro-4-hydroxybenzoic acid{4-[2-(toluene-4-sulfonyl)vinyl]
-1-naphthyl-methylene}hydrazide

EXAMPLE 643:

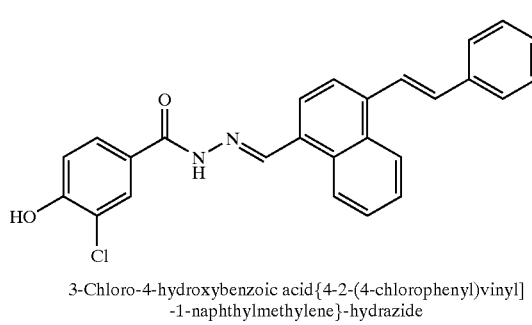

3-Chloro-4-hydroxybenzoic acid{4-2-(4-chlorophenyl)vinyl]
-1-naphthylmethylene}-hydrazide

EXAMPLE 644:

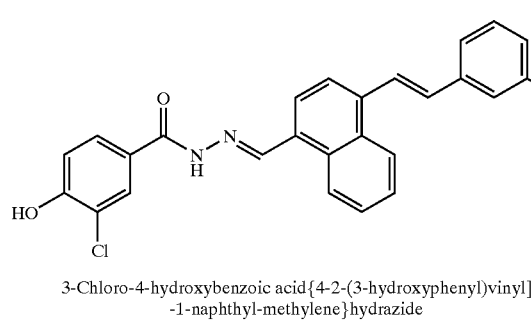

3-Chloro-4-hydroxybenzoic acid{4-2-(3-hydroxyphenyl)vinyl]
-1-naphthyl-methylene}hydrazide

EXAMPLE 645:

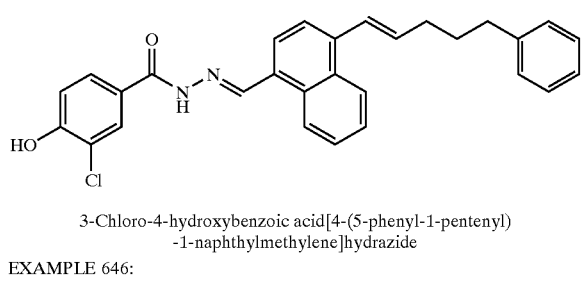

3-Chloro-4-hydroxybenzoic acid[4-(5-phenyl-1-pentenyl)
-1-naphthylmethylene]hydrazide

EXAMPLE 646:

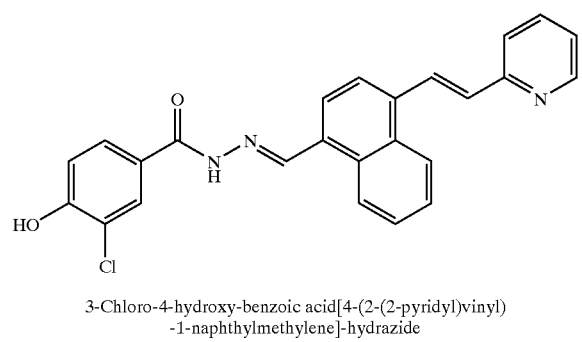

3-Chloro-4-hydroxy-benzoic acid[4-(2-(2-pyridyl)vinyl)
-1-naphthylmethylene]-hydrazide

EXAMPLE 647:

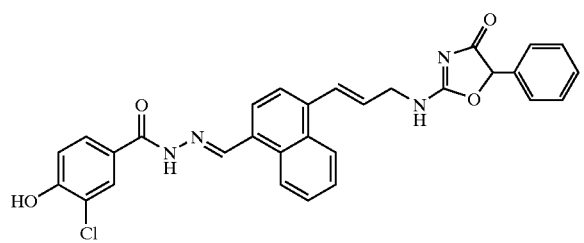

3-Chloro-4-hydroxybenzoic acid{4-[3-(4-oxo-5-phenyl-4, 5-dihydro-
(2-oxazolylamino)-1-propenyl]-1-naphthylmethylene}hydrazide

EXAMPLE 648:

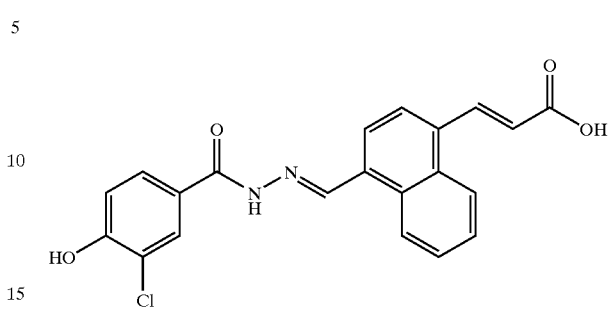

3-(4-[(3-Chloro-4-hydroxybenzoyl)-hydrazonomethyl]
-1-naphthyl}acrylic acid

EXAMPLE 649:

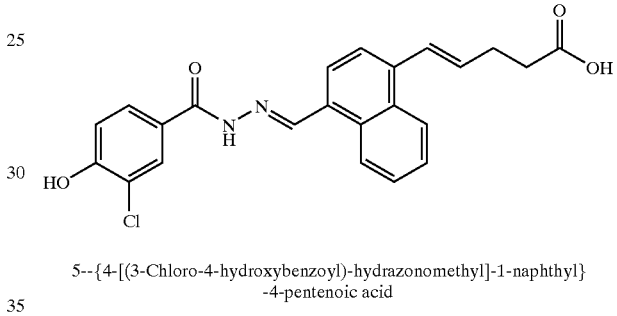

5--{4-[(3-Chloro-4-hydroxybenzoyl)-hydrazonomethyl]-1-naphthyl}
-4-pentenoic acid

EXAMPLE 650:

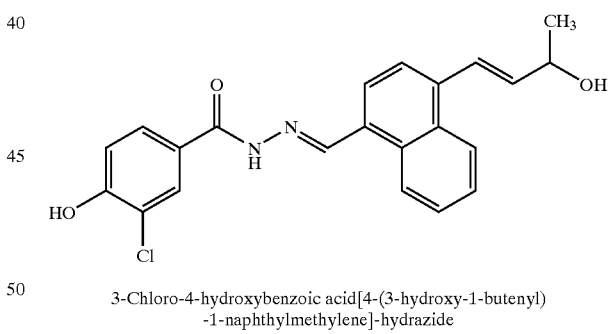

3-Chloro-4-hydroxybenzoic acid[4-(3-hydroxy-1-butenyl)
-1-naphthylmethylene]-hydrazide

EXAMPLE 651:

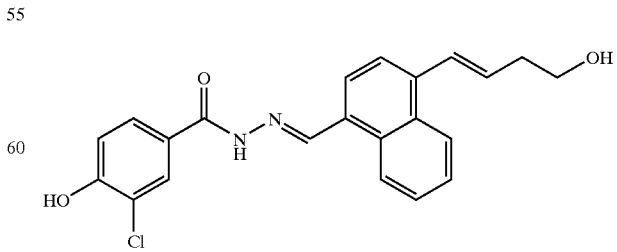

3-Chloro-4-hydroxybenzoic acid[4-(4-hydroxy-1-butenyl)
-1-naphthylmethylene]-hydrazide

EXAMPLE 652:

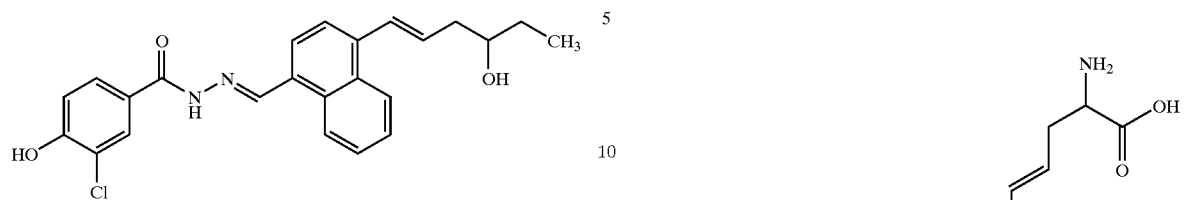

3-Chloro-4-hydroxybenzoic acid[4-(4-hydroxy-1-hexenyl)
-1-naphthylmethylene]-hydrazide

EXAMPLE 653:

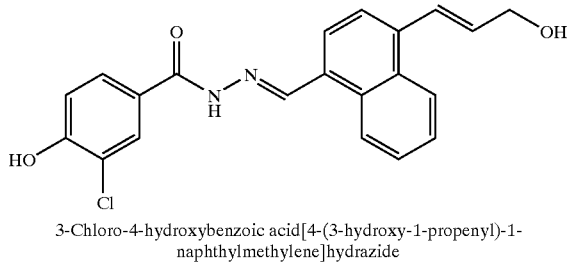

3-Chloro-4-hydroxybenzoic acid[4-(3-hydroxy-1-propenyl)-1-
naphthylmethylene]hydrazide

EXAMPLE 654:

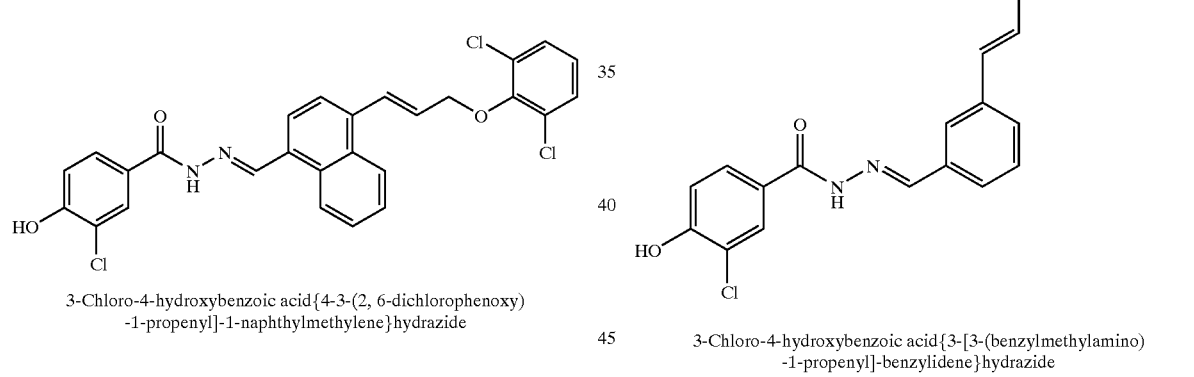

3-Chloro-4-hydroxybenzoic acid{4-3-(2, 6-dichlorophenoxy)
-1-propenyl]-1-naphthylmethylene}hydrazide

EXAMPLE 655:

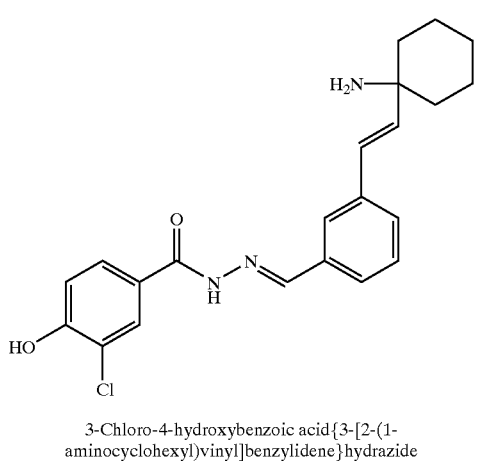

3-Chloro-4-hydroxybenzoic acid{3-[2-(1-
aminocyclohexyl)vinyl]benzylidene}hydrazide

EXAMPLE 656:

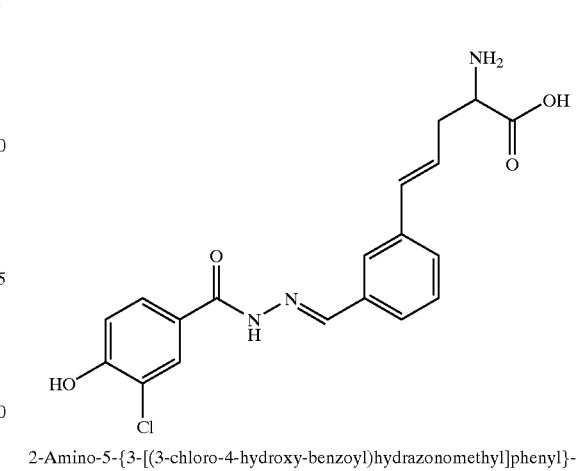

2-Amino-5-{3-[(3-chloro-4-hydroxy-benzoyl)hydrazonomethyl]phenyl}-4-
pentenoic acid

EXAMPLE 657:

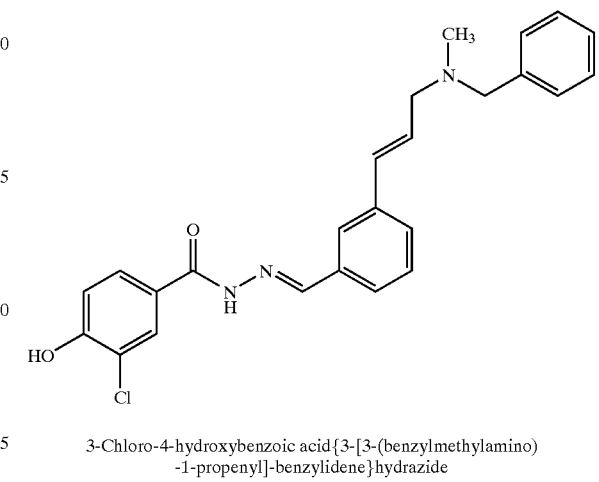

3-Chloro-4-hydroxybenzoic acid{3-[3-(benzylmethylamino)
-1-propenyl]-benzylidene}hydrazide

EXAMPLE 658:

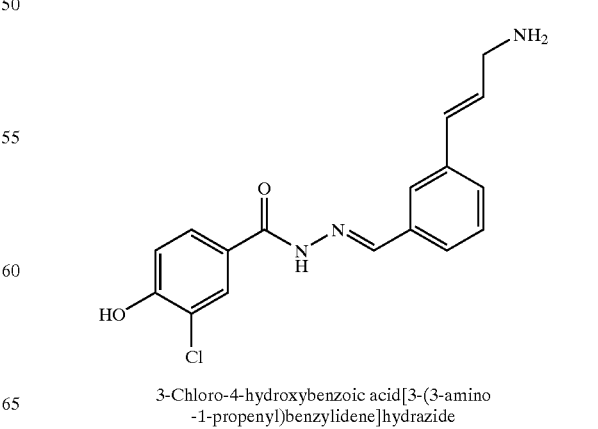

3-Chloro-4-hydroxybenzoic acid[3-(3-amino
-1-propenyl)benzylidene]hydrazide

EXAMPLE 659:

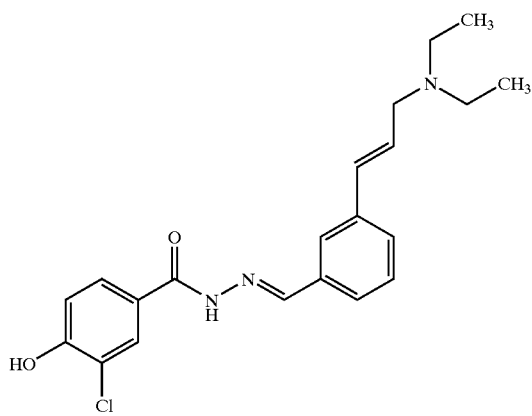

3-Chloro-4-hydroxybenzoic acid[3-(3-diethylamino-1-
propenyl)benzylidene]-hydrazide

EXAMPLE 660:

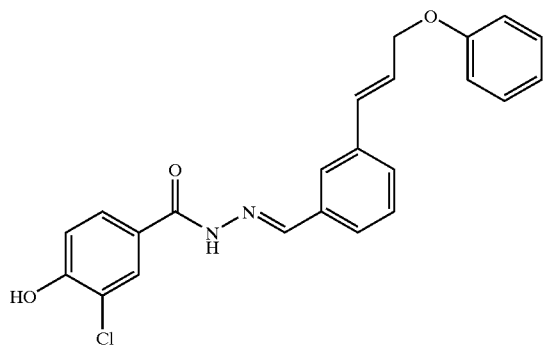

3-Chloro-4-hydroxybenzoic acid[3-(3-phenoxy
-1-propenyl)benzylidene]hydrazide

EXAMPLE 661:

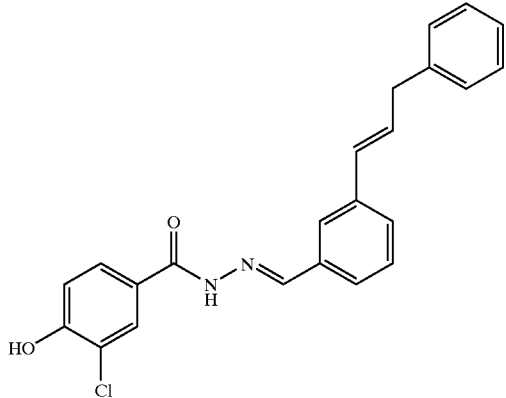

3-Chloro-4-hydroxybenzoic acid[3-(3-phenyl
-1-propenyl)benzylidene]hydrazide

EXAMPLE 662:

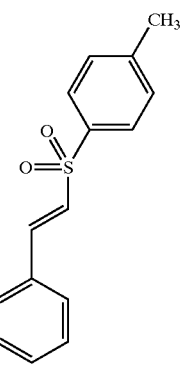

3-Chloro-4-hydroxybenzoic acid{3-[2-(toluene-4-
sulfonyl)vinyl]benzylidene}-hydrazide

EXAMPLE 663:

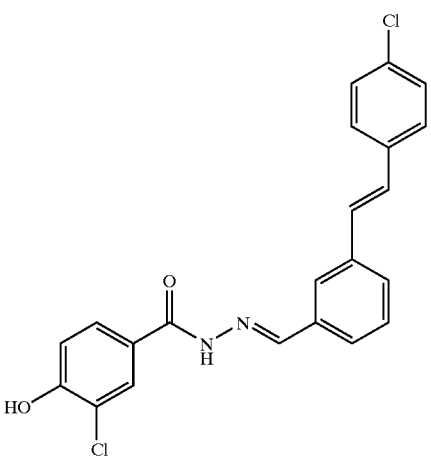

3-Chloro-4-hydroxybenzoic acid{3-[2-(4-
chlorophenyl)vinyl]benzylidene}hydrazide

EXAMPLE 664:

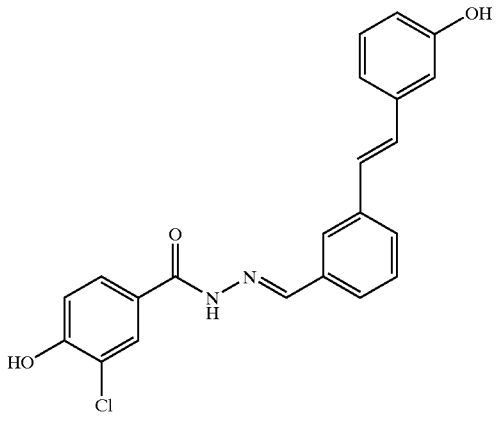

3-Chloro-4-hydroxybenzoic acid{3-[2-(3-
hydroxyphenyl)vinyl]benzylidene}hydrazide

EXAMPLE 665:

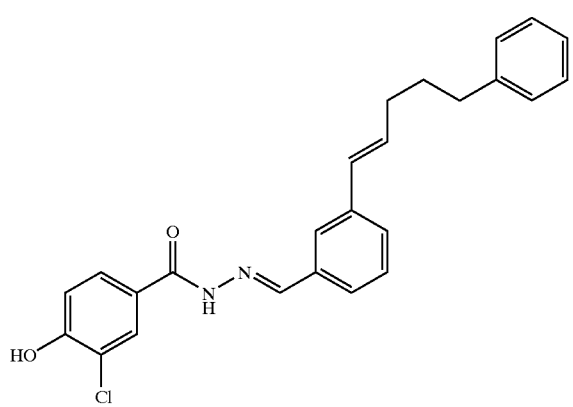

3-Chloro-4-hydroxybenzoic acid[3-(5-phenyl-1-pentenyl)benzylidene]hydrazide

EXAMPLE 666:

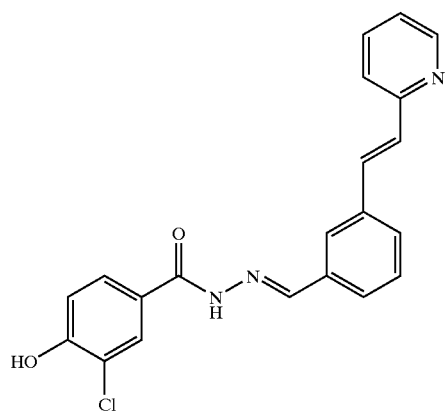

3-Chloro-4-hydroxybenzoic acid[3-(2-(2-pyridyl)vinyl)benzylidene]hydrazide

EXAMPLE 667:

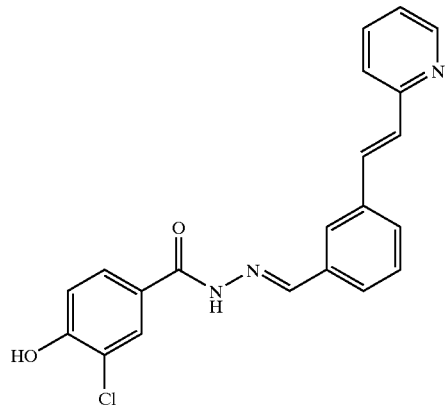

3-Chloro-4-hydroxybenzoic acid{3-[3-(4-oxo-5-phenyl-4, 5-dihydro-(2-oxazolylamino))-1-propenyl]benzylidene}hydrazide

EXAMPLE 668:

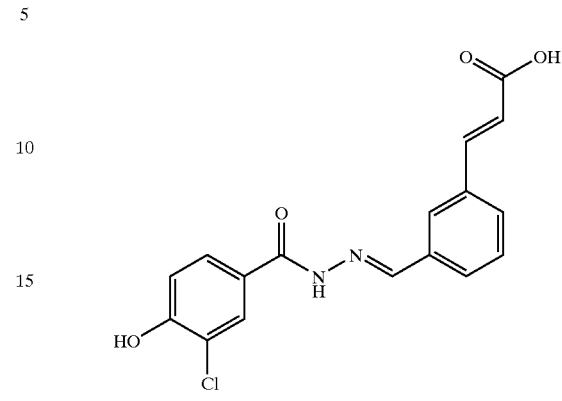

3-{3-[(3-Chloro-4-hydroxybenzoyl)-hydrazonomethyl]phenyl} acrylic acid

EXAMPLE 669:

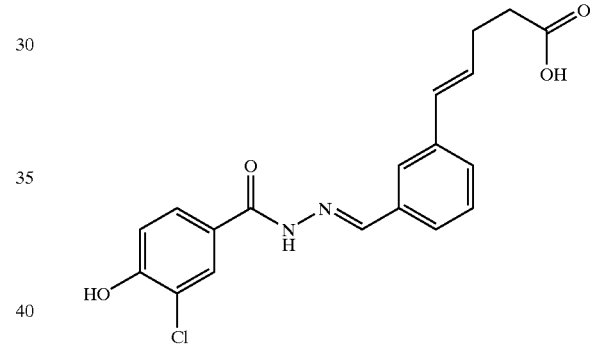

5-{3-[(3-Chloro-4-hydroxybenzoyl)-hydrazonomethyl]phenyl}-4-pentenoic acid

EXAMPLE 670:

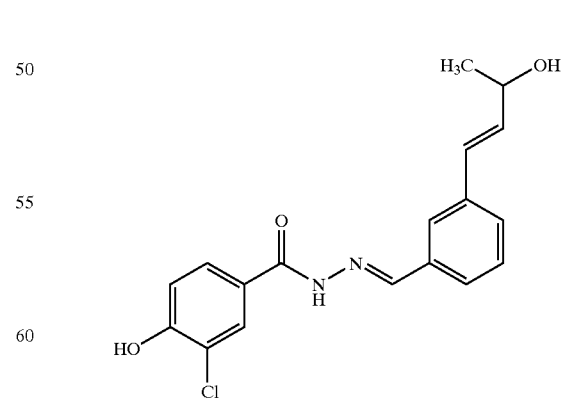

3-Chloro-4-hydroxybenzoic acid[3-(3-hydroxy-1-butenyl)benzylidene]hydrazide

EXAMPLE 671:

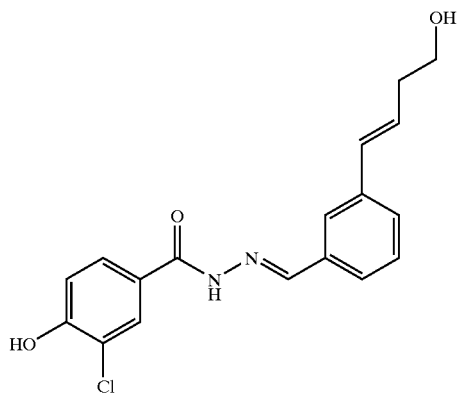

3-Chloro-4-hydroxybenzoic acid[3-(4-hydroxy-1-
butenyl)benzylidene]hydrazide

EXAMPLE 672:

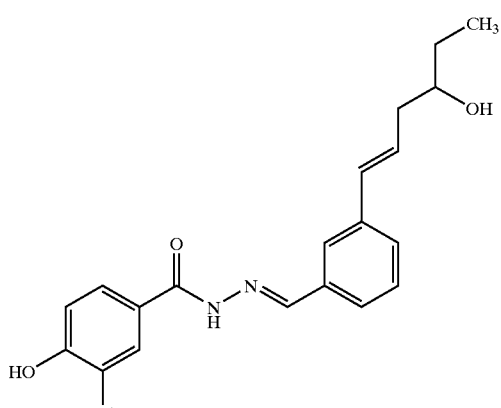

3-Chloro-4-hydroxybenzoic acid[3-(4-hydroxy-1-
hexenyl)benzylidene]hydrazide

EXAMPLE 673:

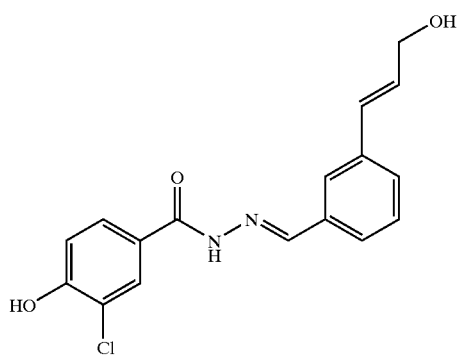

3-Chloro-4-hydroxybenzoic acid[3-(3-hydroxy-1-
propenyl)benzylidene]hydrazide

EXAMPLE 674:

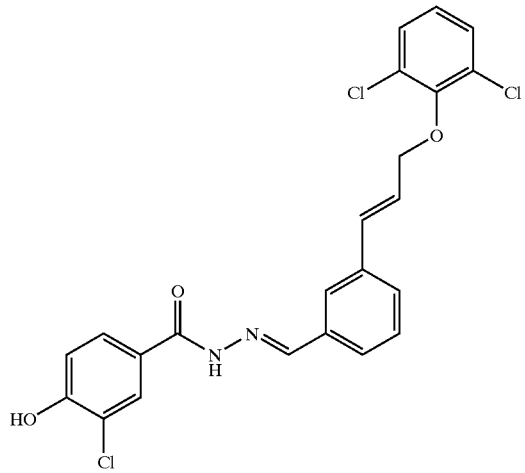

3-Chloro-4-hydroxybenzoic acid{3-[3-(2, 6-dichlorophenoxy)
-1-propenyl]-benzylidene}hydrazide

EXAMPLE 675:

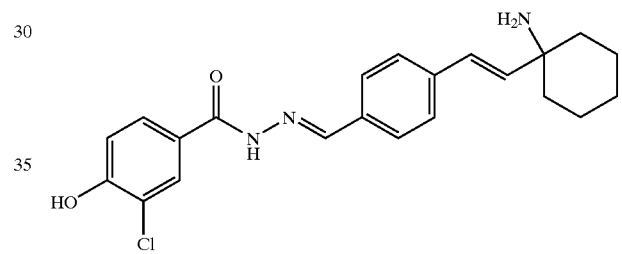

3-Chloro-4-hydroxybenzoic acid{4-[2-(1-
aminocyclohexyl)vinyl]benzylidene}hydrazide

EXAMPLE 676:

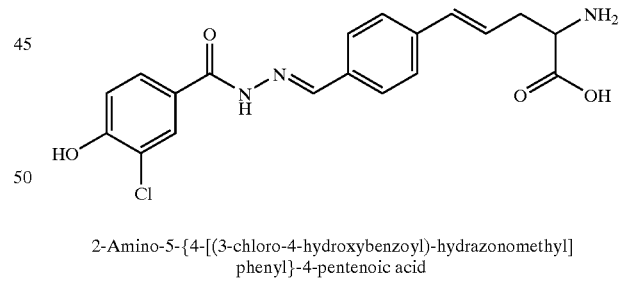

2-Amino-5-{4-[(3-chloro-4-hydroxybenzoyl)-hydrazonomethyl]
phenyl}-4-pentenoic acid

EXAMPLE 677:

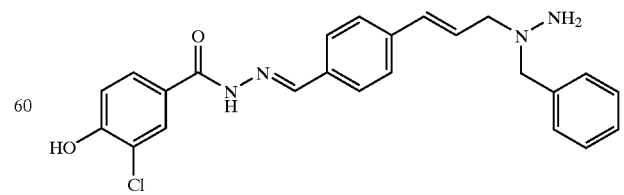

3-Chloro-4-hydroxybenzoic acid{4-[3-(benzylmethylamino)
-1-propenyl]-benzylidene}hydrazide

EXAMPLE 678:

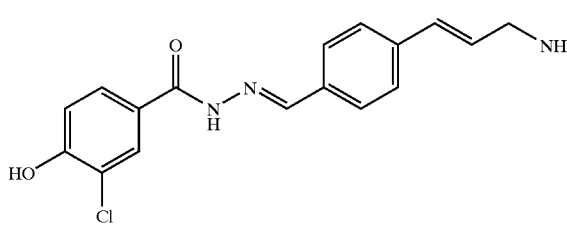

3-Chloro-4-hydroxybenzoic acid[4-(3-amino-1-propenyl)benzylidene]hydrazide

EXAMPLE 679:

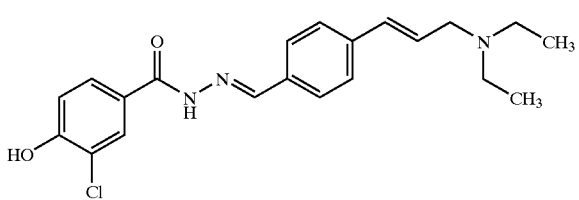

3-Chloro-4-hydroxybenzoic acid[4-(3-diethylaminopropenyl)benzylidene]hydrazide

EXAMPLE 680:

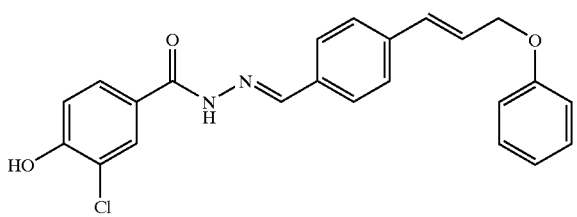

3-Chloro-4-hydroxybenzoic acid[4-(3-phenoxy-1-propenyl]benzylidene]hydrazide

EXAMPLE 681:

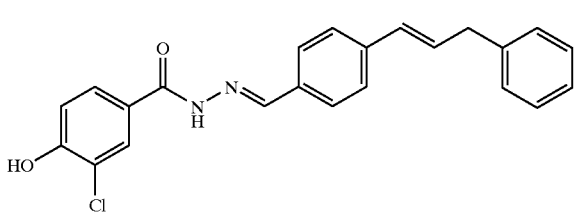

3-Chloro-4-hydroxybenzoic acid[4-(3-phenyl-1-propenyl]benzylidene]hydrazide

EXAMPLE 682:

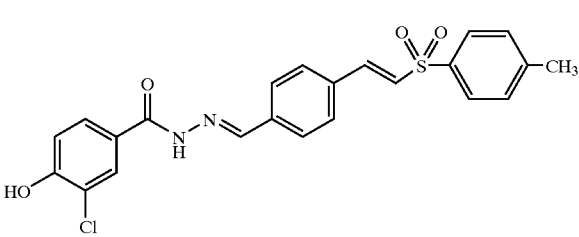

3-Chloro-4-hydroxybenzoic acid{4-[2-(toluene-4-sulfonyl)vinyl]benzylidene}-hydrazide

EXAMPLE 683:

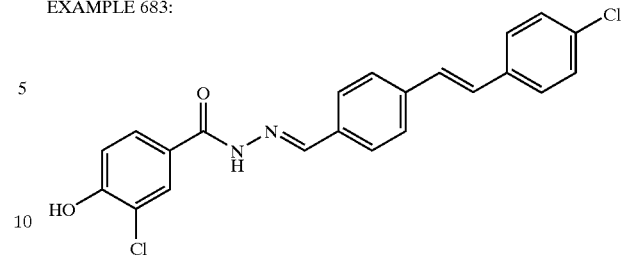

3-Chloro-4-hydroxybenzoic acid{4-[2-(4-chlorophenyl)vinyl]benzylidene}hydrazide

EXAMPLE 684:

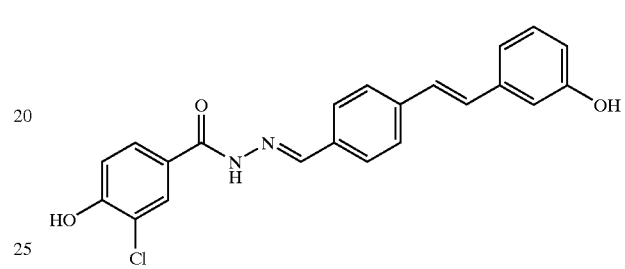

3-Chloro-4-hydroxybenzoic acid{4-[2-(3-hydroxyphenyl)vinyl]benzylidene}hydrazide

EXAMPLE 685:

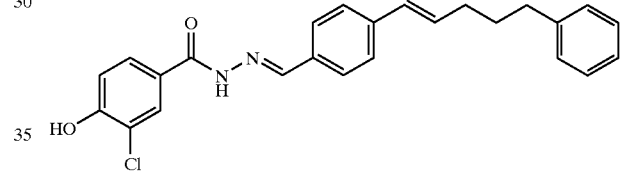

3-Chloro-4-hydroxybenzoic acid[4-(5-phenyl-1-pentenyl)benzylidene]hydrazide

EXAMPLE 686:

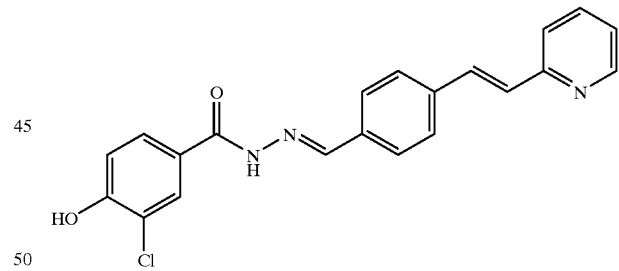

3-Chloro-4-hydroxybenzoic acid{4-[2-(2-pyridinyl)vinyl]benzylidene}hydrazide

EXAMPLE 687:

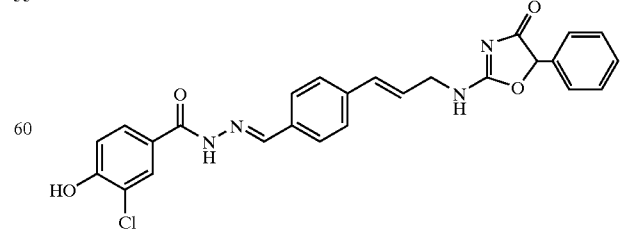

3-Chloro-4-hydroxybenzoic acid{4-[3-(4-oxo-5-phenyl-4, 5-dihydro-(2-oxazolylamino)-1-propenyl]benzylidene}hydrazide

EXAMPLE 688:

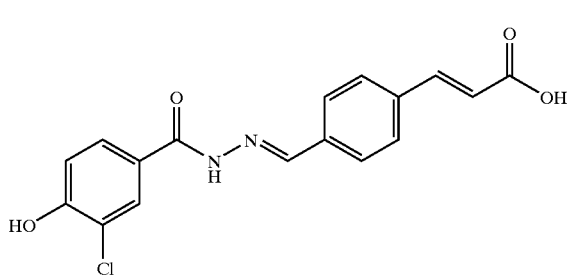

{4-[(3-Chloro-4-hydroxybenzoyl)-hydrazonomethyl]phenyl}
acrylic acid

EXAMPLE 689:

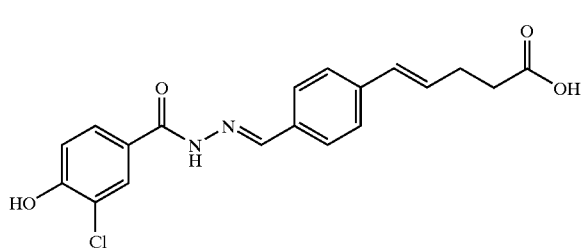

5-{4-[(3-Chloro-4-hydroxybenzoyl)-hydrazonomethyl]
phenyl}-4-pentenoic acid

EXAMPLE 690:

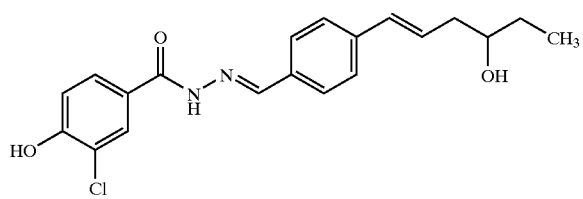

3-Chloro-4-hydroxybenzoic acid[4-(4-hydroxy-1-
hexenyl)benzylidene]hydrazide

EXAMPLE 691:

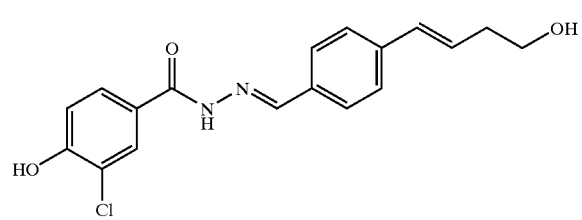

3-Chloro-4-hydroxybenzoic acid[4-(4-hydroxy-1-
butenyl)benzylidene]hydrazide

EXAMPLE 692:

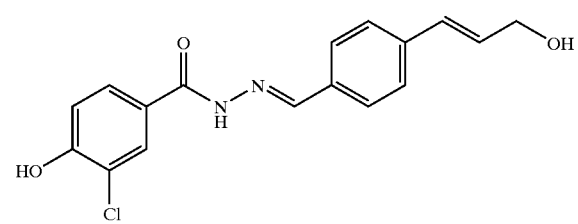

3-Chloro-4-hydroxybenzoic acid[4-(3-hydroxy-1-
propenyl)benzylidene]hydrazide

EXAMPLE 693:

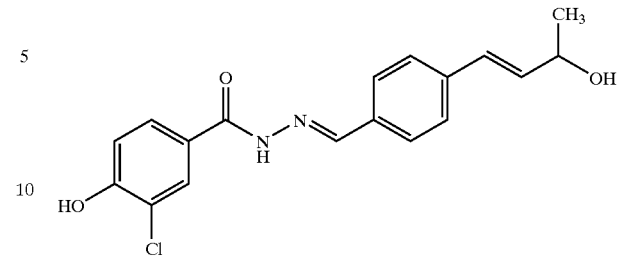

3-Chloro-4-hydroxybenzoic acid[4-(3-hydroxy-1-
butenyl)benzylidene]hydrazide

EXAMPLE 694:

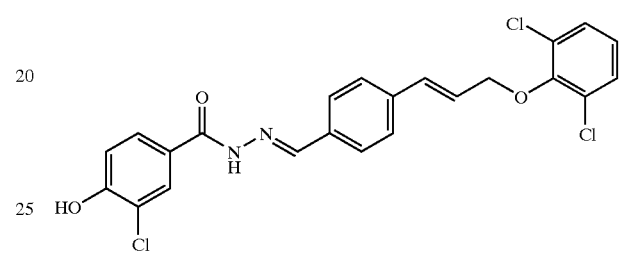

3-Chloro-4-hydroxybenzoic acid{4-[3-(2, 6-dichlorophenoxy)
-1-propenyl]-benzylidene}hydrazide General Procedure for Examples 695 to 701

The compounds were prepared as single entities according to the following equation Resin—[Building block 1]→

Resin—[Building block 1]—[Building block 2]→

Resin—[Building block 1]—[Building block 2]—
[Building block 3]

and were simultaneously deprotected and cleaved from the resin with 50% trifluoroacetic acid in dichloromethane to give the desired compounds as individual entities according to the following formula

[Building block 1]—[Building block 2]—[Building block 3].

The following compounds were prepared as single entities by parallel synthesis on a solid support. Preparation of Resin—[Building block 1] was done manually, whereas the attachment of [Building block 2] and [Building block 3] and cleavage from the resin were performed on an Advanced ChemTech Model 384 HTS.

The starting resin, Resin—[Building block 1], was prepared as described above.

The resin used was a polystyrene resin with a Wang linker and the substitution capacity was 0.9 mmol/g.

All compounds are based on successive attachment of [Building block 2] and [Building block 3] to Resin— [Building block 1] in a combinatorial way using a nucleophilic substitution reaction according to the following formulae, which are included in the general formula II:

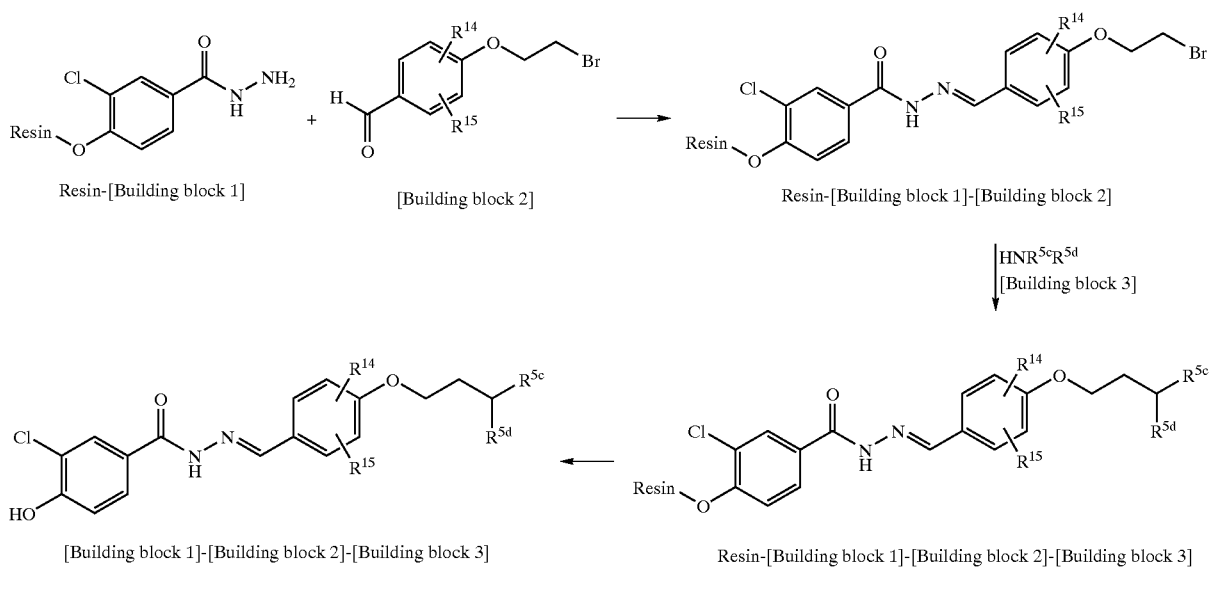

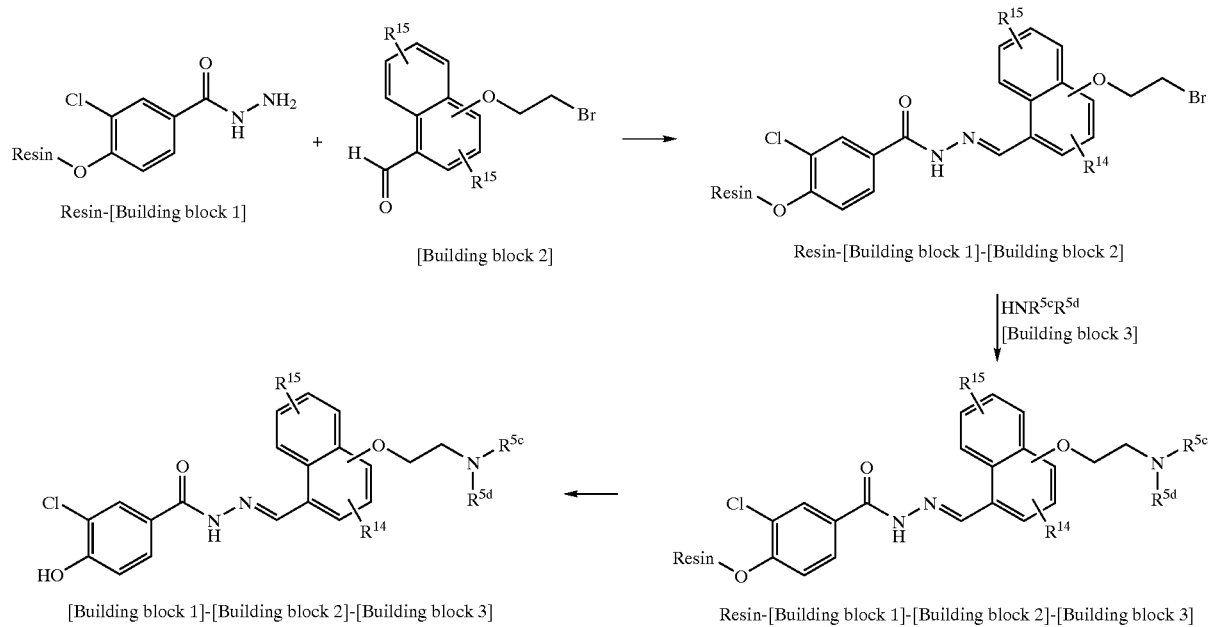

wherein $R^{14}$, $R^{15}$ are as defined for formula I and $-NR^{5c}R^{5d}$ is

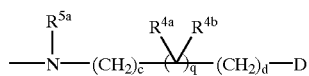

where $R^{5a}$, $R^{4a}$, $R^{4b}$, c, q, d, and D are as defined for formula I or —D' where —D' is defined as a subset of —D that contains a primary or secondary amine that can react as a nucleophile.

The following resin, here depicted as Resin—[Building block 1] was used:

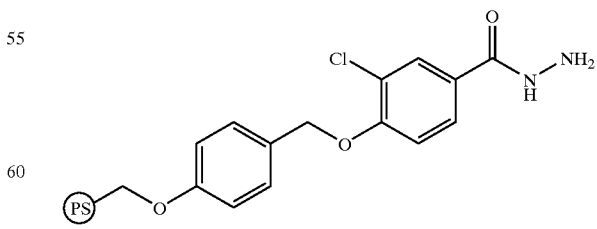

where PS is polystyrene. In the following "Resin" is the polystyrene resin with the Wang linker:

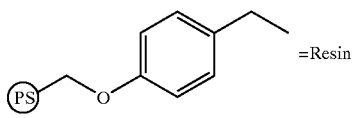 =Resin

5

The following building blocks were used:

| [Building block 2] |
|---|

4-(2-bromoethoxy)-2-methoxybenzaldehyde

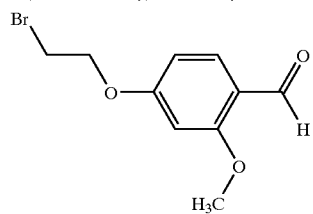

4-(2-bromoethoxy)-3-methoxybenzaldehyde

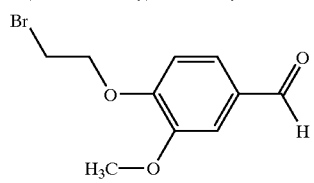

4-(2-bromoethoxy)-3-chloro-5-methoxybenzaldehyde

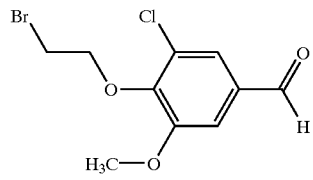

4-(2-bromoethoxy)-1-naphthaldehyde

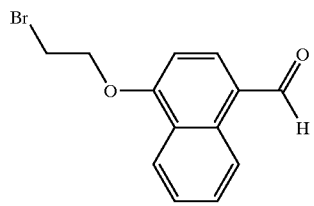

4-(2-bromoethoxy)-3,5-dimethylbenzaldehyde

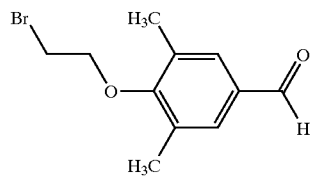

4-(2-bromoethoxy)-3,5-dibromobenzaldehyde

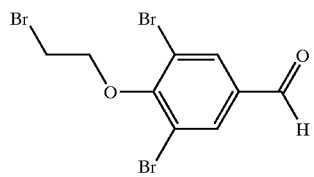

4-(2-bromoethoxy)-3-methoxy-5-phenylbenzaldehyde

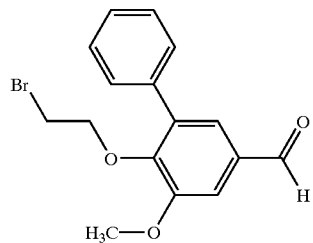

4-(2-bromoethoxy)-3,5-dimethoxybenzaldehyde

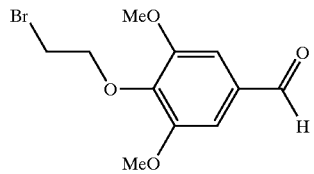

4-(2-bromoethoxy)-3-bromo-5-methoxybenzaldehyde

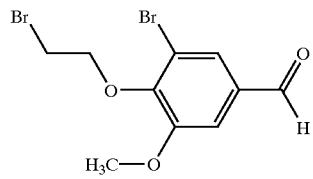

3-(2-bromoethoxy)-4-methoxybenzaldehyde

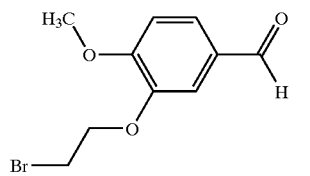

2-(2-bromoethoxy)-1-naphthaldehyde 4-(2-bromoethoxy)-3-methoxyacetophenone

-continued
| [Building block 2] |
|---|
| 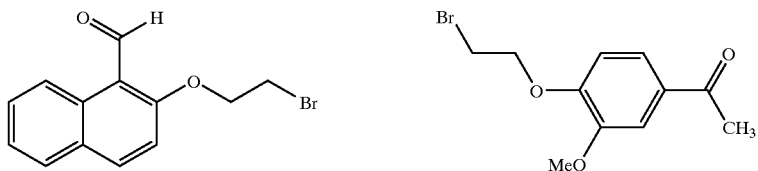 |
[Building block 3]
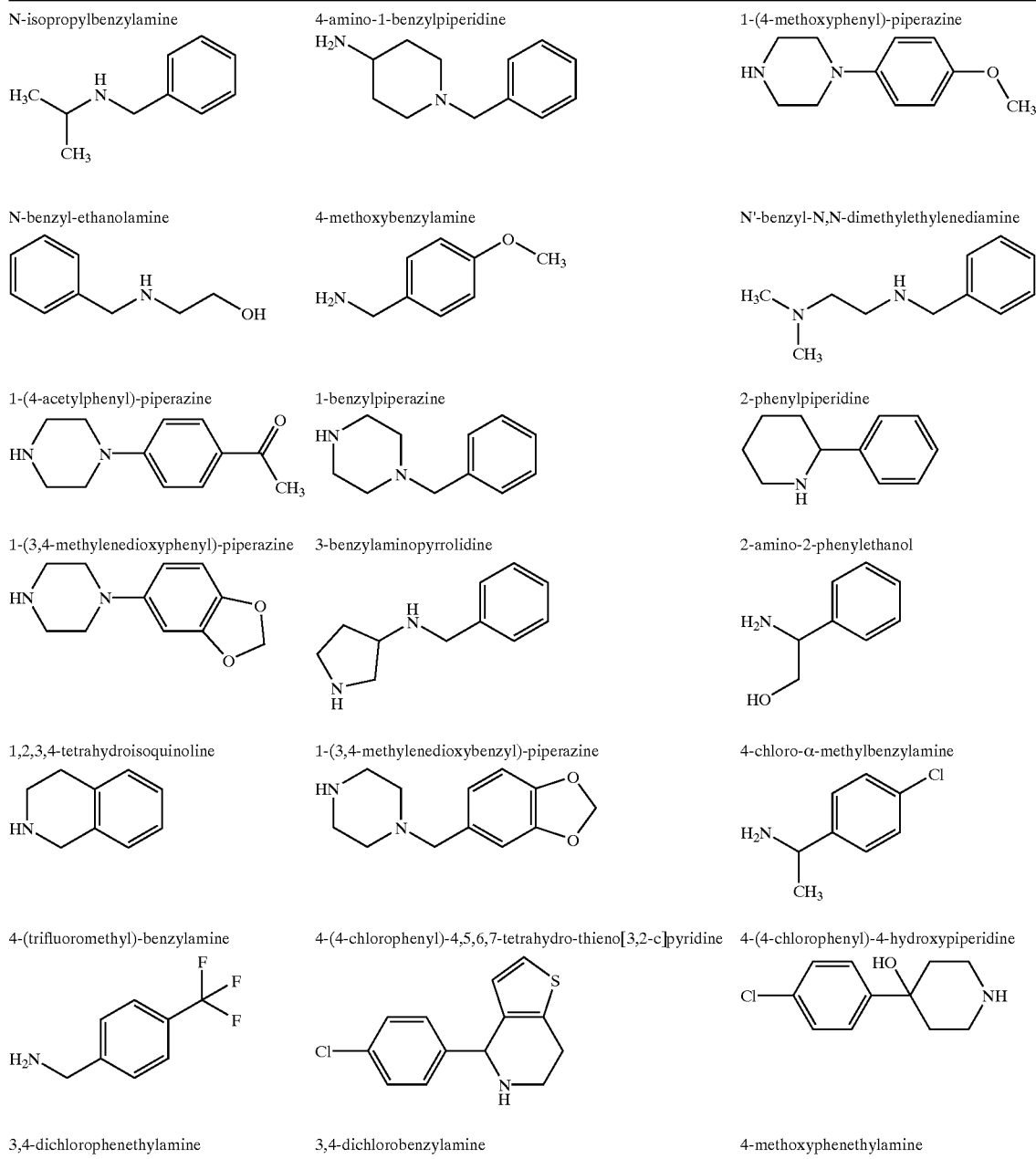

[Building block 3]

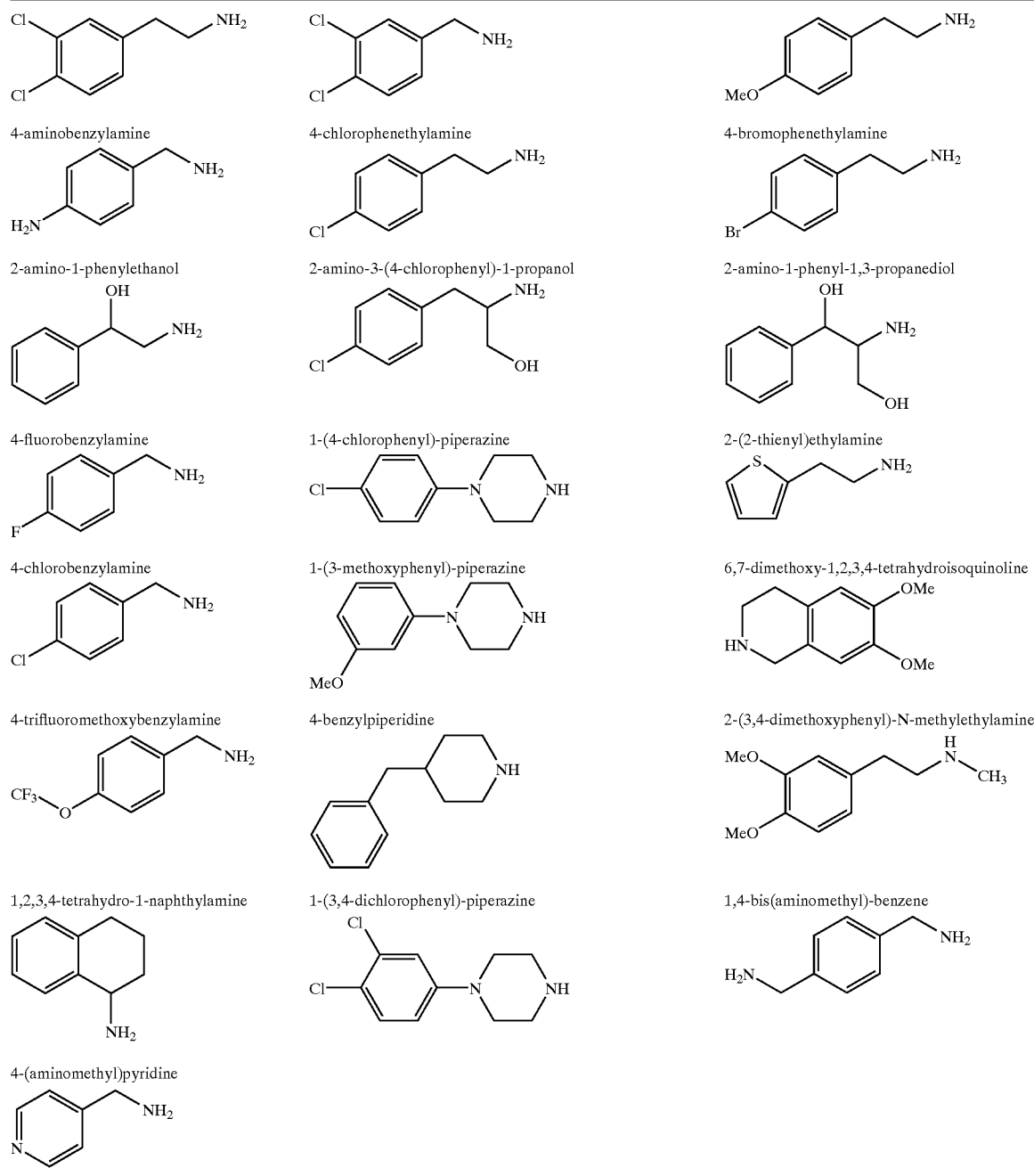

Preparation of Resin—[Building Block 1]

This resin was prepared as described above.

Preparation of [Building Block 21]

Preparation of 4-(2-Bromoethoxy)-2-methoxybenzaldehyde 1,2-Dibromoethane (57 mL, 0.66 moles) was added to a mixture of 4-hydroxy-2-methoxybenzaldehyde (10 g, 66 mmoles) and potassium carbonate (45 g, 0.33 moles) in DMF (130 ml) and the resulting mixture was stirred vigorously at room temperature for 16 hours. The mixture was poured into water (0.8 L) and extracted with ethyl acetate (3×300 mL). The combined organic phases were washed with saturated sodium chloride (400 mL), dried over MgSO$_4$ and evaporated in vacuo to afford 17.4 g (99%) of 4-(2-bromoethoxy)-2-methoxybenzaldehyde, M.p. 78–79° C.

Preparation of 4-(2-Bromoethoxy)-3-methoxybenzaldehyde 1,2-Dibromoethane (57 mL, 0.66 moles) was added to a mixture of 4-hydroxy-3-methoxybenzaldehyde (10 g, 66 mmoles) and potassium carbonate (45 g, 0.33 moles) in DMF (130 ml) and the resulting mixture was stirred vigorously at room temperature for 16 hours. The mixture was poured into water (1.2 L) and extracted with ethyl acetate (500+4×300 mL). The combined organic phases were washed with saturated sodium chloride (500 mL), dried over MgSO$_4$ and evaporated in vacuo to afford 16.3 g (95%) of 4-(2-bromoethoxy)-3-methoxybenzaldehyde. M.p. 61–64° C.

Preparation of 4-(2-Bromoethoxy)-3-chloro-5-methoxybenzaldehyde 1,2-Dibromoethane (46 mL, 0.54 moles) was added to a mixture of 3-chloro-4-hydroxy-5-methoxybenzaldehyde (10 g, 54 mmoles) and potassium carbonate (37 g, 0.27 moles) in DMF (180 ml) and the resulting mixture was stirred vigorously at room temperature for 16 hours. The mixture was poured into water (100 mL) and extracted with ethyl acetate (2×100 mL). The combined organic phases were washed with saturated sodium chloride (150 mL), dried over MgSO$_4$ and evaporated in vacuo to afford 9.33 g (59%) of 4-(2-bromoethoxy)-3-chloro-5-methoxybenzaldehyde. M.p. 52–54° C.

Preparation of 4-(2-Bromoethoxy)-3,5-dimethylbenzaldehyde 1,2-Dibromoethane (26 mL, 0.3 moles) was added to a mixture of 3,5-dimethyl-4-hydroxybenzaldehyde (4.57 g, 30 mmoles) and potassium carbonate (21 g, 150 mmoles) in DMF (90 ml) and the resulting mixture was stirred vigorously at room temperature for 16 hours. The mixture was poured into water (0.3 L), added saturated sodium chloride (200 mL) and extracted with ethyl acetate (2×200 mL). The combined organic phases were washed with saturated sodium chloride (300 mL), dried over MgSO$_4$ and evaporated in vacuo to afford 8.2 g (95%) of 4-(2-bromoethoxy)-3,5-dimethylbenzaldehyde as an oil.

$^1$H-NMR (300 MHz, CDCl$_3$): δ=2.33 (6H, s), 3.83 (2H, t), 4.18 (2H, t), 7.60 (2H, s), 9.88 (1H, s).

Preparation of 4-(2-Bromoethoxy)-3,5-dibromobenzaldehyde 1,2-Dibromoethane (62 mL, 0.72 moles) was added to a mixture of 3,5-dibromo-4-hydroxybenzaldehyde (10 g, 36 mmoles) and potassium carbonate (25 g, 180 mmoles) in DMF (100 ml) and the resulting mixture was stirred vigorously at 70° C. for 16 hours. After cooling, the mixture was poured into water (300 mL) and extracted with ethyl acetate (400 mL). Water (200 mL) was added to the aqueous phase and this was extracted with ethyl acetate (150 mL). The combined organic phases were washed with saturated sodium chloride (3×150 mL), dried over MgSO$_4$ and evaporated in vacuo. The residue was dissolved in refluxing 96% ethanol (60 mL). Water (15 mL) was added and after cooling, filtration, washing with 60% ethanol and drying 10.7 g (77%) of 4-(2-bromoethoxy)-3,5-dibromobenzaldehyde was isolated in two crops. M.p. 84–85° C.

Preparation of 4-(2-Bromoethoxy)-3-methoxy-5-phenylbenzaldehyde

A mixture of 4-hydroxy-3-iodo-5-methoxybenzaldehyde (20 g, 72 mmoles), ethylene glycol (8.0 mL, 144 mmoles), and chlorotrimethylsilane 36.5 mL, 0.29 moles) in dichloromethane (300 mL) was heated at reflux for 16 hours. The mixture was cooled to room temperature and washed with saturated sodium hydrogencarbonate (3×200 mL). The combined aqueous phases were; extracted with dichloromethane (3×150 mL). The combined organic extracts were washed with saturated sodium chloride (200 mL), dried over MgSO$_4$ and evaporated in vacuo to afford 22.1 g (95%) of 4-[1,3]dioxolan-2-yl-2-iodo-6-methoxy-phenol. M.p. 120–121° C.

Under N$_2$, tetrakis-triphenylphosphinepalladium(0) was added to a mixture of the above dioxolane (10 g, 31 mmoles), benzeneboronic acid (4.5 g, 37 mmoles), toluene (67 mL), 2 M aqueous sodium carbonate (33 mL) and methanol (20 mL). The resulting mixture was heated at reflux under N$_2$ for 16 hours. After cooling the mixture was diluted with water (150 mL) and washed with heptane (400 mL). The aqueous phase was made acidic with 3N hydrochloric acid and extracted with ethyl acetate (3×300 mL). The combined organic extracts were dried over MgSO$_4$ and evaporated in vacuo. The residue was purified by column chromatography over silica gel (800 mL) eluting with a mixture of ethyl acetate and heptane (1:2) to afford 5.49 g (77%) of 4-hydroxy-3-methoxy-5-phenylbenzaldehyde. M.p. 107–108° C. 1,2-Dibromoethane (41 mL, 0.48 moles) was added to a mixture of the above 4-hydroxy-3-methoxy-5-phenylbenzaldehyde (5.49 g, 24 mmoles) and potassium carbonate (17 g, 123 mmoles) in DMF (80 ml) and the resulting mixture was stirred vigorously at room temperature for 16 hours. The mixture was poured into water (1 L) and extracted with ethyl acetate (3×300 mL). The combined organic phases were washed with saturated sodium chloride (200 mL), dried over MgSO$_4$ and evaporated in vacuo to afford 8.1 g (100%) of 4-(2-bromoethoxy)-3-methoxy-5-phenylbenzaldehyde as an oil.

$^1$H-NMR (300 MHz, DMSO-d$_6$): δ=3.50 (2H, t), 3.96 (3H, s), 4.19 (2H, t), 7.4–7.6 (11H, m).

Preparation of 4-(2-Bromoethoxy)-1-naphthaldehyde 1,2-Dibromoethane (30 mL, 0.35 moles) was added to a mixture of 4-hydroxy-1-naphthaldehyde (6 g, 35 mmoles) and potassium carbonate (24 g, 175 mmoles) in DMF (110 ml) and the resulting mixture was stirred vigorously at room temperature for 16 hours. The mixture was poured into water (0.5 L) and extracted with ethyl acetate (3×300 mL). The combined organic phases were washed with saturated sodium chloride (300 mL), dried over MgSO$_4$ and evaporated in vacuo. The residue was purified by column chromatography on silica gel (800 mL) eluting with a mixture of ethyl acetate and heptane (1:1) to afford 8.5 g (88%) of 4-(2-bromoethoxy)-1-naphthaldehyde as a solid. M.p.: 83–84° C.

Calculated for C$_{13}$H$_{11}$BrO$_2$: C, 55.94%; H, 3.97%. Found: C, 56.10%; H, 3.98%; C, 56.30%; H, 3.97%.

Preparation of 4-(2-Bromoethoxy)-3,5-dimethoxybenzaldehyde 1,2-Dibromoethane (47 mL, 0.55 moles) was added to a mixture of syringaldehyde (10 g, 55 mmoles) and potassium carbonate (38 g, 275 mmoles) in DMF (150 ml) and the resulting mixture was stirred vigorously at room temperature for 16 hours. The mixture was poured into water (0.5 L) and extracted with ethyl acetate (3×300 mL). The combined organic phases were washed with saturated sodium chloride (500 mL), dried over MgSO$_4$ and evaporated in vacuo to afford 3.44 g (22%) of 4-(2-bromoethoxy)-3,5-dimethoxybenzaldehyde.

$^1$H-NMR (300 MHz, DMSO-d$_6$): δ=3.70 (2H, t), 3.88 (3H, s), 4.27 (2H, t), 7.27 (2H, s).

Preparation of 3-(2-Bromoethoxy)-4-methoxybenzaldehyde 1,2-Dibromoethane (56 mL, 0.66 moles) was added to a mixture of 3-hydroxy-4-methoxybenzaldehyde (10 g, 66 mmoles) and potassium carbonate (45 g, 328 mmoles) in DMF (170 ml) and the resulting mixture was stirred vigorously at room temperature for 16 hours. The mixture was poured into water (0.5 L) and extracted with ethyl acetate (3×200 mL). The combined organic phases were washed with saturated sodium chloride (500 mL), dried over $MgSO_4$ and evaporated in vacuo. The residue was purified by column chromatography on silica gel (800 mL) eluting with a mixture of ethyl acetate and heptane (1:1) to afford 9.8 g (58%) of 3-(2-bromoethoxy)-4-methoxybenzaldehyde.

$^1$H-NMR (300 MHz, DMSO-$d_6$): δ=3.82 (2H, t), 3.90 (3H, s), 4.40 (2H, t), 7.22 (1H, d), 7.44 (1H, d), 7.59 (1H, dd).

Preparation of 4-(2-Bromoethoxy)-3-bromo-5-methoxybenzaldehyde 1,2-Dibromoethane (37 mL, 0.43 moles) was added to a mixture of 5-bromovanillin (10 g, 43 mmoles) and potassium carbonate (30 g, 216 mmoles) in DMF (150 ml) and the resulting mixture was stirred vigorously at room temperature for 16 hours followed by vigorously stirring at 60° C. for 16 hours. The cooled mixture was poured into water (1 L) and extracted with ethyl acetate (3×250 mL). The combined organic phases were washed with saturated sodium chloride (300 mL), dried over $MgSO_4$ and evaporated in vacuo to afford 13.7 g (94%) of 4-(2-bromoethoxy)-3-bromo-5-methoxybenzaldehyde.

$^1$H-NMR (300 MHz, DMSO-$d_6$): δ=3.79 (2H, t), 3.93 (3H, s), 4.40 (2H, t), 7.55 (1H, d), 7.79 (1H, d).

EXAMPLE 695
Preparation of 3-Chloro-4-hydroxybenzoic Acid {4-[2-(1,2,3,4-Tetrahydroisoquinolin-2-yl)ethoxy]-2-methoxybenzylidene}hydrazide

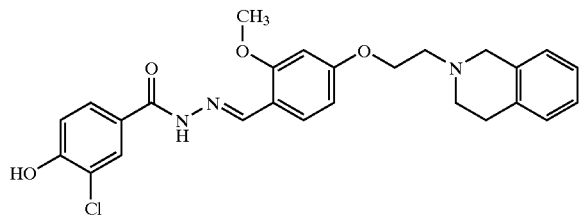

The resin bound 3-chloro-4-hydroxybenzoic acid hydrazide (resin—[building block 1]) (3 g, ~3 mmoles) was swelled in DMF (35 mL) for 30 minutes. Then 4-(2-bromoethoxy)-2-methoxybenzaldehyde (2.33 g, 9 mmoles) and triethyl orthoformate (18 mL) were added and the mixture was shaken at room temperature for 16 hours. The resin was repeatedly swelled in DMF (35 ml, 4 times), $CH_2Cl_2$ (35 mL, 6 times) and N-methyl-2-pyrrolidinone (NMP) (35 mL, 2 times) and filtered. The resin was swelled in NMP (40 mL) and 1,2,3,4-tetrahydroisoquinoline (3.75 mL, 30 mmoles) and potassium iodide (1.0 g, 6 mmoles) were added. The resin was shaken at room temperature for 16 hours and filtered. The resin was repeatedly swelled in DMF (40 ml, 5 times), $CH_2Cl_2$ (40 mL, 10 times) and filtered. The compound was cleaved off the resin by shaking for 1 hour at room temperature with a 50% solution of trifluoroacetic acid in $CH_2Cl_2$ (40 mL). The mixture was filtered and the resin was extracted with $CH_2Cl_2$ (40 mL, 2 times). The combined $CH_2Cl_2$ extracts were concentrated in vacuo. The residue was dissolved in $CH_2Cl_2$ (40 mL) and concentrated in vacuo. The residue was dissolved in methanol (40 mL) and concentrated in vacuo. The residue was partitioned between ethyl acetate (50 mL) and saturated sodium hydrogencarbonate (50 mL). The aqueous phase was extracted with ethyl acetate (50 mL), and the combined organic extracts were dried over $MgSO_4$ and concentrated in vacuo. The residue was purified by coloumn chromatography over silica gel (200 mL) eluting with a mixture of $CH_2Cl_2$ and methanol (9:1). This afforded 280 mg of the title compound.

HPLC-MS (METHOD A): $R_t$=8.44 min; m/z=480 (M+1).

$^1$H-NMR (300 MHz, DMSO-$d_6$) δ=2.80 (4H, m), 2.90 (2H, t), 3.69 (2H, s), 3.86 (3H, s), 4.25 (2H, t), 6.68 (2H, m), 7.04 (1H, d), 7.07–7.14 (5H, m), 7.75 (1H, dd), 7.80 (1H, bs), 7.96 (1H, d), 8.58 (1H, s), 11.6 (1H, s). HR-MS: Calcd. for $C_{26}H_{26}ClN_3O_4$: 479.1611; Found: 479.1604.

EXAMPLE 696
3-Chloro-4-hydroxybenzoic Acid {2-Methoxy-4-[2-(4-Trifluoromethylbenzylamino)ethoxy]-benzylidene}hydrazide

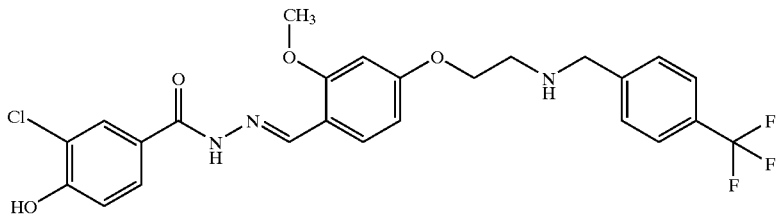

This compound was prepared analogously to the compound described in the previous example starting from resin bound 3-chloro-4-hydroxybenzoic acid hydrazide (resin—[building block 1]) (2 g, ~2 mmoles), 4-(2-bromoethoxy)-2-methoxybenzaldehyde ([building block 2]) (0.73 g, 1.5 equivs.), and 4-trifluoromethylbenzylamine ([building block 3]) (3.3 g, 10 equivs.). After cleavage with 50% trifluoroacetic acid, the residue (1 g) was purified by column chromatography on silica gel (20 g) eluting with a mixture of 25% aq. ammonia, ethanol and dichloromethane (1:9:115). This afforded 130 mg of the title compound.

HPLC-MS (METHOD A): $R_t$=9.4 min; m/z=522 (M+1).

EXAMPLE 697

3-Chloro-4-hydroxybenzoic Acid {4-[2-(4-Benzylpiperazin-1-yl)ethoxy]-2-methoxybenzylidene}hydrazide

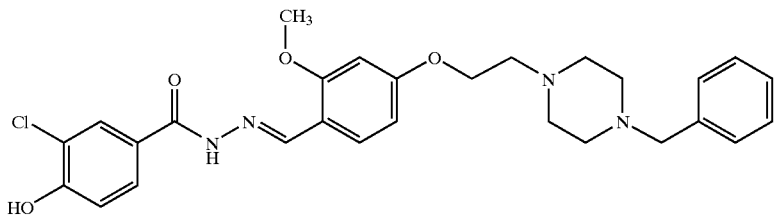

This compound was prepared analogously to the compound described in the previous example starting from resin bound 3-chloro-4-hydroxybenzoic acid hydrazide (resin—[building block 1]) (2 g, ~2 mmoles), 4-(2-bromoethoxy)-2-methoxybenzaldehyde ([building block 2]) (0.73 g, 1.5 equivs.), and 1-benzylpiperazine ([building block 3]) (3.3 g, 10 equivs.). After cleavage with 50% trifluoroacetic acid, the residue (1.4 g) was dissolved in 2-propanol (50 ml) and concentrated to 20 ml. The mixture was allowed to stand at 5° C. for 1 h and filtered. The mother liquor was concentrated in vacuo and the residue was purified by column chromatography on silica gel (20 g) eluting with a mixture of methanol and dichloromethane (1:9). This afforded 0.98 g of the title compound.

$^1$H-NMR (400 MHz, DMSO-d$_6$): $\delta_H$=2.4 (2H, bs), 2.55 (2H, bs), 2.62 (2H, bs), 3.50 (2H, bs), 3.85 (3H, s), 4.15 (2H, t), 6.62 (2H, m), 7.05 (1H, d), 7.30 (5H, m), 7.75 (2H, t), 7.97 (1H, s), 8.67 (1H, s), 11 (1H, bs), 11.5 (1H, s).

HPLC-MS (METHOD A): R$_t$=7.7 min; m/z=523 (M+1).

EXAMPLE 698

3-Chloro-4-hydroxybenzoic Acid {2-Methoxy-4-[2-(2-phenylpiperidin-1-yl)ethoxy]benzylidene}hydrazide

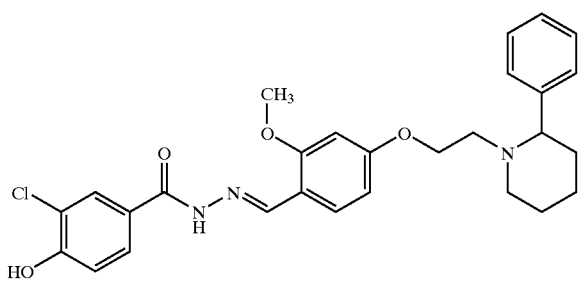

This compound was prepared analogously to the compound described in the previous example starting from resin bound 3-chloro-4-hydroxybenzoic acid hydrazide (resin—[building block 1]) (2 g, ~2 mmoles), 4-(2-bromoethoxy)-2-methoxybenzaldehyde ([building block 2]) (0.73 g, 1.5 equivs.), and 2-phenylpiperidine ([building block 3]) (3.0 g, 10 equivs.). After cleavage with 50% trifluoroacetic acid, the residue (1.0 g) was purified by column chromatography on silica gel (28 g) eluting with a mixture of methanol and dichloromethane (1:13). This afforded 0.24 g of the title compound.

$^1$H-NMR (400 MHz, DMSO-d$_6$): $\delta_H$=1.4 (2H, m), 1.65 (4H, m), 2.25 (2H, m), 2.75 (1H, m), 3.16 (1H, d), 3.25 (2H, d), 3.83 (3H, s), 4.0 (2H, m), 6.50 (1H, d), 6.54 (1H, s), 7.07 (1H, d), 7.23 (1H, t), 7.35 (4H, m), 7.73 (1H, d), 7.77 (1H, dd), 7.96 (1H, d), 8.65 (1H, s), 10.9 (1H, s), 11.6 (1H, s).

HPLC-MS (METHOD A): R$_t$=9.1 min; m/z=508 (M+1).

EXAMPLE 699

3-Chloro-4-hydroxybenzoic Acid {3-Chloro-4-[2-(1,2,3,4-tetrahydro-isoquinolin-2-yl)ethoxy]-5-methoxybenzylidene}hydrazide

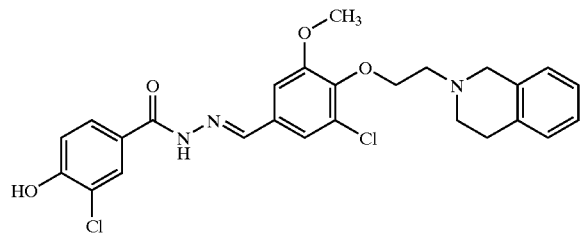

This compound was prepared analogously to the compound described in the previous example starting from resin bound 3-chloro-4-hydroxybenzoic acid hydrazide (resin—[building block 1]) (2 g, 2 mmoles), 4-(2-bromoethoxy)-3-chloro-5-methoxybenzaldehyde ([building block 2]) (0.81 g, 1.5 equivs.), and 1,2,3,4-tetrahydroisoquinoline ([building block 3]) (2.5 g, 10 equivs.). After cleavage with 50% trifluoroacetic acid, the residue (1.0 g) was dissolved in 15 ml of a mixture of 25% aq. ammonia, methanol and dichloromethane (1:9:90) and purified by column chromatography on silica gel (25 g) eluting with a mixture of methanol and dichloromethane (1:12). This afforded 0.11 g of the title compound.

$^1$H-NMR (400 MHz, DMSO-d$_6$): $\delta_H$=1.9 (1H, p), 2.18 (1H, t), 2.90 (2H, t), 3.70 (2H, s), 3.90 (3H, s), 4.19 (2H, t), 7.05 (5H, m), 7.37 (2H, s), 7.78 (1H, d), 7.95 (1H, s), 8.33 (1H, s), 11 (1H, bs), 11.8 (1H, s).

HPLC-MS (METHOD A): R$_t$=9.0 min; m/z=514 (M+1).

EXAMPLE 700

3-Chloro-4-hydroxybenzoic Acid {6-[2-(1,2,3,4-Tetrahydro-isoquinolin-2-yl)ethoxy]-5-methoxybiphenyl-3-ylmethylene}hydrazide

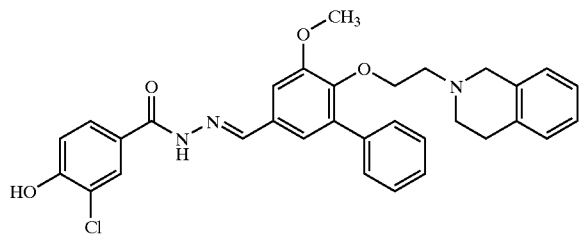

This compound was prepared analogously to the compound described in the previous example starting from resin bound 3-chloro-4-hydroxybenzoic acid hydrazide (resin—[building block 1]) (2 g, ~2 mmoles), 4-(2-bromoethoxy)-3-methoxy-5-phenylbenzaldehyde ([building block 2]) (0.93 g, 1.5 equivs.), and 1,2,3,4-tetrahydroisoquinoline ([building block 3]) (2.5 g, 10 equivs.). After cleavage with 50% trifluoroacetic acid, the residue was dissolved in 15 ml of a mixture of 25% aq. ammonia, methanol and dichloromethane (1:9:90) and purified by column chromatography on silica gel (25 g) eluting with a mixture of methanol and dichloromethane (1:12). This afforded 0.31 g of the title compound.

$^1$H-NMR (400 MHz, DMSO-d$_6$): $\delta_H$=2.60 (4H, m), 2.70 (2H, m), 3.48 (2H, s), 3.92 (3H, s), 3.96 (2H, t), 6.98 (1H, m), 7.10 (4H, m), 7.22 (1H, s), 7.40 (4H, m), 7.55 (2H, d), 7.78 (1H, d), 8.00 (1H, s), 8.40 (1H, s), 11 (1H, bs), 11.7 (1H, s).

HPLC-MS (METHOD A): R$_t$=9.6 min; m/z=557 (M+1).

EXAMPLE 701

3-Chloro-4-hydroxybenzoic Acid (3,5-Dibromo-4-{2-[4-(4-chlorophenyl)piperazin-1-yl]-ethoxy}benzylidene)hydrazide

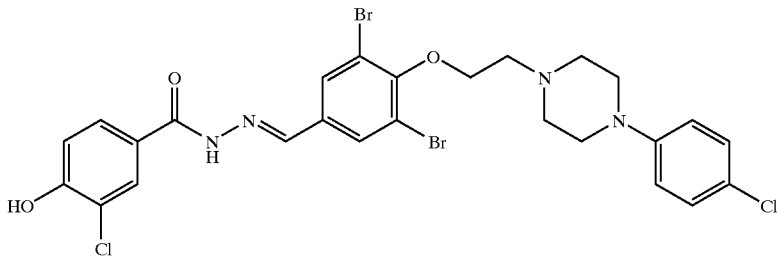

A solution of 4-(2-bromoethoxy)-3,5-dibromobenzaldehyde ([building block 2]) in DMF (0.6 M, 1 mL) was added to the resin bound 3-chloro-4-hydroxybenzoic acid hydrazide (resin—[building block 1]) (0.05 mmoles) followed by addition of triethyl orthoformate (0.5 mL) and the mixture was shaken at room temperature for 15 hours. The resin was repeatedly swelled in DMF (1.5 mL, 3 times), CH$_2$Cl$_2$ (1.5 mL, 2 times) and NMP (1.5 mL, 2 times) for 5 minutes and filtered. The resulting resin (resin—[building block 1]—[building block 2]) was added a solution of 1-(4-chlorophenyl)piperazine (0.4 M, 1 mL) and a solution of potassium iodide in NMP (0.08 M, 0.5 mL) were added and the mixture was shaken at room temperature for 16 hours. The resin was repeatedly swelled in DMF (1.5 mL, 3 times) and CH$_2$Cl$_2$ (1.5 mL, 6 times) for 2 minutes and filtered.

The compound was cleaved off the resin by shaking for 1 hour at room temperature with a 50% solution of trifluoroacetic acid in CH$_2$Cl$_2$ (1.5 mL). The mixture was filtered and the resin was extracted with CH$_2$Cl$_2$ (0.5 mL). The combined CH$_2$Cl$_2$ extracts were concentrated in vacuo. The residue was dissolved in methanol (1 mL) and concentrated in vacuo. The residue was dissolved in a 1:1 mixture of methanol and CH$_2$Cl$_2$ (1 mL) and concentrated in vacuo to give the title compound.

HPLC-MS (METHOD B): R$_t$=15.02 min; m/z=671.

EXAMPLES 702 TO 791

The following 90 compounds were prepared in parallel as individual entities analogously to the previous example on an Advanced ChemTech Model 384 HTS using the following ChemFile to control the operation of the synthesizer.

Further, a library of compounds of all the possible combinations of the above listed building blocks ([building block 1], [building block 2] and [building block 3]) was prepared in parallel as individual entities analogously to the previous example on an Advanced ChemTech Model 384 HTS using the following ChemFile to control the operation of the synthesizer. The compounds are all expected to be present in the respective wells.

The resin bound 3-chloro-4-hydroxybenzoic acid hydrazide (resin—[building block 1]) is equally distributed in the wells in the synthesizer prior to the initialization of the device.

ChemFile C:\ACT_1328\90250012.CHM:
1 REM Filtration of resin
2 Empty RB1__1to96 for 5.000 minute(s)
3 Empty RB2__1to96 for 5.000 minute(s)
4 Empty RB3__1to96 for 5.000 minute(s)
5 Empty RB4__1to96 for 5.000 minute(s)
6 Pause
7
8 REM Washing of resin
9
10 Dispense System Fluid Disdu1__4* 1500 ul to RB1__1to96[1–96]
11 Dispense System Fluid Disdu1__4* 1500 ul to RB2__1to96[1–96]
12 Dispense System Fluid Disdu1__4* 1500 ul to RB3__1to96[1–96]
13 Dispense System Fluid Disdu1__4* 1500 ul to RB4__1to96[1–96]
14 Start mixing "RB1__1to96" for 5.00 minutes at 600 rpm(s) and continue.

15 Start mixing "RB2_1to96" for 5.00 minutes at 600 rpm(s) and continue.
16 Start mixing "RB3__1to96" for 5.00 minutes at 600 rpm(s) and continue.
17 Mix "RB4__1to96" for 5.00 minutes at 600 rpm(s) and wait.
18 Wait for 25.000 minute(s)
19 Repeat from step 14, 1000 times
20 Empty RB1__1to96 for 5.000 minute(s)
21 Empty RB2__1to96 for 5.000 minute(s)
22 Empty RB3__1to96 for 5.000 minute(s)
23 Empty RB4__1to96 for 5.000 minute(s)
24 Pause
25
26 REM Coupling with aldehydes
27
28 Dispense System Fluid Disdu2__3* 1500 ul to RB1__1to96[1–96]
29 Dispense System Fluid Disdu2__3* 1500 ul to RB2__1to96[1–96]
30 Dispense System Fluid Disdu2__3* 1500 ul to RB3__1to96[1–96]
31 Dispense System Fluid Disdu2__3* 1500 ul to RB4__1to96[1–96]
32 Start mixing "RB1__1to96" for 5.00 minutes at 600 rpm(s) and continue.
33 Start mixing "RB2__1to96" for 5.00 minutes at 600 rpm(s) and continue.
34 Start mixing "RB3__1to96" for 5.00 minutes at 600 rpm(s) and continue.
35 Mix "RB4__1to96" for 5.00 minutes at 600 rpm(s) and wait.
36 Empty RB1__1to96 for 5.000 minute(s)
37 Empty RB2__1to96 for 5.000 minute(s)
38 Empty RB3__1to96 for 5.000 minute(s)
39 Empty RB4__1to96 for 5.000 minute(s)
40 Pause
41
42 Dispense Sequence c:\ACT13__28\R2-A.DSP with 1000 ul to RB1__1to96 rack using DMF
43 Mix "RB1__1to96" for 2.00 minutes at 600 rpm(s) and wait.
44 Dispense Sequence c:\ACT13__28\R2-B.DSP with 1000 ul to RB2__1to96 rack using DMF
45 Start mixing "RB1__1to96" for 2.00 minutes at 600 rpm(s) and continue.
46 Mix "RB2__1to96" for 2.00 minutes at 600 rpm(s) and wait.
47 Dispense Sequence c:\ACT13__28\R2-C.DSP with 1000 ul to RB3__1to96 rack using DMF
48 Start mixing "RB1__1to96" for 2.00 minutes at 600 rpm(s) and continue.
49 Start mixing "RB2__1to96" for 2.00 minutes at 600 rpm(s) and continue.
50 Mix "RB3__1to96" for 2.00 minutes at 600 rpm(s) and wait.
51 Dispense Sequence c:\ACT13__28\R2-D.DSP with 1000 ul to RB4__1to96 rack using DMF
52 Start mixing "RB1__1to96" for 2.00 minutes at 600 rpm(s) and continue.
53 Start mixing "RB2__1to96" for 2.00 minutes at 600 rpm(s) and continue.
54 Start mixing "RB3__1to96" for 2.00 minutes at 600 rpm(s) and continue.
55 Mix "RB4__1to96" for 2.00 minutes at 600 rpm(s) and wait.
56
57 Pause
58 REM Manual addition of CH(OC2H5)3
59 Start mixing "RB1__1to96" for 5.00 minutes at 600 rpm(s) and continue.
60 Start mixing "RB2__1to96" for 5.00 minutes at 600 rpm(s) and continue.
61 Start mixing "RB3__1to96" for 5.00 minutes at 600 rpm(s) and continue.
62 Mix "RB4__1to96" for 5.00 minutes at 600 rpm(s) and wait.
63 Wait for 25.000 minute(s)
64 Repeat from step 59, 200 times
65 Empty RB1__1to96 for 5.000 minute(s)
66 Empty RB2__1to96 for 5.000 minute(s)
67 Empty RB3__1to96 for 5.000 minute(s)
68 Empty RB4__1to96 for 5.000 minute(s)
69 Pause
70
71 REM Wash after coupling with aldehydes
72
73 Flush Arm1 with Flush Diluter1 and Flush Diluter 2, Arm2 with Flush Diluter
74 Dispense System Fluid Disdu2__3* 1500 ul to RB1__1to96[1–96]
75 Dispense System Fluid Disdu2__3* 1500 ul to RB2__1to96[1–96]
76 Dispense System Fluid Disdu2__3* 1500 ul to RB3__1to96[1–96]
77 Dispense System Fluid Disdu2__3* 1500 ul to RB4__1to96[1–96]
78 Start mixing "RB1__1to96" for 5.00 minutes at 600 rpm(s) and continue.
79 Start mixing "RB2__1to96" for 5.00 minutes at 600 rpm(s) and continue.
80 Start mixing "RB3__1to96" for 5.00 minutes at 600 rpm(s) and continue.
81 Mix "RB4__1to96" for 5.00 minutes at 600 rpm(s) and wait.
82 Empty RB1__1to96 for 5.000 minute(s)
83 Empty RB2__1to96 for 5.000 minute(s)
84 Empty RB3__1to96 for 5.000 minute(s)
85 Empty RB4__1to96 for 5.000 minute(s)
86 Repeat from step 74, 2 times
87 Pause
88 Dispense System Fluid Disdu1__4* 1500 ul to RB1__1to96[1–96]
89 Dispense System Fluid Disdu1__4* 1500 ul to RB2__1to96[1–96]
90 Dispense System Fluid Disdu1__4* 1500 ul to RB3__1to96[1–96]
91 Dispense System Fluid Disdu1__4* 1500 ul to RB4__1to96[1–96]
92 Start mixing "RB1__1to96" for 5.00 minutes at 600 rpm(s) and continue.

93 Start mixing "RB2_1to96" for 5.00 minutes at 600 rpm(s) and continue.
94 Start mixing "RB3_1to96" for 5.00 minutes at 600 rpm(s) and continue.
95 Mix "RB4_1to96" for 5.00 minutes at 600 rpm(s) and wait.
96 Empty RB1_1to96 for 5.000 minute(s)
97 Empty RB2_1to96 for 5.000 minute(s)
98 Empty RB3_1to96 for 5.000 minute(s)
99 Empty RB4_1to96 for 5.000 minute(s)
100 Repeat from step 88, 1 times
101 Dispense System Fluid Disdu2_3* 1500 ul to RB1_1to96[1–96]
102 Dispense System Fluid Disdu2_3* 1500 ul to RB2_1to96[1–96]
103 Dispense System Fluid Disdu2_3* 1500 ul to RB3_1to96[1–96]
104 Dispense System Fluid Disdu2_3* 1500 ul to RB4_1to96[1–96]
105 Start mixing "RB1_1to96" for 5.00 minutes at 600 rpm(s) and continue.
106 Start mixing "RB2_1to96" for 5.00 minutes at 600 rpm(s) and continue.
107 Start mixing "RB3_1to96" for 5.00 minutes at 600 rpm(s) and continue.
108 Mix "RB4_1to96" for 5.00 minutes at 600 rpm(s) and wait.
109 Wait for 25.000 minute(s)
110 Repeat from step 105, 1000 times
111 Pause
112 Empty RB1_1to96 for 5.000 minute(s)
113 Empty RB2_1to96 for 5.000 minute(s)
114 Empty RB3_1to96 for 5.000 minute(s)
115 Empty RB4_1to96 for 5.000 minute(s)
116 Repeat from step 101, 1 times
117
118 REM Coupling with amines
119 Flush Arm1 with Disdu2_3*, Arm2 with Disdu2_3*
120 Dispense Sequence c:\ACT13_28\R3-A.DSP with 1000 ul to RB1_1to96 rack using NMP
121 Mix "RB1_1to96" for 2.00 minutes at 600 rpm(s) and wait.
122 Dispense Sequence c:\ACT13_28\R3-B.DSP with 1000 ul to RB2_1to96 rack using NMP
123 Start mixing "RB1_1to96" for 2.00 minutes at 600 rpm(s) and continue.
124 Mix "RB2_1to96" for 2.00 minutes at 600 rpm(s) and wait.
125 Dispense Sequence c:\ACT13_28\R3-C.DSP with 1000 ul to RB3_1to96 rack using NMP
126 Start mixing "RB1_1to96" for 2.00 minutes at 600 rpm(s) and continue.
127 Start mixing "RB2_1to96" for 2.00 minutes at 600 rpm(s) and continue.
128 Mix "RB3_1to96" for 2.00 minutes at 600 rpm(s) and wait.
129 Dispense Sequence c:\ACT13_28\R3-D.DSP with 1000 ul to RB4_1to96 rack using NMP
130 Start mixing "RB1_1to96" for 2.00 minutes at 600 rpm(s) and continue.
131 Start mixing "RB2_1to96" for 2.00 minutes at 600 rpm(s) and continue.
132 Start mixing "RB3_1to96" for 2.00 minutes at 600 rpm(s) and continue.
133 Mix "RB4_1to96" for 2.00 minutes at 600 rpm(s) and wait.
134 Pause
135 Transfer 500 ul from REAGENT_3[1]( ) to RB1_1to96[1–96] using NMP
136 Mix "RB1_1to96" for 2.00 minutes at 600 rpm(s) and wait.
137 Pause
138 Transfer 500 ul from REAGENT_3[1]( ) to RB2_1to96[1–96] using NMP
139 Start mixing "RB1_1to96" for 2.00 minutes at 600 rpm(s) and continue.
140 Mix "RB2_1to96" for 2.00 minutes at 600 rpm(s) and wait.
141 Pause
142 Transfer 500 ul from REAGENT_3[1]( ) to RB3_1to96[1–96] using NMP
143 Start mixing "RB1_1to96" for 2.00 minutes at 600 rpm(s) and continue.
144 Start mixing "RB2_1to96" for 2.00 minutes at 600 rpm(s) and continue.
145 Mix "RB3_1to96" for 2.00 minutes at 600 rpm(s) and wait.
146 Pause
147 Transfer 500 ul from REAGENT_3[1]( ) to RB4_1to96[1–96] using NMP
148 Start mixing "RB1_1to96" for 5.00 minutes at 600 rpm(s) and continue.
149 Start mixing "RB2_1to96" for 5.00 minutes at 600 rpm(s) and continue.
150 Start mixing "RB3_1to96" for 5.00 minutes at 600 rpm(s) and continue.
151 Mix "RB4 1to 96" for 5.00 minutes at 600 rpm(s) and wait.
152 Wait for 25.000 minute(s)
153 Repeat from step 148, 200 times
154 Pause
155
156 Empty RB1_1to96 for 5.000 minute(s)
157 Empty RB2_1to96 for 5.000 minute(s)
158 Empty RB3_1to96 for 5.000 minute(s)
159 Empty RB4_1to96 for 5.000 minute(s)
160
161
162 REM Wash after coupling with amines
163
164 Flush Arm1 with Flush Diluter1 and Flush Diluter 2, Arm2 with Flush Diluter
165
166 Dispense System Fluid Disdu2_3* 1500 ul to RB1_1to96[1–96]
167 Dispense System Fluid Disdu2_3* 1500 ul to RB2_1to96[1–96]
168 Dispense System Fluid Disdu2_3* 1500 ul to RB3_1to 96[1–96]
169 Dispense System Fluid Disdu2_3* 1500 ul to RB4_1to96[1–96]

170 Start mixing "RB1__1to96" for 5.00 minutes at 600 rpm(s) and continue.
171 Start mixing "RB2__1to96" for 5.00 minutes at 600 rpm(s) and continue.
172 Start mixing "RB3__1to96" for 5.00 minutes at 600 rpm(s) and continue.
173 Mix "RB4__1to96" for 5.00 minutes at 600 rpm(s) and wait.
174 Empty RB1__1to96 for 5.000 minute(s)
175 Empty RB2__1to96 for 5.000 minute(s)
176 Empty RB3__1to96 for 5.000 minute(s)
177 Empty RB4__1to96 for 5.000 minute(s)
178 Repeat from step 166, 2 times
179 Pause
180 Dispense System Fluid Disdu1_4* 1500 ul to RB1__1to96[1–96]
181 Dispense System Fluid Disdu1_4* 1500 ul to RB2__1to96[1–96]
182 Dispense System Fluid Disdu1_4* 1500 ul to RB3__1to96[1–96]
183 Dispense System Fluid Disdu1_4* 1500 ul to RB4__1to96[1–96]
184 Start mixing "RB1__1to96" for 5.00 minutes at 600 rpm(s) and continue.
185 Start mixing "RB2__1to96" for 5.00 minutes at 600 rpm(s) and continue.
186 Start mixing "RB3__1to96" for 5.00 minutes at 600 rpm(s) and continue.
187 Mix "RB4__1to96" for 5.00 minutes at 600 rpm(s) and wait.
188 Empty RB1__1to96 for 5.000 minute(s)
189 Empty RB2__1to96 for 5.000 minute(s)
190 Empty RB3__1to96 for 5.000 minute(s)
191 Empty RB4__1to96 for 5.000 minute(s)
192
193 Repeat from step 180, 5 times
194
195 Dispense System Fluid Disdu1_4* 1500 ul to RB1__1to96[1–96]
196 Dispense System Fluid Disdu1_4* 1500 ul to RB2__1to96[1–96]
197 Dispense System Fluid Disdu1_4* 1500 ul to RB3__1to96[1–96]
198 Dispense System Fluid Disdu1_4* 1500 ul to RB4__1to96[1–96]
199 Start mixing "RB1__1to96" for 5.00 minutes at 600 rpm(s) and continue.
200 Start mixing "RB2__1to96" for 5.00 minutes at 600 rpm(s) and continue.
201 Start mixing "RB3__1to96" for 5.00 minutes at 600 rpm(s) and continue.
202 Mix "RB4__1to96" for 5.00 minutes at 600 rpm(s) and wait.
203 Wait for 25.000 minute(s)
204 Repeat from step 199, 1000 times
205
206 Flush Arm1 with Flush Diluter1 and Flush Diluter 2, Arm2 with Flush Diluter 3
207 Empty RB4__1to96 for 5.000 minute(s)
208 Pause
209
210 REM Clevage (50% TFA/DCM manually added, one rack at a time)
211 Flush Arm1 with Flush Diluter1, Arm2 with Flush Diluter 4
212 Mix "RB1 1to 96" for 5.00 minutes at 600 rpm(s) and wait.
213 Wait for 5.000 minute(s)
214 Repeat from step 7, 5 times
215 Empty RB1__1to96 for 1 second(s)
216 Wait for 4 second(s)
217 Repeat from step 10, 25 times
218 Empty RB1__1to96 for 5.000 minute(s)
219
220 Dispense System Fluid Disdu1_4* 500 ul to RB1__1to96[1–96]
221 Wait for 1.000 minute(s)
222 Empty RB1__1to96 for 1 second(s)
223 Wait for 4 second(s)
224 Repeat from step 17, 25 times
225 Empty RB1__1to96 for 5.000 minute(s)
226

Dispense sequence files C:\ACT13__28\R3-A.DSP, C:\ACT13__28\R3-B.DSP, C:\ACT13__28\R3-C.DSP and C:\ACT13__28\R3-D.DSP are subroutines that control the combinatorial addition of the amines into the 4 reaction blocks each containing 96 wells in the syntheziser.

The library containing the following compounds was synthesized, and the products were characterised by HPLC-MS (molecular mass & retention time).

| Ex No. | Structure | HPLC-MS (METHOD B) m/z | HPLC-MS (METHOD B) R$_t$ (minutes) |
|---|---|---|---|
| 702 | 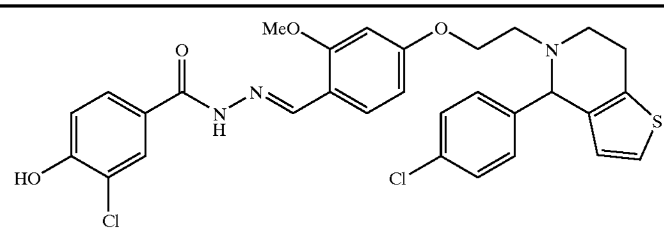 | 596 | 15.9 |

| Ex No. | Structure | HPLC-MS (METHOD B) m/z | HPLC-MS (METHOD B) R$_t$ (minutes) |
|---|---|---|---|
| 703 | 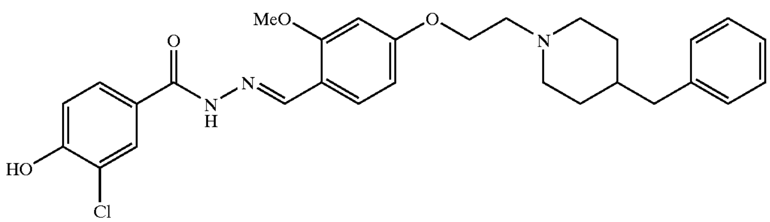 | 522 | 8.82 |
| 704 | 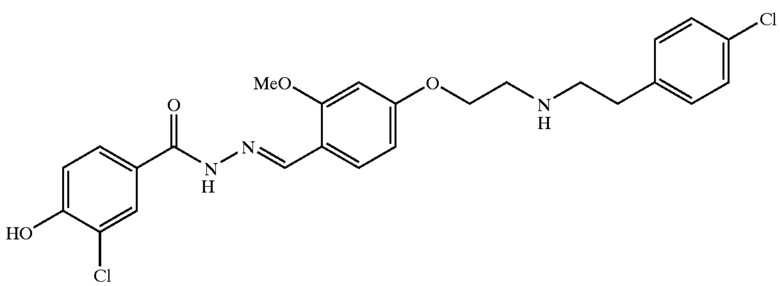 | 502 | 6.62 |
| 705 | 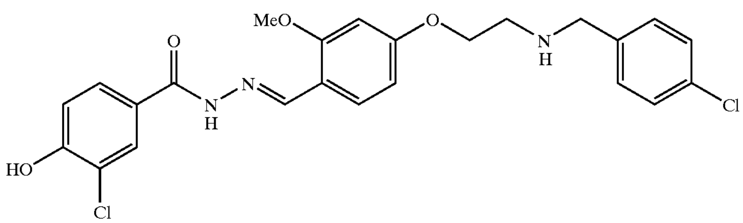 | 488 | 6.68 |
| 706 | 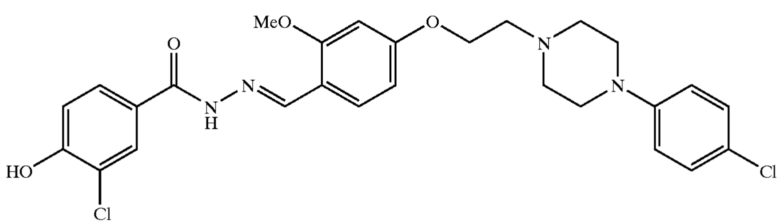 | 543 | 10.93 |
| 707 | 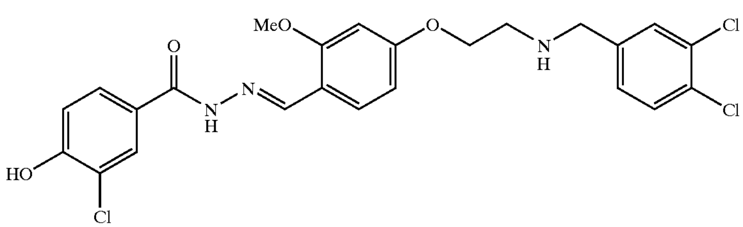 | 522 | 9.40 |
| 708 | 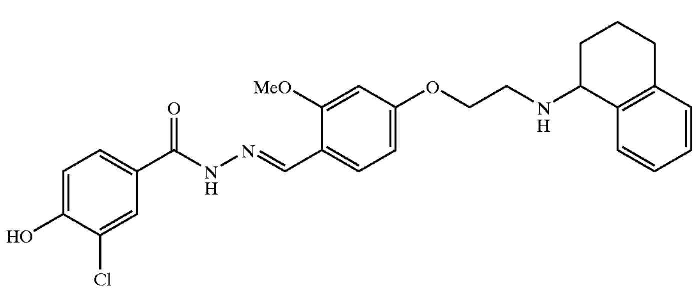 | 494 | 7.87 |

-continued
| Ex No. | Structure | HPLC-MS (METHOD B) m/z | HPLC-MS (METHOD B) R_t (minutes) |
|---|---|---|---|
| 709 | 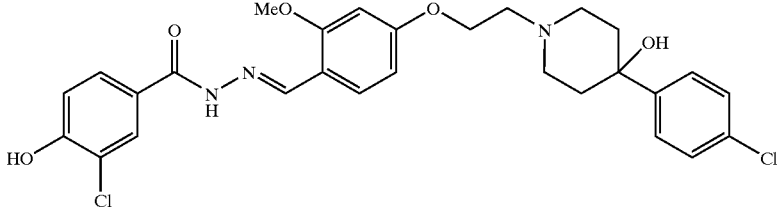 | 558 | 5.37 |
| 710 | 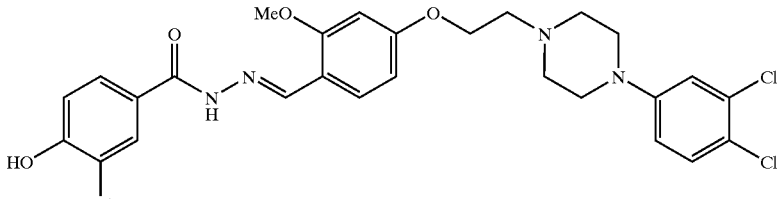 | 577 | 13.50 |
| 711 | 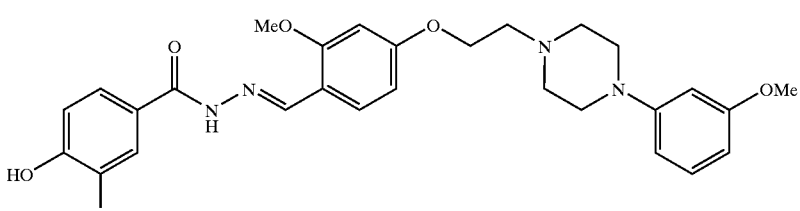 | 539 | 7.43 |
| 712 | 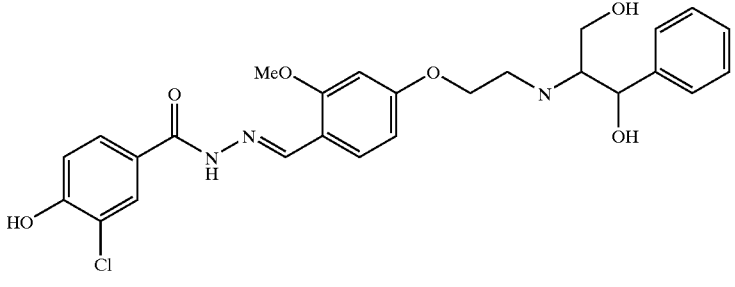 | 214 | 2.05 |
| 713 | 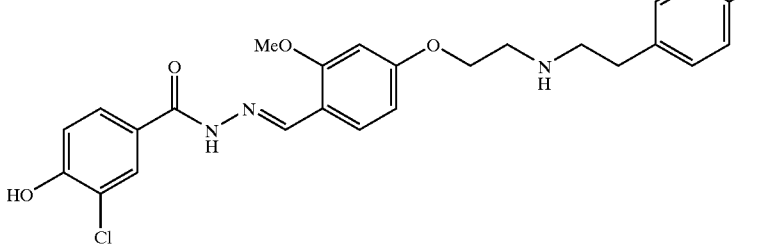 | 548 | 7.10 |

-continued

| Ex No. | Structure | HPLC-MS (METHOD B) m/z | HPLC-MS (METHOD B) R_t (minutes) |
|---|---|---|---|
| 714 | 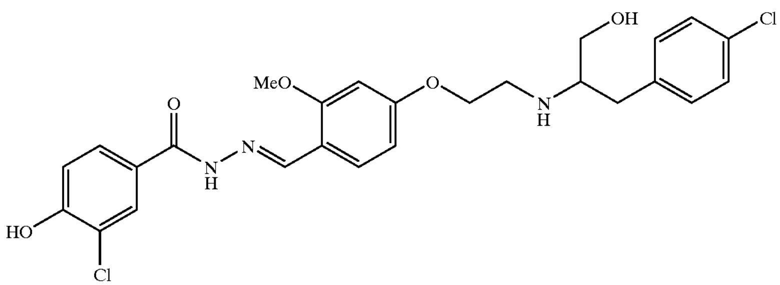 | 532 | 5.38 |
| 715 | 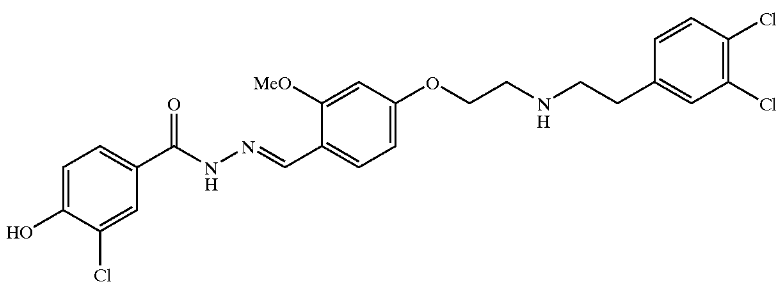 | 536 | 8.43 |
| 716 | 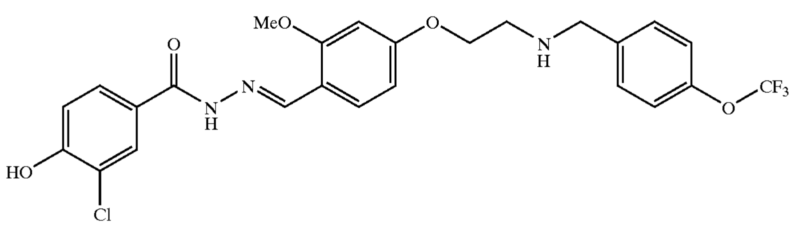 | 538 | 9.05 |
| 717 | 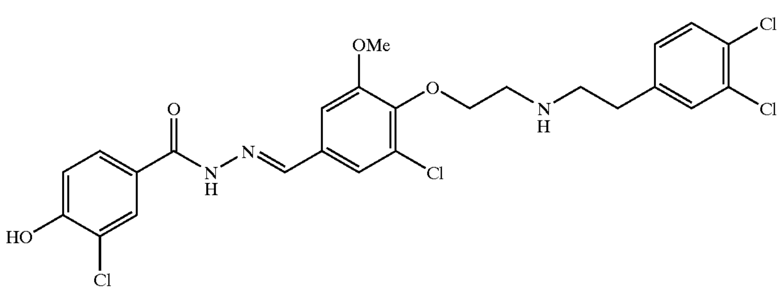 | 572 | 9.93 |
| 718 | 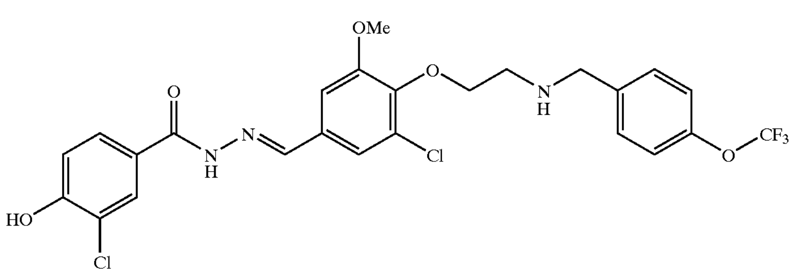 | 572 | 10.78 |

-continued

| Ex No. | Structure | HPLC-MS (METHOD B) m/z | HPLC-MS (METHOD B) R$_t$ (minutes) |
|---|---|---|---|
| 719 | 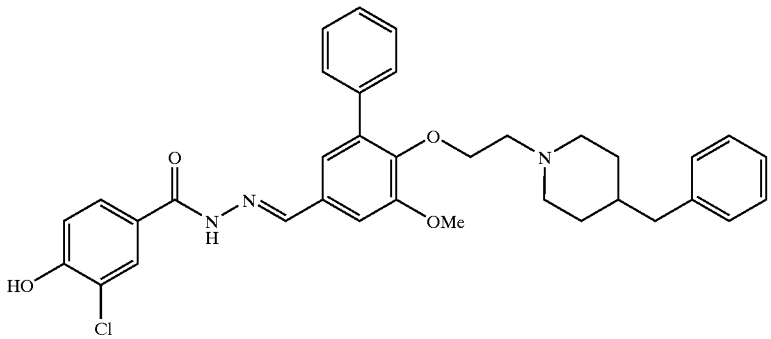 | 598 | 11.47 |
| 720 | 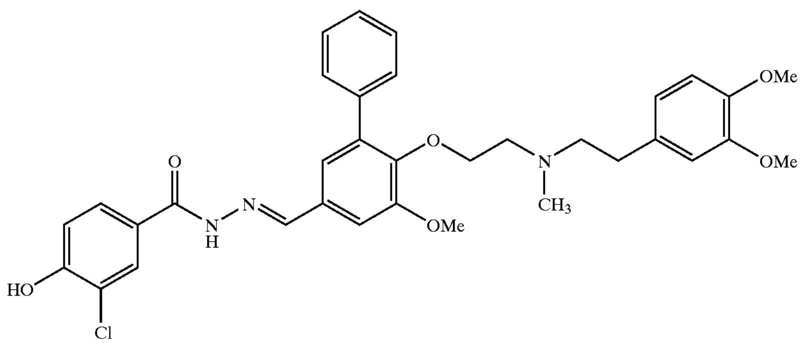 | 618 | 7.35 |
| 721 | 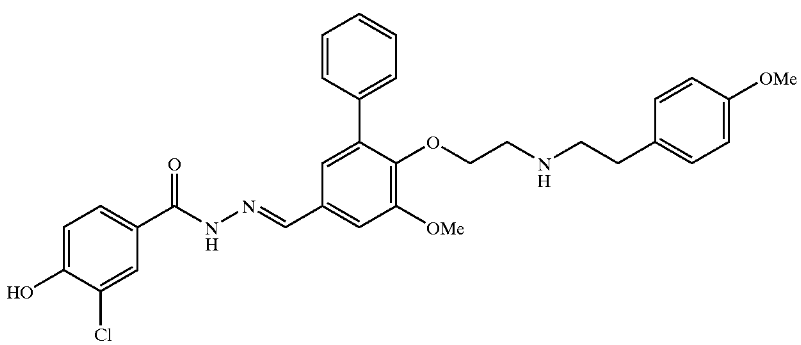 | 574 | 7.27 |
| 722 | 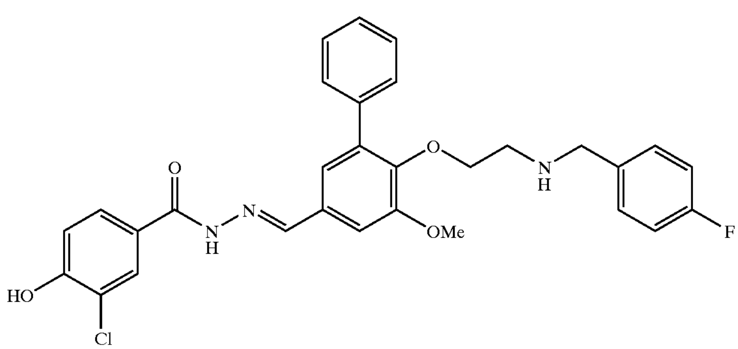 | 548 | 8.50 |

| Ex No. | Structure | HPLC-MS (METHOD B) m/z | HPLC-MS (METHOD B) R$_t$ (minutes) |
| --- | --- | --- | --- |
| 723 | 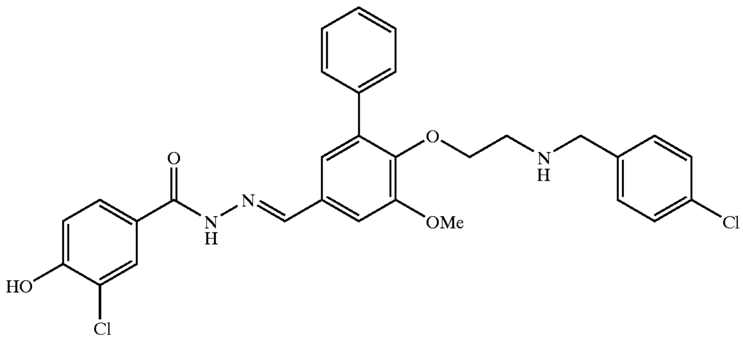 | 564 | 11.38 |
| 724 | 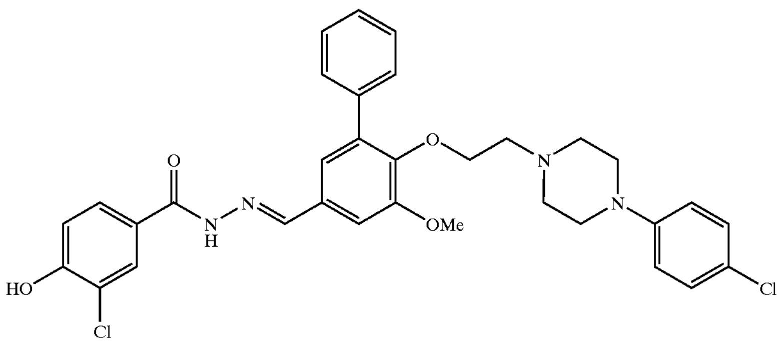 | 619 | 14.47 |
| 725 | 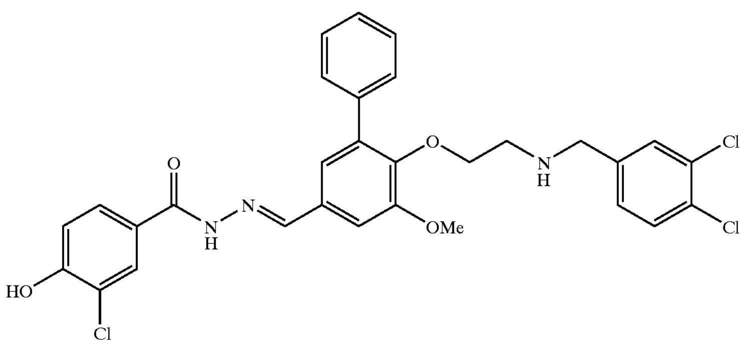 | 598 | 13.87 |
| 726 | 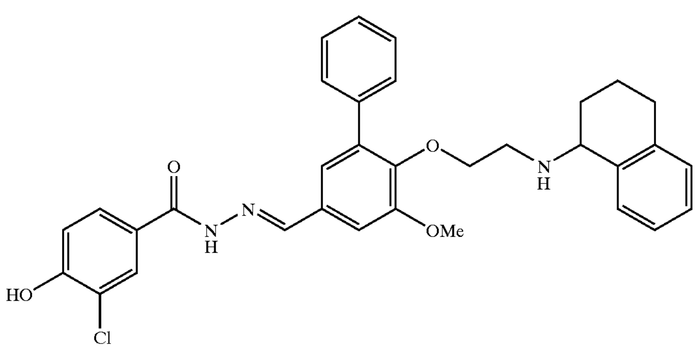 | 570 | 12.50 |

-continued

| Ex No. | Structure | HPLC-MS (METHOD B) m/z | HPLC-MS (METHOD B) $R_t$ (minutes) |
|---|---|---|---|
| 727 | 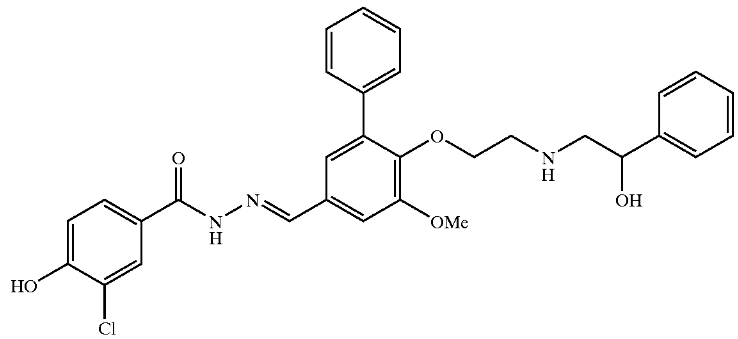 | 560 | 6.02 |
| 728 | 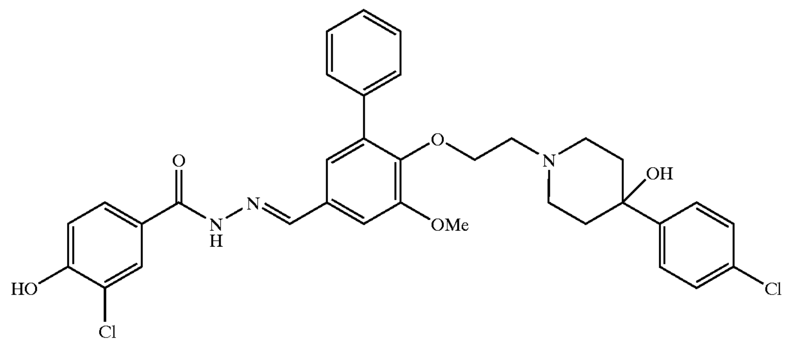 | 634 | 8.05 |
| 729 | 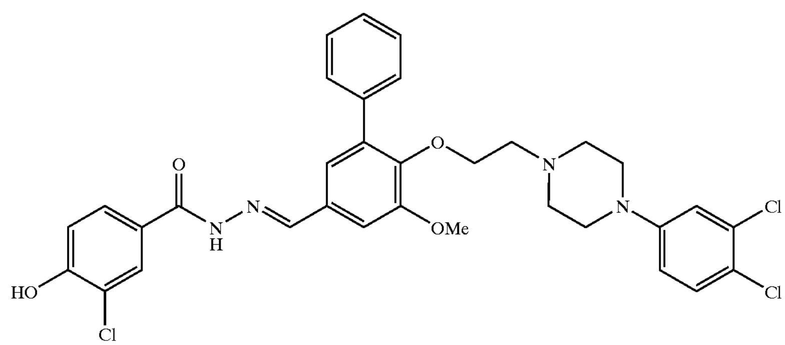 | 655 | 16.35 |
| 730 | 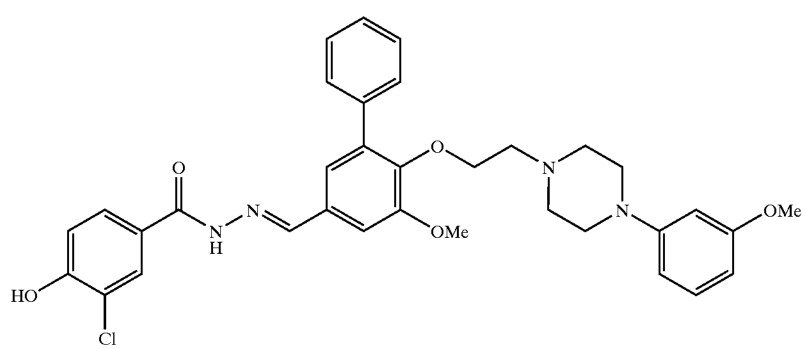 | 615 | 12.15 |

-continued

| Ex No. | Structure | HPLC-MS (METHOD B) m/z | HPLC-MS (METHOD B) R_t (minutes) |
|---|---|---|---|
| 731 | 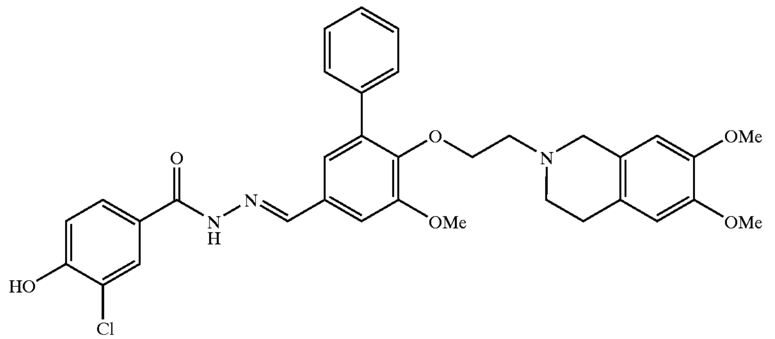 | 616 | 8.30 |
| 732 | 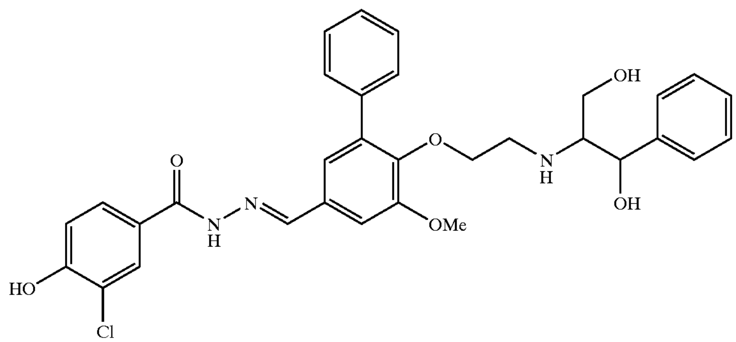 | 590 | 5.30 |
| 733 | 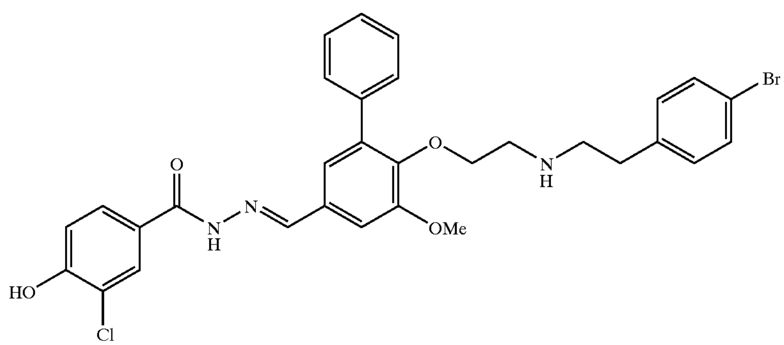 | 624 | 10.90 |
| 734 | 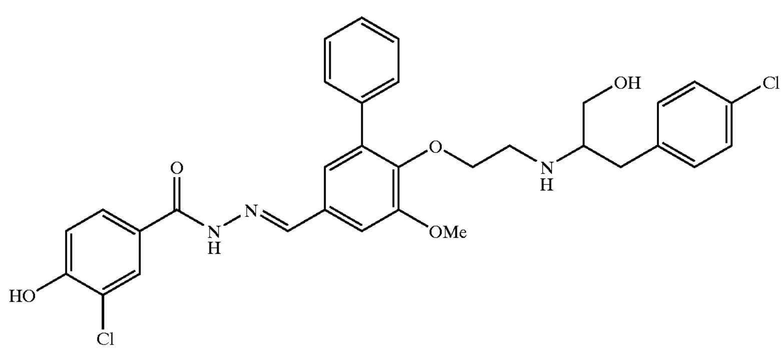 | 608 | 8.95 |

-continued
| Ex No. | Structure | HPLC-MS (METHOD B) m/z | HPLC-MS (METHOD B) R$_t$ (minutes) |
|---|---|---|---|
| 735 | 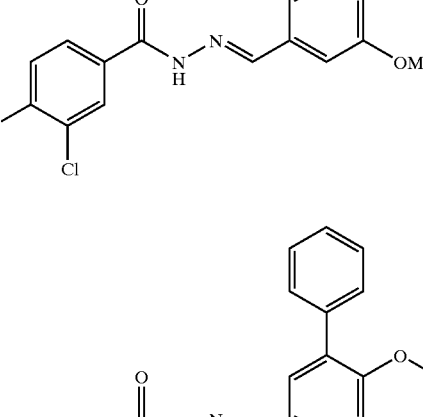 | 612 | 12.65 |
| 736 | 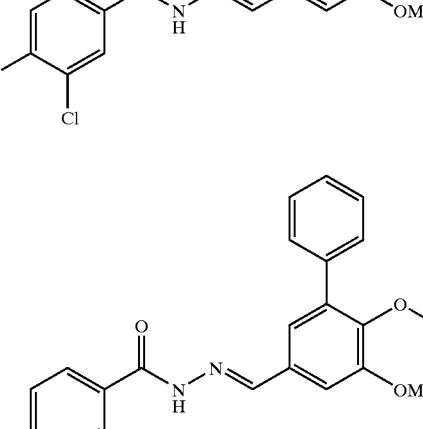 | 550 | 7.88 |
| 737 | 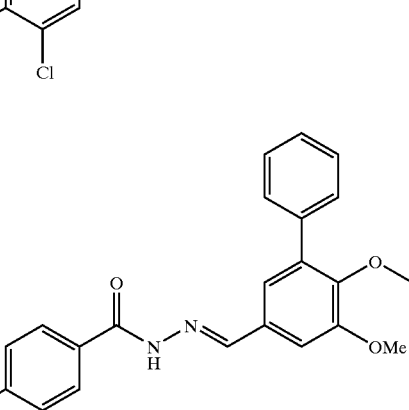 | 614 | 13.07 |
| 738 | 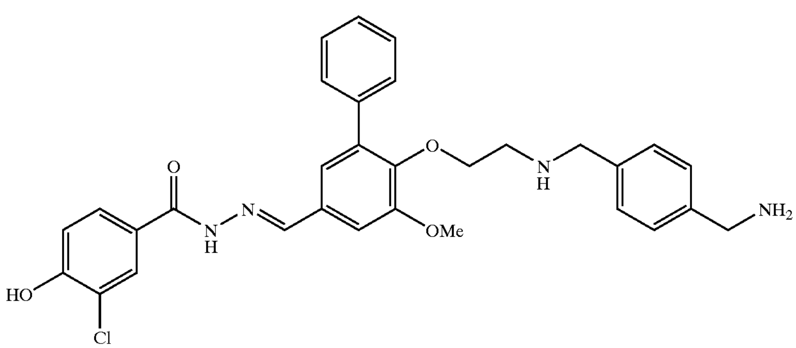 | 559 | 2.33 |

-continued

| Ex No. | Structure | HPLC-MS (METHOD B) m/z | HPLC-MS (METHOD B) R$_t$ (minutes) |
|---|---|---|---|
| 739 | 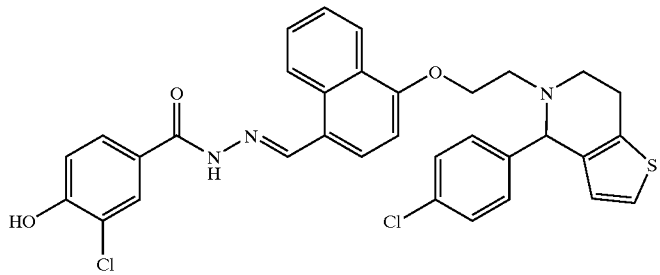 | 616 | 17.98 |
| 740 | 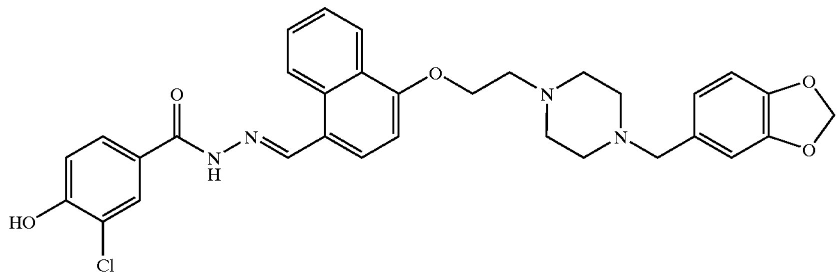 | 587 | 7.87 |
| 741 | 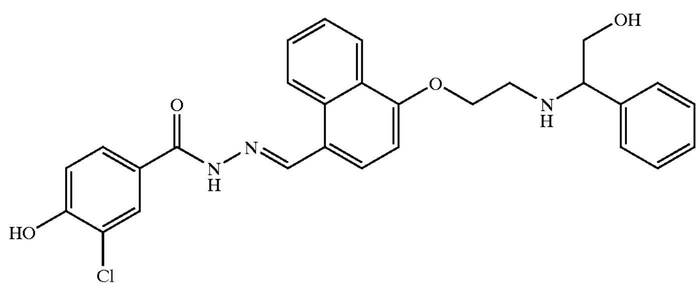 | 504 | 5.40 |
| 742 | 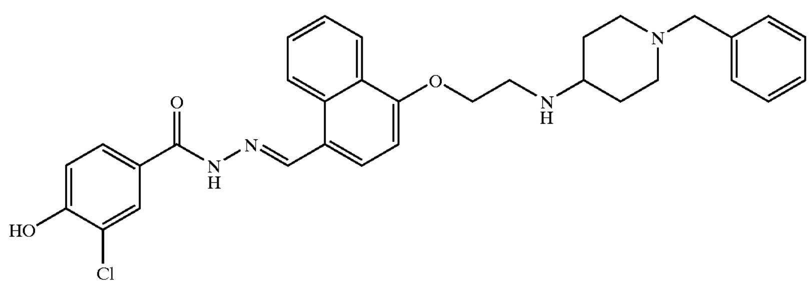 | 557 | 6.57 |
| 743 | 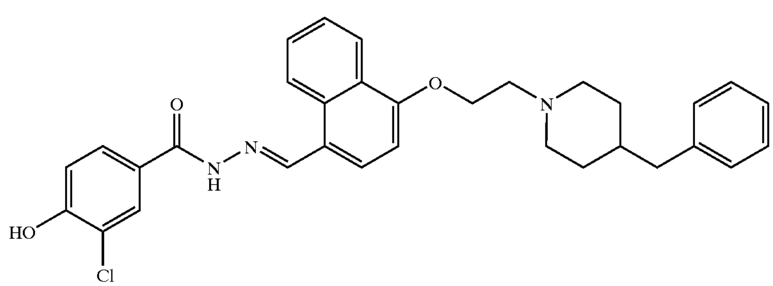 | 5.42 | 12.68 |

-continued

| Ex No. | Structure | HPLC-MS (METHOD B) m/z | HPLC-MS (METHOD B) R$_t$ (minutes) |
|---|---|---|---|
| 744 | 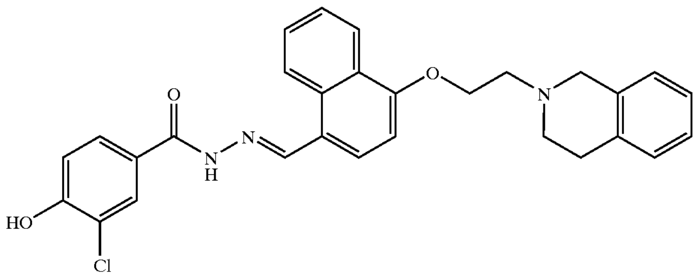 | 500 | 11.95 |
| 745 | 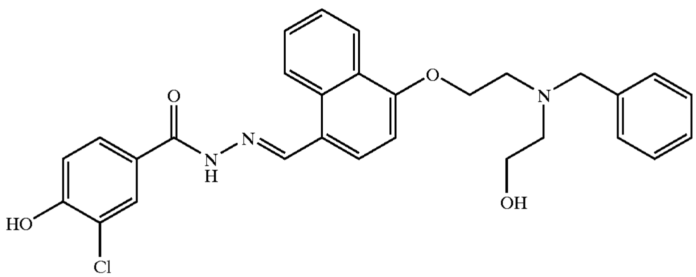 | 518 | 8.83 |
| 746 | 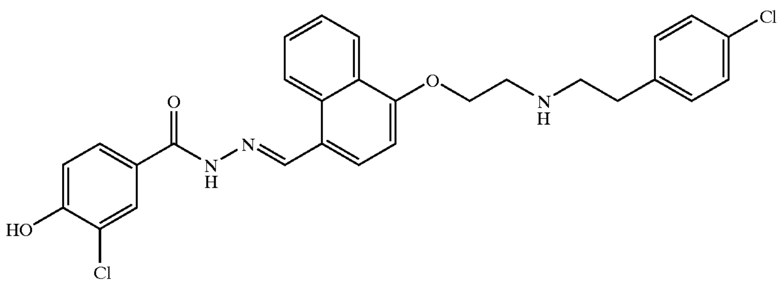 | 522 | 9.53 |
| 747 | 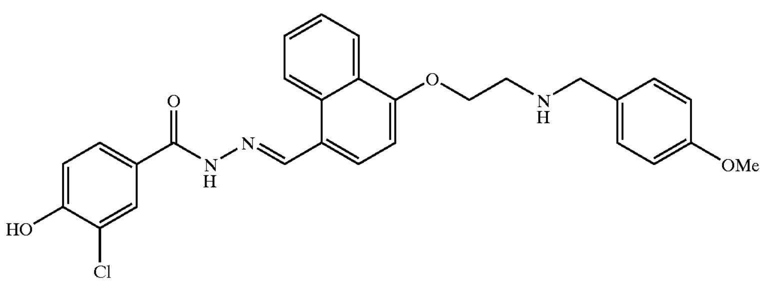 | 504 | 6.42 |
| 748 | 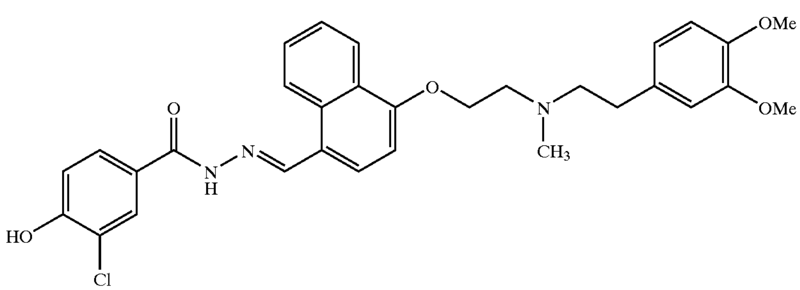 | 562 | 7.35 |

-continued

| Ex No. | Structure | HPLC-MS (METHOD B) m/z | HPLC-MS (METHOD B) R_t (minutes) |
|---|---|---|---|
| 749 | 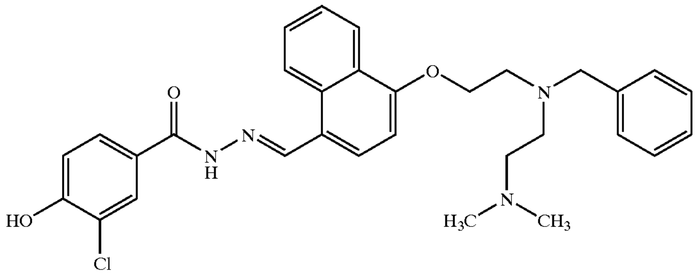 | 545 | 7.54 |
| 750 | 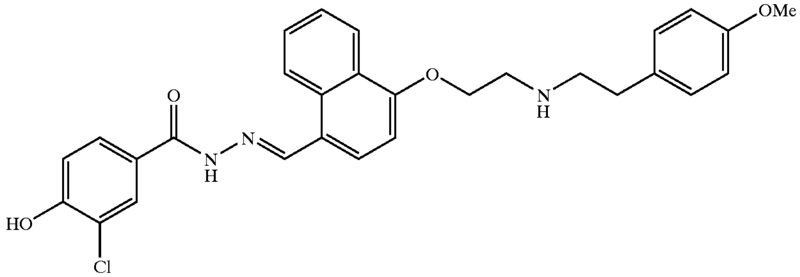 | 518 | 6.52 |
| 751 | 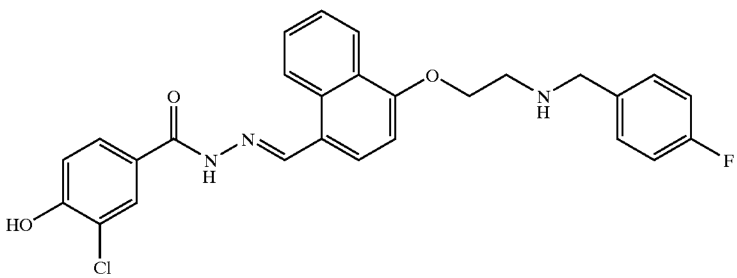 | 492 | 7.57 |
| 752 | 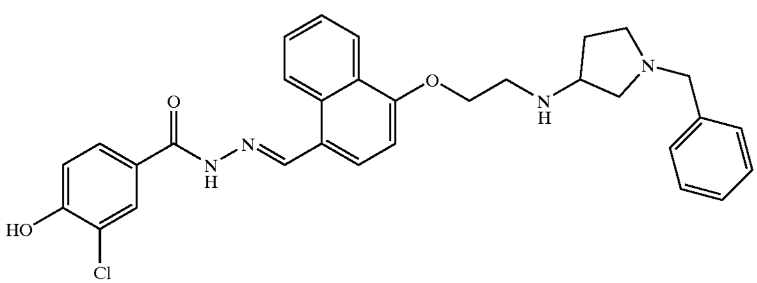 | 543 | 6.13 |
| 753 | 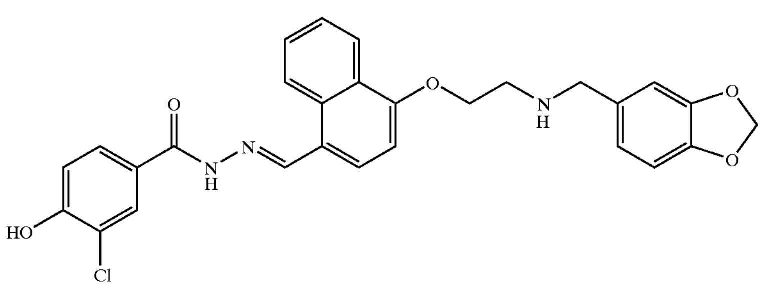 | 518 | 6.43 |

| Ex No. | Structure | HPLC-MS (METHOD B) m/z | HPLC-MS (METHOD B) R$_t$ (minutes) |
|---|---|---|---|
| 754 | 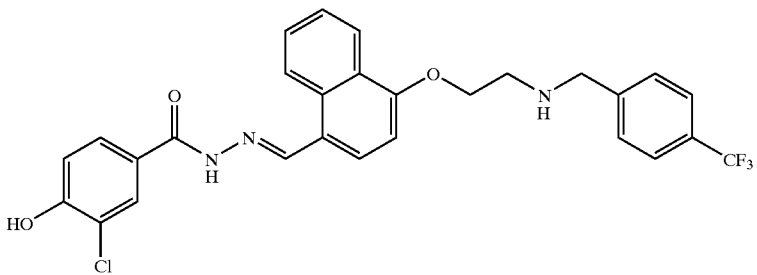 | 542 | 12.03 |
| 755 | 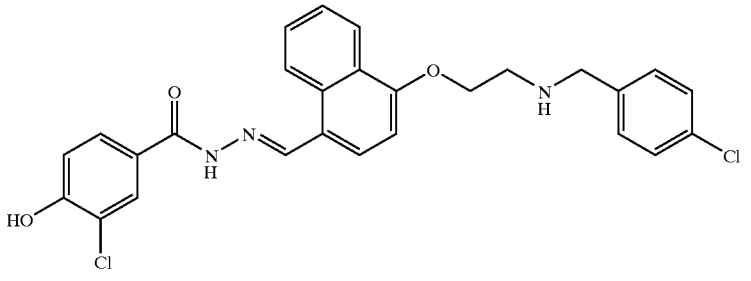 | 508 | 10.32 |
| 756 | 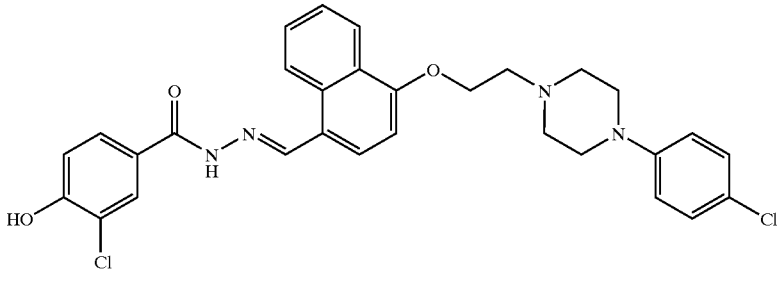 | 563 | 14.17 |
| 757 | 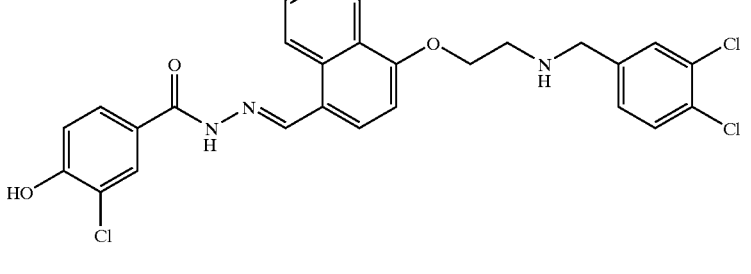 | 544 | 13.07 |
| 758 | 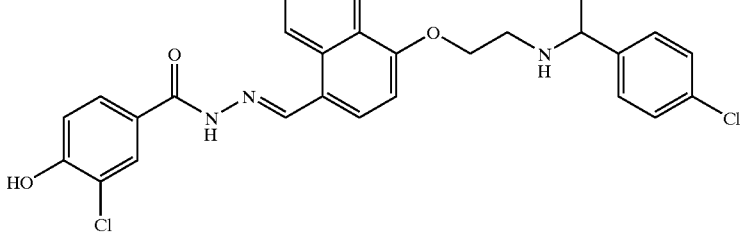 | 522 | 12.65 |

-continued
| Ex No. | Structure | HPLC-MS (METHOD B) m/z | HPLC-MS (METHOD B) $R_t$ (minutes) |
|---|---|---|---|
| 759 | 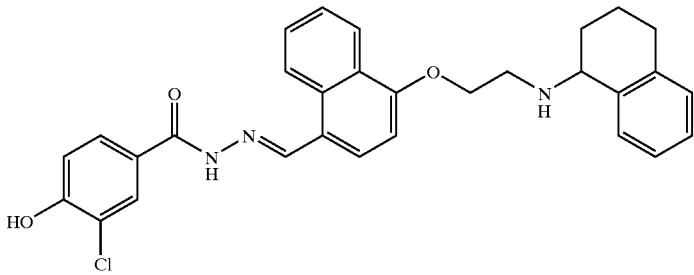 | 514 | 12.03 |
| 760 | 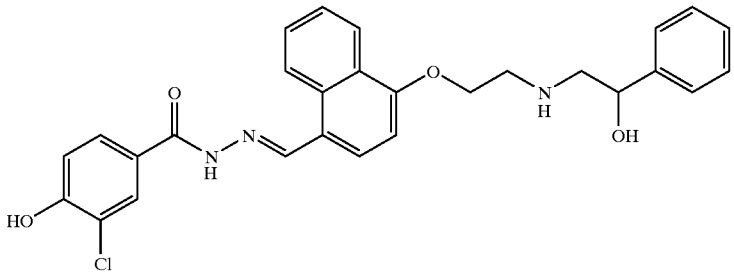 | 504 | 4.57 |
| 761 | 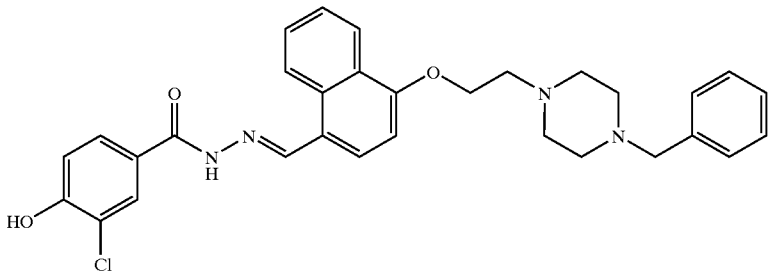 | 543 | 9.30 |
| 762 | 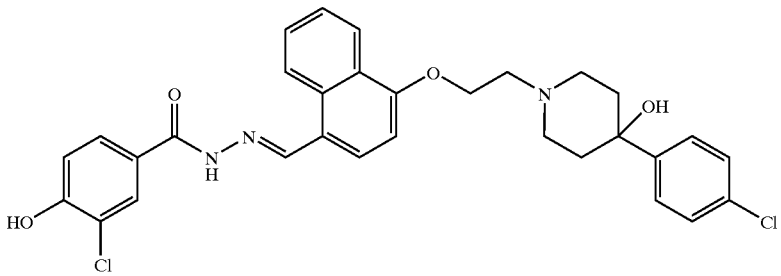 | 578 | 7.77 |
| 763 | 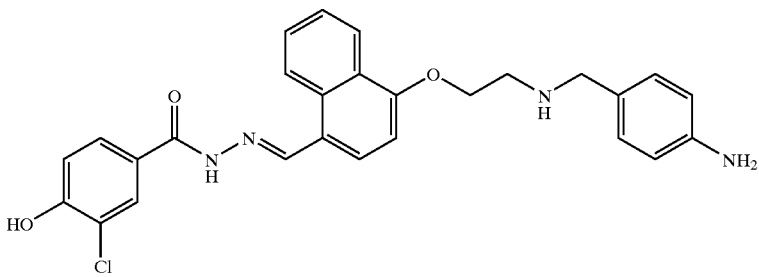 | 489 | 2.23 |

-continued
| Ex No. | Structure | HPLC-MS (METHOD B) m/z | HPLC-MS (METHOD B) $R_t$ (minutes) |
|---|---|---|---|
| 764 | 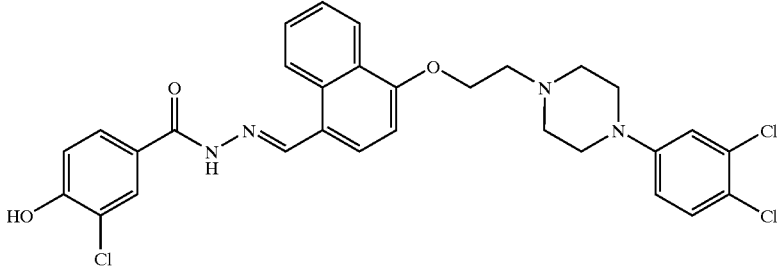 | 597 | 15.73 |
| 765 | 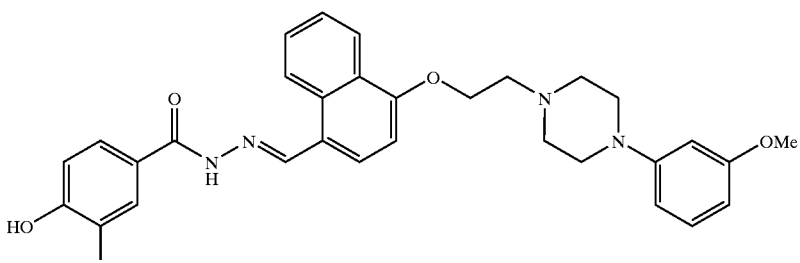 | 559 | 11.25 |
| 766 | 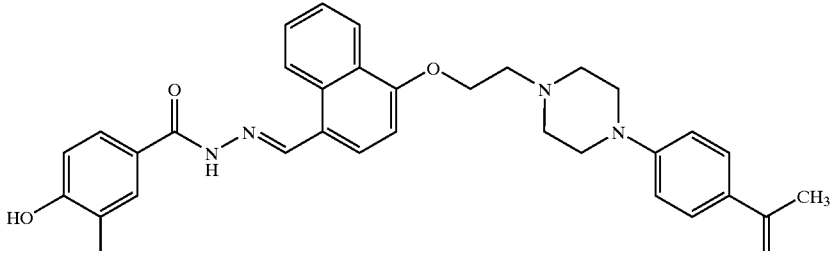 | 571 | 8.38 |
| 767 | 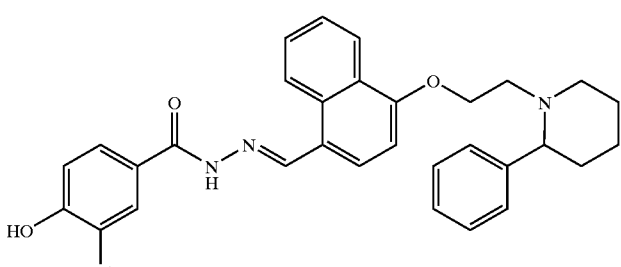 | 528 | 15.38 |
| 768 | 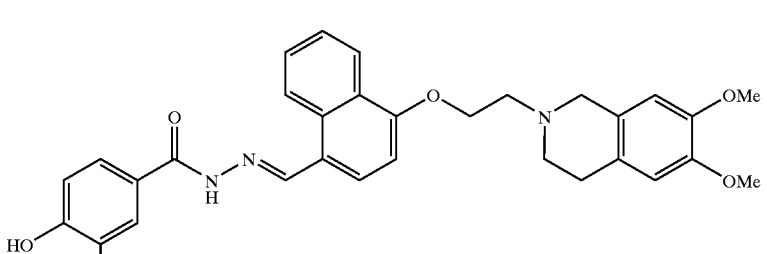 | 560 | 8.00 |

-continued
| Ex No. | Structure | HPLC-MS (METHOD B) m/z | HPLC-MS (METHOD B) R$_t$ (minutes) |
|---|---|---|---|
| 769 | 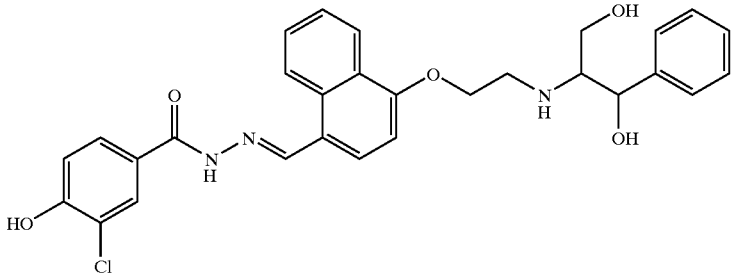 | 5.34 | 3.33 |
| 770 | 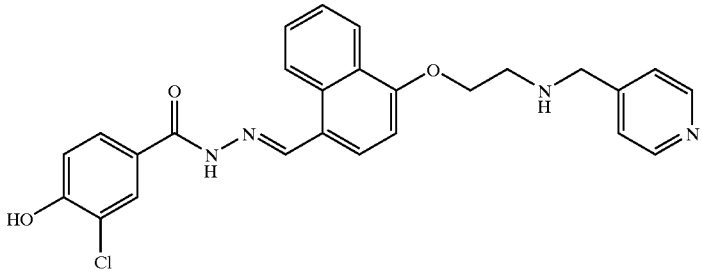 | 475 | 2.23 |
| 771 | 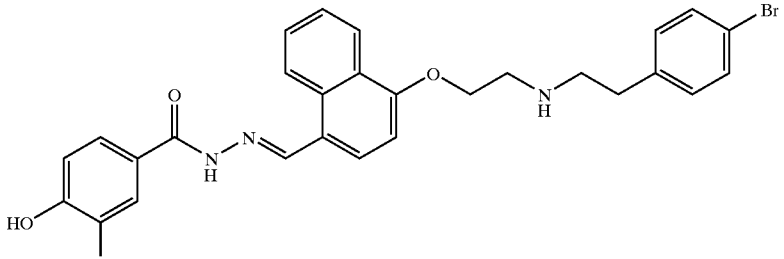 | 568 | 10.07 |
| 772 | 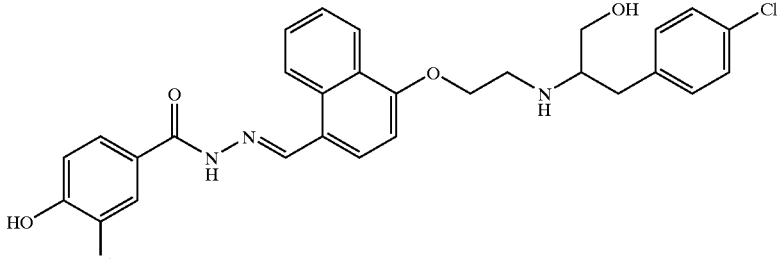 | 552 | 6.93 |
| 773 | 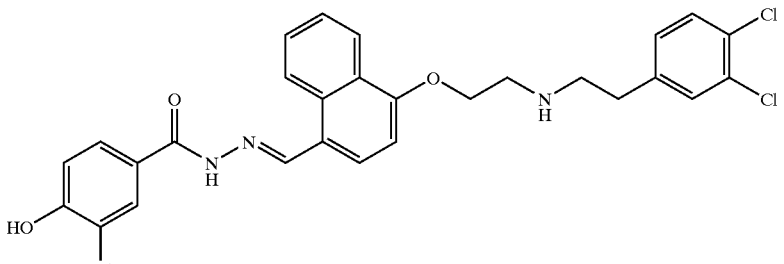 | 556 | 12.02 |

-continued

| Ex No. | Structure | HPLC-MS (METHOD B) m/z | HPLC-MS (METHOD B) R_t (minutes) |
|---|---|---|---|
| 774 | 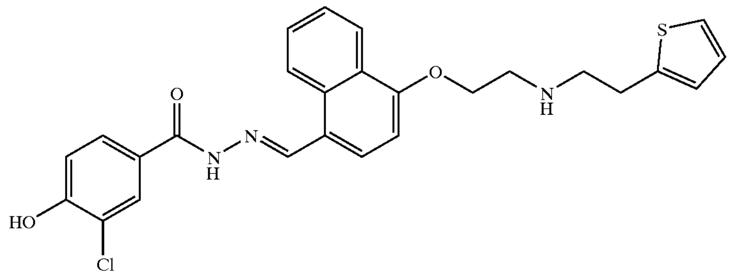 | 494 | 7.12 |
| 775 | 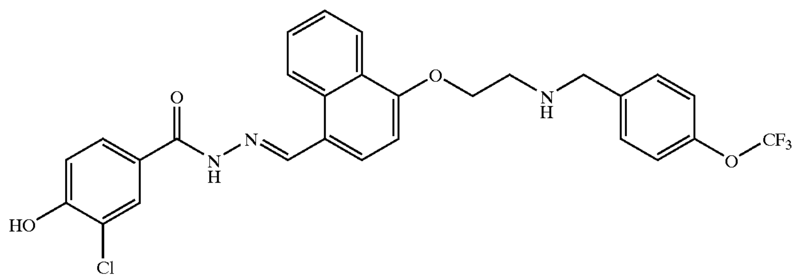 | 558 | 12.58 |
| 776 | 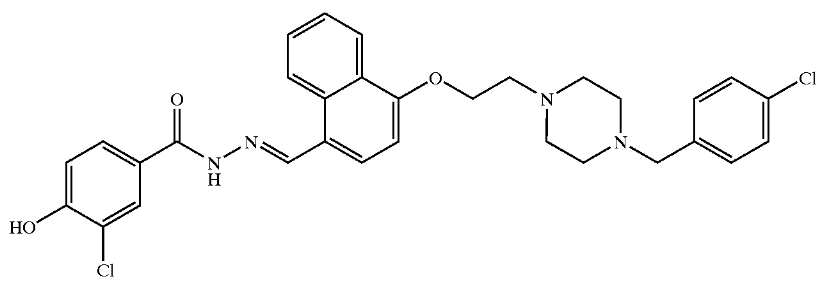 | 577 | 12.68 |
| 777 | 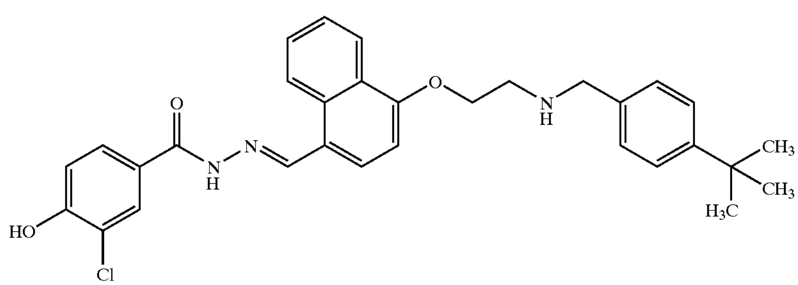 | 530 | 13.23 |
| 778 | 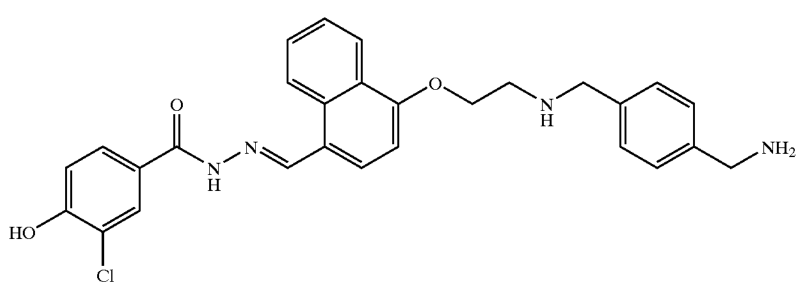 | 503 | 1.88 |

-continued

| Ex No. | Structure | HPLC-MS (METHOD B) m/z | HPLC-MS (METHOD B) R$_t$ (minutes) |
|---|---|---|---|
| 779 | 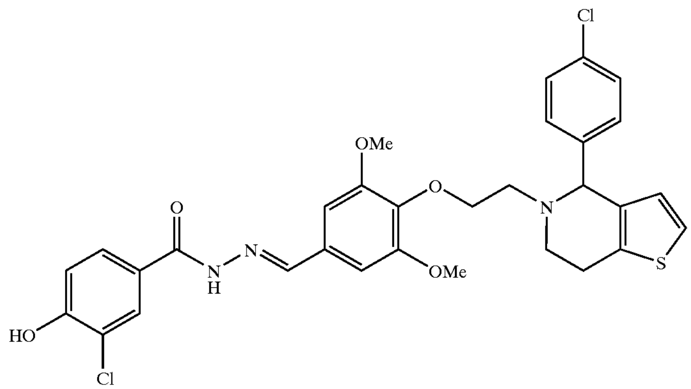 | 626 | 15.23 |
| 780 | 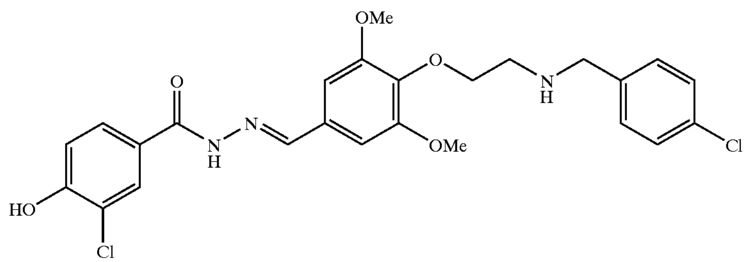 | 518 | 5.23 |
| 781 | 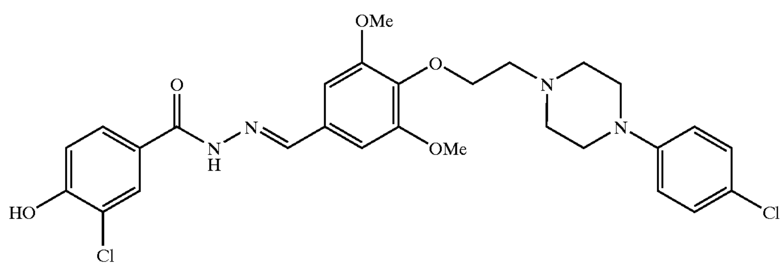 | 573 | 8.48 |
| 782 | 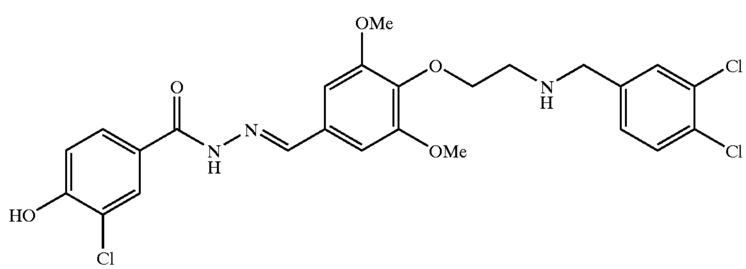 | 552 | 7.52 |
| 783 | 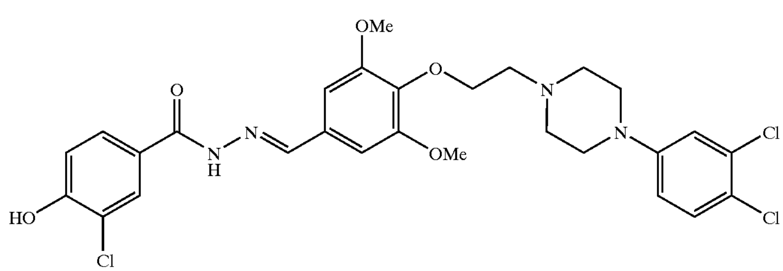 | 607 | 12.25 |

-continued

| Ex No. | Structure | HPLC-MS (METHOD B) m/z | HPLC-MS (METHOD B) $R_t$ (minutes) |
|---|---|---|---|
| 784 | 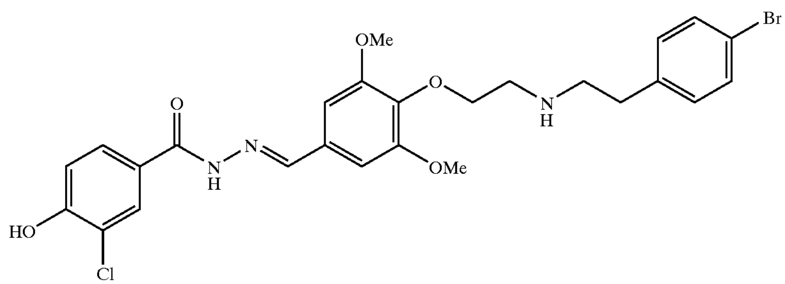 | 578 | 5.70 |
| 785 | 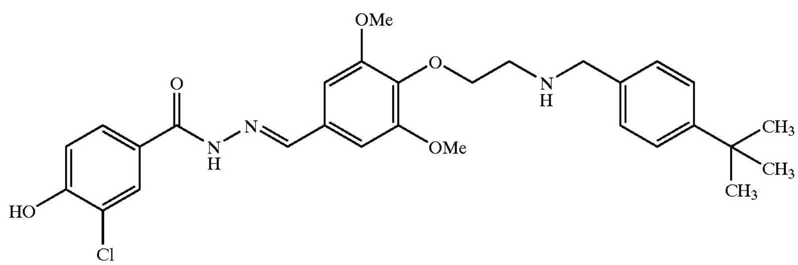 | 540 | 7.98 |
| 786 | 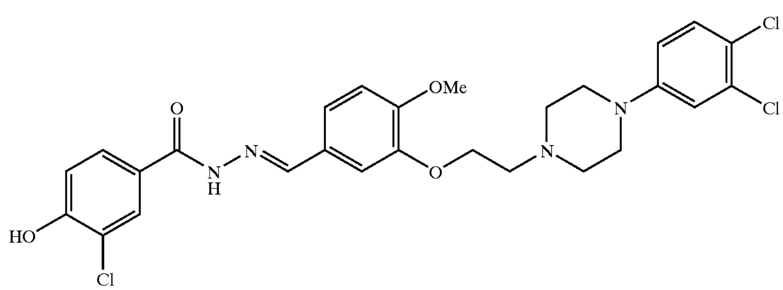 | 577 | 11.48 |
| 787 | 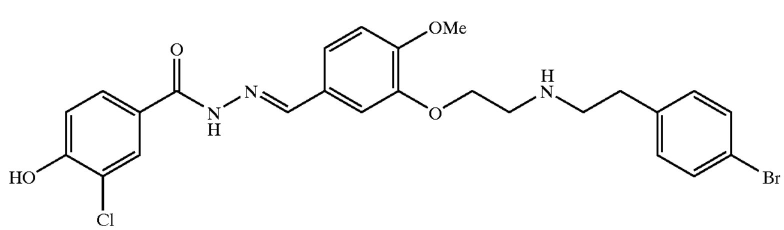 | 548 | 5.63 |
| 788 | 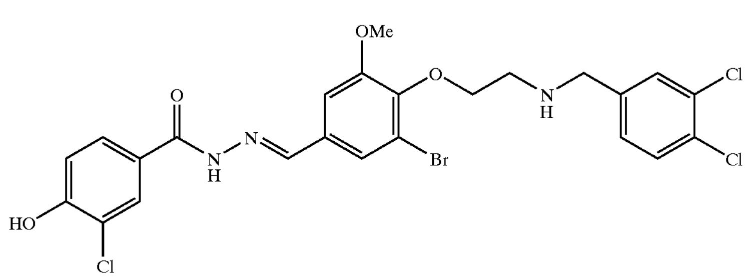 | 602 | 12.13 |

| Ex No. | Structure | HPLC-MS (METHOD B) m/z | HPLC-MS (METHOD B) $R_t$ (minutes) |
|---|---|---|---|
| 789 | 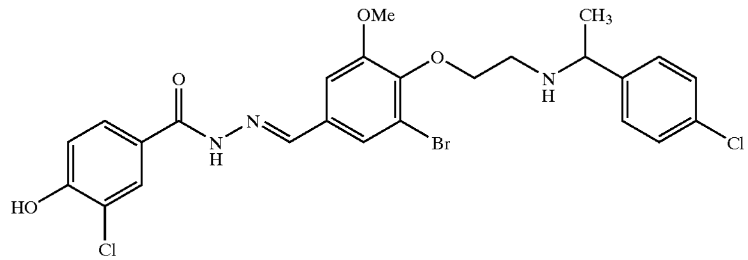 | 582 | 11.67 |
| 790 | 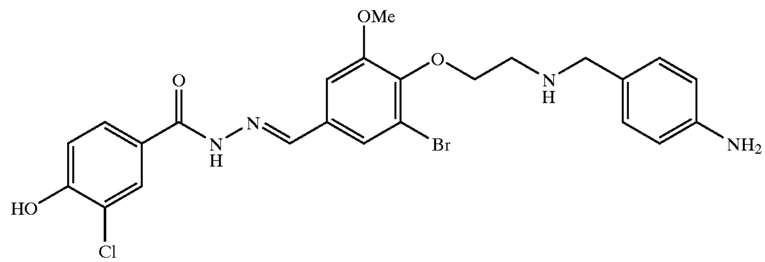 | 549 | 1.70 |
| 791 | 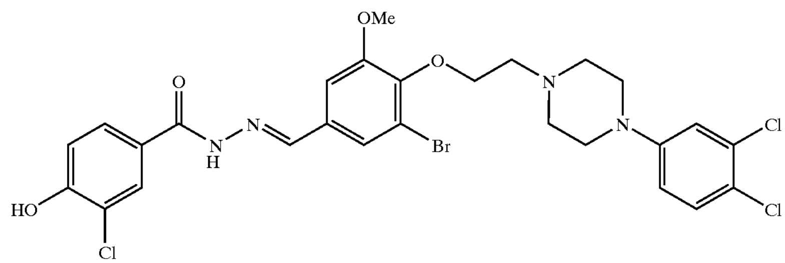 | 549 | 15.33 |

EXAMPLE 792

3-Amino-4-hydroxybenzoic Acid {4-[2-(1,2,3,4-Tetrahydro-isoquinolin-2-yl)ethoxy]-2-methoxybenzylidene}hydrazide

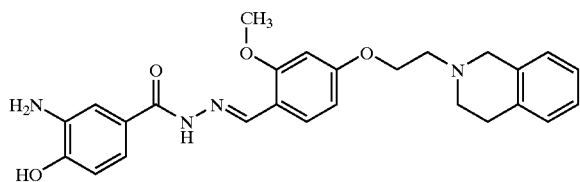

The above 4-(2-bromoethoxy)-2-methoxybenzaldehyde (16.8 g, 65 mmol) ([building block 2]) was dissolved in acetone (300 ml) and potassium carbonate (44.9 g, 0.33 mol), potassium iodide (2 g) were added followed by addition of 1,2,3,4-tetrahydroisoquinoline (9.07 g, 72 mmol). The resulting mixture was stirred vigorously at reflux temperature for 16 hours. After cooling, the mixture was filtered and the inorganic precipitate was washed with acetone (100 ml). The combined acetone filtrates were concentrated in vacuo. The residue was dissolved in ethyl acetate (50 ml) and washed with water (2×20 ml) saturated sodium chloride (20 ml), dried over MgSO$_4$ and concentrated in vacuo. The residue (23 g) was purified by column chromatography on silica gel (400 g) eluting first with a mixture of ethyl acetate and heptane (1:1, 2 liters) then with a mixture of ethyl acetate and heptane (2:1, 5 liters) to afford 12 9 (60%) of 4-[2-(1,2,3,4-tetrahydroisoquinolin-2-yl)ethoxyl-2-methoxybenzaldehyde as a solid.

M.p.: 69–71° C.

Calculated for C$_{19}$H$_{21}$NO$_3$.0.25H$_2$O: C, 72.24%; H, 6.86%; N, 4.43%. Found: C, 72.79%; H, 6.86%; N, 4.46%; C, 72.65%; H, 6.88%; N, 4.47%.

Methyl 3-amino-4-hydroxybenzoate (5.0 g, 30 mmol) was dissolved in ethanol (50 ml) and hydrazine hydrate (4.4 ml, 90 mmol) was added and the resulting mixture was heated at reflux temperature for 16 hours. After cooling the mixture was filtered and solid was washed with ethanol to afford after drying 1.4 g (28%) of 3-amino-4-hydroxybenzoic acid hydrazide as a solid. M.p.: 242–243° C.

Calculated for C$_7$H$_9$N$_3$O$_2$: C, 50.30%; H, 5.43%; N, 25.14%. Found: C, 50.27%; H, 5.46%; N, 24.35%; C, 50.41%; H, 5.47%; N, 24.38%.

The above 3-amino-4-hydroxybenzoic acid hydrazide (50 mg, 0.3 mmol) and the above 4-[2-(1,2,3,4-tetrahydroisoquinolin-2-yl)ethoxy]-2-methoxybenzaldehyde (93 mg, 0.3 mmol) were dissolved in 2-propanol (4 ml) and the mixture was heated at reflux temperature for 16 hours. The cooled mixture was filtered and the precipitate was washed with 2-propanol (2×4 ml) and dried by suction to afford 66 mg (48%) of the title compound as a solid. M.p.: 162–164° C.

HPLC-MS (METHOD B): R$_t$=6.50 minutes. m/z=461.

EXAMPLE 793

3-Amino-4-hydroxybenzoic Acid [4-(4-Isopropylbenzyloxy)-3,5-dimethoxybenzylidene]-hydrazide

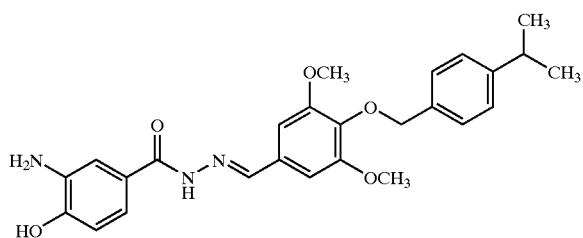

Syringaldehyde (4-hydroxy-3,5-dimethoxybenzaldehyde) (10.2 g, 55 mmol) was dissolved in DMF (45 ml), and 4-isopropylbenzylchloride (9.7 g, 55 mmol) and potassium carbonate (11.5 g) were added successively. The resulting mixture was heated at 60° C. for 16 hours. After cooling, the mixture was partitioned between water (150 ml) and ethyl acetate (3×100 ml). The combined organic extracts were washed with water (100 ml), saturated NaCl (100 ml), dried (MgSO$_4$), treated with activated carbon, filtered and concentrated in vacuo to afford 15 g (100%) of 4-(4-isopropylbenzyloxy)-3,5-dimethoxybenzaldehyde as an oil.

$^1$H-NMR (400 MHz, DMSO-d$_6$): δ$_H$=1.20 (9H, d), 2.89 (1H, h), 3.86 (6H, s), 4.98 (2H, s), 7.23 (2H, d), 7.27 (2H, s), 7.36 (2H, d).

The above 3-amino-4-hydroxybenzoic acid hydrazide (50 mg, 0.3 mmol) and the above 4-(4-isopropylbenzyloxy)-3,5-dimethoxybenzaldehyde(93 mg, 0.3 mmol) were dissolved in 2-propanol (4 ml) and the mixture was heated at reflux temperature for 16 hours. The cooled mixture was filtered and the precipitate was washed with 2-propanol (2×4 ml) and dried by suction to afford 144 mg (100%) of the title compound as a solid. M.p.: 174–175° C.

HPLC-MS (METHOD B): R$_t$=10.40 minutes. m/z=464.

EXAMPLE 794

(R)-2-{4-[(3-Amino-4-hydroxybenzoyl) hydrazonomethyl]-3-methoxyphenoxy}-N-(1-benzylpyrrolidin-3-yl)acetamide

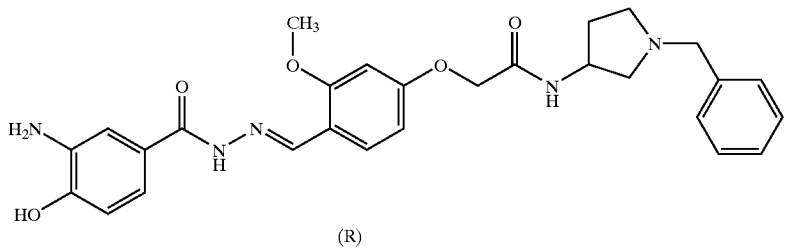

(R)-(−)-1-Benzyl-3-aminopyrrolidine (5 g, 28 mmol) was dissolved in dichloromethane (10 ml). To this solution, a solution of bromoacetyl chloride (4.55 g, 28 mmol) in dichloromethane (5 ml) was added at room temperature. The mixture was stirred at room temperature for 16 hours. The mixture was filtered, washed with dichloromethane and dried in vacuo to afford 6.8 g (72%) of (3R)-N-(1-benzylpyrrolidin-3-yl)-2-bromoacetamide hydrochloride as a solid which was used directly in the next step. 4-Hydroxy-2-methoxybenzaldehyde (2.05 g , 13 mmol) was dissolved in DMF (7 ml) and potassium carbonate (6.2 g, 45 mmol) was added followed by a suspension of the above (3R)-N-(1-Benzylpyrrolidin-3-yl)-2-bromoacetamide hydrochloride (3.0 g, 9 mmol) in DMF (16 ml). The resulting mixture was stirred at room temperature for 16 hours. The mixture was then partitioned between water (100 ml) and ethyl acetate (30 ml). The aqueous phase was extracted with ethyl acetate (2×20 ml) and the combined organic extracts were washed with saturated sodium chloride (3×15 ml), dried (MgSO$_4$) and concentrated in vacuo. The residue was crystallized from diethyl ether to afford 2.11 g (64%) (R)-N-(1-benzylpyrrolidin-3-yl)-2-(4-formyl-3-methoxyphenoxy) acetamide as a solid. M.p.: 98–101° C.

Calculated for C$_{21}$H$_{24}$N$_2$O$_4$.0.5H$_2$O: C, 66.83%; H, 6.68%; N, 7.42%. Found: C, 67.15%; H, 6.57%; N, 7.75%; C, 66.96%; H, 6.57%; N, 7.77%.

The above 3-amino-4-hydroxybenzoic acid hydrazide (50 mg, 0.3 mmol) and the above (R)-N-(1-benzylpyrrolidin-3-yl)-2-(4-formyl-3-methoxyphenoxy)acetamide (110 mg, 0.3 mmol) were dissolved in 2-propanol (4 ml) and the mixture was heated at reflux temperature for 16 hours. The cooled mixture was filtered and the precipitate was washed with 2-propanol (2×3 ml) and dried by suction to afford 109 mg (70%) of the title compound as a solid. M.p.: 157–160° C.

HPLC-MS (METHOD B): R$_t$=3.10 minutes. m/z=518.

EXAMPLE 795

(R)-2-{4-[(3-Amino-4-hydroxybenzoyl)hydrazonomethyl]naphthyl-1-yloxy}-N-(1-benzylpyrrolidin-3-yl)acetamide

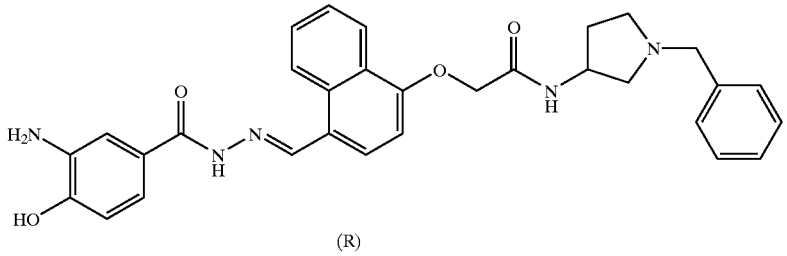

(R)

4-Hydroxy-1-naphthaldehyde (2.32 g, 13 mmol) was dissolved in DMF (7 ml) and potassium carbonate (6.2 g, 45 mmol) was added followed by a suspension of the above (3R)-N-(1-Benzylpyrrolidin-3-yl)-2-bromoacetamide hydrochloride (3.0 g, 9 mmol) in DMF (16 ml). The resulting mixture was stirred at room temperature for 16 hours. The mixture was then partitioned between water (100 ml) and ethyl acetate (30 ml). The aqueous phase was extracted with ethyl acetate (2×20 ml) and the combined organic extracts were washed with saturated sodium chloride (3×15 ml), dried (MgSO$_4$) and concentrated in vacuo. The residue was purified by column chromatography on silica gel (110 g) eluting with ethyl acetate to afford 1.7 g (49%) (R)-N-(1-benzylpyrrolidin-3-yl)-2-(4-formylnaphthyl-1-yloxy)acetamide as a solid. M.p.: 105–107° C.

Calculated for C$_{24}$H$_{24}$N$_2$O$_3$.0.25H$_2$O: C, 73.36%; H, 6.28%; N, 7.13%. Found: C, 73.81%; H. 6.22%; N, 7.11%; C, 73.92%; H, 6.23%; N, 7.11%.

The above 3-amino-4-hydroxybenzoic acid hydrazide (50 mg, 0.3 mmol) and the above (R)-N-(1-benzylpyrrolidin-3-yl)-2-(4-formylnaphthyl-1-yloxy)acetamide (116 mg, 0.3 mmol) were dissolved in 2-propanol (4 ml) and the mixture was heated at reflux temperature for 16 hours. The cooled mixture was filtered and the precipitate was washed with 2-propanol (6×2 ml) and dried by suction to afford 140 mg (87%) of the title compound as a solid. M.p.: 187–192° C.

HPLC-MS (METHOD B): R$_t$=5.72 minutes. m/z=538.

EXAMPLE 796

(S)-2-{4-[(3-Amino-4-hydroxybenzoyl)hydrazonomethyl]-3-methoxyphenoxy}-N-(1-benzylpyrrolidin-3-yl)acetamide

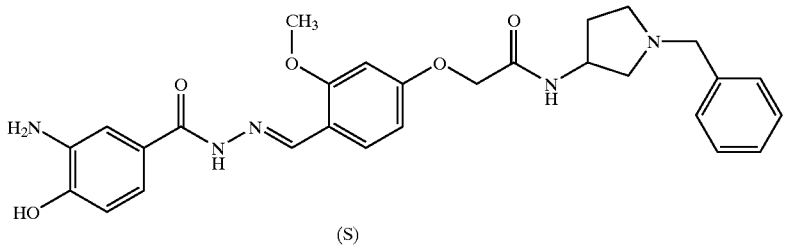

(S)

(S)-(+)-1-Benzyl-3-aminopyrrolidine (6 g, 34 mmol) was dissolved in dichloromethane (12 ml). To this solution, a solution of bromoacetyl chloride (5.46 g, 34 mmol) in dichloromethane (5 ml) was added at room temperature. The mixture was stirred at room temperature for 16 hours. The mixture was filtered, washed with dichloromethane and dried in vacuo to afford 7.3 g (64%) of (3S)-N-(1-benzylpyrrolidin-3-yl)-2-bromoacetamide hydrochloride as a solid which was used directly in the next step. 4-Hydroxy-2-methoxybenzaldehyde (2.39 g, 16 mmol) was dissolved in DMF (10 ml) and potassium carbonate (7.3 g, 52 mmol) was added followed by a suspension of the above (3S)-N-(1-benzylpyrrolidin-3-yl)-2-bromoacetamide hydrochloride (3.5 g, 10 mmol) in DMF (20 ml). The resulting mixture was stirred at room temperature for 16 hours. The mixture was then partitioned between water (100 ml) and ethyl acetate (30 ml). The aqueous phase was extracted with ethyl acetate (2×20 ml) and the combined organic extracts were washed with saturated sodium chloride (3×15 ml), dried (MgSO$_4$) and concentrated in vacuo. The residue (4 g) was crystallised from a mixture of diethyl ether and heptane, filtered and dried in vacuo to afford 2.7 g (71%) (S)-N-(1-benzylpyrrolidin-3-yl)-2-(4-formyl-3-methoxyphenoxy)-acetamide as a solid. M.p.: 96–100° C.

Calculated for C$_{21}$H$_{24}$N$_2$O$_4$.0.25H$_2$O: C, 67.63%; H, 6.62%; N, 7.51%. Found: C, 67.35%; H, 6.61%; N, 7.85%; C, 67.24%; H, 6.59%; N, 7.82%.

The above 3-amino-4-hydroxybenzoic acid hydrazide (50 mg, 0.3 mmol) and the above (S)-N-(1-benzylpyrrolidin-3-yl)-2-(4-formyl-3-methoxyphenoxy)acetamide (110 mg, 0.3 mmol) were dissolved in 2-propanol (4 ml) and the mixture was heated at reflux temperature for 16 hours. The cooled mixture was filtered and the precipitate was washed with 2-propanol (6×2 ml) and dried by suction to afford 109 mg (70%) of the title compound as a solid. M.p.: 139–141° C.

HPLC-MS (METHOD B): R$_t$=3.15 minutes. m/z=518.

EXAMPLE 797

(S)-2-{4-[(3-Amino-4-hydroxybenzoyl)hydrazonomethyl]naphthyl-1-yloxy}-N-(1-benzylpyrrolidin-3-yl)acetamide

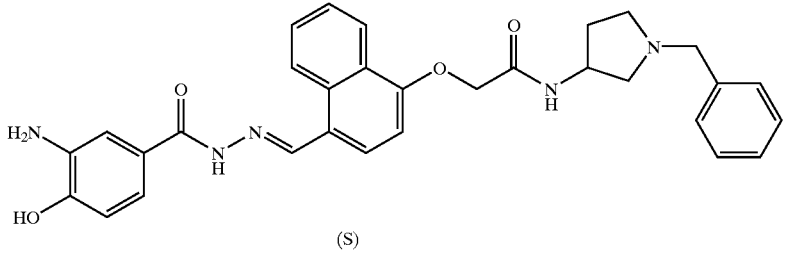

(S)

4-Hydroxy-1-naphthaldehyde (2.71 g, 16 mmol) was dissolved in DMF (10 ml) and potassium carbonate (7.25 g, 52 mmol) was added followed by a suspension of the above (3S)-N-(1-benzylpyrrolidin-3-yl)-2-bromoacetamide hydrochloride (3.0 g, 10 mmol) in DMF (20 ml). The resulting mixture was stirred at room temperature for 16 hours. The mixture was then partitioned between water (100 ml) and ethyl acetate (30 ml). The aqueous phase was extracted with ethyl acetate (2×20 ml) and the combined organic extracts were washed with saturated sodium chloride (3×15 ml), dried (MgSO$_4$) and concentrated in vacuo. The residue (4 g) was purified by column chromatography on silica gel (110 g) eluting with ethyl acetate to give an oil (2 g), which was crystallized from a mixture of diethyl ether and heptane to afford 1.8 g (45%) (S)-N-(1-benzylpyrrolidin-3-yl)-2-(4-formylnaphthyl-1-yloxy)-acetamide as a solid. M.p.: 96–97° C.

Calculated for $C_{24}H_{24}N_2O_3 \cdot 0.25H_2O$: C, 73.36%; H, 6.28%; N, 7.13%. Found: C, 73.58%; H, 6.28%; N, 7.05%; C, 73.55%; H, 6.27%; N, 7.03%.

The above 3-amino-4-hydroxybenzoic acid hydrazide (50 mg, 0.3 mmol) and the above (S)-N-(1-benzylpyrrolidin-3-yl)-2-(4-formylnaphthyl-1-yloxy)acetamide (116 mg, 0.3 mmol) were dissolved in 2-propanol (4 ml) and the mixture was heated at reflux temperature for 16 hours. The cooled mixture was filtered and the precipitate was washed with 2-propanol (3×3 ml) and dried by suction to afford 143 mg (89%) of the title compound as a solid. M.p.: 192–193° C.

HPLC-MS (METHOD B): Rt=5.18 minutes. m/z=538.

EXAMPLE 798

(S)-2-{4-[(3-Fluoro-4-hydroxybenzoyl)hydrazonomethyl]naphthyl-1-yloxy}-N-(1-benzylpyrrolidin-3-yl)acetamide

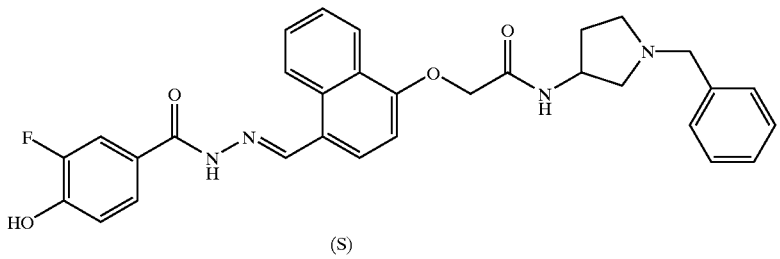

(S)

This compound was prepared on solid phase using resin bound 3-fluoro-4-hydroxybenzoic acid hydrazide, prepared similarly as described above for the resin bound 3-chloro-4-hydroxybenzoic acid hydrazide. Thus, methyl 3-fluoro-4-hydroxybenzoate was attached to the resin. Hydrolysis of the methyl ester (aq. LiOH, dioxane, 60° C.) followed by reaction with hydrazine (PyBOP, hydrazine, DMF) afforded resin bound 3-fluoro-4-hydroxybenzoic acid hydrazide.

The resin bound 3-fluoro-4-hydroxybenzoic acid hydrazide (1 g, 0.94 mmol) was swelled in DMF (10 ml) for 30 minutes and filtered. This was repeated once more. DMF (4 ml) and the above (S)-N-(1-benzylpyrrolidin-3-yl)-2-(4-formylnaphthyl-1-yloxy)acetamide (0.4 g, 0.94 mmol) were added followed by triethyl orthoformate (1.5 ml) and the resulting mixture was shaken at room temperature for 16 hours. The mixture was filtered and the resin was successively washed with DMF (5×4 ml) and dichloromethane (5×4 ml). The compound was cleaved off the resin by addition of 50% TFA in dichloromethane (6 ml) and shaking at room temperature for 1 hour. Filtration followed by extraction of the resin with a mixture of methanol and dichloromethane (4:6) (2×4 ml) followed by extraction with dichloromethane (4 ml). The combined filtrates were concentrated in vacuo, stripped successively with wet methanol, dichloromethane, methanol and dichloromethane. The residue (0.39 g) was purified by column chromatography on silica gel (40 g) eluting first with a mixture of dichloromethane, ethanol and 25% aq. ammonia (90:9:1), then with (85:13.5:1.5) and finally with (80:18:2). Pure fractions were pooled and concentrated in vacuo to afford 0.15 g of the title compound.

HPLC-MS (METHOD B): $R_t$=8.82 minutes. m/z=541. Calculated for $C_{31}H_{29}N_4O_4F \cdot 0.25CH_2Cl_2$: C, 66.81%; H, 5.29%; N, 9.97%. Found: C, 67.30%; H, 5.48%; N, 10.03%; C, 67.33%; H, 5.49%; N, 10.02%.

EXAMPLE 799

(R)-2-{4-[(3-Fluoro-4-hydroxybenzoyl)hydrazonomethyl]naphthyl-1-yloxy}-N-(1-benzylpyrrolidin-3-yl)acetamide

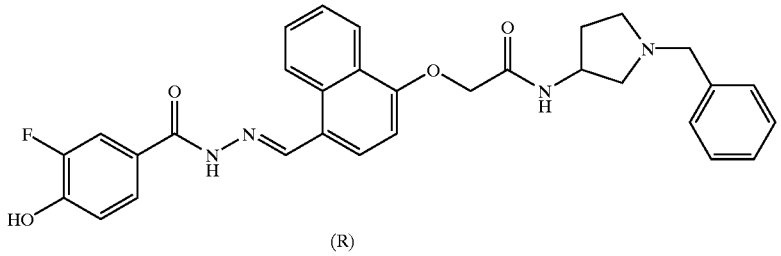

(R)

This compound was prepared similarly as described in the previous example starting from resin bound 3-fluoro-4-hydroxybenzoic acid hydrazide (1 g, 0.94 mmol) and the above (R)-N-(1-benzylpyrrolidin-3-yl)-2-(4-formylnaphthyl-1-yloxy)acetamide (0.4 g, 0.94 mmol). After cleavage the compound was purified by column chromatography to afford 0.14 g of the title compound.

HPLC-MS (METHOD B): $R_t$=9.02 minutes. m/z=541. Calculated for $C_{31}H_{29}N_4O_4F.0.25CH_2Cl_2$: C, 66.81%; H, 5.29%; N, 9.97%. Found: C, 66.77%; H, 5.46%; N, 10.02%; C, 67.14%; H, 5.42%; N, 9.97%.

EXAMPLE 800

(S)-2-{4-[(3-Fluoro-4-hydroxybenzoyl)hydrazonomethyl]-3-methoxyphenoxy)-(1-benzylpyrrolidin-3-yl)acetamide

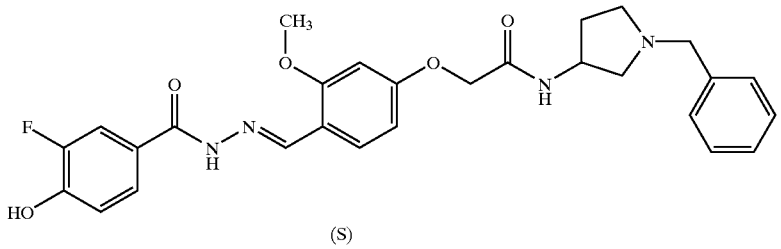

(S)

This compound was prepared similarly as described in the previous example starting from resin bound 3-fluoro-4-hydroxybenzoic acid hydrazide (1 g, 0.94 mmol) and the above (S)-N-(1-benzylpyrrolidin-3-yl)-2-(4-formyl-3-methoxyphenoxy)acetamide (0.4 g, 0.94 mmol). After cleavage the compound was purified by column chromatography to afford 0.13 g of the title compound.

HPLC-MS (METHOD B): $R_t$=3.68 minutes. m/z=521. Calculated for $C_{28}H_{29}N_4O_5F.0.25CH_2Cl_2$: C, 62.63%; H, 5.49%; N, 10.34%. Found: C, 62.92%; H, 5.83%; N, 10.15%; C, 62.71%; H, 5.81%; N, 10.16%.

EXAMPLE 801

(R)-2-{4-f(3-Fluoro-4-hydroxybenzoyl)-hydrazonomethyl]-3-methoxyphenoxyl-N-(1-benzylpyrrolidin-3-yl)acetamide

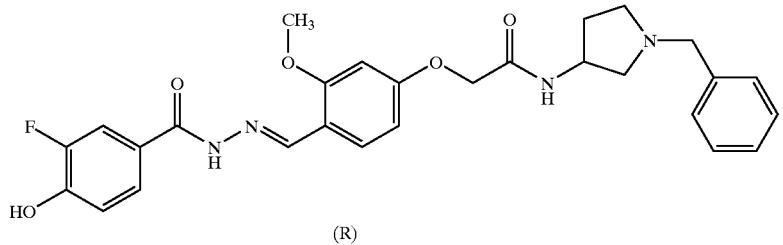

(R)

This compound was prepared similarly as described in the previous example starting from resin bound 3-fluoro-4- hydroxybenzoic acid hydrazide (1 g, 0.94 mmol) and the above (R)-N-(1-benzylpyrrolidin-3-yl)-2-(4-formyl-3-methoxyphenoxy)acetamide (0.4 g, 0.94 mmol). After cleavage the compound was purified by column chromatography to afford 0.16 g of the title compound.

HPLC-MS (METHOD B): $R_t$=4.18 minutes. m/z=521. Calculated for $C_{28}H29N_4O_5F\cdot0.25CH_2Cl_2$: C, 62.63%; H, 5.49%; N, 10.34%. Found: C, 62.65%; H, 5.73%; N, 10.31%; C, 62.84%; H, 5.81%; N, 10.30%.

EXAMPLE 802

3-Fluoro-4-hydroxybenzoic Acid {4-[2-(1,2,3,4-Tetrahydro-isoquinolin-2-yl)ethoxy]-2-methoxybenzylidene}hydrazide

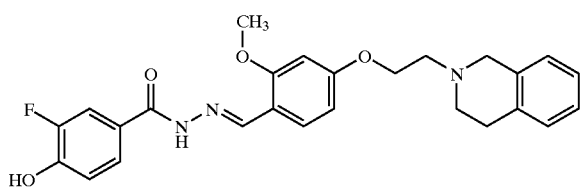

This compound was prepared similarly as described in the previous example starting from resin bound 3-fluoro-4-hydroxybenzoic acid hydrazide (1 g, 0.94 mmol) and the above 4-[2-(1,2,3,4-tetrahydroisoquinolin-2-yl)ethoxy]-2-methoxybenzaldehyde (0.4 g, 0.94 mmol). After cleavage the compound was purified by column chromatography to afford 0.13 g of the title compound.

HPLC-MS (METHOD B): $R_t$=7.60 minutes. m/z=464. Calculated for $C_{26}H_{26}N_3O_4F\cdot0.5CH_2Cl_2$: C, 62.91%; H, 5.38%; N, 8.30%. Found: C, 62.68%; H, 5.47%; N, 8.02%; C, 62.48%; H, 5.43%; N, 8.01%.

The HPLC-MS (METHOD A) analyses were performed on a PE Sciex API 100 LC/MS System using a Waters™ 3 mm×150 mm 3.5μ C-18 Symmetry column and positive ionspray with a flow rate of 20 μL/minute. The column was eluted with a linear gradient of 5–90% A, 85–0% B and 10% C in 15 minutes at a flow rate of 1 ml/min (solvent A=acetonitrile, solvent B=water and solvent C=0.1% trifluoroacetic acid in water).

The HPLC-MS (METHOD B) analyses were performed on a system identical to the one described above, the only difference being the eluent. The column was eluted with a linear gradient of 30–80% A, 60–10% B and 10% D in 15 minutes at a flow rate of 1 ml/min (solvent A=acetonitrile, solvent B=water and solvent D=20 mM ammonium acetate in water, pH 7).

EXAMPLE 803

3-Chloro-4-hydroxy-benzoic Acid {4-[2-(1,2,3,4-Tetrahydro-isoquinolin-2-yl)-ethoxy]-8-methoxy-naphthalen-1-ylmethylene}-hydrazide

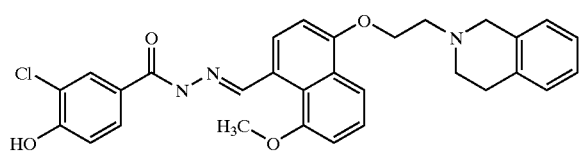

4-hydroxy-8-methoxynaphthalene-1-carbaldehyde (1 g, 5 mmol) was dissolved in DMF (15 mL). To this mixture potassium carbonate (3.4 g, 25 mmol) and 1,2-dibromoethane (4 mL, 50 mmol) were added and the resulting mixture was stirred at room temperature for 16 hours. Water (150 mL) was added and the resulting mixture was extracted with ethyl acetate (3×90 mL). The combined organic extracts were washed with saturated sodium chloride (100 mL), dried (MgSO$_4$) and evaporated in vacuo to afford 1.13 g (74%) of 4-(2-bromoethoxy)-8-methoxynaphthalene-1-carbaldehyde.

HPLC-MS (Method A): $R_t$=14.1 minutes. m/z=309. $^1$H-NMR (300 MHz, DMSO-d$_6$): $\delta_H$=3.99 (3H, s), 7.00 (1H, d), 7.20 (1H, d), 7.47 (1H, t), 7.88 (2H, m), 10.9 (1H, s).

The above resin bound 3-chloro-4-hydroxybenzoic acid hydrazide (2 g, 1.8 mmol) was swelled in DMF (25 mL) for 30 minutes and the above 4-(2-bromoethoxy)-8-methoxynaphthalene-1-carbaldehyde (1.7 g, 5.4 mmol) was added followed by triethyl orthoformate (1.2 mL) and the resulting mixture was shaken at room temperature for 16 hours. The mixture was filtered and the resin was successively washed with DMF (3×25 mL), dichloromethane (4×25 mL) and N-methyl pyrrolidin-2-one (NMP) (2×25 mL). NMP (25 mL) was added followed by potassium iodide (0.6 g) and 1,2,3,4-tetrahydro-isoquinoline (2.25 mL, 18 mmol) and the resulting mixture was shaken at room temperature for 16 hours. The mixture was filtered and the resin was successively washed with NMP (2×25 mL) and dichloromethane (6×25 mL). The compound was cleaved off the resin by addition of 50% TFA in dichloromethane (30 mL) and shaking at room temperature for 1 hour. After filtration followed by extraction of the resin with dichloromethane (2×30 mL) the combined filtrates were concentrated in vacuo. The residue was partitioned between ethyl acetate (80 mL) and saturated sodium hydrogen carbonate (100 mL). The aqueous phase was extracted with ethyl acetate (2×80 mL) and the combined organic extracts were dried (MgSO$_4$) and concentrated in vacuo. The residue was purified by column chromatography on silica gel (200 mL) eluting with a mixture of dichloromethane and methanol (9:1). This afforded 217 mg of the title compound.

HPLC-MS (Method A): $R_t$=9.14 minutes. m/z=530.

General Procedure for Examples 804 to 824

The compounds were prepared as single entities according to the following equation Resin—[Building block 1]→

Resin—[Building block 1]—[Building block 2]→

Resin—[Building block 1]—[Building block 2]—
[Building block 3]

and were simultaneously deprotected (when required) and cleaved from the resin with 50% trifluoroacetic acid in dichloromethane to give the desired compounds as individual entities according to the following formula

[Building block 1]—[Building block 2]—[Building block 3].

The following compounds were prepared as single entities by parallel synthesis on a solid support. Preparation of Resin—[Building block 1] and attachment of [Building block 2] was done manually, whereas the attachment of [Building block 3] and cleavage from the resin were performed on an Advanced ChemTech Model 496 HTS in several runs.

The starting resin, Resin—[Building block 1], was prepared as described above.

The resin used was a polystyrene resin with a Wang linker and the substitution capacity was 0.9 mmol/g.

All compounds are based on successive attachment of [Building block 2] and [Building block 3] to Resin—[Building block 1] in a combinatorial way according to the following formulae, which are included in the general formula II:

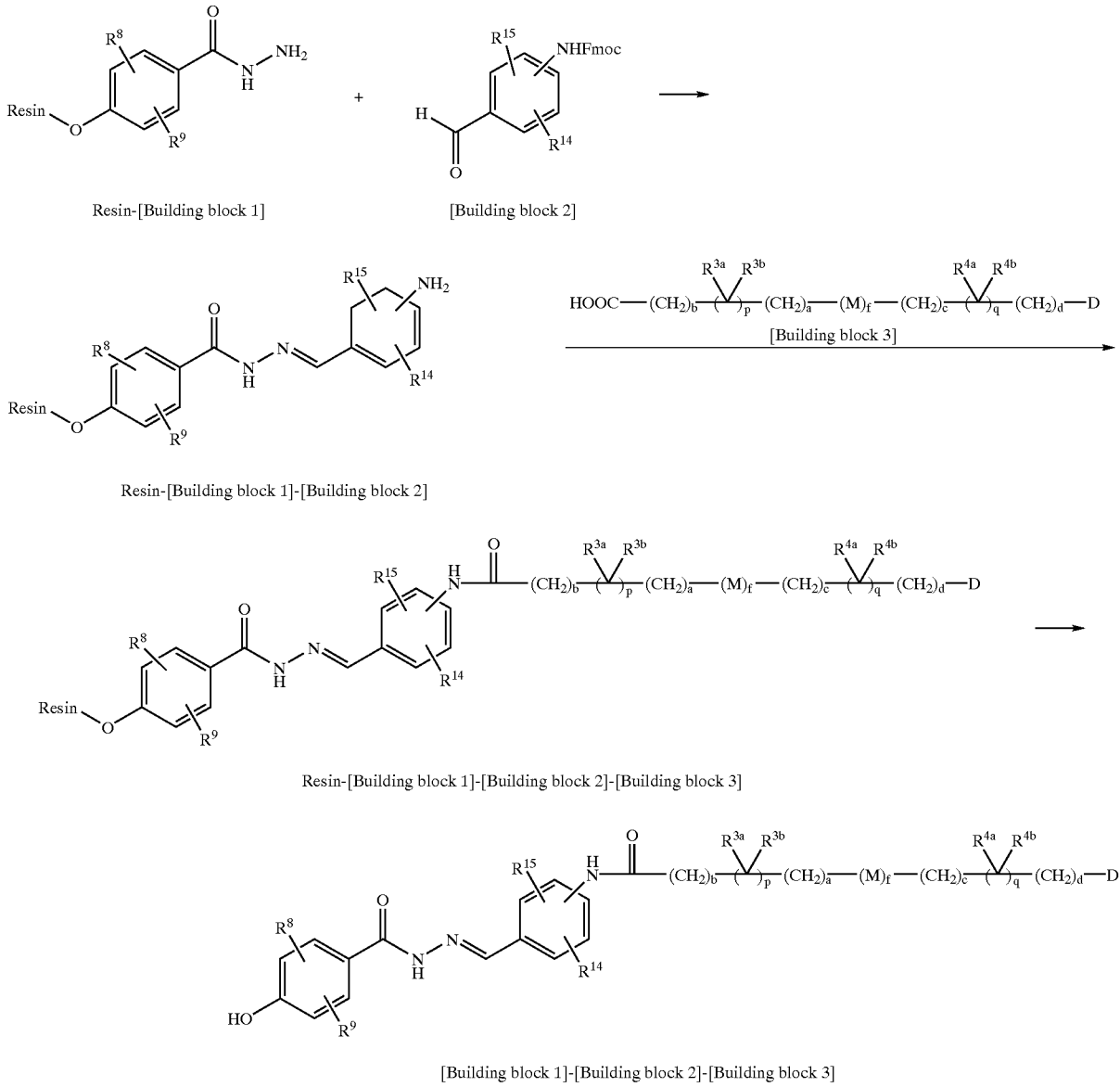

Resin-[Building block 1]    [Building block 2]

Resin-[Building block 1]-[Building block 2]

Resin-[Building block 1]-[Building block 2]-[Building block 3]

[Building block 1]-[Building block 2]-[Building block 3]

wherein $R^8$, $R^9$, $R^{14}$, $R^{15}$ and

are as defined for formula I.

The following resin, here depicted as Resin—[Building block 1] was used:

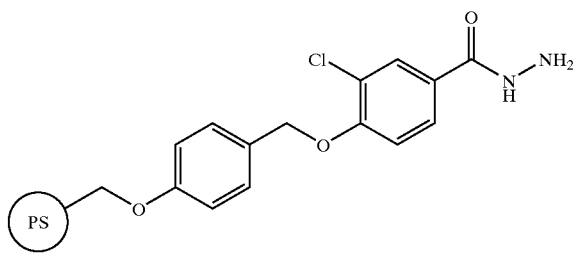

where PS is polystyrene. In the following "Resin" is the polystyrene resin with the Wang linker:

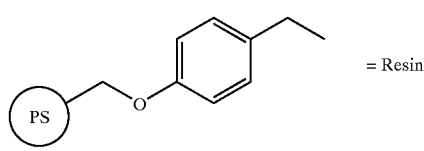 = Resin

The following building blocks were used:

| Building block 2 | |
|---|---|
| (4-Formyl-3-methoxyphenyl)carbamic acid 9H-fluoren-9-ylmethyl ester: | (4-Formyl-2-methoxyphenyl)carbamic acid 9H-fluoren-9-ylmethyl ester |

-continued

| Building block 2 | |
|---|---|
| 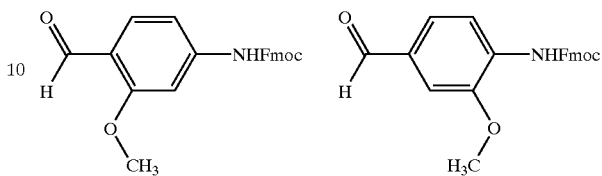 | |
| 3-(tert-Butyldimethylsilanyloxy)-4-formylphenyl)carbamic acid 9H-fluoren-9-ylmethyl ester: | (5-Formyl-2-methoxyphenyl)carbamic acid 9H-fluoren-9-ylmethyl ester: |
| 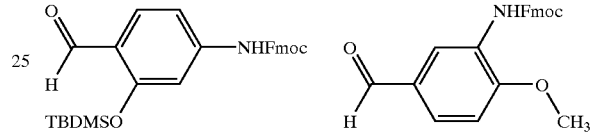 | |

| Building block 3 | | |
|---|---|---|
| 4-Methoxy-2-quinolinecarboxylic acid | N-Methylpyrrole-2-carboxylic acid | Succinylsulfathiazole |
| 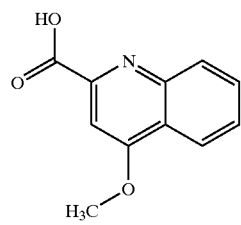 | 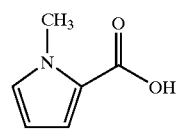 | 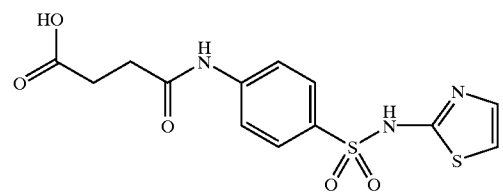 |
| 7-Ethoxybenzofuran-2-carboxylic acid | 4-Toluenesulfonylacetic acid | 3-(2-Thienoyl)propionic acid |
| 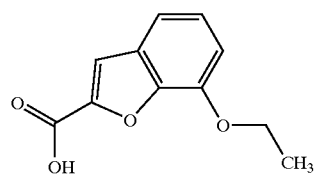 | 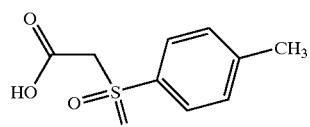 | 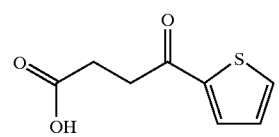 |
| Boc-Hyp-OH | N-fmoc-O-t-butyl-L-serine | Fmoc-His(Boc)-OH |

Building block 3

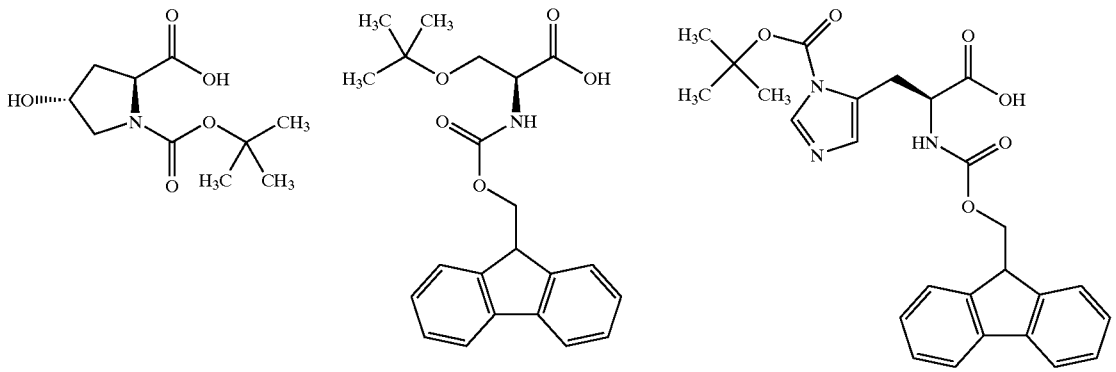

Preparation of Resin—[Building Block 1]

This resin was prepared as described above.

Preparation of [Building Block 2]

(4-Formyl-3-methoxyphenyl)carbamic Acid 9H-Fluoren-9-ylmethyl Ester:

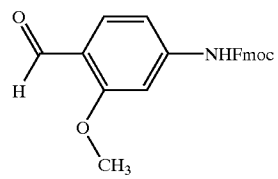

Methyl 4-amino-2-methoxybenzoate (14.7 g, 7.3 mmol) and Fmoc-Osu (26.1 g, 77.3 mmol) were stirred in a mixture of acetonitrile and water (1:1, 320 mL) at reflux for 16 hr. The reaction mixture was concentrated to half the volume and the precipitate isolated by filtration. The isolated solid was dissolved in ethyl acetate (300 mL) and washed with 0.4 N hydrochloric acid (200 mL), 0.2 N hydrochloric acid (200 mL), water (200 mL) and a 20% saturated solution of sodium chloride (200 mL). After drying (magnesium sulphate) the organic phase was concentrated in vacuo and the solid residue was washed with methanol and dried.

The crude product (12 g) was dissolved in dichloromethane (1 L) under nitrogen and a solution of diisobutylaluminium hydride (90 mL, 1.2 M in toluene) was dropwise added at 0–5° C. The reaction mixture was stirred at 20° C. for 16 hr and quenched by dropwise addition of water (58 mL) at 0–5° C. The reaction mixture was stirred at 20° C. for 3 hr and filtered. The filtrate was concentrated in vacuo. The crude product (6.8 g) was suspended in dichloromethane (400 mL) and manganese dioxide (15.6 g, 180 mmol) was added. The mixture was stirred for 16 hr at 20° C. and filtered. The filtrate was concentrated in vacuo to give 5.1 g of the title compound.

m.p. 187–188° C. HPLC-MS (METHOD A): $R_t$=15.1 min, m/z=374. Micro analysis: calculated: C, 73.98; H, 5.13; N, 3.75% found: C, 73.44; H, 5.20; N, 3.56%

(4-Formyl-2-methoxyphenyl)carbamic Acid 9H-Fluoren-9-ylmethyl Ester:

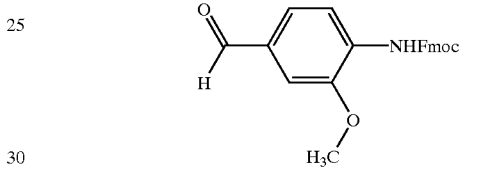

Thionylchloride (12.8 g, 108 mmol) was dropwise added to an ice cold suspension of 4-amino-3-methoxybenzoic acid (12.3 g, 72 mmol) in methanol (250 mL). The reaction mixture was stirred at 20° C. for 16 hr and concentrated in vacuo. Ethyl acetate (250 mL) and a saturated solution of sodium hydrogen carbonate (150 mL) were added and the organic phase was washed with saturated solutions of sodium hydrogen carbonate (2×50 mL), dried (magnesium sulphate) and concentrated in vacuo. The crude product (12.5 g) and Fmoc-Osu (28 g, 83 mmol) was stirred in a mixture of acetonitrile and water (1:1, 240 mL) at 90° C. for 16 hr. The reaction mixture was concentrated to half the volume. Ethyl acetate (200 mL) was added together with 0.4N hydrochloric acid (150 mL). The organic phase was washed with 0.2N hydrochloric acid (100 mL), water (100 mL) and a saturated solution of sodium chloride (2×100 mL). After drying (magnesium sulphate) the organic phase was concentrated in vacuo, and the residue was crystallized from methanol and dried.

m.p. 96–98° C. HPLC (Method 1) $R_t$=32.4 min, Micro analysis: calculated: C, 71.45; H, 5.25; N, 3.47%; found: C, 71.32; H, 5.24; N, 3.41%.

The product (12 g, 29.7 mmol)) was dissolved in dichloromethane (800 mL) under nitrogen and a solution of diisobutylaluminium hydride (90 mL, 1.2M in toluene) was dropwise added at 0–5° C. The reaction mixture was stirred at 20° C. for 16 hr and quenched by dropwise addition of water (58 mL) at 0–5° C. The reaction mixture was stirred at 20° C. for 3 hr and filtered. The filtrate was concentrated in vacuo to give 5.5 g of product (m.p. 169–171° C.). The product (5.5 g) was suspended in dichloromethane (325 mL) and manganese dioxide (12.8 g, 148 mmol) was added. The mixture was stirred for 16 hr at 20° C. and filtered. The filtrate was concentrated in vacuo to give 3.5 g of the title compound. Recrystallization from ethyl acetate.

m.p. 150–152° C. HPLC (Method 1) $R_6$=30.6 min; Micro analysis: calculated: C, 73.98; H, 5.13; N, 3.75%; found: C, 73.54; H, 5.18; N, 3.65%.

3-(tert-Butyldimethylsilanyloxy)-4-formylphenyl)carbamic Acid 9H-fluoren-9-ylmethyl Ester:

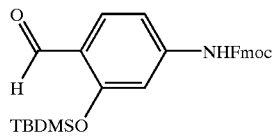

4-(9H-Fluoren-9-ylmethoxycarbonylamino)-2-hydroxybenzoic Acid Methyl Ester:

Thionylchloride (19.4 g, 163 mmol) was dropwise added to an ice cold solution of 4-amino salicylic acid (10.0 g, 65.3 mmol) in methanol (200 mL). The reaction mixture was hereafter heated to 65° C. for 6 days. The reaction mixture was concentrated in vacuo and the crude product was dissolved in a mixture of acetonitrile and water (1:1, 220 mL). Fmoc-Osu (22.0 g, 65.3 mmol) was added and the reaction mixture was stirred at 90° C. for 16 hr. The reaction mixture was concentrated to 100 mL in vacuo, and water (50 mL) and ethyl acetate (250 mL) added. The organic phase was isolated and washed with water (2×50 mL), a saturated solution of sodium chloride (2×50 mL), dried (magnesium sulphate) and concentrated in vacuo.

The residue was purified on silica (300 g) using ethyl acetate and n-heptane (1:2) as eluent. The product was recrystallized from methanol to give 4-(9H-fluoren-9-ylmethoxycarbonylamino)-2-hydroxybenzoic acid methyl ester.

m.p.156–9° C. HPLC (Method 1) $R_t$=31.7 min; Micro analysis: calculated: C, 70.94; H, 4.92; N, 3.60%; found: C, 70.73; H, 4.98; N, 3.37%.

4-(9H-Fluoren-9-ylmethoxycarbonylamino)-2-hydroxybenzoic acid methyl ester (4.36 g, 11.2 mmol) was dissolved in dimethylformamide (20 mL) and imidazole (1.92 g, 28 mmol) was added. tert-Butyldimethylsilylchloride (2.09 g, 13.4 mmol) dissolved in dimethylformamide (10 mL) was dropwise added and the reaction mixture was stirred at 20° C. for 16 hr. The reaction mixture was poured into water (160 mL) and extracted with ethyl acetate (4×50 mL). The collected organic phases were washed with a saturated solution of sodium chloride (4×50 mL), dried (magnesium sulphate) and concentrated in vacuo. The residue was purified on silica (150 g) using ethyl acetate and n-heptane (15:85) as eluent. The isolated product (3.10 g, 6.15 mmol) was dissolved in dichloromethane (200 mL) under nitrogen. A solution of diisobutylaluminiumhydride (18.5 mL, 1.2M in toluene) was dropwise added 0–5° C. The mixture was stirred at 20° C. for 3.5 hr, and quenched by dropwise addition of water at 0–5° C. After 2.5 hr at 20° C. the mixture was filtered and the filtrate was concentrated in vacuo. The residue was purified on silica using ethyl acetate and n-heptane (1:3) as eluent. The isolated product (2.40 g) was dissolved in dichloromethane (120 mL) and manganese dioxide (4.39 g, 50.5 mmol) was added. The reaction mixture was stirred at 0° C. for 16 hr and filtered. The filtrate was concentrated in vacuo and the residue purified on silica using ethyl acetate and n-heptane (15:85) as eluent to give 1.0 g of the title compound.

HPLC (Method 1) $R_t$=30.7 min and 36.8 min.

(5-Formyl-2-methoxyphenyl)carbamic Acid 9H-Fluoren-9-ylmethyl Ester:

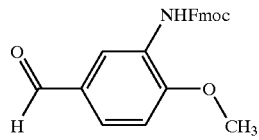

Thionylchloride (10.3 g, 85 mmol) was dropwise added to an ice cold suspension of 3-amino-4-methoxybenzoic acid (9.48 g, 56.7 mmol) in methanol (180 mL). The reaction mixture was stirred at 20° C. for 16 hr and concentrated in vacuo. Ethyl acetate (100 mL) and a saturated solution of sodium hydrogen carbonate (100 mL) were added and the organic phase was washed with saturated solutions of sodium hydrogen carbonate (2×40 mL), dried (magnesium sulphate) and concentrated in vacuo. The crude product (7.7 g) and Fmoc-Osu (12.9 g, 38.2 mmol) were stirred in a mixture of acetonitrile and water (1:1, 75 mL) at 20° C. for 16 hr, and at reflux for 3.5 hr. The reaction mixture was concentrated to half the volume and the precipitate isolated by filtering the mixture to give 15 g of intermediate crude product.

The product (5 g, 12 mmol) was dissolved in dichloromethane (400 mL) under nitrogen and a solution of diisobutylaluminium hydride (38 mL, 1.2M in toluene) was dropwise added at 0–5° C. The reaction mixture was stirred at 20° C. for 16 hr and quenched by dropwise addition of water (23 mL) at 0–5° C. The reaction mixture was stirred at 20° C. for 1.5 hr and filtered. The filtrate was concentrated in vacuo to give 4.9 g of intermediate product. The product (4.9 g) was suspended in dichloromethane (180 mL) and manganese dioxide (11.2 g, 129 mmol) was added. The mixture was stirred for 16 hr at 20° C. and filtered. The filtrate was concentrated in vacuo to give 4.3 g crude product that was purified on silica (150 g) using ethyl acetate and n-heptane (3:7) as eluent to give 1.9 g of the title compound.

m.p. 139–142° C. HPLC (Method 1) $R_t$=29.8 min; Micro analysis: calculated: C, 73.98; H, 5.13; N, 3.75%; found: C, 73.45; H, 5.17; N, 3.72%.

EXAMPLE 804

N-(4-[3-Chloro-4-hydroxybenzoyl)hydrazonomethyl]-3-methoxyphenyl)-2-(4-trifluoromethoxyphenoxy)acetamide

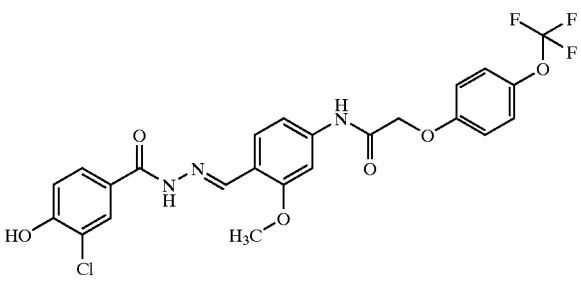

Step 1: Coupling of aldehyde [Building Block 2] to Resin[Building Block 1]

0.75 g resin (Wang resin loaded with 3-chloro-4-hydroxybenzoic acid hydrazide) was swelled in dimethylformamide (6 mL) for 30 min and drained. The aldehyde (4-formyl-3-methoxyphenyl)carbamic acid 9H-fluoren-9-ylmethyl ester, 0.5 g, 1.36 mmol) dissolved in dimethylformamide (3 mL) was added followed by addition of triethylorthoformate (1.5 mL).The mixture was shaken for 16 hr at 20° C. and drained. The resin was washed with dimethylformamide (5×4 mL), dichloromethane (5×4 mL) and dimethylformamide (5×4 mL). The coupling of the aldehyde was repeated twice.

Step 2: Deprotection of Aniline

The resin was swelled in dimethylformamide (5 mL) and piperidine added (1.25 mL). After shaking for 30 min, the resin was drained and washed with dimethylformamide (5×4 mL), N-methylpyrrolidinone (5×4 mL) and dimethylformamide (5×4 mL).

Step 3: Coupling of Acid [Building Block 3] to Resin [Building Block 1][Building Block 2]

The resin[building block 1][building block 2] was swelled in dimethylformamide (2.5 mL) and the acid (4-trifluoromethoxy)phenoxy acetic acid (0.64 g, 2.7 mmol) was added together with diisopropylcarbodiimide (0.21 mL). After 5 min of shaking dimethylaminopyridine (0.34 mL) was added and the mixture was shaken for 3 hr and drained. The resin was washed with dimethylformamide (5×4 mL), dichloromethane (5×4 mL) and dimethylformamide (5×4 mL). The coupling of the acid was repeated twice, but with 16 hr reaction time for the repetition.

Step 4: Cleavage From the Resin

The resin was swelled in dichloromethane (2.5 mL) and trifluoroacetic acid (2.5 mL) was added. After shaking for 1 hr the resin was drained. The eluent was collected and concentrated in vacuo. The residue was crystallized from methanol to give 0.2 g of the title compound.

m.p. 235–236.5° C. HPLC-MS (METHOD A) $R_t$=13.5 min m/z=538; Micro analysis: calculated: C, 53.59; H, 3.56; N, 7.81%; found: C, 53.57; H, 3.58; N, 7.51%.

Further, a library of compounds of all the possible combinations of the above listed building blocks ([building block 1], [building block 2] and [building block 3]) was prepared in parallel as individual entities analogously to the previous example on an Advanced ChemTech Model 384 HTS using the following ChemFile to control the operation of the synthesizer. The compounds are all expected to be present in the respective wells.

The four [building block 2] aldehydes, (4-Formyl-3-methoxyphenyl)carbamic acid 9H-fluoren-9-ylmethyl ester, (4-Formyl-2-methoxyphenyl)carbamic acid 9H-fluoren-9-ylmethyl ester, 3-(tert-Butyidimethylsilanyloxy)-4-formylphenyl)carbamic acid 9H-fluoren-9-ylmethyl ester and (5-Formyl-2-methoxyphenyl)carbamic acid 9H-fluoren-9-ylmethyl ester, were coupled to four individually batches of the resin bound 3-chloro-4-hydroxybenzoic acid hydrazide (resin—[building block 1]) using the same procedure as described for step 1 in the example above. Subsequently the Fmoc deprotection of the anilino group was carried out as described in step 2 in the example above.

The four different examples of resin[building block 1][building block 2] thus prepared were equally distributed in the wells in the synthesizer prior to the initialization of the device. The attachment of the array of [building block 3] mentioned above was carried out in a fully combinatorial way with the four types of resin[building block 1][building block 2] using the general procedure as described in step 3 in the example above. The final cleavage was performed using the same general procedure as described in step 4 in the example above. During this cleavage step deprotection of acid sensible protection groups was also taken place. These two steps 3 and 4 were carried out (in several runs) on an ACT 496 HTS automated synthesizer using the following ChemFile to control the device.

ChemFile: C:\DATA\90250017.CHM
1 Empty RB1to96 for 2.000 minute(s)
2 Flush Arm1 with NMParm1 and DCMarm1
3
4 REM Adding acids 1 to 36
5
6 Dispense Sequence C:\act\ACID1-36.DSP with 1000 ul to RB1to96 rack using NMParm1
7 Mix for 2.00 minutes at 600 rpm(s)
8 Pause
9 Mix for 2.00 minutes at 600 rpm(s)
10
11 REM Adding acids 37 to 48
12
13 Dispense Sequence AC137-48.DSP with 1000 ul to RB1to96 rack using NMParm1
14 Mix for 2.00 minutes at 600 rpm(s)
15
16 Pause
17
18 REM Adding DIC
19
20 Transfer 300 ul from Monomer1to36[12]( ) to RB1to96[2–48] using NMParm1
21 Mix for 2.00 minutes at 600 rpm(s)
22 Transfer 300 ul from Monomer1to36[13]( ) to RB1to96[50–96 ] using NMParm1
23 Mix for 10.00 minutes at 600 rpm(s)
24
25 REM Adding DMAP
26
27 Transfer 200 ul from Monomer1to36[14]( ) to RB1to96[2–48] using NMParm1
28 Transfer 200 ul from Monomer1to36[14]( ) to RB1to96[50–96] using NMParm1
29
30 REM Mixing overnight
31
32 Mix for 10.00 minutes at 600 rpm(s)
33 Wait for 20.000 minute(s)
34 Repeat from step 32, 150 times
35
36 REM wash
37
38 Empty RB1to96 for 2.000 minute(s)
39 Dispense System Fluid NMPdualarms* 1000 ul to RB1to96[1–96]

40 Mix for 3.00 minutes at 600 rpm(s)
41 Empty RB1to96 for 2.000 minute(s)
42 Repeat from step 39, 5 times
43
44 REM de fmoc
45 Mix for 3.00 minutes at 600 rpm(s)
46 Dispense Sequence C:\act\DEFMOC.DSP with 1500 ul to RB1to96 rack using NMParm1
47 Mix for 15.00 minutes at 600 rpm(s)
48 Empty RB1to96 for 3.000 minute(s)
49 Empty RB1to24 for 3.000 minute(s)
50 Empty RB49to72 for 2.000 minute(s)
51 Pause
52
53 REM wash
54 Dispense System Fluid NMPdualarms* 1000 ul to RB1to96[1–96]
55 Mix for 3.00 minutes at 600 rpm(s)
56 Empty RB1to96 for 3.000 minute(s)
57 Repeat from step 54, 2 times
58 Flush Arm1 with NMParm1 and DCMarm1, Arm2 with DCMarm2
59 Dispense System Fluid DCMdualarm* 1000 ul to RB1to96[1–96]
60 Mix for 3.00 minutes at 600 rpm(s)
61 Empty RB1to96 for 3.000 minute(s)
62 Repeat from step 59, 5 times
63
64 REM TFA CLEAVAGE
65
66 Mix for 1.00 minutes at 300 rpm(s)
67 Transfer 1000 ul from Reagent2[1]( ) to RBcleavage1 to 96[1–96] using DCMarm1

68 Mix for 1.00 hours at 600 rpm(s)
69 Empty RBcleavage1to 96 for 30 second(s)
70 Dispense System Fluid DCMdualarm* 500 ul to RBcleavage1to 96[1–96]
71 Mix for 5.00 minutes at 300 rpm(s)
72 Empty RBcleavage1to 96 for 30 second(s)
73
Dispense sequence files C:\act\ACID1-36.DSP are subroutines that control the combinatorial addition of the amines into the 4 reaction blocks each containing 96 wells in the syntheziser.

Examples of compounds from this library were characterized by HPLC-MS (molecular mass & retention time) and includes:

EXAMPLE 805

Quinoline-2-carboxylic Acid (4-[(3-Chloro-4-hydroxybenzoyl)hydrazonomethyl]-3-methoxyphenyl}amide

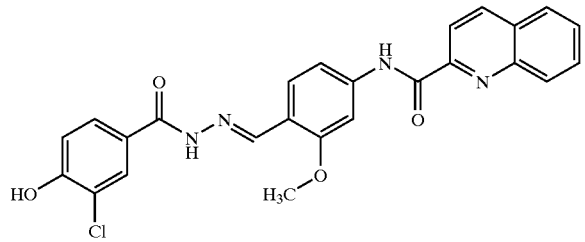

m.p. 236–238° C. HPLC (Method 1) $R_t$=26.2 min.

EXAMPLE 806

N-{4-[(3-Chloro-4-hydroxybenzoyl)hydrazonomethyl]-2-methoxyphenyl}-2-(4-trifluoromethoxyphenoy)acetamide

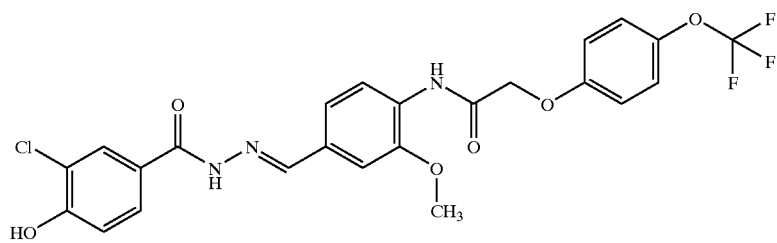

m.p. 216–218° C. HPLC (Method 1) $R_t$=26.6 min.

EXAMPLE 807

Quinoline-2-carboxylic Acid {4-[(3-Chloro-4-hydroxybenzoyl)hydrazonomethyl]-2-methoxyphenyl}amide

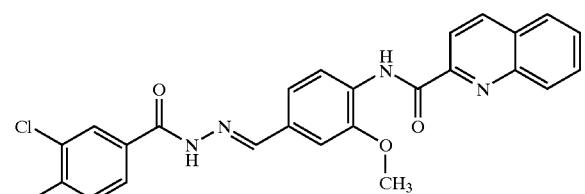

m.p. 159–162° C. HPLC (Method 1) $R_t$=27.7 min.

EXAMPLE 808

N-(4-[(3-Chloro-4-hydroxybenzoyl)hydrazonomethyl]-3-methoxyphenyl}-2-(4-chlorophenoxy)acetamide

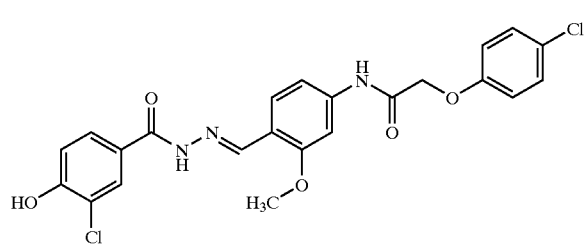

m.p. 216–218° C. HPLC-MS (METHOD A) R$_t$=13.4 min. m/z=488.

EXAMPLE 809

N-{4-[(3-Chloro-4-hydroxybenzoyl)hydrazonomethyl]-3-methoxyphenyl}-6-methylnicotinamide

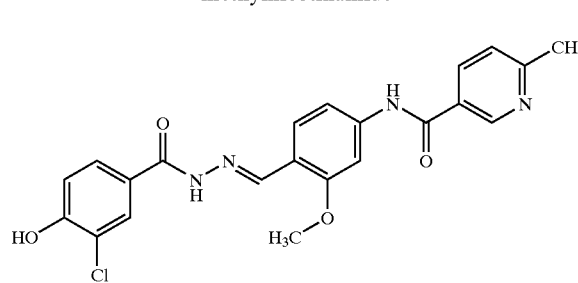

HPLC-MS (METHOD A) R$_t$=8.2 min, m/z=439.

EXAMPLE 810

N-{4-[(3-Chloro-4-hydroxybenzoyl)hydrazonomethyl]-3-methoxyphenyl}-2-(3-trifluoromethylphenyl)acetamide

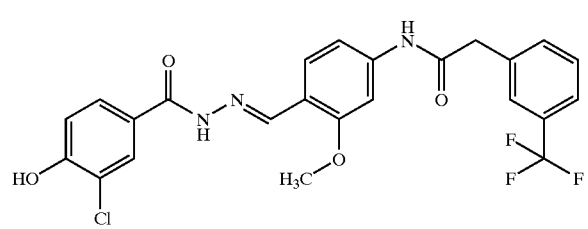

HPLC-MS (METHOD A) R$_t$=13.4 min, m/z=506.

EXAMPLE 811

N-{4-[(3-Chloro-4-hydroxybenzoyl)hydrazonomethyl]-3-methoxyphenyl}-2-(2,4-dichlorophenoxy)acetamide

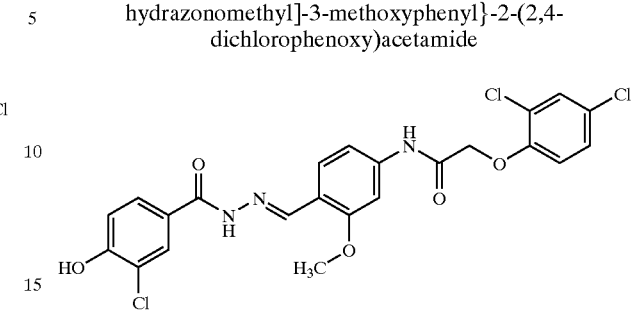

HPLC-MS (METHOD A) R$_t$=14.3 min, m/z=524.

EXAMPLE 812

N-{4-[(3-Chloro-4-hydroxybenzoyl)hydrazonomethyl]-3-methoxyphenyl}-3-(4-trifluoromethylphenyl)propionamide

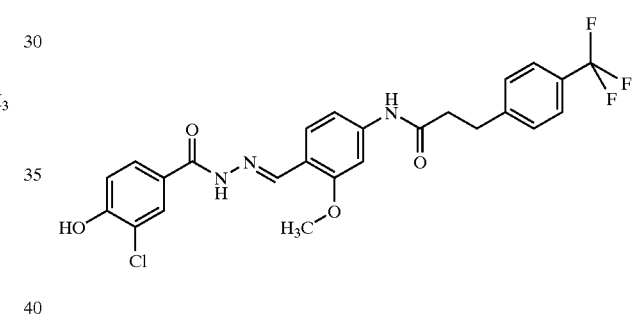

HPLC-MS (METHOD A) R$_t$=14.0 min, m/z=520.

EXAMPLE 813

Isoquinoline-1-carboxylic Acid {4-[(3-Chloro-4-hydroxybenzoyl)hydrazonomethyl]-3-methoxyphenyl}amide

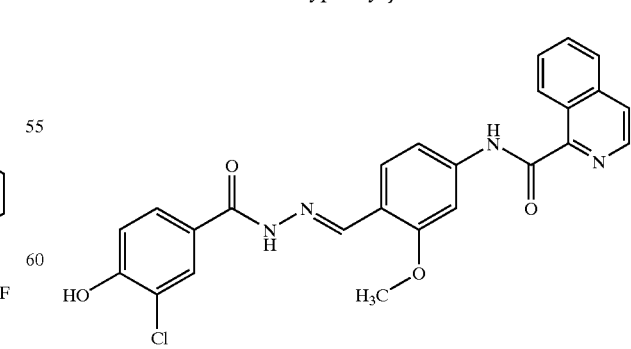

HPLC-MS (METHOD A) R$_t$=13.0 min, m/z=475.

EXAMPLE 814

7-Ethoxybenzofuran-2-carboxylic Acid {4-[(3-Chloro-4-hydroxybenzoyl)hydrazonomethyl]-3-methoxyphenyl}amide

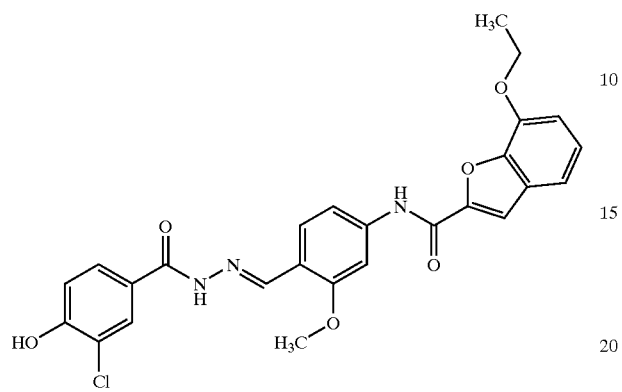

HPLC-MS (METHOD A) $R_t$=13.3 min, m/z=508.

EXAMPLE 815

N-{4-[(3-Chloro-4-hydroxybenzoyl)hydrazonomethyl]-3-methoxyphenyl}-2-(toluene-4-sulonyl)acetamide

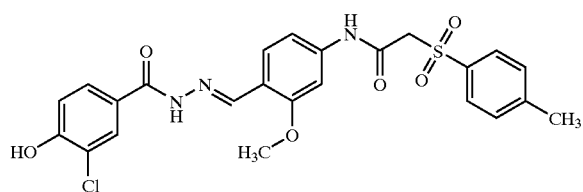

HPLC-MS (METHOD A) $R_t$=10.8 min, m/z=517.

EXAMPLE 816

Benzofuran-2-carboxylic Acid {4-[(3-Chloro-4-hydroxybenzoyl)hydrazonomethyl]-3-methoxyphenyl}-amide

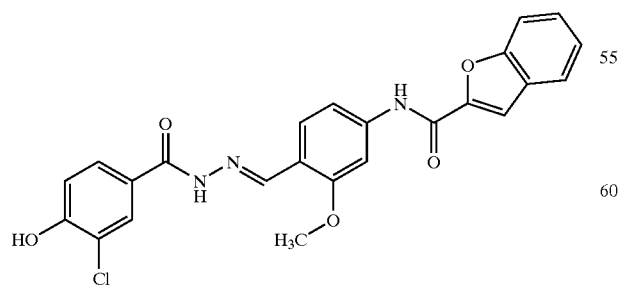

HPLC-MS (METHOD A) $R_t$=12.3 min, m/z=465.

EXAMPLE 817

N-{4-[(3-Chloro-4-hydroxybenzoyl)hydrazonomethyl]-3-methoxyphenyl}-3-cyanobenzamide

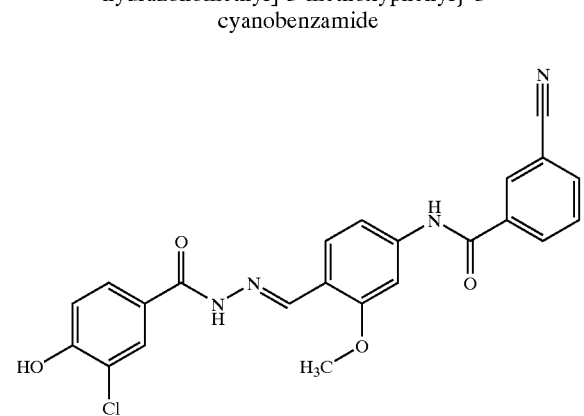

HPLC-MS (METHOD A) $R_t$=10.8 min, m/z=450.

EXAMPLE 818

5-Chloro-4-methoxythiophene-3-carboxylic Acid {4-[(3-Chloro-4-hydroxybenzoyl)hydrazonomethyl]-3-methoxyphenyl}amide

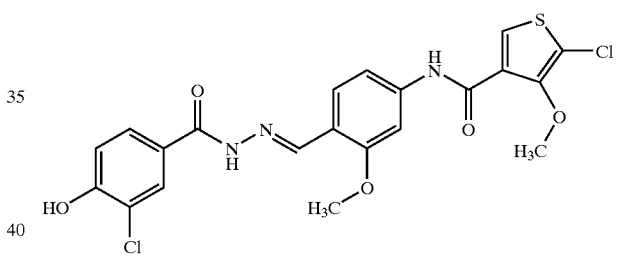

HPLC-MS (METHOD A) $R_t$=9.8 min, m/z=495.

EXAMPLE 819

5-Bromofuran-2-carboxylic Acid {4-[(3-Chloro-4-hydroxybenzoyl)hydrazonomethyl]-3-methoxyphenyl}amide

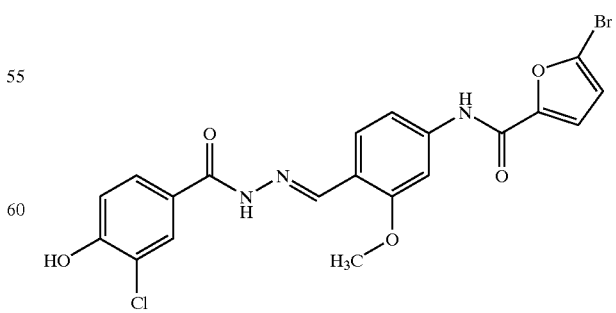

HPLC-MS (METHOD A) $R_t$=11.4 min, m/z=494.

EXAMPLE 820

2-Benzo[b]thien-3-yl-N-{4-[(3-chloro-4-hydroxybenzoyl)hydrazonomethyl]-2-methoxyphenyl}acetamide

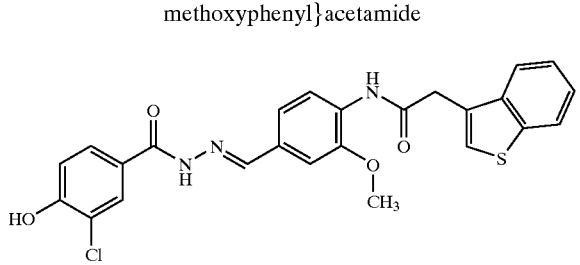

HPLC-MS (METHOD A) $R_t$=13.4 min, m/z=494.

EXAMPLE 821

N-{4-[(3-Chloro-4-hydroxybenzoyl)hydrazonomethyl]-2-methoxyphenyl}-2-(4-chlorophenoxy)-2-methylpropionamide

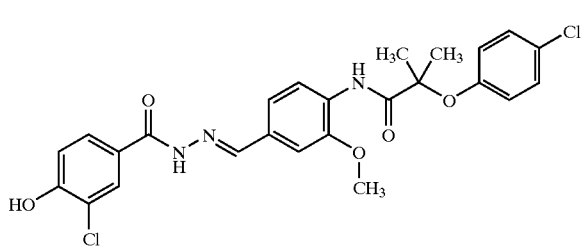

HPLC-MS (METHOD A) $R_t$=14.7 min, m/z=516.

EXAMPLE 822

N-{4-[(3-Chloro-4-hydroxybenzoyl)hydrazonomethyl]-2-methoxyphenyl}-3-(3-trifluoromethylphenyl)acrylamide

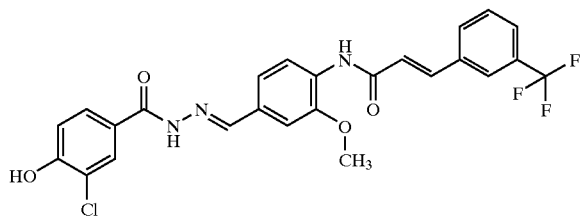

HPLC-MS (METHOD A) $R_t$=14.3 min, m/z=518.

EXAMPLE 823

N-{4-[(3-Chloro-4-hydroxybenzoyl)hydrazonomethyl]-2-methoxyphenyl}-2-fluoro-3-phenylacrylamide

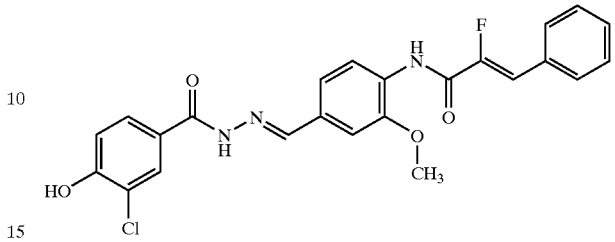

HPLC-MS (METHOD A) $R_t$=14.3 min, m/z=468.

EXAMPLE 824

2-Benzo[b]thieophene-2-carboxylic Acid {4-[(3-Chloro-4-hydroxybenzoyl)hydrazonomethyl]-2-methoxyphenyl}amide

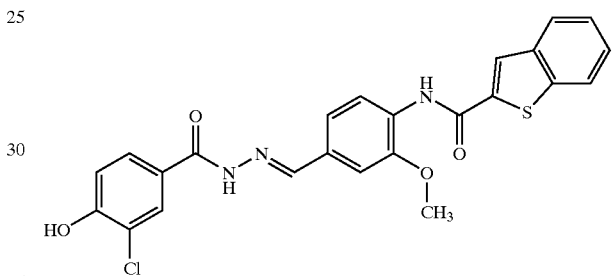

HPLC-MS (METHOD A) $R_t$=13.8 min, m/z=480.

HPLC Method 1.

The RP-HPLC analysis was performed using UV detection at 254 nm and a Merck Hibar LiChrosorb RP-18 (5 μm) prepacked column (Cat. No. 50333), which was eluted at 1 mL/minute. Two solvent systems were used:

Solvent system I: 0.1% Trifluoroacetic acid in acetonitrile.
Solvent system II: 0.1%
Trifluoroacetic acid in water.

The column was equilibrated with a mixture composed of 20% of solvent system I and 80% of solvent system II. After injection of the sample a gradient of 20% to 80% of solvent system I in solvent system II was run over 30 minutes. The gradient was then extended to 100% of solvent system I over 5 minutes followed by isocratic elution with 100% of this system for 6 minutes.

General Procedure for Examples 825 to 875

The compounds were prepared as single entities according to the following equation Resin—[Building block 1]→

Resin—[Building block 1]—[Building block 2]→

Resin—[Building block 1]—[Building block 2]—[Building block 3]

and were simultaneously deprotected and cleaved from the resin with 50% trifluoroacetic acid in dichloromethane to give the desired compounds as individual entities according to the following formula

[Building block 1]—[Building block 2]—[Building block 3].

The following compounds were prepared as single entities by parallel synthesis on a solid support. Preparation of Resin—[Building block 1]—[Building block 2] was done manually, whereas the attachment of [Building block 3] and cleavage from the resin were performed on an Advanced ChemTech Model 384 HTS.

The starting resin, Resin—[Building block 1], was prepared as described above.

The resin used was a polystyrene resin with a Wang linker and the substitution capacity was 0.9 mmol/g.

All compounds are based on successive attachment of [Building block 2] and [Building block 3] to Resin—[Building block 1] in a combinatorial way using a nucleophilic substitution reaction according to the following formulae, which are included in the general formula II:

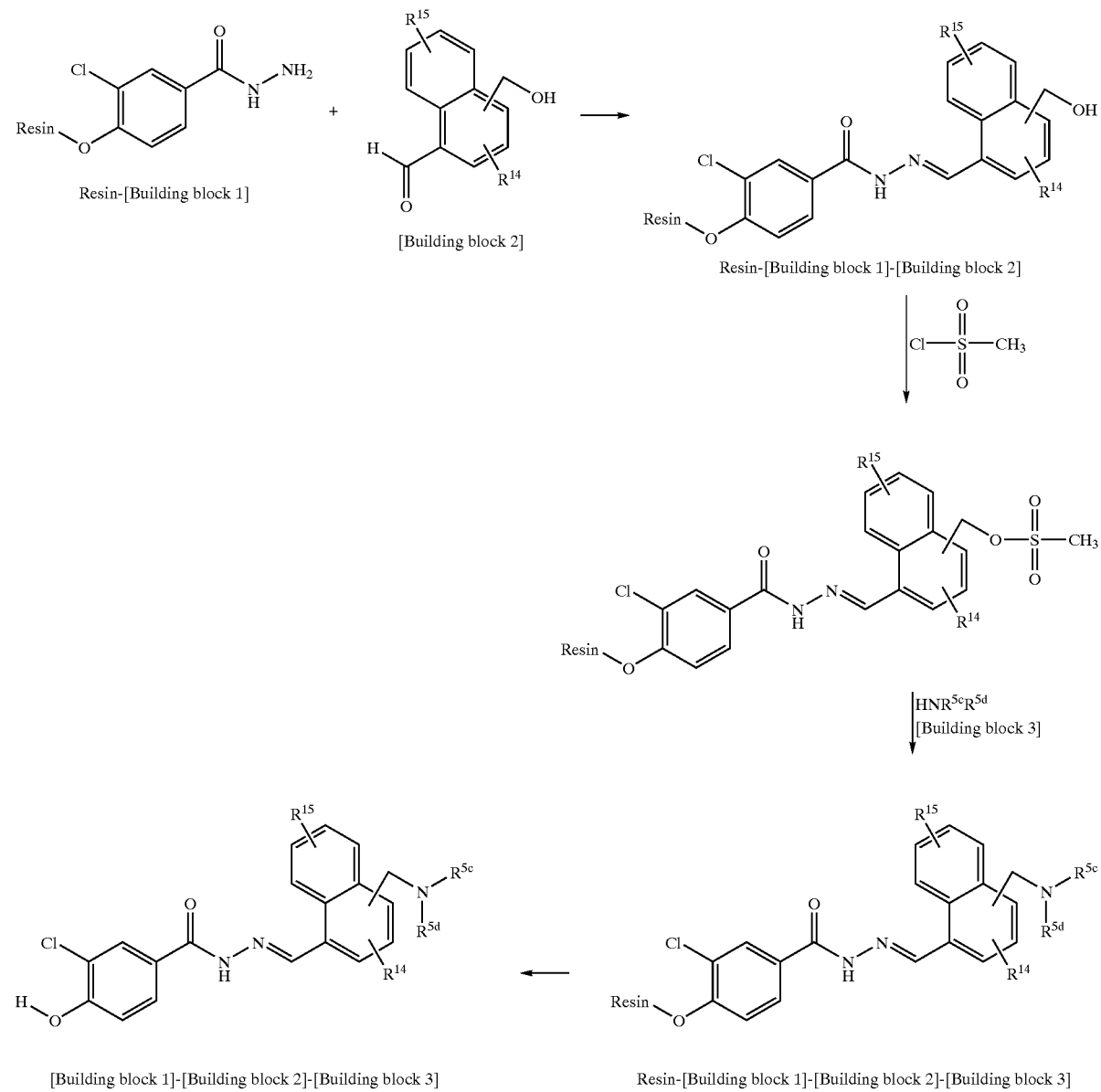

and

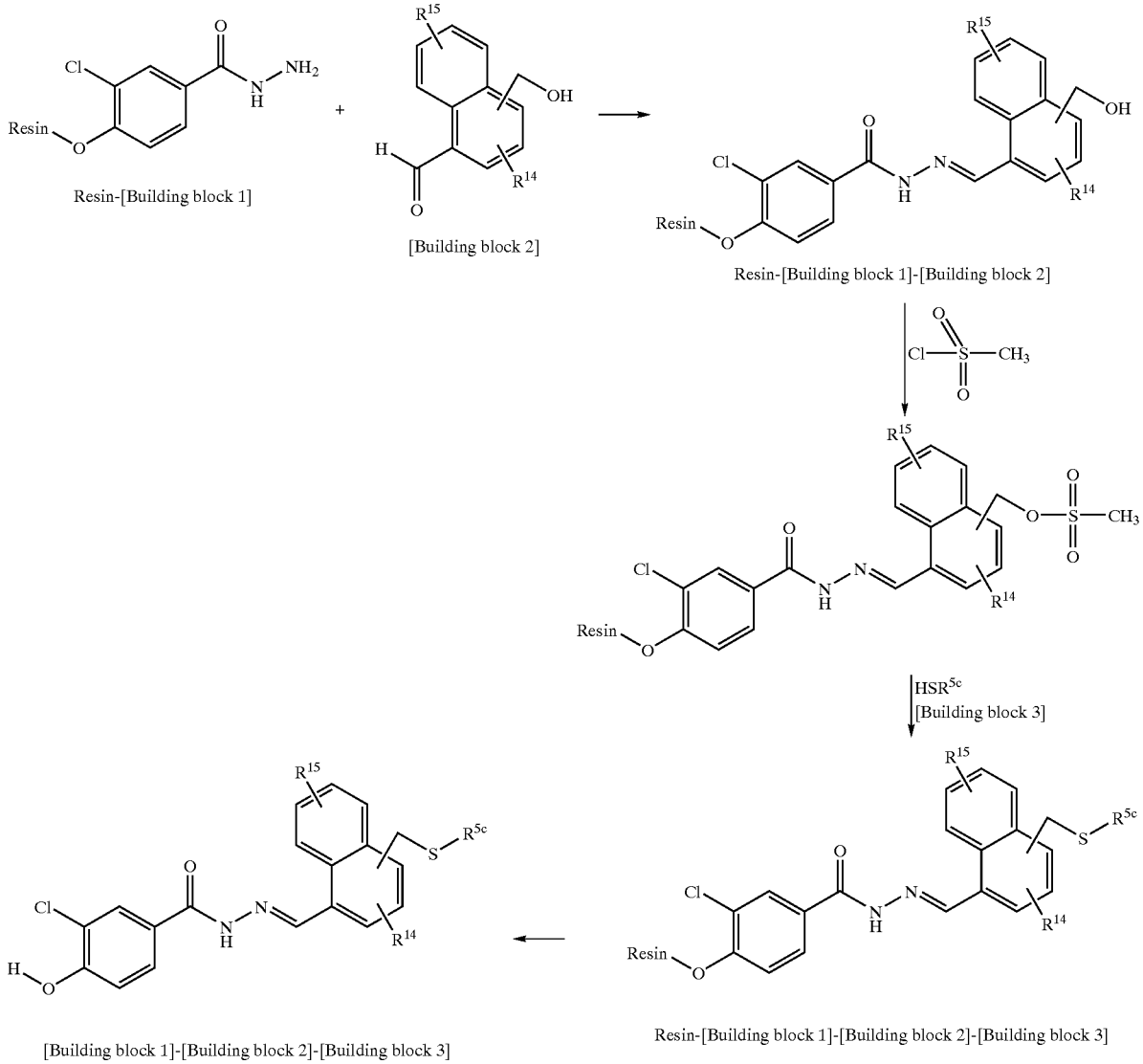

where $R^{14}$, $R^{15}$ are as defined for formula I and $-NR^{5c}R^{5d}$ is

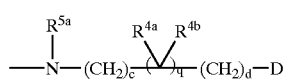

where $R^{5a}$, $R^{4a}$, $R^{4b}$, c, q, d, and D are as defined for formula I or —D' where —D' is defined as a subset of —D that contains a primary or a secondary amine that can react as a nucleophile;

and $-SR^{5c}$ is

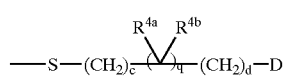

where $R^{4a}$, $R^{4b}$, c, q, d, and D are as defined for formula I or

—D' where —D' is defined as a subset of —D that contains a thiol that can react as a nucleophile.

The following resin, here depicted as Resin—[Building block 1] was used:

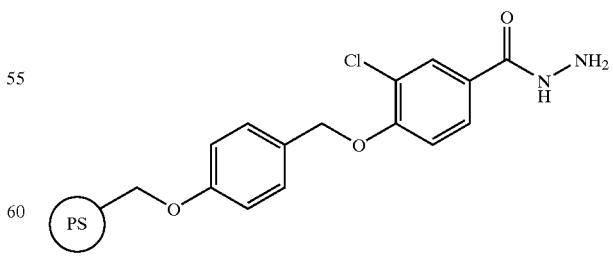

where PS is polystyrene. In the following "Resin" is the polystyrene resin with the Wang linker:

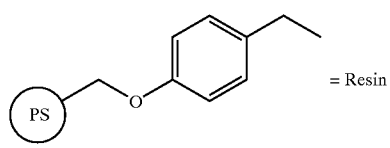 = Resin

The following building blocks were used:

| Building block 2 |
|---|
| 4-Hydroxymethylnaphthalene-1-carbaldehyde 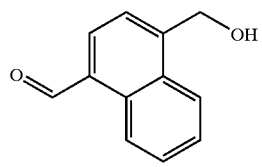 |

| [Building block 3]: |
|---|
| (1,4'-Bipiperidine)-4'carboxamide 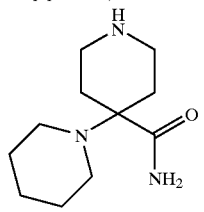 |
| 2-Thiophenemethylamine 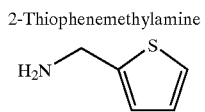 |
| 5-Methyl-2-furanmethylamine 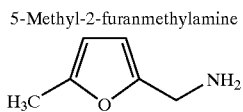 |
| 1-Pyrrolidinocarbonylmethyl)piperazine 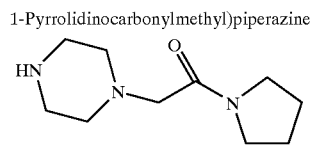 |
| 1-(2-Furoyl)piperazine 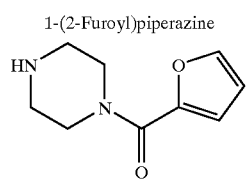 |

-continued

| [Building block 3]: |
|---|
| 2-Amino-2-phenylethanol 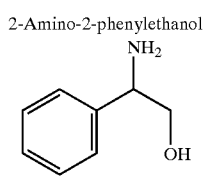 |
| L-Methionine ethyl ester 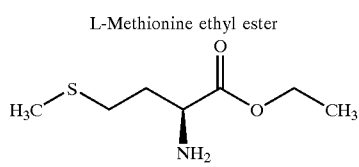 |
| DL-Serine methyl ester 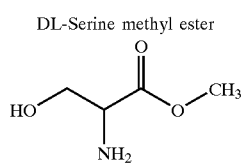 |
| 4-Acetyl-4-phenylpiperidine 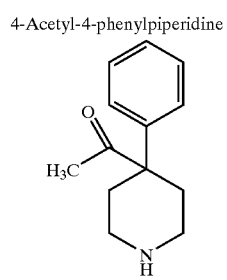 |
| 4-Piperidinopiperidine 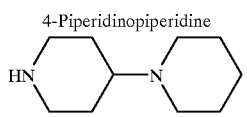 |
| N-Ethylpiperazine 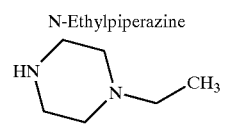 |
| 1-Acetylpiperazine 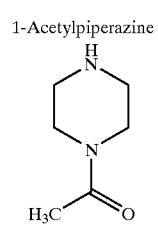 |
| Piperazine 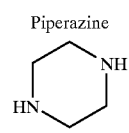 |
| 2-(Aminomethyl)pyridine 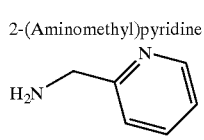 |

[Building block 3]:

4-(Aminomethyl)piperidine

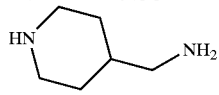

1,3-Diaminocyclohexane

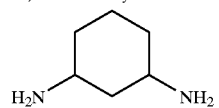

Pyrrolidine

4-(2-Aminoethyl)pyridine

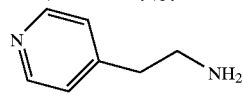

4-(Hydroxymethyl)piperidine

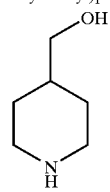

Thiomorpholine

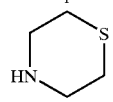

2-(2-Methylaminoethyl)pyridine

(s)-2-Amino-3-cyclohexyl-1-propanol

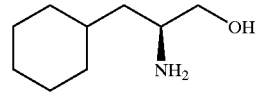

3-Isopropylamino-n-propylamine

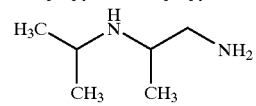

L-Prolinol

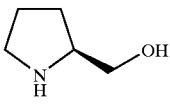

4-Hydroxypiperidine

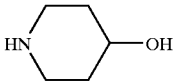

[Building block 3]:

1-Amino-2-propanol

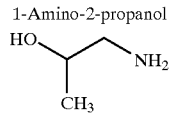

Furfurylamine

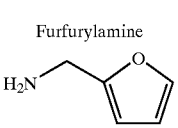

2-Methoxyisopropylamine

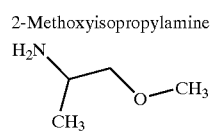

L-Isoleucinol

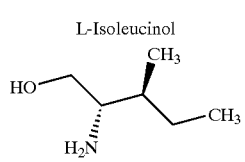

3-Aminopentane

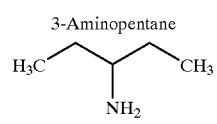

2-Piperidineethanol

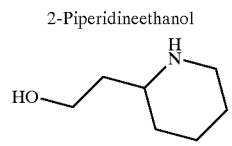

3-Amino-1,2-propanediol

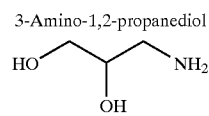

Cyclopropylamine

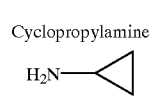

Ethylenediamine

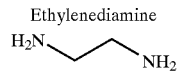

1-Benzyl-3-Aminopyrrolidine

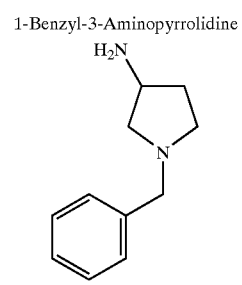

3-Pyrrolidinol

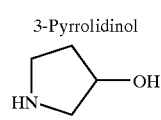

-continued

[Building block 3]:

2-Aminocyclohexanol

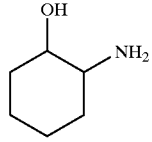

Morpholine

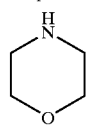

3-Mercaptopropionic acid

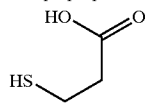

Glycine tert butylester

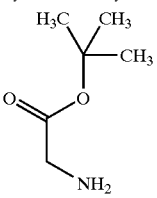

3-Mercaptopropionic acid ethyl ester

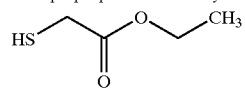

Ethylamine

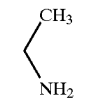

Methylamine

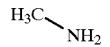

2-Aminoethanol

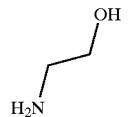

Isopropylamine

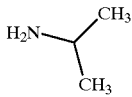

Isopentylamine

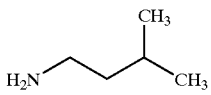

-continued

[Building block 3]:

Dimethylamine

Propylamine

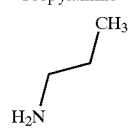

Cyclopentylamine

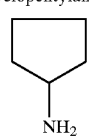

2-Furanylmethylamine

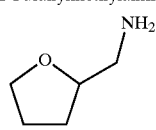

2-Methylimidazole

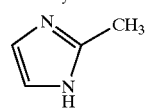

3-Amino-5-mercapto-1,2,4-triazole

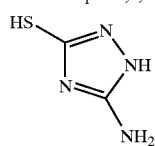

Captopril

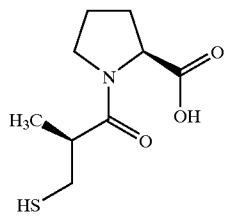

2,2-Dimethylpropylamine

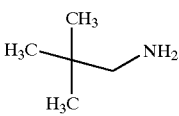

N,N-Dimethylethylenediamine

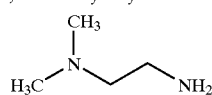

-continued

[Building block 3]:

2,4-Dimethylimidazole

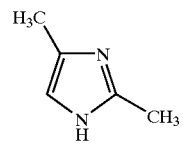

3-Mercapto-1H-1,2,4-triazol

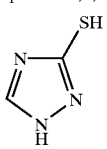

Cyclopropylmethylamine

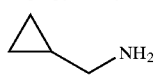

Cyclobutylamine

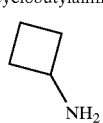

4-Mercaptopyridine

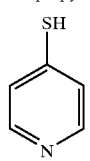

Thiazolidine

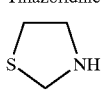

Isopropylmercaptane

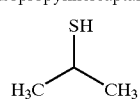

4-(4-Trifluoromethylphenyl)-4-piperidinol

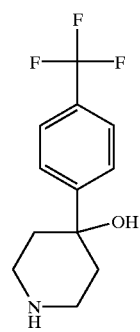

-continued

[Building block 3]:

4-(2-Thienyl)-4-piperidinol

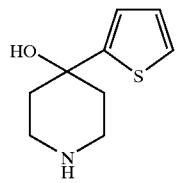

4-(3-Trifluoromethylphenyl)-3-piperidinol

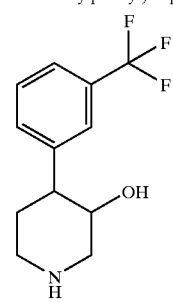

Glutamic Acid di tert butylester

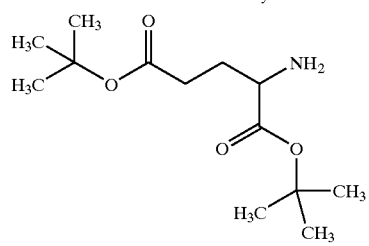

2,2,2-Trifluoroethylamine

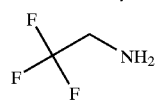

S-1-amino-2-propanol

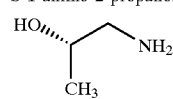

4-(Aminomethyl)-piperidine

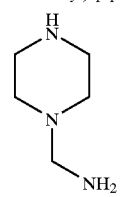

D-Valinol

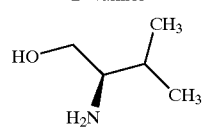

[Building block 3]:

Thiophene-2-ethylamine

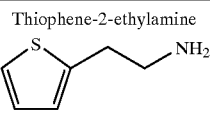

Tetrahydro-3-thiophenamine 1,1-dioxide

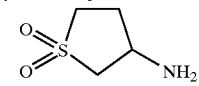

2,3-Dimethoxybenzylamine

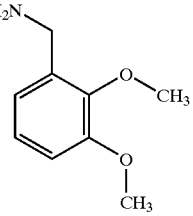

Alfa-methylbenzylamine

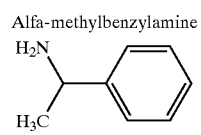

1,2,3,4-Tetrahydroisoquinoline

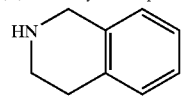

1,2,3,4-Tetrahydro-1-naphthylamine

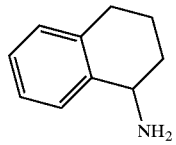

N-Benzylethanolamine

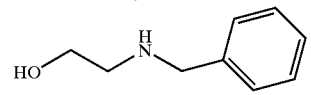

4-Methoxybenzylamine

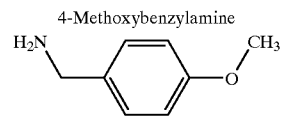

N'-Benzyl-N,Nn-dimethylethylenediamine

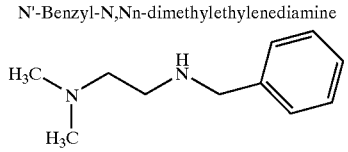

2-Benzylamino-1-propanol

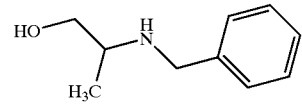

[Building block 3]:

N-Isopropylbenzylamine

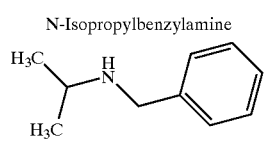

1,2-Dimethylpropylamine

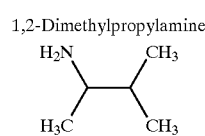

D-(−)-apha-Phenylglycinol

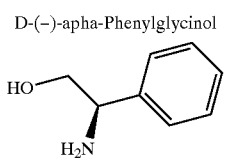

4-Fluorobenzylamine

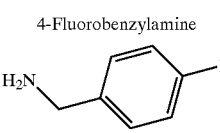

N-Ethylbenzylamine

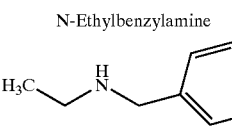

N-(n-propyl) Benzylamine

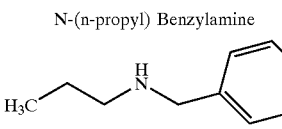

2-Amino-2-methyl-1-propanol

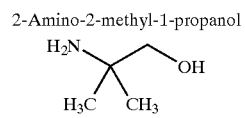

Piperonylamine

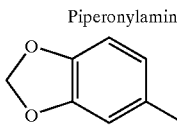

4-(Trifluoromethyl)benzylamine

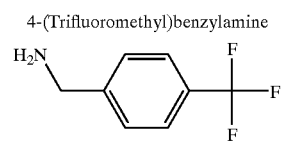

(−)-Norephedrine

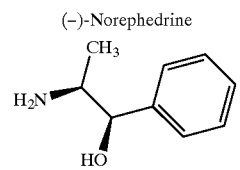

| [Building block 3]: | [Building block 3]: |
|---|---|
| 2-Methylaminoethanol 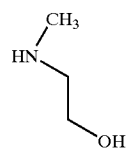 | N,N-Diethyl nipecotamide 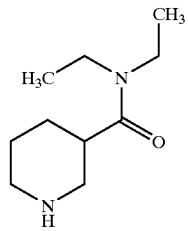 |
| 2-Butylamine 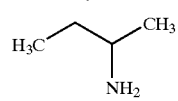 | 4-Aminocyclohexanol 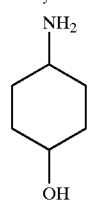 |
| Benzylmethylamine 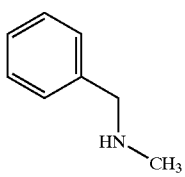 | 2-Isopropylaminoethanol 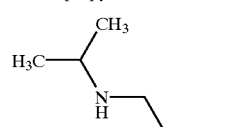 |
| Diisobutylamine 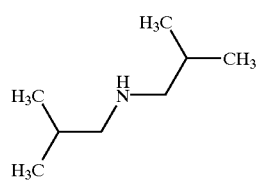 | 1,3-Dimethylbutanamine 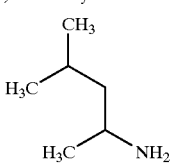 |
| Cyclohexylamine 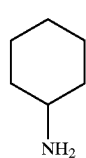 | 4-Methylcyclohexylamine 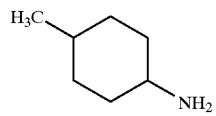 |
| N-Benzylhydroxylamine 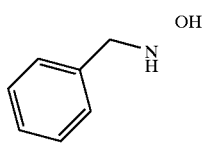 | Alfa-methyl-4-chlorobenzylamine 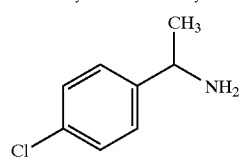 |
| Methylaminoacetonitril 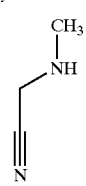 | 4-Methoxybenzylhydroxylamine 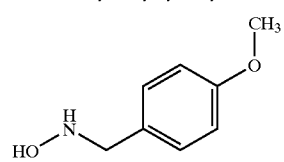 |

-continued

[Building block 3]:

2-Phenylglycinonitrile

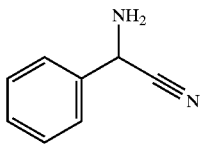

3-(Benzylamino)propionitrile

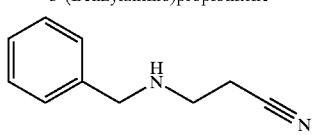

3-Methoxybenzylamine

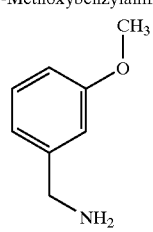

1-Methyl-2-phenoxyethylamine

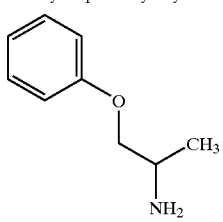

3-Fluorobenzylamine

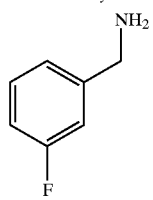

1-Aminoindan

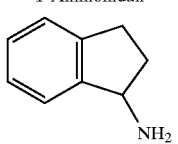

3-Piperidinemethanol

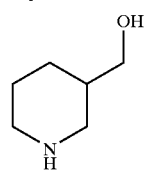

-continued

[Building block 3]:

3,4-Dimethoxybenzylamine

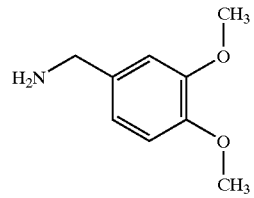

2-Mercapto-5-methylthiadiazole

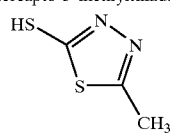

1-Methyl-5-mercaptotetrazole

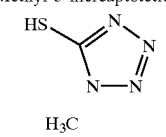

3-Methylaminopropionitril

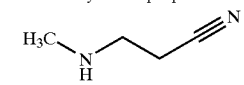

Isopropylmethylamine

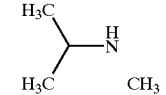

2-Mercaptothiazole

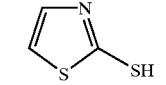

2-Amino-1-propanol

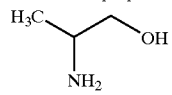

exo-2-Aminonorbornane

4-Aminobenzylamine

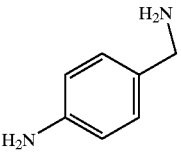

2-Mercaptoimidazol

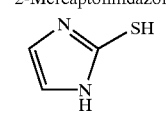

-continued

[Building block 3]:

2-Mercapto-1-methylimidazol

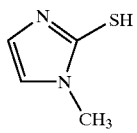

3-Mercapto-4-methyl-1,2,4-triazol

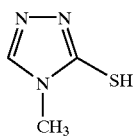

2-Methyl-4-amino-5-aminomethylpyrimidine

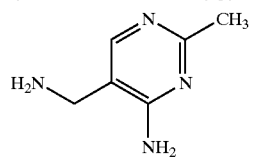

2-Phenylpiperidine

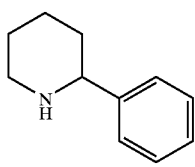

3-benzylamino-1-propanol

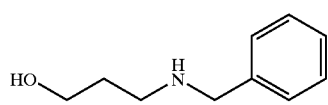

4-Aminomethylpyridine

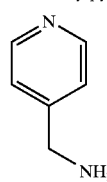

3-Aminomethylpyridine

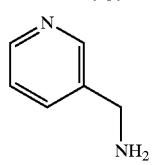

R-2-Amino-1-propanol

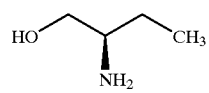

-continued

[Building block 3]:

4-(Ethylaminomethyl)pyridine

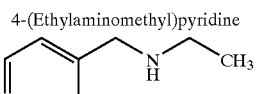

4-Trifluoromethoxybenzylamine

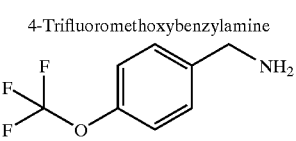

4-tert-Butylbenzylamine

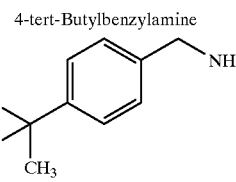

3-Aminobenzylamine

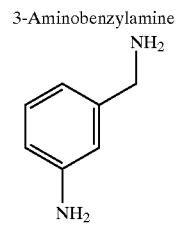

3-(Methylaminomethyl)pyridine

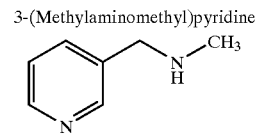

DL-Phenylalanine methyl ester

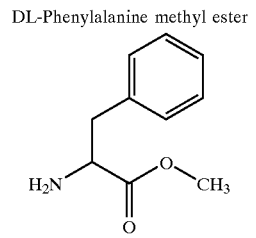

Preparation of Resin—[Building Block 1]

This resin was prepared as described above.

Preparation of 4-Hydroxymethylnaphtaldehyde ([Building Block 2])

The preparation of this compound is described above.

Preparation of Resin—[Building Block 1]—[Building Block 2]

573

Preparation of Resin Bound 3-Chloro-4-hydroxybenzoic Acid (4-Hydroxymethylnaphthylmethylene)hydrazide

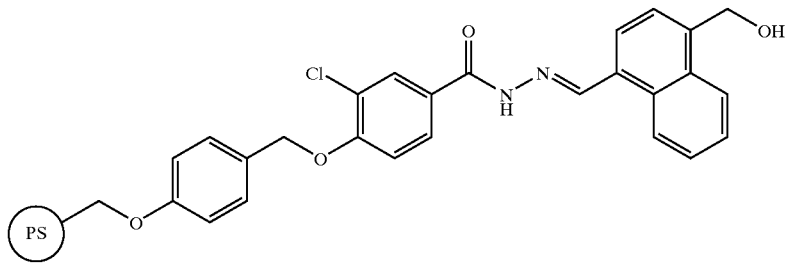

Resin—[Building block 1] (4 g) was suspended in DMF (40 mL) and was allowed to swell for 15 min. and then washed with DMF (2×40 mL), DCM (3×40 mL) and DMSO (2×40 mL). The solvent was removed by filtration. 1.488 g (8 mmol) 4-hydroxymethylnaphtaldehyde was dissolved in 40 mL DMSO and was added to the resin followed by 4 mL glacial acetic acid. The suspension was shaken for 16 hours at 25° C. The resin was successively washed with DMSO (2×40 mL), THF (3×40 mL), CH$_3$OH (40 mL), CH$_2$Cl$_2$ (40 mL), CH$_3$OH (40 mL), CH$_2$Cl$_2$ (40 mL) and dried in vacuo at 40° C. for 16 hours to afford resin bound 3-chloro-4-hydroxybenzoic acid (4-hydroxymethylnaphthylmethylene) hydrazide.

EXAMPLE 825

3-Chloro-4-hydroxybenzoic Acid (4-(1H-1,2,4-Triazol-3-ylsulfanylmethyl)naphthylmethylene) hydrazide

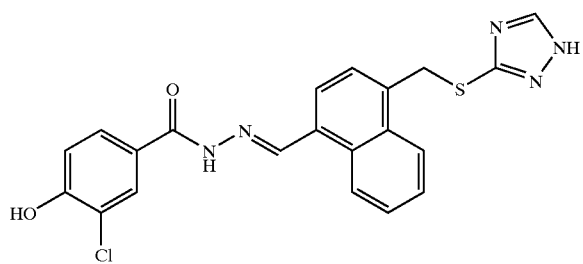

The resin bound 3-chloro-4-hydroxybenzoic acid (4-hydroxymethylnaphthylmethylene)-hydrazide (Resin—[Building block 1]—[Building block 2]) (2 g, ~2 mmoles) was swelled in CH$_2$Cl$_2$ (20 mL) for 15 min, then washed twice with CH$_2$Cl$_2$ (20 mL). 8 mL CH$_2$Cl$_2$ and 8 ml diisopropylethylamine was subsequently added and the suspension was cooled to 0° C. Methanesulfonylchloride (2 mL) was dissolved in CH$_2$Cl$_2$ (6 mL) and added to the suspension. The mixture was allowed to react at 0° C. for 30 min, then at 25° C. for 1 hour. The resin was isolated by filtration and washed with CH$_2$Cl$_2$ (2×20 mL) and N-methyl-2-pyrrolidone (2×20 mL). 1H-1,2,4-Triazole-3-thiol (0.8 g) and KI (0.4 g) was dissolved in a mixture of 10 mL N-methyl-2-pyrrolidone and 10 mL dimethylsulfoxide and was added to the resin. Then 4 mL diisopropylethylamine was added and the mixture was shaken at 25° C. for 2 days. The solvent was removed by suction and the resin was washed with N-methyl-2-pyrrolidone (3×20 mL) THF (3×20 mL), CH$_3$OH (20 mL), CH$_2$Cl$_2$ (20 mL), CH$_3$OH (20 mL), CH$_2$Cl$_2$ (4×20 mL). The compound was cleaved from the resin by shaking for 1 hour at 25° C. with a 50% solution of trifluoroacetic acid in CH$_2$Cl$_2$ (20 mL). The mixture was filtered and the resin was extracted with acetonitrile (20 mL). The combined extracts were concentrated in vacuo. The residue was redissolved in a mixture of CH$_3$OH (10 mL) and acetonitrile (10 mL) and concentrated in vacuo. The residue was treated with CH$_3$OH (4 mL) at 25° C. providing an off-white precipitate which was isolated by filtration. The solid was washed with CH$_3$OH (3×2 mL) and dried in vacuo at 40° C. This afforded 275 mg of the title compound.

HPLC-MS (METHOD B): R$_t$=2.48 min; m/z=438 (M+1). $^1$H-NMR (300 MHz, DMSO-d$_6$) δ=4.9 (2H, s), 7.1 (1H, d), 7.5–7.9 (5H, m), 8.0 (1H, s), 8.25 (1H, d), 8.9 (1H, d), 9.1 (1H, s), 11.0 (1H, s), 11.8 (1H, s).

EXAMPLE 826

3-Chloro-4-hydroxybenzoic Acid (4-(Isobutylaminomethyl)naphthylmethylene)hydrazide

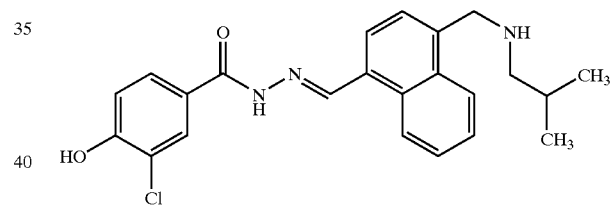

The resin bound 3-chloro-4-hydroxybenzoic acid (4-hydroxymethylnaphthylmethylene)hydrazide (Resin—[Building block 1]—[Building block 2]) (50 mg, ~0.05 mmoles) was swelled in CH$_2$Cl$_2$ (1 mL) for 15 min, then washed with CH$_2$Cl$_2$(2×0.5 mL). 0.4 mL CH$_2$Cl$_2$ and 0.4 mL diisopropylethylamine was subsequently added and the suspension was cooled to 0° C. Methanesulfonylchloride (0.1 mL) was dissolved in CH$_2$Cl$_2$ (0.3 mL) and added to the suspension. The mixture was allowed to react at 0° C. for 30 min, then at 25° C. for 1 hour. The resin was isolated by filtration and washed with CH$_2$Cl$_2$ (2×0.5 mL) and DMSO (0.5 mL). DMSO (0.5 mL) was added followed by 50 µL isobutylamine and 100 µL diisopropylethylamine. The mixture was shaken at 25° C. for 16 hours, filtered and washed successively with DMSO (2×0.5 mL), THF (3×0.5 mL), CH$_3$OH (0.5 mL), CH$_2$Cl$_2$ (0.5 mL), CH$_3$OH (0.5 mL), CH$_2$Cl$_2$ (4×0.5 mL). The compound was cleaved from the resin by shaking for 1 hour at 25° C. with a 50% solution of trifluoroacetic acid in CH$_2$Cl$_2$ (1 mL). The mixture was filtered and the resin was extracted with acetonitrile (1 mL). The combined extracts were concentrated in vacuo. The residue was redissolved in a mixture of CH$_3$OH (0.5 mL) and acetonitrile (0.5 mL) and concentrated in vacuo to give the title compound HPLC-MS (METHOD B): $R_t$=4.20 min; m/z=410 (M+1).

EXAMPLE 827

3-Chloro-4-hydroxybenzoic Acid ((4-(4-Trifluoromethoxybenzylamino)methyl)naphthylmethylene)hydrazide

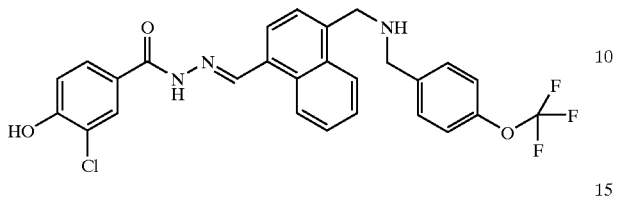

Resin bound 3-chloro-4-hydroxybenzoic acid (4-hydroxymethylnaphthylmethylene)hydrazide: (resin—[building block 1]—[building block 2]) (50 mg) was swelled in a 1:1 mixture of $CH_2Cl_2$ and N-methyl-2-pyrrolidone (0.5 mL) for 15 minutes and then washed with $CH_2Cl_2$ (3×0.5 mL). 800 µL of a 1:1 mixture of $CH_2Cl_2$ and diisopropylethylamine was added to the resin which subsequently was cooled to −3° C. A solution of 100 µL methanesulfonylchloride dissolved in 300 µL was added and allowed to react at −3° C. for 30 minutes then at 25° C. for 1 hour. Filtration of the resin was followed by washing with $CH_2Cl_2$ (2×1 mL) and N-methyl-2-pyrrolidone (2×0.5 mL). 600 µL of a solution of 4-trifluoromethoxybenzylamine (45.8 mg, 0.24 mmol, 0.4M) and KI (10 mg, 0.06 mmol, 0.1M) in N-methyl-2-pyrrolidone (0.5 mL) and diisopropylethylamine (0.1 mL) was added and allowed to react at 25° C. for 16 hours. The resin was isolated by filtration and washed successively with N-methyl-2-pyrrolidone (5×0.5 mL), THF (3×0.8 mL), $CH_3OH$ (0.8 mL), $CH_2Cl_2$ (0.8 mL), $CH_3OH$ (0.8 mL) and $CH_2Cl_2$ (3×0.8 mL). The compound was cleaved from the resin by shaking 1 hour at 25° C. with a solution of 50% trifluoroacetic acid in $CH_2Cl_2$ (1 mL) The mixture was filtered and the resin was extracted with acetonitrile (1 mL). The combined extracts were concentrated in vacuo. The residue was redissolved in a mixture of $CH_3OH$ (0.5 mL) and acetonitrile (0.5 mL) and concentrated in vacuo to give the title compound.

HPLC-MS (METHOD A): $R_t$=10.07 min; m/z=528 (M+1).

EXAMPLES 828 TO 875

A library of compounds of all the possible combinations of the above listed building blocks ([building block 1], [building block 2] and [building block 3]) was prepared in parallel as individual entities analogously to the previous example on an Advanced ChemTech Model 384 HTS using the following ChemFile to control the operation of the synthesizer. The compounds are all expected to be present in the respective wells.

A suspension of the resin bound 3-chloro-4-hydroxybenzoic acid (4-hydroxymethyl-naphthylmethylene)hydrazide: (resin—[building block 1]—[building block 2]) (50 mg) in a 1:1 mixture of $CH_2Cl_2$ and N-methyl-2-pyrrolidone (0.5 mL) is equally distributed in the wells in the synthesizer prior to the initialization of the device.

ChemFile C:\ACT_1328\MAIN.CHM
1 REM Nucleophilic displacement of benzylic alcohol
2 REM via mesylation
3
4
5 REM Dipense resin bound benzylic alchohol to wells
6
7
8 REM Setup Diluter1=DCM, D2=NMP (N-methyl-2-pyrrolidone), D3=NMP, D4=DCM
9 REM Adjust pressure
10 REM Add 100 mL DIEA/DCM 1:1 mixture to Reagent1
11 REM Add 70 mL MsCl/DCM 1:3 mixture to Reagent2
12 REM Add 100 mL TFA/DCM 1:1 mixture to Reagent3
13 REM Add 100 mL CH3CN to Reagent4
14 REM Nitrogen for cooling
15
16 Pause
17 REM Initialising.
18
19 REM Subroutine Empty1__72__3 min is called twice to remove DCM/NMP from dispensed resin
20 Go to ChemFile MTY72__3M.CHM, line 1
21 Go to ChemFile MTY72__3M.CHM, line 1
22
23 Flush Arm1 with Flush Diluter1 and Flush Diluter 2, Arm2 with Flush Diluter 3 and with Flush Diluter 4
24
25 REM Washing with DCM, 3 times
26 Dispense System Fluid Disdu1__4* 500 ul to RB1__1to96[1–72]
27 Mix "RB1__1to96" for 3.00 minutes at 300 rpm(s) and wait.
28 REM Subroutine Empty1__72__3 min
29 Go to ChemFile MTY72__3M.CHM, line 1
30 Repeat from step 26, 2 times
31
32 REM Adding DCM/DIEA mixture from Reagent1
33 Transfer 800 ul from REAGENT__1[1](DCM/DIEA) to RB1__1to96[1–72] using Flush Diluter1
34 Mix "RB1__1to96" for 1.00 minutes at 300 rpm(s) and wait.
35 Set Temperature of rack "RB1__1to96" to −3.0 degrees Celsius and wait for Tempererature to reach setpoint
36 Mix "RB1__1to96" for 1.00 minutes at 300 rpm(s) and wait.
37 REM Ensure complete cooling
38 Wait for 15.000 minute(s)
39
40 REM Adding mesylchloride
41 Transfer 400 ul from REAGENT__2[1](MsCl/DCM) to RB1__1to96[1–72] using Flush Diluter1
42 REM Reacts 30 min @ −3° C.
43 Mix "RB1__1to96" for 1.00 minutes at 300 rpm(s) and wait.
44 Wait for 4.000 minute(s)
45 Repeat from step 43, 5 times
46
47 REM Reacts 60 min @ 25° C.
48 Set Temperature of rack "RB1__1to96" to 25.0 degrees Celsius and wait for Tempererature to reach setpoint
49 Mix "RB1__1to96" for 1.00 minutes at 300 rpm(s) and wait.

50 Wait for 4.000 minute(s)
51 Repeat from step 46, 11 times
52
53 REM Subroutine Empty1_72_3 min
54 Go to ChemFile MTY72_3M.CHM, line 1
55
56 REM Initiate washing procedure, 2XDCM
57 Dispense System Fluid Disdu1_4* 1000 ul to RB1_1to96[1–72]
58 Mix "RB1_1to96" for 3.00 minutes at 300 rpm(s) and wait.
59 Go to ChemFile MTY72_3M.CHM, line 1
60 Repeat from step 57, 1 times
61
62 REM NMP wash
63
64 Dispense System Fluid Disdu2_3* 500 ul to RB1_1to96[1–72]
65 Mix "RB1_1to96" for 5.00 minutes at 300 rpm(s) and wait.
66 Go to ChemFile MTY72_3M.CHM, line 1
67
68 Go to ChemFile MTY72_3M.CHM, line 1
69 Repeat from step 64, 1 times
70
71 REM Make sure that nucleophiles are dissolved and ready for addition
72 Pause
73
74 Dispense Sequence C:\ACT_1328\R2-A.DSP with 600 ul to RB1_1to96 rack using Flush Diluter 2
75 REM Nucleophiles react @ 25° C. for 16 hr
76 Mix "RB1_1to96" for 1.00 minutes at 300 rpm(s) and wait.
77 Wait for 4.000 minute(s)
78 Repeat from step 76, 11 times
79 Repeat from step 76, 15 times
80
81 REM End of reaction
82 Go to ChemFile MTY72_3M.CHM, line 1
83 Go to ChemFile MTY72_3M.CHM, line 1
84
85 REM Commence final washing procedure
86 Dispense System Fluid Disdu2_3* 500 ul to RB1_1to96[1–72]
87 Mix "RB1_1to96" for 10.00 minutes at 300 rpm(s) and wait.
88 Go to ChemFile MTY72_3M.CHM, line 1
89 Go to ChemFile MTY72_3M.CHM, line 1
90 Repeat from step 86, 4 times
91
92 REM Change systemfluids:
93 REM*Diluter2: THF
94 REM*Diluter3: MeOH
95 Pause
96
97 Flush Arm1 with Flush Diluter1 and Flush Diluter 2, Arm2 with Flush Diluter 3 and Flush Diluter 4
98 REM THF wash 3 times
99 Dispense System Fluid Flush Diluter 2 800 ul to RB1_1to96[1–72]
100 Mix "RB1_1to96" for 10.00 minutes at 300 rpm(s) and wait.
101 Go to ChemFile MTY72_3M.CHM, line 1
102 Go to ChemFile MTY72_3M.CHM, line 1
103 Repeat from step 99, 2 times
104
105 REM Alternating MeOH/DCM wash, 2 cycles
106 Dispense System Fluid Flush Diluter 3 800 ul to RB1_1to96[1–72]
107 Mix "RB1_1to96" for 3.00 minutes at 300 rpm(s) and wait.
108 Go to ChemFile MTY72_3M.CHM, line 1
109
110 Dispense System Fluid Disdu1_4* 800 ul to RB1_1to96[1–72]
111 Mix "RB1_1to96" for 10.00 minutes at 300 rpm(s) and wait.
112 Go to ChemFile MTY72_3M.CHM, line 1
113 Go to ChemFile MTY72_3M.CHM, line 1
114
115 Repeat from step 106, 1 times
116
117 Dispense System Fluid Disdu1_4* 800 ul to RB1_1to96[1–72]
118 Mix "RB1_1to96" for 10.00 minutes at 300 rpm(s) and wait.
119 Go to ChemFile MTY72_3M.CHM, line 1
120 Repeat from step 117, 1 times
121
122 REM Washing procedure has ended
123
124 REM Setup for cleavage:
125 REM*Cleavage vials
126 REM*Lower pressure
127 REM*Add 100 mL TFA/DCM 1:1 mixture to Reagent3
128 REM*Add 100 mL CH3CN to Reagent4
129 Pause
130
131 REM Adding cleavage solution, 1 hr
132 Transfer 1000 ul from REAGENT_3[1](TFA/DCM) to RB1_1to96[1–72] using Flush Diluter1
133 Mix "RB1_1to96" for 1.00 minutes at 300 rpm(s) and wait.
134 Wait for 4.000 minute(s)
135 Repeat from step 133, 11 times
136 REM PULSE EMPTY!
137 Go to ChemFile PULSEMP1.CHM, line 1
138
139 REM Washing with CH3CN
140 Transfer 500 ul from REAGENT_4[1](CH3CN) to RB1_1to96[1–72] using Flush Diluter1
141 Mix "RB1_1to96" for 10.00 minutes at 300 rpm(s) and wait.
142 REM PULSE EMPTY!
143 Go to ChemFile PULSEMP1.CHM, line 1

144
145 REM The End
146

The following chemfile is called to empty the wells of the reaction block.:
ChemFile C:\ACT_1328\MTY72_3M.CHM
1 REM Subroutine Empty1_72_3 min
2 Empty RB1_1to96 for 5.000 minute(s)
3 Return The following chemfile is called to empty the wells of the reaction block into the cleavage vials containing the final product in a controlled manner.

ChemFile C:\ACT 1328\PULSEMP1.CHM
1 Empty RB1_1to96 for 1 second(s)
2 Wait for 4 second(s)
3 Repeat from step 1, 11 times
4 Empty RB1_1to96 for 5.000 minute(s)
5 Return Dispense sequence C:\ACT_1328\R2-A.DSP is a subroutine that controls the combinatorial addition of the amines into the reaction block in the syntheziser.

Examples of compounds from this library were characterised by HPLC-MS (molecular mass & retention time) including the following examples 828 to 875:

| Ex No. | Structure | HPLC-MS m/z (M + 1) | HPLC-MS R$_t$ (minutes) |
|---|---|---|---|
| | | (METHOD B) | (METHOD B) |
| 828 | 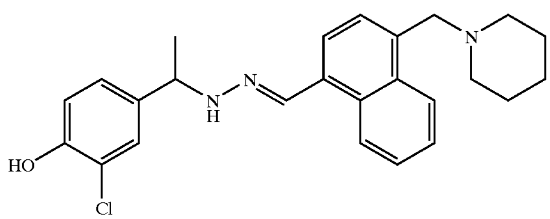 | 422 | 6.10 |
| 829 | 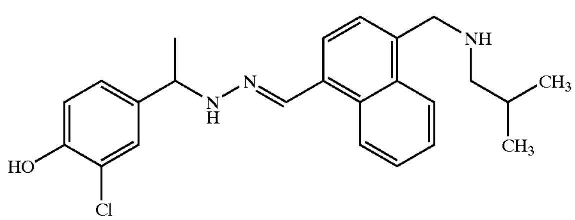 | 410 | 4.20 |
| 830 | 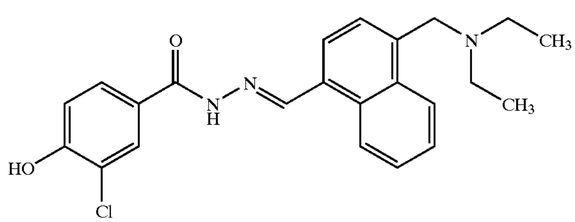 | 410 | 4.93 |
| 831 | 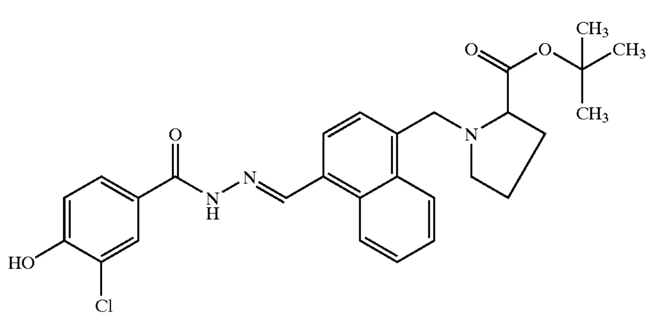 | 508 | 13.30 |

-continued
| Ex No. | Structure | HPLC-MS m/z (M + 1) | HPLC-MS R_t (minutes) |
|---|---|---|---|
| 832 | 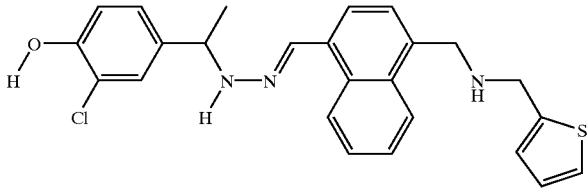 | 450 | 7.87 |
| 833 | 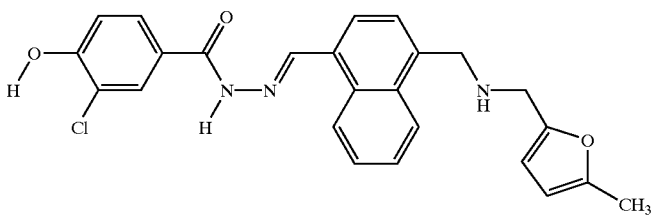 | 448 | 7.07 |
| 834 | 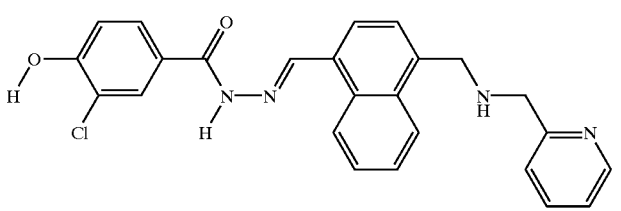 | 474 | 6.10 |
| 835 | 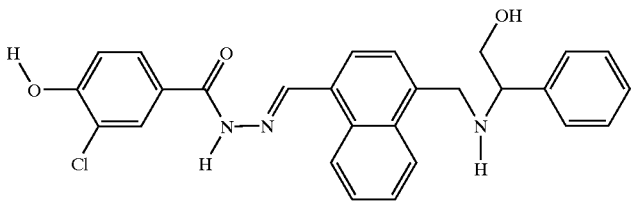 | 445 | 3.32 |
| 836 | 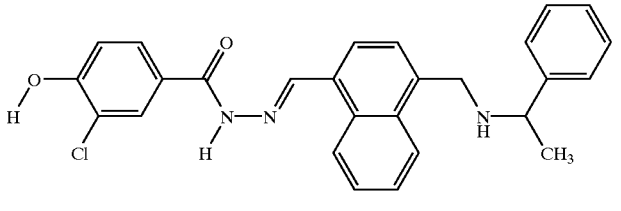 | 458 | 9.55 |
| 837 | 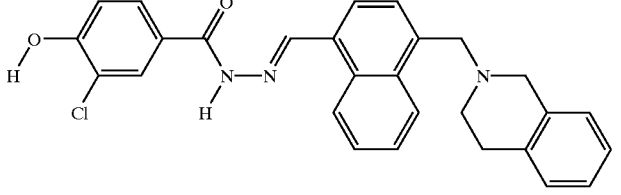 | 470 | 14.13 |
| 838 | 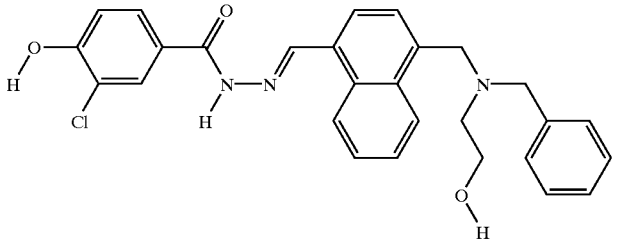 | 488 | 9.85 |

-continued

| Ex No. | Structure | HPLC-MS m/z (M + 1) | HPLC-MS R_t (minutes) |
|---|---|---|---|
| 839 | 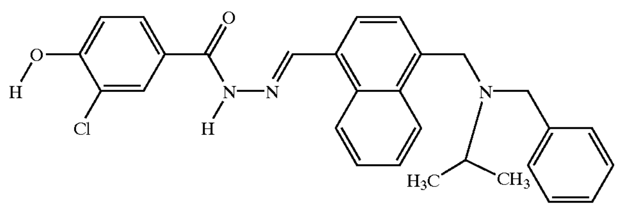 | 486 | 17.00 |
| 840 | 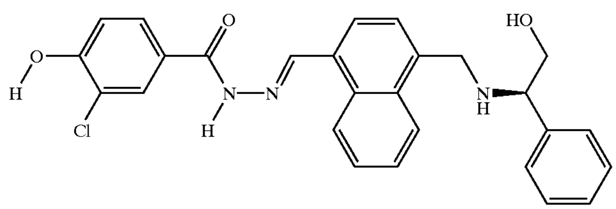 | 474 | 6.35 |
| 841 | 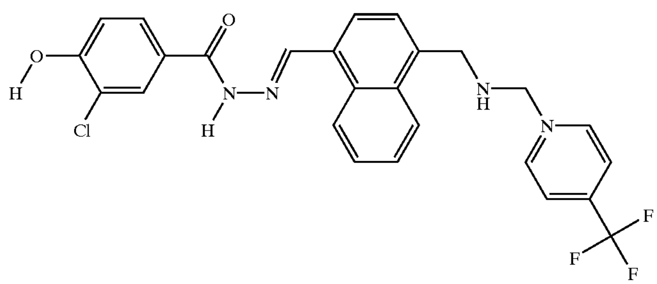 | 512 | 12.82 |
| 842 | 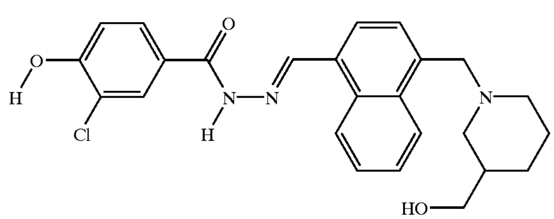 | 452 | 3.25 |
| 843 | 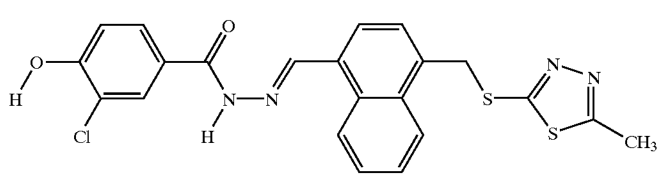 | 468 | 6.25 |
| 844 | 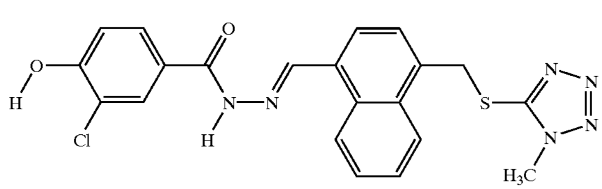 | 453 | 4.87 |
| 845 | 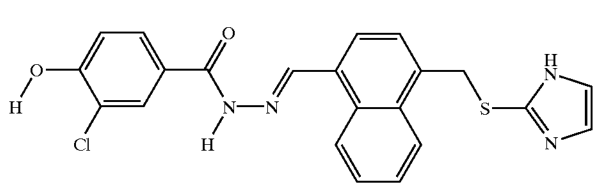 | 437 | 2.68 |

-continued

| Ex No. | Structure | HPLC-MS m/z (M + 1) | HPLC-MS R$_t$ (minutes) |
|---|---|---|---|
| 846 | 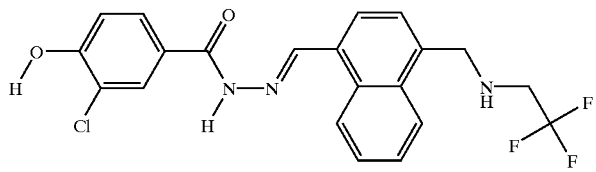 | 436 | 7.88 |
| 847 | 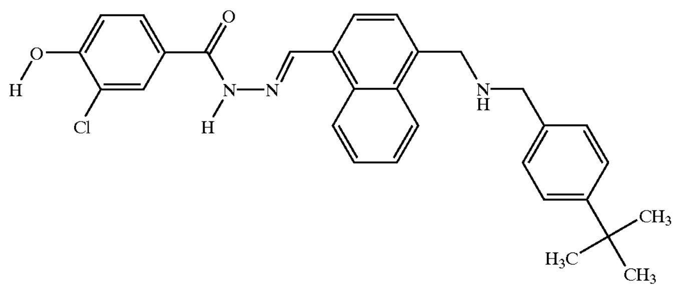 | 500 | 14.12 |
| | | (METHOD A) | (METHOD A) |
| 848 | 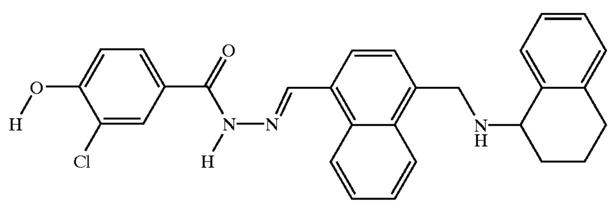 | 484 | 9.80 |
| 849 | 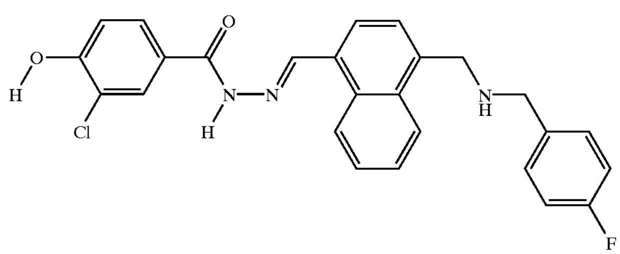 | 462 | 9.38 |
| 850 | 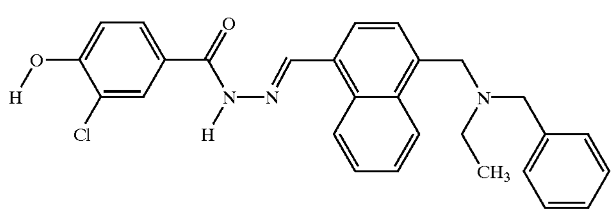 | 472 | 9.37 |
| 851 | 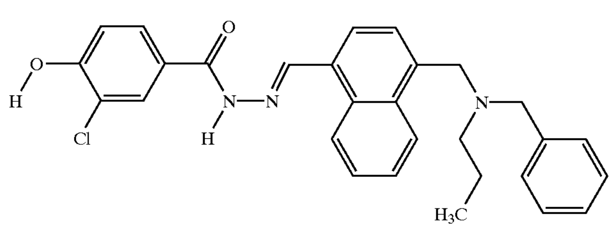 | 486 | 9.55 |

| Ex No. | Structure | HPLC-MS m/z (M + 1) | HPLC-MS R$_t$ (minutes) |
|---|---|---|---|
| 852 | 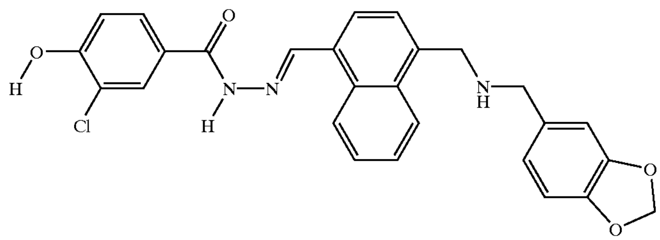 | 488 | 9.18 |
| 853 | 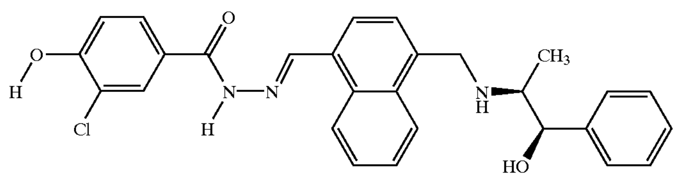 | 488 | 9.37 |
| 854 | 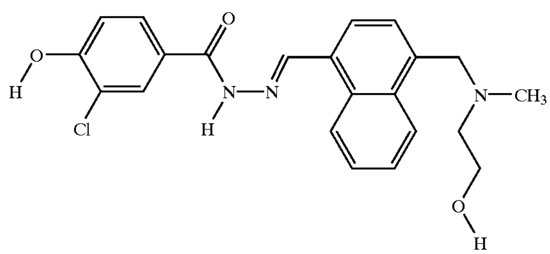 | 412 | 7.83 |
| 855 | 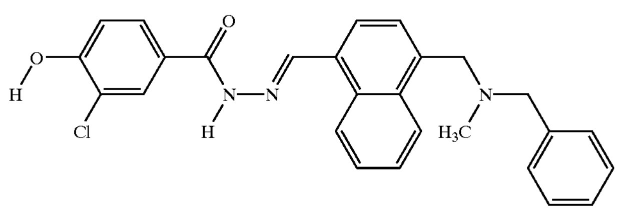 | 458 | 9.30 |
| 856 | 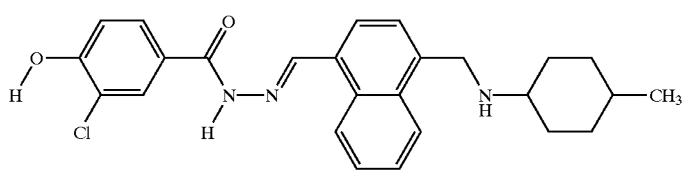 | 450 | 9.62 |
| 857 | 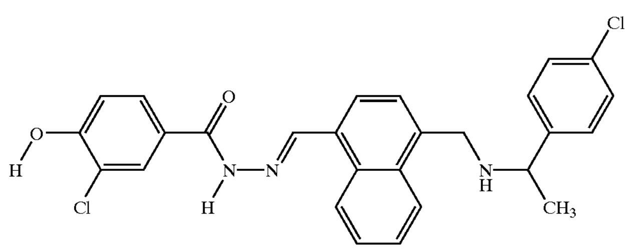 | 492 | 10.03 |
| 858 | 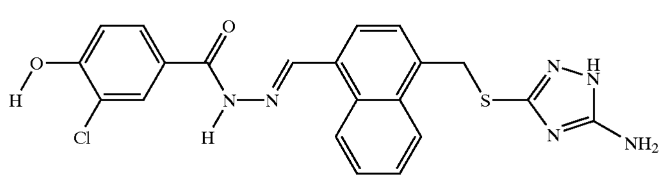 | 453 | 8.90 |

-continued

| Ex No. | Structure | HPLC-MS m/z (M + 1) | HPLC-MS R_t (minutes) |
| --- | --- | --- | --- |
| 859 | 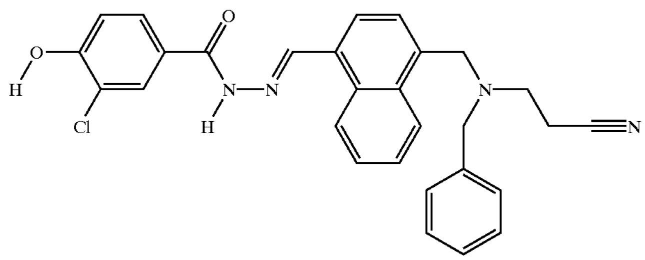 | 497 | 10.73 |
| 860 | 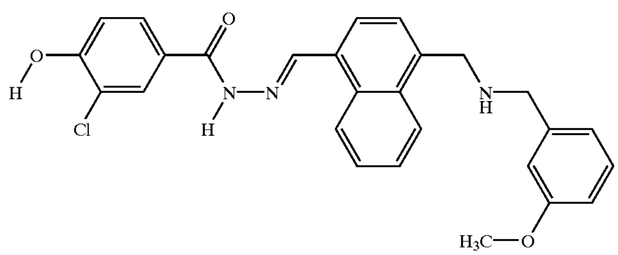 | 474 | 9.15 |
| 861 | 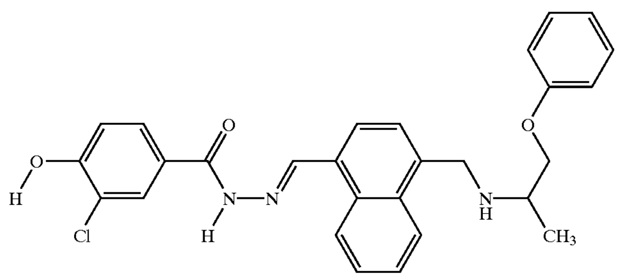 | 488 | 9.55 |
| 862 | 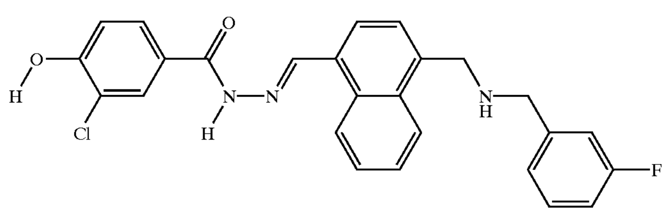 | 462 | 9.27 |
| 863 | 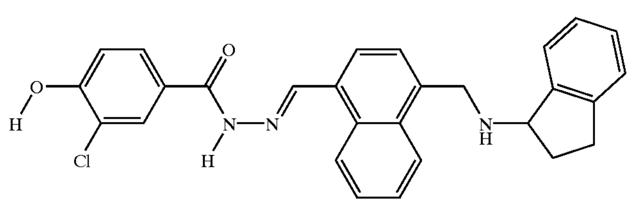 | 470 | 9.43 |
| 864 | 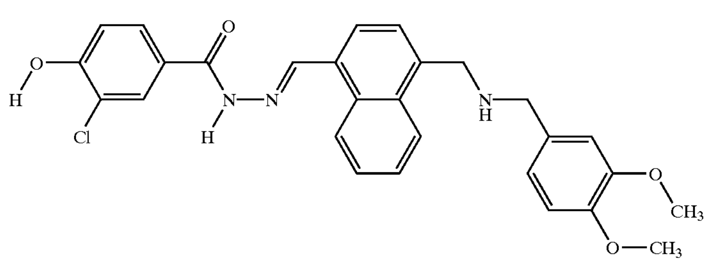 | 504 | 8.98 |

-continued

| Ex No. | Structure | HPLC-MS m/z (M + 1) | HPLC-MS R$_t$ (minutes) |
|---|---|---|---|
| 865 | 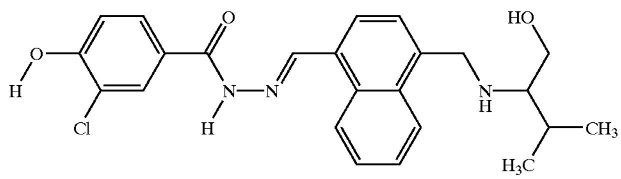 | 440 | 8.35 |
| 866 | 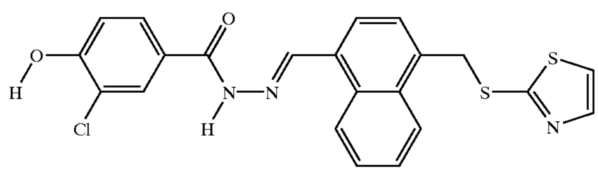 | 454 | 12.90 |
| 867 | 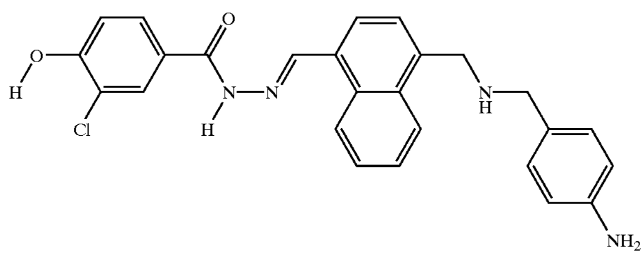 | 459 | 7.63 |
| 868 | 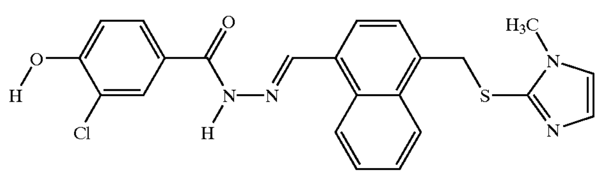 | 451 | 8.45 |
| 869 | 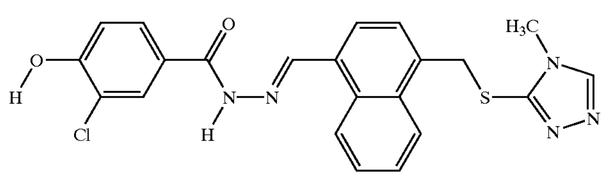 | 452 | 9.31 |
| 870 | 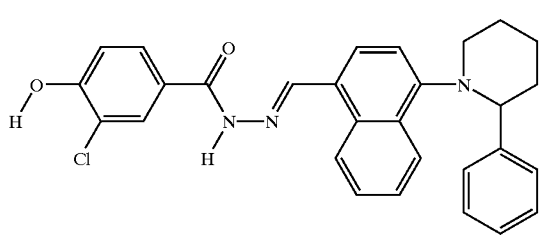 | 498 | 9.65 |
| 871 | 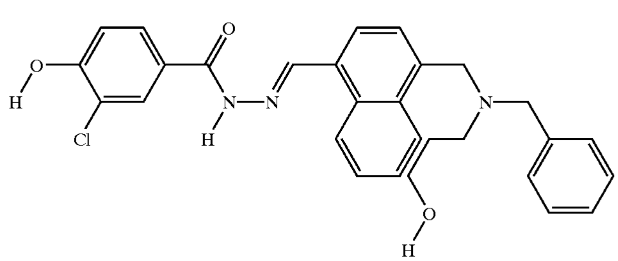 | 502 | 9.03 |

-continued

| Ex No. | Structure | HPLC-MS m/z (M + 1) | HPLC-MS $R_t$ (minutes) |
|---|---|---|---|
| 872 | 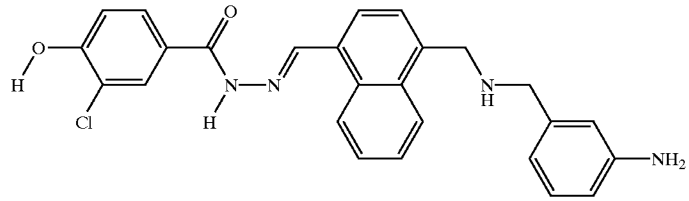 | 459 | 7.60 |
| 873 | 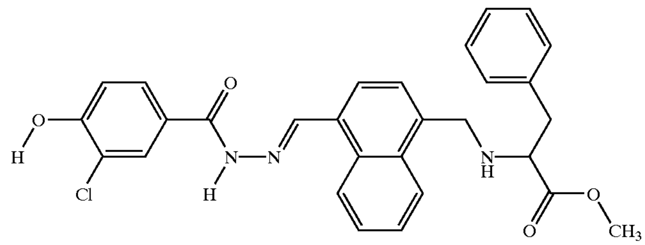 | 516 | 9.33 |

EXAMPLE 874

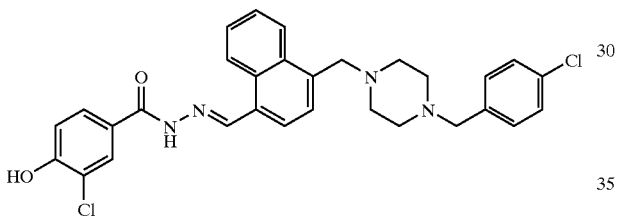

$^1$H NMR (DMSO-D6) d 2.37 (m, 8H), 3.44 (s, 2H), 3.90 (s, 2H), 7.10 (d, J=8.5 Hz, 1H), 7.30 (d, J=8.5 Hz, 2H), 7.37 (d, J=8.5 Hz, 2H), 7.55 (d, J=7.4 Hz, 1H), 7.67 (m, 2H), 7.81 (d, J=8.7 Hz, 1H), 7.86 (d, J=7.3 Hz, 1H), 8.02 (d, J=1.8 Hz, 1H), 8.36 (dd, J=1.7, 7.0 Hz, 1H), 8.83 (d, J=8.0 Hz, 1H), 9.08 (s, 1H), 10.99 (s, 1H), 11.78 (s, 1H). MS (APCI, pos.): 547.1, 550.1.

EXAMPLE 875

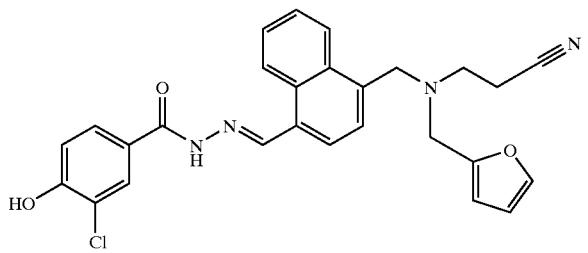

$^1$H NMR (DMSO-D$_6$) d 2.66–2.75 (m, 4H), 3.69 (s, 2H), 4.06 (s, 2H), 6.36 (m, 1H), 6.40 (m, 1H), 7.06 (d, J=8.5 Hz, 1H), 7.51–7.66 (m, 4H), 7.77 (d, J=8.0 Hz, 1H), 7.83 (d, J=7.1 Hz, 1H), 7.98 (s, 1H), 8.26 (d, J=8.5 Hz, 1H), 8.80 (d, J=8.5 Hz, 1H), 9.04 (s, 1H), 10.94 (s, 1H), 11.77 (s, 1H). MS (APCI, pos.): 485.1, 487.1.

General Procedure for Examples 876 to 877

The compounds were prepared as single entities according to the following equation Resin—[Building block 1]→

Resin—[Building block 1]—[Building block 2]→

Resin—[Building block 1]—[Building block 2]—[Building block 3]→

Resin—[Building block 1]—[Building block 2]—[Building block 3]—[Building block 4]

and were simultaneously deprotected and cleaved from the resin with 50% trifluoroacetic acid in dichloromethane to give the desired compounds as individual entities according to the following formula

[Building block 1]—[Building block 2]—[Building block 3]—[Building block 4].

The following compounds were prepared as single entities by parallel synthesis on a solid support. Preparation of Resin—[Building block 1]—[Building block 2] was done manually, whereas the attachment of [Building block 3], attachment of [Building block 4] and cleavage from the resin were performed on an Advanced ChemTech Model 384 HTS.

The starting resin, Resin—[Building block 1], was prepared as described above.

The resin used was a polystyrene resin with a Wang linker and the substitution capacity was 0.9 mmol/g.

All compounds are based on successive attachment of [Building block 2] and [Building block 3] to Resin—[Building block 1] in a combinatorial way using a nucleophilic substitution reaction followed by an acylation reaction attaching [Building block 4] according to the following formulae, which are included in the general formula II:

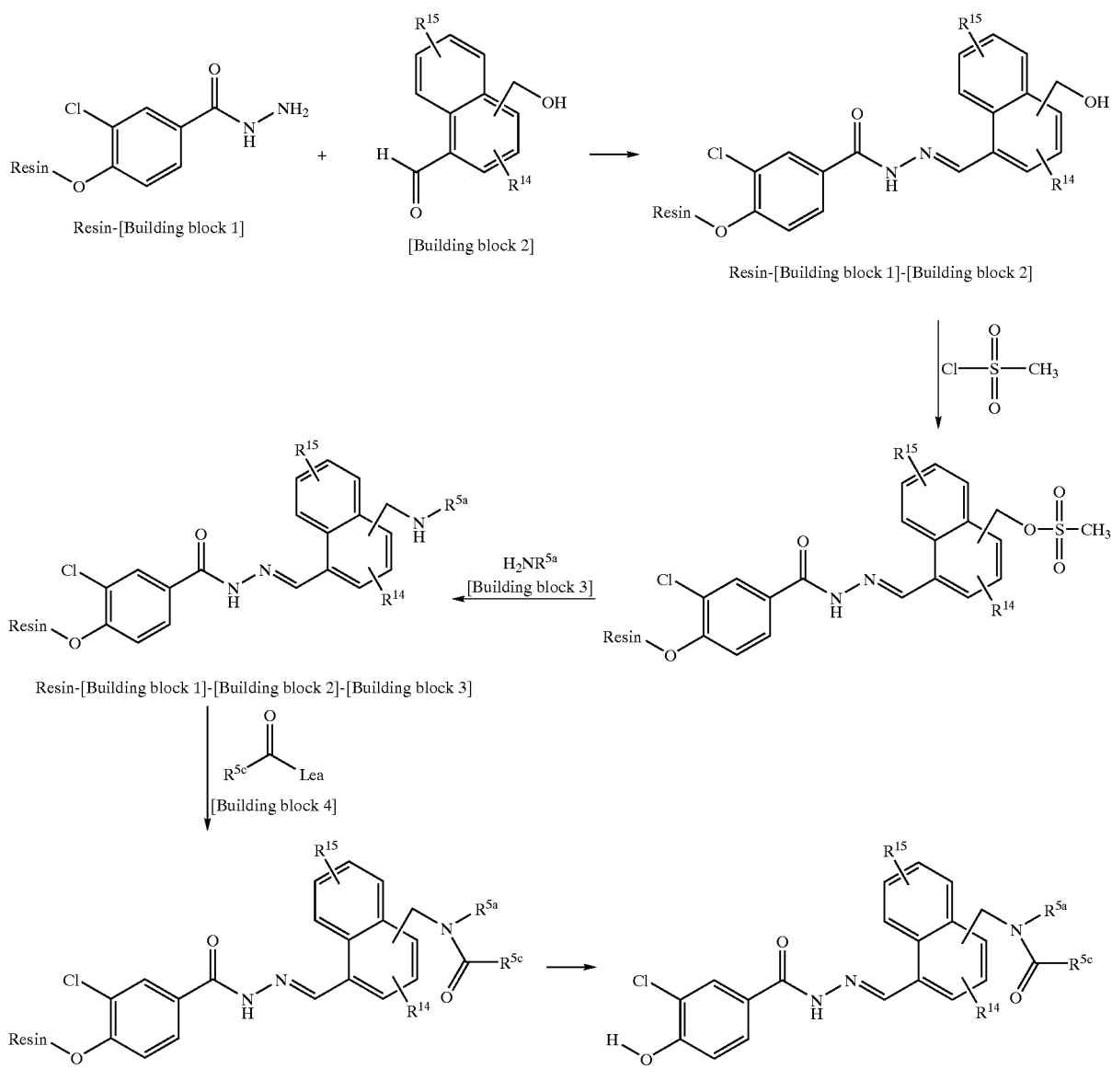
wherein $R^{5a}$, $R^{14}$, $R^{15}$ are as defined for formula I and $R^{5c}$ is
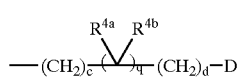
where $R^{4a}$, $R^{4b}$, c, q, d, and D are as defined for formula I or
—D' where —D' is defined as a subset of —D that contains an activated carboxylic acid capable of reacting as an electrophile and
Lea is a leaving group such as chloro, bromo, iodo, carboxylate,
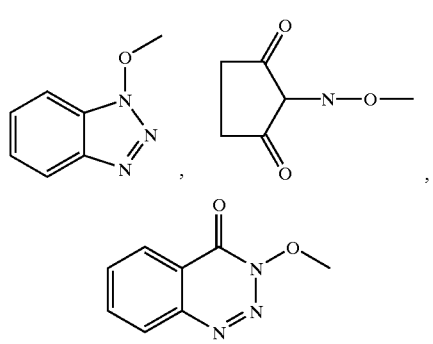

The following resin, here depicted as Resin—[Building block 1] was used:

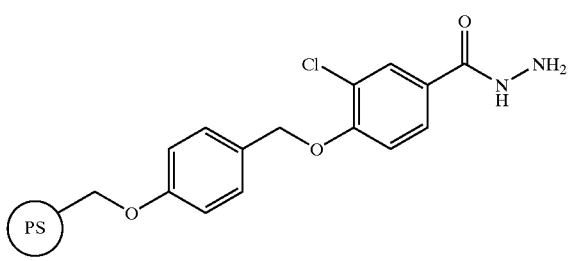

where PS is polystyrene. In the following "Resin" is the polystyrene resin with the Wang linker:

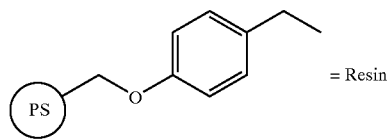

The following building blocks were used:

[Building block 2]:

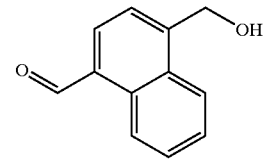

4-Hydroxymethylnaphthalene-1-carbaldehyde

| [Building block 3]: | | |
|---|---|---|
| 2-Thiophenemethylamine 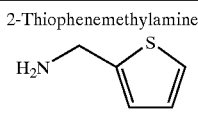 | 5-Methyl-2-furanmethylamine 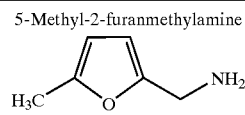 | L-Methionine ethyl ester 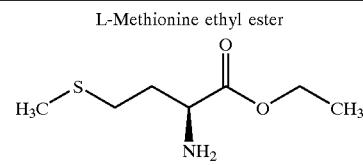 |
| 2-(Aminomethyl)pyridine 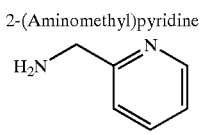 | 4-(2-Aminoethyl)pyridine 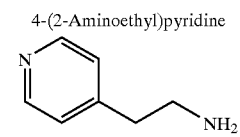 | 3-Aminopentane 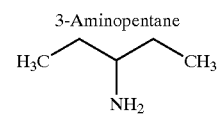 |
| Furfurylamine 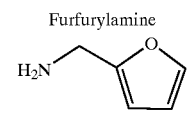 | 2-Methoxyisopropylamine 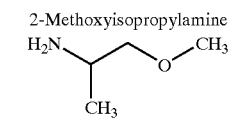 | Cyclopropylamine 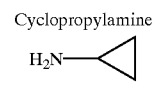 |
| Glycine 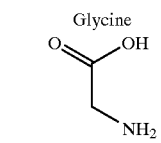 | 2-Furanylmethylamine 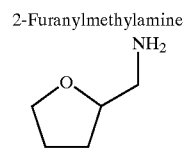 | N,N-Dimethylethylenediamine 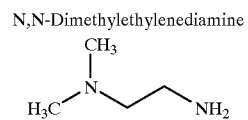 |
| Ethylamine 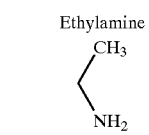 | Methylamine 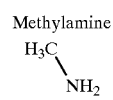 | Propylamine 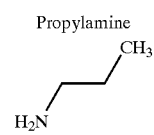 |
| Isopropylamine 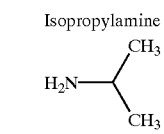 | Isopentylamine 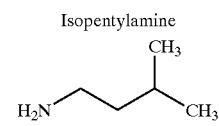 | Cyclopentylamine 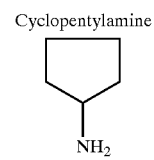 |
| Cyclopropylmethylamine 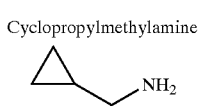 | Cyclobutylamine 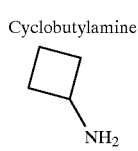 | Thiophene-2-ethylamine 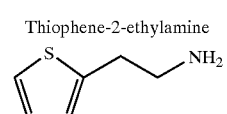 |

[Building block 3]:

Glutamic Acid di tert butylester 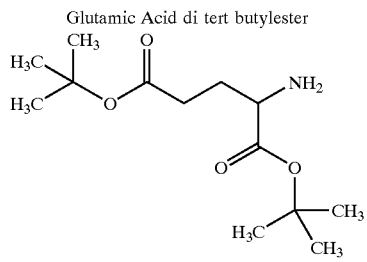

2,2,2-Trifluoroethylamine 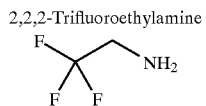

Tetrahydro-3-thiophenamine 1,1-dioxide 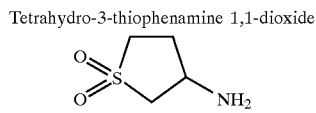

[Building block 4]:

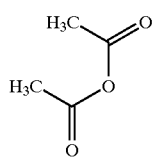

Acetic anhydride

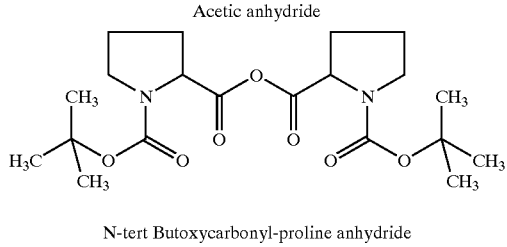

N-tert Butoxycarbonyl-proline anhydride

Preparation of Resin—[Building Block 1]

This resin was prepared as described above.

Preparation of Resin—[Building Block 1]—[Building Block 2]

This resin was prepared as described above.

EXAMPLE 876

N-{4-[(3-Chloro-4-hydrobenzoyl)-hydrazonomethyl]naphtylmethyl}N-isobutylprolinamine

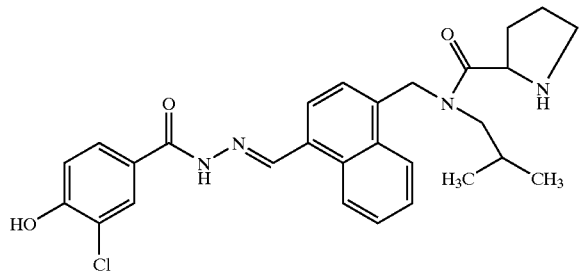

The resin bound 3-chloro-4-hydroxybenzoic acid (4-hydroxymethylnaphthylmethylene)hydrazide (Resin—[Building block 1]—[Building block 2]) (50 mg, ~50 µmoles) was swelled in $CH_2Cl_2$ (0.5 mL) for 15 min, then washed twice with $CH_2Cl_2$ (0.5 mL). 0.4 mL $CH_2Cl_2$ and 0.4 mL diisopropylethylamine were subsequently added and the suspension was cooled to 0° C. Methanesulfonylchloride (0.1 mL) was dissolved in $CH_2Cl_2$ (0.3 mL) and added to the suspension. The mixture was allowed to react at 0° C. for 30 min, then at 25° C. for 1 hour. The resin was isolated by filtration and washed with $CH_2Cl_2$ (2×0.5 mL) and DMSO (0.5 mL). 0.5 mL DMSO was added to the resin followed by isobutylamine (50 µL) and diisopropylethylamine (100 µL). The mixture was shaken at 25° C. for 16 hours. The solvent was removed by suction and the resin was washed with DMSO (2×0.5 mL) and THF (3×0.5 mL). To a solution of N-tert-butoxycarbonyl-proline (46 mg, 0.21 mmol) in THF (0.5 mL) was added diisopropylcarbodiimide (16 µL, 0.2 mmol). This solution was allowed to react at 25° C. for 10 minutes and then added to the resin. The suspension was shaken at 25° C. for 16 hours after which the resin was isolated by suction and washed with THF (3×0.5 mL), DMF (3×0.5 mL) THF (3×0.5 mL), $CH_3OH$ (0.5 mL), $CH_2Cl_2$ (0.5 mL), $CH_3OH$ (0.5 mL), $CH_2Cl_2$ (4×0.5 mL). The compound was cleaved from the resin by shaking for 1 hour at 25° C. with a 50% solution of trifluoroacetic acid in $CH_2Cl_2$ (1 mL). The mixture was filtered and the resin was extracted with acetonitrile (1 mL). The combined extracts were concentrated in vacuo. The residue was redissolved in a mixture of $CH_3OH$ (0.5 mL) and acetonitrile (0.5 mL) and concentrated in vacuo to give the title compound.

HPLC-MS (METHOD B): $R_t$=3.90 min; m/z=507 (M+1).

EXAMPLE 877

3-Chloro-4-hydroxybenzoic Acid ((4-(4-Trifluoromethoxybenzylamino)methyl)naphthylmethylene)hydrazide

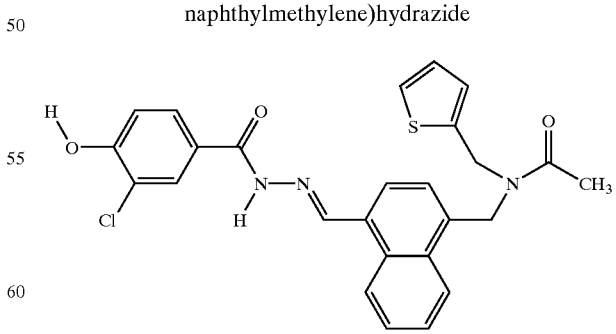

Resin bound 3-chloro-4-hydroxybenzoic acid (4-hydroxymethylnaphthylmethylene)hydrazide (resin—[building block 1]—[building block 2]) (50 mg) was swelled in a 1:1 mixture of $CH_2Cl_2$ and N-methyl-2-pyrrolidone (0.5 mL) for 15 minutes and then washed with $CH_2Cl_2$ (3×0.5 mL). 800 µL of a 1:1 mixture of $CH_2Cl_2$ and diisopropylethylamine was added to the resin which subsequently was cooled to −3° C. A solution of 100 µL methanesulfonylchloride dissolved in 300 µL was added and allowed to react at −3° C for 30 minutes then at 25° C. for 1 hour. Filtration of the resin was followed by washing with $CH_2Cl_2$ (2×1 mL) and N-methyl-2-pyrrolidone (2×0.5 mL). 600 µL of a solution of 4-trifluoromethoxybenzylamine (45.8 mg, 0.24 mmol, 0.4M) and KI (10 mg, 0.06 mmol, 0.1M) in N-methyl-2-pyrrolidone (0.5 mL) and diisopropylethylamine (0.1 mL) was added and allowed to react at 25° C. for 16 hours. The resin was isolated by filtration and washed successively with N-methyl-2-pyrrolidone (5×0.5 mL) and THF (3×0.5 mL). 600 µL of a solution of acetic anhydride (120 µL, 130 mg, 1.27 mmol) in THF (480 µL) was added to the resin. The mixture was allowed to react at 25° C. for 16 hr. The resin was filtered and washed successively with THF (2×0.8 mL), $CH_3OH$ (0.8 mL), $CH_2Cl_2$ (0.8 mL), $CH_3OH$ (0.8 mL) and $CH_2Cl_2$ (3×0.8 mL). The compound was cleaved from the resin by shaking for 1 hour at 25° C. with a solution of 50% trifluoroacetic acid in $CH_2Cl_2$ (1 mL). The mixture was filtered and the resin was extracted with acetonitrile (1 mL). The combined extracts were concentrated in vacuo. The residue was redissolved in a mixture of $CH_3OH$ (0.5 mL) and acetonitrile (0.5 mL) and concentrated in vacuo to give the title compound.

HPLC-MS (METHOD B): $R_t$=6.42 min; m/z=492 (M+1).

EXAMPLES 877 TO 880

A library of compounds of all the possible combinations of the above listed building blocks ([building block 1], [building block 2], [building block 3] and acetic anhydride as [building block 4]) was prepared in parallel as individual entities analogously to the previous example on an Advanced ChemTech Model 384 HTS using the following ChemFile to control the operation of the synthesizer. The compounds are all expected to be present in the respective wells.

A suspension of the resin bound 3-chloro-4-hydroxybenzoic acid (4-hydroxymethyl-naphthylmethylene)hydrazide (resin—[building block 1]—[building block 2]) (50 mg) in a 1:1 mixture of $CH_2Cl_2$, and N-methyl-2-pyrrolidone (0.5 mL) is equally distributed in the wells in the synthesizer prior to the initialization of the device.

ChemFile C:\ACT_1328\MAIN.CHM
1 REM Nucleophilic displacement of benzylic alcohol
2 REM via mesylation
3
4
5 REM Dipense resin bound benzylic alchohol to wells
6
7
8 REM Setup Diluter1=DCM, D2=NMP (N-methyl-2-pyrrolidone), D3=NMP, D4=DCM
9 REM Adjust pressure
10 REM Add 100 mL DIEA/DCM 1:1 mixture to Reagent1
11 REM Add 70 mL MsCl/DCM 1:3 mixture to Reagent2
12 REM Add 100 mL TFA/DCM 1:1 mixture to Reagent3
13 REM Add 100 mL CH3CN to Reagent4
14 REM Nitrogen for cooling
15
16 Pause
17 REM Initialising.
18
19 REM Subroutine Empty1_72_3 min is called twice to remove DCM/NMP from dispensed resin
20 Go to ChemFile MTY72_3M.CHM, line 1
21 Go to ChemFile MTY72_3M.CHM, line 1
22
23 Flush Arm1 with Flush Diluter1 and Flush Diluter 2, Arm2 with Flush Diluter 3 and with Flush Diluter 4
24
25 REM Washing with DCM, 3 times
26 Dispense System Fluid Disdu1_4* 500 ul to RB1_1to96[1–72]
27 Mix "RB1_1to96" for 3.00 minutes at 300 rpm(s) and wait.
28 REM Subroutine Empty1_72_3 min
29 Go to ChemFile MTY72_3M.CHM, line 1
30 Repeat from step 26, 2 times
31
32 REM Adding DCM/DIEA mixture from Reagent1
33 Transfer 800 ul from REAGENT_1[1](DCM/DIEA) to RB1_1to96[1–72] using Flush Diluter1
34 Mix "RB1_1to96" for 1.00 minutes at 300 rpm(s) and wait.
35 Set Temperature of rack "RB1_1to96" to −3.0 degrees Celsius and wait for Temperature to reach setpoint
36 Mix "RB1_1to96" for 1.00 minutes at 300 rpm(s) and wait.
37 REM Ensure complete cooling
38 Wait for 15.000 minute(s)
39
40 REM Adding mesylchloride
41 Transfer 400 ul from REAGENT_2[1](MsCl/DCM) to RB1_1to96[1–72] using Flush Diluter1
42 REM Reacts 30 min @ −3° C.
43 Mix "RB1_1to96" for 1.00 minutes at 300 rpm(s) and wait.
44 Wait for 4.000 minute(s)
45 Repeat from step 43, 5 times
46
47 REM Reacts 60 min @ 25° C.
48 Set Temperature of rack "RB1_1to96" to 25.0 degrees Celsius and wait for Temperature to reach setpoint
49 Mix "RB1_1to96" for 1.00 minutes at 300 rpm(s) and wait.
50 Wait for 4.000 minute(s)
51 Repeat from step 46, 11 times
52
53 REM Subroutine Empty1_72_3 min
54 Go to ChemFile MTY72_3M.CHM, line 1
55
56 REM Initiate washing procedure, 2XDCM
57 Dispense System Fluid Disdu1_4* 1000 ul to RB1_1to96[1–72]
58 Mix "RB1_1to96" for 3.00 minutes at 300 rpm(s) and wait.
59 Go to ChemFile MTY72_3M.CHM, line 1
60 Repeat from step 57, 1 times 61
62 REM NMP wash
63
64 Dispense System Fluid Disdu2_3* 500 ul to RB1_1to96[1–72]
65 Mix "RB1_1to96" for 5.00 minutes at 300 rpm(s) and wait.
66 Go to ChemFile MTY72_3M.CHM, line 1
67
68 Go to ChemFile MTY72_3M.CHM, line 1
69 Repeat from step 64, 1 times
70
71 REM Make sure that nucleophiles are dissolved and ready for addition
72 Pause
73
74 Dispense Sequence C:\ACT_1328\R2-A.DSP with 600 ul to RB1_1to96 rack using Flush Diluter 2
75 REM Nucleophiles react @ 25° C. for 16 hr
76 Mix "RB1_1to96" for 1.00 minutes at 300 rpm(s) and wait.
77 Wait for 4.000 minute(s)
78 Repeat from step 76, 11 times
79 Repeat from step 76, 15 times
80
81 REM End of nucleophilic substitution reaction
82 Go to ChemFile MTY72_3M.CHM, line 1
83 Go to ChemFile MTY72_3M.CHM, line 1
84
85 REM Commence washing procedure
86 Dispense System Fluid Disdu2_3* 500 ul to RB1_1to96[1–72]
87 Mix "RB1_1to96" for 10.00 minutes at 300 rpm(s) and wait.
88 Go to ChemFile MTY72_3M.CHM, line 1
89 Go to ChemFile MTY72_3M.CHM, line 1
90 Repeat from step 86, 4 times
91
92 REM Change systemfluids:
93 REM*Diluter2: THF
94 REM*Diluter3: MeOH
95 Pause
96
97 Flush Arm1 with Flush Diluter1 and Flush Diluter 2, Arm2 with Flush Diluter 3 and Flush Diluter 4
98 REM THF wash 3 times
99 Dispense System Fluid Flush Diluter 2 500 ul to RB1_1to96[1–72]
100 Mix "RB1_1to96" for 10.00 minutes at 300 rpm(s) and wait.
101 Go to ChemFile MTY72_3M.CHM, line 1
102 Go to ChemFile MTY72_3M.CHM, line 1
103 Repeat from step 99, 2 times
104 Go to ChemFile Acylation.CHM, line 1
105 Go to ChemFile WASH.CHM, line 1
106 Go to ChemFile Cleavage.CHM, line 1
107 REM The End The following chemfile is called to acylate the amines:
ChemFile C:\ACT_1328\Acetyl.CHM
1 REM Acetylation procedure
2 REM Charge REAGENT_5 with 100 mL Acetic anhydride/THF 1:4 v/v
3 REM*Diluter2: THF
4 REM Addition of acylation reagent
5 Dispense Sequence C:\R3-A.DSP with 600 μL to RB1to96 rack using Flush Diluter 2
6 Mix for 1.00 minutes at 300 rpm(s)
7 Wait for 5.000 minute(s)
8 Repeat from step 6, 60 times
9 Go to ChemFile MTY72_3M.CHM, line 1
10 Go to ChemFile MTY72_3M.CHM, line 1
11 Return The following chemfile is called to wash the resin bound products:
ChemFile C:\ACT_1328\WASH.CHM
1 REM Washing procedure
2 REM Systemfluids:
3
4 REM*Diluter2: THF
5 REM*Diluter3: MeOH
6
7 Flush Arm1 with Flush Diluter1 and Flush Diluter 2, Arm2 with Flush Diluter 3 and Flush Diluter 4
8 REM THF wash 3 times
9 Dispense System Fluid Flush Diluter 2 800 ul to RB1_1to96[1–72]
10 Mix "RB1_1to96" for 10.00 minutes at 300 rpm(s) and wait.
11 Go to ChemFile MTY72_3M.CHM, line 1
12 Go to ChemFile MTY72_3M.CHM, line 1
13 Repeat from step 9, 2 times
14
15 REM Alternating MeOH/DCM wash, 2 cycles
16 Dispense System Fluid Flush Diluter 3 800 ul to RB1_1to96[1–72]
17 Mix "RB1_1to96" for 3.00 minutes at 300 rpm(s) and wait.
18 Go to ChemFile MTY72_3M.CHM, line 1
19
20 Dispense System Fluid Disdu1_4* 800 ul to RB1_1_1to96[1–72]
21 Mix "RB1_1to96" for 10.00 minutes at 300 rpm(s) and wait.
22 Go to ChemFile MTY72_3M.CHM, line 1
23 Go to ChemFile MTY72_3M.CHM, line 1
24
25 Repeat from step 16, 1 times
26
27 Dispense System Fluid Disdu1_4* 800 ul to RB1_1to96[1–72]
28 Mix "RB1_1to96" for 10.00 minutes at 300 rpm(s) and wait.
29 Go to ChemFile MTY72_3M.CHM, line 1
30 Repeat from step 117, 1 times
31
32 REM Washing procedure has ended
33 Return The following chemfile is called to cleave the products from the resin:

ChemFile C:\ACT_1328\Cleavage.CHM
1 REM Setup for cleavage:
2 REM*Cleavage vials
3 REM*Lower pressure
4 REM*Add 100 mL TFA/DCM 1:1 mixture to Reagent3
5 REM*Add 100 mL CH3CN to Reagent4
6 Pause
7
8 REM Adding cleavage solution, 1 hr
9 Transfer 1000 ul from REAGENT_3[1](TFA/DCM) to RB1_1to96[1–72] using Flush Diluter1
10 Mix "RB1_1to96" for 1.00 minutes at 300 rpm(s) and wait.
11 Wait for 4.000 minute(s)
12 Repeat from step 133, 11 times
13 REM PULSE EMPTY!
14 Go to ChemFile PULSEMP1.CHM, line 1
15
16 REM Washing with CH3CN
17 Transfer 500 ul from REAGENT_4[1](CH3CN) to RB1_1to96[1–72] using Flush Diluter1
18 Mix "RB1_1to96" for 10.00 minutes at 300 rpm(s) and wait.
19 REM PULSE EMPTY!
20 Go to ChemFile PULSEMP1.CHM, line 1
21 Return The following chemfile is called to empty the wells of the reaction block.:

ChemFile C:\ACT_1328\MTY72_3M.CHM Page 1
1 REM Subroutine Empty1_72_3 min
2 Empty RB1_1to96 for 5.000 minute(s)
3 Return The following chemfile is called to empty the wells of the reaction block into the cleavage vials containing the final product in a controlled manner.

ChemFile C:\ACT_1328\PULSEMP1.CHM Page 1
1 Empty RB1_1to96 for 1 second(s)
2 Wait for 4 second(s)
3 Repeat from step 1, 11 times
4 Empty RB1_1to96 for 5.000 minute(s)
5 Return Dispense sequence C:\ACT_1328\R2-A.DSP is a subroutines that control the combinatorial addition of the amines into the reaction block in the syntheziser.

Dispense sequence C:\ACT_1328\R3-A.DSP is a subroutines that control the combinatorial addition of the acylating agents into reaction block in the syntheziser.

Examples of compounds from this library were characterised by HPLC-MS (molecular mass & retention time) including the following examples 878 to 881.

| Ex No. | Structure | HPLC-MS (METHOD B) m/z (M + 1) | HPLC-MS (METHOD B) R$_t$ (minutes) |
|---|---|---|---|
| 878 | 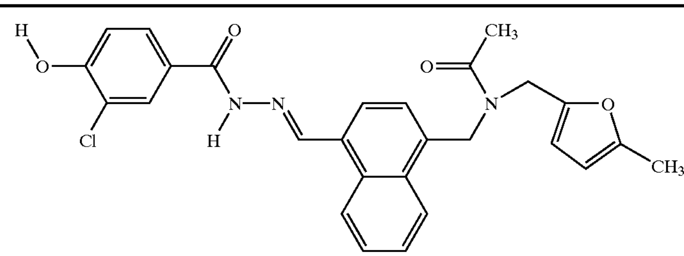 | 490 | 6.22 |
| 879 | 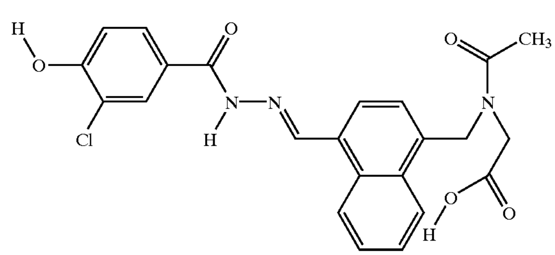 | 454 | 1.05 |
| 880 | 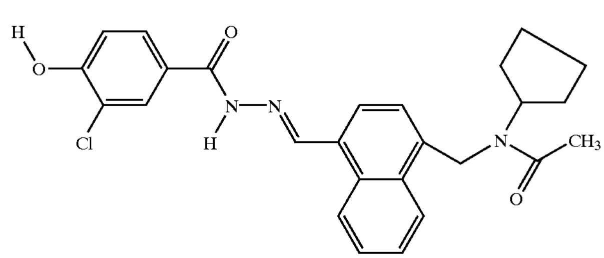 | 464 | 6.33 |

| Ex No. | Structure | HPLC-MS (METHOD B) m/z (M + 1) | HPLC-MS (METHOD B) R$_t$ (minutes) |
|---|---|---|---|
| 881 | 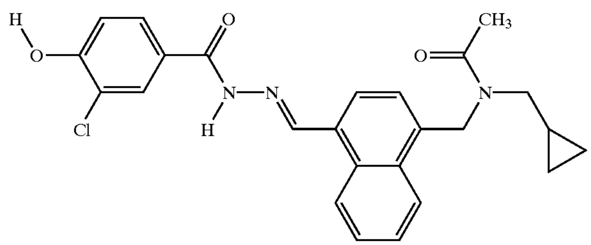 | 450 | 5.30 |

EXAMPLE 882

N-{4-[3-Chloro-4-hydroxybenzoyl)-hydrazonemethyl]-1-naphthyl}methyl iso-Propyl Amide

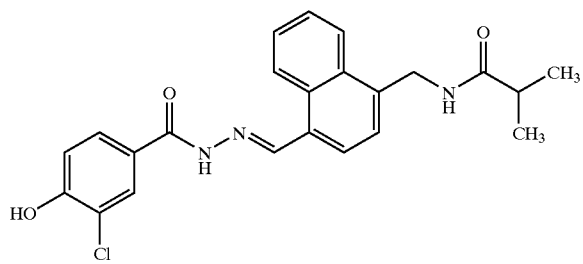

Preparation of N-4-Formylnaphthylmethyl Isopropyl Amide

A mixture of 4-bromomethyl-1-naphthaldehyde ethyleneacetal (447 mg, 1.52 mmol) and NaN$_3$ (221 mg, 3.4 mmol) in 10 mL DMF was warmed up to 100° C. and stirred for 30 min. Solution turned orange. The reaction was filtered and the clear solution was concentrated to 391 mg of yellow oil. This oil (249 mg) together with triphenylphosphine (260 mg, 0.99 mmol) was dissolved in 10 mL of THF. The reaction mixture was left overnight followed by the addition of water. Ninhydrin test revealed the formation of an amine. This amine was extracted into ethyl acetate layer, dried to give an oil. This oil was dissolved in CH$_2$Cl$_2$, EDC, DMAP and 2-methylpropionic acid were added. The reaction mixture was left for 2 days. Column chromatography eluted with ethyl acetate afforded the amide. Deprotection of diethyleneacetal was achieved by 10% HCl in THF to give the title compound (50 mg).

$^1$H NMR (CDCl$_3$): d 1.2 (d, 6H), 2.4 (m, 1H), 4.9 (d, 2H), 6.1 (b, 1H), 7.5 (d, 1H), 7.6 (m, 2H), 7.8 (d, 1H), 8.0 (d, 1H), 9.2 (d, 1H), 10.3 (s, 1H).

The title compound was prepared similarly as described above.

$^1$H NMR (DMSO-D$_6$): d 1.0 (d, 6H), 2.4 (m, 1H), 4.7 (s, 2H), 7.0 (d, 1H), 7.4 (d, 1H), 7.6 (m, 2H), 7.7 (d, 1H), 7.8 (d, 1H), 7.9 (s, 1H), 8.1 (d, 1H), 8.3 (s, 1H), 8.8 (d, 1H), 9.0 (s, 1H), 10.9 (s, 1H), 11.7 (s, 1H); ms (APCI negative); 422.

EXAMPLE 883

4-[3-Chloro-4-hydroxybenzoyl)-hydrazonomethyl]-1-naphthylmethyl iso-Propylsulfoxide

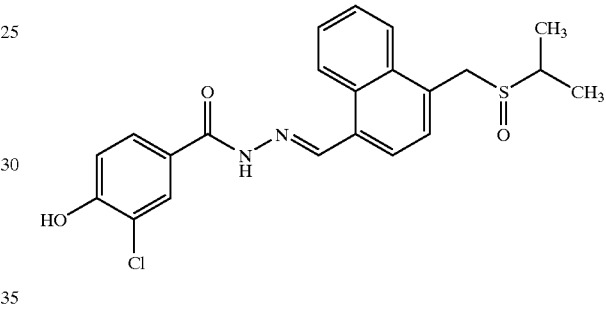

4-Ethyleneacetal-4-formyl-naphthylmethyl iso-Propylthioether:

A mixture of 4-bromomethyl naphthaldehyde ethyleneacetal (232 mg, 0.79 mmol) and iso-propyl thioalcohol (0.08 mL, 0.81 mmol) and 0.12 mL of triethylamine was left at room temperature for 12 h. The reaction mixture was concentrated and the residue was purified by column chromatography eluted with ethyl acetate/hexane (1/5) to afford 93 mg of the desired product as pale radish oil.

$^1$H NMR (CDCl$_3$): d 1.3 (d, 6H), 2.9 (m, 1H), 4.2 (m, 6H), 6.5 (s, 1H), 7.4 (d, 1H), 7.6 (m, 2H), 7.7 (d, 1H), 8.2 (m, 1H).

4-Ethyleneacetal-naphthylmethyl iso-Propylsulfoxide:

To a mixture of the above 4-ethyleneacetal-naphthylmethyl iso-propylthioether (79 mg, 0.27 mmol) in 5 mL of dichloromethane at −78° C. was added m-chloro perbenzoic acid (82 mg, 55% purity, 0.28 mmol). The reaction mixture was left for 1 hour and 40 min. Then, NaHSO$_3$ solution was added followed by NaHCO$_3$. The mixture was extracted with water and dichloromethane. The organic layer was combined and dried over MgSO$_4$. Solvent was removed and the residue was purified by column chromatography eluted with ethyl acetate to yield 56 mg of desired product as an oil.

$^1$H NMR (CDCl$_3$): d 1.3 (d, 3H), 1.4 (d, 3H), 2.7 (m, 1H), 4.2 (m, 4H), 4.4 (dd, 2H), 6.5 (s, 1H), 7.5 (d, 1H), 7.6 (m, 2H), 7.7 (d, 1H), 8.1 (m, 1H), 8.2 (m, 1H). This compound was hydrolyzed in aqueous 10% HCl in THF for 1 hr to give the corresponding aldehyde.

4-[3-Chloro-4-hydroxybenzoyl)-hydrazonomethyl]-1-naphthylmethyl iso-Propylsulfoxide:

The title compound was prepared similarly as described above.

¹H NMR (DMSO-D₆): d 1.3 (dd, 6H), 3.0 (m, 1H), 4.3 (d, 1H), 4.7 (d, 1H), 7.1 (d, 1H), 7.6 (m, 3H), 7.8 (d, 1H), 7.9 (d, 1H), 8.0 (s, 1H), 8.2 (d, 1H), 8.8 (d, 1H), 9.1 (s, 1H), 11.0 (s, 1H), 11.8 (s, 1H); ms (APCI negative); 427, 337.

EXAMPLE 884

4-[3-Chloro-4-hydroxybenzoyl)-hydrazonomethyl]-1-naphthylmethyl iso-Propylsulfone

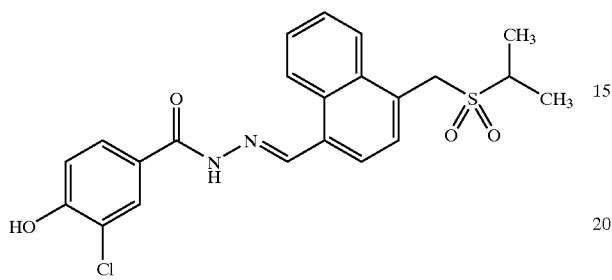

Similarly, the title compound was prepared.

¹H NMR (DMSO-D₆): d 1.3 (d, 6H), 3.4 (m, 1H), 5.0 (s, 2H), 7.0 (d, 1H), 7.6 (m, 3H), 7.7 (d, 1H), 7.9 (d, 2H), 8.2 (d, 1H), 8.7 (d, 1H), 9.0 (s, 1H), 10.9 (s, 1H), 11.8 (s, 1H); ms (APCI negative); 443, 336.

EXAMPLE 885

4-[3-Chloro-4-hydroxybenzoyl)-hydrazonomethyl]-1-naphthylmethyl iso-Propylsulfide

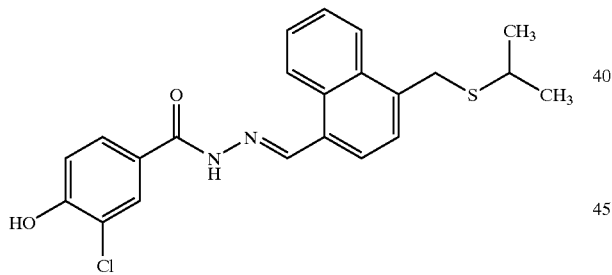

Similarly, the title compound was prepared.

Further examples of the invention are the following compounds:

EXAMPLE 886

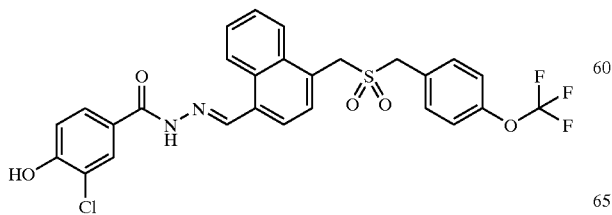

EXAMPLE 887

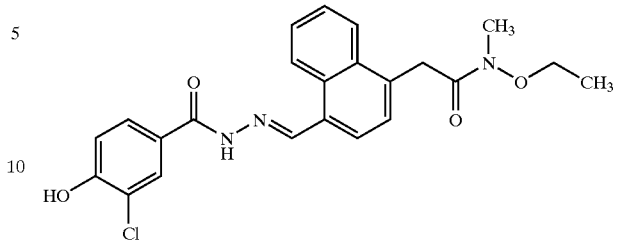

EXAMPLE 888

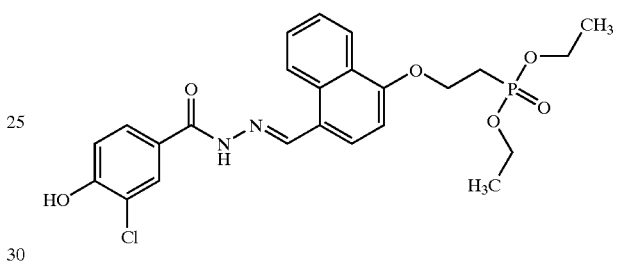

EXAMPLE 889

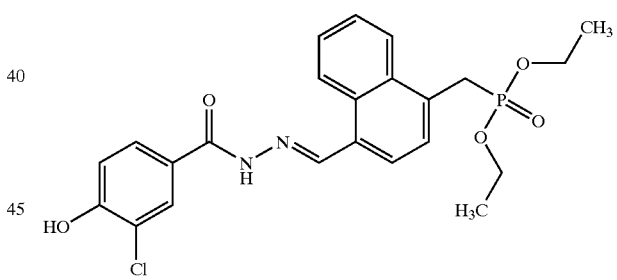

EXAMPLE 890

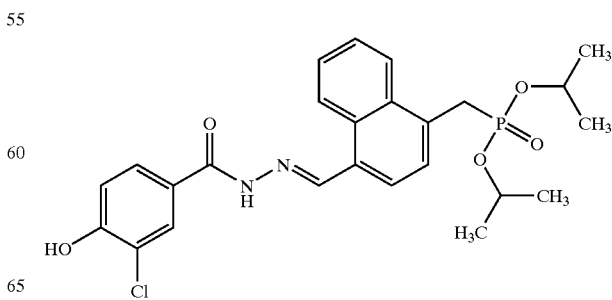

EXAMPLE 891

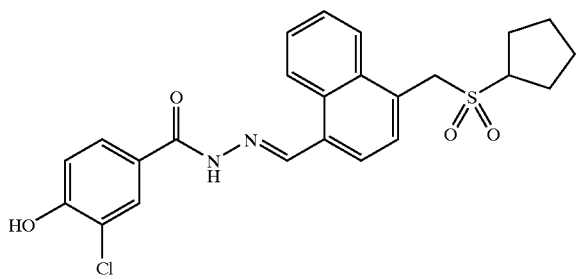

EXAMPLE 892

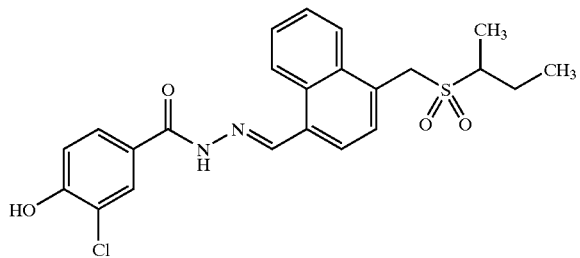

EXAMPLE 893

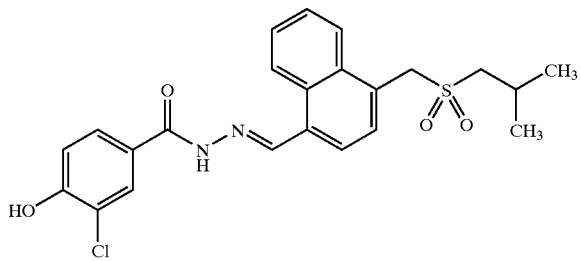

EXAMPLE 894

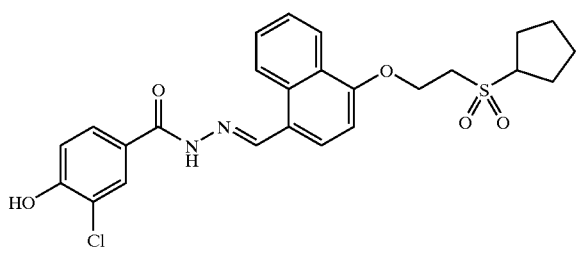

In a further aspect the invention relates to naphthyl anilides of the general formula (XVI):

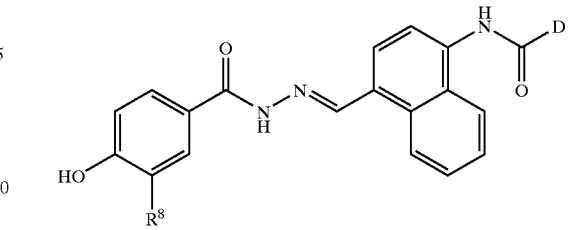

(XVI)

wherein
$R^8$ is chloro, fluoro, nitro or cyano; and
D is $C_{1-6}$-alkyl, $C_{3-8}$-cycloalkyl,

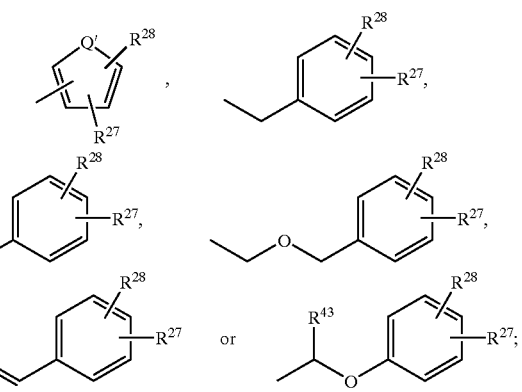

wherein
$R^{27}$ and $R^{28}$ independently are hydrogen, halogen, cyano, nitro, acetoxy, $C_{1-6}$-alkoxy, benzyloxy, trifluoromethyl, methylsulfonyl or $C_{1-6}$-alkyl;
Q' is —O— or —S—; and
$R^{43}$ is hydrogen, $C_{1-6}$-alkyl, $C_{1-6}$-alkylene-NH$_2$, $C_{1-6}$-alkylene-NH($C_{1-3}$-alkyl) or $C_{1-6}$-alkylene-N($C_{1-3}$-alkyl)$_2$;
as well as any optical or geometric isomer or tautomeric form thereof including mixtures of these or a pharmaceutically acceptable salt thereof.

The compounds are active glucagon antagonists or inverse agonists and the foregoing description of applications, pharmaceutical formulations and administration methods, and assays for evaluating the efficacy of the compounds etc also applies to these compounds.

The term "$C_{1-6}$-alkyl" as used in the definition of the formula (XVI), alone or in combination, represents a branched or straight hydrocarbon group having from 1 to 6 carbon atoms. Typical $C_{1-6}$-alkyl groups include, but are not limited to, methyl, ethyl, n-propyl, isopropyl, butyl, isobutyl, sec-butyl, tert-butyl, pentyl, isopentyl, hexyl, isohexyl and the like.

The term "$C_{1-6}$-alkoxy" as used in the definition of the formula (XVI), alone or in combination, refers to the group —O—$C_{1-6}$-alkyl where $C_{1-6}$-alkyl is as defined above. Representative examples are methoxy, ethoxy, n-propoxy, isopropoxy, butoxy, sec-butoxy, tert-butoxy, pentoxy, isopentoxy, hexoxy, isohexoxy and the like.

The term "$C_{3-8}$-cycloalkyl" as used in the definition of the formula (XVI), alone or in combination, represents a carbocyclic group having from 3 to 8 carbon atoms eg cyclopropyl, cyclobutyl, cyclopentyl, cyclohexyl, cycloheptyl, cyclooctyl and the like.

The term "halogen" as used in the definition of the formula (XVI) means Cl, Br, I, or F.

In a preferred embodiment D is

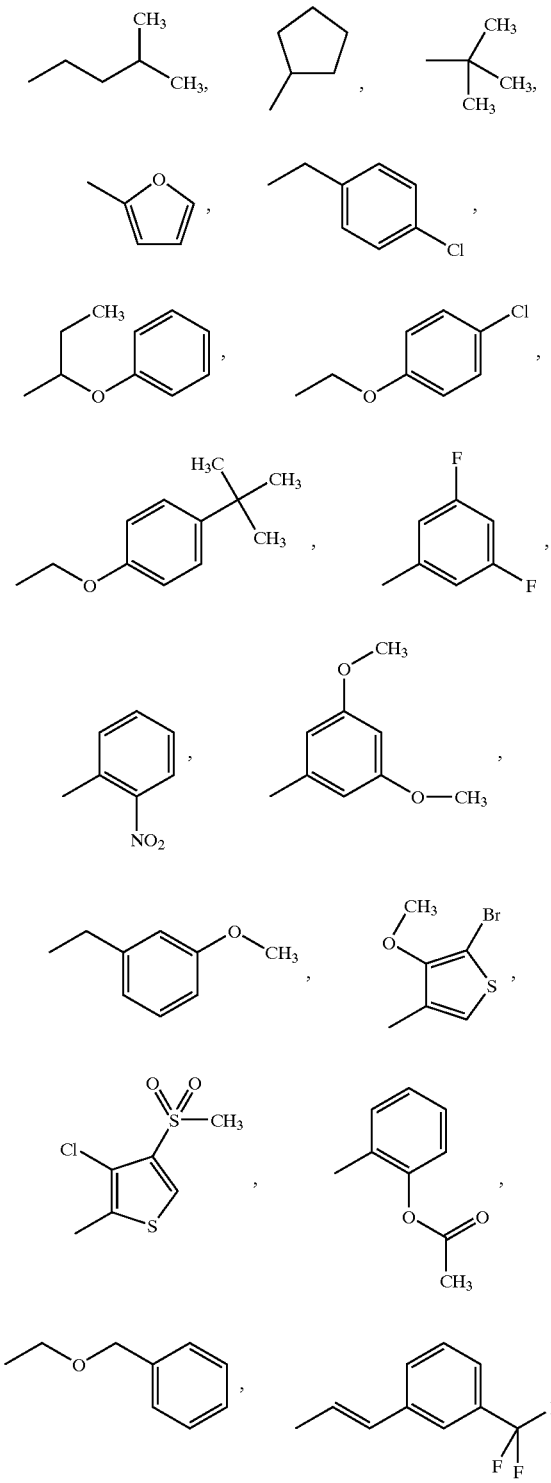

or

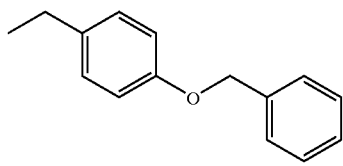

In another preferred embodiment $R^8$ is chloro.

More preferred $R^8$ is cyano.

The present invention is further illustrated by the following representative examples which are, however, not intended to limit the scope of the invention in any way.

The compounds of the general formula (XVI) may be prepared according to the general procedure outlined in the below reaction scheme:

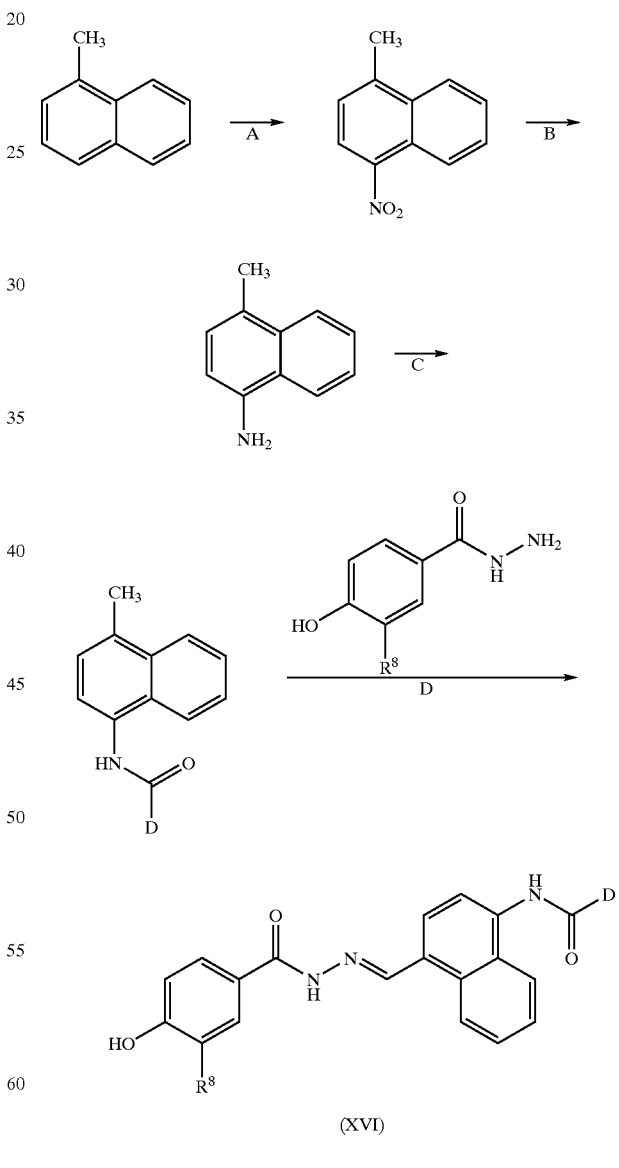

(XVI)

Step A: 4-Nitro-1-methylnaphthalene.

To a cold (0° C.) suspension of 1-methylnaphthalene (5 g) in HNO$_3$ was added H$_2$SO$_4$ (5 mL) dropwise. After stirring the reaction for one hour, the solution was diluted with ethyl acetate and washed with water (3×), aqueous saturated NaHCO$_3$ (2×) and brine, dried over MgSO$_4$, and concentrated. The product was purified by silica gel column chromatography using ethyl acetate:hexane (5:95) and recrystallized from methanol to give yellow needles.

$^1$H NMR (CDCl$_3$): δ 2.79 (s, 3H), 7.38 (d, 1H), 7.65–7.73 (m, 2H), 8.10 (d, 1H), 8.14 (d, 1H), 8.61 (d, 1H).

Step B: 4-Aminonaphthaldehyde.

To a stirring boiling solution of sulfur (3.7 g) in 12% aqueous NaOH (50 mL) was added a solution of 4-nitro-1-methylnaphthalene (8 g) in ethanol (50 mL). After refluxing the solution for one hour, the reaction was diluted with 500 mL of ethyl acetate and washed with water and brine, dried over MgSO$_4$, and concentrated. The product was purified via silica gel column chromatography using ethyl acetate:hexane (5:95 to 10:90). The product (2.54 g, 34%) was stored at −78° C.

$^1$H NMR (DMSO-d$_6$): δ 6.55 (d, 1H), 6.95 (brd s, 2H), 7.25 (t, 1H), 7.45 (t, 1H), 7.60 (d, 1H), 8.05 (d, 1H), 9.10 (d, 1H), 9.68 (s, 1H).

Step C: General Procedure for the Acylation of 4-Aminonaphthaldehyde With Acid Chlorides.

To a solution of 4-aminonaphthaldehyde, diisopropylethylamine (1.1 eq), and 4-dimethylaminopyridine (1.1 eq) in minimum volume of anhydrous DMF was added the desired acid chloride (1.1 eq). After stirring the mixture overnight, the mixture was diluted with ethyl acetate and washed with 1N HCl (2×), water, aqueous NaHCO$_3$ (3×), water and brine, dried over MgSO$_4$, and concentrated. The acylated products were purified by silica gel column chromatography using ethyl acetate/hexane. The yield ranged from 50–90% yield.

Step D: General Procedure for the Preparation of Hydrazones.

Hydrazones were prepared according to the general procedure for the synthesis of alkylidene hydrazones from the condensation of the appropriate 3-substituted 4-hydroxybenzoic acid hydrazide and the above acylated aldehydes.

Combinatorial Format: General procedure for the formation of acylated hydrazones in parallel synthesis format.

To a solution of 4-aminonaphthylmethyl 3-substituted hydroxybenzoic acid hydrazone (50 μL, 0.2 M) was added a solution of the desired acid chloride (55 μL, 0.2 M), a solution of diisopropylethylamine (55 μL, 0.2 M), and a solution of 4-dimethylaminopyridine (55 μL, 0.2 M). The reaction mixtures were left under stirring overnight to give the desired products. The products were purified by HPLC equipped with a reverse phase column. All solutions were prepared using anhydrous DMF.

Examples of Products of the Formula (XVI)

EXAMPLE 895

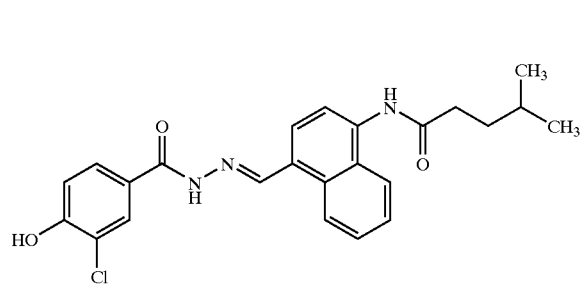

$^1$H-NMR (DMSO-d$_6$): δ 0.96 (d, 6H), 1.55–1.68 (m, 4H), 2.55 (m, 1H), 7.10 (d, 1H), 7.63–7.71 (m, 2H), 7.80 (d, 1H), 7.89 (qt, 2H), 8.02 (s, 1H), 8.20 (d, 1H), 8.91 (d, 1H), 9.04 (s, 1H), 10.04 (s, 1H), 10.99 (s, 1H), 11.78 (s, 1H); MS (APCI=atmospheric pressure chemical ionization): 438.1.

EXAMPLE 896

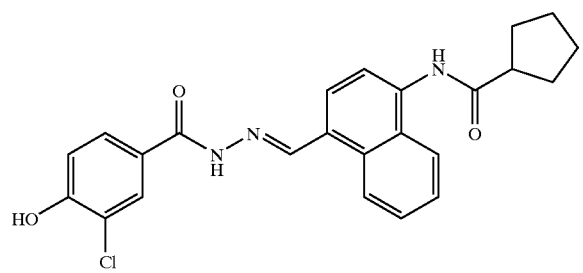

$^1$H-NMR (DMSO-d$_6$): δ 1.61 (m, 2H), 1.71 (m 2H), 1.82 (m, 2H), 1.90 (m, 2H), 3.06 (quintet, 1H), 7.10 (d, 1H), 7.65 (quintet, 2H), 7.83 (qt, 2H), 7.90 (d, 1H), 8.02 (s, 1H), 8.18 (d, 1H), 8.90 (d, 1H), 9.04 (s, 1H), 10.01 (s, 1H), 10.99 (s, 1H), 11.78 (s, 1H); MS (APCI): 436.1, 438.2.

EXAMPLE 897

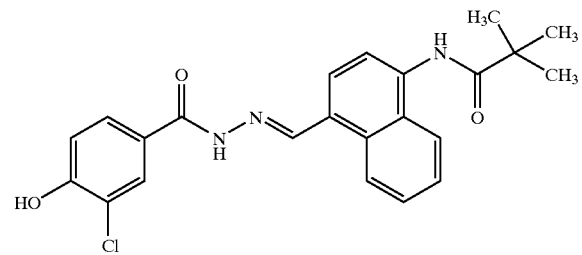

$^1$H-NMR (DMSO-d$_6$): δ 1.34 (s, 9H), 7.17 (d, 1H), 7.54 (d, 1H), 7.66 (quintet, 2H), 7.88 (d, 1H), 7.96 (t, 2H), 8.06 (s, 1H), 8.83 (d, 1H), 9.27 (s, 1H), 9.63 (s, 1H), 11.18 (brd s, 1H), 12.09 (s, 1H); MS (APCI): 424.0.

EXAMPLE 898

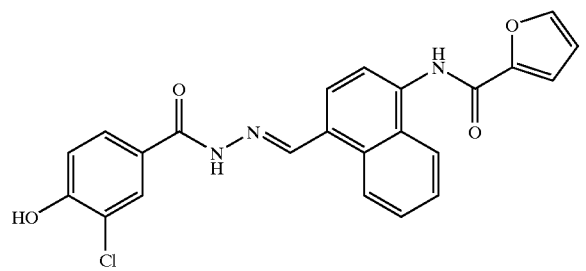

$^1$H-NMR (DMSO-d$_6$): δ 6.76 (s, 1H), 7.11 (d, 1H), 7.44 (d, 1H), 7.65–7.74 (m, 3H), 7.82 (d, 1H), 8.02 (m, 3H), 8.07

(d, 1H), 8.90 (d, 1H), 9.09 (s, 1H), 10.49 (s, 1H), 11.01 (s, 1H), 11.84 (s, 1H); MS (APCI): 434.0, 436.0.

EXAMPLE 899

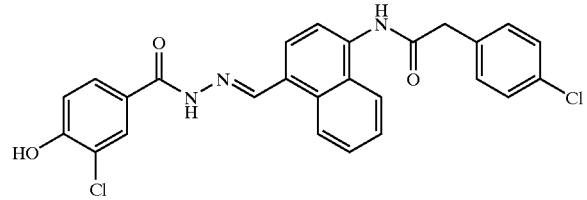

¹H-NMR (DMSO-d₆): δ 3.87 (s, 2H), 7.08 (d, 1H), 7.44 (s, 4H), 7.66 (m, 2H), 7.80–7.89 (m, 3H), 8.01 (s, 1H), 8.20 (d, 1H), 8.90 (d, 1H), 9.04 (s, 1H), 10.32 (s, 1H), 11.99 (s, 1H), 11.78 (s, 1H); MS (APCI): 490.3, 492.1, 493.1.

EXAMPLE 900

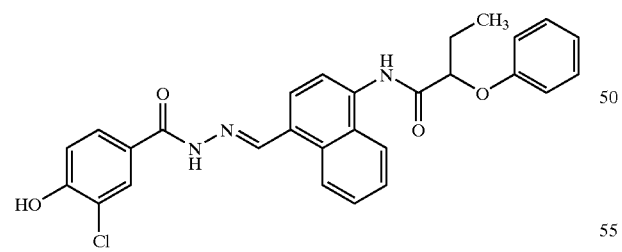

¹H-NMR (DMSO-d₆): δ 1.12 (s, 3H), 2.01 (quintet, 1H), 5.00 (t, 1H), 7.00 (t, 1H), 7.10 (m, 3H), 7.40 (t, 2H), 7.60 (t, 1H), 7.70 (t, 1H), 7.72 (d, 1H), 7.80 (d, 1H), 7.90 (d, 1H), 7.95 (d, 1H), 8.00 (s, 1H), 8.80 (d, 1H), 9.10 (s, 1H), 10.40 (s, 1H), 10.90 (s, 1H), 11.80 (s, 1H); MS (APCI): 502.2, 503.2, 504.2.

EXAMPLE 901

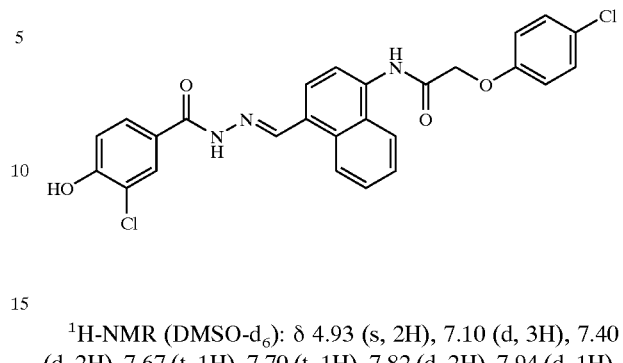

¹H-NMR (DMSO-d₆): δ 4.93 (s, 2H), 7.10 (d, 3H), 7.40 (d, 2H), 7.67 (t, 1H), 7.70 (t, 1H), 7.82 (d, 2H), 7.94 (d, 1H), 8.02 (s, 1H), 8.11 (d, 1H), 8.90 (d, 1H), 9.06 (s, 1H), 10.33 (s, 1H), 11.02 (s, 1H), 11.82 (s, 1H); MS (APCI): 508.1, 509.1, 510.1.

EXAMPLE 902

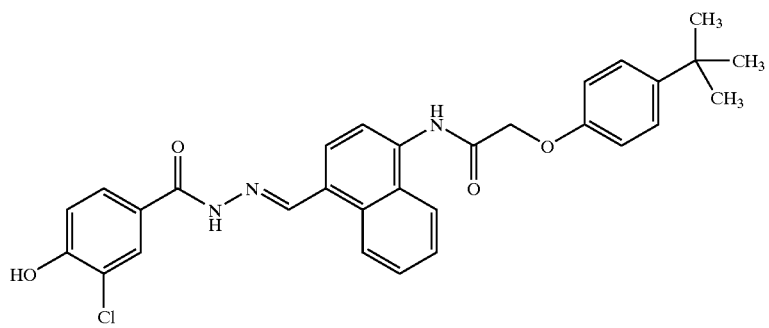

¹H-NMR (DMSO-d₆): δ 1.27 (s, 9H), 4.88 (s, 2H), 6.99 (d, 2H), 7.10 (d, 1H), 7.35 (d, 2H), 7.61 (t, 1H), 7.69 (t, 1H), 7.81 (d, 2H), 7.93 (d, 1H), 8.02 (s, 1H), 8.06 (d, 1H), 8.90 (d, 1H), 9.09 (s, 1H), 10.30 (s, 1H), 11.04 (brd s, 1H), 11.86 (s, 1H); MS (APCI): 530.2, 532.2.

EXAMPLE 903

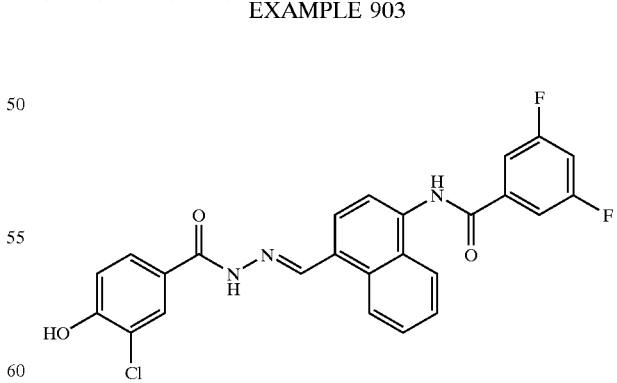

¹H-NMR (DMSO-d₆): δ 7.00 (d, 1H), 7.55–7.75 (m, 2H), 7.80 (d, 2H), 7.85 (d, 3H), 8.00 (d, 1H), 8.10 (s, 1H), 8.20 (d, 1H), 8.90 (d, 1H), 9.20 (s, 1H), 10.70 (s, 1H), 11.00 (s, 1H), 11.80 (s, 1H); MS (APCI): 480.1.

The following compounds may also be prepared using the above mentioned synthesis methodologies:

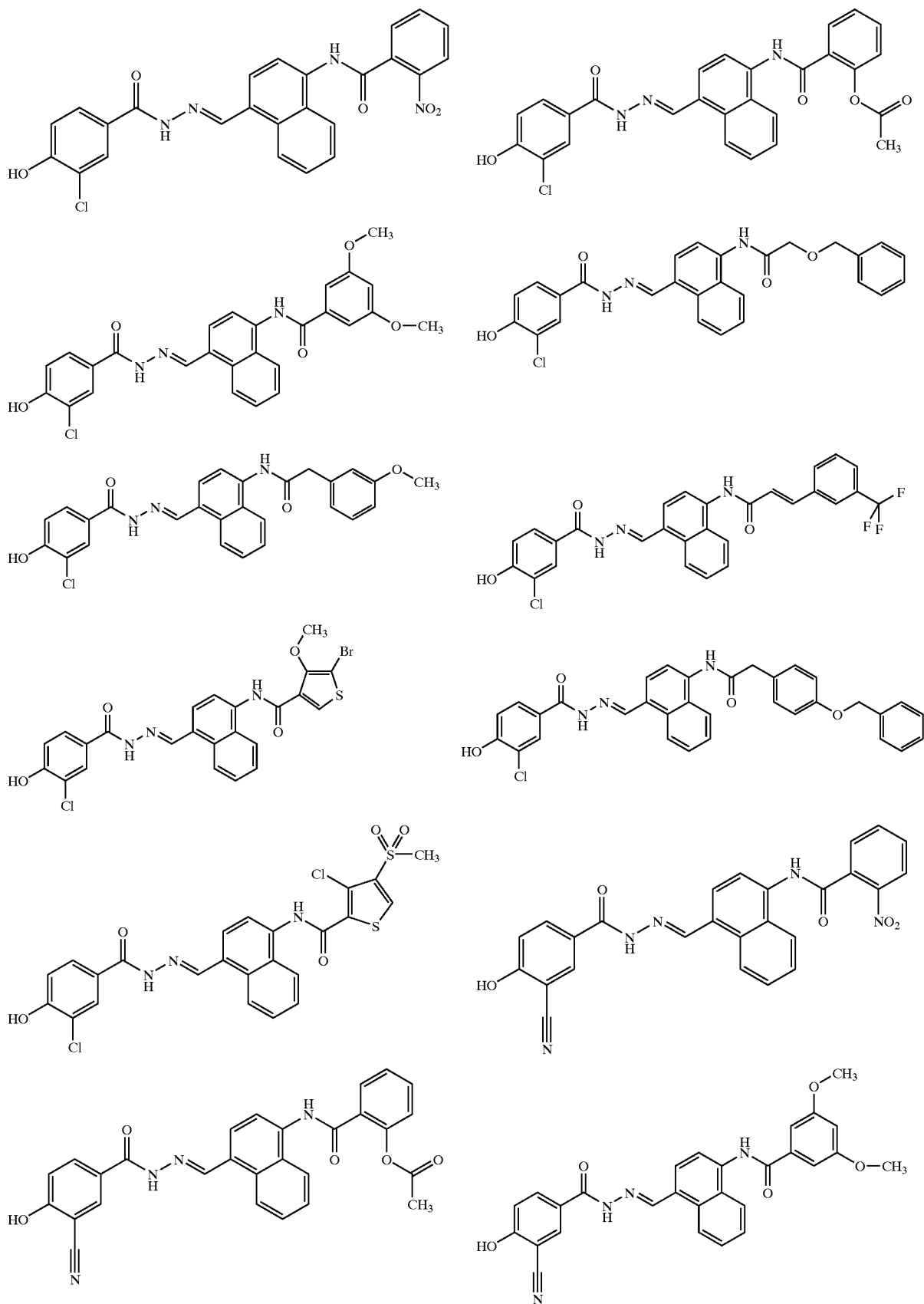

621 622
-continued
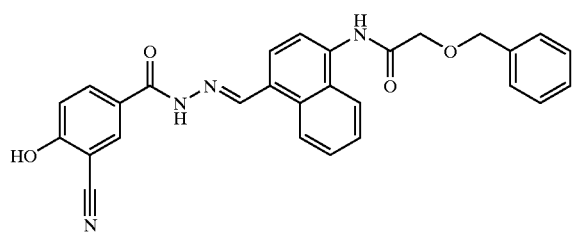
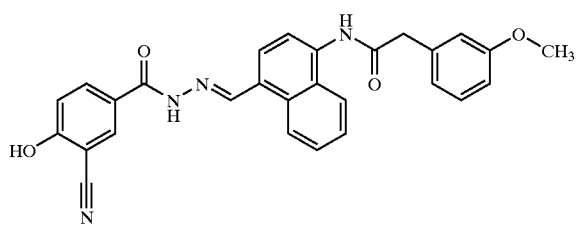
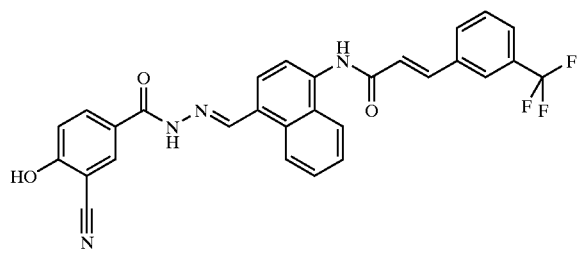
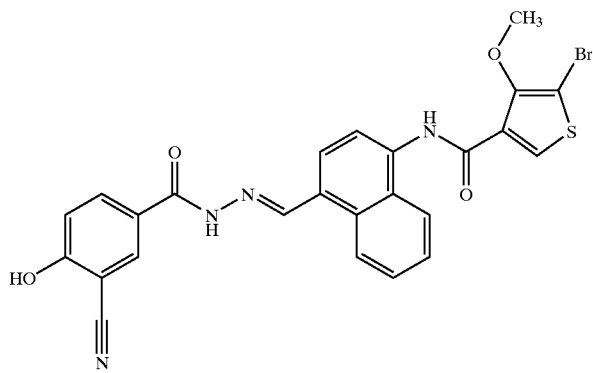
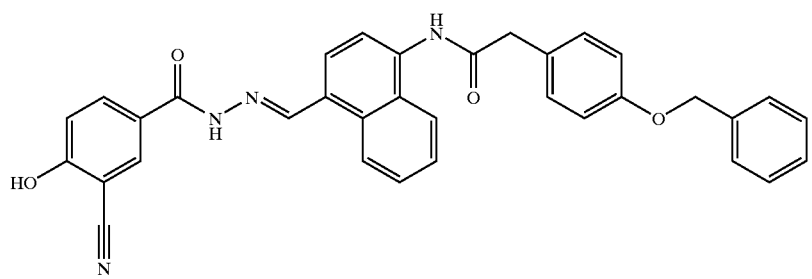
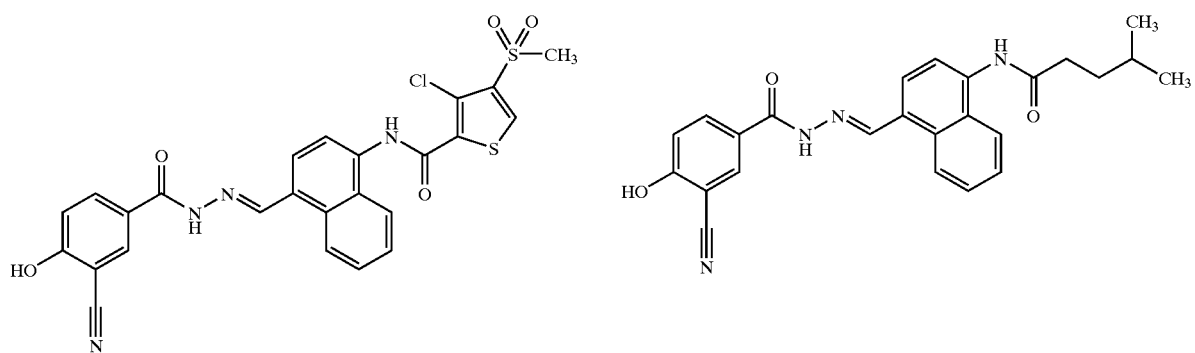
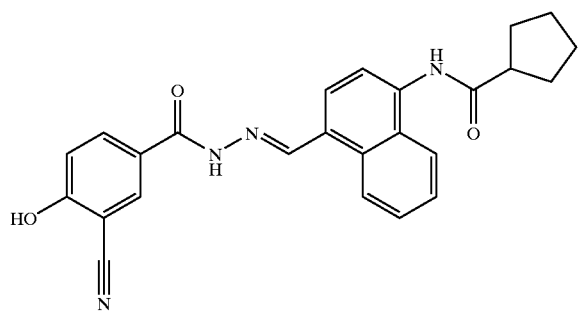
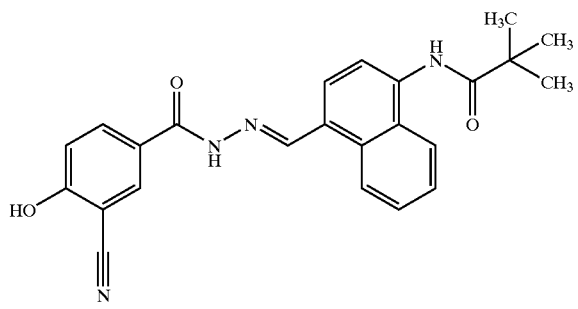

-continued

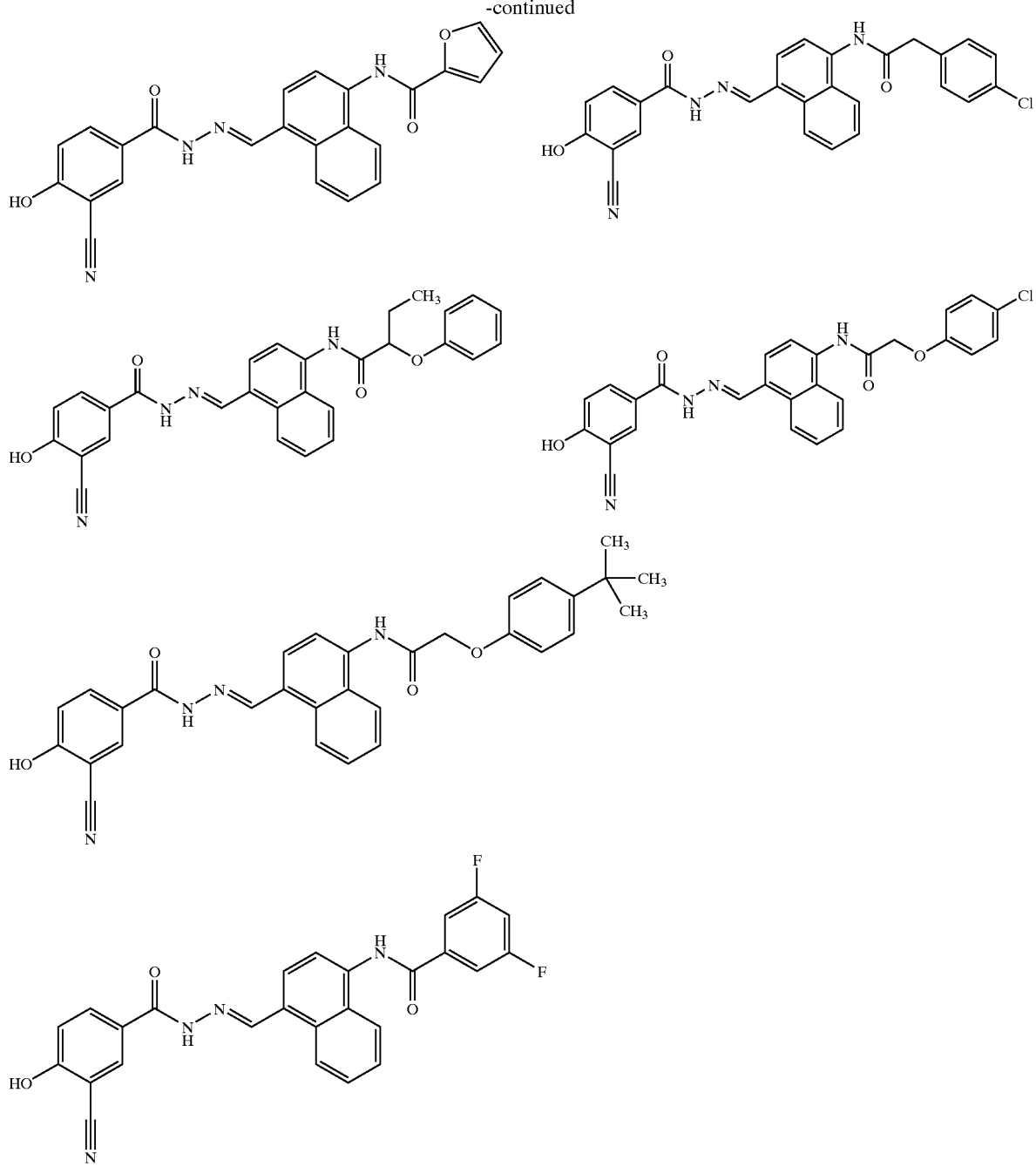

In a further aspect the invention relates to the following compounds:

N-{4-[(3-chloro-4-hydroxybenzoyl)hydrazonomethyl]-3-methoxyphenyl}-2-(2-trifluoromethylphenyl)acetamide;

3-phenylpropynoic acid {4-[(3-chloro-4-hydroxybenzoyl)hydrazonomethyl]-3-methoxyphenyl}amide;

N-{4-[(3-chloro-4-hydroxybenzoyl)hydrazonomethyl]-3-methoxyphenyl}-2-(4-chlorophenyl)acetamide;

N-{4-[(3-chloro-4-hydroxybenzoyl)hydrazonomethyl]-3-methoxyphenyl}-2-(3-chlorophenyl)acetamide;

N-{4-[(3-chloro-4-hydroxybenzoyl)hydrazonomethyl]-3-methoxyphenyl}-2-(4-trifluoromethylphenylsulfanyl)acetamide;

5-methoxybenzofuran-2-carboxylic acid {4-[(3-chloro-4-hydroxybenzoyl)hydrazonomethyl]-3-methoxyphenyl}amide;

2-benzo[b]thiophen-3-yl-N-{4-[(3-chloro-4-hydroxybenzoyl)hydrazonomethyl]-3-methoxyphenyl}acetamide;

N-{4-[(3-chloro-4-hydroxybenzoyl)hydrazonomethyl]-3-methoxyphenyl}-2-(3,4-difluorophenyl)acetamide;

N-{4-[(3-chloro-4-hydroxybenzoyl)hydrazonomethyl]-3-methoxyphenyl}-2-(4-chlorophenylsulfanyl)acetamide;

N-{4-[(3-chloro-4-hydroxybenzoyl)hydrazonomethyl]-3-methoxyphenyl}-3-(4-chlorophenyl)propionamide;

N-{4-[(3-chloro-4-hydroxybenzoyl)hydrazonomethyl]-3-methoxyphenyl}-3-(4-cyanophenoxy)acetamide;

N-{4-[(3-cyano-4-hydroxybenzoyl)hydrazonomethyl]-3-methoxyphenyl}-2-(2-trifluoromethylphenyl)acetamide;

3-phenylpropynoic acid {4-[(3-cyano-4-hydroxybenzoyl)hydrazonomethyl]-3-methoxy-phenyl}amide;

N-{4-[(3-cyano-4-hydroxybenzoyl)hydrazonomethyl]-3-methoxyphenyl}-2-(4-chlorophenyl)acetamide;

N-{4-[(3-cyano-4-hydroxybenzoyl)hydrazonomethyl]-3-methoxyphenyl}-2-(3-chlorophenyl)acetamide;

N-{4-[(3-cyano-4-hydroxybenzoyl)hydrazonomethyl]-3-methoxyphenyl}-2-(4-trifluoromethylphenylsulfanyl)acetamide;

5-methoxybenzofuran-2-carboxylic acid {4-[(3-cyano-4-hydroxybenzoyl)hydrazonomethyl]-3-methoxyphenyl}amide;

2-benzo[b]thiophen-3-yl-N-(4-[(3-cyano-4-hydroxybenzoyl)hydrazonomethyl]-3-methoxyphenyl}acetamide;

N-{4-[(3-cyano-4-hydroxybenzoyl)hydrazonomethyl]-3-methoxyphenyl}-2-(3,4-difluorophenyl)acetamide;

N-{4-[(3-cyano-4-hydroxybenzoyl)hydrazonomethyl]-3-methoxyphenyl}-2-(3-trifluoromethylphenyl)acetamide;

N-{4-[(3-cyano-4-hydroxybenzoyl)hydrazonomethyl]-3-methoxyphenyl}-3-(4-trifluoromethylphenyl)propionamide;

N-{4-[(3-cyano-4-hydroxybenzoyl)hydrazonomethyl]-3-methoxyphenyl}-2-(4-chlorophenylsulfanyl)acetamide;

N-{4-[(3-cyano-4-hydroxybenzoyl)hydrazonomethyl]-3-methoxyphenyl}-3-(4-chlorophenyl)propionamide;

N-{4-[(3-cyano-4-hydroxybenzoyl)hydrazonomethyl]-3-methoxyphenyl}-3-(4-cyanophenoxy)acetamide;

as well as any optical or geometric isomer or tautomeric form thereof including mixtures of these or a pharmaceutically acceptable salt thereof.

The compounds are active glucagon antagonists or inverse agonists. Accordingly, the foregoing description of applications, pharmaceutical formulations and administration methods, and assays for evaluating the efficacy of the compounds etc also applies to these compounds.

General Procedure for Synthesis of the Compounds

Preparation of [Building Block 2] (4-Formyl-3-methoxyphenyl)carbamic Acid 9H-Fluoren-9-ylmethyl Ester:

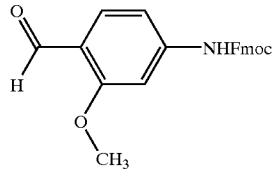

Methyl 4-amino-2-methoxybenzoate (14.7 g, 7.3 mmol) and Fmoc-Osu (26.1 g, 77.3 mmol) were stirred in a mixture of acetonitrile and water (1:1, 320 mL) at reflux for 16 hr. The reaction mixture was concentrated to half the volume and the precipitate isolated by filtration. The isolated solid was dissolved in ethyl acetate (300 mL) and washed with 0.4 N hydrochloric acid (200 mL), 0.2 N hydrochloric acid (200 mL), water (200 mL) and a 20% saturated solution of sodium chloride (200 mL). After drying (magnesium sulphate) the organic phase was concentrated in vacuo, and the solid residue was washed with methanol and dried.

The crude product (12 g) was dissolved in dichloromethane (1 L) under nitrogen and a solution of diisobutylaluminium hydride (90 mL, 1.2 M in toluene) was dropwise added at 0–5° C. The reaction mixture was stirred at 20° C. for 16 hr and quenched by dropwise addition of water (58 mL) at 0–5° C. The reaction mixture was stirred at 20° C. for 3 hr and filtered. The filtrate was concentrated in vacuo. The crude product (6.8 g) was suspended in dichloromethane (400 mL) and manganese dioxide (15.6 g, 180 mmol) was added. The mixture was stirred for 16 hr at 20° C. and filtered. The filtrate was concentrated in vacuo to give 5.1 g of the title compound.

m.p. 187–188° C.; HPLC-MS (METHOD A): $R_t$=15.1 min; m/z=374. Micro analysis: Calculated: C, 73.98; H, 5.13; N, 3.75; Found: C, 73.44; H, 5.20; N, 3.56%.

HPLC-MS (METHOD A):

The following instrumentation is used:

Sciex API 100 Single quadropole mass spectrometer

Perkin Elmer Series 200 Quard pump

Perkin Elmer Series 200 autosampler

Applied Biosystems 785A UV detector

Sedex 55 evaporative light scattering detector

A Valco column switch with a Valco actuator controlled by timed events from the pump.

The instrument control and data acquisition is done by the Sciex Sample control software running on a Macintosh PowerPC 7200 computer.

The HPLC pump is connected to four eluent reservoirs containing:

A: acetonitrile

B: water

C: 0.5% TFA in water

D: 0.02 M ammonium acetate

The requirements for samples are that they contain approximately 500 µg/mL of the compound to be analysed in an acceptable solvent such as methanol, ethanol, acetonitrile, THF, water and mixtures thereof. (High concentrations of strongly eluting solvents will interfere with the chromatography at low acetonitrile concentration.)

The analysis is performed at room temperature by injecting 20 µL of the sample solution on the column which is eluted with a gradient of acetonitrile in either 0.05% TFA or 0.002 M ammonium acetate. Depending on the analysis method varying elution conditions are used.

The eluate from the column is passed through a flow splitting T-connector which passes approximately 20 µl/min (1/50) through approx. 1 m. 75µ fused silica capillary to the API interface of API 100 spectrometer.

The remaining 1.48 mL/min (49/50) is passed through the UV detector and to the ELS detector.

During the LC-analysis the detection data are acquired concurrently from mass spectrometer, UV detector and ELS detector.

The LC conditions, detector settings and mass spectrometer settings used for the different methods are given in the following tables.

| Method | h8 LC-MS 100–800 YMC |
|---|---|
| Column | YMC ODS-A 120 Å s - 5μ 50 mm × mm id |
| Gradient | 5%–90% acetonitrile in 0.05% TFA linearly during 15 min at 1 mL/min |
| Detection | UV: 214 nm ELS: 40° C. |
| MS | Experiment: Start: 100 amu Stop: 800 amu Step: 0.2 amu Dwell: 0.571 msec Method Scan 284 times = 9.5 min State file* PPG-POS ddmmyy Cal file** Q1 MCAL ddmmyy |

*The conditions for the ion source and ion analyser given in the state file are adjusted during the weekly tuning and maintenance of the instrument.
**The mass calibration values given in the Calibration file is adjusted during the weekly tuning and maintenance of the instrument.

EXAMPLE 904

N-{4-[(3-Chloro-4-hydroxybenzoyl)hydrazonomethyl]-3-methoxyphenyl}-2-(2-trifluoromethylphenyl)acetamide

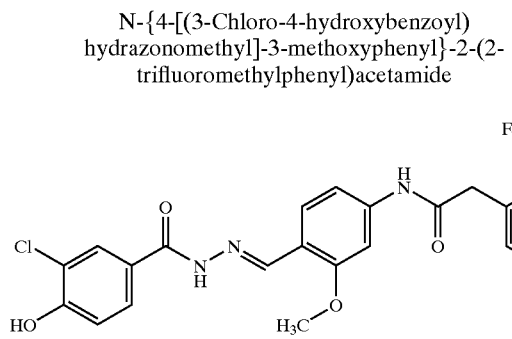

Step 1: Coupling of Aldehyde [Building Block 2] to Resin [Building Block 1].

0.75 g resin (Wang resin loaded with 3-chloro-4-hydroxybenzoic acid hydrazide) was swelled in dimethylformamide (6 mL) for 30 min and drained. The aldehyde (4-formyl-3-methoxyphenyl)carbamic acid 9H-fluoren-9-ylmethyl ester, 0.5 g, 1.36 mmol) dissolved in dimethylformamide (3 mL) was added followed by addition of triethylorthoformate (1.5 mL). The mixture was shaken for 16 hr at 20° C. and drained. The resin was washed with dimethylformamide (5×4 mL), dichloromethane (5×4 mL) and dimethylformamide (5×4 mL). The coupling of the aldehyde was repeated twice.

Step 2: Deprotection of Aniline.

The resin was swelled in dimethylformamide (5 mL) and piperidine added (1.25 mL). After shaking for 30 min, the resin was drained and washed with dimethylformamide (5×4 mL), N-methylpyrrolidinone (5×4 mL) and dimethylformamide (5×4 mL).

Step 3: Coupling of Acid [Building Block 3] to Resin [Building Block 1][Building Block 2].

The resin[building block 1][building block 2] (0.5 g) was swelled in dimethylformamide (2.5 mL) and drained. The acid (2-trifluorophenylacetic acid, 2.3 mmol) was dissolved in DMF (2 mL) together with diisopropylcarbodiimide (2.3 mmol) and after 10 min this mixture was added to the drained resin. After 30 min of shaking a 1M solution of dimethylaminopyridine in DMF (0.32 mL) was added and the mixture was shaken for 16 hr and drained. The resin was washed with dimethylformamide (5×4 mL) and dichloromethane (5×4 mL). The coupling of the acid was repeated twice.

Step 4: Cleavage From the Resin.

The resin was swelled in dichloromethane (2 mL) and trifluoroacetic acid (2 mL) was added. After shaking for 30 min the resin was drained. The eluent was collected and concentrated in vacuo. The residue was crystallized from methanol to the title compound.

HPLC-MS (METHOD A) $R_t$=6.5 min; m/z=506.

$^1$H-NMR, 400 MHz, DMSO-$d_6$: δ 11.6 (s, 1H), 10.9 (s, 1H), 10.45 (s, 1H), 8.7 (s, 1H), 7.95 (s, 1H), 7.8–7.4 (m, 7H), 7.15 (d, 1H), 7.05 (d, 1H), 3.95 (s, 2H), 3.8 (s, 3H).

The following examples were prepared using the same synthesis methodology as described for the example above and can be prepared in parallel on solid support:

EXAMPLE 905

3-Phenylpropynoic Acid {4-[(3-Chloro-4-hydroxybenzoyl)hydrazonomethyl]-3-methoxyphenyl}amide

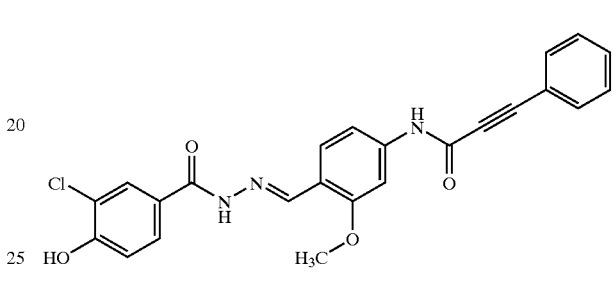

HPLC-MS (METHOD A) $R_t$=5.95 min; m/z=448.

EXAMPLE 906

N-{4-[(3-Chloro-4-hydroxybenzoyl)hydrazonomethyl]-3-methoxyphenyl}-2-(4-chlorophenyl)acetamide

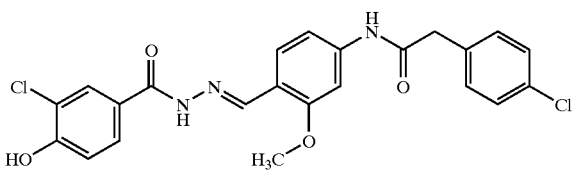

HPLC-MS (METHOD A) $R_t$=6.33 min; m/z=472.

$^1$H-NMR, 400 MHz, DMSO-$d_6$: δ 11.6 (s, 1H), 10.9 (s, 1H), 10.4 (s, 1H), 8.7 (s, 1H), 7.95 (s, 1H), 7.8–7.7 (m, 2H), 7.55 (s, 1H), 7.4–7.3 (m, 4H), 7.25 (d, 1H), 7.05 (d, 1H), 3.8 (s, 3H), 3.7 (s, 2H).

EXAMPLE 907

N-{4-[(3-Chloro-4-hydroxybenzoyl)hydrazonomethyl]-3-methoxyphenyl}-2-(3-chlorophenyl)acetamide

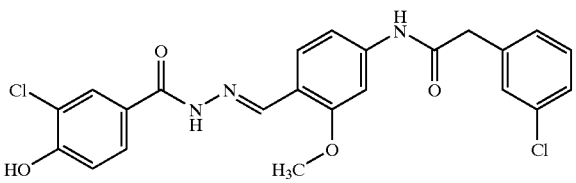

HPLC-MS (METHOD A) $R_t$=6.33 min; m/z=472.

$^1$H-NMR, 400 MHz, DMSO-$d_6$: δ 11.6 (s, 1H), 10.9 (s, 1H), 10.4 (s, 1H), 8.7 (s, 1H), 7.95 (s, 1H), 7.8–7.7 (m, 2H), 7.55 (s, 1H), 7.4–7.25 (m, 4H), 7.15 (d, 1H), 7.05 (d, 1H), 3.8 (s, 3H), 3.7 (s, 2H).

EXAMPLE 908

N-{4-[(3-Chloro-4-hydroxybenzoyl)hydrazonomethyl]-3-methoxyphenyl}-2-(4-trifluoromethylphenylsulfanyl)acetamide

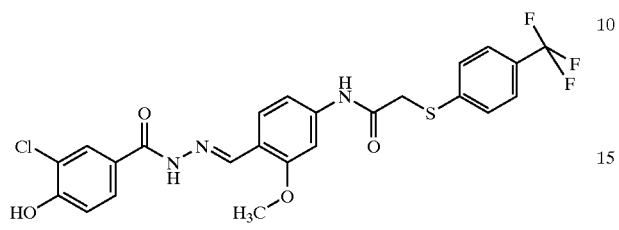

HPLC-MS (METHOD A) $R_t$=6.88 min; m/z=538.

$^1$H-NMR, 400 MHz, DMSO-$d_6$: δ 11.6 (s, 1H), 10.9 (s, 1H), 10.5(s, 1H), 8.7 (s, 1H), 8.0 (s, 1H), 7.8–7.7 (m, 2H), 7.65 (d, 2H), 7.6 (d, 2H), 7.5 (s, 1H), 7.15 (d, 1H), 7.05 (d, 1H), 4.05 (s, 2H), 3.8 (s, 3H).

EXAMPLE 909

5-Methoxybenzofuran-2-carboxylic Acid {4-[(3-Chloro-4-hydroxybenzoyl)hydrazonomethyl]-3-methoxyphenyl)amide

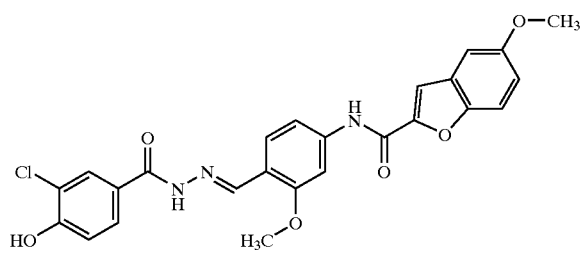

HPLC-MS (METHOD A) $R_t$=6.42 min; m/z=494.

Micro analysis: Calculated for $C_{25}H_{20}N_3O_6Cl$, 0.2 mol $CH_2Cl_2$: C, 58.87; H, 4.01; N, 8.16% Found: C, 59.33; H, 4.31; N, 8.17%.

$^1$H-NMR, 400 MHz, DMSO-$d_6$: δ 11.7 (s, 1H), 10.9 (s, 1H), 10.6 (s, 1H), 8.7 (s, 1H), 8.0 (s, 1H), 7.9–7.7 (m, 4H), 7.6 (d, 1H), 7.55 (d, 1H), 7.3 (d, 1H), 7.1 (dd, 1H), 7.05 (d, 1H), 3.9 (s, 3H), 3.8 (s, 3H).

EXAMPLE 910

2-Benzo[b]thiophen-3-yl-N-{4-[(3-chloro-4-hydroxybenzoyl)hydrazonomethyl]-3-methoxyphenyl}acetamide

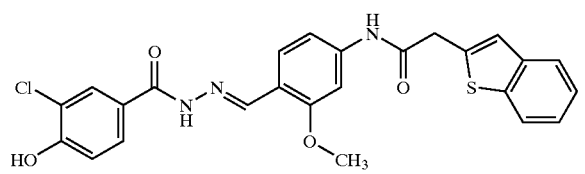

HPLC-MS (METHOD A) $R_t$=6.1 min; m/z=494.

Micro analysis: Calculated for $C_{25}H_{20}N_3O_4SCl$, 1½$H_2O$: C, 57.64; H, 4.45; N, 8.07% Found: C, 57.79; H, 3.96; N, 7.78%.

$^1$H-NMR, 400 MHz, DMSO-$d_6$: δ 11.6 (s, 1H), 10.9 (s, 1H), 10.5 (s, 1H), 8.7 (s, 1H), 8.1–7.7 (m, 4H), 7.6 (d, 2H), 7.45–7.35 (m, 3H), 7.2 (d, 1H), 7.05 (d, 1H), 3.95 (s, 2H), 3.8 (s, 3H).

EXAMPLE 911

N-{4-[(3-Chloro-4-hydroxybenzoyl)hydrazonomethyl]-3-methoxyphenyl}-2-(3,4-difluorophenyl)acetamide

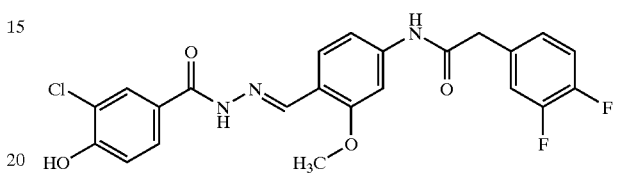

HPLC-MS (METHOD A) $R_t$=6.12 min; m/z=474.

$^1$H-NMR, 400 MHz, DMSO-$d_6$: δ 11.6 (s, 1H), 10.9 (s, 1H), 10.4 (s, 1H), 8.7 (s, 1H), 7.95 (s, 1H), 7.8–7.7 (m, 2H), 7.55 (s, 1H), 7.45–7.3 (m, 2H), 7.15 (d, 2H), 7.05 (d, 1H), 3.8 (s, 3H), 3.7 (s, 2H).

EXAMPLE 912

N-{4-[(3-Cyano-4-hydroxybenzoyl)hydrazonomethyl]-3-methoxyphenyl}-2-(3-trifluoromethylphenyl)acetamide

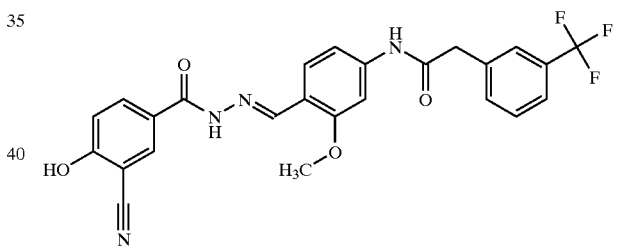

2-Methoxy-4-[2-(3-trifluoromethylphenyl)acetylamino]benzoic Acid Methyl Ester:

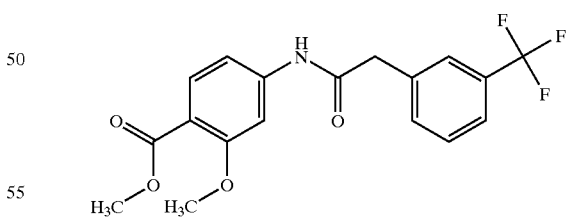

Ethyldiisopropylcarbodiimide (8.1 g, 42 mmol) was added to a solution of 3-(trifluoromethyl)phenylacetic acid (17 g, 83 mmol) in DCM (50 mL). After 10 min methyl 4-amino-2-methoxybenzoate (5.0 g, 28 mmol) was added and the mixture was stirred at reflux temperature for 4 hr and at 20° C. for 16 hr. The mixture was diluted with DCM (100 mL) and extracted with a saturated solution of sodium hydrogen carbonate (3×50 mL) and water (3×50 mL). The organic phase was dried (magnesium sulphate), filtered and evaporated in vacuo to give crude 2-methoxy-4-[2-(3- trifluoromethylphenyl)acetetylamino]benzoic acid methyl ester that was purified by column chromatography on silica (120 g) using heptane and ethyl acetate (3:2) as eluent.

HPLC-MS (METHOD A) $R_t$=6.17 min; m/z=368.

Micro analysis: Calculated for $C_{18}H_{16}NO_4$: C, 58.86; H, 4.39; N, 3.81% Found: C, 58.97; H, 4.41; N, 3.75%.

$^1$H-NMR, 300 MHz, DMSO-$d_6$: δ 10.5 (s, 1H), 7.7–7.5 (m, 6H), 7.2 (d, 1H), 3.85 (s, 2H), 3.75 (s, 3H), 3.7 (s, 3H).
N-(4-Hydroxymethyl-3-methoxyphenyl)-2-(3-trifluoromethylphenyl)acetamide:

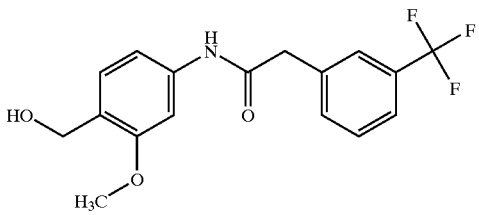

2-Methoxy-4-[2-(3-trifluoromethylphenyl)acetylamino]benzoic acid methyl ester (2.0 g, 5.4 mmol) was dissolved in dry DCM (100 mL) under nitrogen and cooled to −20° C. Diisobutylaluminum hydride (1.2 M in toluene, 18.9 mmol, 16 mL) was dropwise added over 40min. The reaction mixture was heated to 20° C. and stirred at this temperature for 2 hr. After dilution with DCM (100 mL) the reaction mixture was quenched by dropwise addition of water (10 mL) at 20–25° C. The mixture was filtered after 16 hr and the organic phase was dried (magnesium sulphate), filtered and concentrated in vacuo to give crude N-(4-hydroxymethyl-3-methoxyphenyl)-2-(3-trifluoromethylphenyl)acetamide that was purified by column chromatography on silica (30 g) using heptane and ethyl acetate (3:2) as eluent.

$^1$H-NMR, 300 MHz, DMSO-$d_6$: δ 10.2 (s, 1H), 7.7–7.5 (m, 4H), 7.35 (s, 1H), 7.25 (d, 1H), 7.1 (d, 1H), 4.9 (t, 1H), 4.4 (d, 2H), 3.8 (s, 2H), 3.7 (s, 3H).
N-(4-Formyl-3-methoxyphenyl)-2-(3-trifluoromethylphenyl)acetamide:

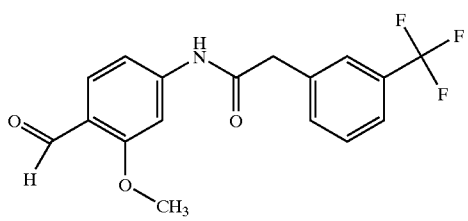

N-(4-Hydroxymethyl-3-methoxyphenyl)-2-(3-trifluoromethylphenyl)acetamide (0.7 g, 2 mmol) was dissolved in ethyl acetate (40 mL) and manganese dioxide (3 g, 34 mmol) was added. The reaction mixture was stirred at 20° C. for 3 hr and filtered. The organic phase was concentrated in vacuo to give crude N-(4-formyl-3-methoxyphenyl)-2-(3-trifluoromethylphenyl)acetamide that was used for the next step without further purification.

$^1$H-NMR, 300 MHz, DMSO-$d_6$: δ 10.65 (s, 1H), 10.2 (s, 1H), 7.7–7.5 (m, 6H), 7.2 (d, 1H), 3.85 (s, 5H).

N-(4-Formyl-3-methoxyphenyl)-2-(3-trifluoromethylphenyl)acetamide (0.67 g, 2 mmol) was dissolved in DMSO (10 mL). 3-cyano-4-hydroxybenzoic acid hydrazide (0.35 g, 2 mmol) was added followed by addition of glacial acetic acid (0.3 mL). The reaction mixture was stirred for 16 hr at 20° C., diluted with ethyl acetate (125 mL) and washed with water (100 mL). The aqueous phase was extracted with ethyl acetate (100 mL) and the organic phases combined, dried (magnesium sulphate) and concentrated in vacuo. The crude product was crystallised from methanol and DCM (1:9) to give 0.5 g of the title compound.

HPLC-MS (METHOD A) $R_t$=6.03 min; m/z=497.

$^1$H-NMR, 400 MHz, DMSO-$d_6$: δ 11.8 (s, 1H), 11.7 (s, 1H), 10.5 (s, 1H), 8.7 (s, 1H), 8.2 (s, 1H), 8.05 (dd, 1H), 7.8 (d, 1H), 7.7 (s, 1H), 7.65–7.5 (m, 4H), 7.15 (d, 1H), 7.1 (d, 1H), 3.8 (s, 5H).

EXAMPLE 913

N-{4-[(3-Cyano-4-hydroxybenzoyl)hydrazonomethyl]-3-methoxyphenyl}-3-(4-trifluoromethyl-phenyl)propionamide

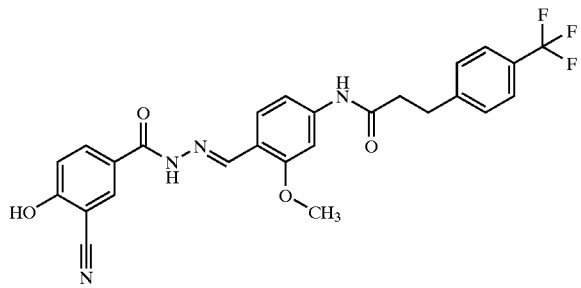

$^1$H-NMR, 300 MHz, DMSO-$d_6$: δ 11.8 (s, 1H), 11.7 (s, 1H), 10.2 (s, 1H), 8.68 (s, 1H), 8.24 (d, 1H), 8.06 (dd, 1H), 7.80 (d, 1H), 7.68 (d, 2H), 7.5 (m, 3H), 7.18 (d, 1H), 7.12 (d, 1H), 3.83 (s, 3H), 3.03 (t, 2H), 2.72 (t, 2H).

HPLC-MS (METHOD A) $R_t$=5.62 min; m/z=511.

Micro analysis: Calculated for $C_{26}H_{21}N_4O_4F_3$, ½DMSO, 1 $H_2O$: C, 57.14; H, 4.62; N, 9.87%. Found: C, 57.18; H, 4.60; N, 9.78%.

EXAMPLE 914

N-{4-[(3-Cyano-4-hydroxybenzoyl)hydrazonomethyl]-3-methoxyphenyl}-2-(4-chlorophenyl)acetamide

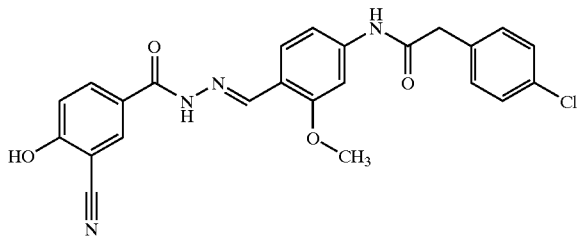

$^1$H-NMR, 300 MHz, DMSO-$d_6$: δ 11.8 (bs, 1H), 11.6 (s, 1H), 10.4 (s, 1H), 8.68 (s, 1H), 8.24 (d, 1H), 8.07 (dd, 1H), 7.80 (d, 1H), 7.55 (s, 1H), 7.4–7.35 (m, 5H), 7.18 (d, 1H), 7.10 (d, 2H), 3.82 (s, 3H), 3.68 (s, 2H).

HPLC-MS (METHOD A) $R_t$=5.33 min; m/z=463.

The following compounds may be prepared using the same synthesis methodology as described above:

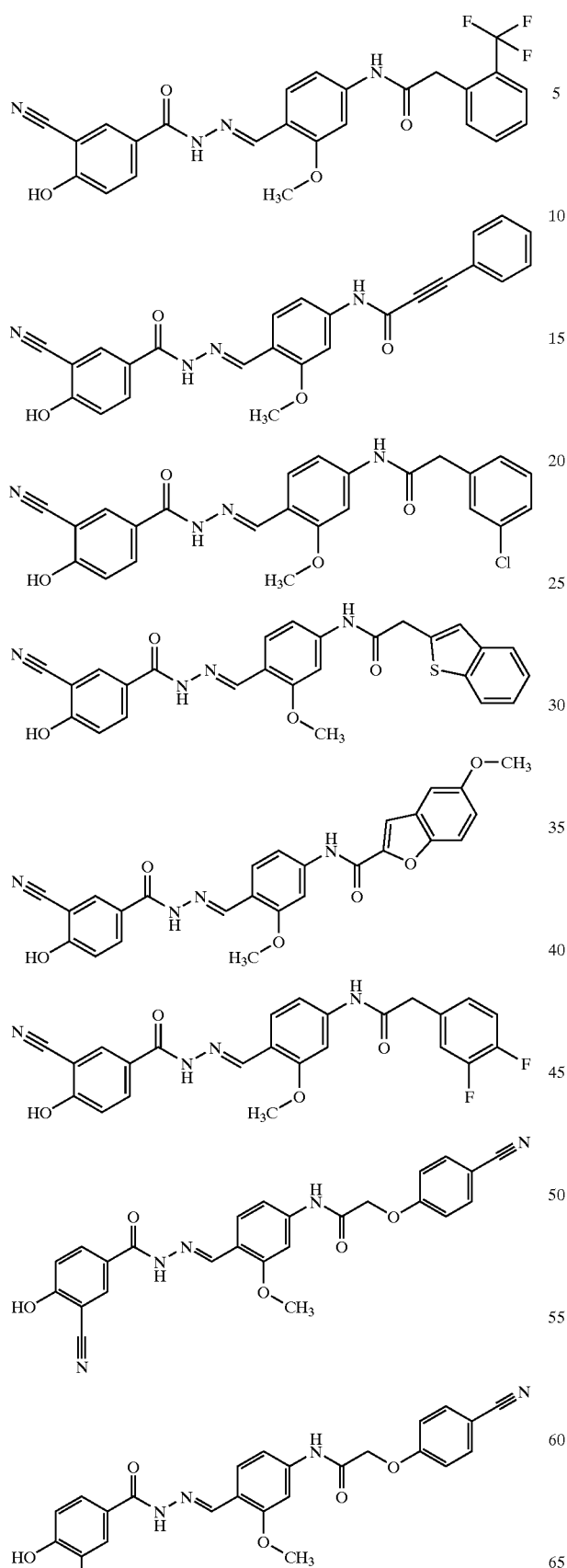
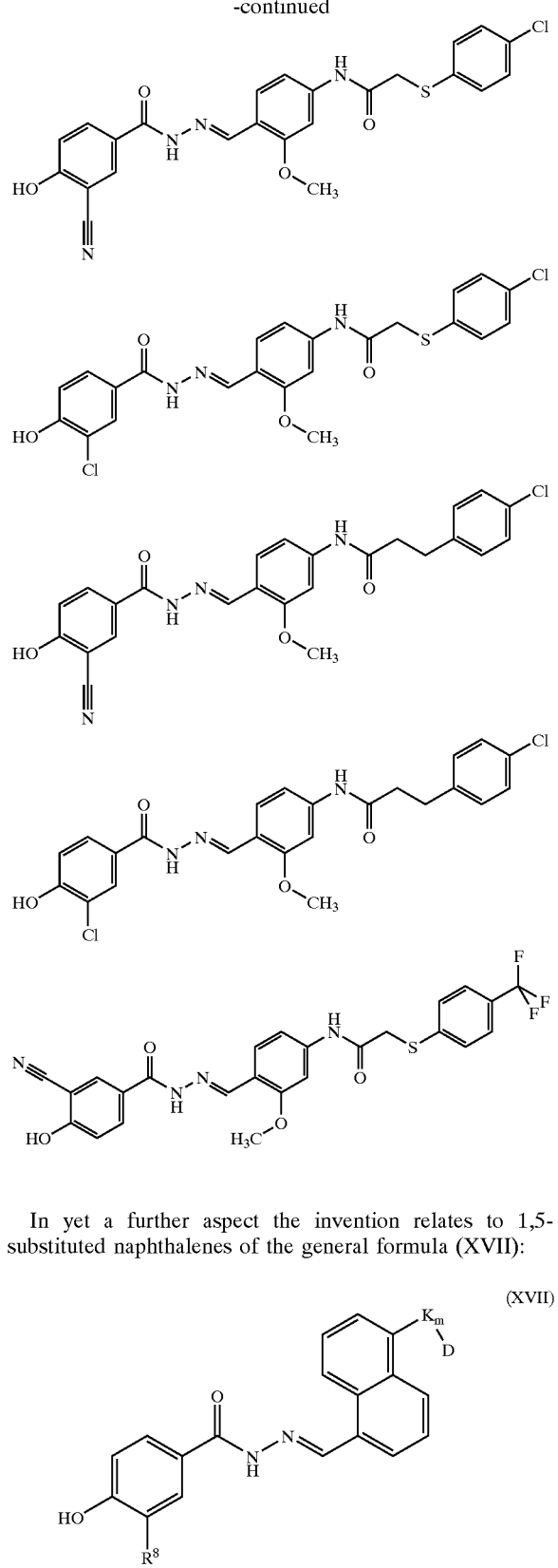
In yet a further aspect the invention relates to 1,5-substituted naphthalenes of the general formula (XVII):
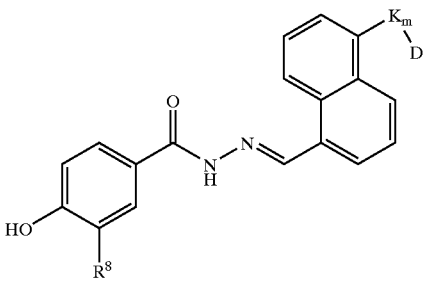
wherein
R[8] is chloro, fluoro, nitro or cyano;

K is

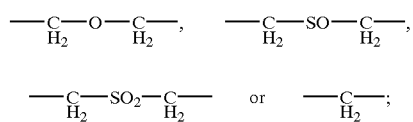

m is 0 or 1;
D is halogen, hydroxy,

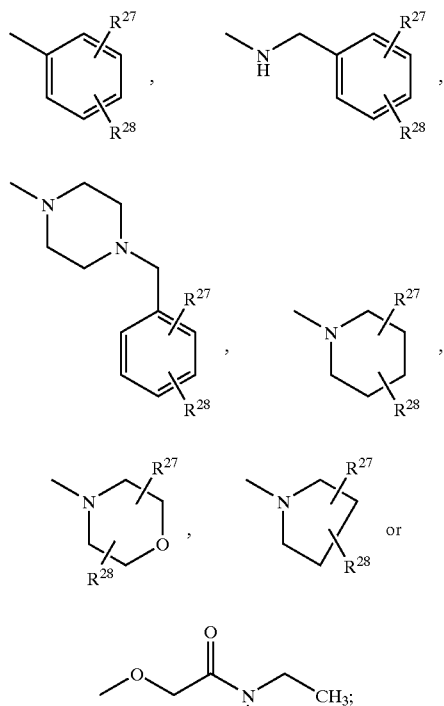

wherein
$R^{27}$ and $R^{28}$ independently are hydrogen, halogen, cyano, trifluoromethyl, trifluoromethoxy or $C_{1-6}$-alkyl;
with the proviso that
when K is

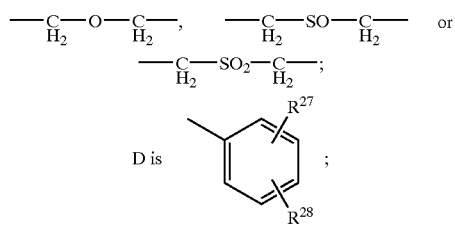

as well as any optical or geometric isomer or tautomeric form thereof including mixtures of these or a pharmaceutically acceptable salt thereof.

The compounds are active glucagon antagonists or inverse agonists and the foregoing description of applications, pharmaceutical formulations and administration methods, and as says for evaluating the efficacy of the compounds etc also applies to these compounds.

The term "$C_{1-6}$-alkyl" as used in the definition of the formula (XVII), alone or in combination, represents a branched or straight hydrocarbon group having from 1 to 6 carbon atoms. Typical $C_{1-6}$-alkyl groups include, but are not limited to, methyl, ethyl, n-propyl, isopropyl, butyl, isobutyl, sec-butyl, tert-butyl, pentyl, isopentyl, hexyl, isohexyl and the like.

The term "halogen" as used in the definition of the formula (XVII) means Cl, Br, I, or F.

In a preferred embodiment $R^8$ is chloro.
More preferred $R^8$ is cyano.
In still a preferred embodiment m is 1, K is

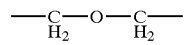

and D is

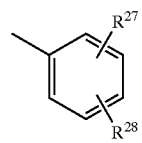

wherein $R^{27}$ and $R^{28}$ are as defined for formula (XVII) above.
In another preferred embodiment m is 1, K is

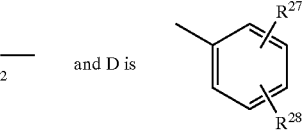

wherein $R^{27}$ and $R^{28}$ are as defined for formula (XVII) above.
In another preferred embodiment m is 1, K is

and D is halogen, hydroxy,

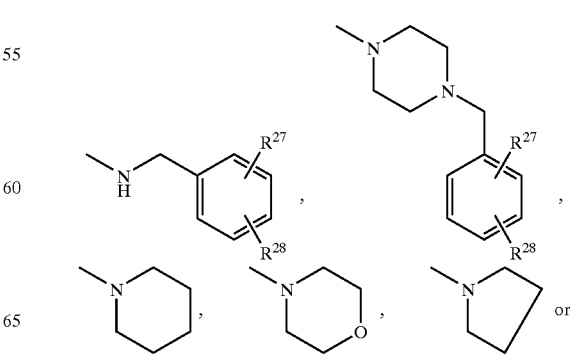

-continued

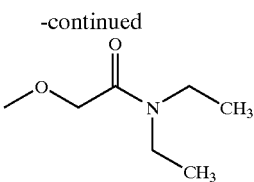

wherein R[27] and R[28] are as defined above for formula (XVII).

In the above preferred embodiments R[27] is preferably hydrogen and R[28] is halogen, cyano, trifluoromethyl, trifluoromethoxy or $C_{1-6}$-alkyl.

In a further preferred embodiment the invention relates to the following compounds:

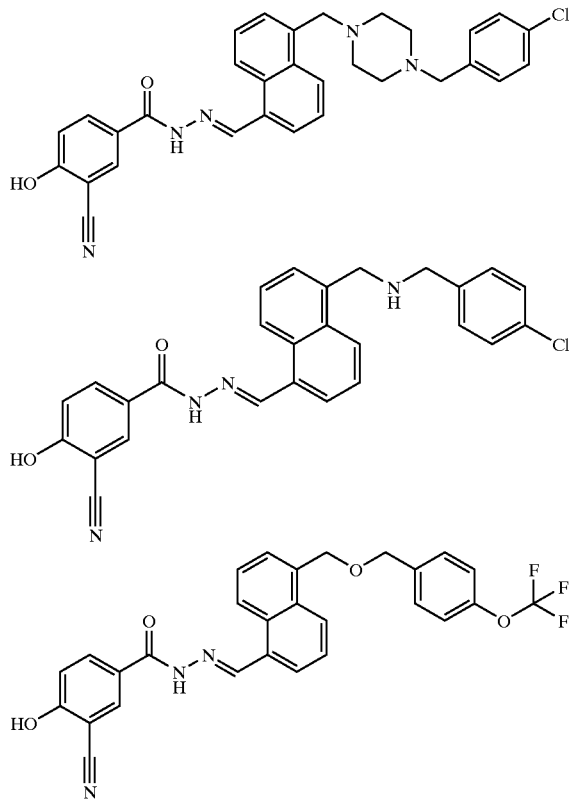

as well as any optical or geometric isomer or tautomeric form thereof including mixtures of these or a pharmaceutically acceptable salt thereof.

The present invention is further illustrated by the following representative examples which are, however, not intended to limit the scope of the invention in any way.

Preparation of Intermediates

5-Hydroxymethyl-1-naphthaldehyde
Methyl 5-Bromo-1-naphthylcarboxylate:

To a suspension of 5-bromo-1-naphthylcarboxylic acid (5 g, 20 mmol) in 200 mL anhydrous MeOH was added 5 mL concentrated $H_2SO_4$ and refluxed overnight. The reaction was cooled to room temperature and concentrated to one-third the volume. The residue was diluted with water and extracted with diethyl ether. The organic layer was separated and washed with water (2×), dried over $MgSO_4$, and concentrated. Silica gel column chromatography using hexane/ethyl acetate (2/11) gave 4.91 g (92%) of the product.

$^1$H NMR (CDCl$_3$-d: δ 4.01 (s, 3H), 7.44 (dd, 1H), 7.61 (dd, 1H), 7.85 (dd, 1H), 8.22 (dd, 1H), 8.51 (d, 1H), 8.90 (d, 1H).

Methyl 5-Cyano-1-naphthylcarboxylate:

A mixture of methyl 5-bromo-1-naphthylcarboxylate (5.2 g, 19 mmol) and CuCN (3.4 g, 38 mmol) in 100 mL anhydrous DMF was refluxed overnight. After cooling the reaction to 70° C., a solution of NaCN (2 g) in 50 mL water was added to destroy the copper complex. Ethyl acetate was added and the two layers were separated. The organic layer was washed with brine, dried over $MgSO_4$, and concentrated. Silica gel column chromatography using hexane/ethyl acetate (5/1) gave the product (3.8 g, 95%).

$^1$H NMR (CDCl$_3$-d: δ 4.01 (s, 3H), 7.60–7.80 (m, 3H), 7.98 (d, 1H), 8.30 (d, 1H), 8.45 (d, 1H), 9.21 (d, 1H).

5-Hydroxymethyl-1-naphthaldehyde:

To a cooled (0° C.) solution of methyl 5-cyano-1-naphthylcarboxylate (1 g, 5 mmol) in 20 mL anhydrous THF was added DIBAL (1M in hexane, 20 mL, 20 mmol) via syringe. The mixture was then kept between 50–60° C. overnight. The mixture was then cooled to room temperature. The mixture was poured into a cold (0° C.) solution of 2 N HCl (100 mL). The product was extracted with ether (2×). The organic layer was washed with brine, dried over $MgSO_4$ and concentrated. Silica gel column chromatography using hexane/ethyl acetate (2/1) gave the 0.85 g (91%) of the product.

$^1$H NMR (CDCl$_3$-d: δ 4.95 (s, 2H), 7.45–7.58 (m, 3H), 7.82 (dd, 1H), 8.24 (d, 1H), 9.03 (dd, 1H), 10.21 (s, 1H).

General Procedure for the Alkylation of 5-Hydroxymethylnaphthaldehyde

To a solution of the above 5-hydroxymethyl-1-naphthaldehyde (1 mmol), alkyl halide (1.5 mmol) and 100 mg n-Bu$_4$NCl in 20 mL CH$_2$Cl$_2$ was added aqueous 5% KOH (20 mL) solution. The reaction was refluxed overnight, and the two layers were separated. The organic layer was washed with water, brine, dried over $MgSO_4$ and concentrated. The desired product was purified via silica gel column chromatography using hexane/ethyl acetate.

Examples of alkylated products:

5-(4-Isopropylbenzyloxy)methyl-1-naphthaldehyde:

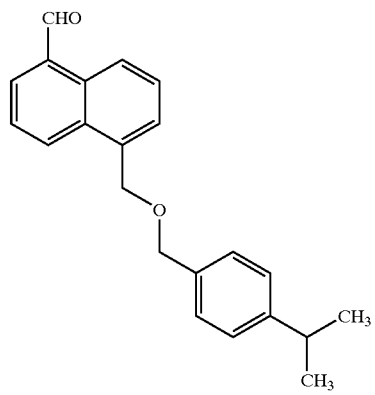

$^1$H NMR (CDCl$_3$): δ 1.25 (d, 6H), 2.90 (m, 1H), 4.56 (s, 2H), 4.98 (s, 2H), 7.25 (dd, 4H), 7.52–7.68 (m, 3H), 7.97 (d, 1H), 8.42 (d, 1H), 9.24 (d, 1H), 10.38 (s, 1H).

5-(4-Trifluoromethoxybenzyloxy)methyl-1-naphthaldehyde

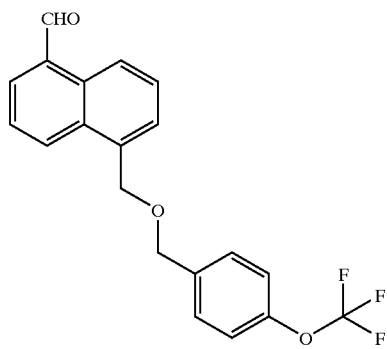

¹H NMR (CDCl₃): δ 4.54 (s, 2H), 5.05 (s, 2H), 7.21 (d, 2H), 7.39 (d, 2H), 7.59–7.74 (m, 3H), 8.01 (d, 1H), 8.45 (d, 1H), 9.30 (d, 1H), 10.43 (s, 1H).

General Procedure for the Formation of the 1,5-Substituted Naphthalenes of the General Formula (XVII)

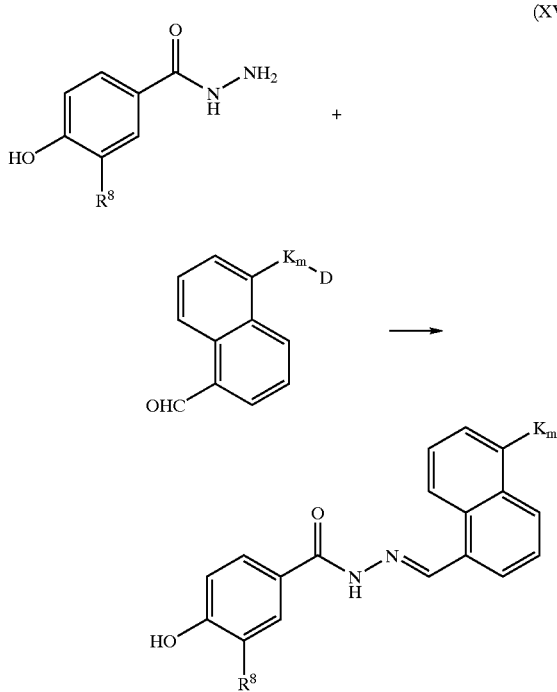

(XVII)

wherein $R^8$, K, m and D are as defined for formula (XVII) above.

The resulting carbonyl compounds, prepared as described above, are treated with the corresponding acylhydrazide prepared as decribed in the foregoing in a solvent. The solvent may be one of the following: ethyl alcohol, methyl alcohol, isopropyl alcohol, tert-butyl alcohol, dioxane, tetrahydrofuran, toluene, chlorobenzene, anisole, benzene, chloroform, dichloromethane, DMSO, acetic acid, water or a compatible mixture of two or more of the above solvents. A catalyst such as acetic acid can be added. A dehydrating reagent such as triethylorthoformate can also be added to the reaction mixture. The reaction is performed by stirring the reaction mixture preferably under an inert atmosphere of $N_2$ or Ar at temperatures between 0° C. to 140° C., preferably between 10° C. to 80° C. In many cases the product simply crystallizes out when the reaction is completed and is isolated by suction filtration. It can be further recrystallized if necessary from a solvent such as the above described reaction solvents. The product can also be isolated by concentration of the reaction mixture in vacuo, followed by column chromatography on silica gel using a solvent system such as chloroform/methanol or dichloromethane/methanol or chloroform/ethyl acetate.

The following compounds of the general formula (XVII) according to the invention were prepared as examples of compounds that can be prepared using this methodology:

EXAMPLE 915

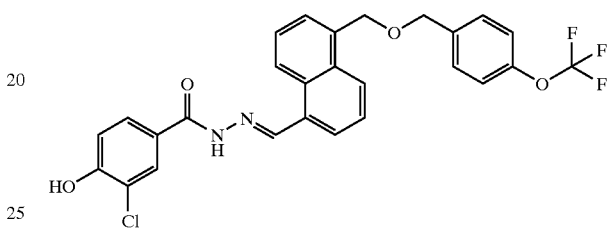

¹H NMR (DMSO-d₆): δ 4.67 (s, 2H), 5.05 (s, 2H), 7.11 (d, 1H), 7.35 (d, 2H), 7.50 (d, 2H), 7.57–7.75 (m, 3H), 7.82 (d, 1H), 7.95–8.08 (m, 2H), 8.22 (d, 1H), 8.78 (s, 1H), 9.14 (s, 1H), 11.01 (s, 1H), 11.85 (s, 1H); LC-MS (APCI, neg.): 527.

EXAMPLE 916

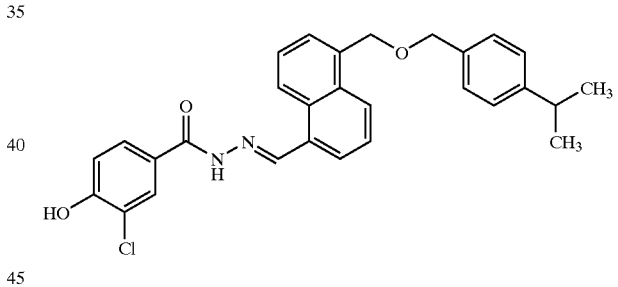

¹H NMR (DMSO-d₆): δ 1.13 (d, 6H), 2.82 (m, 1H), 4.53 (s, 2H), 4.95 (d, 2H), 7.04 (d, 1H), 7.15–7.24 (dd, 4H), 7.57–7.62 (m, 3H), 7.76 (d, 1H), 7.90–7.97 (m, 2H), 8.14 (d, 1H), 8.70 (s, 1H), 9.08 (s, 1H), 10.99 (s, 1H), 11.78 (s, 1H). LC-MS (APCI, neg.): 485.1.

EXAMPLE 917

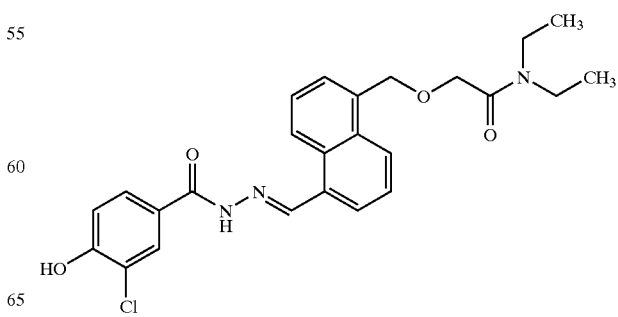

EXAMPLE 918

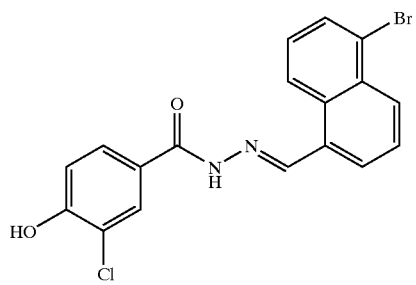

¹H NMR (DMSO-d₆): δ 7.09 (d, 1H), 7.58 (t, 1H), 7.79 (m, 2H), 7.96–8.01 (m, 3H), 8.27 (d, 1H), 8.86 (d, 1H), 9.09 (s, 1H), 11.0 (s, 1H), 11.88 (s, 1H); LC-MS (APCI, neg.): 403.1.

EXAMPLE 919

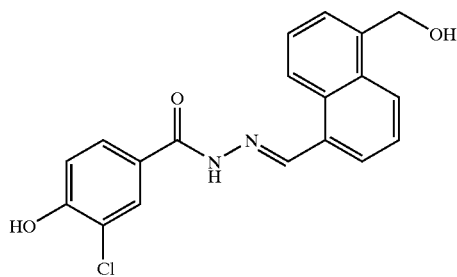

¹H NMR (DMSO-d₆) δ 4.98 (d, 2H), 5.37 (t, 1H), 7.08 (d, 1H), 7.62 (dr, 3H), 7.79 (d, 1H), 7.94 (d, 1H), 8.00 (s, 1H), 8.18 (d, 1H), 8.67 (s, 1H), 9.12 (s, 1H); LC-MS (APCI, pos.): 355.

EXAMPLE 920

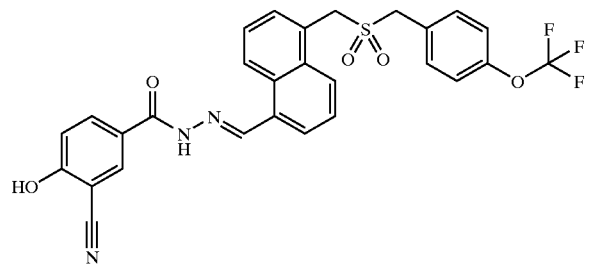

¹H NMR (DMSO-d₆): δ 11.8 (b, 1H), 10.5 (b, 1H), 9.0 (s, 1H), 8.7 (d, 1H), 8.1 (m, 2H), 8.0 (d, 1H), 7.9 (d, 1H), 7.5 (m, 6H), 7.3 (d, 2H), 7.0 (d, 2H), 5.0 (s, 1H), 4.6 (s, 1H); MS (M+1): 568.

General Procedure for the Synthesis of Further Derivatized Hydrazides of the General Formula (XVIIa)

According to one embodiment of the invention the compounds of the general formula (XVIIa) may be prepared as indicated in the below Scheme, that is, by converting an alkylidene hydrazide (prepared according to the general method shown above) into a further derivatized alkylidene hydrazide. Thus, by reacting an amine with an alkylidene hydrazide that contains a leaving group $X_L$ such as Cl, Br or OSO₂Me, a new alkylidene hydrazide of formula (XVIIa) can be formed.

SCHEME

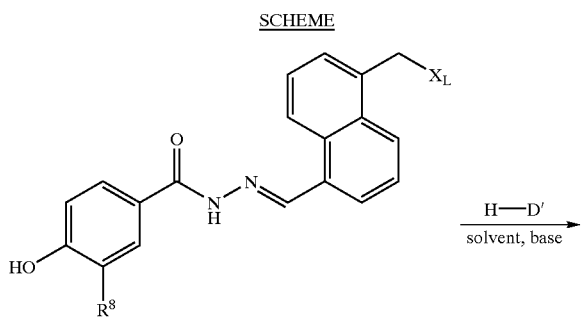

(XVIIa)

wherein $X_L$ is a leaving group, such as chloro, bromo or OSO₂CH₃, $R^8$ is as defined for formula (XVII) and D' is the subset of D that contains a primary or secondary amine that can react as a nucleophile.

Specific examples illustrating the preparation of further derivatized hydrazides of formula (XVII) are provided below:

EXAMPLE 921

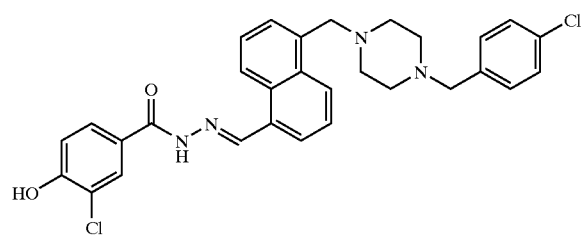

EXAMPLE 922

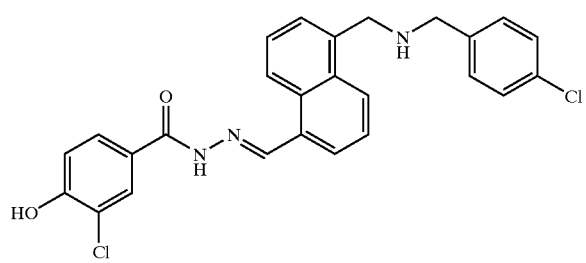

EXAMPLE 923
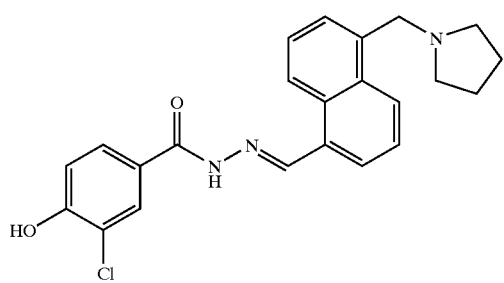
EXAMPLE 924
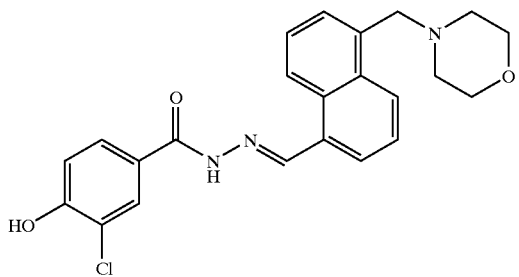
EXAMPLE 925
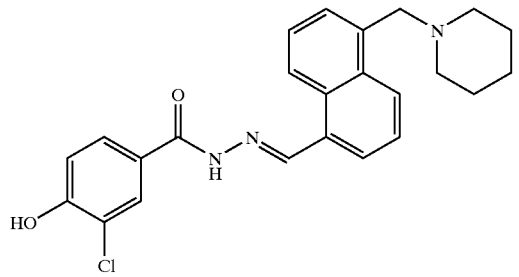
The following compounds may also be prepared using the above mentioned methodologies:
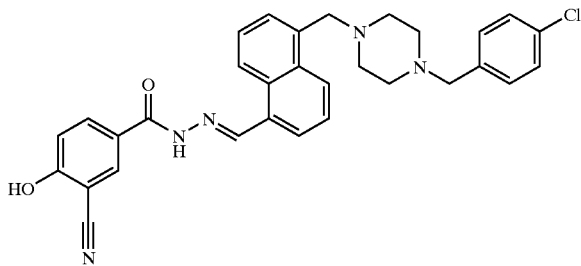
-continued
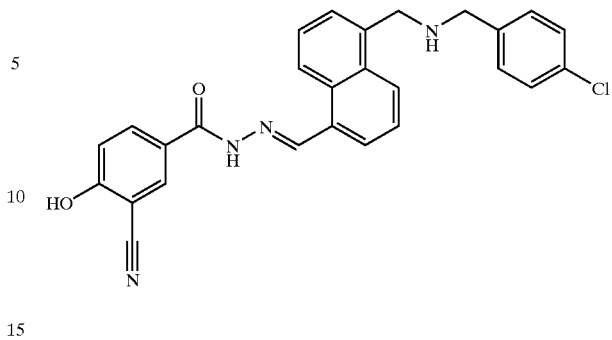
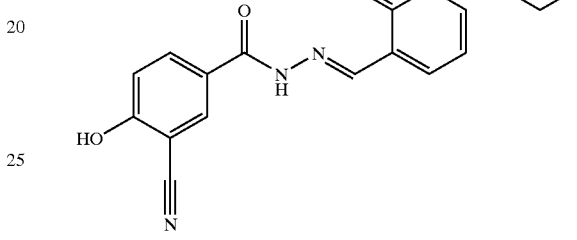
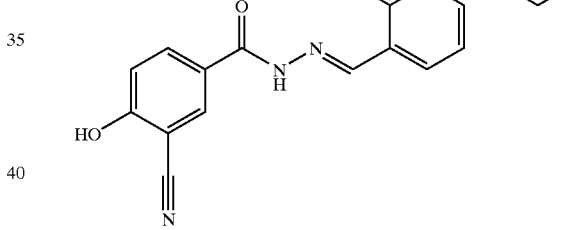
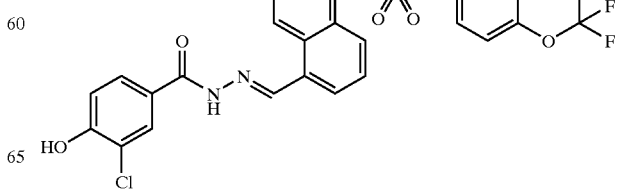

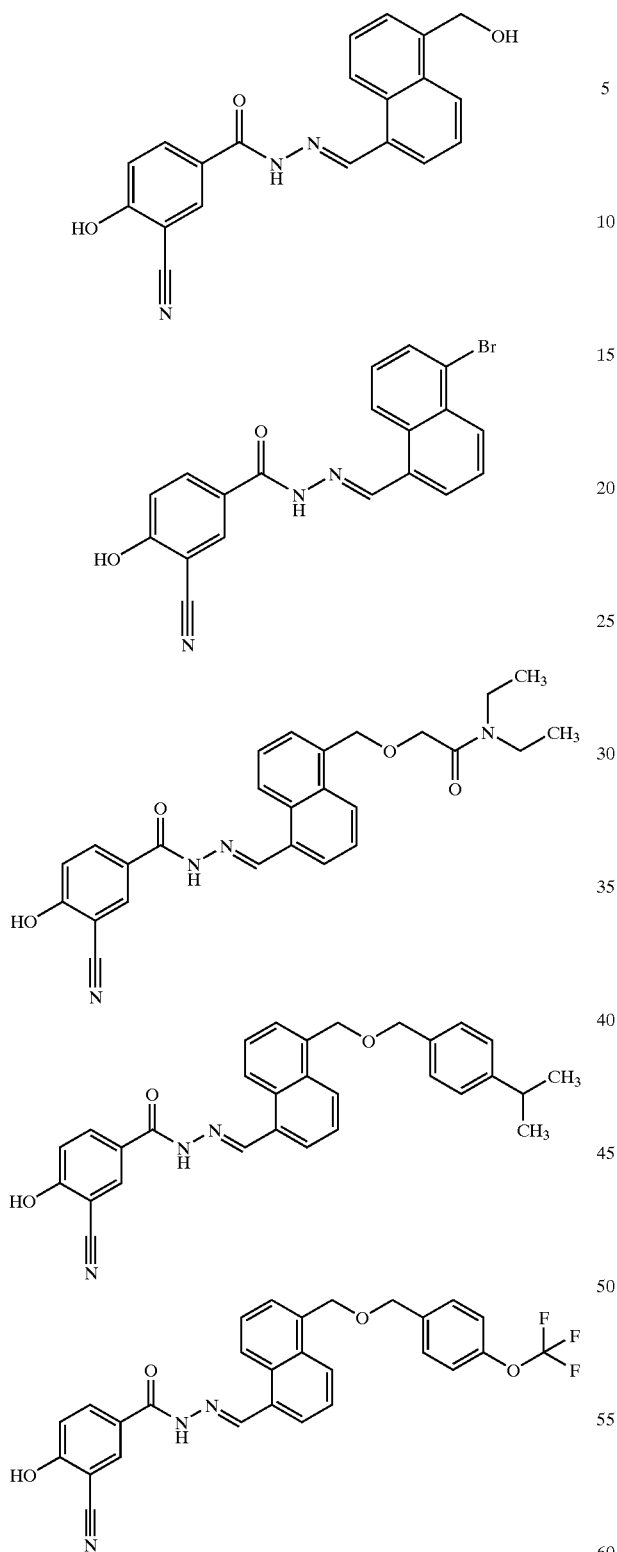

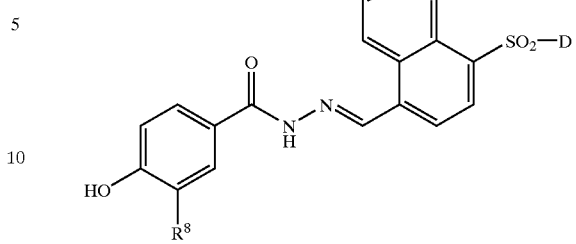

wherein
R[8] is chloro, fluoro, nitro or cyano;
D is

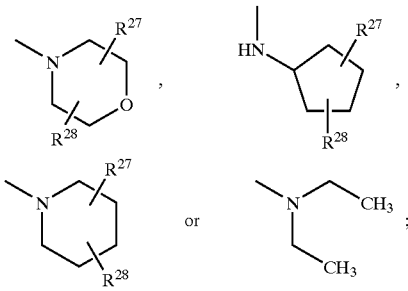

wherein
R[27] and R[28] independently are hydrogen, halogen, cyano, trifluoromethyl, trifluoromethoxy or $C_{1-6}$-alkyl;
as well as any optical or geometric isomer or tautomeric form thereof including mixtures of these or a pharmaceutically acceptable salt thereof.

The compounds are active glucagon antagonists or inverse agonists and the foregoing description of applications, pharmaceutical formulations and administration methods, and assays for evaluating the efficacy of the compounds etc also applies to these compounds.

The term "$C_{1-6}$-alkyl" as used in the definition of the formula (XVIII), alone or in combination, represents a branched or straight hydrocarbon group having from 1 to 6 carbon atoms. Typical $C_{1-6}$-alkyl groups include, but are not limited to, methyl, ethyl, n-propyl, isopropyl, butyl, isobutyl, sec-butyl, tert-butyl, pentyl, isopentyl, hexyl, isohexyl and the like.

The term "halogen" as used in the definition of the formula (XVIII) means Cl, Br, I, or F.

In a preferred embodiment of the invention D is

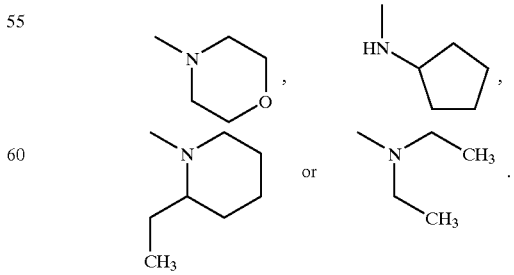

In yet a further aspect the invention relates to the naphthalene sulfonamides of the general formula (XVIII):

In another preferred embodiment of the invention $R^8$ is chloro.

More preferred $R^8$ is cyano.

The present invention is further illustrated by the following representative examples which are, however, not intended to limit the scope of the invention in any way.

General Procedure for the Preparation of Hydrazones of Naphthalene Sulfonamides of the Formula (XVIII)

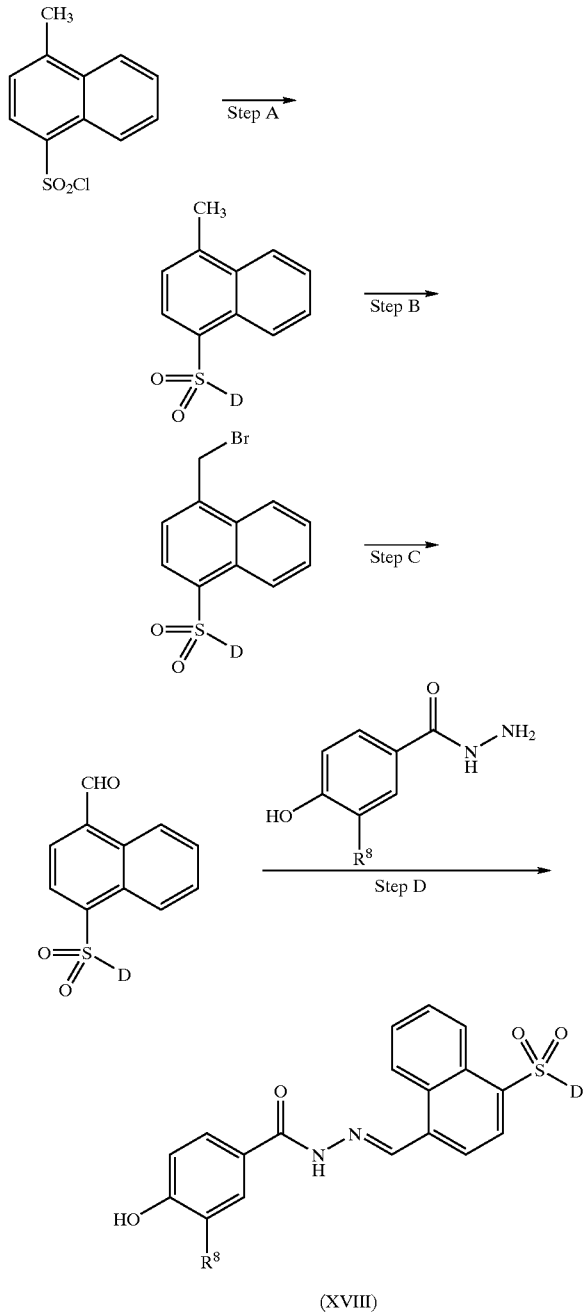

(XVIII)

Step A: General Procedure for the Synthesis of 4-Methyl-1-naphthalene Sulfonamides:

To a solution of 4-methyl-1-naphthalene sulfonylchloride (2.0 g, 8.3 mmol) (prepared according to P. Cagniant, D. Cagniant, Bull. Soc. Chim. Fr. 1966, 2037–2042) in dichloromethane was added dropwise the amine (1 eq) at 0° C. The mixture was stirred at room temperature for 16 hr, diluted with dichloromethane (15 mL), extracted with 1N HCl (10 mL), brine (10 mL), dried (MgSO$_4$), and concentrated to give the corresponding 4-methyl-1-naphthalene sulfonamide.

Examples of sulfonamides prepared:
4-Methyl-1-naphthalene Diethylsulfonamide:

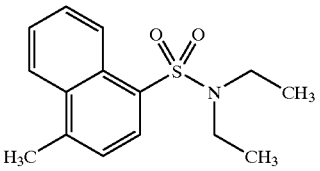

$^1$H NMR (CDCl$_3$): δ 1.08 (t, J=6.8 Hz, 6H), 2.76 (s, 3H), 3.37 (q, J=6.8 Hz, 4H), 7.37 (d, J=7.5 Hz, 1H), 7.61–7.66 (m, 2H), 8.08 (dd, J=2.1, 4.2 Hz, 1H), 8.11 (d, J=7.5 Hz, 1H), 8.67 (dd, J=2.1, 8.6 Hz, 1H). GC-MS (pos.): 278.

1-(2-Ethylpiperidinylsulnyl)-4-methylnaphthalene:

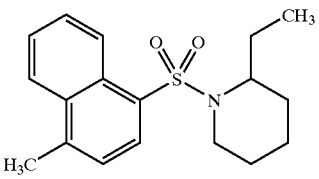

$^1$H NMR (CDCl$_3$): δ 0.74 (t, J=6.8 Hz, 3H), 1.21 (m, 2H), 1.47–1.66 (m, 6H), 2.76 (s, 3H), 3.01 (t, J=13.4 Hz, 1H), 3.69 (dd, J=3.5, 13.4 Hz, 1H), 3.99 (m, 1H), 7.37 (d, J=7.5 Hz, 1H), 7.61–7.66 (m, 2H), 8.08 (dd, J=2.1, 6.5 Hz, 1H), 8.20 (d, J=7.5 Hz, 1H), 8.62 (dd, J=2.1, 9.5 Hz, 1H). GC-MS (pos.): 318.

1-(4-Morpholinosulfonyl)-4-methylnaphthalene:

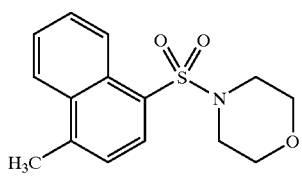

$^1$H NMR (CDCl$_3$): δ 2.78 (s, 3H), 3.15 (t, J=4.7 Hz, 4H), 3.68 (t, J=4.7 Hz, 4H), 7.42 (d, J=7.5 Hz, 1H), 7.63–7.67 (m, 2H), 8.09–8.14 (m, 2H), 8.78–8.81 (m, 1H). GC-MS (pos.): 292.

4-Methyl-1-naphthalene Cyclopentylsulfonamide:

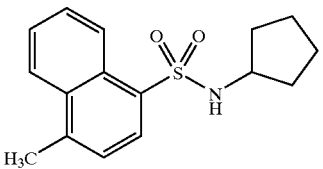

$^1$H NMR (CDCl$_3$): δ 1.21–1.66 (m, 8H), 2.78 (s, 3H), 3.54 (m, 1H), 4.60 (d, J=7.3 Hz, 1H), 7.40 (d, J=7.5 Hz, 1H), 7.63–7.68 (m, 2H), 8.12 (dd, J=2.0,7.6 Hz, 1H), 8.19 (d, J=7.5 Hz,1H), 8.65 (dd, J=1.8, 7.2 Hz, 1H); GC-MS (pos.): 290.

Step B: General Procedure for the Synthesis of 4-Bromomethyl-1-naphthalene Sulfonamides:

A mixture of 4-methyl-1-naphthalene sulfonamide (1 eq), N-bromosuccinimide (1.1 eq) and a catalytic amount of benzoyl peroxide in CCl$_4$ was refluxed for 2 hr. The mixture was filtered, and the filtrate was concentrated. Flash chromatography (hexane:ethyl acetate, 5:1) provided a mixture of starting material and desired product, which was used without further purification in the next step.

Step C: General Procedure for the Synthesis of 4-Formyl-1-naphthalene Sulfonamides:

Nitrogen was bubbled through a suspension of 1.3 g sodium bicarbonate in DMSO (5 mL) for 20 min. The 4-bromomethyl-1-naphthalene sulfonamide from step B dissolved in 5 mL DMSO was added. The mixture was placed in oil bath at 110° C. for 1.5 hr. The mixture was cooled, diluted with water (10 mL), and extracted with ethyl acetate (3×10 mL). The combined organic extracts were dried (MgSO$_4$), and concentrated. Flash chromatography (silicagel, hexane:ethyl acetate, 5:1) provided the title compound.

Examples of 4-Formyl-1-naphthalene Sulfonamides:

4-Formyl-1-naphthalene Diethylsulfonamide:

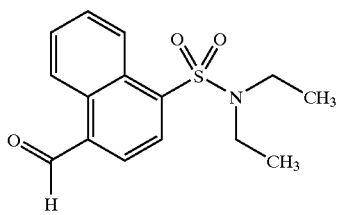

$^1$H NMR (CDCl$_3$): δ 1.12 (t, J=6.8 Hz, 6H), 3.41 (q, J=6.8 Hz, 4H), 7.74–7.79 (m, 2H), 8.04 (d, J=7.5 Hz, 1H), 8.32 (d, J=7.5 Hz, 1H), 8.78 (dd, J=2.1, 7.7 Hz, 1H), 9.28 (dd, J=2.1, 6.7 Hz, 1H), 10.50 (s, 1H). GC-MS (pos.): 292.

1-(2-Ethylpiperidinylsulfonyl)-4-formylnaphthalene:

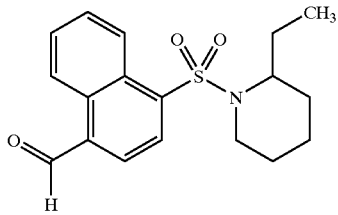

$^1$H NMR (CDCl$_3$): δ 0.74 (t, J=6.8 Hz, 3H), 1.21 (m, 2H), 1.47–1.66 (m, 6H), 3.02 (dd, J=2.2, 11.2 Hz, 1H), 3.72 (dd, J=3.6 Hz, 1H), 3.97 (m, 1H), 7.73–7.78 (m, 2H), 8.04 (d, J=7.6 Hz, 1H), 8.45 (d, J=7.5 Hz, 1H), 8.73 (dd, J=2.1, 7.8 Hz, 1H), 9.28 (dd, J=2.1, 6.7 Hz, 1H), 10.50 (s, 1H).

1-(4-Morpholinosulfonyl)-4-formylnaphthalene:

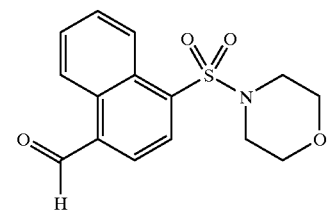

$^1$H NMR (CDCl$_3$): δ 3.21 (t, J=4.7 Hz, 4H), 3.70 (t, J=4.7 Hz, 4H), 7.73–7.78 (m, 2H), 8.08 (d, J=7.6 Hz, 1H), 8.37 (d, J=7.5 Hz, 1H), 8.87 (d, J=7.5 Hz, 1H), 9.30 (dd, J=8.0 Hz, 1H), 10.52 (s, 1H).

4-Formyl-1-naphthalene Cyclopentylsulfonamide:

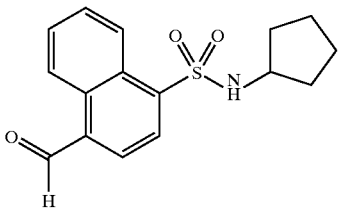

$^1$H NMR (CDCl$_3$): δ 1.23–1.27 (m, 2H), 1.42–1.53 (m, 4H), 1.62–1.69 (m, 2H), 3.65 (m, 1H), 4.82 (d, J=7.5 Hz, 1H), 7.73–7.82 (m, 2H), 8.07 (d, J=7.6 Hz, 1H), 8.46 (d, J=7.5 Hz, 1H), 8.75 (dd, J=2.2, 7.6 Hz, 1H), 9.31 (dd, J=2.2, 6.7 Hz, 1H), 10.51 (s, 1H).

Step D: General Procedure for the Synthesis of the Naphthalene Sulfonamides of the General Formula (XVIII):

These compounds were prepared according to the general procedure for the synthesis of alkylidene hydrazones from the condensation of 4-formyl-1-naphthalene sulfonamides from step C and the appropriate 3-substituted 4-hydroxy benzoic acid hydrazide.

EXAMPLE 926

4-{[2-(3-Chloro-4-hydroxybenzoyl)hydrazono]methyl}-N,N-diethyl-1-naphthalenesulfonamide

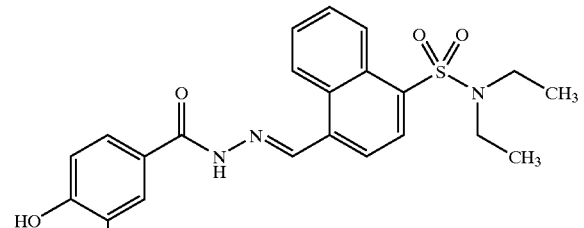

$^1$H NMR (DMSO-D$_6$): δ 1.11 (t, J=7.0 Hz, 6H), 3.32 (q, J=7.0 Hz, 4H), 7.09 (d, J=8.5 Hz, 1H), 7.79 (m, 3H), 8.01–8.17 (m, 3H), 8.63 (m, 1H), 7.79 (m, 1H), 9.16 (s, 1H), 11.20 (bs, 1H), 12.02 (s, 1H); MS (APCI, pos.): 460.1, 462.1.

EXAMPLE 927

3-Chloro-4-hydroxybenzoyl)-N-4[-(4-morpholinosulfonyl)-1-naphthyl]-methylene Hydrazide

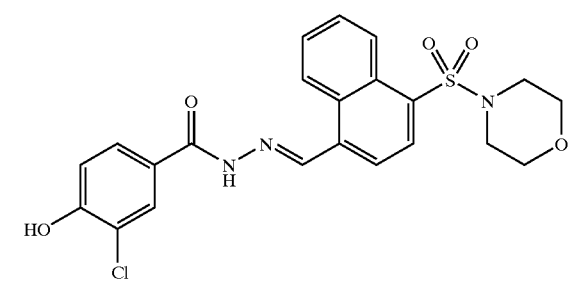

$^1$H NMR (DMSO-D$_6$): δ 3.08 (m, 4H), 3.74 (m, 4H), 7.09 (d, J=8.3 Hz, 1H), 7.78–7.83 (m, 4H), 8.00 (s, 1H), 8.13 (m,

1H), 8.21 (d, J=8.0 Hz, 1H), 8.72–8.76 (m, 2H), 9.17 (s, 1H), 12.06 (s, 1H); MS (APCI, pos.): 474.0, 476.1.

EXAMPLE 928

4-{[2-(3-Chloro-4-hydroxybenzoyl)hydrazono]methyl}-N-cyclopentyl-1-naphthalenesulfonamide

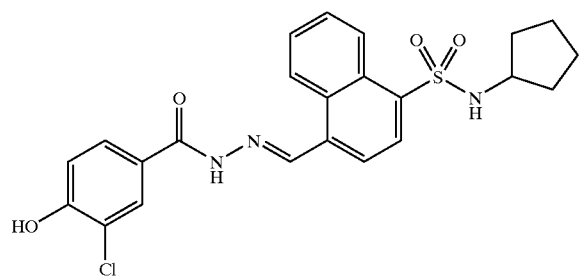

$^1$H NMR (DMSO-D$_6$): δ 1.15–1.25 (m, 4H), 1.27 (m, 4H), 3.40 (m, 1H), 7.08 (d, J=8.5 Hz, 1H), 7.75–7.80 (m, 3H), 7.98 (s, 1H), 8.04–8.07 (m, 2H), 8.22 (d, J=7.8 Hz, 1H), 8.73–8.77 (m, 2H), 9.15 (s, 1H), 12.00 (s, 1H); MS (APCI, pos.): 472, 474.

EXAMPLE 929

3-Chloro-4-hydroxybenzoic Acid 4-[(2-Ethyl-1-piperidinyl)sulfonyl]-1-naphthylmethylene Hydrazide

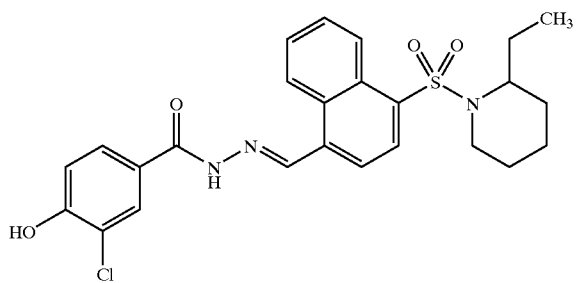

$^1$H NMR (DMSO-D$_6$): δ 0.64 (t, J=6.8 Hz, 3H), 0.93 (m, 2H), 1.22–1.66 (m, 6H), 3.02 (t, J=11.2 Hz, 1H), 3.72 (m, 1H), 3.85 (m, 1H), 7.08 (d, J=8.5 Hz, 1H), 7.75–7.80 (m, 3H), 8.01 (s, 1H), 8.07 (d, J=8.7 Hz, 1H), 8.30 (d, J=7.8 Hz, 1H), 8.62 (m, 1H), 8.76 (m, 1H), 9.17 (s, 1H), 12.00 (s, 1H); MS (APCI, pos.): 500, 502.

The following compounds may also be prepared using the above mentioned methodologies:

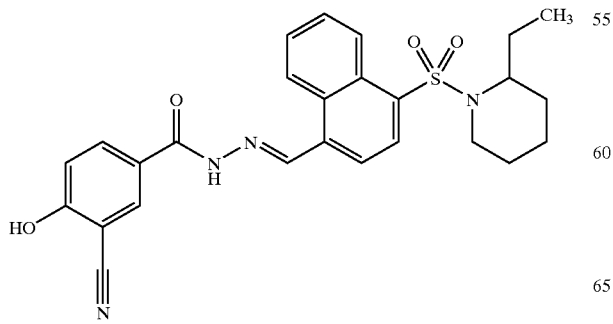

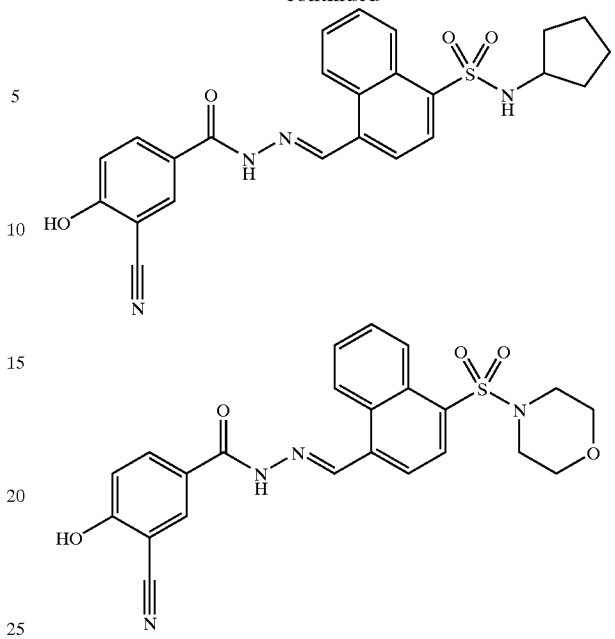

In another aspect the invention relates to 1,4-substituted indoles of the formula (IXX):

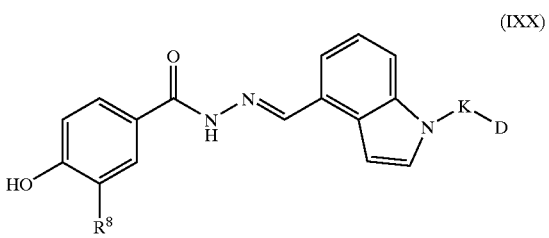

(IXX)

wherein

R$^8$ is chloro, fluoro, nitro or cyano;

K is —C(O)—(CH$_2$)$_d$—, —CH$_2$—CH$_2$—O— or —CHR$^{5a}$—;

wherein d is 0 or 1;

R$^{5a}$ is hydrogen or C$_{1-6}$-alkyl

D is

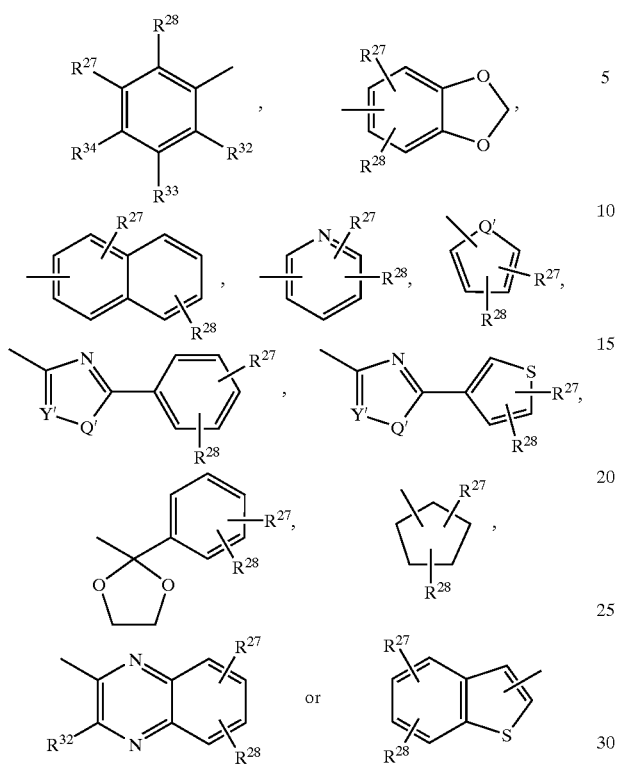

wherein

Q' is —O— or —S—;
Y' is —CH= or —N=;
$R^{27}$, $R^{28}$, $R^{32}$, $R^{33}$ and $R^{34}$ independently are hydrogen, $C_{1-6}$-alkyl, trifluoromethyl, difluoromethoxy, trifluoromethoxy, halogen, carboxamido, hydroxymethyl, phenyl, dimethylamino, $C_{1-6}$-alkoxy or nitro;

as well as any optical or geometric isomer or tautomeric form thereof including mixtures of these or a pharmaceutically acceptable salt thereof.

The compounds are active glucagon antagonists or inverse agonists and the foregoing description of applications, pharmaceutical formulations and administration methods, and assays for evaluating the efficacy of the compounds etc also applies to these compounds.

The term "$C_{1-6}$-alkyl" as used in the definition of the formula (IXX), alone or in combination, represents a branched or straight hydrocarbon group having from 1 to 6 carbon atoms. Typical $C_{1-6}$-alkyl groups include, but are not limited to, methyl, ethyl, n-propyl, isopropyl, butyl, isobutyl, sec-butyl, tert-butyl, pentyl, isopentyl, hexyl, isohexyl and the like.

The term "$C_{1-6}$-alkoxy" as used in the definition of the formula (IXX), alone or in combination, refers to the group —O—$C_{1-6}$-alkyl where $C_{1-6}$-alkyl is as defined above. Representative examples are methoxy, ethoxy, n-propoxy, isopropoxy, butoxy, sec-butoxy, tert-butoxy, pentoxy, isopentoxy, hexoxy, isohexoxy and the like.

The term "halogen" as used in the definition of the formula (IXX) means Cl, Br, I, or F.

In a preferred embodiment $R^8$ is chloro.
More preferred $R^8$ is cyano.
In a further preferred embodiment K is —CH$_2$— or —CH($C_{1-6}$-alkyl)-.

In another preferred embodiment K is —C(O)— or —C(O)—CH$_2$-.

In yet another preferred embodiment D is

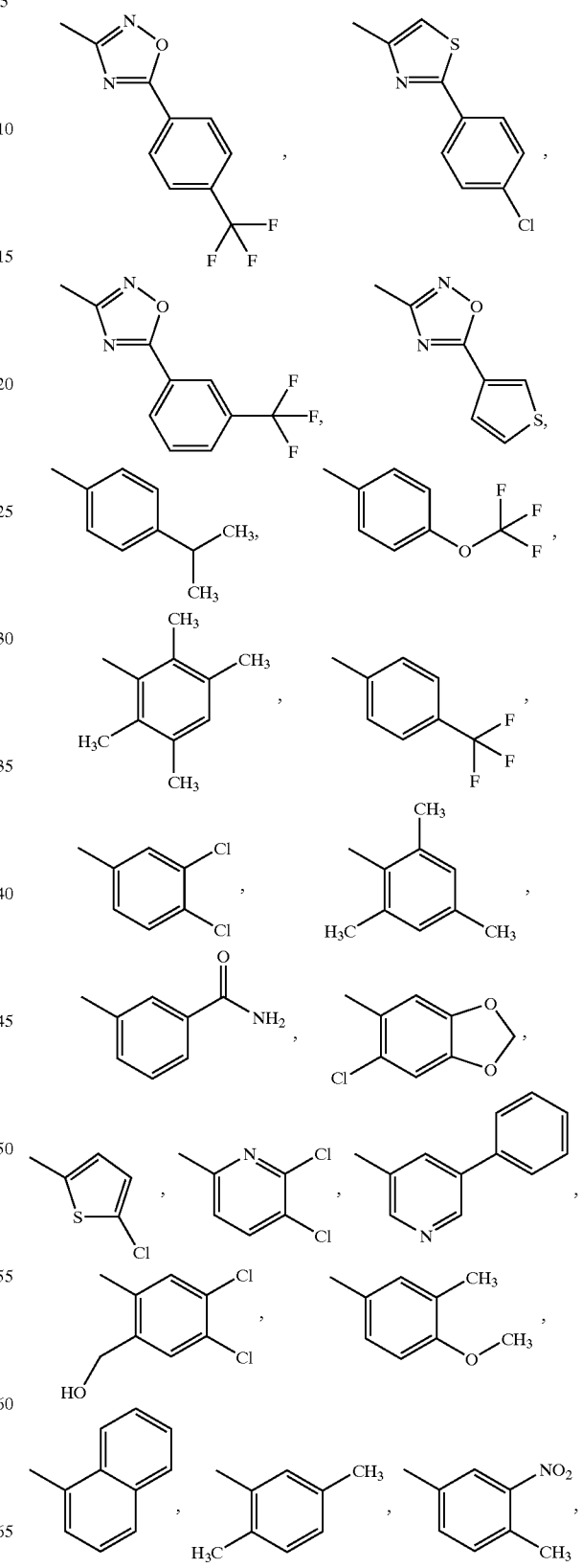

655
-continued
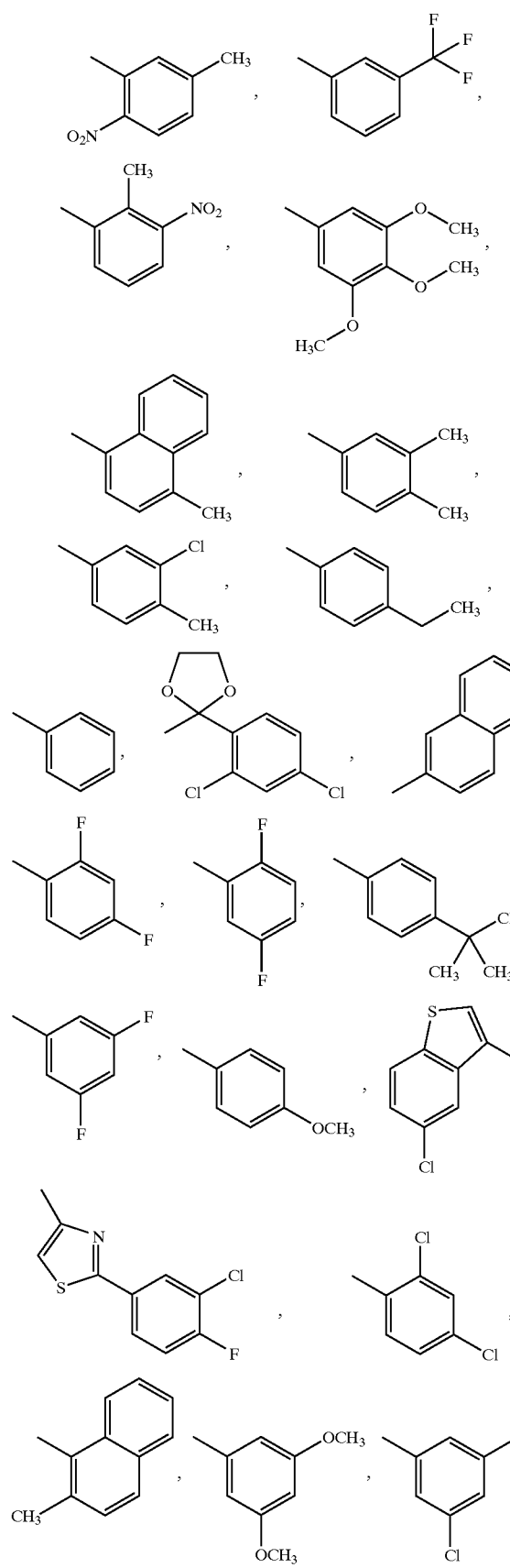
656
-continued
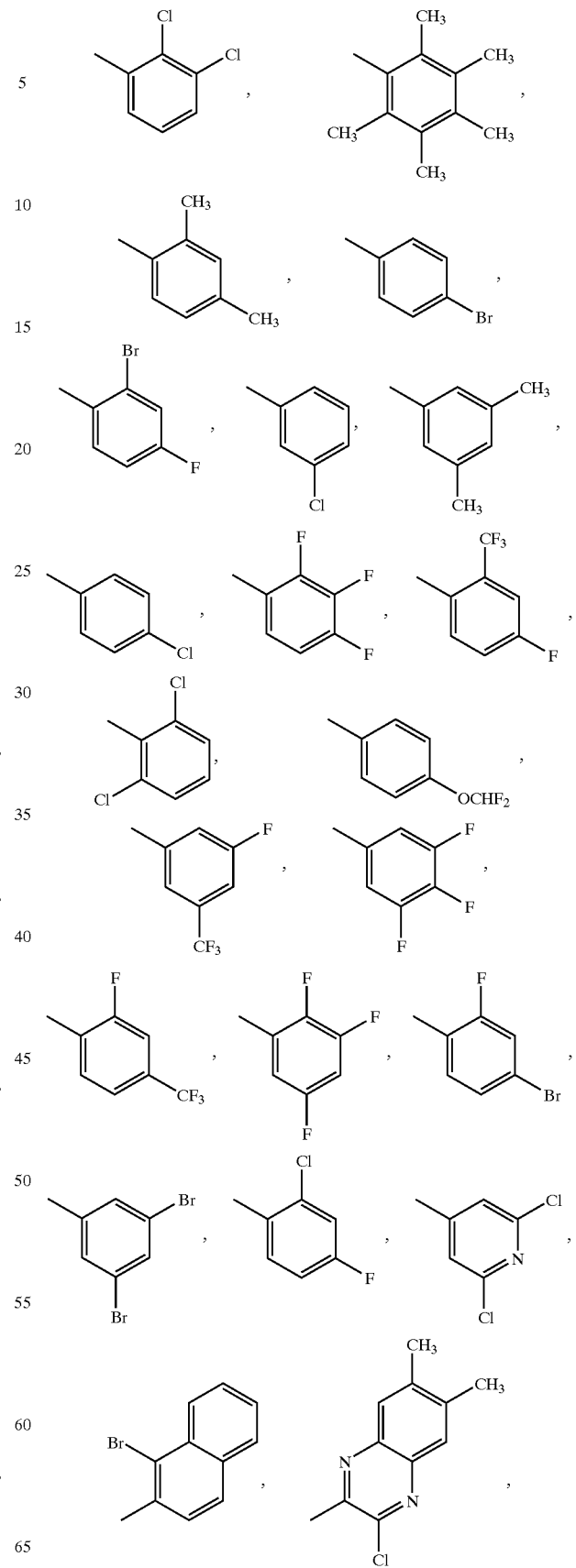

-continued
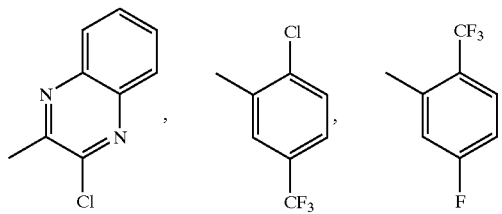
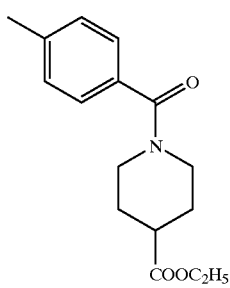
In yet a preferred embodiment D is
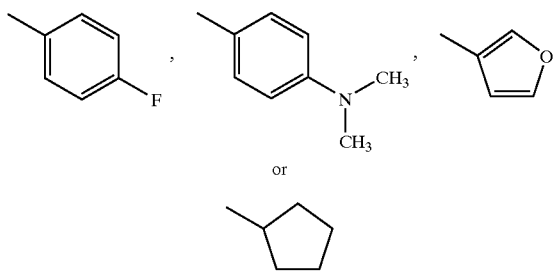
In still a further preferred embodiment D is
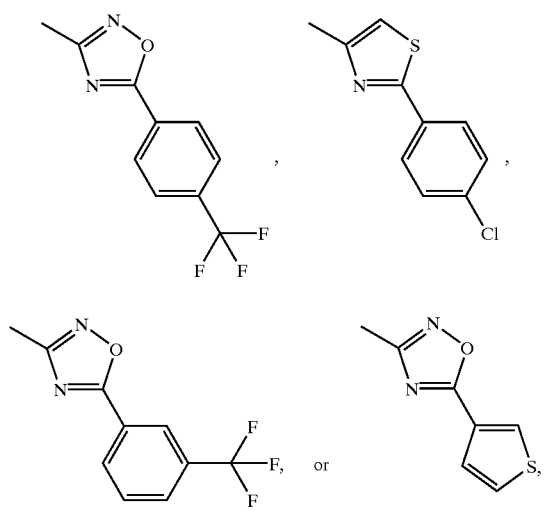
In another preferred embodiment the invention relates to the following compounds of the formula (IXX):
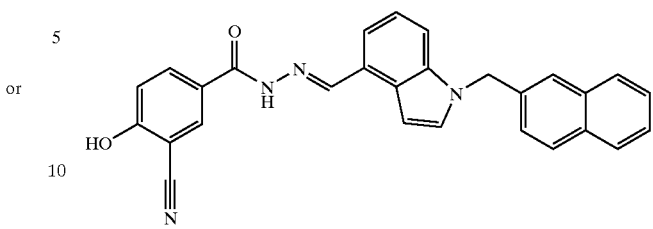
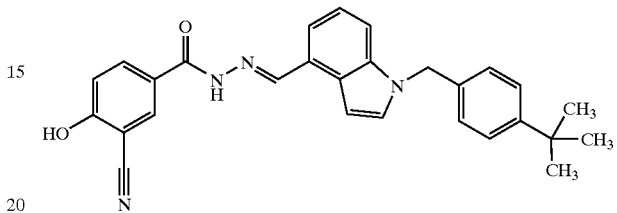
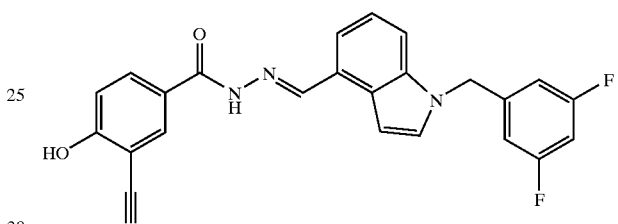
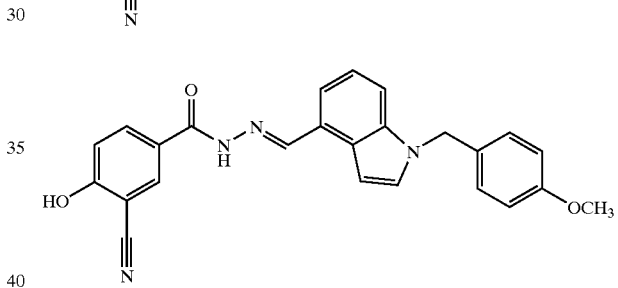
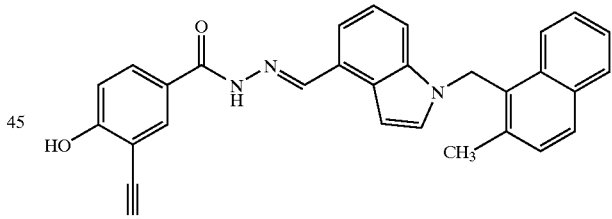
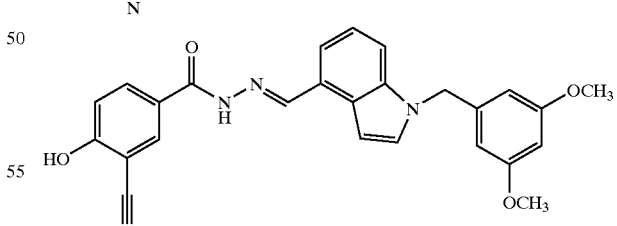
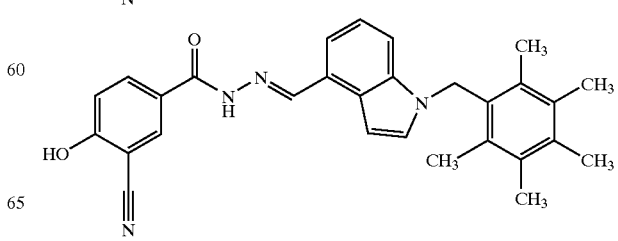

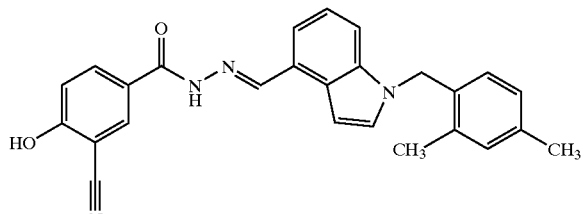

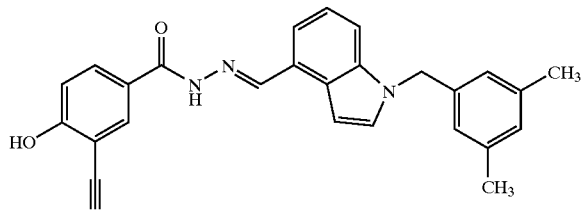

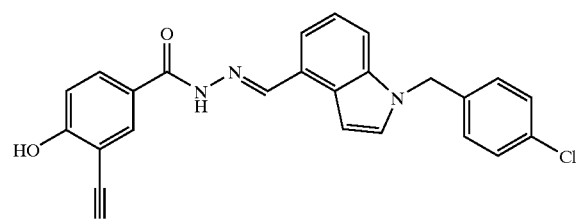

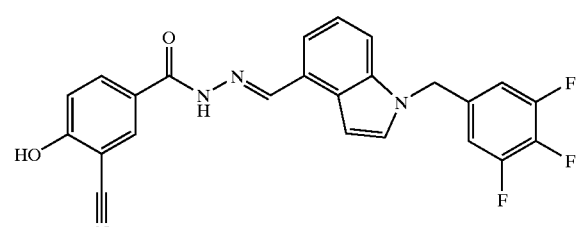

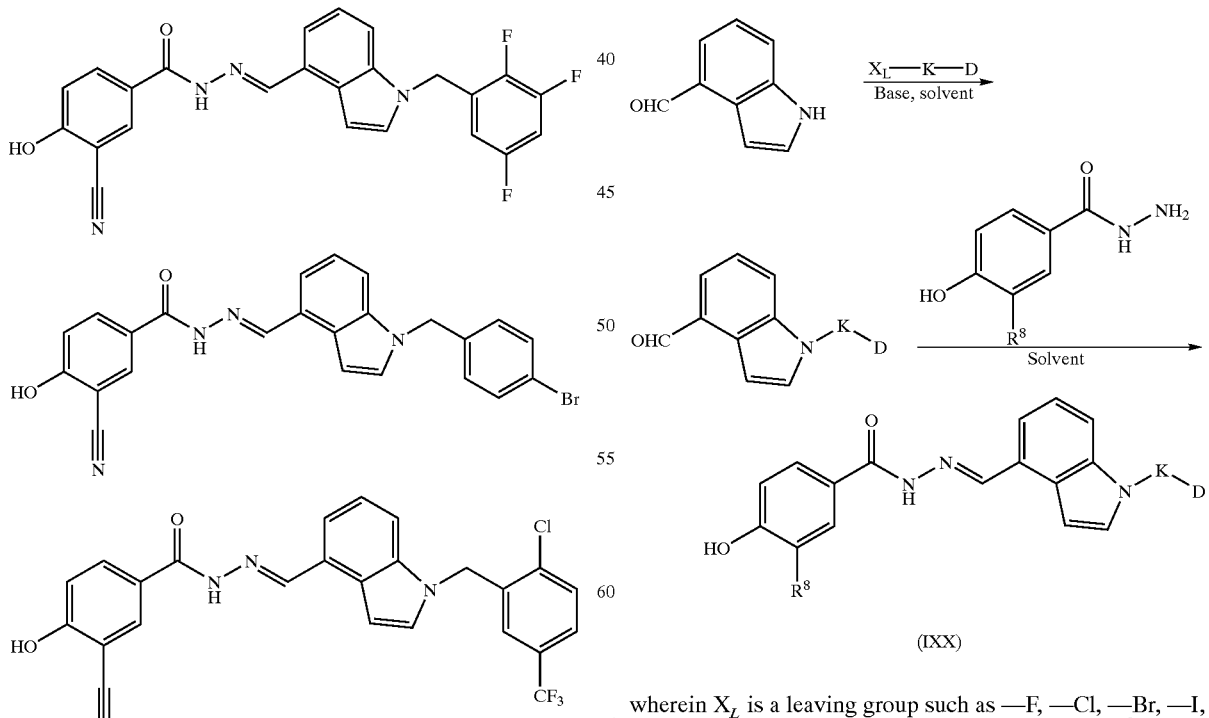

as well as any optical or geometric isomer or tautomeric form thereof including mixtures of these or a pharmaceutically acceptable salt thereof.

The present invention is further illustrated by the following representative examples which are, however, not intended to limit the scope of the invention in any way.

General Procedure for the Synthesis of 1-Substituted Indole-4-carboxaldehydes Followed by Hydrazone Formation The 1-substituted indole-4-carboxaldehydes may be prepared according to the scheme below by N-alkylation of the indole-4-carboxaldehyde using various electrophilic alkylating agents that introduce the —K—D moiety as defined above, such as halides (fluorides, chlorides, bromides, odides), methanesulfonates, toluenesulfonates or triflates.

SCHEME wherein $X_L$ is a leaving group such as —F, —Cl, —Br, —I, —OSO$_2$CH$_3$, —OSO$_2$p-tolyl or —OSO$_2$CF$_3$ and $R^8$, K and D are as defined for formula (IXX).

According to the scheme the 1-substituted indole-4-carboxaldehydes can be prepared by stirring indole-4-carboxaldehyde in an organic solvent such as acetone, methylethyl ketone, dimethylformamide, dioxane, tetrahydrofuran, toluene, ethylene glycol dimethyl ether, sulfolane, diethylether, dimethylsulfoxide, water or a compatible mixture of two or more of the above solvents with an equimolar amount of an alkyl halide, an aryl-lower alkyl halide, an acyl halide or a carboxylic acid anhydride in the presence of 1 to 15 equivalents (preferably 1 to 5 equivalents) of a base such as sodium hydride, potassium hydride, sodium or potassium methoxide, ethoxide or tert-butoxide, sodium, potassium or cesium carbonate, potassium or cesium fluoride, sodium or potassium hydroxide or organic bases such as diisopropylethylamine, 2,4,6-collidine or benzyldimethyl ammonium methoxide or hydroxide. The reaction can be performed at 0° C. to 150° C., preferably at 20° C. to 100° C. and preferably in an inert atmosphere of $N_2$ or Ar. When the reaction is complete the mixture is filtered, concentrated in vacuo and the resulting product optionally purified by column chromatography on silica gel using ethyl acetate/hexane as eluent. The compound can also (when appropriate) be purified by recrystallization from a suitable solvent such as ethyl alcohol, ethyl acetate, isopropyl alcohol, water, hexane, toluene or their compatible mixture.

The resulting carbonyl compounds are then treated with the corresponding acylhydrazide in a solvent. The solvent may be one of the following: ethyl alcohol, methyl alcohol, isopropyl alcohol, tert-butyl alcohol, dioxane, tetrahydrofuran, toluene, chlorobenzene, anisole, benzene, chloroform, dichloromethane, DMSO, acetic acid, water or a compatible mixture of two or more of the above solvents. A catalyst such as acetic acid can be added. A dehydrating reagent such as triethylorthoformate can also be added to the reaction mixture. The reaction is performed by stirring the reaction mixture preferably under an inert atmosphere of $N_2$ or Ar at temperatures between 0° C. to 140° C., preferably between 10° C. to 80° C. In many cases the product simply crystallizes out when the reaction is completed and is isolated by suction filtration. It can be further recrystallized if necessary from a solvent such as the above described reaction solvents. The product can also be isolated by concentration of the reaction mixture in vacuo, followed by column chromatography on silica gel using a solvent system such as chloroform/methanol or dichloromethane/methanol or chloroform/ethyl acetate.

Library Procedure for Indole Alkylation
Preparation of the Sodium Salt of the Indole:
Indole-4-carboxaldehyde (1.45 g) was dissolved into 8.6 mL of dry DMF in a dried and cooled 100 mL 3-necked round bottom flask.

While maintaining a steady flow of nitrogen or argon through the 3-necked round bottomed flask, 1.1 equivalent of sodium hydride (0.27 g of dry 95% reagent) was transferred to the indole solution. The mixture was stirred for 15 minutes, while maintaining flow of inert gas. Proceeded promptly to the next step.

Preparation of the Alkyl Halide Solutions:
Amber glass vials (for preparing stock solutions) were dried for at least four hours at 110° C., then were allowed to cool under an argon atmosphere in a desiccator. Alkyl halides solutions (1.0 M) were prepared in anhydrous DMF in the dried vials. Each alkyl halide solution (100 µL) was added to its corresponding well of a deep-well plate.

Alkylation of the Indole Sodium Salt:
100 µL of the 1.0 M indole salt solution was quickly delivered to each alkyl halide in the deep-well plates. The plates were vortexed briefly to mix, then allowed to react for two hours.

Library Procedure for Hydrazone Formation

3-Substituted 4-hydroxybenzoic acid hydrazides (10 mmoles) were dissolved in 5 mL of dry DMSO, followed by trifluoroacetic acid (0.77 mL). The resulting solutions were diluted to final volumes of 10.0 mL. 100 µL of the 1.0 M acid hydrazide TFA salt solution was added to each well of the deep-well plate. The plate was vortexed for one minute to mix, then allowed to react for 30 minutes.

The products were purified by chromatography on silica gel with ethyl acetate/hexane eluent.

EXAMPLE 930

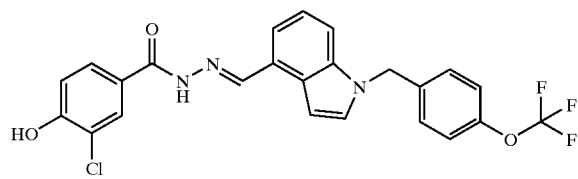

$^1$H NMR (DMSO-$d_6$): δ 5.54 (s, 2H), 7.07 (d, 1H), 7.20 (t, 1H), 7.26 (m, 2H), 7.31 (s, 4H), 7.58 (d, 1H), 7.68 (s, 1H), 7.80 (d, 1H), 8.01 (d, 1H), 8.66 (s, 1H), 11.98 (brd s, 1H), 11.71 (s, 1H); MS (APCI, negative): 486.0, 487.0, 488.0.

EXAMPLE 931

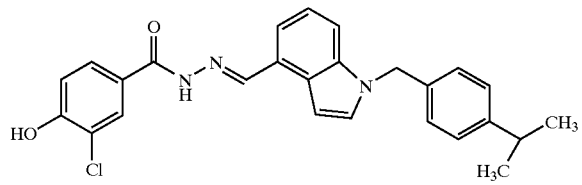

$^1$H NMR (DMSO-$d_6$): δ 1.13 (s, 3H), 1.15 (s, 3H), 2.83 (sept, 1H), 5.43 (s, 2H), 7.07–7.30 (m, 7H), 7.58 (d, 1H), 7.64 (s, 1H), 7.80 (d, 1H), 8.00 (s, 1H), 8.66 (s, 1H), 10.95 (s, 1H), 11.70 (s, 1H); MS (APCI, neg.): 444.0, 446.1.

EXAMPLE 932

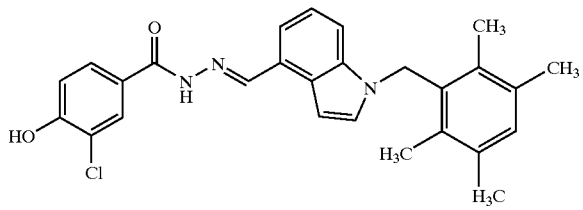

$^1$H NMR (DMSO-$d_6$): δ 2.08 (s, 6H), 2.21 (s, 6H), 5.37 (s, 2H), 6.77 (d, 1H), 7.04 (m, 3H), 7.26 (t, 1H), 7.35 (d, 1H), 7.77 (m, 2H), 7.97 (s, 1H), 8.67 (s, 1H), 11.00 (brd s, 1H), 11.67 (s, 1H); MS (APCI): 460.2, 461.2, 462.2.

EXAMPLE 933

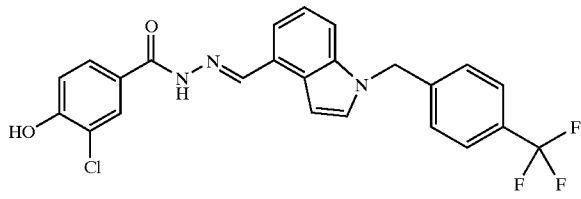

¹H NMR (DMSO-d₆): δ 5.61 (s, 2H), 7.04 (d, 1H), 7.17 (t, 1H), 7.30 (m, 2H), 7.34 (d, 2H), 7.52 (d, 1H), 7.67 (m, 3H), 7.79 (d, 1H), 7.80 (d, 1H), 8.66 (s, 1H), 10.97 (brd s, 1H), 11.72 (s, 1H); MS (APCI): 472.1.

EXAMPLE 934

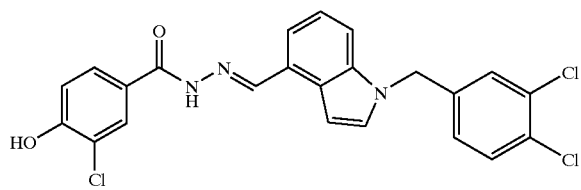

¹H NMR (DMSO-d₆): δ 5.51 (s, 2H), 7.01 (d, 1H), 7.12 (d, 1H), 7.22 (t, 1H), 7.27 (m, 1H), 7.30 (d, 1H), 7.49 (s, 1H), 7.58 (d, 2H), 7.68 (d, 1H), 7.80 (d, 1H), 8.01 (d, 1H), 8.66 (brd s, 1H), 10.95 (brd s, 1H), 11.72 (brd s, 1H); MS (APCI, negative): 470.9, 471.9, 473.9.

EXAMPLE 935

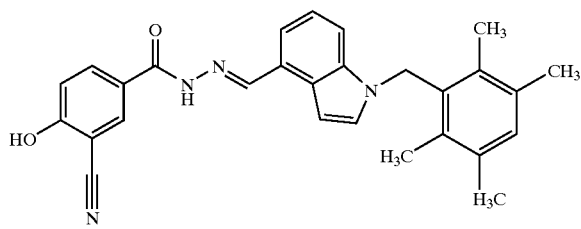

¹H NMR (DMSO-d₆): δ 2.08 (s, 6H), 2.21 (s, 6H), 5.37 (s, 2H), 6.78 (s, 1H), 7.05 (m, 3H), 7.26 (t, 1H), 7.34 (d, 1H), 7.76 (d, 1H), 8.01 (d, 1H), 8.19 (s, 1H), 8.64 (s, 1H), 11.68 (s, 1H). MS (APCI): 451.2, 452.2, 453.2.

EXAMPLE 936

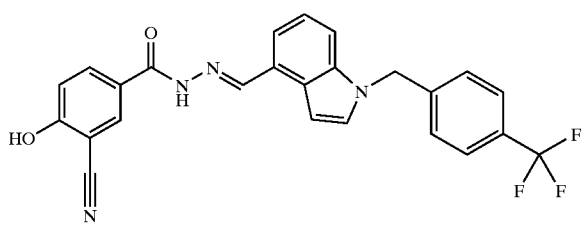

¹H NMR (DMSO-d₆): δ 5.61 (s, 2H), 7.12 (d, 1H), 7.18 (t, 1H), 7.27 (,2H), 7.34 (d, 2H), 7.54 (d, 1H), 7.66 (s, 1H), 7.69 (d, 2H), 8.08 (d, 1H), 8.25 (s, 1H), 8.64 (s, 1H), 11.78 (s, 1H); MS (APCI): 463.1, 464.2.

EXAMPLE 937

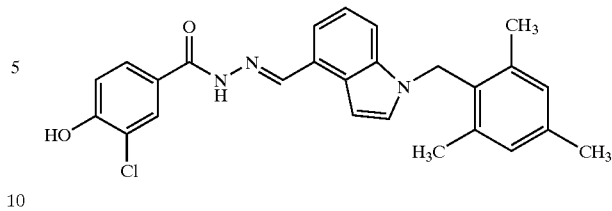

¹H NMR (DMSO-d₆): δ 2.17 (s, 6H), 2.26 (s, 3H), 5.33 (s, 2H), 6.88 (s, 1H), 6.94 (s, 2H), 7.07 (d, 1H), 7.11 (s, 1H), 7.24 (t, 1H), 7.32 (d, 1H), 7.69 (d, 1H), 7.78 (d, 1H), 7.99 (s, 1H), 8.66 (s, 1H), 11.00 (brd S, 1H), 11.68 (s, 1H); MS (APCI): 4461.1, 448.1.

EXAMPLE 938

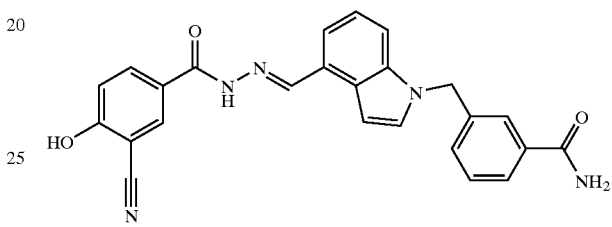

¹H NMR (DMSO-d₆): 85.53 (s, 2H), 7.14 (d, 1H), 7.20 (d, 1H), 7.25 (d, 1H), 7.30 (d, 1H), 7.41 (t, 1H), 7.57 (d, 1H), 7.67 (d, 1H), 7.75 (d, 1H), 7.79 (s, 1H), 7.97 (s, 1H), 8.10 (d, 1H), 8.26 (s, 1H), 8.65 (s, 1H), 11.77 (s, 1H); MS (APCI, negative): 436.1, 437.1.

EXAMPLE 939

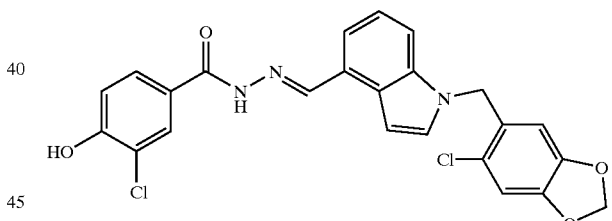

¹H NMR (DMSO-d₆): δ 5.45 (s, 2H), 6.03 (s, 2H), 6.37 (s, 1H), 7.08 (d, 1H), 7.15 (s, 1H), 7.22 (t, 1H), 7.25 (d, 1H), 7.32 (d, 1H), 7.53 (s, 1H), 7.56 (m, 1H), 7.79 (d, 1H), 8.00 (s, 1H), 8.67 (s, 1H), 10.97 (brd s, 1H), 11.73 (brd s, 1H); MS (APCI, negative): 480.0, 481.0, 482.0.

EXAMPLE 940

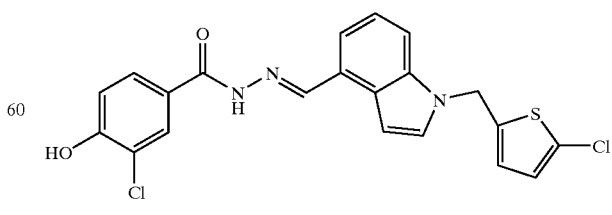

¹H NMR (DMSO-d₆): δ 5.60 (s, 2H), 6.58 (d, 1H), 6.88 (d, 1H), 6.98 (d, 1H), 7.06 (d, 1H), 7.53 (d, 1H), 7.64 (s, 2H), 7.77 (dd, 1H), 7.85 (s, 1H), 7.98 (d, 1H), 8.49 (s, 1H), 10.94 (brd s, 1H), 11.60 (s, 1H); MS (APCI, negative): 441.9, 442.9, 443.9.

EXAMPLE 941

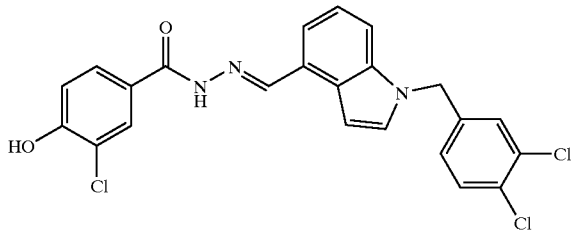

$^1$H NMR (DMSO-d$_6$): δ 5.56 (s, 2H), 7.08 (d, 1H), 7.22 (t, 1H), 7.27–7.32 (m, 2H), 7.66 (d, 1H), 7.72 (s, 1H), 7.80 (dd, 1H), 7.99 (t, 2H), 8.33 (d, 1H), 8.65 (s, 1H), 10.86 (brd s, 1H), 11.72 (s, 1H); MS (APCI): 473.0, 475.0.

EXAMPLE 942

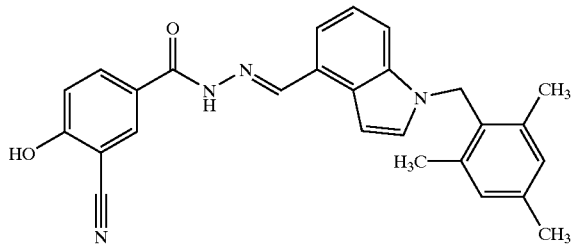

$^1$H NMR (DMSO-d$_6$): δ 2.17 (s, 6H), 2.25 (s, 3H), 5.33 (s, 2H), 6.88 (s, 1H), 6.93 (s, 2H), 7.08 (s, 1H), 7.11 (s, 1H), 7.22 (t, 1H), 7.28 (d, 1H), 7.70 (d, 1H), 8.05 (d, 1H), 8.23 (s, 1H), 8.65 (s, 1H), 11.72 (brd s, 1H); MS (APCI): 437.2, 438.2, 439.2.

EXAMPLE 943

3-Cyano-4-hydroxybenzoic Acid {1-[(4,5-Dichloro-2-hydroxymethyl)benzyl]-indol-4-yl}methylidene Hydrazide

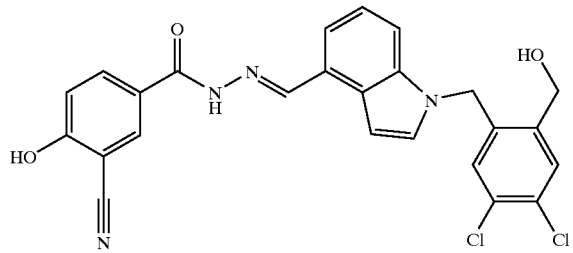

4-Formyl-1-(4,5-dichloro-2-hydroxymethylbenzyl)-indole:

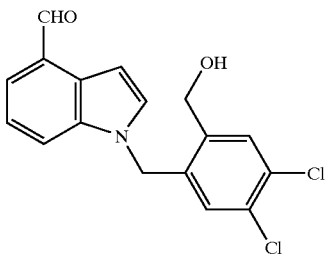

This compound was prepared from 4-formylindole and 4,5-dichloro-2-tetrahydropyranyloxy benzylchloride [prep. from 1,2-dihydroxymethyl-4,5-dichloro benzene acc. W. Y. Lee et al. J. Org. Chem. 57, 1992, 4074–4079] following the general procedure for alkylation of indoles. After treatment of the product with 1N HCl in THF, 4-formyl-1-(4,5-dichloro-2-hydroxymethylbenzyl)-indole was obtained.

$^1$H NMR (CDCl$_3$): δ 4.65 (s, 2H), 5.45 (s, 2H), 6.81 (s, 1H), 7.26 (s, 1H), 7.27 (d, J=3.4 H8 Hz, 1H), 7.32 (d, J=7.9 Hz, 1H), 7.36 (d, J=3.8 Hz, 1H), 7.51 (d, J=6.8 Hz, 1H), 7.52 (s, 1H), 7.66 (d, J=7.2 Hz, 1H), 10.25 (s, 1H).

The title compound was prepared according to the general procedure for the synthesis of alkylidene hydrazones from the condensation of 4-formyl-1-(4.5-dichloro-2-hydroxymethylbenzyl)-indole and 3-cyano-4-hydroxy benzoic acid hydrazide.

$^1$H NMR (DMSO-D$_6$): δ 4.55 (s, 2H), 5.51 (s, 3H), 6.60 (s, 1H), 7.13 (d, J=8.5 Hz, 1H), 7.20 (m, 1H), 7.30 (m, 2H), 7.49 (d, J=8.0 Hz, 1H), 7.55 (s, 1H), 7.66 (s, 1H), 8.8 (d, J=8.5 Hz, 1H), 8.26 (s, 1H), 8.65 (s, 1H), 11.79 (s, 2H); MS (APCI, pos.): 493.

EXAMPLE 944

3-Cyano-4-hydroxybenzoic Acid {1-[(5-Phenyl-3-pyridinyl)methyl]-indol-4-yl}methylidene Hydrazide

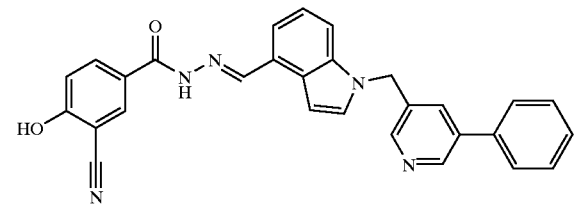

4-Formyl-1-[(5-phenyl-3-pyridinyl)methyl]-indole:

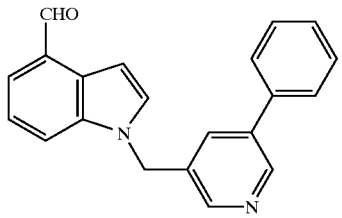

The compound was prepared from 4-formylindole and 3-chloromethyl-5-phenyl pyridine [prep. from 5-methyl-3-phenylpyridine by chlorination with NCS/AIBN] following the general procedure for alkylation of indoles.

$^1$H NMR (CDCl$_3$): δ 5.49 (s, 2H), 7.40 (m, 2H), 7.43–7.46 (m, 3H), 7.50 (m, 1H), 7.66 (dd, J=0.8, 7.2 Hz, 1H), 7.67 (s, 1H), 8.78 (s, 1H), 10.26 (s, 1H).

The title compound was prepared according to the general procedure for the synthesis of alkylidene hydrazones from the condensation of 4-formyl-1-[(5-phenyl-3-pyridinyl)methyl]-indole and 3-cyano-4-hydroxy benzoic acid hydrazide.

$^1$H NMR (DMSO-D$_6$): δ 5.61 (s, 2H), 6.97 (d, 1H), 7.20 (dd, 1H), 7.27 (dd, 1H), 7.37–7.47 (m, 3H), 7.59–7.66 (m, 3H), 7.74 (d, 1H), 7.90 (s, 1H), 7.97 (d, 1H), 8.14 (d, 1H), 8.42 (s, 1H), 8.60 (s, 1H), 8.73 (s, 1H), 11.67 (s, 2H); Ms (APCI, pos.): 472.

EXAMPLE 945

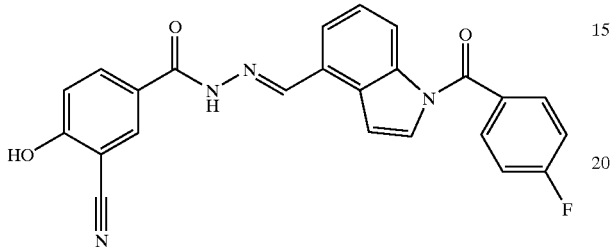

$^1$H NMR (DMSO-d$_6$): δ 6.88 (d, 1H), 7.45 (t, 4H), 7.55 (d, 2H), 7.85–7.90 (m, 2H), 7.94 (d, 1H), 8.15 (s, 1H), 8.32 (d, 1H), 8.66 (brd s, 1H), 11.77 (s, 1H); MS (APCI): 427.1, 428.1.

EXAMPLE 946

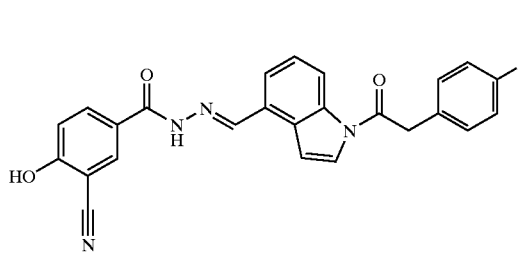

$^1$H NMR (DMSO-d$_6$): d 2.85 (s, 6H), 4.28 (s, 2H), 6.68 (d, 2H), 7.06 (d, 1H), 7.18 (d, 1H), 7.39 (t, 1H), 7.47–7.51 (m, 2H), 8.05 (d, 1H), 8.21 (s, 1H), 8.40 (d, 1H), 8.62 (s, 1H), 11.82 (s, 1H); MS (APCI): 466.2, 467.3.

EXAMPLE 947

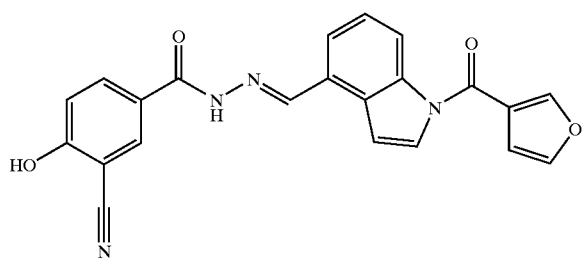

$^1$H NMR (DMSO-d$_6$): δ 7.01 (s, 1H), 7.10 (d, 1H), 7.45 (t, 1H), 7.55 (m, 2H), 7.95 (s, 1H), 7.98 (d, 1H), 8.10 (d, 1H), 8.24 (s, 1H), 8.39 (d, 1H), 8.53 (s, 1H), 8.65 (s, 1H), 11.86 (s, 1H); MS (APCI, neg.): 397.1, 398.1.

EXAMPLE 948

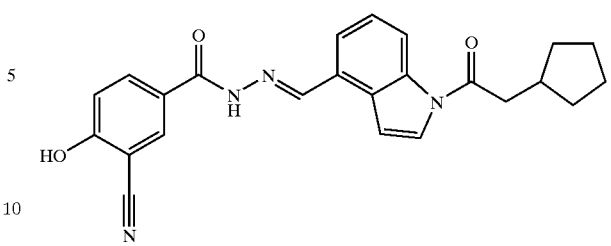

$^1$H NMR (DMSO-d$_6$): δ 1.20–1.27 (m, 2H), 1.50–1.65 (m, 5H), 1.80–1.86 (m, 2H), 2.33 (sept, 1H), 3.09 (d, 2H), 7.05 (d, 1H), 7.39 (t, 1H), 7.49 (m, 3H), 8.02 (d, 1H), 8.07 (s, 1H), 8.21 (s, 1H), 8.44 (d, 1H), 8.63 (s, 1H), 11.82 (s, 1H); MS (APCI): 415.2, 416.2.

EXAMPLE 949

3-Cyano-4-hydroxybenzoic Acid {1-[(2-Hydroxymethyl)benzyl]-indol-4-yl}methylidene Hydrazide

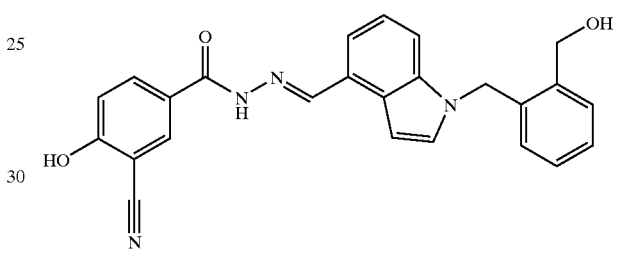

4-Formyl-1-(2-hydroxymethylbenzyl)-indole:

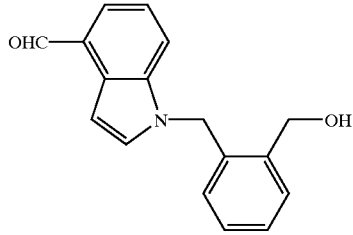

This compound was prepared from 4-formylindole and 2-tetrahydropyranyloxy benzylchloride [prep. from 1,2-benzene dimethanol acc. W. Y. Lee et al. J. Org. Chem. 57, 1992, 4074–4079] following the general procedure for alkylation of indoles. After treatment of the product with 1N HCl in THF, 4-formyl-1-(2-hydroxymethylbenzyl)-indole was obtained.

$^1$H NMR (CDCl$_3$): δ 4.72 (s, 2H), 5.53 (s, 2H), 6.73 (d, J=7.5 Hz, 1H), 7.20 (d, J=7.5 Hz, 1H), 7.27–7.35 (m, 4H), 7.39 (d, J=7.1 Hz, 1H), 7.56 (d, J=8.1 Hz, 1H), 7.63 (d, J=7.2 Hz, 1H), 10.24 (s, 1H).

The title compound was prepared according to the general procedure for the synthesis of alkylidene hydrazones from the condensation of 4-formyl-1-(2-hydroxymethylbenzyl)-indole and 3-cyano-4-hydroxy benzoic acid hydrazide.

$^1$H NMR (DMSO-D$_6$): δ 4.60 (s, 1H), 5.30 (s, 1H), 5.55 (s, 2H), 6.47 (d, J=7.5 Hz, 1H), 7.08 (d, J=7.5 Hz, 1H), 7.12 (d, J=8.7 Hz, 1H), 7.18 (d, J=7.8 Hz, 1H), 7.20–7.32 (m, 3H), 7.43 (d, J=7.9 Hz, 1H), 7.46 (d, J=8.5 Hz, 1H), 7.53 (d, J=2.5 Hz, 1H), 8.08 (d, J=8.7 Hz, 1H), 8.26 (s, 1H), 8.65 (s, 1H), 11.78 (s, 2H).

EXAMPLE 950

3-Cyano-4-hydroxybenzoic Acid {1-[(4-Methyl-2-pyridinyl)methyl]-indol-4-yl}methylidene Hydrazide

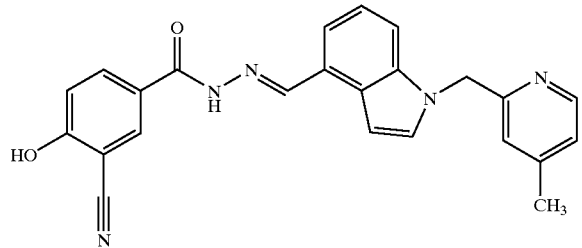

4-Formyl-1-[(4-methyl-2-pyridinyl)methyl]-indole:

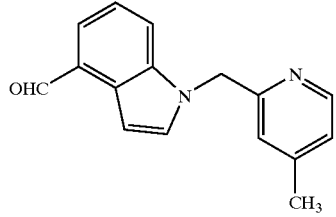

The compound was prepared from 4-formylindole and 2-chloromethyl-4-methyl pyridine [prep. from 2,4-lutidine acc. G. E. Jeromin et al. Chem. Ber. 120, 1987, 640–451] following the general procedure for alkylation of indoles.

$^1$H NMR (CDCl$_3$): δ 2.19 (s, 3H), 5.48 (s, 2H), 6.54 (s, 1H), 7.01 (d, J=4.8 Hz, 1H), 7.29 (t, J=7.8 Hz, 1H), 7.39 (d, J=3.0 Hz, 1H), 7.43 (d, J=3.0 Hz, 1H), 8.45 (s, 1H), 10.27 (s, 1H).

The title compound was prepared according to the general procedure for the synthesis of alkylidene hydrazones from the condensation of 4-formyl-1-[(4-methyl-2-pyridinyl)methyl]-indole and 3-cyano-4-hydroxy benzoic acid hydrazide.

$^1$H NMR (DMSO-D$_6$): δ 1.53 (s, 3H), 5.50 (s, 2H), 6.86 (s, 1H), 7.10 (d, J=5.0 Hz, 1H), 7.13 (d, J=8.7 Hz, 1H), 7.17 (dd, J=J=7.8 Hz, 1H), 7.24 (d, J=2.7 Hz, 1H), 7.30 (d, J=7.8 Hz, 1H), 7.54 (d, J=7.8 Hz, 1H), 7.63 (d, J=2.7 Hz, 1H), 8.07 (d, J=8.7 Hz, 1H), 8.25 (s, 1H), 8.37 (d, J=4.9 Hz, 1H), 11.76 (s, 2H); MS (APCI, pos.): 410.

The following preferred group of compounds were made according to the above Library Procedures:

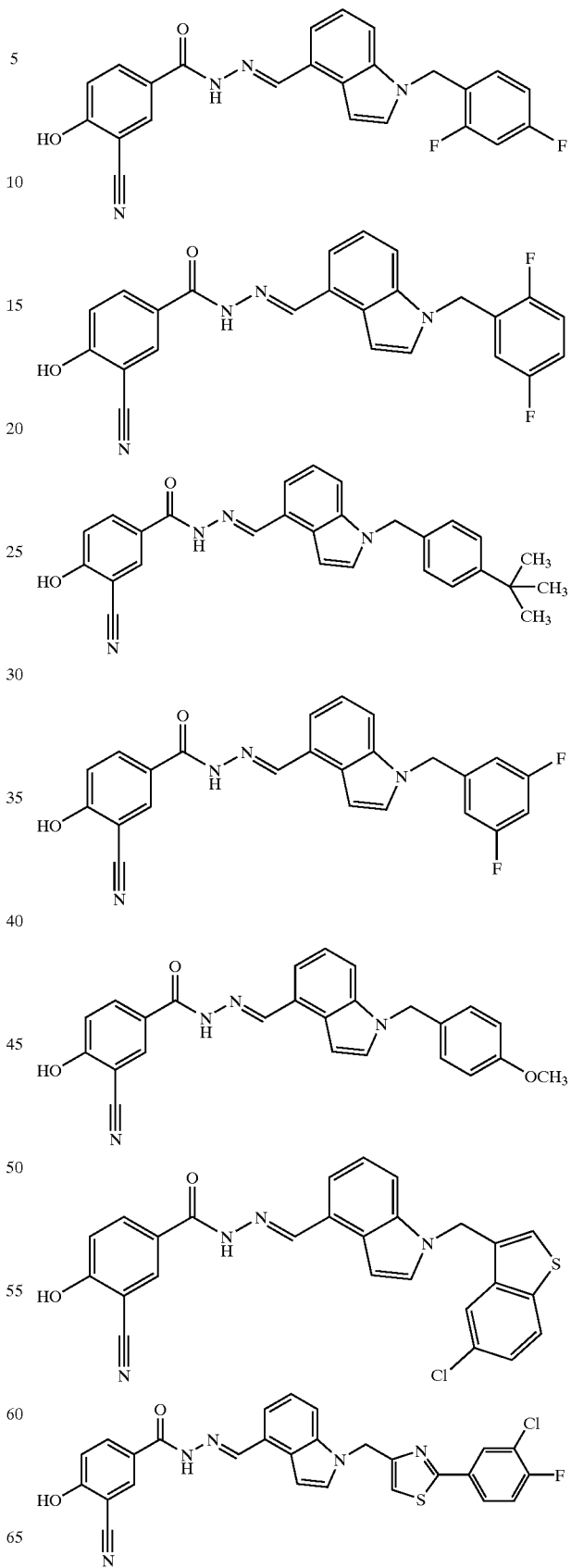

671
-continued
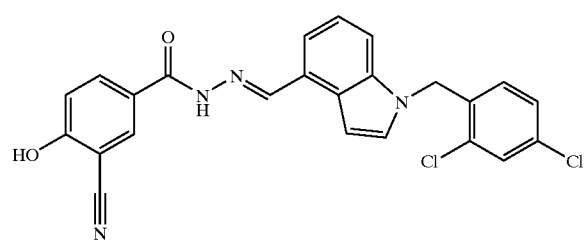
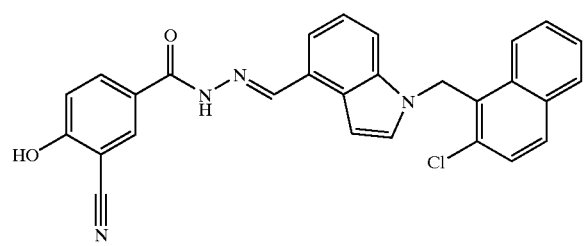
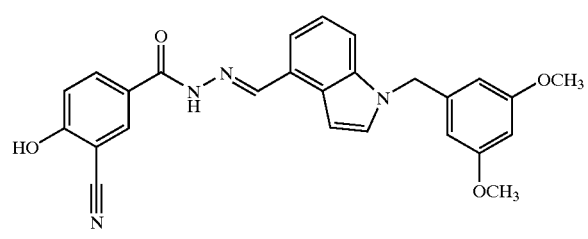
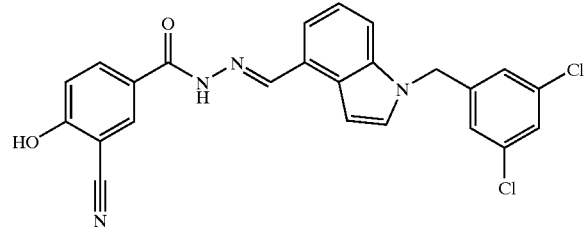
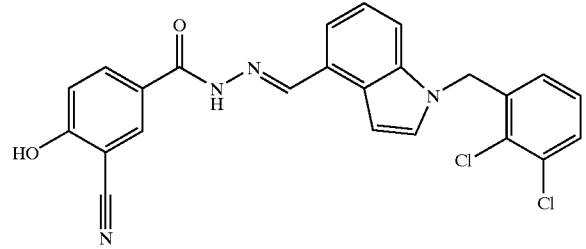
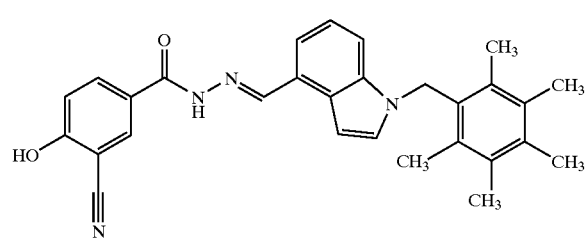
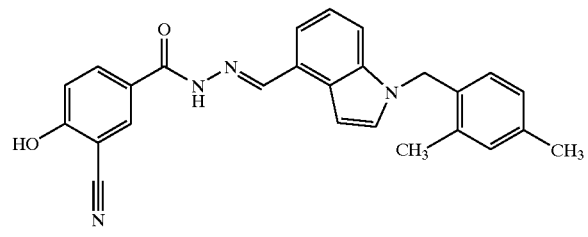
672
-continued
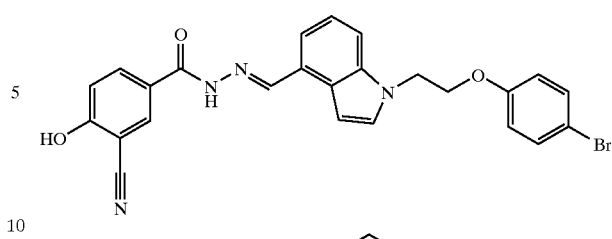
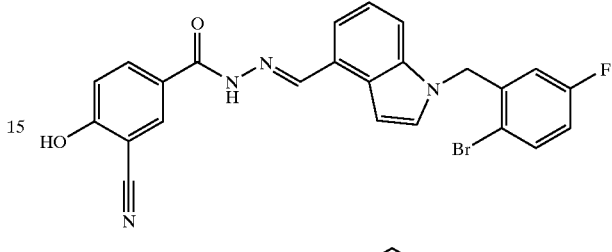
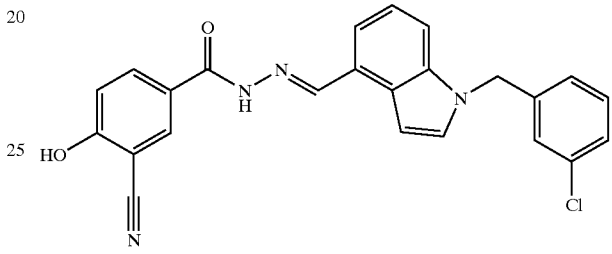
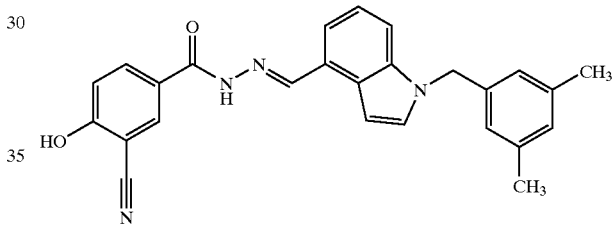
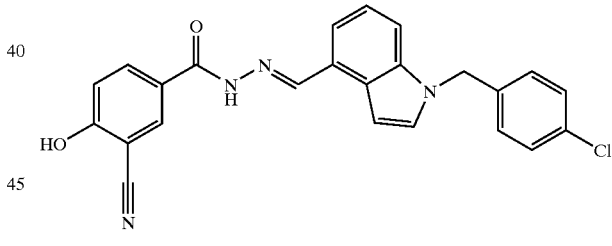
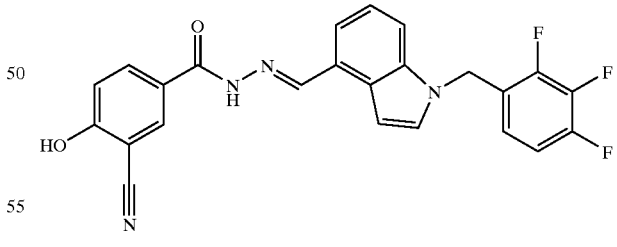
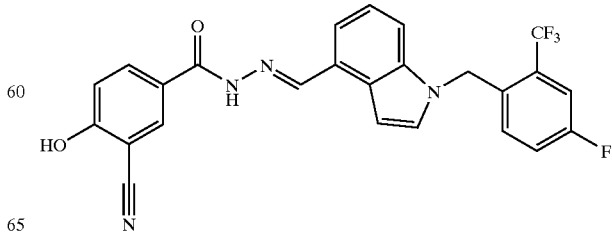

673
-continued
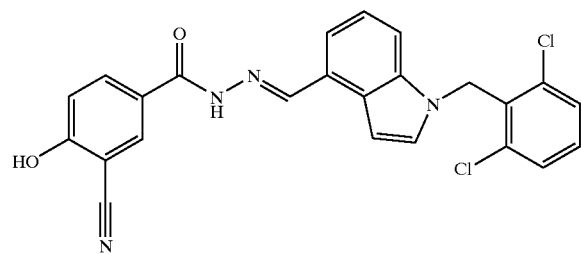
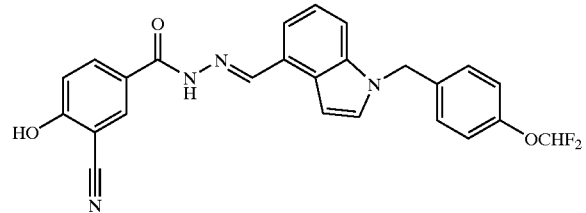
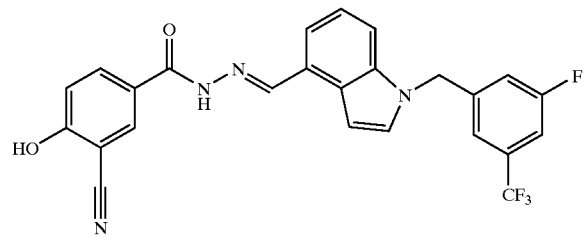
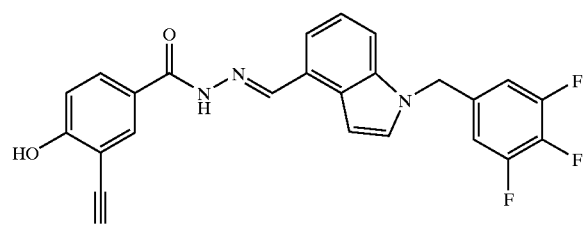
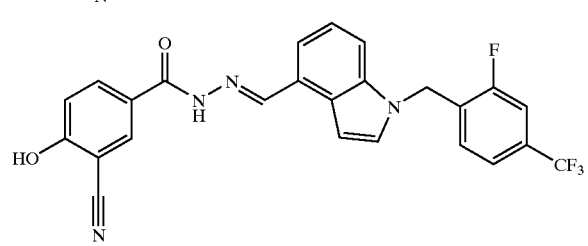
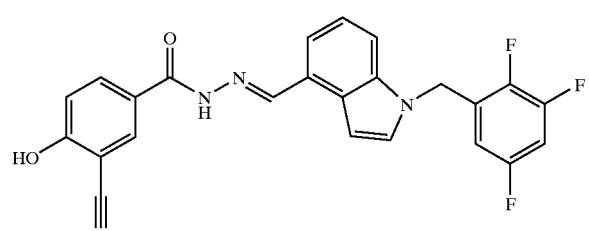
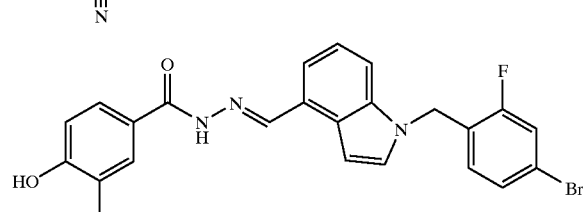
674
-continued
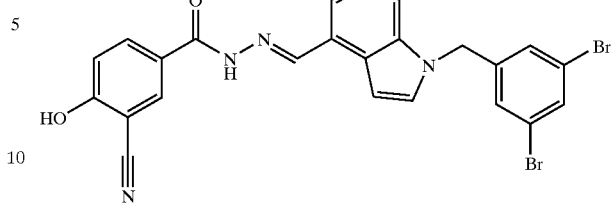
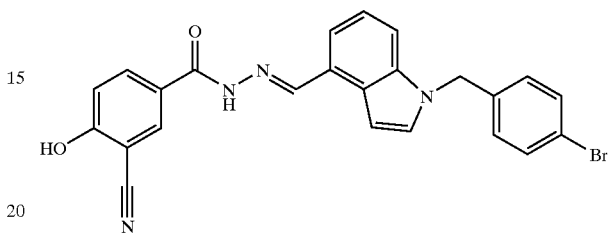
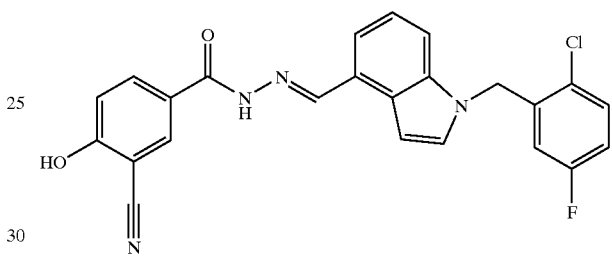
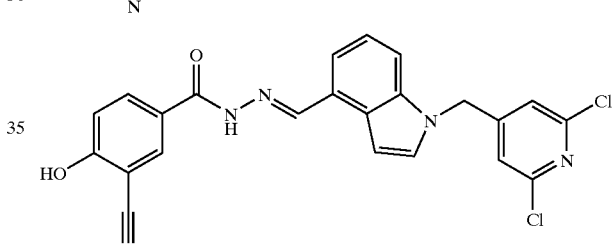
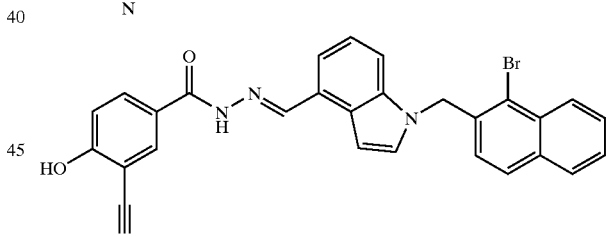
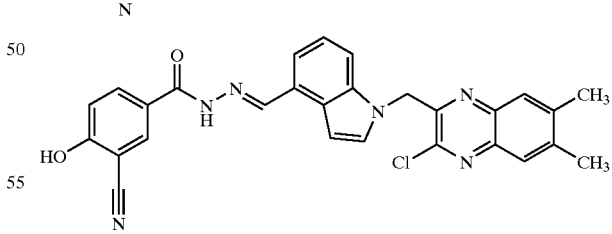
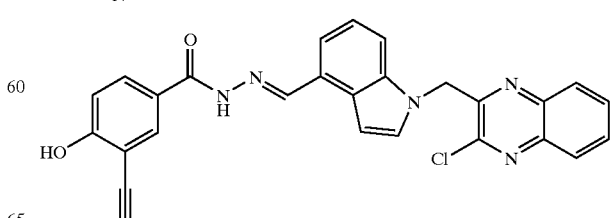

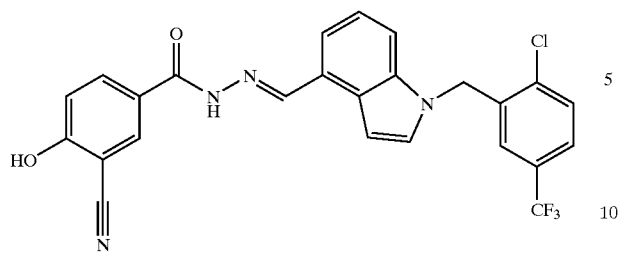
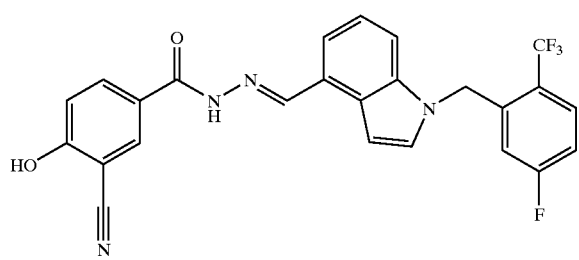
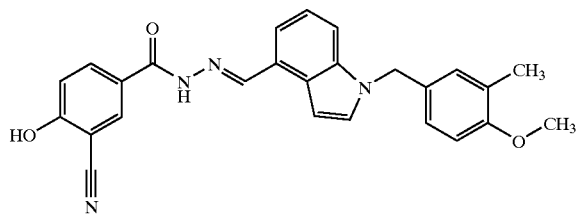
A further preferred embodiment of the invention are the following compounds:
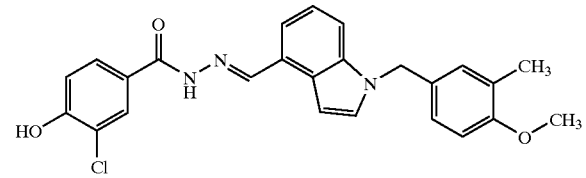
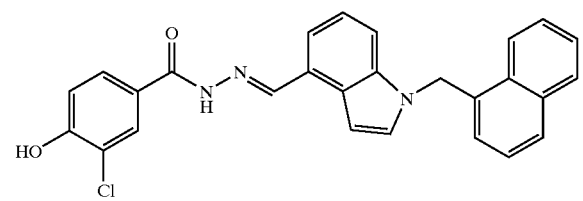
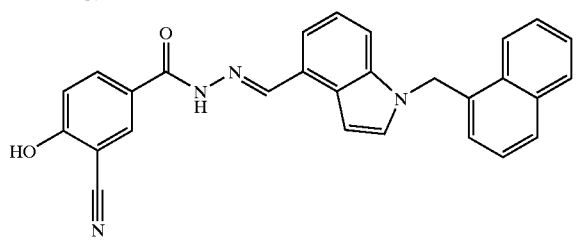
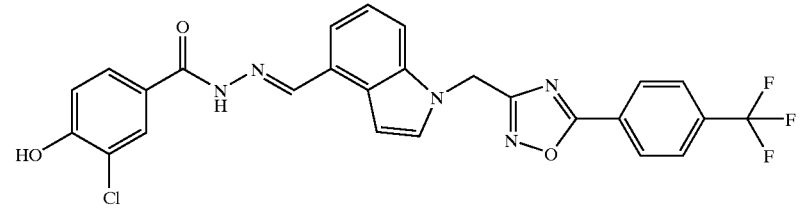
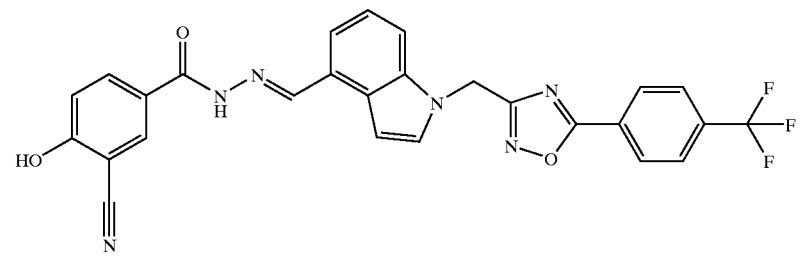
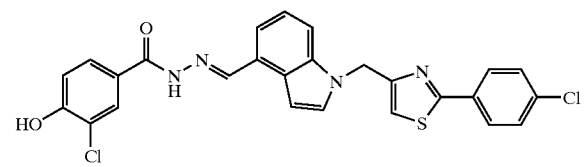

| 677 | 678 |
|---|---|
| 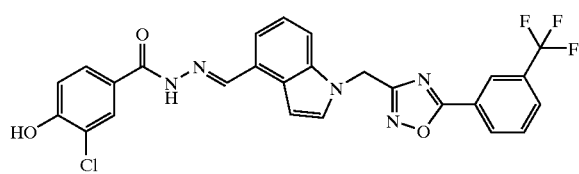 | 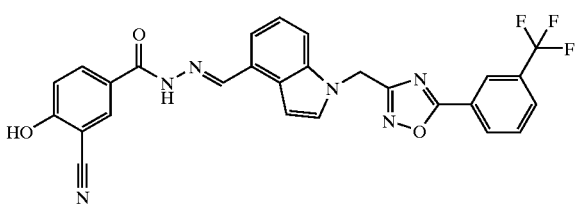 |
| 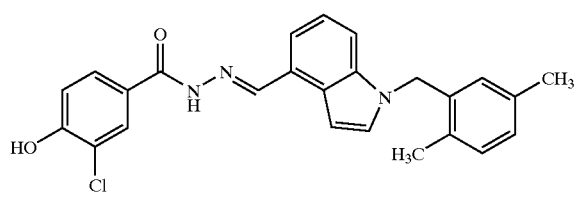 | 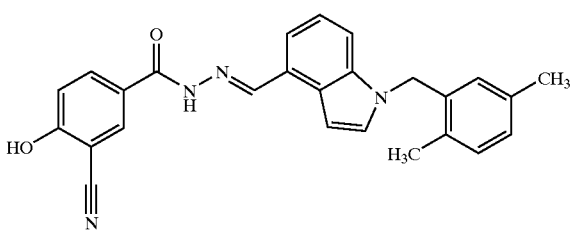 |
| 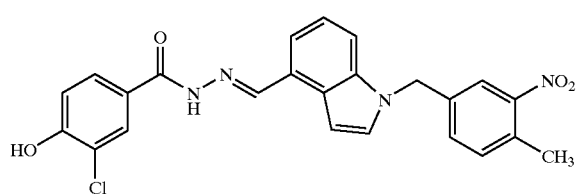 | 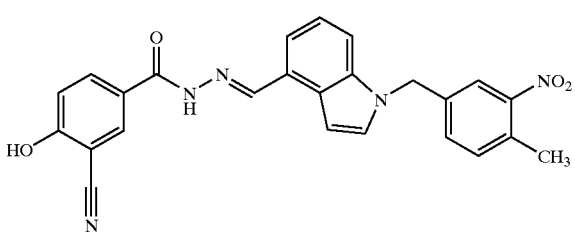 |
| 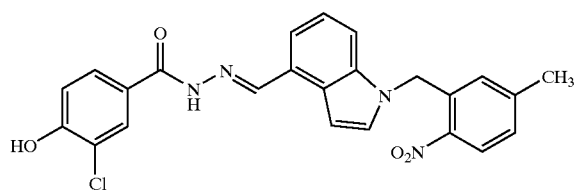 | 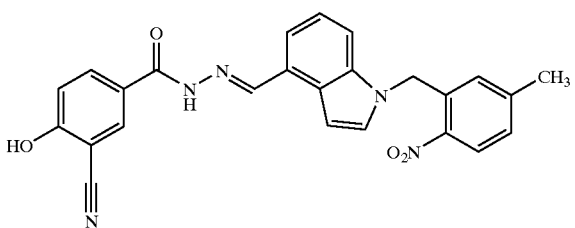 |
| 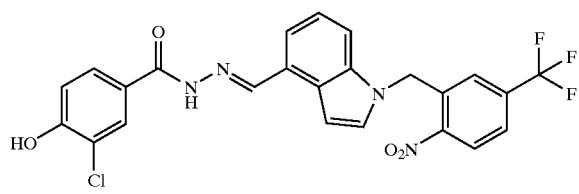 | 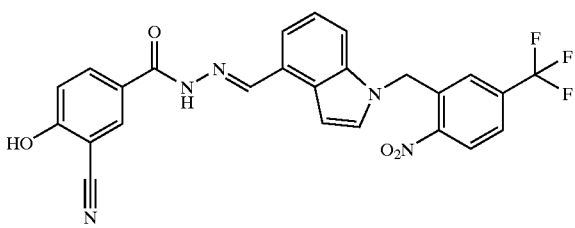 |
| 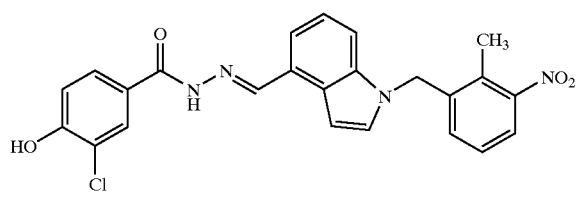 | 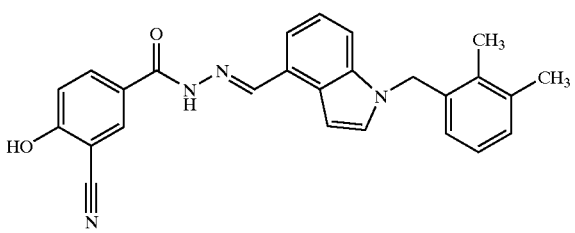 |
| 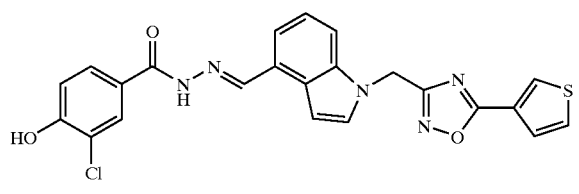 | 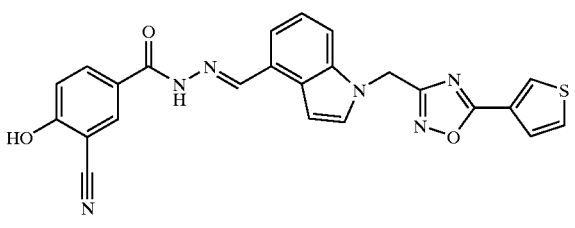 |

679 680
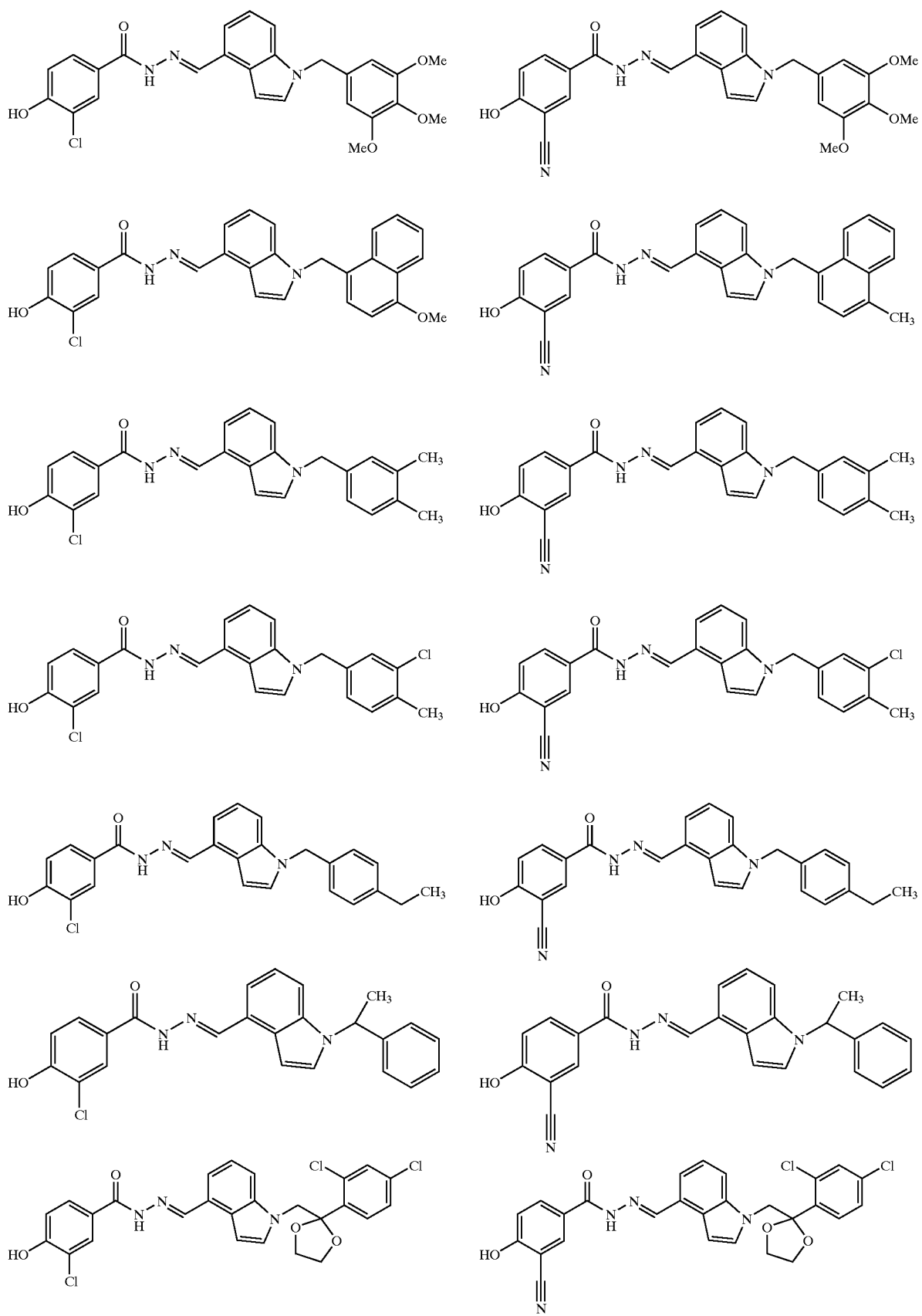

681                                           682
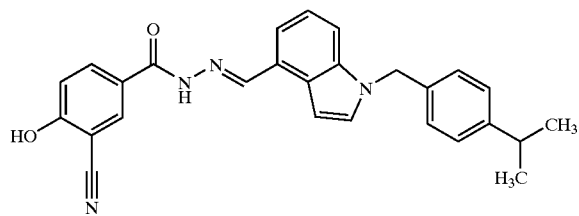
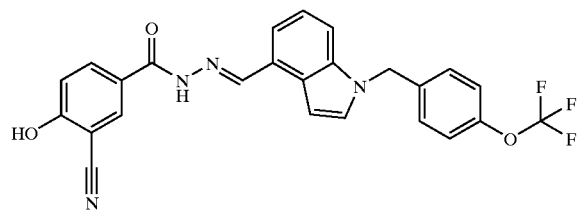
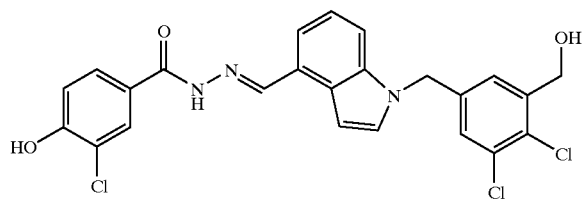
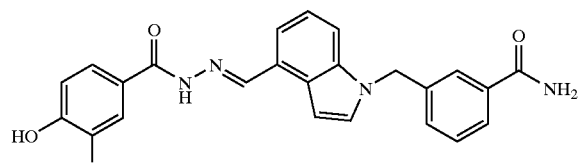
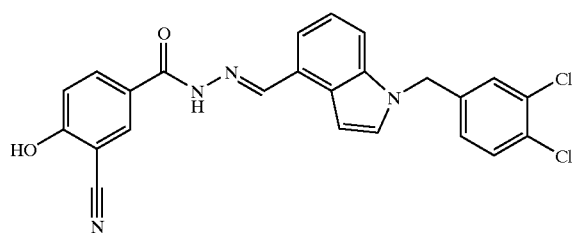
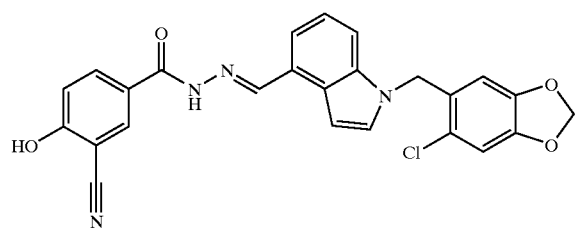
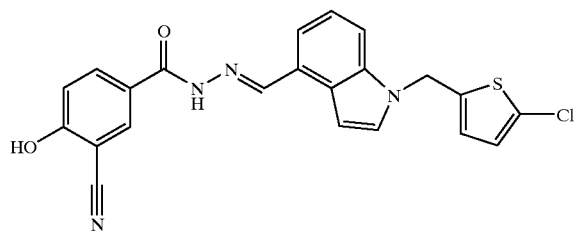
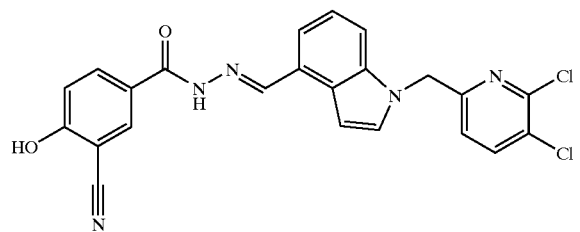
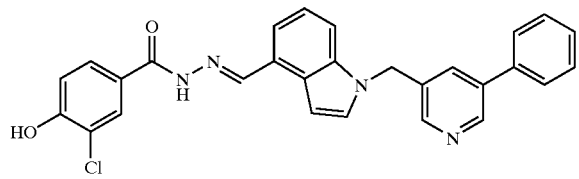
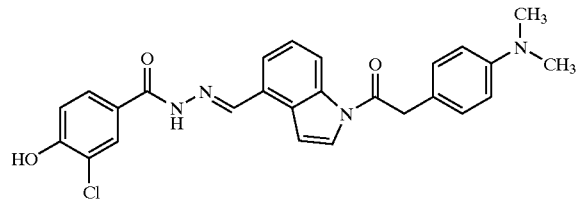
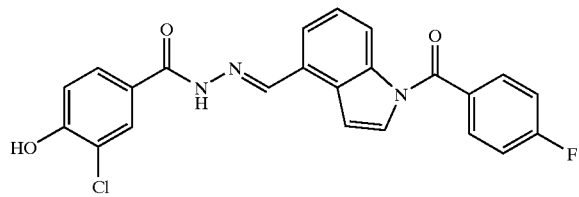
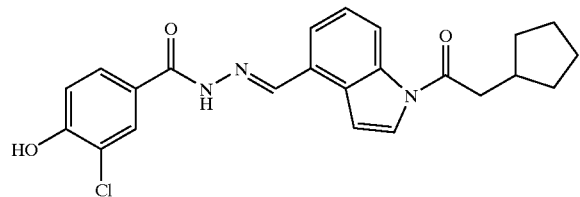
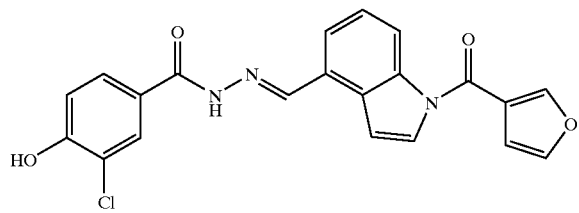

In another aspect the invention relates to 1,5-alkylated indoles of the formula (XX):

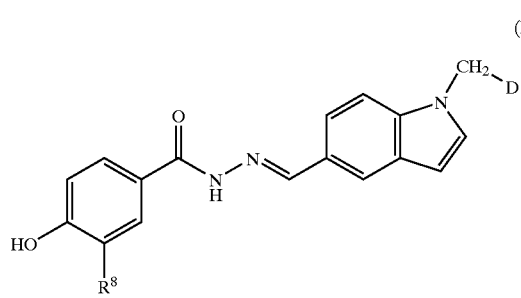

(XX)

wherein

R[8] is chloro, fluoro, nitro or cyano;

D is

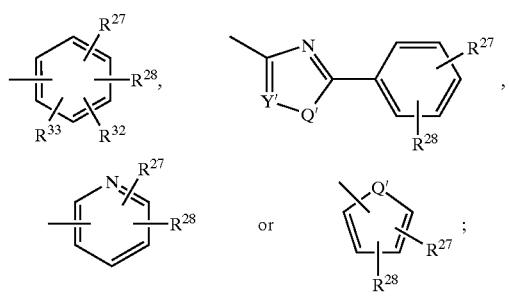

wherein

Q' is —O— or —S—;

Y' is —CH= or —N=;

R[27], R[28], R[32] and R[33] independently are hydrogen, $C_{1-6}$-alkyl, trifluoromethyl, trifluoromethoxy, halogen or $C_{1-6}$-alkoxy;

as well as any optical or geometric isomer or tautomeric form thereof including mixtures of these or a pharmaceutically acceptable salt thereof.

The compounds are active glucagon antagonists or inverse agonists and the foregoing description of applications, pharmaceutical formulations and administration methods, and assays for evaluating the efficacy of the compounds etc also applies to these compounds.

The term "$C_{1-6}$-alkyl" as used in the definition of the formula (XX), alone or in combination, represents a branched or straight hydrocarbon group having from 1 to 6 carbon atoms. Typical $C_{1-6}$-alkyl groups include, but are not limited to, methyl, ethyl, n-propyl, isopropyl, butyl, isobutyl, sec-butyl, tert-butyl, pentyl, isopentyl, hexyl, isohexyl and the like.

The term "$C_{1-6}$-alkoxy" as used in the definition of the formula (XX), alone or in combination, refers to the group —O—$C_{1-6}$-alkyl where $C_{1-6}$-alkyl is as defined above. Representative examples are methoxy, ethoxy, n-propoxy, isopropoxy, butoxy, sec-butoxy, tert-butoxy, pentoxy, isopentoxy, hexoxy, isohexoxy and the like.

The term "halogen" as used in the definition of the formula (XX) means Cl, Br, I, or F.

In a preferred embodiment R[8] is chloro.

More preferred R[8] is cyano.

In still another preferred embodiment D is

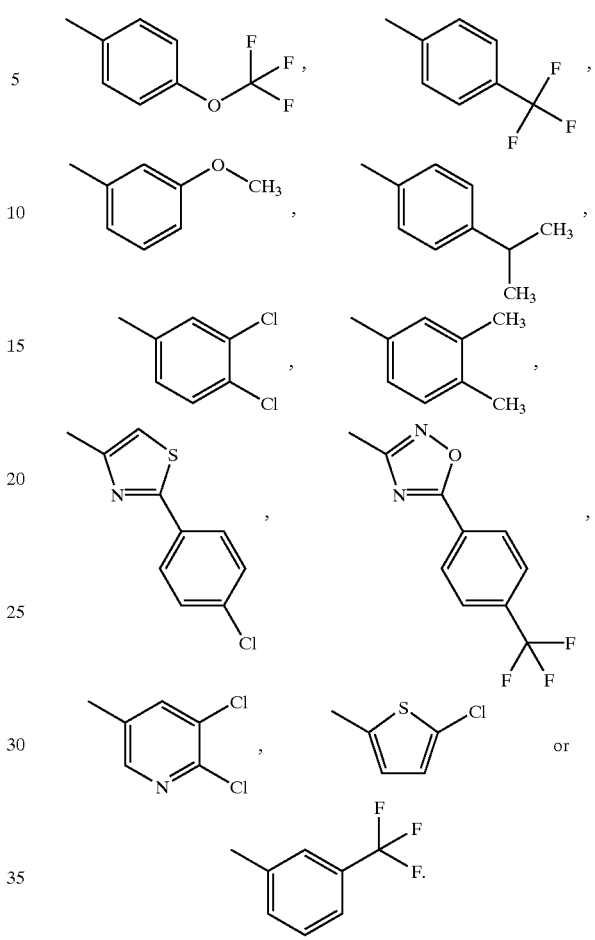

The present invention is further illustrated by the following representative examples which are, however, not intended to limit the scope of the invention in any way.

General Procedure for the Synthesis of 1-Substituted Indole-5-carboxaldehydes Followed by Hydrazone Formation The 1-substituted indole-5-carboxaldehydes may be prepared according to the below Scheme by N-alkylation of the indole4-carboxaldehyde using various electrophilic alkylating agents that introduce the —K—D moiety as defined above, such as for example lower alkyl or aryl-lower alkyl derivatives, such as halides (fluorides, chlorides, bromides, iodides), methanesulfonates, toluenesulfonates or triflates.

SCHEME

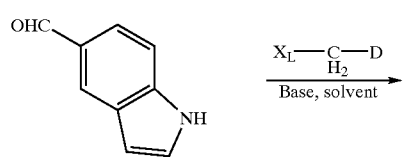

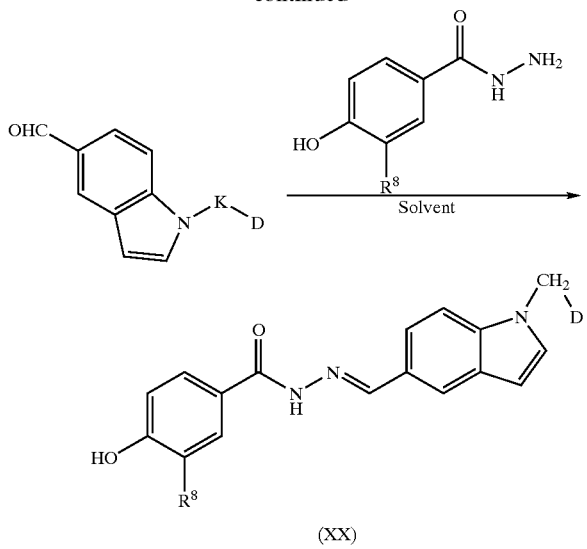

wherein $X_L$ is a leaving group such as —F, —Cl, —Br, —I, —OSO$_2$CH$_3$, —OSO$_2$p-tolyl or —OSO$_2$CF$_3$ and D and R$^8$ are as defined for formula (XX).

According to the Scheme 1-substituted indole-5-carboxaldehydes can be prepared by stirring indole-5-carboxaldehyde in an organic solvent such as acetone, methylethyl ketone, dimethylformamide, dioxane, tetrahydrofuran, toluene, ethylene glycol dimethyl ether, sulfolane, diethylether, dimethylsulfoxide, water or a compatible mixture of two or more of the above solvents with an equimolar amount of an alkyl halide or an aryl-lower alkyl halide in the presence of 1 to 15 equivalents (preferably 1 to 5 equivalents) of a base such as sodium hydride, potassium hydride, sodium or potassium methoxide, ethoxide or tert-butoxide, sodium, potassium or cesium carbonate, potassium or cesium fluoride, sodium or potassium hydroxide or organic bases such as diisopropylethylamine, 2,4,6-collidine or benzyldimethyl-ammonium methoxide or hydroxide. The reaction can be performed at 0° C. to 150° C., preferably at 20° C. to 100° C. and preferably in an inert atmosphere of N$_2$ or Ar. When the reaction is complete the mixture is filtered, concentrated in vacuo and the resulting product optionally purified by column chromatography on silica gel using ethyl acetate/hexane as eluent. The compound can also (when appropriate) be purified by recrystallization from a suitable solvent such as ethyl alcohol, ethyl acetate, isopropyl alcohol, water, hexane, toluene or their compatible mixture.

The resulting carbonyl compounds are then treated with the corresponding acylhydrazide in a solvent. The solvent may be one of the following: ethyl alcohol, methyl alcohol, isopropyl alcohol, tert-butyl alcohol, dioxane, tetrahydrofuran, toluene, chlorobenzene, anisole, benzene, chloroform, dichloromethane, DMSO, acetic acid, water or a compatible mixture of two or more of the above solvents. A catalyst such as acetic acid or TFA can be added. A dehydrating reagent such as triethylorthoformate can also be added to the reaction mixture. The reaction is performed by stirring the reaction mixture preferably under an inert atmosphere of N$_2$ or Ar at temperatures between 0° C. to 140° C., preferably between 10° C. to 80° C. In many cases the product simply crystallizes out when the reaction is completed and is isolated by suction filtration. It can be further recrystallized if necessary from a solvent such as the above described reaction solvents. The product can also be isolated by concentration of the reaction mixture in vacuo, followed by column chromatography on silica gel using a solvent system such as chloroform/methanol or dichloromethane/methanol or chloroform/ethyl acetate.

Library Procedure for Indole Alkylation

Preparation of the Sodium Salt of the Indole:

Indole-5-carboxaldehyde (1.45 g) was dissolved into 8.6 mL of dry DMF in a dried and cooled 3 100 mL 3-necked round bottom flask.

Evolution of large amounts of hydrogen gas occurs during this step. Care should be taken to keep the flow of inert gas steady and maintain adequate venting to accommodate the hydrogen gas evolution.

While maintaining a steady flow of nitrogen or argon through the 3-necked round bottomed flask, 1.1 equivalent of sodium hydride (0.27 g of dry 95% reagent) was transferred to the indole solution. The mixture was stirred for 15 minutes, while maintaining flow of inert gas. Proceeded Promptly to the next step.

Preparation of the Alkyl Halide Solutions:

Amber glass vials (for preparing stock solutions) were dried for at least four hours at 110° C., then were allowed to cool under an argon atmosphere in a desiccator. Alkyl halides solutions (1.0 M) were prepared in anhydrous DMF in the dried vials. Each alkyl halide solution (100 μL) was added to its corresponding well of a deep-well plate.

Alkylation of the Indole Sodium Salt:

100 μL of the 1.0 M indole salt solution was quickly delivered to each alkyl halide in the deep-well plates. The plates were vortexed briefly to mix, then allowed to react for two hours.

Library Procedure for Hydrazone Formation

3-Substituted 4-hydroxybenzoic acid hydrazides (10 mmoles) were dissolved in 5 mL of dry DMSO, followed by trifluoroacetic acid (0.77 mL). The resulting solutions were diluted to final volumes of 10.0 mL. 100 μL of the 1.0 M acid hydrazide TFA salt solution was added to each well of the deep-well plate. The plate was vortexed for one minute to mix, then allowed to react for 30 minutes.

The products were purified by chromatography on silica gel with ethyl acetate/hexane eluent.

EXAMPLE 951

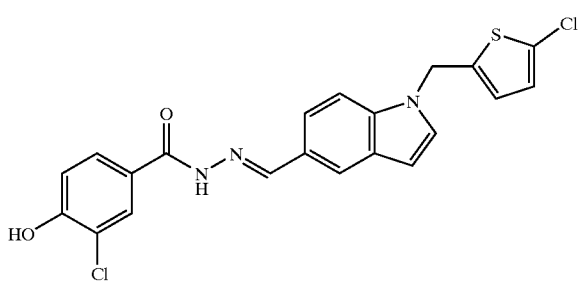

$^1$H NMR (DMSO-d$_6$): δ 5.54 (s, 2H), 7.07 (d, 1H), 7.20 (t, 1H), 7.26 (m, 2H), 7.31 (s, 4H), 7.58 (d, 1H), 7.68 (s, 1H), 7.80 (d, 1H), 8.01 (d, 1H), 8.66 (s, 1H), 11.98 (brd s, 1H), 11.71 (s, 1H); MS (APCI, negative): 486.0, 487.0, 488.0.

EXAMPLE 952
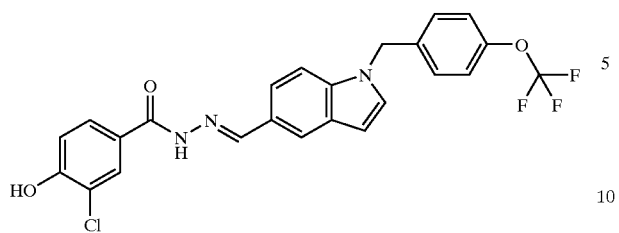
$^1$H NMR (DMSO-d$_6$): δ 5.54 (s, 2H), 7.08 (d, 1H), 7.19 (t, 1H), 7.27–7.31 (m, 5H), 7.57 (d, 1H), 7.67 (s, 1H), 7.80 (d, 1H), 8.01 (d, 1H), 8.66 (s, 1H), 10.97 (brd s, 1H), 11.71 (s, 1H); MS (APCI, neg.): 486.0, 487.0, 488.0.
Similarly, the following compounds may be prepared:
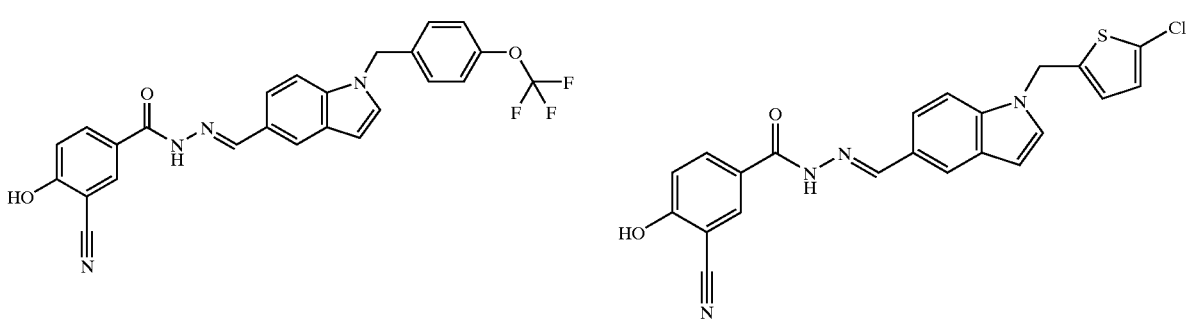
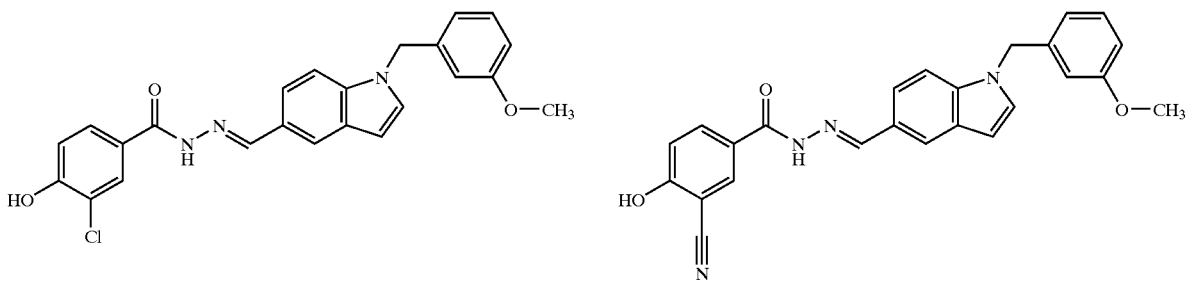
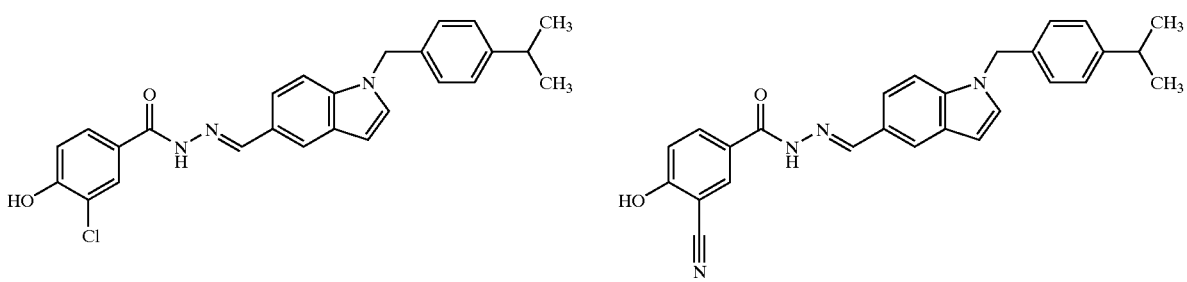
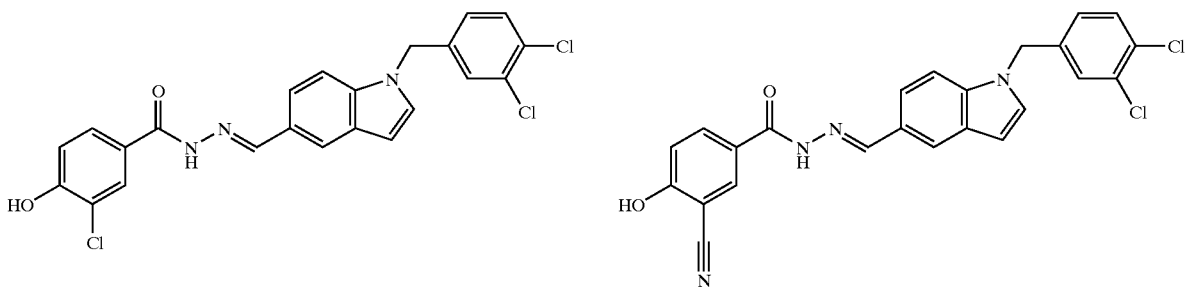

689 690
-continued
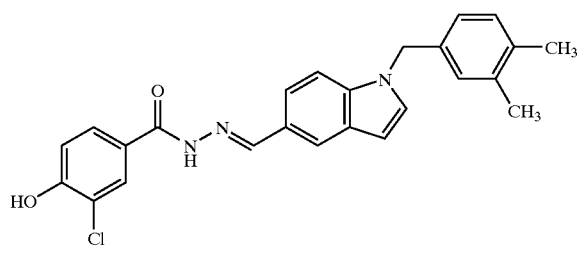
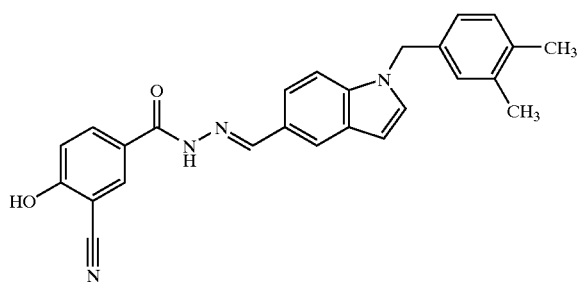
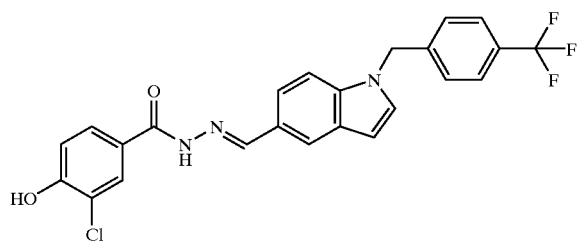
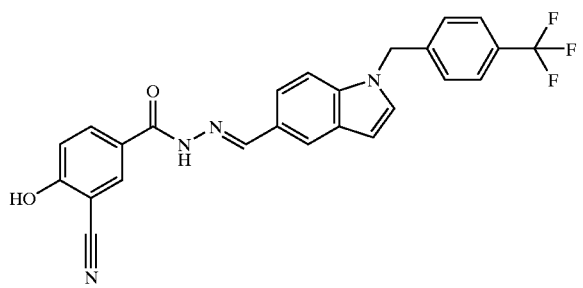
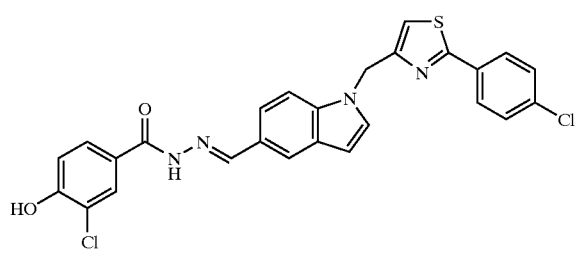
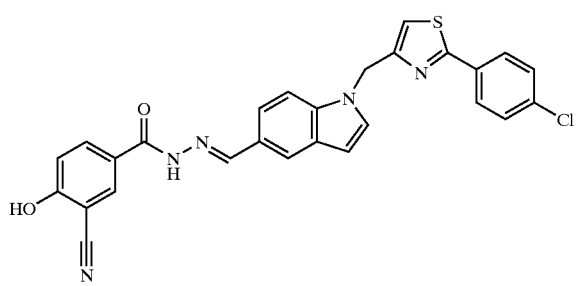
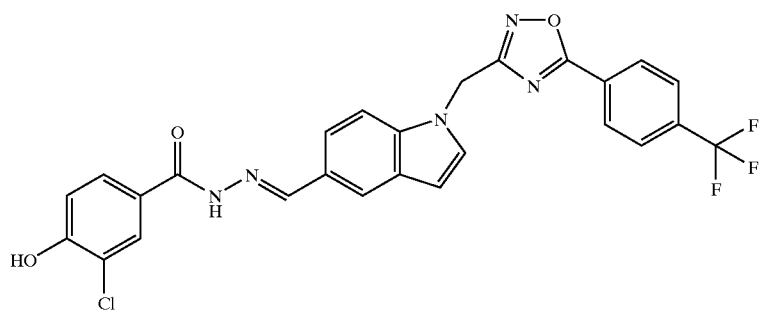
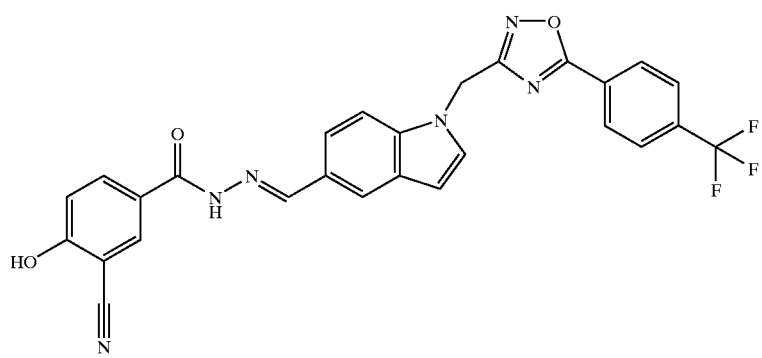

691
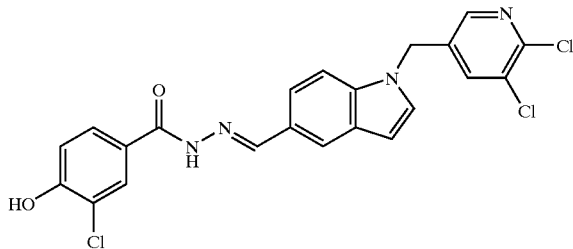
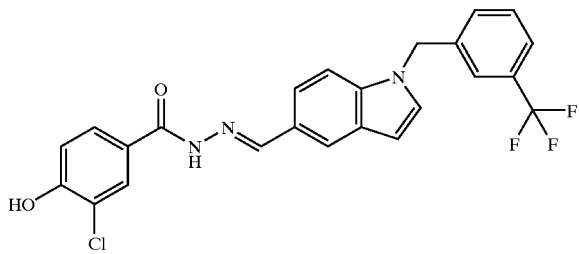
In a further aspect the invention relates to the following compounds:
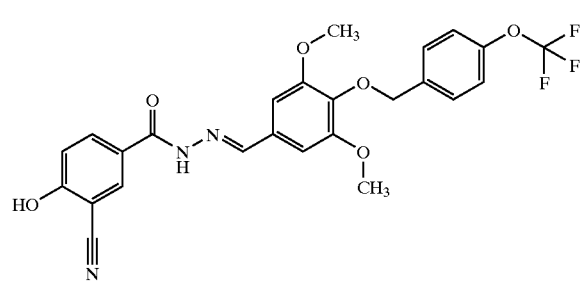
¹H NMR (DMSO-d₆): δ 3.83 (s, 6H), 4.98 (s, 2H), 7.03 (s, 2H), 7.14 (d, 1H), 7.36 (d, 2H), 7.58 (d, 2H), 8.04 (d, 1H), 8.21 (s, 1H), 8.35 (s, 1H), 11.80 (bs, 2H); MS (APCI, pos.): 517.2;
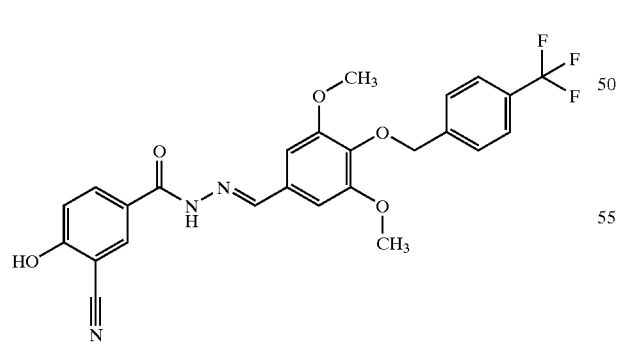
¹H NMR (DMSO-d₆): δ 3,83 (s, 6H), 5.05 (s, 2H), 7.03 (s, 2H), 7.12 (d, 1H), 7.69 (d, 2H), 7.74 (d, 2H), 8.03 (dd, 1H), 8.20 (d, 1H), 8.34 (s, 1H), 11.80 (s, 1H), 11.89 (s, 1H); MS (APCI, pos.): 500.1;
692
-continued
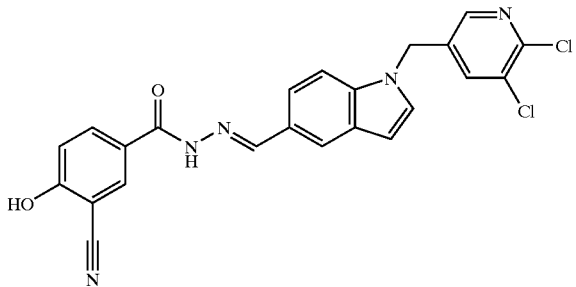
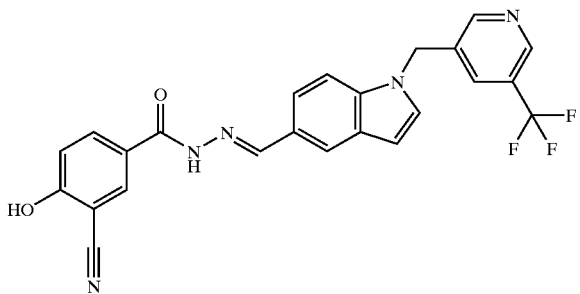
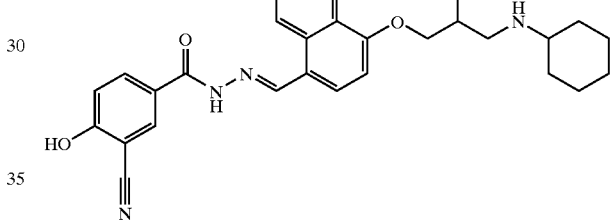
¹H NMR (DMSO-d₆): δ 1.00–2.00 (m, 10H), 2.76 (m, 1H), 2.97 (m, 1H), 3.09 (m, 1H), 4.20 (s, 3H), 6.58 (d, 1H), 7.07 (d, 1H), 7.53–7.70 (m, 2H), 7.78–7.81 (d, 2H), 8.02 (s, 1H), 8.35 (d, 1H), 8.90–8.97 (d, 2H), 11.47 (s, 1H); LC-MS (APCI, pos.): 487;
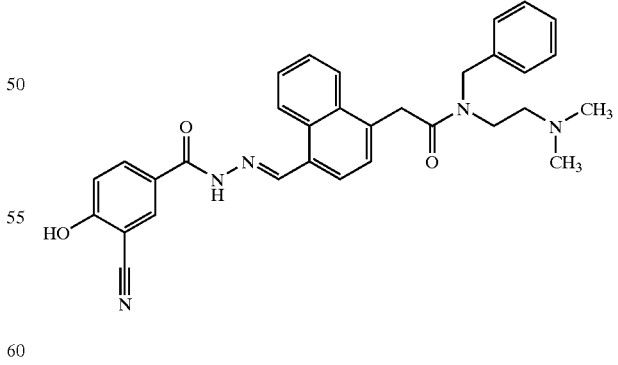
¹H NMR (DMSO-d₆): δ 2.37 (s, 3H), 2.53 (s, 3H), 2.75–2.92 (d, 2H), 3.58–3.61 (d, 2H), 4.22 (s, 1H), 4.38 (s, 1H), 4.58 (s, 1H), 4.82 (s, 1H), 7.12 (d, 1H), 7.21–7.75 (m, 10H), 7.84 (d, 1H), 8.10 (t, 1H), 8.26 (s, 1H), 8.82 (t, 1H), 9.11 (s, 1H), 11.91 (s, 1H); LC-MS (APCI, pos.): 534;

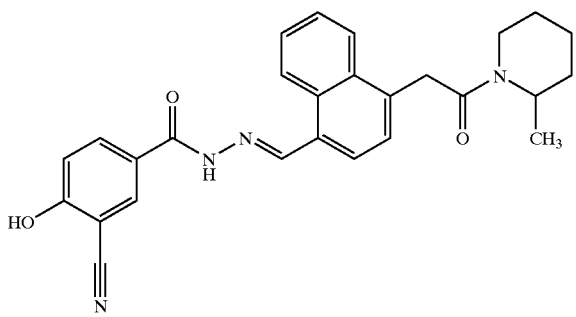

¹H NMR (DMSO-d₆): δ 1.08–1.32 (m, 4H), 1.50–1.59 (m, 5H), 2.66 (m, 0.5H), 3.12 (m, 0.5H), 3.77 (m, 0.5H), 4.17 (s, 2H), 4.27–4.32 (m, 1H), 4.74 (m, 0.5H), 7.14 (d, 1H), 7.43 (m, 1H), 7.64 (m, 2H), 7.87 (d, 1H), 8.01 (d, 1H), 8.10 (d, 1H), 8.27 (s, 1H), 8.85 (d, 1H), 9.05 (s, 1H), 11.86 (s, 2H); IR (KBr): 2230, 1608 cm⁻¹; MS (APCI, pos.): 455;

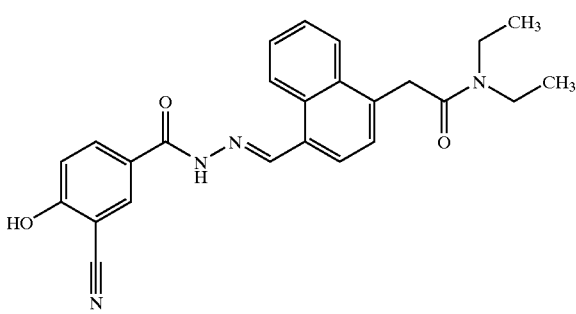

¹H NMR (DMSO-d₆): δ 1.04 (t, 3H), 1.15 (t, 3H), 3.9 (q, 2H), 3.45 (q, 2H), 4.18 (s, 2H), 7.15 (d, 1H), 3.45 (q, 2H), 4.18 (s, 2H), 7.15 (d, 1H), 7.43 (d, 1H), 7.57–7.68 (m, 2H), 7.87 (d, 1H), 8.09 (dd, 1H), 8.26 (s, 1H), 8.84 (d, 1H), 9.05 (s, 1H), 11.87 (bs, 2H); IR (KBr): 2229, 1607 cm⁻¹; MS (APCI, pos.): 429.2;

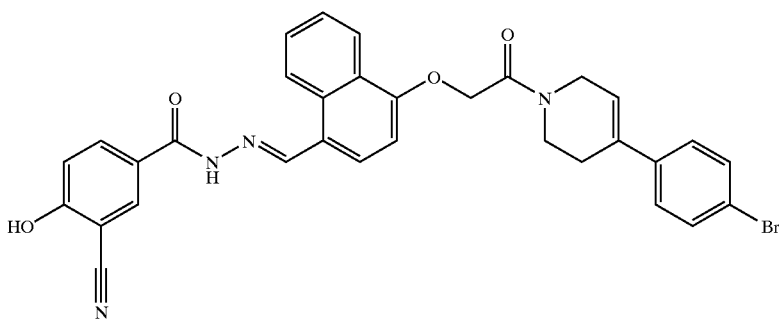

¹H NMR (DMSO-d₆): δ 2.54 (m, 1H), 2.61 (m, 1H), 3.74 (m, 2H), 4.15 (m, 1H), 4.28 (m, 1H), 5.19 (m, 1H), 5.24 (m, 1H), 6.26 (s, 1H), 7.07 (t, 1H), 7.16 (d, 1H), 7.41 (dd, 2H), 7.55 (d, 2H), 7.63 (dd, 1H), 7.71 (dd, 1H), 7.81 (d, 1H), 8.09 (d, 1H), 8.26 (s, 1H), 8.36 (d, 1H), 8.92 (s, 1H), 9.01 (d, 1H), 11.74 (s, 1H), 11.88 (s, 1H); MS (APCI, pos.): 610.0, 612.0;

¹H NMR (DMSO-d₆): δ 2.21 (m, 1H), 2.29 (m, 1H), 2.50 (m, 2H), 3.11 (m, 2H), 3.49 (s, 2H), 3.84 (m, 1H), 3.88 (m, 1H), 7.16 (d, 1H), 7.31 (d, 2H), 7.37 (d, 2H), 7.52 (d, 1H), 7.66 (m, 2H), 7.83 (d, 1H), 7.96 (d, 1H), 8.11 (d, 1H), 8.28 (s, 1H), 8.87 (d, 1H), 9.08 (s, 1H), 11.95 (s, 1H); MS (APCI, pos.): 552.2;

as well as any optical or geometric isomers or tautomeric forms thereof including mixtures of these or a pharmaceutically acceptable salts thereof.

The compounds are active glucagon antagonists or inverse agonists. Accordingly, the foregoing description of applications, pharmaceutical formulations and administration methods, and assays for evaluating the efficacy of the compounds etc also applies to these compounds.

The compounds were prepared in analogy with the foregoing methods of preparation.

In another aspect the invention relates to the compounds of the general formula (XXI):

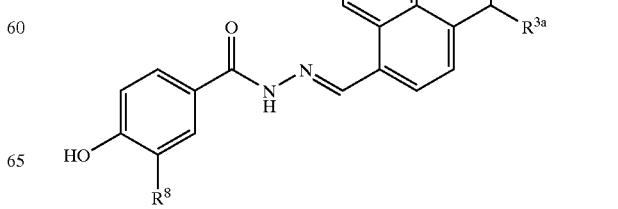

(XXI)

wherein

R[8] is chloro, fluoro, nitro or cyano;

R[3a] is $C_{1-6}$-alkyl;

as well as any optical or geometric isomer or tautomeric form thereof including mixtures of these or a pharmaceutically acceptable salt thereof.

The compounds are active glucagon antagonists or inverse agonists and the foregoing description of applications, pharmaceutical formulations and administration methods, and assays for evaluating the efficacy of the compounds etc also applies to these compounds.

The term "$C_{1-6}$-alkyl" as used in the definition of the formula (XXI), alone or in combination, represents a branched or straight hydrocarbon group having from 1 to 6 carbon atoms. Typical $C_{1-6}$-alkyl groups include, but are not limited to, methyl, ethyl, n-propyl, isopropyl, butyl, isobutyl, sec-butyl, tert-butyl, pentyl, isopentyl, hexyl, isohexyl and the like.

In a preferred embodiment R[8] is chloro.

More preferred R[8] is cyano.

In another preferred embodiment the invention relates to 3-cyano-4-hydroxybenzoic acid [4-(1-hydroxy-3-methylbutyl)-naphth-1-ylmethylene] hydrazide as well as any optical or geometric isomer or tautomeric form thereof including mixtures of these or a pharmaceutically acceptable salt thereof.

In yet another preferred embodiment the invention relates to 3-cyano-4-hydroxy-benzoic acid [4-(1-hydroxy-2-methylpropyl)-naphth-1-ylmethylene] hydrazide as well as any optical or geometric isomer or tautomeric form thereof including mixtures of these or a pharmaceutically acceptable salt thereof.

The present invention is further illustrated by the following representative examples which are, however, not intended to limit the scope of the invention in any way.

General Procedure for the Preparation of Compounds According to Formula (XXI)

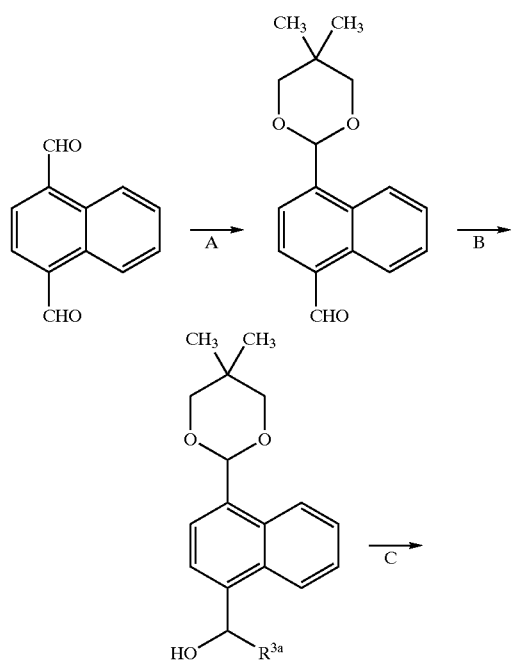

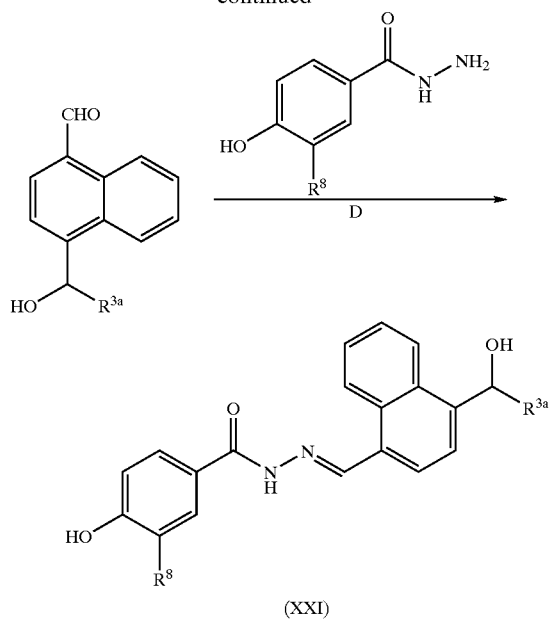

(XXI)

Step A: General Procedure for the Preparation of Mono-protected Naphthalene-1,4-dicarboxaldehydes To a solution of naphthalene-1,4-dicarboxaldehyde in a solvent, such as THF, dichloromethane, toluene, benzene, or ethylenglycol dimethyl ether, is added a slight excess (1.1 equivalent) of a diol, such as 1,2-ethanediol, 1,3-propanediol, 2,2-dimethyl-1,3-propanedol (neopentylglycol) and the like and an acidic catalyst, such as p-toluenesulfonic acid, methanesulfonic acid, trifluoroacetic acid, $BF_3$-etherate. The resulting mixture is stirred at 20–150° C., preferably at room temperature or at the boiling point of the mixture. Extraction and/or flash chromatography affords the desired mono-protected naphthalene-1,4-dicarboxaldehyde.

Step B: General Procedure for the Preparation of Protected 4-(1-Hydroxyalkyl)-naphthalene-1-carboxaldehydes To a solution of the mono-protected naphthalene-1,4-dicarboxaldehyde in THF is added the desired alkyl magnesium chloride dissolved in THF. The mixture is stirred at room temperature for 3 hr, diluted with satd. $NH_4Cl$, and extracted with ethyl acetate. The combined organic extracts are dried ($MgSO_4$) and concentrated. The product is isolated by flash chromatography.

Step C: General Procedure for the Preparation of 4-(1-Hydroxyalkyl)-naphthalene-1-carboxaldehydes Hydrolysis of the protected aldehyde is performed under acidic aqueous conditions, eg with a mixture of water and one of the following acids: hydrochloric acid, hydrobromic acid, trifluoroacetic acid, p-toluenesulfonic acid, methanesulfonic acid, perchloric acid or sulfuric acid. Extraction and flash chromatography affords the desired 4-(1-hydroxyalkyl)-naphthalene-1-carboxaldehyde.

In certain cases the protection/deprotection sequence (Step A and Step C) in the preparation of the 4-(1-hydroxyalkyl)-naphthalene-1-carboxaldehyd can be omitted as described below:

To a solution of 1,4-diformylnaphthalene in THF is added the desired alkyl magnesium chloride dissolved in THF. The mixture is stirred at room temperature for 3 hr, diluted with satd. $NH_4Cl$, and extracted with ethyl acetate. The combined organic extracts are dried (MgSO₄) and concentrated. The product is isolated by flash chromatography.

Step D: General Procedure for the Preparation of Hydrazones

Hydrazones are prepared according to the general procedure for the synthesis of alkylidene hydrazones from the condensation of the appropriate 3-substituted 4-hydroxybenzoic acid hydrazide and the above 4-(1-hydroxy-alkyl)-naphthaldehydes.

EXAMPLE 953

3-Chloro-4-hydroxybenzoic Acid [4-(1-Hydroxy-2-methylpropyl)-naphth-1-ylmethylene]hydrazide

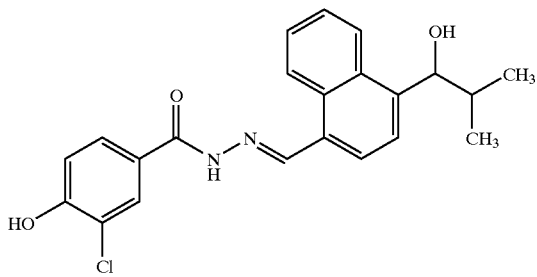

4-Formyl-1-(1-hydroxy-2-methylpropyl)naphthalene

To a solution of 1,4-diformylnaphthalene (490 mg, 2.66 mmol) in THF (12 mL) was added dropwise at 0° C. isopropyl magnesium chloride (1.3 mL of a 2 M solution in THF). The mixture was stirred at room temperature for 3 hr, diluted with satd. NH₄Cl (10 mL), and extracted with ethyl acetate (3×10 mL). The combined organic extracts were dried (MgSO₄) and concentrated. Flash chromatography (silicagel, hexane:ethyl acetate, 5:1) provided the title compound (81 mg, 14%).

$^1$H NMR (CDCl₃): δ 0.83 (d, J=6.5 Hz, 3H), 1.03 (d, J=6.5 Hz, 3H), 2.24 (m, 1H), 5.21 (m, 1H), 5.33 (d, J=4.5 Hz, 1H), 7.62–7.64 (m, 1H), 7.70 (d, J=8.5 Hz, 1H), 7.84 (d, J=7.4 Hz, 1H), 8.01 (d, J=7.4 Hz, 1H), 8.15 (d, J=7.8 Hz, 1H), 9.35 (d, J=7.8 Hz, 1H), 10.29 (s, 1H); GC-MS: 228.

3-Chloro-4-hydroxybenzoic Acid 4-(1-Hydroxy-2-methylpropyl)naphthyl Methylene Hydrazide The compound was prepared according to the general procedure for the synthesis of alkylidene hydrazones from the condensation of 4-formyl-1-(1-hydroxy-2-methylpropyl) naphthalene and 3-chloro-4-hydroxy benzoic acid hydrazide.

$^1$H NMR (DMSO-d₆): δ 0.88 (d, J=6.5 Hz, 3H), 0.95 (d, J=6.5 Hz, 3H), 2.03 (m, 1H), 5.11 (dd, J=J'=4.5 Hz, 1H), 5.38 (d, J=4.5 Hz, 1H), 7.08 (d, J=8.5 Hz, 1H), 7.62 (m, 2H), 7.69 (d, J=7.6 Hz, 1H), 7.80 (d, J=8.5 Hz, 1H), 7.92 (d, J=7.5 Hz, 1H), 8.00 (d, J=1.8 Hz, 1H), 8.24 (d, J=8.0 Hz, 1H), 8.82 (d, J=8.0 Hz, 1H), 9.07 (s, 1H), 11.04 (s, 1H), 11.78 (s, 1H); MS (APCI, pos.): 397.1, 399.1.

EXAMPLE 954

3-Cyano-4-hydroxybenzoic Acid [4-(1-Hydroxy-3-methylbutyl)-naphth-1-ylmethylene]hydrazide

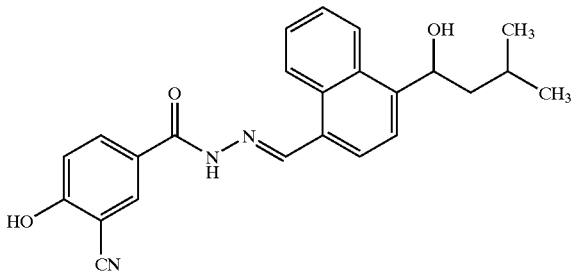

4-(5,5-Dimethyl-1,3-dioxan-2-yl)-1-naphthaldehyde (step A):

A solution of 1,4-diformylnaphthalene (4.1 g, 22 mmol) [prep. acc. Ried et al. Chem. Ber. 91, 1958, 2479] neopentylglycole (2.1 g, 24 mmol), and p-TsOH (250 mg) in toluene (100 mL) was refluxed for 16 hours using a Dean-Stark-trap to remove water. The solution was extracted with satd. NaHCO₃ solution (3×30 mL), dried (MgSO₄) and concentrated. The residue was purified by flash chromatography (silicagel, hexane:ethyl acetate, 9:1) to provide 4.0 g (66%) of the desired product.

$^1$H NMR (CDCl₃): δ 0.88 (s, 3H), 1.37 (s, 3H), 3.80 (d, J=11.0 Hz, 2H), 3.91 (d, J=11.0 Hz, 2H), 6.04 (s, 1H), 7.09 (m, 2H), 7.45 (m, 2H), 7.65 (d, J=7.7 Hz, 1H), 8.75 (d, J=7.7 Hz, 1H), 9.83 (s, 1H); GC-MS (pos.): 270.

1-[4-(5,5-Dimethyl-1,3-dioxan-2-yl)-1-naphthyl]-3-methyl-1-butanol (step B):

4-(5,5-dimethyl-1,3-dioxan-2-yl)-1-naphthaldehyde (4.0 g, 14.8 mmol) was dissolved in diethyl ether (80 mL). Magnesium bromide diethyl etherate (2.8 g, 10.8 mol) was added followed by a 2M solution of isobutyl magnesium chloride in diethyl ether (8.0 mL, 16 mmol). The mixture was stirred at room temperature for 16 hours, diluted with methanol (1 mL), water (1 mL), and 1 N HCl (20 mL). The phases were separated, and the aqueous phase was extracted with ether (3×50 mL). The combined organic extracts were dried (MgSO₄), and concentrated. Flash chromatography of the residue provided the 1.76 g (36%) desired product.

$^1$H NMR (CDCl₃): δ 0.87 (s, 3H), 0.97 (d, J=6.7 Hz, 3H), 1.14 (d, J=6.7 Hz, 3H), 1.67–2.11 (m, 4H), 5.65 (d, J=8.0 Hz, 1H), 5.98 (s, 1H), 7.60–7.72 (m, 2H), 7.90 (d, J=7.5 Hz, 1H), 8.00 (d, J=7.5 Hz, 1H), 8.11 (d, J=8.3 Hz, 1H), 9.34 (d, J=8.2 Hz, 1H), 10.36 (s, 1H); GC-MS (pos.): 243.

4-(1-Hydroxy-3-methylbutyl)-1-naphthaldehyde (step C):

To a solution of 1-[4-(5,5-Dimethyl-1,3-dioxan-2-yl)-1-naphthyl]-3-methyl-1-butanol (1.76 g, 5.35 mmol) in THF (10 mL) was added water (1 mL) and conc. HCl (1 mL). The solution was stirred at room temp. for 16 hours, diluted with NaHCO₃-solution (20 mL), and extracted with ether (3×30 mL). The combined organic extracts were dried and concentrated. Flash chromatography (silicagel, hexanes:ethyl acetate, 4:1) provided 900 mg (70%) colorless oil.

$^1$H NMR (CDCl₃): δ 0.99 (d, J=6.7 Hz, 3H), 1.08 (d, J=6.7 Hz, 3H), 1.36 (s, 3H), 1.67–1.92 (m, 4H), 5.55 (d, J=8.9 Hz, 1H), 5.98 (s, 1H), 7.57 (m, 2H), 7.67 (d, J=7.5 Hz, 1H), 7.83 (d, J=7.5 Hz, 1H), 8.11 (dd, J=2.5, 7.2 Hz, 1H), 8.24 (dd, J=2.5, 8.5 Hz, 1H).

3-Cyano-4-hydroxybenzoic Acid 4-(1-Hydroxy-3-methylbutyl)naphthyl Methylidene Hydrazide (step D):

The compound was prepared according to the general procedure for the synthesis of alkylidene hydrazones from the condensation of 4-(1-hydroxy-3-methylbutyl)-1-naphthaldehyde from step C and 3-cyano-4-hydroxy benzoic acid hydrazide.

$^1$H NMR (DMSO-D$_6$): δ 0.89 (d, J=6.6 Hz, 3H), 1.05 (d, j=6.6 Hz, 3H), 1.50 (m, 1H), 1.61 (m, 1H), 1.63 (m, 1H), 5.39 (m, 2H), 7.15 (d, J=8.8 Hz, 1H), 7.64 (m, 2H), 7.76 (d, J=7.6 Hz, 1H), 7.92 (d, J=7.6 Hz, 1H), 8.09 (d, J=8.7 Hz, 1H), 8.17 (d, J=8.8 Hz, 1H), 8.27 (s, 1H), 8.85 (d, J=7.8 Hz, 1H), 9.05 (s, 1H), 11.84 (s, 1H), 11.89 (s, 1H); MS (APCI, pos.): 402.

By use of the aforementioned methodology the following compounds may be produced:

| 3-Cyano-4-hydroxy-benzoic acid[4-(1-hydroxy-2-methylpropyl)-naphth-1-ylmethylene]hydrazide | 3-Chloro-4-hydroxy-benzoic acid[4-(1-hydroxy-3-methylbutyl)-naphth-1-ylmethylene]hydrazide |
| --- | --- |

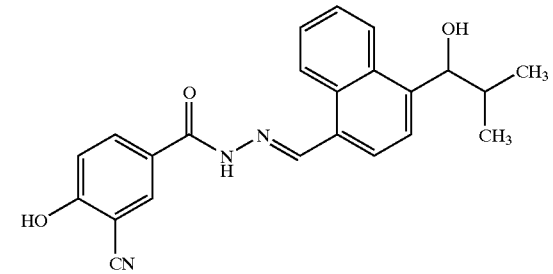

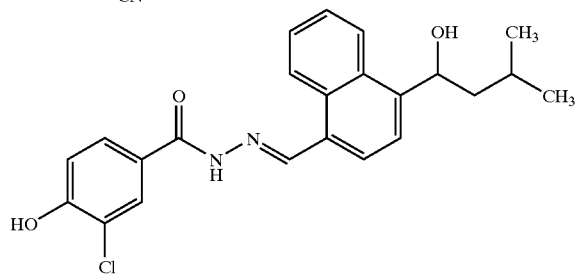

In another aspect the invention relates to the compounds of the general formula (XXII):

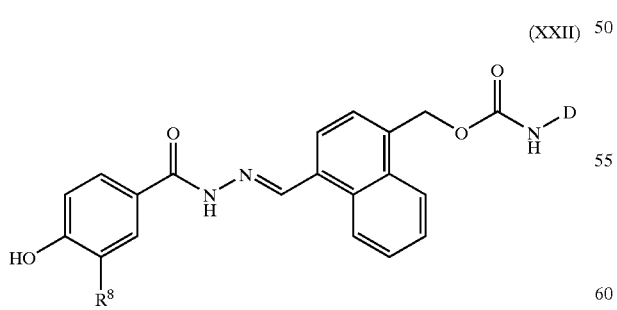

(XXII)

wherein

R$^8$ is chloro, fluoro, nitro or cyano;

D is C$_{1-6}$-alkyl,

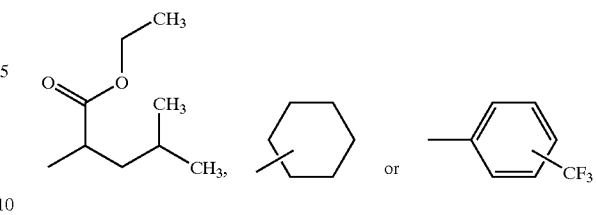

as any optical or geometric isomer or tautomeric form thereof including mixtures of these or a pharmaceutically acceptable salt thereof.

The compounds are active glucagon antagonists or inverse agonists and the foregoing description of applications, pharmaceutical formulations and administration methods, and assays for evaluating the efficacy of the compounds etc also applies to these compounds.

The term "C$_{1-6}$-alkyl" as used in the definition of the formula (XXII), alone or in combination, represents a branched or straight hydrocarbon group having from 1 to 6 carbon atoms. Typical C$_{1-6}$-alkyl groups include, but are not limited to, methyl, ethyl, n-propyl, isopropyl, butyl, isobutyl, sec-butyl, tert-butyl, pentyl, isopentyl, hexyl, isohexyl and the like.

In a preferred embodiment R$^8$ is chloro.

More preferred R$^8$ is cyano.

In another preferred embodiment D is isopropyl,

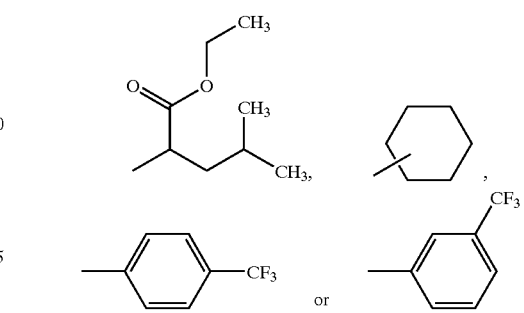

The present invention is further illustrated by the following representative examples which are, however, not intended to limit the scope of the invention in any way.

General Procedure for the Preparation of Compounds Described by the General Formula (XXII)

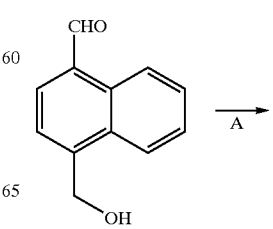

-continued

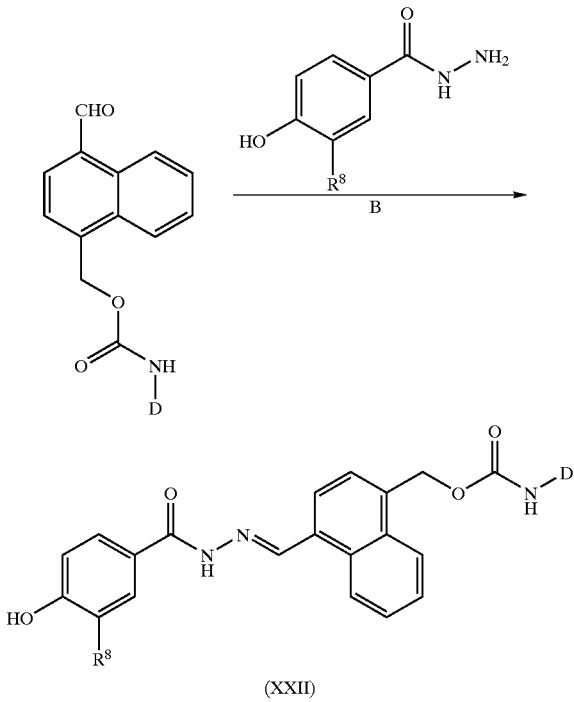

(XXII)

Step A: General Procedure for the Preparation of Carbamates.

To a solution of hydroxymethylnaphthaldehyde dissolved in anhydrous DMF is added the desired isocyanate (excess). After stirring the reaction overnight at room temperature, hexane was added to help precipitate the product. The crude product was collected by filtration and recrystallized from dichloromethane, Step B: General Procedure for the Preparation of Hydrazones.

Hydrazones were prepared according to the general procedure for the synthesis of alkylidene hydrazones from the condensation of the appropriate 3-substituted 4-hydroxybenzoic acid hydrazide and the above carbamate-aldehydes.

EXAMPLE 955

(4-Trifluoromethylphenyl)-carbamic Acid 4-[(3-Chloro-4-hydroxybenzoyl)-hydrazonomethyl]-naphth-1-ylmethyl Ester

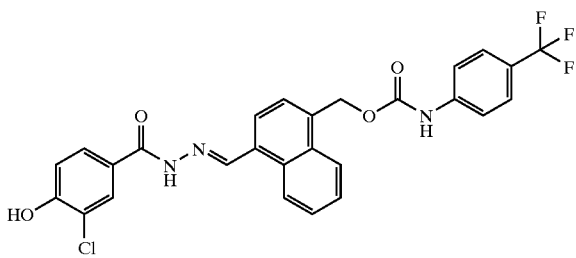

$^1$H NMR (DMSO-D$_6$): δ 5.70 (s, 2H), 7.09 (d, 1H), 7.66 (m, 4H), 7.73 (m, 3H), 7.80 (d, 1H), 7.94 (d, 1H), 8.00 (d, 1H), 8.20 (m, 1H), 8.90 (d, 1H), 9.10 (d, 1H), 10.24 (s, 1H), 10.99 (brd s, 1H), 11.85 (brd s, 1H); MS (APCI): 541.8, 543.8.

EXAMPLE 956

(3-Trifluoromethylphenyl)-carbamic Acid 4-[(3-Chloro-4-hydroxybenzoyl)-hydrazonomethyl]-naphth-1-ylmethyl Ester

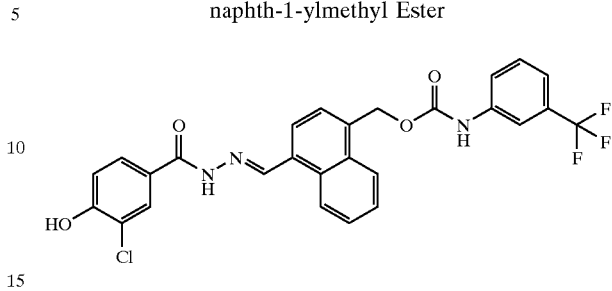

$^1$H NMR (DMSO-D$_6$): δ 5.69 (s, 2H), 7.12 (d, 1H), 7.33 (d, 1H), 7.51 (t, 3H), 7.68–7.75 (m, 2H), 7.84 (d, 1H), 7.93 (s, 1H), 7.96 (d, 1H), 8.04 (s, 1H), 8.20 (m, 1H), 8.86 (d, 1H), 9.22 (s, 1H), 10.20 (s, 1H), 11.10 (brd s, 1H), 12.01 (brd s, 1H); MS (APCI): 541.8, 543.8.

EXAMPLE 957

Isopropylcarbamic Acid 4-[(3-Chloro-4-hydroxybenzoyl)-hydrazonomethyl]-naphth-1-ylmethylester

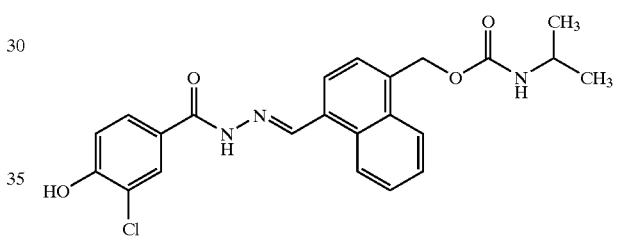

$^1$H NMR (DMSO-D$_6$): δ 1.06 (d, 6H), 3.62 (oct, 1H), 5.51 (s, 2H), 7.08 (d, 1H), 7.22 (d, 1H), 7.62–7.69 (m, 3H), 7.80 (dd, 1H), 7.90 (d, 1H), 8.00 (d, 1H), 8.10 (d, 1H), 8.86 (d, 1H), 9.08 (s, 1H), 11.00 (brd s, 1H), 11.82 (brd s, 1H); MS (APCI): 439.8

EXAMPLE 958

Cyclohexylcarbamic Acid 4-[(3-Chloro-4-hydroxybenzoyl)-hydrazonomethyl]-naphth-1-ylmethyl Ester

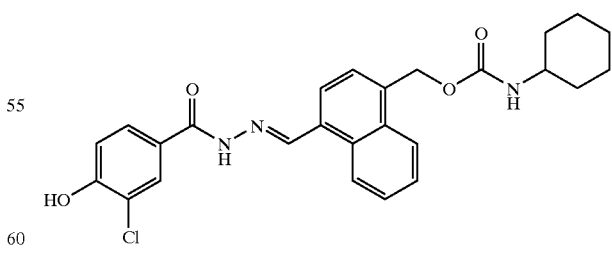

$^1$H NMR (DMSO-D$_6$): δ 1.03–1.21 (m, 6H), 1.63–1.77 (m, 4H), 3.28 (m, 1H), 5.49 (s, 2H), 6.54 (d, 1H), 7.23 (d, 1H), 7.57–7.70 (m, 4H), 7.84 (d, 1H), 7.87 (d, 1H), 8.07 (m, 1H), 8.83 (d, 1H), 9.05 (s, 1H), 11.53 (s, 1H); MS (APCI): 479.9, 480.9.

EXAMPLE 959

2-{4-[(3-Chloro-4-hydroxybenzoyl)-hydrazonomethyl]-naphth-1-ylmethoxycarbonylamino}-4-methylpentanoic Acid Ethyl Ester

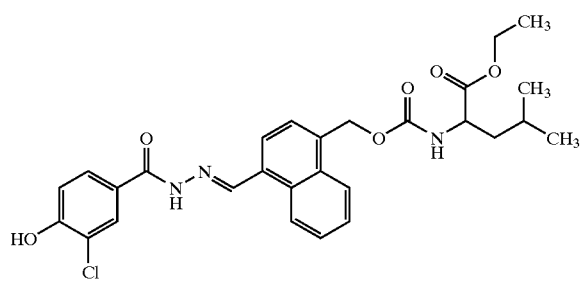

By use of the aforementioned methodology the following compounds may be produced:

In a further aspect the invention relates to the compounds of the general formula (XXIII):

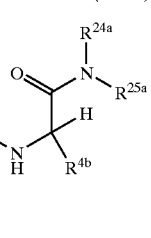

(XXIII)

wherein
R$^8$ is chloro, fluoro, nitro or cyano;
R$^{4b}$ is hydrogen, C$_{1-6}$-alkyl or phenyl-C$_{1-6}$-alkyl; R$^{24a}$ and R$^{25a}$ independently are hydrogen, C$_{1-6}$-alkyl, phenyl or phenyl-C$_{1-6}$-alkyl;

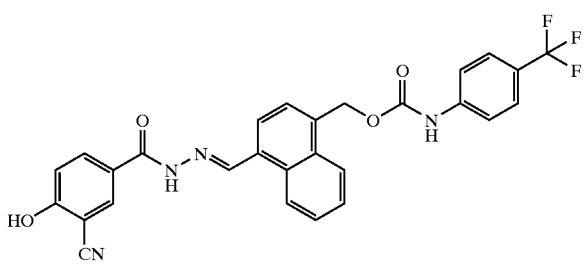

(4-Trifluoromethylphenyl)-carbamic acid 4-[(3-cyano-4-hydroxybenzoyl)-hydrazonomethyl]-naphth-1-ylmethyl ester

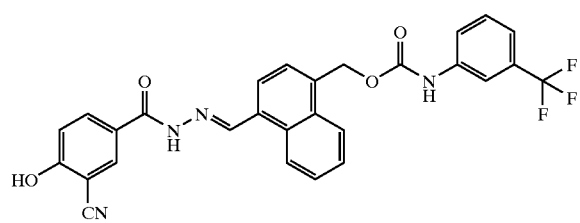

(3-Trifluoromethylphenyl)-carbamic acid 4-[(3-cyano-4-hydroxybenzoyl)-hydrazonomethyl]-naphth-1-ylmethyl ester

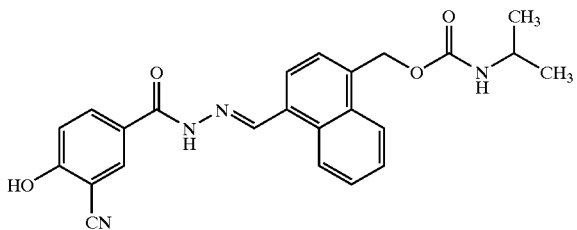

Isopropylcarbamic acid 4-[(3-cyano-4-hydroxybenzoyl)-hydrazonomethyl]-naphth-1-ylmethylester

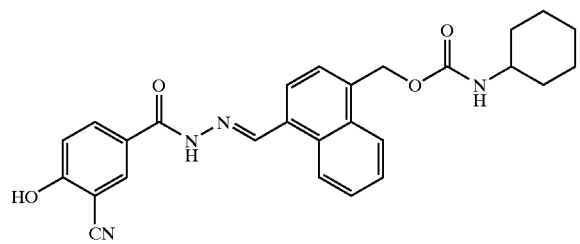

Cyclohexylcarbamic acid 4-[(3-cyano-4-hydroxybenzoyl)-hydrazonomethyl]-naphth-1-ylmethyl ester

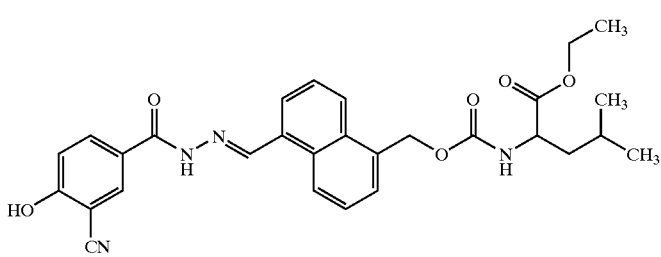

2-{4-[(3-Cyano-4-hydroxybenzoyl)-hydrazonomethyl]-naphth-1-ylmethoxycarbonylamino-4-methylpentanoic acid ethyl ester as well as any optical or geometric isomer or tautomeric form thereof including mixtures of these or a pharmaceutically acceptable salt thereof.

The compounds are active glucagon antagonists or inverse agonists and the foregoing description of applications, pharmaceutical formulations and administration methods, and assays for evaluating the efficacy of the compounds etc also applies to these compounds.

The term "$C_{1-6}$-alkyl" as used in the definition of the formula (XXIII), alone or in combination, represents a branched or straight hydrocarbon group having from 1 to 6 carbon atoms. Typical $C_{1-6}$-alkyl groups include, but are not limited to, methyl, ethyl, n-propyl, isopropyl, butyl, isobutyl, sec-butyl, tert-butyl, pentyl, isopentyl, hexyl, isohexyl and the like.

In a preferred embodiment $R^8$ is chloro.

More preferred $R^8$ is cyano.

In another preferred embodiment $R^{24a}$ and $R^{25a}$ are both hydrogen.

In yet another preferred embodiment $R^{4b}$ is benzyl, sec-butyl or isobutyl, preferably benzyl.

The present invention is further illustrated by the following representative examples which are, however, not intended to limit the scope of the invention in any way.

General Procedure for the Preparation of Compounds Described by the Formula (XXIII)

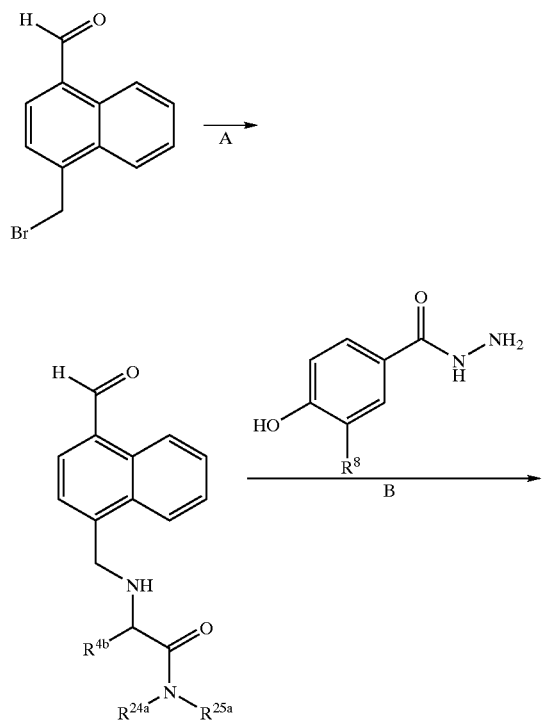

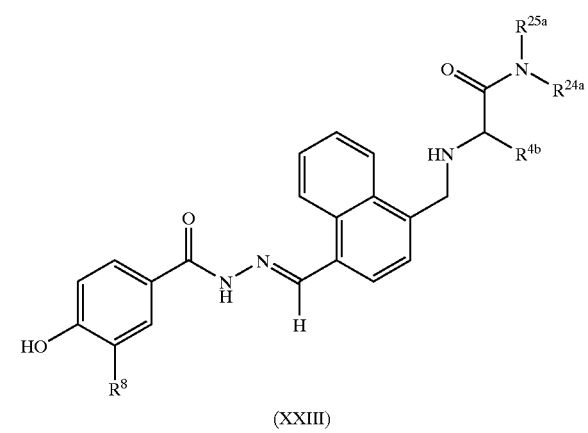

(XXIII)

Step A: General Procedure for the Preparation of Naphthylmethyl-amino-amides.

To a solution of bromomethyinaphthaldehyde in anhydrous DMF was added diisopropylethylamine (1.2 eq) and the desired amino-amide (1.1 eq). After stirring the reaction for four hours the mixture was diluted with ethyl acetate and washed with 1N HCl (2x), water (2x), brine, dried over $MgSO_4$, and concentrated. The products were purified via silica gel column chromatography.

Step B: General Procedure for the Preparation of Hydrazones.

Hydrazones were prepared according to the general procedure for the synthesis of alkylidene hydrazones from the condensation of the appropriate 3-substituted 4-hydroxybenzoic acid hydrazide and the above aminoamide-aldehydes.

EXAMPLE 960

2-({4-[(3-Chloro-4-hydroxybenzoyl)-hydrazonomethyl]-naphth-1-ylmethyl}-amino)-3-methylpentanoic Acid Amide

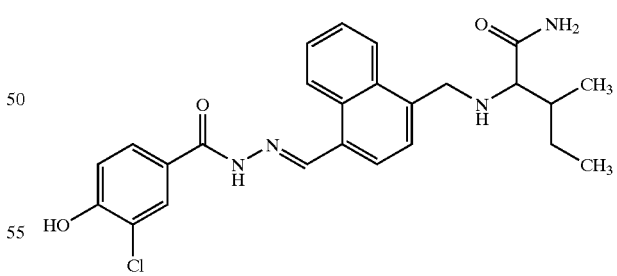

$^1$H NMR (DMSO-$d_6$): δ 0.77 (t, 3H), 0.82 (d, 3H), 1.09 (m, 1H), 1.54 (m 2H), 2.86 (d, 1H), 3.95 (d, 1H), 4.20 (d, 1H), 7.09 (m 2H), 7.44 (brd s, 1H), 7.59–7.64 (m, 3H), 7.80 (d, 1H), 7.87 (d, 1H), 8.02 (s, 1H), 8.29 (d, 1H), 8.85 (d, 1H), 9.08 (s, 1H), 10.90 (brd s, 1H), 11.79 (s, 1H); MS (APCI): 466.9, 468.9.

EXAMPLE 961

2-({4-[(3-Chloro-4-hydroxybenzoyl)-hydrazonomethyl]-naphth-1-ylmethyl}-amino)-4-methylpentanoic Acid Amide

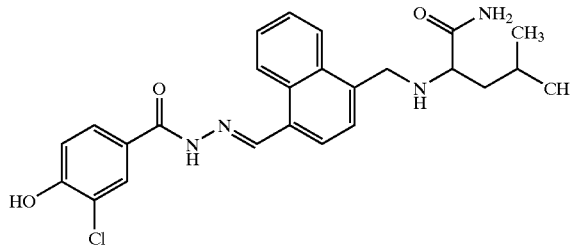

$^1$H NMR (DMSO-$d_6$): δ 0.76 (d, 3H), 0.86 (d, 3H), 1.35 (d, 2H), 1.72 (oct, 1H), 3.09 (t, 1H), 3.17 (s, 1H), 3.36 (m, 3H), 4.00 (d, 1H), 4.20 (d, 1H), 7.08 (s, 1H), 7.10 (d, 1H), 7.47 (d, 1H), 7.59–7.67 (m, 3H), 7.80 (d, 1H), 7.87 (d, 2H), 8.01 (d, 1H), 8.26 (d, 1H), 8.84 (s, 1H), 9.08 (s, 1H), 11.80 (s, 1H); MS (APCI): 466.9, 468.9.

EXAMPLE 962

S-2-({4-[(3-Chloro-4-hydroxybenzoyl)-hydrazonomethyl]-naphth-1-ylmethyl}-amino)-4-methylpentanoic Acid Amide

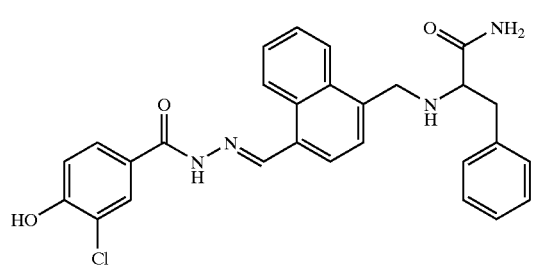

$^1$H NMR (DMSO-$d_6$): δ 2.79 (m, 1H), 2.89 (m, 1H), 3.99 (d, 1H), 4.14 (d, 1H), 7.12 (m, 2H), 7.24 (m, 5H), 7.48 (m, 2H), 7.60 (m, 1H), 7.64 (m, 1H), 7.80 (m, 2H), 8.01 (s, 1H), 8.11 (d, 1H), 8.82 (d, 1H), 9.06 (s, 1H), 11.00 (brd s, 1H), 11.79 (s, 1H); MS (APCI): 501.0, 502.0.

EXAMPLE 963

R-2-({4-[(3-Chloro-4-hydroxybenzoyl)-hydrazonomethyl]-naphth-1-ylmethyl}-amino)-3-phenylpropionamide

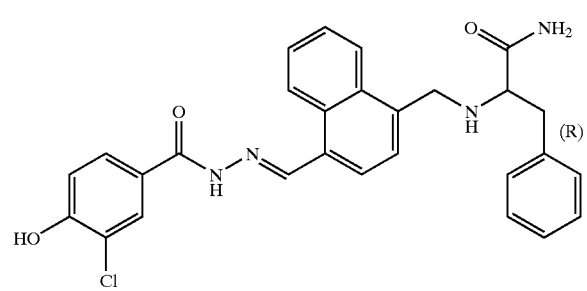

$^1$H NMR (DMSO-$d_6$): δ 2.74 (m, 1H), 2.88 (m, 1H), 3.98 (d, 1H), 4.16 (d, 1H), 7.11 (s, 1H), 7.20 (m, 1H), 7.24 (m, 5H), 7.47–7.60 (m, 3H), 7.64 (t, 1H), 7.79 (m, 2H), 8.01 (s, 1H), 8.11 (d, 1H), 8.80 (d, 1H), 9.06 (s, 1H), 11.78 (s, 1H); MS (APCI): 500.9, 502.9.

By use of the aforementioned methodology the following compounds may be produced:

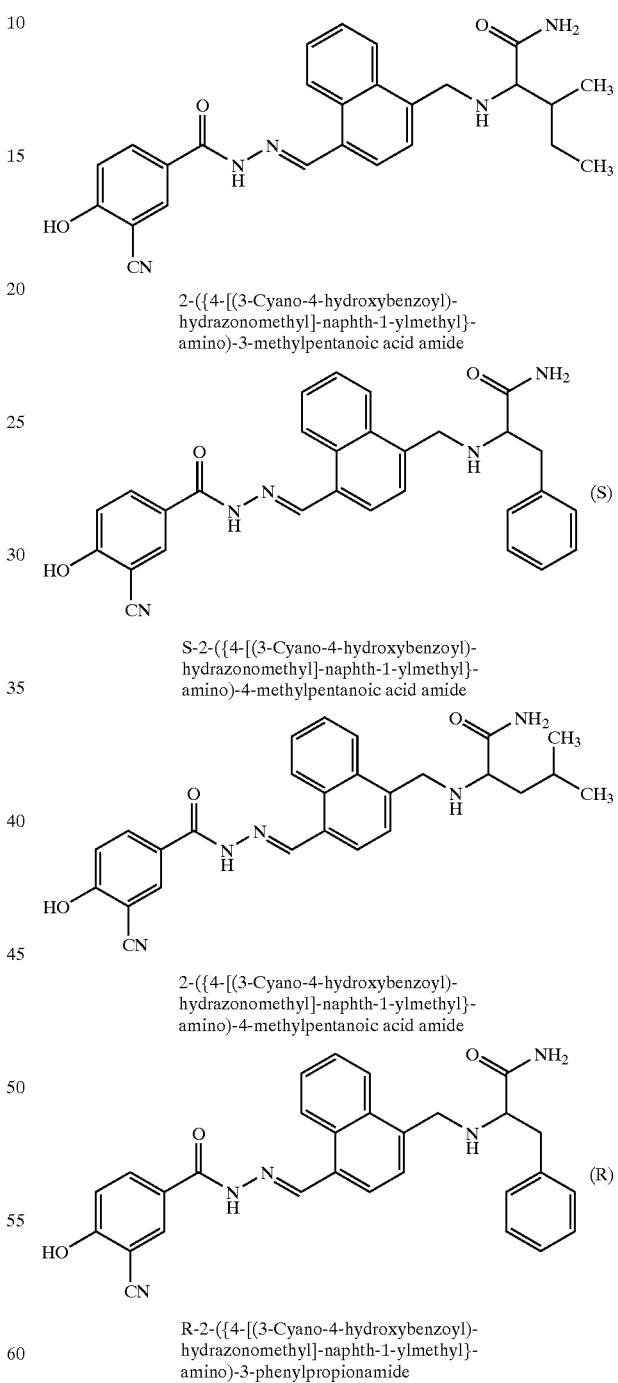

2-({4-[(3-Cyano-4-hydroxybenzoyl)-hydrazonomethyl]-naphth-1-ylmethyl}-amino)-3-methylpentanoic acid amide S-2-({4-[(3-Cyano-4-hydroxybenzoyl)-hydrazonomethyl]-naphth-1-ylmethyl}-amino)-4-methylpentanoic acid amide 2-({4-[(3-Cyano-4-hydroxybenzoyl)-hydrazonomethyl]-naphth-1-ylmethyl}-amino)-4-methylpentanoic acid amide R-2-({4-[(3-Cyano-4-hydroxybenzoyl)-hydrazonomethyl]-naphth-1-ylmethyl}-amino)-3-phenylpropionamide In a further aspect the invention relates to the compounds of the general formula (XXIV):

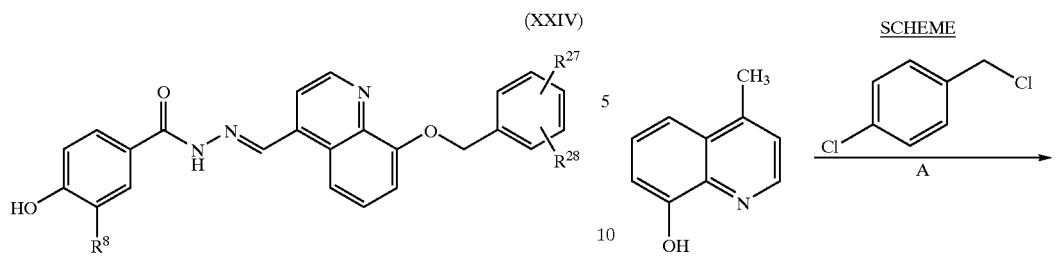

(XXIV)

wherein $R^8$ is chloro, fluoro, nitro or cyano; and $R^{27}$ and $R^{28}$ independently are hydrogen, halogen, cyano, nitro, acetoxy, $C_{1-6}$-alkoxy, benzyloxy, trifluoromethyl, methylsulfonyl or $C_{1-6}$-alkyl;

as well as any optical or geometric isomer or tautomeric form thereof including mixtures of these or a pharmaceutically acceptable salt thereof.

The compounds are active glucagon antagonists or inverse agonists and the foregoing description of applications, pharmaceutical formulations and administration methods, and assays for evaluating the efficacy of the compounds etc also applies to these compounds.

The term "$C_{1-6}$-alkyl" as used in the definition of the formula (XXIV), alone or in combination, represents a branched or straight hydrocarbon group having from 1 to 6 carbon atoms. Typical $C_{1-6}$-alkyl groups include, but are not limited to, methyl, ethyl, n-propyl, isopropyl, butyl, isobutyl, sec-butyl, tert-butyl, pentyl, isopentyl, hexyl, isohexyl and the like.

The term "$C_{1-6}$-alkoxy" as used in the definition of the formula (XXIV), alone or in combination, refers to the group —O—$C_{1-6}$-alkyl where $C_{1-6}$-alkyl is as defined above. Representative examples are methoxy, ethoxy, n-propoxy, isopropoxy, butoxy, sec-butoxy, tert-butoxy, pentoxy, isopentoxy, hexoxy, isohexoxy and the like.

The term "halogen" as used in the definition of the formula (XXIV) means Cl, Br, I, or F.

In a preferred embodiment $R^8$ is chloro.

More preferred $R^8$ is cyano.

In a further preferred embodiment $R^{27}$ is hydrogen and $R^{28}$ is halogen. The present invention is further illustrated by the following representative examples which are, however, not intended to limit the scope of the invention in any way.

EXAMPLE 964

3-Cyano-4-hydroxybenzoic Acid {[8-(4-Chlorobenzyloxy])-4-quinolinyl]methylidene}hydrazide

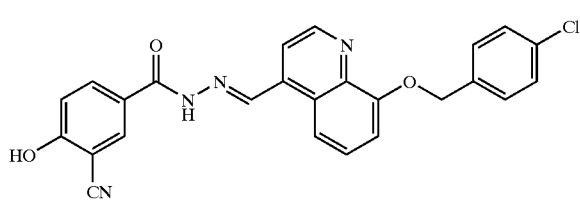

8-(4-Chlorobenzyloxy)-4-methylquinoline (Step A):

4-methyl-8-hydroxy quinoline (2.65 g, 16.6 mmol) [prep. acc. P. Belser, S. Bernhard, U. Guerig, Tetrahedron 52, 1996, 2937–2944] was dissolved in a warm solution of KOH (930 mg, 16.6 mmol) in ethanol (50 mL). The mixture was heated to reflux and a solution of 4-chlorobenzyl chloride (3.5 g, 21.7 mmol) in ethanol (20 ml) was added dropwise to the refluxing solution during a period of 30 min. Refluxing was continued for 16 h. The solution was filtered by suction, and the filtrate was concentrated. The residue was diluted with ethyl acetate (100 ml), extracted with water (100 mL), dried (MgSO$_4$) and concentrated. Flash chromatography (silicagel, hexane:ethyl acetate, 3:1) provided 1.69 (34%) beige solid.

$^1$H NMR (CDCl$_3$): δ 2.69 (s, 3H), 5.41 (s, 2H), 7.00 (d, J=7.7 Hz, 1H), 7.30 (d, J=4.3 Hz, 1H), 7.33 (d, J=8.5 Hz, 2H), 7.40 (dd, J=7.7, 8.3 Hz, 1H), 7.47 (d, J=8.5 Hz, 2H), 7.58 (d, J=8.5 Hz, 1H), 8.85 (d, J=4.3 Hz, 1H); GC-MS (pos.): 283.

8-(4-Chlorobenzyloxy)-4-formylquinoline (Step B):

Selenium dioxide (620 mg, 5.6 mmol) was suspended in dioxane (5 mL); a few drops of water was added until a clear solution was obtained. The mixture was heated to 100° C. and 8-(4-chlorobenzyloxy)-4-methyl quinoline (1.6 g, 5.6 mmol) in dioxane (20 mL) was added dropwise during a period of 2 hours. The mixture kept at 100° C. for 4 hours, filtered hot and concentrated. The residue was treated with 1N HCl (200 ml), and filtered. The filtrate was neutralized with 3N NaOH, and extracted with ethyl acetate (3×100 mL). The combined organic extracts were dried (Na$_2$SO$_4$), and concentrated. Recrystallization from toluene provided 1.02 g (62%) yellow needles.

$^1$H NMR (CDCl$_3$): δ 5.42 (s, 2H), 7.12 (d, J=7.3 Hz, 1H), 7.36 (d, J=8.5 Hz, 2H), 7.46 (d, J=8.5 Hz, 2H), 7.58 (dd, J=8.1,8.5 Hz, 1H), 7.85 (d, J=4.3 Hz, 1H), 8.57 (d, J=8.5 Hz, 1H), 9.25 (d, J=4.3 Hz, 1H), 10.53 (s, 1H); GC-MS (pos.): 297.

3-Cyano-4-hydroxybenzoic Acid {[8-(4-Chlorobenzyloxy])-4-quinolinyl]methylidene}hydrazide (Step C):

The title compound was prepared according to the general procedure for the synthesis of alkylidene hydrazones from the condensation 8-(4-chlorobenzyloxy)-4-formylquinoline from step B and 3-cyano-4-hydroxy benzoic acid hydrazide.

$^1$H NMR (DMSO-d$_6$): δ 5.33 (s, 2H), 7.13 (d, J=8.8 Hz, 1H), 7.36 (d, J=7.8 Hz, 1H), 7.49 (d, J=8.3 Hz, 2H), 7.58 (d, J=8.3 Hz, 2H), 7.63 (dd, J=J'=7.6 Hz, 1H), 7.86 (s, 1H), 8.08 (d, J=8.6 Hz, 1H), 8.21 (d, J=7.6 Hz, 1H), 8.26 (s, 1H), 8.95 (d, J=4.6 Hz, 1H), 9.04 (s, 1H), 12.10 (s, 1H); IR (KBr): 2230, 1653, 1605 cm$^{-1}$; MS (APCI, pos.): 457.

EXAMPLE 965

3-Chloro-4-hydroxybenzoic Acid {[8-(4-chlorobenzyloxy])-4-quinolinyl] methylidene}hydrazide

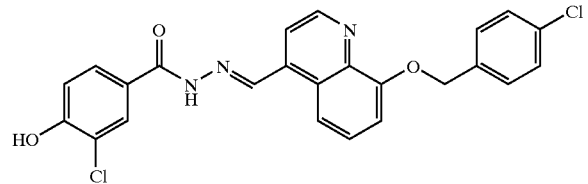

This compound was prepared according to the general procedure for the synthesis of alkylidene hydrazones from the condensation 8-(4-chlorobenzyloxy)-4-formylquinoline from step B and 3-chloro4-hydroxy benzoic acid hydrazide.

$^1$H NMR (DMSO-d$_6$): δ 5.33 (s, 2H), 7.06 (d, J=8.5 Hz, 1H), 7.35 (d, J=7.8 Hz, 1H), 7.49 (d, J=8.4 Hz, 2H), 7.58 (d J=8.3 Hz, 2H), 7.59 (m, 1H), 7.79 (dd, J=1.9, 8.5 Hz, 1H), 7.85 (d, J=4.4 Hz, 1H), 8.00 (d, J=1.8 Hz, 1H), 8.20 (d, J=8.5 Hz, 1H), 8.26 (s, 1H), 8.94 (d, J=4.4 Hz, 1H), 9.05 (s, 1H), 12.05 (s, 1H); MS (APCI, pos.): 466.

It should be apparent from the foregoing that other starting materials and other intermediate compounds can be substituted in the above procedures to prepare all of the compounds of the invention. The methods disclosed herein are based on established chemical techniques, as will be apparent to those skilled in the art, and therefore all of the compounds of the invention are broadly enabled by the preceding disclosure.

Accordingly, the invention may be embodied in other specific forms without departing from its spirit or essential characteristics. The described embodiments are to be considered in all respects only as illustrative and not restrictive, and the scope of the invention is, therefore, indicated by the appended claims rather than by the foregoing description. All modifications which come within the meaning and range of the lawful equivalency of the claims are to be embraced within their scope.

What is claimed is:

1. A compound of formula I:

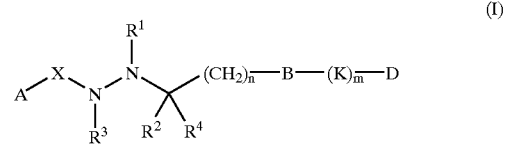

(I)

wherein:

$R^1$ and $R^2$ together form a valence bond;

$R^3$ is hydrogen or lower alkyl and $R^4$ is hydrogen;

n is 0, 1, 2 or 3;

m is 0 or 1;

X is >C=O,

A is

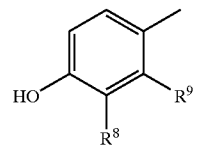

wherein:

$R^8$ is halogen, —CN, —F$_3$, —OCF$_3$, —OCH$_2$CF$_3$, —NO$_2$, —OCOR$^{13}$, —OSO$_2$R$^{13}$, -Olower alkyl, —Oaryl, —NR$^{11}$R$^{12}$, lower alkyl, aryl, —SCF$_3$, —SR$^{11}$, —CHF$_2$, —OCHF$_2$, —OSO$_2$R$^{11}$, —CONR$^{11}$R$^{12}$, —CH$_2$OR$^{11}$, —CH$_2$NR$^{11}$R$^{12}$, —OCOR$^{11}$, —CO$_2$R$^{13}$ or —OSO$_2$CF$_3$, and $R^9$ is hydrogen, halogen, —CN, —CF$_3$, —OCF$_3$, —OCH$_2$CF$_3$, —NO$_2$, —OR$^{11}$, —NR$^{11}$R$^{12}$, lower alkyl, aryl, —SCF$_3$, —SR$^{11}$, —CHF$_2$, —OCHF$_2$, —OSO$_2$R$^{11}$, —CONR$^{11}$R$^{12}$, —CH$_2$OR$^{11}$, —CH$_2$NR$^{11}$R$^{12}$, —OCOR$^{11}$, —CO$_2$R$^{13}$ or —OSO$_2$CF$_3$, or $R^8$ and $R^9$ together form a bridge —OCH$_2$O— or —OCH$_2$CH$_2$O—;

wherein $R^{11}$ and $R^{12}$ independently are hydrogen, —COR$^{13}$, —SO$_2$R$^{13}$, lower alkyl or aryl;

wherein $R^{13}$ is hydrogen, lower alkyl, aryl-lower alkyl or aryl; and $R^{10}$ is hydrogen, lower alkyl, aryl-lower alkyl or aryl;

B is

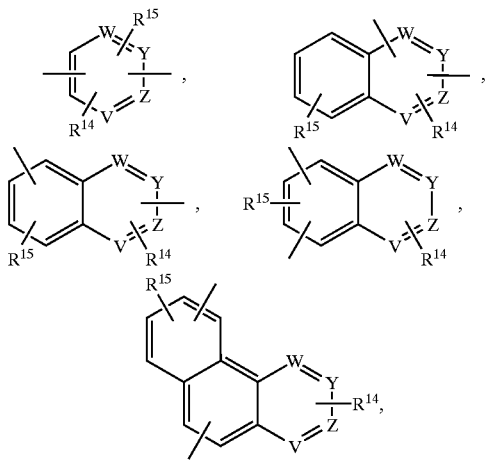

wherein:

$R^{14}$ and $R^{15}$ independently are hydrogen, halogen, —CN, —CF$_3$, —OCF$_3$, —O(CH$_2$)$_l$CF$_3$, —NO$_2$, —OR$^{16}$, —NR$^{16}$R$^{17}$, lower alkyl, aryl, aryl-lower alkyl, —SCF$_3$, —SR$^{16}$, —CHF$_2$, —OCHF$_2$, —OCF$_2$CHF$_2$, —OSO$_2$CF$_3$, —CONR$^{16}$R$^{17}$, —(CH$_2$)$_l$CONR$^{16}$R$^{17}$, —O(CH$_2$)$_l$CONR$^{16}$R$^{17}$, —(CH$_2$)$_l$COR$^{16}$, —(CH$_2$)$_l$COR$^{16}$, —(CH$_2$)$_l$OR$^{16}$, —O(CH$_2$)$_l$OR$^{16}$, —(CH$_2$)$_l$NR$^{16}$R$^{17}$, —O(CH$_2$)$_l$NR$^{16}$R$^{17}$, —OCOR$^{16}$, —CO$_2$R$^{18}$, —O(CH$_2$)$_l$CO$_2$R$^{18}$, —O(CH$_2$)$_l$CN, —O(CH$_2$)$_l$Cl, or $R^{14}$ and $R^{15}$ together form a bridge —O(CH$_2$)$_l$O— or —(CH$_2$)$_l$—;

wherein l is 1, 2, 3 or 4;

$R^{16}$ and $R^{17}$ independently are hydrogen, —COR$^{18}$, —SO$_2$R$^{18}$, lower alkyl, aryl, or $R^{16}$ and $R^{17}$ together form a cyclic alkyl bridge containing from 2 to 7 carbon atoms;

wherein $R^{18}$ is hydrogen, lower alkyl, aryl or aryl-lower alkyl;

W is CR$^{19}$=;

Y is —CR$^{20}$=;

Z is —CR$^{21}$=; and

V is —CR$^{22}$=;

wherein:

$R^{19}$, $R^{20}$, $R^{21}$ and $R^{22}$ independently are hydrogen, halogen, —CN, —CF$_3$, —OCF$_3$, —OCH$_2$CF$_3$, —NO$_2$, —OR$^{24}$, —NR$^{24}$R$^{25}$, lower alkyl, aryl, aryl-lower alkyl, —SCF$_3$, —SR$^{24}$, —CHF$_2$, 13 OCHF$_2$, —OCF$_2$CHF$_2$, —OSO$_2$CF$_3$, —CONR$^{24}$R$^{25}$, —CH$_2$CONR$^{24}$R$^{25}$, —OCH$_2$CONR$^{24}$R$^{25}$, —CH$_2$OR$^{24}$, —CH$_2$NR$^{24}$R$^{25}$, —OCOR$^{24}$ or —COR$^2$R$^{24}$, or $R^{19}$ and $R^{20}$, $R^{20}$ and $R^{21}$, or $R^{21}$ and $R^{22}$ together form a bridge —OCH$_2$O—;

wherein $R^{24}$ and $R^{25}$ independently are hydrogen, —COR$^{26}$, —SO$_2$R$^{26}$, lower alkyl, aryl or aryl-lower alkyl; and wherein $R^{26}$ is hydrogen, lower alkyl, aryl or aryl-lower alkyl;

K is

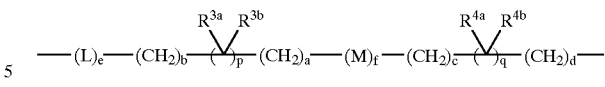

wherein:

$R^{3a}$, $R^{3b}$, $R^{4a}$ and $R^{4b}$ independently are hydrogen, halogen, —CN, —CF$_3$, —OCF$_3$, —OCH$_2$CF$_3$, —NO$_2$, —OR$^{24n}$, —NR$^{24n}$R$^{25a}$, lower alkyl, aryl, aryl-lower alkyl, —SCF$_3$, —SR$^{24n}$, —CHF$_2$, —OCH$_2$, —OCF$_2$CHF$_2$, —OSO$_2$CF$_3$, —CONR$^{24n}$R$^{25a}$, —CH$_2$CONR$^{24a}$R$^{25n}$, —OCH$_2$CONR$^{24a}$R$^{25n}$, —CH$_2$OR$^{24n}$, —CH$_2$NR$^{24a}$R$^{25n}$, —OCOR$^{24n}$ or —CO$_2$R$^{24n}$;

wherein $R^{24n}$ and $R^{25a}$ independently are hydrogen, —COR$^{26n}$, —SO$_2$R$^{26a}$, lower alkyl, aryl or aryl-lower alkyl;

wherein $R^{26a}$ is hydrogen, lower alkyl, aryl or aryl-lower alkyl;

or $R^{3n}$ and $R^{3b}$, $R^{4n}$ and $R^{4b}$, or $R^{3n}$ and $R^{4b}$ together form a bridge —(CH$_2$)$_i$—;

wherein i is 1, 2, 3 or 4;

a, b, c and d independently are 0, 1, 2, 3 or 4;

e, f and p independently are 0 or 1;

q is 0, 1 or 2; and

L and M independently are —O—, —S—, —CH=CH—, —C≡C—, —NR$^{5a}$—, —CH$_2$NR$^{5a}$—, —CO—, —OCO—, —COO—, —CONR$^{5a}$—, —CONR$^{5b}$—, —NR$^{5n}$CO—, —SO—, —SO$_2$—, —OSO$_2$—, —SO$_2$NR$^{5a}$—, —NR$^{5n}$SO$_2$—, —NR$^{5a}$CON R$^{5b}$—, —CONR$^{5a}$NR$^{5b}$—, —NR$^{5a}$CSNR$^{5b}$—, —OCONR$^{5b}$—, —CH$_2$CONR$^{5b}$—, —OCH$_2$CONR$^{5b}$, —P(O)(OR$^{5a}$)O—, —NR$^{5a}$C(O)O— or

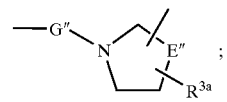

wherein $R^{5a}$ and $R^{5b}$ independently are hydrogen, lower alkyl, —OH, —(CH$_2$)$_k$OR$^{6n}$, —COR$^{6n}$, —(CH$_2$)$_k$—CH(OR$^{6n}$)$_z$, —(CH$_2$)$_k$—CN, —(CH$_2$)$_k$—NR$^{6a}$R$^{6b}$, aryl, aryl-lower alkyl, —(CH$_2$)$_E$—COOR$^{43}$ or —(CH$_2$)$_E$—CF$_3$;

wherein k is 1, 2, 3 or 4;

$R^{6a}$ and $R^{6b}$ independently are hydrogen, lower alkyl, aryl or aryl-lower alkyl;

g is 0, 1, 2, 3 or 4;

$R^{43}$ is hydrogen or lower alkyl;

G" is —OCH$_2$CO—, —CH$_2$CO—, —CO— or a valence bond; and

E" is —CH$_2$—, —CH$_2$CH$_2$—, —CH=CH—, —CH$_2$NH— or —CH$_2$CH$_2$NH—;

D is hydrogen,

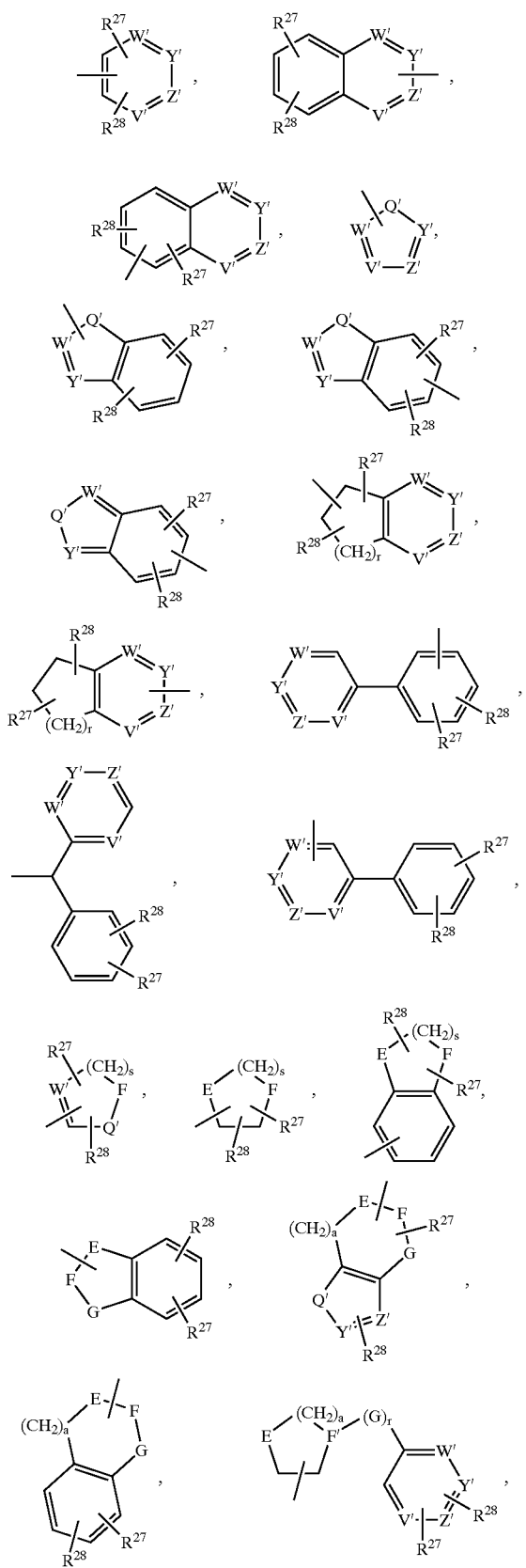

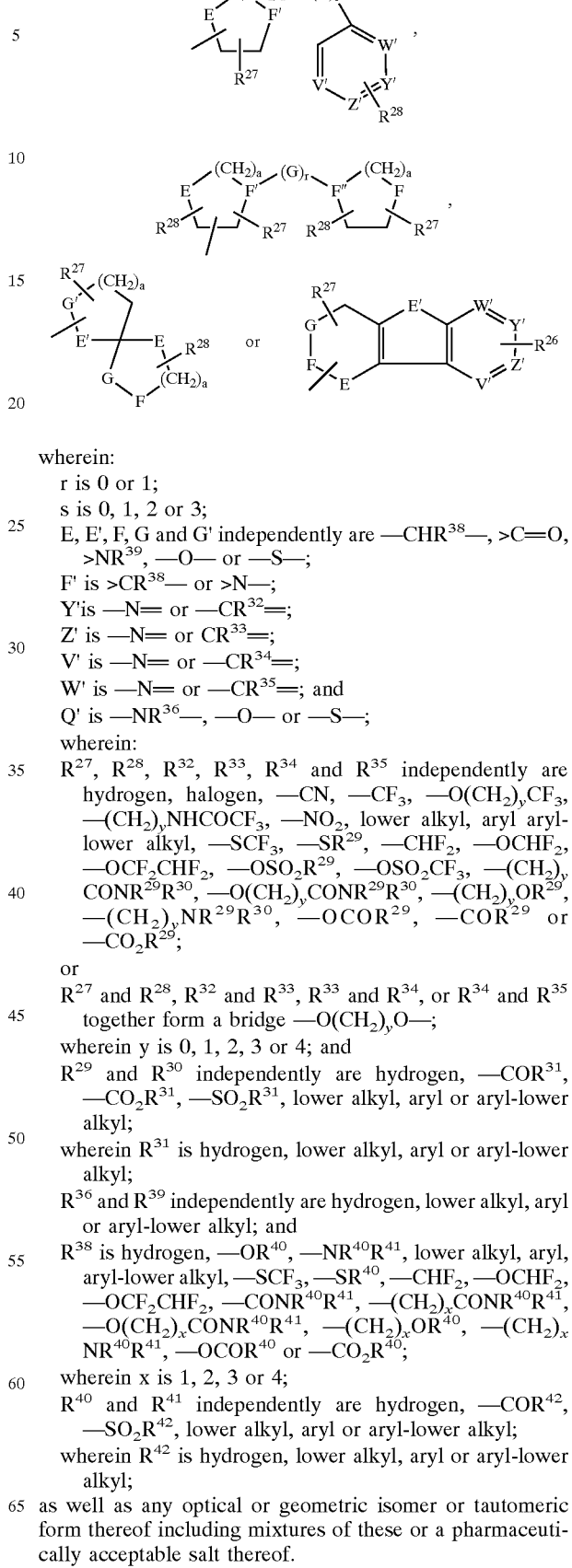

wherein:
r is 0 or 1;
s is 0, 1, 2 or 3;
E, E', F, G and G' independently are —CHR$^{38}$—, >C=O, >NR$^{39}$, —O— or —S—;
F' is >CR$^{38}$— or >N—;
Y' is —N= or —CR$^{32}$=;
Z' is —N= or CR$^{33}$=;
V' is —N= or —CR$^{34}$=;
W' is —N= or —CR$^{35}$=; and
Q' is —NR$^{36}$—, —O— or —S—;
wherein:
R$^{27}$, R$^{28}$, R$^{32}$, R$^{33}$, R$^{34}$ and R$^{35}$ independently are hydrogen, halogen, —CN, —CF$_3$, —O(CH$_2$)$_y$CF$_3$, —(CH$_2$)$_y$NHCOCF$_3$, —NO$_2$, lower alkyl, aryl aryl-lower alkyl, —SCF$_3$, —SR$^{29}$, —CHF$_2$, —OCHF$_2$, —OCF$_2$CHF$_2$, —OSO$_2$R$^{29}$, —OSO$_2$CF$_3$, —(CH$_2$)$_y$CONR$^{29}$R$^{30}$, —O(CH$_2$)$_y$CONR$^{29}$R$^{30}$, —(CH$_2$)$_y$OR$^{29}$, —(CH$_2$)$_y$NR$^{29}$R$^{30}$, —OCOR$^{29}$, —COR$^{29}$ or —CO$_2$R$^{29}$;
or
R$^{27}$ and R$^{28}$, R$^{32}$ and R$^{33}$, R$^{33}$ and R$^{34}$, or R$^{34}$ and R$^{35}$ together form a bridge —O(CH$_2$)$_y$O—;
wherein y is 0, 1, 2, 3 or 4; and
R$^{29}$ and R$^{30}$ independently are hydrogen, —COR$^{31}$, —CO$_2$R$^{31}$, —SO$_2$R$^{31}$, lower alkyl, aryl or aryl-lower alkyl;
wherein R$^{31}$ is hydrogen, lower alkyl, aryl or aryl-lower alkyl;
R$^{36}$ and R$^{39}$ independently are hydrogen, lower alkyl, aryl or aryl-lower alkyl; and
R$^{38}$ is hydrogen, —OR$^{40}$, —NR$^{40}$R$^{41}$, lower alkyl, aryl, aryl-lower alkyl, —SCF$_3$, —SR$^{40}$, —CHF$_2$, —OCHF$_2$, —OCF$_2$CHF$_2$, —CONR$^{40}$R$^{41}$, —(CH$_2$)$_x$CONR$^{40}$R$^{41}$, —O(CH$_2$)$_x$CONR$^{40}$R$^{41}$, —(CH$_2$)$_x$OR$^{40}$, —(CH$_2$)$_x$NR$^{40}$R$^{41}$, —OCOR$^{40}$ or —CO$_2$R$^{40}$;
wherein x is 1, 2, 3 or 4;
R$^{40}$ and R$^{41}$ independently are hydrogen, —COR$^{42}$, —SO$_2$R$^{42}$, lower alkyl, aryl or aryl-lower alkyl;
wherein R$^{42}$ is hydrogen, lower alkyl, aryl or aryl-lower alkyl;
as well as any optical or geometric isomer or tautomeric form thereof including mixtures of these or a pharmaceutically acceptable salt thereof.

2. A compound according to claim 1, wherein $R^3$ is hydrogen.

3. A compound according to claim 1, wherein $R^8$ is halogen, —$NO_2$, —$NH_2$, —CN, —$OCF_3$, —$SCF_3$, —$CF_3$, —$OCH_2CF_3$, —O-lower alkyl, lower alkyl or phenyl and $R^9$ is hydrogen, halogen, —OH, —$NO_2$, —$NH_2$, —CN, —$OCF_3$, —$SCF_3$, —$CF_3$, —$OCH_2CF_3$, —O-lower alkyl, lower alkyl or phenyl.

4. A compound according to claim 3, wherein $R^8$ is halogen, —O-lower alkyl, —$NH_2$, —CN or —$NO_2$ and $R^9$ is hydrogen, halogen, —O-lower alkyl, —$NH_2$, —CN or —$NO_2$.

5. A compound according to claim 1, wherein $R^8$ is halogen, —O-lower alkyl, —$NH_2$, —CN or —$NO_2$; and $R^9$ is hydrogen or halogen.

6. A compound according to claim 1, wherein B is

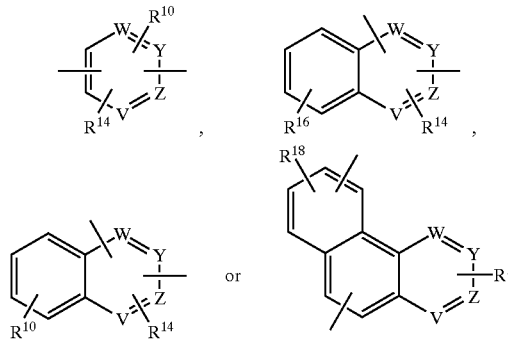

wherein $R^{14}$ and $R^{15}$ independently are hydrogen, halogen, —$CF_3$, —$OCF_3$, —$OR^{16}$, —$NR^{16}R^{17}$, lower alkyl, aryl, aryl-lower alkyl, —$OSO_2CF_3$, —$CONR^{16}R^{17}$, —$CH_2OR^{16}$, —$CH_2NR^{16}R^{17}$, —$OCOR^{16}$ or —$CO_2R^{18}$; or $R^{14}$ and $R^{15}$ together form a bridge —$OCH_2O$— or —$(CH_2)_1$—.

7. A compound according to claim 6 wherein B is

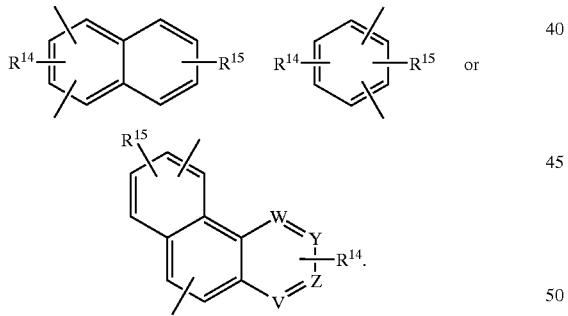

wherein $R^{14}$ and $R^{15}$ are as defined in claim 6.

8. A compound according to claim 6, wherein $R^{14}$ and $R^{15}$ independently are hydrogen, halogen, lower alkyl, —O-lower alkyl or aryl.

9. A compound according to claim 1, wherein K is selected from the group consisting of

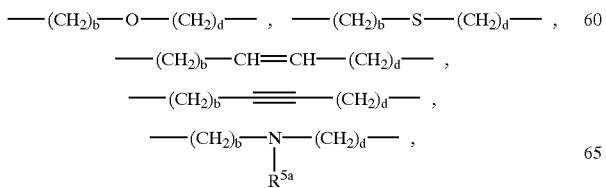

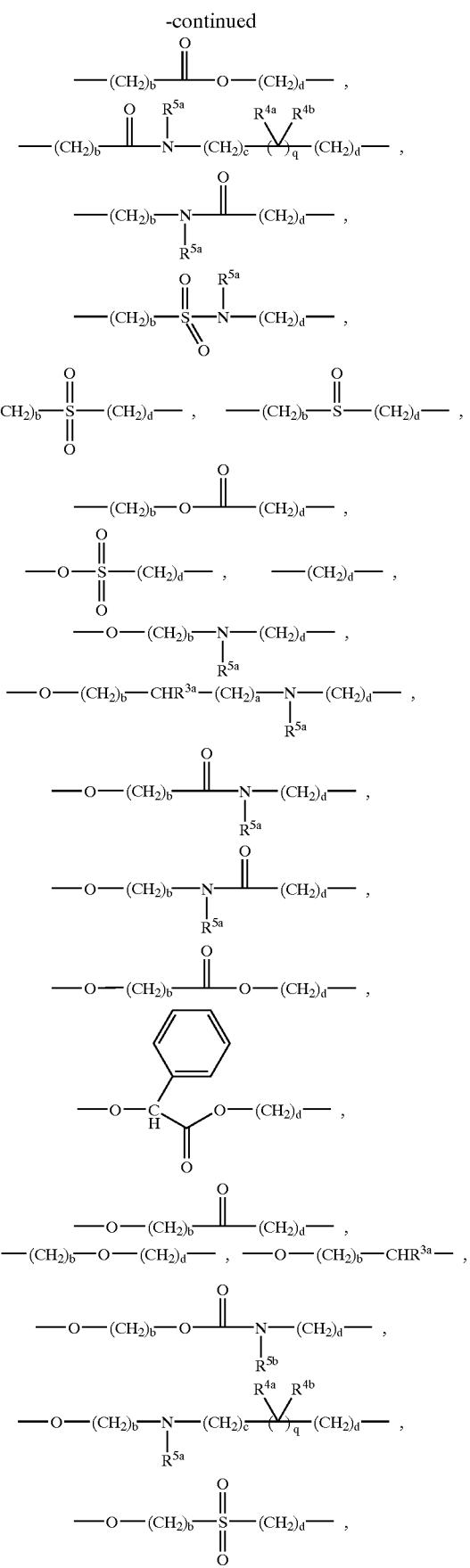

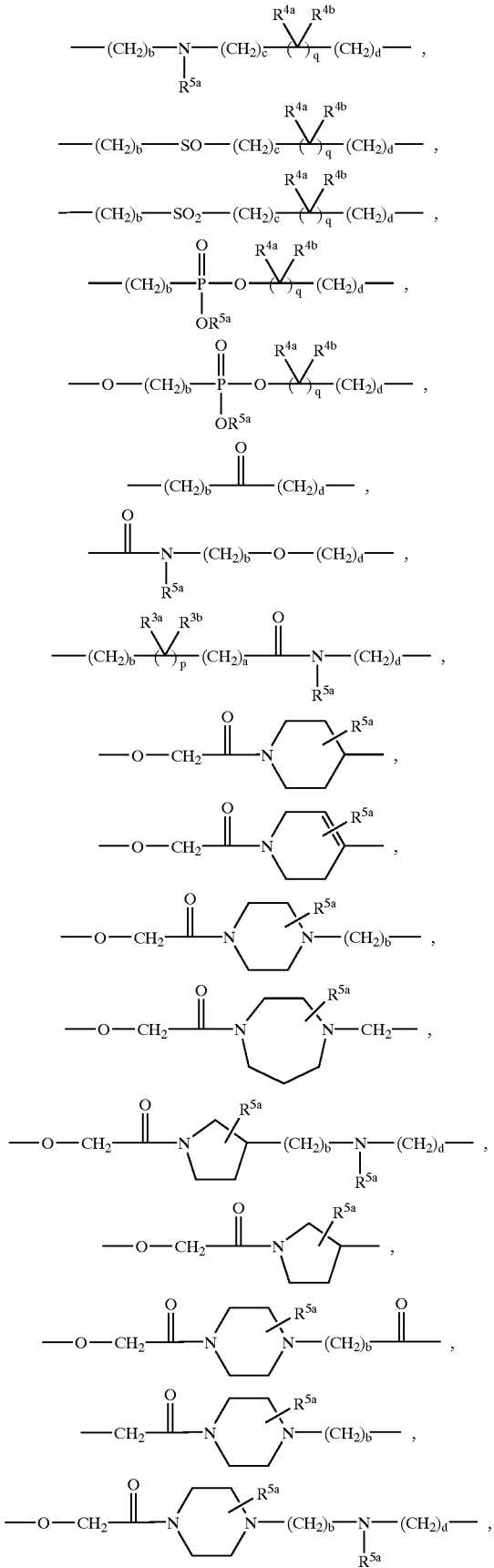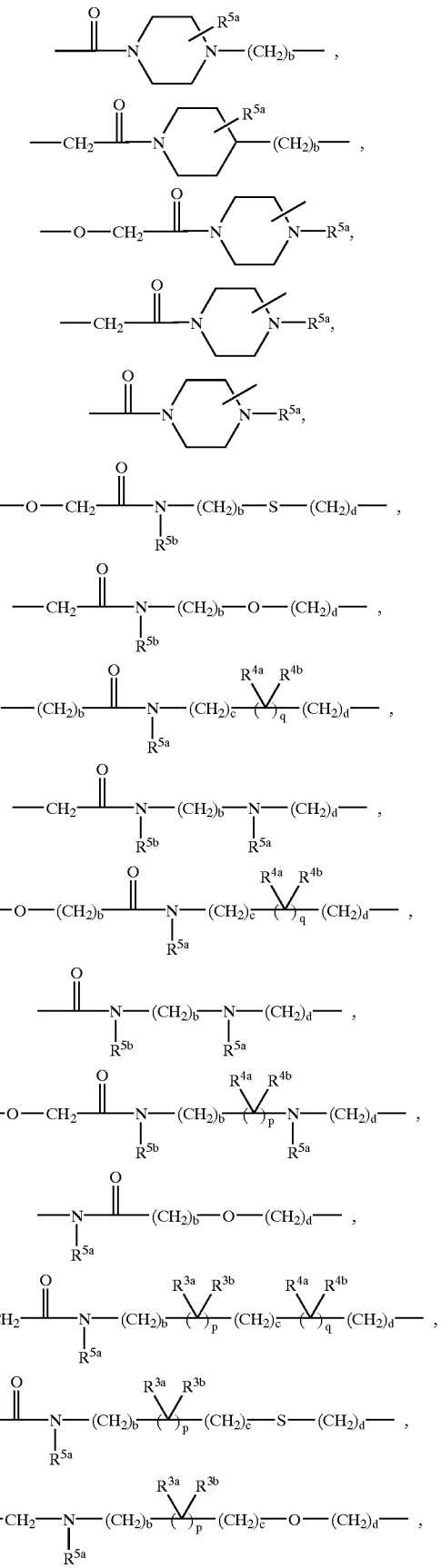

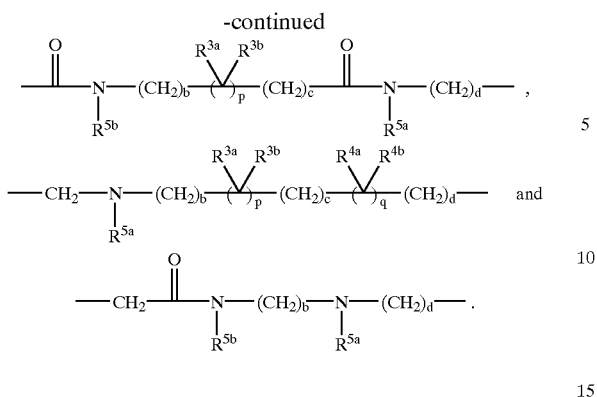
10. A compound according to claim 9, wherein K is selected from the group consisting of
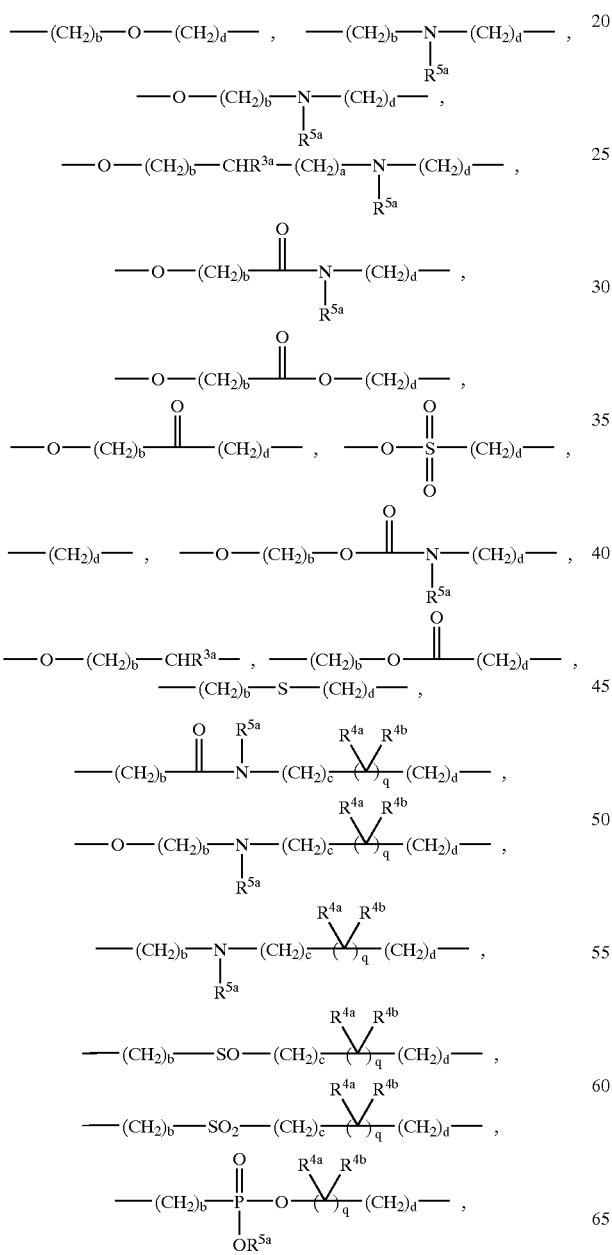
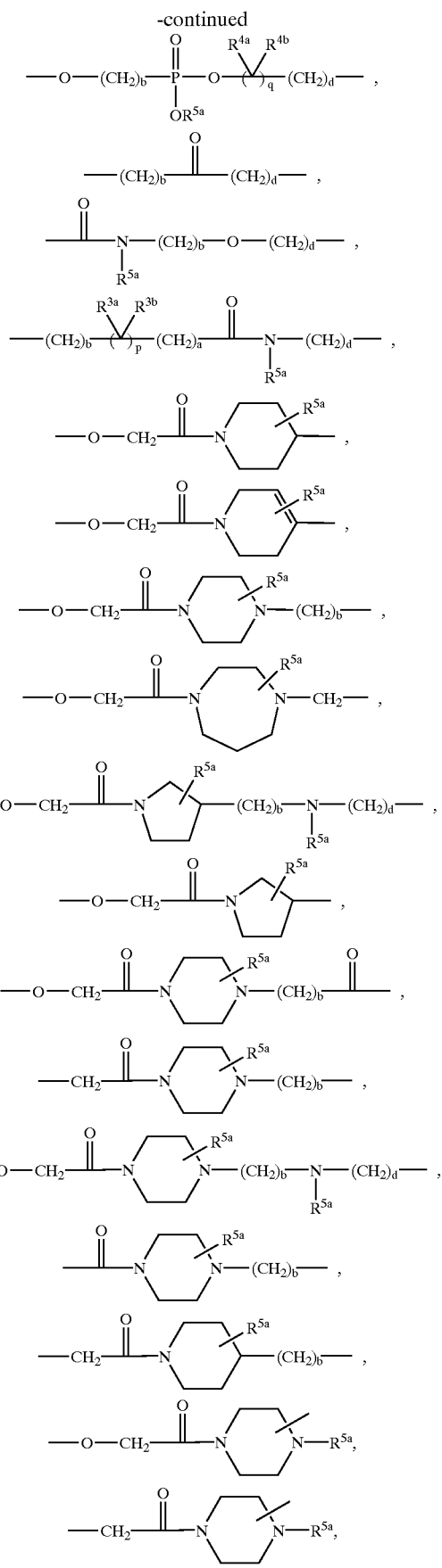

11. A compound according to claim 10, wherein K is selected from the group consisting of

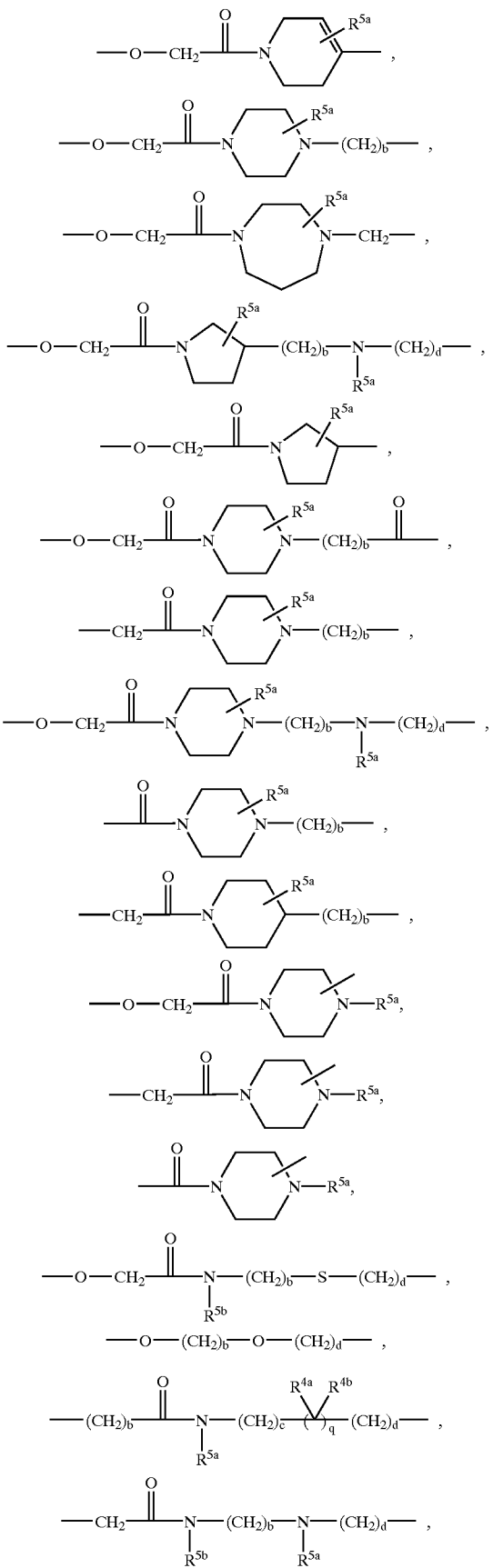

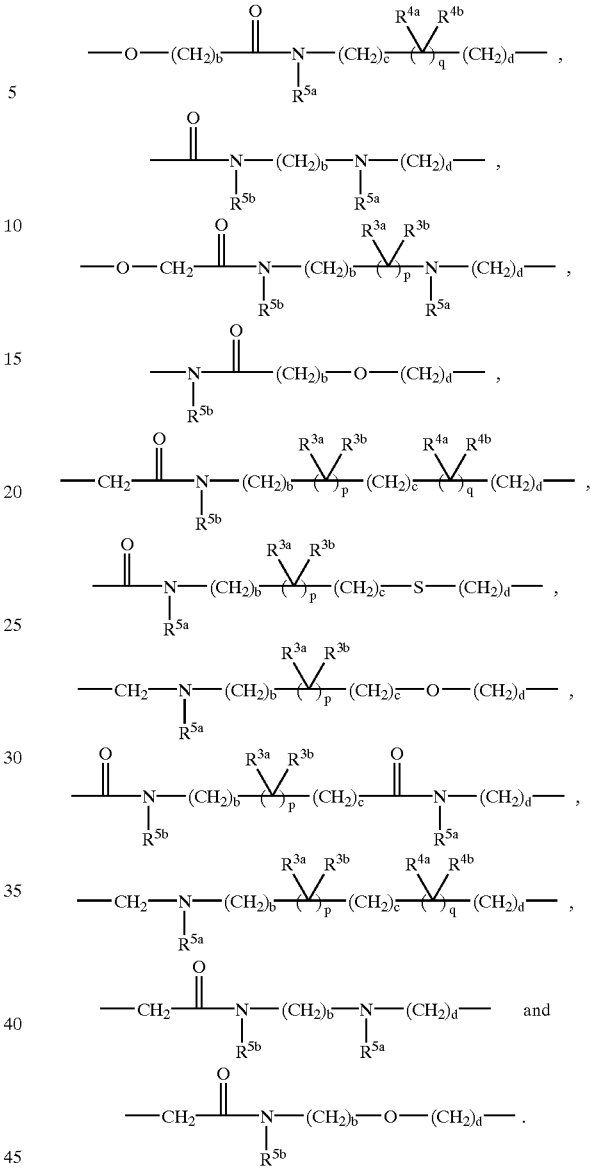

12. A compound according to claim 9, wherein $R^{5a}$ and $R^{5b}$ independently are hydrogen, lower alkyl, —OH, —$(CH_2)_k OR^{6a}$, aryl, aryl-lower alkyl, —$CH_2CF_3$, —$(CH_2)_g$—$COOR^{43}$, —$COOR^{43}$, —$(CH_2)_k$—CN or —$(CH_2)_k$—$NR^{6a}R^{6b}$.

13. A compound according to claim 12, wherein g and k independently are 1, 2 or 3, $R^{6a}$ and $R^{6b}$ independently are hydrogen, lower alkyl or aryl.

14. A compound according to claim 9, wherein $R^{3a}$ and $R^{3b}$ independently are hydrogen, halogen, —OH, —O-lower alkyl, —COO-lower alkyl, lower alkyl or aryl-lower alkyl.

15. A compound according to claim 9, wherein $R^{4a}$ and $R^{4b}$ independently are hydrogen, —CN, —$CONH_2$, —$(CH_2)$—$N(CH_3)_2$, —O-lower alkyl, —$CH_2OH$, —$CH_2O$-aryl, —$N(CH_3)_2$, —OH, —$CO_2$-lower alkyl or lower alkyl.

16. A compound according to claim 1, wherein D is hydrogen,

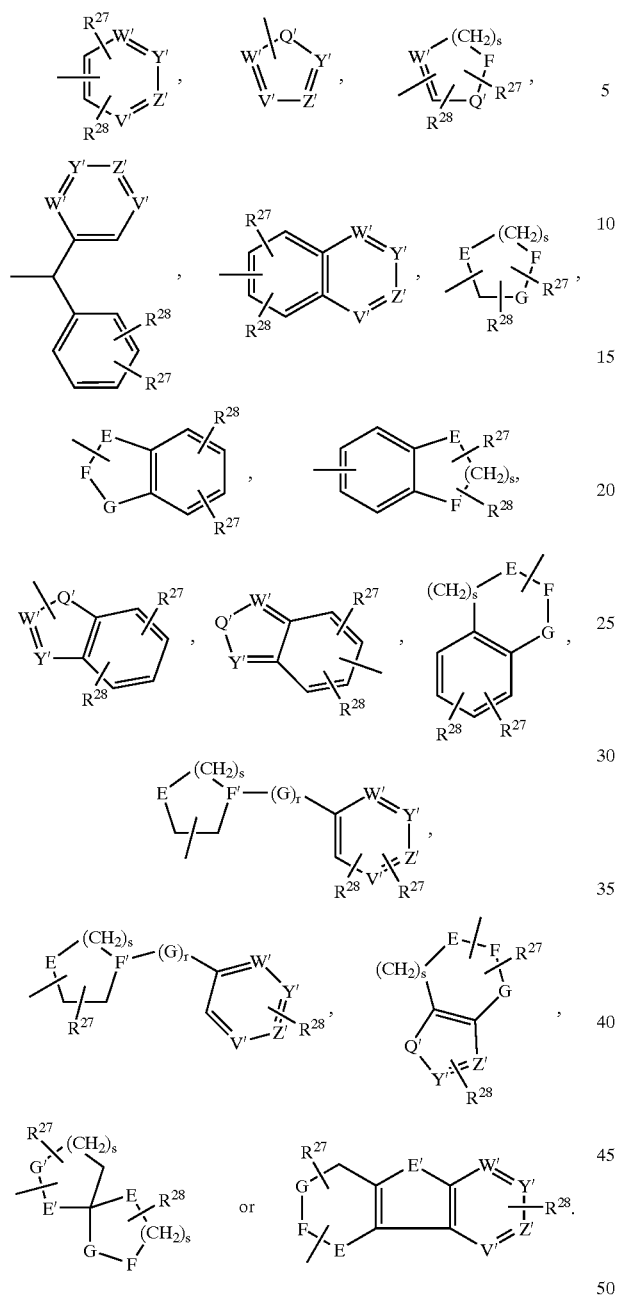
17. A compound according to claim 16, wherein D is hydrogen,
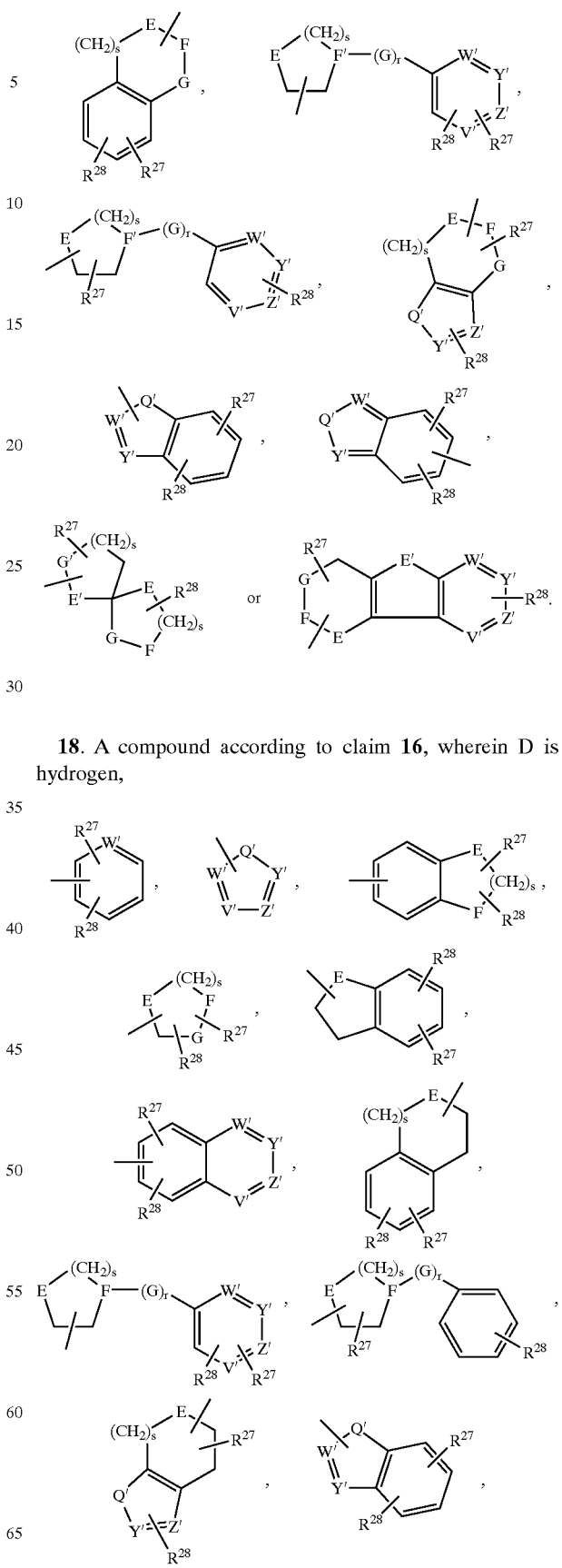
18. A compound according to claim 16, wherein D is hydrogen, -continued

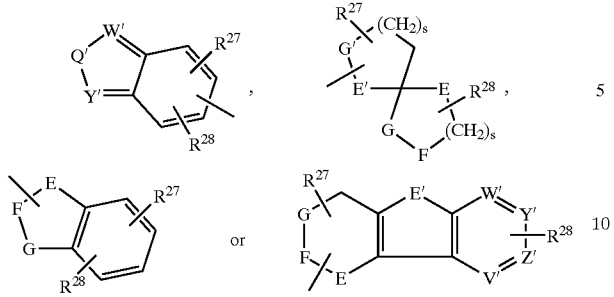

wherein E and E' independently are >CHR$^{38}$, >NR$^{39}$ and/or —O—; F, G and G' independently are >CHR$^{38}$, >C=O or >NR$^{39}$; F' is >CR$^{38}$— or >N.

19. A compound according to claim 16, wherein R$^{27}$ and R$^{28}$ independently are hydrogen; halogen —CF$_3$; —OCF$_3$; —OCHF$_2$; —OCH$_2$CF$_3$; —(CH$_2$)$_y$NHCOCF$_3$; —NHCOCF$_3$; —CN; —NO$_2$; —COR$^{29}$; —COOR$^{29}$, —(CH$_2$)$_y$OR$^{29}$ or —OR$^{29}$ wherein R$^{29}$ is hydrogen, aryl or lower alkyl and y is 1, 2, 3 or 4; lower alkyl lower alkylthio; —SCF$_3$; aryl —(CH$_2$)$_y$NR$^{29}$R$^{30}$ or —NR$^{29}$R$^{30}$ wherein R$^{29}$ and R$^{30}$ independently are hydrogen, —COO-lower alkyl or lower alkyl and y is 1, 2, 3 or 4; or —CONH$_2$; or R$^{27}$ and R$^{28}$ together form a bridge —OCH$_2$O—; R$^{38}$ is hydrogen; —OCHF$_2$; —OR$^{40}$ wherein R$^{40}$ is hydrogen or lower alkyl; lower alkyl lower alkylthio; —SCF$_3$; —CH$_2$OH; —COO-lower alkyl or —CONH$_2$; and R$^{39}$ is hydrogen, lower alkyl, aryl or aryl-lower alkyl.

20. A pharmaceutical composition comprising, as an active ingredient a compound according to claim 1 together with one or more pharmaceutically acceptable carriers or excipients.

21. A pharmaceutical composition according to claim 20 in unit dosage form, comprising from about 0.05 mg to about 1000 mg, of the compound.

22. A method of treating type I or type II diabetes, comprising administering to a subject in need thereof an effective amount of a compound according to claim 1.

23. A method of treating hyperglycemia, comprising administering to a subject in need thereof an effective amount of a compound according to claim 1.

24. A method of lowering blood glucose in a mammal, comprising administering to said mammal an effective amount of a compound according to claim 1.

25. The method according to claim 22 comprising administering to a subject in need thereof an amount of the compound as defined in claim 1 to 33 in the range of from about 0.05 mg to about 1000 mg, one or more times per day.

26. A compound according to claim 1 characterized by having a glucagon antagonistic activity as determined by the Glucagon Binding Assay I or Glucagon By Binding Assay II corresponding to an IC$_{50}$ value of less than 1 μM.

27. A compound of formula (XVI):

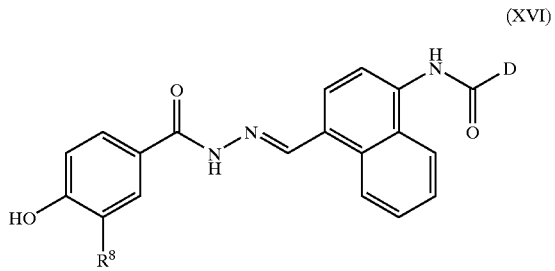

(XVI)

wherein

R$^8$ is chloro, fluoro, nitro or cyano; and

D is C$_{1-6}$-alkyl, C$_{3-8}$-cycloalkyl,

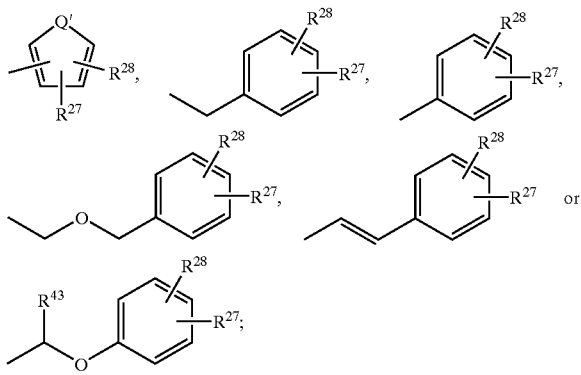

wherein R$^{27}$ and R$^{28}$ independently are hydrogen, halogen, cyano, nitro, acetoxy, C$_{1-6}$-alkoxy, benzyloxy, trifluoromethyl, methylsulfonyl or C$_{1-6}$-alkyl;

Q' is —O— or —S—; and

R$^{43}$ is hydrogen, C$_{1-6}$-alkyl, C$_{1-6}$-alkylene-NH$_2$, C$_{1-6}$-alkylene-NH(C$_{1-3}$-alkyl) or C$_{1-6}$-alkylene-N(C$_{1-3}$-alkyl)$_2$;

as well as any optical or geometric isomer or tautomeric form thereof including mixtures of these or a pharmaceutically acceptable salt thereof.

28. A compound according to claim 27 wherein D is

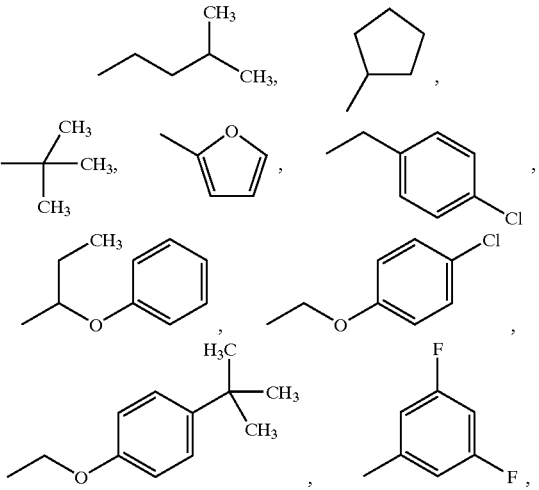

-continued

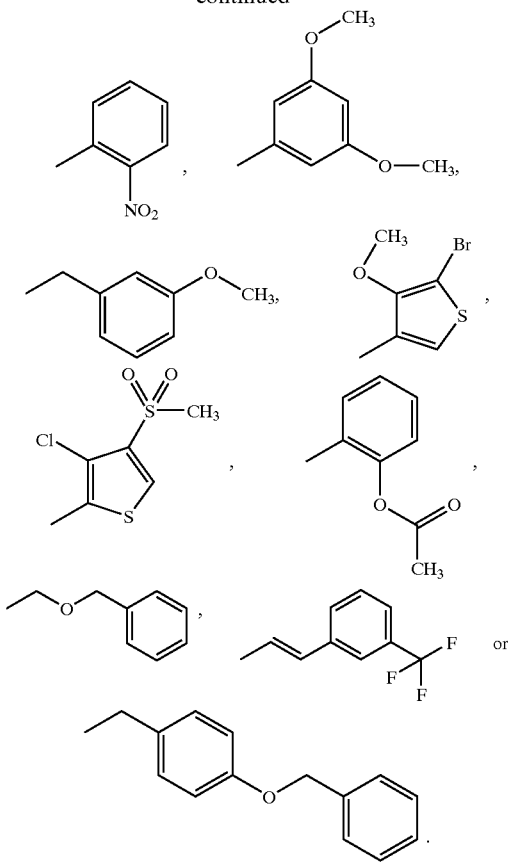

29. A compound according to claim 27 wherein $R^8$ is chloro.

30. A compound according to claim 27 wherein $R^8$ is cyano.

31. A pharmaceutical composition comprising, as an active ingredient, a compound according to claim 27 together with one or more pharmaceutically acceptable carriers or excipients.

32. A pharmaceutical composition according to claim 31 in unit dosage form, comprising from about 0.05 mg to about 1000 mg of the compound according to claim 29.

33. A method of treating type I or type II diabetes, comprising administering to a subject in need thereof an effective amount of a compound according to claim 29.

34. A method of treating hyperglycemia, comprising administering to a subject in need thereof an effective amount of a compound according to claim 29.

35. A method of lowering blood glucose in a mammal, comprising administering to said mammal an effective amount of a compound according to claim 29.

36. The method according to claim 33 comprising administering to a subject in need thereof an amount of the compound as defined in claim 27 in the range of from about 0.05 mg to about 1000 mg, one or more times per day.

37. A compound selected from the group consisting of:

N-(4-[(3-chloro-4-hydroxybenzoyl)hydrazonomethyl]-3-methoxyphenyl)-2-(2-trifluoromethylphenyl) acetamide as well as any optical or geometric isomer or tautomeric form thereof including mixtures of these or a pharmaceutically acceptable salt thereof;

3-phenylpropynoic acid {4-[(3-chloro-4-hydroxybenzoyl)hydrazonomethyl]-3-methoxyphenyl}amide as well as any optical or geometric isomer or tautomeric form thereof including mixtures of these or a pharmaceutically acceptable salt thereof;

N-{4-[(3-chloro-4-hydroxybenzoyl)hydrazonomethyl]-3-methoxyphenyl}-2-(4-chlorophenyl)-acetamide as well as any optical or geometric isomer or tautomeric form thereof including mixtures of these or a pharmaceutically acceptable salt thereof;

N-{4-[(3-chloro-4-hydroxybenzoyl)hydrazonomethyl]-3-methoxyphenyl}-2-(3-chlorophenyl)acetamide as well as any optical or geometric isomer or tautomeric form thereof including mixtures of these or a pharmaceutically acceptable salt thereof;

N-{4-[(3-chloro-4-hydroxybenzoyl)hydrazonomethyl]-3-methoxyphenyl}-2-(4-trifluoromethylphenylsulfanyl) acetamide as well as any optical or geometric isomer or tautomeric form thereof including mixtures of these or a pharmaceutically acceptable salt thereof;

5-methoxybenzofuran-2-carboxylic acid {4-[(3-chloro-4-hydroxybenzoyl)hydrazonomethyl]-3-methoxyphenyl) amide as well as any optical or geometric isomer or tautomeric form thereof including mixtures of these or a pharmaceutically acceptable salt thereof;

2-benzo[b]thiophen-3-yl-N-{4-[(3-chloro-4-hydroxybenzoyl)hydrazonomethyl]-3-methoxyphenyl}acetamide as well as any optical or geometric isomer or tautomeric form thereof including mixtures of these or a pharmaceutically acceptable salt thereof;

N-(4-[(3-chloro-4-hydroxybenzoyl)hydrazonomethyl]-3-methoxyphenyl}-2-(3,4-difluorophenyl)acetamide as well as any optical or geometric isomer or tautomeric form thereof including mixtures of these or a pharmaceutically acceptable salt thereof;

N-{4-[(3-chloro-4-hydroxybenzoyl)hydrazonomethyl]-3-methoxyphenyl}-2-(4-chlorophenylsulfanyl)acetamide as well as any optical or geometric isomer or tautomeric form thereof including mixtures of these or a pharmaceutically acceptable salt thereof;

N-{4-[(3-chloro-4-hydroxybenzoyl)hydrazonomethyl]-3-methoxyphenyl}-3-(4-chlorophenyl)propionamide as well as any optical or geometric isomer or tautomeric form thereof including mixtures of these or a pharmaceutically acceptable salt thereof; and N-{4-[(3-chloro-4-hydroxybenzoyl)hydrazonomethyl]-3-methoxyphenyl}-3-(4-cyanophenoxy)acetamide as well as any optical or geometric isomer or tautomeric form thereof including mixtures of these or a pharmaceutically acceptable salt thereof.

38. A compound selected from the group consisting of:

N-{4-[(3-cyano-4-hydroxybenzoyl)hydrazonomethyl]-3-methoxyphenyl}-2-(2-trifluoromethylphenyl) acetamide as well as any optical or geometric isomer or tautomeric form thereof including mixtures of these or a pharmaceutically acceptable salt thereof;

3-phenylpropynoic acid {4-[(3-cyano-4-hydroxybenzoyl) hydrazonomethyl]-3-methoxyphenyl}amide as well as any optical or geometric isomer or tautomeric form thereof including mixtures of these or a pharmaceutically acceptable salt thereof;

N-{4-[(3-cyano-4-hydroxybenzoyl)hydrazonomethyl]-3-methoxyphenyl}-2-(4-chlorophenyl)acetamide as well as any optical or geometric isomer or tautomeric form thereof including mixtures of these or a pharmaceutically acceptable salt thereof;

N-{4-[(3-cyano-4-hydroxybenzoyl)hydrazonomethyl]-3-methoxyphenyl}-2-(3-chlorophenyl)acetamide as well as any optical or geometric isomer or tautomeric form thereof including mixtures of these or a pharmaceutically acceptable salt thereof;

N-{4-[(3-cyano-4-hydroxybenzoyl)hydrazonomethyl]-3-methoxyphenyl}-2-(4-trifluoromethylphenylsulfanyl)acetamide as well as any optical or geometric isomer or tautomeric form thereof including mixtures of these or a pharmaceutically acceptable salt thereof;

5-methoxybenzofuran-2-carboxylic acid {4-[(3-cyano-4-hydroxybenzoyl)hydrazonomethyl]-3-methoxyphenyl) amide as well as any optical or geometric isomer or tautomeric form thereof including mixtures of these or a pharmaceutically acceptable salt thereof;

2-benzo[b]thiophen-3-yl-N-{4-[(3-cyano-4-hydroxybenzoyl)hydrazonomethyl]-3-methoxyphenyl}acetamide as well as any optical or geometric isomer or tautomeric form thereof including mixtures of these or a pharmaceutically acceptable salt thereof;

N-{4-[(3-cyano-4-hydroxybenzoyl)hydrazonomethyl]-3-methoxyphenyl)-2-(3,4-difluorophenyl)acetamide as well as any optical or geometric isomer or tautomeric form thereof including mixtures of these or a pharmaceutically acceptable salt thereof;

N-{4-[(3-cyano-4-hydroxybenzoyl)hydrazonomethyl]-3-methoxyphenyl}-2-(3-trifluoromethylphenyl)acetamide as well as any optical or geometric isomer or tautomeric form thereof including mixtures of these or a pharmaceutically acceptable salt thereof;

N-{4-[(3-cyano-4-hydroxybenzoyl)hydrazonomethyl]-3-methoxyphenyl}-3-(4-trifluoromethylphenyl)propionamide as well as any optical or geometric isomer or tautomeric form thereof including mixtures of these or a pharmaceutically acceptable salt thereof;

N-{4-[(3-cyano-4-hydroxybenzoyl)hydrazonomethyl]-3-methoxyphenyl}-2-(4-chlorophenylsulfanyl)acetamide as well as any optical or geometric isomer or tautomeric form thereof including mixtures of these or a pharmaceutically acceptable salt thereof;

N-(4-[(3-cyano-4-hydroxybenzoyl)hydrazonomethyl]-3-methoxyphenyl}-3-(4-chlorophenyl)propionamide as well as any optical or geometric isomer or tautomeric form thereof including mixtures of these or a pharmaceutically acceptable salt thereof; and N-{4-[(3-cyano-4-hydroxybenzoyl)hydrazonomethyl]-3-methoxyphenyl}-3-(4-cyanophenoxy)acetamide as well as any optical or geometric isomer or tautomeric form thereof including mixtures of these or a pharmaceutically acceptable salt thereof.

39. A pharmaceutical composition comprising, as an active ingredient a compound according to claim 37 together with one or more pharmaceutically acceptable carriers or excipients.

40. A pharmaceutical composition according to claim 39 in unit dosage form, comprising from about 0.05 mg to about 1000 mg of the compound according to claim 37.

41. A method of treating type I or type II diabetes, comprising administering to a subject in need thereof an effective amount of a compound according to claim 37.

42. A method of treating hyperglycemia, comprising administering to a subject in need thereof an effective amount of a compound according to claim 37.

43. A method of lowering blood glucose in a mammal, comprising administering to said mammal an effective amount of a compound according to claim 37.

44. The method according to claim 41 comprising administering to a subject in need thereof an amount of the compound as defined in claim 37 in the range of from about 0.05 mg to about 1000 mg.

45. A method of treating type I or type II diabetes, comprising administering to a subject in need thereof an effective amount of a composition according to claim 31.

46. A method of treating hyperglycemia, comprising administering to a subject in need thereof an effective amount of a composition according to claim 31.

47. A method of lowering blood glucose in a mammal, comprising administering to said mammal an effective amount of a composition according to claim 31.

48. A method of treating type I or type II diabetes, comprising administering to a subject in need thereof an effective amount of a composition according to claim 39.

49. A method of treating hyperglycemia, comprising administering to a subject in need thereof an effective amount of a composition according to claim 39.

50. A method of lowering blood glucose in a mammal, comprising administering to said mammal an effective amount of a composition according to claim 39.

* * * * *